US010246456B2

(12) United States Patent
Chan et al.

(10) Patent No.: US 10,246,456 B2
(45) Date of Patent: Apr. 2, 2019

(54) IRAK4 INHIBITING AGENTS

(71) Applicant: BIOGEN MA INC., Cambridge, MA (US)

(72) Inventors: Timothy Chan, Cambridge, MA (US); Kevin Guckian, Cambridge, MA (US); Tracy Jenkins, Cambridge, MA (US); Jermaine Thomas, Cambridge, MA (US); Jeffery Vessels, Cambridge, MA (US); Gnanasambandam Kumaravel, Cambridge, MA (US); Robert Meissner, Cambridge, MA (US); Joseph Lyssikatos, Cambridge, MA (US); Brian Lucas, Cambridge, MA (US); Irina Leaf, Cambridge, MA (US); Jeremy Duffield, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 15/326,740

(22) PCT Filed: Jul. 17, 2015

(86) PCT No.: PCT/US2015/040967
§ 371 (c)(1),
(2) Date: Jan. 17, 2017

(87) PCT Pub. No.: WO2016/011390
PCT Pub. Date: Jan. 21, 2016

(65) Prior Publication Data
US 2017/0204093 A1    Jul. 20, 2017

Related U.S. Application Data

(60) Provisional application No. 62/026,214, filed on Jul. 18, 2014.

(51) Int. Cl.
| | |
|---|---|
| *C07D 471/04* | (2006.01) |
| *C07D 413/14* | (2006.01) |
| *C07D 405/14* | (2006.01) |
| *C07D 401/14* | (2006.01) |
| *A61K 31/416* | (2006.01) |
| *A61P 13/12* | (2006.01) |
| *C07B 59/00* | (2006.01) |
| *C07D 401/12* | (2006.01) |
| *C07D 417/14* | (2006.01) |

(52) U.S. Cl.
CPC .......... *C07D 471/04* (2013.01); *A61K 31/416* (2013.01); *C07B 59/002* (2013.01); *C07D 401/12* (2013.01); *C07D 401/14* (2013.01); *C07D 405/14* (2013.01); *C07D 413/14* (2013.01); *C07D 417/14* (2013.01); *A61P 13/12* (2018.01); *C07B 2200/05* (2013.01)

(58) Field of Classification Search
CPC .. C07D 231/56; C07D 231/46; A61K 31/416; A61P 13/12
USPC ....................................... 548/361.1; 514/403
See application file for complete search history.

(56) References Cited

U.S. PATENT DOCUMENTS

| | | | |
|---|---|---|---|
| 8,232,411 B2 * | 7/2012 | Lukin .................. | C07D 231/56 548/361.1 |
| 2004/0236110 A1 * | 11/2004 | Ladouceur ........... | C07D 401/04 546/277.4 |
| 2009/0281115 A1 | 11/2009 | Bornmann et al. | |
| 2011/0130384 A1 | 6/2011 | Setoh et al. | |

FOREIGN PATENT DOCUMENTS

| | | |
|---|---|---|
| WO | WO-2014/092351 A1 | 6/2014 |

OTHER PUBLICATIONS

Cecil Textbook of Medicine, edited by Bennet, J.C., and Plum F., 20th edition, vol. 1, 1004-1010, 1996.*
Cohen et al., Current Opinion in Chemical Biology, 3,459-465, 1999.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531 -537, 1999.*
Jain et al. Frontiers in Immunology, Nov. 2004, vol. 5, Article 563, pp. 1-8.*
WO 2014092351, Jun. 19, 2014, Machine Translation.*
Buckley et al., "IRAK-4 inhibitors. Part III: A series of imidazo[1,2-a]pyridines", Bioorganic & Medicinal Chemistry Letters, 18(12):3656-3660 (Jun. 15, 2008).

* cited by examiner

*Primary Examiner* — Venkataraman Balasubramanian
(74) *Attorney, Agent, or Firm* — McCarter & English, LLP; Steven G. Davis; Xin Zhang

(57) ABSTRACT

Provided are compounds of Formula (I), or pharmaceutically acceptable salts thereof, and methods for their use and production.

4 Claims, 3 Drawing Sheets

(a)

(b)

(c)

(d)

IRAK4 INHIBITING AGENTS

RELATED APPLICATIONS

This application is a 35 U.S.C. § 371 national stage filing of International Application No. PCT/US2015/040967, filed Jul. 17, 2015, which claims the benefit of U.S. Provisional Patent Application No. 62/026,214, filed Jul. 18, 2014. The entire contents of each of these applications are hereby incorporated by reference.

Provided are certain agents that inhibit IRAK4, and methods of making and using such agents.

Cellular immune responses depend on the ability of immune cells (e.g., macrophages, natural killer cells, T-cells) to detect and respond to cues in the extracellular environment by transmitting (transducing) signals across the cell membrane and into the intracellular (cytoplasmic) environment. Signals transmitted across the cell membrane may then effect a variety of "downstream" cytoplasmic and nuclear signal transduction pathways that subsequently produce a variety of immune cell responses (for example up- or down-regulation of gene transcription and translation or by releasing cytoplasmically stored components into the extracellular environment).

One cytoplasmic molecule responsible for the transmission of such downstream signals is known as "IRAK4". IRAK4 functions in cytoplasmic signal transduction pathways by interacting with components ("adaptor proteins") associated with the cytoplasmic portion of the Interleukin-1 receptor (IL-1R), Interleukin-18 receptor (IL-18R), and Toll-Like receptors (TLRs). These receptors (ILRs and the vertebrate TLRs) play important roles in innate immunity (i.e., general, non-specific immune system mechanisms of defense). In particular, TLRs play important roles in responding to microbial pathogens. TLRs are capable of eliciting a generalized immune response to pathogens via recognition of pathogen-associated molecular patterns (PAMPs). In response to such PAMPs, IL-1R/TLR signal transduction is initiated, across the cell membrane, by recruiting cytoplasmic adaptor proteins. Such adaptor proteins interact with homologous Toll/IL-1R (TIR) domains located in the cytoplasmic portion of IL-1R/TLR receptors.

The importance of adaptor proteins to immune system function is well established, as elimination of such adaptor proteins has been shown to induce significant disruptions of innate immune responses. Some examples of known IL-1R/TLR adaptor proteins are: MyD88; TIRAP/Mal; Trif/Ticam; and TRAM. MyD88, in particular, has a modular "death domain" (DD) that functions to recruit IRAK family proteins such as IRAK4. IRAK4 is thought to associate with MyD88 via IRAK4's own death domain. Moreover, loss of IRAK4/MyD88 association disrupts IL-1R/TLR signal transduction by preventing IRAK4 from phosphorylating (i.e., activating) IRAK1. Biologically, IRAK4 has been demonstrated to play a critical role in innate immunity.

SUMMARY

A first embodiment of the invention is a compound of Formula (I):

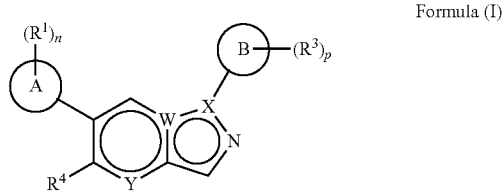

Formula (I)

or a pharmaceutically acceptable salt thereof, wherein:

Ring A is selected from phenyl and 5- or 6-membered heteroaryl;

Ring B is selected from phenyl and 5- or 6-membered heteroaryl;

n is 0, 1, or 2;

p is 0, 1, or 2;

one of W and X is N, and the other of W and X is C;

Y is N or C—$R^2$;

$R^1$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{1a}$)=NR(O$R^{1a}$), —C($R^{1a}$)=N($R^{1a}$), —C(O)$R^{1a}$, —C(O)$_2R^{1a}$, —C(O)N($R^{1a}$)$_2$, —NO$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^{15}$;

$R^{1a}$ in each occurrence is independently selected from H, $C_{1-6}$alkyl, $C_{2-6}$alkenyl, $C_{2-6}$alkynyl, 3- to 6-membered monocyclic carbocyclyl, and 3- to 6-membered monocyclic heterocyclyl wherein said $C_{1-6}$alkyl, $C_{2-6}$alkenyl, $C_{2-6}$alkynyl, 3- to 6-membered monocyclic carbocyclyl, and 3- to 6-membered monocyclic heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{10a}$)=NR(O$R^{10a}$), —C($R^{10a}$)=N($R^{10a}$), —C(O)$R^{10a}$, —C(O)$_2R^{10a}$, —C(O)N($R^{1a}$)$_2$, —NO$_2$, —N($R^{10a}$)$_2$, —N($R^{10a}$)C(O)$_2R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently selected from H and $C_{1-6}$alkyl, wherein said $C_{1-6}$alkyl is optionally substituted with one or more halo;

$R^{15}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{15a}$)=NR(O$R^{15a}$), —C($R^{15a}$)=N($R^{15a}$), —C(O)$R^{15a}$, —C(O)$_2R^{15a}$, —C(O)N($R^{15a}$)$_2$, —NO$_2$, —N($R^{15a}$)$_2$, —N($R^{15a}$)C(O)$R^{15a}$, —N($R^{15a}$)C(O)$_2R^{15a}$, —N($R^{15a}$)C(O)N($R^{15a}$)$_2$, —N($R^{15a}$)S(O)$_2R^{15a}$, —O$R^{15a}$, —OC(O)$R^{15a}$, —OC(O)N($R^{15a}$)$_2$, —S$R^{15a}$, —S(O)$R^{15a}$, —S(O)$_2R^{15a}$, —S(O)N($R^{15a}$)$_2$, and —S(O)$_2$N($R^{15a}$)$_2$;

$R^{15a}$ in each occurrence is independently selected from H and $C_{1-6}$alkyl, wherein said $C_{1-6}$alkyl is optionally substituted with one or more halo;

$R^2$ is selected from H, $C_{1-6}$alkyl, $C_{2-6}$alkenyl, $C_{2-6}$alkynyl, 3- to 7-membered carbocyclyl, 3- to 7-membered heterocyclyl, halo, —CN, —C($R^{2a}$)=NR(O$R^{2a}$), —C($R^{2a}$)=N($R^{2a}$), —C(O)$R^{2a}$, —C(O)$_2R^{2a}$, —C(O)N($R^{2a}$)$_2$, —NO$_2$, —N($R^{2a}$)$_2$, —N($R^{2a}$)C(O)$R^{2a}$, —N($R^{2a}$)C(O)$_2R^{2a}$, —N($R^{2a}$)C(O)N($R^{2a}$)$_2$, —N($R^{2a}$)S(O)$_2R^{2a}$, —O$R^{2a}$, —OC(O)$R^{2a}$, —OC(O)N($R^{2a}$)$_2$, —S$R^{2a}$, —S(O)$R^{2a}$, —S(O)$_2R^{2a}$, —S(O)N($R^{2a}$)$_2$, and —S(O)$_2$N($R^{2a}$)$_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one or more $R^{20}$;

$R^{2a}$ in each occurrence is independently selected from H and $C_{1-6}$alkyl, wherein said $C_{1-6}$alkyl in each occurrence is optionally and independently substituted with one or more $R^{20}$;

$R^{20}$ in each occurrence is independently selected from $C_{1-6}$alkyl, $C_{2-6}$alkenyl, $C_{2-6}$alkynyl, $C_{3-7}$cycloalkyl, 3- to 7-membered saturated heterocyclyl, halo, —CN, —C($R^{20a}$)=NR(O$R^{20a}$), —C($R^{20a}$)=N($R^{20a}$), —C(O)$R^{20a}$, —C(O)$_2R^{20a}$, —C(O)N($R^{20a}$)$_2$, —NO$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one or more $R^{25}$;

$R^{20a}$ in each occurrence is independently selected from H and $C_{1-6}$alkyl, wherein said $C_{1-6}$alkyl is optionally substituted with $R^{25}$;

$R^{25}$ is selected from halo and —O$R^{25a}$;

$R^{25a}$ is selected from H and $C_{1-6}$alkyl;

$R^3$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{3a}$)=NR(O$R^{3a}$), —C($R^{3a}$)=N($R^{3a}$), —C(O)$R^{3a}$, —C(O)$_2R^{3a}$, —C(O)N($R^{3a}$)$_2$, —NO$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{30}$;

$R^{3a}$ in each occurrence is independently selected from H, $C_{1-6}$alkyl, 3- to 6-membered carbocyclyl, and 3- to 6-membered heterocyclyl, wherein said $C_{1-6}$alkyl, 3- to 6-membered carbocyclyl, and 3- to 6-membered heterocyclyl in each occurrence are optionally and independently substituted with one or more $R^{30}$;

$R^{30}$ in each occurrence is independently selected from $C_{1-6}$alkyl, $C_{2-6}$alkenyl, $C_{2-6}$alkynyl, 3- to 6-membered carbocyclyl, 3- to 6-membered heterocyclyl, halo, —CN, —C($R^{30a}$)=NR(O$R^{30a}$), —C($R^{30a}$)=N($R^{30a}$), —C(O)$R^{30a}$, —C(O)$_2R^{30a}$, —C(O)N($R^{30a}$)$_2$, —NO$_2$, —N($R^{30a}$)$_2$, —N($R^{30a}$)C(O)$R^{3a}$, —N($R^{30a}$)C(O)$_2R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, 3-6 membered carboyclyl, 3- to 6-membered heterocyclyl in each occurrence are optionally and independently substituted with one or more $R^{35}$;

$R^{30a}$ in each occurrence is independently selected from H and $C_{1-6}$alkyl, wherein said $C_{1-6}$alkyl is optionally substituted with one or more $R^{35}$;

$R^{35}$ in each occurrence is independently selected from halo and —O$R^{35a}$;

$R^{35a}$ in each occurrence is independently selected from H and $C_{1-6}$alkyl;

$R^4$ is selected from H, halo, $C_{1-6}$alkyl, N($R^{4a}$)$_2$, and —O$R^{4a}$; and $R^{4a}$ in each occurrence is independently selected from H and $C_{1-6}$alkyl, wherein the compound is not:
3-(1-(2,4-dichlorophenyl)-1H-indazol-6-yl)-N-(2-hydroxyethyl)benzamide,
ethyl 3-(1-(2,4-dichlorophenyl)-1H-indazol-6-yl)benzoate,
3-(1-(2,4-dichlorophenyl)-1H-indazol-6-yl)benzoic acid, or
N-(3-(1-(4-methoxyphenyl)-1H-pyrazolo[4,3-b]pyridin-6-yl)phenyl)acetamide.

In a particular aspect, $R^1$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{1a}$)=NR(O$R^{1a}$), —C($R^{1a}$)=N($R^{1a}$), —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^{15}$.

In another particular aspect, the compound is not 6-(5-bromo-2-nitrophenyl)-1-phenyl-1H-indazole or 6-(2-nitrophenyl)-1-phenyl-1H-indazole.

Also provided is a pharmaceutical composition comprising at least one compound described herein, or a pharmaceutically acceptable salt thereof, and at least one pharmaceutically acceptable excipient.

Also provided is a method of decreasing the expression or activity of IRAK-4, or to otherwise affect the properties and/or behavior of IRAK-4 polypeptides or polynucleotides comprising administering to said mammal an effective amount of at least one compound described herein, or a pharmaceutically acceptable salt thereof.

Also provided is a method for treating an inflammatory disease in a subject, the method comprising administering to the patient a therapeutically effective amount of a compound described herein, or a pharmaceutically acceptable salt thereof, thereby treating the inflammatory disease in the subject.

Also provided is a method for treating an autoimmune disease, cancer, cardiovascular disease, a disease of the central nervous system, a disease of the skin, an ophthalmic disease and condition, and bone disease in a subject, the method comprising administering to the patient a therapeutically effective amount of a compound disclosed herein, or a pharmaceutically acceptable salt thereof, thereby treating the autoimmune disease, cancer, cardiovascular disease, disease of the central nervous system, disease of the skin, ophthalmic disease and condition, and bone disease in the subject.

Other features or advantages will be apparent from the following detailed description of several embodiments, and also from the appended claims.

DETAILED DESCRIPTION

Figure 1:
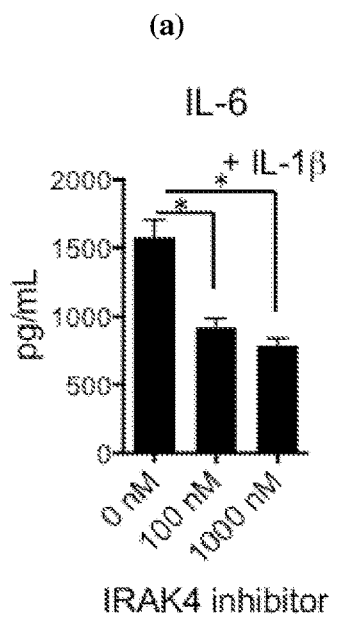
FIG. 1 is a graph showing the effect of administration of an IRAK4 inhibitor on the inflammatory responses of primary mouse kidney fibroblasts that were treated for 24 hours with 10 ng/ml recombinant IL-1β (a) or 100 ng/ml ultrapure LPS (b).
Figure 1:
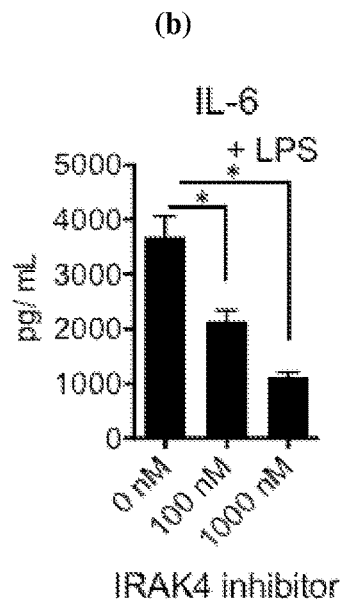

The compounds or pharmaceutically acceptable salts thereof as described herein, can have activity as IRAK4 modulators. In particular, compounds or pharmaceutically acceptable salts thereof as described herein, can be IRAK4 inhibitors.

A second embodiment of the invention is a compound of Formula (II):

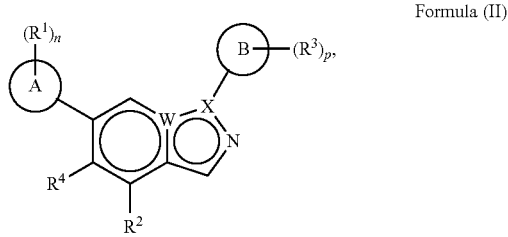

Formula (II)

or a pharmaceutically acceptable salt thereof, wherein the values of the variables are as defined for the first embodiment.

A third embodiment of the invention is a compound of Formula (III):

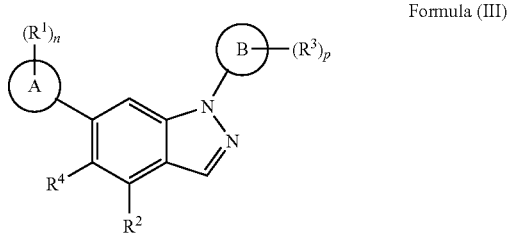

Formula (III)

or a pharmaceutically acceptable salt thereof, wherein the values of the variables are as defined for the first embodiment.

A fourth embodiment of the invention is a compound of Formula (IV):

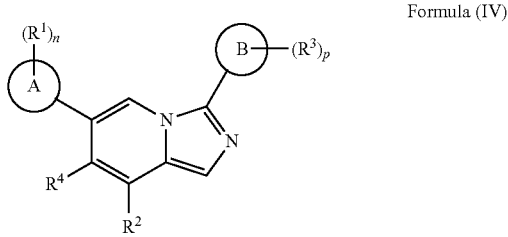

Formula (IV)

or a pharmaceutically acceptable salt thereof, wherein the values of the variables are as defined for the first embodiment.

In a fifth embodiment of the invention, the compound is represented by the formula (I), (II), (III), or (IV), wherein Ring A is 5- or 6-membered heteroaryl and Ring B is 5- or 6-membered heteroaryl, wherein the values of the other variables are as defined for the first embodiment.

In a sixth embodiment of the invention, the compound is represented by the formula (I), (II), (III), or (IV), wherein Ring A is a 5- or 6-membered heteroaryl and Ring B is phenyl, wherein the values of the other variables are as defined for the first embodiment.

In a seventh embodiment of the invention, the compound is represented by the formula (I), (II), (III), or (IV), wherein Ring A is a phenyl and Ring B is a 5- or 6-membered heteroaryl, wherein the values of the other variables are as defined for the first embodiment.

In an eighth embodiment of the invention, the compound is represented by the formula (I), (II), (III), or (IV), wherein the 5- or 6-membered heteroaryl in each occurrence is independently selected from pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, or tetrazinyl, wherein the values of the other variables are as defined for the first, fifth, sixth, and seventh embodiments.

In a ninth embodiment of the invention, the compound is represented by the formula (I), (II), (III), or (IV), wherein the 5- or 6-membered heteroaryl in each occurrence is independently selected from pyridinyl, pyrimidinyl, pyrazinyl, thiazolyl, imidazolyl, oxazolyl pyrazolyl, and thiophenyl, wherein the values of the other variables are as defined for the first, fifth, sixth, seventh and eighth embodiments.

In a tenth embodiment of the invention, the compound is represented by the formula (I), (II), (III), or (IV), wherein Ring A is a phenyl and Ring B is phenyl, wherein the values of the other variables are as defined for the first embodiment.

In an eleventh embodiment of the invention, the compound is represented by the formula (I), (II), (III), or (IV), wherein n is 1 or 2, and each $R^1$ is in each occurrence independently selected from $C_{1-6}$alkyl, $C_{3-6}$cycloalkyl selected from cyclopropyl, cyclobutyl, cyclopentyl, and cyclohexyl; 3- to 6-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, and trithianyl; halo, —CN, —C($R^{1a}$)=NR(O$R^{1a}$), —C($R^{1a}$)=N($R^{1a}$), —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —O$R^{1a}$, —OC(O)$R^{1a}$, and —OC(O)N($R^{1a}$)$_2$, wherein said $C_{1-6}$alkyl, $C_{3-6}$cycloalkyl, and 3- to 6-membered saturated heterocyclyl are optionally substituted with one to four $R^{10}$;

$R^{1a}$ in each occurrence is independently selected from H, $C_{1-6}$alkyl, 3- to 6-membered monocyclic carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl; and 3- to 6-membered monocyclic heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, dihydrofuranyl, imidazolinyl, dihydropyranyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl, wherein said $C_{1-6}$alkyl, 3- to 6-membered monocyclic carbocyclyl, and 3- to 6-membered monocyclic heterocyclyl in each occurrence are optionally and independently substituted with one to three $R^{10}$;

$R^{10}$ in each occurrence is independently selected from $C_{1-6}$alkyl, 3- to 6-membered carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl; 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, dihydrofuranyl, imidazolinyl, dihydropyranyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl, halo, —CN, —C($R^{10a}$)=NR(OR$^{10a}$), —C($R^{10a}$)=N($R^{10a}$), —C(O)$R^{10a}$, —C(O)$_2R^{10a}$, —C(O)N($R^{10a}$)$_2$, —NO$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —OR$^{10a}$, —OC(O)$R^{10a}$, and —OC(O)N($R^{10a}$)$_2$; and $R^{10a}$ in each occurrence is independently selected from H and $C_{1-6}$alkyl, wherein said $C_{1-6}$alkyl is optionally substituted with one to three halo, wherein the values of the other variables are as defined for the first and fifth, sixth, seventh, eighth, ninth and tenth embodiments.

In a twelfth embodiment of the invention, the compound is represented by the formula (I), (II), (III), or (IV), wherein n is 1 or 2, and each $R^1$ is in each occurrence independently selected from $C_{1-6}$alkyl, $C_{3-6}$cycloalkyl selected from cyclopropyl, cyclobutyl, cyclopentyl, and cyclohexyl, 3- to 6-membered saturated heterocyclyl selected from aziridinyl, azetidinyl, pyrrolidinyl, imidazolidinyl, pyrazolidinyl, oxazolidinyl, isoxazolidinyl, thiazolidinyl, isothiazolidinyl, piperidinyl, piperazinyl, and morpholinyl; halo, —CN, —C(O)$_2R^{1a}$, —C(O)N($R^{1a}$)$_2$, —N($R^{1a}$)$_2$, and —OR$^{1a}$, wherein said $C_{1-6}$alkyl, $C_{3-6}$cycloalkyl, and 3- to 6-membered saturated heterocyclyl are optionally substituted with one to four $R^{10}$;

$R^{1a}$ in each occurrence is independently selected from H and $C_{1-4}$alkyl, wherein said $C_{1-4}$alkyl is optionally substituted with one to three $R^{10}$;

$R^{10}$ in each occurrence is independently selected from $C_{1-4}$alkyl, 3- to 6-membered carbocyclyl selected from cyclopropyl, cyclobutyl, cyclopentyl, cyclohexyl, and phenyl; halo, —CN, —C(O)$_2R^{10a}$, —C(O)N($R^{10a}$)$_2$, —N($R^{10a}$)C(O)$R^{10a}$, —N($R^{10a}$)$_2$, and —OR$^{10a}$; and $R^{10a}$ in each occurrence is independently selected from H and $C_{1-4}$alkyl, wherein the values of the other variables are as defined for the first and fifth, sixth, seventh, eighth, ninth, tenth and eleventh embodiments.

In a thirteenth embodiment of the invention, the compound is represented by the formula (I), (II), (III), or (IV), wherein n is 1 and $R^1$ is $C_{1-6}$alkyl optionally substituted with —N($R^{10a}$)$_2$; and $R^{10a}$ in each occurrence is independently selected from H and $C_{1-4}$alkyl, wherein the values of the other variables are as defined for the first and fifth, sixth, seventh, eighth, ninth, tenth, eleventh and twelfth embodiments.

In a fourteenth embodiment of the invention, the compound is represented by the formula (I), (II), (III), or (IV), wherein $R^1$ is selected from $C_{1-6}$alkyl, $C_{2-6}$alkenyl, $C_{2-6}$alkynyl, $C_{3-6}$cycloalkyl 3- to 6-membered saturated heterocyclyl, halo, —CN, —C($R^{1a}$)=NR(OR$^{1a}$), —C($R^{1a}$)=N($R^{1a}$), —C(O)$R^{1a}$, —NO$_2$, —N($R^{1a}$)$_2$, N($R^{1a}$)C(O)$R^{1a}$, N($R^{1a}$)C(O)$_2R^{1a}$, —N($R^{1a}$)C(O)N($R^{1a}$)$_2$, —N($R^{1a}$)C(O)$_2R^{1a}$, —N($R^{1a}$)S(O)$_2R^{1a}$, —OR$^{1a}$, —OC(O)$R^{1a}$, —OC(O)N($R^{1a}$)$_2$, —SR$^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^{15}$, wherein the values of the other variables are as defined for the first and fifth, sixth, seventh, eighth, ninth, and tenth, embodiments. Alternatively, the compound is represented by the formula (I), (II), (III), or (VI) wherein $R^1$ is selected from $C_{1-6}$alkyl, $C_{2-6}$alkenyl, $C_{2-6}$alkynyl, $C_{3-6}$cycloalkyl 3- to 6-membered saturated heterocyclyl, halo, —CN, —C($R^{1a}$)=NR(OR$^{1a}$), —C($R^{1a}$)=N($R^{1a}$), —C(O)$R^{1a}$, —NO$_2$, —N($R^{1a}$)$_2$, —N($R^{1a}$)C(O)$_2R^{1a}$, —N($R^{1a}$)C(O)N($R^{1a}$)$_2$, —N($R^{1a}$)S(O)$_2R^{1a}$, —OR$^{1a}$, —OC(O)$R^{1a}$, —OC(O)N($R^{1a}$)$_2$, —SR$^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl and 3- to 6-membered saturated heterocyclyl are optionally substituted with one or more $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one or more $R^{15}$, wherein the values of the other variables are as defined for the first and fifth, sixth, seventh, eighth, ninth, and tenth, embodiments.

In a fifteenth embodiment of the invention, the compound is represented by the formula (I), (II), (III), or (IV), wherein if X is N, Ring A and Ring B are phenyl, then $R^1$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{1a}$)=NR(OR$^{1a}$), —C($R^{1a}$)=N($R^{1a}$), —C(O)$R^{1a}$, NO$_2$, —N($R^{1a}$)$_2$, N($R^{1a}$)C(O)$R^{1a}$, N($R^{1a}$)C(O)$_2R^{1a}$, —N($R^{1a}$)C(O)N($R^{1a}$)$_2$, —N($R^{1a}$)S(O)$_2R^{1a}$, —OR$^{1a}$, —OC(O)$R^{1a}$, —OC(O)N($R^{1a}$)$_2$, —SR$^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one to four $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one to four $R^{15}$, wherein the values of the other variables are as defined for the first and fifth, sixth, seventh, eighth, ninth, tenth, eleventh, twelfth and fourteenth embodiments. Alternatively, the compound is represented by the formula (I), (II), or (III), or (IV), wherein X is N, Ring A and Ring B are phenyl, and $R^1$ is selected from $C_{1-6}$alkyl, $C_{2-6}$alkenyl, $C_{2-6}$alkynyl, $C_{3-6}$cycloalkyl, 3- to 6-membered saturated heterocyclyl, halo, —CN, —C($R^{1a}$)=NR(OR$^{1a}$), —C($R^{1a}$)=N($R^{1a}$), —C(O)$R^{1a}$, NO$_2$, —N($R^{1a}$)$_2$, N($R^{1a}$)C(O)$_2R^{1a}$, —N($R^{1a}$)C(O)N($R^{1a}$)$_2$, —N($R^{1a}$)S(O)$_2R^{1a}$, —OR$^{1a}$, —OC(O)$R^{1a}$, —OC(O)N($R^{1a}$)$_2$, —SR$^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, $C_{3-6}$cycloalkyl, and 3- to 6-membered saturated heterocyclyl are optionally substituted with one to four $R^{10}$; or two $R^1$ substituents, together with their intervening atoms, form a $C_{5-7}$cycloalkyl or a saturated 5- to 7-membered heterocyclic ring, wherein said $C_{5-7}$cycloalkyl or a saturated 5- to 7-membered heterocyclic ring are optionally substituted with one to four $R^{15}$ wherein the values of the other variables are as defined for the first and fifth, sixth, seventh, eighth, ninth, tenth, and fourteenth embodiments.

In a sixteenth embodiment of the invention, the compound is represented by the formula (I), (II), (III), or (IV), wherein n is 1 or 2, and each $R^1$ is in each occurrence independently selected from $C_{1-6}$alkyl, $C_{3-6}$cycloalkyl selected from cyclopropyl, cyclobutyl, cyclopentyl, and cyclohexyl, 3- to 6-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, and trithianyl; halo, —CN, —C($R^{1a}$)=NR(O$R^{1a}$), —C($R^{1a}$)=N($R^{1a}$), —C(O)$R^{1a}$, —N($R^{1a}$)$_2$, —O$R^{1a}$, —OC(O)$R^{1a}$, and —OC(O)N($R^{1a}$)$_2$, wherein said $C_{1-6}$alkyl, $C_{3-6}$cycloalkyl, and 3- to 6-membered saturated heterocyclyl are optionally substituted with one to four $R^{10}$;

$R^{1a}$ in each occurrence is independently selected from H, $C_{1-6}$alkyl, 3- to 6-membered monocyclic carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl; and 3- to 6-membered monocyclic heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, dihydrofuranyl, imidazolinyl, dihydropyranyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl, wherein said $C_{1-6}$alkyl, 3- to 6-membered monocyclic carbocyclyl, and 3- to 6-membered monocyclic heterocyclyl in each occurrence are optionally and independently substituted with one to three $R^{10}$;

$R^{10}$ in each occurrence is independently selected from $C_{1-6}$alkyl, 3- to 6-membered carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl; 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, dihydrofuranyl, imidazolinyl, dihydropyranyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl, halo, —CN, —C($R^{10a}$)=NR(O$R^{10a}$), —C($R^{10a}$)=N($R^{10a}$), —C(O)$R^{10a}$, —C(O)$_2R^{10a}$, —C(O)N($R^{10a}$)$_2$, —NO$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —O$R^{10a}$, —OC(O)$R^{10a}$, and —OC(O)N($R^{10a}$)$_2$; and $R^{10a}$ in each occurrence is independently selected from H and $C_{1-6}$alkyl, wherein said $C_{1-6}$alkyl is optionally substituted with one to three halo.; wherein the values of the other variables are as defined for the first and fifth, sixth, seventh, eighth, ninth, tenth, fourteenth and fifteenth embodiments.

In a seventeenth embodiment of the invention, the compound is represented by the formula (I), (II), (III), or (IV), n is 1 or 2, and each $R^1$ is in each occurrence independently selected from $C_{1-6}$alkyl, $C_{3-6}$cycloalkyl selected from cyclopropyl, cyclobutyl, cyclopentyl, and cyclohexyl; 3- to 6-membered saturated heterocyclyl selected from aziridinyl, azetidinyl, pyrrolidinyl, imidazolidinyl, pyrazolidinyl, oxazolidinyl, isoxazolidinyl, thiazolidinyl, isothiazolidinyl, piperidinyl, piperazinyl, and morpholinyl; halo, —CN, —N($R^{1a}$)$_2$, and —O$R^{1a}$, wherein said $C_{1-6}$alkyl, $C_{3-6}$cycloalkyl, and 3- to 6-membered saturated heterocyclyl are optionally substituted with one to four $R^{10}$. In an alternative aspect, $R^1$ may also include $C_{2-6}$alkenyl, $C_{2-6}$alkynyl, and tetrahydrofuranyl.

$R^{1a}$ in each occurrence is independently selected from H and $C_{1-4}$alkyl, wherein said $C_{1-4}$alkyl is optionally substituted with one to three $R^{10}$;

$R^{10}$ in each occurrence is independently selected from $C_{1-4}$alkyl, 3- to 6-membered carbocyclyl selected from cyclopropyl, cyclobutyl, cyclopentyl, cyclohexyl, and phenyl; halo, —CN, —C(O)$_2R^{10a}$, —C(O)N($R^{10a}$)$_2$, —N($R^{10a}$)C(O)$R^{10a}$, —N($R^{1a}$)$_2$, and —O$R^{10a}$; and $R^{10a}$ in each occurrence is independently selected from H and $C_{1-4}$alkyl, wherein the values of the other variables are as defined for the first and fifth, sixth, seventh, eighth, ninth, tenth, fourteenth, fifteenth and sixteenth embodiments. In an alternative aspect of this embodiment, $R^{10}$ may also include —S$R^{10a}$, $C_{2-6}$alkenyl, $C_{2-6}$alkynyl, —C(O)$R^{10a}$, —S(O)$_2R^{10a}$ and —S(O)$R^{10a}$.

In an alternative seventeenth embodiment, the compound is represented by the formula (I), (II), (III), or (IV), n is 1, and $R^1$ is $C_{1-6}$alkyl substituted with one, two, three or four groups selected from halo, —O$R^{1a}$, —N($R^{1a}$)$_2$, cyclobutyl, and oxetanyl, wherein $R^{1a}$ in each occurrence is independently selected from H and $C_{1-4}$alkyl, wherein the values of the other variables are as defined for the first and fifth, sixth, seventh, eighth, ninth, tenth, fourteenth, fifteenth and sixteenth embodiments.

In an eighteenth embodiment of the invention, the compound is represented by the formula (I), (II), (III), or (IV), wherein n is 2 and two $R^1$ substituents, together with their intervening atoms, form a $C_{5-7}$cycloalkyl ring or a saturated 5- to 7-membered heterocyclic ring, wherein said $C_{5-7}$cycloalkyl ring or a saturated 5- to 7-membered heterocyclic ring are optionally substituted with one to three $R^{15}$;

$R^{15}$ in each occurrence is independently selected from $C_{1-4}$alkyl, halo, —CN, —C(O)$R^{15a}$, —C(O)$_2R^{15a}$, —C(O)N($R^{15a}$)$_2$, —N($R^{15a}$)$_2$, —N($R^{15a}$)C(O)$R^{15a}$, —N($R^{15a}$)C(O)$_2R^{15a}$, —N($R^{15a}$)C(O)N($R^{15a}$)$_2$, —O$R^{15a}$, —OC(O)$R^{15a}$, and —OC(O)N($R^{15a}$)$_2$; and $R^{15a}$ in each occurrence is independently selected from H and $C_{1-6}$alkyl, wherein said $C_{1-6}$alkyl is optionally substituted with one to three halo, wherein the values of the other variables are as defined for the first and fifth, sixth, seventh, eighth, ninth, and tenth embodiments.

In a nineteenth embodiment of the invention, the compound is represented by the formula (I), (II), (III), or (IV), wherein the $C_{5-7}$cycloalkyl ring selected from cyclopentyl, cyclohexyl, and cycloheptyl and the saturated 5- to 7-membered heterocyclic ring selected from pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, and thiepanyl, said $C_{5-7}$cycloalkyl ring or a saturated 5- to 7-membered heterocyclic ring are optionally substituted with $C_{1-4}$alkyl or $—N(R^{15a})_2$; and $R^{15a}$ in each occurrence is independently selected from H and $C_{1-4}$alkyl; wherein the values of the other variables are as defined for the first and fifth, sixth, seventh, eighth, ninth, tenth and eighteenth embodiments.

In a twentieth embodiment of the invention, the compound is represented by the formula (I), (II), (III), or (IV), wherein the $C_{5-7}$cycloalkyl ring is selected from cyclopentyl, cyclohexyl, and cycloheptyl and the saturated 5- to 7-membered heterocyclic ring selected from pyrrolidinyl, imidazolidinyl, pyrazolidinyl, oxazolidinyl, isoxazolidinyl, thiazolidinyl, isothiazolidinyl, piperidinyl, piperazinyl, and azepanyl, said $C_{5-7}$cycloalkyl ring or a saturated 5- to 7-membered heterocyclic ring are optionally substituted with $C_{1-4}$alkyl or $—N(R^{15a})_2$; and $R^{15a}$ in each occurrence is independently selected from H and $C_{1-4}$alkyl, wherein the values of the other variables are as defined for the first and fifth, sixth, seventh, eighth, ninth, tenth, eighteenth and nineteenth embodiments.

In a twenty-first embodiment of the invention, the compound is represented by the formula (I), (II), (III), or (IV), wherein $R^2$ is selected from H, $C_{1-6}$alkyl, $C_{2-6}$alkenyl, $C_{2-6}$alkynyl, 3- to 7-membered carbocyclyl selected from cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, cycloheptatrienyl, and phenyl; 3- to 7-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, thiazepinyl, dihydrofuranyl, imidazolinyl, and dihydropyranyl; halo, $—CN$, $—C(O)R^{2a}$, $—C(O)_2R^{2a}$, $—C(O)N(R^{2a})_2$, $—NO_2$, $—N(R^{2a})_2$, $—N(R^{2a})C(O)R^{2a}$, $—N(R^{2a})C(O)_2R^{2a}$, $—N(R^{2a})C(O)N(R^{2a})_2$, $—OR^{2a}$, $—OC(O)R^{2a}$, and $—OC(O)N(R^{2a})_2$, wherein said $C_{1-6}$alkyl, $C_{2-6}$alkenyl, $C_{2-6}$alkynyl, 3- to 7-membered carbocyclyl, and 3-7 membered heterocyclyl are optionally substituted with one to three $R^{20}$;

$R^{2a}$ in each occurrence is independently selected from H and $C_{1-6}$alkyl, wherein said $C_{1-4}$alkyl in each occurrence is optionally and independently substituted with one to three $R^{20}$;

$R^{20}$ in each occurrence is independently selected from $C_{1-6}$alkyl, $C_{2-6}$alkenyl, $C_{2-6}$alkynyl, $C_{3-7}$cycloalkyl selected from cyclopropyl, cyclobutyl, cyclopentyl, cyclohexyl, and cycloheptyl, 3- to 7-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, and thiepanyl; halo, $—CN$, $—C(O)R^{20a}$, $—C(O)_2R^{20a}$, $—C(O)N(R^{20a})_2$, $—N(R^{20a})_2$, $—N(R^{20a})C(O)R^{20a}$, $—N(R^{20a})C(O)_2R^{20a}$, $—N(R^{20a})C(O)N(R^{20a})_2$, $—OR^{20a}$, $—OC(O)R^{20a}$, and $—OC(O)N(R^{20a})_2$, wherein said $C_{1-6}$alkyl, $C_{2-6}$alkenyl, $C_{2-6}$alkynyl, $C_{3-7}$cycloalkyl, and 3-7 membered saturated heterocyclyl in each occurrence are optionally and independently substituted with one to three $R^{25}$;

$R^{20a}$ in each occurrence is independently selected from H and $C_{1-4}$alkyl, wherein said $C_{1-4}$alkyl is optionally substituted with $R^{25}$;

$R^{25}$ is selected from halo and $—OR^{25a}$; and $R^{25a}$ is selected from H and $C_{1-4}$alkyl, wherein the values of the other variables are as defined for the first and fifth, sixth, seventh, eighth, ninth, tenth, eleventh, twelfth, thirteenth, fourteenth, fifteenth, sixteenth, seventeenth, eighteenth, nineteenth and twentieth embodiments.

In a twenty-second embodiment of the invention, the compound is represented by the formula (I), (II), (III), or (IV), wherein $R^2$ is H, $C_{1-4}$alkyl, $C_{2-4}$alkenyl, halo, $—C(O)_2R^{2a}$, $—C(O)N(R^{2a})_2$, $—N(R^{2a})_2$, $—N(R^{2a})C(O)R^{2a}$, $—CN$, $—OR^{2a}$, cyclopropyl, aziridinyl, azetidinyl, oxetanyl, pyrrolidinyl, imidazolidinyl, pyrazolidinyl, oxazolidinyl, isoxazolidinyl, piperidinyl, piperazinyl, azepanyl, oxepanyl, azirinyl, azetyl, pyrrolyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, pyrazinyl, pyrimidinyl, pyridazinyl, triazinyl, tetrazinyl, azepinyl, diazepinyl, thiazepinyl, and imidazolinyl, wherein said $C_{1-4}$alkyl is optionally substituted with one to three groups selected from cyclopropyl, cyclobutyl, cyclopentyl, cyclohexyl, cycloheptyl, $—OR^{20a}$, $—N(R^{20a})_2$, $N(R^{20a})C(O)R^{20a}$, and halo. In an alternative aspect, $R^2$ also includes $C_{2-4}$alkynyl, phenyl, tetrahydrofuranyl, tetrahydropyranyl, dihydro-2H-pyranyl, tetrahydropyridinyl, morpholinyl, thiomorpholinyl, thiomorpholine 1,1-dioxidyl, morpholin-3-onyl, and dihydrooxazolyl; wherein the $C_{1-4}$alkyl, $C_{2-4}$alkynyl, phenyl, tetrahydrofuranyl, tetrahydropyranyl, dihydro-2H-pyranyl, tetrahydropyridinyl, morpholinyl, thiomorpholine 1,1-dioxidyl, morpholin-3-onyl, dihydrooxazolyl, thiomorpholinyl, cyclopropyl, aziridinyl, azetidinyl, oxetanyl, pyrrolidinyl, imidazolidinyl, pyrazolidinyl, oxazolidinyl, isoxazolidinyl, piperidinyl, piperazinyl, azepanyl, oxepanyl, azirinyl, azetyl, pyrrolyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, pyrazinyl, pyrimidinyl, pyridazinyl, triazinyl, tetrazinyl, azepinyl, diazepinyl, thiazepinyl, and imidazolinyl are optionally substituted with one to three groups selected from $C_{1-4}$alkyl, halo, $—OR^{20a}$, CN, $—C(O)R^{20a}$, $—C(O)_2R^{20a}$ and morpholinyl; wherein the $C_{1-4}$alkyl is optionally substituted with one to three groups selected from halo and $—OR^{25a}$; wherein $R^{25a}$ is H or $C_{1-4}$alkyl.

$R^{2a}$ in each occurrence is independently selected from H and $C_{1-4}$alkyl, wherein said $C_{1-4}$alkyl is optionally substituted with cyclopropyl, cyclobutyl, cyclopentyl, cyclohexyl, and cycloheptyl. In an alternative aspect, the wherein the $C_{1-4}$alkyl is also optionally substituted with one to three groups selected from halo, —OR$^{20a}$, —N(R$^{20a}$)$_2$, —C(O)R$^{20a}$, piperdinyl and cyclobutyl; wherein the piperidinyl and cyclobutyl are optionally substituted with one to three halo; wherein R$^{20a}$ is H and C$_{1-4}$alkyl.

R$^{20a}$ in each occurrence is independently selected from H and C$_{1-4}$alkyl. In an alternative aspect, C$_{1-4}$alkyl is also optionally substituted with halo and S(O)$_2$R$^{20a}$. The values of the other variables are as defined for the first and fifth, sixth, seventh, eighth, ninth, tenth, eleventh, twelfth, thirteenth, fourteenth, fifteenth, sixteenth, seventeenth, eighteenth, nineteenth, twentieth and twenty-first embodiments.

In a twenty-third embodiment of the invention, the compound is represented by the formula (I), (II), (III), or (IV), wherein R$^2$ is H or —OR$^{2a}$; R$^{2a}$ in each occurrence is independently selected from H and C$_{1-4}$alkyl, wherein the values of the other variables are as defined for the first and fifth, sixth, seventh, eighth, ninth, tenth, eleventh, twelfth, thirteenth, fourteenth, fifteenth, sixteenth, seventeenth, eighteenth, nineteenth, twentieth, twenty-first and twenty-second embodiments.

In an alternative twenty-third embodiment of the invention, the compound is represented by the formula (I), (II), (III), or (IV), wherein R$^2$ is H, —OR$^{2a}$, tetrahydrofuranyl, or pyrazolyl; wherein the tetrahydrofuranyl and pyrazolyl are optionally substituted with C$_{1-4}$alkyl; R$^{2a}$ in each occurrence is independently selected from H and C$_{1-4}$alkyl, wherein the C$_{1-4}$alkyl is optionally substituted with —OR$^{20a}$, wherein R$^{20a}$ is H and C$_{1-4}$alkyl, wherein the values of the other variables are as defined for the first and fifth, sixth, seventh, eighth, ninth, tenth, eleventh, twelfth, thirteenth, fourteenth, fifteenth, sixteenth, seventeenth, eighteenth, nineteenth, twentieth, twenty-first and twenty-second embodiments.

In a twenty-fourth embodiment of the invention, the compound is represented by the formula (I), (II), (III), or (IV), wherein p is 1 or 2; each R$^3$ is independently selected from C$_{1-6}$alkyl, C$_{3-6}$cycloalkyl selected from cyclopropyl, cyclobutyl, cyclopentyl, and cyclohexyl, 3- to 6-membered saturated heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, and trithianyl; halo, —CN, —C(O)R$^{3a}$, —C(O)$_2$R$^{3a}$, —C(O)N(R$^{3a}$)$_2$, —N(R$^{3a}$)$_2$, —N(R$^{3a}$)C(O)R$^{3a}$, —N(R$^{3a}$)C(O)$_2$R$^{3a}$, —N(R$^{3a}$)C(O)N(R$^{3a}$)$_2$, —OR$^{3a}$, —OC(O)R$^{3a}$, —OC(O)N(R$^{3a}$)$_2$, —SR$^{3a}$, —S(O)R$^{3a}$, —S(O)$_2$R$^{3a}$, —S(O)N(R$^{3a}$)$_2$, and —S(O)$_2$N(R$^{3a}$)$_2$, wherein said C$_{1-6}$alkyl, C$_{3-6}$cycloalkyl, and 3- to 6-membered saturated heterocyclyl are optionally substituted with one to three R$^{30}$;

R$^{3a}$ in each occurrence is independently selected from H, C$_{1-6}$alkyl, 3- to 6-membered carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl, and 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, dihydrofuranyl, imidazolinyl, and dihydropyranyl; wherein said C$_{1-6}$alkyl, 3- to 6-membered carbocyclyl, and 3- to 6-membered saturated heterocyclyl in each occurrence are optionally and independently substituted with one to three R$^{30}$;

R$^{30}$ in each occurrence is independently selected from C$_{1-6}$alkyl, 3- to 6-membered carbocyclyl selected from cyclopropyl, cyclobutyl, cyclopentyl, cyclohexyl, cyclopropenyl, cyclobutenyl, cyclopenentyl, cyclohexenyl, cyclobutadienyl, cyclopentadienyl, cyclohexadienyl, and phenyl; 3- to 6-membered heterocyclyl selected from aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azirinyl, oxirenyl, thiirenyl, diazirinyl, azetyl, oxetyl, thietyl, pyrrolyl, furanyl, thiophenyl, imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, dihydrofuranyl, imidazolinyl, and dihydropyranyl; halo, —CN, —C(O)R$^{30a}$, —C(O)$_2$R$^{30a}$, —C(O)N(R$^{30a}$)$_2$, —N(R$^{30a}$)$_2$, —N(R$^{30a}$)C(O)R$^{30a}$, —N(R$^{30a}$)C(O)$_2$R$^{30a}$, —N(R$^{30a}$)C(O)N(R$^{30a}$)$_2$, —OR$^{30a}$, —OC(O)R$^{30a}$, and —OC(O)N(R$^{30a}$)$_2$, SR$^{30a}$, —S(O)R$^{30a}$, —S(O)$_2$R$^{30a}$, —S(O)N(R$^{30a}$)$_2$, and —S(O)$_2$N(R$^{30a}$)$_2$, wherein said C$_{1-6}$alkyl, 3-6 membered carboyclyl, and 3- to 6-membered heterocyclyl in each occurrence are optionally and independently substituted with one to three R$^{35}$;

R$^{30a}$ in each occurrence is independently selected from H and C$_{1-6}$alkyl, wherein said C$_{1-6}$alkyl is optionally substituted with one to three R$^{35}$;

R$^{35}$ in each occurrence is independently selected from halo and —OR$^{35a}$; and R$^{35a}$ in each occurrence is independently selected from H and C$_{1-6}$alkyl, wherein the values of the other variables are as defined for the first and fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second and twenty-third embodiments.

In a twenty-fifth embodiment of the invention, the compound is represented by the formula (I), (II), (III), or (IV), wherein R$^3$ in each occurrence is independently selected from C$_{1-4}$alkyl, —CN, halo, C(O)$_2$R$^{3a}$, C(O)N(R$^{3a}$)$_2$, —NR$^{3a}$$_2$, cyclopropyl, cyclobutyl, and —C(O)R$^{3a}$, wherein said C$_{1-4}$alkyl, cyclopropyl and cyclobutyl are optionally substituted with one to three groups selected from halo, N(R$^{30a}$)$_2$, —CN, —S(O)$_2$R$^{30a}$, —C(O)N(R$^{3a}$)$_2$, and —OR$^{3a}$;

R$^{3a}$ in each occurrence is independently selected from H, C$_{1-4}$alkyl, and azetidinyl, wherein said C$_{1-4}$alkyl and azetidinyl are optionally substituted with —OR$^{30a}$, N(R$^{30a}$)$_2$, —CN, —S(O)$_2$R$^{30a}$, —C(O)$_2$R$^{30a}$, and —C(O)N(R$^{30a}$)$_2$; and R$^{30a}$ in each occurrence is independently selected from H and C$_{1-4}$alkyl, wherein the values of the other variables are as defined for the first and fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third and twenty-fourth embodiments.

In a twenty-sixth embodiment of the invention, the compound is represented by the formula (I), (II), (III), or (IV), wherein $R^3$ is selected from $C_{1-4}$alkyl and $C(O)N(R^{3a})_2$, wherein said $C_{1-4}$alkyl is optionally substituted with 1 to 3 groups selected from halo and —$OR^{3a}$; and $R^{3a}$ in each occurrence is independently selected from H and $C_{1-4}$alkyl, wherein the values of the other variables are as defined for the first and fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, and twenty-fifth embodiments. In an alternative aspect, $R^3$ is $C_{1-4}$alkyl, $C(O)N(R^{3a})_2$, $C(O)_2R^{3a}_2$, halo, —CN, —$C(O)R^{3a}$, —$C(O)_2R^{3a}$, and cyclobutyl, wherein the $C_{1-4}$alkyl and cyclobutyl are optionally substituted with 1 to 4 groups selected from halo and —$OR^{30a}$ and $N(R^{30a})_2$; and each $R^{3aa}$ and $R^{30a}$ in each occurrence is independently selected from H and $C_{1-4}$alkyl. In a specific aspect, $R^3$ is $C_{1-4}$alkyl substituted with —$OR^{3a}$; and $R^{3a}$ in each occurrence is independently selected from H and $C_{1-4}$alkyl.

In a twenty-seventh embodiment of the invention, the compound is represented by the formula (I), (II), (III), or (IV), wherein $R^4$ is selected from H, halo, and $C_{1-4}$alkyl, wherein the values of the other variables are as defined for the first and fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth and twenty-sixth embodiments.

In a twenty-eighth embodiment of the invention, the compound is represented by the formula (I), (II), (III), or (IV), wherein the compound is represented by the formula structural formula

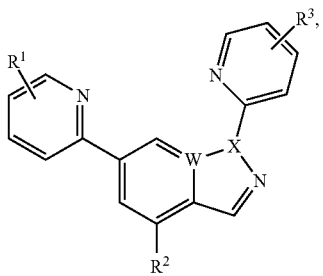

or a pharmaceutically acceptable salt thereof, wherein
$R^1$ is $C_{1-6}$alkyl optionally substituted with $N(R^{10})_2$;
$R^{10}$ is H or $C_{1-4}$alkyl;
$R^2$ is H, F or —$OR^{2a}$;
$R^{2a}$ is H or $C_{1-4}$alkyl;
$R^3$ is $C(O)N(R^{3a})_2$ or $C_{1-4}$alkyl, wherein said $C_{1-4}$alkyl is optionally substituted with one to three halo or —$OR^{3a}$; and
$R^{3a}$ in each occurrence is independently selected from H and $C_{1-4}$alkyl, wherein the values of the other variables are as defined for the first embodiment. In an alternative aspect of this embodiment, $R^1$ is $C_{1-6}$alkyl optionally substituted one to three groups selected from $N(R^{10})_2$, $OR^{10}$, halo, cyclobutyl, oxetanyl;
$R^{10}$ is H or $C_{1-4}$alkyl;
$R^2$ is H, F, —$OR^{2a}$, tetrahydrofuranyl, or pyrazolyl, wherein the tetrahydrofuranyl, or pyrazolyl is optionally substituted with $C_{1-4}$alkyl;
$R^{2a}$ is H or $C_{1-4}$alkyl optionally substituted with —$OR^{20a}$;
$R^{20a}$ is H or $C_{1-4}$alkyl;

$R^3$ is $C(O)N(R^{3a})_2$ or $C_{1-4}$alkyl, wherein said $C_{1-4}$alkyl is optionally substituted with one to three halo or —$OR^{3a}$; and
$R^{3a}$ in each occurrence is independently selected from H and $C_{1-4}$alkyl, wherein the values of the other variables are as defined for the first embodiment.

In a twenty-ninth embodiment, the invention is any one the compounds disclosed in the Exemplification section as a neutral compound or a pharmaceutically acceptable salt thereof.

In a thirtieth embodiment of the invention, there is provided a compound selected from:
6-(1-(6-methylpyridin-2-yl)-1H-indazol-6-yl)pyridin-2-amine;
2-(1-(6-methylpyridin-2-yl)-1H-indazol-6-yl)pyrimidin-4-amine;
2-(1-(6-methylpyridin-2-yl)-1H-indazol-6-yl)pyridin-4-amine;
(6-(1-(6-methylpyridin-2-yl)-1H-indazol-6-yl)pyridin-2-yl)methanamine;
(2-(1-(6-methylpyridin-2-yl)-1H-indazol-6-yl)pyridin-4-yl)methanamine;
4-(1-(6-methylpyridin-2-yl)-1H-indazol-6-yl)pyridin-2-amine;
5-(1-(6-methylpyridin-2-yl)-1H-indazol-6-yl)pyridin-3-amine;
3-(1-(6-methylpyridin-2-yl)-1H-indazol-6-yl)aniline;
(2-(1-(6-methylpyridin-2-yl)-1H-indazol-6-yl)pyrimidin-4-yl)methanamine;
4-methyl-5-(1-(6-methylpyridin-2-yl)-1H-indazol-6-yl)pyridin-3-amine;
3-(1-(6-methylpyridin-2-yl)-1H-indazol-6-yl)-5-nitropyridin-2-ol;
3-amino-5-(1-(6-methylpyridin-2-yl)-1H-indazol-6-yl)pyridin-4-ol;
N-methyl-5-(1-(6-methylpyridin-2-yl)-1H-indazol-6-yl)pyridin-3-amine;
N,N-dimethyl-1-(6-(1-(6-methylpyridin-2-yl)-1H-indazol-6-yl)pyridin-2-yl)methanamine;
5-(1-(6-methylpyridin-2-yl)-1H-indazol-6-yl)-1,2,3,4-tetrahydroisoquinoline;
2-methyl-5-(1-(6-methylpyridin-2-yl)-1H-indazol-6-yl)-1,2,3,4-tetrahydroisoquinoline;
6-(2-methylisoindolin-4-yl)-1-(6-methylpyridin-2-yl)-1H-indazole;
N-methyl-1-(3-(1-(6-methylpyridin-2-yl)-1H-indazol-6-yl)phenyl)methanamine;
3-(6-(3-aminophenyl)-1H-indazol-1-yl)benzonitrile;
3-(1-(pyridin-2-yl)-1H-indazol-6-yl)aniline;
6-(6-(3-aminophenyl)-1H-indazol-1-yl)picolinonitrile;
3-(1-(4,6-dimethylpyridin-2-yl)-1H-indazol-6-yl)aniline;
3-(1-(5,6-dimethylpyridin-2-yl)-1H-indazol-6-yl)aniline;
3-(1-(6-(trifluoromethyl)pyridin-2-yl)-1H-indazol-6-yl)aniline;
5-(1-(6-cyclopropylpyridin-2-yl)-1H-indazol-6-yl)pyridin-3-amine;
5-(1-(6-cyclobutylpyridin-2-yl)-1H-indazol-6-yl)pyridin-3-amine;
6-(6-(5-aminopyridin-3-yl)-1H-indazol-1-yl)picolinonitrile;
6-(6-(5-aminopyridin-3-yl)-1H-indazol-1-yl)picolinic acid;
6-(6-(5-aminopyridin-3-yl)-1H-indazol-1-yl)picolinamide;
6-(6-(5-aminopyridin-3-yl)-1H-indazol-1-yl)-N-methylpicolinamide;
3-(6-(5-aminopyridin-3-yl)-1H-indazol-1-yl)benzonitrile;
2-(6-(5-aminopyridin-3-yl)-1H-indazol-1-yl)-6-methylisonicotinonitrile;

2-(6-(5-aminopyridin-3-yl)-1H-indazol-1-yl)isonicotinonitrile;
5-(1-(4-methylpyrimidin-2-yl)-1H-indazol-6-yl)pyridin-3-amine;
2-(6-(5-aminopyridin-3-yl)-1H-indazol-1-yl)pyrimidine-4-carbonitrile;
5-(1-(3-chloro-6-methylpyridin-2-yl)-1H-indazol-6-yl)pyridin-3-amine;
5-(1-(4-methylpyridin-2-yl)-1H-indazol-6-yl)pyridin-3-amine;
5-(1-(6-(trifluoromethyl)pyridin-2-yl)-1H-indazol-6-yl)pyridin-3-amine;
5-(3-(6-methylpyridin-2-yl)imidazo[1,5-a]pyridin-6-yl)pyridin-3-amine;
3-(3-(6-methylpyridin-2-yl)imidazo[1,5-a]pyridin-6-yl)aniline;
5-(5-fluoro-1-(6-methylpyridin-2-yl)-1H-indazol-6-yl)pyridin-3-amine;
5-(5-methyl-1-(6-methylpyridin-2-yl)-1H-indazol-6-yl)pyridin-3-amine;
6-(6-(6-(aminomethyl)pyridin-2-yl)-1H-indazol-1-yl)picolinonitrile;
6-(6-(6-(aminomethyl)pyridin-2-yl)-1H-indazol-1-yl)picolinamide;
(6-(1-(6-(trifluoromethyl)pyridin-2-yl)-1H-indazol-6-yl)pyridin-2-yl)methanamine;
methyl 6-(5-aminopyridin-3-yl)-1-(6-cyanopyridin-2-yl)-1H-indazole-4-carboxylate;
methyl 6-(5-aminopyridin-3-yl)-1-(6-(trifluoromethyl)pyridin-2-yl)-1H-indazole-4-carboxylate;
6-(5-aminopyridin-3-yl)-1-(6-(trifluoromethyl)pyridin-2-yl)-1H-indazole-4-carboxylic acid;
6-(5-aminopyridin-3-yl)-1-(6-(trifluoromethyl)pyridin-2-yl)-1H-indazole-4-carboxamide;
5-(4-(aminomethyl)-1-(6-(trifluoromethyl)pyridin-2-yl)-1H-indazol-6-yl)pyridin-3-amine;
(6-(5-aminopyridin-3-yl)-1-(6-(trifluoromethyl)pyridin-2-yl)-1H-indazol-4-yl)methanol;
1-(6-(1-(6-methylpyridin-2-yl)-1H-indazol-6-yl)pyridin-2-yl)ethanamine;
methyl 6-(6-(1-aminoethyl)pyridin-2-yl)-1-(6-(trifluoromethyl)pyridin-2-yl)-1H-indazole-4-carboxylate;
(6-(6-(1-aminoethyl)pyridin-2-yl)-1-(6-(trifluoromethyl)pyridin-2-yl)-1H-indazol-4-yl)methanol;
6-(6-(1-aminoethyl)pyridin-2-yl)-N,N-dimethyl-1-(6-(trifluoromethyl)pyridin-2-yl)-1H-indazole-4-carboxamide;
6-(6-(1-aminoethyl)pyridin-2-yl)-N-methyl-1-(6-(trifluoromethyl)pyridin-2-yl)-1H-indazole-4-carboxamide;
6-(5-aminopyridin-3-yl)-N,N-dimethyl-1-(6-(trifluoromethyl)pyridin-2-yl)-1H-indazole-4-carboxamide;
6-(5-aminopyridin-3-yl)-N-methyl-1-(6-(trifluoromethyl)pyridin-2-yl)-1H-indazole-4-carboxamide;
2-(1-(6-(trifluoromethyl)pyridin-2-yl)-1H-indazol-6-yl)-6,7-dihydro-5H-cyclopenta[b]pyridin-7-amine;
2-(1-(6-(trifluoromethyl)pyridin-2-yl)-1H-indazol-6-yl)-5,6,7,8-tetrahydroquinolin-8-amine;
6-(6-(5-aminopyridin-3-yl)-1H-indazol-1-yl)-N,N-dimethylpicolinamide;
6-(6-(5-aminopyridin-3-yl)-1H-indazol-1-yl)-N-(2-hydroxyethyl)picolinamide;
6-(6-(5-aminopyridin-3-yl)-1H-indazol-1-yl)-N-(3-hydroxypropyl)picolinamide;
6-(6-(5-aminopyridin-3-yl)-1H-indazol-1-yl)-N-(2-hydroxypropyl)picolinamide;
(6-(6-(5-aminopyridin-3-yl)-1H-indazol-1-yl)pyridin-2-yl)(3-hydroxyazetidin-1-yl)methanone;
6-(6-(5-aminopyridin-3-yl)-1H-indazol-1-yl)-N-(2-(dimethylamino)ethyl)picolinamide;
6-(6-(5-aminopyridin-3-yl)-1H-indazol-1-yl)-N-(2-cyanoethyl)picolinamide;
6-(6-(5-aminopyridin-3-yl)-1H-indazol-1-yl)-N-(3-cyanopropyl)picolinamide;
N-(2-aminoethyl)-6-(6-(5-aminopyridin-3-yl)-1H-indazol-1-yl)picolinamide;
6-(6-(5-aminopyridin-3-yl)-1H-indazol-1-yl)-N-(cyanomethyl)picolinamide;
6-(6-(5-aminopyridin-3-yl)-1H-indazol-1-yl)-N-(2-(methylsulfonyl)ethyl)picolinamide;
3-(6-(5-aminopyridin-3-yl)imidazo[1,5-a]pyridin-3-yl)benzonitrile;
6-(6-(5-aminopyridin-3-yl)imidazo[1,5-a]pyridin-3-yl)picolinonitrile;
6-(6-(5-aminopyridin-3-yl)imidazo[1,5-a]pyridin-3-yl)picolinamide;
5-(3-(6-(trifluoromethyl)pyridin-2-yl)imidazo[1,5-a]pyridin-6-yl)pyridin-3-amine;
1-(6-(3-(6-(trifluoromethyl)pyridin-2-yl)imidazo[1,5-a]pyridin-6-yl)pyridin-2-yl)ethanamine;
2-(aminomethyl)-6-(1-(6-(trifluoromethyl)pyridin-2-yl)-1H-indazol-6-yl)pyridin-4-amine;
2-(6-(6-(5-aminopyridin-3-yl)-1H-indazol-1-yl)pyridin-2-yl)acetonitrile;
2-(6-(6-(5-aminopyridin-3-yl)-1H-indazol-1-yl)pyridin-2-yl)acetic acid;
1-(6-(1-(6-(trifluoromethyl)pyridin-2-yl)-1H-indazol-6-yl)pyridin-2-yl)ethanamine;
3-amino-5-(1-(6-(trifluoromethyl)pyridin-2-yl)-1H-indazol-6-yl)benzoic acid;
3-amino-N-(cyanomethyl)-5-(1-(6-(trifluoromethyl)pyridin-2-yl)-1H-indazol-6-yl)benzamide;
6-amino-N-(cyanomethyl)-4-(1-(6-(trifluoromethyl)pyridin-2-yl)-1H-indazol-6-yl)picolinamide;
3-amino-N-(2-aminoethyl)-5-(1-(6-(trifluoromethyl)pyridin-2-yl)-1H-indazol-6-yl)benzamide;
1-(3-(1-(6-(trifluoromethyl)pyridin-2-yl)-1H-indazol-6-yl)phenyl)ethanamine;
1-(5-(1-(6-(trifluoromethyl)pyridin-2-yl)-1H-indazol-6-yl)pyridin-3-yl)ethanamine;
1-(4-(1-(6-(trifluoromethyl)pyridin-2-yl)-1H-indazol-6-yl)pyridin-2-yl)ethanamine;
6-(1-(6-(trifluoromethyl)pyridin-2-yl)-1H-indazol-6-yl)pyrazine-2-carbonitrile;
(6-(1-(6-(trifluoromethyl)pyridin-2-yl)-1H-indazol-6-yl)pyrazin-2-yl)methanamine;
4-(1-(6-(trifluoromethyl)pyridin-2-yl)-1H-indazol-6-yl)pyrimidine-2-carbonitrile;
(4-(1-(6-(trifluoromethyl)pyridin-2-yl)-1H-indazol-6-yl)pyrimidin-2-yl)methanamine;
6-(1-(6-(trifluoromethyl)pyridin-2-yl)-1H-indazol-6-yl)pyrazin-2-amine;
6-(6-(pyrrolidin-2-yl)pyridin-2-yl)-1-(6-(trifluoromethyl)pyridin-2-yl)-1H-indazole;
6-(6-(1-methylpyrrolidin-2-yl)pyridin-2-yl)-1-(6-(trifluoromethyl)pyridin-2-yl)-1H-indazole;
1-(6-(3-(6-methylpyridin-2-yl)imidazo[1,5-a]pyridin-6-yl)pyridin-2-yl)ethanamine;
6-(6-(1-aminoethyl)pyridin-2-yl)-1-(6-methylpyridin-2-yl)-1H-indazol-4-amine;
6-(6-(1-aminoethyl)pyridin-2-yl)-N-methyl-1-(6-methylpyridin-2-yl)-1H-indazol-4-amine;
6-(6-(1-aminoethyl)pyridin-2-yl)-N,N-dimethyl-1-(6-methylpyridin-2-yl)-1H-indazol-4-amine;

N-(6-(6-(1-aminoethyl)pyridin-2-yl)-1-(6-methylpyridin-2-yl)-1H-indazol-4-yl)acetamide;
1-(6-(4-(aminomethyl)-1-(6-methylpyridin-2-yl)-1H-indazol-6-yl)pyridin-2-yl)ethanamine;
N-((6-(6-(1-aminoethyl)pyridin-2-yl)-1-(6-methylpyridin-2-yl)-1H-indazol-4-yl)methyl)acetamide;
1-(6-(4-chloro-1-(6-methylpyridin-2-yl)-1H-indazol-6-yl)pyridin-2-yl)ethanamine;
1-(6-(4-cyclopropyl-1-(6-methylpyridin-2-yl)-1H-indazol-6-yl)pyridin-2-yl)ethanamine;
1-(6-(1-(6-methylpyridin-2-yl)-4-(prop-1-en-2-yl)-1H-indazol-6-yl)pyridin-2-yl)ethanamine;
1-(6-(4-ethyl-1-(6-methylpyridin-2-yl)-1H-indazol-6-yl)pyridin-2-yl)ethanamine;
1-(6-(4-isopropyl-1-(6-methylpyridin-2-yl)-1H-indazol-6-yl)pyridin-2-yl)ethanamine;
1-(6-(1-(6-methylpyridin-2-yl)-4-(trifluoromethyl)-1H-indazol-6-yl)pyridin-2-yl)ethanamine;
methyl 6-(6-(1-aminoethyl)pyridin-2-yl)-1-(6-methylpyridin-2-yl)-1H-indazole-4-carboxylate;
6-(6-(1-aminoethyl)pyridin-2-yl)-1-(6-methylpyridin-2-yl)-1H-indazole-4-carboxylic acid;
6-(6-(1-aminoethyl)pyridin-2-yl)-1-(6-methylpyridin-2-yl)-1H-indazol-4-yl)methanol;
6-(6-(1-aminoethyl)pyridin-2-yl)-N-methyl-1-(6-methylpyridin-2-yl)-1H-indazole-4-carboxamide;
N-methyl-1-(6-(1-(6-methylpyridin-2-yl)-1H-indazol-6-yl)pyridin-2-yl)ethanamine;
N-methyl-1-(6-(1-(6-(trifluoromethyl)pyridin-2-yl)-1H-indazol-6-yl)pyridin-2-yl)ethanamine;
1-(6-(1-(6-cyclopropylpyridin-2-yl)-1H-indazol-6-yl)pyridin-2-yl)ethanamine;
1-(6-(1-(6-ethylpyridin-2-yl)-1H-indazol-6-yl)pyridin-2-yl)ethanamine;
1-(6-(1-(6-isopropylpyridin-2-yl)-1H-indazol-6-yl)pyridin-2-yl)ethanamine;
1-(6-(1-(pyridin-2-yl)-1H-indazol-6-yl)pyridin-2-yl)ethanamine;
(6-(6-(6-(1-aminoethyl)pyridin-2-yl)-1H-indazol-1-yl)pyridin-2-yl)methanol;
1-(4-methyl-6-(1-(6-methylpyridin-2-yl)-1H-indazol-6-yl)pyridin-2-yl)ethanamine;
1-(6-(1-(6-methylpyridin-2-yl)-1H-indazol-6-yl)-4-(trifluoromethyl)pyridin-2-yl)ethanamine;
6-(6-(6-(1-aminoethyl)pyridin-2-yl)-1H-indazol-1-yl)picolinamide;
1-(6-(1-(6-(trifluoromethyl)pyridin-2-yl)-1H-indazol-6-yl)pyridin-2-yl)propan-1-amine;
cyclopropyl(6-(1-(6-(trifluoromethyl)pyridin-2-yl)-1H-indazol-6-yl)pyridin-2-yl)methanamine;
2-(6-(1-(6-(trifluoromethyl)pyridin-2-yl)-1H-indazol-6-yl)pyridin-2-yl)propan-2-amine;
1-(6-(1-(6-methylpyridin-2-yl)-1H-indazol-6-yl)pyridin-2-yl)ethanol;
cyclopropyl(6-(1-(6-methylpyridin-2-yl)-1H-indazol-6-yl)pyridin-2-yl)methanamine;
1-(6-(1-(6-methylpyridin-2-yl)-1H-indazol-6-yl)pyridin-2-yl)butan-1-amine;
1-(6-(1-(4-methylthiazol-2-yl)-1H-indazol-6-yl)pyridin-2-yl)ethanamine;
1-(6-(1-(5-methylthiazol-2-yl)-1H-indazol-6-yl)pyridin-2-yl)ethanamine;
1-(6-(1-(2-methylthiazol-4-yl)-1H-indazol-6-yl)pyridin-2-yl)ethanamine;
1-(6-(1-(1-methyl-1H-pyrazol-3-yl)-1H-indazol-6-yl)pyridin-2-yl)ethanamine;
1-(6-(1-(1-methyl-1H-imidazol-4-yl)-1H-indazol-6-yl)pyridin-2-yl)ethanamine;
(2-(1-(6-methylpyridin-2-yl)-1H-indazol-6-yl)thiazol-4-yl)methanamine;
(2-(1-(6-methylpyridin-2-yl)-1H-indazol-6-yl)thiazol-5-yl)methanamine;
(R)-1-(6-(1-(6-methylpyridin-2-yl)-1H-indazol-6-yl)pyridin-2-yl)ethanamine;
(S)-1-(6-(1-(6-methylpyridin-2-yl)-1H-indazol-6-yl)pyridin-2-yl)ethanamine;
(S)-(6-(6-(6-(1-aminoethyl)pyridin-2-yl)-1H-indazol-1-yl)pyridin-2-yl)methanol;
(R)-(6-(6-(6-(1-aminoethyl)pyridin-2-yl)-1H-indazol-1-yl)pyridin-2-yl)methanol;
(S)-(6-(6-(6-(1-aminobutyl)pyridin-2-yl)-1H-indazol-1-yl)pyridin-2-yl)methanol;
(R)-(6-(6-(6-(1-aminobutyl)pyridin-2-yl)-1H-indazol-1-yl)pyridin-2-yl)methanol;
1-(6-methylpyridin-2-yl)-1H-pyrazolo[4,3-c]pyridin-7-amine;
2-(1-(6-methylpyridin-2-yl)-1H-indazol-6-yl)isonicotinamide;
N,N-dimethyl-5-(1-(6-methylpyridin-2-yl)-1H-indazol-6-yl)pyridin-3-amine;
1-(6-methylpyridin-2-yl)-6-(5-(pyrrolidin-1-yl)pyridin-3-yl)-1H-indazole;
6-methyl-5-(1-(6-methylpyridin-2-yl)-1H-indazol-6-yl)pyridin-3-amine;
5-(1-(6-cyclopentylpyridin-2-yl)-1H-indazol-6-yl)pyridin-3-amine;
5-(1-(6-methylpyridin-2-yl)-1H-indazol-6-yl)-3,4-dihydroisoquinolin-1(2H)-one;
1-(6-(4-fluoro-1-(6-(trifluoromethyl)pyridin-2-yl)-1H-indazol-6-yl)pyridin-2-yl)ethanone;
N-(5-(4-cyano-1-(6-(trifluoromethyl)pyridin-2-yl)-1H-indazol-6-yl)pyridin-3-yl)-2,2,2-trifluoroacetamide;
1-(6-(1-(6-(trifluoromethyl)pyridin-2-yl)-1H-indazol-6-yl)pyridin-2-yl)ethanamine;
2-(1-(6-(trifluoromethyl)pyridin-2-yl)-1H-indazol-6-yl)-5H-cyclopenta[b]pyridin-7 (6H)-one;
6-(1-(6-(trifluoromethyl)pyridin-2-yl)-1H-indazol-6-yl)picolinonitrile;
2-(1-(6-(trifluoromethyl)pyridin-2-yl)-1H-indazol-6-yl)-6,7-dihydroquinolin-8 (5H)-one;
6-amino-4-(1-(6-(trifluoromethyl)pyridin-2-yl)-1H-indazol-6-yl)picolinic acid;
6-(6-(1-aminoethyl)pyridin-2-yl)-1-(6-methylpyridin-2-yl)-1H-indazole-4-carbonitrile;
1-(6-(4-(aminomethyl)-2-(6-methylpyridin-2-yl)-2H-indazol-6-yl)pyridin-2-yl)ethanamine;
N,N-dimethyl-1-(6-(1-(6-(trifluoromethyl)pyridin-2-yl)-1H-indazol-6-yl)pyridin-2-yl)ethanamine;
N-((6-(6-(1-aminoethyl)pyridin-2-yl)-2-(6-methylpyridin-2-yl)-2H-indazol-4-yl)methyl)acetamide;
1-(6-(4-chloro-1-(6-methylpyridin-2-yl)-1H-indazol-6-yl)pyridin-2-yl)ethanone;
(Z)-1-(6-(4-chloro-1-(6-methylpyridin-2-yl)-1H-indazol-6-yl)pyridin-2-yl)ethanone oxime;
N,N-dimethyl-1-(6-(1-(6-methylpyridin-2-yl)-1H-indazol-6-yl)pyridin-2-yl)ethanamine;
N,N-dimethyl-1-(6-(1-(6-(trifluoromethyl)pyridin-2-yl)-1H-indazol-6-yl)pyridin-2-yl)ethanamine;
1-(6-(3-(6-(trifluoromethyl)pyridin-2-yl)imidazo[1,5-a]pyridin-6-yl)pyridin-2-yl)ethanamine;
1-(6-(3-(6-(trifluoromethyl)pyridin-2-yl)imidazo[1,5-a]pyridin-6-yl)pyridin-2-yl)ethanamine;

(Z)-1-(6-(3-(6-(trifluoromethyl)pyridin-2-yl)imidazo[1,5-a]pyridin-6-yl)pyridin-2-yl)ethanone oxime;
tert-butyl(6-(6-acetylpyridin-2-yl)-1-(6-methylpyridin-2-yl)-1H-indazol-4-yl)(methyl)carbamate;
(Z)-tert-butyl(6-(6-(1-(hydroxyimino)ethyl)pyridin-2-yl)-1-(6-methylpyridin-2-yl)-1H-indazol-4-yl)(methyl)carbamate;
(Z)-1-(6-(4-(methylamino)-1-(6-methylpyridin-2-yl)-1H-indazol-6-yl)pyridin-2-yl)ethanone oxime;
1-(6-(1-(6-ethylpyridin-2-yl)-1H-indazol-6-yl)pyridin-2-yl)ethanone;
1-(6-(1-(pyridin-2-yl)-1H-indazol-6-yl)pyridin-2-yl)ethanone;
(E)-1-(6-(1-(pyridin-2-yl)-1H-indazol-6-yl)pyridin-2-yl)ethanone oxime;
2-(aminomethyl)-6-(1-(6-methylpyridin-2-yl)-1H-indazol-6-yl)pyridin-4-amine;
N,N-dimethyl-1-(6-(1-(6-methylpyridin-2-yl)-1H-indazol-6-yl)pyridin-2-yl)ethanamine;
1-(6-(4-(dimethylamino)-1-(6-methylpyridin-2-yl)-1H-indazol-6-yl)pyridin-2-yl)ethanone;
(E)-1-(6-(4-(dimethylamino)-1-(6-methylpyridin-2-yl)-1H-indazol-6-yl)pyridin-2-yl)ethanone oxime;
(E)-1-(6-(1-(6-ethylpyridin-2-yl)-1H-indazol-6-yl)pyridin-2-yl)ethanone oxime;
6-(6-(6-acetylpyridin-2-yl)-1H-indazol-1-yl)picolinonitrile;
(E)-methyl 6-(6-(6-(1-(hydroxyimino)ethyl)pyridin-2-yl)-1H-indazol-1-yl)picolinate;
1-(6-(1-(4-methylthiazol-2-yl)-1H-indazol-6-yl)pyridin-2-yl)ethanone;
1-(6-(4-fluoro-1-(6-(trifluoromethyl)pyridin-2-yl)-1H-indazol-6-yl)pyridin-2-yl)ethanamine;
(S)-1-(6-(1-(6-methylpyridin-2-yl)-1H-indazol-6-yl)pyridin-2-yl)ethanamine;
1-(3-fluoro-6-(1-(6-methylpyridin-2-yl)-1H-indazol-6-yl)pyridin-2-yl)ethanamine;
methyl 3-amino-6-(1-(6-methylpyridin-2-yl)-1H-indazol-6-yl)picolinate;
2,2,2-trifluoro-1-(6-(1-(6-methylpyridin-2-yl)-1H-indazol-6-yl)pyridin-2-yl)ethanol;
1-(6-(4-ethoxy-1-(6-methylpyridin-2-yl)-1H-indazol-6-yl)pyridin-2-yl)ethanamine;
1-(6-(4-methoxy-1-(6-methylpyridin-2-yl)-1H-indazol-6-yl)pyridin-2-yl)ethanamine;
3-amino-3-(6-(1-(6-methylpyridin-2-yl)-1H-indazol-6-yl)pyridin-2-yl)propan-1-ol;
6-(1-(6-methylpyridin-2-yl)-1H-indazol-6-yl)picolinamide;
2-(6-(1-(6-methylpyridin-2-yl)-1H-indazol-6-yl)pyridin-2-yl)acetonitrile;
6-(6-(1-aminoethyl)pyridin-2-yl)-1-(6-methylpyridin-2-yl)-1H-indazol-4-ol;
1-(6-(4-(cyclopropylmethoxy)-1-(6-methylpyridin-2-yl)-1H-indazol-6-yl)pyridin-2-yl)ethanamine;
(4-(1-(6-methylpyridin-2-yl)-1H-indazol-6-yl)thiazol-2-yl)methanamine;
N-((6-(1-(6-methylpyridin-2-yl)-1H-indazol-6-yl)pyridin-2-yl)methyl)acetamide;
2-(6-(1-(6-methylpyridin-2-yl)-1H-indazol-6-yl)pyridin-2-yl)ethanamine;
1-(6-(1-(6-methylpyridin-2-yl)-1H-indazol-6-yl)-3-(trifluoromethyl)pyridin-2-yl)ethanamine;
2-(1-aminoethyl)-6-(1-(6-methylpyridin-2-yl)-1H-indazol-6-yl)pyridin-4-amine;
(1-methyl-4-(1-(6-methylpyridin-2-yl)-1H-indazol-6-yl)-1H-imidazol-2-yl)methanol;
2-amino-2-(6-(1-(6-methylpyridin-2-yl)-1H-indazol-6-yl)pyridin-2-yl)acetonitrile;
2,2,2-trifluoro-1-(6-(1-(6-methylpyridin-2-yl)-1H-indazol-6-yl)pyridin-2-yl)ethanamine;
3-amino-3-(6-(1-(6-methylpyridin-2-yl)-1H-indazol-6-yl)pyridin-2-yl)propanoic acid;
methyl 3-amino-3-(6-(1-(6-methylpyridin-2-yl)-1H-indazol-6-yl)pyridin-2-yl)propanoate;
1-(6-(1-(6-methylpyridin-2-yl)-1H-indazol-6-yl)pyridin-2-yl)cyclopropanamine;
1-(6-(1-(6-methylpyridin-2-yl)-1H-indazol-6-yl)pyridin-2-yl)propan-1-amine;
(R)-1-(6-(1-(6-methylpyridin-2-yl)-1H-indazol-6-yl)pyridin-2-yl)butan-1-amine;
(S)-1-(6-(1-(6-methylpyridin-2-yl)-1H-indazol-6-yl)pyridin-2-yl)butan-1-amine;
1-(3-chloro-6-(1-(6-methylpyridin-2-yl)-1H-indazol-6-yl)pyridin-2-yl)ethanamine;
2-amino-2-(6-(1-(6-methylpyridin-2-yl)-1H-indazol-6-yl)pyridin-2-yl)acetamide;
1-(6-(1-(6-(trifluoromethyl)pyridin-2-yl)-1H-indazol-6-yl)pyridin-2-yl)butan-1-amine;
6-(6-(6-(1-aminopropyl)pyridin-2-yl)-1H-indazol-1-yl)picolinamide;
2-(1-aminoethyl)-6-(1-(6-(trifluoromethyl)pyridin-2-yl)-1H-indazol-6-yl)pyridin-4-amine;
2-amino-2-(6-(1-(6-methylpyridin-2-yl)-1H-indazol-6-yl)pyridin-2-yl)ethanol;
methyl 2-amino-2-(6-(1-(6-methylpyridin-2-yl)-1H-indazol-6-yl)pyridin-2-yl)acetate;
2-amino-2-(6-(1-(6-methylpyridin-2-yl)-1H-indazol-6-yl)pyridin-2-yl)acetic acid;
6-(6-(6-(1-aminobutyl)pyridin-2-yl)-1H-indazol-1-yl)picolinamide;
1-(6-(3-(6-methylpyridin-2-yl)imidazo[1,5-a]pyridin-6-yl)pyridin-2-yl)propan-1-amine;
1-(6-(3-(6-methylpyridin-2-yl)imidazo[1,5-a]pyridin-6-yl)pyridin-2-yl)butan-1-amine;
2-(6-(6-(6-(1-aminoethyl)pyridin-2-yl)-1H-indazol-1-yl)pyridin-2-yl)propan-2-ol;
1-(6-(1-(6-(methoxymethyl)pyridin-2-yl)-1H-indazol-6-yl)pyridin-2-yl)ethanamine;
(6-(6-(6-(1-aminobutyl)pyridin-2-yl)-1H-indazol-1-yl)pyridin-2-yl)methanol;
1-(3-methyl-6-(1-(6-methylpyridin-2-yl)-1H-indazol-6-yl)pyridin-2-yl)ethanamine;
1-(6-(1-(4-methylthiophen-2-yl)-1H-indazol-6-yl)pyridin-2-yl)ethanamine;
1-(6-(1-(6-propylpyridin-2-yl)-1H-indazol-6-yl)pyridin-2-yl)ethanamine;
1-(6-(6-(6-(1-aminoethyl)pyridin-2-yl)-1H-indazol-1-yl)pyridin-2-yl)ethanol;
(4-(1-(6-methylpyridin-2-yl)-1H-indazol-6-yl)oxazol-2-yl)methanamine;
1-(6-(1-(6-(tert-butyl)pyridin-2-yl)-1H-indazol-6-yl)pyridin-2-yl)ethanamine;
1-(6-(1-(6-(aminomethyl)pyridin-2-yl)-1H-indazol-6-yl)pyridin-2-yl)ethanamine;
2-(6-(6-(6-(1-aminoethyl)pyridin-2-yl)-1H-indazol-1-yl)pyridin-2-yl)-2-methylpropanenitrile;
1-(6-(1-(6-(2-(methylsulfonyl)propan-2-yl)pyridin-2-yl)-1H-indazol-6-yl)pyridin-2-yl)ethanamine;
1-(6-(6-(6-(1-aminoethyl)pyridin-2-yl)-1H-indazol-1-yl)pyridin-2-yl)cyclopropanecarbonitrile;
(6-(6-(6-(aminomethyl)pyridin-2-yl)-1H-indazol-1-yl)pyridin-2-yl)methanol;
2-(6-(6-(6-(1-aminoethyl)pyridin-2-yl)-1H-indazol-1-yl)pyridin-2-yl)propan-2-amine;

1-(6-(3-(6-ethylpyridin-2-yl)imidazo[1,5-a]pyridin-6-yl)
pyridin-2-yl)ethanamine;
(6-(6-(6-(1-aminopropyl)pyridin-2-yl)-1H-indazol-1-yl)
pyridin-2-yl)methanol;
1-(6-(4-(1H-imidazol-2-yl)-1-(6-methylpyridin-2-yl)-1H-
indazol-6-yl)pyridin-2-yl)ethanamine;
1-(6-(1-(4-methylpyrimidin-2-yl)-1H-indazol-6-yl)pyridin-
2-yl)ethanamine;
1-(6-(1-(4-(trifluoromethyl)pyrimidin-2-yl)-1H-indazol-6-
yl)pyridin-2-yl)ethanamine;
2-(6-(1-(6-methylpyridin-2-yl)-1H-indazol-6-yl)pyridin-2-
yl)propan-2-amine;
1-(1-methyl-4-(1-(6-methylpyridin-2-yl)-1H-indazol-6-yl)-
1H-imidazol-2-yl)ethanol;
(1-methyl-4-(1-(6-methylpyridin-2-yl)-1H-indazol-6-yl)-
1H-imidazol-2-yl)methanamine;
2-(6-(6-(6-(1-aminoethyl)pyridin-2-yl)-1H-indazol-1-yl)
pyridin-2-yl)-2-methylpropanamide;
(6-(6-(6-(1-aminoethyl)pyridin-2-yl)imidazo[1,5-a]pyridin-
3-yl)pyridin-2-yl)methanol;
1-(6-(1-(6-methylpyridin-2-yl)-4-(thiazol-2-yl)-1H-indazol-
6-yl)pyridin-2-yl)ethanamine;
1-(6-(1-(6-methylpyridin-2-yl)-1H-indazol-6-yl)pyridin-2-
yl)cyclobutanecarbonitrile;
1-(1-methyl-4-(1-(6-methylpyridin-2-yl)-1H-indazol-6-yl)-
1H-imidazol-2-yl)ethanamine;
1-(6-methylpyridin-2-yl)-6-(pyridin-2-yl)-1H-indazole;
(6-(6-(6-(1-aminoethyl)pyridin-2-yl)-4-methoxy-1H-inda-
zol-1-yl)pyridin-2-yl)methanol;
2-(1-(6-methylpyridin-2-yl)-1H-indazol-6-yl)-6,7,8,9-tetra-
hydro-5H-cyclohepta[b]pyridin-9-amine;
(6-(6-(1-aminoethyl)pyridin-2-yl)-1-(6-(hydroxymethyl)
pyridin-2-yl)-1H-indazol-4-yl)methanol;
1-(4-(1-(6-methylpyridin-2-yl)-1H-indazol-6-yl)thiazol-2-
yl)ethanamine;
1-(6-(8-chloro-3-(6-(trifluoromethyl)pyridin-2-yl)imidazo
[1,5-a]pyridin-6-yl)pyridin-2-yl)ethanamine;
1-(6-(1-(6-methylpyridin-2-yl)-1H-indazol-6-yl)pyridin-2-
yl)cyclobutanecarboxamide;
1-(6-methylpyridin-2-yl)-6-(6-(3,3,3-trifluoropropyl)pyri-
din-2-yl)-1H-indazole;
2-(6-(6-(6-(1-aminoethyl)pyridin-2-yl)-1H-indazol-1-yl)
pyridin-2-yl)ethanol;
1-(6-(1-(4,6-dimethylpyridin-2-yl)-1H-indazol-6-yl)pyri-
din-2-yl)ethanamine;
6-(6-(1-aminoethyl)pyridin-2-yl)-1-(6-(hydroxymethyl)
pyridin-2-yl)-N-methyl-1H-indazole-4-carboxamide;
1-(6-(8-fluoro-3-(6-(trifluoromethyl)pyridin-2-yl)imidazo
[1,5-a]pyridin-6-yl)pyridin-2-yl)ethanamine;
(S)-(6-(6-(6-(1-aminopropyl)pyridin-2-yl)-1H-indazol-1-yl)
pyridin-2-yl)methanol;
1-(6-(1-(6-methylpyridin-2-yl)-4-(1H-pyrazol-3-yl)-1H-in-
dazol-6-yl)pyridin-2-yl)ethanamine;
(4-(1-(6-methylpyridin-2-yl)-1H-indazol-6-yl)thiazol-2-yl)
methanol;
(6-(6-(6-(1-aminoethyl)pyridin-2-yl)-4-fluoro-1H-indazol-
1-yl)pyridin-2-yl)methanol;
(R)-(6-(6-(6-(1-aminopropyl)pyridin-2-yl)-1H-indazol-1-
yl)pyridin-2-yl)methanol; and
6-(1-methyl-1H-imidazol-4-yl)-1-(6-methylpyridin-2-yl)-
1H-indazole,
or a pharmaceutically acceptable salt thereof.
In an alternative thirtieth embodiment, the compound is further selected from:
(6-(6-(6-ethylpyridin-2-yl)-4-(5-methyl-1,3,4-oxadiazol-2-
yl)-1H-indazol-1-yl)pyridin-2-yl)methanol;
1-(6-(6-((S)-1-aminobutyl)pyridin-2-yl)-1-(6-(hydroxym-
ethyl)pyridin-2-yl)-1H-indazol-4-yl)pyrrolidin-3-ol;
(S)-(6-(6-(6-(1-aminopropyl)pyridin-2-yl)-1H-indazol-1-yl)
pyrazin-2-yl)methanol;
(1-(6-(6-((S)-1-aminobutyl)pyridin-2-yl)-1-(6-(hydroxym-
ethyl)pyridin-2-yl)-1H-indazol-4-yl)pyrrolidin-2-yl)
methanol;
(S)-(6-(6-(6-(1-aminobutyl)pyridin-2-yl)-4-(methylamino)-
1H-indazol-1-yl)pyridin-2-yl)methanol;
(S)-(6-(6-(6-(1-aminoethyl)pyridin-2-yl)-4-(oxazol-2-yl)-
1H-indazol-1-yl)pyridin-2-yl)methanol;
(S)-(6-(6-(6-(1-aminobutyl)pyridin-2-yl)-1H-indazol-1-yl)
pyrazin-2-yl)methanol;
(S)-(6-(6-(6-(1-aminopropyl)pyridin-2-yl)-4-(1-methyl-1H-
pyrazol-3-yl)-1H-indazol-1-yl)pyridin-2-yl)methanol;
(S)-(6-(6-(6-(1-aminobutyl)pyridin-2-yl)-4-(2-methoxy-
ethoxy)-1H-indazol-1-yl)pyridin-2-yl)methanol;
(6-(6-(6-((1R,2R)-1-amino-2-fluorobutyl)pyridin-2-yl)-4-
(2-methoxyethoxy)-1H-indazol-1-yl)pyridin-2-yl)metha-
nol;
(S)-(6-(6-(6-(1-aminobutyl)pyridin-2-yl)-4-(ethylamino)-
1H-indazol-1-yl)pyridin-2-yl)methanol;
(S)-(6-(6-(6-(1-aminobutyl)pyridin-2-yl)-4-(1-methyl-1H-
pyrazol-3-yl)-1H-indazol-1-yl)pyridin-2-yl)methanol;
(S)-1-(6-(6-(1-aminobutyl)pyridin-2-yl)-1-(6-(hydroxym-
ethyl)pyridin-2-yl)-1H-indazol-4-yl)piperidin-4-ol;
1-(6-(6-((S)-1-aminobutyl)pyridin-2-yl)-1-(6-(hydroxym-
ethyl)pyridin-2-yl)-1H-indazol-4-yl)piperidin-3-ol;
(S)-(6-(6-(6-(1-aminoethyl)pyridin-2-yl)-1H-indazol-1-yl)
pyrazin-2-yl)methanol;
(S)-(6-(6-(6-(1-aminobutyl)pyridin-2-yl)-4-(3,3-difluoro-
azetidin-1-yl)-1H-indazol-1-yl)pyridin-2-yl)methanol;
(S)-(6-(6-(6-(1-aminopropyl)pyridin-2-yl)-4-(methyl-
amino)-1H-indazol-1-yl)pyridin-2-yl)methanol;
(S)-1-(6-(1-(4-(difluoromethyl)pyrimidin-2-yl)-1H-indazol-
6-yl)pyridin-2-yl)butan-1-amine;
(S)-(6-(6-(6-(1-aminoethyl)pyridin-2-yl)-4-(1-methyl-1H-
pyrazol-4-yl)-1H-indazol-1-yl)pyridin-2-yl)methanol;
(S)-(6-(6-(6-(1-aminobutyl)pyridin-2-yl)-4-(fluoromethyl)-
1H-indazol-1-yl)pyridin-2-yl)methanol;
(S)-1-(4-(6-(6-(1-aminobutyl)pyridin-2-yl)-1-(6-(hy-
droxymethyl)pyridin-2-yl)-1H-indazol-4-yl)-5,6-dihy-
dropyridin-1(2H)-yl)ethanone;
(S)-(6-(6-(6-(1-aminobutyl)pyridin-2-yl)-4-methoxy-1H-in-
dazol-1-yl)pyrazin-2-yl)methanol;
(S)-(6-(6-(6-(1-aminoethyl)pyridin-2-yl)-4-(5-methyl-1,3,4-
thiadiazol-2-yl)-1H-indazol-1-yl)pyridin-2-yl)methanol;
(S)-(6-(6-(6-(1-aminobutyl)pyridin-2-yl)-4-chloro-1H-inda-
zol-1-yl)pyridin-2-yl)methanol;
(S)-(1-(6-(6-(1-aminobutyl)pyridin-2-yl)-1-(6-(hydroxym-
ethyl)pyridin-2-yl)-1H-indazol-4-yl)-3-(chloromethyl)
azetidin-3-yl)methanol;
(S)-(6-(6-(6-(1-aminoethyl)pyridin-2-yl)-4-(1-methyl-1H-
imidazol-4-yl)-1H-indazol-1-yl)pyridin-2-yl)methanol;
(S)-(6-(6-(6-(1-aminobutyl)pyridin-2-yl)-4-(3,3-difluoropy-
rrolidin-1-yl)-1H-indazol-1-yl)pyridin-2-yl)methanol;
(6-(6-(6-((S)-1-aminobutyl)pyridin-2-yl)-4-(2-methylmor-
pholino)-1H-indazol-1-yl)pyridin-2-yl)methanol;
(S)-(6-(6-(6-(1-aminobutyl)pyridin-2-yl)-4-(1-methyl-1,2,3,
6-tetrahydropyridin-4-yl)-1H-indazol-1-yl)pyridin-2-yl)
methanol;
(6-(6-(6-((1R,2S)-1-amino-2-fluorobutyl)pyridin-2-yl)-4-
(2-methoxyethoxy)-1H-indazol-1-yl)pyridin-2-yl)metha-
nol;
(S)-(6-(6-(6-(1-aminoethyl)pyridin-2-yl)-4-(pyrimidin-2-
yl)-1H-indazol-1-yl)pyridin-2-yl)methanol;

(S)-(6-(6-(6-(1-aminobutyl)pyridin-2-yl)-4-(difluoromethyl)-1H-indazol-1-yl)pyridin-2-yl)methanol;
(S)-(6-(6-(6-(1-aminobutyl)pyridin-2-yl)-1-(6-(hydroxymethyl)pyridin-2-yl)-1H-indazol-4-yl)methanol;
(S)-(6-(6-(6-(1-aminobutyl)pyridin-2-yl)-4-(3-methoxypropoxy)-1H-indazol-1-yl)pyridin-2-yl)methanol;
(S)-(6-(6-(6-(1-aminopentyl)pyridin-2-yl)-1H-indazol-1-yl)pyridin-2-yl)methanol;
(S)-(6-(6-(6-(1-aminoethyl)pyridin-2-yl)-4-(1H-imidazol-1-yl)-1H-indazol-1-yl)pyridin-2-yl)methanol;
(S)-(6-(6-(6-(1-aminobutyl)pyridin-2-yl)-4-(3,6-dihydro-2H-pyran-4-yl)-1H-indazol-1-yl)pyridin-2-yl)methanol;
(S)-(6-(6-(6-(1-aminopropyl)pyridin-2-yl)-4-(3-methoxypropoxy)-1H-indazol-1-yl)pyridin-2-yl)methanol;
(S)-(6-(6-(6-(1-aminoethyl)pyridin-2-yl)-4-(1,5-dimethyl-1H-pyrazol-3-yl)-1H-indazol-1-yl)pyridin-2-yl)methanol;
(S)-(6-(6-(6-(1-aminoethyl)pyridin-2-yl)-4-(5-methyl-1H-pyrazol-3-yl)-1H-indazol-1-yl)pyridin-2-yl)methanol;
(S)-(6-(6-(6-(1-aminobutyl)pyridin-2-yl)-4-(methoxymethyl)-1H-indazol-1-yl)pyridin-2-yl)methanol;
(S)-(6-(6-(6-(amino(cyclopropyl)methyl)pyridin-2-yl)-4-methoxy-1H-indazol-1-yl)pyrazin-2-yl)methanol;
(6-(6-(6-((S)-1-aminobutyl)pyridin-2-yl)-4-(2,6-dimethylmorpholino)-1H-indazol-1-yl)pyridin-2-yl)methanol;
(S)-(6-(6-(4-(1-aminobutyl)pyrimidin-2-yl)-1H-indazol-1-yl)pyridin-2-yl)methanol;
3-((6-(6-(((S)-1-aminobutyl)pyridin-2-yl)-1-(6-(hydroxymethyl)pyridin-2-yl)-1H-indazol-4-yl)amino)-2-(chloromethyl)propanoic acid;
(S)-(6-(6-(6-(1-aminobutyl)pyridin-2-yl)-4-((difluoromethoxy)methyl)-1H-indazol-1-yl)pyridin-2-yl)methanol;
(S)-(6-(6-(6-(1-aminobutyl)pyridin-2-yl)-4-(morpholinomethyl)-1H-indazol-1-yl)pyridin-2-yl)methanol;
(S)-4-(6-(6-(1-aminobutyl)pyridin-2-yl)-1-(6-(hydroxymethyl)pyridin-2-yl)-1H-indazol-4-yl)thiomorpholine 1,1-dioxide;
(S)-(6-(6-(6-(1-amino-4,4,4-trifluorobutyl)pyridin-2-yl)-1H-indazol-1-yl)pyridin-2-yl)methanol;
(S)-(6-(6-(6-(1-aminobutyl)pyridin-2-yl)-4-thiomorpholino-1H-indazol-1-yl)pyridin-2-yl)methanol;
1-(6-(6-(6-((S)-1-aminoethyl)pyridin-2-yl)-1H-indazol-1-yl)pyridin-2-yl)ethanol;
(S)-(6-(6-(6-(1-aminoethyl)pyridin-2-yl)-4-ethoxy-1H-indazol-1-yl)pyrazin-2-yl)methanol;
(S)-(6-(6-(6-(1-aminoethyl)pyridin-2-yl)-4-(1-methyl-1H-pyrazol-3-yl)-1H-indazol-1-yl)pyridin-2-yl)methanol;
(S)-(6-(6-(6-(1-aminoethyl)pyridin-2-yl)-4-(2-methylthiazol-4-yl)-1H-indazol-1-yl)pyridin-2-yl)methanol;
(S)-(6-(6-(6-(1-aminopropyl)pyridin-2-yl)-4-ethoxy-1H-indazol-1-yl)pyrazin-2-yl)methanol;
(S)-(6-(6-(6-(1-aminoethyl)pyridin-2-yl)-4-(3-methoxypropoxy)-1H-indazol-1-yl)pyridin-2-yl)methanol;
(S)-(6-(6-(6-(amino(cyclopropyl)methyl)pyridin-2-yl)-4-ethoxy-1H-indazol-1-yl)pyrazin-2-yl)methanol;
(S)-(6-(6-(6-(1-aminoethyl)pyridin-2-yl)-4-(1H-1,2,4-triazol-1-yl)-1H-indazol-1-yl)pyridin-2-yl)methanol;
(S)-2-(6-(6-(1-aminoethyl)pyridin-2-yl)-1-(6-(hydroxymethyl)pyridin-2-yl)-1H-indazol-4-yl)thiazole-4-carbonitrile;
(S)-(6-(6-(6-(1-aminoethyl)pyridin-2-yl)-4-(isothiazol-3-yl)-1H-indazol-1-yl)pyridin-2-yl)methanol;
(S)-(6-(6-(6-(amino(cyclobutyl)methyl)pyridin-2-yl)-1H-indazol-1-yl)pyridin-2-yl)methanol;
(S)-(6-(6-(6-(1-aminobutyl)pyridin-2-yl)-4-(tetrahydro-2H-pyran-4-yl)-1H-indazol-1-yl)pyridin-2-yl)methanol;
(6-(6-(6-((1R,2S)-1-amino-2-fluorobutyl)pyridin-2-yl)-4-ethoxy-1H-indazol-1-yl)pyridin-2-yl)methanol;
(S)-(6-(6-(6-(1-aminobutyl)pyridin-2-yl)-4-morpholino-1H-indazol-1-yl)pyridin-2-yl)methanol;
(6-(6-(6-((1R,2R)-1-amino-2-fluorobutyl)pyridin-2-yl)-4-ethoxy-1H-indazol-1-yl)pyridin-2-yl)methanol;
1-(6-(6-(6-((S)-1-aminobutyl)pyridin-2-yl)-1H-indazol-1-yl)pyridin-2-yl)ethanol;
(S)-(6-(6-(6-(1-aminobutyl)pyridin-2-yl)-4-(3,3-dimethylazetidin-1-yl)-1H-indazol-1-yl)pyridin-2-yl)methanol;
(S)-(6-(6-(6-(1-amino-4,4,4-trifluorobutyl)pyridin-2-yl)-4-methoxy-1H-indazol-1-yl)pyridin-2-yl)methanol;
(S)-(6-(6-(6-(1-aminopropyl)pyridin-2-yl)-4-methoxy-1H-indazol-1-yl)pyrazin-2-yl)methanol;
(S)-(6-(6-(6-(1-amino-3,3-difluorobutyl)pyridin-2-yl)-4-ethoxy-1H-indazol-1-yl)pyridin-2-yl)methanol;
(S)-1-(6-(4-methoxy-1-(4-(trifluoromethyl)pyrimidin-2-yl)-1H-indazol-6-yl)pyridin-2-yl)butan-1-amine;
(6-(6-(6-(amino(oxetan-3-yl)methyl)pyridin-2-yl)-4-ethoxy-1H-indazol-1-yl)pyridin-2-yl)methanol;
(S)-1-(6-(4-ethoxy-1-(4-(trifluoromethyl)pyrimidin-2-yl)-1H-indazol-6-yl)pyridin-2-yl)butan-1-amine;
(6-{6-[6-((S)-1-Amino-ethyl)-pyridin-2-yl]-4-fluoro-indazol-1-yl}-pyridin-2-yl)-methanol;
(S)-(6-(6-(6-(1-aminoethyl)pyridin-2-yl)-4-phenyl-1H-indazol-1-yl)pyridin-2-yl)methanol;
(S)-(6-(6-(6-(1-amino-3,3-difluorobutyl)pyridin-2-yl)-1H-indazol-1-yl)pyridin-2-yl)methanol;
(S)-(6-(6-(6-(1-aminoethyl)pyridin-2-yl)-4-(5-methylthiazol-2-yl)-1H-indazol-1-yl)pyridin-2-yl)methanol;
(6-(6-(6-((S)-1-aminobutyl)pyridin-2-yl)-4-(piperidin-3-ylmethoxy)-1H-indazol-1-yl)pyridin-2-yl)methanol;
(6-{6-[6-((S)-1-Amino-butyl)-pyridin-2-yl]-4-isopropoxy-indazol-1-yl}-pyridin-2-yl)-methanol;
(S)-(6-(6-(6-(1-aminoethyl)pyridin-2-yl)-4-(pyridin-2-yl)-1H-indazol-1-yl)pyridin-2-yl)methanol;
1-(6-(6-((S)-1-aminobutyl)pyridin-2-yl)-1-(6-(hydroxymethyl)pyridin-2-yl)-1H-indazol-4-yl)pyrrolidine-3-carboxylic acid;
(S)-(6-(6-(6-(1-aminoethyl)pyridin-2-yl)-4-(pyrrolidin-1-yl)-1H-indazol-1-yl)pyridin-2-yl)methanol;
(6-(6-(6-(amino(oxetan-3-yl)methyl)pyridin-2-yl)-1H-indazol-1-yl)pyridin-2-yl)methanol;
(R)-(6-(6-(4-(1-aminobutyl)pyrimidin-2-yl)-1H-indazol-1-yl)pyridin-2-yl)methanol;
1-amino-1-(6-(1-(6-(hydroxymethyl)pyridin-2-yl)-1H-indazol-6-yl)pyridin-2-yl)butan-2-ol;
(6-{6-[6-((S)-1-Amino-butyl)-pyridin-2-yl]-4-fluoro-indazol-1-yl}-pyridin-2-yl)-methanol;
4-amino-4-(6-(1-(6-(hydroxymethyl)pyridin-2-yl)-1H-indazol-6-yl)pyridin-2-yl)butan-2-ol;
(S)-(6-(6-(6-(1-aminobutyl)pyridin-2-yl)-4-(4-methylpiperazin-1-yl)-1H-indazol-1-yl)pyridin-2-yl)methanol;
(S)-(6-(6-(6-(1-amino-4-methoxybutyl)pyridin-2-yl)-4-methoxy-1H-indazol-1-yl)pyridin-2-yl)methanol;
(S)-(6-(6-(6-(1-amino-4,4,4-trifluorobutyl)pyridin-2-yl)-4-ethoxy-1H-indazol-1-yl)pyridin-2-yl)methanol;
(S)-6-(6-(1-aminobutyl)pyridin-2-yl)-1-(6-(hydroxymethyl)pyridin-2-yl)-1H-indazole-4-carbonitrile;
(S)-1-(6-(1-(4-(difluoromethyl)pyrimidin-2-yl)-1H-indazol-6-yl)pyridin-2-yl)propan-1-amine;
(S)-(6-(6-(6-(1-amino-4-methoxybutyl)pyridin-2-yl)-4-ethoxy-1H-indazol-1-yl)pyridin-2-yl)methanol;
(S)-(6-(6-(6-(1-aminobutyl)pyridin-2-yl)-4-(2,2,2-trifluoroethoxy)-1H-indazol-1-yl)pyridin-2-yl)methanol;

(S)-1-(4-(6-(6-(1-aminobutyl)pyridin-2-yl)-1-(6-(hydroxymethyl)pyridin-2-yl)-1H-indazol-4-yl)piperidin-1-yl)ethanone;
1-amino-1-(6-(1-(6-(hydroxymethyl)pyridin-2-yl)-1H-indazol-6-yl)pyridin-2-yl)butan-2-ol;
(S)-(6-(6-(6-(1-aminoethyl)pyridin-2-yl)-4-(4-(trifluoromethyl)oxazol-2-yl)-1H-indazol-1-yl)pyridin-2-yl)methanol;
(S)-(6-(6-(6-(1-aminobutyl)pyridin-2-yl)-4-((dimethylamino)methyl)-1H-indazol-1-yl)pyridin-2-yl)methanol;
(S)-(6-(6-(6-(1-aminobutyl)pyridin-2-yl)-4-((3-chloro-2,2-dimethylpropyl)amino)-1H-indazol-1-yl)pyridin-2-yl)methanol;
(S)-(6-(6-(6-(1-aminobutyl)pyridin-2-yl)-4-ethoxy-1H-indazol-1-yl)pyridin-2-yl)methanol;
(S)-1-(6-(1-(6-(fluoromethyl)pyridin-2-yl)-1H-indazol-6-yl)pyridin-2-yl)butan-1-amine;
(S)-(6-(6-(6-(1-aminobutyl)pyridin-2-yl)-4-(azetidin-1-yl)-1H-indazol-1-yl)pyridin-2-yl)methanol;
(S)-(6-(6-(6-(1-aminobutyl)pyridin-2-yl)-4-(4,4-difluoropiperidin-1-yl)-1H-indazol-1-yl)pyridin-2-yl)methanol;
(S)-1-(6-(1-(6-(difluoromethyl)pyridin-2-yl)-1H-indazol-6-yl)pyridin-2-yl)butan-1-amine;
(S)-(6-(6-(6-(1-aminobutyl)pyridin-2-yl)-4-(3,3-difluoropiperidin-1-yl)-1H-indazol-1-yl)pyridin-2-yl)methanol;
(S)-1-(6-(6-(1-aminobutyl)pyridin-2-yl)-1-(6-(hydroxymethyl)pyridin-2-yl)-1H-indazol-4-yl)azetidine-3-carboxylic acid;
(6-(6-(6-(1-amino-2-(methylthio)ethyl)pyridin-2-yl)-1H-indazol-1-yl)pyridin-2-yl)methanol;
(R)-1-(6-(6-(6-((S)-1-aminobutyl)pyridin-2-yl)-1H-indazol-1-yl)pyridin-2-yl)-2,2,2-trifluoroethanol;
(S)-(6-(6-(6-(1-aminoethyl)pyridin-2-yl)-4-(4-methylthiazol-2-yl)-1H-indazol-1-yl)pyridin-2-yl)methanol;
(S)-(6-(6-(6-(1-amino-3-methylbutyl)pyridin-2-yl)-1H-indazol-1-yl)pyridin-2-yl)methanol;
(R)-(6-(6-(6-(amino(phenyl)methyl)pyridin-2-yl)-4-ethoxy-1H-indazol-1-yl)pyridin-2-yl)methanol;
(6-(6-(6-(((1R,2R)-1-amino-2-methoxybutyl)pyridin-2-yl)-4-ethoxy-1H-indazol-1-yl)pyridin-2-yl)methanol;
(S)-(6-(6-(6-(1-aminobutyl)pyridin-2-yl)-4-(2-cyclopropylethoxy)-1H-indazol-1-yl)pyridin-2-yl)methanol;
(S)-(6-(6-(6-(1-aminobutyl)pyridin-2-yl)-4-methoxy-1H-indazol-1-yl)pyridin-2-yl)methanol;
(S)-(6-(6-(6-(1-aminobutyl)pyridin-2-yl)-4-(trifluoromethoxy)-1H-indazol-1-yl)pyridin-2-yl)methanol;
(S)-(6-(6-(6-(1-aminoethyl)pyridin-2-yl)-4-(4,5-dihydrooxazol-2-yl)-1H-indazol-1-yl)pyridin-2-yl)methanol;
4-amino-4-(6-(1-(6-(hydroxymethyl)pyridin-2-yl)-1H-indazol-6-yl)pyridin-2-yl)butan-2-ol;
(S)-(6-(6-(6-(1-aminobutyl)pyridin-2-yl)-4-(difluoromethoxy)-1H-indazol-1-yl)pyrazin-2-yl)methanol;
(S)-(6-(6-(6-(1-(methylamino)butyl)pyridin-2-yl)-1H-indazol-1-yl)pyridin-2-yl)methanol;
(6-(6-(6-((S)-1-aminoethyl)pyridin-2-yl)-4-(4-methyl-4,5-dihydrooxazol-2-yl)-1H-indazol-1-yl)pyridin-2-yl)methanol;
(S)-(6-(6-(6-(1-aminoethyl)pyridin-2-yl)-4-(1-(trifluoromethyl)-1H-pyrazol-4-yl)-1H-indazol-1-yl)pyridin-2-yl)methanol;
(S)-1-(6-(1-(6-(difluoromethyl)pyridin-2-yl)-1H-indazol-6-yl)pyridin-2-yl)ethanamine;
2-amino-2-(6-(1-(6-(hydroxymethyl)pyridin-2-yl)-1H-indazol-6-yl)pyridin-2-yl)ethanol;
(S)-(6-(6-(6-(1-amino-3-methylbut-3-en-1-yl)pyridin-2-yl)-1H-indazol-1-yl)pyridin-2-yl)methanol;
(S)-1-(6-(1-(4-(trifluoromethyl)pyrimidin-2-yl)-1H-indazol-6-yl)pyridin-2-yl)butan-1-amine;
(6-(6-(6-(1-amino-2-(methylsulfonyl)ethyl)pyridin-2-yl)-1H-indazol-1-yl)pyridin-2-yl)methanol;
1-(6-(6-(((S)-1-aminobutyl)pyridin-2-yl)-1-(6-(hydroxymethyl)pyridin-2-yl)-1H-indazol-4-yl)piperidine-3-carboxylic acid;
(S)-6-(6-(1-aminopropyl)pyridin-2-yl)-1-(6-(hydroxymethyl)pyridin-2-yl)-1H-indazole-4-carbonitrile;
(S)-(6-(6-(6-(1-aminoethyl)pyridin-2-yl)-4-(4,5-dimethylthiazol-2-yl)-1H-indazol-1-yl)pyridin-2-yl)methanol;
(S)-(6-(6-(6-(1-aminobutyl)pyridin-2-yl)-4-(piperidin-1-yl)-1H-indazol-1-yl)pyridin-2-yl)methanol;
(6-(6-(6-(1-amino-2-cyclopropylethyl)pyridin-2-yl)-1H-indazol-1-yl)pyridin-2-yl)methanol;
1-(6-(6-(6-((S)-1-aminoethyl)pyridin-2-yl)-1H-indazol-1-yl)pyridin-2-yl)ethanol;
(6-{6-[6-((S)-1-Amino-butyl)-pyridin-2-yl]-4-fluoro-indazol-1-yl}-pyridin-2-yl)-methanol;
1-(6-(1-(6-methylpyridin-2-yl)-4-(oxazol-5-yl)-1H-indazol-6-yl)pyridin-2-yl)ethanamine;
(S)-(6-(6-(4-(1-aminoethyl)pyrimidin-2-yl)-1H-indazol-1-yl)pyridin-2-yl)methanol;
(S)-6-(6-(1-aminoethyl)pyridin-2-yl)-1-(6-(hydroxymethyl)pyridin-2-yl)-1H-indazole-4-carbonitrile;
(6-(6-(6-(amino(cyclopropyl)methyl)pyridin-2-yl)-1H-indazol-1-yl)pyridin-2-yl)methanol;
(S)-1-(6-(1-(6-(difluoromethyl)pyridin-2-yl)-1H-indazol-6-yl)pyridin-2-yl)propan-1-amine;
(S)-6-(6-(1-aminoethyl)pyridin-2-yl)-N-(1-hydroxy-2-methylpropan-2-yl)-1-(6-(hydroxymethyl)pyridin-2-yl)-1H-indazole-4-carboxamide;
(S)-1-(6-(1-(4-(difluoromethyl)pyrimidin-2-yl)-1H-indazol-6-yl)pyridin-2-yl)ethanamine;
1-(6-(1-(6-methylpyridin-2-yl)-4-(oxazol-2-yl)-1H-indazol-6-yl)pyridin-2-yl)ethanamine;
(S)-(6-(6-(6-(1-aminoethyl)pyridin-2-yl)-4-(4-(trifluoromethyl)thiazol-2-yl)-1H-indazol-1-yl)pyridin-2-yl)methanol;
(6-(6-(6-(1-amino-2-methoxyethyl)pyridin-2-yl)-1H-indazol-1-yl)pyridin-2-yl)methanol;
2-amino-2-(6-(1-(6-(hydroxymethyl)pyridin-2-yl)-1H-indazol-6-yl)pyridin-2-yl)-N,N-dimethylacetamide;
(S)-(6-(6-(6-(1-aminoethyl)pyridin-2-yl)-4-(thiazol-2-yl)-1H-indazol-1-yl)pyridin-2-yl)methanol;
(S)-1-(6-(6-(6-((S)-1-aminobutyl)pyridin-2-yl)-1H-indazol-1-yl)pyridin-2-yl)-2,2,2-trifluoroethanol;
(S)-(6-(6-(6-(1-aminoethyl)pyridin-2-yl)-4-(5-(trifluoromethyl)thiazol-2-yl)-1H-indazol-1-yl)pyridin-2-yl)methanol;
(S)-1-(6-(6-(1-aminobutyl)pyridin-2-yl)-1-(6-(hydroxymethyl)pyridin-2-yl)-1H-indazol-4-yl)piperidine-4-carboxylic acid;
(S)-(6-(6-(6-(1-aminoethyl)pyridin-2-yl)-1H-indazol-1-yl)-3-fluoropyridin-2-yl)methanol;
(6-(6-(6-(((1R,2S)-1-amino-2-methoxybutyl)pyridin-2-yl)-4-ethoxy-1H-indazol-1-yl)pyridin-2-yl)methanol;
(S)-1-(6-(1-(6-(trifluoromethyl)pyrazin-2-yl)-1H-indazol-6-yl)pyridin-2-yl)butan-1-amine;
(S)-6-(6-(6-(1-aminobutyl)pyridin-2-yl)-1H-indazol-1-yl)picolinaldehyde;
(S)-(6-(6-(6-(1-aminoethyl)pyridin-2-yl)-4-(3-(trifluoromethyl)-1H-pyrazol-1-yl)-1H-indazol-1-yl)pyridin-2-yl)methanol;
6-(6-((S)-1-aminoethyl)pyridin-2-yl)-N-(2-aminopropyl)-1-(6-(hydroxymethyl)pyridin-2-yl)-1H-indazole-4-carboxamide;

(S)-(6-(6-(6-(1-aminoethyl)pyridin-2-yl)-4-(1H-pyrazol-3-yl)-1H-indazol-1-yl)pyridin-2-yl)methanol;
1-(6-(1-(6-(hydroxymethyl)pyridin-2-yl)-1H-indazol-6-yl)pyridin-2-yl)butan-1-ol;
1-(6-(1-(6-(hydroxymethyl)pyridin-2-yl)-1H-indazol-6-yl)pyridin-2-yl)butan-1-ol;
(6-(6-(6-(1-amino-2-(3-methyloxetan-3-yl)ethyl)pyridin-2-yl)-1H-indazol-1-yl)pyridin-2-yl)methanol;
3,3,3-trifluoro-1-(6-(1-(6-methylpyridin-2-yl)-1H-indazol-6-yl)pyridin-2-yl)propan-1-amine;
1-(6-(4-(5-methyl-1,3,4-oxadiazol-2-yl)-1-(6-methylpyridin-2-yl)-1H-indazol-6-yl)pyridin-2-yl)ethanamine;
1-(6-(1-(6-methylpyrazin-2-yl)-1H-indazol-6-yl)pyridin-2-yl)ethanamine;
6-{6-[6-((S)-1-Amino-ethyl)-pyridin-2-yl]-indazol-1-yl}-pyridine-2-carboxylic acid;
2-amino-2-(6-(1-(6-(hydroxymethyl)pyridin-2-yl)-1H-indazol-6-yl)pyridin-2-yl)acetonitrile;
2-amino-2-(6-(1-(6-(hydroxymethyl)pyridin-2-yl)-1H-indazol-6-yl)pyridin-2-yl)acetamide;
4-(6-(6-(1-aminoethyl)pyridin-2-yl)-1H-indazol-1-yl)pyrimidine-2-carbonitrile;
(6-(6-(3-(1-aminoethyl)phenyl)-1H-indazol-1-yl)pyridin-2-yl)methanol;
(6-(6-(6-(1-aminoethyl)-3-fluoropyridin-2-yl)-1H-indazol-1-yl)pyridin-2-yl)methanol;
(R)-(6-(6-(4-(1-aminoethyl)pyrimidin-2-yl)-1H-indazol-1-yl)pyridin-2-yl)methanol;
(S)-(6-(6-(6-(1-aminoethyl)pyridin-2-yl)-1H-indazol-1-yl)-5-fluoropyridin-2-yl)methanol;
(S)-(6-(6-(6-(1-(dimethylamino)butyl)pyridin-2-yl)-1H-indazol-1-yl)pyridin-2-yl)methanol;
1-(6-(6-(6-((S)-1-aminobutyl)pyridin-2-yl)-1H-indazol-1-yl)pyridin-2-yl)ethanol;
2-amino-2-(6-(1-(6-(hydroxymethyl)pyridin-2-yl)-1H-indazol-6-yl)pyridin-2-yl)-N-methylacetamide;
(6-(6-(6-(1-amino-2-(methylsulfinyl)ethyl)pyridin-2-yl)-1H-indazol-1-yl)pyridin-2-yl)methanol;
(6-(6-(6-((S)-1-aminobutyl)pyridin-2-yl)-4-(1-methoxyethyl)-1H-indazol-1-yl)pyridin-2-yl)methanol;
(S)-4-amino-4-(6-(1-(6-(hydroxymethyl)pyridin-2-yl)-1H-indazol-6-yl)pyridin-2-yl)butan-1-ol;
(S)-(6-(6-(6-(1-aminobut-3-en-1-yl)pyridin-2-yl)-1H-indazol-1-yl)pyridin-2-yl)methanol;
(S)-4-amino-4-(6-(1-(6-(hydroxymethyl)pyridin-2-yl)-1H-indazol-6-yl)pyridin-2-yl)butan-2-one;
(S)-1-(6-(4-chloro-1-(4-(difluoromethyl)pyrimidin-2-yl)-1H-indazol-6-yl)pyridin-2-yl)butan-1-amine;
(6-(6-(6-(pyrrolidin-2-yl)pyridin-2-yl)-1H-indazol-1-yl)pyridin-2-yl)methanol;
(S)-4-(6-(6-(1-aminobutyl)pyridin-2-yl)-1-(6-(hydroxymethyl)pyridin-2-yl)-1H-indazol-4-yl)-2-methylbut-3-yn-2-ol;
(S)-(6-(6-(6-(1-aminoethyl)pyridin-2-yl)-4-(2-(trifluoromethyl)thiazol-4-yl)-1H-indazol-1-yl)pyridin-2-yl)methanol;
(S)-1-(6-(1-(4-(difluoromethyl)pyrimidin-2-yl)-4-methoxy-1H-indazol-6-yl)pyridin-2-yl)butan-1-amine;
(S)-(6-(6-(6-(1-aminopent-3-yn-1-yl)pyridin-2-yl)-4-ethoxy-1H-indazol-1-yl)pyridin-2-yl)methanol;
(S)-(6-(6-(6-(amino(phenyl)methyl)pyridin-2-yl)-4-ethoxy-1H-indazol-1-yl)pyridin-2-yl)methanol;
(6-(6-(6-((S)-1-aminobutyl)pyridin-2-yl)-4-((S)-pyrrolidin-2-yl)-1H-indazol-1-yl)pyridin-2-yl)methanol;
(6-(6-(6-((S)-1-aminobutyl)pyridin-2-yl)-4-(tetrahydrofuran-2-yl)-1H-indazol-1-yl)pyridin-2-yl)methanol;
(S)-4-(6-(6-(1-aminobutyl)pyridin-2-yl)-1-(6-(hydroxymethyl)pyridin-2-yl)-1H-indazol-4-yl)morpholin-3-one;
(S)-(6-(6-(4-(1-aminobutyl)pyrimidin-2-yl)-4-methoxy-1H-indazol-1-yl)pyridin-2-yl)methanol;
(S)-(6-(6-(6-(1-amino-4-methoxybutyl)pyridin-2-yl)-4-(1-methyl-1H-pyrazol-3-yl)-1H-indazol-1-yl)pyridin-2-yl)methanol;
(R)-(6-(6-(4-(1-aminobutyl)pyrimidin-2-yl)-4-methoxy-1H-indazol-1-yl)pyridin-2-yl)methanol;
(S)-(6-(6-(6-(1-aminoethyl)pyridin-2-yl)-4-(5-(trifluoromethyl)-1H-pyrazol-3-yl)-1H-indazol-1-yl)pyridin-2-yl)methanol;
(S)-(6-(6-(6-(1-aminobutyl)pyridin-2-yl)-4-(pyrimidin-2-yl)-1H-indazol-1-yl)pyridin-2-yl)methanol;
deutero (S)-(6-(6-(6-(1-aminobutyl)pyridin-2-yl)-1H-indazol-1-yl)pyridin-2-yl)methanol;
(S)-(6-(6-(6-(1-aminoethyl)pyridin-2-yl)-4-(5-fluoropyrimidin-2-yl)-1H-indazol-1-yl)pyridin-2-yl)methanol;
(S)-(4-(6-(6-(1-aminobutyl)pyridin-2-yl)-1H-indazol-1-yl)pyridin-2-yl)methanol;
(S)-(3-(6-(6-(1-aminobutyl)pyridin-2-yl)-1H-indazol-1-yl)phenyl)methanol;
(S)-(6-(6-(6-(1-aminoethyl)pyridin-2-yl)-4-(5-methyloxazol-2-yl)-1H-indazol-1-yl)pyridin-2-yl)methanol;
(S)-(6-(6-(6-(1-aminobutyl)pyridin-2-yl)-4-(1H-1,2,3-triazol-1-yl)-1H-indazol-1-yl)pyridin-2-yl)methanol;
(S)-(6-(6-(6-(1-aminobutyl)pyridin-2-yl)-4-((trifluoromethoxy)methyl)-1H-indazol-1-yl)pyridin-2-yl)methanol;
(S)-(6-(6-(6-(1-aminoethyl)pyridin-2-yl)-4-(1-(difluoromethyl)-1H-pyrazol-3-yl)-1H-indazol-1-yl)pyridin-2-yl)methanol;
(S)-(6-(6-(6-(1-aminoethyl)pyridin-2-yl)-4-(1-(difluoromethyl)-1H-pyrazol-5-yl)-1H-indazol-1-yl)pyridin-2-yl)methanol;
(S)-(6-(6-(6-(1-aminoethyl)pyridin-2-yl)-4-(pyrazin-2-yl)-1H-indazol-1-yl)pyridin-2-yl)methanol;
(S)-(6-(6-(4-(1-aminopentyl)pyrimidin-2-yl)-1H-indazol-1-yl)pyridin-2-yl)methanol;
(R)-3-amino-3-(6-(1-(6-(hydroxymethyl)pyridin-2-yl)-1H-indazol-6-yl)pyridin-2-yl)propanenitrile;
(S)-4-amino-4-(6-(1-(6-(hydroxymethyl)pyridin-2-yl)-4-methoxy-1H-indazol-6-yl)pyridin-2-yl)butan-1-ol;
(S)-4-amino-4-(6-(4-ethoxy-1-(6-(hydroxymethyl)pyridin-2-yl)-1H-indazol-6-yl)pyridin-2-yl)butan-1-ol;
(S)-(6-(6-(6-(1-aminobutyl)pyridin-2-yl)-4-(2-methoxyethoxy)-1H-indazol-1-yl)pyrazin-2-yl)methanol;
(S)-(6-(6-(6-(1-aminoethyl)pyridin-2-yl)-4-(2-methoxyethoxy)-1H-indazol-1-yl)pyrazin-2-yl)methanol;
(S)-(6-(6-(4-(1-aminobutyl)pyrimidin-2-yl)-1H-indazol-1-yl)pyridin-2-yl)methanol;
(S)-(6-(6-(6-(1-aminobutyl)pyridin-2-yl)-4-(5-methyloxazol-2-yl)-1H-indazol-1-yl)pyridin-2-yl)methanol;
(S)-(6-(6-(4-(1-aminobutyl)pyrimidin-2-yl)-4-ethoxy-1H-indazol-1-yl)pyridin-2-yl)methanol;
(R)-(6-(6-(4-(1-aminobutyl)pyrimidin-2-yl)-4-ethoxy-1H-indazol-1-yl)pyridin-2-yl)methanol;
(S)-2-((6-(6-(1-aminobutyl)pyridin-2-yl)-1-(6-(hydroxymethyl)pyridin-2-yl)-1H-indazol-4-yl)oxy)ethanol;
(S)-(6-(6-(6-(1-aminobutyl)pyridin-2-yl)-4-(1,5-dimethyl-1H-pyrazol-3-yl)-1H-indazol-1-yl)pyridin-2-yl)methanol;
(S)-(2-(6-(6-(1-aminobutyl)pyridin-2-yl)-1H-indazol-1-yl)pyrimidin-4-yl)methanol;
(S)-(6-(6-(6-(1-aminopropyl)pyridin-2-yl)-4-(2-methoxyethoxy)-1H-indazol-1-yl)pyrazin-2-yl)methanol;

2-(6-(6-((S)-1-aminobutyl)pyridin-2-yl)-1-(6-(hydroxymethyl)pyridin-2-yl)-1H-indazol-4-yl)-3-chloropropan-1-ol;
(S)-(6-(6-(6-(1-aminoethyl)pyridin-2-yl)-4-(2-methoxyethoxy)-1H-indazol-1-yl)pyridin-2-yl)methanol;
(S)-(6-(6-(6-(1-aminopropyl)pyridin-2-yl)-4-(2-methoxyethoxy)-1H-indazol-1-yl)pyridin-2-yl)methanol;
(S)-(6-(6-(6-(amino(cyclopropyl)methyl)pyridin-2-yl)-4-(2-methoxyethoxy)-1H-indazol-1-yl)pyridin-2-yl)methanol;
(S)-(6-(6-(6-(1-amino-3,3-difluorobutyl)pyridin-2-yl)-4-(2-methoxyethoxy)-1H-indazol-1-yl)pyridin-2-yl)methanol;
(S)-4-amino-4-(6-(1-(6-(hydroxymethyl)pyridin-2-yl)-4-(1-methyl-1H-pyrazol-3-yl)-1H-indazol-6-yl)pyridin-2-yl)butan-1-ol;
(R)-(6-(6-(6-(1-aminopropyl)pyridin-2-yl)-4-(1,5-dimethyl-1H-pyrazol-3-yl)-1H-indazol-1-yl)pyridin-2-yl)methanol;
(R)-(6-(6-(6-(1-amino-2-fluoroethyl)pyridin-2-yl)-1H-indazol-1-yl)pyridin-2-yl)methanol;
(S)-1-(6-(1-(6-methylpyrazin-2-yl)-1H-indazol-6-yl)pyridin-2-yl)butan-1-amine;
(S)-3-amino-3-(6-(1-(6-(hydroxymethyl)pyridin-2-yl)-1H-indazol-6-yl)pyridin-2-yl)propanenitrile;
(S)-4-amino-4-(6-(1-(6-(hydroxymethyl)pyridin-2-yl)-1H-indazol-6-yl)pyridin-2-yl)butanenitrile;
(S)-(6-(6-(2-(1-aminobutyl)pyrimidin-4-yl)-1H-indazol-1-yl)pyridin-2-yl)methanol;
(4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;
(R)-(6-(6-(6-(1-amino-2-fluoroethyl)pyridin-2-yl)-4-(1,5-dimethyl-1H-pyrazol-3-yl)-1H-indazol-1-yl)pyridin-2-yl)methanol;
(S)-4-amino-4-(6-(1-(6-(hydroxymethyl)pyridin-2-yl)-4-(2-methoxyethoxy)-1H-indazol-6-yl)pyridin-2-yl)butan-1-ol;
(4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;
(4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;
(R)-(6-(6-(2-(1-aminobutyl)pyrimidin-4-yl)-1H-indazol-1-yl)pyridin-2-yl)methanol;
(S)-4-amino-4-(6-(4-(1,5-dimethyl-1H-pyrazol-3-yl)-1-(6-(hydroxymethyl)pyridin-2-yl)-1H-indazol-6-yl)pyridin-2-yl)butan-1-ol;
(S)-(6-(6-(6-(1-aminoethyl)pyridin-2-yl)-4-(pyrimidin-4-yl)-1H-indazol-1-yl)pyridin-2-yl)methanol;
(S)-(6-(6-(6-(1-aminoethyl)pyridin-2-yl)-4-(pyridazin-3-yl)-1H-indazol-1-yl)pyridin-2-yl)methanol;
(R)-(6-(6-(6-(1-amino-2-fluoroethyl)pyridin-2-yl)-4-(2-methoxyethoxy)-1H-indazol-1-yl)pyridin-2-yl)methanol;
(S)-4-amino-4-(6-(1-(6-(hydroxymethyl)pyrazin-2-yl)-4-(2-methoxyethoxy)-1H-indazol-6-yl)pyridin-2-yl)butan-1-ol;
(S)-(6-(6-(4-(1-aminobutyl)pyrimidin-2-yl)-4-(2-methoxyethoxy)-1H-indazol-1-yl)pyridin-2-yl)methanol;
(6-(6-(6-(1-aminocyclobutyl)pyridin-2-yl)-4-(2-methoxyethoxy)-1H-indazol-1-yl)pyridin-2-yl)methanol;
(R)-(6-(6-(4-(1-aminobutyl)pyrimidin-2-yl)-4-(2-methoxyethoxy)-1H-indazol-1-yl)pyridin-2-yl)methanol;
(4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;
(S)-3-((6-(6-(1-aminobutyl)pyridin-2-yl)-1-(6-(hydroxymethyl)pyridin-2-yl)-1H-indazol-4-yl)oxy)propan-1-ol;
(S)-3-((6-(6-(1-aminopropyl)pyridin-2-yl)-1-(6-(hydroxymethyl)pyridin-2-yl)-1H-indazol-4-yl)oxy)propan-1-ol;
(S)-3-((6-(6-(1-aminoethyl)pyridin-2-yl)-1-(6-(hydroxymethyl)pyridin-2-yl)-1H-indazol-4-yl)oxy)propan-1-ol;
(6-(6-(6-((S)-1-aminobutyl)pyridin-2-yl)-4-((2S,5R)-5-methyltetrahydrofuran-2-yl)-1H-indazol-1-yl)pyridin-2-yl)methanol;
(6-(6-(6-((S)-1-aminobutyl)pyridin-2-yl)-4-((2R,5R)-5-methyltetrahydrofuran-2-yl)-1H-indazol-1-yl)pyridin-2-yl)methanol;
(6-(6-(6-((S)-1-aminobutyl)pyridin-2-yl)-4-(tetrahydrofuran-3-yl)-1H-indazol-1-yl)pyridin-2-yl)methanol;
(R)-(6-(6-(6-(1-aminobutyl)pyrazin-2-yl)-1H-indazol-1-yl)pyridin-2-yl)methanol;
(6-(6-(6-(((1R)-1-amino-2-fluoropropyl)pyridin-2-yl)-4-(2-methoxyethoxy)-1H-indazol-1-yl)pyridin-2-yl)methanol;
(6-(6-(6-(1-aminocyclobutyl)pyridin-2-yl)-4-(2-methoxyethoxy)-1H-indazol-1-yl)pyrazin-2-yl)methanol;
(6-(6-(6-(1-aminocyclopentyl)pyridin-2-yl)-4-(2-methoxyethoxy)-1H-indazol-1-yl)pyridin-2-yl)methanol;
(6-(6-(6-(3-aminotetrahydrofuran-3-yl)pyridin-2-yl)-4-(2-methoxyethoxy)-1H-indazol-1-yl)pyridin-2-yl)methanol;
(S)-1-((6-(6-(1-aminobutyl)pyridin-2-yl)-1-(6-(hydroxymethyl)pyridin-2-yl)-1H-indazol-4-yl)oxy)-2-methylpropan-2-ol;
(S)-(6-(6-(6-(1-aminobutyl)pyrazin-2-yl)-1H-indazol-1-yl)pyridin-2-yl)methanol;
(6-(6-(6-((1S)-1-amino-2-fluoropropyl)pyridin-2-yl)-4-(2-methoxyethoxy)-1H-indazol-1-yl)pyridin-2-yl)methanol;
(S)-(6-(6-(6-(1-aminoethyl)pyridin-2-yl)-4-(3-methyl-1H-pyrazol-1-yl)-1H-indazol-1-yl)pyridin-2-yl)methanol;
(S)-(6-(6-(6-(1-aminoethyl)pyridin-2-yl)-4-(1H-pyrazol-1-yl)-1H-indazol-1-yl)pyridin-2-yl)methanol;
(S)-(4-(6-(6-(1-aminobutyl)pyridin-2-yl)-1H-indazol-1-yl)pyrimidin-2-yl)methanol;
(6-(6-(8-amino-8-methyl-5,6,7,8-tetrahydroquinolin-2-yl)-1H-indazol-1-yl)pyridin-2-yl)methanol;
(6-(6-(8-amino-8-propyl-5,6,7,8-tetrahydroquinolin-2-yl)-1H-indazol-1-yl)pyridin-2-yl)methanol;
(6-(6-(3-aminooxetan-3-yl)pyridin-2-yl)-4-(2-methoxyethoxy)-1H-indazol-1-yl)pyridin-2-yl)methanol;
(S)-(6-(6-(6-(1-aminobutyl)pyridin-2-yl)-4-(2-(methylsulfonyl)ethoxy)-1H-indazol-1-yl)pyridin-2-yl)methanol;
(S)-(6-(6-(6-(1-aminobutyl)pyridin-2-yl)-4-((3,3-difluorocyclobutyl)methoxy)-1H-indazol-1-yl)pyridin-2-yl)methanol;
(S)-(6-(6-(6-(1-aminobutyl)pyridin-2-yl)-4-(1-methylpiperidin-4-yl)-1H-indazol-1-yl)pyridin-2-yl)methanol;
or a pharmaceutically acceptable salt thereof.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x\text{-}xx}$", wherein x and xx are integers. For example, "$C_{1\text{-}4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., bridged or spiro ring systems) ring system which has from 3- to 7-ring members, or in particular 3- to 6-ring members or 5- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. As used herein, the term "heteroaryl" refers to an aromatic 5 or 6 membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or -7-membered bicyclic ring. The heterocyclyl group can be attached at a heteroatom or a carbon atom. Examples of heterocyclyls include aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azirinyl, oxirenyl, thiirenyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like. Examples of bicyclic heterocyclic ring systems include 3-azabicyclo[3.1.0]hexanyl, 3-azabicyclo[3.1.1]heptanyl, 2-azaspiro[3.3]heptanyl, 2-oxa-6-azaspiro[3.3]heptanyl, and 5-azaspiro[2.3]hexanyl.

As used herein, the term "carbocyclyl" refers to saturated or unsaturated monocyclic or bicyclic hydrocarbon groups of 3-7 carbon atoms, 3-6, or 5-7 carbon atoms. The term "carbocyclyl" encompasses cycloalkyl groups and aromatic groups. The term "cycloalkyl" refers to completely saturated monocyclic or bicyclic hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopentenyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6-7 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 7 ring members.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The disclosed compounds, or pharmaceutically acceptable salts thereof, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The disclosed compounds may exist in tautomeric forms and mixtures and separate individual tautomers are contemplated. In addition, some compounds may exhibit polymorphism.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). When a particular enantiomer of a compound used in the disclosed methods is depicted by name or structure, the stereochemical purity of the compounds is at least 20%, 30%, 40%, 50%, 60%, 70%, 80%, 90%, 95%, 97%, 99%, 99.5% or 99.9%. "Stererochemical purity" means the weight percent of the desired stereoisomer relative to the combined weight of all stereoisomers.

Unless otherwise indicated, any position occupied by hydrogen is meant to include enrichment by deuterium or tritium above the natural abundance of deuterium or tritium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the expression or activity of IRAK-4, or to otherwise affect the properties and/or behavior of IRAK-4 polypeptides or polynucleotides, e.g., stability, phosphorylation, kinase activity, interactions with other proteins, etc.

One embodiment of the invention includes a method of decreasing the expression or activity of IRAK-4, or to otherwise affect the properties and/or behavior of IRAK-4 polypeptides or polynucleotides comprising administering to said mammal an effective amount of at least one compound described herein, or a pharmaceutically acceptable salt thereof.

One embodiment of the invention includes a method for treating an inflammatory disease in a subject, the method comprising administering to the patient a therapeutically effective amount of a compound described herein, or a pharmaceutically acceptable salt thereof, thereby treating the inflammatory disease in the subject.

In one embodiment, the inflammatory disease is a pulmonary disease or a disease of the airway.

In one embodiment, the pulmonary disease and disease of the airway is selected from Adult Respiratory Disease Syndrome (ARDS), Chronic Obstructive Pulmonary Disease (OPD), pulmonary fibrosis, interstitial lung disease, asthma, chronic cough, and allergic rhinitis.

In one embodiment, the inflammatory disease is selected from transplant rejection, CD14 mediated sepsis, non-CD14 mediated sepsis, inflammatory bowel disease, Behcet's syndrome, ankylosing spondylitis, sarcoidosis, and gout.

One embodiment of the invention includes a method for treating an autoimmune disease, cancer, cardiovascular disease, a disease of the central nervous system, a disease of the skin, an ophthalmic disease and condition, and bone disease in a subject, the method comprising administering to the patient a therapeutically effective amount of a compound disclosed herein, or a pharmaceutically acceptable salt thereof, thereby treating the autoimmune disease, cancer, cardiovascular disease, disease of the central nervous system, disease of the skin, ophthalmic disease and condition, and bone disease in the subject.

In one embodiment, the autoimmune disease is selected from rheumatoid arthritis, systemic lupus erythematosus, multiple sclerosis, diabetes, systemic sclerosis, and Sjogren's syndrome.

In one embodiment, the autoimmune disease is type 1 diabetes.

In one embodiment, the cancer is selected from Waldenström's macroglobulinemia, solid tumors, skin cancer, and lymphoma.

In one embodiment, the cardiovascular disease is selected from stroke and atherosclerosis.

In one embodiment, the disease of the central nervous system is a neurodegenerative disease.

In one embodiment, the disease of the skin is selected from rash, contact dermatitis, psoriasis, and atopic dermatitis.

In one embodiment, the bone disease is selected from osteoporosis and osteoarthritis.

In one embodiment, the inflammatory bowel disease is selected from Crohn's disease and ulcerative colitis.

One embodiment of the invention includes a method for treating an ischemic fibrotic disease, the method comprising administering to the patient a therapeutically effective amount of a compound described herein, or a pharmaceutically acceptable salt thereof, thereby treating the ischemic fibrotic disease in the subject. In one embodiment, the ischemic fibrotic disease is selected from stroke, acute lung injury, acute kidney injury, ischemic cardiac injury, acute liver injury, and ischemic skeletal muscle injury.

One embodiment of the invention includes a method for treating post-organ transplantation fibrosis, the method comprising administering to the patient a therapeutically effective amount of a compound described herein, or a pharmaceutically acceptable salt thereof, thereby treating post-organ transplantation fibrosis in the subject.

One embodiment of the invention includes a method for treating hypertensive or diabetic end organ disease, the method comprising administering to the patient a therapeutically effective amount of a compound described herein, or a pharmaceutically acceptable salt thereof, thereby treating hypertensive or diabetic end organ disease in the subject.

One embodiment of the invention includes a method for treating hypertensive kidney disease, the method comprising administering to the patient a therapeutically effective amount of a compound described herein, or a pharmaceutically acceptable salt thereof, thereby treating hypertensive kidney disease in the subject.

One embodiment of the invention includes a method for treating idiopathic pulmonary fibrosis (IPF), the method comprising administering to the patient a therapeutically effective amount of a compound described herein, or a pharmaceutically acceptable salt thereof, thereby treating IPF in the subject.

One embodiment of the invention includes a method for treating scleroderma or systemic sclerosis, the method comprising administering to the patient a therapeutically effective amount of a compound described herein, or a pharmaceutically acceptable salt thereof, thereby treating scleroderma or systemic sclerosis in the subject.

One embodiment of the invention includes a method for treating liver cirrhosis, the method comprising administering to the patient a therapeutically effective amount of a compound described herein, or a pharmaceutically acceptable salt thereof, thereby treating liver cirrhosis in the subject.

One embodiment of the invention includes a method for treating fibrotic diseases wherein tissue injury and/or inflammation are present, the method comprising administering to the patient a therapeutically effective amount of a compound described herein, or a pharmaceutically acceptable salt thereof, thereby treating fibrotic diseases where tissue injury and/or inflammation are present in the subject. The fibrotic diseases include, for example, pancreatitis, peritonitis, burns, glomerulonephritis, complications of drug toxicity, and scarring following infections.

Scarring of the internal organs is a major global health problem, which is the consequence of subclinical injury to the organ over a period of time or as the sequela of acute severe injury or inflammation. All organs may be affected by scarring and currently there are few therapies the specifically target the evolution of scarring. Increasing evidence indicates that scarring per se provokes further decline in organ function, inflammation and tissue ischemia. This may be directly due the deposition of the fibrotic matrix which impairs function such as in contractility and relaxation of the heart and vasculature or impaired inflation and deflation of lungs, or by increasing the space between microvasculature and vital cells of the organ that are deprived of nutrients and distorting normal tissue architecture. However recent studies have shown that myofibroblasts themselves are inflammatory cells, generating cytokines, chemokines and radicals that promote injury; and myofibroblasts appear as a result of a transition from cells that normally nurse and maintain the microvasculature, known as pericytes. The consequence of this transition of phenotype is an unstable microvasculature that leads to aberrant angiogenesis, or rarefaction.

The present disclosure relates to methods and compositions for treating, preventing, and/or reducing scarring in organs. More particularly, the present disclosure relates to methods and composition for treating, preventing, and/or reducing scarring in kidneys.

It is contemplated that the present disclosure, methods and compositions described herein can be used as an anti-fibrotic, or used to treat, prevent, and/or reduce the severity and damage from fibrosis.

It is additionally contemplated that the present disclosure, methods and compositions described herein can be used to treat, prevent, and/or reduce the severity and damage from fibrosis.

It is further contemplated that the present disclosure, methods and compositions described herein can used as an anti-inflammatory, used to treat inflammation.

Some non-limiting examples of organs include: kidney, hearts, lungs, stomach, liver, pancreas, hypothalamus, stomach, uterus, bladder, diaphragm, pancreas, intestines, colon, and so forth.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The dose of a compound provided herein, or a pharmaceutically acceptable salt thereof, administered to a subject can be 10 μg-500 mg; 10 μg to 1 mg; or 1 to 500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

Example 1. 6-(1-(6-methylpyridin-2-yl)-1H-indazol-6-yl)pyridin-2-amine

Synthesis of 6-bromo-1-(6-methylpyridin-2-yl)-1H-indazole and 6-bromo-2-(6-methylpyridin-2-yl)-2H-indazole

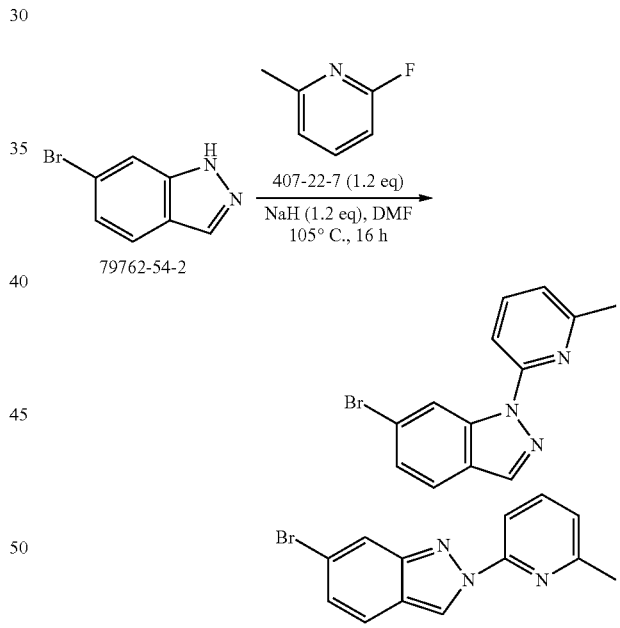

To a solution of 6-bromo-1H-indazole (CAS#79762-54-2) (3.0 g, 15.3 mmol) in DMF (10 mL) was added NaH (440 mg, 18.36 mmol, 1.2 eq) at 0° C. After stirring at room temperature for 1 h, 2-fluoro-6-methylpyridine (CAS#407-22-7) (2.04 g, 18.36 mmol, 1.2 eq) was added to the mixture. The mixture was stirred at 105° C. for 16 h. After cooling down to room temperature, the mixture was diluted with water (50 mL) and stirred for 1 h. The residue was filtrated to give a yellow solid which was purified by Pre-TLC (PE/EA (10/1)).

6-bromo-1-(6-methylpyridin-2-yl)-1H-indazole, 1.0 g, as a yellow solid, Y: 23%. ESI-MS (M+H)+: 288.0. $^1$H NMR (400 MHz, CDCl$_3$) δ: 9.09 (s, 1H), 8.13 (s, 1H), 7.79 (d, J=8.4 Hz, 1H), 7.71 (t, J=8.0 Hz, 1H), 7.61 (d, J=8.4 Hz, 1H), 7.37 (dd, J=8.0, 1.2 Hz, 1H), 7.02 (d, J=7.6 Hz, 1H), 2.66 (s, 3H).

6-bromo-2-(6-methylpyridin-2-yl)-2H-indazole, 1.05 g, as a yellow solid, Y: 24%. ESI-MS (M+H)⁺: 288.0. ¹H NMR (400 MHz, CDCl₃) δ: 9.04 (s, 1H), 7.96 (d, J=8.0 Hz, 1H), 7.86 (s, 1H), 7.70 (t, J=8.0 Hz, 1H), 7.53 (d, J=8.8 Hz, 1H), 7.11-7.08 (m, 2H), 2.54 (s, 3H).

Synthesis of 1-(6-methylpyridin-2-yl)-6-(4,4,5,5-tetramethyl-1,3,2-dioxaborolan-2-yl)-1H-indazole

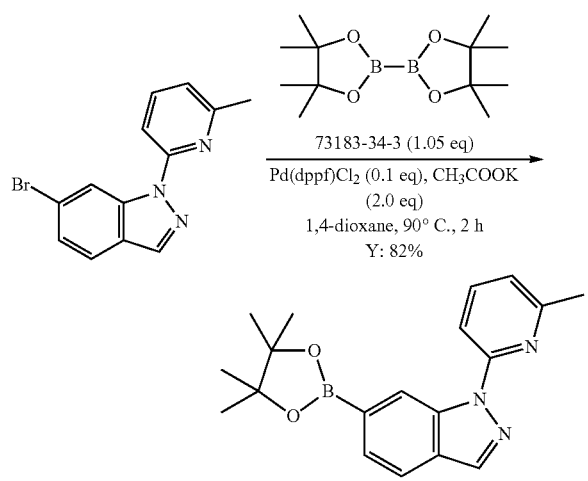

A mixture of 6-bromo-1-(6-methylpyridin-2-yl)-1H-indazole (1.0 g, 3.5 mmol), 4,4,4',4',5,5,5',5'-octamethyl-2,2'-bi(1,3,2-dioxaborolane) (CAS#73183-34-3) (930 mg, 3.66 mmol, 1.05 eq) and CH₃COOK (686 mg, 7.0 mmol, 2.0 eq) in 1, 4-dioxane (25 mL) was stirred while purging N₂ at rt for 10 min. To this system was added Pd(dppf)Cl₂ (256 mg, 0.35 mmol, 0.1 eq) and heated to 90° C. for 2 h. The mixture was diluted with EtOAc (50 mL) and washed with saturated aqueous NaHCO₃ solution (50 mL) and brine (50 mL). The organics were dried (MgSO₄) and concentrated in vacuo. The crude mixture was purified by silica gel chromatography with PE/EA (10/1) as eluent to give 1-(6-methylpyridin-2-yl)-6-(4,4,5,5-tetramethyl-1,3,2-dioxaborolan-2-yl)-1H-indazole. 960 mg, as a yellow solid, Y: 82%. ESI-MS (M+H)⁺: 336.2.

Synthesis of 6-(1-(6-methylpyridin-2-yl)-1H-indazol-6-yl)pyridin-2-amine

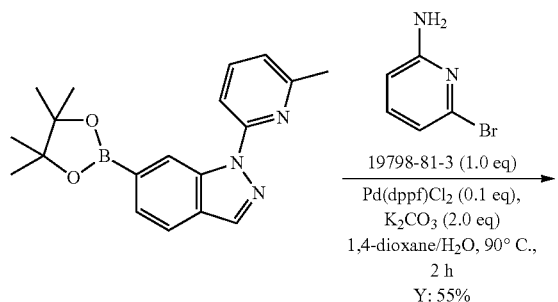

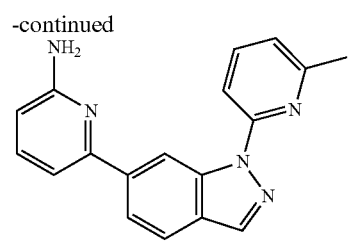

A mixture of 1-(6-methylpyridin-2-yl)-6-(4,4,5,5-tetramethyl-1,3,2-dioxaborolan-2-yl)-1H-indazole (100 mg, 0.3 mmol), 6-bromopyridin-2-amine (CAS#19798-81-3) (51 mg, 0.3 mmol, 1.0 eq) and K₂CO₃ (83 mg, 0.6 mmol, 2.0 eq) in 1, 4-dioxane/H₂O (5 mL/0.5 mL) was stirred while purging N₂ at room temperature for 10 min. To this system was added Pd(dppf)Cl₂ (22 mg, 0.03 mmol, 0.1 eq) and heated to 90° C. for 2 h. The mixture was diluted with EtOAc (10 mL) and washed with saturated aqueous NaHCO₃ solution (10 mL) and brine (10 mL). The organics were dried (MgSO₄) and concentrated in vacuo. The crude mixture was purified by pre-HPLC to give 6-(1-(6-methylpyridin-2-yl)-1H-indazol-6-yl)pyridin-2-amine. 54 mg, as a yellow solid, Y: 55%. ESI-MS (M+H)⁺: 302.1. HPLC: 100.00%. ¹H NMR (400 MHz, CD₃OD) δ: 9.28 (s, 1H), 8.25 (s, 1H), 7.85 (d, J=8.4 Hz, 1H), 7.80-7.77 (m, 3H), 7.57 (t, J=7.2 Hz, 1H), 7.12-7.10 (m, 2H), 6.58 (d, J=8.4 Hz, 1H), 2.64 (s, 3H).

Example 2. 2-(1-(6-methylpyridin-2-yl)-1H-indazol-6-yl)pyrimidin-4-amine

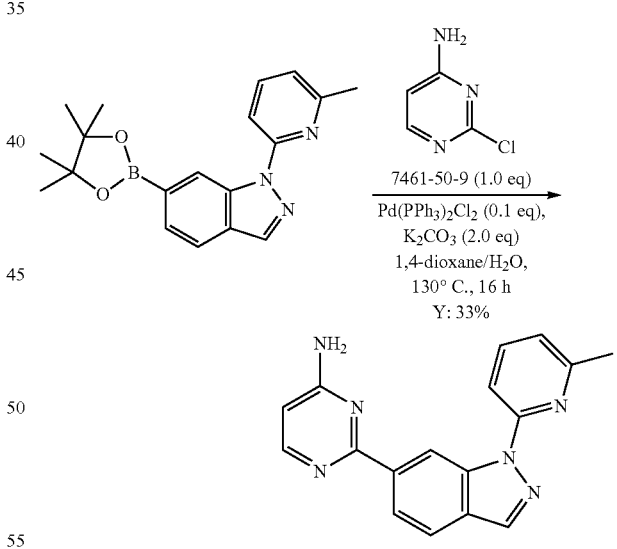

A mixture of 1-(6-methylpyridin-2-yl)-6-(4,4,5,5-tetramethyl-1,3,2-dioxaborolan-2-yl)-1H-indazole (134 mg, 0.4 mmol), 2-chloropyrimidin-4-amine (CAS#7461-50-9) (52 mg, 0.4 mmol, 1.0 eq) and K₂CO₃ (110 mg, 0.8 mmol, 2.0 eq) in 1, 4-dioxane/H₂O (5 mL/0.5 mL) was stirred while purging N₂ at rt for 10 min. To this system was added Pd(PPh₃)₂Cl₂ (28 mg, 0.04 mmol, 0.1 eq) and heated to 130° C. for 16 h. The mixture was diluted with EA (50 mL) and washed with brine (20 mL). The organic phase was dried over Na₂SO₄ and concentrated in vacuo. The residue was purified by pre-HPLC (MeOH/H₂O with 0.05% NH₄OH as mobile phase from 5% to 95%) to give 2-(1-(6-methylpyridin-2-yl)-1H-indazol-6-yl)pyrimidin-4-amine. 40 mg, as a yellow solid, Y: 33%. ESI-MS (M+H)⁺: 303.1. HPLC: 100.00%. ¹H NMR (400 MHz, CDCl₃) δ: 9.80 (s, 1H), 8.41 (d, J=6.0 Hz, 1H), 8.28 (dd, J=8.4, 1.2 Hz, 1H), 8.21 (s, 1H), 7.83 (d, J=8.0 Hz, 1H), 7.81 (d, J=8.0 Hz, 1H), 7.73 (t, J=7.6 Hz, 1H), 7.04 (d, J=7.2 Hz, 1H), 6.40 (d, J=5.6 Hz, 1H), 4.94 (s, 2H), 2.72 (s, 3H).

Example 3. 2-(1-(6-methylpyridin-2-yl)-1H-indazol-6-yl)pyridin-4-amine

Synthesis of 2-(1-(6-methylpyridin-2-yl)-1H-indazol-6-yl)pyridin-4-amine

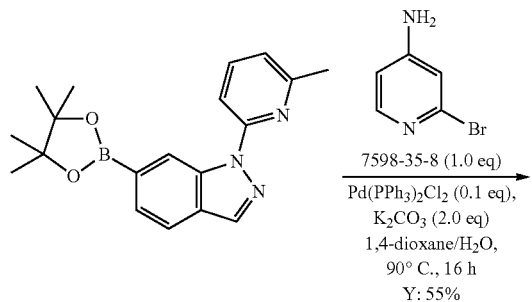

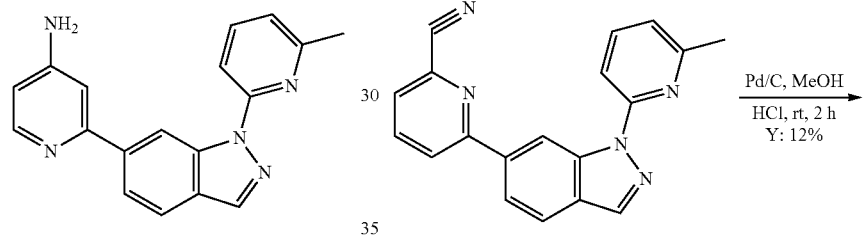

The preparation of 2-(1-(6-methylpyridin-2-yl)-1H-indazol-6-yl)pyridin-4-amine was the same as that of 2-(1-(6-methylpyridin-2-yl)-1H-indazol-6-yl)pyrimidin-4-amine except the temperature was decreased to 90. 50 mg, as a yellow solid, Y: 55%. ESI-MS (M+H)⁺: 302.1. HPLC: 100.00%. ¹H NMR (400 MHz, CD₃OD) δ: 9.18 (s, 1H), 8.22 (s, 1H), 8.07 (d, J=5.6 Hz, 1H), 7.83 (d, J=8.0 Hz, 1H), 7.79-7.73 (m, 2H), 7.67 (dd, J=8.8, 1.6 Hz, 1H), 7.08 (dd, J=6.0, 2.0 Hz, 1H), 7.02 (d, J=2.0 Hz, 1H), 6.57 (dd, J=5.6, 2.0 Hz, 1H), 2.62 (s, 3H).

Example 4. (6-(1-(6-methylpyridin-2-yl)-1H-indazol-6-yl)pyridin-2-yl)methanamine Synthesis of 6-(1-(6-methylpyridin-2-yl)-1H-indazol-6-yl)picolinonitrile

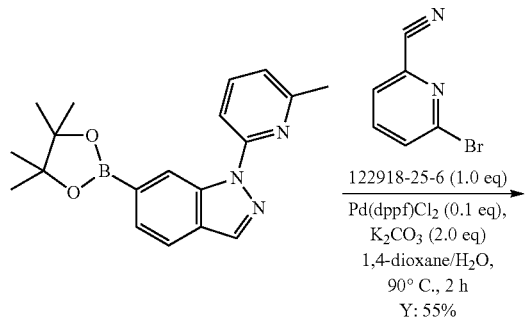

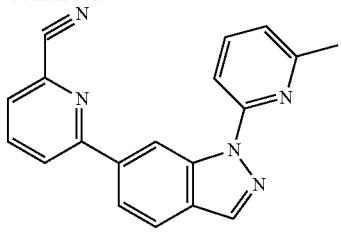

The preparation of 6-(1-(6-methylpyridin-2-yl)-1H-indazol-6-yl)picolinonitrile was the same as that of 6-(1-(6-methylpyridin-2-yl)-1H-indazol-6-yl)pyridin-2-amine. 90 mg, as a yellow solid, Y: 55%. ESI-MS (M+H)⁺: 312.1.

Synthesis of (6-(1-(6-methylpyridin-2-yl)-1H-indazol-6-yl)pyridin-2-yl)methanamine

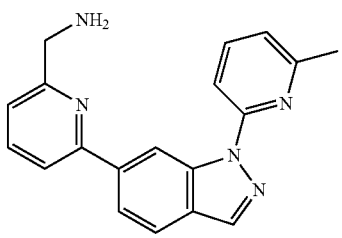

To a solution of 6-(1-(6-methylpyridin-2-yl)-1H-indazol-6-yl)picolinonitrile (90 mg, 0.29 mmol) in MeOH/HCl (5 mL/0.5 mL) was added Pd/C (9 mg, 10% w/w). Then the mixture was stirred at rt for 2 h under H₂ atmosphere. After filtration, the filtrate was concentrated and purified by pre-HPLC to give (6-(1-(6-methylpyridin-2-yl)-1H-indazol-6-yl)pyridin-2-yl)methanamine. 12 mg, as a white solid, Y: 12%. ESI-MS (M+H)⁺: 316.1. HPLC: 93.18%. ¹H NMR (400 MHz, CD₃OD) δ: 9.51 (s, 1H), 8.24 (s, 1H), 8.02 (dd, J=8.8, 1.6 Hz, 1H), 7.89-7.86 (m, 3H), 7.79-7.78 (m, 2H), 7.35 (dd, J=6.4, 2.4 Hz, 1H), 7.10 (dd, J=6.0, 1.6 Hz, 1H), 4.14 (s, 2H), 2.63 (s, 3H).

Example 5. (2-(1-(6-methylpyridin-2-yl)-1H-indazol-6-yl)pyridin-4-yl)methanamine Synthesis of 2-(1-(6-methylpyridin-2-yl)-1H-indazol-6-yl)isonicotinonitrile

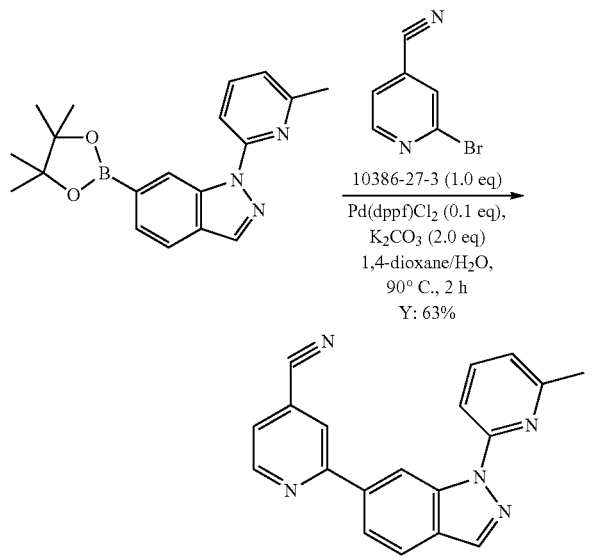

The preparation of 2-(1-(6-methylpyridin-2-yl)-1H-indazol-6-yl)isonicotinonitrile was the same as that of 6-(1-(6-methylpyridin-2-yl)-1H-indazol-6-yl)pyridin-2-amine. 102 mg, as a yellow solid, Y: 63%. ESI-MS (M+H)+: 312.1.

Synthesis of (2-(1-(6-methylpyridin-2-yl)-1H-indazol-6-yl)pyridin-4-yl)methanamine

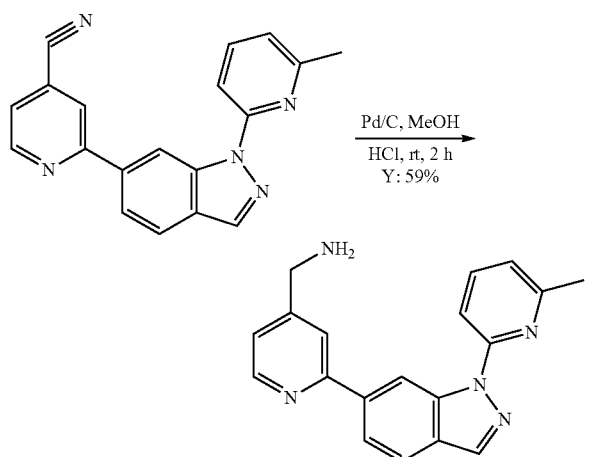

The preparation of (2-(1-(6-methylpyridin-2-yl)-1H-indazol-6-yl)pyridin-4-yl)methanamine was the same as that of (6-(1-(6-methylpyridin-2-yl)-1H-indazol-6-yl)pyridin-2-yl)methanamine. 60 mg, as a yellow solid, Y: 59%. ESI-MS (M+H)+: 316.1. HPLC: 94.08%. $^1$H NMR (400 MHz, CD$_3$OD) δ: 9.48 (s, 1H), 8.76 (d, J=5.2 Hz, 1H), 8.32 (s, 1H), 8.04 (s, 1H), 7.97 (d, J=8.4 Hz, 1H), 7.90 (dd, J=8.4, 2.0 Hz, 1H), 7.85-7.84 (m, 2H), 7.48 (d, J=3.6 Hz, 1H), 7.16 (dd, J=6.0, 2.0 Hz, 1H), 4.31 (s, 2H), 2.68 (s, 3H).

Example 6. 4-(1-(6-methylpyridin-2-yl)-1H-indazol-6-yl)pyridin-2-amine

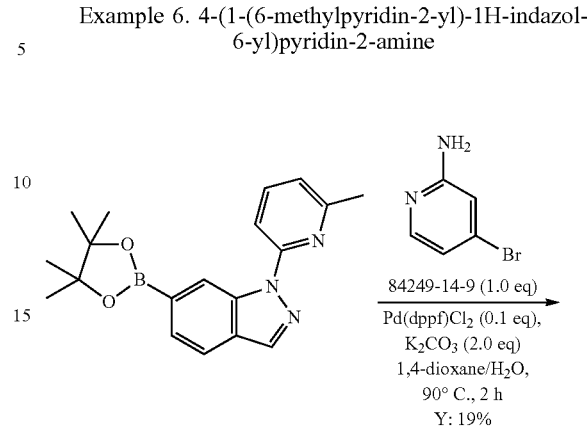

The preparation of 4-(1-(6-methylpyridin-2-yl)-1H-indazol-6-yl)pyridin-2-amine was the same as that of 6-(1-(6-methylpyridin-2-yl)-1H-indazol-6-yl)pyridin-2-amine. 20 mg, as a yellow solid, Y: 19%. ESI-MS (M+H)+: 302.1. HPLC: 99.29%. $^1$H NMR (400 MHz, CD$_3$OD) δ: 9.11 (s, 1H), 8.25 (s, 1H), 7.97 (d, J=4.0 Hz, 1H), 7.87 (dd, J=6.8, 1.2 Hz, 1H), 7.81-7.77 (m, 2H), 7.54 (d, J=6.8 Hz, 1H), 7.11 (d, J=4.8 Hz, 1H), 6.98 (d, J=4.8 Hz, 1H), 6.96 (s, 1H), 2.63 (s, 3H).

Example 7. 5-(1-(6-methylpyridin-2-yl)-1H-indazol-6-yl)pyridin-3-amine

Synthesis of 5-(1-(6-methylpyridin-2-yl)-1H-indazol-6-yl)pyridin-3-amine

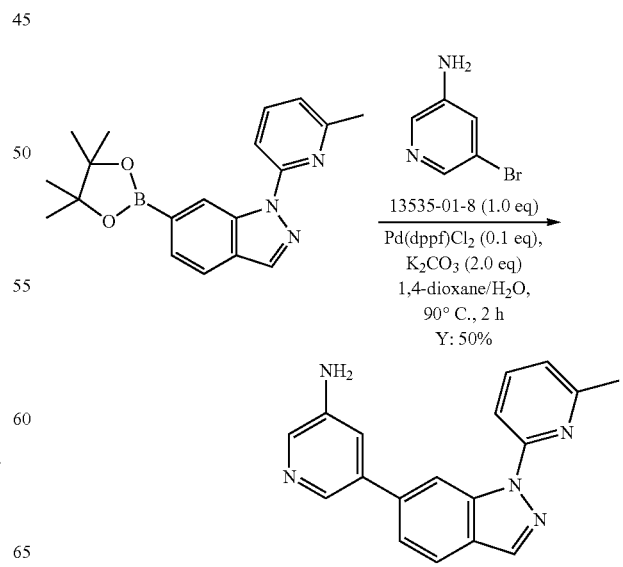

The preparation of 5-(1-(6-methylpyridin-2-yl)-1H-indazol-6-yl)pyridin-3-amine was the same as that of 6-(1-(6-methylpyridin-2-yl)-1H-indazol-6-yl)pyridin-2-amine. 58 mg, as a yellow solid, Y: 50%. ESI-MS (M+H)+: 302.1. HPLC: 92.66%. $^1$H NMR (400 MHz, CD$_3$OD) δ: 9.06 (s, 1H), 8.26 (s, 1H), 8.13 (d, J=1.6 Hz, 1H), 7.98 (d, J=2.4 Hz, 1H), 7.89 (d, J=8.8 Hz, 1H), 7.83-7.77 (m, 2H), 7.51 (d, J=8.4 Hz, 1H), 7.41 (t, J=2.0 Hz, 1H), 7.11 (d, J=6.0 Hz, 1H), 2.63 (s, 3H).

Example 8. 3-(1-(6-methylpyridin-2-yl)-1H-indazol-6-yl)aniline

Synthesis of 3-(1-(6-methylpyridin-2-yl)-1H-indazol-6-yl)aniline

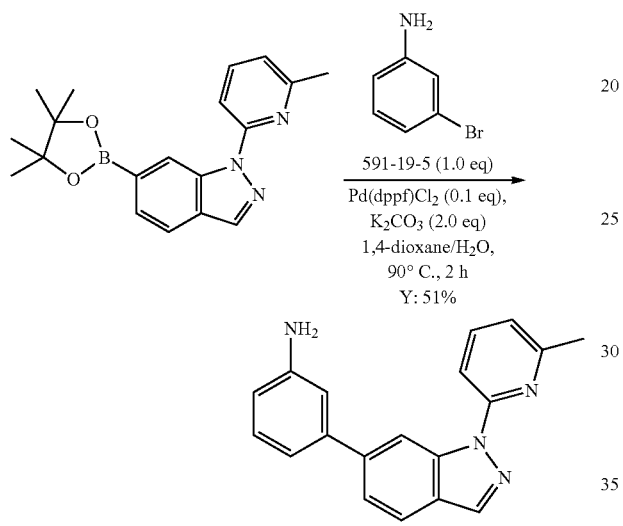

The preparation of 3-(1-(6-methylpyridin-2-yl)-1H-indazol-6-yl)aniline was the same as that of 6-(1-(6-methylpyridin-2-yl)-1H-indazol-6-yl)pyridin-2-amine. 54 mg, as a yellow solid, Y: 51%. ESI-MS (M+H)+: 301.1. HPLC: 95.87%. $^1$H NMR (400 MHz, CD$_3$OD) δ: 9.02 (s, 1H), 8.23 (s, 1H), 7.84-7.78 (m, 3H), 7.52 (dd, J=6.8, 1.2 Hz, 1H), 7.22 (t, J=6.8 Hz, 1H), 7.12-7.10 (m, 2H), 7.05 (d, J=6.0 Hz, 1H), 6.77 (dd, J=6.4, 1.2 Hz, 1H), 2.63 (s, 3H).

Example 9. (2-(1-(6-methylpyridin-2-yl)-1H-indazol-6-yl)pyrimidin-4-yl)methanamine Synthesis of 2-(1-(6-methylpyridin-2-yl)-1H-indazol-6-yl)pyrimidine-4-carbonitrile

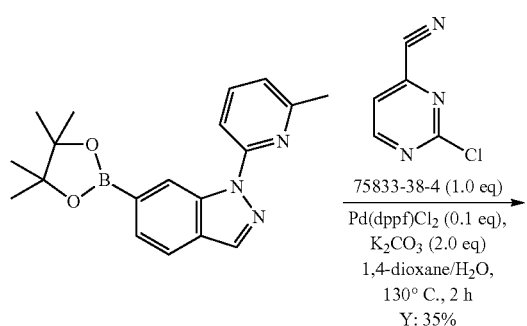

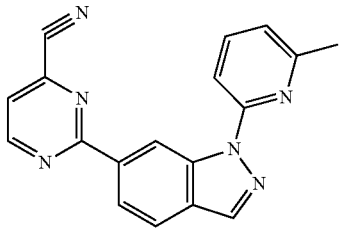

The preparation of 2-(1-(6-methylpyridin-2-yl)-1H-indazol-6-yl)pyrimidine-4-carbonitrile was the same as that of 6-(1-(6-methylpyridin-2-yl)-1H-indazol-6-yl)pyridin-2-amine except the reaction temperature was 130. 60 mg, as a yellow solid, Y: 35%. ESI-MS (M+H)+: 313.1.

Synthesis of (2-(1-(6-methylpyridin-2-yl)-1H-indazol-6-yl)pyrimidin-4-yl)methanamine

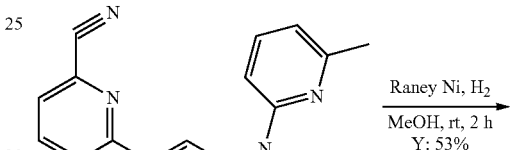

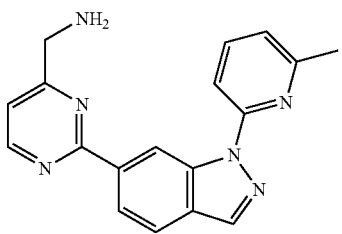

To a solution of 2-(1-(6-methylpyridin-2-yl)-1H-indazol-6-yl)pyrimidine-4-carbonitrile (60 mg, 0.19 mmol) in MeOH (5 mL) was added Raney Ni (6 mg, 10% w/w). Then the mixture was stirred at room temperature for 2 h under H$_2$ atmosphere. After filtration, the filtrate was concentrated and purified by pre-HPLC (MeOH/H$_2$O with 0.05% NH$_4$OH as mobile phase from 5% to 95%) to give (2-(1-(6-methylpyridin-2-yl)-1H-indazol-6-yl)pyrimidin-4-yl)methanamine. 32 mg, as a yellow solid, Y: 53%. ESI-MS (M+H)+: 317.0. HPLC: 95.54%. $^1$H NMR (400 MHz, CD$_3$OD) δ: 9.99 (s, 1H), 8.82 (d, J=4.8 Hz, 1H), 8.42 (dd, J=4.8, 1.2 Hz, 1H), 8.30 (d, J=0.8 Hz, 1H), 7.92 (d, J=8.4 Hz, 1H), 7.85-7.83 (m, 2H), 7.39 (d, J=4.8 Hz, 1H), 7.17 (dd, J=5.6, 2.0 Hz, 1H), 4.05 (s, 2H), 2.71 (s, 3H).

49

Example 10. 4-methyl-5-(1-(6-methylpyridin-2-yl)-1H-indazol-6-yl)pyridin-3-amine Synthesis of 4-methyl-5-(1-(6-methylpyridin-2-yl)-1H-indazol-6-yl)pyridin-3-amine

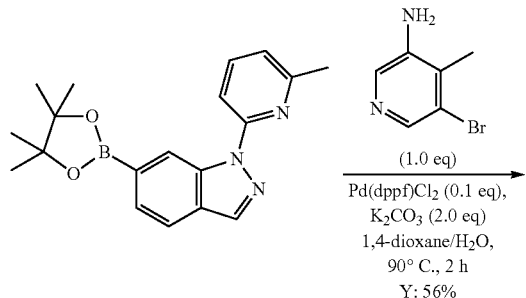

The preparation of 4-methyl-5-(1-(6-methylpyridin-2-yl)-1H-indazol-6-yl)pyridin-3-amine was the same as that of 6-(1-(6-methylpyridin-2-yl)-1H-indazol-6-yl)pyridin-2-amine. 54 mg, as a yellow solid, Y: 56%. ESI-MS (M+H)$^+$: 316.1. HPLC: 100.00%. $^1$H NMR (400 MHz, CDCl$_3$) δ: 8.83 (s, 1H), 8.23 (s, 1H), 8.17 (s, 1H), 8.05 (s, 1H), 7.86-7.81 (m, 2H), 7.73 (t, J=8.0 Hz, 1H), 7.20 (d, J=8.0 Hz, 1H), 7.01 (d, J=7.6 Hz, 1H), 3.96 (br, 2H), 2.58 (s, 3H), 2.19 (s, 3H).

Example 11. 3-(1-(6-methylpyridin-2-yl)-1H-indazol-6-yl)-5-nitropyridin-2-ol

Synthesis of 3-(1-(6-methylpyridin-2-yl)-1H-indazol-6-yl)-5-nitropyridin-2-ol

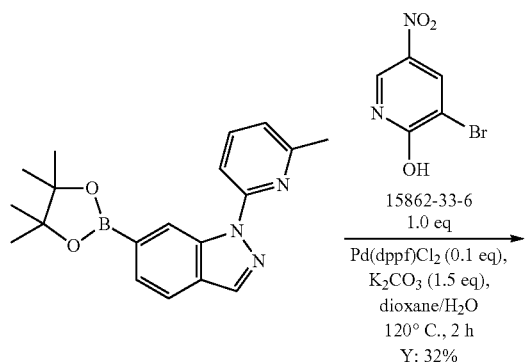

50

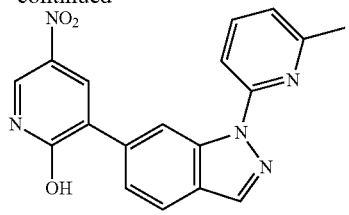

The preparation of 3-(1-(6-methylpyridin-2-yl)-1H-indazol-6-yl)-5-nitropyridin-2-ol was the same as that of 6-(1-(6-methylpyridin-2-yl)-1H-indazol-6-yl)pyridin-2-amine except the reaction temperature was at 120. 50 mg, as a yellow solid, Y: 32%. ESI-MS (M+H)$^+$: 348.1.

Synthesis of 5-amino-3-(1-(6-methylpyridin-2-yl)-1H-indazol-6-yl)pyridin-2-ol

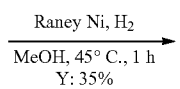

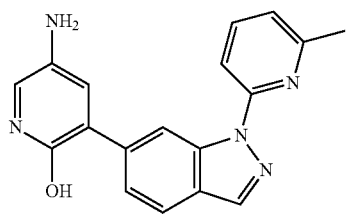

To a solution of 3-(1-(6-methylpyridin-2-yl)-1H-indazol-6-yl)-5-nitropyridin-2-ol (50 mg, 0.14 mmol) in MeOH (5 mL) was added Raney Ni (5 mg, 10% w/w). Then the mixture was stirred at 45° C. for 1 h under H$_2$ atmosphere. After filtration, the filtrate was concentrated and purified by pre-HPLC (MeOH/H$_2$O with 0.05% NH$_4$OH as mobile phase from 5% to 95%) to give 5-amino-3-(1-(6-methylpyridin-2-yl)-1H-indazol-6-yl)pyridin-2-ol. 16 mg, as a yellow solid, Y: 35%. ESI-MS (M+H)$^+$: 318.0. HPLC: 95.53%. $^1$H NMR (400 MHz, CD$_3$OD) δ: 9.12 (s, 1H), 8.26 (s, 1H), 7.85 (d, J=8.0 Hz, 1H), 7.82 (d, J=4.4 Hz, 2H), 7.61 (d, J=2.8 Hz, 1H), 7.59 (d, J=8.0 Hz, 1H), 7.14-7.12 (m, 1H), 7.00 (d, J=2.8 Hz, 1H), 2.64 (s, 3H).

Example 12. Synthesis of 3-amino-5-(1-(6-methyl-pyridin-2-yl)-1H-indazol-6-yl)pyridin-4-ol Synthesis of 3-(1-(6-methylpyridin-2-yl)-1H-indazol-6-yl)-5-nitropyridin-4-ol

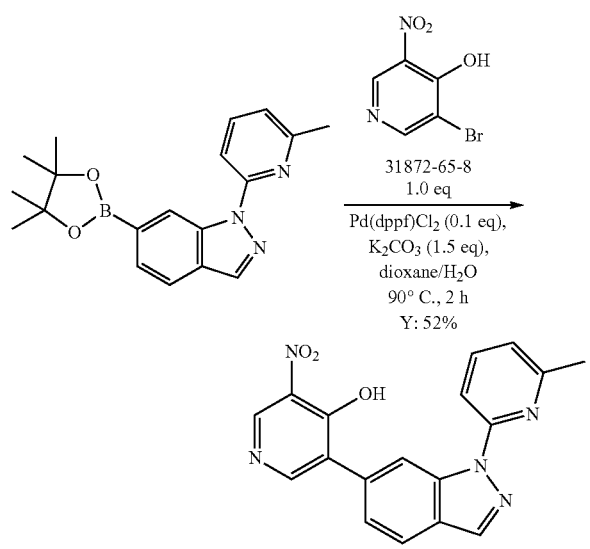

The preparation of 3-(1-(6-methylpyridin-2-yl)-1H-indazol-6-yl)-5-nitropyridin-4-ol was the same as that of 6-(1-(6-methylpyridin-2-yl)-1H-indazol-6-yl)pyridin-2-amine. 91 mg, as a yellow solid, Y: 52%. ESI-MS (M+H)$^+$: 348.1.

Synthesis of 3-amino-5-(1-(6-methylpyridin-2-yl)-1H-indazol-6-yl)pyridin-4-ol

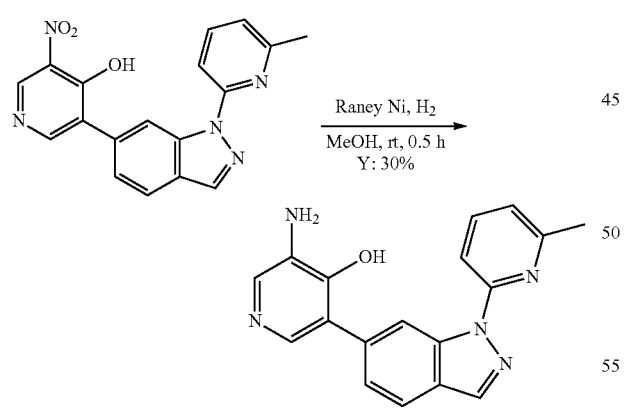

The preparation of 3-amino-5-(1-(6-methylpyridin-2-yl)-1H-indazol-6-yl)pyridin-4-ol was the same as that of 5-amino-3-(1-(6-methylpyridin-2-yl)-1H-indazol-6-yl)pyridin-2-ol. 25 mg, as a yellow solid, Y: 30%. ESI-MS (M+H)$^+$: 318.0. HPLC: 93.43%. $^1$H NMR (400 MHz, DMSO-d$_6$) δ: 11.42 (br, 1H), 9.14 (s, 1H), 8.38 (s, 1H), 7.90-7.78 (m, 3H), 7.71 (d, J=1.6 Hz, 1H), 7.65 (dd, J=8.4, 1.6 Hz, 1H), 7.18 (d, J=1.2 Hz, 1H), 7.17 (d, J=8.0 Hz, 1H), 4.76 (br, 2H), 2.58 (s, 3H).

Example 13. N-methyl-5-(1-(6-methylpyridin-2-yl)-1H-indazol-6-yl)pyridin-3-amine Synthesis of N-(5-(1-(6-methylpyridin-2-yl)-1H-indazol-6-yl)pyridin-3-yl)acetamide

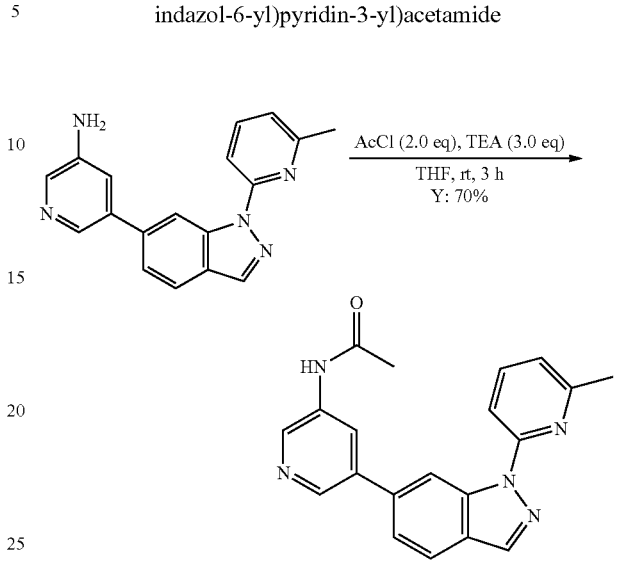

To a mixture of 5-(1-(6-methylpyridin-2-yl)-1H-indazol-6-yl)pyridin-3-amine (65 mg, 0.22 mmol) and TEA (67 mg, 0.66 mmol, 3.0 eq) in THF (5 mL) was added AcCl (34 mg, 0.44 mmol, 2.0 eq) at room temperature. The mixture was stirred at rt for 3 h. After concentration, the residue was purified by pre-HPLC to give N-(5-(1-(6-methylpyridin-2-yl)-1H-indazol-6-yl)pyridin-3-yl)acetamide as a white solid. (52 mg, Y: 70%). ESI-MS (M+H)$^+$: 344.1.

Synthesis of N-methyl-N-(5-(1-(6-methylpyridin-2-yl)-1H-indazol-6-yl)pyridin-3-yl)acetamide

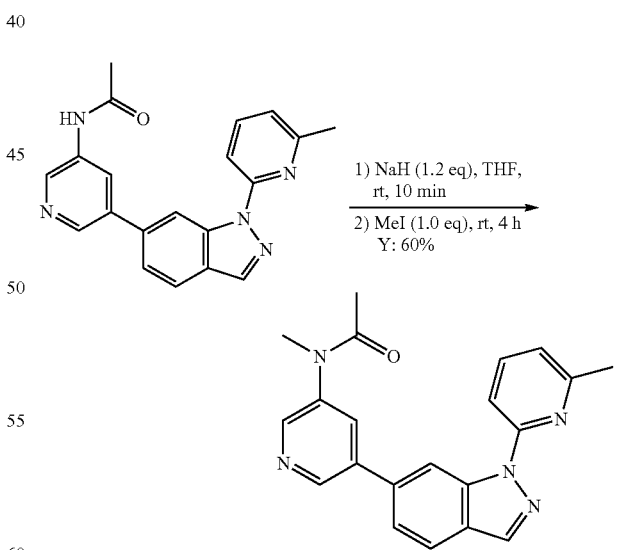

To a solution of N-(5-(1-(6-methylpyridin-2-yl)-1H-indazol-6-yl)pyridin-3-yl)acetamide (52 mg, 0.15 mmol) in THF (3 mL) was added NaH (7 mg, 0.18 mmol, 1.2 eq). The resulting solution was stirred at rt for 10 min and then MeI (0.01 mL, 0.15 mmol, 1.0 eq) was added. The reaction mixture was stirred at rt for 4 h and concentrated in vacuo.

The residue was partitioned between DCM/H₂O (10 mL/5 mL), then the aqueous phase was washed with DCM (3×10 mL). The combined organic phase was washed with brine (10 mL) and dried over Na₂SO₄. After filtration and concentration, the residue was purified by column chromatography (silica gel, PE/EA=1/1) to afford N-methyl-N-(5-(1-(6-methylpyridin-2-yl)-1H-indazol-6-yl)pyridin-3-yl)acetamide as yellow oil (32 mg, Y: 60%). ¹H NMR (400 MHz, CDCl₃) δ: 9.18 (s, 1H), 8.97 (s, 1H), 8.55 (s, 1H), 8.23 (s, 1H), 7.95-7.83 (m, 3H), 7.74 (t, J=7.6 Hz, 1H), 7.49 (dd, J=8.8 Hz, 1.6 Hz, 1H), 7.04 (d, J=7.6 Hz, 1H), 3.39 (s, 3H), 2.63 (s, 3H), 2.02 (s, 3H).

Synthesis of N-methyl-5-(1-(6-methylpyridin-2-yl)-1H-indazol-6-yl)pyridin-3-amine

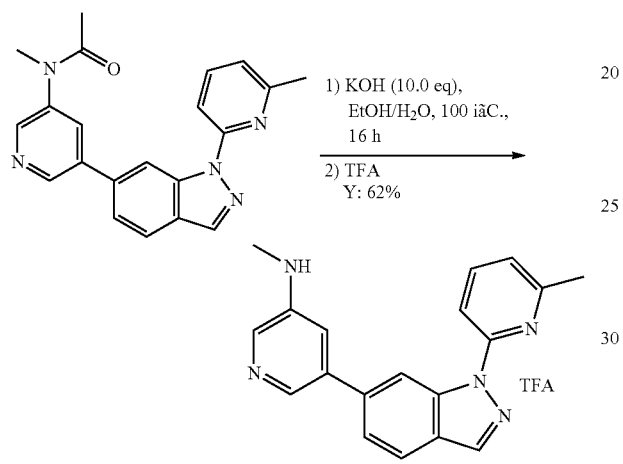

To a solution of N-methyl-N-(5-(1-(6-methylpyridin-2-yl)-1H-indazol-6-yl)pyridin-3-yl)acetamide (65 mg, 0.18 mmol, 1.0 eq) in EtOH/H₂O (1 mL/2 mL) was added KOH (100 mg, 1.8 mmol, 10.0 eq). The reaction mixture was heated to 100° C. for 16 h. The reaction mixture was allowed to cool to rt and extracted with DCM (3×10 mL), then washed with brine (10 mL), dried over Na₂SO₄. After removing solvent in vacuo, the residue was suspended in MeOH and acidified with TFA, then purified by prep-HPLC to afford N-methyl-5-(1-(6-methylpyridin-2-yl)-1H-indazol-6-yl)pyridin-3-amine as a white solid (30 mg, Y: 62%) 1H NMR (400 MHz, CD₃OD) δ: 9.14-9.00 (m, 1H), 8.27-8.13 (m, 2H), 7.96-7.67 (m, 5H), 7.56-7.42 (m, 1H), 7.01-6.98 (m, 1H), 2.91-2.84 (m, 3H), 2.57-2.50 (m, 3H).

Example 14. N,N-dimethyl-1-(6-(1-(6-methylpyridin-2-yl)-1H-indazol-6-yl)pyridin-2-yl)methanamine Synthesis of N,N-dimethyl-1-(6-(1-(6-methylpyridin-2-yl)-1H-indazol-6-yl)pyridin-2-yl)methanamine

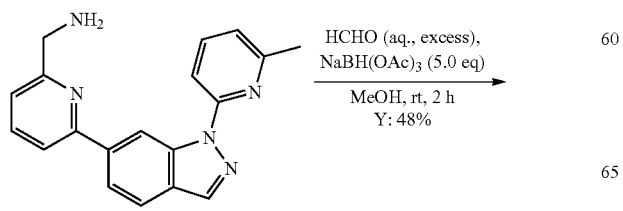

To a mixture of (6-(1-(6-methylpyridin-2-yl)-1H-indazol-6-yl)pyridin-2-yl)methanamine (115 mg, 0.36 mmol) and HCHO (aq., excess) in MeOH (10 mL) was added NaBH(OAc)₃ (382 mg, 1.80 mmol, 5.0 eq) at rt. The mixture was stirred at rt for 2 h. After concentration, the residue was purified by pre-HPLC to give N,N-dimethyl-1-(6-(1-(6-methylpyridin-2-yl)-1H-indazol-6-yl)pyridin-2-yl)methanamine as a white solid (60 mg, Y: 48%). ESI-MS (M+H)⁺: 344.1. HPLC: 94.59%. ¹H NMR (400 MHz, CD₃OD) δ: 9.44 (s, 1H), 8.22 (s, 1H), 7.93-7.74 (m, 6H), 7.39 (dd, J=7.2, 1.2 Hz, 1H), 7.08 (dd, J=7.2, 2.0 Hz, 1H), 3.70 (s, 2H), 2.60 (s, 3H), 2.33 (s, 6H).

Example 15. 5-(1-(6-methylpyridin-2-yl)-1H-indazol-6-yl)-1,2,3,4-tetrahydroisoquinoline Synthesis of tert-butyl 5-(1-(6-methylpyridin-2-yl)-1H-indazol-6-yl)-3,4-dihydroisoquinoline-2(1H)-carboxylate

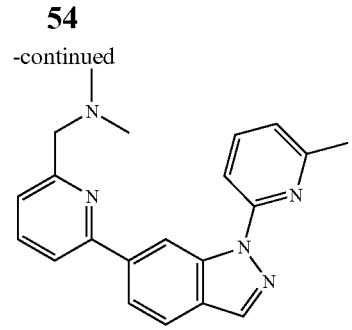

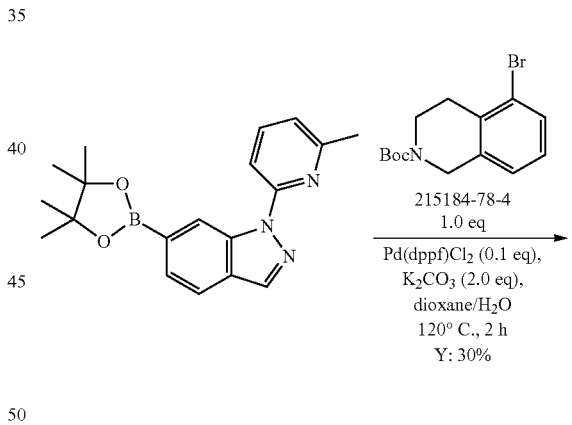

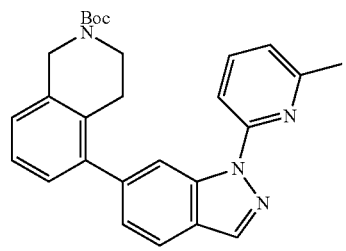

The preparation of tert-butyl 5-(1-(6-methylpyridin-2-yl)-1H-indazol-6-yl)-3,4-dihydroisoquinoline-2(1H)-carboxylate was the same as that of 6-(1-(6-methylpyridin-2-yl)-1H-indazol-6-yl)pyridin-2-amine. 100 mg, as a yellow solid, Y: 30%. ESI-MS (M+H)⁺: 441.2.

Synthesis of 5-(1-(6-methylpyridin-2-yl)-1H-indazol-6-yl)-1,2,3,4-tetrahydroisoquinoline

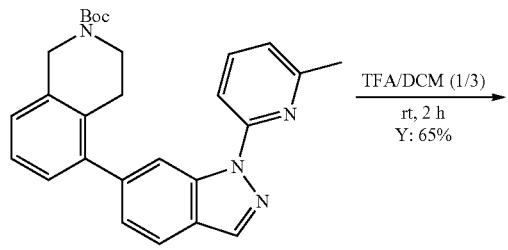

A solution of tert-butyl 5-(1-(6-methylpyridin-2-yl)-1H-indazol-6-yl)-3,4-dihydroisoquinoline-2(1H)-carboxylate (100 mg, 0.23 mmol) in TFA/DCM (1 mL/3 mL) was stirred at rt for 2 h. After concentration, the residue was purified by pre-HPLC to give 5-(1-(6-methylpyridin-2-yl)-1H-indazol-6-yl)-1,2,3,4-tetrahydroisoquinoline as a white solid (50 mg, Y: 65%). ESI-MS (M+H)$^+$: 341.2. HPLC: 100.00%. $^1$H NMR (400 MHz, CD$_3$OD) δ: 8.70 (s, 1H), 8.20-8.18 (m, 1H), 7.75-7.70 (m, 3H), 7.16-7.00 (m, 5H), 3.99 (s, 2H), 2.92-2.89 (m, 2H), 2.67-2.65 (m, 2H), 2.47 (s, 3H).

Example 16. 2-methyl-5-(1-(6-methylpyridin-2-yl)-1H-indazol-6-yl)-1,2,3,4-tetrahydroisoquinoline Synthesis of 2-methyl-5-(1-(6-methylpyridin-2-yl)-1H-indazol-6-yl)-1,2,3,4-tetrahydroisoquinoline

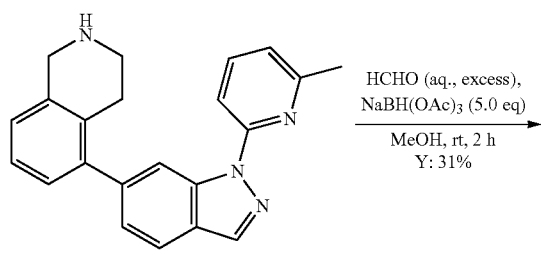

The preparation of 2-methyl-5-(1-(6-methylpyridin-2-yl)-1H-indazol-6-yl)-1,2,3,4-tetrahydroisoquinoline was the same as that of N,N-dimethyl-1-(6-(1-(6-methylpyridin-2-yl)-1H-indazol-6-yl)pyridin-2-yl)methanamine. 19 mg, as a white solid, Y: 31%. ESI-MS (M+H)$^+$: 355.2. HPLC: 97.75%. $^1$H NMR (400 MHz, CD$_3$OD) δ: 8.68 (s, 1H), 8.18 (d, J=0.8 Hz, 1H), 7.74-7.70 (m, 3H), 7.16-6.98 (m, 5H), 3.62 (s, 2H), 2.76-2.74 (m, 2H), 2.57-2.55 (m, 2H), 2.45 (s, 3H), 2.36 (s, 3H).

Example 17. 6-(2-methylisoindolin-4-yl)-1-(6-methylpyridin-2-yl)-1H-indazole

Synthesis of 6-(2-methylisoindolin-4-yl)-1-(6-methylpyridin-2-yl)-1H-indazole

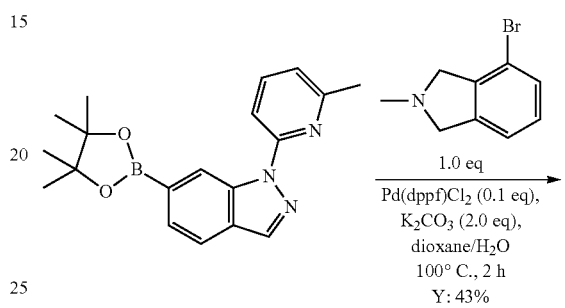

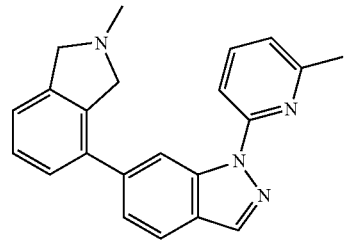

The preparation of 6-(2-methylisoindolin-4-yl)-1-(6-methylpyridin-2-yl)-1H-indazole was the same as that of 6-(1-(6-methylpyridin-2-yl)-1H-indazol-6-yl)pyridin-2-amine except the reaction was performed at a temperature of 100. 47 mg, as a white solid, Y: 43%. ESI-MS (M+H)$^+$: 341.2. HPLC: 95.23%. $^1$H NMR (400 MHz, CD$_3$OD) δ: 8.74 (s, 1H), 8.13 (s, 1H), 7.72-7.66 (m, 3H), 7.31-7.21 (m, 4H), 6.97-6.95 (m, 1H), 4.04 (s, 2H), 3.92 (s, 2H), 2.52 (s, 3H), 2.49 (s, 3H).

Example 18. N-methyl-1-(3-(1-(6-methylpyridin-2-yl)-1H-indazol-6-yl)phenyl)methanamine Synthesis of tert-butyl methyl((6-(1-(6-methylpyridin-2-yl)-1H-indazol-6-yl)pyridin-2-yl)methyl)carbamate

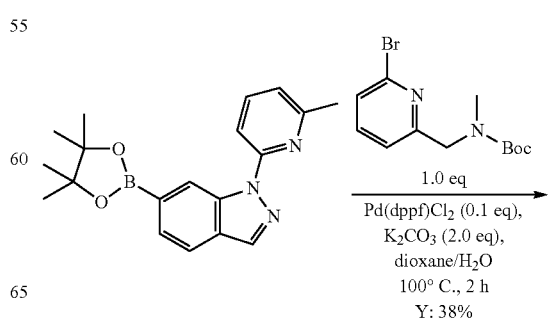

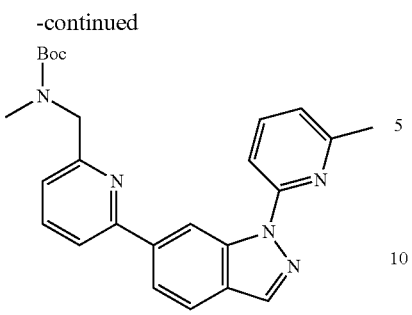

The preparation of tert-butyl methyl(((6-(1-(6-methylpyridin-2-yl)-1H-indazol-6-yl)pyridin-2-yl)methyl)carbamate was the same as that of 6-(1-(6-methylpyridin-2-yl)-1H-indazol-6-yl)pyridin-2-amine except the reaction temperature was 100. 110 mg, as a yellow solid, Y: 38%. ESI-MS (M+H)⁺: 430.2.

Synthesis of N-methyl-1-(3-(1-(6-methylpyridin-2-yl)-1H-indazol-6-yl)phenyl)methanamine

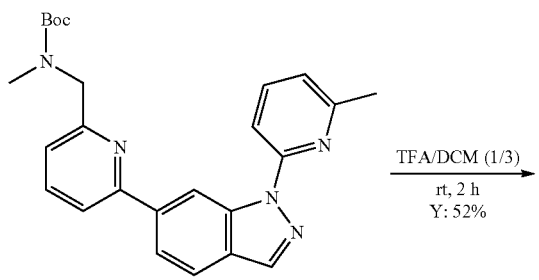

The preparation of N-methyl-1-(3-(1-(6-methylpyridin-2-yl)-1H-indazol-6-yl)phenyl)methanamine was the same as that of 5-(1-(6-methylpyridin-2-yl)-1H-indazol-6-yl)-1,2,3,4-tetrahydroisoquinoline. 53 mg, as a yellow solid, Y: 52%. ESI-MS (M+H)⁺: 330.2. HPLC: 91.60%. $^1$H NMR (400 MHz, CDCl$_3$) δ: 9.56 (s, 1H), 8.20 (s, 1H), 7.99 (d, J=8.4 Hz, 1H), 7.86-7.71 (m, 5H), 7.29-7.26 (m, 1H), 7.04 (d, J=7.2 Hz, 1H), 4.02 (s, 2H), 3.69 (s, 3H), 2.59 (s, 3H).

Example 20. 3-(6-(3-aminophenyl)-1H-indazol-1-yl)benzonitrile

Synthesis of 3-(6-bromo-1H-indazol-1-yl)benzonitrile

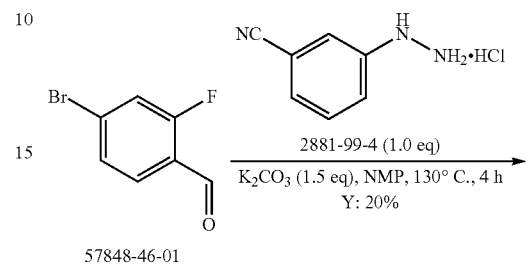

A mixture of 4-bromo-2-fluorobenzaldehyde (CAS#57848-46-01) (350 mg, 1.73 mmol), 3-hydrazinylbenzonitrile hydrochloride (CAS#2881-99-4) (293 mg, 1.73 mmol, 1.0 eq) and K$_2$CO$_3$ (358 mg, 2.60 mmol, 1.5 eq) in NMP (5 mL) was stirred at 130° C. for 4 h. After cooling down to rt, the mixture was diluted with H$_2$O (20 mL) and stirred at rt for 30 min. After filtration, the solid was purified by silica gel chromatography with PE/EA (10/1) as eluent to give 3-(6-bromo-1H-indazol-1-yl)benzonitrile. 102 mg, as a yellow solid, Y: 20%. ESI-MS (M+H)⁺: 298.1. $^1$H NMR (400 MHz, CDCl$_3$) δ: 8.20 (s, 1H), 8.02 (s, 1H), 7.97 (dd, J=7.2, 2.0 Hz, 1H), 7.90 (s, 1H), 7.69-7.64 (m, 3H), 7.39 (dd, J=8.4, 1.2 Hz, 1H).

Synthesis of 3-(6-(4,4,5,5-tetramethyl-1,3,2-dioxaborolan-2-yl)-1H-indazol-1-yl)benzonitrile

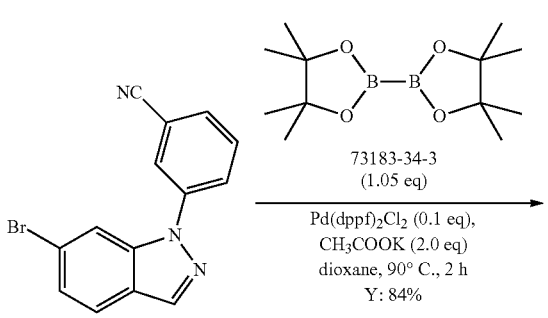

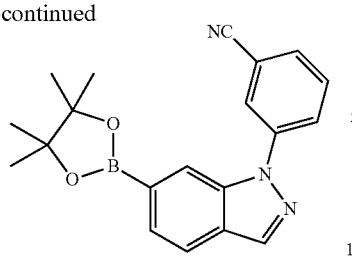

The preparation of 3-(6-(4,4,5,5-tetramethyl-1,3,2-dioxaborolan-2-yl)-1H-indazol-1-yl)benzonitrile was the same as that of 1-(6-methylpyridin-2-yl)-6-(4,4,5,5-tetramethyl-1,3,2-dioxaborolan-2-yl)-1H-indazole. 100 mg, as a yellow solid, Y: 84%. ESI-MS (M+H)$^+$: 346.2.

Synthesis of 3-(6-(3-aminophenyl)-1H-indazol-1-yl)benzonitrile

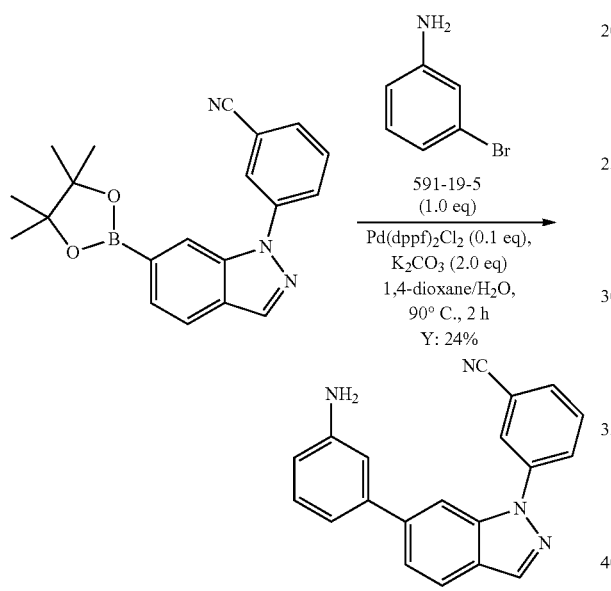

The preparation of 3-(6-(3-aminophenyl)-1H-indazol-1-yl)benzonitrile was the same as that of 6-(1-(6-methylpyridin-2-yl)-1H-indazol-6-yl)pyridin-2-amine. 25 mg, as a yellow solid, Y: 24%. ESI-MS (M+H)$^+$: 311.1. HPLC: 95.39%. $^1$H NMR (400 MHz, CD$_3$OD) δ: 8.20 (s, 1H), 8.03-8.00 (m, 2H), 7.79-7.77 (m, 2H), 7.69-7.63 (m, 2H), 7.43 (dd, J=8.4, 1.2 Hz, 1H), 7.13 (t, J=7.6 Hz, 1H), 6.97 (s, 1H), 6.92 (d, J=7.6 Hz, 1H), 6.70 (dd, J=8.0, 1.2 Hz, 1H).

Example 21. 3-(1-(pyridin-2-yl)-1H-indazol-6-yl)aniline

Synthesis of 6-bromo-1-(pyridin-2-yl)-1H-indazole

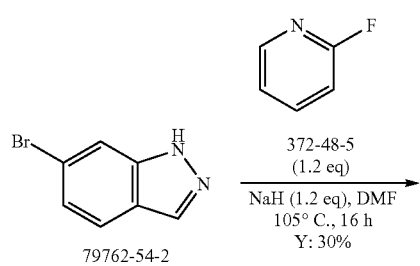

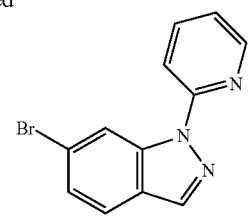

The preparation of 6-bromo-1-(pyridin-2-yl)-1H-indazole was the same as that of 6-bromo-1-(6-methylpyridin-2-yl)-1H-indazole. 100 mg, as a yellow solid, Y: 30%. ESI-MS (M+H)$^+$: 274.0. $^1$H NMR (400 MHz, CDCl$_3$) δ: 9.10 (s, 1H), 8.54 (d, J=3.6 Hz, 1H), 8.16 (s, 1H), 8.03 (d, J=8.4 Hz, 1H), 7.86-7.82 (m, 1H), 7.63 (d, J=8.4 Hz, 1H), 7.39 (dd, J=8.4, 1.6 Hz, 1H), 7.18 (dd, J=6.8, 1.2 Hz, 1H).

Synthesis of 1-(pyridin-2-yl)-6-(4,4,5,5-tetramethyl-1,3,2-dioxaborolan-2-yl)-1H-indazole

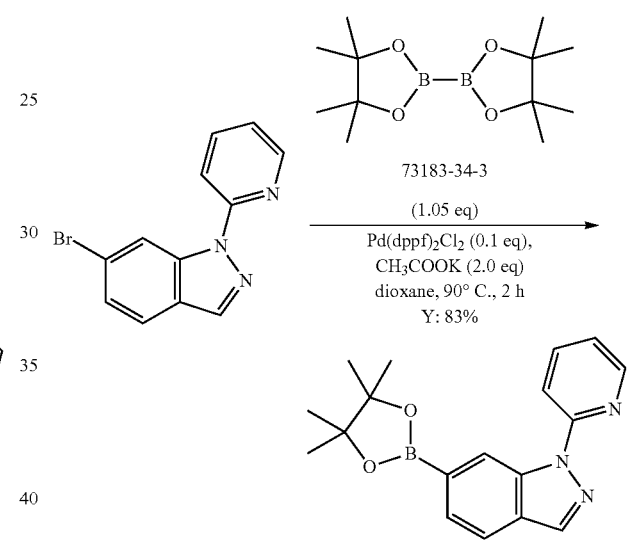

The preparation of 1-(pyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 95 mg, as a yellow solid, Y: 83%. ESI-MS (M+H)$^+$: 322.2.

Synthesis of 3-(1-(pyridin-2-yl)-1H-indazol-6-yl)aniline

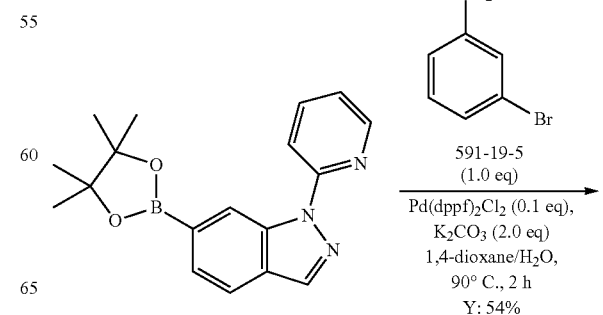

-continued

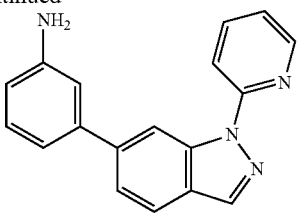

The preparation of 3-(1-(pyridin-2-yl)-1H-indazol-6-yl) aniline was the same as that of 6-(1-(6-methylpyridin-2-yl)-1H-indazol-6-yl)pyridin-2-amine. 54 mg, as a yellow solid, Y: 54%. ESI-MS (M+H)$^+$: 287.1. $^1$H NMR (400 MHz, CD$_3$OD) δ: 8.97 (s, 1H), 8.55 (dd, J=5.2, 1.2 Hz, 1H), 8.25 (s, 1H), 8.03 (d, J=8.4 Hz, 1H), 7.93 (dd, J=7.6, 2.0 Hz, 1H), 7.83 (d, J=8.4 Hz, 1H), 7.53 (dd, J=8.4, 1.6 Hz, 1H), 7.26-7.19 (m, 2H), 7.11 (d, J=2.0 Hz, 1H), 7.04 (d, J=7.6 Hz, 1H), 6.76 (dd, J=8.0, 1.6 Hz, 1H).

Example 22. 6-(6-(3-aminophenyl)-1H-indazol-1-yl)picolinonitrile

Synthesis of 6-(6-bromo-1H-indazol-1-yl)picolinonitrile

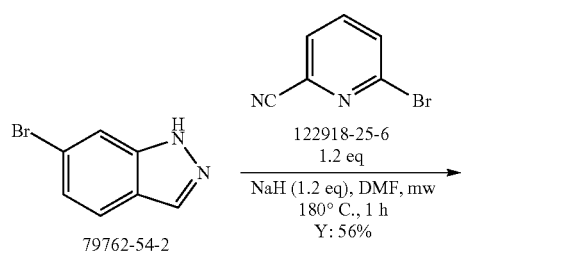

The preparation of 6-(6-bromo-1H-indazol-1-yl)picolinonitrile was the same as that of 6-bromo-1-(6,7-dihydro-5H-cyclopenta[b]pyridin-2-yl)-1H-indazole. 170 mg, as a yellow solid, Y: 56%. ESI-MS (M+H)$^+$: 299.0. $^1$H NMR (400 MHz, CDCl$_3$) δ: 9.01 (s, 1H), 8.31 (d, J=7.6 Hz, 1H), 8.19 (s, 1H), 7.96 (t, J=8.4 Hz, 1H), 7.64 (d, J=8.4 Hz, 1H), 7.58 (d, J=7.6 Hz, 1H), 7.47 (dd, J=8.4, 1.2 Hz, 1H).

Synthesis of 6-(6-(4,4,5,5-tetramethyl-1,3,2-dioxaborolan-2-yl)-1H-indazol-1-yl)picolinonitrile

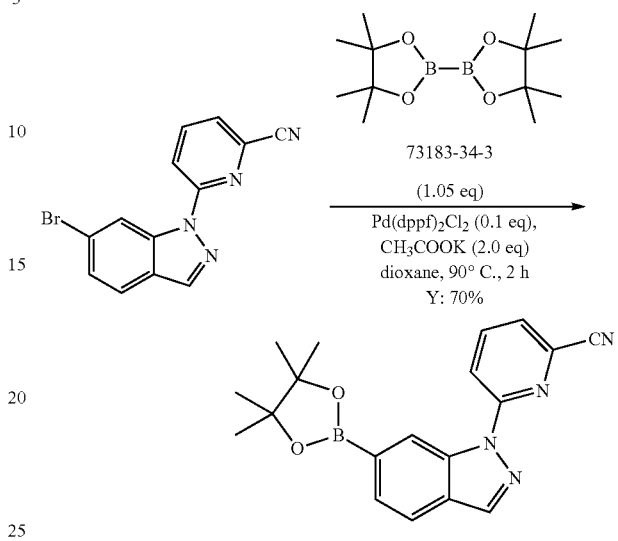

The preparation of 6-(6-(4,4,5,5-tetramethyl-1,3,2-dioxaborolan-2-yl)-1H-indazol-1-yl)picolinonitrile was the same as that of 1-(6-methylpyridin-2-yl)-6-(4,4,5,5-tetramethyl-1,3,2-dioxaborolan-2-yl)-1H-indazole. 109 mg, as a yellow solid, Y: 70%. ESI-MS (M+H)$^+$: 347.2.

Synthesis of 6-(6-(3-aminophenyl)-1H-indazol-1-yl)picolinonitrile

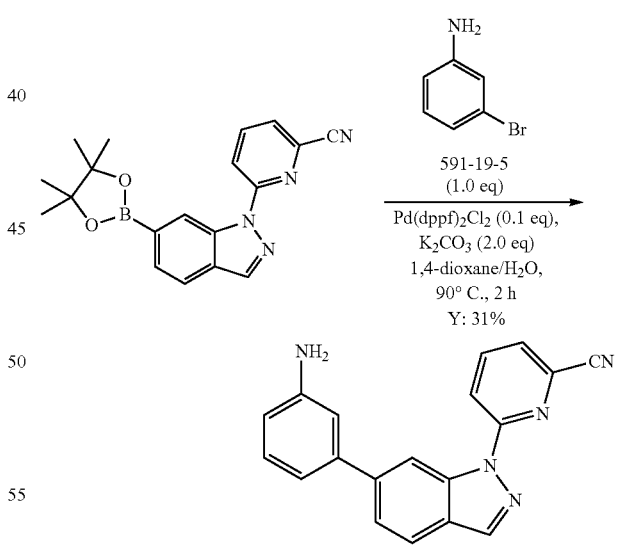

The preparation of 6-(6-(3-aminophenyl)-1H-indazol-1-yl)picolinonitrile was the same as that of 6-(1-(6-methylpyridin-2-yl)-1H-indazol-6-yl)pyridin-2-amine. 31 mg, as a yellow solid, Y: 31%. ESI-MS (M+H)$^+$: 312.1. HPLC: 100.00%. $^1$H NMR (400 MHz, DMSO-d$_6$) δ: 8.80 (s, 1H), 8.57 (s, 1H), 8.35 (d, J=8.8 Hz, 1H), 8.25 (t, J=7.6 Hz, 1H), 7.99-7.97 (m, 2H), 7.56 (dd, J=8.4, 1.2 Hz, 1H), 7.18 (t, J=7.6 Hz, 1H), 6.91 (s, 1H), 6.84 (d, J=7.6 Hz, 1H), 6.64 (dd, J=7.6, 1.2 Hz, 1H), 5.29 (br, 2H).

Example 23. 3-(1-(4,6-dimethylpyridin-2-yl)-1H-indazol-6-yl)aniline

Synthesis of 6-bromo-1-(4,6-dimethylpyridin-2-yl)-1H-indazole

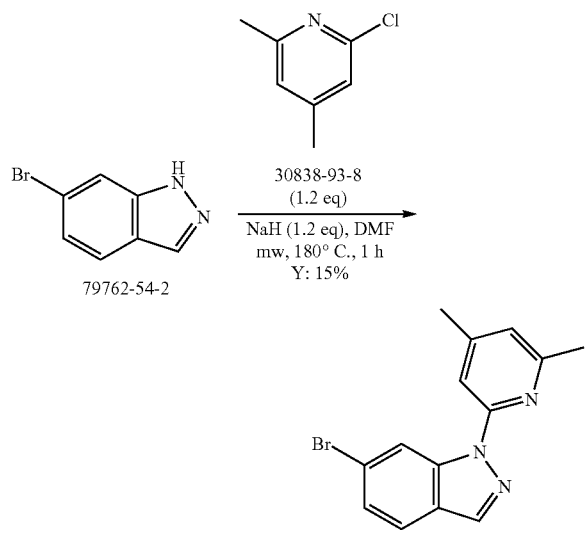

The preparation of 6-bromo-1-(4,6-dimethylpyridin-2-yl)-1H-indazole was the same as that of 6-bromo-1-(6,7-dihydro-5H-cyclopenta[b]pyridin-2-yl)-1H-indazole. 70 mg, as a yellow solid, Y: 15%. ESI-MS (M+H)+: 302.2. 1H NMR (400 MHz, CD3OD) δ: 9.08 (s, 1H), 8.12 (s, 1H), 7.64 (s, 1H), 7.60 (d, J=8.4 Hz, 1H), 7.36 (dd, J=8.4, 1.6 Hz, 1H), 6.87 (s, 1H), 2.61 (s, 3H), 2.40 (s, 3H).

Synthesis of 1-(4,6-dimethylpyridin-2-yl)-6-(4,4,5,5-tetramethyl-1,3,2-dioxaborolan-2-yl)-1H-indazole The preparation of 1-(4,6-dimethylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 64 mg, as a yellow solid, Y: 80%. ESI-MS (M+H)+: 350.2.

Synthesis of 3-(1-(4,6-dimethylpyridin-2-yl)-1H-indazol-6-yl)aniline

The preparation of 3-(1-(4,6-dimethylpyridin-2-yl)-1H-indazol-6-yl)aniline was the same as that of 6-(1-(6-methylpyridin-2-yl)-1H-indazol-6-yl)pyridin-2-amine. 30 mg, as a yellow solid, Y: 52%. ESI-MS (M+H)+: 315.2. HPLC: 98.79%. 1H NMR (400 MHz, CDCl3) δ: 9.06 (s, 1H), 8.17 (s, 1H), 7.77 (d, J=7.6 Hz, 1H), 7.67 (s, 1H), 7.48 (dd, J=8.4, 1.6 Hz, 1H), 7.29 (d, J=7.6 Hz, 1H), 7.13 (d, J=7.2 Hz, 1H), 7.05 (t, J=2.0 Hz, 1H), 6.86 (s, 1H), 6.75-6.72 (m, 1H), 3.79 (s, 2H), 2.60 (s, 3H), 2.41 (s, 3H).

Example 24. 3-(1-(5,6-dimethylpyridin-2-yl)-1H-indazol-6-yl)aniline

Synthesis of 6-bromo-1-(5,6-dimethylpyridin-2-yl)-1H-indazole

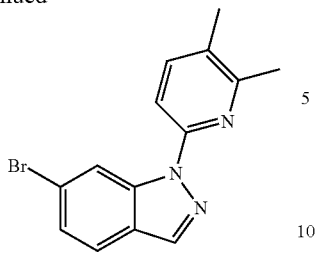

The preparation of 6-bromo-1-(5,6-dimethylpyridin-2-yl)-1H-indazole was the same as that of 6-bromo-1-(6,7-dihydro-5H-cyclopenta[b]pyridin-2-yl)-1H-indazole. 30 mg, as a yellow solid, Y: 13%. ESI-MS (M+H)+: 302.2.

Synthesis of 1-(5,6-dimethylpyridin-2-yl)-6-(4,4,5,5-tetramethyl-1,3,2-dioxaborolan-2-yl)-1H-indazole

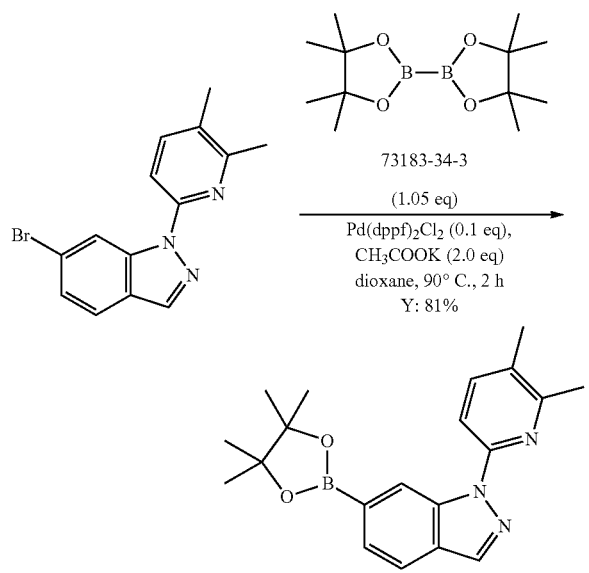

The preparation of 1-(5,6-dimethylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 28 mg, as a yellow solid, Y: 81%. ESI-MS (M+H)+: 350.2.

Synthesis of 3-(1-(5,6-dimethylpyridin-2-yl)-1H-indazol-6-yl)aniline

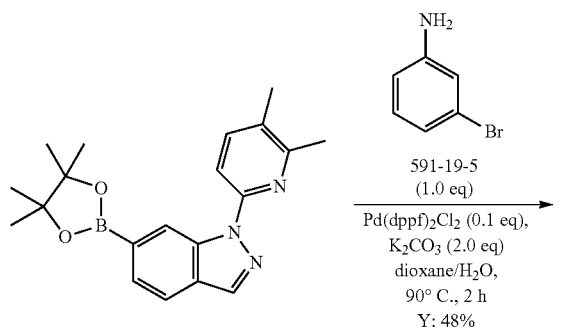

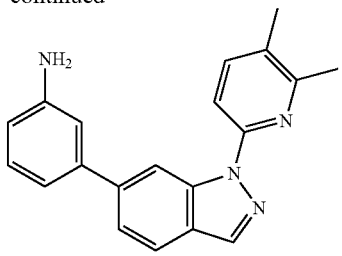

The preparation of 3-(1-(5,6-dimethylpyridin-2-yl)-1H-indazol-6-yl)aniline was the same as that of 6-(1-(6-methylpyridin-2-yl)-1H-indazol-6-yl)pyridin-2-amine. 15 mg, as a yellow solid, Y: 48%. ESI-MS (M+H)+: 315.2. HPLC: 100.00%. 1H NMR (400 MHz, CD3OD) δ: 8.97 (s, 1H), 8.20 (s, 1H), 7.82 (d, J=8.4 Hz, 1H), 7.71 (d, J=8.0 Hz, 1H), 7.65 (d, J=8.0 Hz, 1H), 7.50 (dd, J=8.4, 1.6 Hz, 1H), 7.21 (t, J=7.6 Hz, 1H), 7.09 (t, J=1.6 Hz, 1H), 7.03 (d, J=7.6 Hz, 1H), 6.75 (dd, J=7.6, 1.6 Hz, 1H), 2.59 (s, 3H), 2.34 (s, 3H).

Example 25. 3-(1-(6-(trifluoromethyl)pyridin-2-yl)-1H-indazol-6-yl)aniline

Synthesis of 6-bromo-1-(6-(trifluoromethyl)pyridin-2-yl)-1H-indazole

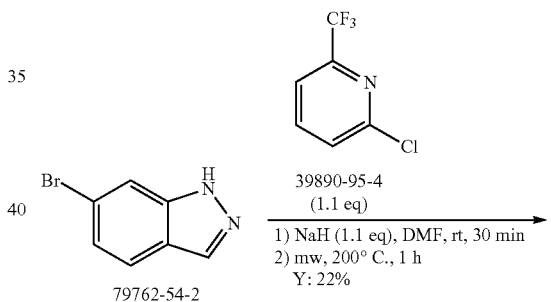

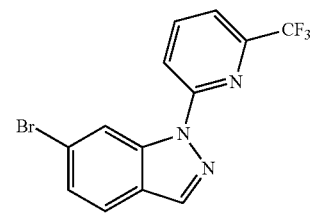

The preparation of 6-bromo-1-(6-(trifluoromethyl)pyridin-2-yl)-1H-indazole was the same as that of 6-bromo-1-(6,7-dihydro-5H-cyclopenta[b]pyridin-2-yl)-1H-indazole except the reaction was run at 200 for 1 h. 300 mg, as a yellow solid, Y: 22%. ESI-MS (M+H)+: 342.0. 1H NMR (400 MHz, CDCl3) δ: 9.07 (s, 1H), 8.24 (d, J=8.8 Hz, 1H), 8.18 (s, 1H), 8.00 (t, J=7.6 Hz, 1H), 7.64 (d, J=8.4 Hz, 1H), 7.54 (d, J=7.2 Hz, 1H), 7.44 (dd, J=8.8, 2.0 Hz, 1H).

Synthesis of 6-(4,4,5,5-tetramethyl-1,3,2-dioxaborolan-2-yl)-1-(6-(trifluoromethyl)pyridin-2-yl)-1H-indazole

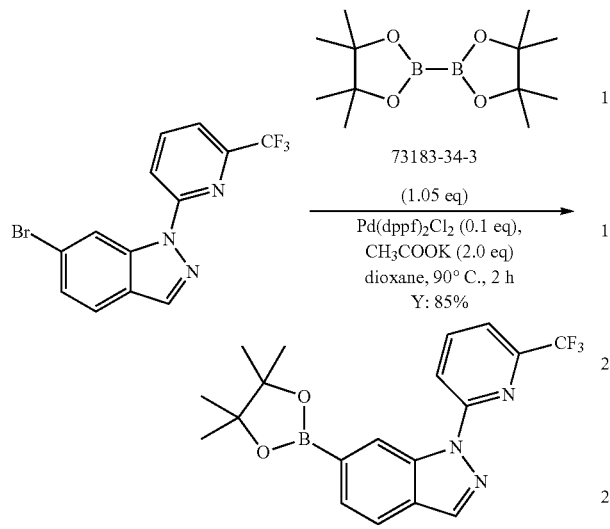

The preparation of 6-(4,4,5,5-tetramethyl-1,3,2-dioxaborolan-2-yl)-1-(6-(trifluoromethyl)pyridin-2-yl)-1H-indazole was the same as that of 1-(6-methylpyridin-2-yl)-6-(4,4,5,5-tetramethyl-1,3,2-dioxaborolan-2-yl)-1H-indazole. 145 mg, as a yellow solid, Y: 85%. ESI-MS (M+H)+: 390.2.

Synthesis of 3-(1-(6-(trifluoromethyl)pyridin-2-yl)-1H-indazol-6-yl)aniline

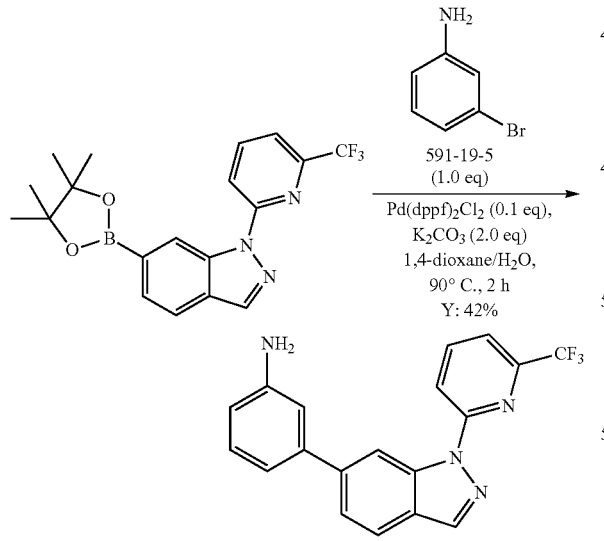

The preparation of 3-(1-(6-(trifluoromethyl)pyridin-2-yl)-1H-indazol-6-yl)aniline was the same as that of 6-bromo-1-(6,7-dihydro-5H-cyclopenta[b]pyridin-2-yl)-1H-indazole. 55 mg, as a yellow solid, Y: 42%. ESI-MS (M+H)+: 355.1. HPLC: 98.79%. ¹H NMR (400 MHz, CDCl₃) δ: 9.16 (s, 1H), 8.26 (d, J=8.4 Hz, 1H), 8.22 (s, 1H), 7.99 (t, J=8.0 Hz, 1H), 7.79 (d, J=8.4 Hz, 1H), 7.58 (dd, J=8.0, 1.6 Hz, 1H), 7.51 (d, J=7.6 Hz, 1H), 7.29 (t, J=8.0 Hz, 1H), 7.16 (d, J=8.0 Hz, 1H), 7.09 (t, J=2.0 Hz, 1H), 6.74 (dd, J=8.0, 1.6 Hz, 1H), 3.79 (s, 2H).

Example 27. 5-(1-(6-cyclopropylpyridin-2-yl)-1H-indazol-6-yl)pyridin-3-amine

Synthesis of 6-bromo-1-(6-cyclopropylpyridin-2-yl)-1H-indazole

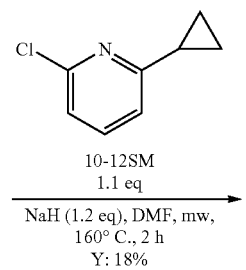

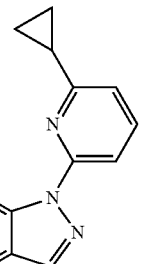

The preparation of 6-bromo-1-(6-cyclopropylpyridin-2-yl)-1H-indazole was the same as that of 6-bromo-1-(6,7-dihydro-5H-cyclopenta[b]pyridin-2-yl)-1H-indazole. 40 mg, as a yellow solid, Y: 18%. ESI-MS (M+H)+: 314.0.

Synthesis of 1-(6-cyclopropylpyridin-2-yl)-6-(4,4,5,5-tetramethyl-1,3,2-dioxaborolan-2-yl)-1H-indazole

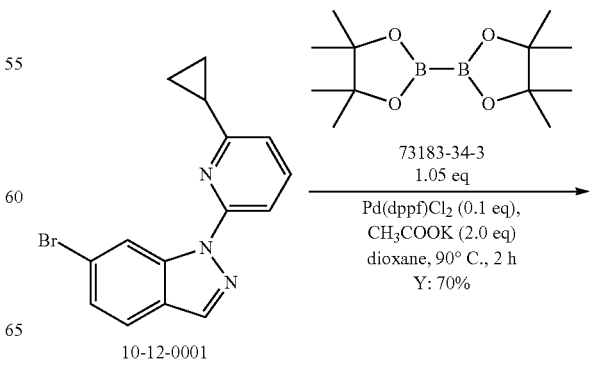

-continued

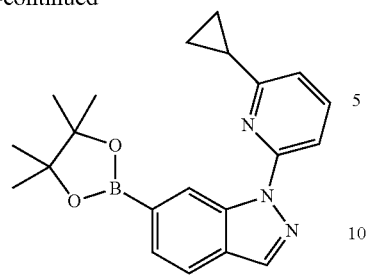

The preparation of 1-(6-cyclopropylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 32 mg, as a yellow solid, Y: 70%. ESI-MS (M+H)+: 362.2.

Synthesis of 5-(1-(6-cyclopropylpyridin-2-yl)-1H-indazol-6-yl)pyridin-3-amine

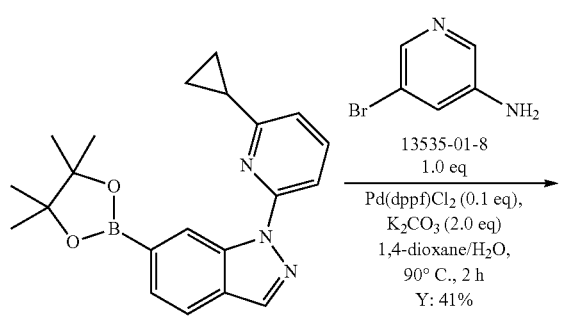

The preparation of 5-(1-(6-cyclopropylpyridin-2-yl)-1H-indazol-6-yl)pyridin-3-amine was the same as that of 6-bromo-1-(6,7-dihydro-5H-cyclopenta[b]pyridin-2-yl)-1H-indazole. 12 mg, as a yellow solid, Y: 41%. ESI-MS (M+H)+: 328.1. HPLC: 100.00%. 1H NMR (400 MHz, CDCl3) δ: 9.04 (s, 1H), 8.43 (d, J=1.6 Hz, 1H), 8.17 (s, 1H), 8.14 (d, J=2.4 Hz, 1H), 7.81-7.78 (m, 2H), 7.67 (t, J=8.0 Hz, 1H), 7.47 (dd, J=8.4, 1.6 Hz, 1H), 7.32 (dd, J=8.4, 2.8 Hz, 1H), 7.07 (d, J=7.6 Hz, 1H), 3.80 (br, 2H), 2.14-2.10 (m, 1H), 1.28-1.24 (m, 2H), 1.12-1.08 (m, 2H).

Example 28. 5-(1-(6-cyclobutylpyridin-2-yl)-1H-indazol-6-yl)pyridin-3-amine

Synthesis of 6-bromo-1-(6-cyclobutylpyridin-2-yl)-1H-indazole

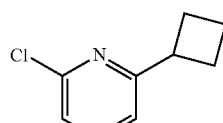

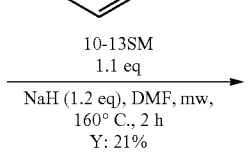

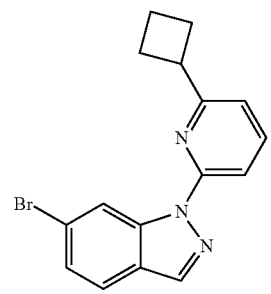

The preparation of 6-bromo-1-(6-cyclobutylpyridin-2-yl)-1H-indazole was the same as that of 6-bromo-1-(6,7-dihydro-5H-cyclopenta[b]pyridin-2-yl)-1H-indazole. 140 mg, as a yellow solid, Y: 21%. ESI-MS (M+H)+: 328.0.

Synthesis of 1-(6-cyclobutylpyridin-2-yl)-6-(4,4,5,5-tetramethyl-1,3,2-dioxaborolan-2-yl)-1H-indazole

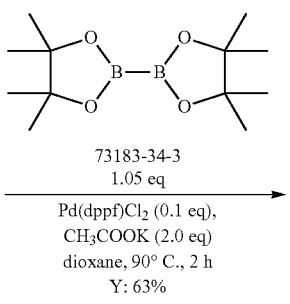

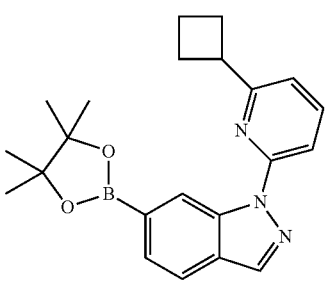

The preparation of 1-(6-cyclobutylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 100 mg, as a yellow solid, Y: 63%. ESI-MS (M+H)+: 376.2.

Synthesis of 5-(1-(6-cyclobutylpyridin-2-yl)-1H-indazol-6-yl)pyridin-3-amine

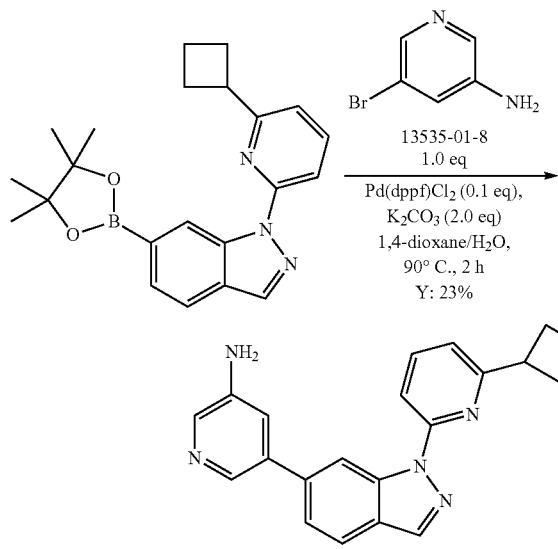

The preparation of 5-(1-(6-cyclobutylpyridin-2-yl)-1H-indazol-6-yl)pyridin-3-amine was the same as that of 6-bromo-1-(6,7-dihydro-5H-cyclopenta[b]pyridin-2-yl)-1H-indazole. 21 mg, as a yellow solid, Y: 23%. ESI-MS (M+H)+: 342.2. HPLC: 100.00%. $^1$H NMR (400 MHz, CDCl$_3$) δ: 9.22 (s, 1H), 8.37 (d, J=1.6 Hz, 1H), 8.11 (d, J=1.6 Hz, 1H), 8.08 (d, J=8.0 Hz, 1H), 7.92 (s, 1H), 7.82 (d, J=8.8 Hz, 1H), 7.79 (d, J=8.0 Hz, 1H), 7.32 (dd, J=8.4, 1.2 Hz, 1H), 7.26 (s, 1H), 7.15 (d, J=7.6 Hz, 1H), 3.80 (br, 2H), 3.75-3.70 (m, 1H), 2.48-2.39 (m, 4H), 2.12-1.97 (m, 2H).

Example 29. 6-(6-(5-aminopyridin-3-yl)-1H-indazol-1-yl)picolinonitrile

Synthesis of 6-(6-(5-aminopyridin-3-yl)-1H-indazol-1-yl)picolinonitrile

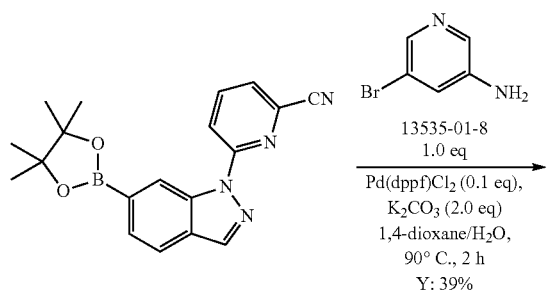

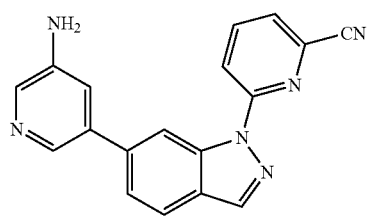

The preparation of 6-(6-(5-aminopyridin-3-yl)-1H-indazol-1-yl)picolinonitrile was the same as that of 6-bromo-1-(6,7-dihydro-5H-cyclopenta[b]pyridin-2-yl)-1H-indazole. 120 mg, as a yellow solid, Y: 39%. ESI-MS (M+H)+: 313.1. HPLC: 94.59%. $^1$H NMR (400 MHz, CD$_3$OD) δ: 8.98 (s, 1H), 8.41-8.38 (m, 2H), 8.16 (d, J=1.6 Hz, 1H), 8.12 (d, J=8.4 Hz, 1H), 8.02 (d, J=2.4 Hz, 1H), 7.96 (d, J=8.0 Hz, 1H), 7.75 (d, J=7.6 Hz, 1H), 7.61 (d, J=8.0 Hz, 1H), 7.44 (s, 1H).

Example 30. 6-(6-(5-aminopyridin-3-yl)-1H-indazol-1-yl)picolinic acid

Synthesis of 6-(6-(5-aminopyridin-3-yl)-1H-indazol-1-yl)picolinic acid

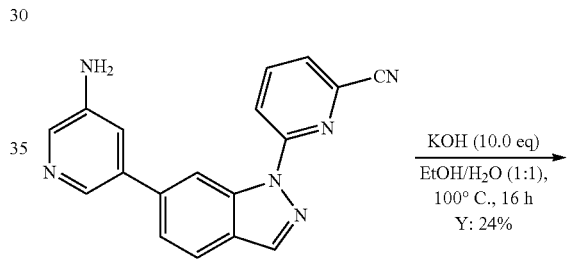

A mixture of 6-(6-(5-aminopyridin-3-yl)-1H-indazol-1-yl)picolinonitrile (60 mg, 0.19 mmol, 1.0 eq) and KOH (106 mg, 1.90 mmol, 10.0 eq) in EtOH/H$_2$O (1 mL/1 mL) was stirred at 100° C. for 16 h. After cooling to rt, the mixture was adjusted pH=7 with 3 N HCl. After concentration, the residue was purified by pre-HPLC (CH$_3$CN/0.5% TFA in H$_2$O, 5%-95%) to give 6-(6-(5-aminopyridin-3-yl)-1H-indazol-1-yl)picolinic acid as a white solid. 15 mg, Y: 24%. ESI-MS (M+H)+: 332.1. HPLC: 97.10%. $^1$H NMR (400 MHz, DMSO-d$_6$) δ: 9.45 (s, 1H), 8.57 (s, 1H), 8.32 (s, 1H), 8.23-8.20 (m, 2H), 8.07-7.99 (m, 2H), 7.98 (d, J=7.2 Hz, 1H), 7.68-7.66 (m, 2H).

Example 31. 6-(6-(5-aminopyridin-3-yl)-1H-indazol-1-yl)picolinamide

Synthesis of 6-(6-(5-aminopyridin-3-yl)-1H-indazol-1-yl)picolinamide

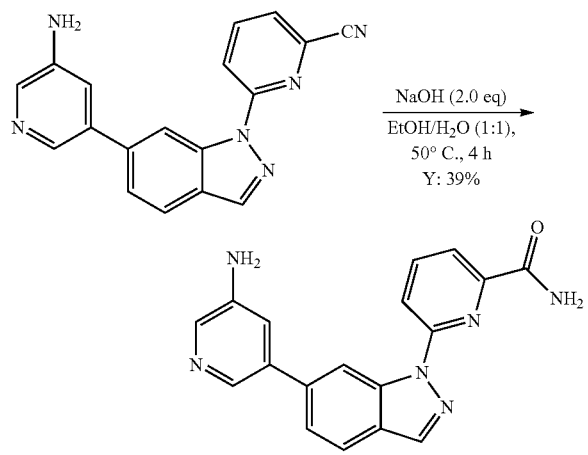

A mixture of 6-(6-(5-aminopyridin-3-yl)-1H-indazol-1-yl)picolinonitrile (65 mg, 0.21 mmol, 1.0 eq) and NaOH (17 mg, 0.42 mmol, 2.0 eq) in EtOH/H$_2$O (1 mL/1 mL) was stirred at 50° C. for 4 h. After cooling to rt, the mixture was adjusted pH=7 with 3 N HCl. After concentration, the residue was purified by pre-HPLC (CH$_3$CN/0.5% TFA in H$_2$O, 5%-95%) to give 6-(6-(5-aminopyridin-3-yl)-1H-indazol-1-yl)picolinamide as a white solid. 27 mg, Y: 39%. ESI-MS (M+H)$^+$: 331.1. HPLC: 99.33%. $^1$H NMR (400 MHz, DMSO-d$_6$) δ: 8.94 (s, 1H), 8.54 (s, 1H), 8.22 (d, J=2.0 Hz, 1H), 8.19-8.17 (m, 2H), 8.07 (s, 1H), 8.02-7.98 (m, 2H), 7.90-7.59 (m, 2H), 7.61 (dd, J=8.4, 0.4 Hz, 1H), 7.29 (t, J=2.0 Hz, 1H), 5.45 (s, 2H).

Example 32. 6-(6-(5-aminopyridin-3-yl)-1H-indazol-1-yl)-N-methylpicolinamide Synthesis of 6-(6-(5-aminopyridin-3-yl)-1H-indazol-1-yl)-N-methylpicolinamide

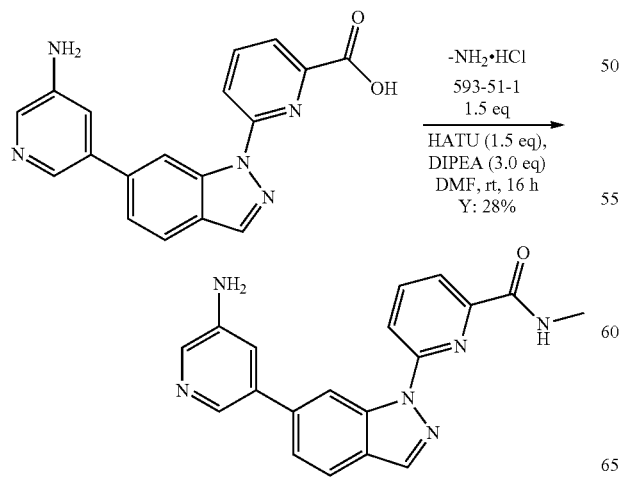

A mixture of 6-(6-(5-aminopyridin-3-yl)-1H-indazol-1-yl)picolinic acid (38 mg, 0.11 mmol, 1.0 eq), DIPEA (43 mg, 0.33 mmol, 3.0 eq) and HATU (65 mg, 0.17 mmol, 1.5 eq) in DMF (2 mL) was stirred at rt for 20 min, then, methylamine hydrochloride (CAS#593-51-1) (11 mg, 0.17 mmol, 1.5 eq) was added to the mixture. The mixture was stirred at rt for 16 h. The mixture was purified by pre-HPLC (CH$_3$CN/0.5% NH$_4$OH in H$_2$O, 5%-95%) to give 6-(6-(5-aminopyridin-3-yl)-1H-indazol-1-yl)-N-methylpicolinamide as a white solid. 11 mg, Y: 28%). ESI-MS (M+H)$^+$: 345.0. HPLC: 96.81%. $^1$H NMR (400 MHz, DMSO-d$_6$) δ: 8.98 (s, 1H), 8.65 (q, J=4.4 Hz, 1H), 8.54 (d, J=0.4 Hz, 1H), 8.27 (d, J=1.6 Hz, 1H), 8.18-8.16 (m, 2H), 8.02-7.99 (m, 2H), 7.87 (dd, J=6.0, 2.0 Hz, 1H), 7.61 (dd, J=8.0, 1.6 Hz, 1H), 7.32 (t, J=2.4 Hz, 1H), 5.43 (s, 2H), 2.93 (d, J=4.8 Hz, 3H).

Example 33. 3-(6-(5-aminopyridin-3-yl)-1H-indazol-1-yl)benzonitrile

Synthesis of 3-(6-(5-aminopyridin-3-yl)-1H-indazol-1-yl)benzonitrile

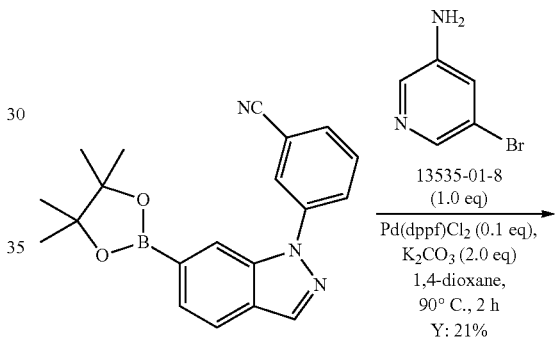

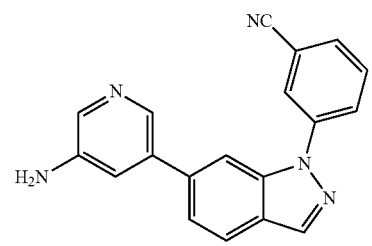

The preparation of 3-(6-(5-aminopyridin-3-yl)-1H-indazol-1-yl)benzonitrile was the same as that of 6-bromo-1-(6,7-dihydro-5H-cyclopenta[b]pyridin-2-yl)-1H-indazole. 17 mg, as a yellow solid. Y: 21%. ESI-MS (M+H)$^+$: 312.1. HPLC: 94.59%. $^1$H NMR (400 MHz, CD$_3$OD) δ: 8.34 (s, 1H), 8.19-8.15 (m, 2H), 8.11 (d, J=2.0 Hz, 1H), 7.97-7.95 (m, 3H), 7.77-7.74 (m, 2H), 7.53 (dd, J=8.4, 1.2 Hz, 1H), 7.40 (t, J=2.0 Hz, 1H).

Example 34. 2-(6-(5-aminopyridin-3-yl)-1H-indazol-1-yl)-6-methylisonicotinonitrile Synthesis of 2-(6-bromo-1H-indazol-1-yl)-6-methylisonicotinonitrile

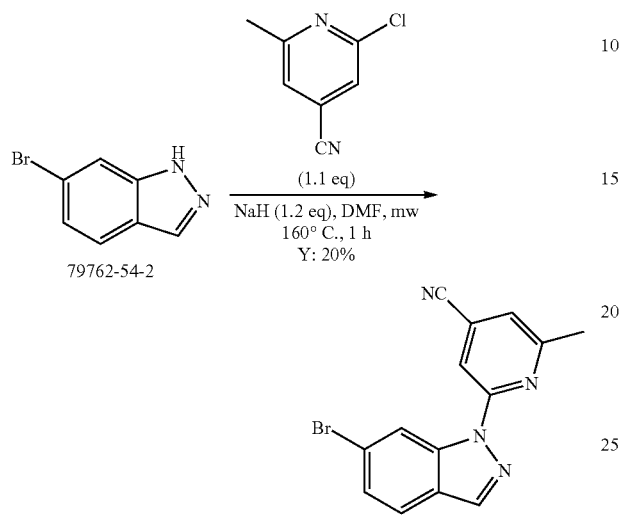

The preparation of 2-(6-bromo-1H-indazol-1-yl)-6-methylisonicotinonitrile was the same as that of 6-bromo-1-(6,7-dihydro-5H-cyclopenta[b]pyridin-2-yl)-1H-indazole. 80 mg, as a yellow solid, Y: 20%. ESI-MS (M+H)$^+$: 313.0.

Synthesis of 2-methyl-6-(6-(4,4,5,5-tetramethyl-1,3,2-dioxaborolan-2-yl)-1H-indazol-1-yl)isonicotinonitrile

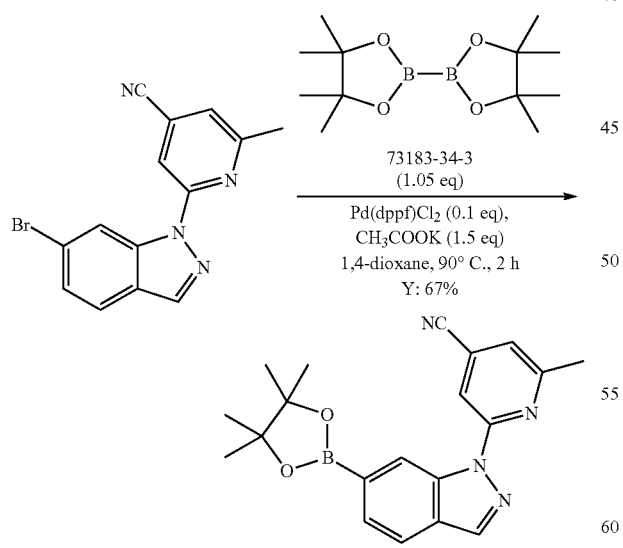

The preparation of 2-methyl-6-(6-(4,4,5,5-tetramethyl-1,3,2-dioxaborolan-2-yl)-1H-indazol-1-yl)isonicotinonitrile was the same as that of 1-(6-methylpyridin-2-yl)-6-(4,4,5,5-tetramethyl-1,3,2-dioxaborolan-2-yl)-1H-indazole. 62 mg, as a yellow solid, Y: 67%. ESI-MS (M+H)$^+$: 361.2.

Synthesis of 2-(6-(5-aminopyridin-3-yl)-1H-indazol-1-yl)-6-methylisonicotinonitrile

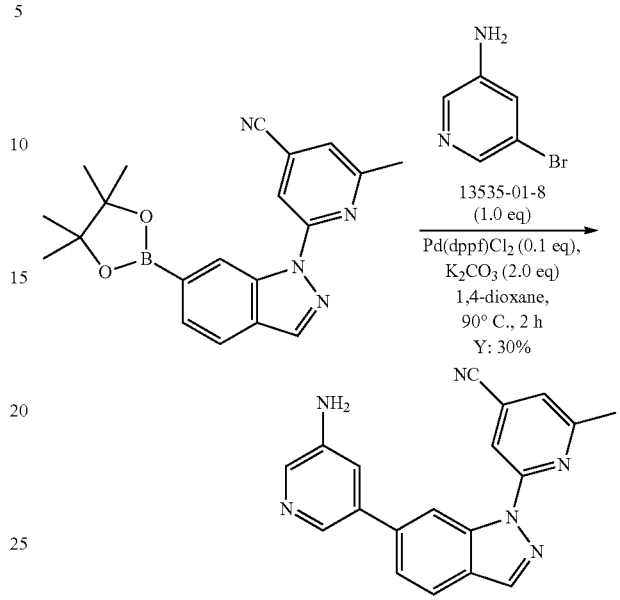

The preparation of 2-(6-(5-aminopyridin-3-yl)-1H-indazol-1-yl)-6-methylisonicotinonitrile was the same as that of 6-bromo-1-(6,7-dihydro-5H-cyclopenta[b]pyridin-2-yl)-1H-indazole. 17 mg, as a yellow solid, Y: 30%. ESI-MS (M+H)$^+$: 327.1. HPLC: 100.00%. $^1$H NMR (400 MHz, CD$_3$OD) δ: 9.05 (s, 1H), 8.35 (s, 1H), 8.14 (s, 1H), 8.13 (s, 1H), 8.01 (d, J=2.4 Hz, 1H), 7.94 (d, J=8.4 Hz, 1H), 7.58 (dd, J=8.0, 1.6 Hz, 1H), 7.43-7.41 (m, 2H), 2.72 (s, 3H).

Example 35. 2-(6-(5-aminopyridin-3-yl)-1H-indazol-1-yl)isonicotinonitrile

Synthesis of 2-(6-bromo-1H-indazol-1-yl)isonicotinonitrile

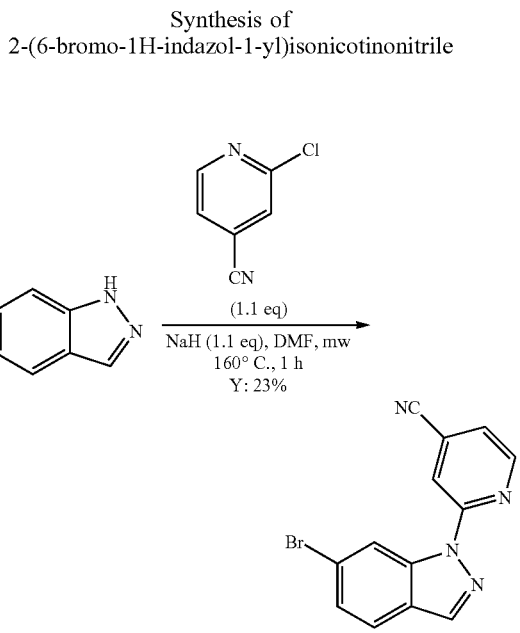

The preparation of 2-(6-bromo-1H-indazol-1-yl)isonicotinonitrile was the same as that of 6-bromo-1-(6,7-dihydro- 5H-cyclopenta[b]pyridin-2-yl)-1H-indazole. 76 mg, as a yellow solid, Y: 23%. ESI-MS (M+H)⁺: 299.0.

Synthesis of 2-(6-(4,4,5,5-tetramethyl-1,3,2-dioxaborolan-2-yl)-1H-indazol-1-yl)isonicotinonitrile

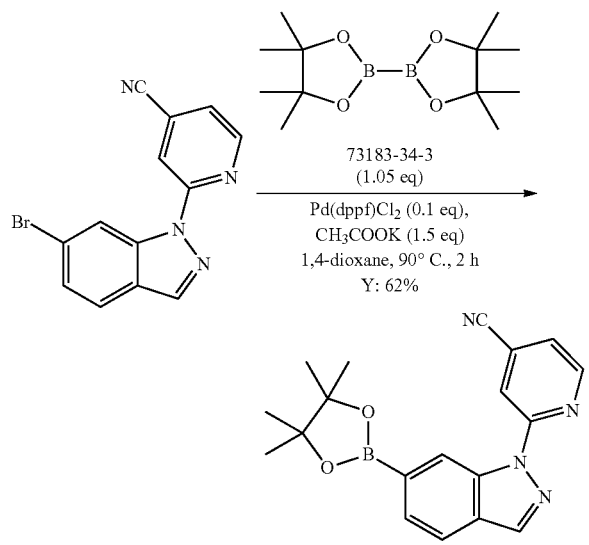

The preparation of 2-(6-(4,4,5,5-tetramethyl-1,3,2-dioxaborolan-2-yl)-1H-indazol-1-yl)isonicotinonitrile was the same as that of 1-(6-methylpyridin-2-yl)-6-(4,4,5,5-tetramethyl-1,3,2-dioxaborolan-2-yl)-1H-indazole. 54 mg, as a yellow solid, Y: 62%. ESI-MS (M+H)⁺: 347.2.

Synthesis of 2-(6-(5-aminopyridin-3-yl)-1H-indazol-1-yl)isonicotinonitrile

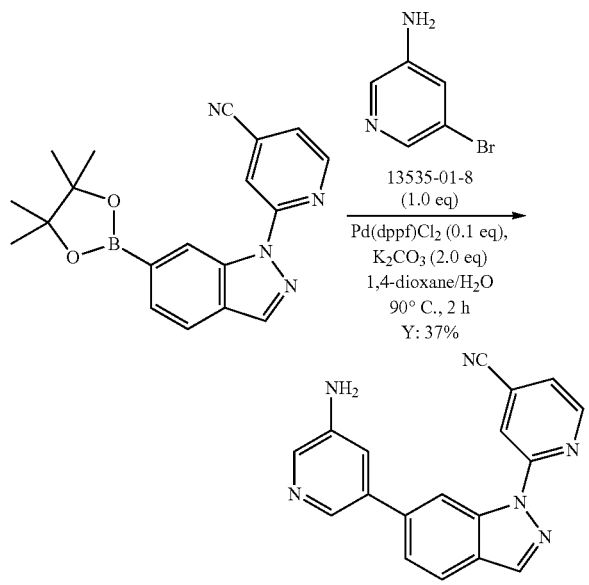

The preparation of 2-(6-(5-aminopyridin-3-yl)-1H-indazol-1-yl)isonicotinonitrile was the same as that of 6-bromo-1-(6,7-dihydro-5H-cyclopenta[b]pyridin-2-yl)-1H-indazole.

18 mg, as a yellow solid, Y: 37%. ESI-MS (M+H)⁺: 313.1. HPLC: 100.00%. ¹H NMR (400 MHz, CD₃OD) δ: 9.02 (s, 1H), 8.77 (dd, J=4.8, 0.4 Hz, 1H), 8.38 (s, 2H), 8.13 (d, J=1.6 Hz, 1H), 8.01 (d, J=2.4 Hz, 1H), 7.95 (d, J=8.4 Hz, 1H), 7.59 (dd, J=8.4, 1.6 Hz, 1H), 7.45 (d, J=5.6 Hz, 1H), 7.44-7.43 (m, 1H).

Example 36. 5-(1-(4-methylpyrimidin-2-yl)-1H-indazol-6-yl)pyridin-3-amine

Synthesis of 6-bromo-1-(4-methylpyrimidin-2-yl)-1H-indazole

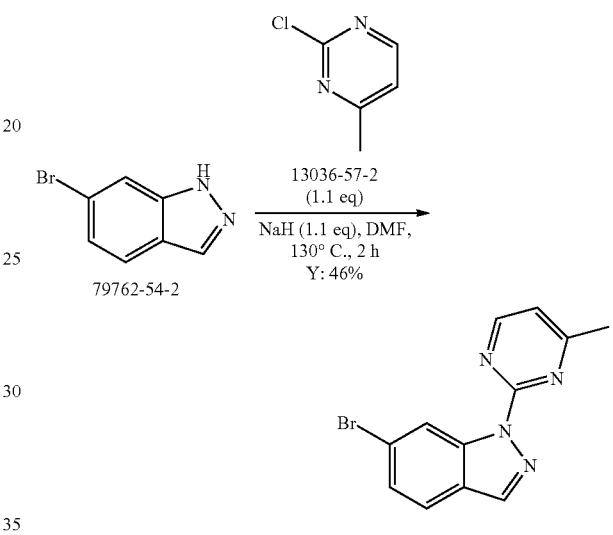

The preparation of 6-bromo-1-(4-methylpyrimidin-2-yl)-1H-indazole was the same as that of 6-bromo-1-(6,7-dihydro-5H-cyclopenta[b]pyridin-2-yl)-1H-indazole. 200 mg, as a yellow solid, Y: 46%. ESI-MS (M+H)⁺: 289.0.

Synthesis of 1-(4-methylpyrimidin-2-yl)-6-(4,4,5,5-tetramethyl-1,3,2-dioxaborolan-2-yl)-1H-indazole

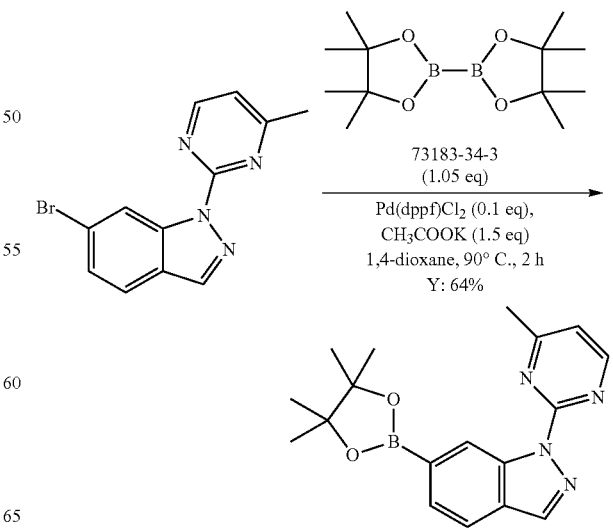

The preparation of 1-(4-methylpyrimidin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 150 mg, as a yellow solid, Y: 64%. ESI-MS (M+H)+: 337.2.

Synthesis of 5-(1-(4-methylpyrimidin-2-yl)-1H-indazol-6-yl)pyridin-3-amine

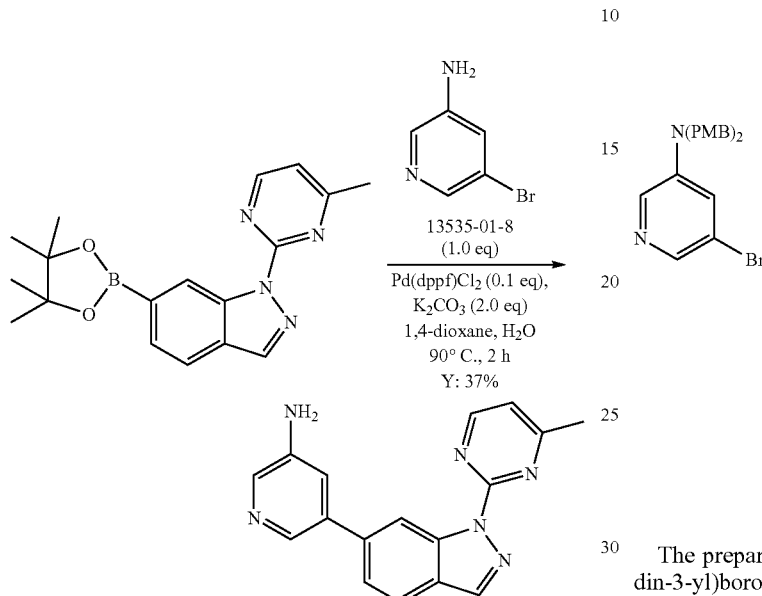

The preparation of 5-(1-(4-methylpyrimidin-2-yl)-1H-indazol-6-yl)pyridin-3-amine was the same as that of 6-bromo-1-(6,7-dihydro-5H-cyclopenta[b]pyridin-2-yl)-1H-indazole. 47 mg, as a yellow solid, Y: 37%. ESI-MS (M+H)+: 312.1. HPLC: 98.55%. $^1$H NMR (400 MHz, CD$_3$OD) δ: 9.06 (s, 1H), 8.74 (d, J=5.2 Hz, 1H), 8.44 (s, 1H), 8.17 (d, J=1.2 Hz, 1H), 8.03 (d, J=2.0 Hz, 1H), 7.99 (d, J=8.4 Hz, 1H), 7.63 (dd, J=8.4, 1.6 Hz, 1H), 7.46 (t, J=2.0 Hz, 1H), 7.28 (d, J=4.8 Hz, 1H), 2.69 (s, 3H).

Example 37. 2-(6-(5-aminopyridin-3-yl)-1H-indazol-1-yl)pyrimidine-4-carbonitrile Synthesis of 5-bromo-N,N-bis(4-methoxybenzyl)pyridin-3-amine

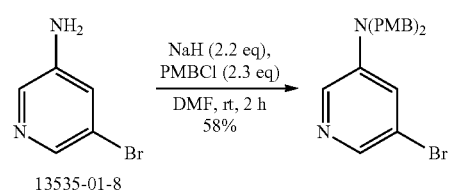

To a solution of 5-bromopyridin-3-amine (CAS#13535-01-8) (1 g, 5.81 mmol) in DMF (10 mL) was added NaH (512 mg, 12.8 mmol, 2.2 eq) at 0° C. Then, PMBCl (2.09 g, 13.37 mmol, 2.3 eq) was added to the mixture. The mixture was stirred at rt for 2 h and diluted with water (50 mL). After filtration, the residue was purified by silica gel chromatography with PE/EA (10/1) as eluent to give 5-bromo-N,N-bis(4-methoxybenzyl)pyridin-3-amine as yellow oil. 1.4 g, Y: 58%. ESI-MS (M+H)+: 413.0.

Synthesis of (5-(bis(4-methoxybenzyl)amino)pyridin-3-yl)boronic acid

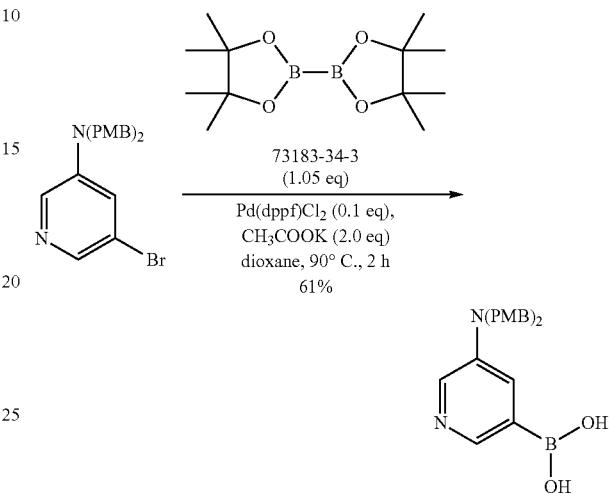

The preparation of (5-(bis(4-methoxybenzyl)amino)pyridin-3-yl)boronic acid was the same as that of 1-(6-methylpyridin-2-yl)-6-(4,4,5,5-tetramethyl-1,3,2-dioxaborolan-2-yl)-1H-indazole. 280 mg, as a yellow solid, Y: 61%. ESI-MS (M+H)+: 379.1.

Synthesis of 5-(1H-indazol-6-yl)-N,N-bis(4-methoxybenzyl)pyridin-3-amine

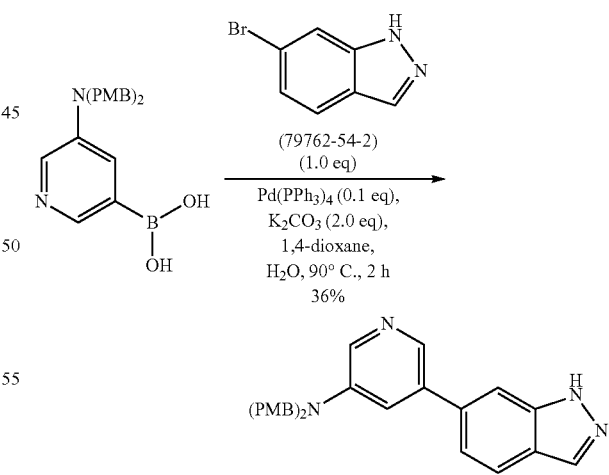

The preparation of 5-(1H-indazol-6-yl)-N,N-bis(4-methoxybenzyl)pyridin-3-amine was the same as that of 6-bromo-1-(6,7-dihydro-5H-cyclopenta[b]pyridin-2-yl)-1H-indazole except palladiumtetrakis was used. 120 mg, as a yellow solid, Y: 36%. ESI-MS (M+H)+: 451.1. $^1$H NMR (400 MHz, DMSO-d$_6$) δ: 13.16 (s, 1H), 8.14 (d, J=1.2 Hz, 1H), 8.09 (s, 1H), 8.04 (d, J=2.8 Hz, 2H), 7.81 (d, J=8.0 Hz, 1H), 7.30-7.28 (m, 2H), 7.24 (d, J=8.4 Hz, 4H), 6.91 (d, J=8.4 Hz, 4H), 4.74 (s, 4H), 3.72 (s, 6H).

Synthesis of 2-(6-(5-(bis(4-methoxybenzyl)amino) pyridin-3-yl)-1H-indazol-1-yl)pyrimidine-4-carbonitrile

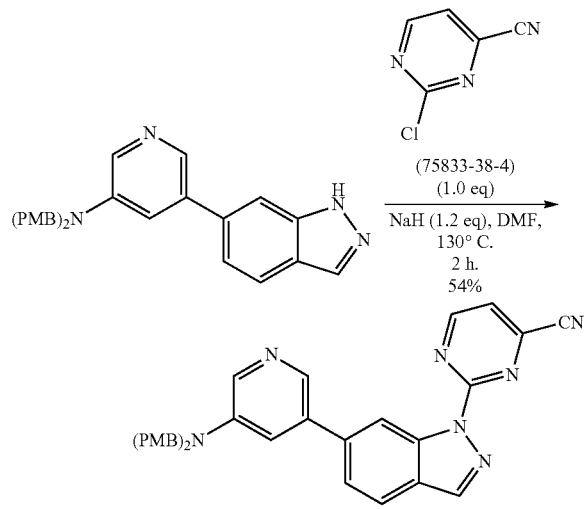

The preparation of 2-(6-(5-(bis(4-methoxybenzyl)amino)pyridin-3-yl)-1H-indazol-1-yl)pyrimidine-4-carbonitrile was the same as that of 6-bromo-1-(6,7-dihydro-5H-cyclopenta[b]pyridin-2-yl)-1H-indazole. 80 mg, as yellow oil, Y: 54%. ESI-MS (M+H)$^+$: 554.1.

Synthesis of 2-(6-(5-aminopyridin-3-yl)-1H-indazol-1-yl)pyrimidine-4-carbonitrile

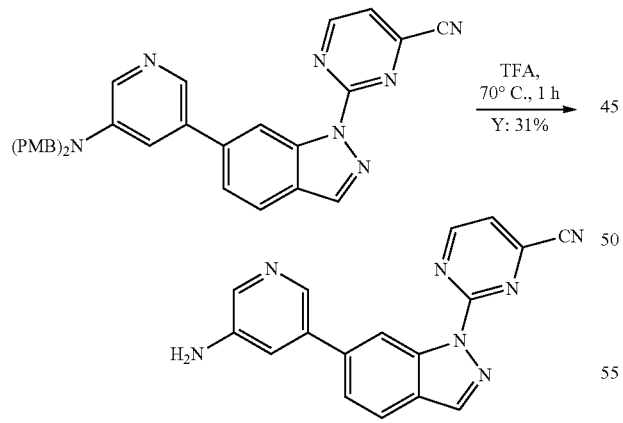

A solution of 2-(6-(5-(bis(4-methoxybenzyl)amino)pyridin-3-yl)-1H-indazol-1-yl)pyrimidine-4-carbonitrile (80 mg, 0.267 mmol) in TFA (5 mL) was stirred at 70° C. for 1 h. After concentration, the residue was purified by pre-HPLC (CH$_3$CN/0.5% TFA in H$_2$O, 5%-95%) to give 2-(6-(5-aminopyridin-3-yl)-1H-indazol-1-yl)pyrimidine-4-carbonitrile as yellow oil. 14 mg, Y: 31%. ESI-MS (M+H)$^+$: 313.1. HPLC: 98.15% $^1$H NMR (400 MHz, CD$_3$OD) δ: 9.03 (s, 1H), 8.91 (d, J=5.6 Hz, 1H), 8.56 (d, J=0.4 Hz, 1H), 8.34 (s, 1H), 8.31 (d, J=6.0 Hz, 1H), 8.10-8.07 (m, 2H), 8.00-7.99 (m, 1H), 7.74 (dd, J=8.4, 1.6 Hz, 1H).

Example 38. 5-(1-(3-chloro-6-methylpyridin-2-yl)-1H-indazol-6-yl)pyridin-3-amine Synthesis of 6-bromo-1-(3-chloro-6-methylpyridin-2-yl)-1H-indazole

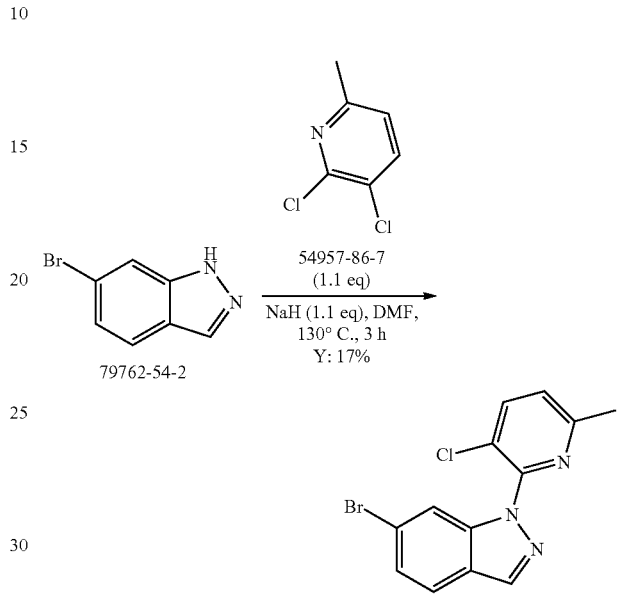

The preparation of 6-bromo-1-(3-chloro-6-methylpyridin-2-yl)-1H-indazole was the same as that of 6-bromo-1-(6,7-dihydro-5H-cyclopenta[b]pyridin-2-yl)-1H-indazole. 80 mg, as a yellow solid, Y: 17%. ESI-MS (M+H)$^+$: 322.0.

Synthesis of 1-(3-chloro-6-methylpyridin-2-yl)-6-(4,4,5,5-tetramethyl-1,3,2-dioxaborolan-2-yl)-1H-indazole

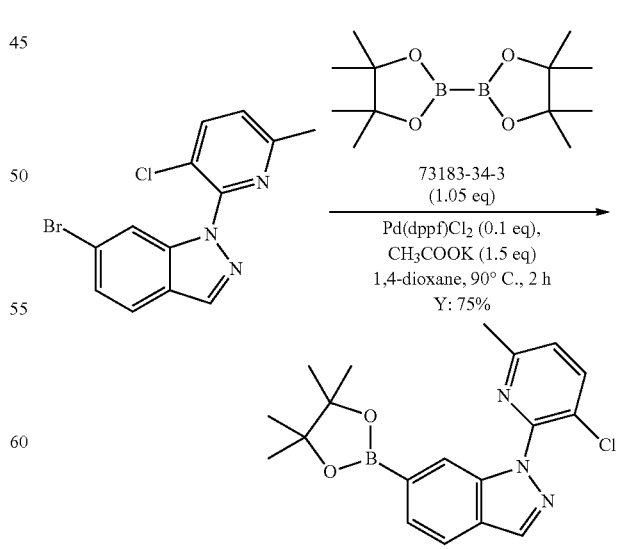

The preparation of 1-(3-chloro-6-methylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 70 mg, as a yellow solid, Y: 75%. ESI-MS (M+H)+: 370.1.

Synthesis of 5-(1-(3-chloro-6-methylpyridin-2-yl)-1H-indazol-6-yl)pyridin-3-amine

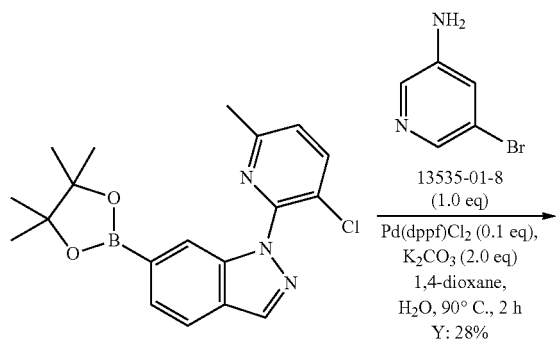

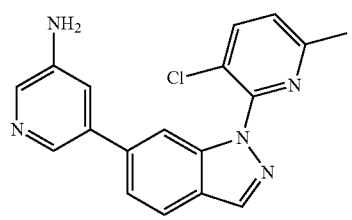

The preparation of 5-(1-(3-chloro-6-methylpyridin-2-yl)-1H-indazol-6-yl)pyridin-3-amine was the same as that of 6-bromo-1-(6,7-dihydro-5H-cyclopenta[b]pyridin-2-yl)-1H-indazole. 18 mg, as a yellow solid, Y: 28%. ESI-MS (M+H)+: 336.1. HPLC: 100.00%. $^1$H NMR (400 MHz, CD$_3$OD) δ: 8.22 (d, J=0.8 Hz, 1H), 7.49 (d, J=1.6 Hz, 1H), 7.91 (d, J=8.0 Hz, 1H), 7.86-7.82 (m, 2H), 7.58 (s, 1H), 7.40 (dd, J=8.8, 1.6 Hz, 1H), 7.30 (d, J=8.0 Hz, 1H), 7.24 (t, J=2.4 Hz, 1H), 2.48 (s, 3H).

Example 39. 5-(1-(4-methylpyridin-2-yl)-1H-indazol-6-yl)pyridin-3-amine

Synthesis of 6-bromo-1-(4-methylpyridin-2-yl)-1H-indazole

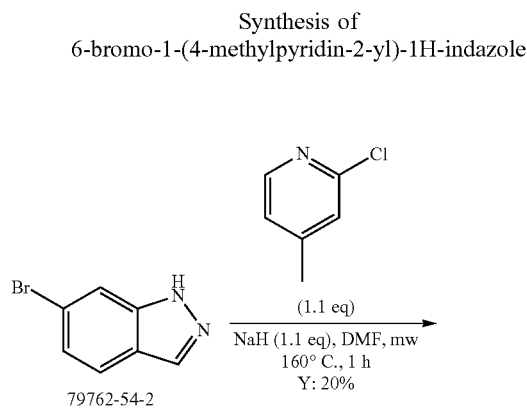

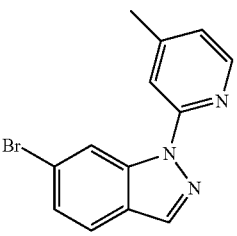

The preparation of 6-bromo-1-(4-methylpyridin-2-yl)-1H-indazole was the same as that of 6-bromo-1-(6,7-dihydro-5H-cyclopenta[b]pyridin-2-yl)-1H-indazole. 150 mg, as a yellow solid, Y: 20%. ESI-MS (M+H)+: 288.0.

Synthesis of 1-(4-methylpyridin-2-yl)-6-(4,4,5,5-tetramethyl-1,3,2-dioxaborolan-2-yl)-1H-indazole

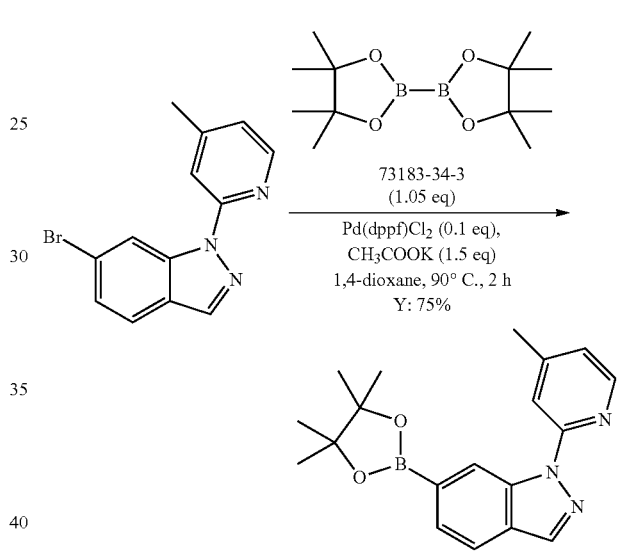

The preparation of 1-(4-methylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 131 mg, as a yellow solid, Y: 75%. ESI-MS (M+H)+: 336.2.

Synthesis of 5-(1-(4-methylpyridin-2-yl)-1H-indazol-6-yl)pyridin-3-amine

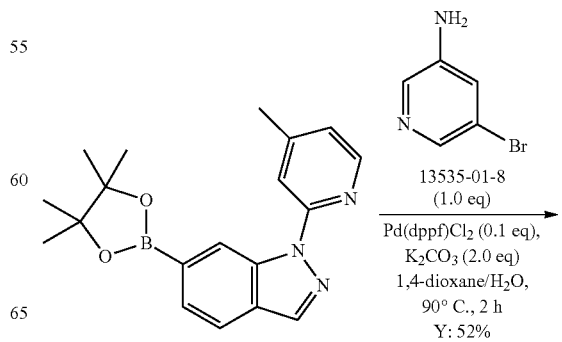

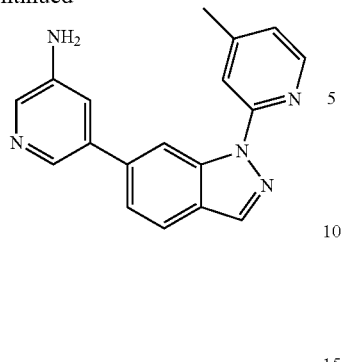

The preparation of 5-(1-(4-methylpyridin-2-yl)-1H-indazol-6-yl)pyridin-3-amine was the same as that of 6-bromo-1-(6,7-dihydro-5H-cyclopenta[b]pyridin-2-yl)-1H-indazole. 62 mg, as a yellow solid, Y: 52%. ESI-MS (M+H)⁺: 302.0. HPLC: 95.23%. ¹H NMR (400 MHz, CDCl₃) δ: 9.04 (s, 1H), 8.40-8.39 (m, 2H), 8.21 (d, J=0.8 Hz, 1H), 8.13 (d, J=2.4 Hz, 1H), 7.90 (s, 1H), 7.83 (dd, J=8.4, 0.4 Hz, 1H), 7.46 (dd, J=8.0, 1.6 Hz, 1H), 7.32 (s, 1H), 7.00 (d, J=0.8 Hz, 1H), 3.83 (br, 2H), 2.46 (s, 3H).

Example 40. 5-(1-(6-(trifluoromethyl)pyridin-2-yl)-1H-indazol-6-yl)pyridin-3-amine Synthesis of 6-bromo-1-(6-(trifluoromethyl)pyridin-2-yl)-1H-indazole

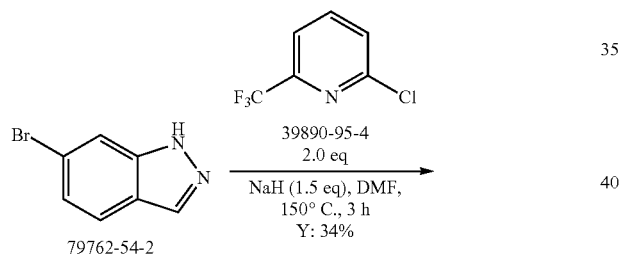

The preparation of 6-bromo-1-(6-(trifluoromethyl)pyridin-2-yl)-1H-indazole was the same as that of 6-bromo-1-(6,7-dihydro-5H-cyclopenta[b]pyridin-2-yl)-1H-indazole. 600 mg, as a yellow solid, Y: 34%. ESI-MS (M+H)⁺: 342.0.

Synthesis of 6-(4,4,5,5-tetramethyl-1,3,2-dioxaborolan-2-yl)-1-(6-(trifluoromethyl)pyridin-2-yl)-1H-indazole

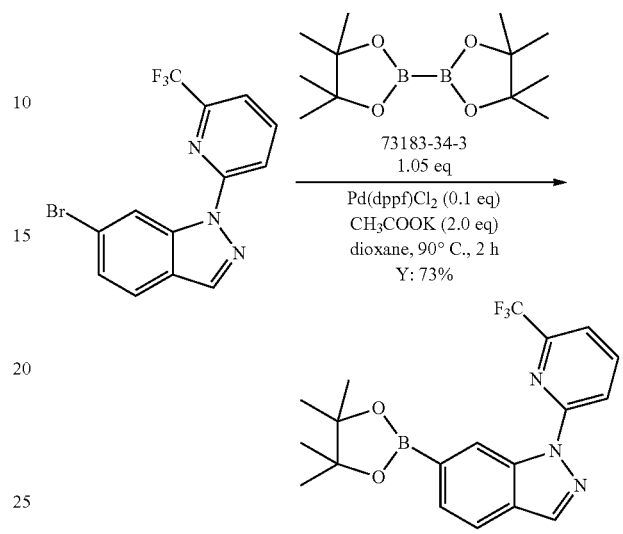

The preparation of 6-(4,4,5,5-tetramethyl-1,3,2-dioxaborolan-2-yl)-1-(6-(trifluoromethyl)pyridin-2-yl)-1H-indazole was the same as that of 1-(6-methylpyridin-2-yl)-6-(4,4,5,5-tetramethyl-1,3,2-dioxaborolan-2-yl)-1H-indazole. 500 mg, as a yellow solid, Y: 73%. ESI-MS (M+H)⁺: 390.2.

Synthesis of 5-(1-(6-(trifluoromethyl)pyridin-2-yl)-1H-indazol-6-yl)pyridin-3-amine

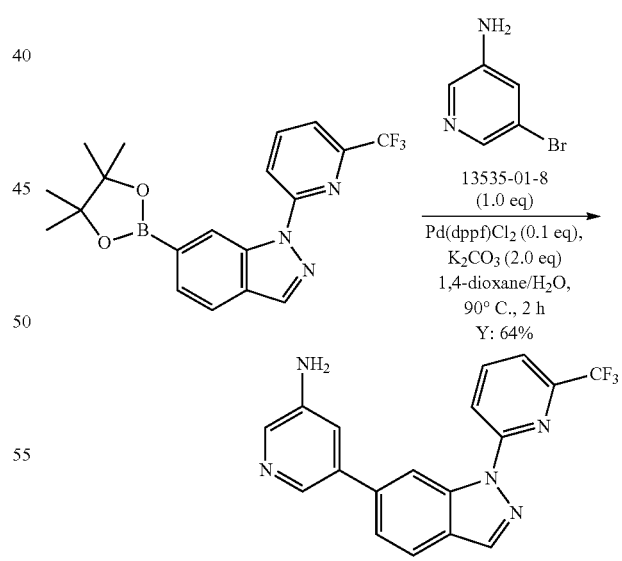

The preparation of 5-(1-(6-(trifluoromethyl)pyridin-2-yl)-1H-indazol-6-yl)pyridin-3-amine was the same as that of 6-bromo-1-(6,7-dihydro-5H-cyclopenta[b]pyridin-2-yl)-1H-indazole. 146 mg, as a yellow solid, Y: 64%. ESI-MS (M+H)⁺: 356.1. HPLC: 94.10%. ¹H NMR (400 MHz, CD₃OD) δ: 9.12 (s, 1H), 8.38 (s, 1H), 8.35 (d, J=8.4 Hz, 1H), 8.19-8.17 (m, 2H), 8.03 (d, J=2.4 Hz, 1H), 7.97 (d, J=8.4 Hz, 1H), 7.69 (d, J=7.6 Hz, 1H), 7.61 (dd, J=8.4, 1.6 Hz, 1H), 7.44 (t, J=2.4 Hz, 1H).

Example 41. 5-(3-(6-methylpyridin-2-yl)imidazo[1,5-a]pyridin-6-yl)pyridin-3-amine Synthesis of N-((5-bromopyridin-2-yl)methyl)-6-methylpicolinamide

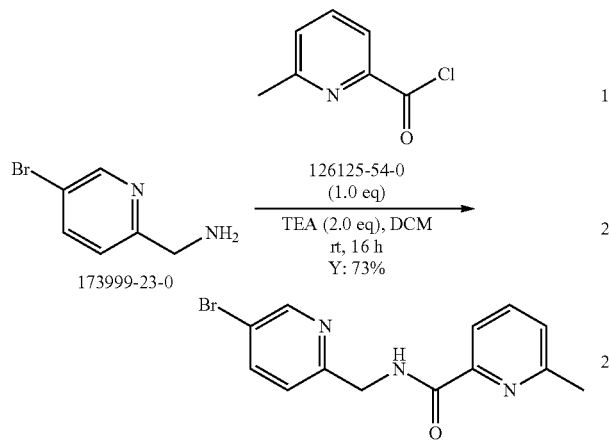

A mixture of (5-bromopyridin-2-yl)methanamine (CAS#173999-23-0) (250 mg, 1.34 mmol), 6-methylpicolinoyl chloride (CAS#126125-54-0) (208 mg, 1.34 mmol, 1.0 eq) and TEA (270 mg, 2.68 mmol, 2.0 eq) in DCM (10 mL) was stirred at rt for 16 h. After concentration, the residue was purified by silica gel chromatography with PE/EA (8/1) as eluent. 300 mg, as a yellow solid, Y: 73%. ESI-MS (M+H)$^+$: 306.1.

Synthesis of 6-bromo-3-(6-methylpyridin-2-yl)imidazo[1,5-a]pyridine

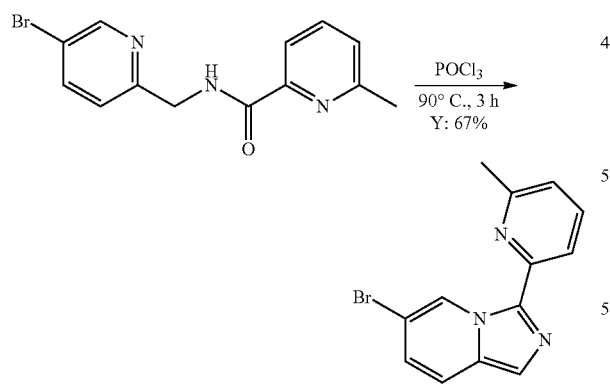

A solution of N-((5-bromopyridin-2-yl)methyl)-6-methylpicolinamide (250 mg, 0.82 mmol) in POCl$_3$ (5 mL) was stirred at 90° C. for 3 h. After cooling down to rt, the mixture was poured into ice-water (30 mL) and stirred for 30 min. After filtration, the residue was purified by pre-TLC (PE/EA=10/1). 190 mg, as a yellow solid, Y: 67%. ESI-MS (M+H)$^+$: 288.0. $^1$H NMR (400 MHz, CDCl$_3$) δ: 10.28 (s, 1H), 8.16 (d, J=8.0 Hz, 1H), 7.70 (t, J=7.6 Hz, 1H), 7.61 (s, 1H), 7.44 (d, J=9.2 Hz, 1H), 7.11 (d, J=7.6 Hz, 1H), 6.93 (dd, J=9.6, 1.6 Hz, 1H), 2.67 (s, 3H).

Synthesis of 3-(6-methylpyridin-2-yl)-6-(4,4,5,5-tetramethyl-1,3,2-dioxaborolan-2-yl)imidazo[1,5-a]pyridine

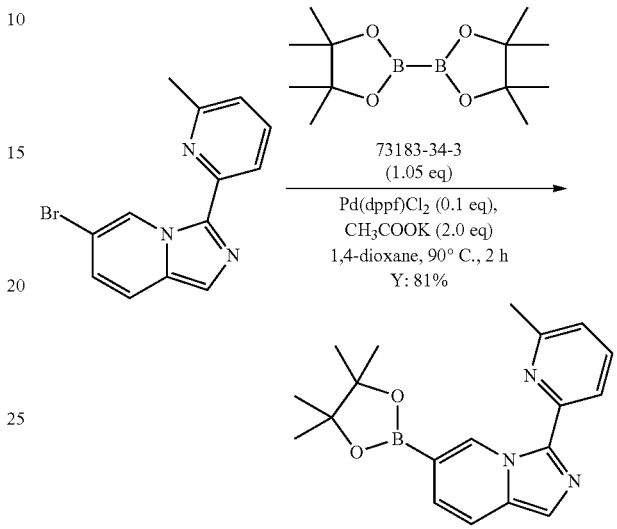

The preparation of 3-(6-methylpyridin-2-yl)-6-(4,4,5,5-tetramethyl-1,3,2-dioxaborolan-2-yl)imidazo[1,5-a]pyridine was the same as that of 1-(6-methylpyridin-2-yl)-6-(4,4,5,5-tetramethyl-1,3,2-dioxaborolan-2-yl)-1H-indazole. 180 mg, as a yellow solid, Y: 81%. ESI-MS (M+H)$^+$: 336.2.

Synthesis of 5-(3-(6-methylpyridin-2-yl)imidazo[1,5-a]pyridin-6-yl)pyridin-3-amine

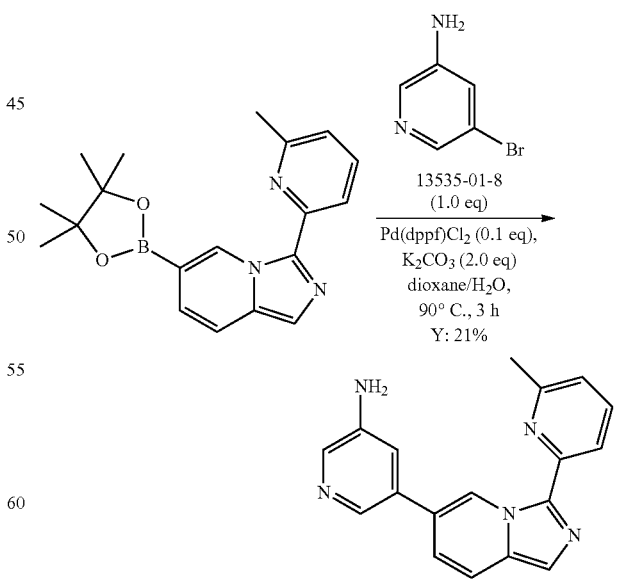

The preparation of 5-(3-(6-methylpyridin-2-yl)imidazo[1,5-a]pyridin-6-yl)pyridin-3-amine was the same as that of 6-bromo-1-(6,7-dihydro-5H-cyclopenta[b]pyridin-2-yl)-

1H-indazole. 17 mg, as a yellow solid, Y: 21%. ESI-MS (M+H)+: 301.9. HPLC: 96.34%. 1H NMR (400 MHz, CD3OD) δ: 10.29 (s, 1H), 8.07 (d, J=1.6 Hz, 1H), 7.98-7.96 (m, 2H), 7.76 (d, J=8.0 Hz, 1H), 7.72 (d, J=8.0 Hz, 1H), 7.58 (s, 1H), 7.25 (t, J=2.0 Hz, 1H), 7.21-7.17 (m, 2H), 2.62 (s, 3H).

Example 42. 3-(3-(6-methylpyridin-2-yl)imidazo[1,5-a]pyridin-6-yl)aniline

Synthesis of 3-(3-(6-methylpyridin-2-yl)imidazo[1,5-a]pyridin-6-yl)aniline

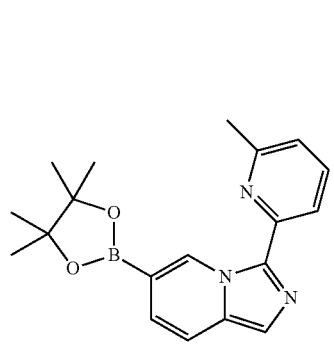
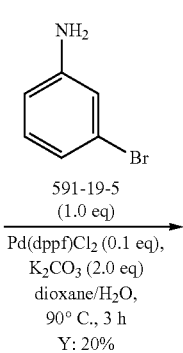

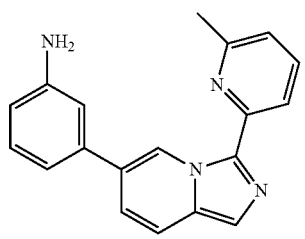

The preparation of 3-(3-(6-methylpyridin-2-yl)imidazo[1,5-a]pyridin-6-yl)aniline was the same as that of 6-bromo-1-(6,7-dihydro-5H-cyclopenta[b]pyridin-2-yl)-1H-indazole. 16 mg, as a yellow solid, Y: 20%. ESI-MS (M+H)+: 301.0. HPLC: 97.85%. 1H NMR (400 MHz, CDCl3) δ: 10.33 (s, 1H), 8.14 (d, J=8.0 Hz, 1H), 7.69 (t, J=7.6 Hz, 1H), 7.59-7.57 (m, 2H), 7.29 (d, J=8.0 Hz, 1H), 7.14 (dd, J=9.2, 1.6 Hz, 1H), 7.07 (d, J=7.6 Hz, 2H), 6.98 (t, J=1.6 Hz, 1H), 6.73 (dd, J=8.4, 2.0 Hz, 1H), 3.81 (br, 2H), 2.65 (s, 3H).

Example 43. 5-(5-fluoro-1-(6-methylpyridin-2-yl)-1H-indazol-6-yl)pyridin-3-amine Synthesis of 6-bromo-5-fluoro-1-(6-methylpyridin-2-yl)-1H-indazole

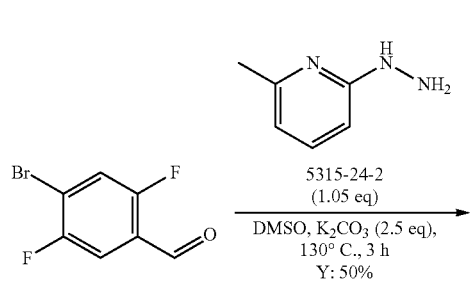

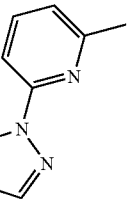

A mixture of 4-bromo-2,5-difluorobenzaldehyde (CAS#357405-75-5) (220 mg, 1.0 mmol), 2-hydrazinyl-6-methylpyridine (CAS#5315-24-2) (129 g, 1.05 mmol, 1.05 eq) and K2CO3 (2.5 eq) in DMSO (2 mL) was stirred at 130° C. for 3 h. The mixture was diluted with H2O (15 mL) and extracted with DCM (20 mL×2). The combined organic fractions were dried, concentrated and purified by silica gel chromatography with PE/EA (8/1) as eluent to give 6-bromo-5-fluoro-1-(6-methylpyridin-2-yl)-1H-indazole. 153 mg, as a white solid, Y: 50%. ESI-MS (M+H)+: 306.2, 308.2.

Synthesis of 5-fluoro-1-(6-methylpyridin-2-yl)-6-(4,4,5,5-tetramethyl-1,3,2-dioxaborolan-2-yl)-1H-indazole

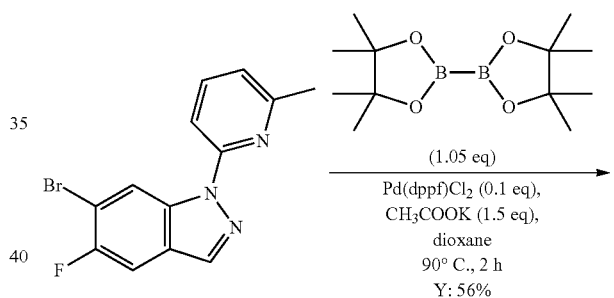

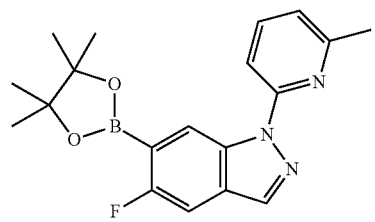

The preparation of 5-fluoro-1-(6-methylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 100 mg, as a yellow solid, Y: 56%. ESI-MS (M+H)+: 354.2.

Synthesis of 5-(5-fluoro-1-(6-methylpyridin-2-yl)-1H-indazol-6-yl)pyridin-3-amine

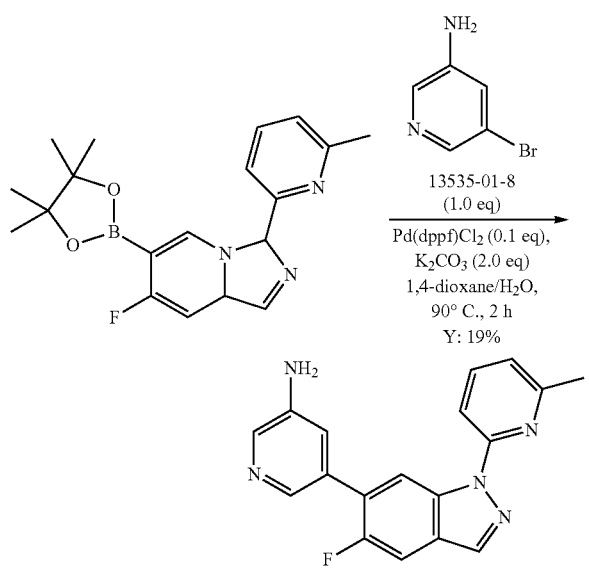

The preparation of 5-(5-fluoro-1-(6-methylpyridin-2-yl)-1H-indazol-6-yl)pyridin-3-amine was the same as that of 6-bromo-1-(6,7-dihydro-5H-cyclopenta[b]pyridin-2-yl)-1H-indazole. 16 mg, as a yellow solid, Y: 19%. ESI-MS (M+H)+: 320.2. HPLC: 100.00%. $^1$H NMR (400 MHz, CD$_3$OD) δ: 8.99 (d, J=6.4 Hz, 1H), 8.27 (s, 1H), 8.04-8.03 (m, 2H), 7.86-7.80 (m, 2H), 7.65 (d, J=10.0 Hz, 1H), 7.38-7.36 (m, 1H), 7.14 (d, J=6.8 Hz, 1H), 2.61 (s, 3H).

Example 44. 5-(5-methyl-1-(6-methylpyridin-2-yl)-1H-indazol-6-yl)pyridin-3-amine Synthesis of 6-bromo-5-methyl-1-(6-methylpyridin-2-yl)-1H-indazole

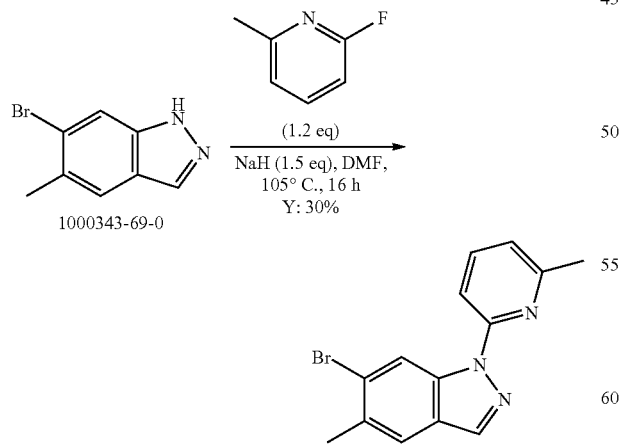

The preparation of 6-bromo-5-methyl-1-(6-methylpyridin-2-yl)-1H-indazole was the same as that of 6-bromo-1-(6,7-dihydro-5H-cyclopenta[b]pyridin-2-yl)-1H-indazole. 210 mg, as a yellow solid, Y: 30%. ESI-MS (M+H)+: 302.1.

$^1$H NMR (400 MHz, CDCl$_3$) δ: 9.14 (s, 1H), 8.07 (s, 1H), 7.79 (d, J=8.0 Hz, 1H), 7.70 (t, J=8.0 Hz, 1H), 7.60 (s, 1H), 7.02 (d, J=8.0 Hz, 1H), 2.66 (s, 3H), 2.53 (s, 3H).

Synthesis of 5-methyl-1-(6-methylpyridin-2-yl)-6-(4,4,5,5-tetramethyl-1,3,2-dioxaborolan-2-yl)-1H-indazole

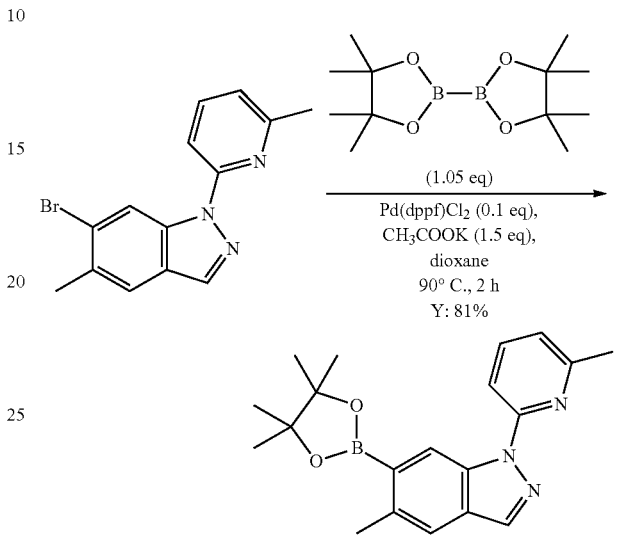

The preparation of 5-methyl-1-(6-methylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 197 mg, as a yellow solid, Y: 81%. ESI-MS (M+H)+: 350.2.

Synthesis of 5-(5-methyl-1-(6-methylpyridin-2-yl)-1H-indazol-6-yl)pyridin-3-amine

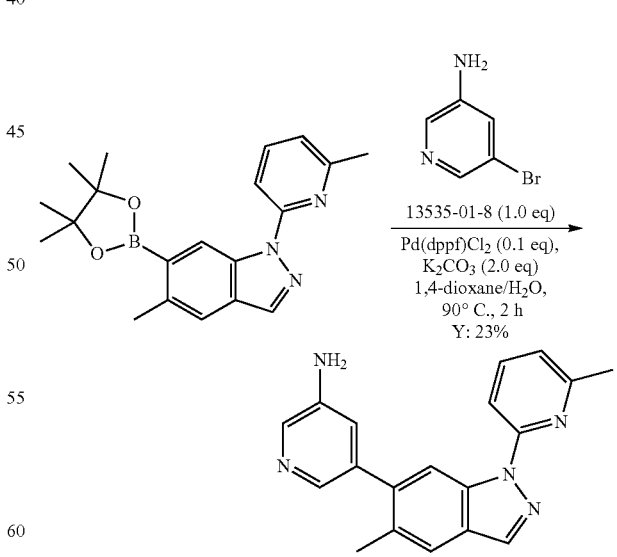

The preparation of 5-(5-methyl-1-(6-methylpyridin-2-yl)-1H-indazol-6-yl)pyridin-3-amine was the same as that of 6-bromo-1-(6,7-dihydro-5H-cyclopenta[b]pyridin-2-yl)-1H-indazole. 45 mg, as a yellow solid, Y: 23%. ESI-MS (M+H)+: 316.1. HPLC: 96.91%. $^1$H NMR (400 MHz, CD₃OD) δ: 8.55 (s, 1H), 8.08 (s, 1H), 7.94 (d, J=2.8 Hz, 1H), 7.74 (d, J=2.0 Hz, 1H), 7.68-7.66 (m, 2H), 7.58 (s, 1H), 7.06 (t, J=2.0 Hz, 1H), 6.96 (d, J=8.0 Hz, 1H), 2.43 (s, 3H), 2.24 (s, 3H).

Example 46. 6-(6-(6-(aminomethyl)pyridin-2-yl)-1H-indazol-1-yl)picolinonitrile

Synthesis of tert-butyl((6-bromopyridin-2-yl)methyl)(2,4-dimethoxybenzyl)carbamate

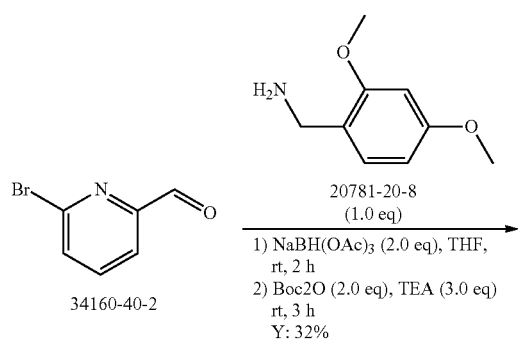

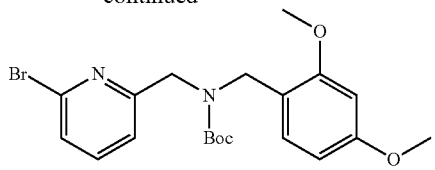

To a mixture of 6-bromopicolinaldehyde (CAS#34160-40-2) (2.0 g, 10.81 mmol, 1.0 eq) and (2,4-dimethoxyphenyl)methanamine (CAS#20781-20-8) (1.81 g, 10.83 mmol, 1.0 eq) in THF (50 mL) was added NaBH(OAc)₃ (4.58 g, 21.62 mmol, 2.0 eq). The mixture was stirred at rt for 2 h. TEA (3.28 g, 32.43 mmol, 3.0 eq) and Boc₂O (4.71 g, 21.62 mmol, 2.0 eq) were added into the mixture. The mixture was stirred at rt for 3 h. After concentration, the residue was purified by silica gel chromatography with PE/EA (6/1) as eluent to give tert-butyl ((6-bromopyridin-2-yl)methyl)(2,4-dimethoxybenzyl)carbamate. 1.51 g, as a white solid, Y: 32%. ESI-MS (M+H)⁺: 437.1. ¹H NMR (400 MHz, CDCl₃) δ: 7.43 (t, J=8.0 Hz, 1H), 7.30 (d, J=8.0 Hz, 1H), 7.24-7.01 (m, 2H), 6.43 (d, J=8.0 Hz, 1H), 6.35 (d, J=2.4 Hz, 1H), 4.57-4.41 (m, 4H), 3.81 (s, 3H), 3.68 (s, 3H), 1.50-1.38 (m, 9H).

Synthesis of tert-butyl ((6-(1-(6-cyanopyridin-2-yl)-1H-indazol-6-yl)pyridin-2-yl)methyl) (2,4-dimethoxybenzyl)carbamate

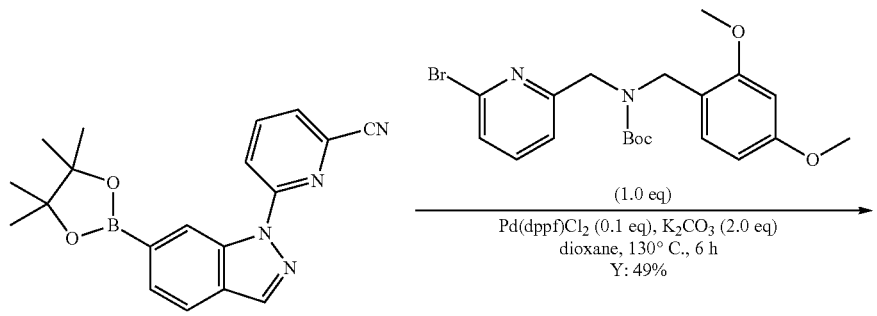

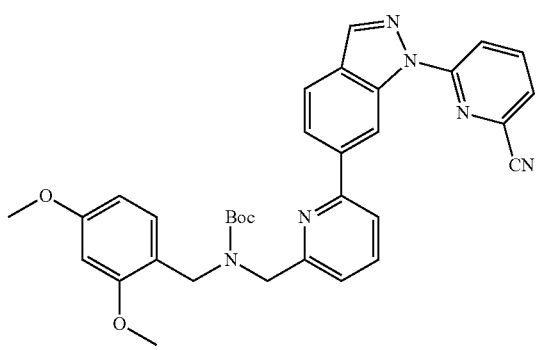

The preparation of tert-butyl ((6-(1-(6-cyanopyridin-2-yl)-1H-indazol-6-yl)pyridin-2-yl)methyl)(2,4-dimethoxybenzyl)carbamate was the same as that of 6-bromo-1-(6,7-dihydro-5H-cyclopenta[b]pyridin-2-yl)-1H-indazole. 350 mg, as a white solid, Y: 49%. ESI-MS (M+H)⁺: 577.2.

Synthesis of 6-(6-(6-(aminomethyl)pyridin-2-yl)-1H-indazol-1-yl)picolinonitrile

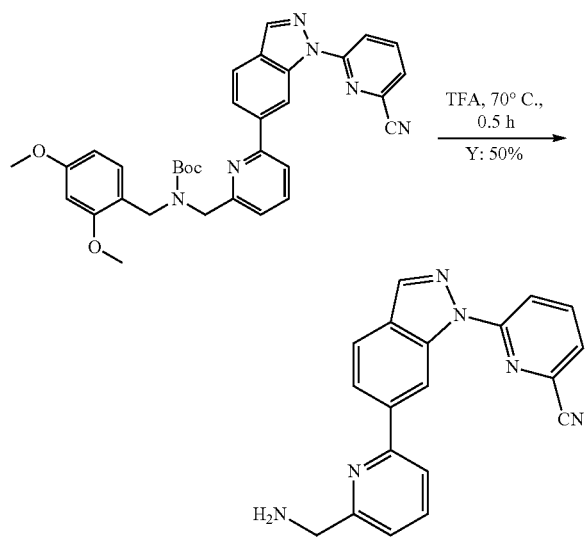

A solution of tert-butyl ((6-(1-(6-cyanopyridin-2-yl)-1H-indazol-6-yl)pyridin-2-yl)methyl)(2,4-dimethoxybenzyl)carbamate (350 mg, 0.61 mmol, 1.0 eq) in TFA (3 mL) was stirred at 70° C. for 0.5 h. After concentration, the residue was purified by pre-HPLC to give 6-(6-(6-(aminomethyl)pyridin-2-yl)-1H-indazol-1-yl)picolinonitrile as a white solid. (100 mg, Y: 50%). ESI-MS (M+H)⁺: 327.1. HPLC: 99.11%. ¹H NMR (400 MHz, CD₃OD) δ: 9.21 (s, 1H), 8.13 (d, J=0.8 Hz, 1H), 8.11 (d, J=8.8, 0.8 Hz, 1H), 7.92 (d, J=8.8, 7.6 Hz, 1H), 7.87 (d, J=8.4, 1.2 Hz, 1H), 7.78 (t, J=7.6 Hz, 1H), 7.71 (d, J=8.8 Hz, 1H), 7.68 (d, J=7.6 Hz, 1H), 7.54 (dd, J=7.2, 0.4 Hz, 1H), 7.27 (d, J=7.6 Hz, 1H), 3.97 (s, 2H).

Example 47. 6-(6-(6-(aminomethyl)pyridin-2-yl)-1H-indazol-1-yl)picolinamide

Synthesis of 6-(6-(6-(aminomethyl)pyridin-2-yl)-1H-indazol-1-yl)picolinamide

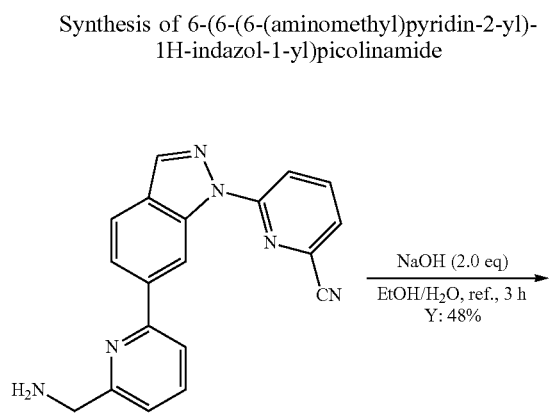

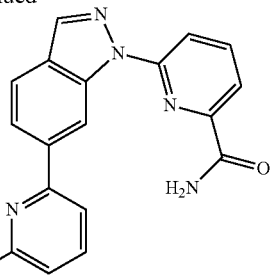

A mixture of 6-(6-(6-(aminomethyl)pyridin-2-yl)-1H-indazol-1-yl)picolinonitrile (51 mg, 0.16 mmol, 1.0 eq) and NaOH (13 mg, 0.32 mmol, 2.0 eq) in EtOH/H₂O (3 mL/1 mL) was refluxed for 3 h. After concentration, the mixture was purified by pre-HPLC to give 6-(6-(6-(aminomethyl)pyridin-2-yl)-1H-indazol-1-yl)picolinamide as a white solid. (26 mg, Y: 48%). ESI-MS (M+H)⁺: 345.0. HPLC: 100.00%. ¹H NMR (400 MHz, CDCl₃) δ: 9.48 (s, 1H), 8.26 (d, J=0.8 Hz, 1H), 8.24 (d, J=8.4, 1.2 Hz, 1H), 8.11 (d, J=7.6, 0.8 Hz, 1H), 8.03 (t, J=8.0 Hz, 1H), 7.94-7.87 (m, 2H), 7.81-7.73 (m, 2H), 7.29 (d, J=7.2 Hz, 1H), 6.06 (br, 2H), 4.08 (s, 2H).

Example 48. (6-(1-(6-(trifluoromethyl)pyridin-2-yl)-1H-indazol-6-yl)pyridin-2-yl)methanamine Synthesis of 6-(1-(6-(trifluoromethyl)pyridin-2-yl)-1H-indazol-6-yl)picolinonitrile

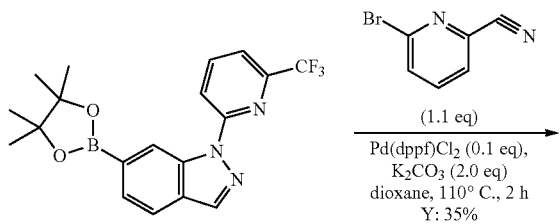

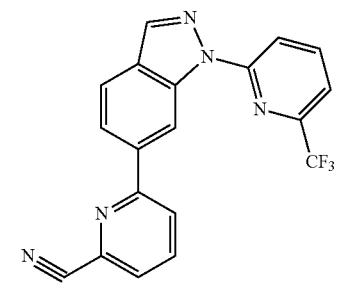

The preparation of 6-(1-(6-(trifluoromethyl)pyridin-2-yl)-1H-indazol-6-yl)picolinonitrile was the same as that of 6-bromo-1-(6,7-dihydro-5H-cyclopenta[b]pyridin-2-yl)-1H-indazole. 74 mg, as a white solid, Y: 35%. ESI-MS (M+H)⁺: 366.1.

Synthesis of (6-(1-(6-(trifluoromethyl)pyridin-2-yl)-1H-indazol-6-yl)pyridin-2-yl)methanamine

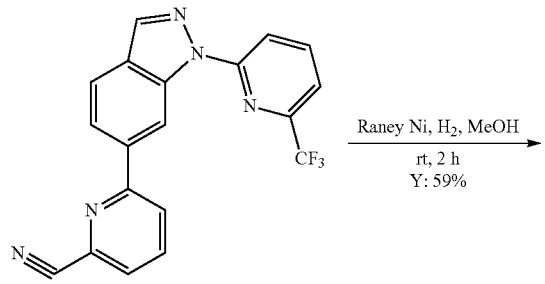

Example 49. methyl 6-(5-aminopyridin-3-yl)-1-(6-cyanopyridin-2-yl)-1H-indazole-4-carboxylate Synthesis of methyl 6-bromo-1-(6-cyanopyridin-2-yl)-1H-indazole-4-carboxylate and methyl 6-bromo-2-(6-cyanopyridin-2-yl)-2H-indazole-4-carboxylate

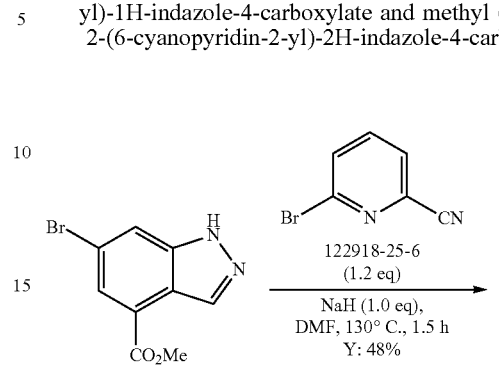

The preparation of methyl 6-bromo-1-(6-cyanopyridin-2-yl)-1H-indazole-4-carboxylate and methyl 6-bromo-2-(6-cyanopyridin-2-yl)-2H-indazole-4-carboxylate was the same as that of 6-bromo-1-(6-methylpyridin-2-yl)-1H-indazole. 400 mg, as a yellow solid, Y: 48%. The mixture of methyl 6-bromo-1-(6-cyanopyridin-2-yl)-1H-indazole-4-carboxylate and methyl 6-bromo-2-(6-cyanopyridin-2-yl)-2H-indazole-4-carboxylate was difficult to be purified due to poor solubility. The mixture was directly used for next step. ESI-MS (M+H)+: 356.9.

The preparation of (6-(1-(6-(trifluoromethyl)pyridin-2-yl)-1H-indazol-6-yl)pyridin-2-yl)methanamine was the same as that of 6-(1-(6-(trifluoromethyl)pyridin-2-yl)-1H-indazol-6-yl)picolinonitrile. 44 mg, as a white solid, Y: 59%. ESI-MS (M+H)+: 370.1. HPLC: 96.14%. ¹H NMR (400 MHz, CD₃OD) δ: 9.55 (s, 1H), 8.36-8.24 (m, 3H), 8.16-8.14 (m, 1H), 7.99-7.94 (m, 3H), 7.69-7.67 (m, 1H), 7.45-7.43 (m, 1H), 4.40 (s, 2H).

Synthesis of methyl 1-(6-cyanopyridin-2-yl)-6-(4,4,5,5-tetramethyl-1,3,2-dioxaborolan-2-yl)-1H-indazole-4-carboxylate and methyl 2-(6-cyanopyridin-2-yl)-6-(4,4,5,5-tetramethyl-1,3,2-dioxaborolan-2-yl)-2H-indazole-4-carboxylate

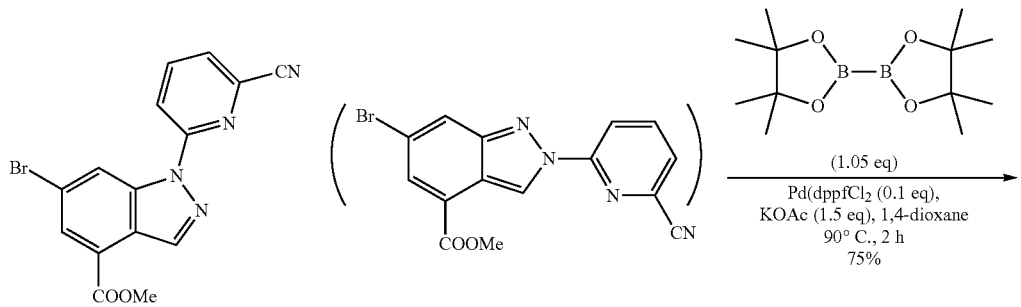

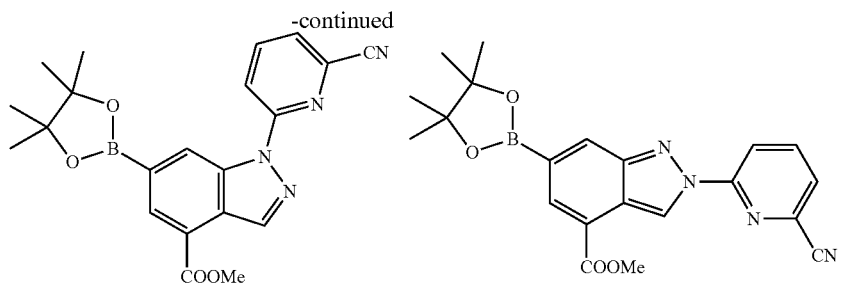

The preparation of methyl 1-(6-cyanopyridin-2-yl)-6-(4,4,5,5-tetramethyl-1,3,2-dioxaborolan-2-yl)-1H-indazole-4-carboxylate and methyl 2-(6-cyanopyridin-2-yl)-6-(4,4,5,5-tetramethyl-1,3,2-dioxaborolan-2-yl)-2H-indazole-4-carboxylate was the same as that of 1-(6-methylpyridin-2-yl)-6-(4,4,5,5-tetramethyl-1,3,2-dioxaborolan-2-yl)-1H-indazole. 340 mg, as a yellow solid, Y: 75%. The mixture of methyl 1-(6-cyanopyridin-2-yl)-6-(4,4,5,5-tetramethyl-1,3,2-dioxaborolan-2-yl)-1H-indazole-4-carboxylate and methyl 2-(6-cyanopyridin-2-yl)-6-(4,4,5,5-tetramethyl-1,3,2-dioxaborolan-2-yl)-2H-indazole-4-carboxylate was directly used for next step without further purification. ESI-MS (M+H)+: 405.1.

Synthesis of methyl 6-(5-aminopyridin-3-yl)-1-(6-cyanopyridin-2-yl)-1H-indazole-4-carboxylate

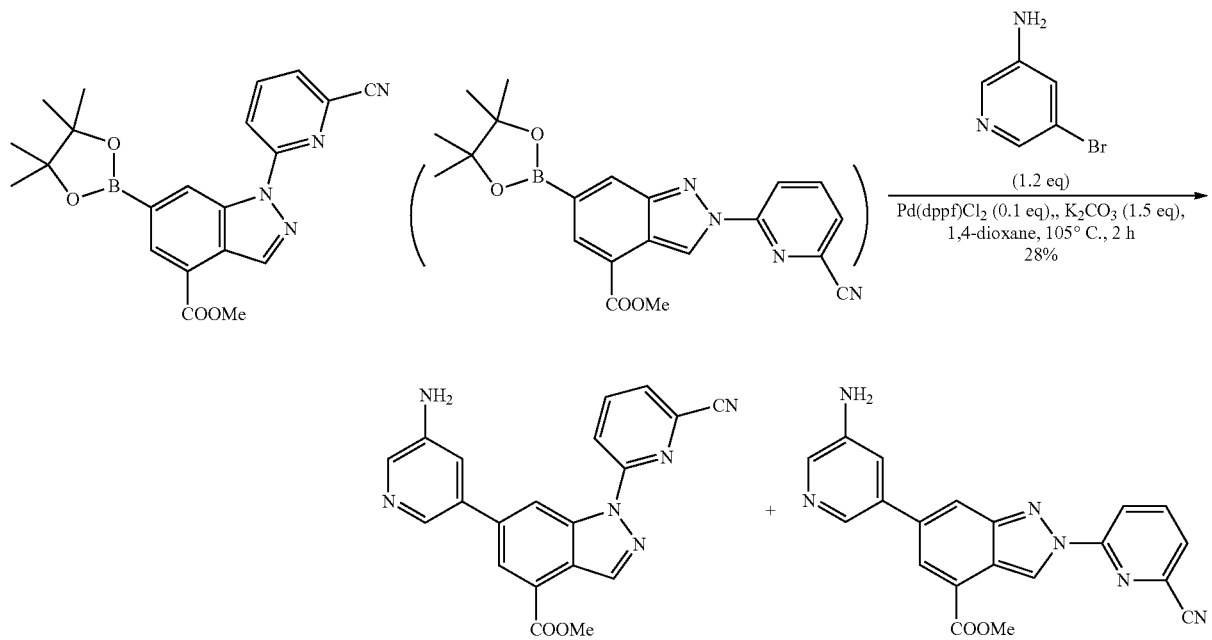

The preparation of methyl 6-(5-aminopyridin-3-yl)-1-(6-cyanopyridin-2-yl)-1H-indazole-4-carboxylate was the same as that of 6-bromo-1-(6,7-dihydro-5H-cyclopenta[b]pyridin-2-yl)-1H-indazole. The mixture of methyl 6-(5-aminopyridin-3-yl)-1-(6-cyanopyridin-2-yl)-1H-indazole-4-carboxylate and methyl 6-(5-aminopyridin-3-yl)-2-(6-cyanopyridin-2-yl)-2H-indazole-4-carboxylate was purified by silica gel chromatography with PE/EA (2/1) as eluent to give methyl 6-(5-aminopyridin-3-yl)-1-(6-cyanopyridin-2-yl)-1H-indazole-4-carboxylate and EA/MeOH (10/1) as eluent to give methyl 6-(5-aminopyridin-3-yl)-2-(6-cyanopyridin-2-yl)-2H-indazole-4-carboxylate. 18 mg of methyl 6-(5-aminopyridin-3-yl)-1-(6-cyanopyridin-2-yl)-1H-indazole-4-carboxylate, as a yellow solid, Y: 28%. ESI-MS (M+H)+: 371.1. HPLC: 93.60%. $^1$H NMR (400 MHz, DMSO-$d_6$) δ: 9.10 (s, 1H), 8.82 (d, J=0.4 Hz, 1H), 8.34 (dd, J=8.4, 0.4 Hz, 1H), 8.27 (t, J=8.0 Hz, 1H), 8.13-8.11 (m, 2H), 8.04 (d, J=2.4 Hz, 1H), 8.01 (dd, J=7.6, 0.8 Hz, 1H), 7.29 (t, J=2.4 Hz, 1H), 5.60 (s, 2H), 4.02 (s, 3H).

Example 50. methyl 6-(5-aminopyridin-3-yl)-1-(6-(trifluoromethyl)pyridin-2-yl)-1H-indazole-4-carboxylate Synthesis of methyl 6-bromo-1-(6-(trifluoromethyl)pyridin-2-yl)-1H-indazole-4-carboxylate and methyl 6-bromo-2-(6-(trifluoromethyl)pyridin-2-yl)-2H-indazole-4-carboxylate

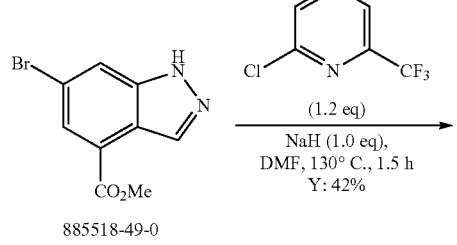

885518-49-0

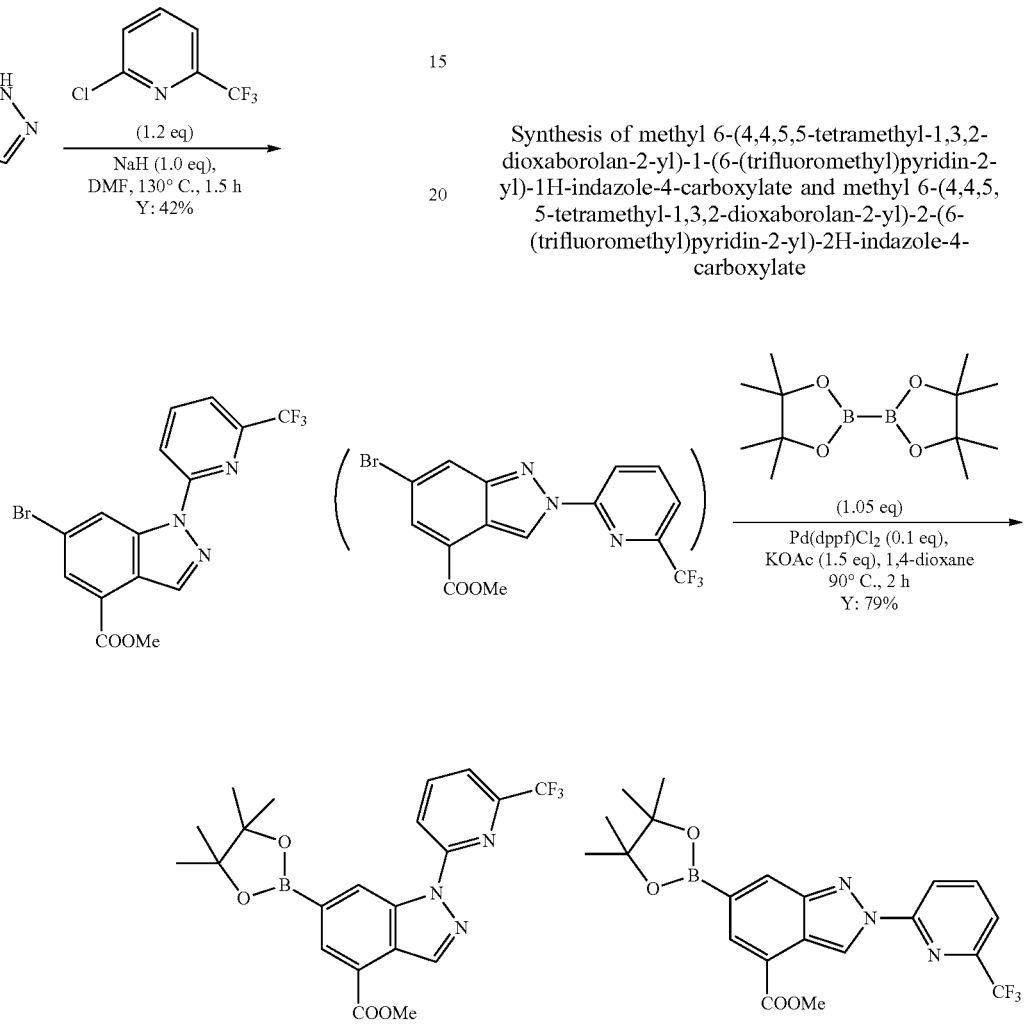

-continued

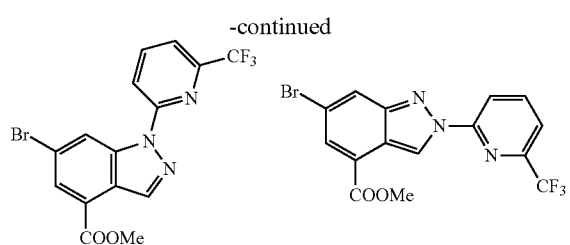

The preparation of methyl 6-bromo-1-(6-(trifluoromethyl)pyridin-2-yl)-1H-indazole-4-carboxylate and methyl 6-bromo-2-(6-(trifluoromethyl)pyridin-2-yl)-2H-indazole-4-carboxylate was the same as that of 6-bromo-1-(6-methylpyridin-2-yl)-1H-indazole. 950 mg, as a yellow solid, Y: 42%. The mixture of methyl 6-bromo-1-(6-(trifluoromethyl)pyridin-2-yl)-1H-indazole-4-carboxylate and methyl 6-bromo-2-(6-(trifluoromethyl)pyridin-2-yl)-2H-indazole-4-carboxylate was difficult to be purified due to poor solubility. The mixture was directly used for next step. ESI-MS (M+H)$^+$: 400.1.

Synthesis of methyl 6-(4,4,5,5-tetramethyl-1,3,2-dioxaborolan-2-yl)-1-(6-(trifluoromethyl)pyridin-2-yl)-1H-indazole-4-carboxylate and methyl 6-(4,4,5,5-tetramethyl-1,3,2-dioxaborolan-2-yl)-2-(6-(trifluoromethyl)pyridin-2-yl)-2H-indazole-4-carboxylate The preparation of methyl 6-(4,4,5,5-tetramethyl-1,3,2-dioxaborolan-2-yl)-1-(6-(trifluoromethyl)pyridin-2-yl)-1H-indazole-4-carboxylate and methyl 6-(4,4,5,5-tetramethyl-1,3-dioxolan-2-yl)-2-(6-(trifluoromethyl)pyridin-2-yl)-2H-indazole-4-carboxylate was the same as that of 1-(6-methylpyridin-2-yl)-6-(4,4,5,5-tetramethyl-1,3,2-dioxaborolan-2-yl)-1H-indazole. 700 mg, as a yellow solid, Y: 79%. The mixture of methyl 6-(4,4,5,5-tetramethyl-1,3,2-dioxaborolan-2-yl)-1-(6-(trifluoromethyl)pyridin-2-yl)-1H-indazole-4-carboxylate and methyl 6-(4,4,5,5-tetramethyl-1,3-dioxolan-2-yl)-2-(6-(trifluoromethyl)pyridin-2-yl)-2H-indazole-4-carboxylate was directly used for next step without further purification. ESI-MS (M+H)$^+$: 448.2.

Synthesis of methyl 6-(5-aminopyridin-3-yl)-1-(6-(trifluoromethyl)pyridin-2-yl)-1H-indazole-4-carboxylate

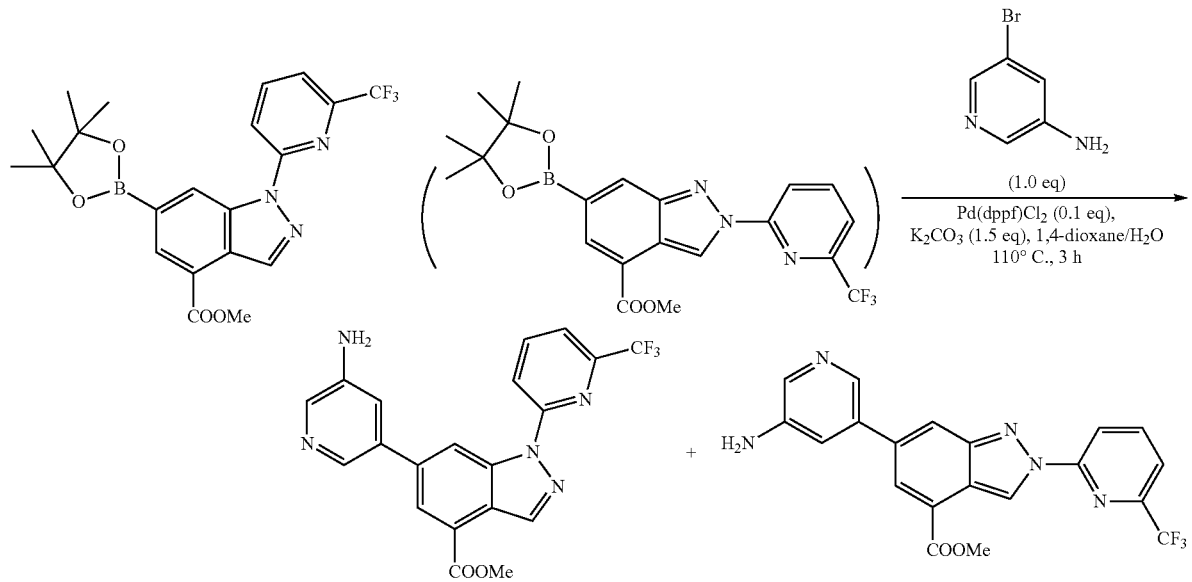

The preparation of methyl 6-(5-aminopyridin-3-yl)-1-(6-(trifluoromethyl)pyridin-2-yl)-1H-indazole-4-carboxylate was the same as that of 6-bromo-1-(6,7-dihydro-5H-cyclopenta[b]pyridin-2-yl)-1H-indazole. The mixture of methyl 6-(5-aminopyridin-3-yl)-1-(6-(trifluoromethyl)pyridin-2-yl)-1H-indazole-4-carboxylate and methyl 6-(5-aminopyridin-3-yl)-2-(6-(trifluoromethyl)pyridin-2-yl)-2H-indazole-4-carboxylate was purified by pre-HPLC (MeOH/H$_2$O with 0.05% TFA as mobile phase from 5% to 95%) to give methyl 6-(5-aminopyridin-3-yl)-1-(6-(trifluoromethyl)pyridin-2-yl)-1H-indazole-4-carboxylate and 19-06-a. R$_f$ value of methyl 6-(5-aminopyridin-3-yl)-2-(6-(trifluoromethyl)pyridin-2-yl)-2H-indazole-4-carboxylate is more than that of methyl 6-(5-aminopyridin-3-yl)-1-(6-(trifluoromethyl)pyridin-2-yl)-1H-indazole-4-carboxylate.

methyl 6-(5-aminopyridin-3-yl)-1-(6-(trifluoromethyl)pyridin-2-yl)-1H-indazole-4-carboxylate: 20 mg, as a white solid, ESI-MS (M+H)$^+$: 414.1, HPLC: 100.00%. $^1$H NMR (400 MHz, CD$_3$OD) δ: 9.37 (s, 1H), 8.78 (s, 1H), 8.36 (d, J=8.4 Hz, 1H), 8.26 (d, J=1.6 Hz, 1H), 8.21 (t, J=8.0 Hz, 1H), 8.16 (d, J=1.6 Hz, 1H), 8.04 (d, J=2.4 Hz, 1H), 7.72 (d, J=7.6 Hz, 1H), 7.44 (t, J=2.4 Hz, 1H), 4.07 (s, 3H).

methyl 6-(5-aminopyridin-3-yl)-2-(6-(trifluoromethyl)pyridin-2-yl)-2H-indazole-4-carboxylate: 15 mg, as a white solid, ESI-MS (M+H)$^+$: 414.1, HPLC: 93.65%. $^1$H NMR (400 MHz, CD$_3$OD) δ: 9.57 (d, J=0.8 Hz, 1H), 8.61 (d, J=8.0 Hz, 1H), 8.41-8.25 (m, 3H), 8.25 (d, J=1.6 Hz, 1H), 8.05 (s, 2H), 7.96 (d, J=7.2 Hz, 1H), 4.09 (s, 3H).

Example 51. 6-(5-aminopyridin-3-yl)-1-(6-(trifluoromethyl)pyridin-2-yl)-1H-indazole-4-carboxylic acid Synthesis of 6-(5-aminopyridin-3-yl)-1-(6-(trifluoromethyl)pyridin-2-yl)-1H-indazole-4-carboxylic acid

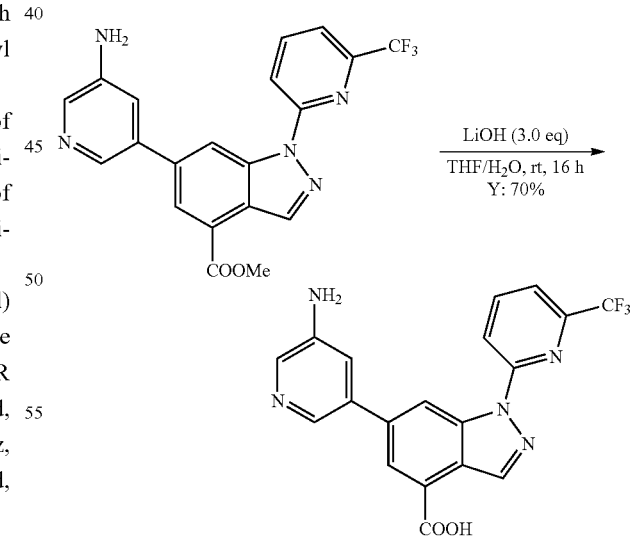

A mixture of methyl 6-(5-aminopyridin-3-yl)-1-(6-(trifluoromethyl)pyridin-2-yl)-1H-indazole-4-carboxylate (100 mg, 0.24 mmol, 1.0 eq) and LiOH.H$_2$O (30 mg, 0.72 mmol, 3.0 eq) in THF/H$_2$O (4 mL/1 mL) was stirred at rt for 16 h. The mixture was adjusted pH=6 with 1 N HCl and extracted with DCM (100 mL×2). The combined organic phase was washed with water (20 mL). After concentration, the residue was purified by pre-HPLC (MeOH/H₂O as mobile phase from 5% to 95%) to give 6-(5-aminopyridin-3-yl)-1-(6-(trifluoromethyl)pyridin-2-yl)-1H-indazole-4-carboxylic acid. 67 mg, as a white solid, Y: 70%. ESI-MS (M+H)⁺: 400.1. HPLC: 98.77%. ¹H NMR (400 MHz, CD₃OD) δ: 9.41 (s, 1H), 8.86 (s, 1H), 8.40 (d, J=8.8 Hz, 1H), 8.32 (d, J=1.2 Hz, 1H), 8.29 (d, J=8.0 Hz, 1H), 8.25 (t, J=8.0 Hz, 1H), 8.08 (d, J=2.4 Hz, 1H), 7.96 (t, J=2.0 Hz, 1H), 7.75 (d, J=7.2 Hz, 1H).

Example 52. 6-(5-aminopyridin-3-yl)-1-(6-(trifluoromethyl)pyridin-2-yl)-1H-indazole-4-carboxamide Synthesis of 6-(5-aminopyridin-3-yl)-1-(6-(trifluoromethyl)pyridin-2-yl)-1H-indazole-4-carboxamide

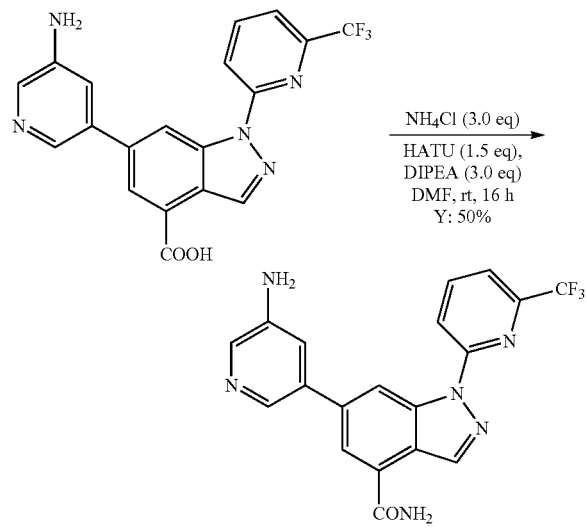

The preparation of 6-(5-aminopyridin-3-yl)-1-(6-(trifluoromethyl)pyridin-2-yl)-1H-indazole-4-carboxamide was the same as that of 6-(6-(5-aminopyridin-3-yl)-1H-indazol-1-yl)-N-methylpicolinamide. 30 mg, as a yellow solid, Y: 50%. ESI-MS (M+H)⁺: 399.1. HPLC: 93.73%. ¹H NMR (400 MHz, CD₃OD) δ: 9.35 (s, 1H), 8.81 (s, 1H), 8.41 (d, J=8.8 Hz, 1H), 8.32 (d, J=0.8 Hz, 1H), 8.25 (t, J=8.0 Hz, 1H), 8.09-8.08 (m, 2H), 8.00 (t, J=2.0 Hz, 1H), 7.75 (d, J=7.6 Hz, 1H).

Example 53. 5-(4-(aminomethyl)-1-(6-(trifluoromethyl)pyridin-2-yl)-1H-indazol-6-yl)pyridin-3-amine Synthesis of N-(5-(4-cyano-1-(6-(trifluoromethyl)pyridin-2-yl)-1H-indazol-6-yl)pyridin-3-yl)-2,2,2-trifluoroacetamide

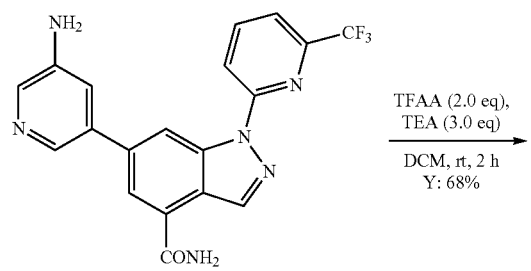

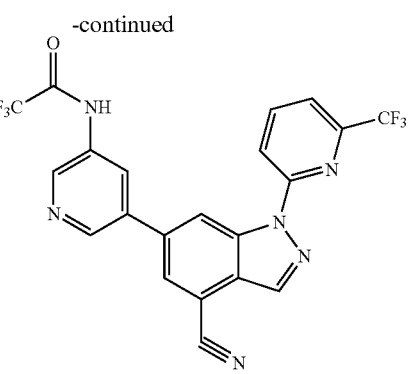

To a mixture of 6-(5-aminopyridin-3-yl)-1-(6-(trifluoromethyl)pyridin-2-yl)-1H-indazole-4-carboxamide (50 mg, 0.13 mmol, 1.0 eq) and TEA (39 mg, 0.39 mmol, 3.0 eq) in DCM (4 mL) was added TFAA (55 mg, 0.26 mmol, 2.0 eq) at rt. The mixture was stirred at rt for 2 h. The mixture was diluted with water (5 mL) and DCM (10 mL). The organic phase was washed with brine (5 mL) and dried over Na₂SO₄. After filtration and concentration, 42 mg of N-(5-(4-cyano-1-(6-(trifluoromethyl)pyridin-2-yl)-1H-indazol-6-yl)pyridin-3-yl)-2,2,2-trifluoroacetamide was obtained. Y: 68%. ESI-MS (M+H)⁺: 477.0. HPLC: 95.77%. ¹H NMR (400 MHz, CD₃OD) δ: 9.49 (s, 1H), 8.91 (d, J=2.4 Hz, 1H), 8.81 (d, J=1.6 Hz, 1H), 8.61 (s, 2H), 8.42 (d, J=8.8 Hz, 1H), 8.28 (t, J=7.6 Hz, 1H), 8.18 (d, J=1.6 Hz, 1H), 7.79 (d, J=7.6 Hz, 1H).

Synthesis of 6-(5-aminopyridin-3-yl)-1-(6-(trifluoromethyl)pyridin-2-yl)-1H-indazole-4-carbonitrile

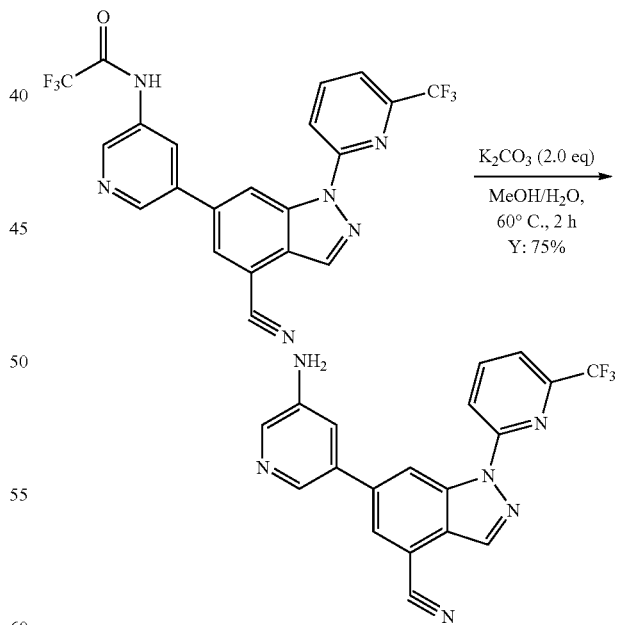

A mixture of 6-(5-aminopyridin-3-yl)-1-(6-(trifluoromethyl)pyridin-2-yl)-1H-indazole-4-carbonitrile (40 mg, 0.09 mmol, 1.0 eq) and K₂CO₃ (25 mg, 0.18 mmol, 2.0 eq) in MeOH/H₂O (4 mL/2 mL) was stirred at 60° C. for 2 h. After concentration, the residue was diluted with DCM (10 mL) and water (5 mL). The organic phase was concentrated and the residue was directly used for next step without further purification. 26 mg, as a yellow solid, Y: 75%. ESI-MS (M+H)⁺: 381.1.

Synthesis of 5-(4-(aminomethyl)-1-(6-(trifluoromethyl)pyridin-2-yl)-1H-indazol-6-yl)pyridin-3-amine

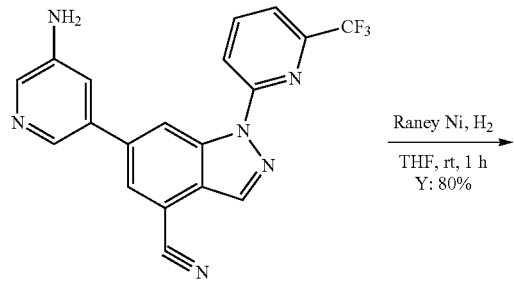

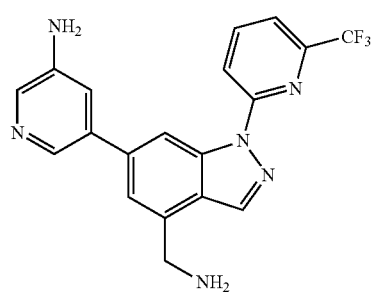

The preparation of 5-(4-(aminomethyl)-1-(6-(trifluoromethyl)pyridin-2-yl)-1H-indazol-6-yl)pyridin-3-amine was the same as that of 6-(1-(6-(trifluoromethyl)pyridin-2-yl)-1H-indazol-6-yl)picolinonitrile except THF was used as a solvent. 21 mg, as a yellow solid, Y: 80%. ESI-MS (M+H)⁺: 385.1. HPLC: 100.00%. ¹H NMR (400 MHz, CD₃OD) δ: 9.23 (s, 1H), 8.69 (s, 1H), 8.41 (d, J=8.8 Hz, 1H), 8.28-8.24 (m, 2H), 8.10 (s, 1H), 7.90 (s, 1H), 7.79 (s, 1H), 7.77 (d, J=7.6 Hz, 1H), 4.66 (s, 2H).

Example 54. (6-(5-aminopyridin-3-yl)-1-(6-(trifluoromethyl)pyridin-2-yl)-1H-indazol-4-yl)methanol Synthesis of (6-(5-aminopyridin-3-yl)-1-(6-(trifluoromethyl)pyridin-2-yl)-1H-indazol-4-yl)methanol

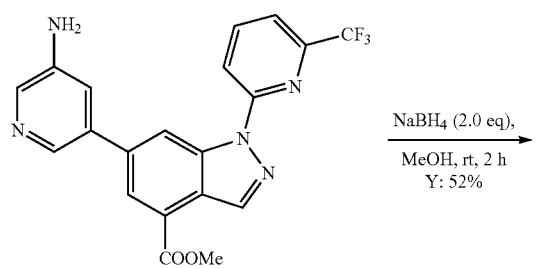

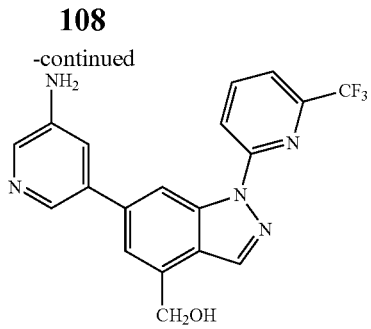

To a solution of methyl 6-(5-aminopyridin-3-yl)-1-(6-(trifluoromethyl)pyridin-2-yl)-1H-indazole-4-carboxylate (50 mg, 0.12 mmol, 1.0 eq) in MeOH (5 mL) was added NaBH₄ (9.0 mg, 0.24 mmol, 2.0 eq) at rt. The mixture reaction was at rt for 2 h. After concentration, the residue was purified by pre-HPLC (MeOH/H₂O with 0.05% TFA as mobile phase from 5% to 95%) to give (6-(5-aminopyridin-3-yl)-1-(6-(trifluoromethyl)pyridin-2-yl)-1H-indazol-4-yl)methanol. 20 mg, as a yellow solid, Y: 52%. ESI-MS (M+H)⁺: 386.1. HPLC: 93.73%. ¹H NMR (400 MHz, CD₃OD) δ: 9.05 (s, 1H), 8.52 (d, J=1.2 Hz, 1H), 8.35 (d, J=8.8 Hz, 1H), 8.20 (d, J=8.0 Hz, 1H), 8.17 (s, 1H), 8.01 (d, J=2.8 Hz, 1H), 7.68 (d, J=7.2 Hz, 1H), 7.72 (d, J=7.6 Hz, 1H), 7.60 (s, 1H), 7.44 (s, 1H), 5.08 (s, 2H).

Example 55. 1-(6-(1-(6-methylpyridin-2-yl)-1H-indazol-6-yl)pyridin-2-yl)ethanamine Synthesis of 1-(6-(1-(6-methylpyridin-2-yl)-1H-indazol-6-yl)pyridin-2-yl)ethanone

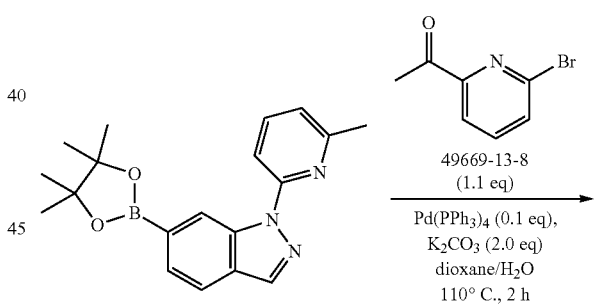

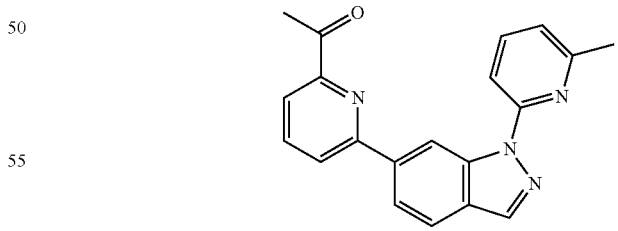

A mixture of 1-(6-methylpyridin-2-yl)-6-(4,4,5,5-tetramethyl-1,3,2-dioxaborolan-2-yl)-1H-indazole (275 mg, 0.82 mmol), 1-(6-bromopyridin-2-yl)ethanone (CAS#49669-13-8) (180 mg, 0.90 mmol, 1.1 eq), Pd(PPh₃)₄ (95 mg, 0.082 mmol, 0.1 eq) and K₂CO₃ (226 mg, 1.64 mmol, 2.0 eq) in 1,4-dioxane/H₂O (5 mL/0.5 mL) was stirred at 110° C. for 2 h under N₂. After concentration, the residue was purified by column chromatography (silica gel, PE/EA=8/1) to afford 1-(6-(1-(6-methylpyridin-2-yl)-1H-indazol-6-yl)pyridin-2-yl)ethanone as a yellow solid (200 mg, Y: 74%). ESI-MS (M+H)+: 330.1.

Synthesis of N-(4-methoxybenzyl)-1-(6-(1-(6-methylpyridin-2-yl)-1H-indazol-6-yl)pyridin-2-yl)ethanamine

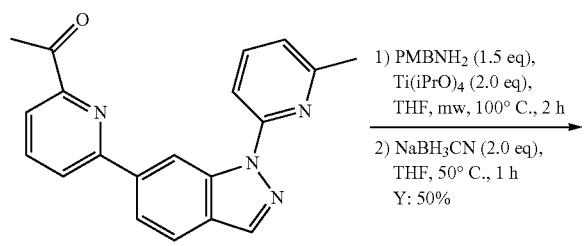

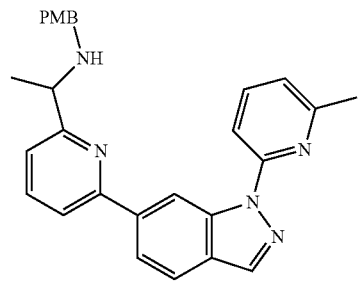

A mixture of 1-(6-(1-(6-methylpyridin-2-yl)-1H-indazol-6-yl)pyridin-2-yl)ethanone (260 mg, 0.79 mmol), PMBNH₂ (162 mg, 1.18 mmol, 1.5 eq) and Ti(iPrO)₄ (168 mg, 1.58 mmol, 2.0 eq) in THF (10 mL) was stirred at 100° C. under mw for 2 h. After cooling to rt, NaBH₃CN (98 mg, 1.58 mmol, 2.0 eq) was added into the mixture reaction. The mixture was stirred at 50° C. for 1 h. The mixture was poured into water (10 mL) and extracted with EA (20 mL). The organic phase was concentrated and the residue was purified by column chromatography (silica gel, PE/EA=6/1) to afford N-(4-methoxybenzyl)-1-(6-(1-(6-methylpyridin-2-yl)-1H-indazol-6-yl)pyridin-2-yl)ethanamine as a yellow solid (180 mg, Y: 50%). ESI-MS (M+H)+: 450.1.

Synthesis of 1-(6-(1-(6-methylpyridin-2-yl)-1H-indazol-6-yl)pyridin-2-yl)ethanamine

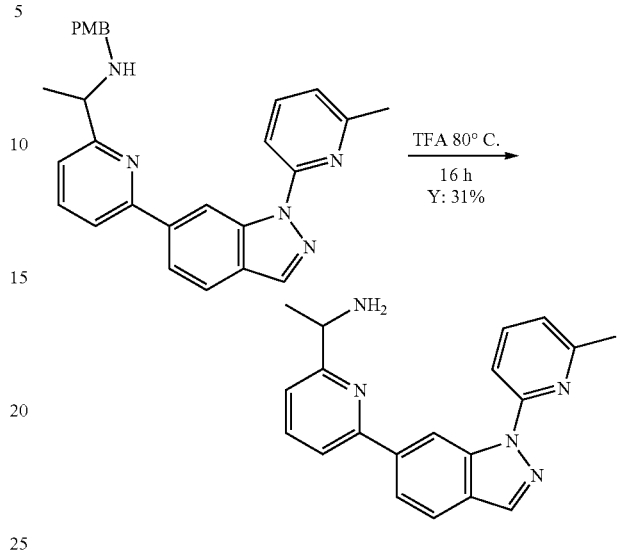

A solution of N-(4-methoxybenzyl)-1-(6-(1-(6-methylpyridin-2-yl)-H-indazol-6-yl)pyridin-2-yl)ethanamine (70 mg, 0.19 mmol) in TFA (2 mL) was stirred at 80° C. for 16 h. After concentration, the residue was dissolved in EA (10 mL) and washed with saturated aqueous NaHCO₃ solution (10 mL) and brine (10 mL). The organics were dried (MgSO₄) and concentrated in vacuo. The crude product was purified by pre-HPLC (MeOH/H₂O with 0.05% NH₄OH as mobile phase from 5% to 95%) to give 1-(6-(1-(6-methylpyridin-2-yl)-1H-indazol-6-yl)pyridin-2-yl)ethanamine. 40 mg, as a white solid, Y: 31%. ESI-MS (M+H)+: 330.1. HPLC: 100.00%. ¹H NMR (400 MHz, CD₃OD) δ: 9.64 (s, 1H), 8.20 (s, 1H), 7.99 (dd, J=8.8, 1.6 Hz, 1H), 7.86-7.82 (m, 2H), 7.76-7.71 (m, 3H), 7.25 (dd, J=4.4, 3.2 Hz, 1H), 7.03 (d, J=7.2 Hz, 1H), 4.27-4.22 (m, 1H), 2.69 (s, 3H), 1.55 (d, J=6.8 Hz, 3H).

Example 56. methyl 6-(6-(1-aminoethyl)pyridin-2-yl)-1-(6-(trifluoromethyl)pyridin-2-yl)-1H-indazole-4-carboxylate Synthesis of methyl 6-(6-acetylpyridin-2-yl)-1-(6-(trifluoromethyl)pyridin-2-yl)-1H-indazole-4-carboxylate and methyl 6-(6-acetylpyridin-2-yl)-2-(6-(trifluoromethyl)pyridin-2-yl)-2H-indazole-4-carboxylate

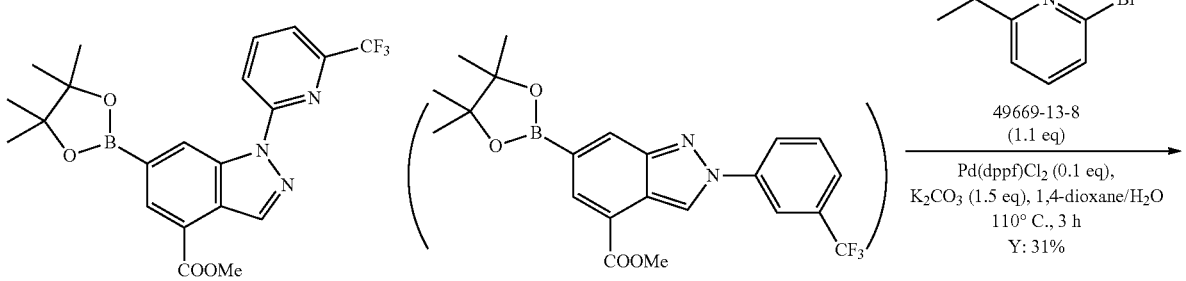

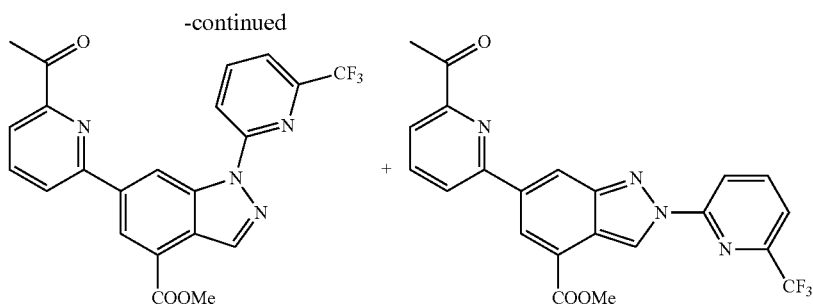

The preparation of methyl 6-(6-acetylpyridin-2-yl)-1-(6-(trifluoromethyl)pyridin-2-yl)-1H-indazole-4-carboxylate and methyl 6-(6-acetylpyridin-2-yl)-2-(6-(trifluoromethyl)pyridin-2-yl)-2H-indazole-4-carboxylate was the same as that of 6-bromo-1-(6-methylpyridin-2-yl)-1H-indazole. The mixture of methyl 6-(6-acetylpyridin-2-yl)-1-(6-(trifluoromethyl)pyridin-2-yl)-1H-indazole-4-carboxylate and methyl 6-(6-acetylpyridin-2-yl)-2-(6-(trifluoromethyl)pyridin-2-yl)-2H-indazole-4-carboxylate was purified by silica gel chromatography with PE/EA (2/1) as eluent to give methyl 6-(6-acetylpyridin-2-yl)-1-(6-(trifluoromethyl)pyridin-2-yl)-1H-indazole-4-carboxylate. 400 mg, as a yellow solid, Y: 31%. ESI-MS (M+H)+: 441.1.

Synthesis of methyl 6-(6-(1-((4-methoxybenzyl)amino)ethyl)pyridin-2-yl)-1-(6-(trifluoromethyl)pyridin-2-yl)-1H-indazole-4-carboxylate

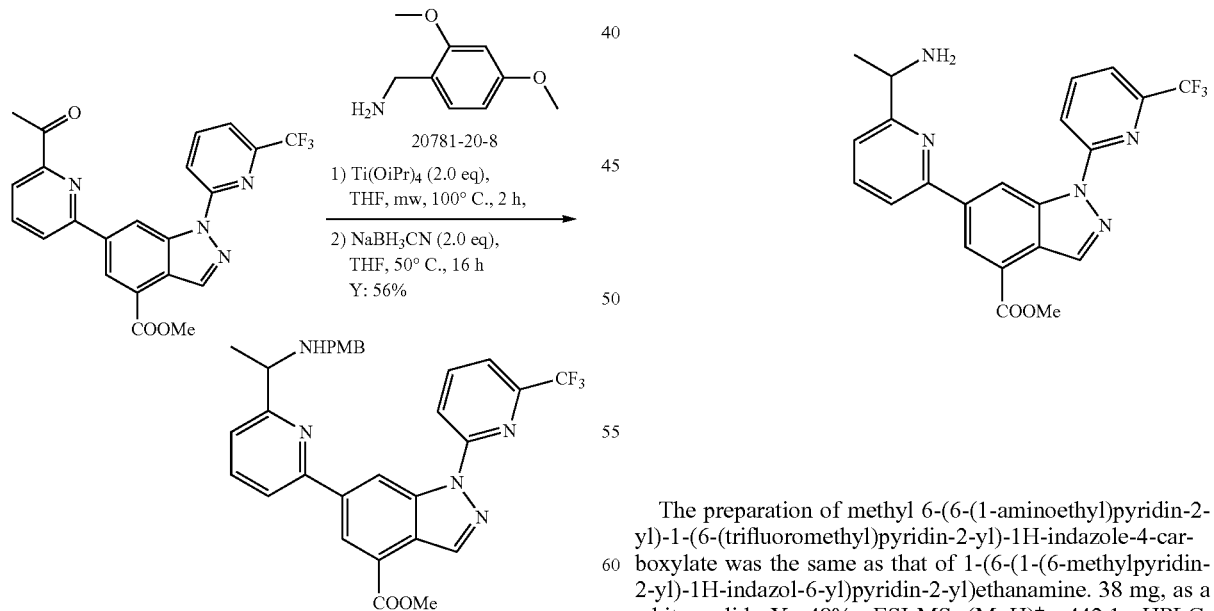

The preparation of methyl 6-(6-(1-((4-methoxybenzyl)amino)ethyl)pyridin-2-yl)-1-(6-(trifluoromethyl)pyridin-2-yl)-1H-indazole-4-carboxylate was the same as that of N-(4-methoxybenzyl)-1-(6-(1-(6-methylpyridin-2-yl)-1H-indazol-6-yl)pyridin-2-yl)ethanamine. 285 mg, as a yellow solid, Y: 56%. ESI-MS (M+H)+: 562.1.

Synthesis of methyl 6-(6-(1-aminoethyl)pyridin-2-yl)-1-(6-(trifluoromethyl)pyridin-2-yl)-1H-indazole-4-carboxylate

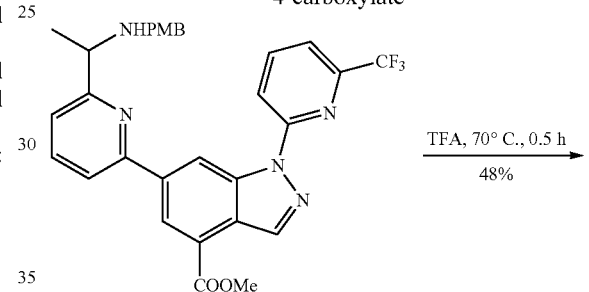

The preparation of methyl 6-(6-(1-aminoethyl)pyridin-2-yl)-1-(6-(trifluoromethyl)pyridin-2-yl)-1H-indazole-4-carboxylate was the same as that of 1-(6-(1-(6-methylpyridin-2-yl)-1H-indazol-6-yl)pyridin-2-yl)ethanamine. 38 mg, as a white solid, Y: 48%. ESI-MS (M+H)+: 442.1. HPLC: 96.49%. $^1$H NMR (400 MHz, CD$_3$OD) δ: 9.68-9.65 (m, 1H), 8.59-8.54 (m, 2H), 8.19 (d, J=8.0 Hz, 1H), 8.08 (d, J=8.0 Hz, 1H), 7.78-7.71 (m, 2H), 7.61 (d, J=7.2 Hz, 1H), 7.31 (d, J=7.6 Hz, 1H), 4.11 (q, J=6.8 Hz, 1H), 3.96 (s, 3H), 1.45 (d, J=6.8 Hz, 3H).

Example 57. (6-(6-(1-aminoethyl)pyridin-2-yl)-1-(6-(trifluoromethyl)pyridin-2-yl)-1H-indazol-4-yl)methanol Synthesis of (6-(6-(1-aminoethyl)pyridin-2-yl)-1-(6-(trifluoromethyl)pyridin-2-yl)-1H-indazol-4-yl)methanol

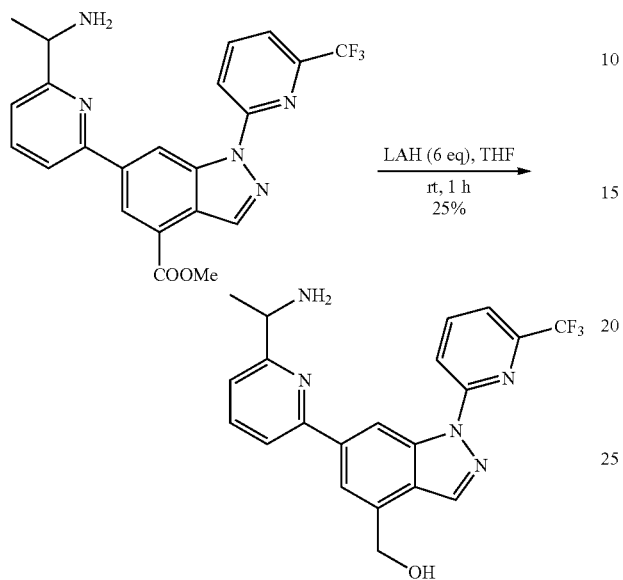

To a solution of methyl 6-(6-(1-aminoethyl)pyridin-2-yl)-1-(6-(trifluoromethyl)pyridin-2-yl)-1H-indazole-4-carboxylate (84 mg, 0.19 mmol, 1.0 eq) in THF (5 mL) was added LAH (43.0 mg, 1.14 mmol, 6.0 eq) at rt. The mixture reaction was at rt for 1 h. After concentration, the residue was purified by pre-HPLC (MeOH/H$_2$O with 0.05% TFA as mobile phase from 5% to 95%) to give (6-(6-(1-aminoethyl)pyridin-2-yl)-1-(6-(trifluoromethyl)pyridin-2-yl)-1H-indazol-4-yl)methanol. 20 mg, as a white solid, Y: 25%. ESI-MS (M+H)$^+$: 414.1. HPLC: 100.00%. $^1$H NMR (400 MHz, CD$_3$OD) δ: 9.51 (s, 1H), 8.55 (s, 1H), 8.38 (d, J=8.0 Hz, 1H), 8.24 (s, 1H), 8.21 (t, J=8.0 Hz, 1H), 8.06-8.01 (m, 2H), 7.72 (d, J=7.6 Hz, 1H), 7.50 (dd, J=6.8, 2.0 Hz, 1H), 5.12 (s, 2H), 4.70 (q, J=6.8 Hz, 1H), 1.74 (d, J=6.8 Hz, 3H).

Example 58. 6-(6-(1-aminoethyl)pyridin-2-yl)-N,N-dimethyl-1-(6-(trifluoromethyl)pyridin-2-yl)-1H-indazole-4-carboxamide Synthesis of 6-(6-(1-((4-methoxybenzyl)amino)ethyl)pyridin-2-yl)-1-(6-(trifluoromethyl)pyridin-2-yl)-1H-indazole-4-carboxylic acid

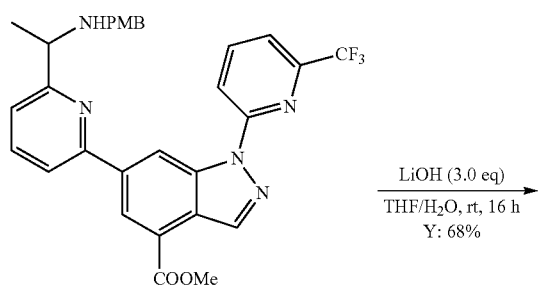

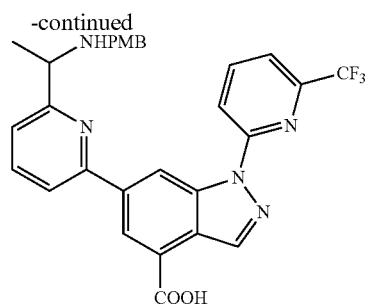

The preparation of 6-(6-(1-((4-methoxybenzyl)amino)ethyl)pyridin-2-yl)-1-(6-(trifluoromethyl)pyridin-2-yl)-1H-indazole-4-carboxylic acid was the same as that of 6-(5-aminopyridin-3-yl)-1-(6-(trifluoromethyl)pyridin-2-yl)-1H-indazole-4-carboxylic acid. 200 mg, as a white solid, Y: 68%. ESI-MS (M+H)$^+$: 548.1.

Synthesis of 6-(6-(1-((4-methoxybenzyl)amino)ethyl)pyridin-2-yl)-N,N-dimethyl-1-(6-(trifluoromethyl)pyridin-2-yl)-1H-indazole-4-carboxamide

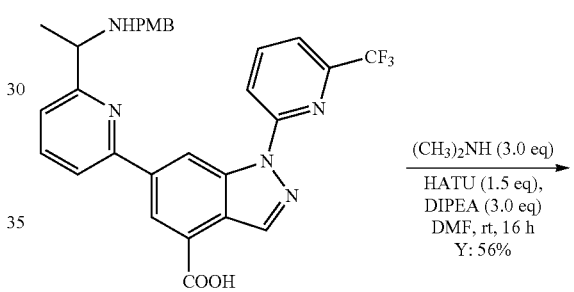

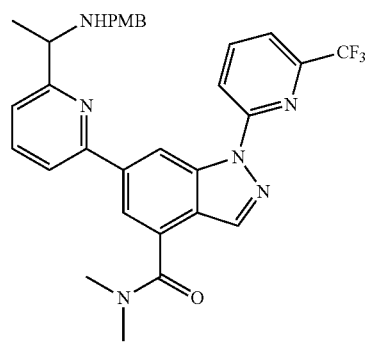

The preparation of 6-(6-(1-((4-methoxybenzyl)amino)ethyl)pyridin-2-yl)-N,N-dimethyl-1-(6-(trifluoromethyl)pyridin-2-yl)-1H-indazole-4-carboxamide was the same as that of 6-(6-(5-aminopyridin-3-yl)-1H-indazol-1-yl)-N-methylpicolinamide. 90 mg, as a yellow solid, Y: 56%. ESI-MS (M+H)$^+$: 575.2.

115

Synthesis of 6-(6-(1-aminoethyl)pyridin-2-yl)-N,N-dimethyl-1-(6-(trifluoromethyl)pyridin-2-yl)-1H-indazole-4-carboxamide

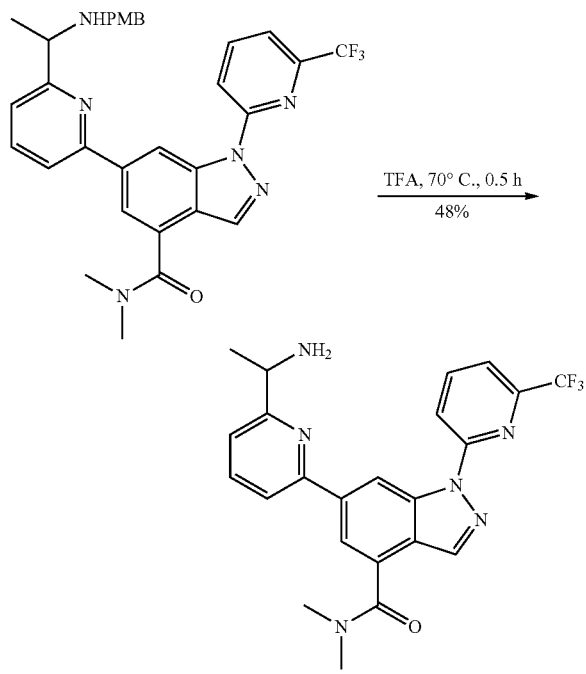

The preparation of 6-(6-(1-aminoethyl)pyridin-2-yl)-N,N-dimethyl-1-(6-(trifluoromethyl)pyridin-2-yl)-1H-indazole-4-carboxamide was the same as that of 1-(6-(1-(6-methylpyridin-2-yl)-1H-indazol-6-yl)pyridin-2-yl)ethanamine. 34 mg, as a white solid, Y: 48%. ESI-MS (M+H)+: 455.1. HPLC: 99.18%. $^1$H NMR (400 MHz, CD$_3$OD) δ: 9.75 (s, 1H), 8.41-8.38 (m, 2H), 8.23 (t, J=8.0 Hz, 1H), 8.18 (d, J=1.2 Hz, 1H), 7.93-7.91 (m, 2H), 7.75 (d, J=7.6 Hz, 1H), 7.42 (dd, J=6.4, 2.0 Hz, 1H), 4.26 (q, J=6.4 Hz, 1H), 3.28 (s, 3H), 3.10 (s, 3H), 1.55 (d, J=6.8 Hz, 3H).

Example 59. 6-(6-(1-aminoethyl)pyridin-2-yl)-N-methyl-1-(6-(trifluoromethyl)pyridin-2-yl)-1H-indazole-4-carboxamide Synthesis of 6-(6-(1-((4-methoxybenzyl)amino)ethyl)pyridin-2-yl)-N-methyl-1-(6-(trifluoromethyl)pyridin-2-yl)-1H-indazole-4-carboxamide

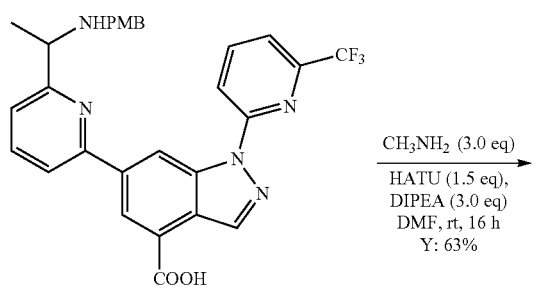

116

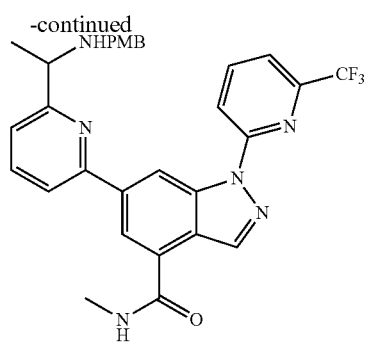

The preparation of 6-(6-(1-((4-methoxybenzyl)amino)ethyl)pyridin-2-yl)-N-methyl-1-(6-(trifluoromethyl)pyridin-2-yl)-1H-indazole-4-carboxamide was the same as that of 6-(6-(5-aminopyridin-3-yl)-1H-indazol-1-yl)-N-methylpicolinamide. (Example 32) 102 mg, as a yellow solid, Y: 63%. ESI-MS (M+H)+: 561.2.

Synthesis of 6-(6-(1-aminoethyl)pyridin-2-yl)-N-methyl-1-(6-(trifluoromethyl)pyridin-2-yl)-1H-indazole-4-carboxamide

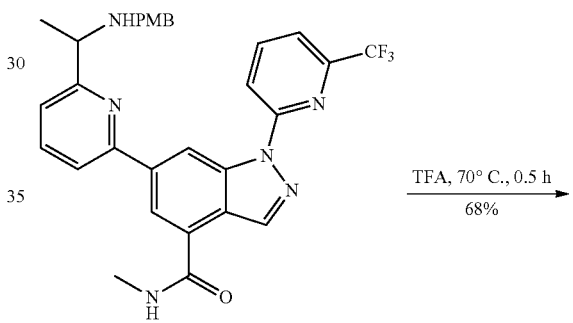

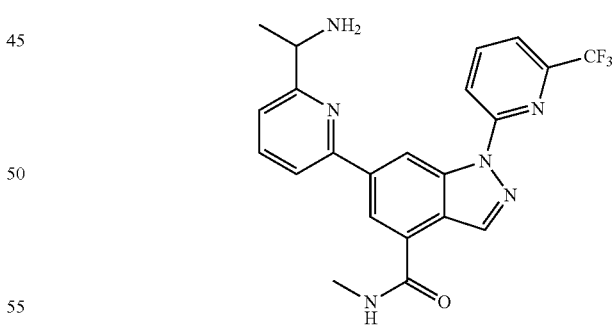

The preparation of 6-(6-(1-aminoethyl)pyridin-2-yl)-N-methyl-1-(6-(trifluoromethyl)pyridin-2-yl)-1H-indazole-4-carboxamide was the same as that of 1-(6-(1-(6-methylpyridin-2-yl)-1H-indazol-6-yl)pyridin-2-yl)ethanamine. 54 mg, as a white solid, Y: 68%. ESI-MS (M+H)+: 441.1. HPLC: 99.59%. $^1$H NMR (400 MHz, CD$_3$OD) δ: 9.78 (s, 1H), 8.75 (d, J=0.8 Hz, 1H), 8.58 (d, J=1.2 Hz, 1H), 8.42 (d, J=8.4 Hz, 1H), 8.27 (t, J=7.6 Hz, 1H), 8.09-8.07 (m, 2H), 7.76 (d, J=7.6 Hz, 1H), 7.54 (dd, J=5.6, 2.8 Hz, 1H), 4.73 (q, J=7.2 Hz, 1H), 3.08 (s, 3H), 1.75 (d, J=6.8 Hz, 3H).

Example 60. 6-(5-aminopyridin-3-yl)-N,N-dimethyl-1-(6-(trifluoromethyl)pyridin-2-yl)-1H-indazole-4-carboxamide Synthesis of 6-(5-aminopyridin-3-yl)-N,N-dimethyl-1-(6-(trifluoromethyl)pyridin-2-yl)-1H-indazole-4-carboxamide

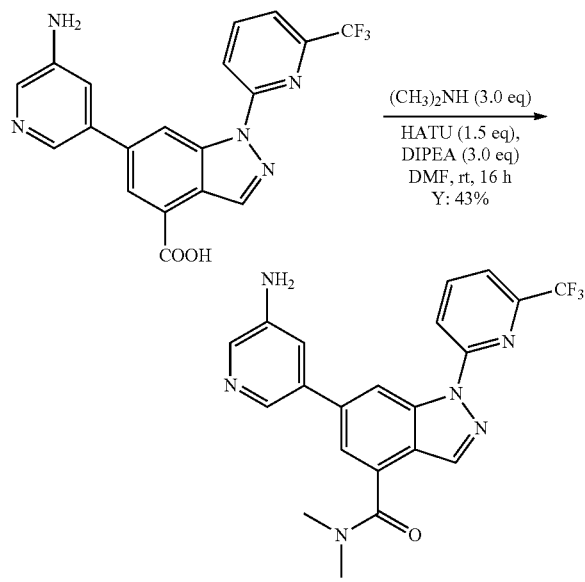

The preparation of 6-(5-aminopyridin-3-yl)-N,N-dimethyl-1-(6-(trifluoromethyl)pyridin-2-yl)-1H-indazole-4-carboxamide was the same as that of 6-(6-(5-aminopyridin-3-yl)-1H-indazol-1-yl)-N-methylpicolinamide (Example 32). 32 mg, as a yellow solid, Y: 43%. ESI-MS (M+H)$^+$: 427.1. HPLC: 99.74%. $^1$H NMR (400 MHz, CD$_3$OD) δ: 9.23 (s, 1H), 8.38 (d, J=8.4 Hz, 1H), 8.37 (s, 1H), 8.23 (t, J=8.0 Hz, 1H), 8.17 (d, J=1.6 Hz, 1H), 8.03 (d, J=2.4 Hz, 1H), 7.73 (d, J=7.2 Hz, 1H), 7.65 (d, J=1.6 Hz, 1H), 7.44 (t, J=2.0 Hz, 1H), 3.26 (s, 3H), 3.09 (s, 3H).

Example 61. 6-(5-aminopyridin-3-yl)-N-methyl-1-(6-(trifluoromethyl)pyridin-2-yl)-1H-indazole-4-carboxamide Synthesis of 6-(5-aminopyridin-3-yl)-N-methyl-1-(6-(trifluoromethyl)pyridin-2-yl)-1H-indazole-4-carboxamide

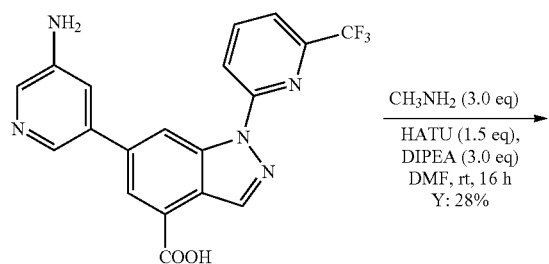

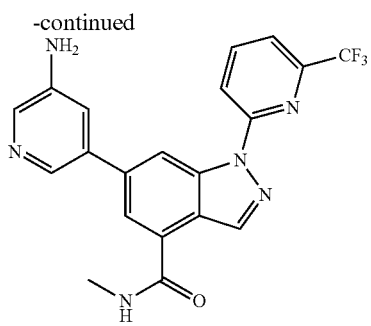

The preparation of 6-(5-aminopyridin-3-yl)-N-methyl-1-(6-(trifluoromethyl)pyridin-2-yl)-1H-indazole-4-carboxamide was the same as that of 6-(6-(5-aminopyridin-3-yl)-1H-indazol-1-yl)-N-methylpicolinamide (Example 32). 20 mg, as a brown solid, Y: 28%. ESI-MS (M+H)$^+$: 413.1. HPLC: 94.83%. $^1$H NMR (400 MHz, CD$_3$OD) δ: 9.26 (s, 1H), 8.71 (s, 1H), 8.35 (d, J=8.4 Hz, 1H), 8.20-8.18 (m, 2H), 8.04 (d, J=2.4 Hz, 1H), 7.94 (d, J=1.2 Hz, 1H), 7.70 (d, J=7.6 Hz, 1H), 7.45 (t, J=2.0 Hz, 1H), 3.04 (s, 3H).

Example 62. 2-(1-(6-(trifluoromethyl)pyridin-2-yl)-1H-indazol-6-yl)-6,7-dihydro-5H-cyclopenta[b]pyridin-7-amine Synthesis of 2-chloro-6,7-dihydro-5H-cyclopenta[b]pyridine 1-oxide

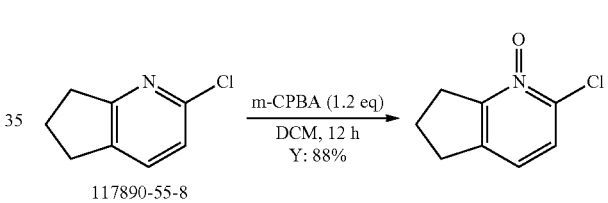

A solution of m-CPBA (4.7 g, 23.5 mmol, 1.2 eq, 85%) in DCM (25 mL) was added dropwise to a stirring solution of 2-chloro-6,7-dihydro-5H-cyclopenta[b]pyridine (CAS#117890-55-8) (3.0 g, 19.6 mmol, 1.0 eq) in DCM (50 mL) and the resulting solution was allowed to stir at rt for 12 h. The reaction mixture was quenched with a saturated aqueous solution of Na$_2$S$_2$O$_3$ and the organic layer was separated. The aqueous phase was then extracted with DCM (3×30 mL), and the combined organic extracts were washed with aqueous NaHCO$_3$, brine, dried over anhydrous Na$_2$SO$_4$ and concentrated in vacuo to afford crude product as pale yellow solid (2.9 g, Y: 88%), which was used directly in the next step without further purification. ESI-MS (M+H)$^+$: 170.0. $^1$H NMR (400 MHz, CDCl$_3$) δ: 7.33 (d, J=7.8 Hz, 1H), 7.11 (d, J=8.0 Hz, 1H), 3.31-3.13 (m, 2H), 3.12-2.96 (m, 2H), 2.31-2.16 (m, 2H).

Synthesis of 2-chloro-6,7-dihydro-5H-cyclopenta[b]pyridin-7-yl acetate

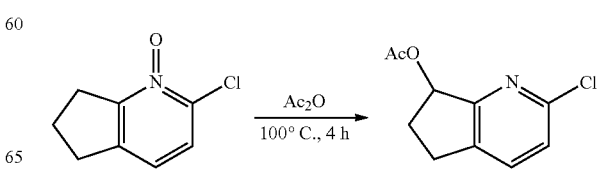

In round bottom flask equipped with a condenser, 2-chloro-6,7-dihydro-5H-cyclopenta[b]pyridine 1-oxide (2.9 g, 17.2 mmol, 1.0 eq) was dissolved in acetic anhydride (10 mL) and heated at 100° C. for 4 h. The reaction mixture was allowed to cool and the solvent was removed under reduced pressure. The resulting residue was dissolved up in DCM, and washed successively with saturated aqueous solution of NaHCO$_3$ (20 mL) and brine. After drying over anhydrous Na$_2$SO$_4$, the solution was removed under reduce pressure to afford crude product 2-chloro-6,7-dihydro-5H-cyclopenta[b]pyridin-7-yl acetate, which was used directly in the next step without further purification. ESI-MS (M+H)$^+$: 212.0.

Synthesis of 2-chloro-6,7-dihydro-5H-cyclopenta[b]pyridin-7-ol

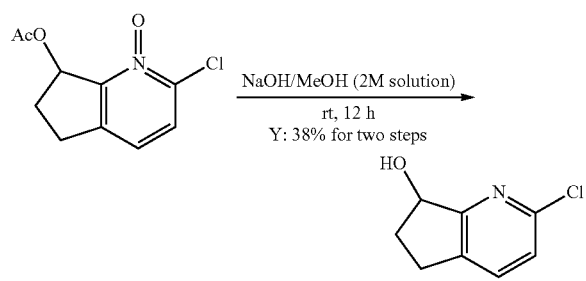

2-chloro-6,7-dihydro-5H-cyclopenta[b]pyridin-7-yl acetate was added to a 2 M solution of NaOH in MeOH (40 mL) and the mixture was stirred at rt for 12 h. The reaction mixture was extracted with DCM (3×40 mL), washed with brine and dried over anhydrous Na$_2$SO$_4$. After removing solvent under reduced pressure, the residue was purified by column chromatography (silica gel, PE/EA=4/1) to afford the compound 2-chloro-6,7-dihydro-5H-cyclopenta[b]pyridin-7-ol as off-white solid (1.1 g, Y: 38% for two steps). ESI-MS (M+H)$^+$: 170.0. $^1$H NMR (400 MHz, CDCl$_3$) δ: 7.53 (d, J=8.0 Hz, 1H), 7.18 (d, J=8.0 Hz, 1H), 5.32-5.09 (m, 1H), 3.56 (br, 1H), 3.11-2.93 (m, 1H), 2.88-2.71 (m, 1H), 2.65-2.48 (m, 1H), 2.17-2.02 (m, 1H).

Synthesis of 2-chloro-5H-cyclopenta[b]pyridin-7(6H)-one

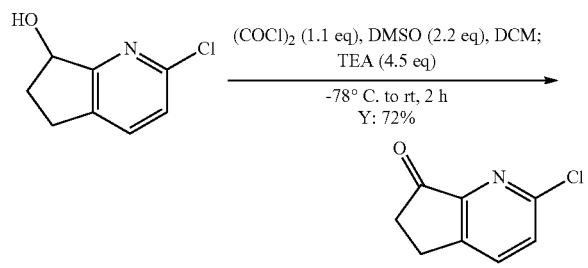

To a stirred solution of oxalyl chloride (0.49 mL, 5.5 mmol, 1.1 eq) in DCM (12 mL) was slowly added DMSO (0.79 mL, 11.0 mmol, 2.2 eq) at −78° C., and the resulting mixture was stirred for 30 min at this temperature. A solution of 2-chloro-6,7-dihydro-5H-cyclopenta[b]pyridin-7-ol (845 mg, 5.0 mmol, 1.0 eq) in DCM (10 mL) was added to this mixture slowly over 10 min, and then TEA (3.1 mL, 22.5 mmol, 4.5 eq) was added dropwise. The reaction mixture was allowed to warm slowly to rt and stirred at rt for 1 h, then quenched with water (10 mL). After extraction with DCM (3×20 mL), the organic layer was washed successively with HCl (10 mL, 1 M), saturated aqueous Na$_2$CO$_3$, and then brine. The organic layer was dried over anhydrous Na$_2$SO$_4$ and concentrated in vacuo. The residue was purified by column chromatography (silica gel, PE/EA=2/1) to afford the compound 2-chloro-5H-cyclopenta[b]pyridin-7(6H)-one as off-white solid (600 mg, Y: 72%). ESI-MS (M+H)$^+$: 168.0. $^1$H NMR (400 MHz, CDCl$_3$) δ: 7.86 (d, J=8.2 Hz, 1H), 7.49 (d, J=8.2 Hz, 1H), 3.20-3.12 (m, 2H), 2.84-2.76 (m, 2H).

Synthesis of 6-(4,4,5,5-tetramethyl-1,3,2-dioxaborolan-2-yl)-1-(6-(trifluoromethyl)pyridin-2-yl)-1H-indazole

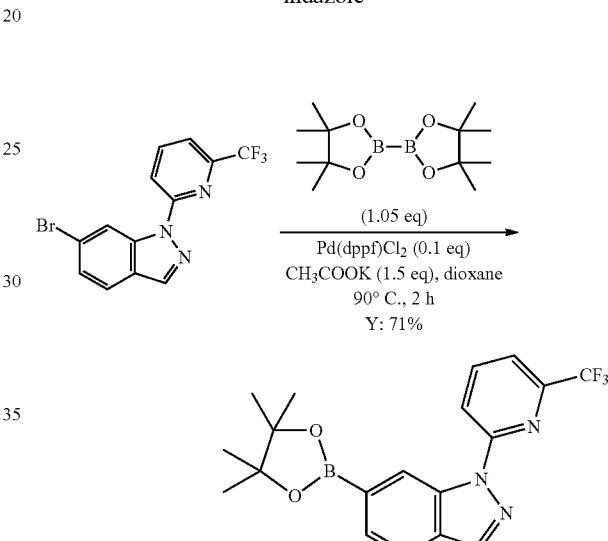

The preparation of 6-(4,4,5,5-tetramethyl-1,3,2-dioxaborolan-2-yl)-1-(6-(trifluoromethyl)pyridin-2-yl)-1H-indazole was the same as that of 1-(6-methylpyridin-2-yl)-6-(4,4,5,5-tetramethyl-1,3,2-dioxaborolan-2-yl)-1H-indazole. 550 mg, as a white solid, Y: 71%. ESI-MS (M+H)$^+$: 390.2.

Synthesis of 2-(1-(6-(trifluoromethyl)pyridin-2-yl)-1H-indazol-6-yl)-5H-cyclopenta[b]pyridin-7(6H)-one

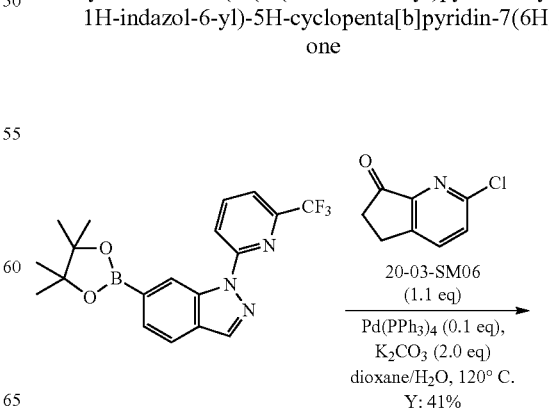

122
Synthesis of 2-(1-(6-(trifluoromethyl)pyridin-2-yl)-1H-indazol-6-yl)-6,7-dihydro-5H-cyclopenta[b]pyridin-7-amine

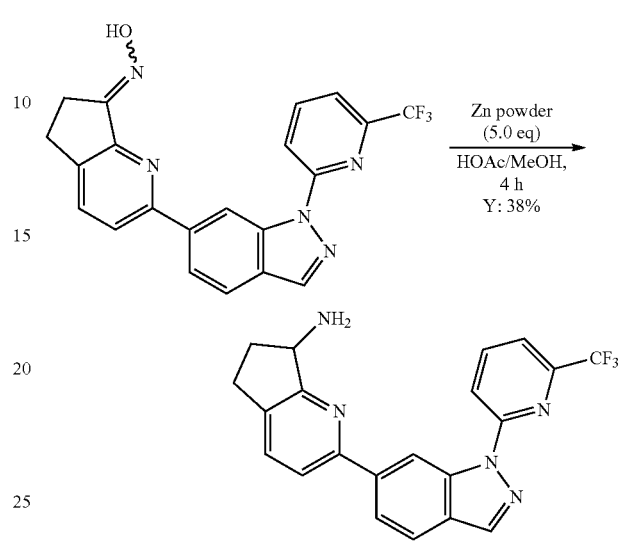

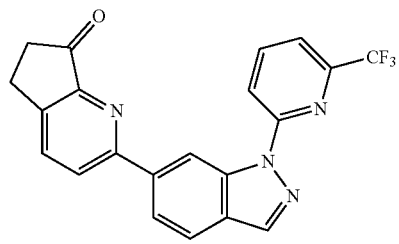

6-(4,4,5,5-tetramethyl-1,3,2-dioxaborolan-2-yl)-1-(6-(trifluoromethyl)pyridin-2-yl)-1H-indazole (550 mg, 1.41 mmol), 2-chloro-5H-cyclopenta[b]pyridin-7(6H)-one (262 mg, 1.56 mmol, 1.1 eq), Pd(PPh₃)₄ (162 mg, 0.14 mmol, 0.1 eq), K₂CO₃ (389 mg, 2.82 mmol, 2.0 eq) were dissolved in 1,4-dioxane/H₂O (1/1, 12 mL). The mixture was degassed with N₂ and heated to reflux for 4 h. The reaction mixture was cooled to rt and concentrated in vacuo. The residue was purified by column chromatography (silica gel, PE/EA=2/1) to afford the compound 2-(1-(6-(trifluoromethyl)pyridin-2-yl)-1H-indazol-6-yl)-5H-cyclopenta[b]pyridin-7(6H)-one as red solid (230 mg, Y: 41%). ESI-MS (M+H)⁺: 395.1. ¹H NMR (400 MHz, CDCl₃) δ: 9.50 (s, 1H), 8.37 (dd, J=8.4, 1.5 Hz, 1H), 8.31-8.21 (m, 2H), 8.12 (d, J=8.2 Hz, 1H), 8.07-7.97 (m, 2H), 7.87 (d, J=8.4 Hz, 1H), 7.54 (d, J=7.5 Hz, 1H), 3.27-3.19 (m, 2H), 2.90-2.80 (m, 2H).

Synthesis of 2-(1-(6-(trifluoromethyl)pyridin-2-yl)-1H-indazol-6-yl)-5H-cyclopenta[b]pyridin-7(6H)-one oxime

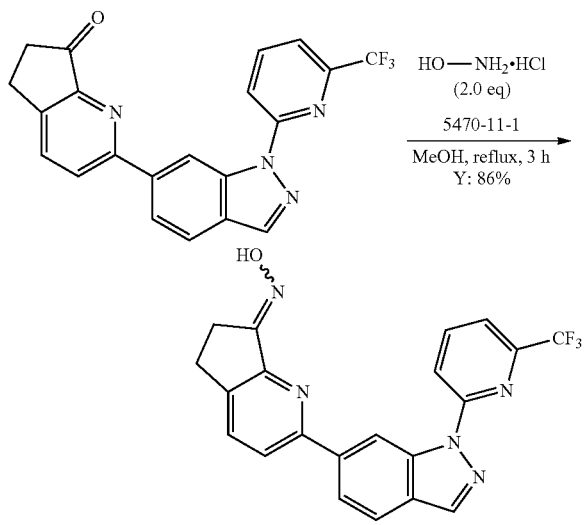

To a stirred solution of 2-(1-(6-(trifluoromethyl)pyridin-2-yl)-1H-indazol-6-yl)-5H-cyclopenta[b]pyridin-7(6H)-one (120 mg, 0.3 mmol, 1.0 eq) in MeOH (10 mL) was added Hydroxyamine*HCl (CAS#5470-11-1) (42 mg, 0.6 mmol, 2.0 eq), and the resulting mixture was heated to reflux for 3 h. The reaction mixture was cooled to rt and concentrated in vacuo. The residue could be used in the next step without further purification (brown solid, 107 mg, Y: 86%). ESI-MS (M+H)⁺: 410.1.

To a stirred solution of 2-(1-(6-(trifluoromethyl)pyridin-2-yl)-1H-indazol-6-yl)-5H-cyclopenta[b]pyridin-7(6H)-one oxime (100 mg, 0.25 mmol, 1.0 eq) in MeOH/HOAc (1/1, 10 mL) was added Zn powder (82 mg, 1.25 mmol, 5.0 eq), and the resulting mixture was stirred at rt for 3 h. The mixture was filtered, and the filtrate was concentrated in vacuo. The residue was basified with aq. NaOH and purified by prep-HPLC (MeOH/H₂O with 0.05% NH₄OH as mobile phase from 5% to 95%) to afford the product as white solid (37 mg, Y: 38%). ESI-MS (M+H)⁺: 396.1. HPLC: 99.25%. ¹H NMR (400 MHz, CD₃OD) δ: 9.55 (s, 1H), 8.40-8.29 (m, 2H), 8.17 (t, J=8.0 Hz, 1H), 8.03 (d, J=8.4 Hz, 1H), 7.93 (d, J=8.4 Hz, 1H), 7.84-7.73 (m, 2H), 7.67 (d, J=7.5 Hz, 1H), 4.39 (t, J=7.9 Hz, 1H), 3.11-3.00 (m, 1H), 3.00-2.85 (m, 1H), 2.69-2.54 (m, 1H), 1.94-1.81 (m, 1H).

Example 63. 2-(1-(6-(trifluoromethyl)pyridin-2-yl)-1H-indazol-6-yl)-5,6,7,8-tetrahydroquinolin-8-amine Step 1. Synthesis of 2-chloro-5,6,7,8-tetrahydroquinoline 1-oxide

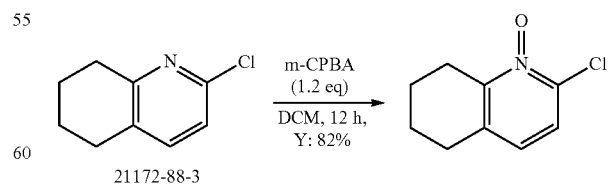

21172-88-3

The preparation of 2-chloro-5,6,7,8-tetrahydroquinoline 1-oxide was the same as that of 2-chloro-6,7-dihydro-5H-cyclopenta[b]pyridine 1-oxide (Example 62). 900 mg, as a yellow solid, Y: 82%. ESI-MS (M+H)⁺: 184.1.

Step 2. Synthesis of 2-chloro-5,6,7,8-tetrahydroquinolin-8-yl acetate

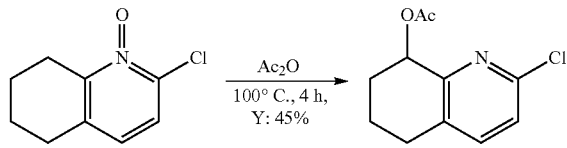 [SMILES: "Ac2O" ; [O-][n+]1c(Cl)ccc2c1CCCC2 ; CC(=O)OC1CCCc2ccc(Cl)nc21]

The preparation of 2-chloro-5,6,7,8-tetrahydroquinolin-8-yl acetate was the same as that of 2-chloro-6,7-dihydro-5H-cyclopenta[b]pyridin-7-yl acetate. 500 mg, as yellow oil, Y: 45%. ESI-MS (M+H)⁺: 226.1. ¹H NMR (400 MHz, CD₃OD) δ: 7.61 (d, J=7.6 Hz, 1H), 7.31 (d, J=8.0 Hz, 1H), 5.81 (t, J=4.4 Hz, 1H), 3.12-2.84 (m, 1H), 2.80-2.72 (m, 1H), 2.16-2.01 (m, 5H), 1.93-1.81 (m, 2H).

Step 3. Synthesis of 2-chloro-5,6,7,8-tetrahydroquinolin-8-ol

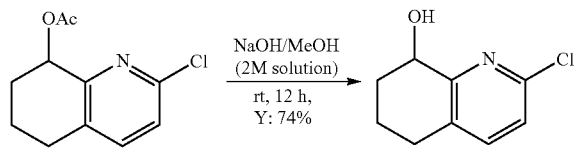 [SMILES: CC(=O)OC1CCCc2ccc(Cl)nc21 ; "NaOH/MeOH(2M solution)" ; OC1CCCc2ccc(Cl)nc21]

The preparation of 2-chloro-5,6,7,8-tetrahydroquinolin-8-ol was the same as that of 2-chloro-6,7-dihydro-5H-cyclopenta[b]pyridin-7-ol. 300 mg, as off-white solid, Y: 74%. ESI-MS (M+H)⁺: 184.1. ¹H NMR (400 MHz, CD₃OD) δ: 7.45 (d, J=8.4 Hz, 1H), 7.15 (d, J=8.0 Hz, 1H), 4.55 (t, J=4.8 Hz, 1H), 2.76-2.59 (m, 2H), 1.95-1.80 (m, 3H), 1.75-1.62 (m, 1H).

Step 4. Synthesis of 2-chloro-6,7-dihydroquinolin-8(5H)-one

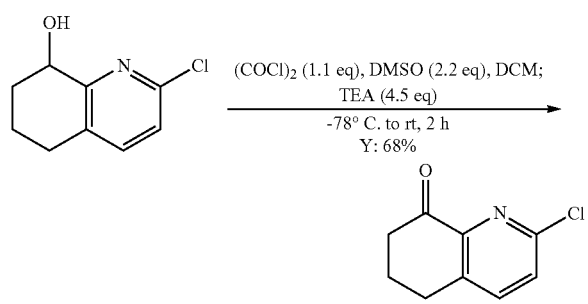

The preparation of 2-chloro-6,7-dihydroquinolin-8(5H)-one was the same as that of 2-chloro-5H-cyclopenta[b]pyridin-7(6H)-one. 200 mg, as off-white solid, Y: 68%. ESI-MS (M+H)⁺: 182.1. ¹H NMR (400 MHz, DMSO-d₆) δ: 7.93 (d, J=8.0 Hz, 1H), 7.66 (d, J=8.0 Hz, 1H), 2.99 (t, J=6.0 Hz, 2H), 2.71-2.68 (m, 2H), 2.10-2.04 (m, 2H).

Step 5. Synthesis of 2-(1-(6-(trifluoromethyl)pyridin-2-yl)-1H-indazol-6-yl)-6,7-dihydroquinolin-8(5H)-one

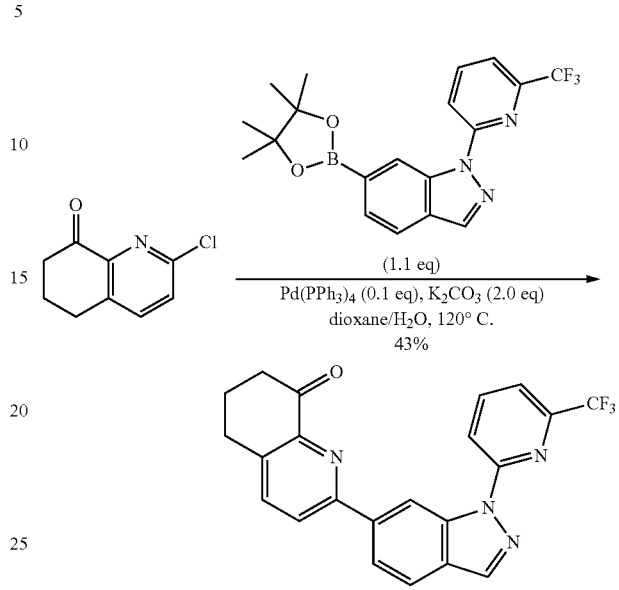

The preparation of 2-(1-(6-(trifluoromethyl)pyridin-2-yl)-1H-indazol-6-yl)-6,7-dihydroquinolin-8(5H)-one was the same as that of 2-(1-(6-(trifluoromethyl)pyridin-2-yl)-1H-indazol-6-yl)-5H-cyclopenta[b]pyridin-7(6H)-one. 180 mg, as white solid, Y: 43%. ESI-MS (M+H)⁺: 409.1. ¹H NMR (400 MHz, DMSO-d₆) δ: 9.44 (s, 1H), 8.62 (d, J=0.8 Hz, 1H), 8.34-8.29 (m, 2H), 8.16 (dd, J=8.4, 1.6 Hz, 1H), 8.10-8.02 (m, 3H), 7.86 (dd, J=6.0, 2.4 Hz, 1H), 3.07 (t, J=6.0 Hz, 2H), 2.79-2.75 (m, 2H), 2.17-2.11 (m, 2H).

Step 6. Synthesis of (E)-2-(1-(6-(trifluoromethyl)pyridin-2-yl)-1H-indazol-6-yl)-6,7-dihydroquinolin-8(5H)-one oxime

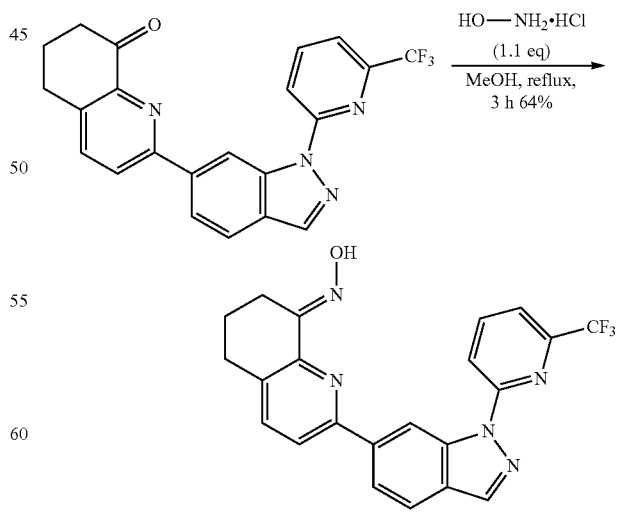

The preparation of (E)-2-(1-(6-(trifluoromethyl)pyridin-2-yl)-1H-indazol-6-yl)-6,7-dihydroquinolin-8(5H)-one oxime was the same as that of 2-(1-(6-(trifluoromethyl)

pyridin-2-yl)-1H-indazol-6-yl)-5H-cyclopenta[b]pyridin-7 (6H)-one oxime. 100 mg, as white solid, Y: 64%. ESI-MS (M+H)⁺: 424.1.

Step 7. Synthesis of 2-(1-(6-(trifluoromethyl)pyridin-2-yl)-1H-indazol-6-yl)-5,6,7,8-tetrahydroquinolin-8-amine

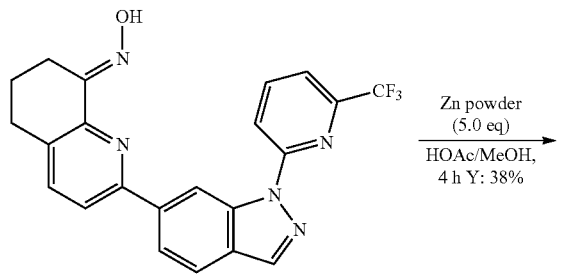

The preparation of 2-(1-(6-(trifluoromethyl)pyridin-2-yl)-1H-indazol-6-yl)-5,6,7,8-tetrahydroquinolin-8-amine was the same as that of 2-(1-(6-(trifluoromethyl)pyridin-2-yl)-1H-indazol-6-yl)-6,7-dihydro-5H-cyclopenta[b]pyridin-7-amine. 40 mg, as white solid, Y: 38%. ESI-MS (M+H)⁺: 410.1. ¹H NMR (400 MHz, CD₃OD) δ: 9.58 (s, 1H), 8.28 (d, J=8.0 Hz, 1H), 8.24 (d, J=0.8 Hz, 1H), 8.05 (dd, J=8.4, 1.2 Hz, 1H), 8.00 (t, J=8.0 Hz, 1H), 7.85 (dd, J=8.4, 0.8 Hz, 1H), 7.70 (d, J=8.0 Hz, 1H), 7.53 (d, J=7.2 Hz, 2H), 4.14-4.10 (m, 1H), 2.90-2.85 (m, 2H), 2.34-2.31 (m, 1H), 2.05-2.01 (m, 1H), 1.80-1.73 (m, 2H).

Example 64. 6-(6-(5-aminopyridin-3-yl)-1H-indazol-1-yl)-N,N-dimethylpicolinamide Synthesis of 6-(6-(5-aminopyridin-3-yl)-1H-indazol-1-yl)-N,N-dimethylpicolinamide

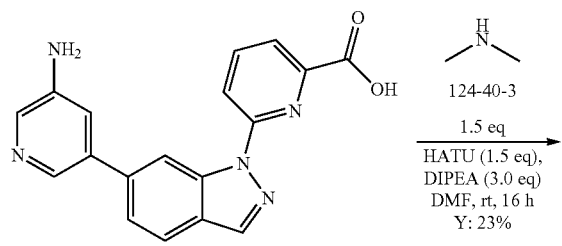

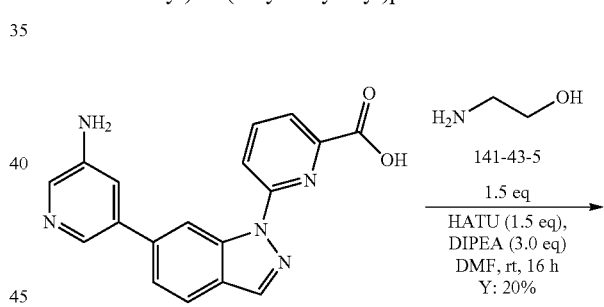

A mixture of 6-(6-(5-aminopyridin-3-yl)-1H-indazol-1-yl)picolinic acid (100 mg, 0.30 mmol, 1.0 eq), DIPEA (116 mg, 0.90 mmol, 3.0 eq) and HATU (171 mg, 0.45 mmol, 1.5 eq) in DMF (2 mL) was stirred at rt for 20 min, then, dimethylamine (CAS#124-40-3) (1 M, in THF, 0.45 mL, 0.45 mmol, 1.5 eq) was added to the mixture. The mixture was stirred at rt for 16 h. The mixture was purified by pre-HPLC to give 6-(6-(5-aminopyridin-3-yl)-1H-indazol-1-yl)-N,N-dimethylpicolinamide as a yellow solid. (25 mg, Y: 23%). ESI-MS (M+H)⁺: 359.1. HPLC: 97.92%. ¹H NMR (400 MHz, CD₃OD) δ: 9.09 (s, 1H), 8.42 (s, 1H), 8.30 (d, J=1.2 Hz, 1H), 8.22 (d, J=7.6 Hz, 1H), 8.14-8.10 (m, 1H), 8.06-8.04 (m, 2H), 7.95-7.94 (m, 1H), 7.62 (dd, J=8.4, 1.6 Hz, 1H), 7.49 (d, J=7.6 Hz, 1H), 3.20 (s, 3H), 3.13 (s, 3H).

Example 65. 6-(6-(5-aminopyridin-3-yl)-1H-indazol-1-yl)-N-(2-hydroxyethyl)picolinamide Synthesis of 6-(6-(5-aminopyridin-3-yl)-1H-indazol-1-yl)-N-(2-hydroxyethyl)picolinamide

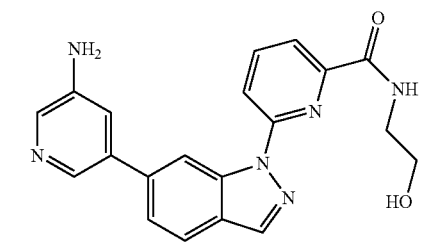

The preparation of 6-(6-(5-aminopyridin-3-yl)-1H-indazol-1-yl)-N-(2-hydroxyethyl)picolinamide was the same as that of 6-(6-(5-aminopyridin-3-yl)-1H-indazol-1-yl)-N,N-dimethylpicolinamide. 18 mg, yellow solid. Y: 20%. ESI-MS (M+H)⁺: 375.1. HPLC: 100.00%. ¹H NMR (400 MHz, CD₃OD) δ: 9.02 (d, J=0.8 Hz, 1H), 8.44 (d, J=2.0 Hz, 2H), 8.31 (d, J=8.4, 0.8 Hz, 1H), 8.19-8.15 (m, 1H), 8.07-8.02 (m, 4H), 7.67 (dd, J=8.4, 1.6 Hz, 1H), 3.79 (t, J=4.8 Hz, 2H), 3.64 (t, J=4.8 Hz, 2H).

Example 66. 6-(6-(5-aminopyridin-3-yl)-1H-indazol-1-yl)-N-(3-hydroxypropyl)picolinamide Synthesis of 6-(6-(5-aminopyridin-3-yl)-1H-indazol-1-yl)-N-(3-hydroxypropyl)picolinamide

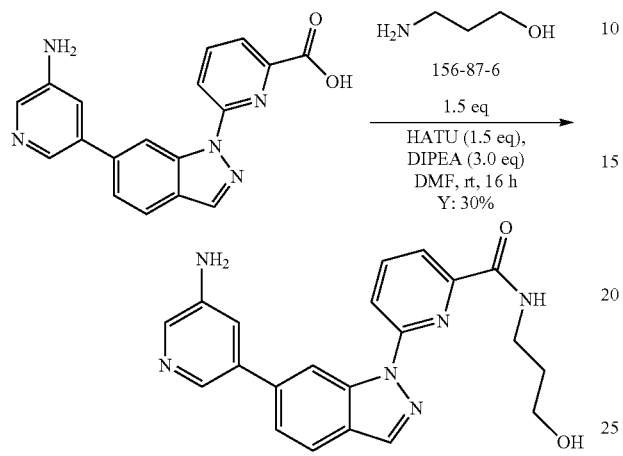

The preparation of 6-(6-(5-aminopyridin-3-yl)-1H-indazol-1-yl)-N-(3-hydroxypropyl)picolinamide was the same as that of 6-(6-(5-aminopyridin-3-yl)-1H-indazol-1-yl)-N,N-dimethylpicolinamide. 27 mg, yellow solid. Y: 30%. ESI-MS (M+H)$^+$: 389.1. HPLC: 97.38%. $^1$H NMR (400 MHz, CD$_3$OD) δ: 8.82 (s, 1H), 8.29 (s, 1H), 8.27 (s, 1H), 8.10 (d, J=8.0 Hz, 1H), 7.99 (d, J=7.6 Hz, 1H), 7.98-7.96 (m, 1H), 7.91-7.89 (m, 2H), 7.82 (d, J=7.2 Hz, 1H), 7.50 (dd, J=8.0, 1.2 Hz, 1H), 3.54-3.47 (m, 4H), 1.75-1.71 (m, 2H).

Example 67. 6-(6-(5-aminopyridin-3-yl)-1H-indazol-1-yl)-N-(2-hydroxypropyl)picolinamide Synthesis of 6-(6-(5-aminopyridin-3-yl)-1H-indazol-1-yl)-N-(2-hydroxypropyl)picolinamide

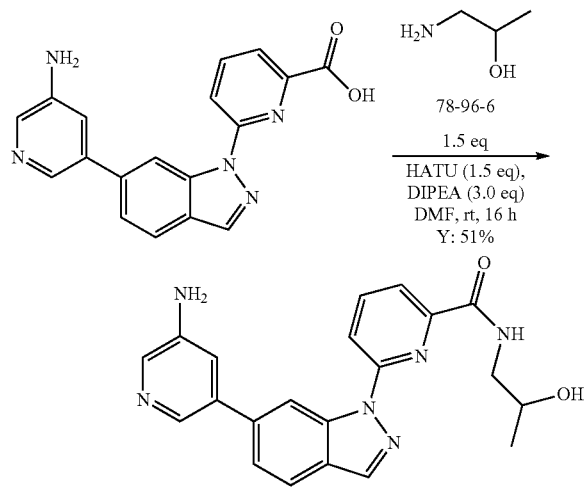

The preparation of 6-(6-(5-aminopyridin-3-yl)-1H-indazol-1-yl)-N-(2-hydroxypropyl)picolinamide was the same as that of 6-(6-(5-aminopyridin-3-yl)-1H-indazol-1-yl)-N,N-dimethylpicolinamide. 58 mg, yellow solid. Y: 51%. ESI-MS (M+H)$^+$: 389.1. HPLC: 97.83%. $^1$H NMR (400 MHz, CD$_3$OD) δ: 8.52 (s, 1H), 8.19 (s, 1H), 8.12 (s, 1H), 7.99-7.93 (m, 2H), 7.86-7.82 (m, 2H), 7.76-7.73 (m, 2H), 7.39 (dd, J=8.4, 1.6 Hz, 1H), 3.88-3.84 (m, 1H), 3.53 (dd, J=14.0, 3.2 Hz, 1H), 3.17 (dd, J=13.6, 8.0 Hz, 1H), 1.11 (d, J=6.4 Hz, 3H).

Example 68. (6-(6-(5-aminopyridin-3-yl)-1H-indazol-1-yl)pyridin-2-yl)(3-hydroxyazetidin-1-yl)methanone Synthesis of (6-(6-(5-aminopyridin-3-yl)-1H-indazol-1-yl)pyridin-2-yl)(3-hydroxyazetidin-1-yl)methanone

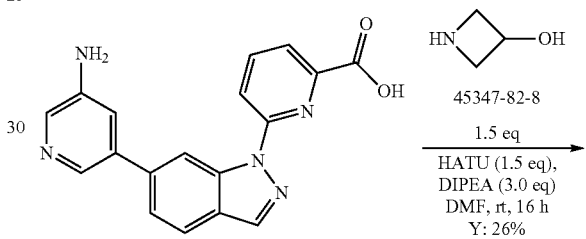

The preparation of (6-(6-(5-aminopyridin-3-yl)-1H-indazol-1-yl)pyridin-2-yl)(3-hydroxyazetidin-1-yl)methanone was the same as that of 6-(6-(5-aminopyridin-3-yl)-1H-indazol-1-yl)-N,N-dimethylpicolinamide. 22 mg, yellow solid. Y: 26%. ESI-MS (M+H)$^+$: 387.1. HPLC: 97.48%. $^1$H NMR (400 MHz, CD$_3$OD) δ: 9.06 (s, 1H), 8.42 (d, J=0.8 Hz, 1H), 8.34 (s, 1H), 8.24 (dd, J=8.4, 0.8 Hz, 1H), 8.14 (t, J=8.0 Hz, 1H), 8.06-8.04 (m, 3H), 7.81 (dd, J=7.6, 1.2 Hz, 1H), 7.65 (dd, J=8.0, 1.6 Hz, 1H), 4.70-4.62 (m, 2H), 4.59-4.50 (m, 2H), 4.07-4.03 (m, 1H).

Example 69. 6-(6-(5-aminopyridin-3-yl)-1H-indazol-1-yl)-N-(2-(dimethylamino)ethyl)picolinamide Synthesis of 6-(6-(5-aminopyridin-3-yl)-1H-indazol-1-yl)-N-(2-(dimethylamino)ethyl)picolinamide

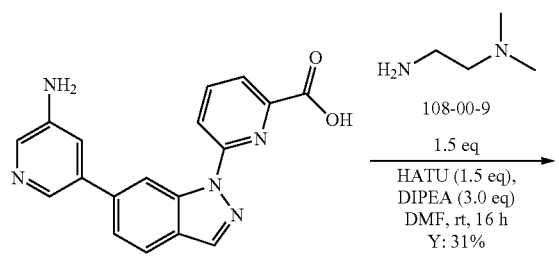

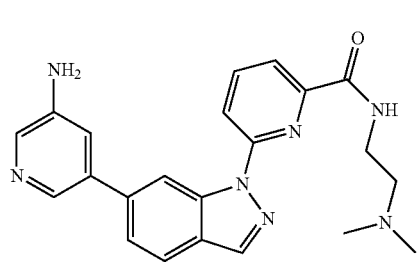

The preparation of 6-(6-(5-aminopyridin-3-yl)-1H-indazol-1-yl)-N-(2-(dimethylamino)ethyl)picolinamide was the same as that of 6-(6-(5-aminopyridin-3-yl)-1H-indazol-1-yl)-N,N-dimethylpicolinamide. 29 mg, yellow solid. Y: 31%. ESI-MS (M+H)+: 402.2. HPLC: 97.39%. $^1$H NMR (400 MHz, CD$_3$OD) δ: 8.95 (s, 1H), 8.46-8.45 (m, 2H), 8.29 (d, J=8.4 Hz, 1H), 8.22-8.17 (m, 1H), 8.08-8.05 (m, 4H), 7.67 (d, J=8.4 Hz, 1H), 3.90 (t, J=6.0 Hz, 2H), 3.43 (t, J=6.0 Hz, 2H), 3.01 (s, 6H).

Example 70. 6-(6-(5-aminopyridin-3-yl)-1H-indazol-1-yl)-N-(2-cyanoethyl)picolinamide Synthesis of 6-(6-(5-aminopyridin-3-yl)-1H-indazol-1-yl)-N-(2-cyanoethyl)picolinamide

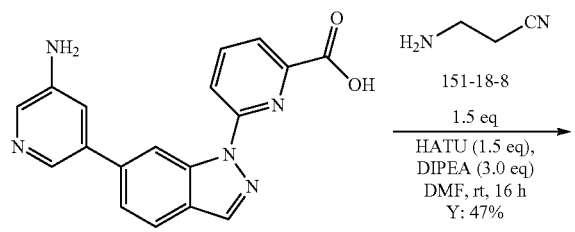

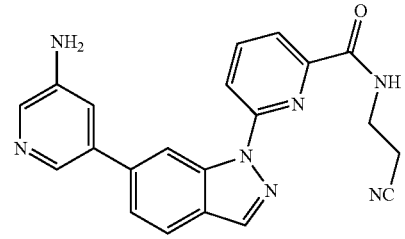

The preparation of 6-(6-(5-aminopyridin-3-yl)-1H-indazol-1-yl)-N-(2-cyanoethyl)picolinamide was the same as that of 6-(6-(5-aminopyridin-3-yl)-1H-indazol-1-yl)-N,N-dimethylpicolinamide. 55 mg, yellow solid. Y: 47%. ESI-MS (M+H)+: 384.1. HPLC: 96.87%. $^1$H NMR (400 MHz, CD$_3$OD) δ: 8.92 (s, 1H), 8.40 (s, 1H), 8.34 (d, J=1.2 Hz, 1H), 8.27 (dd, J=8.4, 0.8 Hz, 1H), 8.16 (t, J=8.0 Hz, 1H), 8.03-7.98 (m, 3H), 7.83-7.82 (m, 1H), 7.61 (dd, J=8.4, 1.2 Hz, 1H), 3.74 (t, J=6.4 Hz, 2H), 2.84 (t, J=6.4 Hz, 2H).

Example 71. 6-(6-(5-aminopyridin-3-yl)-1H-indazol-1-yl)-N-(3-cyanopropyl)picolinamide Synthesis of 4-((2,4-dimethoxybenzyl)amino)butanenitrile

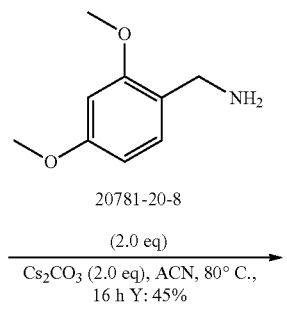

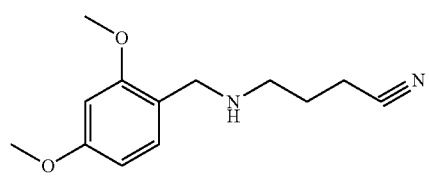

A mixture of 4-bromobutanenitrile (CAS#5332-06-9) (500 mg, 3.40 mmol, 1.0 eq), (2,4-dimethoxyphenyl)methanamine (CAS#20781-20-8) (1.14 g, 6.80 mmol, 2.0 eq) and Cs$_2$CO$_3$ (2.21 g, 6.80 mmol, 2.0 eq) in ACN (10 mL) was stirred at 80° C. for 16 h. After concentration, the residue was purified by column chromatography on silica gel (PE/EA=6/1) to afford 4-((2,4-dimethoxybenzyl)amino)butanenitrile. 358 mg, as a yellow solid, Y: 45%. ESI-MS (M+H)+: 235.1. $^1$H NMR (400 MHz, CD$_3$OD) δ: 7.30 (d, J=8.8 Hz, 1H), 6.66 (d, J=2.4 Hz, 1H), 6.60 (dd, J=8.4, 2.4 Hz, 1H), 4.17 (s, 2H), 3.91 (s, 3H), 3.83 (s, 3H), 3.15-3.11 (m, 2H), 2.62 (t, J=7.2 Hz, 2H), 2.09-2.02 (m, 2H).

Synthesis of 6-(6-(5-aminopyridin-3-yl)-1H-indazol-1-yl)-N-(3-cyanopropyl)-N-(2,4-dimethoxybenzyl)picolinamide

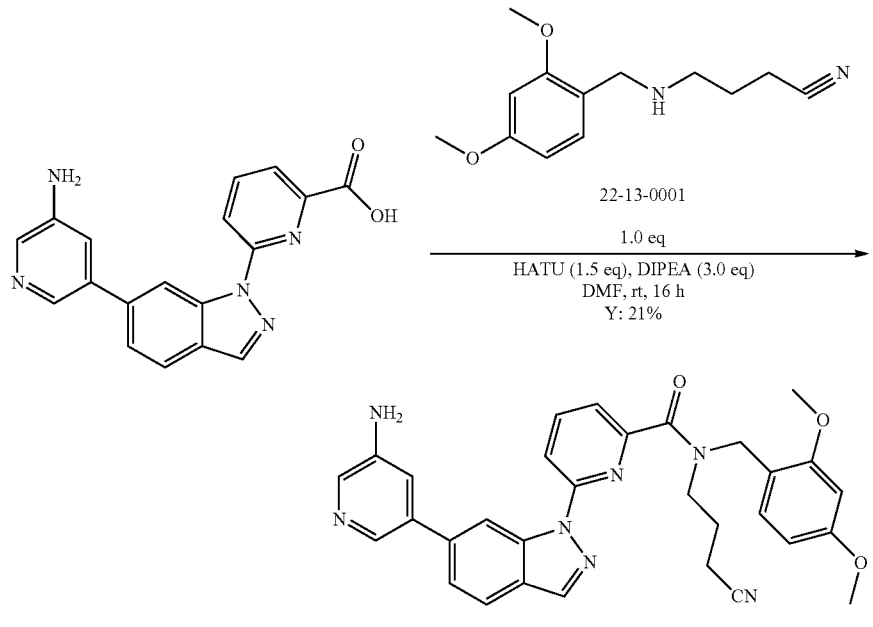

The preparation of 6-(6-(5-aminopyridin-3-yl)-1H-indazol-1-yl)-N-(3-cyanopropyl)-N-(2,4-dimethoxybenzyl)picolinamide was the same as that of 6-(6-(5-aminopyridin-3-yl)-1H-indazol-1-yl)-N,N-dimethylpicolinamide. 62 mg, yellow solid. Y: 21%. ESI-MS (M+H)$^+$: 548.2.

Synthesis of 6-(6-(5-aminopyridin-3-yl)-1H-indazol-1-yl)-N-(3-cyanopropyl)picolinamide A solution of 6-(6-(5-aminopyridin-3-yl)-1H-indazol-1-yl)-N-(3-cyanopropyl)-N-(2,4-dimethoxybenzyl)picolinamide (62 mg, 0.11 mmol, 1.0 eq) in TFA (0.5 mL) was stirred at 70° C. for 0.5 h. After concentration, the residue was purified by pre-HPLC to give 6-(6-(5-aminopyridin-3-yl)-1H-indazol-1-yl)-N-(3-cyanopropyl)picolinamide as a yellow solid. (15 mg, Y: 33%). ESI-MS (M+H)$^+$: 398.1. HPLC: 100.00%. $^1$H NMR (400 MHz, CD$_3$OD) δ: 9.00 (s, 1H), 8.43 (s, 1H), 8.38 (s, 1H), 8.28 (dd, J=8.4, 0.8 Hz, 1H), 8.17 (t, J=8.0 Hz, 1H), 8.067-8.05 (m, 2H), 7.99-7.97 (m, 2H), 7.64 (dd, J=8.0, 1.6 Hz, 1H), 3.59 (t, J=6.8 Hz, 2H), 2.53 (t, J=7.2 Hz, 2H), 1.98-1.94 (m, 2H).

Example 72. N-(2-aminoethyl)-6-(6-(5-aminopyridin-3-yl)-1H-indazol-1-yl)picolinamide Synthesis of N-(2-aminoethyl)-6-(6-(5-aminopyridin-3-yl)-1H-indazol-1-yl)picolinamide

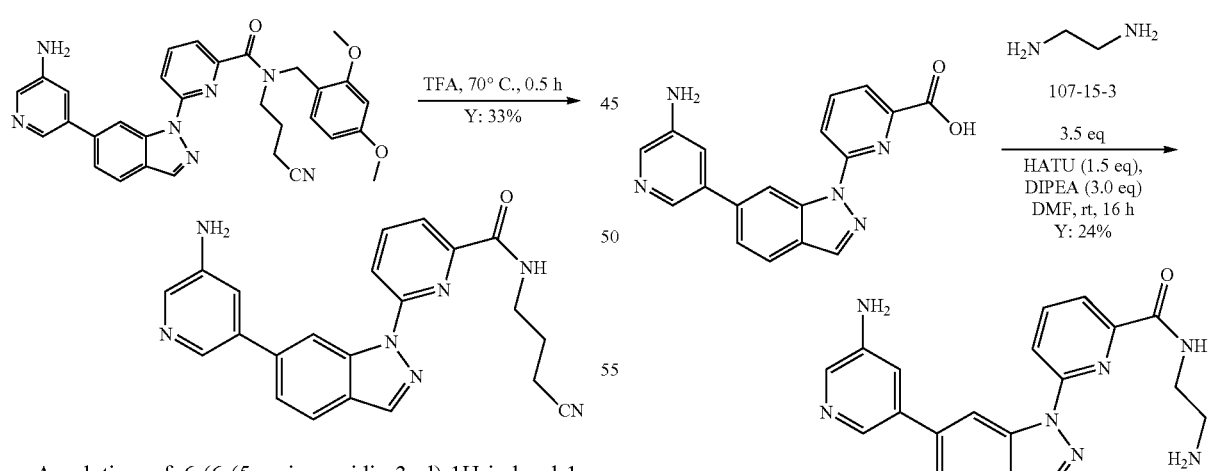

The preparation of N-(2-aminoethyl)-6-(6-(5-aminopyridin-3-yl)-1H-indazol-1-yl)picolinamide was the same as that of 6-(6-(5-aminopyridin-3-yl)-1H-indazol-1-yl)-N,N-dimethylpicolinamide. 25 mg, yellow solid. Y: 24%. ESI-MS (M+H)$^+$: 374.1. HPLC: 95.00%. $^1$H NMR (400 MHz, CD$_3$OD) δ: 8.96 (s, 1H), 8.45 (d, J=0.4 Hz, 1H), 8.43 (d, J=1.2 Hz, 1H), 8.30 (dd, J=8.4, 0.8 Hz, 1H), 8.20 (t, J=8.0

Hz, 1H), 8.08-7.97 (m, 3H), 7.97 (s, 1H), 7.67 (dd, J=8.0, 1.2 Hz, 1H), 3.81 (t, J=6.0 Hz, 2H), 3.23 (t, J=6.0 Hz, 2H).

Example 73. 6-(6-(5-aminopyridin-3-yl)-1H-indazol-1-yl)-N-(cyanomethyl)picolinamide Synthesis of 6-(6-(5-aminopyridin-3-yl)-1H-indazol-1-yl)-N-(cyanomethyl)picolinamide

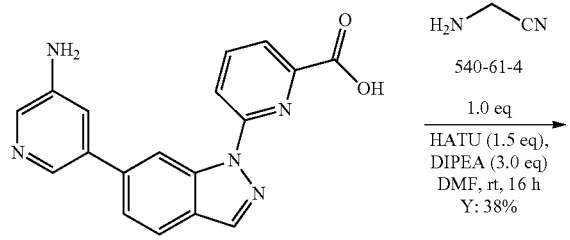

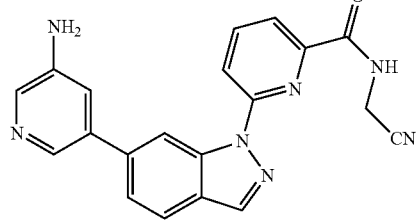

The preparation of 6-(6-(5-aminopyridin-3-yl)-1H-indazol-1-yl)-N-(cyanomethyl)picolinamide was the same as that of 6-(6-(5-aminopyridin-3-yl)-1H-indazol-1-yl)-N,N-dimethylpicolinamide. 47 mg, yellow solid. Y: 38%. ESI-MS (M+H)+: 370.1. HPLC: 100.00%. 1H NMR (400 MHz, CD3OD) δ: 8.99 (s, 1H), 8.42 (d, J=0.8 Hz, 1H), 8.41 (d, J=1.2 Hz, 1H), 8.29 (dd, J=8.4, 0.8 Hz, 1H), 8.18 (t, J=8.0 Hz, 1H), 8.06-8.04 (m, 2H), 8.01-7.99 (m, 2H), 7.66 (dd, J=8.4, 1.6 Hz, 1H), 4.48 (s, 2H).

Example 74. 6-(6-(5-aminopyridin-3-yl)-1H-indazol-1-yl)-N-(2-(methylsulfonyl)ethyl)picolinamide Synthesis of 6-(6-(5-aminopyridin-3-yl)-1H-indazol-1-yl)-N-(2-(methylsulfonyl)ethyl)picolinamide

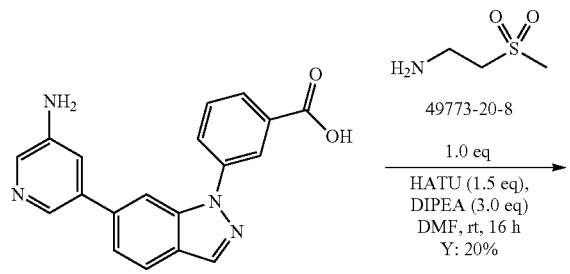

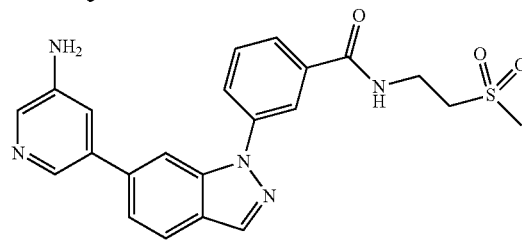

The preparation of 6-(6-(5-aminopyridin-3-yl)-1H-indazol-1-yl)-N-(2-(methylsulfonyl)ethyl)picolinamide was the same as that of 6-(6-(5-aminopyridin-3-yl)-1H-indazol-1-yl)-N,N-dimethylpicolinamide. 25 mg, yellow solid. Y: 20%. ESI-MS (M+H)+: 437.1. HPLC: 96.20%. 1H NMR (400 MHz, CD3OD) δ: 8.71 (s, 1H), 8.26 (d, J=0.4 Hz, 1H), 8.21 (d, J=0.4 Hz, 1H), 8.10 (dd, J=8.4, 1.2 Hz, 1H), 7.98 (t, J=8.0 Hz, 1H), 7.92-7.85 (m, 4H), 7.45 (dd, J=8.4, 1.6 Hz, 1H), 3.90-3.87 (m, 2H), 3.60-3.30 (m, 2H), 2.86 (s, 3H).

Example 75. 3-(6-(5-aminopyridin-3-yl)imidazo[1,5-a]pyridin-3-yl)benzonitrile

Synthesis of N-((5-bromopyridin-2-yl)methyl)-3-cyanobenzamide

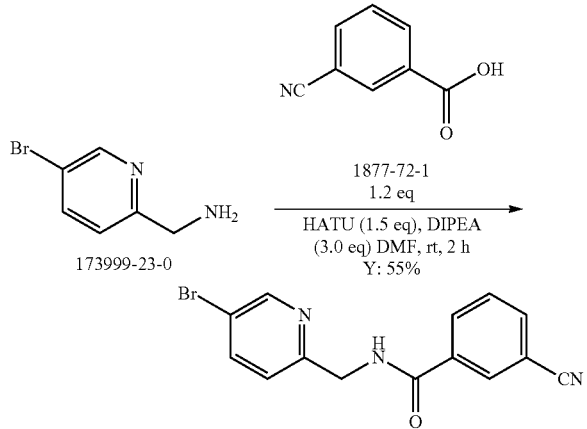

The preparation of N-((5-bromopyridin-2-yl)methyl)-3-cyanobenzamide was the same as that of 6-(6-(5-aminopyridin-3-yl)-1H-indazol-1-yl)-N,N-dimethylpicolinamide. 160 mg, yellow solid, Y: 55%. ESI-MS (M+H)+: 316.0. 1H NMR (400 MHz, CDCl3) δ: 8.65 (d, J=2.0 Hz, 1H), 8.16 (d, J=1.6 Hz, 1H), 8.10 (dt, J=8.0, 1.2 Hz, 1H), 7.86 (dd, J=8.4, 2.8 Hz, 1H), 7.81 (dt, J=7.6, 1.2 Hz, 1H), 7.62-7.58 (m, 2H), 7.28 (d, J=8.0 Hz, 1H), 4.73 (d, J=5.2 Hz, 2H).

Synthesis of 3-(6-bromoimidazo[1,5-a]pyridin-3-yl)benzonitrile

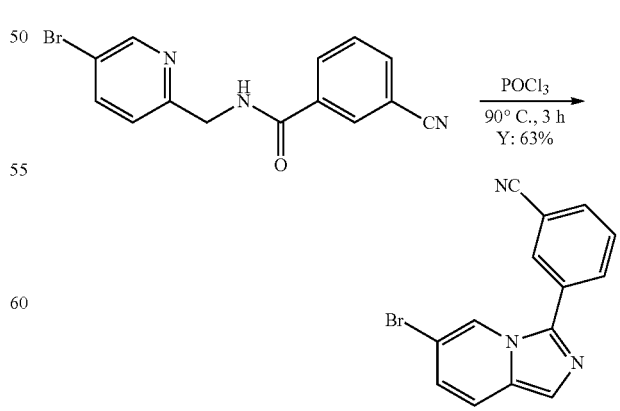

A solution of N-((5-bromopyridin-2-yl)methyl)-3-cyanobenzamide (160 mg, 0.50 mmol, 1.0 eq) in POCl3 (5 ml)

was stirred at 90° C. for 3 h. After concentration, the residue was purified by silica gel chromatography with PE/EA (10/1) as eluent to give 3-(6-bromoimidazo[1,5-a]pyridin-3-yl)benzonitrile. 95 mg, yellow solid, Y: 63%. ESI-MS (M+H)⁺: 298.1. ¹H NMR (400 MHz, CDCl₃) δ: 8.35 (d, J=0.8 Hz, 1H), 8.03 (t, J=1.2 Hz, 1H), 7.98 (dt, J=7.6, 1.2 Hz, 1H), 7.68 (dt, J=8.0, 1.2 Hz, 1H), 7.61 (d, J=8.0 Hz, 1H), 7.56 (s, 1H), 7.38 (dd, J=9.6, 1.2 Hz, 1H), 6.81 (dd, J=9.6, 1.2 Hz, 1H).

Synthesis of 3-(6-(4,4,5,5-tetramethyl-1,3,2-dioxaborolan-2-yl)imidazo[1,5-a]pyridin-3-yl)benzonitrile

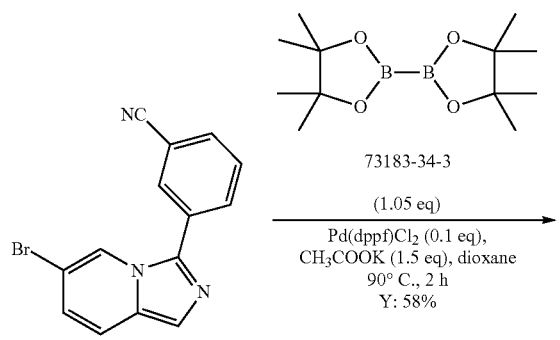

The preparation of 3-(6-(4,4,5,5-tetramethyl-1,3,2-dioxaborolan-2-yl)imidazo[1,5-a]pyridin-3-yl)benzonitrile was the same as that of 1-(6-methylpyridin-2-yl)-6-(4,4,5,5-tetramethyl-1,3,2-dioxaborolan-2-yl)-1H-indazole. 65 mg, as a white solid, Y: 58%. ESI-MS (M+H)⁺: 346.2.

Synthesis of 3-(6-(5-aminopyridin-3-yl)imidazo[1,5-a]pyridin-3-yl)benzonitrile NH₂

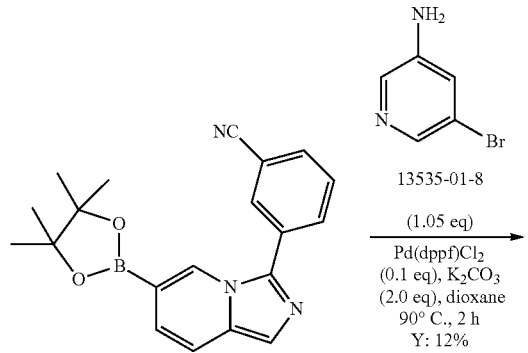

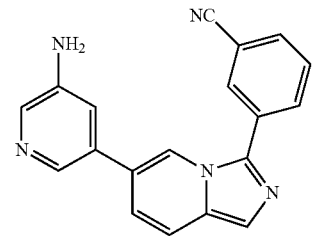

The preparation of 3-(6-(5-aminopyridin-3-yl)imidazo[1,5-a]pyridin-3-yl)benzonitrile was the same as that of 6-(1-(6-methylpyridin-2-yl)-1H-indazol-6-yl)pyridin-2-amine. 7 mg, as a yellow solid, Y: 12%. ESI-MS (M+H)⁺: 312.1. HPLC: 100.00%. ¹H NMR (400 MHz, CD₃OD) δ: 8.52 (d, J=0.8 Hz, 1H), 8.13 (s, 1H), 8.08 (d, J=8.0 Hz, 1H), 7.98 (d, J=2.0 Hz, 1H), 7.89 (d, J=2.4 Hz, 1H), 7.76 (d, J=8.0 Hz, 1H), 7.70-7.66 (m, 2H), 7.55 (s, 1H), 7.25 (t, J=2.0 Hz, 1H), 7.09 (dd, J=9.6, 1.2 Hz, 1H).

Example 76. 6-(6-(5-aminopyridin-3-yl)imidazo[1,5-a]pyridin-3-yl)picolinonitrile Synthesis of 6-((benzyloxy)carbonyl)picolinic acid

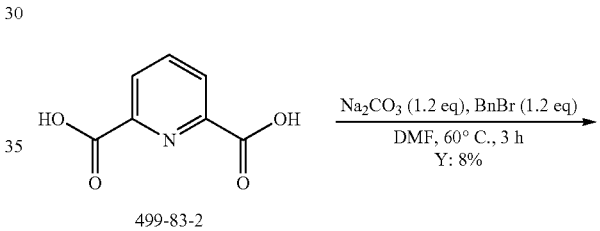

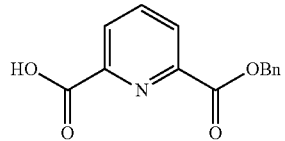

A mixture of pyridine-2,6-dicarboxylic acid (CAS#499-83-2) (8.12 g, 48.6 mmol, 1.0 eq) and Na₂CO₃ (6.18 g, 58.3 mmol, 1.2 eq) in DMF (20 mL) was stirred at rt for 10 min. Then, BnBr (9.97 g, 58.3 mmol, 1.2 eq) was added into the mixture. The mixture was stirred at 60° C. for 3 h. The mixture was diluted with water (200 mL), adjusted pH=5-6 with 6 N HCl and extracted with EA (2×200 mL). The combined organic phase was washed with water (50 mL) and dried over Na₂SO₄. After filtration and concentration, the residue was purified by silica gel chromatography with DCM/MeOH (10/1) as eluent to give 6-((benzyloxy)carbonyl)picolinic acid as a yellow solid. 1.0 g, Y: 8%. ESI-MS (M+H)⁺: 258.0. ¹H NMR (400 MHz, DMSO-d₆) δ: 8.08-8.03 (m, 2H), 7.96 (d, J=7.6 Hz, 1H), 7.50-7.49 (m, 2H), 7.43-7.36 (m, 3H), 5.40 (s, 2H).

Synthesis of benzyl 6-(chlorocarbonyl)picolinate

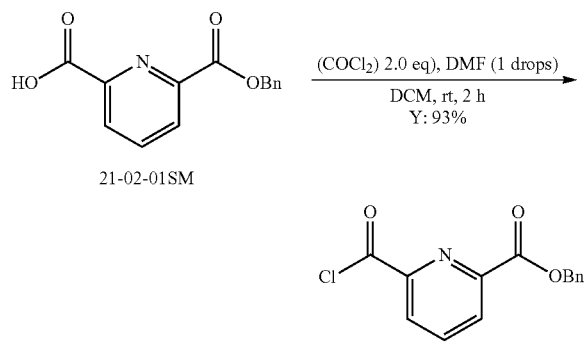

To a mixture of 6-((benzyloxy)carbonyl)picolinic acid (603 mg, 2.35 mmol, 1.0 eq) and DMF (cat.) in DCM (10 mL) was added (COCl)$_2$ (592 mg, 4.70 mmol, 2.0 eq) at rt. The mixture was stirred at rt for 2 h. After concentration, the residue was directly used for next step without further purification. 600 mg, yellow solid, Y: 93%. ESI-MS (M+H)$^+$: 276.0.

Synthesis of benzyl 6-(((5-bromopyridin-2-yl)methyl)carbamoyl)picolinate

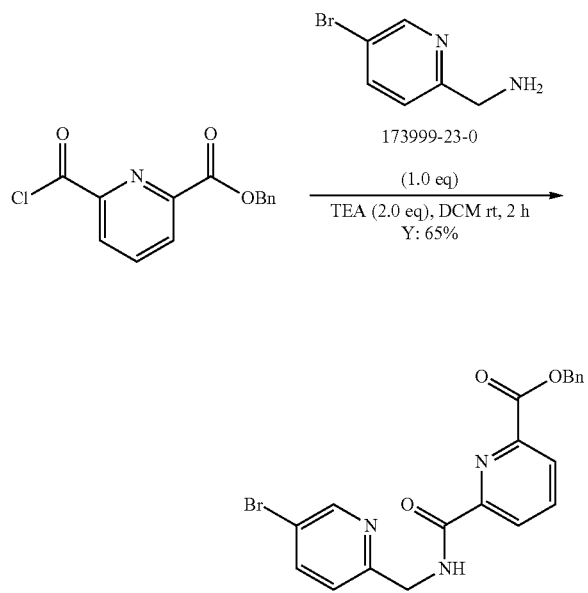

To a mixture of (5-bromopyridin-2-yl)methanamine (CAS#173999-23-0) (404 mg, 2.17 mmol, 1.0 eq) and TEA (438 mg, 4.34 mmol, 2.0 eq) in DCM (20 mL) was added benzyl 6-(((5-bromopyridin-2-yl)methyl)carbamoyl)picolinate (597 mg, 2.17 mmol, 1.0 eq) at rt. The mixture was stirred at rt for 2 h. After concentration, the residue was purified by silica gel chromatography with PE/EA (2/1) as eluent to give benzyl 6-(((5-bromopyridin-2-yl)methyl)carbamoyl)picolinate. 600 mg, yellow solid, Y: 65%. ESI-MS (M+H)$^+$: 426.0.

Synthesis of benzyl 6-(6-bromoimidazo[1,5-a]pyridin-3-yl)picolinate

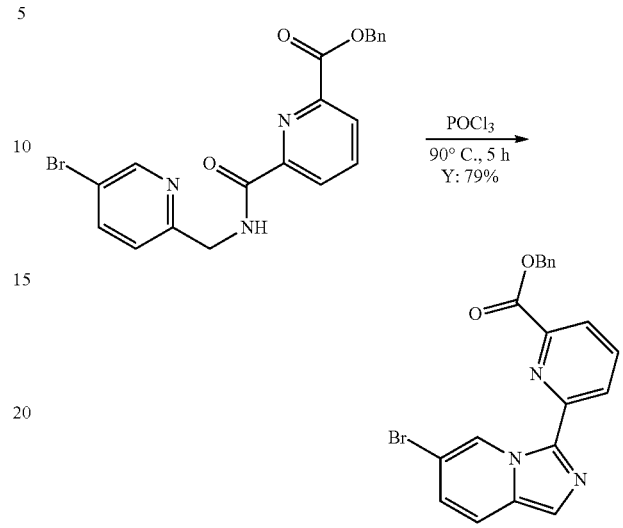

The preparation of benzyl 6-(6-bromoimidazo[1,5-a]pyridin-3-yl)picolinate was the same as that of 3-(6-bromoimidazo[1,5-a]pyridin-3-yl)benzonitrile. 380 mg, yellow solid, Y: 79%. ESI-MS (M+H)$^+$: 408.0.

Synthesis of 6-(6-bromoimidazo[1,5-a]pyridin-3-yl)picolinic acid

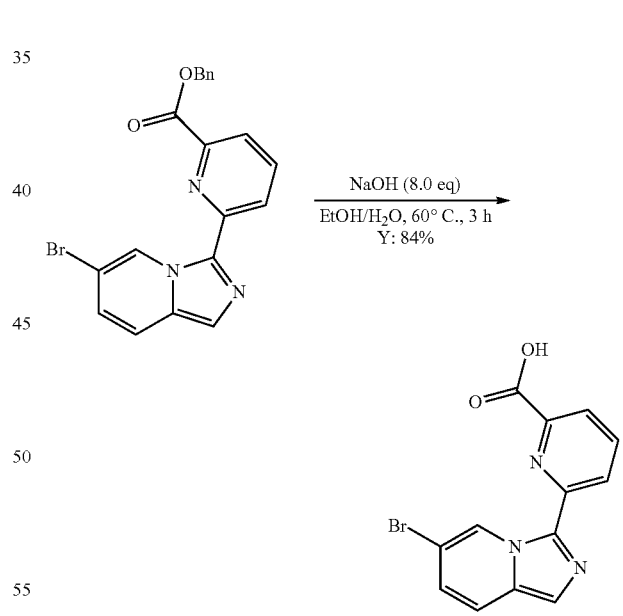

A mixture of benzyl 6-(6-bromoimidazo[1,5-a]pyridin-3-yl)picolinate (380 mg, 0.94 mmol, 1.0 eq) and NaOH (301 mg, 7.52 mmol, 8.0 eq) in EtOH/H$_2$O (10 mL/4 mL) was stirred at 60° C. for 3 h. After cooling to rt, the mixture was adjusted pH=6 with 3 N HCl and extracted with EA (3×100 mL). The combined organic phase was washed with brine (50 mL) and dried over Na$_2$SO$_4$. After filtration and concentration, the residue was directly used for next step without further purification. 250 mg, yellow solid, Y: 84%. ESI-MS (M+H)$^+$: 318.0.

Synthesis of 6-(6-bromoimidazo[1,5-a]pyridin-3-yl)picolinamide

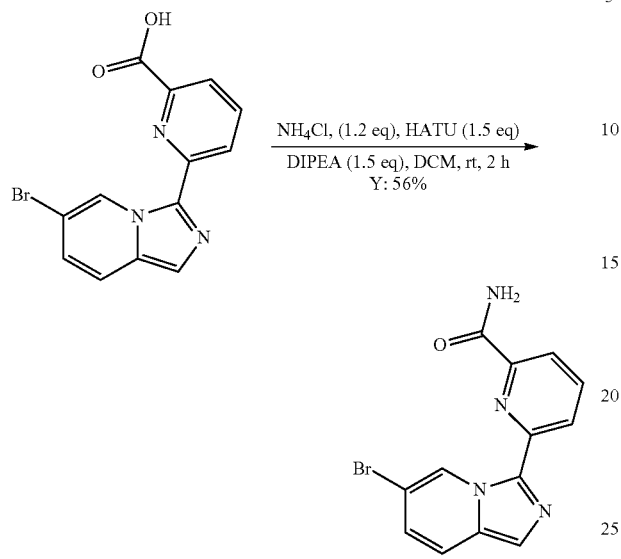

The preparation of 6-(6-bromoimidazo[1,5-a]pyridin-3-yl)picolinamide was the same as that of 6-(6-(5-aminopyridin-3-yl)-1H-indazol-1-yl)-N,N-dimethylpicolinamide. 240 mg, yellow solid, Y: 56%. ESI-MS (M+H)+: 317.0.

Synthesis of 6-(6-bromoimidazo[1,5-a]pyridin-3-yl)picolinonitrile

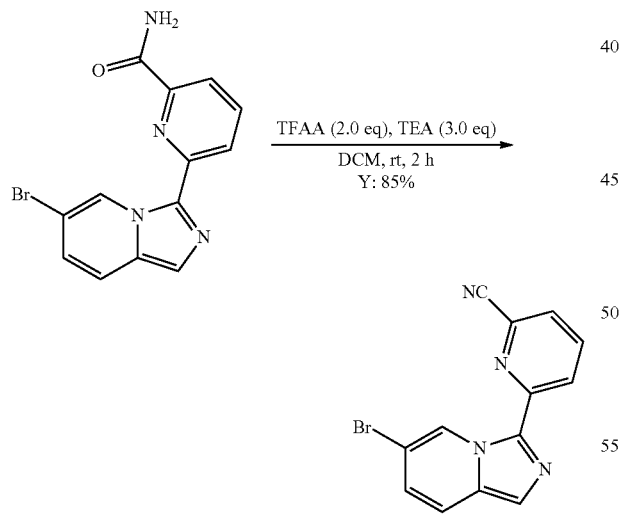

The preparation of 6-(6-bromoimidazo[1,5-a]pyridin-3-yl)picolinonitrile was the same as that of N-(5-(4-cyano-1-(6-(trifluoromethyl)pyridin-2-yl)-1H-indazol-6-yl)pyridin-3-yl)-2,2,2-trifluoroacetamide. 200 mg, yellow solid, Y: 85%. ESI-MS (M+H)+: 299.0. $^1$H NMR (400 MHz, CD$_3$OD) δ: 10.04 (s, 1H), 8.58 (dd, J=8.4, 0.8 Hz, 1H), 7.94 (d, J=7.6 Hz, 1H), 7.70 (s, 1H), 7.64 (dd, J=7.6, 0.4 Hz, 1H), 7.52 (d, J=9.2 Hz, 1H), 7.07 (dd, J=9.2, 1.2 Hz, 1H).

Synthesis of 6-(6-(4,4,5,5-tetramethyl-1,3,2-dioxaborolan-2-yl)imidazo[1,5-a]pyridin-3-yl)picolinonitrile

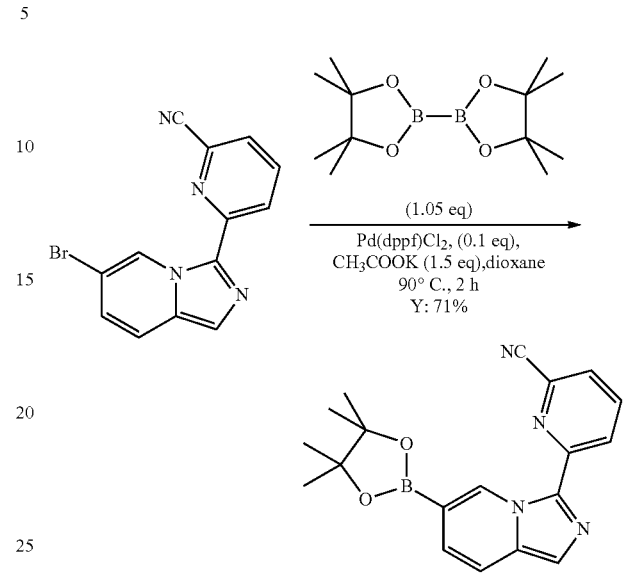

The preparation of 6-(6-(4,4,5,5-tetramethyl-1,3,2-dioxaborolan-2-yl)imidazo[1,5-a]pyridin-3-yl)picolinonitrile was the same as that of 1-(6-methylpyridin-2-yl)-6-(4,4,5,5-tetramethyl-1,3,2-dioxaborolan-2-yl)-1H-indazole. 220 mg, yellow solid, Y: 71%. ESI-MS (M+H)+: 347.2

Synthesis of 6-(6-(5-aminopyridin-3-yl)imidazo[1,5-a]pyridin-3-yl)picolinonitrile

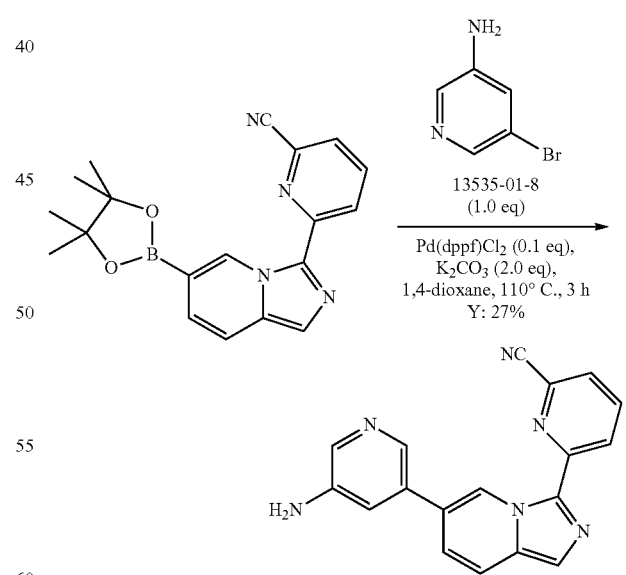

The preparation of 6-(6-(5-aminopyridin-3-yl)imidazo[1,5-a]pyridin-3-yl)picolinonitrile was the same as that of 6-(1-(6-methylpyridin-2-yl)-1H-indazol-6-yl)pyridin-2-amine. 13 mg, yellow solid, Y: 27%. ESI-MS (M+H)+: 313.1. HPLC: 99.55%. $^1$H NMR (400 MHz, DMSO-d$_6$) δ: 9.95 (s, 1H), 8.56 (dd, J=8.0, 0.4 Hz, 1H), 8.17 (t, J=8.0 Hz, 1H), 8.08 (d, J=2.0 Hz, 1H), 8.01-7.99 (m, 2H), 7.95 (dd, J=9.2, 0.8 Hz, 1H), 7.80 (d, J=0.8 Hz, 1H), 7.34 (dd, J=9.2, 1.2 Hz, 1H), 7.20 (t, J=2.0 Hz, 1H), 5.57 (s, 2H).

Example 77. 6-(6-(5-aminopyridin-3-yl)imidazo[1,5-a]pyridin-3-yl)picolinamide Synthesis of 6-(6-(5-aminopyridin-3-yl)imidazo[1,5-a]pyridin-3-yl)picolinamide

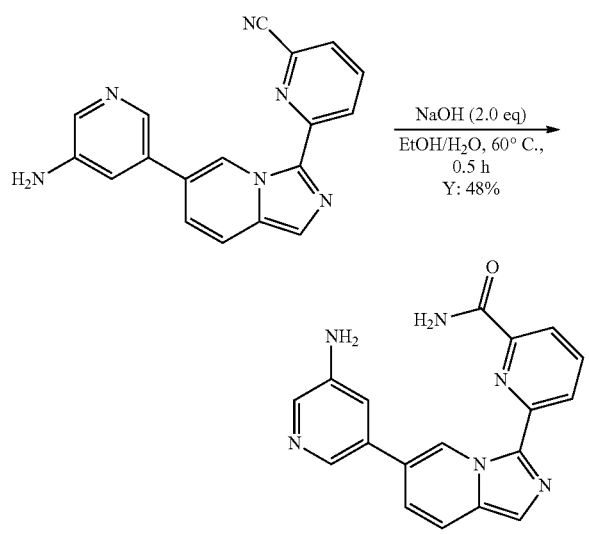

The preparation of 6-(6-(5-aminopyridin-3-yl)imidazo[1,5-a]pyridin-3-yl)picolinamide was the same as that of 6-(6-(5-aminopyridin-3-yl)-1H-indazol-1-yl)picolinamide. 8.1 mg, yellow solid, Y: 48%. ESI-MS (M+H)+: 331.1. HPLC: 95.29%. 1H NMR (400 MHz, CD3OD) δ: 10.07 (s, 1H), 8.39 (d, J=8.0 Hz, 1H), 8.18 (d, J=2.0 Hz, 1H), 8.11 (t, J=8.0 Hz, 1H), 8.05-8.01 (m, 2H), 7.84 (d, J=9.2 Hz, 1H), 7.70 (s, 1H), 7.43 (t, J=2.4 Hz, 1H), 7.33 (dd, J=9.2, 1.2 Hz, 1H).

Example 78. 5-(3-(6-(trifluoromethyl)pyridin-2-yl)imidazo[1,5-a]pyridin-6-yl)pyridin-3-amine Synthesis of 6-(trifluoromethyl)picolinoyl chloride

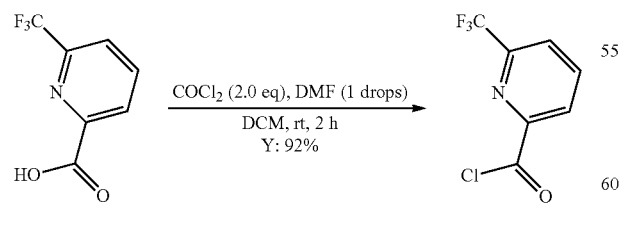

The preparation of 6-(trifluoromethyl)picolinoyl chloride was the same as that of benzyl 6-(chlorocarbonyl)picolinate. 180 mg, yellow solid, Y: 92%. ESI-MS (M+H)+: 210.1.

Synthesis of N-((5-bromopyridin-2-yl)methyl)-6-(trifluoromethyl)picolinamide

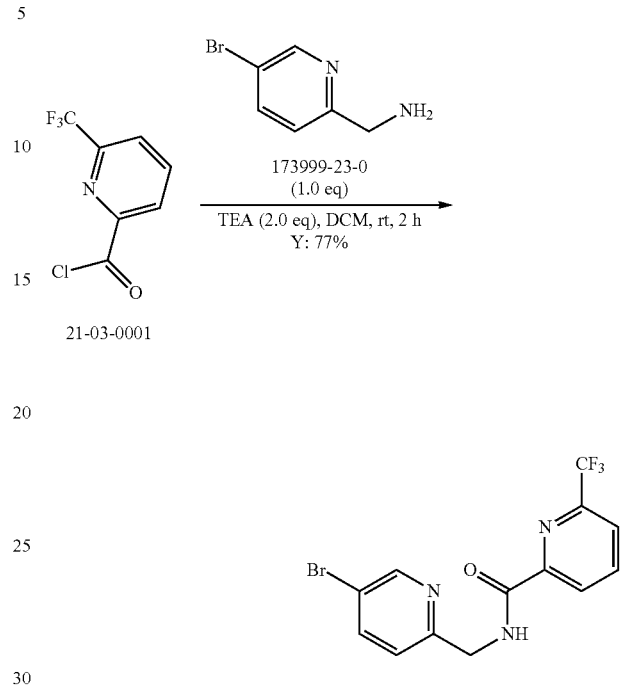

The preparation of N-((5-bromopyridin-2-yl)methyl)-6-(trifluoromethyl)picolinamide was the same as that of benzyl 6-(((5-bromopyridin-2-yl)methyl)carbamoyl)picolinate. 140 mg, yellow solid, Y: 77%. ESI-MS (M+H)+: 360.1. 1H NMR (400 MHz, CDCl3) δ: 8.73 (s, 1H), 8.67 (d, J=2.4 Hz, 1H), 8.41 (d, J=8.0 Hz, 1H), 8.08 (t, J=7.6 Hz, 1H), 7.85-7.81 (m, 2H), 7.30 (d, J=8.4 Hz, 1H), 4.78 (d, J=6.0 Hz, 2H).

Synthesis of 6-bromo-3-(6-(trifluoromethyl)pyridin-2-yl)imidazo[1,5-a]pyridine

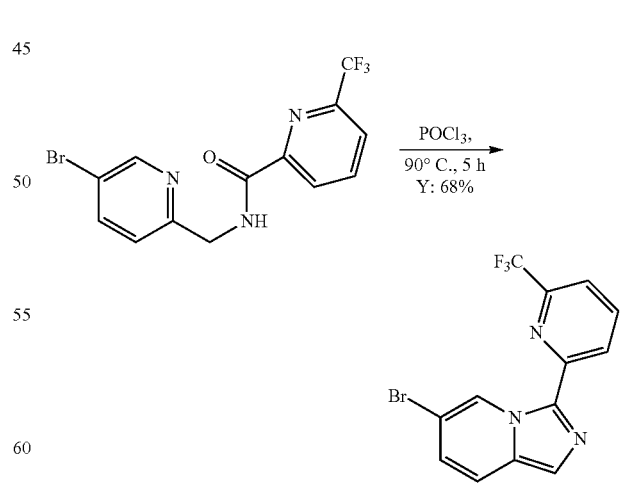

The preparation of 6-bromo-3-(6-(trifluoromethyl)pyridin-2-yl)imidazo[1,5-a]pyridine was the same as that of 3-(6-bromoimidazo[1,5-a]pyridin-3-yl)benzonitrile. 90 mg, yellow solid, Y: 68%. ESI-MS (M+H)+: 342.1.

Synthesis of 6-(4,4,5,5-tetramethyl-1,3,2-dioxaborolan-2-yl)-3-(6-(trifluoromethyl)pyridin-2-yl)imidazo[1,5-a]pyridine

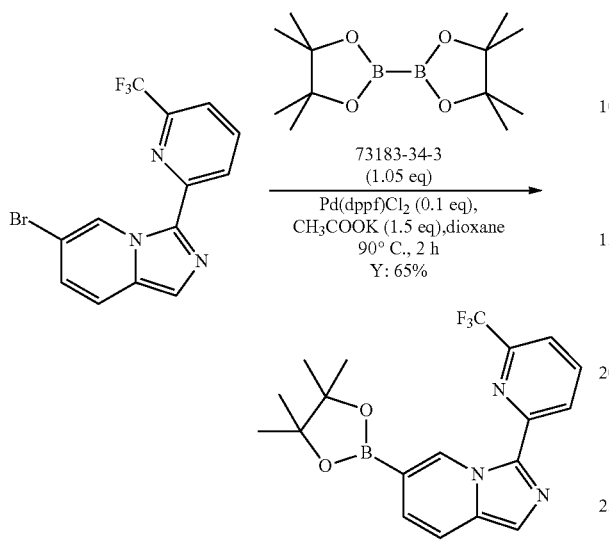

The preparation of 6-(4,4,5,5-tetramethyl-1,3,2-dioxaborolan-2-yl)-3-(6-(trifluoromethyl)pyridin-2-yl)imidazo[1,5-a]pyridine was the same as that of 1-(6-methylpyridin-2-yl)-6-(4,4,5,5-tetramethyl-1,3,2-dioxaborolan-2-yl)-1H-indazole. 85 mg, yellow solid, Y: 65%. ESI-MS (M+H)+: 390.1.

Synthesis of 5-(3-(6-(trifluoromethyl)pyridin-2-yl)imidazo[1,5-a]pyridin-6-yl)pyridin-3-amine

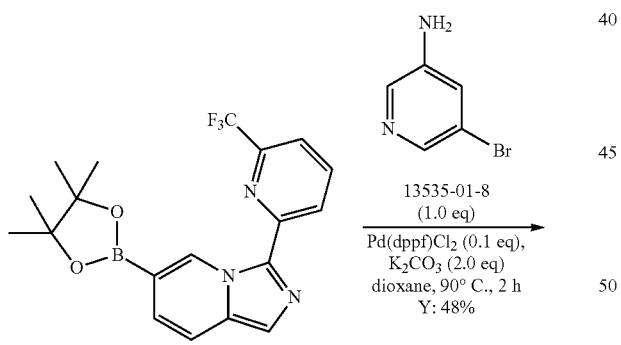

The preparation of 5-(3-(6-(trifluoromethyl)pyridin-2-yl)imidazo[1,5-a]pyridin-6-yl)pyridin-3-amine was the same as that of 6-(1-(6-methylpyridin-2-yl)-1H-indazol-6-yl)pyridin-2-amine. 45 mg, yellow solid, Y: 48%. ESI-MS (M+H)+: 390.1. HPLC: 100.00%. $^1$H NMR (400 MHz, CD$_3$OD) δ: 10.40 (s, 1H), 8.52 (d, J=8.4 Hz, 1H), 8.24 (d, J=2.0 Hz, 1H), 8.18 (t, J=8.0 Hz, 1H), 8.06 (d, J=2.4 Hz, 1H), 7.94-7.91 (m, 2H), 7.80-7.78 (m, 2H), 7.36 (dd, J=8.0, 1.2 Hz, 1H).

Example 79. 1-(6-(3-(6-(trifluoromethyl)pyridin-2-yl)imidazo[1,5-a]pyridin-6-yl)pyridin-2-yl)ethanamine

Synthesis of 1-(6-(3-(6-(trifluoromethyl)pyridin-2-yl)imidazo[1,5-a]pyridin-6-yl)pyridin-2-yl)ethanone

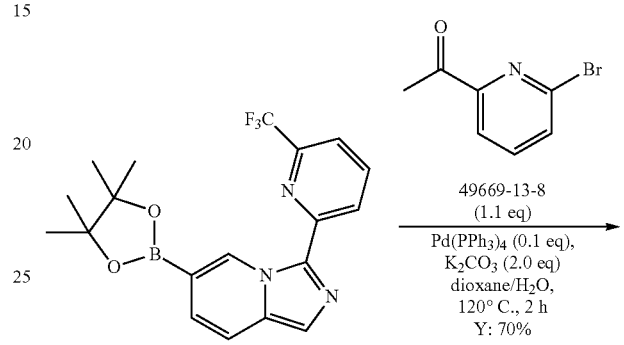

The preparation of 1-(6-(3-(6-(trifluoromethyl)pyridin-2-yl)imidazo[1,5-a]pyridin-6-yl)pyridin-2-yl)ethanone was the same as that of 1-(6-(1-(6-methylpyridin-2-yl)-1H-indazol-6-yl)pyridin-2-yl)ethanone. 200 mg, yellow solid, Y: 70%. ESI-MS (M+H)+: 381.1. $^1$H NMR (400 MHz, CDCl$_3$) δ: 10.76 (s, 1H), 8.59 (d, J=8.0 Hz, 1H), 8.06-7.97 (m, 4H), 7.83 (dd, J=9.2, 1.6 Hz, 1H), 7.74-7.69 (m, 2H), 7.61 (d, J=7.6 Hz, 1H), 2.86 (s, 3H).

Synthesis of (E)-1-(6-(3-(6-(trifluoromethyl)pyridin-2-yl)imidazo[1,5-a]pyridin-6-yl)pyridin-2-yl)ethanone oxime

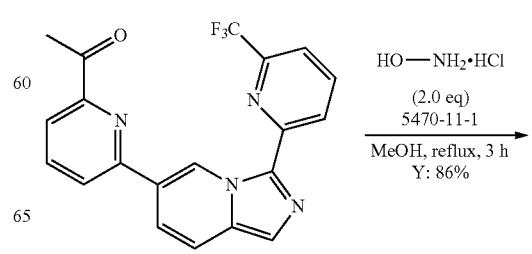

-continued

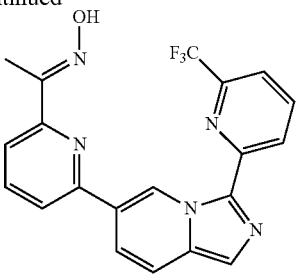

The preparation of (E)-1-(6-(3-(6-(trifluoromethyl)pyridin-2-yl)imidazo[1,5-a]pyridin-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 80 mg, yellow solid, Y: 86%. ESI-MS (M+H)+: 398.1. HPLC: 95.37%. $^1$H NMR (400 MHz, DMSO-d$_6$) δ: 11.64 (br, 1H), 10.51 (d, J=0.4 Hz, 1H), 8.57 (d, J=8.0 Hz, 1H), 8.23 (t, J=8.0 Hz, 1H), 7.97-7.88 (m, 5H), 7.81-7.79 (m, 2H), 2.34 (s, 3H).

Synthesis of 1-(6-(3-(6-(trifluoromethyl)pyridin-2-yl)imidazo[1,5-a]pyridin-6-yl)pyridin-2-yl)ethanamine

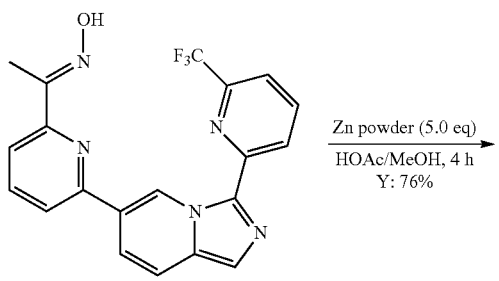

The preparation of 1-(6-(3-(6-(trifluoromethyl)pyridin-2-yl)imidazo[1,5-a]pyridin-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 55 mg, yellow solid, Y: 76%. ESI-MS (M+H)+: 384.2. HPLC: 100.00%. $^1$H NMR (400 MHz, CD$_3$OD) δ: 10.62 (s, 1H), 8.41 (d, J=8.0 Hz, 1H), 8.07 (t, J=8.0 Hz, 1H), 7.81 (t, J=8.0 Hz, 1H), 7.74-7.73 (m, 2H), 7.70 (d, J=8.0 Hz, 2H), 7.62 (d, J=0.4 Hz, 1H), 7.33 (d, J=7.6 Hz, 1H), 4.14 (q, J=6.8 Hz, 1H), 1.46 (d, J=6.8 Hz, 3H).

Example 80. 2-(aminomethyl)-6-(1-(6-(trifluoromethyl)pyridin-2-yl)-1H-indazol-6-yl)pyridin-4-amine Synthesis of 2,6-dibromo-N,N-bis(4-methoxybenzyl)pyridin-4-amine

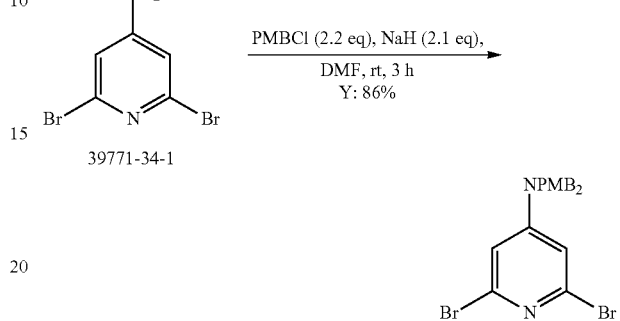

To a solution of 2,6-dibromopyridin-4-amine (CAS#39771-34-1) (2.0 g, 8.0 mmol, 1.0 eq) in DMF (10 mL) was added NaH (672 mg, 16.8 mmol, 2.1 eq) at rt. The mixture was stirred at rt for 10 min, then PMBCl (2.74 g, 17.6 mmol, 2.2 eq) was added into the mixture reaction. The mixture was stirred at rt for 3 h and diluted with water (80 mL). After filtration, the solid was directly used for next step without further purification. 3.2 g, as a white solid, Y: 86%. ESI-MS (M+H)+: 491.1. $^1$H NMR (400 MHz, DMSO-d$_6$) δ: 7.15 (d, J=8.4 Hz, 4H), 6.92 (d, J=8.8 Hz, 4H), 6.86 (s, 2H), 4.67 (s, 4H), 3.73 (s, 6H).

Synthesis of 4-(bis(4-methoxybenzyl)amino)-6-bromopicolinonitrile

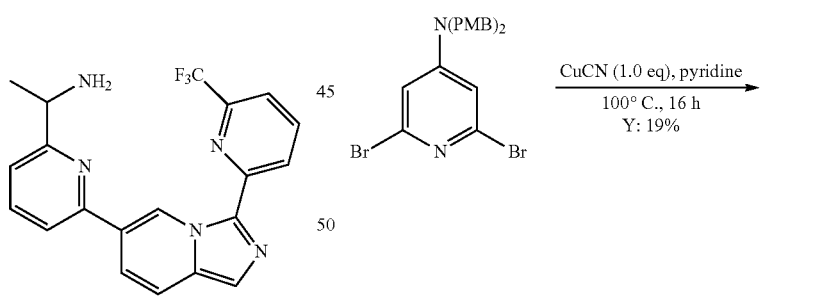

To a solution of 2,6-dibromo-N,N-bis(4-methoxybenzyl)pyridin-4-amine (3.5 g, 7.14 mmol, 1.0 eq) in pyridine (10 mL) was added CuCN (636 mg, 7.14 mmol, 1.0 eq) at rt. The mixture was stirred at 100° C. for 16 h. After concentration, the residue was purified by silica gel column (PE/EA=10/1) to give 4-(bis(4-methoxybenzyl)amino)-6-bromopicolinonitrile as a white solid. 550 mg, Y: 19%. ESI-MS (M+H)+: 438.1 $^1$H NMR (400 MHz, CD$_3$OD) δ: 7.05 (d, J=8.4 Hz, 4H), 6.91-6.88 (m, 6H), 4.56 (s, 4H), 3.82 (s, 6H).

Synthesis of 4-(bis(4-methoxybenzyl)amino)-6-(1-(6-(trifluoromethyl)pyridin-2-yl)-1H-indazol-6-yl)picolinonitrile

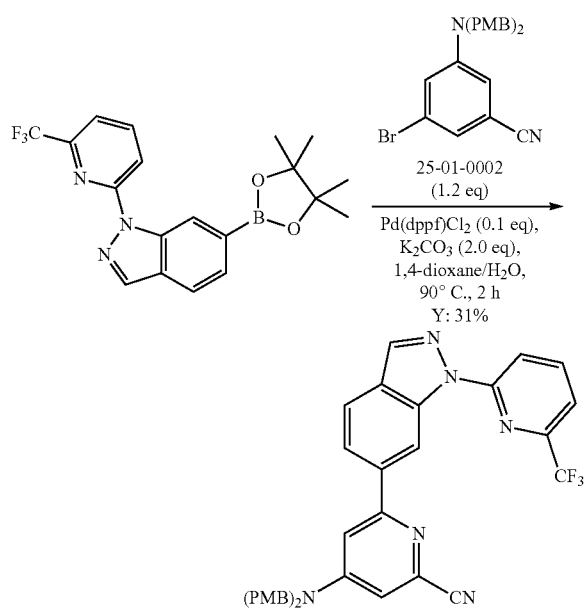

The preparation of 4-(bis(4-methoxybenzyl)amino)-6-(1-(6-(trifluoromethyl)pyridin-2-yl)-1H-indazol-6-yl)picolinonitrile was the same as that of 6-(1-(6-methylpyridin-2-yl)-1H-indazol-6-yl)pyridin-2-amine. 220 mg, as a yellow solid, Y: 31%. ESI-MS (M+H)$^+$: 621.1.

Synthesis of 2-(aminomethyl)-N,N-bis(4-methoxybenzyl)-6-(1-(6-(trifluoromethyl)pyridin-2-yl)-1H-indazol-6-yl)pyridin-4-amine

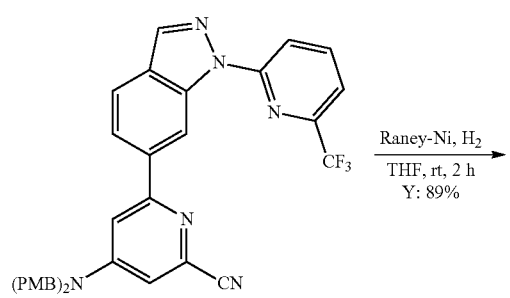

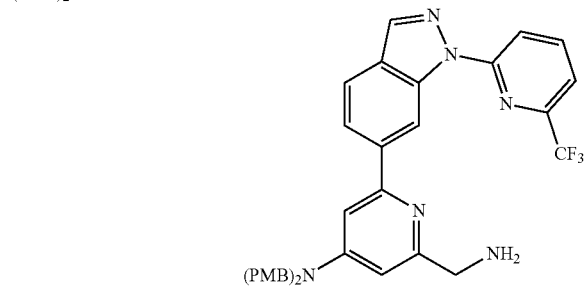

The preparation of 2-(aminomethyl)-N,N-bis(4-methoxybenzyl)-6-(1-(6-(trifluoromethyl)pyridin-2-yl)-1H-indazol- 6-yl)pyridin-4-amine was the same as that of 6-(1-(6-(trifluoromethyl)pyridin-2-yl)-1H-indazol-6-yl)picolinonitrile. 150 mg, as a yellow solid, Y: 89%. ESI-MS (M+H)$^+$: 625.1.
$^1$H NMR (400 MHz, CD$_3$OD) δ: 9.30 (s, 1H), 8.24-8.21 (m, 2H), 8.06 (t, J=8.0 Hz, 1H), 7.78 (d, J=8.4 Hz, 1H), 7.71 (d, J=7.6 Hz, 1H), 7.56 (d, J=6.8 Hz, 1H), 7.10 (d, J=8.4 Hz, 4H), 7.02 (s, 1H), 6.79 (d, J=8.8 Hz, 4H), 6.68 (d, J=2.4 Hz, 1H), 4.65 (s, 4H), 3.73 (s, 2H), 3.68 (s, 6H).

Synthesis of N-((4-amino-6-(1-(6-(trifluoromethyl)pyridin-2-yl)-1H-indazol-6-yl)pyridin-2-yl)methyl)-2,2,2-trifluoroacetamide

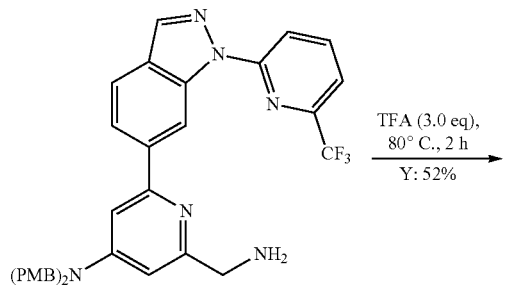

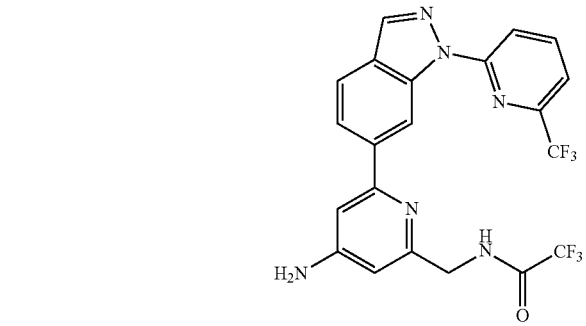

The preparation of N-((4-amino-6-(1-(6-(trifluoromethyl)pyridin-2-yl)-1H-indazol-6-yl)pyridin-2-yl)methyl)-2,2,2-trifluoroacetamide was the same as that of 2-(6-(5-aminopyridin-3-yl)-1H-indazol-1-yl)pyrimidine-4-carbonitrile. 60 mg, as a yellow solid, Y: 52%. ESI-MS (M+H)$^+$: 481.1.

Synthesis of 2-(aminomethyl)-6-(1-(6-(trifluoromethyl)pyridin-2-yl)-1H-indazol-6-yl)pyridin-4-amine

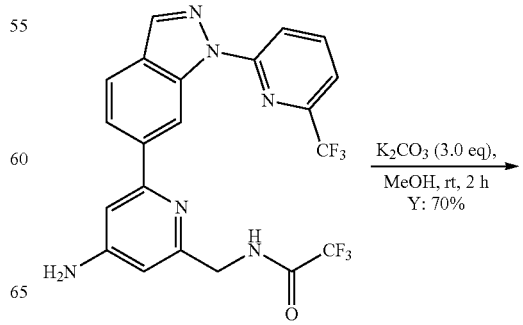

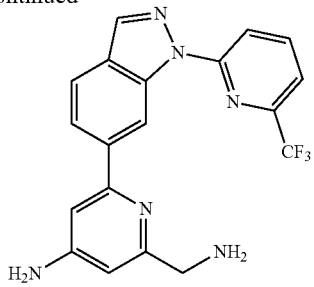

To a solution of N-((4-amino-6-(1-(6-(trifluoromethyl)pyridin-2-yl)-1H-indazol-6-yl)pyridin-2-yl)methyl)-2,2,2-trifluoroacetamide (60 mg, 0.28 mmol, 1.0 eq) in MeOH (5 mL) was added K₂CO₃ (116 mg, 0.84 mmol, 3.0 eq) at rt. The mixture was stirred at rt for 2 h. After filtration and concentration, the residue was purified by pre-HPLC (MeOH/H₂O with 0.05% TFA as mobile phase from 5% to 95%) to give 2-(aminomethyl)-6-(1-(6-(trifluoromethyl)pyridin-2-yl)-1H-indazol-6-yl)pyridin-4-amine as a yellow solid. 40 mg, Y: 83%. ESI-MS (M+H)⁺: 385.1. HPLC: 98.36%. ¹H NMR (400 MHz, CD₃OD) δ: 9.25 (s, 1H), 8.50 (s, 1H), 8.40 (d, J=8.4 Hz, 1H), 8.24 (t, J=8.0 Hz, 1H), 8.11 (d, J=8.4 Hz, 1H), 7.77-7.73 (m, 2H), 7.11 (d, J=2.4 Hz, 1H), 6.95 (d, J=8.0 Hz, 1H), 4.36 (s, 2H).

Example 81. 2-(6-(6-(5-aminopyridin-3-yl)-1H-indazol-1-yl)pyridin-2-yl)acetonitrile Synthesis of 6-bromo-1-(6-fluoropyridin-2-yl)-1H-indazole and 6-bromo-2-(6-fluoropyridin-2-yl)-2H-indazole

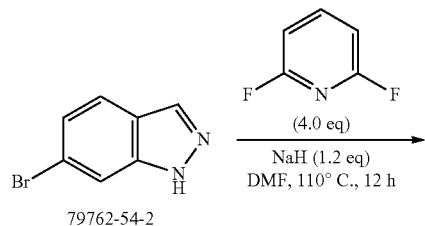

The preparation of 6-bromo-1-(6-fluoropyridin-2-yl)-1H-indazole and 6-bromo-2-(6-fluoropyridin-2-yl)-2H-indazole was the same as that of 6-bromo-1-(6-methylpyridin-2-yl)-1H-indazole. 600 mg, as a yellow solid, Y: 65%. The mixture of 6-bromo-1-(6-fluoropyridin-2-yl)-1H-indazole and 6-bromo-2-(6-fluoropyridin-2-yl)-2H-indazole was difficult to be separated and was directly used for next step. ESI-MS (M+H)⁺: 292.0, 294.0.

Synthesis of tert-butyl 2-(6-(6-bromo-1H-indazol-1-yl)pyridin-2-yl)-2-cyanoacetate

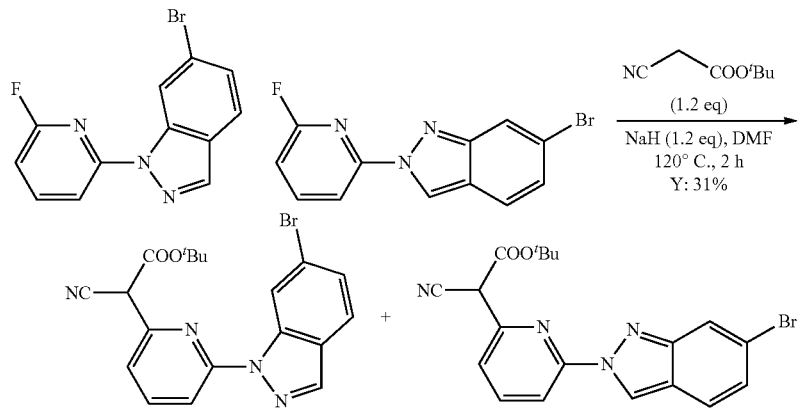

The preparation of tert-butyl 2-(6-(6-bromo-1H-indazol-1-yl)pyridin-2-yl)-2-cyanoacetate and tert-butyl 2-(6-(6-bromo-2H-indazol-2-yl)pyridin-2-yl)-2-cyanoacetate was the same as that of 6-bromo-1-(6-methylpyridin-2-yl)-1H-indazole. The mixture of tert-butyl 2-(6-(6-bromo-1H-indazol-1-yl)pyridin-2-yl)-2-cyanoacetate and tert-butyl 2-(6-(6-bromo-2H-indazol-2-yl)pyridin-2-yl)-2-cyanoacetate was purified by silica gel chromatography with PE/EA (5/1) as eluent to give tert-butyl 2-(6-(6-bromo-1H-indazol-1-yl)pyridin-2-yl)-2-cyanoacetate as a yellow solid (150 mg, Y: 31%) and PE/EA (1/1) as eluent to give tert-butyl 2-(6-(6-bromo-2H-indazol-2-yl)pyridin-2-yl)-2-cyanoacetate as a yellow solid (80 mg, Y: 17%). ESI-MS (M+H)⁺: 413.0, 415.0.

Synthesis of 2-(6-(6-bromo-1H-indazol-1-yl)pyridin-2-yl)acetonitrile

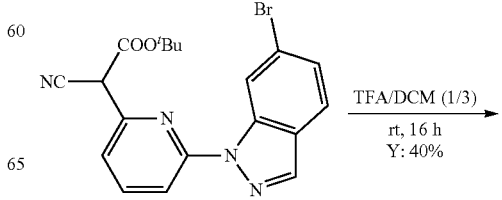

-continued

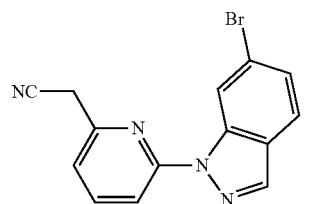

A solution of tert-butyl 2-(6-(6-bromo-1H-indazol-1-yl)pyridin-2-yl)-2-cyanoacetate (150 mg, 0.48 mmol, 1.0 eq) in TFA (1 mL)/DCM (3 mL) was stirred at rt for 16 h. After concentration, the residue was purified by pre-HPLC (CH$_3$CN/H$_2$O with 0.05% TFA as mobile phase from 5% to 95%) to give 2-(6-(6-bromo-1H-indazol-1-yl)pyridin-2-yl)acetonitrile as a yellow solid. 60 mg, Y: 40%. ESI-MS (M+H)$^+$: 313.0, 315.0.

Synthesis of 2-(6-(6-(4,4,5,5-tetramethyl-1,3,2-dioxaborolan-2-yl)-1H-indazol-1-yl)pyridin-2-yl)acetonitrile

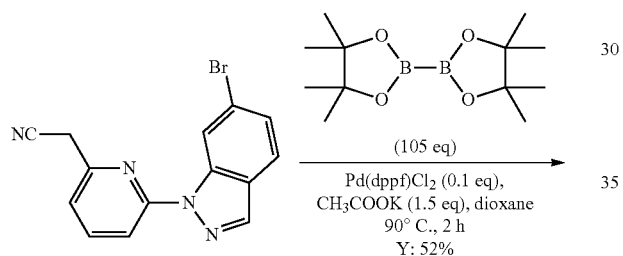

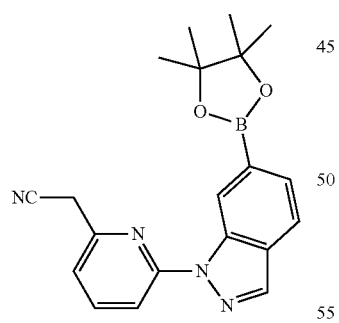

The preparation of 2-(6-(6-(4,4,5,5-tetramethyl-1,3,2-dioxaborolan-2-yl)-1H-indazol-1-yl)pyridin-2-yl)acetonitrile was the same as that of 1-(6-methylpyridin-2-yl)-6-(4,4,5,5-tetramethyl-1,3,2-dioxaborolan-2-yl)-1H-indazole. 36 mg, as a yellow solid, Y: 52%. ESI-MS (M+H)$^+$: 361.1.

Synthesis of 2-(6-(6-(5-aminopyridin-3-yl)-1H-indazol-1-yl)pyridin-2-yl)acetonitrile

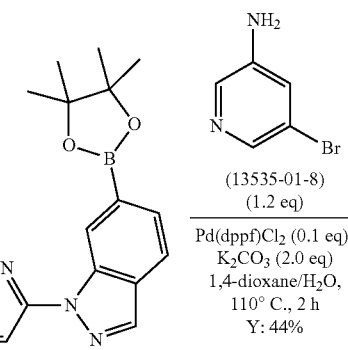

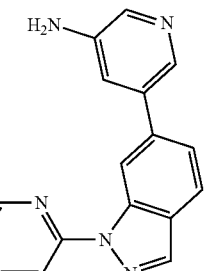

The preparation of 2-(6-(6-(5-aminopyridin-3-yl)-1H-indazol-1-yl)pyridin-2-yl)acetonitrile was the same as that of 6-(1-(6-methylpyridin-2-yl)-1H-indazol-6-yl)pyridin-2-amine. 14 mg, as a yellow solid, Y: 21%. ESI-MS (M+H)$^+$: 327.1. HPLC: 100.00% $^1$H NMR (400 MHz, CDCl$_3$) δ: 9.30 (s, 1H), 8.42 (d, J=1.6 Hz, 1H), 8.23 (s, 1H), 8.10 (d, J=2.0 Hz, 1H), 8.07 (d, J=8.4 Hz, 1H), 7.86-7.82 (m, 2H), 7.74 (t, J=6.0 Hz, 1H), 7.63 (dd, J=8.4, 1.2 Hz, 1H), 7.09 (d, J=7.6 Hz, 1H), 4.06 (s, 2H), 3.92 (br, 2H).

Example 82. 2-(6-(6-(5-aminopyridin-3-yl)-1H-indazol-1-yl)pyridin-2-yl)acetic acid Synthesis of 2-(6-(6-(5-aminopyridin-3-yl)-1H-indazol-1-yl)pyridin-2-yl)acetic acid

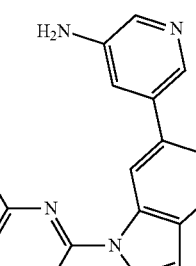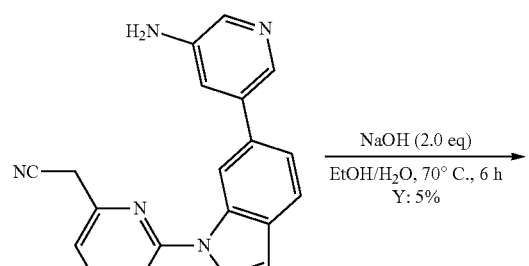

153
-continued

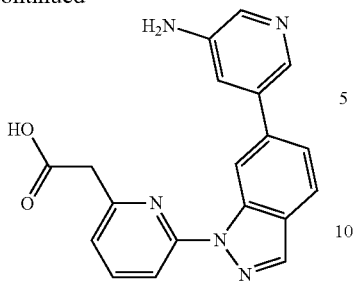

The preparation of 2-(6-(6-(5-aminopyridin-3-yl)-1H-indazol-1-yl)pyridin-2-yl)acetic acid was the same as that of 6-(6-(5-aminopyridin-3-yl)-1H-indazol-1-yl)picolinic acid. 3.0 mg, as a yellow solid, Y: 5%. ESI-MS (M+H)+: 346.2. HPLC: 100.00% $^1$H NMR (400 MHz, CD$_3$OD) δ: 9.35 (s, 1H), 8.45 (s, 1H), 8.37 (s, 1H), 8.11 (s, 1H), 8.03-7.93 (m, 4H), 7.66 (dd, J=8.4, 0.8 Hz, 1H), 7.28 (d, J=7.6 Hz, 1H), 3.97 (s, 2H).

Example 209, 83 and 84. 1-(6-(1-(6-(trifluoromethyl)pyridin-2-yl)-1H-indazol-6-yl)pyridin-2-yl)ethanamine

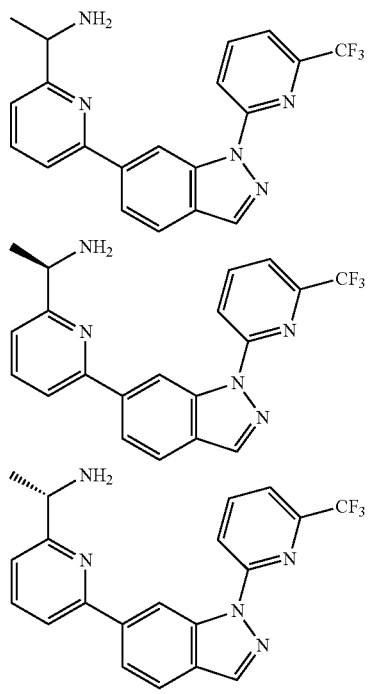

Synthesis of 1-(6-(1-(6-(trifluoromethyl)pyridin-2-yl)-1H-indazol-6-yl)pyridin-2-yl)ethanone

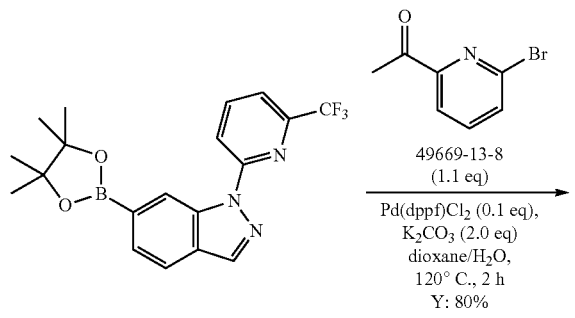

154
-continued

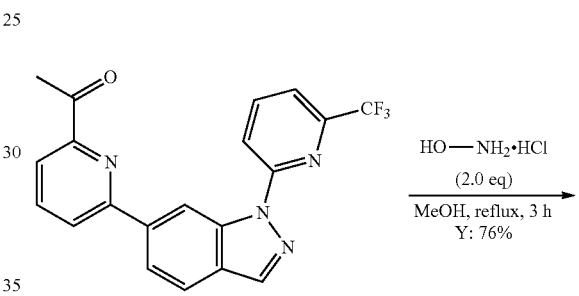

The preparation of 1-(6-(1-(6-(trifluoromethyl)pyridin-2-yl)-1H-indazol-6-yl)pyridin-2-yl)ethanone was the same as that of 6-(1-(6-methylpyridin-2-yl)-1H-indazol-6-yl)pyridin-2-amine. 502 mg, as a white solid, Y: 80%. ESI-MS (M+H)+: 383.1. $^1$H NMR (400 MHz, CDCl$_3$) δ: 9.61 (s, 1H), 8.25 (d, J=8.4 Hz, 1H), 8.21 (s, 1H), 8.08-8.01 (m, 2H), 8.00-7.87 (m, 3H), 7.84 (d, J=8.4 Hz, 1H), 7.49 (d, J=7.5 Hz, 1H), 2.83 (s, 3H).

Synthesis of (E)-1-(6-(1-(6-(trifluoromethyl)pyridin-2-yl)-1H-indazol-6-yl)pyridin-2-yl)ethanone oxime

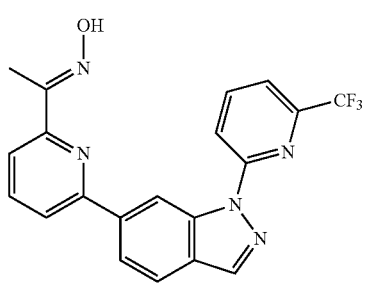

The preparation of (E)-1-(6-(1-(6-(trifluoromethyl)pyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 631 mg, as white solid, Y: 76%. ESI-MS (M+H)+: 398.1. $^1$H NMR (400 MHz, DMSO-d$_6$) δ: 11.62 (s, 1H), 9.54 (s, 1H), 8.60 (d, J=0.6 Hz, 1H), 8.36-8.25 (m, 2H), 8.11 (dd, J=8.5, 1.4 Hz, 1H), 8.08-8.00 (m, 2H), 7.96 (t, J=7.7 Hz, 1H), 7.89 (dd, J=7.7, 0.9 Hz, 1H), 7.84 (d, J=7.0 Hz, 1H), 2.39 (s, 3H).

Synthesis of 1-(6-(1-(6-(trifluoromethyl)pyridin-2-yl)-1H-indazol-6-yl)pyridin-2-yl)ethanamine

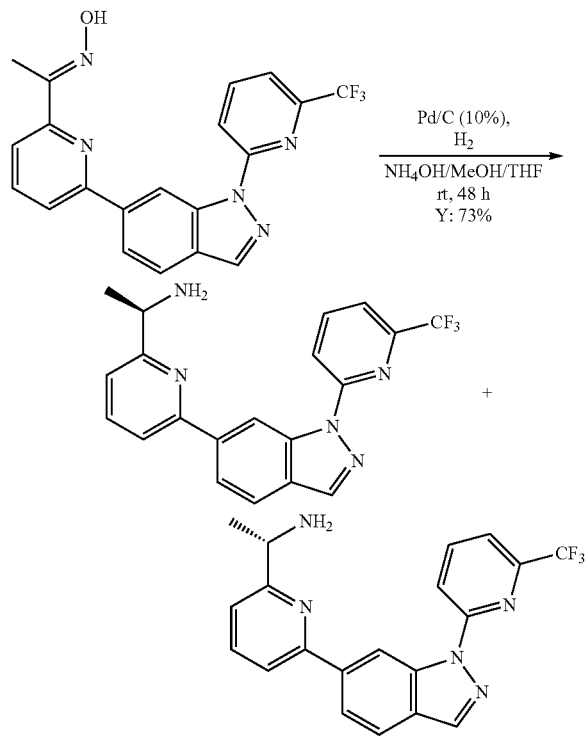

A solution of (E)-1-(6-(1-(6-(trifluoromethyl)pyridin-2-yl)-1H-indazol-6-yl)pyridin-2-yl)ethanone oxime (500 mg, 1.26 mmol, 1.0 eq) in NH₄OH/MeOH/THF solution (1/5/5, 33 mL) was added Pd/C (50 mg). The mixture was stirred at rt under H₂ atmosphere for 48 h. The mixture was filtered and the filtrate was concentrated in vacuo to afford target compound 1-(6-(1-(6-(trifluoromethyl)pyridin-2-yl)-1H-indazol-6-yl)pyridin-2-yl)ethanamine as a white solid (410 mg, Y: 85%). ESI-MS (M+H)⁺: 384.1. HPLC: 100.00% ¹H NMR (400 MHz, CD₃OD) δ: 9.56 (s, 1H), 8.30 (s, 1H), 8.28 (d, J=8.8 Hz, 1H), 8.11 (t, J=8.0 Hz, 1H), 8.00 (dd, J=8.4, 1.2 Hz, 1H), 7.87 (d, J=8.4 Hz, 1H), 7.83-7.77 (m, 2H), 7.61 (d, J=7.6 Hz, 1H), 7.30 (dd, J=7.6, 1.6 Hz, 1H), 4.14 (q, J=6.8 Hz, 1H), 1.46 (d, J=6.4 Hz, 3H).

SFC (Chiralpak IC column, 4.6*250 mm 5 μm, MeOH with 0.5% DEA, CO₂ flow rate=2.1, Co-Solvent Flow Rate=0.9, Detection wavelength=230 nm) t_R=5.25 min, 6.22 min.

Example 83. 1-(6-(1-(6-(trifluoromethyl)pyridin-2-yl)-1H-indazol-6-yl)pyridin-2-yl)ethanamine-isomer A 80 mg, as a yellow solid, ESI-MS (M+H)⁺: 384.2, HPLC: 100.00%. t_R=5.25 min (Chiral HPLC). ¹H NMR (400 MHz, CD₃OD) δ: 9.58 (s, 1H), 8.32 (d, J=0.8 Hz, 1H), 8.31 (d, J=8.8 Hz, 1H), 8.13 (t, J=8.0 Hz, 1H), 8.03 (dd, J=8.4, 1.2 Hz, 1H), 7.90 (d, J=8.4 Hz, 1H), 7.84-7.81 (m, 2H), 7.64 (d, J=7.6 Hz, 1H), 7.33 (dd, J=7.2, 1.2 Hz, 1H), 4.17 (q, J=6.4 Hz, 1H), 1.49 (d, J=6.4 Hz, 3H).

Example 84. 1-(6-(1-(6-(trifluoromethyl)pyridin-2-yl)-1H-indazol-6-yl)pyridin-2-yl)ethanamine-isomer B 80 mg, as a yellow solid, ESI-MS (M+H)⁺: 384.2, HPLC: 100.00%. t_R=6.22 min (Chiral HPLC). ¹H NMR (400 MHz, CD₃OD) δ: 9.56 (d, J=0.4 Hz, 1H), 8.30 (d, J=0.8 Hz, 1H), 8.28 (d, J=8.4 Hz, 1H), 8.11 (t, J=8.0 Hz, 1H), 8.01 (dd, J=8.8, 2.0 Hz, 1H), 7.88 (d, J=8.4 Hz, 1H), 7.83-7.77 (m, 2H), 7.61 (d, J=7.6 Hz, 1H), 7.31 (dd, J=7.2, 1.6 Hz, 1H), 4.14 (q, J=6.8 Hz, 1H), 1.46 (d, J=6.4 Hz, 3H).

Example 85. 3-amino-5-(1-(6-(trifluoromethyl)pyridin-2-yl)-1H-indazol-6-yl)benzoic Acid Synthesis of methyl 3-nitro-5-(1-(6-(trifluoromethyl)pyridin-2-yl)-1H-indazol-6-yl)benzoate

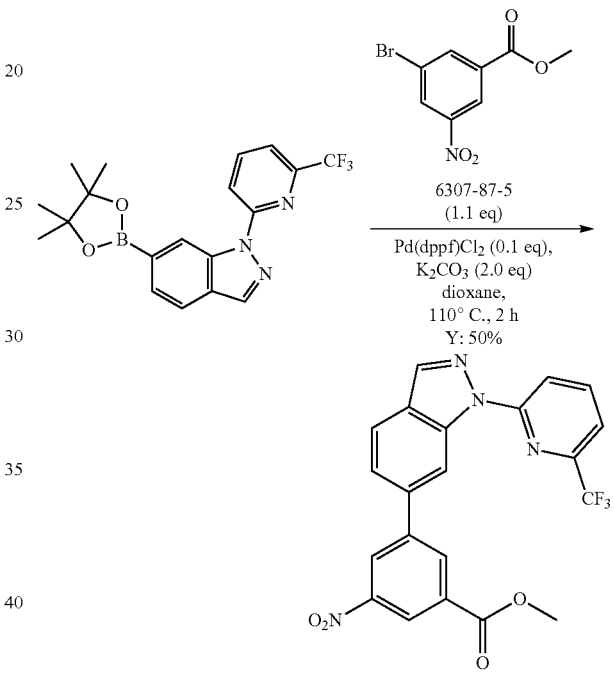

The preparation of methyl 3-nitro-5-(1-(6-(trifluoromethyl)pyridin-2-yl)-1H-indazol-6-yl)benzoate was the same as that of 6-(1-(6-methylpyridin-2-yl)-1H-indazol-6-yl)pyridin-2-amine. 163 mg, as a yellow solid, Y: 50%. ESI-MS (M+H)⁺: 443.1.

Synthesis of methyl 3-amino-5-(1-(6-(trifluoromethyl)pyridin-2-yl)-1H-indazol-6-yl)benzoate

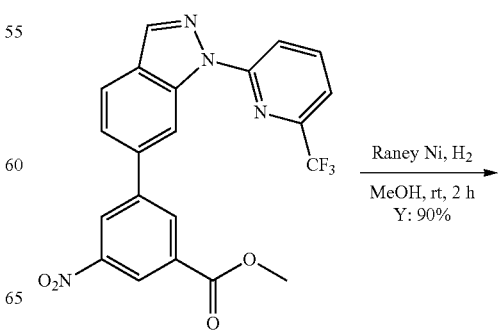

-continued

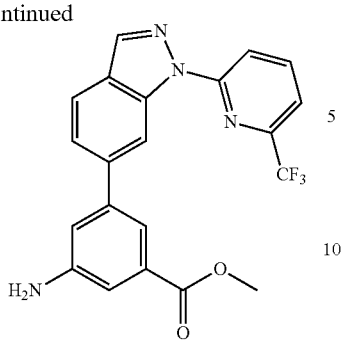

A mixture of methyl 3-nitro-5-(1-(6-(trifluoromethyl)pyridin-2-yl)-1H-indazol-6-yl)benzoate (150 mg, 0.34 mmol, 1.0 eq), Raney Ni (30 mg) in MeOH (10 mL) was stirred at rt for 2 h under $H_2$ atmosphere. After filtration and concentration, the residue was directly used in the next step without further purification. 126 mg, as a white solid, Y: 90%. ESI-MS (M+H)$^+$: 413.1.

Synthesis of 3-amino-5-(1-(6-(trifluoromethyl)pyridin-2-yl)-1H-indazol-6-yl)benzoic acid

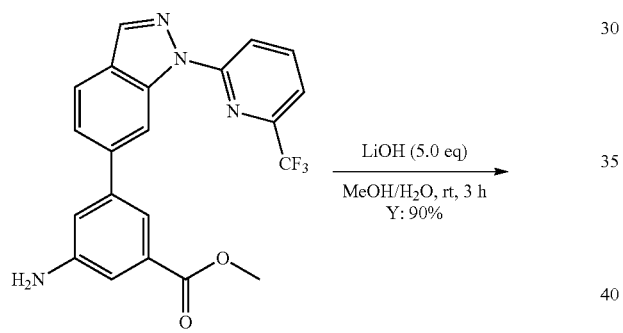

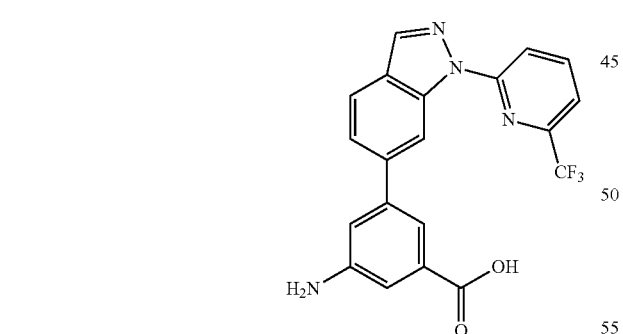

A mixture of 3-amino-5-(1-(6-(trifluoromethyl)pyridin-2-yl)-1H-indazol-6-yl)benzoate (126 mg, 0.3 mmol, 1.0 eq), LiOH (37 mg, 1.5 mmol, 5.0 eq) in MeOH (5 mL)/MeOH (1 mL) was stirred at rt for 3 h. Then, pH value of the mixture was adjusted to 5-6. After filtration, 110 mg of 3-amino-5-(1-(6-(trifluoromethyl)pyridin-2-yl)-1H-indazol-6-yl)benzoic acid as a white solid was obtained. Y: 90%, ESI-MS (M+H)$^+$: 399.1. $^1$H NMR (400 MHz, CD$_3$OD) δ: 9.11 (s, 1H), 8.31-8.25 (m, 3H), 8.10 (t, J=8.0 Hz, 1H), 7.92-7.87 (m, 2H), 7.75-7.74 (m, 1H), 7.60-7.57 (m, 2H).

Example 86. 3-amino-N-(cyanomethyl)-5-(1-(6-(trifluoromethyl)pyridin-2-yl)-1H-indazol-6-yl)benzamide Synthesis of 3-amino-N-(cyanomethyl)-5-(1-(6-(trifluoromethyl)pyridin-2-yl)-1H-indazol-6-yl)benzamide

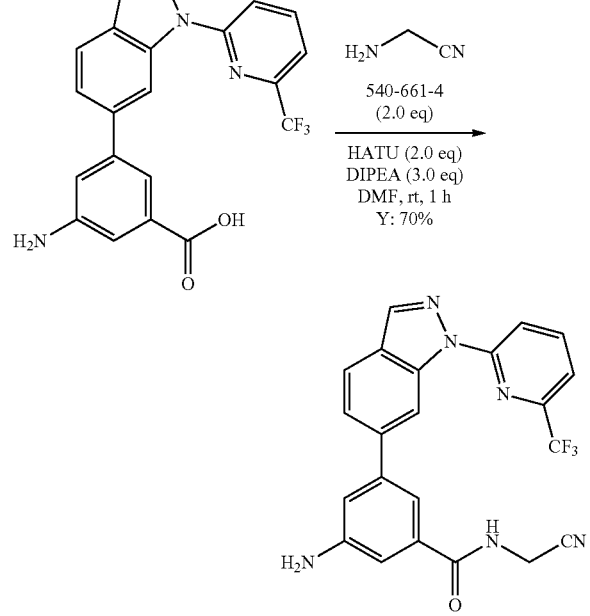

The preparation of 3-amino-N-(cyanomethyl)-5-(1-(6-(trifluoromethyl)pyridin-2-yl)-1H-indazol-6-yl)benzamide was the same as that of 6-(6-(5-aminopyridin-3-yl)-1H-indazol-1-yl)-N,N-dimethylpicolinamide. 80 mg, as a white solid, Y: 70%. ESI-MS (M+H)$^+$: 413.1. HPLC: 97.40%. $^1$H NMR (400 MHz, DMSO-d$_6$) δ: 9.13 (t, J=5.2 Hz, 1H), 8.96 (s, 1H), 8.59 (s, 1H), 8.34-8.31 (m, 2H), 8.03 (d, J=8.4 Hz, 1H), 7.84 (dd, J=6.0, 2.2 Hz, 1H), 7.64 (d, J=8.4 Hz, 1H), 7.34 (s, 1H), 7.12 (s, 1H), 7.07 (s, 1H), 5.56 (s, 2H), 4.31 (d, J=5.6 Hz, 2H).

Example 87. 6-amino-N-(cyanomethyl)-4-(1-(6-(trifluoromethyl)pyridin-2-yl)-1H-indazol-6-yl)picolinamide Synthesis of 4-bromo-6-(methoxycarbonyl)picolinic acid

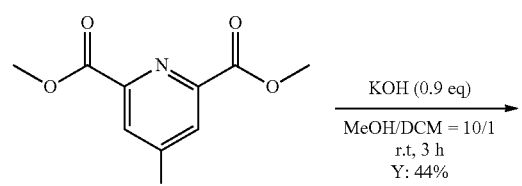

-continued

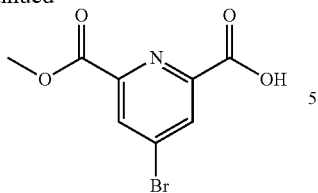

To a solution of dimethyl 4-bromopyridine-2,6-dicarboxylate (CAS#162102-79-6) (2.40 g, 8.8 mmol, 1.0 eq) in MeOH/DCM solution (10/1, 88 mL) was added KOH (896 mg, 8.0 mmol, 0.9 eq) at rt. The reaction mixture was stirred at rt for 3 h and Et$_2$O (80 mL) was added thereto. The resulting white solid was filtered and then redissolved in water (50 mL). 2 M HCl solution (8 mL) was added. The mixture extracted with DCM (2×50 mL). The combined organic layers were washed with brine and dried over anhydrous Na$_2$SO$_4$. After removing the solvent, the residue as brown solid was used directly in the next step without further purification (1.0 g, Y: 44%). ESI-MS (M+H)$^+$: 259.9. $^1$H NMR (400 MHz, CDCl$_3$) δ: 8.56 (d, J=1.7 Hz, 1H), 8.50 (d, J=1.7 Hz, 1H), 4.04 (s, 3H).

Synthesis of methyl 4-bromo-6-((tert-butoxycarbonyl)amino)picolinate

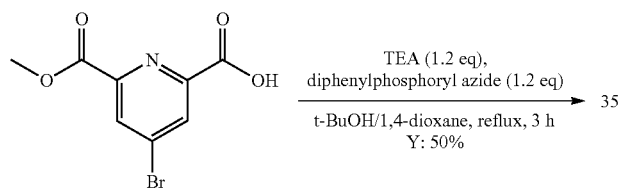

To a mixture of 4-bromo-6-(methoxycarbonyl)picolinic acid (1.25 g, 3.84 mmol, 1.0 eq), TEA (0.6 mL, 4.61 mmol, 1.2 eq), t-BuOH (8 mL) and 1,4-dioxane (20 mL) was added diphenylphosphoryl azide (1.27 g, 4.61 mmol, 1.2 eq) at rt. The reaction mixture was heated to reflux for 3 h and concentrated in vacuo. The residue was purified by silica gel column chromatography with PE/EA (6/1) as eluent to give methyl 4-bromo-6-((tert-butoxycarbonyl)amino)picolinate as a brown solid (793 mg, Y: 50%). ESI-MS (M+H)$^+$: 331.0. $^1$H NMR (400 MHz, CDCl$_3$) δ: 8.42 (d, J=1.4 Hz, 1H), 7.93 (d, J=1.6 Hz, 1H), 7.65 (s, 1H), 3.98 (s, 3H), 1.51 (s, 9H).

Synthesis of methyl 6-((tert-butoxycarbonyl)amino)-4-(1-(6-(trifluoromethyl)pyridin-2-yl)-1H-indazol-6-yl)picolinate

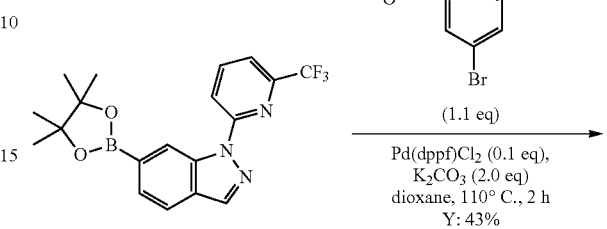

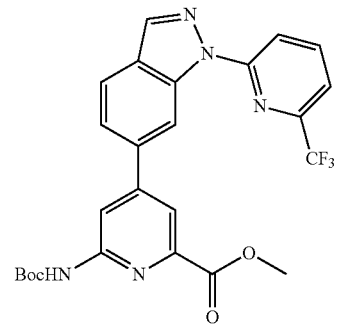

The preparation of methyl 6-((tert-butoxycarbonyl)amino)-4-(1-(6-(trifluoromethyl)pyridin-2-yl)-1H-indazol-6-yl)picolinate was the same as that of 6-(1-(6-methylpyridin-2-yl)-1H-indazol-6-yl)pyridin-2-amine. 320 mg, as a white solid, Y: 43%. ESI-MS (M+H)$^+$: 513.1. $^1$H NMR (400 MHz, DMSO-d$_6$) δ: 10.38 (s, 1H), 9.22 (s, 1H), 8.65 (s, 1H), 8.56 (d, J=1.3 Hz, 1H), 8.33 (d, J=6.1 Hz, 2H), 8.11 (dd, J=9.9, 4.8 Hz, 2H), 7.88-7.79 (m, 2H), 3.92 (s, 3H), 1.50 (s, 9H).

Synthesis of methyl 6-amino-4-(1-(6-(trifluoromethyl)pyridin-2-yl)-1H-indazol-6-yl)picolinate

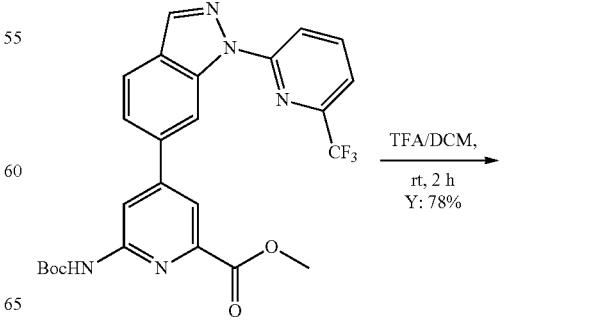

-continued

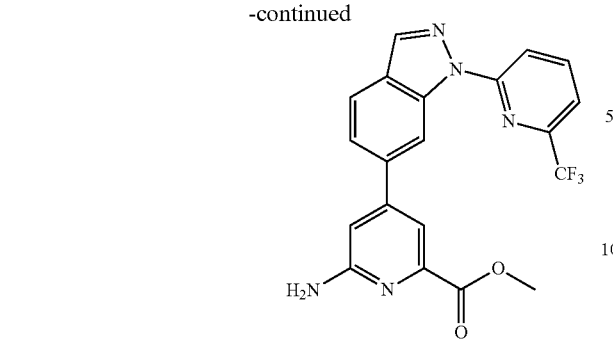

To a solution of methyl 6-((tert-butoxycarbonyl)amino)-4-(1-(6-(trifluoromethyl)pyridin-2-yl)-1H-indazol-6-yl)picolinate (320 mg, 0.6 mmol, 1.0 eq) in DCM (10 mL) was added TFA (0.6 mL) at rt. The reaction mixture was stirred at rt for 2 h and then concentrated in vacuo. The residue as a yellow solid could be used directly in the next step without further purification (200 mg, Y: 78%). ESI-MS (M+H)$^+$: 414.1.

Synthesis of 6-amino-4-(1-(6-(trifluoromethyl)pyridin-2-yl)-1H-indazol-6-yl)picolinic acid

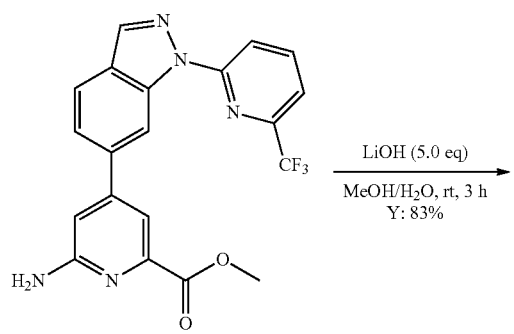

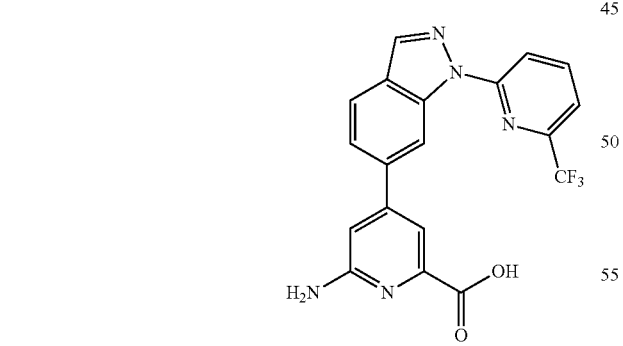

The preparation of 6-amino-4-(1-(6-(trifluoromethyl)pyridin-2-yl)-1H-indazol-6-yl)picolinic acid was the same as that of 3-amino-5-(1-(6-(trifluoromethyl)pyridin-2-yl)-1H-indazol-6-yl)benzoic acid. 160 mg, as a white solid, Y: 83%. ESI-MS (M+H)$^+$: 399.1. HPLC: 100.00%. $^1$H NMR (400 MHz, DMSO-d$_6$) δ: 9.11 (s, 1H), 8.65 (s, 1H), 8.36-8.30 (m, 2H), 8.11 (d, J=8.4 Hz, 1H), 7.87 (dd, J=5.1, 3.1 Hz, 1H), 7.72 (d, J=8.3 Hz, 1H), 7.62 (s, 1H), 7.20 (s, 1H).

Synthesis of 6-amino-N-(cyanomethyl)-4-(1-(6-(trifluoromethyl)pyridin-2-yl)-1H-indazol-6-yl)picolinamide

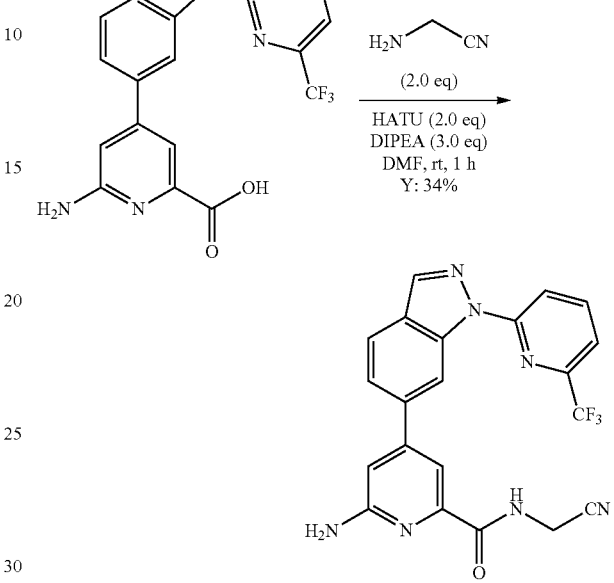

The preparation of 6-amino-N-(cyanomethyl)-4-(1-(6-(trifluoromethyl)pyridin-2-yl)-1H-indazol-6-yl)picolinamide was the same as that of 6-(6-(5-aminopyridin-3-yl)-1H-indazol-1-yl)-N,N-dimethylpicolinamide. 64 mg, as a white solid, Y: 34%. ESI-MS (M+H)$^+$: 437.1. HPLC: 93.37%. $^1$H NMR (400 MHz, CDCl$_3$) δ: 9.25 (s, 1H), 8.32-8.24 (m, 3H), 8.03 (t, J=8.0 Hz, 1H), 7.96 (d, J=1.3 Hz, 1H), 7.87 (d, J=8.3 Hz, 1H), 7.65 (dd, J=8.4, 1.4 Hz, 1H), 7.55 (d, J=7.5 Hz, 1H), 7.05 (d, J=1.3 Hz, 1H), 4.66 (br, 2H), 4.37 (d, J=6.0 Hz, 2H).

Example 88. 3-amino-N-(2-aminoethyl)-5-(1-(6-(trifluoromethyl)pyridin-2-yl)-1H-indazol-6-yl)benzamide Synthesis of 3-amino-N-(2-aminoethyl)-5-(1-(6-(trifluoromethyl)pyridin-2-yl)-1H-indazol-6-yl)benzamide

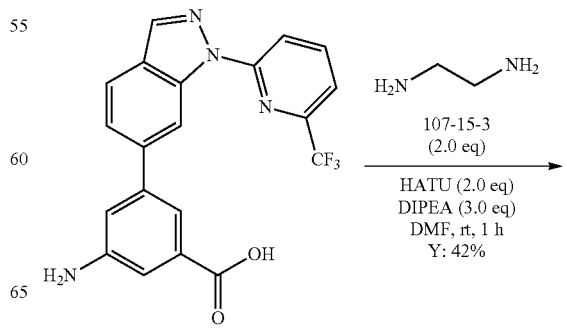

163
-continued

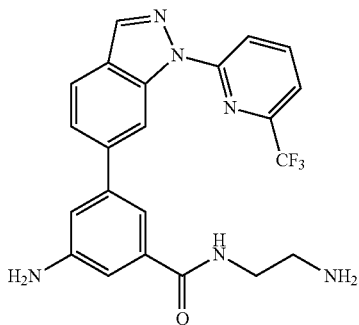

The preparation of 3-amino-N-(2-aminoethyl)-5-(1-(6-(trifluoromethyl)pyridin-2-yl)-1H-indazol-6-yl)benzamide was the same as that of 6-(6-(5-aminopyridin-3-yl)-1H-indazol-1-yl)-N,N-dimethylpicolinamide. 15 mg, as a white solid, Y: 42%. ESI-MS (M+H)$^+$: 441.2. HPLC: 100.00%. $^1$H NMR (400 MHz, CD$_3$OD) δ: 9.10 (s, 1H), 8.26 (s, 1H), 8.24 (d, J=8.4 Hz, 1H), 8.08 (t, J=8.0 Hz, 1H), 7.82 (d, J=8.8 Hz, 1H), 7.57 (d, J=7.6 Hz, 1H), 7.50 (dd, J=8.8, 1.2 Hz, 1H), 7.40 (s, 1H), 7.13 (d, J=1.6 Hz, 1H), 7.08 (d, J=2.0 Hz, 1H), 3.43 (t, J=2.4 Hz, 2H), 2.85 (t, J=2.4 Hz, 2H).

Example 89. 1-(3-(1-(6-(trifluoromethyl)pyridin-2-yl)-1H-indazol-6-yl)phenyl)ethanamine Synthesis of 1-(3-(1-(6-(trifluoromethyl)pyridin-2-yl)-1H-indazol-6-yl)phenyl)ethanone

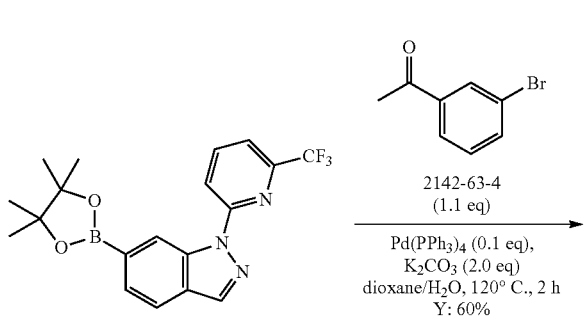

The preparation of 1-(3-(1-(6-(trifluoromethyl)pyridin-2-yl)-1H-indazol-6-yl)phenyl)ethanone was the same as that of 6-(1-(6-methylpyridin-2-yl)-1H-indazol-6-yl)pyridin-2-amine. 320 mg, as a white solid, Y: 60%. ESI-MS (M+H)$^+$: 382.1.

164
Synthesis of (Z)-1-(3-(1-(6-(trifluoromethyl)pyridin-2-yl)-1H-indazol-6-yl)phenyl)ethanone oxime

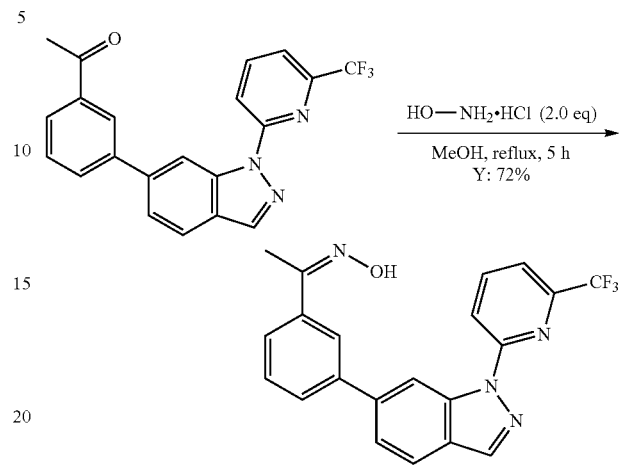

The preparation of (Z)-1-(3-(1-(6-(trifluoromethyl)pyridin-2-yl)-1H-indazol-6-yl)phenyl)ethanone oxime was the same as that of 2-(1-(6-(trifluoromethyl)pyridin-2-yl)-1H-indazol-6-yl)-5H-cyclopenta[b]pyridin-7(6H)-one oxime. 150 mg, as a yellow solid, Y: 72%. ESI-MS (M+H)$^+$: 397.1.

Synthesis of 1-(3-(1-(6-(trifluoromethyl)pyridin-2-yl)-1H-indazol-6-yl)phenyl)ethanamine

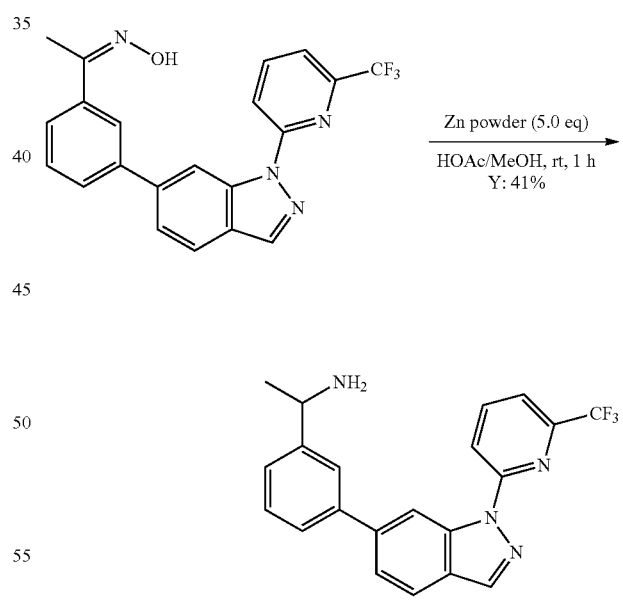

The preparation of 1-(3-(1-(6-(trifluoromethyl)pyridin-2-yl)-1H-indazol-6-yl)phenyl)ethanamine was the same as that of 2-(1-(6-(trifluoromethyl)pyridin-2-yl)-1H-indazol-6-yl)-6,7-dihydro-5H-cyclopenta[b]pyridin-7-amine. 60 mg, as a white solid, Y: 41%. ESI-MS (M+H)$^+$: 383.1. HPLC: 95.27%. $^1$H NMR (400 MHz, CD$_3$OD) δ: 9.06 (s, 1H), 8.25-8.21 (m, 2H), 8.09-8.05 (m, 1H), 7.83 (d, J=8.4 Hz, 1H), 7.68 (s, 1H), 7.60-7.53 (m, 3H), 7.41-7.35 (m, 2H), 4.07 (q, J=6.8 Hz, 1H), 1.43 (d, J=6.8 Hz, 3H).

Example 90. 1-(5-(1-(6-(trifluoromethyl)pyridin-2-yl)-1H-indazol-6-yl)pyridin-3-yl)ethanamine Synthesis of 1-(5-(1-(6-(trifluoromethyl)pyridin-2-yl)-1H-indazol-6-yl)pyridin-3-yl)ethanone

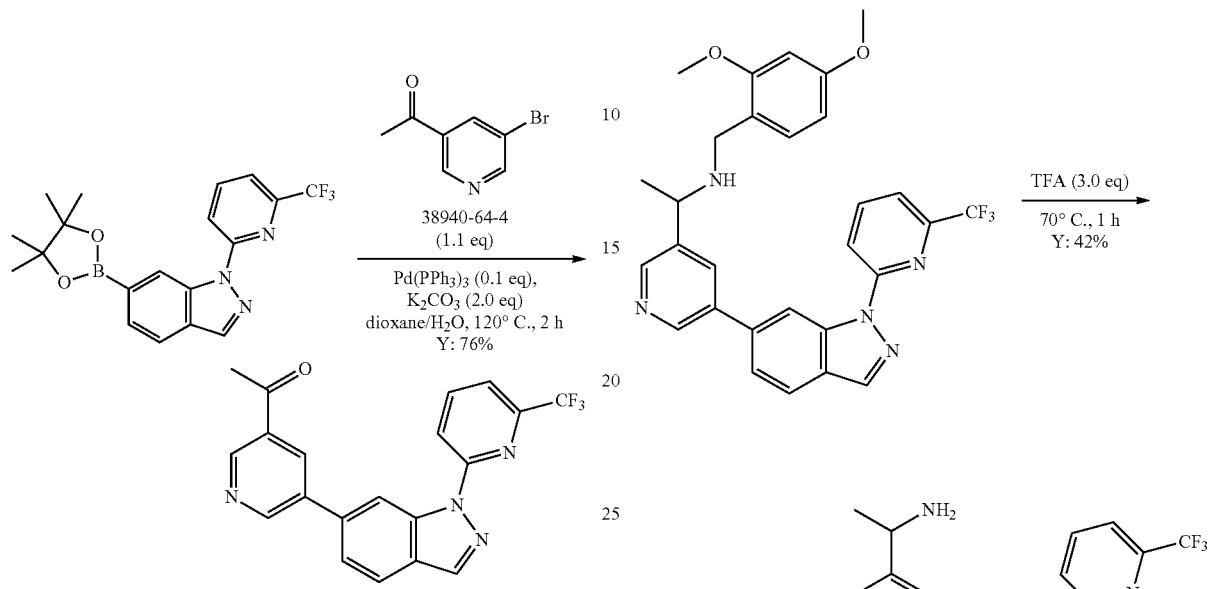

The preparation of 1-(5-(1-(6-(trifluoromethyl)pyridin-2-yl)-1H-indazol-6-yl)pyridin-3-yl)ethanone was the same as that of 6-(1-(6-methylpyridin-2-yl)-1H-indazol-6-yl)pyridin-2-amine. 140 mg, as yellow solid, Y: 76%. ESI-MS (M+H)$^+$: 383.1.

Synthesis of N-(2,4-dimethoxybenzyl)-1-(5-(1-(6-(trifluoromethyl)pyridin-2-yl)-1H-indazol-6-yl)pyridin-3-yl)ethanamine The preparation of N-(2,4-dimethoxybenzyl)-1-(5-(1-(6-(trifluoromethyl)pyridin-2-yl)-1H-indazol-6-yl)pyridin-3-yl)ethanamine was the same as that of N-(4-methoxybenzyl)-1-(6-(1-(6-methylpyridin-2-yl)-1H-indazol-6-yl)pyridin-2-yl)ethanamine. 140 mg, as yellow solid, Y: 71%. ESI-MS (M+H)$^+$: 534.2.

Synthesis of 1-(5-(1-(6-(trifluoromethyl)pyridin-2-yl)-1H-indazol-6-yl)pyridin-3-yl)ethanamine The preparation of 1-(5-(1-(6-(trifluoromethyl)pyridin-2-yl)-1H-indazol-6-yl)pyridin-3-yl)ethanamine was the same as that of 1-(6-(1-(6-methylpyridin-2-yl)-1H-indazol-6-yl)pyridin-2-yl)ethanamine. 40 mg, as a yellow solid, Y: 42%. ESI-MS (M+H)$^+$: 384.1, HPLC: 100.00%. $^1$H NMR (400 MHz, CD$_3$OD) δ: 9.25 (s, 1H), 9.02 (d, J=2.4 Hz, 1H), 8.73 (d, J=2.4 Hz, 1H), 8.44 (s, 1H), 8.39-8.34 (m, 2H), 8.22 (t, J=8.0 Hz, 1H), 8.06 (d, J=8.0 Hz, 1H), 7.73 (t, J=8.2 Hz, 2H), 4.72 (q, J=6.6 Hz, 1H), 1.80 (d, J=6.8 Hz, 3H).

Example 91. 1-(4-(1-(6-(trifluoromethyl)pyridin-2-yl)-1H-indazol-6-yl)pyridin-2-yl)ethanamine Synthesis of 4-bromo-N-methoxy-N-methylpicolinamide

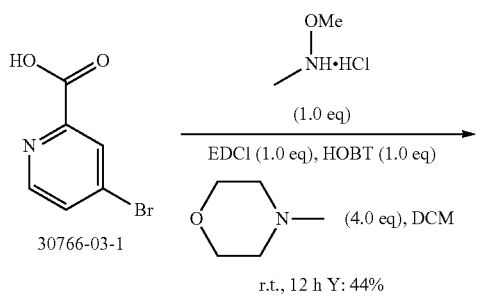

To a solution of 4-bromopicolinic acid (CAS#30766-03-1) (1.01 g, 5.0 mmol, 1.0 eq), methoxymethylamine HCl salt (536 mg, 5.5 mmol, 1.1 eq) and N-methylmorpholine (2.02 g, 20 mmol, 4.0 eq) in DCM (20 mL) were added EDCI (959 mg, 5 mmol, 1.0 eq) and HOBT (676 mg, 5 mmol, 1.0 eq) in portions at 0° C. The reaction mixture was warmed up to rt and stirred for 12 h. The mixture was extracted with DCM (3×30 mL) and washed with brine. The combined organic phase was dried over $Na_2SO_4$ and concentrated in vacuo. The crude mixture was purified by silica gel chromatography with PE/EA (10/1) as eluent to give 4-bromo-N-methoxy-N-methylpicolinamide. 545 mg, as colorless oil, Y: 44%. ESI-MS (M+H)$^+$: 245.0.

Synthesis of 1-(4-bromopyridin-2-yl)ethanone

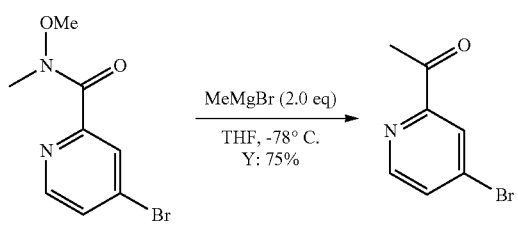

To a solution of 4-bromo-N-methoxy-N-methylpicolinamide (548 mg, 2.2 mmol, 1.0 eq) in anhydrous THF (25 mL) cooled to −78° C. was slowly added MeMgBr (3 M in THF, 1.43 mL, 4.4 mmol, 2.0 eq). After stirring at −78° C. for 2 h, the reaction mixture was quenched with aq. $NH_4Cl$ and extracted with EA (3×30 mL). The combined organic phase was dried over $Na_2SO_4$ and concentrated in vacuo. The crude mixture was purified by silica gel chromatography with PE/EA (2/1) as eluent to give 1-(4-bromopyridin-2-yl)ethanone. 330 mg, as white solid, Y: 75%. ESI-MS (M+H)$^+$: 200.0. $^1$H NMR (400 MHz, $CDCl_3$) δ: 8.50 (d, J=5.0 Hz, 1H), 8.20 (s, 1H), 7.74-7.51 (m, 1H), 2.72 (s, 3H).

Synthesis of 1-(4-(1-(6-(trifluoromethyl)pyridin-2-yl)-1H-indazol-6-yl)pyridin-2-yl)ethanone

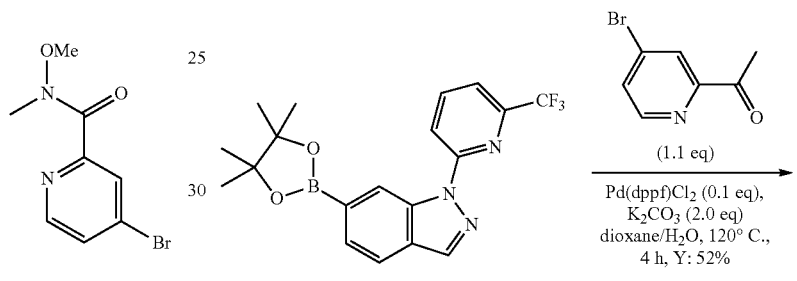

The preparation of 1-(4-(1-(6-(trifluoromethyl)pyridin-2-yl)-1H-indazol-6-yl)pyridin-2-yl)ethanone was the same as that of 6-(1-(6-methylpyridin-2-yl)-1H-indazol-6-yl)pyridin-2-amine. 280 mg, as pale yellow solid, Y: 52%. ESI-MS (M+H)$^+$: 383.1. $^1$H NMR (400 MHz, $CDCl_3$) δ: 9.31 (s, 1H), 8.80 (d, J=5.1 Hz, 1H), 8.44 (d, J=1.7 Hz, 1H), 8.30-8.23 (m, 2H), 8.03 (t, J=7.9 Hz, 1H), 7.90 (d, J=8.3 Hz, 1H), 7.85 (dd, J=5.1, 1.8 Hz, 1H), 7.68 (dd, J=8.3, 1.2 Hz, 1H), 7.55 (d, J=7.5 Hz, 1H), 2.81 (s, 3H).

Synthesis of N-(2,4-dimethoxybenzyl)-1-(4-(1-(6-(trifluoromethyl)pyridin-2-yl)-1H-indazol-6-yl)pyridin-2-yl)ethanamine

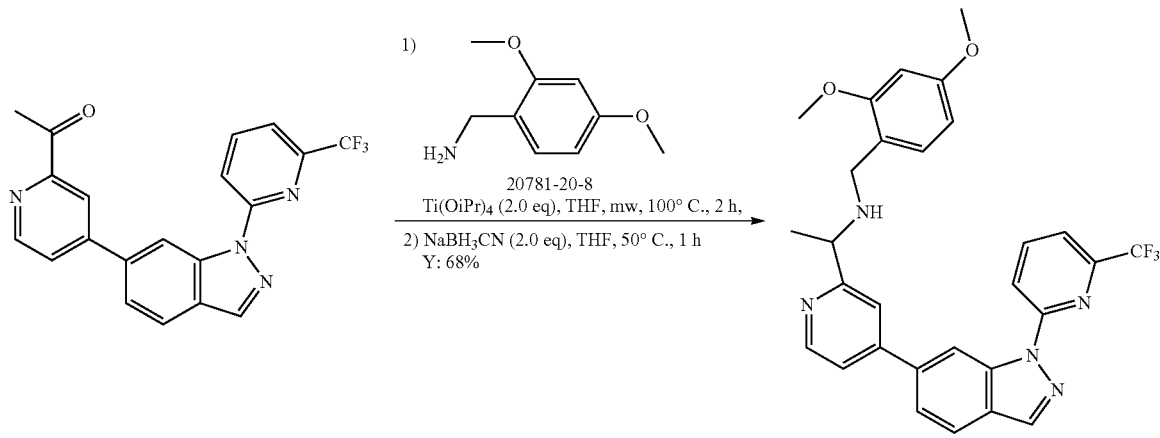 [SMILES: CC(=O)c1cc(-c2ccc3cnn(-c4cccc(C(F)(F)F)n4)c3c2)ccn1 ; COc1ccc(CN)c(OC)c1 ; COc1ccc(CNC(C)c2cc(-c3ccc4cnn(-c5cccc(C(F)(F)F)n5)c4c3)ccn2)c(OC)c1]

The preparation of N-(2,4-dimethoxybenzyl)-1-(4-(1-(6-(trifluoromethyl)pyridin-2-yl)-1H-indazol-6-yl)pyridin-2-yl)ethanamine was the same as that of N-(4-methoxybenzyl)-1-(6-(1-(6-methylpyridin-2-yl)-1H-indazol-6-yl)pyridin-2-yl)ethanamine. 200 mg, as a brown oil, Y: 68%. ESI-MS (M+H)$^+$: 534.2.

Synthesis of 1-(4-(1-(6-(trifluoromethyl)pyridin-2-yl)-1H-indazol-6-yl)pyridin-2-yl)ethanamine

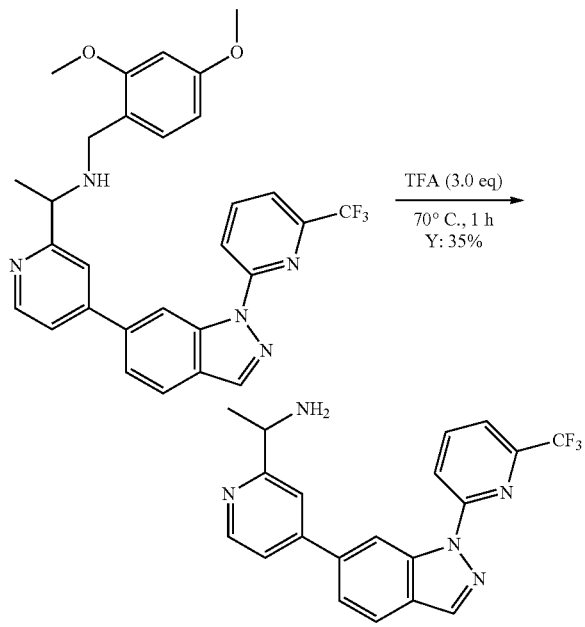

The preparation of 1-(4-(1-(6-(trifluoromethyl)pyridin-2-yl)-1H-indazol-6-yl)pyridin-2-yl)ethanamine was the same as that of 1-(6-(1-(6-methylpyridin-2-yl)-1H-indazol-6-yl)pyridin-2-yl)ethanamine. 38 mg, as a white solid, Y: 35%. ESI-MS (M+H)$^+$: 384.1, HPLC: 96.56%. $^1$H NMR (400 MHz, CD$_3$OD) δ: 9.20 (s, 1H), 8.65 (d, J=5.2 Hz, 1H), 8.32 (s, 1H), 8.26 (d, J=8.5 Hz, 1H), 8.11 (t, J=8.0 Hz, 1H), 7.93 (d, J=8.4 Hz, 1H), 7.75 (s, 1H), 7.69-7.64 (m, 2H), 7.61 (d, J=7.5 Hz, 1H), 4.59 (q, J=6.9 Hz, 1H), 1.63 (d, J=6.9 Hz, 3H).

Example 92. 6-(1-(6-(trifluoromethyl)pyridin-2-yl)-1H-indazol-6-yl)pyrazine-2-carbonitrile Synthesis of 6-(6-bromopyrazin-2-yl)-1-(6-(trifluoromethyl)pyridin-2-yl)-1H-indazole

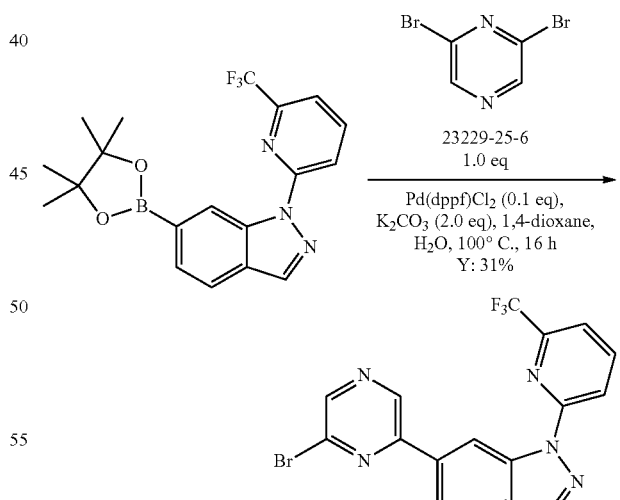

The preparation of 6-(6-bromopyrazin-2-yl)-1-(6-(trifluoromethyl)pyridin-2-yl)-1H-indazole was the same as that of 6-(1-(6-methylpyridin-2-yl)-1H-indazol-6-yl)pyridin-2-amine. 300 mg, as a yellow solid, Y: 31%. ESI-MS (M+H)$^+$: 419.9. $^1$H NMR (400 MHz, CDCl$_3$) δ: 9.57 (s, 1H), 8.97 (s, 1H), 8.79 (s, 1H), 8.30-8.28 (m, 2H), 8.07-8.04 (m, 2H), 7.93 (d, J=8.4 Hz, 1H), 7.58-7.55 (m, 1H).

Synthesis of 6-(1-(6-(trifluoromethyl)pyridin-2-yl)-1H-indazol-6-yl)pyrazine-2-carbonitrile

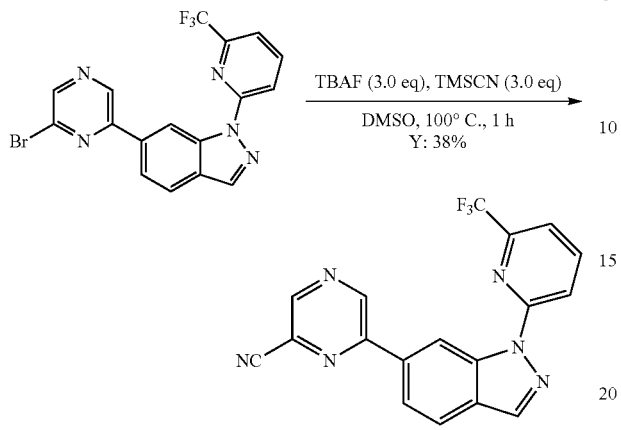

A mixture of 6-(6-bromopyrazin-2-yl)-1-(6-(trifluoromethyl)pyridin-2-yl)-1H-indazole (150 mg, 0.36 mmol, 1.0 eq), TBAF (281 mg, 1.08 mmol, 3.0 eq), TMSCN (107 mg, 1.08 mmol, 3.0 eq) in DMF (3 mL) was stirred at 100° C. for 1 h. After cooling to rt, the mixture was purified by pre-HPLC (MeOH/H₂O with 0.05% NH₄OH as mobile phase from 5% to 95%) to give 6-(1-(6-(trifluoromethyl)pyridin-2-yl)-1H-indazol-6-yl)pyrazine-2-carbonitrile as a white solid. 50 mg, Y: 38%. ESI-MS (M+H)⁺: 367.1. HPLC: 100.00%. ¹H NMR (400 MHz, CD₃OD) δ: 9.61 (s, 1H), 9.48 (d, J=1.6 Hz, 1H), 9.36 (d, J=1.6 Hz, 1H), 8.69 (d, J=0.8 Hz, 1H), 8.34-8.33 (m, 2H), 8.23 (dd, J=9.2, 1.6 Hz, 1H), 8.16 (dd, J=9.2, 0.4 Hz, 1H), 7.90-7.87 (m, 1H).

Example 93. (6-(1-(6-(trifluoromethyl)pyridin-2-yl)-1H-indazol-6-yl)pyrazin-2-yl)methanamine Synthesis of (6-(1-(6-(trifluoromethyl)pyridin-2-yl)-1H-indazol-6-yl)pyrazin-2-yl)methanamine

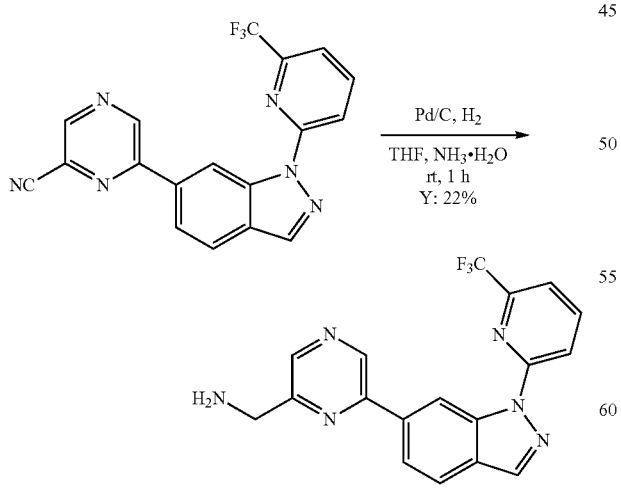

A mixture of 6-(1-(6-(trifluoromethyl)pyridin-2-yl)-1H-indazol-6-yl)pyrazine-2-carbonitrile (45 mg, 0.12 mmol, 1.0 eq) and Pd/C (5 mg) in THF/NH₃.H₂O (2 mL/0.5 mL) was stirred at rt under H₂ for 1 h. After filtration and concentration, the crude product was purified by pre-HPLC (MeOH/H₂O with 0.05% NH₄OH as mobile phase from 5% to 95%) to give (6-(1-(6-(trifluoromethyl)pyridin-2-yl)-1H-indazol-6-yl)pyrazin-2-yl)methanamine as a white solid. 10 mg, Y: 22%. ESI-MS (M+H)⁺: 371.1. HPLC: 98.10%. ¹H NMR (400 MHz, CD₃OD) δ: 9.57 (s, 1H), 9.17 (s, 1H), 8.79 (s, 1H), 8.41 (s, 1H), 8.37 (d, J=8.4 Hz, 1H), 8.20 (t, J=8.0 Hz, 1H), 8.11 (dd, J=8.4, 1.2 Hz, 1H), 8.02 (d, J=8.4 Hz, 1H), 7.71 (d, J=7.6 Hz, 1H), 4.18 (s, 2H).

Example 94. 4-(1-(6-(trifluoromethyl)pyridin-2-yl)-1H-indazol-6-yl)pyrimidine-2-carbonitrile Synthesis of 6-(2-chloropyrimidin-4-yl)-1-(6-(trifluoromethyl)pyridin-2-yl)-1H-indazole

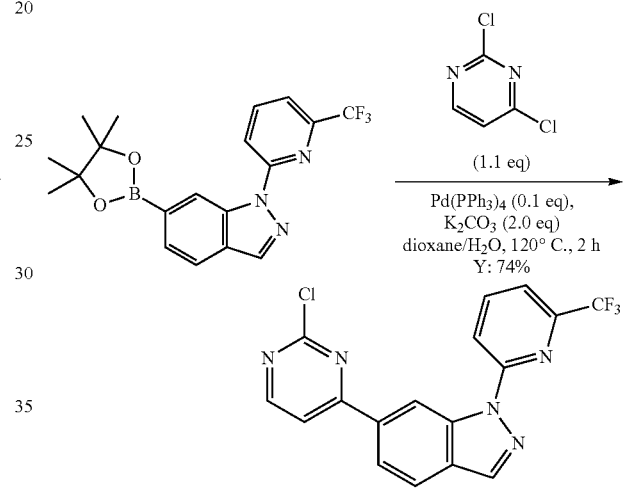

The preparation of 6-(2-chloropyrimidin-4-yl)-1-(6-(trifluoromethyl)pyridin-2-yl)-1H-indazole was the same as that of 6-(1-(6-methylpyridin-2-yl)-1H-indazol-6-yl)pyridin-2-amine. 390 mg, as a white solid, Y: 74%. ESI-MS (M+H)⁺: 376.0.

Synthesis of 4-(1-(6-(trifluoromethyl)pyridin-2-yl)-1H-indazol-6-yl)pyrimidine-2-carbonitrile

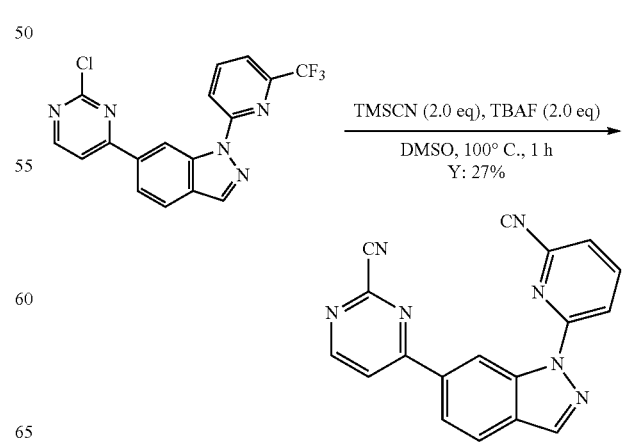

The preparation of 4-(1-(6-(trifluoromethyl)pyridin-2-yl)-1H-indazol-6-yl)pyrimidine-2-carbonitrile was the same as that of 6-(1-(6-(trifluoromethyl)pyridin-2-yl)-1H-indazol-6-yl)pyrazine-2-carbonitrile. 40 mg, as a white solid, Y: 27%. ESI-MS (M+H)$^+$: 367.1. HPLC: 100.00%. $^1$H NMR (400 MHz, CD$_3$OD) δ: 9.76 (s, 1H), 9.15 (d, J=5.6 Hz, 1H), 8.68 (s, 1H), 8.47 (d, J=5.2 Hz, 1H), 8.34 (d, J=3.6 Hz, 2H), 8.22 (dd, J=8.4, 1.6 Hz, 1H), 8.15 (d, J=8.4 Hz, 1H), 7.90-7.88 (m, 1H).

Example 95. (4-(1-(6-(trifluoromethyl)pyridin-2-yl)-1H-indazol-6-yl)pyrimidin-2-yl)methanamine Synthesis of (4-(1-(6-(trifluoromethyl)pyridin-2-yl)-1H-indazol-6-yl)pyrimidin-2-yl)methanamine

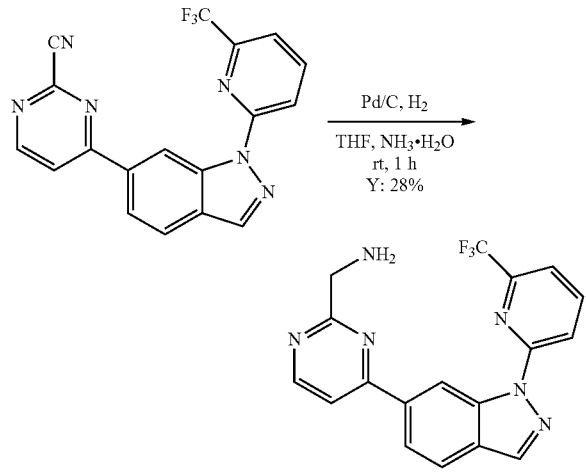

The preparation of (4-(1-(6-(trifluoromethyl)pyridin-2-yl)-1H-indazol-6-yl)pyrimidin-2-yl)methanamine was the same as that of (6-(1-(6-(trifluoromethyl)pyridin-2-yl)-1H-indazol-6-yl)pyrazin-2-yl)methanamine. 23 mg, as a white solid, Y: 28%. ESI-MS (M+H)$^+$: 371.1. HPLC: 96.68%. $^1$H NMR (400 MHz, CDCl$_3$) δ: 9.69 (s, 1H), 8.74 (d, J=4.8 Hz, 1H), 8.30 (s, 1H), 8.26 (d, J=8.4 Hz, 1H), 8.10-8.07 (m, 2H), 7.89 (dd, J=8.4, 0.4 Hz, 1H), 7.83 (d, J=5.2 Hz, 1H), 7.63 (d, J=7.2 Hz, 1H), 4.06 (s, 2H).

Example 96. 6-(1-(6-(trifluoromethyl)pyridin-2-yl)-1H-indazol-6-yl)pyrazin-2-amine Synthesis of 6-bromo-N-(2,4-dimethoxybenzyl)pyrazin-2-amine

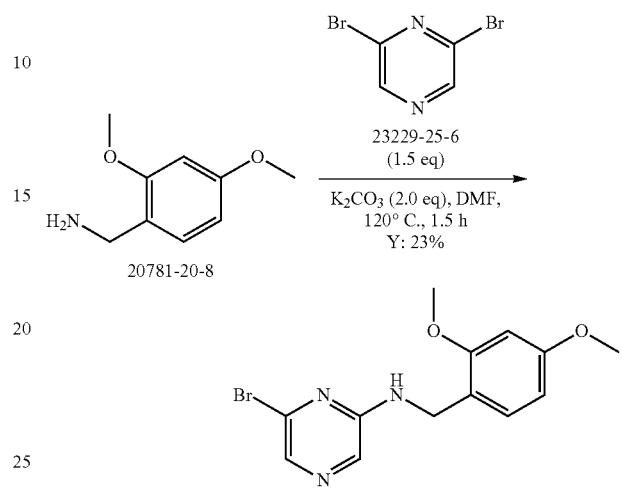

A mixture of (2,4-dimethoxyphenyl)methanamine (CAS#20781-20-8) (668 mg, 4.0 mmol, 1.0 eq), K$_2$CO$_3$ (1.1 g, 8.0 mmol, 2.0 eq) and 2,6-dibromopyrazine (CAS#23229-25-6) (1.42 g, 6.0 mmol, 1.5 eq) in DMF (10 mL) was stirred at 120° C. for 1.5 h. After cooling to rt, the mixture was poured into water (60 mL) and extracted with EA (2×60 mL). The combined organic phase was washed with brine (60 mL) and dried over Na$_2$SO$_4$. After filtration and concentration, the residue was purified by silica gel chromatography with PE/EA (2/1) as eluent to give 6-bromo-N-(2,4-dimethoxybenzyl)pyrazin-2-amine. 300 mg, as a yellow solid, Y: 23%. ESI-MS (M+H)$^+$: 324.0. $^1$H NMR (400 MHz, CDCl$_3$) δ: 8.06 (s, 1H), 7.69 (s, 1H), 7.19 (d, J=8.4 Hz, 1H), 6.48-6.42 (m, 3H), 4.44 (s, 2H), 3.84 (s, 3H), 3.79 (s, 3H).

Synthesis of N-(2,4-dimethoxybenzyl)-6-(1-(6-(trifluoromethyl)pyridin-2-yl)-1H-indazol-6-yl)pyrazin-2-amine

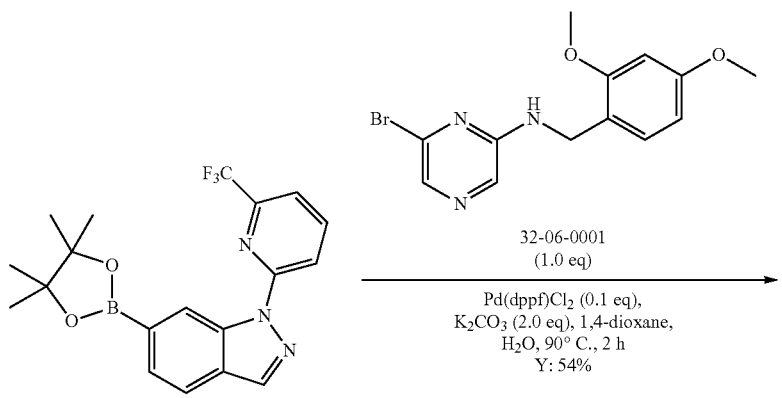

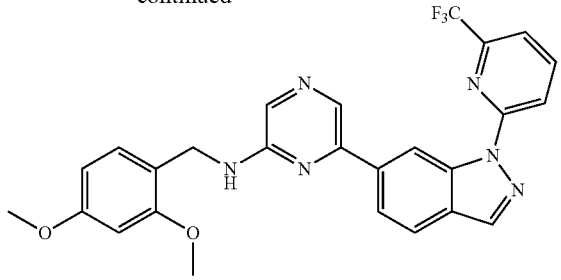

The preparation of N-(2,4-dimethoxybenzyl)-6-(1-(6-(trifluoromethyl)pyridin-2-yl)-1H-indazol-6-yl)pyrazin-2-amine was the same as that of 6-(1-(6-methylpyridin-2-yl)-1H-indazol-6-yl)pyridin-2-amine. 250 mg, as a yellow solid, Y: 54%. ESI-MS (M+H)⁺: 507.2.

Synthesis of 6-(1-(6-(trifluoromethyl)pyridin-2-yl)-1H-indazol-6-yl)pyrazin-2-amine

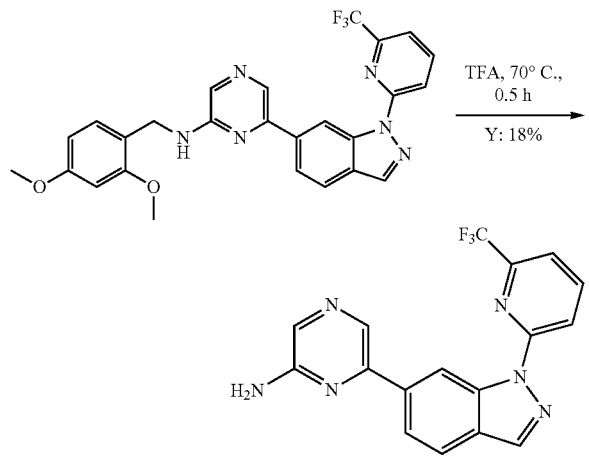

The preparation of 6-(1-(6-(trifluoromethyl)pyridin-2-yl)-1H-indazol-6-yl)pyrazin-2-amine was the same as that of 1-(6-(1-(6-methylpyridin-2-yl)-1H-indazol-6-yl)pyridin-2-yl)ethanamine. 32 mg, as a yellow solid, Y: 18%. ESI-MS (M+H)⁺: 357.1, HPLC: 93.27%. ¹H NMR (400 MHz, DMSO-d₆) δ: 9.28 (d, J=0.8 Hz, 1H), 8.54-8.53 (m, 2H), 8.30-8.28 (m, 2H), 8.04 (d, J=1.6 Hz, 1H), 7.96 (d, J=0.8 Hz, 2H), 7.84-7.82 (m, 1H), 6.77 (br, 2H).

Example 97. 6-(6-(pyrrolidin-2-yl)pyridin-2-yl)-1-(6-(trifluoromethyl)pyridin-2-yl)-1H-indazole Synthesis of 2-bromo-6-(3,4-dihydro-2H-pyrrol-5-yl)pyridine

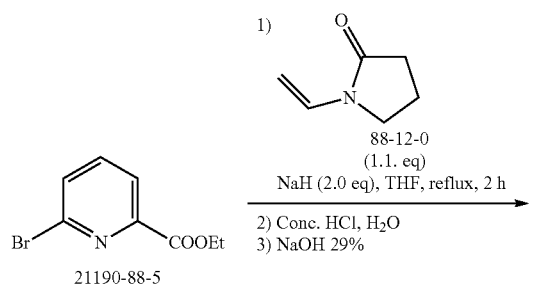

To a solution of ethyl 6-bromopicolinate (CAS#21190-88-5) (1.0 g, 4.3 mmol, 1.0 eq) and N-vinylpyrrolidinone (533 mg, 4.8 mmol, 1.1 eq) in 30 mL of THF was added NaH (3.44 g, 8.6 mmol, 60% dispersion in mineral oil, 2.0 eq) in one portion. The mixture was refluxed for 2 h and then cooled to rt. Conc. HCl (10 mL) diluted with 20 mL of H₂O was added thereto and the mixture was heated under reflux for 12 h. The solution was made basic with concentrated aqueous NaOH (ice-bath cooling), and then extracted with DCM (2×40 mL). The organics were washed with brine (20 mL), dried over Na₂SO₄ and concentrated in vacuo. The crude mixture was purified by silica gel chromatography with PE/EA (4/1) as eluent to give 2-bromo-6-(3,4-dihydro-2H-pyrrol-5-yl)pyridine. 360 mg, as off-white solid, Y: 29%. ESI-MS (M+H)⁺: 225.0. ¹H NMR (400 MHz, CDCl₃) δ: 8.08 (d, J=7.6 Hz, 1H), 7.60 (t, J=7.7 Hz, 1H), 7.51 (d, J=7.5 Hz, 1H), 4.18-4.08 (m, 2H), 3.15-3.01 (m, 2H), 2.10-1.99 (m, 2H).

Synthesis of 2-bromo-6-(pyrrolidin-2-yl)pyridine

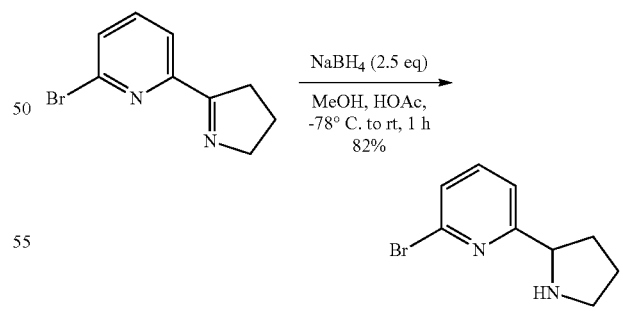

To a solution of 2-bromo-6-(3,4-dihydro-2H-pyrrol-5-yl)pyridine (360 mg, 1.6 mmol, 1.0 eq) in MeOH/HOAc (20 mL, 4/1) was added NaBH₄ (152 mg, 4.0 mmol, 2.5 eq) at −78° C. After warming to rt, most of the solvent was removed with a rotary evaporator. The residue was purified by silica gel chromatography with PE/EA (2/1) as eluent to give 2-bromo-6-(pyrrolidin-2-yl)pyridine. 298 mg, as white solid, Y: 82%. ESI-MS (M+H)⁺: 226.0.

Synthesis of tert-butyl 2-(6-bromopyridin-2-yl)pyrrolidine-1-carboxylate

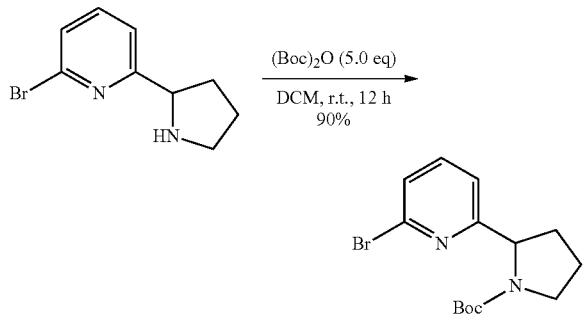

To a solution of 2-bromo-6-(pyrrolidin-2-yl)pyridine (250 mg, 1.1 mmol, 1.0 eq) in 10 mL of DCM was added (Boc)$_2$O (1.2 g, 5.5 mmol, 5.0 eq). The reaction mixture was stirred at rt for 12 h and then concentrated in vacuo. The residue was purified by silica gel chromatography with PE/EA (10/1) as eluent to give tert-butyl 2-(6-bromopyridin-2-yl)pyrrolidine-1-carboxylate. 330 mg, as white solid, Y: 90%. ESI-MS (M+H)$^+$: 327.1. $^1$H NMR (400 MHz, CDCl$_3$) δ: 7.54-7.44 (m, 1H), 7.34 (d, J=7.7 Hz, 1H), 7.13 (d, J=7.7 Hz, 1H), 4.89-4.78 (m, 1H), 3.68-3.54 (m, 2H), 2.45-2.31 (m, 1H), 2.04-1.95 (m, 1H), 1.93-1.83 (m, 2H), 1.23 (s, 9H).

Synthesis of tert-butyl 2-(6-(1-(6-(trifluoromethyl)pyridin-2-yl)-1H-indazol-6-yl)pyridin-2-yl)pyrrolidine-1-carboxylate

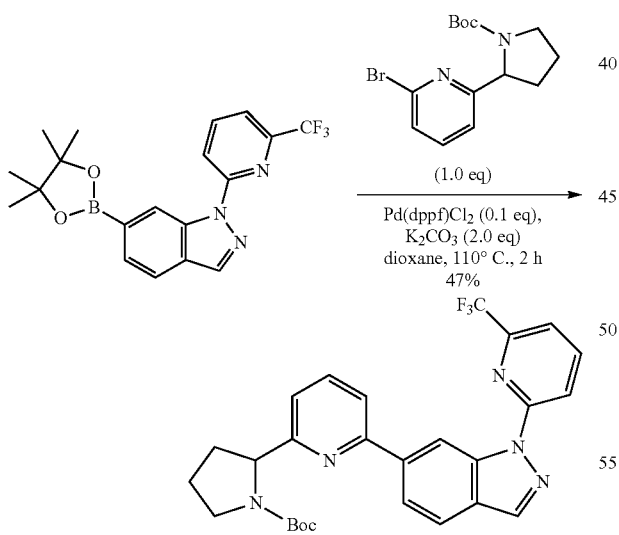

The preparation of tert-butyl 2-(6-(1-(6-(trifluoromethyl)pyridin-2-yl)-1H-indazol-6-yl)pyridin-2-yl)pyrrolidine-1-carboxylate was the same as that of 6-(1-(6-methylpyridin-2-yl)-1H-indazol-6-yl)pyridin-2-amine. 240 mg, as off-white solid, Y: 47%. ESI-MS (M+H)$^+$: 510.2. $^1$H NMR (400 MHz, CDCl$_3$) δ: 9.57 (s, 1H), 8.33-8.20 (m, 2H), 8.09 (d, J=8.4 Hz, 1H), 8.01 (t, J=8.0 Hz, 1H), 7.85 (d, J=8.3 Hz, 1H), 7.81-7.70 (m, 2H), 7.54 (d, J=7.5 Hz, 1H), 7.22-7.13 (m, 1H), 5.01 (dd, J=8.0, 4.0 Hz, 1H), 3.78-3.60 (m, 2H), 2.50-2.39 (m, 1H), 2.26-2.13 (m, 1H), 1.98-1.87 (m, 2H), 1.22 (s, 9H).

Synthesis of 6-(6-(pyrrolidin-2-yl)pyridin-2-yl)-1-(6-(trifluoromethyl)pyridin-2-yl)-1H-indazole

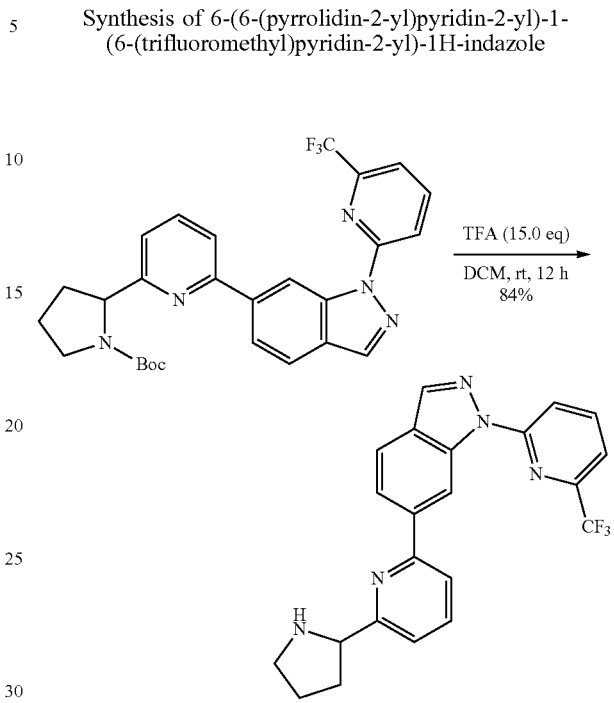

To a solution of tert-butyl 2-(6-(1-(6-(trifluoromethyl)pyridin-2-yl)-1H-indazol-6-yl)pyridin-2-yl)pyrrolidine-1-carboxylate (255 mg, 0.5 mmol, 1.0 eq) in 10 mL of DCM was added TFA (0.55 mL, 7.5 mmol, 15 eq). The mixture was stirred at rt for 12 h and then concentrated in vacuo. The residue was purified by pre-HPLC (ACN/H$_2$O with 0.05% TFA as mobile phase from 5% to 95%) to afford the product 6-(6-(pyrrolidin-2-yl)pyridin-2-yl)-1-(6-(trifluoromethyl)pyridin-2-yl)-1H-indazole. 220 mg, as white solid, Y: 84%. ESI-MS (M+H)$^+$: 410.2. HPLC: 97.60%. $^1$H NMR (400 MHz, CD$_3$OD) δ: 9.11 (s, 1H), 8.07 (d, J=8.8 Hz, 1H), 8.03-7.96 (m, 2H), 7.95-7.83 (m, 2H), 7.76-7.65 (m, 2H), 7.50-7.34 (m, 2H), 4.94 (t, J=7.3 Hz, 1H), 3.67-3.48 (m, 2H), 2.68-2.53 (m, 1H), 2.29-2.11 (m, 3H).

Example 98. 6-(6-(1-methylpyrrolidin-2-yl)pyridin-2-yl)-1-(6-(trifluoromethyl)pyridin-2-yl)-1H-indazole

Synthesis of 6-(6-(1-methylpyrrolidin-2-yl)pyridin-2-yl)-1-(6-(trifluoromethyl)pyridin-2-yl)-1H-indazole

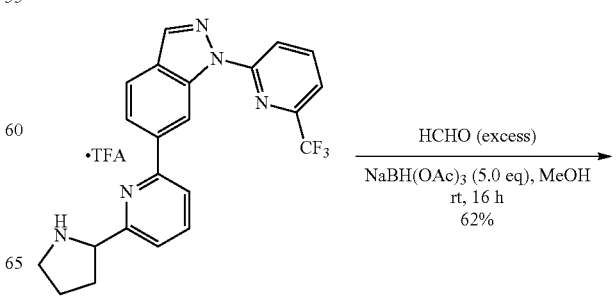

-continued

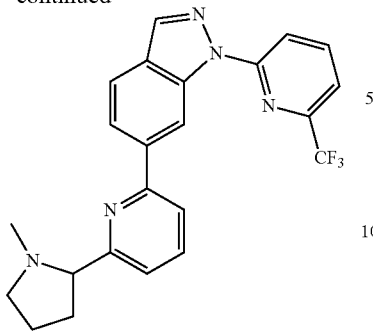

To a mixture of 6-(6-(pyrrolidin-2-yl)pyridin-2-yl)-1-(6-(trifluoromethyl)pyridin-2-yl)-1H-indazole (125 mg, 0.30 mmol) and HCHO (aq., excess) in MeOH (30 mL) was added NaBH(OAc)₃ (318 mg, 1.50 mmol, 5.0 eq) at rt. The mixture was stirred at rt for 2 h. After concentration, the residue was purified by pre-HPLC (MeCN/H₂O with 0.05% TFA as mobile phase from 5% to 95%) to give 6-(6-(1-methylpyrrolidin-2-yl)pyridin-2-yl)-1-(6-(trifluoromethyl)pyridin-2-yl)-1H-indazole as a pale yellow solid (80 mg, Y: 62%). ESI-MS (M+H)⁺: 424.2. HPLC: 98.13%. ¹H NMR (400 MHz, CD₃OD) δ: 9.17 (s, 1H), 8.17 (s, 1H), 8.09-8.00 (m, 2H), 8.01-7.87 (m, 2H), 7.82-7.70 (m, 2H), 7.54-7.42 (m, 2H), 4.71 (t, J=8.1 Hz, 1H), 4.01-3.87 (m, 1H), 3.47-3.35 (m, 1H), 2.96 (s, 3H), 2.75-2.62 (m, 1H), 2.40-2.21 (m, 3H).

Example 99. 1-(6-(3-(6-methylpyridin-2-yl)imidazo[1,5-a]pyridin-6-yl)pyridin-2-yl)ethanamine Synthesis of N-((5-bromopyridin-2-yl)methyl)-6-methylpicolinamide

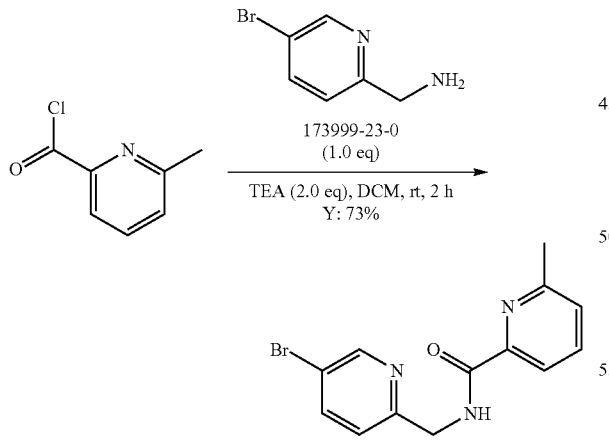

The preparation of N-((5-bromopyridin-2-yl)methyl)-6-methylpicolinamide was the same as that of benzyl 6-(((5-bromopyridin-2-yl)methyl)carbamoyl)picolinate. 420 mg, yellow solid, Y: 73%. ESI-MS (M+H)⁺: 306.1. ¹H NMR (400 MHz, CDCl₃) δ: 8.85 (s, 1H), 8.65 (d, J=2.0 Hz, 1H), 8.02 (d, J=7.6 Hz, 1H), 7.79 (dd, J=8.4, 2.4 Hz, 1H), 7.74 (t, J=7.6 Hz, 1H), 7.30-7.28 (m, 2H), 4.75 (d, J=6.0 Hz, 2H), 2.59 (s, 3H).

Synthesis of 6-bromo-3-(6-methylpyridin-2-yl)imidazo[1,5-a]pyridine

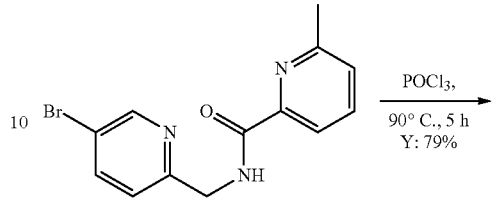

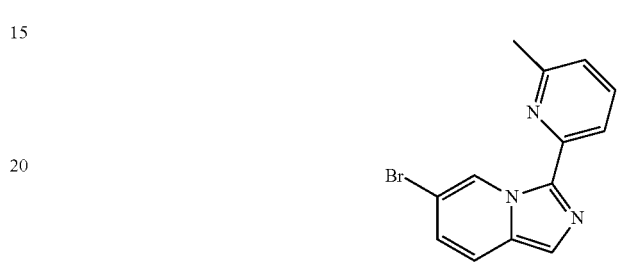

The preparation of 6-bromo-3-(6-methylpyridin-2-yl)imidazo[1,5-a]pyridine was the same as that of 3-(6-bromoimidazo[1,5-a]pyridin-3-yl)benzonitrile. 312 mg, yellow solid, Y: 79%. ESI-MS (M+H)⁺: 288.1. ¹H NMR (400 MHz, CDCl₃) δ: 10.28 (s, 1H), 8.12 (d, J=8.0 Hz, 1H), 7.69 (t, J=8.0 Hz, 1H), 7.59 (s, 1H), 7.43 (dd, J=9.6, 0.8 Hz, 1H), 7.10 (d, J=7.2 Hz, 1H), 6.91 (dd, J=9.6, 1.6 Hz, 1H), 2.67 (s, 3H).

Synthesis of 3-(6-methylpyridin-2-yl)-6-(4,4,5,5-tetramethyl-1,3,2-dioxaborolan-2-yl)imidazo[1,5-a]pyridine

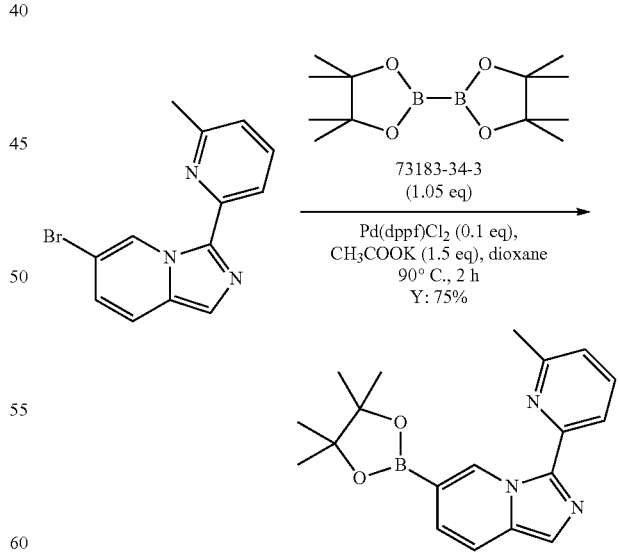

The preparation of 3-(6-methylpyridin-2-yl)-6-(4,4,5,5-tetramethyl-1,3,2-dioxaborolan-2-yl)imidazo[1,5-a]pyridine was the same as that of 1-(6-methylpyridin-2-yl)-6-(4,4,5,5-tetramethyl-1,3,2-dioxaborolan-2-yl)-1H-indazole. 273 mg, yellow solid, Y: 75%. ESI-MS (M+H)⁺: 336.1.

Synthesis of 1-(6-(3-(6-methylpyridin-2-yl)imidazo[1,5-a]pyridin-6-yl)pyridin-2-yl)ethanone

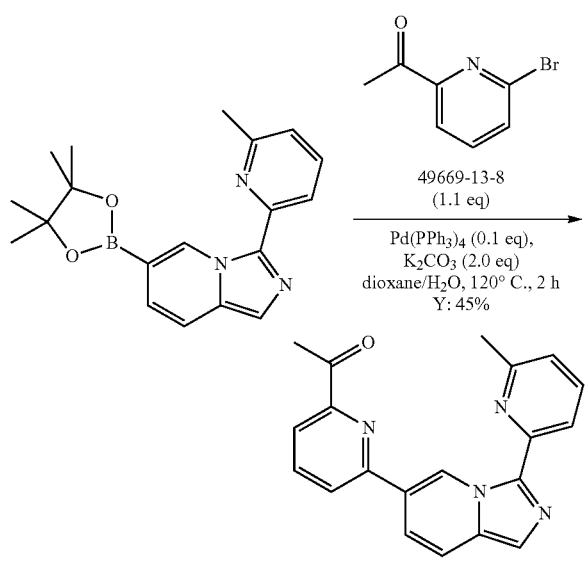

The preparation of 1-(6-(3-(6-methylpyridin-2-yl)imidazo[1,5-a]pyridin-6-yl)pyridin-2-yl)ethanone was the same as that of 6-(1-(6-methylpyridin-2-yl)-1H-indazol-6-yl)pyridin-2-amine. 120 mg, yellow solid, Y: 45%. ESI-MS (M+H)$^+$: 329.1. $^1$H NMR (400 MHz, CDCl$_3$) δ: 10.88 (d, J=1.2 Hz, 1H), 8.19 (d, J=8.4 Hz, 1H), 8.03-8.01 (m, 1H), 7.97-7.95 (m, 2H), 7.72 (t, J=7.6 Hz, 1H), 7.66-7.63 (m, 3H), 7.12 (d, J=8.0 Hz, 1H), 2.89 (s, 3H), 2.70 (s, 3H).

Synthesis of (E)-1-(6-(3-(6-methylpyridin-2-yl)imidazo[1,5-a]pyridin-6-yl)pyridin-2-yl)ethanone oxime

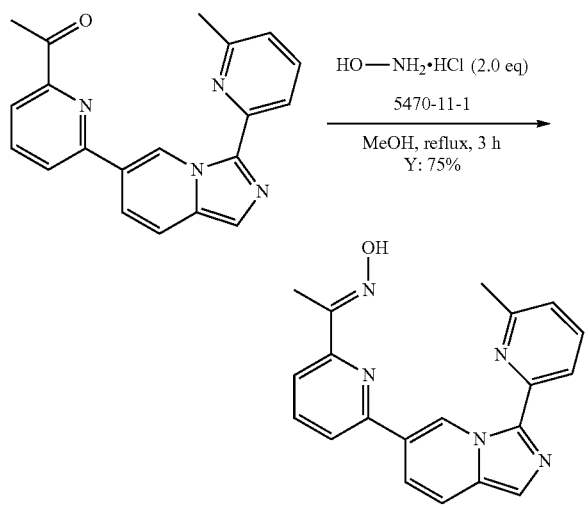

The preparation of (E)-1-(6-(3-(6-methylpyridin-2-yl)imidazo[1,5-a]pyridin-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 94 mg, yellow solid, Y: 75%. ESI-MS (M+H)$^+$: 344.1.

Synthesis of 1-(6-(3-(6-methylpyridin-2-yl)imidazo[1,5-a]pyridin-6-yl)pyridin-2-yl)ethanamine

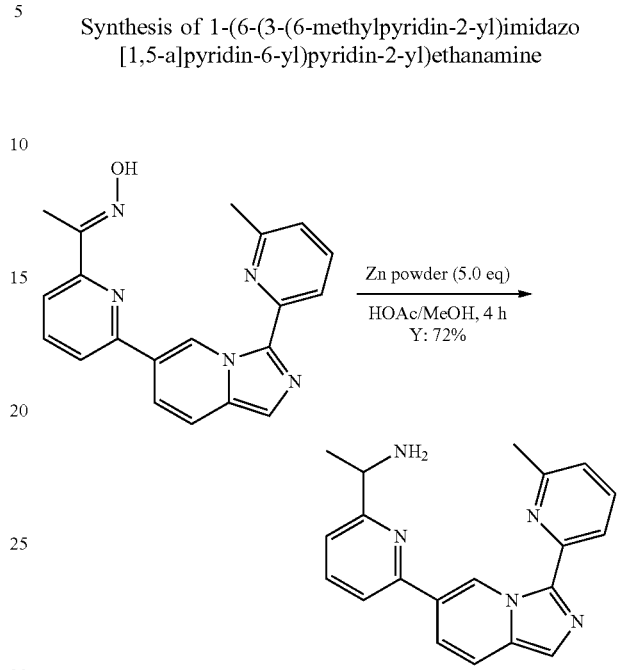

The preparation of 1-(6-(3-(6-methylpyridin-2-yl)imidazo[1,5-a]pyridin-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 65 mg, yellow solid, Y: 72%. ESI-MS (M+H)$^+$: 330.2. HPLC: 98.32%. $^1$H NMR (400 MHz, CD$_3$OD) δ: 10.73 (d, J=1.2 Hz, 1H), 7.94 (d, J=8.0 Hz, 1H), 7.80 (t, J=8.0 Hz, 1H), 7.72 (t, J=8.0 Hz, 1H), 7.68-7.65 (m, 2H), 7.60 (dd, J=9.2, 1.2 Hz, 1H), 7.52 (d, J=0.4 Hz, 1H), 7.31 (d, J=7.6 Hz, 1H), 7.15 (d, J=7.2 Hz, 1H), 4.13 (q, J=6.8 Hz, 1H), 2.62 (s, 3H), 1.47 (d, J=6.8 Hz, 3H).

Example 100. 6-(6-(1-aminoethyl)pyridin-2-yl)-1-(6-methylpyridin-2-yl)-1H-indazol-4-amine Synthesis of 6-bromo-1-(6-methylpyridin-2-yl)-1H-indazole-4-carboxylic acid and 6-bromo-2-(6-methylpyridin-2-yl)-2H-indazole-4-carboxylic acid

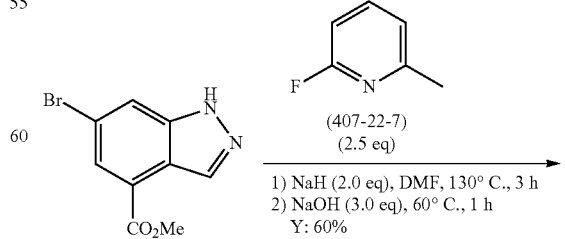

183

-continued

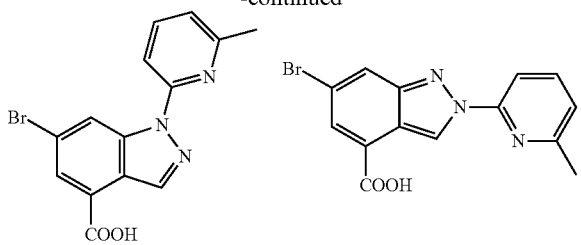

The preparation of 6-bromo-1-(6-methylpyridin-2-yl)-1H-indazole-4-carboxylic acid and 6-bromo-2-(6-methyl-

184 pyridin-2-yl)-2H-indazole-4-carboxylic acid was the same as that of 6-bromo-1-(6-methylpyridin-2-yl)-1H-indazole. 810 mg, as a light brown solid, Y: 60%. The mixture of 6-bromo-1-(6-methylpyridin-2-yl)-1H-indazole-4-carboxylic acid and 6-bromo-2-(6-methylpyridin-2-yl)-2H-indazole-4-carboxylic acid was difficult to be purified due to poor solubility. The mixture was directly used for next step. ESI-MS (M+H)+: 332.9.

Synthesis of tert-butyl (6-bromo-1-(6-methylpyridin-2-yl)-1H-indazol-4-yl)carbamate and tert-butyl (6-bromo-2-(6-methylpyridin-2-yl)-2H-indazol-4-yl)carbamate

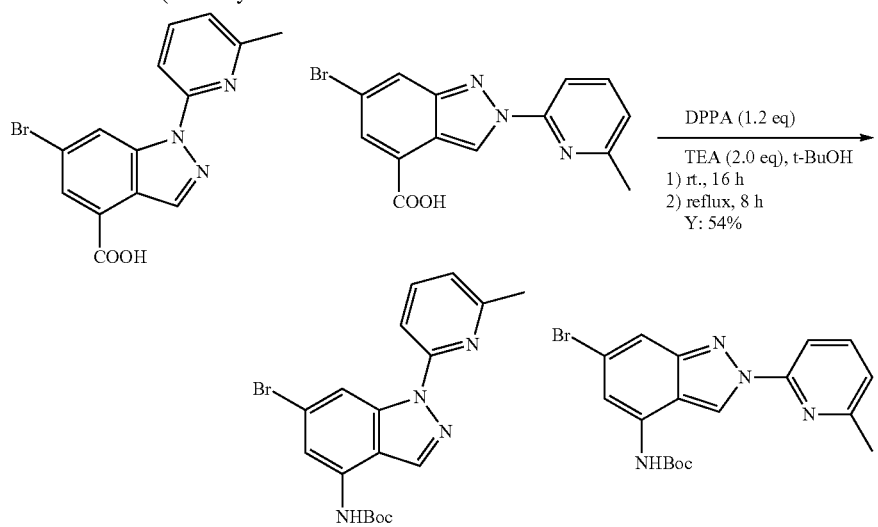

A mixture of 6-bromo-1-(6-methylpyridin-2-yl)-1H-indazole-4-carboxylic acid and 6-bromo-2-(6-methylpyridin-2-yl)-2H-indazole-4-carboxylic acid (350 mg, 1.1 mmol, 1.0 eq), DPPA (413 mg, 1.5 mmol, 1.5 eq) and TEA (165 mg, 1.5 mmol, 1.5 eq) in t-BuOH (15 mL) and anhydrous toluene (15 mL) was stirred at rt for 16 h and then refluxed for 8 h. After concentration, the crude product was purified by column chromatography on silica gel (PE/EA=10/1) to give a mixture of tert-butyl (6-bromo-1-(6-methylpyridin-2-yl)-1H-indazol-4-yl)carbamate and tert-butyl (6-bromo-2-(6-methylpyridin-2-yl)-2H-indazol-4-yl)carbamate as a white solid. 230 mg, Y: 54%. ESI-MS (M+H)+: 403.1

Synthesis of tert-butyl (1-(6-methylpyridin-2-yl)-6-(4,4,5,5-tetramethyl-1,3,2-dioxaborolan-2-yl)-1H-indazol-4-yl)carbamate and tert-butyl (2-(6-methylpyridin-2-yl)-6-(4,4,5,5-tetramethyl-1,3,2-dioxaborolan-2-yl)-2H-indazol-4-yl)carbamate

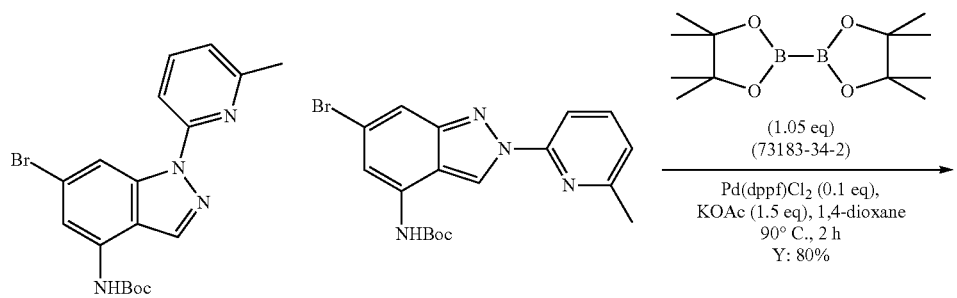

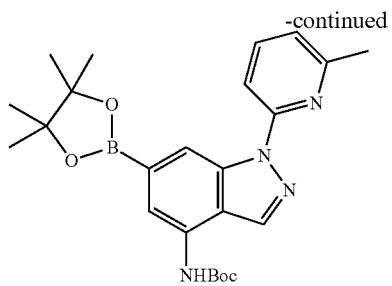
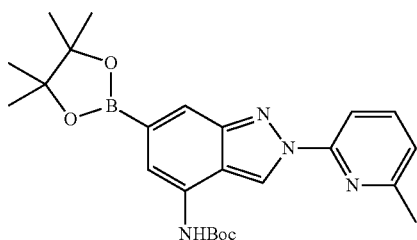

The preparation of tert-butyl (1-(6-methylpyridin-2-yl)-6-(4,4,5,5-tetramethyl-1,3,2-dioxaborolan-2-yl)-1H-indazol-4-yl)carbamate and tert-butyl (2-(6-methylpyridin-2-yl)-6-(4,4,5,5-tetramethyl-1,3,2-dioxaborolan-2-yl)-2H-indazol-4-yl)carbamate was the same as that of 1-(6-methylpyridin-2-yl)-6-(4,4,5,5-tetramethyl-1,3,2-dioxaborolan-2-yl)-1H-indazole. 206 mg, as a white solid, Y: 80%. The mixture of tert-butyl (1-(6-methylpyridin-2-yl)-6-(4,4,5,5-tetramethyl-1,3,2-dioxaborolan-2-yl)-1H-indazol-4-yl)carbamate and tert-butyl (2-(6-methylpyridin-2-yl)-6-(4,4,5,5-tetramethyl-1,3,2-dioxaborolan-2-yl)-2H-indazol-4-yl)carbamate was directly used for next step without further purification. ESI-MS (M+H)$^+$: 451.1.

Synthesis of tert-butyl (6-(6-acetylpyridin-2-yl)-1-(6-methylpyridin-2-yl)-1H-indazol-4-yl)carbamate

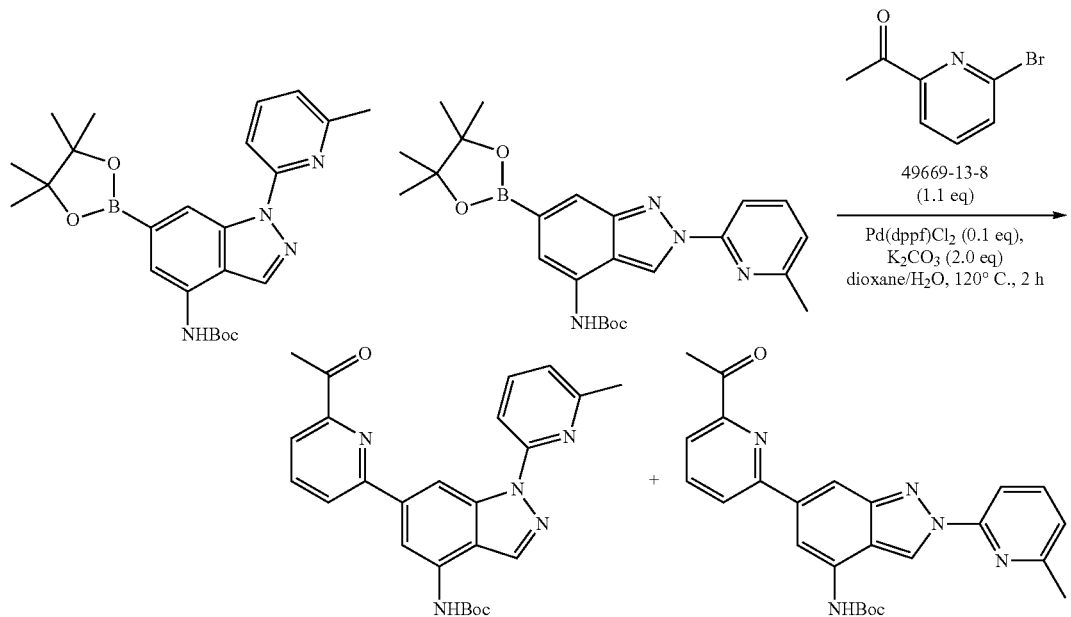

The preparation of tert-butyl (6-(6-acetylpyridin-2-yl)-1-(6-methylpyridin-2-yl)-1H-indazol-4-yl)carbamate was the same as that of 6-(1-(6-methylpyridin-2-yl)-1H-indazol-6-yl)pyridin-2-amine. The mixture of tert-butyl (6-(6-acetylpyridin-2-yl)-1-(6-methylpyridin-2-yl)-1H-indazol-4-yl)carbamate and tert-butyl (6-(6-acetylpyridin-2-yl)-2-(6-methylpyridin-2-yl)-2H-indazol-4-yl)carbamate was purified by silica gel chromatography with PE/EA (5/1) as eluent to give tert-butyl (6-(6-acetylpyridin-2-yl)-1-(6-methylpyridin-2-yl)-1H-indazol-4-yl)carbamate and PE/EA (1/1) as eluent to give tert-butyl (6-(6-acetylpyridin-2-yl)-2-(6-methylpyridin-2-yl)-2H-indazol-4-yl)carbamate as a yellow solid (66 mg, Y: 33%).

tert-butyl (6-(6-acetylpyridin-2-yl)-1-(6-methylpyridin-2-yl)-1H-indazol-4-yl)carbamate, as a yellow solid, 52 mg, Y: 26%. ESI-MS (M+H)$^+$: 444.2. $^1$H NMR (400 MHz, CDCl$_3$) δ: 9.47 (s, 1H), 8.43 (s, 1H), 8.23 (d, J=0.8 Hz, 1H), 8.10 (dd, J=7.6, 0.8 Hz, 1H), 8.01 (dd, J=7.6, 0.8 Hz, 1H), 7.93 (t, J=8.0 Hz, 1H), 7.86 (d, J=8.0 Hz, 1H), 7.75 (t, J=8.0 Hz, 1H), 7.06 (d, J=7.6 Hz, 1H), 6.93 (s, 1H), 2.93 (s, 3H), 2.69 (s, 3H), 1.55 (s, 9H).

Synthesis of (Z)-tert-butyl (6-(6-(1-(hydroxyimino)ethyl)pyridin-2-yl)-1-(6-methylpyridin-2-yl)-1H-indazol-4-yl)carbamate

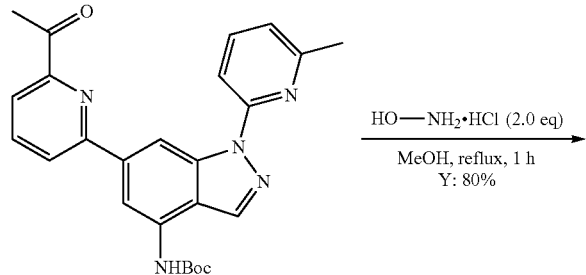

The preparation of (Z)-tert-butyl (6-(6-(1-(hydroxyimino)ethyl)pyridin-2-yl)-1-(6-methylpyridin-2-yl)-1H-indazol-4-yl)carbamate was the same as that of 2-(1-(6-(trifluoromethyl)pyridin-2-yl)-1H-indazol-6-yl)-5H-cyclopenta[b]pyridin-7(6H)-one oxime. 105 mg, as white solid, Y: 80%. ESI-MS (M+H)$^+$: 459.1.

Synthesis of tert-butyl (6-(6-(1-aminoethyl)pyridin-2-yl)-1-(6-methylpyridin-2-yl)-1H-indazol-4-yl)carbamate

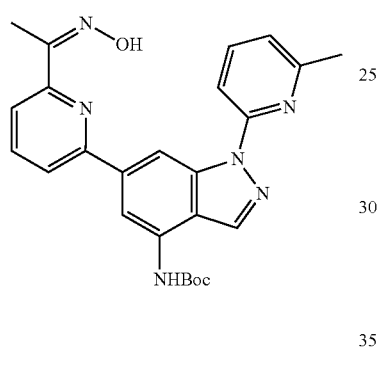

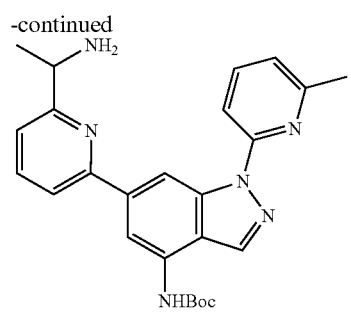

The preparation of tert-butyl (6-(6-(1-aminoethyl)pyridin-2-yl)-1-(6-methylpyridin-2-yl)-1H-indazol-4-yl)carbamate was the same as that of 2-(1-(6-(trifluoromethyl)pyridin-2-yl)-1H-indazol-6-yl)-6,7-dihydro-5H-cyclopenta[b]pyridin-7-amine. 72 mg, as white solid, Y: 53%. ESI-MS (M+H)$^+$: 445.1.

Synthesis of 6-(6-(1-aminoethyl)pyridin-2-yl)-1-(6-methylpyridin-2-yl)-1H-indazol-4-amine

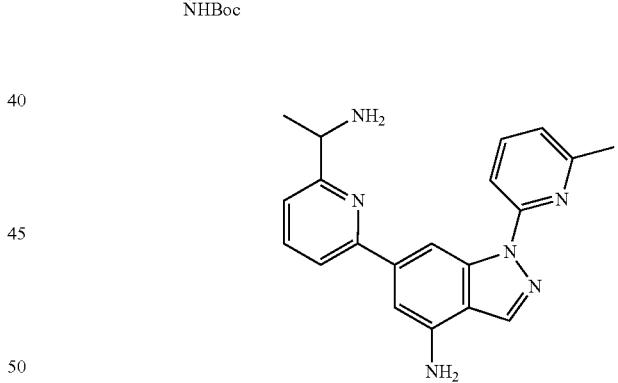

To a solution of tert-butyl (6-(6-(1-aminoethyl)pyridin-2-yl)-1-(6-methylpyridin-2-yl)-1H-indazol-4-yl)carbamate (72 mg, 0.16 mmol, 1.0 eq) in DCM (5 mL) was added TFA (1 mL). The mixture was stirred at rt for 1 h. After concentration, the residue was purified by prep-HPLC (CH$_3$CN/H$_2$O with 0.05% TFA as mobile phase from 5% to 95%) to give 6-(6-(1-aminoethyl)pyridin-2-yl)-1-(6-methylpyridin-2-yl)-1H-indazol-4-amine as a yellow solid. 32 mg, Y: 57%. ESI-MS (M+H)$^+$: 345.1. HPLC: 98.64%. $^1$H NMR (400 MHz, CD$_3$OD) δ: 8.78 (s, 1H), 8.36 (s, 1H), 7.87-7.76 (m, 4H), 7.35 (d, J=7.6 Hz, 1H), 7.21 (d, J=0.8 Hz, 1H), 7.13 (dd, J=6.0, 2.4 Hz, 1H), 4.22 (q, J=6.4 Hz, 1H), 2.66 (s, 3H), 1.54 (d, J=6.8 Hz, 3H).

Example 101. 6-(6-(1-aminoethyl)pyridin-2-yl)-N-methyl-1-(6-methylpyridin-2-yl)-1H-indazol-4-amine Synthesis of tert-butyl (6-bromo-1-(6-methylpyridin-2-yl)-1H-indazol-4-yl)(methyl)carbamate and tert-butyl (6-bromo-2-(6-methylpyridin-2-yl)-2H-indazol-4-yl)(methyl)carbamate

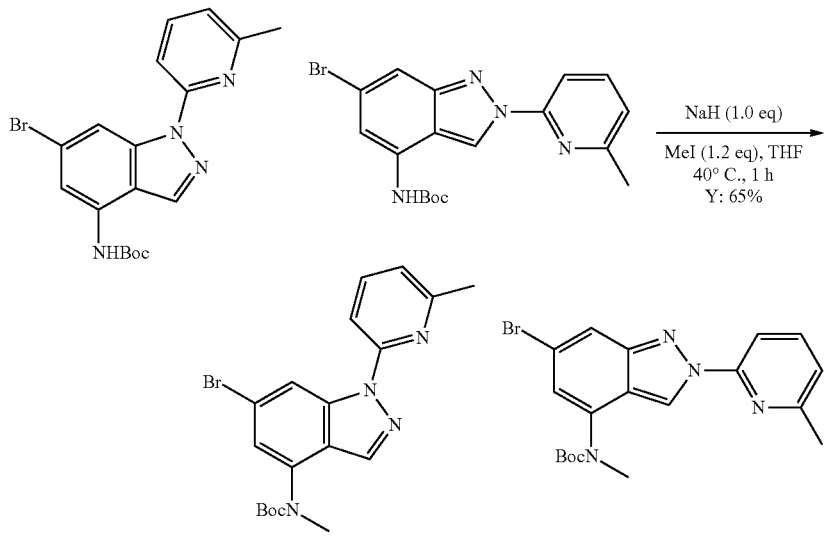

To a mixture of tert-butyl (6-bromo-1-(6-methylpyridin-2-yl)-1H-indazol-4-yl)(methyl)carbamate and tert-butyl (6-bromo-2-(6-methylpyridin-2-yl)-2H-indazol-4-yl)(methyl)carbamate (650 mg, 1.60 mmol, 1.0 eq) in anhydrous THF (10 mL) was added NaH (39 mg, 1.60 mmol, 1.0 eq) at rt. The mixture was stirred at rt for 5 min, then MeI (273 mg, 1.92 mmol, 1.2 eq) was added into the mixture. The mixture was stirred at 40° C. for 1 h. After concentration, the residue was purified by column chromatography on silica gel (PE/EA=10/1) to give a mixture of tert-butyl (6-bromo-1-(6-methylpyridin-2-yl)-1H-indazol-4-yl)(methyl)carbamate and tert-butyl (6-bromo-2-(6-methylpyridin-2-yl)-2H-indazol-4-yl)(methyl)carbamate as a white solid. 439 mg, Y: 65%. ESI-MS (M+H)$^+$: 417.2.

Synthesis of tert-butyl methyl(1-(6-methylpyridin-2-yl)-6-(4,4,5,5-tetramethyl-1,3,2-dioxaborolan-2-yl)-1H-indazol-4-yl)carbamate and tert-butyl methyl(2-(6-methylpyridin-2-yl)-6-(4,4,5,5-tetramethyl-1,3,2-dioxaborolan-2-yl)-2H-indazol-4-yl)carbamate

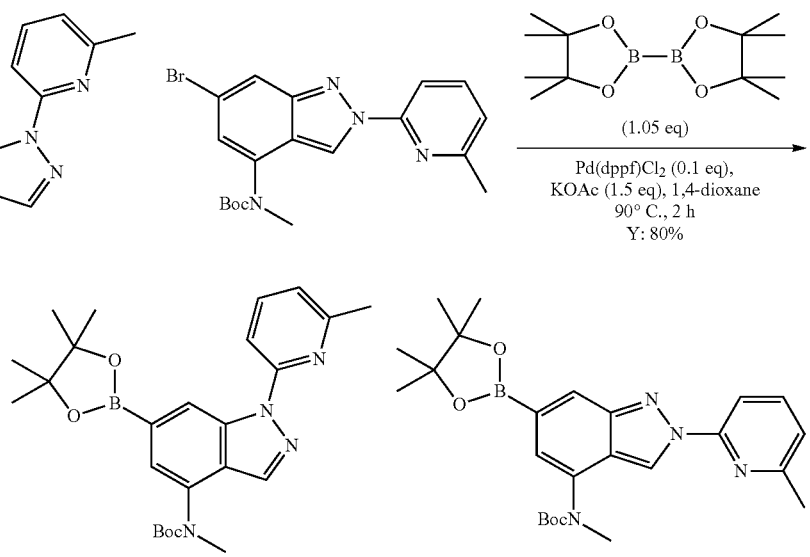

The preparation of tert-butyl methyl(1-(6-methylpyridin-2-yl)-6-(4,4,5,5-tetramethyl-1,3,2-dioxaborolan-2-yl)-1H-indazol-4-yl)carbamate and tert-butyl methyl(2-(6-methylpyridin-2-yl)-6-(4,4,5,5-tetramethyl-1,3,2-dioxaborolan-2-yl)-2H-indazol-4-yl)carbamate was the same as that of 1-(6-methylpyridin-2-yl)-6-(4,4,5,5-tetramethyl-1,3,2-dioxaborolan-2-yl)-1H-indazole. 465 mg, as a white solid, Y: 80%. The mixture of tert-butyl methyl(1-(6-methylpyridin-2-yl)-6-(4,4,5,5-tetramethyl-1,3,2-dioxaborolan-2-yl)-1H-indazol-4-yl)carbamate and tert-butyl methyl(2-(6-methylpyridin-2-yl)-6-(4,4,5,5-tetramethyl-1,3,2-dioxaborolan-2-yl)-2H-indazol-4-yl)carbamate was directly used for next step without further purification. ESI-MS (M+H)$^+$: 465.1.

Synthesis of tert-butyl (6-(6-acetylpyridin-2-yl)-1-(6-methylpyridin-2-yl)-1H-indazol-4-yl)(methyl)carbamate

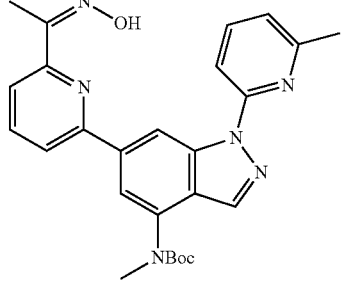

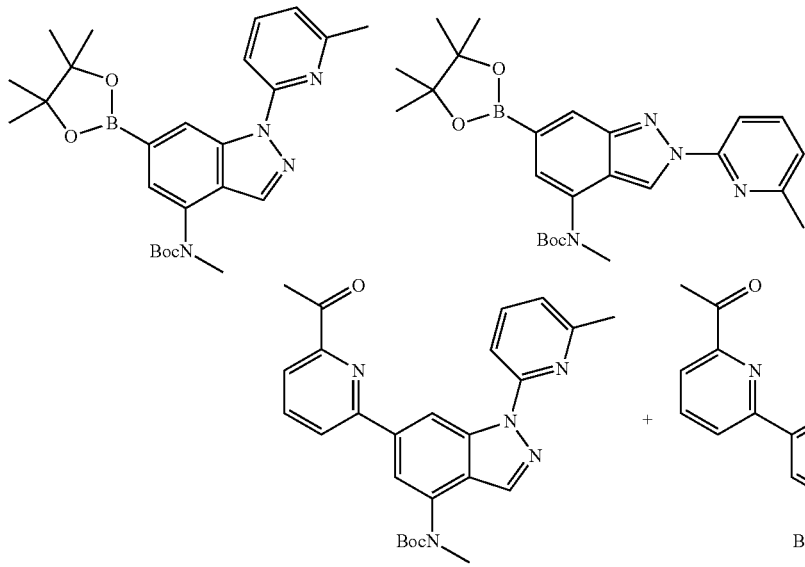

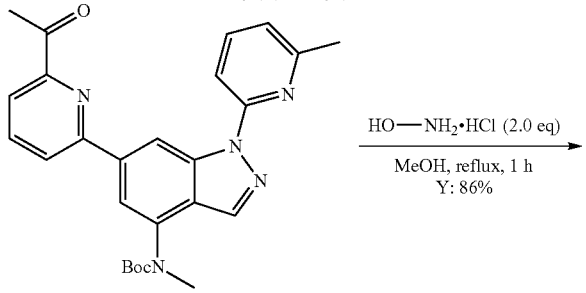

The preparation of tert-butyl (6-(6-acetylpyridin-2-yl)-1-(6-methylpyridin-2-yl)-1H-indazol-4-yl)(methyl)carbamate was the same as tert-butyl (6-(6-acetylpyridin-2-yl)-1-(6-methylpyridin-2-yl)-1H-indazol-4-yl)carbamate. 142 mg, as a yellow solid, Y: 31%. ESI-MS (M+H)$^+$: 458.1. HPLC: 93.37%. $^1$H NMR (400 MHz, CDCl$_3$) δ: 9.52 (s, 1H), 8.07 (s, 1H), 8.00 (d, J=8.0 Hz, 1H), 7.97 (d, J=7.6 Hz, 1H), 7.89 (t, J=8.0 Hz, 1H), 7.81-7.79 (m, 2H), 7.69 (t, J=7.6 Hz, 1H), 7.00 (d, J=7.6 Hz, 1H), 3.41 (s, 3H), 2.84 (s, 3H), 2.63 (s, 3H), 1.37 (s, 9H).

Synthesis of (Z)-tert-butyl (6-(6-(1-(hydroxyimino)ethyl)pyridin-2-yl)-1-(6-methylpyridin-2-yl)-1H-indazol-4-yl)(methyl)carbamate

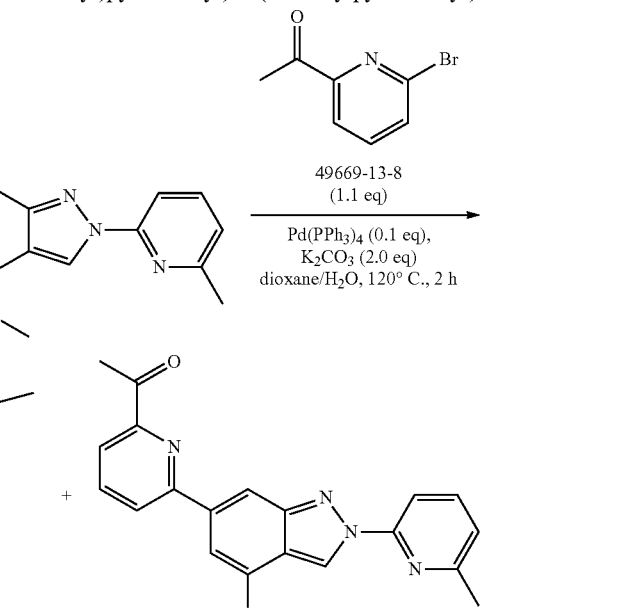

The preparation of (Z)-tert-butyl (6-(6-(1-(hydroxyimino)ethyl)pyridin-2-yl)-1-(6-methylpyridin-2-yl)-1H-indazol-4-yl)(methyl)carbamate was the same as that of 2-(1-(6-(trifluoromethyl)pyridin-2-yl)-1H-indazol-6-yl)-5H-cyclopenta[b]pyridin-7(6H)-one oxime. 126 mg, as white solid, Y: 86%. ESI-MS (M+H)$^+$: 473.2. HPLC: 98.82%. $^1$H NMR (400 MHz, CD$_3$OD) δ: 9.62 (s, 1H), 8.19 (s, 1H), 7.97 (d, J=7.6 Hz, 1H), 7.93-7.82 (m, 5H), 7.17 (d, J=6.4 Hz, 1H), 3.47 (s, 3H), 2.70 (s, 3H), 2.49 (s, 3H), 1.46 (s, 9H).

Synthesis of tert-butyl (6-(6-(1-aminoethyl)pyridin-2-yl)-1-(6-methylpyridin-2-yl)-1H-indazol-4-yl)(methyl)carbamate

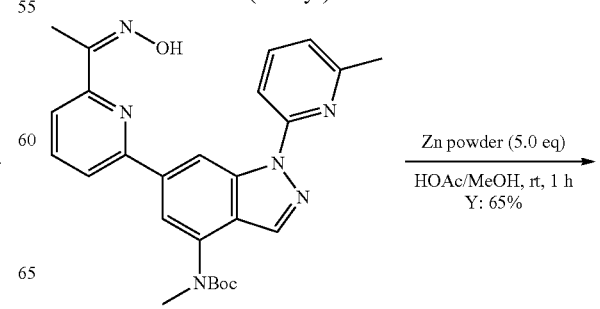

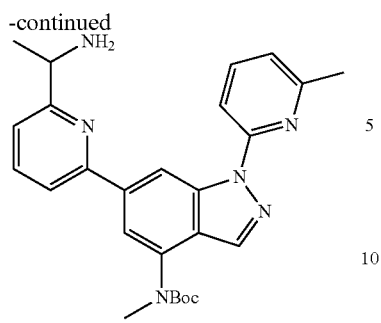

The preparation of (6-(6-(1-aminoethyl)pyridin-2-yl)-1-(6-methylpyridin-2-yl)-1H-indazol-4-yl)(methyl)carbamate was the same as 2-(1-(6-(trifluoromethyl)pyridin-2-yl)-1H-indazol-6-yl)-6,7-dihydro-5H-cyclopenta[b]pyridin-7-amine. 103 mg, as white solid, Y: 65%. ESI-MS (M+H)+: 458.2

Synthesis of 6-(6-(1-aminoethyl)pyridin-2-yl)-N-methyl-1-(6-methylpyridin-2-yl)-1H-indazol-4-amine

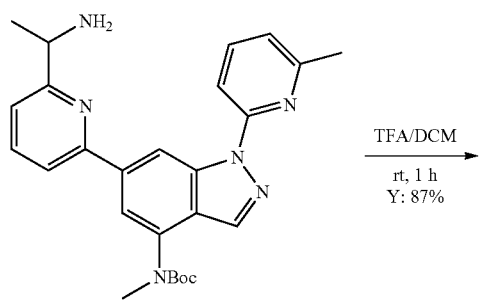

The preparation of 6-(6-(1-aminoethyl)pyridin-2-yl)-N-methyl-1-(6-methylpyridin-2-yl)-1H-indazol-4-amine was the same as 6-(6-(1-aminoethyl)pyridin-2-yl)-1-(6-methylpyridin-2-yl)-1H-indazol-4-amine. 33 mg, as yellow solid, Y: 87%. ESI-MS (M+H)+: 359.2. HPLC: 100.00%. $^1$H NMR (400 MHz, DMSO-$d_6$) δ: 8.79 (s, 1H), 8.51 (s, 1H), 8.45 (br, 2H), 8.04-7.98 (m, 2H), 7.87 (d, J=8.0 Hz, 1H), 7.79 (d, J=8.0 Hz, 1H), 7.50 (dd, J=5.6, 2.8 Hz, 1H), 7.17 (d, J=7.6 Hz, 1H), 7.03 (s, 1H), 4.66-4.63 (m, 1H), 2.99 (s, 3H), 2.64 (s, 3H), 1.61 (d, J=7.2 Hz, 3H).

Example 102. 6-(6-(1-aminoethyl)pyridin-2-yl)-N,N-dimethyl-1-(6-methylpyridin-2-yl)-1H-indazol-4-amine Synthesis of 6-bromo-1-(6-methylpyridin-2-yl)-1H-indazol-4-amine and 6-bromo-2-(m-tolyl)-2H-indazol-4-amine

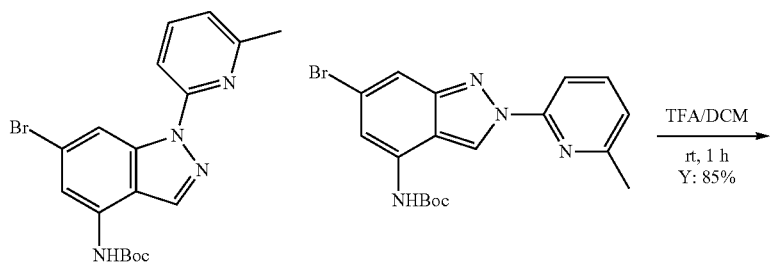

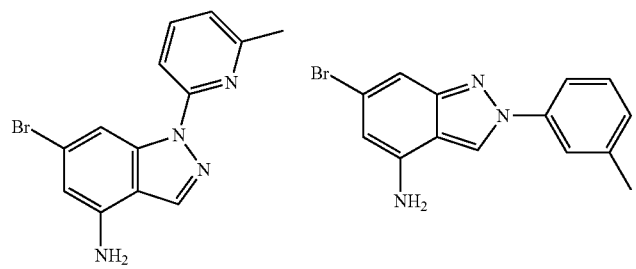

The preparation of 6-bromo-1-(6-methylpyridin-2-yl)-1H-indazol-4-amine and 6-bromo-2-(m-tolyl)-2H-indazol-4-amine was the same as 6-(6-(1-aminoethyl)pyridin-2-yl)-1-(6-methylpyridin-2-yl)-1H-indazol-4-amine. 340 mg, as a light brown solid, Y: 85%. ESI-MS (M+H)⁺: 303.1.

Synthesis of 6-bromo-N,N-dimethyl-1-(6-methylpyridin-2-yl)-1H-indazol-4-amine and 6-bromo-N,N-dimethyl-2-(6-methylpyridin-2-yl)-2H-indazol-4-amine

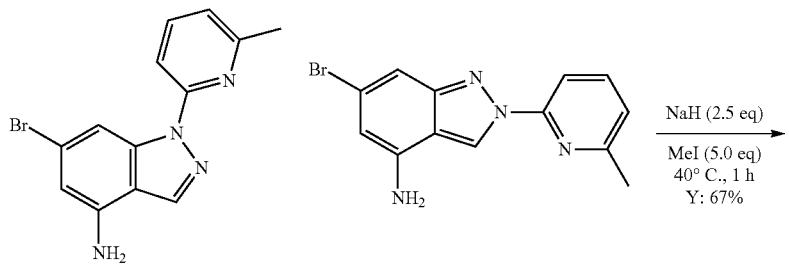

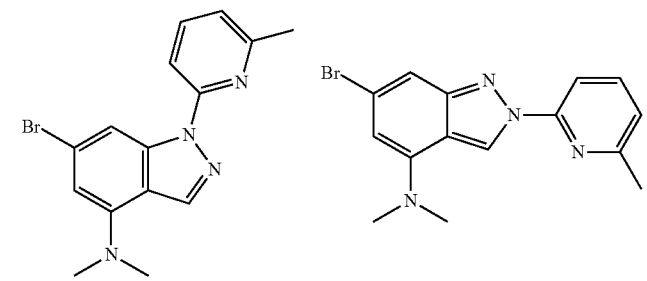

The preparation of 6-bromo-N,N-dimethyl-1-(6-methylpyridin-2-yl)-1H-indazol-4-amine and 6-bromo-N,N-dimethyl-2-(6-methylpyridin-2-yl)-2H-indazol-4-amine was the same as tert-butyl (6-bromo-1-(6-methylpyridin-2-yl)-1H-indazol-4-yl)(methyl)carbamate. 250 mg, as white solid, Y: 67%. ESI-MS (M+H)⁺: 331.2.

Synthesis of N,N-dimethyl-1-(6-methylpyridin-2-yl)-6-(4,4,5,5-tetramethyl-1,3,2-dioxaborolan-2-yl)-1H-indazol-4-amine and N,N-dimethyl-2-(6-methylpyridin-2-yl)-6-(4,4,5,5-tetramethyl-1,3,2-dioxaborolan-2-yl)-2H-indazol-4-amine

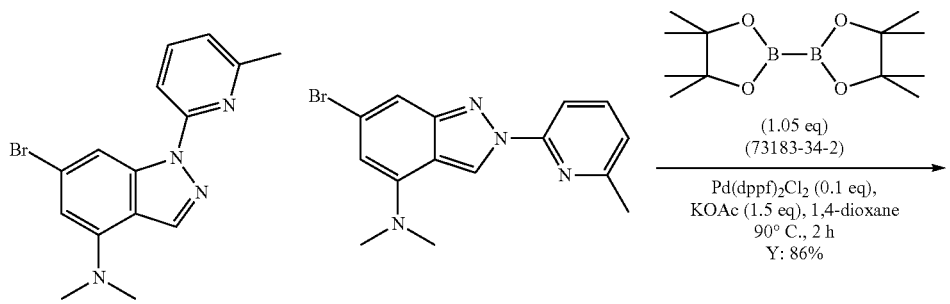

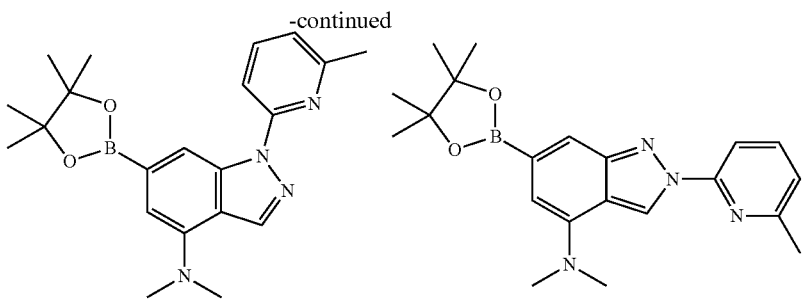

The preparation of N,N-dimethyl-1-(6-methylpyridin-2-yl)-6-(4,4,5,5-tetramethyl-1,3,2-dioxaborolan-2-yl)-1H-indazol-4-amine and N,N-dimethyl-2-(6-methylpyridin-2-yl)-6-(4,4,5,5-tetramethyl-1,3,2-dioxaborolan-2-yl)-2H-indazol-4-amine was the same as that of 1-(6-methylpyridin-2-yl)-6-(4,4,5,5-tetramethyl-1,3,2-dioxaborolan-2-yl)-1H-indazole. 246 mg, as a white solid, Y: 86%. The mixture of N,N-dimethyl-1-(6-methylpyridin-2-yl)-6-(4,4,5,5-tetramethyl-1,3,2-dioxaborolan-2-yl)-1H-indazol-4-amine and N,N-dimethyl-2-(6-methylpyridin-2-yl)-6-(4,4,5,5-tetramethyl-1,3,2-dioxaborolan-2-yl)-2H-indazol-4-amine was directly used for next step without further purification. ESI-MS (M+H)+: 379.1.

Synthesis of 1-(6-(4-(dimethylamino)-1-(6-methylpyridin-2-yl)-1H-indazol-6-yl)pyridin-2-yl)ethanone and 1-(6-(4-(dimethylamino)-2-(6-methylpyridin-2-yl)-2H-indazol-6-yl)pyridin-2-yl)ethanone

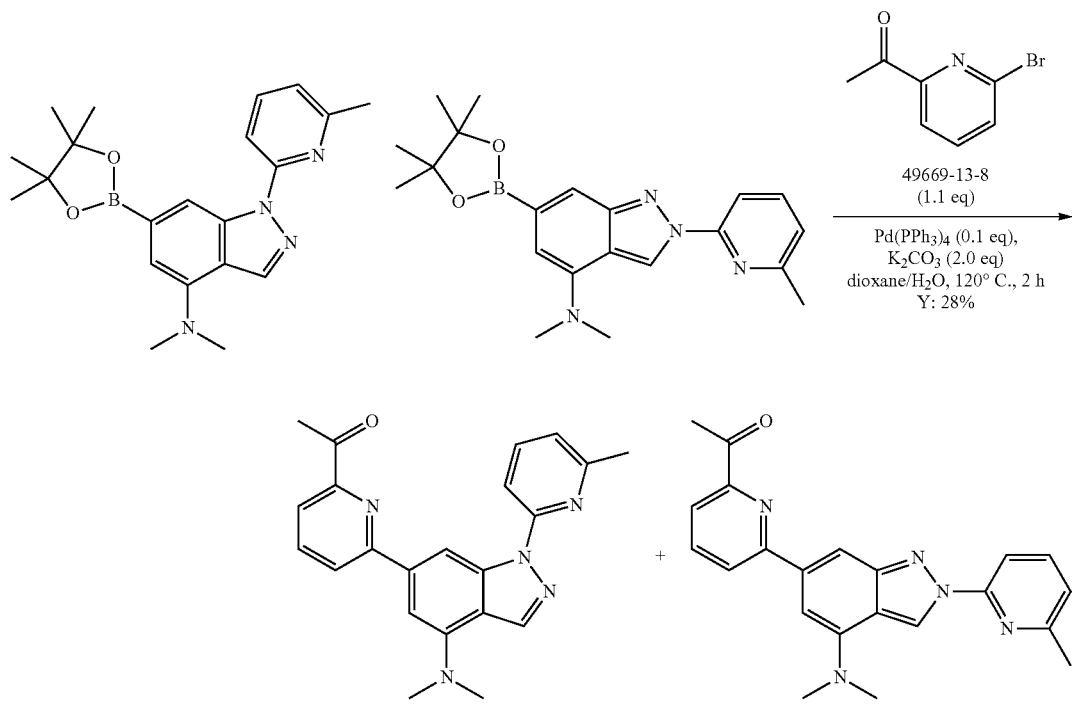

The preparation of 1-(6-(4-(dimethylamino)-1-(6-methylpyridin-2-yl)-1H-indazol-6-yl)pyridin-2-yl)ethanone was the same as tert-butyl (6-(6-acetylpyridin-2-yl)-1-(6-methylpyridin-2-yl)-1H-indazol-4-yl)carbamate. 67 mg, as a yellow solid, Y: 28%. ESI-MS (M+H)+: 372.1. HPLC: 100.00%. $^1$H NMR (400 MHz, CDCl$_3$) δ: 9.04 (s, 1H), 8.26 (s, 1H), 8.00 (d, J=8.0 Hz, 1H), 8.01 (d, J=7.2 Hz, 1H), 7.93 (t, J=8.0 Hz, 1H), 7.85 (d, J=7.6 Hz, 1H), 7.73 (t, J=7.6 Hz, 1H), 7.26 (s, 1H), 7.04 (d, J=7.6 Hz, 1H), 3.27 (s, 6H), 2.90 (s, 3H), 2.68 (s, 3H).

Synthesis of (Z)-1-(6-(4-(dimethylamino)-1-(6-methylpyridin-2-yl)-1H-indazol-6-yl)pyridin-2-yl)ethanone oxime

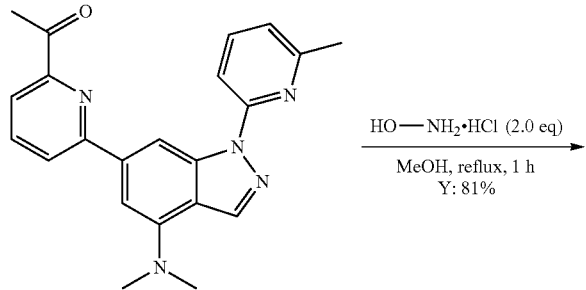

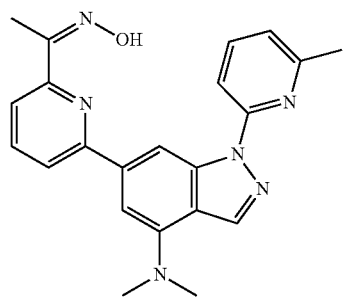

The preparation of (Z)-1-(6-(4-(dimethylamino)-1-(6-methylpyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 51 mg, as white solid, Y: 81%. ESI-MS (M+H)$^+$: 387.2. HPLC: 100.00% $^1$H NMR (400 MHz, CD$_3$OD) δ: 9.05 (s, 1H), 8.41 (s, 1H), 7.95-7.79 (m, 5H), 7.27 (d, J=0.8 Hz, 1H), 7.16-7.13 (m, 1H), 3.26 (s, 6H), 2.67 (s, 3H), 2.47 (s, 3H).

Synthesis of 6-(6-(1-aminoethyl)pyridin-2-yl)-N,N-dimethyl-1-(6-methylpyridin-2-yl)-1H-indazol-4-amine

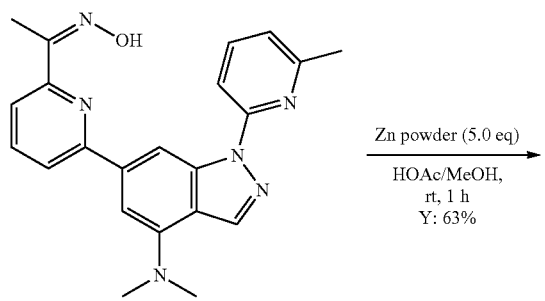

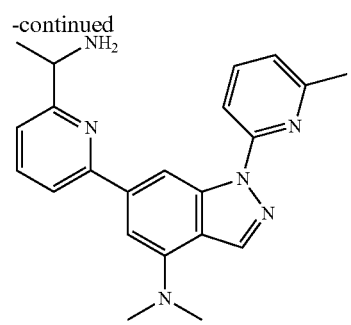

The preparation of 6-(6-(1-aminoethyl)pyridin-2-yl)-N,N-dimethyl-1-(6-methylpyridin-2-yl)-1H-indazol-4-amine was the same as 2-(1-(6-(trifluoromethyl)pyridin-2-yl)-1H-indazol-6-yl)-6,7-dihydro-5H-cyclopenta[b]pyridin-7-amine. 42 mg, as a yellow solid, Y: 63%. ESI-MS (M+H)$^+$: 373.3. HPLC: 100.00%. $^1$H NMR (400 MHz, DMSO-d$_6$) δ: 9.00 (s, 1H), 8.59 (s, 1H), 8.49 (br, 2H), 8.05-8.01 (m, 2H), 7.90 (t, J=8.0 Hz, 1H), 7.81 (d, J=8.0 Hz, 1H), 7.51 (dd, J=8.4, 0.4 Hz, 1H), 7.24 (s, 1H), 7.20 (d, J=7.2 Hz, 1H), 4.67-4.63 (m, 1H), 3.26 (s, 6H), 2.65 (s, 3H), 1.61 (d, J=6.8 Hz, 3H).

Example 103. N-(6-(6-(1-aminoethyl)pyridin-2-yl)-1-(6-methylpyridin-2-yl)-1H-indazol-4-yl)acetamide

Synthesis of 1-(6-(4-amino-1-(6-methylpyridin-2-yl)-1H-indazol-6-yl)pyridin-2-yl)ethanone

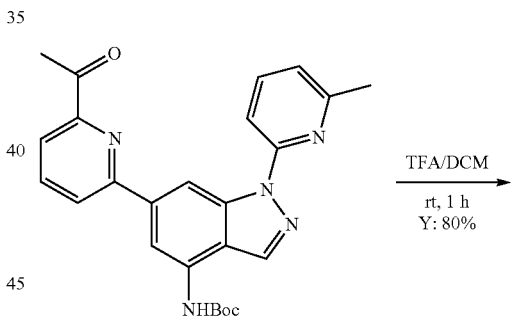

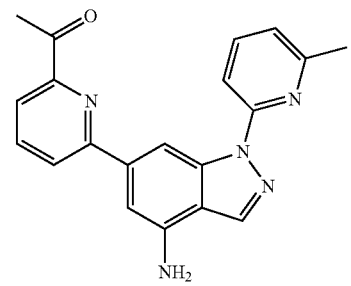

The preparation of 1-(6-(4-amino-1-(6-methylpyridin-2-yl)-H-indazol-6-yl)pyridin-2-yl)ethanone was the same as 6-(6-(1-aminoethyl)pyridin-2-yl)-1-(6-methylpyridin-2-yl)-1H-indazol-4-amine. 140 mg, as a yellow solid, Y: 80%. ESI-MS (M+H)$^+$: 344.1.

Synthesis of N-(6-(6-acetylpyridin-2-yl)-1-(6-methylpyridin-2-yl)-1H-indazol-4-yl)acetamide

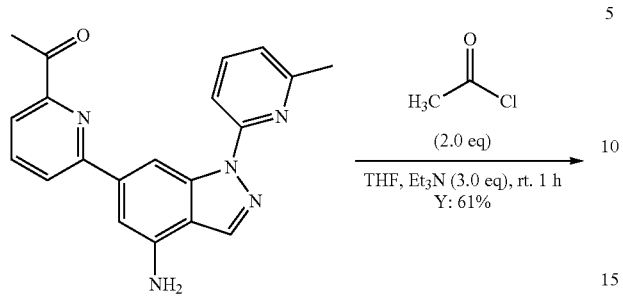

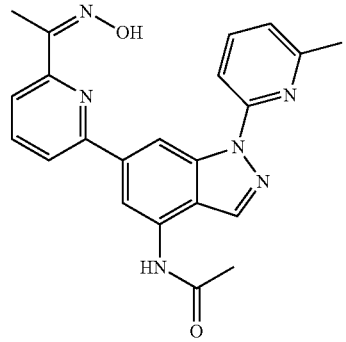

To a mixture of 1-(6-(4-amino-1-(6-methylpyridin-2-yl)-1H-indazol-6-yl)pyridin-2-yl)ethanone (95 mg, 0.28 mmol, 1.0 eq) and TEA (86 mg, 0.84 mmol, 3.0 eq) in THF (5 mL) was added AcCl (44 mg, 0.56 mmol, 2.0 eq). The mixture was stirred at rt for 1 h. After concentration, the residue was purified by pre-HPLC (CH$_3$CN/H$_2$O with 0.05% TFA as mobile phase from 5% to 95%) to give N-(6-(6-acetylpyridin-2-yl)-1-(6-methylpyridin-2-yl)-1H-indazol-4-yl)acetamide as a white solid. 65 mg, Y: 61%. ESI-MS (M+H)$^+$: 386.1.

Synthesis of (Z)—N-(6-(6-(1-(hydroxyimino)ethyl)pyridin-2-yl)-1-(6-methylpyridin-2-yl)-1H-indazol-4-yl)acetamide

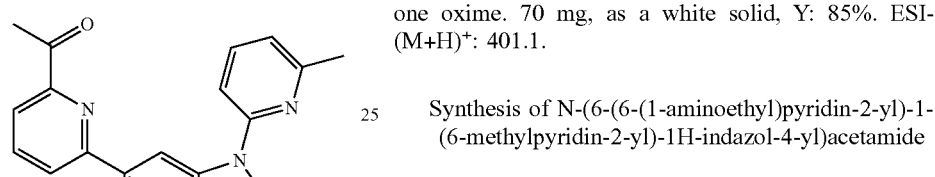

The preparation of (Z)—N-(6-(6-(1-(hydroxyimino)ethyl)pyridin-2-yl)-1-(6-methylpyridin-2-yl)-1H-indazol-4-yl)acetamide was the same as 2-(1-(6-(trifluoromethyl)pyridin-2-yl)-1H-indazol-6-yl)-5H-cyclopenta[b]pyridin-7(6H)-one oxime. 70 mg, as a white solid, Y: 85%. ESI-MS (M+H)$^+$: 401.1.

Synthesis of N-(6-(6-(1-aminoethyl)pyridin-2-yl)-1-(6-methylpyridin-2-yl)-1H-indazol-4-yl)acetamide

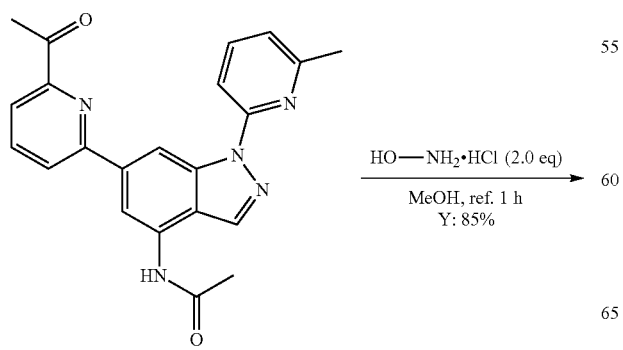

The preparation of N-(6-(6-(1-aminoethyl)pyridin-2-yl)-1-(6-methylpyridin-2-yl)-1H-indazol-4-yl)acetamide was the same as 2-(1-(6-(trifluoromethyl)pyridin-2-yl)-1H-indazol-6-yl)-6,7-dihydro-5H-cyclopenta[b]pyridin-7-amine. 52 mg, as a white solid, Y: 72%. ESI-MS (M+H)$^+$: 387.2. HPLC: 100.00%. $^1$H NMR (400 MHz, CD$_3$OD) δ: 9.40 (s, 1H), 8.44 (d, J=0.8 Hz, 2H), 7.91 (t, J=7.6 Hz, 1H), 7.86-7.83 (m, 3H), 7.40 (d, J=7.6 Hz, 1H), 7.16 (dd, J=6.0, 2.0 Hz, 1H), 4.30 (q, J=6.8 Hz, 1H), 2.68 (s, 3H), 2.32 (s, 3H), 1.57 (d, J=6.8 Hz, 3H).

Example 104. 1-(6-(4-(aminomethyl)-1-(6-methyl-pyridin-2-yl)-1H-indazol-6-yl)pyridin-2-yl)ethan-amine Synthesis of 6-bromo-1-(6-methylpyridin-2-yl)-1H-indazole-4-carboxamide and O-(6-bromo-2-(6-methylpyridin-2-yl)-2H-indazole-4-carbonyl)hydroxylamine

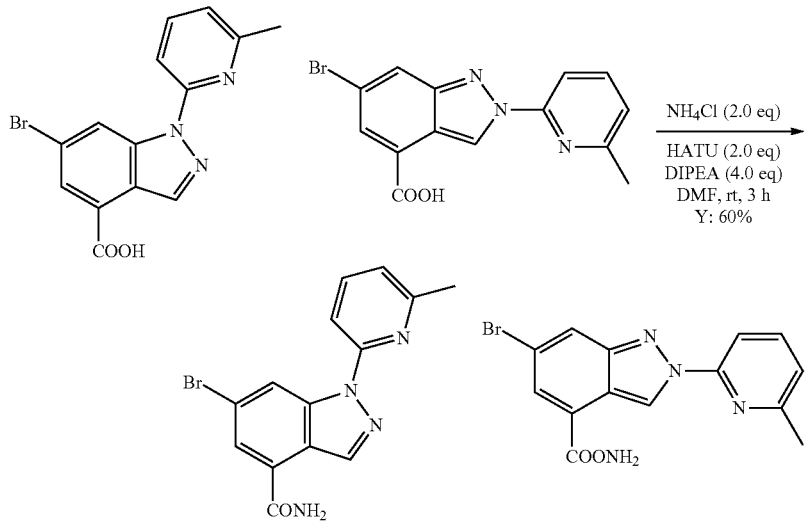

The preparation of 6-bromo-1-(6-methylpyridin-2-yl)-1H-indazole-4-carboxamide and O-(6-bromo-2-(6-methylpyridin-2-yl)-2H-indazole-4-carbonyl)hydroxylamine was the same as that of 6-bromo-1-(6-methylpyridin-2-yl)-1H-indazole-4-carboxamide and O-(6-bromo-2-(6-methylpyridin-2-yl)-2H-indazole-4-carbonyl)hydroxylamine. 1.5 g, as a yellow solid, Y: 60%. The mixture of 36-bromo-1-(6-methylpyridin-2-yl)-1H-indazole-4-carboxamide and O-(6-bromo-2-(6-methylpyridin-2-yl)-2H-indazole-4-carbonyl) hydroxylamine was difficult to be purified due to poor solubility. The mixture was directly used for next step. ESI-MS (M+H)+: 331.1.

Synthesis of 6-bromo-1-(6-methylpyridin-2-yl)-1H-indazole-4-carbonitrile and 6-bromo-2-(6-methyl-pyridin-2-yl)-2H-indazole-4-carbonitrile

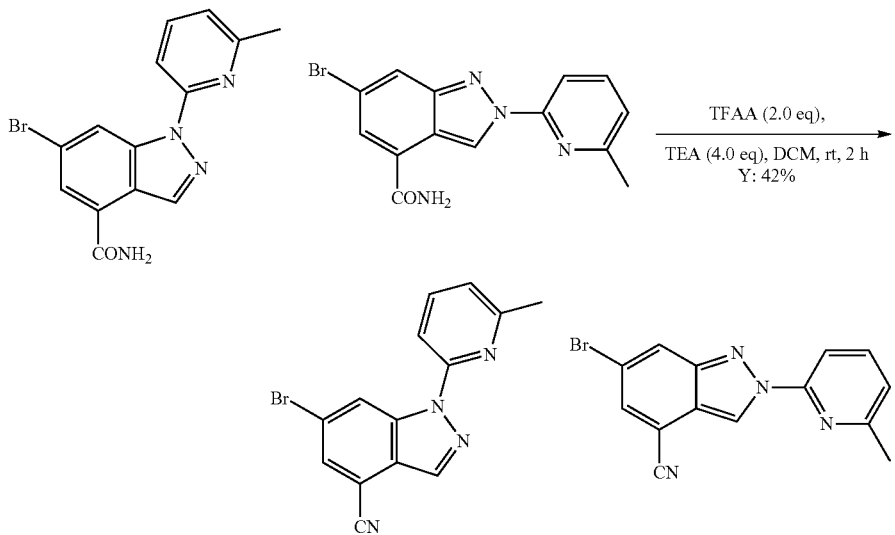

The preparation of 6-bromo-1-(6-methylpyridin-2-yl)-1H-indazole-4-carbonitrile and 6-bromo-2-(6-methylpyridin-2-yl)-2H-indazole-4-carbonitrile was the same as that of N-(5-(4-cyano-1-(6-(trifluoromethyl)pyridin-2-yl)-1H-indazol-6-yl)pyridin-3-yl)-2,2,2-trifluoroacetamide. 596 mg, as a white solid, Y: 42%. The mixture of 6-bromo-1-(6-methylpyridin-2-yl)-1H-indazole-4-carbonitrile and 6-bromo-2-(6-methylpyridin-2-yl)-2H-indazole-4-carbonitrile was difficult to be purified due to poor solubility. The mixture was directly used for next step. ESI-MS (M+H)+: 313.1.

Synthesis of 1-(6-methylpyridin-2-yl)-6-(4,4,5,5-tetramethyl-1,3,2-dioxaborolan-2-yl)-1H-indazole-4-carbonitrile and 2-(6-methylpyridin-2-yl)-6-(4,4,5,5-tetramethyl-1,3,2-dioxaborolan-2-yl)-2H-indazole-4-carbonitrile

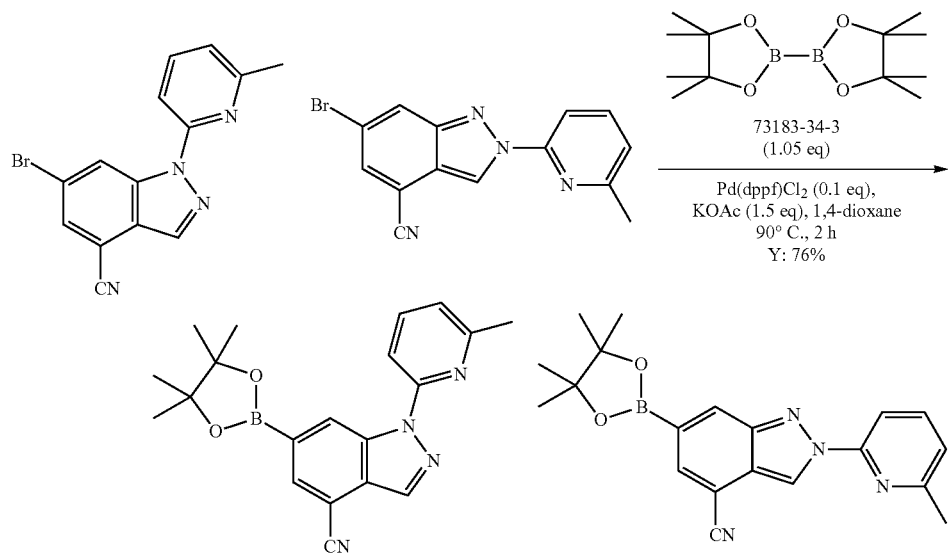

The preparation of 1-(6-methylpyridin-2-yl)-6-(4,4,5,5-tetramethyl-1,3,2-dioxaborolan-2-yl)-1H-indazole-4-carbonitrile and 2-(6-methylpyridin-2-yl)-6-(4,4,5,5-tetramethyl-1,3,2-dioxaborolan-2-yl)-2H-indazole-4-carbonitrile was the same as that of 1-(6-methylpyridin-2-yl)-6-(4,4,5,5-tetramethyl-1,3,2-dioxaborolan-2-yl)-1H-indazole. 523 mg, as a white solid, Y: 76%. The mixture of 1-(6-methylpyridin-2-yl)-6-(4,4,5,5-tetramethyl-1,3,2-dioxaborolan-2-yl)-1H-indazole-4-carbonitrile and 2-(6-methylpyridin-2-yl)-6-(4,4,5,5-tetramethyl-1,3,2-dioxaborolan-2-yl)-2H-indazole-4-carbonitrile was difficult to be purified due to poor solubility. The mixture was directly used for next step. ESI-MS (M+H)+: 361.1.

Synthesis of 6-(6-acetylpyridin-2-yl)-1-(6-methylpyridin-2-yl)-1H-indazole-4-carbonitrile and 6-(6-acetylpyridin-2-yl)-2-(6-methylpyridin-2-yl)-2H-indazole-4-carbonitrile

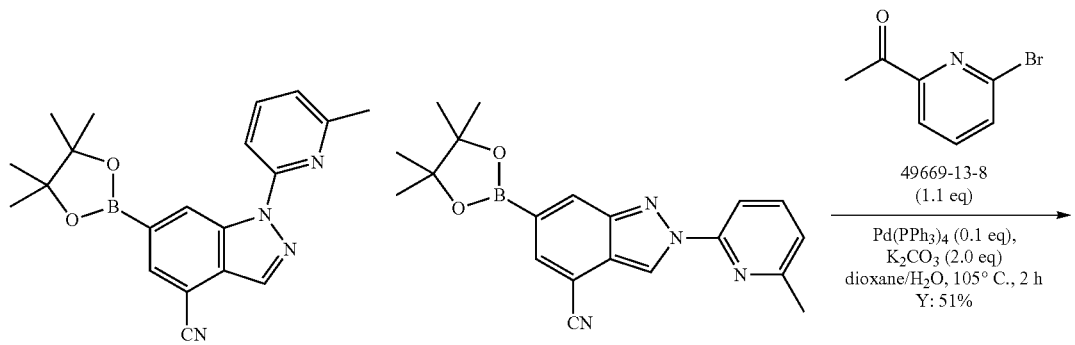

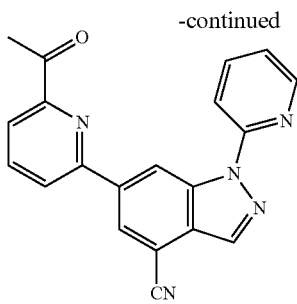
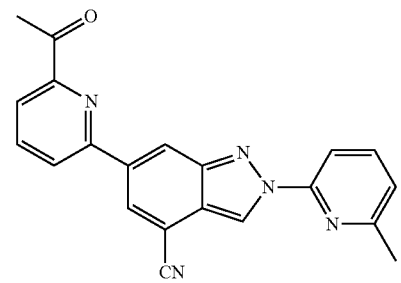

The preparation of 6-(6-acetylpyridin-2-yl)-1-(6-methyl-pyridin-2-yl)-1H-indazole-4-carbonitrile and 6-(6-acetylpyridin-2-yl)-2-(6-methylpyridin-2-yl)-2H-indazole-4-carbonitrile was the same as that of tert-butyl (6-(6-acetylpyridin-2-yl)-1-(6-methylpyridin-2-yl)-1H-indazol-4-yl)carbamate. 262 mg, as a white solid, Y: 51%. The mixture of 6-(6-acetylpyridin-2-yl)-1-(6-methylpyridin-2-yl)-1H-indazole-4-carbonitrile and 6-(6-acetylpyridin-2-yl)-2-(6-methylpyridin-2-yl)-2H-indazole-4-carbonitrile was difficult to be purified due to poor solubility. The mixture was directly used for next step. ESI-MS (M+H)+: 354.1.

Synthesis of (Z)-6-(6-(1-(hydroxyimino)ethyl)pyridin-2-yl)-1-(6-methylpyridin-2-yl)-1H-indazole-4-carbonitrile and (Z)-6-(6-(1-(hydroxyimino)ethyl)pyridin-2-yl)-2-(6-methylpyridin-2-yl)-2H-indazole-4-carbonitrile

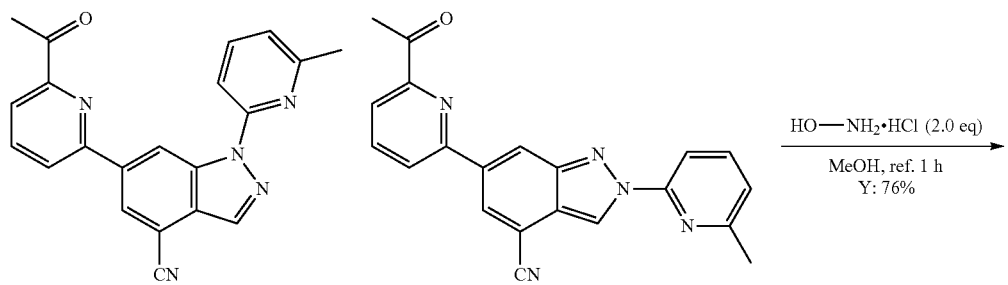

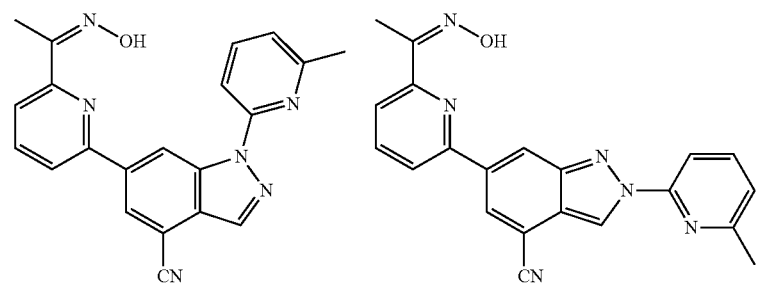

The preparation of (Z)-6-(6-(1-(hydroxyimino)ethyl)pyridin-2-yl)-1-(6-methylpyridin-2-yl)-1H-indazole-4-carbonitrile and (Z)-6-(6-(1-(hydroxyimino)ethyl)pyridin-2-yl)-2-(6-methylpyridin-2-yl)-2H-indazole-4-carbonitrile was the same as that of 2-(1-(6-(trifluoromethyl)pyridin-2-yl)-1H-indazol-6-yl)-5H-cyclopenta[b]pyridin-7(6H)-one oxime. 208 mg, as a white solid, Y: 76%. The mixture of (Z)-6-(6- (1-(hydroxyimino)ethyl)pyridin-2-yl)-1-(6-methylpyridin-2-yl)-1H-indazole-4-carbonitrile and (Z)-6-(6-(1-(hydroxyimino)ethyl)pyridin-2-yl)-2-(6-methylpyridin-2-yl)-2H-indazole-4-carbonitrile was difficult to be purified due to poor solubility. The mixture was directly used for next step. ESI-MS (M+H)+: 369.1.

Synthesis of 6-(6-(1-aminoethyl)pyridin-2-yl)-1-(6-methylpyridin-2-yl)-1H-indazole-4-carbonitrile and 6-(6-(1-aminoethyl)pyridin-2-yl)-2-(6-methylpyridin-2-yl)-2H-indazole-4-carbonitrile

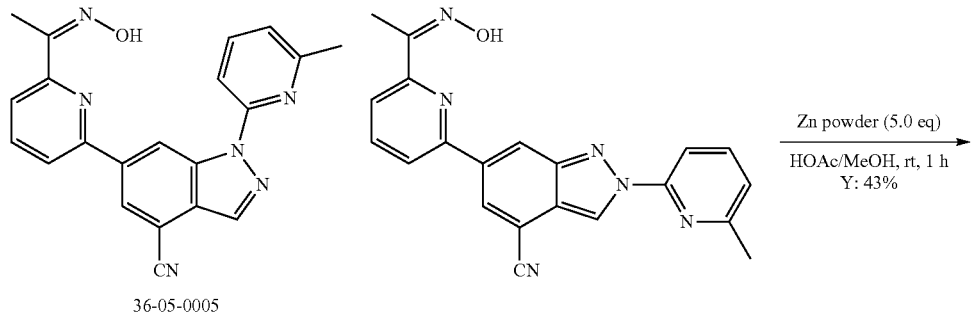

36-05-0005

The preparation of 6-(6-(1-aminoethyl)pyridin-2-yl)-1-(6-methylpyridin-2-yl)-1H-indazole-4-carbonitrile and 6-(6-(1-aminoethyl)pyridin-2-yl)-2-(6-methylpyridin-2-yl)-2H-indazole-4-carbonitrile was the same as that of 2-(1-(6-(trifluoromethyl)pyridin-2-yl)-1H-indazol-6-yl)-6,7-dihydro-5H-cyclopenta[b]pyridin-7-amine. 208 mg, as a white solid, Y: 43%. The mixture of 6-(6-(1-aminoethyl)pyridin-2-yl)-1-(6-methylpyridin-2-yl)-1H-indazole-4-carbonitrile and 6-(6-(1-aminoethyl)pyridin-2-yl)-2-(6-methylpyridin-2-yl)-2H-indazole-4-carbonitrile was difficult to be purified due to poor solubility. The mixture was directly used for next step. ESI-MS (M+H)+: 355.1.

Synthesis of 1-(6-(4-(aminomethyl)-1-(6-methylpyridin-2-yl)-1H-indazol-6-yl)pyridin-2-yl)ethanamine and 1-(6-(4-(aminomethyl)-2-(6-methylpyridin-2-yl)-2H-indazol-6-yl)pyridin-2-yl)ethanamine

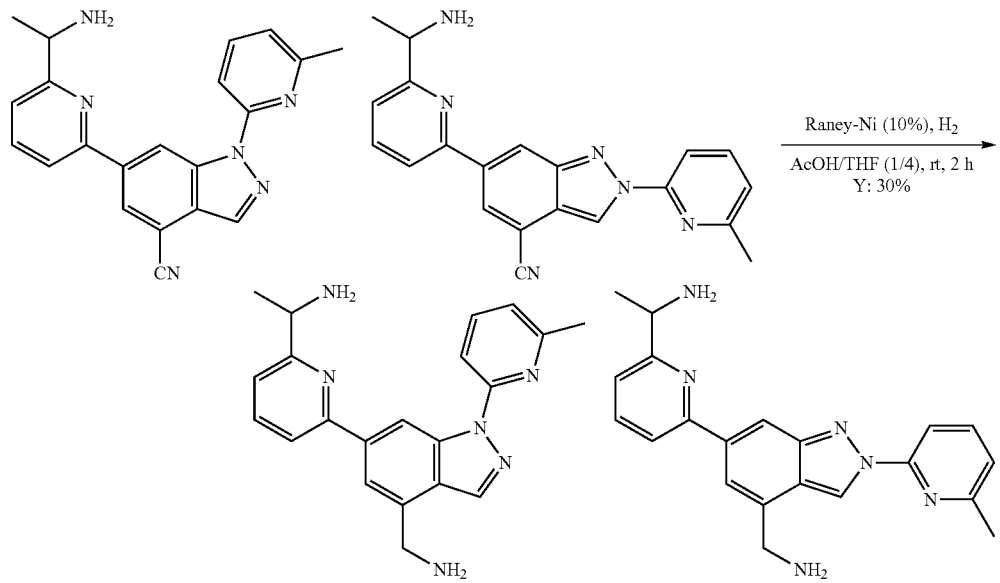

The preparation of 1-(6-(4-(aminomethyl)-1-(6-methyl-pyridin-2-yl)-1H-indazol-6-yl)pyridin-2-yl)ethanamine and 1-(6-(4-(aminomethyl)-2-(6-methylpyridin-2-yl)-2H-indazol-6-yl)pyridin-2-yl)ethanamine was the same as that of 02-04. The mixture of 1-(6-(4-(aminomethyl)-1-(6-methyl-pyridin-2-yl)-1H-indazol-6-yl)pyridin-2-yl)ethanamine and 1-(6-(4-(aminomethyl)-2-(6-methylpyridin-2-yl)-2H-indazol-6-yl)pyridin-2-yl)ethanamine was purified by pre-HPLC (MeOH/H$_2$O with 0.05% TFA as mobile phase from 5% to 95%) to give. 1-(6-(4-(aminomethyl)-1-(6-methylpyridin-2-yl)-1H-indazol-6-yl)pyridin-2-yl)ethanamine: 5 mg, as a yellow oil, ESI-MS (M+H)$^+$: 359.1, t$_R$=2.57 min, HPLC: 100.00%. $^1$H NMR (400 MHz, CD$_3$OD) δ: 9.60 (s, 1H), 8.45 (s, 1H), 8.20 (s, 1H), 7.98-7.92 (m, 2H), 7.81-7.75 (m, 2H), 7.42 (dd, J=7.2, 1.2 Hz, 1H), 7.01 (d, J=6.8 Hz, 1H), 4.62 (q, J=6.8 Hz, 1H), 4.54 (s, 2H), 2.61 (s, 3H), 1.64 (d, J=7.2 Hz, 3H). 1-(6-(4-(aminomethyl)-2-(6-methylpyridin-2-yl)-2H-indazol-6-yl)pyridin-2-yl)ethanamine: 4 mg, as a yellow oil, ESI-MS (M+H)$^+$: 359.1, t$_R$=2.47 min, HPLC: 100.00%. $^1$H NMR (400 MHz, CD$_3$OD) δ: 9.44 (s, 1H), 8.57 (s, 1H), 8.00-7.96 (m, 3H), 7.93-7.84 (m, 2H), 7.38 (d, J=7.2 Hz, 1H), 7.27 (d, J=7.2 Hz, 1H), 4.61 (q, J=6.8 Hz, 1H), 4.48 (s, 2H), 2.55 (s, 3H), 1.62 (d, J=7.2 Hz, 3H).

Example 105. N-((6-(6-(1-aminoethyl)pyridin-2-yl)-1-(6-methylpyridin-2-yl)-1H-indazol-4-yl)methyl) acetamide Synthesis of tert-butyl (1-(6-(4-cyano-1-(6-methyl-pyridin-2-yl)-1H-indazol-6-yl)pyridin-2-yl)ethyl) carbamate and tert-butyl (1-(6-(4-cyano-2-(6-methylpyridin-2-yl)-2H-indazol-6-yl)pyridin-2-yl)ethyl) carbamate

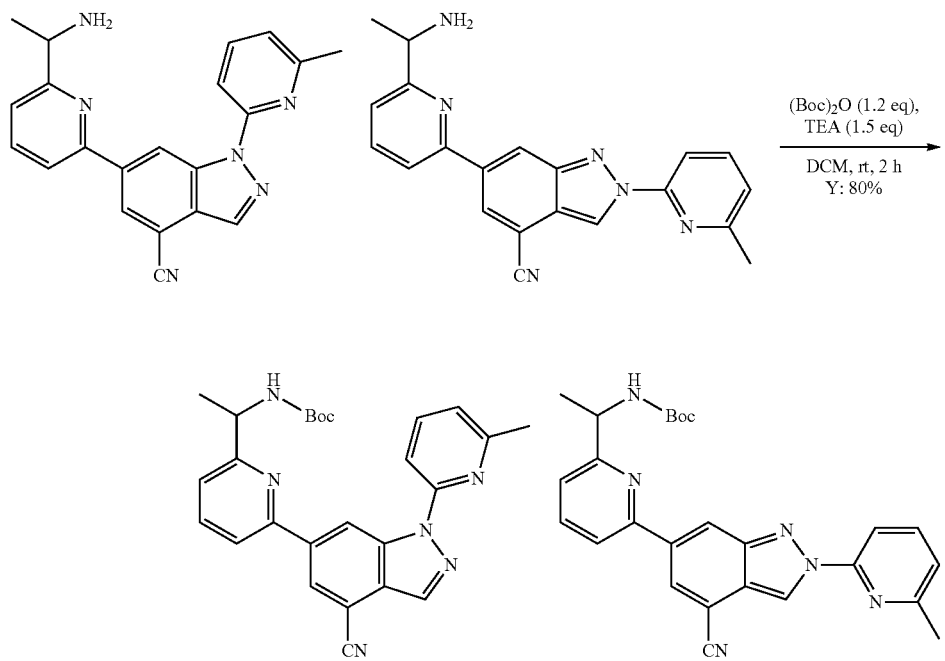

To a mixture of tert-butyl (1-(6-(4-cyano-1-(6-methyl-pyridin-2-yl)-1H-indazol-6-yl)pyridin-2-yl)ethyl)carbamate and tert-butyl (1-(6-(4-cyano-2-(6-methylpyridin-2-yl)-2H-indazol-6-yl)pyridin-2-yl)ethyl)carbamate (120 mg, 0.34 mmol, 1.0 eq) and TEA (51.4 mg, 0.51 mmol, 1.5 eq) in DCM (20 mL) was added (Boc)$_2$O (88 mg, 0.41 mmol, 1.2 eq) at rt. The mixture was stirred at rt for 2 h and diluted with water (10 mL). The organic phase was washed with brine and dried over Na$_2$SO$_4$. After filtration and concentration, the residue was directly used for next step without further purification. 123 mg, as yellow oil, Y: 80%. ESI-MS (M+H)$^+$: 455.1.

Synthesis of tert-butyl (1-(6-(4-(aminomethyl)-1-(6-methylpyridin-2-yl)-1H-indazol-6-yl)pyridin-2-yl)ethyl)carbamate and tert-butyl (1-(6-(4-(aminomethyl)-2-(6-methylpyridin-2-yl)-2H-indazol-6-yl)pyridin-2-yl)ethyl)carbamate

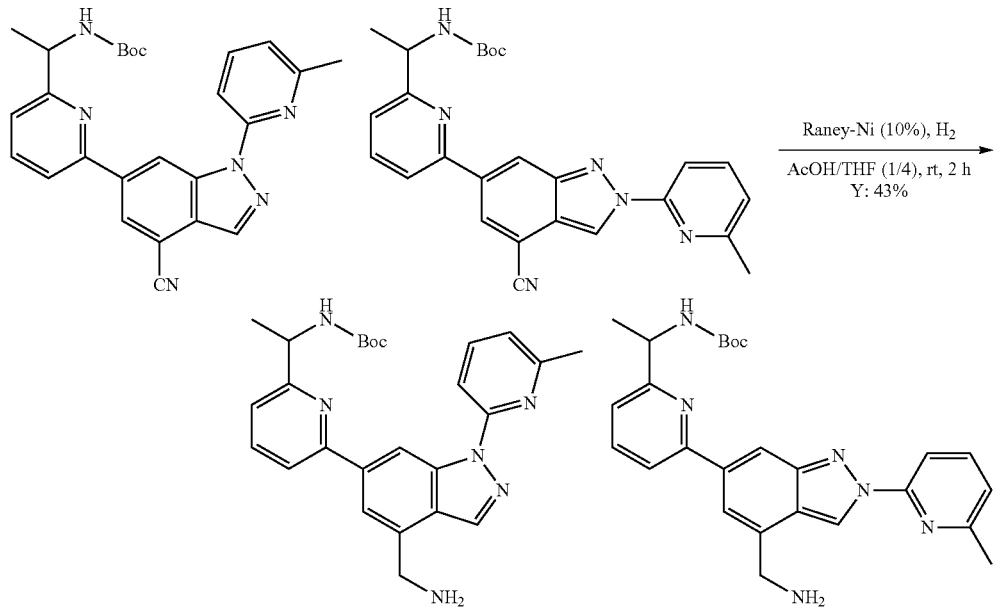

The preparation of tert-butyl (1-(6-(4-(aminomethyl)-1-(6-methylpyridin-2-yl)-1H-indazol-6-yl)pyridin-2-yl)ethyl)carbamate and tert-butyl (1-(6-(4-(aminomethyl)-2-(6-methylpyridin-2-yl)-2H-indazol-6-yl)pyridin-2-yl)ethyl)carbamate was the same as that of 5-(4-(aminomethyl)-1-(6-(trifluoromethyl)pyridin-2-yl)-1H-indazol-6-yl)pyridin-3-amine. 100 mg, as yellow oil, ESI-MS (M+H)$^+$: 459.1.

Synthesis of N-((6-(6-(1-aminoethyl)pyridin-2-yl)-1-(6-methylpyridin-2-yl)-1H-indazol-4-yl)methyl)acetamide and N-((6-(6-(1-aminoethyl)pyridin-2-yl)-2-(6-methylpyridin-2-yl)-2H-indazol-4-yl)methyl)acetamide

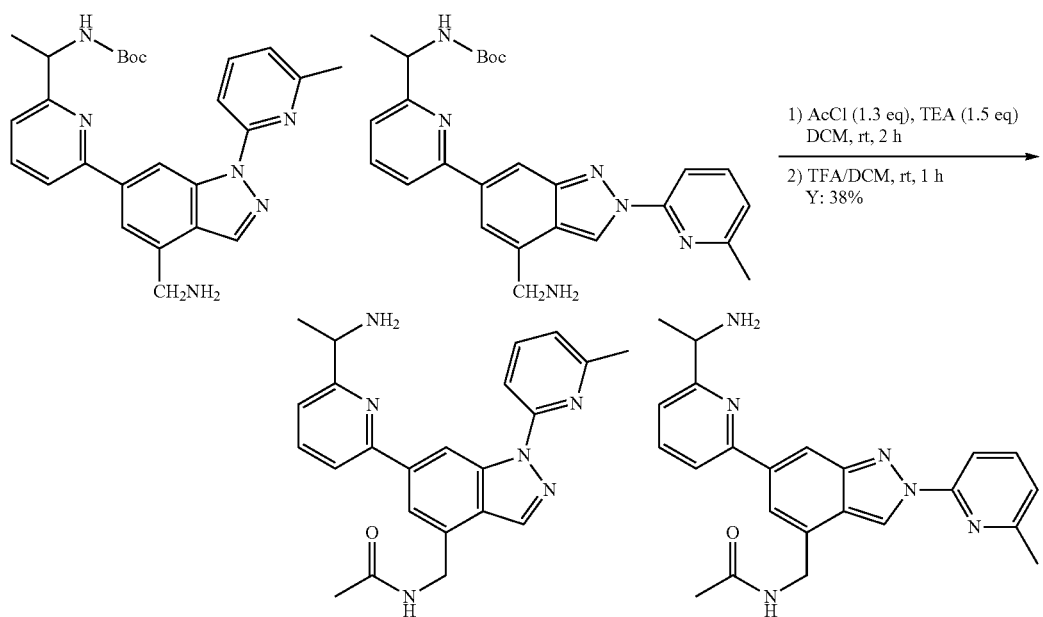

The preparation of N-((6-(6-(1-aminoethyl)pyridin-2-yl)-1-(6-methylpyridin-2-yl)-1H-indazol-4-yl)methyl)acetamide was the same as that of N-(6-(6-acetylpyridin-2-yl)-1-(6-methylpyridin-2-yl)-1H-indazol-4-yl)acetamide. The mixture of N-((6-(6-(1-aminoethyl)pyridin-2-yl)-1-(6-methylpyridin-2-yl)-1H-indazol-4-yl)methyl)acetamide and N-((6-(6-(1-aminoethyl)pyridin-2-yl)-2-(6-methylpyridin-2-yl)-2H-indazol-4-yl)methyl)acetamide was purified by pre-HPLC (MeOH/H$_2$O with 0.05% TFA as mobile phase from 5% to 95%).

N-((6-(6-(1-aminoethyl)pyridin-2-yl)-1-(6-methylpyridin-2-yl)-1H-indazol-4-yl)methyl)acetamide: 9.8 mg, as a yellow oil, ESI-MS (M+H)$^+$: 401.1, t$_R$=1.15 min, HPLC: 100.00%. $^1$H NMR (400 MHz, CD$_3$OD) δ: 9.53 (s, 1H), 8.44 (s, 1H), 8.10 (s, 1H), 8.04-8.02 (m, 2H), 7.89-7.84 (m, 2H), 7.49 (dd, J=5.6, 2.4 Hz, 1H), 7.19 (dd, J=6.0, 1.6 Hz, 1H), 4.82 (s, 2H), 4.71 (q, J=6.8 Hz, 1H), 2.70 (s, 3H), 2.04 (s, 3H), 1.74 (d, J=6.8 Hz, 3H).

N-((6-(6-(1-aminoethyl)pyridin-2-yl)-2-(6-methylpyridin-2-yl)-2H-indazol-4-yl)methyl)acetamide: 4.9 mg, as a yellow oil, ESI-MS (M+H)$^+$: 401.1, t$_R$=1.07 min, HPLC: 100.00%. $^1$H NMR (400 MHz, CD$_3$OD) δ: 9.35 (s, 1H), 8.47 (s, 1H), 8.06-7.92 (m, 5H), 7.46 (d, J=7.6 Hz, 1H), 7.35 (d, J=8.0 Hz, 1H), 4.76 (s, 2H), 4.70 (q, J=6.8 Hz, 1H), 2.66 (s, 3H), 2.04 (s, 3H), 1.72 (d, J=7.2 Hz, 3H).

Example 106. 1-(6-(4-chloro-1-(6-methylpyridin-2-yl)-1H-indazol-6-yl)pyridin-2-yl)ethanamine Synthesis of 6-bromo-4-chloro-1-(6-methylpyridin-2-yl)-1H-indazole

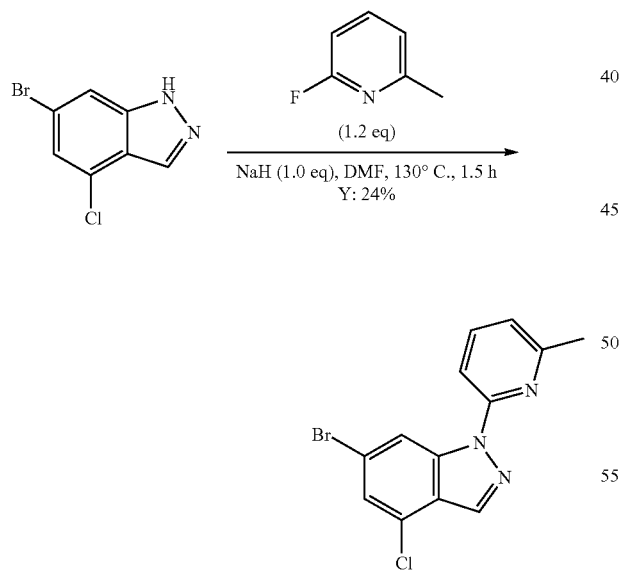

The preparation of 6-bromo-4-chloro-1-(6-methylpyridin-2-yl)-1H-indazole was the same as that of 6-bromo-1-(6-methylpyridin-2-yl)-1H-indazole. 200 mg, as a white solid, Y: 24%. ESI-MS (M+H)$^+$: 321.9. $^1$H NMR (400 MHz, CDCl$_3$) δ: 9.02 (d, J=1.2 Hz, 1H), 8.21 (d, J=0.8 Hz, 1H), 7.82 (d, J=8.4 Hz, 1H), 7.74 (t, J=8.0 Hz, 1H), 7.40 (d, J=1.6 Hz, 1H), 7.07 (d, J=7.2 Hz, 1H), 2.66 (s, 3H).

Synthesis of 4-chloro-1-(6-methylpyridin-2-yl)-6-(4,4,5,5-tetramethyl-1,3,2-dioxaborolan-2-yl)-1H-indazole

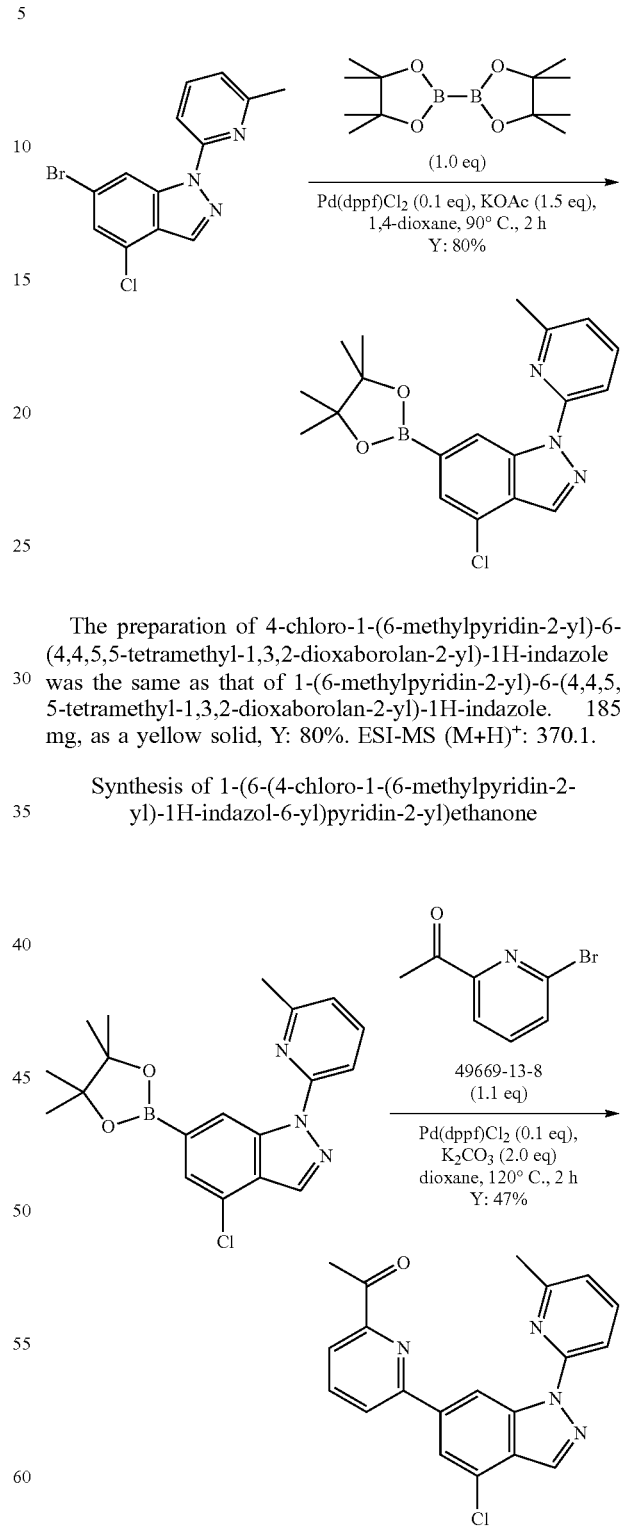

The preparation of 4-chloro-1-(6-methylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 185 mg, as a yellow solid, Y: 80%. ESI-MS (M+H)$^+$: 370.1.

Synthesis of 1-(6-(4-chloro-1-(6-methylpyridin-2-yl)-1H-indazol-6-yl)pyridin-2-yl)ethanone The preparation of 1-(6-(4-chloro-1-(6-methylpyridin-2-yl)-1H-indazol-6-yl)pyridin-2-yl)ethanone was the same as that of tert-butyl (6-(6-acetylpyridin-2-yl)-1-(6-methylpyridin-2-yl)-1H-indazol-4-yl)carbamate. 85 mg, as a white solid, Y: 47%. ESI-MS (M+H)⁺: 362.9. HPLC: 98.26% ¹H NMR (400 MHz, CDCl₃) δ: 9.56 (s, 1H), 8.24 (s, 1H), 8.01-7.97 (m, 3H), 7.90 (t, J=8.0 Hz, 1H), 7.82 (d, J=8.4 Hz, 1H), 7.70 (t, J=8.0 Hz, 1H), 7.02 (d, J=8.0 Hz, 1H), 2.84 (s, 3H), 2.63 (s, 3H).

Synthesis of (Z)-1-(6-(4-chloro-1-(6-methylpyridin-2-yl)-1H-indazol-6-yl)pyridin-2-yl)ethanone oxime

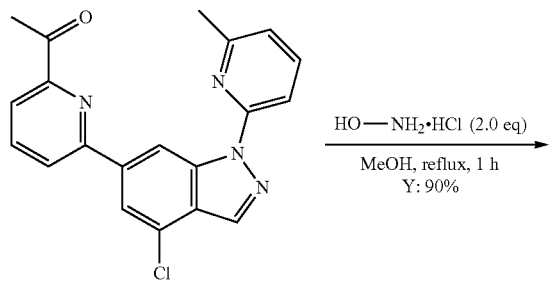

The preparation of (Z)-1-(6-(4-chloro-1-(6-methylpyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 80 mg, as a yellow solid, Y: 90%. ESI-MS (M+H)⁺: 378.0. HPLC: 100.00% ¹H NMR (400 MHz, CD₃OD) δ: 9.66 (s, 1H), 8.36 (s, 1H), 8.09 (d, J=1.2 Hz, 1H), 7.98-7.84 (m, 5H), 7.21 (d, J=6.8 Hz, 1H), 2.70 (s, 3H), 2.49 (s, 3H).

Synthesis of 1-(6-(4-chloro-1-(6-methylpyridin-2-yl)-1H-indazol-6-yl)pyridin-2-yl)ethanamine

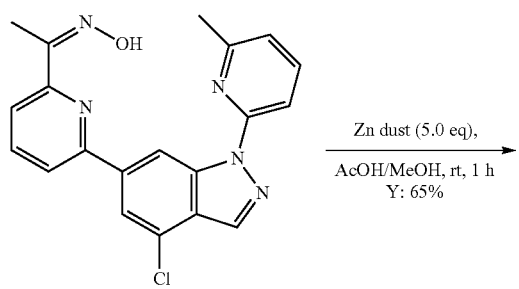

-continued

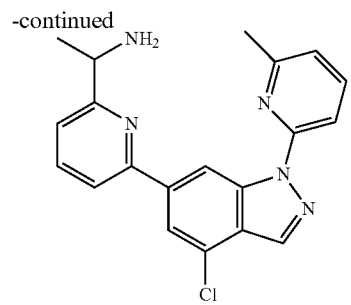

The preparation of 1-(6-(4-chloro-1-(6-methylpyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 50 mg, as a white solid, Y: 65%. ESI-MS (M+H)⁺: 364.2. HPLC: 100.00% ¹H NMR (400 MHz, CD₃OD) δ: 9.38 (s, 1H), 8.17 (s, 1H), 7.92 (s, 1H), 7.89 (t, J=8.0 Hz, 1H), 7.73-7.69 (m, 3H), 7.32 (d, J=7.6 Hz, 1H), 7.06 (t, J=4.0 Hz, 1H), 4.14 (q, J=6.8 Hz, 1H), 2.57 (s, 3H), 1.48 (d, J=6.8 Hz, 3H).

Example 107. 1-(6-(4-cyclopropyl-1-(6-methylpyridin-2-yl)-1H-indazol-6-yl)pyridin-2-yl)ethanamine Synthesis of 1-(6-(4-iodo-1-(6-methylpyridin-2-yl)-1H-indazol-6-yl)pyridin-2-yl)ethanone

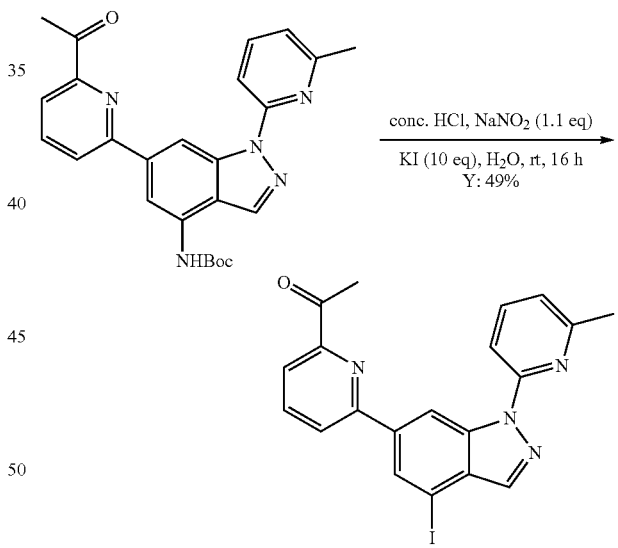

A mixture of tert-butyl (6-(6-acetylpyridin-2-yl)-1-(6-methylpyridin-2-yl)-1H-indazol-4-yl)carbamate (1.1 g, 2.5 mmol, 1.0 eq) and conc. HCl (30 mL) was stirred at rt for 30 min. Then the mixture was cooled down to 0° C. and NaNO₂ (190 mg, 2.75 mmol, 1.1 eq) was added into the mixture. The mixture was stirred at 0° C. for 15 min and a solution of potassium iodide (4.2 g, 25 mmol, 10 eq) in 100 mL of water was added. The mixture was stirred at rt for 16 h. After concentration, the residue was purified by silica gel chromatography with PE/EA (1/1) as eluent to give 1-(6-(4-iodo-1-(6-methylpyridin-2-yl)-1H-indazol-6-yl)pyridin-2-yl)ethanone as a brown solid. (550 mg, Y: 49%). ESI-MS (M+H)⁺: 455.1. ¹H NMR (400 MHz, CDCl₃) δ: 9.62 (s, 1H), 8.33 (d, J=1.2 Hz, 1H), 8.02 (s, 1H), 8.01-7.93 (m, 2H), 7.92-7.85 (m, 1H), 7.80 (d, J=8.4 Hz, 1H), 7.68 (t, J=7.6 Hz, 1H), 7.00 (d, J=7.6 Hz, 1H), 2.83 (s, 3H), 2.61 (s, 3H).

Synthesis of 1-(6-(4-cyclopropyl-1-(6-methylpyridin-2-yl)-1H-indazol-6-yl)pyridin-2-yl)ethanone

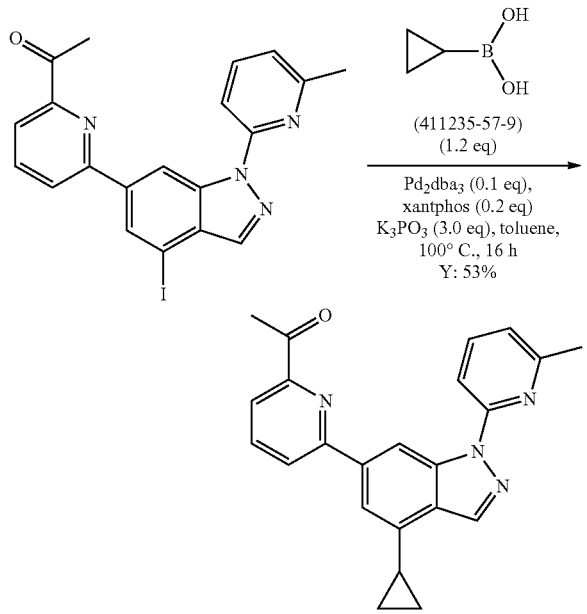

A mixture of 1-(6-(4-iodo-1-(6-methylpyridin-2-yl)-1H-indazol-6-yl)pyridin-2-yl)ethanone (70 mg, 0.15 mmol, 1.0 eq), cyclopropylboronic acid (CAS#411235-57-9) (16 mg, 0.18 mmol, 1.2 eq), Pd$_2$dba$_3$ (14 mg, 0.015 mmol, 0.1 eq), xantphos (17 mg, 0.03 mmol, 0.2 eq) and K$_3$PO$_4$ (95 mg, 0.45 mmol, 3.0 eq) in dry toluene (5 mL) was stirred at 100° C. for 16 h under N$_2$ atmosphere. After concentration, the residue was purified by column chromatography on silica gel (PE/EA=5/1) to give 1-(6-(4-cyclopropyl-1-(6-methylpyridin-2-yl)-1H-indazol-6-yl)pyridin-2-yl)ethanone as a light yellow solid. 30 mg, Y: 53%. ESI-MS (M+H)$^+$: 369.2. $^1$H NMR (400 MHz, CDCl$_3$) δ: 9.43 (s, 1H), 8.29 (s, 1H), 7.97 (dd, J=7.6, 0.8 Hz, 1H), 7.93 (dd, J=7.6, 0.8 Hz, 1H), 7.86 (t, J=8.0 Hz, 1H), 7.79 (d, J=8.0 Hz, 1H), 7.67 (t, J=7.2 Hz, 1H), 7.54 (s, 1H), 6.96 (d, J=7.6 Hz, 1H), 2.83 (s, 3H), 2.61 (s, 3H), 2.33-2.28 (m, 1H), 1.12-1.07 (m, 2H), 0.96-0.92 (m, 2H).

Synthesis of (Z)-1-(6-(4-cyclopropyl-1-(6-methylpyridin-2-yl)-1H-indazol-6-yl)pyridin-2-yl)ethanone oxime

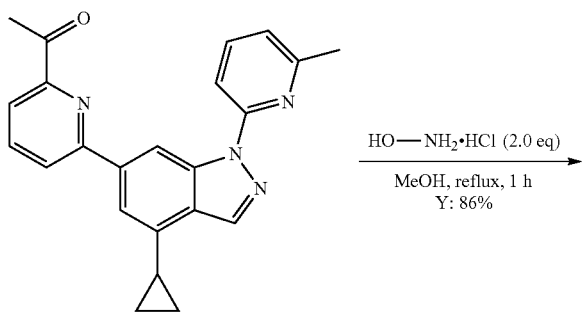

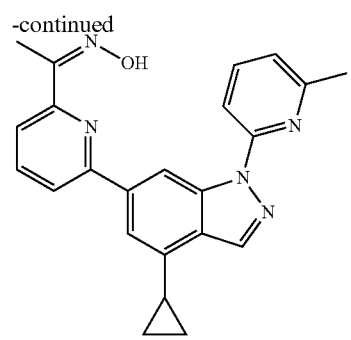

The preparation of (Z)-1-(6-(4-cyclopropyl-1-(6-methylpyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 27 mg, as a white solid, Y: 86%. ESI-MS (M+H)$^+$: 384.2.

Synthesis of 1-(6-(4-cyclopropyl-1-(6-methylpyridin-2-yl)-1H-indazol-6-yl)pyridin-2-yl)ethanamine

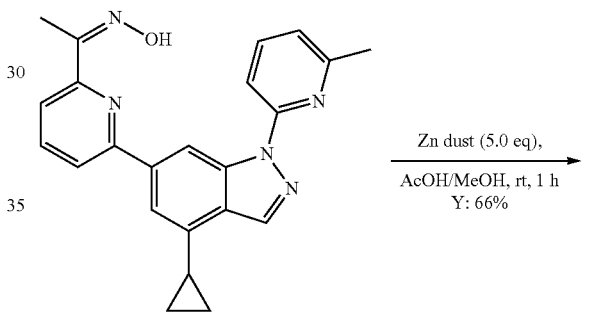

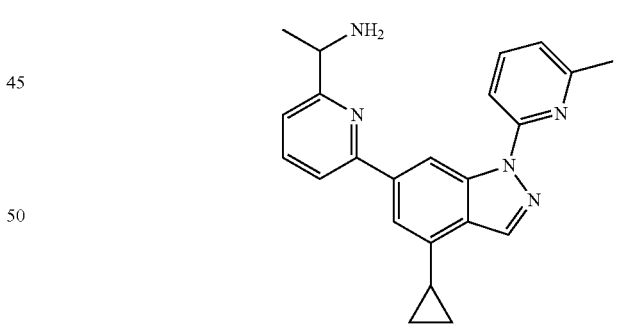

The preparation of 1-(6-(4-cyclopropyl-1-(6-methylpyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 14 mg, as a yellow solid, Y: 66%. ESI-MS (M+H)$^+$: 370.3. HPLC: 97.95%. $^1$H NMR (400 MHz, CD$_3$OD) δ: 9.35 (s, 1H), 8.49 (s, 1H), 8.03-7.98 (m, 2H), 7.88-7.83 (m, 2H), 7.72 (s, 1H), 7.47 (dd, J=5.2, 2.8 Hz, 1H), 7.18 (t, J=1.2 Hz, 1H), 4.71 (q, J=6.8 Hz, 1H), 2.69 (s, 3H), 2.51-2.44 (m, 1H), 1.73 (d, J=6.8 Hz, 3H), 1.22-1.18 (m, 2H), 1.08-1.05 (m, 2H).

Example 108. 1-(6-(1-(6-methylpyridin-2-yl)-4-(prop-1-en-2-yl)-1H-indazol-6-yl)pyridin-2-yl)ethanamine Synthesis of 1-(6-(1-(6-methylpyridin-2-yl)-4-(prop-1-en-2-yl)-1H-indazol-6-yl)pyridin-2-yl)ethanone

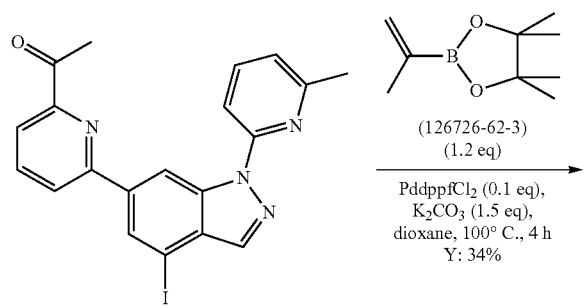

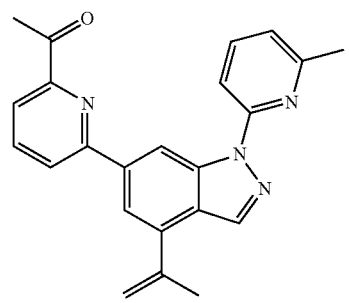

The preparation of 1-(6-(1-(6-methylpyridin-2-yl)-4-(prop-1-en-2-yl)-1H-indazol-6-yl)pyridin-2-yl)ethanone was the same as that of tert-butyl (6-(6-acetylpyridin-2-yl)-1-(6-methylpyridin-2-yl)-1H-indazol-4-yl)carbamate. 103 mg, as a light yellow solid, Y: 34%. ESI-MS (M+H)⁺: 369.2. $^1$H NMR (400 MHz, CDCl$_3$) δ: 9.64 (s, 1H), 8.36 (s, 1H), 8.09 (d, J=7.6 Hz, 1H), 8.03 (d, J=8.0 Hz, 1H), 7.98-7.93 (m, 2H), 7.88 (d, J=8.0 Hz, 1H), 7.75 (t, J=8.0 Hz, 1H), 7.06 (d, J=7.2 Hz, 1H), 5.53 (s, 1H), 5.46 (s, 1H), 2.91 (s, 3H), 2.70 (s, 3H), 2.38 (s, 3H).

Synthesis of (Z)-1-(6-(1-(6-methylpyridin-2-yl)-4-(prop-1-en-2-yl)-1H-indazol-6-yl)pyridin-2-yl)ethanone oxime

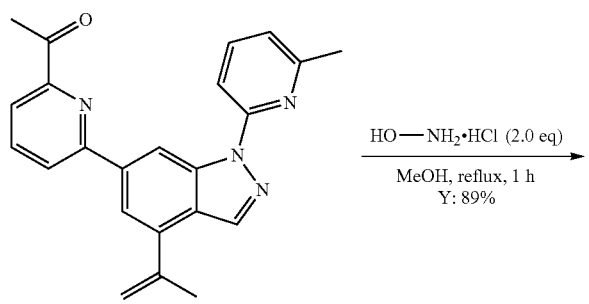

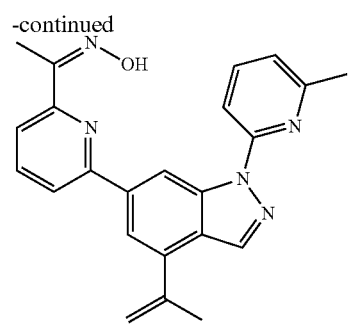

The preparation of (Z)-1-(6-(1-(6-methylpyridin-2-yl)-4-(prop-1-en-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 95 mg, as a yellow solid, Y: 89%. ESI-MS (M+H)⁺: 384.2.

Synthesis of 1-(6-(1-(6-methylpyridin-2-yl)-4-(prop-1-en-2-yl)-1H-indazol-6-yl)pyridin-2-yl)ethanamine

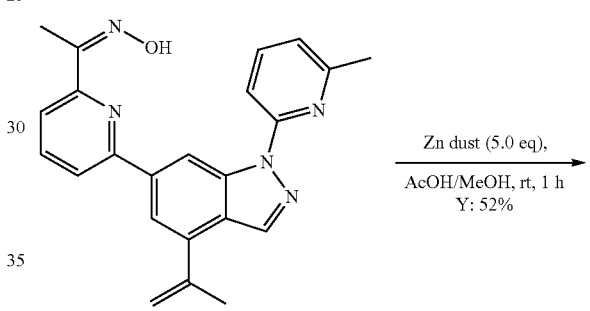

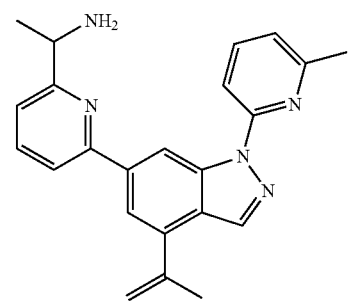

The preparation of 1-(6-(1-(6-methylpyridin-2-yl)-4-(prop-1-en-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 47 mg, as a white solid, Y: 52%. ESI-MS (M+H)⁺: 370.2. HPLC: 95.00%. $^1$H NMR (400 MHz, CD$_3$OD) δ: 9.43 (s, 1H), 8.26 (d, J=0.8 Hz, 1H), 7.84 (s, 1H), 7.83-7.70 (m, 4H), 7.29 (dd, J=7.2, 0.4 Hz, 1H), 7.03 (dd, J=6.4, 0.8 Hz, 1H), 5.42 (s, 1H), 5.38-5.37 (m, 1H), 4.11 (q, J=6.8 Hz, 1H), 2.56 (s, 3H), 2.28 (s, 3H), 1.45 (d, J=6.8 Hz, 3H).

Example 109. 1-(6-(4-ethyl-1-(6-methylpyridin-2-yl)-1H-indazol-6-yl)pyridin-2-yl)ethanamine Synthesis of 1-(6-(1-(6-methylpyridin-2-yl)-4-((trimethylsilyl)ethynyl)-1H-indazol-6-yl)pyridin-2-yl)ethanone

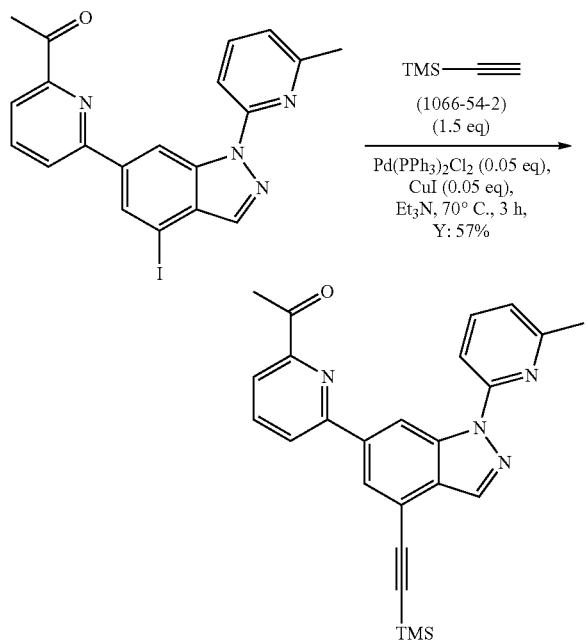

A mixture of 1-(6-(4-iodo-1-(6-methylpyridin-2-yl)-1H-indazol-6-yl)pyridin-2-yl)ethanone (150 mg, 0.33 mmol, 1.0 eq), ethynyltrimethylsilane CAS#1066-54-2 (49 mg, 0.5 mmol, 1.5 eq), Pd(PPh$_3$)$_2$Cl$_2$ (23 mg, 0.033 mmol, 0.1 eq) and CuI (6 mg, 0.033 mmol, 0.1 eq) in Et$_3$N (15 mL) was stirred at 70° C. for 3 h under N$_2$ atmosphere. After concentration, the residue was purified by column chromatography on silica gel (PE/EA=10/1) to give 1-(6-(1-(6-methylpyridin-2-yl)-4-((trimethylsilyl)ethynyl)-1H-indazol-6-yl) pyridin-2-yl)ethanone as a white solid. 90 mg, Y: 64%. ESI-MS (M+H)$^+$: 425.2. $^1$H NMR (400 MHz, CDCl$_3$) δ: 9.63 (s, 1H), 8.21 (s, 1H), 8.02 (d, J=1.2 Hz, 1H), 7.98-7.93 (m, 2H), 7.86 (t, J=7.6 Hz, 1H), 7.79 (d, J=8.0 Hz, 1H), 7.66 (t, J=7.6 Hz, 1H), 6.97 (d, J=7.6 Hz, 1H), 2.84 (s, 3H), 2.59 (s, 3H), 0.28 (s, 9H).

Synthesis of 1-(6-(4-ethynyl-1-(6-methylpyridin-2-yl)-1H-indazol-6-yl)pyridin-2-yl)ethanone

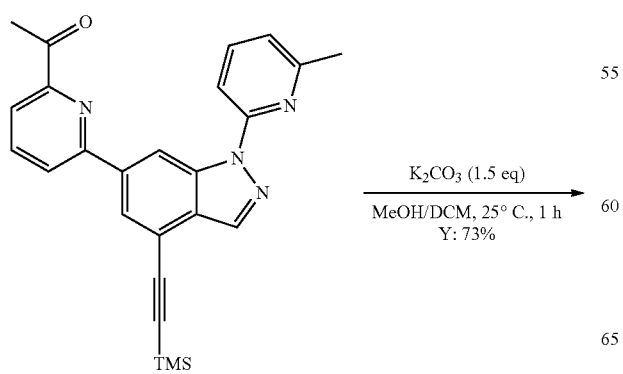

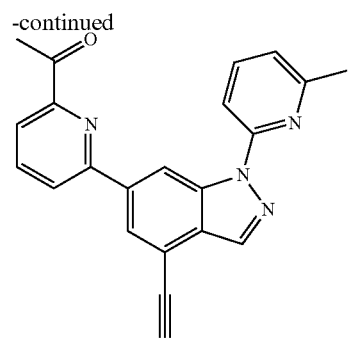

A mixture of 1-(6-(1-(6-methylpyridin-2-yl)-4-((trimethylsilyl)ethynyl)-1H-indazol-6-yl)pyridin-2-yl)ethanone (196 mg, 0.46 mmol, 1.0 eq) and K$_2$CO$_3$ (63 mg, 0.46 mmol, 1.5 eq) in MeOH/DCM (15 mL/15 mL) was stirred at 25° C. for 1 h. The mixture was diluted with DCM (100 mL) and washed with H$_2$O (30 mL). The organic layer was dried over anhydrous sodium sulfate and concentrated under reduced pressure. The residue was purified by column chromatography on silica gel (PE/EA=5/1) to give 1-(6-(4-ethynyl-1-(6-methylpyridin-2-yl)-1H-indazol-6-yl)pyridin-2-yl)ethanone as a white solid. 116 mg, Y: 73%. ESI-MS (M+H)$^+$: 353.2. $^1$H NMR (400 MHz, CDCl$_3$) δ: 9.75 (s, 1H), 8.35 (s, 1H), 8.16 (d, J=1.2 Hz, 1H), 8.09-8.04 (m, 2H), 7.97 (t, J=7.6 Hz, 1H), 7.88 (d, J=8.0 Hz, 1H), 7.76 (t, J=7.6 Hz, 1H), 7.07 (d, J=7.6 Hz, 1H), 3.45 (s, 1H), 2.92 (s, 3H), 2.69 (s, 3H).

Synthesis of (Z)-1-(6-(4-ethynyl-1-(6-methylpyridin-2-yl)-1H-indazol-6-yl)pyridin-2-yl)ethanone oxime

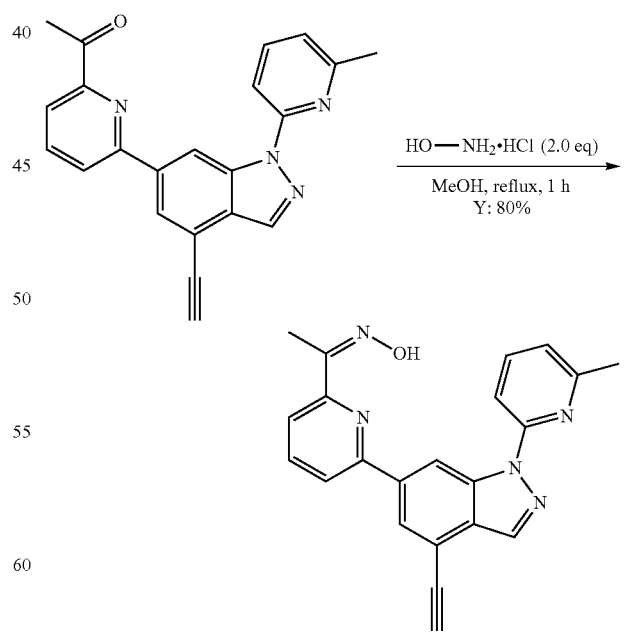

The preparation of (Z)-1-(6-(4-ethynyl-1-(6-methylpyridin-2-yl)-1H-indazol-6-yl)pyridin-2-yl)ethanone oxime was the same as that of 2-(1-(6-(trifluoromethyl)pyridin-2-yl)-

1H-indazol-6-yl)-5H-cyclopenta[b]pyridin-7(6H)-one oxime. 103 mg, as a white solid, Y: 80%. ESI-MS (M+H)+: 368.2.

Synthesis of 1-(6-(4-ethynyl-1-(6-methylpyridin-2-yl)-1H-indazol-6-yl)pyridin-2-yl)ethanamine

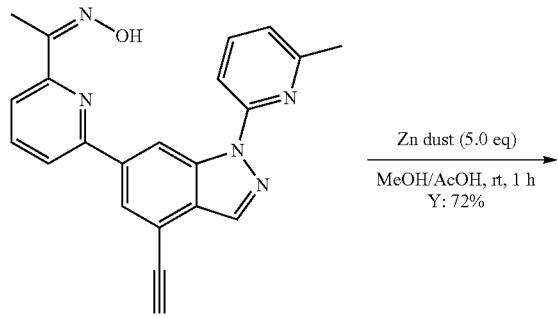

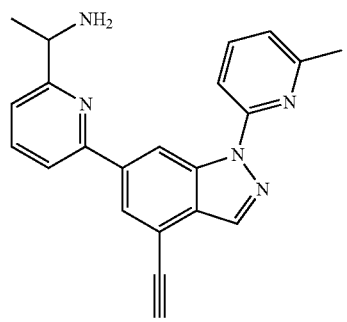

The preparation of 1-(6-(4-ethynyl-1-(6-methylpyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 89 mg, as a yellow solid, Y: 72%. ESI-MS (M+H)+: 354.2. HPLC: 99.40%. $^1$H NMR (400 MHz, CD$_3$OD) δ: 9.61 (s, 1H), 8.38 (s, 1H), 8.36 (s, 1H), 8.07-8.03 (m, 2H), 7.88-7.85 (m, 2H), 7.51-7.49 (m, 1H), 7.18 (dd, J=6.4, 0.8 Hz 1H), 4.71 (q, J=6.8 Hz, 1H), 4.01 (s, 1H), 2.71 (s, 3H), 1.73 (d, J=6.4 Hz, 3H).

Synthesis of 1-(6-(4-ethyl-1-(6-methylpyridin-2-yl)-1H-indazol-6-yl)pyridin-2-yl)ethanamine

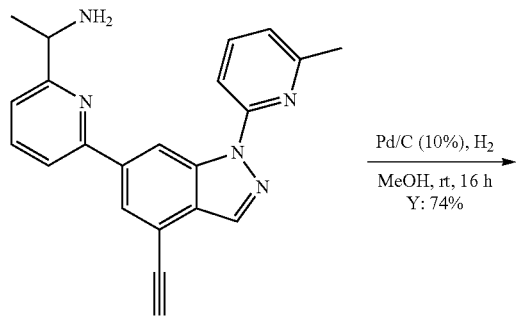

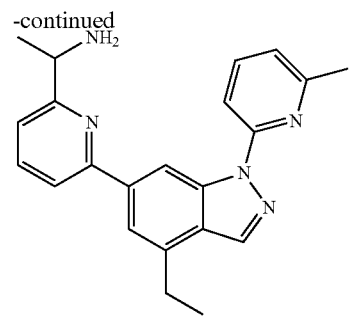

A mixture of 1-(6-(4-ethynyl-1-(6-methylpyridin-2-yl)-1H-indazol-6-yl)pyridin-2-yl)ethanamine (80 mg, 0.23 mmol, 1.0 eq) and Pd/C (8 mg) in MeOH (5 mL) was stirred at rt for 16 h under H$_2$. After filtration and concentration, the residue was purified by pre-HPLC (MeOH/H$_2$O with 0.05% TFA as mobile phase from 5% to 95%) to give 1-(6-(4-ethyl-1-(6-methylpyridin-2-yl)-1H-indazol-6-yl)pyridin-2-yl)ethanamine as a yellow solid. 60 mg, Y: 74%. ESI-MS (M+H)+: 358.2. HPLC: 98.83%. $^1$H NMR (400 MHz, CD$_3$OD) δ: 9.40 (s, 1H), 8.40 (s, 1H), 8.04-7.99 (m, 3H), 7.88-7.82 (m, 2H), 7.47 (dd, J=6.0, 2.8 Hz, 1H), 7.17 (d, J=6.0 Hz, 1H), 4.70 (q, J=6.8 Hz, 1H), 3.14 (q, J=7.6 Hz, 2H), 2.70 (s, 3H), 1.74 (d, J=6.4 Hz, 3H), 1.48 (t, J=7.6 Hz, 3H).

Example 110. 1-(6-(4-isopropyl-1-(6-methylpyridin-2-yl)-1H-indazol-6-yl)pyridin-2-yl)ethanamine Synthesis of 1-(6-(4-isopropyl-1-(6-methylpyridin-2-yl)-1H-indazol-6-yl)pyridin-2-yl)ethanamine

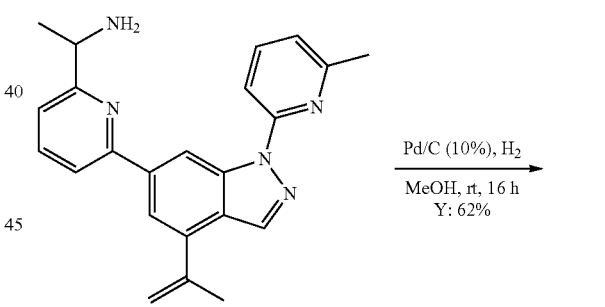

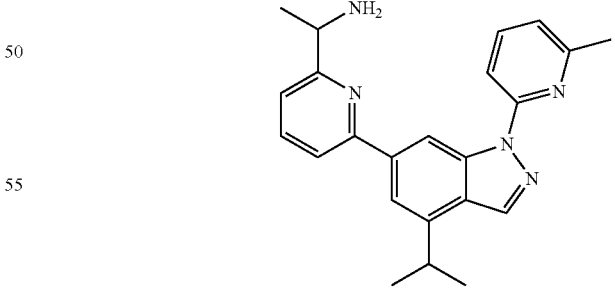

The preparation of 1-(6-(4-isopropyl-1-(6-methylpyridin-2-yl)-1H-indazol-6-yl)pyridin-2-yl)ethanamine was the same as that of 1-(6-(4-ethyl-1-(6-methylpyridin-2-yl)-1H-indazol-6-yl)pyridin-2-yl)ethanamine. 22 mg, as a yellow solid, Y: 62%. ESI-MS (M+H)+: 372.2. HPLC: 96.42%. $^1$H NMR (400 MHz, CD$_3$OD) δ: 9.33 (s, 1H), 8.32 (s, 1H), 7.81-7.73 (m, 5H), 7.29 (d, J=7.6 Hz, 1H), 7.04 (t, J=6.0 Hz, 1H), 4.14 (q, J=6.4 Hz, 1H), 3.44-3.40 (m, 1H), 2.57 (s, 3H), 1.45 (d, J=6.8 Hz, 3H), 1.41 (t, J=6.4 Hz, 6H).

Example 111. 1-(6-(1-(6-methylpyridin-2-yl)-4-(trifluoromethyl)-1H-indazol-6-yl)pyridin-2-yl)ethanamine Synthesis of 1-(6-(1-(6-methylpyridin-2-yl)-4-(trifluoromethyl)-1H-indazol-6-yl)pyridin-2-yl)ethanone

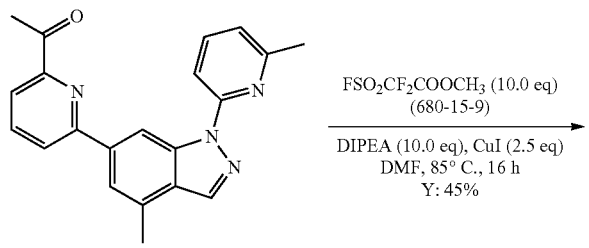

To a solution of 1-(6-(4-iodo-1-(6-methylpyridin-2-yl)-1H-indazol-6-yl)pyridin-2-yl)ethanone (80 mg, 0.18 mmol, 1.0 eq) in DMF (10 mL) were added methyl 2,2-difluoro-2-(fluorosulfonyl)acetate (CAS#680-15-9) (338 mg, 1.76 mmol, 10.0 eq), DIPEA (227 mg, 1.76 mmol, 10.0 eq), CuI (84 mg, 0.44 mmol, 2.5 eq) at rt. The mixture was stirred at 85° C. for 16 h under N$_2$ atmosphere. After concentration, the residue was purified by column chromatography on silica gel (PE/EA=2/1) to give 1-(6-(1-(6-methylpyridin-2-yl)-4-(trifluoromethyl)-1H-indazol-6-yl)pyridin-2-yl)ethanone as a yellow solid. 31 mg, Y: 45%. ESI-MS (M+H)$^+$: 397.2. $^1$H NMR (400 MHz, CDCl$_3$) δ: 9.94 (s, 1H), 8.36 (s, 1H), 8.33 (s, 1H), 8.10 (dd, J=8.0, 1.2 Hz, 1H), 8.06 (dd, J=7.6, 1.2 Hz, 1H), 7.99 (t, J=8.0 Hz, 1H), 7.90 (d, J=8.4 Hz, 1H), 7.78 (t, J=8.0 Hz, 1H), 7.10 (d, J=7.2 Hz, 1H), 2.91 (s, 3H), 2.70 (s, 3H).

Synthesis of (Z)-1-(6-(1-(6-methylpyridin-2-yl)-4-(trifluoromethyl)-1H-indazol-6-yl)pyridin-2-yl)ethanone oxime

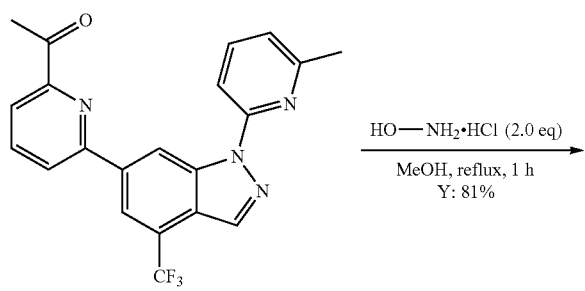

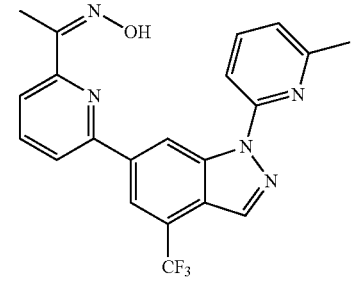

The preparation of (Z)-1-(6-(1-(6-methylpyridin-2-yl)-4-(trifluoromethyl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 26 mg, as a white solid, Y: 81%. ESI-MS (M+H)$^+$: 412.2.

Synthesis of 1-(6-(1-(6-methylpyridin-2-yl)-4-(trifluoromethyl)-1H-indazol-6-yl)pyridin-2-yl)ethanamine

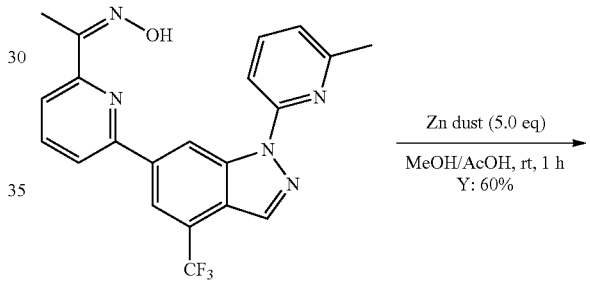

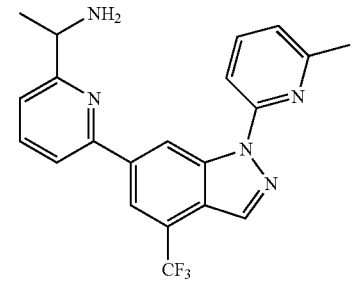

The preparation of 1-(6-(1-(6-methylpyridin-2-yl)-4-(trifluoromethyl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 15 mg, as a yellow solid, Y: 60%. ESI-MS (M+H)$^+$: 398.2. HPLC: 100.00%. $^1$H NMR (400 MHz, CD$_3$OD) δ: 9.88 (s, 1H), 8.58 (s, 1H), 8.43 (s, 1H), 8.13-8.06 (m, 2H), 7.95-7.88 (m, 2H), 7.55 (dd, J=7.2, 0.8 Hz, 1H), 7.25 (d, J=6.8 Hz, 1H), 4.73 (q, J=6.8 Hz, 1H), 2.73 (s, 3H), 1.74 (d, J=6.8 Hz, 3H).

Example 112. methyl 6-(6-(1-aminoethyl)pyridin-2-yl)-1-(6-methylpyridin-2-yl)-1H-indazole-4-carboxylate Synthesis of methyl 1-(6-methylpyridin-2-yl)-6-(4,4,5,5-tetramethyl-1,3,2-dioxaborolan-2-yl)-1H-indazole-4-carboxylate and methyl 2-(6-methylpyridin-2-yl)-6-(4,4,5,5-tetramethyl-1,3,2-dioxaborolan-2-yl)-2H-indazole-4-carboxylate

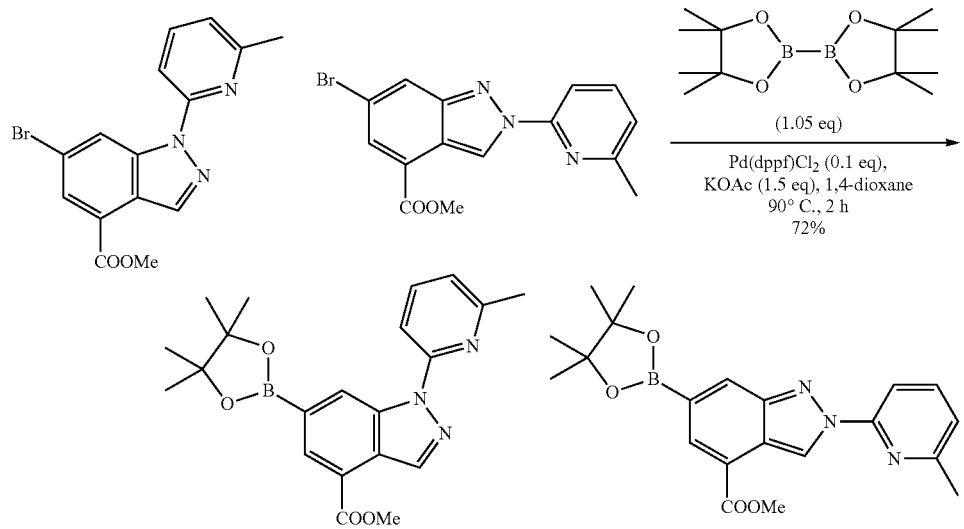

The preparation of methyl 1-(6-methylpyridin-2-yl)-6-(4,4,5,5-tetramethyl-1,3,2-dioxaborolan-2-yl)-1H-indazole-4-carboxylate and methyl 2-(6-methylpyridin-2-yl)-6-(4,4,5,5-tetramethyl-1,3,2-dioxaborolan-2-yl)-2H-indazole-4-carboxylate was the same as that of 1-(6-methylpyridin-2-yl)-6-(4,4,5,5-tetramethyl-1,3,2-dioxaborolan-2-yl)-1H-indazole. 1.1 g, as a yellow solid, Y: 72%. The mixture of methyl 1-(6-methylpyridin-2-yl)-6-(4,4,5,5-tetramethyl-1,3,2-dioxaborolan-2-yl)-1H-indazole-4-carboxylate and methyl 2-(6-methylpyridin-2-yl)-6-(4,4,5,5-tetramethyl-1,3,2-dioxaborolan-2-yl)-2H-indazole-4-carboxylate was difficult to be purified due to poor solubility. The mixture was directly used for next step. ESI-MS (M+H)$^+$: 394.1.

Synthesis of methyl 6-(6-acetylpyridin-2-yl)-1-(6-methylpyridin-2-yl)-1H-indazole-4-carboxylate

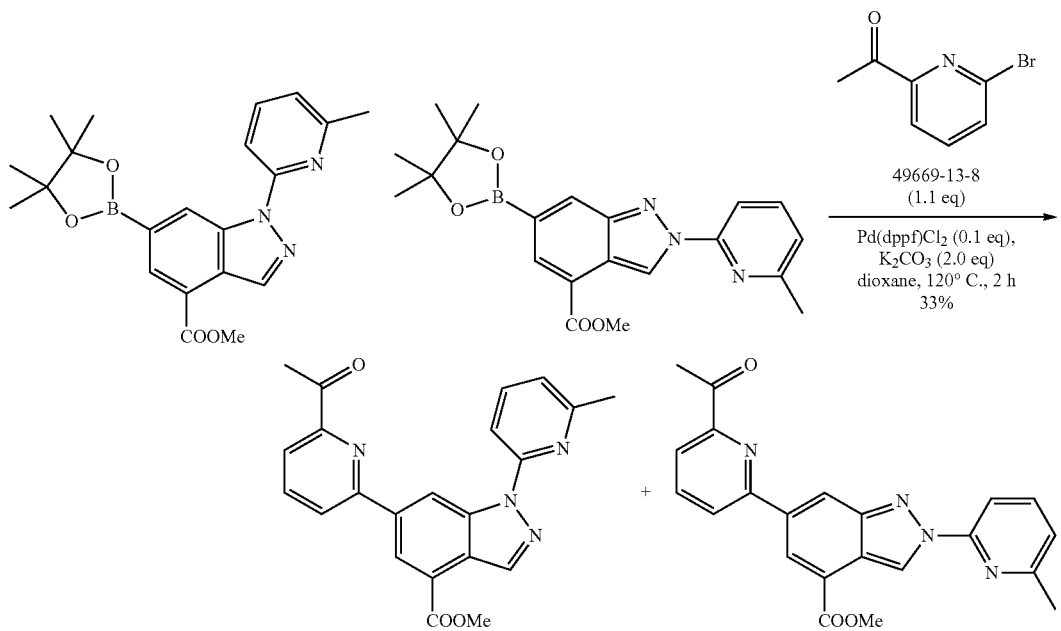

The preparation of methyl 6-(6-acetylpyridin-2-yl)-1-(6-methylpyridin-2-yl)-1H-indazole-4-carboxylate was the same as that of tert-butyl (6-(6-acetylpyridin-2-yl)-1-(6-methylpyridin-2-yl)-1H-indazol-4-yl)carbamate. The mixture was purified by silica gel chromatography with PE/EA (2/1) as eluent to give methyl 6-(6-acetylpyridin-2-yl)-1-(6-methylpyridin-2-yl)-1H-indazole-4-carboxylate and EA as eluent to give methyl 6-(6-acetylpyridin-2-yl)-2-(6-methylpyridin-2-yl)-2H-indazole-4-carboxylate as a yellow solid.

methyl 6-(6-acetylpyridin-2-yl)-1-(6-methylpyridin-2-yl)-1H-indazole-4-carboxylate, as a yellow solid, 300 mg, Y: 33%. ESI-MS (M+H)+: 387.1. $^1$H NMR (400 MHz, CDCl$_3$) δ: 10.05 (s, 1H), 8.76 (s, 1H), 8.73 (d, J=1.6 Hz, 1H), 8.15 (dd, J=8.0, 1.2 Hz, 1H), 8.06 (dd, J=8.0, 1.2 Hz, 1H), 8.00 (t, J=7.6 Hz, 1H), 7.92 (d, J=8.0 Hz, 1H), 7.75 (t, J=8.0 Hz, 1H), 7.09 (d, J=7.6 Hz, 1H), 4.10 (s, 3H), 2.93 (s, 3H), 2.63 (s, 3H).

Synthesis of (Z)-methyl 6-(6-(1-(hydroxyimino)ethyl)pyridin-2-yl)-1-(6-methylpyridin-2-yl)-1H-indazole-4-carboxylate

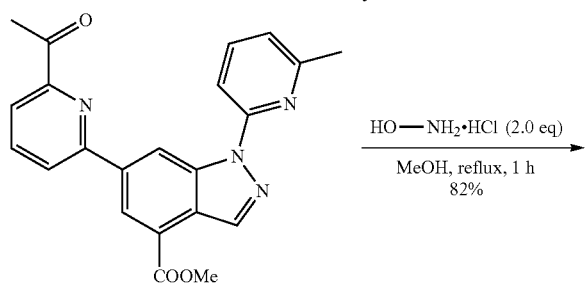

The preparation of (Z)-methyl 6-(6-(1-(hydroxyimino)ethyl)pyridin-2-yl)-1-(6-methylpyridin-2-yl)-1H-indazole-4-carboxylate was the same as that of 2-(1-(6-(trifluoromethyl)pyridin-2-yl)-1H-indazol-6-yl)-5H-cyclopenta[b]pyridin-7(6H)-one oxime. 255 mg, as white solid, Y: 82%. ESI-MS (M+H)+: 402.1.

Synthesis of methyl 6-(6-(1-aminoethyl)pyridin-2-yl)-1-(6-methylpyridin-2-yl)-1H-indazole-4-carboxylate

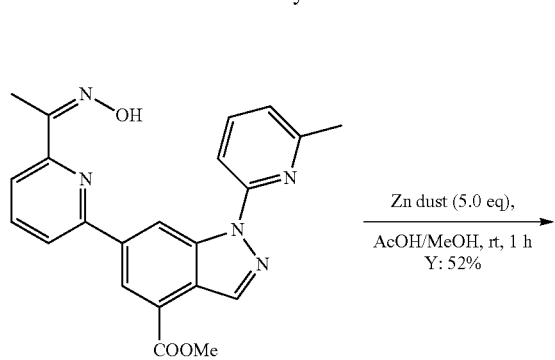

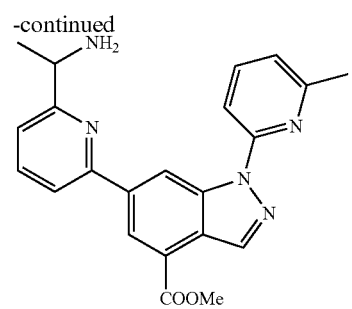

The preparation of methyl 6-(6-(1-aminoethyl)pyridin-2-yl)-1-(6-methylpyridin-2-yl)-1H-indazole-4-carboxylate was the same as that of 2-(1-(6-(trifluoromethyl)pyridin-2-yl)-1H-indazol-6-yl)-6,7-dihydro-5H-cyclopenta[b]pyridin-7-amine. 72 mg, as white solid, Y: 52%. ESI-MS (M+H)+: 388.2. HPLC: 100.00%. $^1$H NMR (400 MHz, CD$_3$OD) δ: 9.46 (d, J=1.2 Hz, 1H), 8.53 (d, J=1.6 Hz, 1H), 8.34 (d, J=0.8 Hz, 1H), 7.87 (t, J=8.0 Hz, 1H), 7.65 (d, J=7.2 Hz, 1H), 7.62 (t, J=8.0 Hz, 1H), 7.57 (d, J=8.0 Hz, 1H), 7.39 (d, J=7.6 Hz, 1H), 6.98 (d, J=7.2 Hz, 1H), 4.61 (q, J=6.4 Hz, 1H), 3.91 (s, 3H), 2.49 (s, 3H), 1.65 (d, J=6.8 Hz, 3H).

Example 113. 6-(6-(1-aminoethyl)pyridin-2-yl)-1-(6-methylpyridin-2-yl)-1H-indazole-4-carboxylic acid Synthesis of 6-(6-(1-aminoethyl)pyridin-2-yl)-1-(6-methylpyridin-2-yl)-1H-indazole-4-carboxylic acid

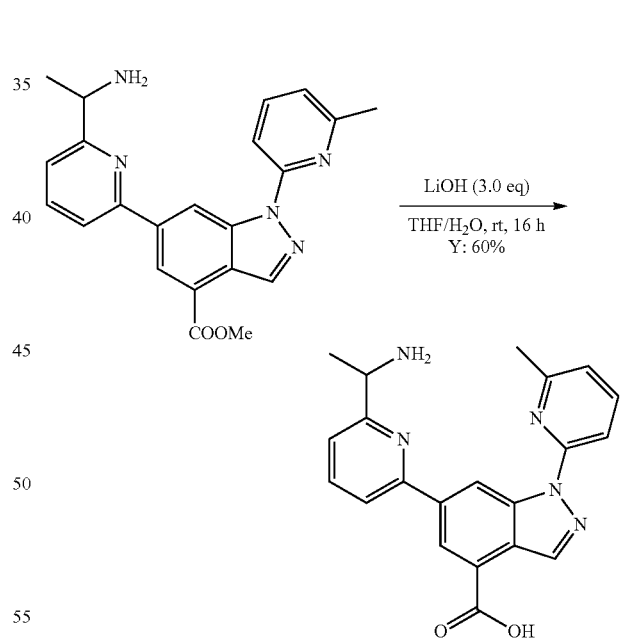

The preparation of 6-(6-(1-aminoethyl)pyridin-2-yl)-1-(6-methylpyridin-2-yl)-1H-indazole-4-carboxylic acid was the same as that of 6-(5-aminopyridin-3-yl)-1-(6-(trifluoromethyl)pyridin-2-yl)-1H-indazole-4-carboxylic acid. 60 mg, as white solid, Y: 60%. ESI-MS (M+H)+: 374.2. HPLC: 100.00%. $^1$H NMR (400 MHz, CD$_3$OD) δ: 9.84 (s, 1H), 8.86 (d, J=2.0 Hz, 1H), 8.72 (s, 1H), 8.07-8.05 (m, 2H), 7.88-7.84 (m, 2H), 7.53 (dd, J=6.0, 3.2 Hz, 1H), 7.20 (d, J=6.8 Hz, 1H), 4.73 (q, J=6.8 Hz, 1H), 2.71 (s, 3H), 1.75 (d, J=6.8 Hz, 3H).

Example 114. 6-(6-(1-aminoethyl)pyridin-2-yl)-1-(6-methylpyridin-2-yl)-1H-indazol-4-yl)methanol Synthesis of (6-(6-(1-aminoethyl)pyridin-2-yl)-1-(6-methylpyridin-2-yl)-1H-indazol-4-yl)methanol

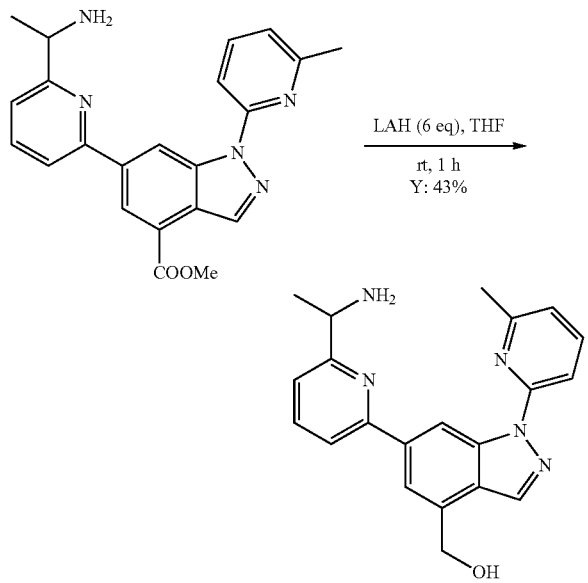

The preparation of (6-(6-(1-aminoethyl)pyridin-2-yl)-1-(6-methylpyridin-2-yl)-1H-indazol-4-yl)methanol was the same as that of (6-(6-(1-aminoethyl)pyridin-2-yl)-1-(6-(trifluoromethyl)pyridin-2-yl)-1H-indazol-4-yl)methanol. 17 mg, as a yellow solid, Y: 43%. ESI-MS (M+H)⁺: 360.2. HPLC: 100.00%. ¹H NMR (400 MHz, CD₃OD) δ: 9.53 (s, 1H), 8.43 (d, J=0.8 Hz, 1H), 8.05 (s, 1H), 7.95-7.90 (m, 2H), 7.87-7.81 (m, 2H), 7.41 (dd, J=6.0, 2.8 Hz, 1H), 7.16 (dd, J=6.4, 1.2 Hz, 1H), 5.08 (s, 2H), 4.38 (q, J=6.8 Hz, 1H), 2.69 (s, 3H), 1.61 (d, J=6.8 Hz, 3H).

Example 115. 6-(6-(1-aminoethyl)pyridin-2-yl)-N-methyl-1-(6-methylpyridin-2-yl)-1H-indazole-4-carboxamide Synthesis of 6-(6-(1-aminoethyl)pyridin-2-yl)-N-methyl-1-(6-methylpyridin-2-yl)-1H-indazole-4-carboxamide

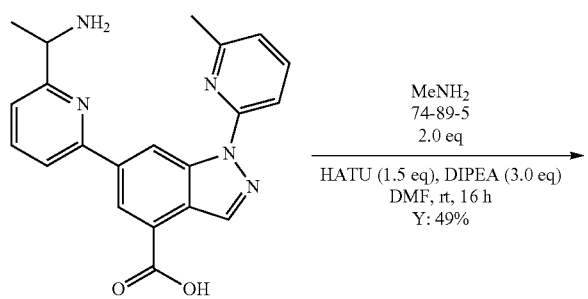

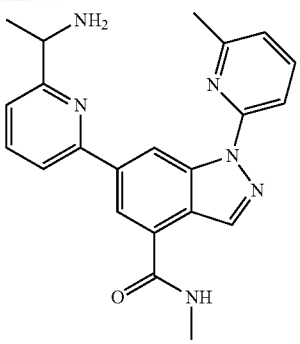

The preparation of 6-(6-(1-aminoethyl)pyridin-2-yl)-N-methyl-1-(6-methylpyridin-2-yl)-1H-indazole-4-carboxamide was the same as that of 6-(6-(5-aminopyridin-3-yl)-1H-indazol-1-yl)-N-methylpicolinamide (Example 32). 22 mg, as a brown solid, Y: 49%. ESI-MS (M+H)⁺: 387.3. HPLC: 100.00%. ¹H NMR (400 MHz, CD₃OD) δ: 9.81 (s, 1H), 8.64 (d, J=0.8 Hz, 1H), 8.43 (d, J=1.6 Hz, 1H), 7.97-7.92 (m, 2H), 7.89-7.83 (m, 2H), 7.43 (dd, J=6.4, 2.0 Hz, 1H), 7.18 (d, J=6.4 Hz, 1H), 4.33 (q, J=6.8 Hz, 1H), 3.06 (s, 3H), 2.69 (s, 3H), 1.59 (d, J=6.8 Hz, 3H).

Example 116. N-methyl-1-(6-(1-(6-methylpyridin-2-yl)-1H-indazol-6-yl)pyridin-2-yl)ethanamine Synthesis of N-methyl-1-(6-(1-(6-methylpyridin-2-yl)-1H-indazol-6-yl)pyridin-2-yl)ethanamine

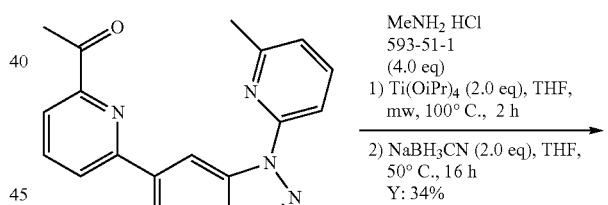

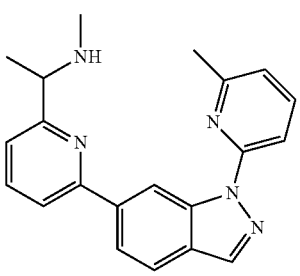

The preparation of N-methyl-1-(6-(1-(6-methylpyridin-2-yl)-1H-indazol-6-yl)pyridin-2-yl)ethanamine was the same as that of N-(4-methoxybenzyl)-1-(6-(1-(6-methylpyridin-2-yl)-1H-indazol-6-yl)pyridin-2-yl)ethanamine. 180 mg, as a white solid, Y: 34%. ESI-MS (M+H)⁺: 344.2.

Example 117 and 118. N-methyl-1-(6-(1-(6-(trifluoromethyl)pyridin-2-yl)-1H-indazol-6-yl)pyridin-2-yl)ethanamine

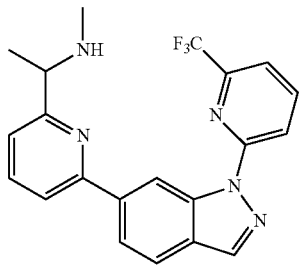 [SMILES: CNC(C)c1cccc(-c2ccc3cnn(-c4cccc(C(F)(F)F)n4)c3c2)n1]

Synthesis of N-methyl-1-(6-(1-(6-(trifluoromethyl)pyridin-2-yl)-1H-indazol-6-yl)pyridin-2-yl)ethanamine

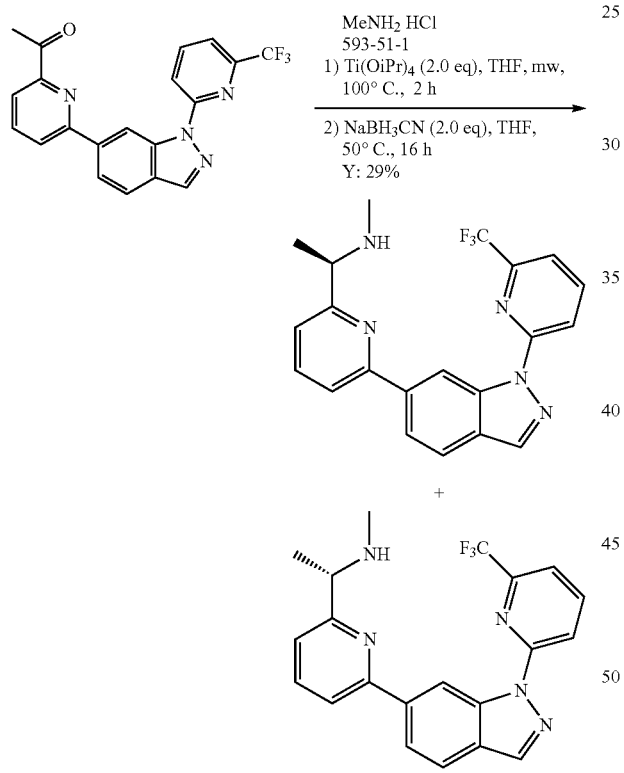

The preparation of N-methyl-1-(6-(1-(6-(trifluoromethyl)pyridin-2-yl)-1H-indazol-6-yl)pyridin-2-yl)ethanamine was the same as that of N-(4-methoxybenzyl)-1-(6-(1-(6-methylpyridin-2-yl)-1H-indazol-6-yl)pyridin-2-yl)ethanamine. 120 mg, as a white solid, Y: 29%. ESI-MS (M+H)$^+$: 398.2.

SFC (Column: IC, 4.6*250 mm 5 μm, IPA:MTBE=1:1 (1% DEA), $CO_2$ flow rate=2.25, Co-Solvent Flow Rate=0.75, Detection wavelength=214 nm) $t_R$=6.58 min, 7.32 min.

Isomer a: 20 mg, as a yellow solid, ESI-MS (M+H)$^+$: 398.2, HPLC: 98.13%. $t_R$=6.58 min (Chiral HPLC). $^1$H NMR (400 MHz, CD$_3$OD) δ: 9.61 (s, 1H), 8.37 (s, 1H), 8.35 (d, J=8.8 Hz, 1H), 8.18 (t, J=8.0 Hz, 1H), 8.06 (dd, J=8.4, 1.2 Hz, 1H), 7.95 (d, J=8.4 Hz, 1H), 7.90-7.88 (m, 2H), 7.68 (d, J=7.6 Hz, 1H), 7.37 (dd, J=6.8, 1.2 Hz, 1H), 3.91 (q, J=6.8 Hz, 1H), 2.34 (s, 3H), 1.50 (d, J=6.4 Hz, 3H). (Example 117)

Isomer b: 25 mg, as a yellow solid, ESI-MS (M+H)$^+$: 398.2, HPLC: 98.13%. $t_R$=7.32 min (Chiral HPLC). $^1$H NMR (400 MHz, CD$_3$OD) δ: 9.52 (s, 1H), 8.28 (s, 1H), 8.27 (d, J=8.8 Hz, 1H), 8.10 (t, J=8.0 Hz, 1H), 8.00 (dd, J=8.8, 1.6 Hz, 1H), 7.88-7.79 (m, 3H), 7.61 (d, J=7.2 Hz, 1H), 7.34 (dd, J=6.4, 2.8 Hz, 1H), 3.90 (q, J=6.8 Hz, 1H), 2.34 (s, 3H), 1.49 (d, J=6.8 Hz, 3H). (Example 118)

Example 119. 1-(6-(1-(6-cyclopropylpyridin-2-yl)-1H-indazol-6-yl)pyridin-2-yl)ethanamine

Synthesis of 1-(6-(1-(6-bromopyridin-2-yl)-1H-indazol-6-yl)pyridin-2-yl)ethanone

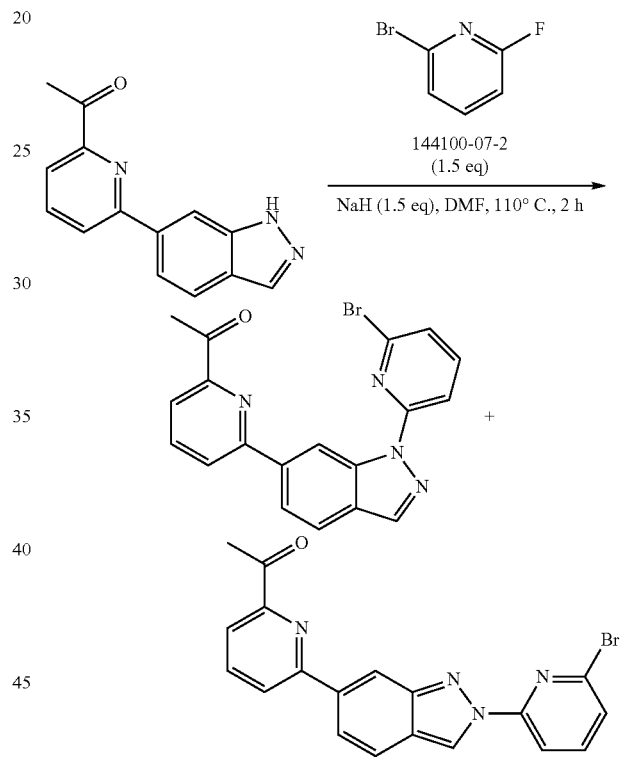

The preparation of 1-(6-(1-(6-bromopyridin-2-yl)-1H-indazol-6-yl)pyridin-2-yl)ethanone was the same as that of 6-bromo-1-(6-methylpyridin-2-yl)-1H-indazole. The mixture of 1-(6-(1-(6-bromopyridin-2-yl)-1H-indazol-6-yl)pyridin-2-yl)ethanone and 1-(6-(2-(6-bromopyridin-2-yl)-2H-indazol-6-yl)pyridin-2-yl)ethanone was purified by pre-TLC (PE/EA=5/1) to give 1-(6-(1-(6-bromopyridin-2-yl)-1H-indazol-6-yl)pyridin-2-yl)ethanone and 1-(6-(2-(6-bromopyridin-2-yl)-2H-indazol-6-yl)pyridin-2-yl)ethanone. R$_f$ value of 1-(6-(1-(6-bromopyridin-2-yl)-1H-indazol-6-yl)pyridin-2-yl)ethanone is more than that of 1-(6-(2-(6-bromopyridin-2-yl)-2H-indazol-6-yl)pyridin-2-yl)ethanone.

1-(6-(1-(6-bromopyridin-2-yl)-1H-indazol-6-yl)pyridin-2-yl)ethanone, 80 mg, as a yellow solid, Y: 15%. ESI-MS (M+H)$^+$: 393.0, 395.0.

1-(6-(2-(6-bromopyridin-2-yl)-2H-indazol-6-yl)pyridin-2-yl)ethanone, 27 mg, as a yellow solid, Y: 5%. ESI-MS (M+H)$^+$: 393.0, 395.0.

Synthesis of 1-(6-(1-(6-cyclopropylpyridin-2-yl)-1H-indazol-6-yl)pyridin-2-yl)ethanone

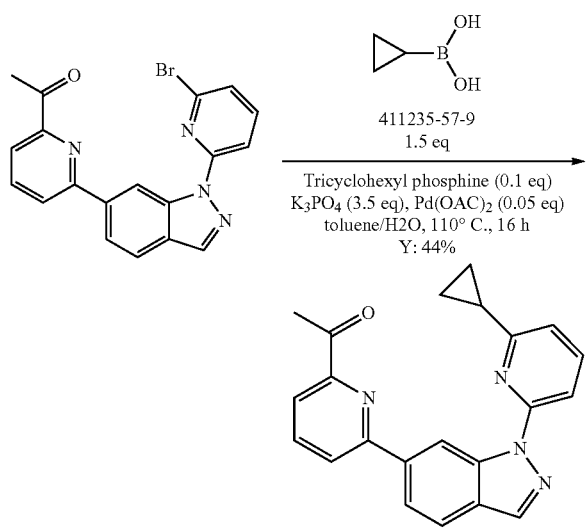

A mixture of 1-(6-(1-(6-bromopyridin-2-yl)-1H-indazol-6-yl)pyridin-2-yl)ethanone (80 mg, 0.20 mmol, 1.0 eq), cyclopropylboronic acid (CAS#411235-57-9) (26 mg, 0.30 mmol, 1.5 eq), tricyclohexyl phosphine (56 mg, 0.02 mmol, 0.1 eq), K$_3$PO$_4$ (74 mg, 0.35 mmol, 3.5 eq), Pd(OAc)$_2$ (3 mg, 0.01 mmol, 0.05 eq) in toluene (2 mL)/H$_2$O (0.2 mL) was stirred at 110° C. for 16 h under N$_2$. After concentration, the residue was purified by silica gel chromatography with PE/EA (4/1) as eluent to give 1-(6-(1-(6-cyclopropylpyridin-2-yl)-1H-indazol-6-yl)pyridin-2-yl)ethanone. 40 mg, as a yellow solid, Y: 44%. ESI-MS (M+H)$^+$: 355.1.

Synthesis of (Z)-1-(6-(1-(6-cyclopropylpyridin-2-yl)-1H-indazol-6-yl)pyridin-2-yl)ethanone oxime

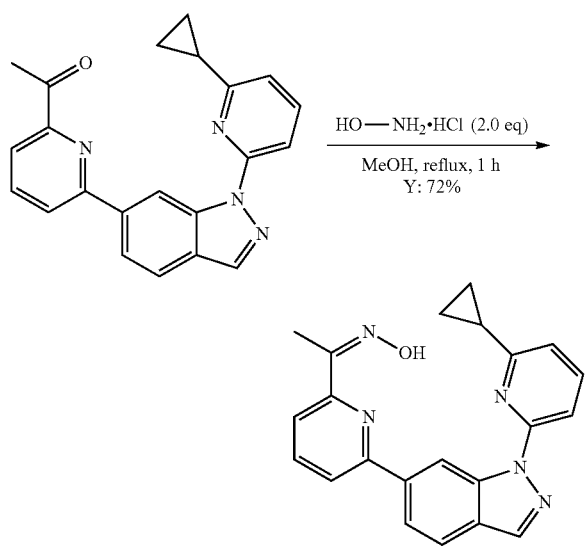

The preparation of (Z)-1-(6-(1-(6-cyclopropylpyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 30 mg, as a yellow solid, Y: 72%. ESI-MS (M+H)$^+$: 370.2.

Synthesis of 1-(6-(1-(6-cyclopropylpyridin-2-yl)-1H-indazol-6-yl)pyridin-2-yl)ethanamine

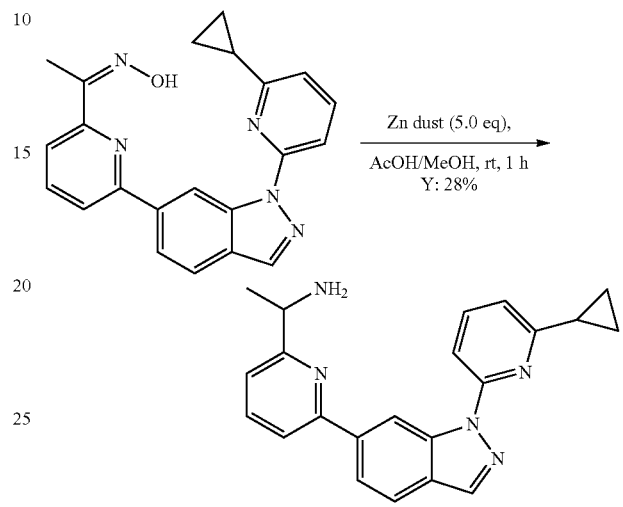

The preparation of 1-(6-(1-(6-cyclopropylpyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 8.2 mg, as a yellow solid, Y: 28%. ESI-MS (M+H)$^+$: 356.2. HPLC: 100.00%. $^1$H NMR (500 MHz, CD$_3$OD) δ: 9.34 (s, 1H), 8.18 (s, 1H), 7.91 (dd, J=7.5, 0.5 Hz, 1H), 7.83-7.80 (m, 2H), 7.71 (d, J=7.5 Hz, 1H), 7.67 (dd, J=7.5, 1.0 Hz, 1H), 7.63 (t, J=7.5 Hz, 1H), 7.27 (d, J=7.5 Hz, 1H), 7.07 (d, J=7.0 Hz, 1H), 4.20 (q, J=6.5 Hz, 1H), 2.16-2.12 (m, 1H), 1.49 (d, J=6.5 Hz, 3H), 1.27-1.09 (m, 2H), 1.07-1.04 (m, 2H).

Example 120. 1-(6-(1-(6-ethylpyridin-2-yl)-1H-indazol-6-yl)pyridin-2-yl)ethanamine Synthesis of 2-bromo-6-ethylpyridine

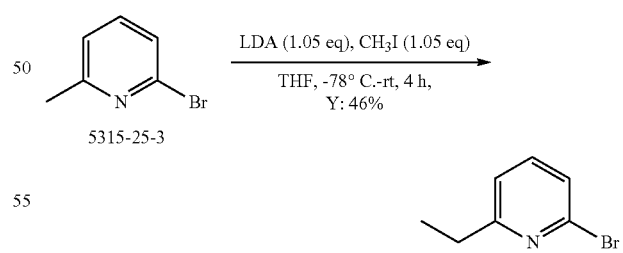

To a solution of 2-bromo-6-methylpyridine (CAS#5315-25-3) (2.0 g, 11.7 mmol, 1.0 eq) in THF (10 mL) was added LDA (12.3 mL, 12.3 mmol, 1.05 eq) at −78° C. After stirring at −78° C. for 1 h, CH$_3$I (1.8 g, 12.3 mmol, 1.05 eq) was added to the mixture. The mixture was stirred at rt for 3 h. The mixture was quenched with sat. NH$_4$Cl (2 mL), diluted with water (50 mL) and extracted with EA (2×100 mL). The combined organic phase was washed with brine and dried over Na$_2$SO$_4$. After concentration, the residue was purified by silica gel chromatography with PE/EA (20/1) as eluent to give 2-bromo-6-ethylpyridine. 1.0 g, as a yellow solid, Y: 46%. ESI-MS (M+H)+: 185.9, 187.9.

Synthesis of 6-bromo-1-(6-ethylpyridin-2-yl)-1H-indazole

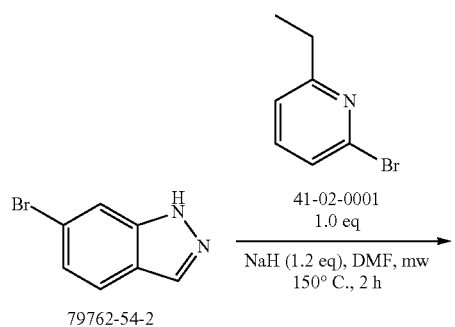

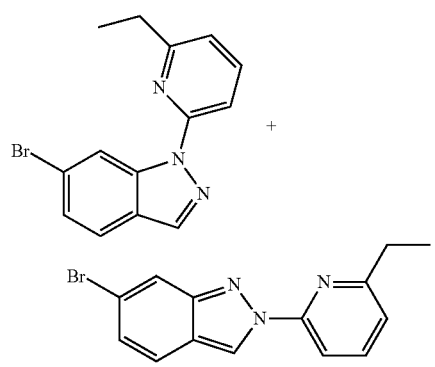

The preparation of 6-bromo-1-(6-ethylpyridin-2-yl)-1H-indazole was the same as that of 6-bromo-1-(6-methylpyridin-2-yl)-1H-indazole. The mixture of 6-bromo-1-(6-ethylpyridin-2-yl)-1H-indazole and 6-bromo-2-(6-ethylpyridin-2-yl)-2H-indazole was purified by pre-TLC (PE/EA=10/1) to give 41-02-0002 and 6-bromo-2-(6-ethylpyridin-2-yl)-2H-indazole. $R_f$ value of 6-bromo-1-(6-ethylpyridin-2-yl)-1H-indazole is more than that of 6-bromo-2-(6-ethylpyridin-2-yl)-2H-indazole.

6-bromo-1-(6-ethylpyridin-2-yl)-1H-indazole, 230 mg, as a yellow solid, Y: 26%. ESI-MS (M+H)+: 302.0, 304.0.

6-bromo-2-(6-ethylpyridin-2-yl)-2H-indazole, 170 mg, as a yellow solid, Y: 19%. ESI-MS (M+H)+: 302.0, 304.0.

Synthesis of 1-(6-ethylpyridin-2-yl)-6-(4,4,5,5-tetramethyl-1,3,2-dioxaborolan-2-yl)-1H-indazole

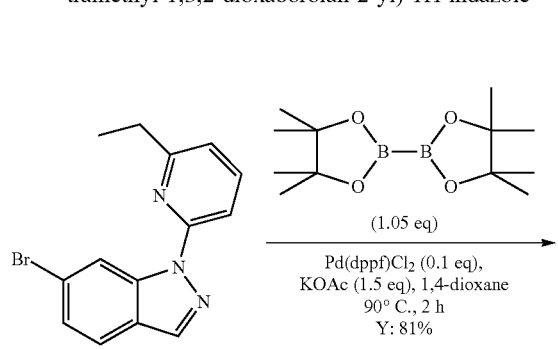

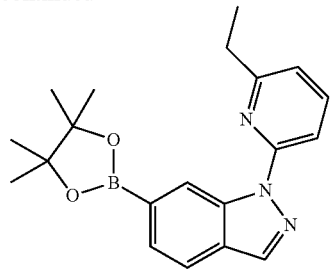

The preparation of 1-(6-ethylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 216 mg, as a yellow solid, Y: 81%. ESI-MS (M+H)+: 350.2.

Synthesis of 1-(6-(1-(6-ethylpyridin-2-yl)-1H-indazol-6-yl)pyridin-2-yl)ethanone

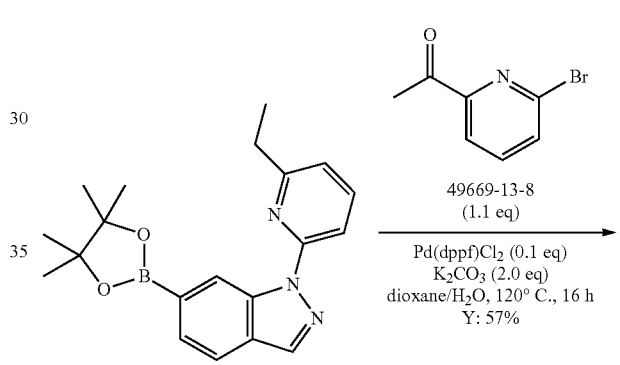

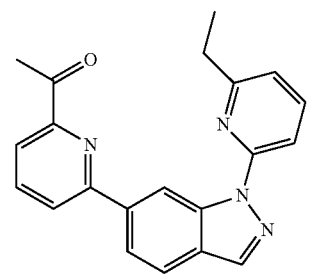

The preparation of 1-(6-(1-(6-ethylpyridin-2-yl)-1H-indazol-6-yl)pyridin-2-yl)ethanone was the same as that of tert-butyl (6-(6-acetylpyridin-2-yl)-1-(6-methylpyridin-2-yl)-1H-indazol-4-yl)carbamate. 120 mg, as a white solid, Y: 57%. ESI-MS (M+H)+: 343.2. HPLC: 95.58%. $^1$H NMR (400 MHz, CDCl$_3$) δ: 9.71 (s, 1H), 8.23 (s, 1H), 8.09-8.02 (m, 3H), 7.95 (t, J=8.0 Hz, 1H), 7.90-7.87 (m, 2H), 7.77 (t, J=8.0 Hz, 1H), 7.06 (d, J=7.6 Hz, 1H), 2.98 (q, J=7.6 Hz, 2H), 2.89 (s, 3H), 1.48 (t, J=7.6 Hz, 3H).

Synthesis of (E)-1-(6-(1-(6-ethylpyridin-2-yl)-1H-indazol-6-yl)pyridin-2-yl)ethanone oxime

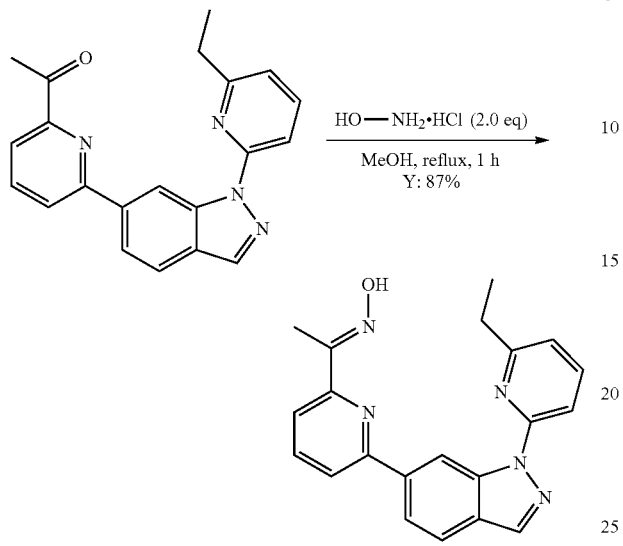

The preparation of (E)-1-(6-(1-(6-ethylpyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 100 mg, as a white solid, Y: 87%. ESI-MS (M+H)+: 358.2. HPLC: 100.00% $^1$H NMR (400 MHz, CD$_3$OD) δ: 9.66 (s, 1H), 8.27 (s, 1H), 8.02 (dd, J=8.4, 1.2 Hz, 1H), 7.92-7.81 (m, 6H), 7.14 (dd, J=6.4, 1.2 Hz, 1H), 2.97 (q, J=7.6 Hz, 2H), 2.47 (s, 3H), 1.46 (t, J=7.6 Hz, 3H).

Synthesis of 1-(6-(1-(6-ethylpyridin-2-yl)-1H-indazol-6-yl)pyridin-2-yl)ethanamine

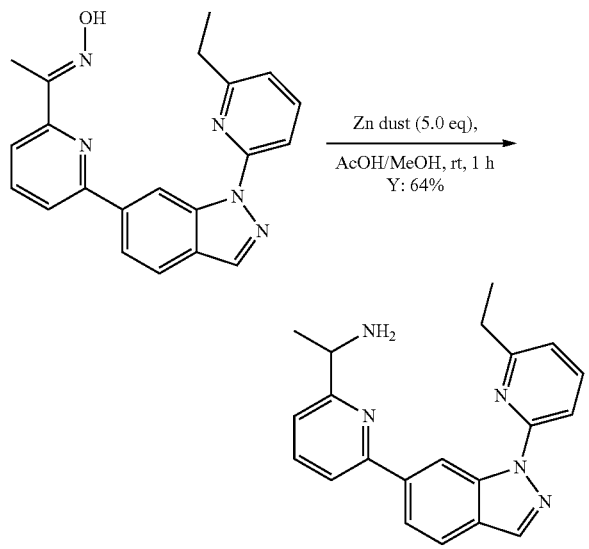

The preparation of 1-(6-(1-(6-ethylpyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 55 mg, as a white solid, Y: 64%. ESI-MS (M+H)+: 344.2. HPLC: 100.00% $^1$H NMR (400 MHz, CD$_3$OD) δ: 9.56 (s, 1H), 8.20 (s, 1H), 7.91 (d, J=8.4 Hz, 1H), 7.83 (d, J=8.8 Hz, 1H), 7.80-7.73 (m, 4H), 7.30 (d, J=7.2 Hz, 1H), 7.06 (d, J=6.4 Hz, 1H), 4.13 (q, J=7.6 Hz, 1H), 2.89 (q, J=7.6 Hz, 2H), 1.46-1.40 (m, 6H).

Example 121. 1-(6-(1-(6-isopropylpyridin-2-yl)-1H-indazol-6-yl)pyridin-2-yl)ethanamine

Synthesis of 6-bromo-1-(6-isopropylpyridin-2-yl)-1H-indazole

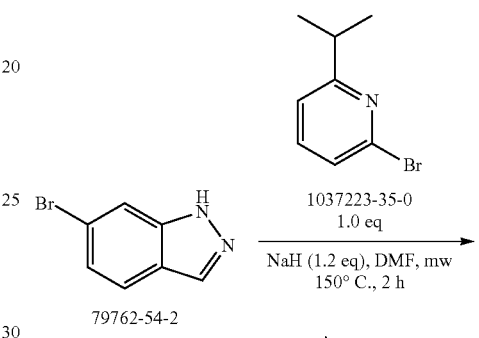

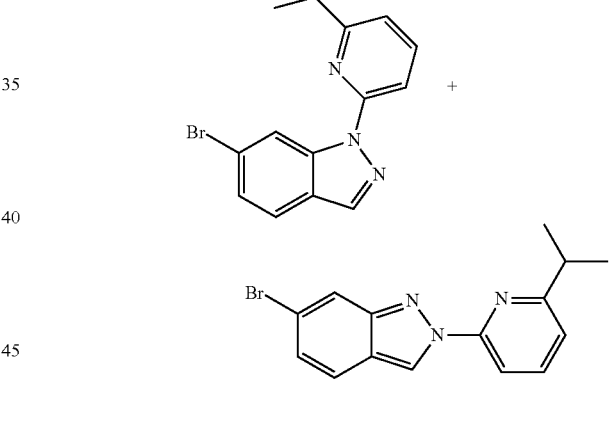

The preparation of 6-bromo-1-(6-isopropylpyridin-2-yl)-1H-indazole was the same as that of 6-bromo-1-(6-methylpyridin-2-yl)-1H-indazole. The mixture of 6-bromo-1-(6-isopropylpyridin-2-yl)-1H-indazole and 6-bromo-2-(6-isopropylpyridin-2-yl)-2H-indazole was purified by pre-TLC (PE/EA=10/1) to give 6-bromo-1-(6-isopropylpyridin-2-yl)-1H-indazole and 6-bromo-2-(6-isopropylpyridin-2-yl)-2H-indazole. R$_f$ value of 6-bromo-1-(6-isopropylpyridin-2-yl)-1H-indazole is more than that of 6-bromo-2-(6-isopropylpyridin-2-yl)-2H-indazole.

6-bromo-1-(6-isopropylpyridin-2-yl)-1H-indazole, 200 mg, as a yellow solid, Y: 23%. ESI-MS (M+H)+: 316.0, 318.0.

6-bromo-2-(6-isopropylpyridin-2-yl)-2H-indazole, 180 mg, as a yellow solid, Y: 21%. ESI-MS (M+H)+: 316.0, 318.0.

243

Synthesis of 1-(6-isopropylpyridin-2-yl)-6-(4,4,5,5-tetramethyl-1,3,2-dioxaborolan-2-yl)-1H-indazole

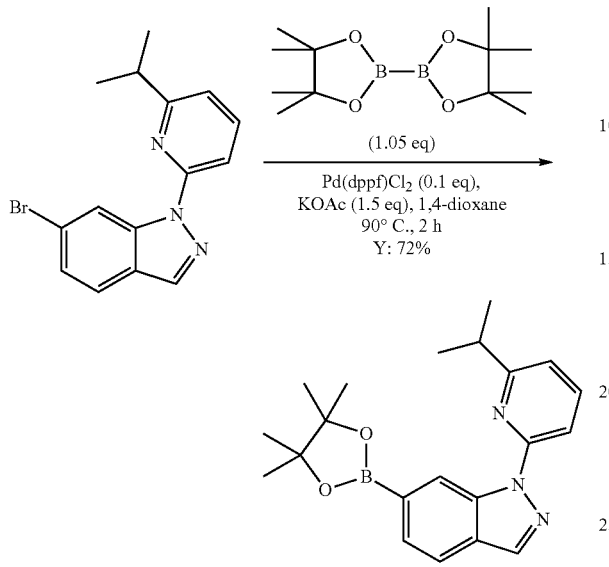

The preparation of 1-(6-isopropylpyridin-2-yl)-6-(4,4,5,5-tetramethyl-1,3,2-dioxaborolan-2-yl)-1H-indazole was the same as that of 1-(6-methylpyridin-2-yl)-6-(4,4,5,5-tetramethyl-1,3,2-dioxaborolan-2-yl)-1H-indazole. 100 mg, as a yellow solid, Y: 72%. ESI-MS (M+H)$^+$: 364.2.

Synthesis of 1-(6-(1-(6-isopropylpyridin-2-yl)-1H-indazol-6-yl)pyridin-2-yl)ethanone

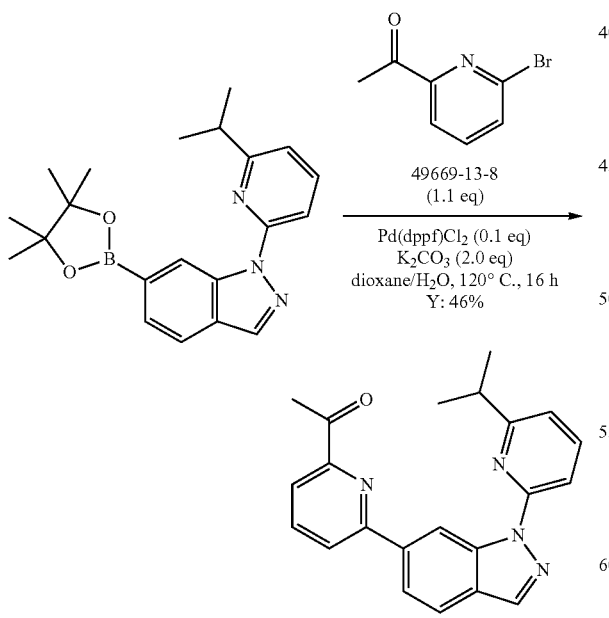

The preparation of 1-(6-(1-(6-isopropylpyridin-2-yl)-1H-indazol-6-yl)pyridin-2-yl)ethanone was the same as that of tert-butyl (6-(6-acetylpyridin-2-yl)-1-(6-methylpyridin-2-yl)-1H-indazol-4-yl)carbamate. 45 mg, as a white solid, Y:

244

46%. ESI-MS (M+H)$^+$: 357.2. $^1$H NMR (400 MHz, CDCl$_3$) δ: 9.67 (s, 1H), 8.24 (s, 1H), 8.09-8.02 (m, 3H), 7.90 (d, J=7.6 Hz, 1H), 7.83 (d, J=8.0 Hz, 2H), 7.71 (t, J=8.0 Hz, 1H), 7.01 (d, J=7.2 Hz, 1H), 3.17-3.10 (m, 1H), 2.87 (s, 3H), 1.39 (d, J=7.6 Hz, 6H).

Synthesis of (E)-1-(6-(1-(6-isopropylpyridin-2-yl)-1H-indazol-6-yl)pyridin-2-yl)ethanone oxime

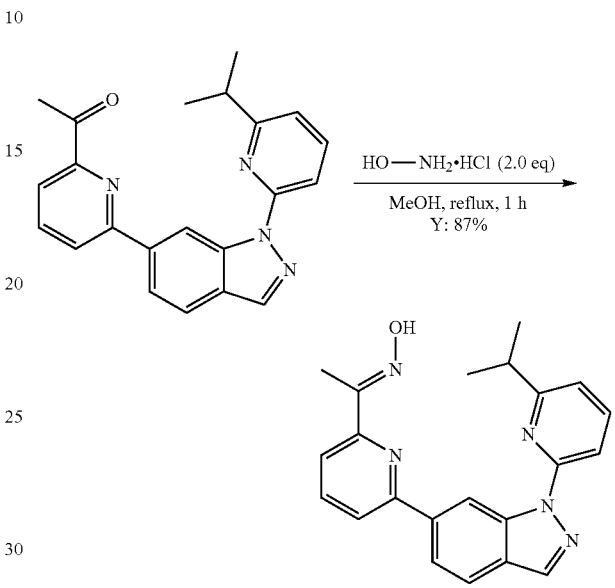

The preparation of (E)-1-(6-(1-(6-isopropylpyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 41 mg, as a yellow solid, Y: 87%. ESI-MS (M+H)$^+$: 372.1.

Synthesis of 1-(6-(1-(6-isopropylpyridin-2-yl)-1H-indazol-6-yl)pyridin-2-yl)ethanamine

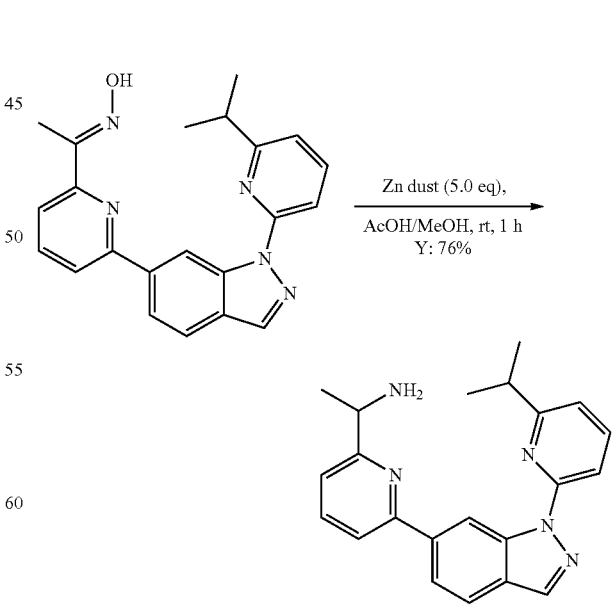

The preparation of 1-(6-(1-(6-isopropylpyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 30 mg, as a yellow solid, Y: 76%. ESI-MS (M+H)+: 358.2. HPLC: 100.00% ¹H NMR (400 MHz, CD₃OD) δ: 9.62 (s, 1H), 8.25 (s, 1H), 7.98 (d, J=8.8 Hz, 1H), 7.89-7.79 (m, 5H), 7.37 (d, J=7.2 Hz, 1H), 7.12 (d, J=6.8 Hz, 1H), 4.24 (q, J=6.4 Hz, 1H), 3.19-3.15 (m, 1H), 1.52 (d, J=6.8 Hz, 3H), 1.46 (d, J=6.8 Hz, 6H).

Example 122. 1-(6-(1-(pyridin-2-yl)-1H-indazol-6-yl)pyridin-2-yl)ethanamine

Synthesis of 1-(6-(1-(pyridin-2-yl)-1H-indazol-6-yl)pyridin-2-yl)ethanone

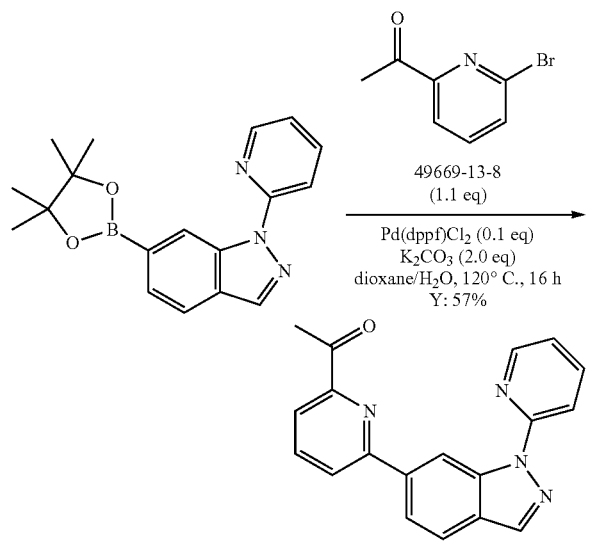

The preparation of 1-(6-(1-(pyridin-2-yl)-1H-indazol-6-yl)pyridin-2-yl)ethanone was the same as that of tert-butyl (6-(6-acetylpyridin-2-yl)-1-(6-methylpyridin-2-yl)-1H-indazol-4-yl)carbamate. 200 mg, as a white solid, Y: 57%. ESI-MS (M+H)+: 315.1. HPLC: 100.00%.

¹H NMR (400 MHz, CDCl₃) δ: 9.52 (s, 1H), 8.52 (dd, J=5.2, 1.2 Hz, 1H), 8.18 (s, 1H), 8.07-8.01 (m, 3H), 7.96 (dd, J=7.6, 0.8 Hz, 1H), 7.89 (t, J=8.0 Hz, 1H), 7.83 (d, J=9.2 Hz, 1H), 7.79 (dd, J=8.4, 1.6 Hz, 1H), 7.13 (dd, J=6.4, 0.8 Hz, 1H), 2.82 (s, 3H).

Synthesis of (E)-1-(6-(1-(pyridin-2-yl)-1H-indazol-6-yl)pyridin-2-yl)ethanone oxime

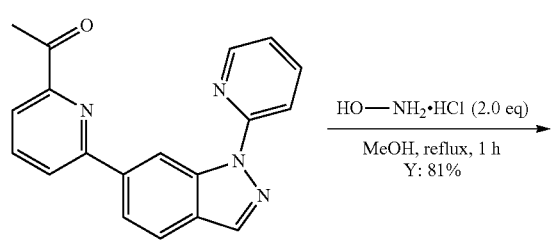

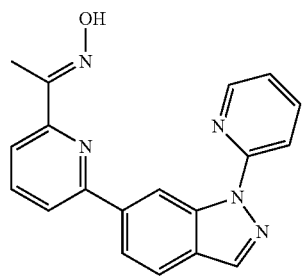

The preparation of (E)-1-(6-(1-(pyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 140 mg, as a yellow solid, Y: 81%. ESI-MS (M+H)+: 330.1. HPLC: 100.00%. ¹H NMR (400 MHz, CD₃OD) δ: 9.45 (s, 1H), 8.50 (d, J=4.0 Hz, 1H), 8.21 (s, 1H), 8.01-7.97 (m, 2H), 7.88-7.76 (m, 5H), 7.19 (dd, J=7.2, 1.2 Hz, 1H), 2.36 (s, 3H).

Synthesis of 1-(6-(1-(pyridin-2-yl)-1H-indazol-6-yl)pyridin-2-yl)ethanamine

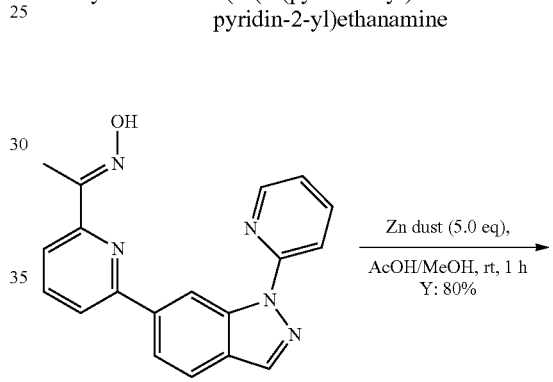

The preparation of 1-(6-(1-(pyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 100 mg, as yellow oil, Y: 80%. ESI-MS (M+H)+: 316.1. HPLC: 100.00% ¹H NMR (400 MHz, CD₃OD) δ: 9.26 (s, 1H), 8.44 (dd, J=4.4, 0.8 Hz, 1H), 8.13 (s, 1H), 7.92-7.87 (m, 2H), 7.80-7.78 (m, 1H), 7.77-7.63 (m, 3H), 7.24 (d, J=7.6 Hz, 1H), 7.12 (dd, J=7.2, 5.2 Hz, 1H), 4.10 (q, J=6.8 Hz, 1H), 1.45 (d, J=6.8 Hz, 3H).

Example 123. (6-(6-(6-(1-aminoethyl)pyridin-2-yl)-1H-indazol-1-yl)pyridin-2-yl)methanol Synthesis of 6-(6-(6-acetylpyridin-2-yl)-1H-indazol-1-yl)picolinonitrile

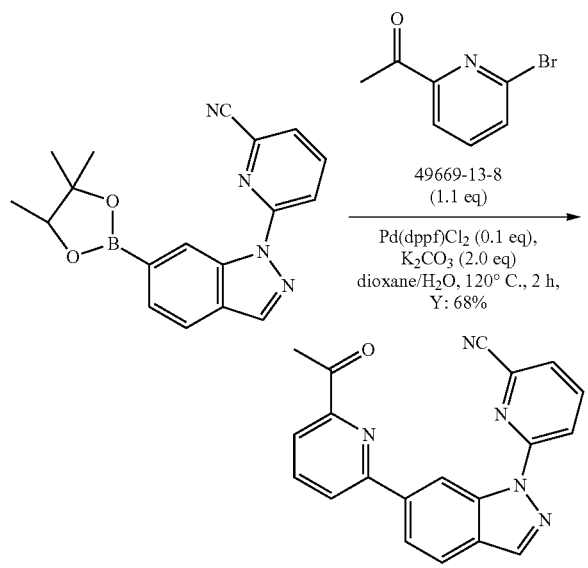

The preparation of 6-(6-(6-acetylpyridin-2-yl)-1H-indazol-1-yl)picolinonitrile was the same as that of tert-butyl (6-(6-acetylpyridin-2-yl)-1-(6-methylpyridin-2-yl)-1H-indazol-4-yl)carbamate. 200 mg, as a white solid, Y: 68%. ESI-MS (M+H)$^+$: 340.1. HPLC: 92.68%. $^1$H NMR (400 MHz, CDCl$_3$) δ: 9.72 (s, 1H), 8.63 (d, J=0.8 Hz, 1H), 8.40 (d, J=8.0 Hz, 1H), 8.37 (d, J=8.8 Hz, 1H), 8.27 (d, J=7.6 Hz, 1H), 8.25 (d, J=7.2 Hz, 1H), 8.21-8.15 (m, 2H), 8.09 (d, J=8.4 Hz, 1H), 7.99 (t, J=8.0 Hz, 1H), 2.86 (s, 3H).

Synthesis of methyl 6-(6-(6-acetylpyridinazol-1-yl)picolinate

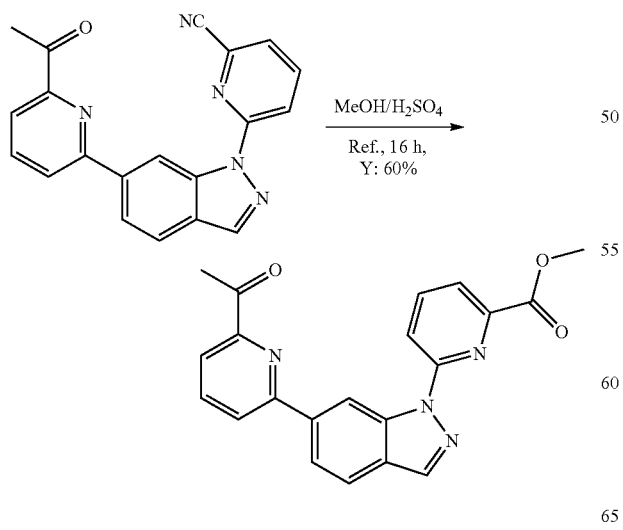

A solution of 6-(6-(6-acetylpyridin-2-yl)-1H-indazol-1-yl)picolinonitrile (180 mg, 0.53 mmol, 1.0 eq) in MeOH (50 mL)/H$_2$SO$_4$ (2 mL) was refluxed for 16 h. After concentration, the residue was dissolved in DCM (100 mL) and adjusted pH=8 with 3 N NaOH solution. The organic phase was concentrated and the residue was purified by silica gel chromatography with PE/EA (1/1) as eluent to give methyl 6-(6-(6-acetylpyridin-2-yl)-1H-indazol-1-yl)picolinate. 118 mg, as a yellow solid, Y: 60%. ESI-MS (M+H)$^+$: 373.1.

Synthesis of (E)-methyl 6-(6-(6-(1-(hydroxyimino)ethyl)pyridin-2-yl)-1H-indazol-1-yl)picolinate

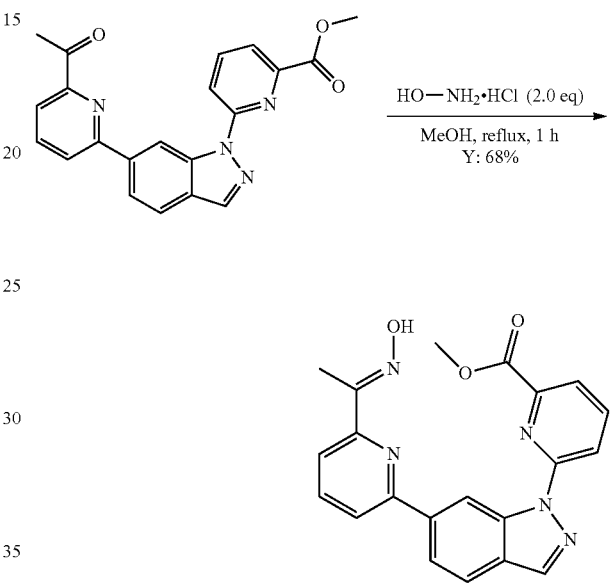

The preparation of (E)-methyl 6-(6-(6-(1-(hydroxyimino)ethyl)pyridin-2-yl)-1H-indazol-1-yl)picolinate was the same as that of 2-(1-(6-(trifluoromethyl)pyridin-2-yl)-1H-indazol-6-yl)-5H-cyclopenta[b]pyridin-7(6H)-one oxime. 83 mg, as a white solid, Y: 68%. ESI-MS (M+H)$^+$: 388.2. HPLC: 98.46%. $^1$H NMR (400 MHz, CD$_3$OD) δ: 9.86 (s, 1H), 8.34 (s, 1H), 8.30 (d, J=8.4 Hz, 1H), 8.24 (dd, J=8.8, 1.6 Hz, 1H), 8.12 (t, J=8.0 Hz, 1H), 8.07 (dd, J=5.6, 4.0 Hz, 1H), 8.01 (d, J=7.6 Hz, 1H), 7.94 (d, J=8.4 Hz, 1H), 7.92-7.90 (m, 2H), 4.07 (s, 3H), 2.46 (s, 3H).

Synthesis of methyl 6-(6-(6-(1-aminoethyl)pyridin-2-yl)-1H-indazol-1-yl)picolinate

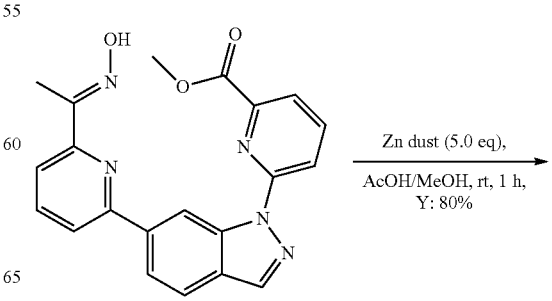

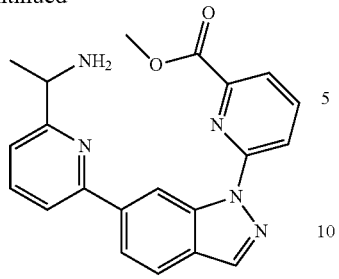

The preparation of methyl 6-(6-(6-(1-aminoethyl)pyridin-2-yl)-1H-indazol-1-yl)picolinate was the same as that of 2-(1-(6-(trifluoromethyl)pyridin-2-yl)-1H-indazol-6-yl)-6,7-dihydro-5H-cyclopenta[b]pyridin-7-amine. 56 mg, as a white solid, Y: 80%. ESI-MS (M+H)$^+$: 374.1.

Synthesis of (6-(6-(6-(1-aminoethyl)pyridin-2-yl)-1H-indazol-1-yl)pyridin-2-yl)methanol

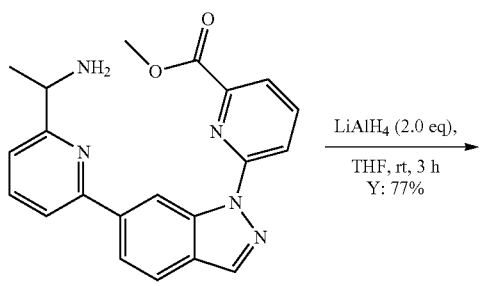

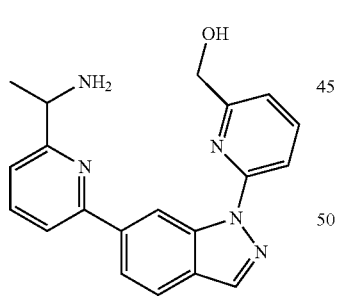

The preparation of (6-(6-(6-(1-aminoethyl)pyridin-2-yl)-1H-indazol-1-yl)pyridin-2-yl)methanol was the same as that of (6-(6-(1-aminoethyl)pyridin-2-yl)-1-(6-(trifluoromethyl)pyridin-2-yl)-1H-indazol-4-yl)methanol. 40 mg, as a white solid, Y: 77%. ESI-MS (M+H)$^+$: 346.2. HPLC: 100.00%. $^1$H NMR (400 MHz, CD$_3$OD) δ: 9.78 (s, 1H), 8.32 (s, 1H), 8.16 (dd, J=8.4, 1.2 Hz, 1H), 8.08 (d, J=7.2 Hz, 1H), 8.03-7.94 (m, 4H), 7.47 (d, J=7.6 Hz, 1H), 7.36 (t, J=4.0 Hz, 1H), 4.89 (s, 2H), 4.71 (q, J=6.8 Hz, 1H), 1.73 (d, J=7.2 Hz, 3H).

Example 124. 1-(4-methyl-6-(1-(6-methylpyridin-2-yl)-1H-indazol-6-yl)pyridin-2-yl)ethanamine Synthesis of 6-chloro-N-methoxy-N,4-dimethylpicolinamide

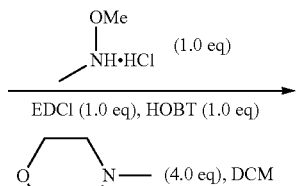

324028-95-7

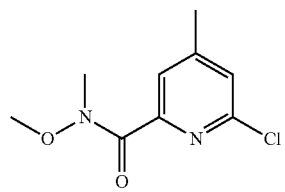

The preparation of 6-chloro-N-methoxy-N,4-dimethylpicolinamide was the same as that of 4-bromo-N-methoxy-N-methylpicolinamide. 600 mg, as a yellow solid, Y: 48%. ESI-MS (M+H)$^+$: 215.1.

Synthesis of 1-(6-chloro-4-methylpyridin-2-yl)ethanone

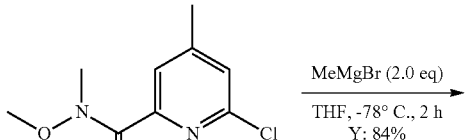

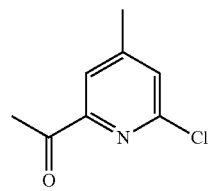

The preparation of 1-(6-chloro-4-methylpyridin-2-yl)ethanone was the same as that of 1-(4-bromopyridin-2-yl)ethanone. 400 mg, as a yellow solid, Y: 84%. ESI-MS (M+H)$^+$: 170.0.

$^1$H NMR (400 MHz, CDCl$_3$) δ: 7.78 (s, 1H), 7.34 (s, 1H), 2.70 (s, 3H), 2.42 (s, 3H).

251

Synthesis of 1-(4-methyl-6-(1-(6-methylpyridin-2-yl)-1H-indazol-6-yl)pyridin-2-yl)ethanone

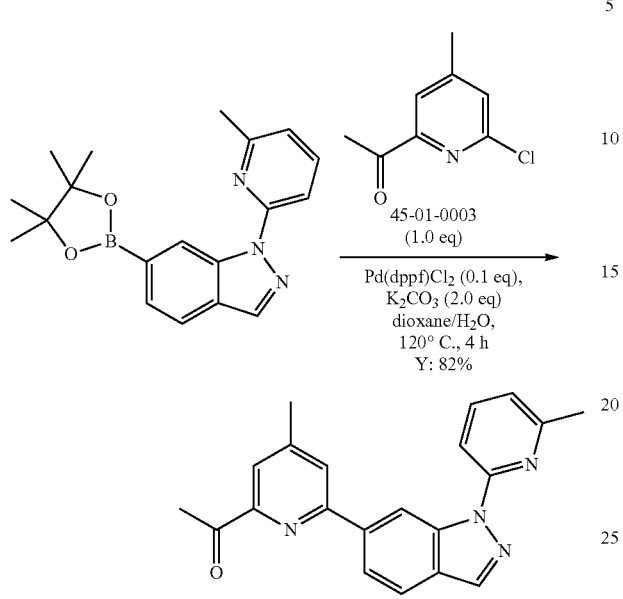

The preparation of 1-(4-methyl-6-(1-(6-methylpyridin-2-yl)-1H-indazol-6-yl)pyridin-2-yl)ethanone was the same as that of tert-butyl (6-(6-acetylpyridin-2-yl)-1-(6-methylpyridin-2-yl)-1H-indazol-4-yl)carbamate. 250 mg, as a yellow solid, Y: 82%. ESI-MS (M+H)$^+$: 343.1. $^1$H NMR (400 MHz, CD$_3$OD) δ: 9.74 (s, 1H), 8.23 (s, 1H), 8.01 (dd, J=8.4, 0.8 Hz, 1H), 7.90-7.86 (m, 4H), 7.75 (t, J=7.6 Hz, 1H), 7.05 (d, J=7.2 Hz, 1H), 2.90 (s, 3H), 2.70 (s, 3H), 2.53 (s, 3H).

Synthesis of (Z)-1-(4-methyl-6-(1-(6-methylpyridin-2-yl)-1H-indazol-6-yl)pyridin-2-yl)ethanone oxime

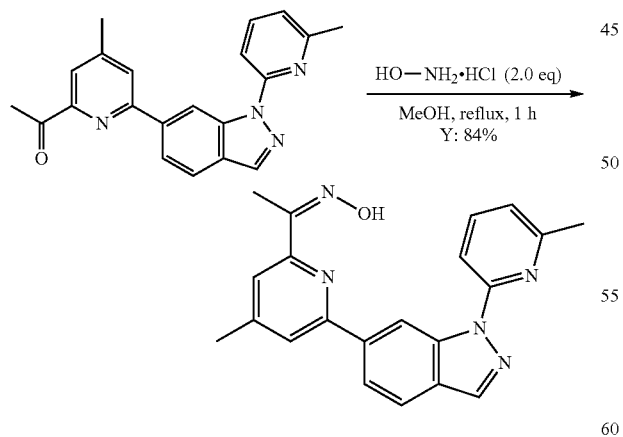

The preparation of (Z)-1-(4-methyl-6-(1-(6-methylpyridin-2-yl)-1H-indazol-6-yl)pyridin-2-yl)ethanone oxime was the same as that of 2-(1-(6-(trifluoromethyl)pyridin-2-yl)-1H-indazol-6-yl)-5H-cyclopenta[b]pyridin-7(6H)-one oxime. 220 mg, as a yellow solid, Y: 84%. ESI-MS (M+H)$^+$: 358.2.

252

Synthesis of 1-(4-methyl-6-(1-(6-methylpyridin-2-yl)-1H-indazol-6-yl)pyridin-2-yl)ethanamine

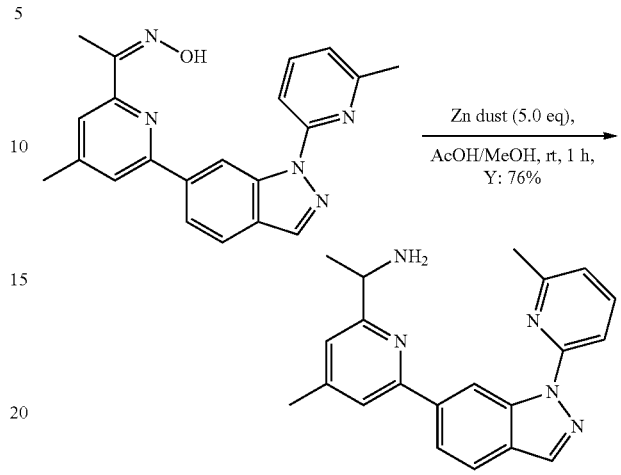

The preparation of 1-(4-methyl-6-(1-(6-methylpyridin-2-yl)-1H-indazol-6-yl)pyridin-2-yl)ethanamine was the same as that of 2-(1-(6-(trifluoromethyl)pyridin-2-yl)-1H-indazol-6-yl)-6,7-dihydro-5H-cyclopenta[b]pyridin-7-amine. 140 mg, as a yellow solid, Y: 76%. ESI-MS (M+H)$^+$:344.1. HPLC: 98.81%. $^1$H NMR (400 MHz, CD$_3$OD) δ: 9.50 (s, 1H), 8.18 (s, 1H), 7.87 (dd, J=6.8, 1.2 Hz, 1H), 7.79 (d, J=6.8 Hz, 1H), 7.74-7.71 (m, 2H), 7.56 (s, 1H), 7.14 (s, 1H), 7.04 (d, J=5.6 Hz, 1H), 4.08 (q, J=5.2 Hz, 1H), 2.59 (s, 3H), 2.40 (s, 3H), 1.47 (d, J=5.2 Hz, 3H).

Example 125. 1-(6-(1-(6-methylpyridin-2-yl)-1H-indazol-6-yl)-4-(trifluoromethyl)pyridin-2-yl)ethanamine Synthesis of 6-(6-chloro-4-(trifluoromethyl)pyridin-2-yl)-1-(6-methylpyridin-2-yl)-1H-indazole

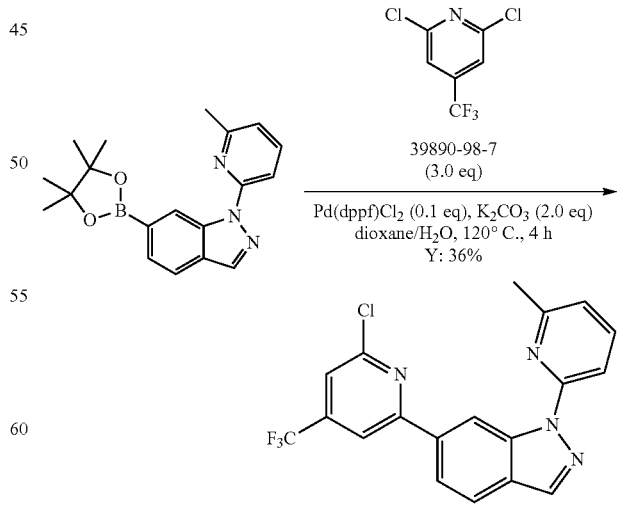

The preparation of 6-(6-chloro-4-(trifluoromethyl)pyridin-2-yl)-1-(6-methylpyridin-2-yl)-1H-indazole was the same as that of tert-butyl (6-(6-acetylpyridin-2-yl)-1-(6- methylpyridin-2-yl)-1H-indazol-4-yl)carbamate. 300 mg, as a yellow solid, Y: 36%. ESI-MS (M+H)+: 389.1.

Synthesis of 6-(1-(6-methylpyridin-2-yl)-1H-indazol-6-yl)-4-(trifluoromethyl)picolinonitrile

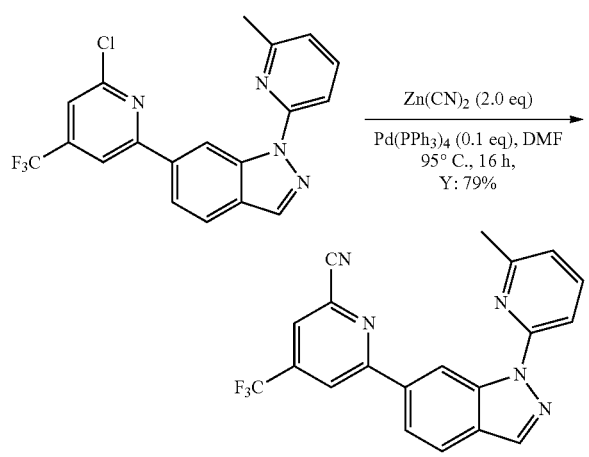

A mixture of 6-(6-chloro-4-(trifluoromethyl)pyridin-2-yl)-1-(6-methylpyridin-2-yl)-1H-indazole (300 mg, 0.77 mmol, 1.0 eq), Zn(CN)₂ (179 mg, 1.54 mmol, 2.0 eq) and Pd(PPh₃)₄(92 mg, 0.08 mmol, 0.1 eq) in DMF (5 mL) was stirred at 95° C. for 16 h. After cooling down to rt, the mixture was diluted with water (50 mL) and extracted with EA (3×60 mL). The combined organic phase was washed with brine and dried over Na₂SO₄. After filtration and concentration, the residue was purified by column chromatography on silica gel (PE/EA=5/1) to give 6-(1-(6-methylpyridin-2-yl)-1H-indazol-6-yl)-4-(trifluoromethyl)picolinonitrile as a brown solid. 480 mg, Y: 79%. ESI-MS (M+H)+: 380.2. ¹H NMR (400 MHz, CD₃OD) δ: 9.67 (s, 1H), 8.30 (s, 1H), 8.24 (s, 1H), 8.02 (dd, J=8.4, 2.0 Hz, 1H), 7.85-7.91 (m, 3H), 7.76 (t, J=8.0 Hz, 1H), 7.06 (t, J=7.6 Hz, 1H), 2.70 (s, 3H).

Synthesis of 1-(6-(1-(6-methylpyridin-2-yl)-1H-indazol-6-yl)-4-(trifluoromethyl)pyridin-2-yl)ethanamine

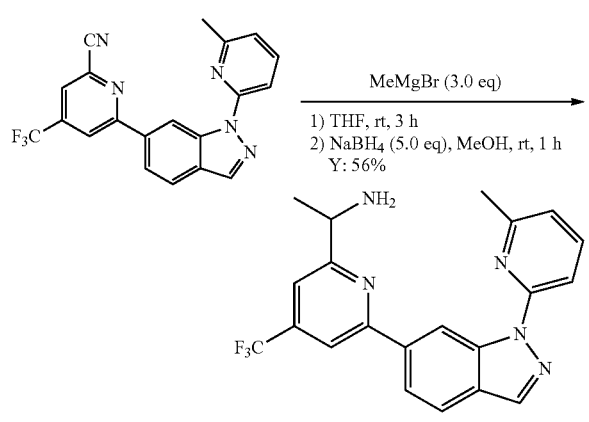

To a solution of 6-(1-(6-methylpyridin-2-yl)-1H-indazol-6-yl)-4-(trifluoromethyl)picolinonitrile (92 mg, 0.24 mmol, 1.0 eq) in anhydrous THF was added MeMgBr (1 M in THF solution, 0.7 mmol, 0.7 ml) at rt. The mixture was stirred at rt for 3 h under N₂. The mixture was added to a solution of NaBH₄ (45 mg, 1.2 mmol, 5.0 eq) in MeOH (20 mL) at rt. The mixture was stirred at rt for 1 h, quenched with H₂O (30 mL) and extracted by DCM (4×30 mL). The combined organic phase was washed with brine (30 mL) and dried over Na₂SO₄. After filtration and concentration, the residue was purified by prep-HPLC (MeOH/H₂O with 0.05% NH₄OH as mobile phase from 5% to 95%) to give 1-(6-(1-(6-methylpyridin-2-yl)-1H-indazol-6-yl)-4-(trifluoromethyl)pyridin-2-yl)ethanamine as a white solid. 54 mg, Y: 56%. ESI-MS (M+H)+: 398.2. HPLC: 95.86%. ¹H NMR (400 MHz, CD₃OD) δ: 9.71 (s, 1H), 8.34 (s, 1H), 8.31 (s, 1H), 8.22 (dd, J=8.4, 1.2 Hz, 1H), 8.01 (d, J=8.8 Hz, 1H), 7.90-7.84 (m, 3H), 7.18 (d, J=6.4 Hz, 1H), 4.84 (q, J=6.8 Hz, 1H), 2.71 (s, 3H), 1.77 (d, J=7.2 Hz, 3H).

Example 126. 6-(6-(6-(1-aminoethyl)pyridin-2-yl)-1H-indazol-1-yl)picolinamide

Synthesis of 6-(6-(6-acetylpyridin-2-yl)-1H-indazol-1-yl)picolinamide

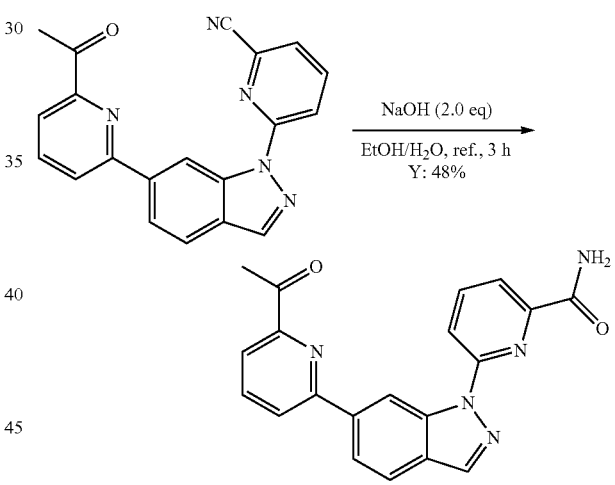

The preparation of 6-(6-(6-acetylpyridin-2-yl)-1H-indazol-1-yl)picolinamide was the same as that of 6-(6-(5-aminopyridin-3-yl)-1H-indazol-1-yl)picolinamide. 120 mg, as a yellow solid, Y: 48%. ESI-MS (M+H)+: 358.1.

Synthesis of (E)-6-(6-(6-(1-(hydroxyimino)ethyl)pyridin-2-yl)-1H-indazol-1-yl)picolinamide

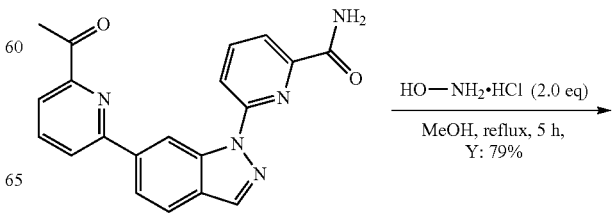

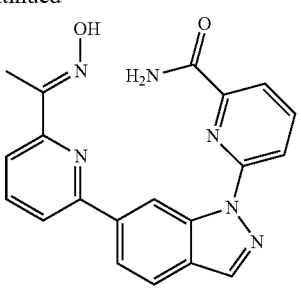

The preparation of (E)-6-(6-(6-(1-(hydroxyimino)ethyl)pyridin-2-yl)-1H-indazol-1-yl)picolinamide was the same as that of 2-(1-(6-(trifluoromethyl)pyridin-2-yl)-1H-indazol-6-yl)-5H-cyclopenta[b]pyridin-7(6H)-one oxime. 100 mg, as yellow oil, Y: 79%. ESI-MS (M+H)$^+$: 373.1. $^1$H NMR (400 MHz, CD$_3$OD) δ: 9.41 (s, 1H), 8.38 (s, 1H), 8.28 (d, J=8.0 Hz 1H), 8.17 (t, J=8.0 Hz, 1H), 8.11 (dd, J=8.4, 1.2 Hz, 1H), 8.03 (d, J=8.0 Hz 1H), 8.01-7.97 (m, 2H), 7.90 (s, 1H), 7.89 (d, J=7.2 Hz 1H), 2.45 (s, 3H).

Synthesis of 6-(6-(6-(1-aminoethyl)pyridin-2-yl)-1H-indazol-1-yl)picolinamide

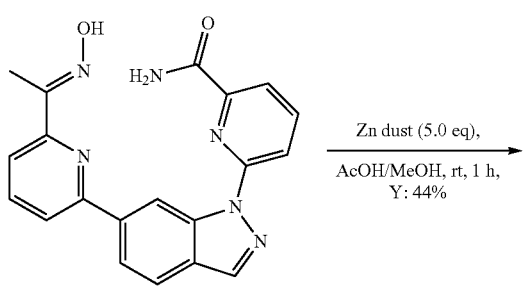

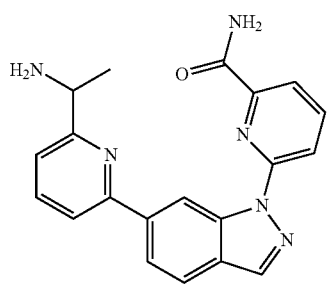

The preparation of 6-(6-(6-(1-aminoethyl)pyridin-2-yl)-1H-indazol-1-yl)picolinamide was the same as that of 2-(1-(6-(trifluoromethyl)pyridin-2-yl)-1H-indazol-6-yl)-6,7-dihydro-5H-cyclopenta[b]pyridin-7-amine. 43 mg, as a yellow solid, Y: 44%. ESI-MS (M+H)$^+$: 359.2. HPLC: 100.00% $^1$H NMR (400 MHz, CD$_3$OD) δ: 9.45 (s, 1H), 8.38 (s, 1H), 8.25 (d, J=8.4 Hz, 1H), 8.21 (dd, J=8.4, 1.2 Hz, 1H), 8.15 (t, J=7.6 Hz, 1H), 8.08 (d, J=8.0 Hz, 1H), 8.02 (d, J=7.6 Hz, 1H), 8.00-7.97 (m, 2H), 7.49 (d, J=7.6 Hz, 1H), 4.71 (q, J=6.8 Hz, 1H), 1.73 (d, J=6.8 Hz, 3H).

Example 127. 1-(6-(1-(6-(trifluoromethyl)pyridin-2-yl)-1H-indazol-6-yl)pyridin-2-yl)propan-1-amine Synthesis of 1-(6-(1-(6-(trifluoromethyl)pyridin-2-yl)-1H-indazol-6-yl)pyridin-2-yl)propan-1-amine

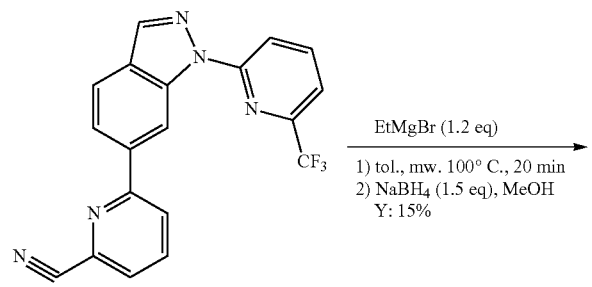

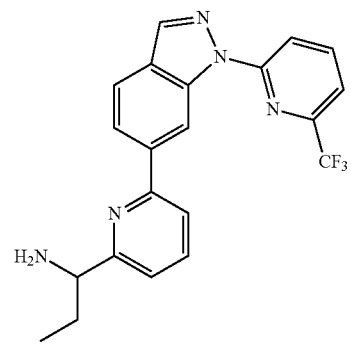

To a solution of 6-(1-(6-(trifluoromethyl)pyridin-2-yl)-1H-indazol-6-yl)picolinonitrile (180 mg, 0.49 mmol, 1.0 eq) in anhydrous toluene was added EtMgBr (1 M in THF solution, 0.6 mmol, 0.6 ml) at rt. The mixture was stirred at 100° C. for 20 min under microwave. After cooling to rt, the mixture was added to a solution of NaBH$_4$ (28 mg, 0.74 mmol, 1.5 eq) in MeOH (20 mL) at 0° C. The mixture was stirred at rt for 30 min, quenched with H$_2$O (30 mL) and extracted by DCM (4×30 mL). The combined organic phase was washed with brine (30 mL) and dried over Na$_2$SO$_4$. After filtration and concentration, the residue was purified by prep-HPLC (MeOH/H$_2$O with 0.05% NH$_4$OH as mobile phase from 5% to 95%) to give 1-(6-(1-(6-(trifluoromethyl)pyridin-2-yl)-1H-indazol-6-yl)pyridin-2-yl)propan-1-amine as a yellow solid. 29 mg, Y: 15%. ESI-MS (M+H)$^+$: 398.1. HPLC: 93.13%. $^1$H NMR (400 MHz, CD$_3$OD) δ: 9.62 (d, J=0.4 Hz, 1H), 8.36 (s, 1H), 8.35 (d, J=8.0 Hz, 1H), 8.17 (t, J=8.0 Hz, 1H), 8.06 (dd, J=8.4, 1.2 Hz, 1H), 7.94 (d, J=8.4 Hz, 1H), 7.90-7.84 (m, 2H), 7.68 (d, J=7.2 Hz, 1H), 7.34 (dd, J=6.8, 2.0 Hz, 1H), 3.94 (t, J=6.8 Hz, 1H), 1.98-1.86 (m, 2H), 0.94 (d, J=7.2 Hz, 3H).

Example 128. cyclopropyl(6-(1-(6-(trifluoromethyl)pyridin-2-yl)-1H-indazol-6-yl)pyridin-2-yl)methanamine Synthesis of cyclopropyl(6-(1-(6-(trifluoromethyl)pyridin-2-yl)-1H-indazol-6-yl)pyridin-2-yl)methanamine

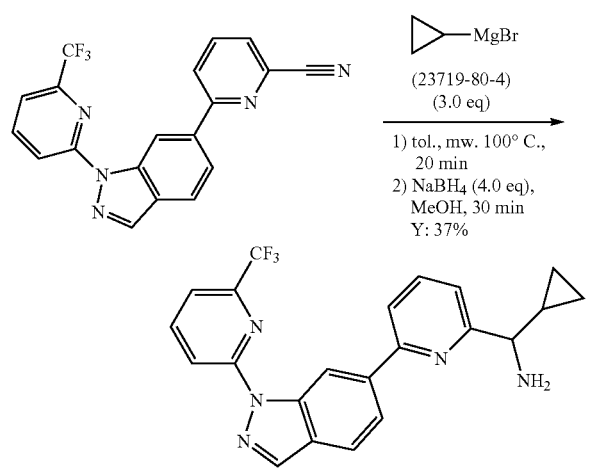

The preparation of cyclopropyl(6-(1-(6-(trifluoromethyl)pyridin-2-yl)-1H-indazol-6-yl)pyridin-2-yl)methanamine was the same as that of 1-(6-(1-(6-(trifluoromethyl)pyridin-2-yl)-1H-indazol-6-yl)pyridin-2-yl)propan-1-amine. 83 mg, as brown oil, Y: 37%. ESI-MS (M+H)$^+$: 410.2. HPLC: 100.00%. $^1$H NMR (400 MHz, CD$_3$OD) δ: 9.62 (s, 1H), 8.36 (s, 1H), 8.35 (d, J=7.6 Hz, 1H), 8.17 (t, J=8.0 Hz, 1H), 8.09 (dd, J=8.4, 1.2 Hz, 1H), 7.94 (dd, J=8.4, 0.8 Hz, 1H), 7.92-7.88 (m, 2H), 7.68 (d, J=7.6 Hz, 1H), 7.41 (dd, J=6.4, 2.4 Hz, 1H), 3.33 (d, J=6.8 Hz, 1H), 1.29-1.27 (m, 1H), 0.72-0.70 (m, 1H), 0.58-0.43 (m, 3H).

Example 129. 2-(6-(1-(6-(trifluoromethyl)pyridin-2-yl)-1H-indazol-6-yl)pyridin-2-yl)propan-2-amine Synthesis of 2-(6-bromopyridin-2-yl)propan-2-ol

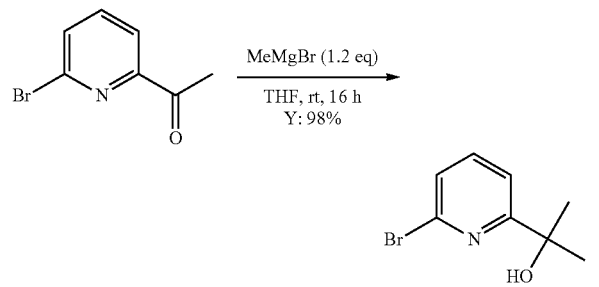

To a solution of 1-(6-bromo-pyridin-2-yl)-ethanone (4.0 g, 20 mmol) in anhydrous THF (50 mL) at 0° C. was added a solution of methyl magnesium bromide (3.0 M, 8.0 mL, 24 mmol, 1.2 eq) in THF dropwise over 20 min. The mixture was stirred at rt for 16 h, quenched with H$_2$O (30 mL) and extracted by EA (4×30 mL). The organic phase was washed with brine (30 mL) and dried over Na$_2$SO$_4$. After filtration and concentration, the residue was directly used for next step without further purification. 4.2 g, Y: 98%. ESI-MS (M+H)$^+$: 216.0

Synthesis of N-(2-(6-bromopyridin-2-yl)propan-2-yl)acetamide

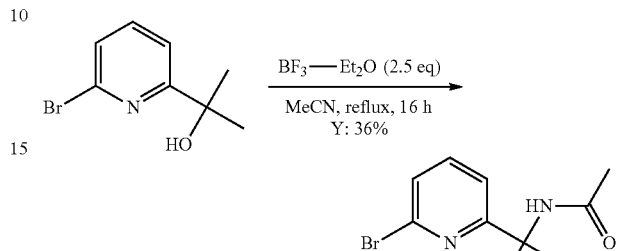

To a solution of 2-(6-bromopyridin-2-yl)propan-2-ol (2.0 g, 9.26 mmol) in MeCN (30 mL) was added BF$_3$-Et$_2$O (3.7 mL, 23.1 mmol, 2.5 eq) at rt. The mixture was refluxed for 16 h. After cooling to rt, the mixture was neutralized with 5 N NaOH and extracted with DCM (100 mL). The organic phase was washed with brine (30 mL) and dried over Na$_2$SO$_4$. After filtration and concentration, the residue was purified by column chromatography (silica gel, PE/EA=1/1) to afford the compound N-(2-(6-bromopyridin-2-yl)propan-2-yl)acetamide (860 mg, Y: 36%). ESI-MS (M+H)$^+$: 257.0

Synthesis of N-(2-(6-(1-(6-(trifluoromethyl)pyridin-2-yl)-1H-indazol-6-yl)pyridin-2-yl)propan-2-yl)acetamide

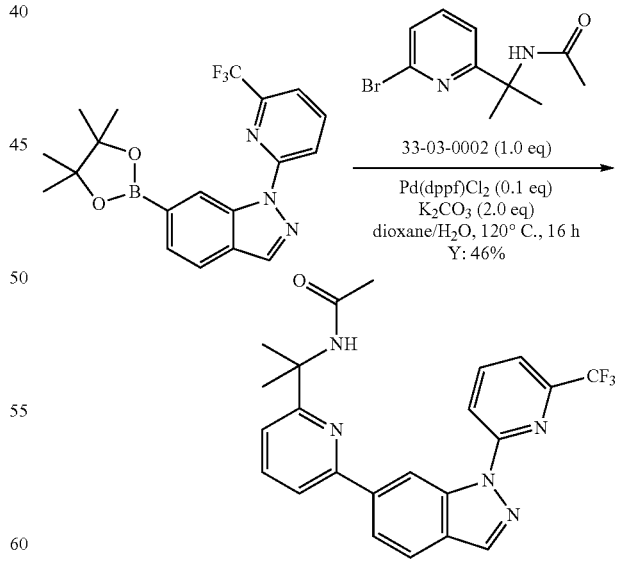

The preparation of N-(2-(6-(1-(6-(trifluoromethyl)pyridin-2-yl)-1H-indazol-6-yl)pyridin-2-yl)propan-2-yl)acetamide was the same as that of tert-butyl (6-(6-acetylpyridin-2-yl)-1-(6-methylpyridin-2-yl)-1H-indazol-4-yl)carbamate. 100 mg, as a white solid, Y: 46%. ESI-MS (M+H)$^+$: 440.1

Synthesis of 2-(6-(1-(6-(trifluoromethyl)pyridin-2-yl)-1H-indazol-6-yl)pyridin-2-yl)propan-2-amine

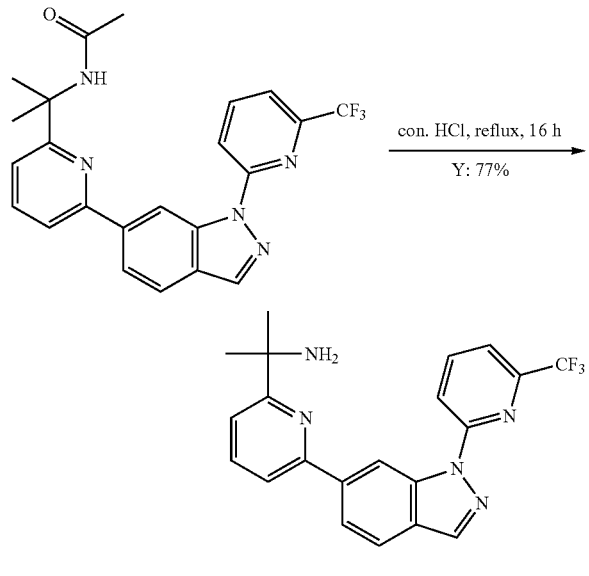

A mixture of N-(2-(6-(1-(6-(trifluoromethyl)pyridin-2-yl)-1H-indazol-6-yl)pyridin-2-yl)propan-2-yl)acetamide (100 mg, 0.23 mmol) in conc. HCl (5 mL) was refluxed for 16 h. After concentration, the residue was basified with sat. NaHCO$_3$ and extracted with DCM (3×30 mL). The combined organic layers were washed with brine and dried over Na$_2$SO$_4$. After filtration and concentration, the residue was purified by prep-HPLC (MeOH/H$_2$O with 0.05% NH$_4$OH as mobile phase from 5% to 95%) to give 2-(6-(1-(6-(trifluoromethyl)pyridin-2-yl)-1H-indazol-6-yl)pyridin-2-yl)propan-2-amine as a brown solid. 70 mg, Y: 77%. ESI-MS (M+H)$^+$: 398.2. HPLC: 100.00%. $^1$H NMR (400 MHz, CDCl$_3$) δ: 9.55 (s, 1H), 8.21 (d, J=8.4 Hz, 1H), 8.17 (s, 1H), 8.02 (d, J=8.4 Hz, 1H), 7.93 (t, J=8.0 Hz, 1H), 7.77 (d, J=8.4 Hz, 1H), 7.73-7.70 (m, 2H), 7.46 (d, J=8.4 Hz, 1H), 7.37-7.35 (m, 1H), 2.29 (br, 2H), 1.56 (s, 6H).

Example 130. 1-(6-(1-(6-methylpyridin-2-yl)-1H-indazol-6-yl)pyridin-2-yl)ethanol Synthesis of 1-(6-(1-(6-methylpyridin-2-yl)-1H-indazol-6-yl)pyridin-2-yl)ethanone

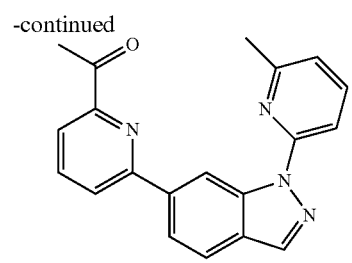

The preparation of 1-(6-(1-(6-methylpyridin-2-yl)-1H-indazol-6-yl)pyridin-2-yl)ethanone was the same as that of tert-butyl (6-(6-acetylpyridin-2-yl)-1-(6-methylpyridin-2-yl)-1H-indazol-4-yl)carbamate. 100 mg, as a yellow solid. Y: 68%. ESI-MS (M+H)$^+$: 329.1.

Synthesis of 1-(6-(1-(6-methylpyridin-2-yl)-1H-indazol-6-yl)pyridin-2-yl)ethanol

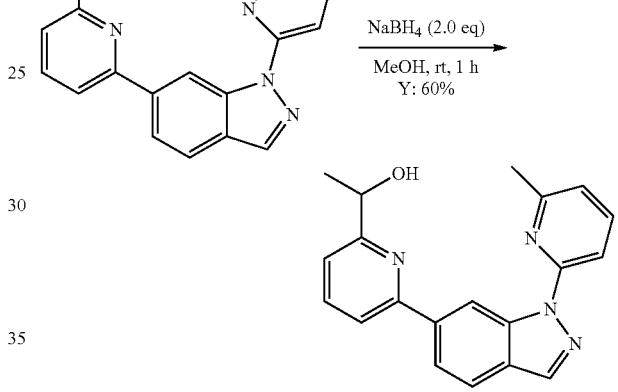

To a solution of 1-(6-(1-(6-methylpyridin-2-yl)-1H-indazol-6-yl)pyridin-2-yl)ethanone (100 mg, 0.3 mmol, 1.0 eq) in MeOH (2 mL) was added NaBH$_4$ (23 mg, 0.6 mmol, 2.0 eq) at rt. The mixture was stirred at rt for 1 h. After concentration, the residue was purified by Pre-HPLC (MeOH/H$_2$O with 0.05% NH$_4$OH as mobile phase from 5% to 95%) to give 1-(6-(1-(6-methylpyridin-2-yl)-1H-indazol-6-yl)pyridin-2-yl)ethanol as a yellow solid. 60 mg, Y: 60%. ESI-MS (M+H)$^+$: 331.1. HPLC: 98.98%. $^1$H NMR (400 MHz, CD$_3$OD) δ: 9.51 (s, 1H), 8.23 (s, 1H), 7.93-7.77 (m, 6H), 7.50 (d, J=7.6 Hz, 1H), 7.10-7.08 (m, 1H), 4.96 (q, J=6.8 Hz, 1H), 2.63 (s, 3H), 1.58 (d, J=6.4 Hz, 3H).

Example 131. cyclopropyl(6-(1-(6-methylpyridin-2-yl)-1H-indazol-6-yl)pyridin-2-yl)methanamine Synthesis of cyclopropyl(6-(1-(6-methylpyridin-2-yl)-1H-indazol-6-yl)pyridin-2-yl)methanamine

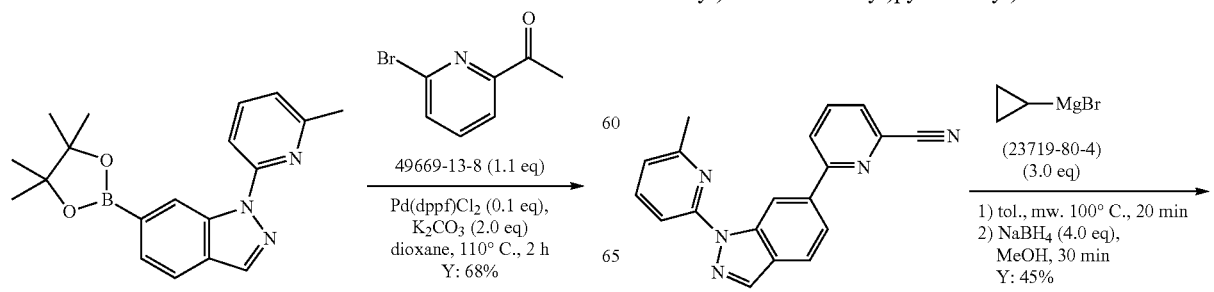

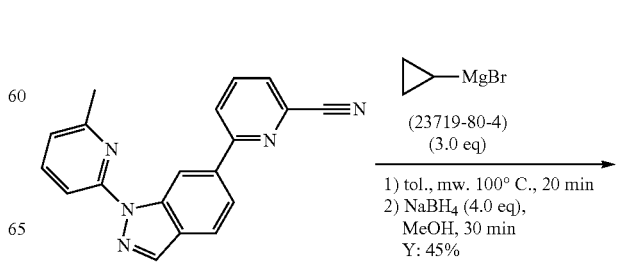

-continued

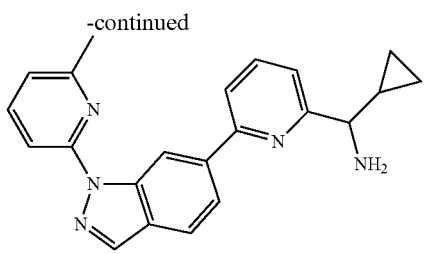

The preparation of cyclopropyl(6-(1-(6-methylpyridin-2-yl)-1H-indazol-6-yl)pyridin-2-yl)methanamine was the same as that of 1-(6-(1-(6-(trifluoromethyl)pyridin-2-yl)-1H-indazol-6-yl)pyridin-2-yl)propan-1-amine. 167 mg, as a yellow solid, Y: 45%. ESI-MS (M+H)⁺: 356.2. HPLC: 96.74%. ¹H NMR (400 MHz, CD₃OD) δ: 9.42 (s, 1H), 8.17 (s, 1H), 8.06 (dd, J=8.0, 0.8 Hz, 1H), 7.89 (s, 1H), 7.88 (d, J=1.2 Hz, 1H), 7.81 (d, J=8.4 Hz, 1H), 7.71-7.68 (m, 2H), 7.42-7.40 (m, 1H), 7.03 (dd, J=6.0, 2.0 Hz, 1H), 3.79 (d, J=6.0 Hz, 1H), 2.56 (s, 3H), 1.31-1.29 (m, 1H), 0.79-0.62 (m, 4H).

Example 132. 1-(6-(1-(6-methylpyridin-2-yl)-1H-indazol-6-yl)pyridin-2-yl)butan-1-amine Synthesis of 1-(6-(1-(6-methylpyridin-2-yl)-1H-indazol-6-yl)pyridin-2-yl)butan-1-amine

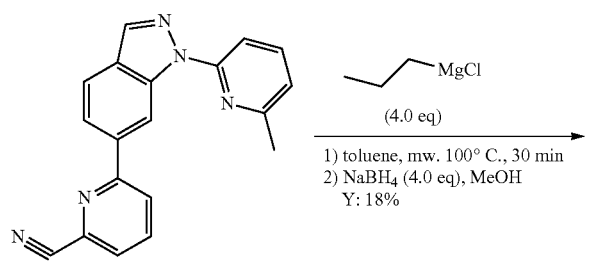

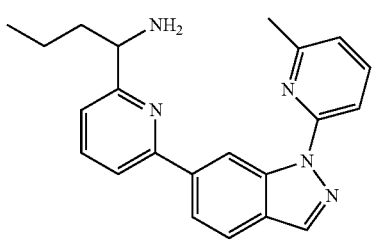

The preparation of 1-(6-(1-(6-methylpyridin-2-yl)-1H-indazol-6-yl)pyridin-2-yl)butan-1-amine was the same as that of 1-(6-(1-(6-(trifluoromethyl)pyridin-2-yl)-1H-indazol-6-yl)pyridin-2-yl)propan-1-amine. 7.9 mg, as yellow oil, Y: 18%. ESI-MS (M+H)⁺: 358.2. HPLC: 100.00%. ¹H NMR (400 MHz, CD₃OD) δ: 9.50 (s, 1H), 8.18 (s, 1H), 7.88 (dd, J=8.4, 1.6 Hz, 1H), 7.81-7.69 (m, 5H), 7.23 (dd, J=7.2, 1.6 Hz, 1H), 7.03 (dd, J=6.8, 1.2 Hz, 1H), 3.94 (t, J=6.0 Hz, 1H), 2.57 (s, 3H), 1.86-1.67 (m, 2H), 1.37-1.21 (m, 2H), 0.86 (t, J=6.8 Hz, 3H).

Example 134. 1-(6-(1-(4-methylthiazol-2-yl)-1H-indazol-6-yl)pyridin-2-yl)ethanamine Synthesis of 2-(6-bromo-1H-indazol-1-yl)-4-methylthiazole

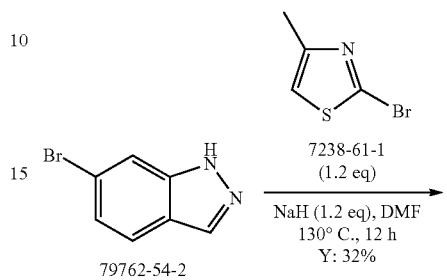

The preparation of 2-(6-bromo-1H-indazol-1-yl)-4-methylthiazole was the similar to that of 6-bromo-1-(6-methylpyridin-2-yl)-1H-indazole. 200 mg, as a brown solid, Y: 32%. ESI-MS (M+H)⁺: 294.0. ¹H NMR (400 MHz, CDCl₃) δ: 8.78 (s, 1H), 8.06 (s, 1H), 7.55 (d, J=8.5 Hz, 1H), 7.36 (dd, J=8.5, 1.5 Hz, 1H), 6.55 (s, 1H), 2.42 (s, 3H).

Synthesis of 4-methyl-2-(6-(4,4,5,5-tetramethyl-1,3,2-dioxaborolan-2-yl)-1H-indazol-1-yl)thiazole

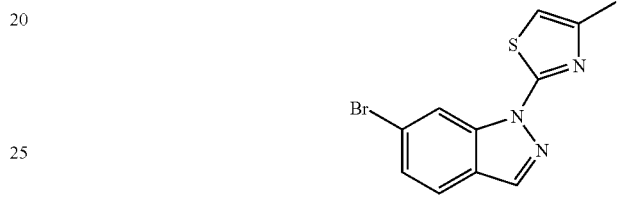

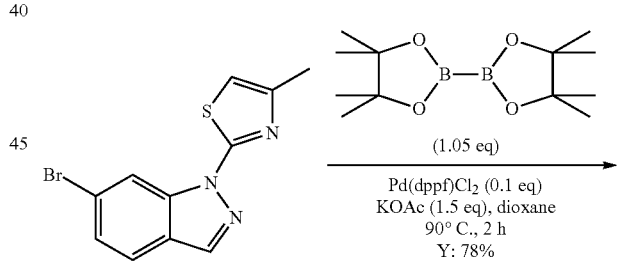

The preparation of 4-methyl-2-(6-(4,4,5,5-tetramethyl-1,3,2-dioxaborolan-2-yl)-1H-indazol-1-yl)thiazole was the similar to that of 1-(6-methylpyridin-2-yl)-6-(4,4,5,5-tetramethyl-1,3,2-dioxaborolan-2-yl)-1H-indazole. 180 mg, as a pale yellow solid, Y: 78%. ESI-MS (M+H)⁺: 342.1.

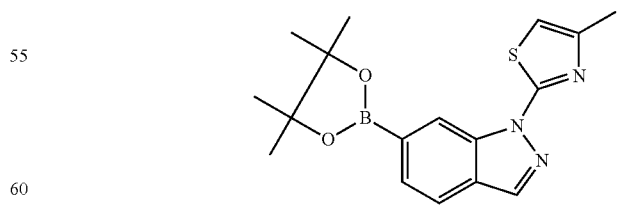

Synthesis of 1-(6-(1-(4-methylthiazol-2-yl)-1H-indazol-6-yl)pyridin-2-yl)ethanone

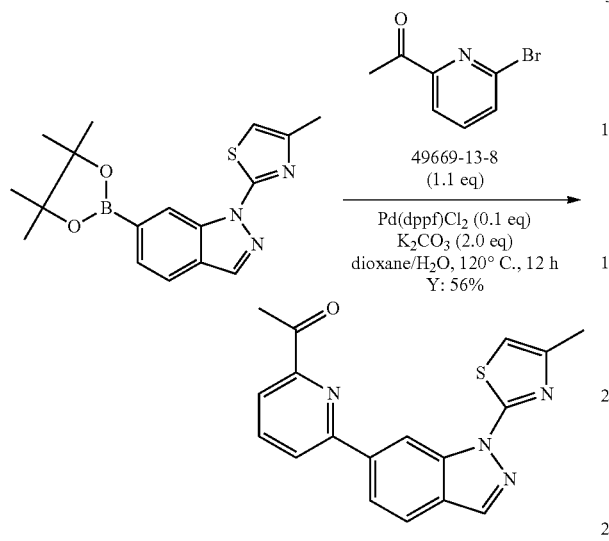

The preparation of 1-(6-(1-(4-methylthiazol-2-yl)-1H-indazol-6-yl)pyridin-2-yl)ethanone was the similar to that of tert-butyl (6-(6-acetylpyridin-2-yl)-1-(6-methylpyridin-2-yl)-1H-indazol-4-yl)carbamate. 114 mg, as a white solid, Y: 56%. ESI-MS (M+H)+: 335.1. HPLC: 98.62%. $^1$H NMR (400 MHz, CDCl$_3$) δ: 9.44 (s, 1H), 8.22 (s, 1H), 8.18-8.07 (m, 2H), 8.04 (d, J=6.9 Hz, 1H), 7.97 (t, J=7.7 Hz, 1H), 7.89 (d, J=8.4 Hz, 1H), 6.64 (s, 1H), 2.90 (s, 3H), 2.51 (s, 3H).

Synthesis of (Z)-1-(6-(1-(4-methylthiazol-2-yl)-1H-indazol-6-yl)pyridin-2-yl)ethanone oxime

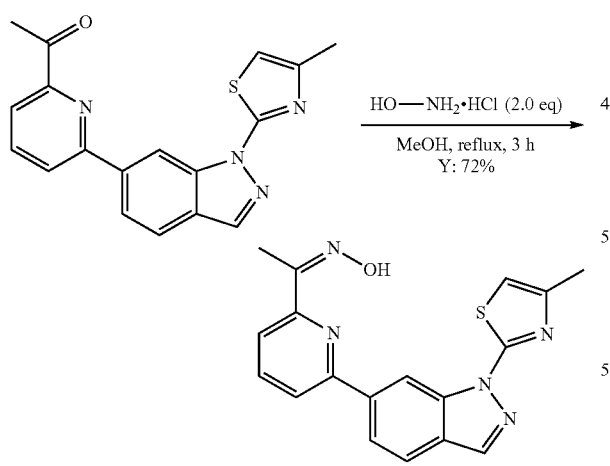

The preparation of (Z)-1-(6-(1-(4-methylthiazol-2-yl)-1H-indazol-6-yl)pyridin-2-yl)ethanone oxime was the similar to that of 2-(1-(6-(trifluoromethyl)pyridin-2-yl)-1H-indazol-6-yl)-5H-cyclopenta[b]pyridin-7(6H)-one oxime. 75 mg, as a white solid, Y: 72%. ESI-MS (M+H)+: 350.1. HPLC: 94.61%. $^1$H NMR (400 MHz, DMSO-d$_6$) δ: 11.63 (s, 1H), 9.50 (s, 1H), 8.54 (s, 1H), 8.16 (dd, J=8.5, 1.3 Hz, 1H), 8.10 (d, J=7.6 Hz, 1H), 8.04 (d, J=8.4 Hz, 1H), 7.97 (t, J=7.8 Hz, 1H), 7.90 (d, J=7.6 Hz, 1H), 7.08 (d, J=1.0 Hz, 1H), 2.45 (s, 3H), 2.41 (s, 3H).

Synthesis of 1-(6-(1-(4-methylthiazol-2-yl)-1H-indazol-6-yl)pyridin-2-yl)ethanamine

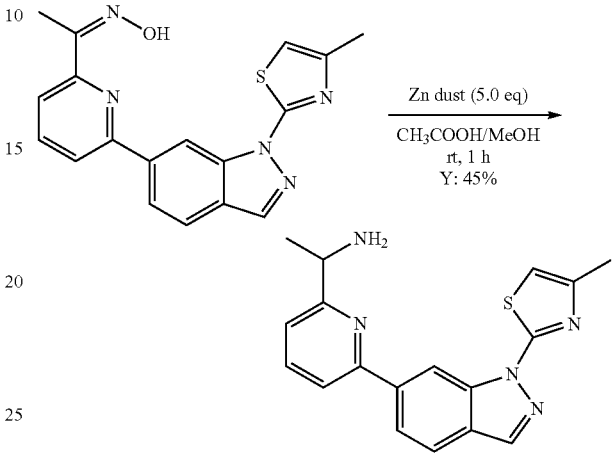

The preparation of 1-(6-(1-(4-methylthiazol-2-yl)-1H-indazol-6-yl)pyridin-2-yl)ethanamine was the similar to that of 2-(1-(6-(trifluoromethyl)pyridin-2-yl)-1H-indazol-6-yl)-6,7-dihydro-5H-cyclopenta[b]pyridin-7-amine. 30 mg, as a white solid, Y: 45%. ESI-MS (M+H)+: 336.1. HPLC: 100.00%. $^1$H NMR (400 MHz, CD$_3$OD) δ: 9.17 (s, 1H), 8.18 (s, 1H), 8.05-7.90 (m, 1H), 7.89-7.70 (m, 3H), 7.30 (d, J=6.6 Hz, 1H), 6.73 (s, 1H), 4.28-4.03 (m, 1H), 2.38 (s, 3H), 1.44 (d, J=6.7 Hz, 3H).

Example 135. 1-(6-(1-(5-methylthiazol-2-yl)-1H-indazol-6-yl)pyridin-2-yl)ethanamine

Synthesis of 2-(6-bromo-1H-indazol-1-yl)-5-methylthiazole

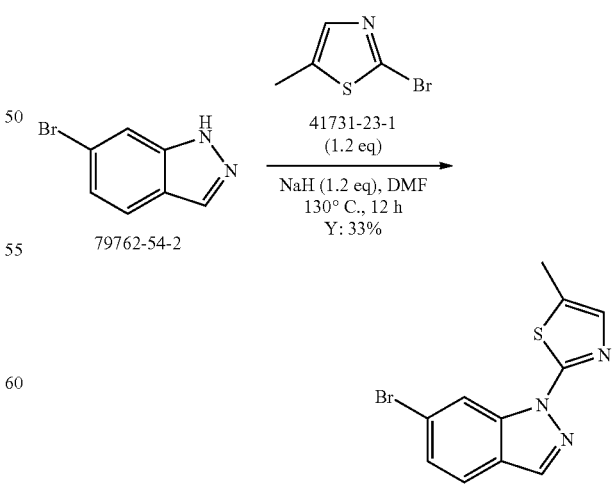

The preparation of 2-(6-bromo-1H-indazol-1-yl)-5-methylthiazole was the similar to that of 6-bromo-1-(6-methylpyridin-2-yl)-1H-indazole. 200 mg, as a brown solid, Y: 33%. ESI-MS (M+H)+: 294.0. ¹H NMR (400 MHz, CDCl₃) δ: 8.81 (s, 1H), 8.11 (s, 1H), 7.62 (d, J=8.5 Hz, 1H), 7.42 (dd, J=8.5, 1.6 Hz, 1H), 7.26 (s, 1H), 2.48 (d, J=1.2 Hz, 3H).

Synthesis of 5-methyl-2-(6-(4,4,5,5-tetramethyl-1,3,2-dioxaborolan-2-yl)-1H-indazol-1-yl)thiazole

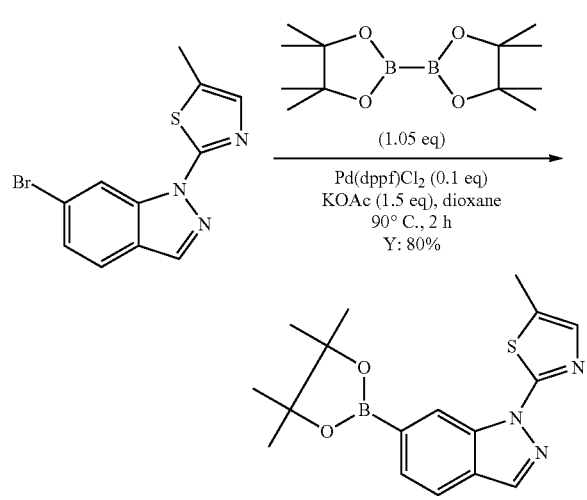

The preparation of 5-methyl-2-(6-(4,4,5,5-tetramethyl-1,3,2-dioxaborolan-2-yl)-1H-indazol-1-yl)thiazole was the similar to that of 1-(6-methylpyridin-2-yl)-6-(4,4,5,5-tetramethyl-1,3,2-dioxaborolan-2-yl)-1H-indazole. 187 mg, as a pale yellow solid, Y: 80%. ESI-MS (M+H)+: 342.1.

Synthesis of 1-(6-(1-(5-methylthiazol-2-yl)-1H-indazol-6-yl)pyridin-2-yl)ethanone

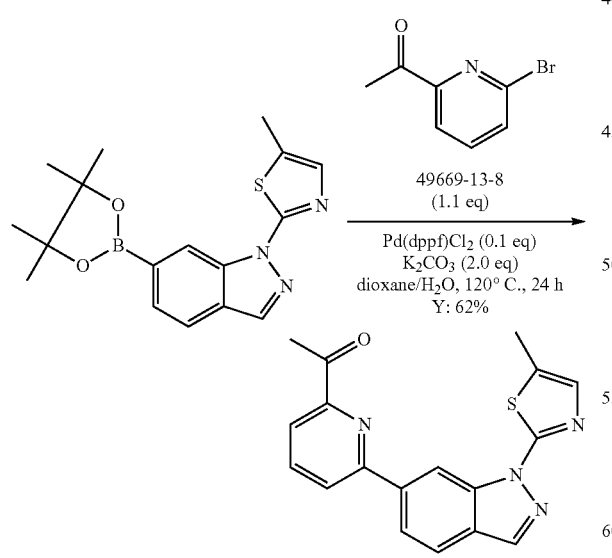

The preparation of 1-(6-(1-(5-methylthiazol-2-yl)-1H-indazol-6-yl)pyridin-2-yl)ethanone was the similar to that of tert-butyl (6-(6-acetylpyridin-2-yl)-1-(6-methylpyridin-2-yl)-1H-indazol-4-yl)carbamate. 114 mg, as a white solid, Y: 62%. ESI-MS (M+H)+: 335.1. HPLC: 100.00%. ¹H NMR (400 MHz, CDCl₃) δ: 9.25 (s, 1H), 8.22-8.10 (m, 3H), 8.06-8.00 (m, 1H), 7.97 (d, J=7.7 Hz, 1H), 7.89 (d, J=8.5 Hz, 1H), 7.30 (d, J=1.3 Hz, 1H), 2.88 (s, 3H), 2.50 (d, J=1.2 Hz, 3H).

Synthesis of (Z)-1-(6-(1-(5-methylthiazol-2-yl)-1H-indazol-6-yl)pyridin-2-yl)ethanone oxime

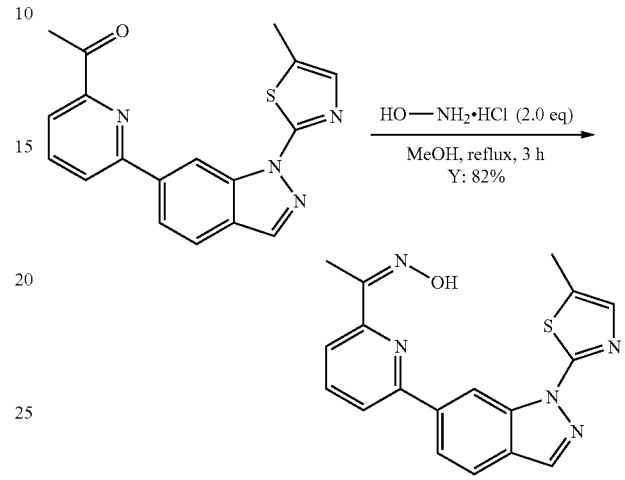

The preparation of (Z)-1-(6-(1-(5-methylthiazol-2-yl)-1H-indazol-6-yl)pyridin-2-yl)ethanone oxime was the similar to that of 2-(1-(6-(trifluoromethyl)pyridin-2-yl)-1H-indazol-6-yl)-5H-cyclopenta[b]pyridin-7(6H)-one oxime. 79 mg, as a white solid, Y: 82%. ESI-MS (M+H)+: 350.1. HPLC: 100.00%. ¹H NMR (400 MHz, DMSO-d₆) δ: 11.63 (s, 1H), 9.50 (s, 1H), 8.54 (s, 1H), 8.16 (dd, J=8.5, 1.3 Hz, 1H), 8.10 (d, J=7.6 Hz, 1H), 8.04 (d, J=8.4 Hz, 1H), 7.97 (t, J=7.8 Hz, 1H), 7.90 (d, J=7.6 Hz, 1H), 7.08 (d, J=1.0 Hz, 1H), 2.45 (s, 3H), 2.41 (s, 3H).

Synthesis of 1-(6-(1-(5-methylthiazol-2-yl)-1H-indazol-6-yl)pyridin-2-yl)ethanamine

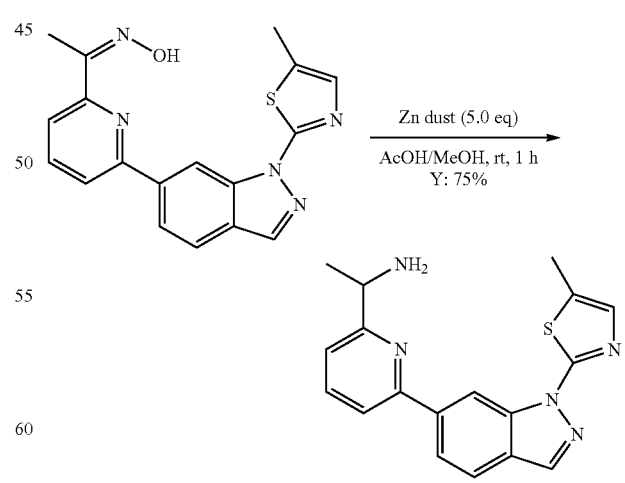

The preparation of 1-(6-(1-(5-methylthiazol-2-yl)-1H-indazol-6-yl)pyridin-2-yl)ethanamine was the similar to that of 2-(1-(6-(trifluoromethyl)pyridin-2-yl)-1H-indazol-6-yl)-6,7-dihydro-5H-cyclopenta[b]pyridin-7-amine. 30 mg, as a white solid, Y: 75%. ESI-MS (M+H)⁺: 336.1. HPLC: 100.00%. ¹H NMR (400 MHz, CD₃OD) δ: 9.04 (s, 1H), 8.17 (s, 1H), 8.00 (dd, J=8.4, 1.4 Hz, 1H), 7.86-7.74 (m, 3H), 7.29 (dd, J=6.3, 2.2 Hz, 1H), 7.24 (d, J=1.3 Hz, 1H), 4.11 (q, J=6.7 Hz, 1H), 2.39 (d, J=1.2 Hz, 3H), 1.42 (d, J=6.7 Hz, 3H).

Example 136. 1-(6-(1-(2-methylthiazol-4-yl)-1H-indazol-6-yl)pyridin-2-yl)ethanamine Synthesis of 6-bromo-1-(tetrahydro-2H-pyran-2-yl)-1H-indazole

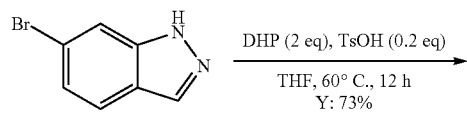

79762-54-2

To a mixture of 6-bromo-1H-indazole (CAS#79762-54-2) (750 mg, 3.83 mmol, 1.0 eq) in THF (15 mL), DHP (2.8 g, 7.66 mmol, 2.0 eq) and TsOH (132 mg, 0.77 mmol, 0.2 eq) were added. The mixture was stirred at 60° C. for 12 h. The solvent was removed in vacuo. The residue was diluted with ethyl acetate (50 mL) and washed with H₂O (10 mL×3). The organic layer was dried over anhydrous sodium sulfate and concentrated under reduced pressure. The residue was purified by column chromatography on silica gel (PE/EA=10/1) to give 6-bromo-1-(tetrahydro-2H-pyran-2-yl)-1H-indazole as a yellow solid. 783 mg, Y: 73%. ESI-MS (M+H)⁺: 281.1. ¹H NMR (400 MHz, CDCl₃) δ: 7.92 (s, 1H), 7.72 (s, 1H), 7.51 (d, J=8.8 Hz, 1H), 7.21 (dd, J=8.4, 1.6 Hz, 1H), 5.60 (dd, J=9.2, 2.8 Hz, 1H), 3.98-3.95 (m, 1H), 3.72-3.65 (m, 1H), 2.48-2.45 (m, 1H), 2.10-1.99 (m, 2H), 1.72-1.48 (m, 3H).

Synthesis of 1-(tetrahydro-2H-pyran-2-yl)-6-(4,4,5,5-tetramethyl-1,3,2-dioxaborolan-2-yl)-1H-indazole

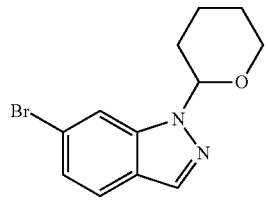

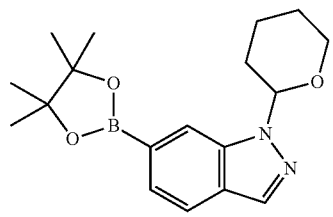

The preparation of 1-(tetrahydro-2H-pyran-2-yl)-6-(4,4,5,5-tetramethyl-1,3,2-dioxaborolan-2-yl)-1H-indazole was the similar to that of 1-(6-methylpyridin-2-yl)-6-(4,4,5,5-tetramethyl-1,3,2-dioxaborolan-2-yl)-1H-indazole. 734 mg, as a yellow solid, Y: 80%. ESI-MS (M+H)⁺: 329.2.

Synthesis of 1-(6-(1-(tetrahydro-2H-pyran-2-yl)-1H-indazol-6-yl)pyridin-2-yl)ethanone

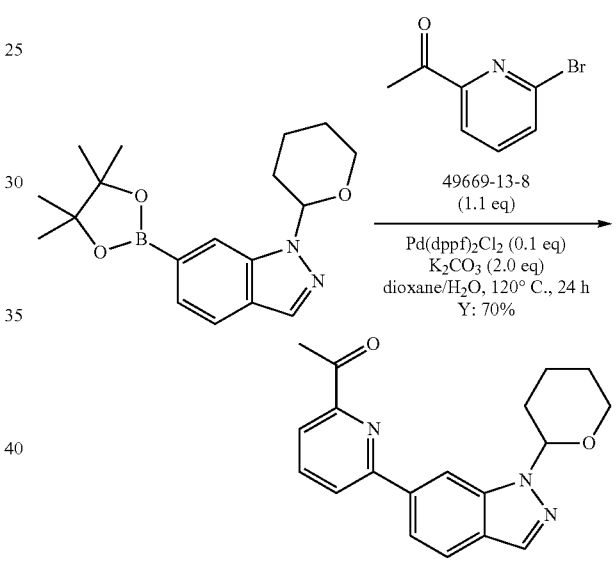

The preparation of 1-(6-(1-(tetrahydro-2H-pyran-2-yl)-1H-indazol-6-yl)pyridin-2-yl)ethanone was the similar to that of tert-butyl (6-(6-acetylpyridin-2-yl)-1-(6-methylpyridin-2-yl)-1H-indazol-4-yl)carbamate. 503 mg, as a yellow solid, Y: 62%. ESI-MS (M+H)⁺: 322.1.

Synthesis of 1-(6-(1H-indazol-6-yl)pyridin-2-yl)ethanone

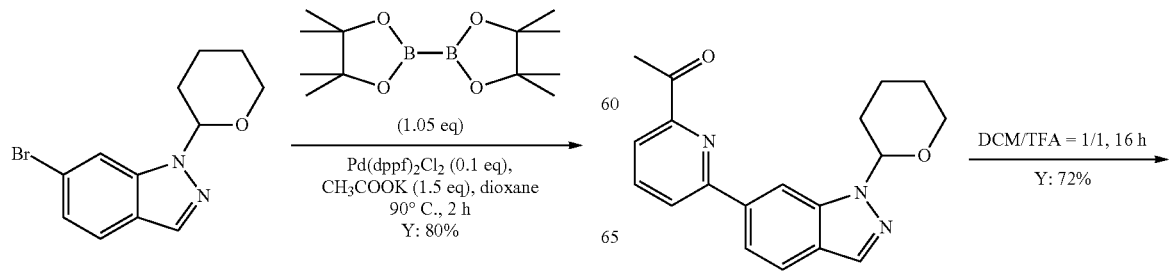

-continued

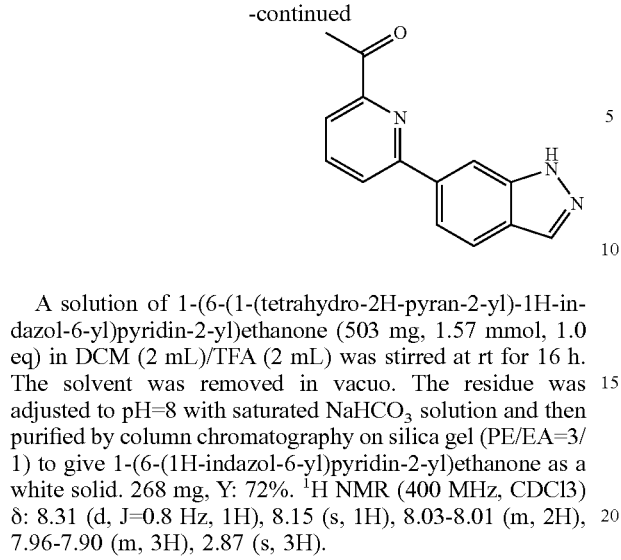

A solution of 1-(6-(1-(tetrahydro-2H-pyran-2-yl)-1H-indazol-6-yl)pyridin-2-yl)ethanone (503 mg, 1.57 mmol, 1.0 eq) in DCM (2 mL)/TFA (2 mL) was stirred at rt for 16 h. The solvent was removed in vacuo. The residue was adjusted to pH=8 with saturated NaHCO$_3$ solution and then purified by column chromatography on silica gel (PE/EA=3/1) to give 1-(6-(1H-indazol-6-yl)pyridin-2-yl)ethanone as a white solid. 268 mg, Y: 72%. $^1$H NMR (400 MHz, CDCl3) δ: 8.31 (d, J=0.8 Hz, 1H), 8.15 (s, 1H), 8.03-8.01 (m, 2H), 7.96-7.90 (m, 3H), 2.87 (s, 3H).

Synthesis of 1-(6-(1-(2-methylthiazol-4-yl)-1H-indazol-6-yl)pyridin-2-yl)ethanone

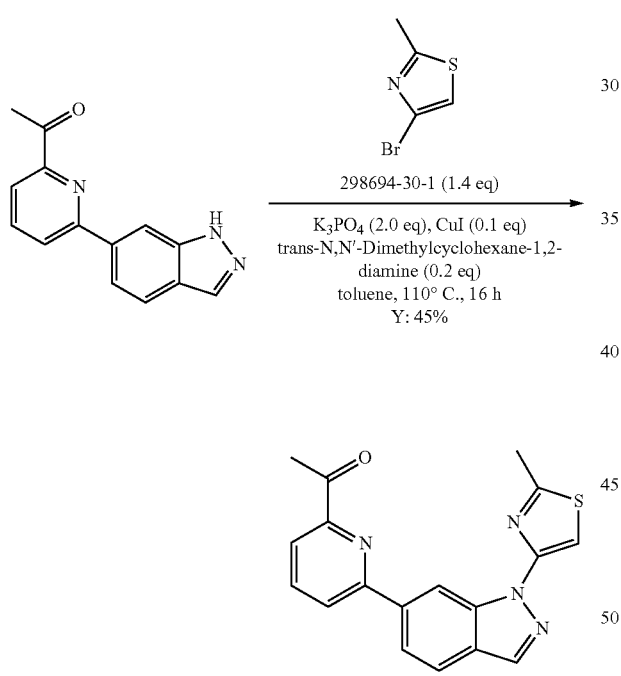

A mixture of 47-SM04 (237 mg, 1.0 mmol), 298694-30-1 (248 mg, 1.4 mmol, 1.4 eq), K$_3$PO$_4$ (424 mg, 2.0 mmol, 2.0 eq) and trans-N,N'-Dimethylcyclohexane-1,2-diamine (28 mg, 0.2 mmol, 0.2 eq) in toluene (5 mL) was stirred at 110° C. for 16 h under N$_2$. After concentration, the residue was purified by column chromatography on silica gel (PE/EA=3/1) to give 1-(6-(1-(2-methylthiazol-4-yl)-1H-indazol-6-yl)pyridin-2-yl)ethanone as a white solid. 150 mg, Y: 45%. ESI-MS (M+H)$^+$: 335.1.

Synthesis of (Z)-1-(6-(1-(2-methylthiazol-4-yl)-1H-indazol-6-yl)pyridin-2-yl)ethanone oxime

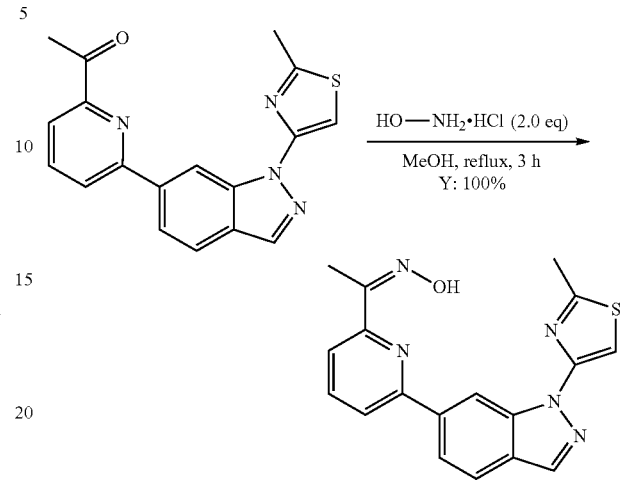

The preparation of (Z)-1-(6-(1-(2-methylthiazol-4-yl)-1H-indazol-6-yl)pyridin-2-yl)ethanone oxime was the similar to that of 2-(1-(6-(trifluoromethyl)pyridin-2-yl)-1H-indazol-6-yl)-5H-cyclopenta[b]pyridin-7(6H)-one oxime. 156 mg, as a white solid, Y: 100%. ESI-MS (M+H)$^+$: 350.1.

Synthesis of 1-(6-(1-(2-methylthiazol-4-yl)-1H-indazol-6-yl)pyridin-2-yl)ethanamine

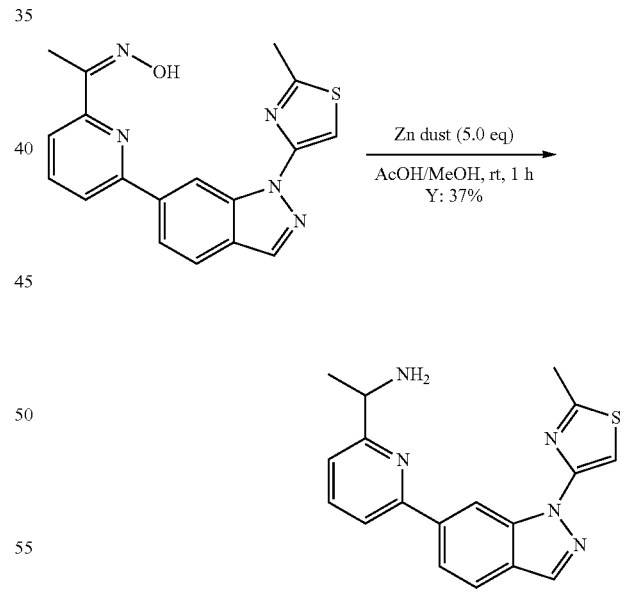

The preparation of 1-(6-(1-(2-methylthiazol-4-yl)-1H-indazol-6-yl)pyridin-2-yl)ethanamine was the similar to that of 2-(1-(6-(trifluoromethyl)pyridin-2-yl)-1H-indazol-6-yl)-6,7-dihydro-5H-cyclopenta[b]pyridin-7-amine. 55 mg, as a yellow solid, Y: 75%. ESI-MS (M+H)$^+$: 336.1. HPLC: 95.88%. $^1$H NMR (400 MHz, CDCl$_3$) δ: 9.00 (s, 1H), 8.12 (s, 1H), 7.90 (d, J=8.4 Hz, 1H), 7.76 (d, J=8.4 Hz, 1H), 7.71-7.65 (m, 2H), 7.19-7.18 (m, 2H), 4.19 (q, J=6.4 Hz, 1H), 2.77 (s, 3H), 2.05 (br, 2H), 1.47 (d, J=6.8 Hz, 3H).

Example 137. 1-(6-(1-(1-methyl-1H-pyrazol-3-yl)-1H-indazol-6-yl)pyridin-2-yl)ethanamine Synthesis of 1-(6-(1-(1-methyl-1H-pyrazol-3-yl)-1H-indazol-6-yl)pyridin-2-yl)ethanone

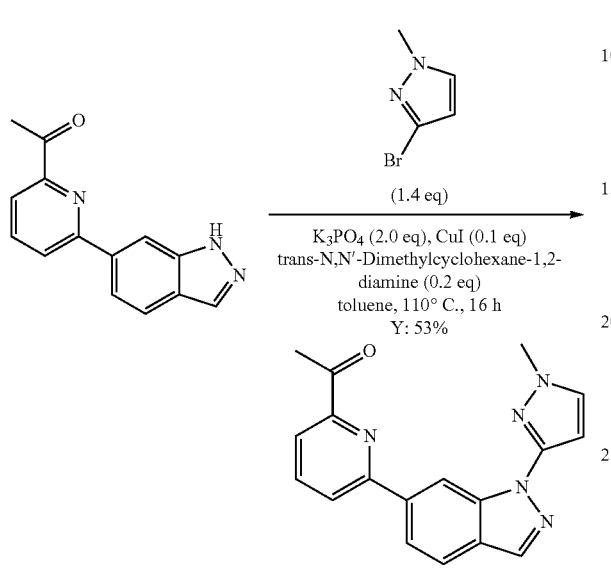

The preparation of 1-(6-(1-(1-methyl-1H-pyrazol-3-yl)-1H-indazol-6-yl)pyridin-2-yl)ethanone was the similar to that of 1-(6-(1-(2-methylthiazol-4-yl)-1H-indazol-6-yl)pyridin-2-yl)ethanone. 166 mg, as a yellow solid, Y: 53%. ESI-MS (M+H)$^+$: 318.1. $^1$H NMR (400 MHz, CD$_3$OD) δ: 9.11 (s, 1H), 8.27 (s, 1H), 8.25 (d, J=8.0 Hz, 1H), 8.13-7.95 (m, 4H), 7.71 (d, J=2.0 Hz, 1H), 6.61 (d, J=2.4 Hz, 1H), 4.01 (s, 3H), 2.86 (s, 3H).

Synthesis of (Z)-1-(6-(1-(1-methyl-1H-pyrazol-3-yl)-1H-indazol-6-yl)pyridin-2-yl)ethanone oxime

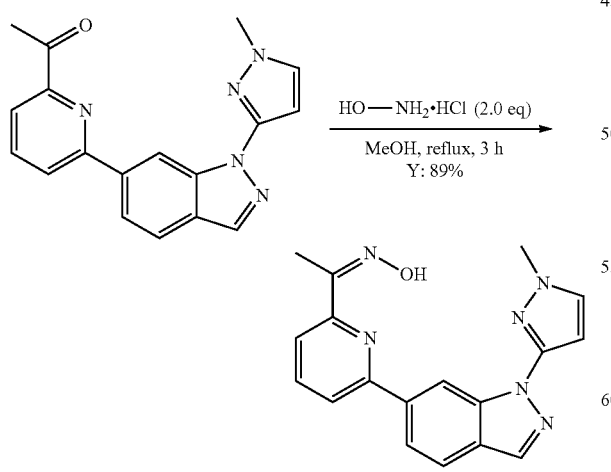

The preparation of (Z)-1-(6-(1-(1-methyl-1H-pyrazol-3-yl)-1H-indazol-6-yl)pyridin-2-yl)ethanone oxime was the similar to that of 2-(1-(6-(trifluoromethyl)pyridin-2-yl)-1H-indazol-6-yl)-5H-cyclopenta[b]pyridin-7(6H)-one oxime. 155 mg, as a white solid, Y: 89%. ESI-MS (M+H)$^+$: 333.1.

Synthesis of 1-(6-(1-(1-methyl-1H-pyrazol-3-yl)-1H-indazol-6-yl)pyridin-2-yl)ethanamine

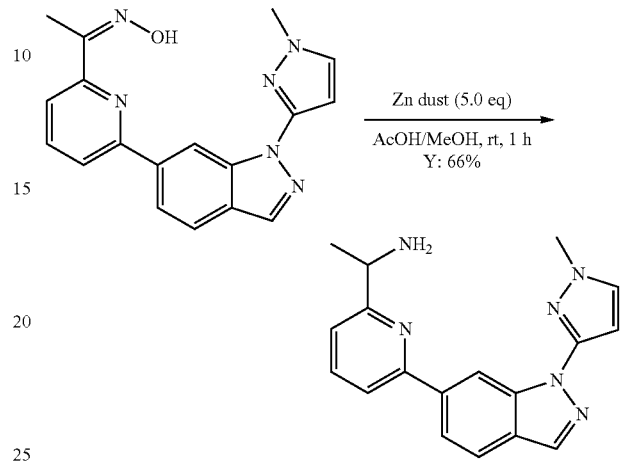

The preparation of 1-(6-(1-(1-methyl-1H-pyrazol-3-yl)-1H-indazol-6-yl)pyridin-2-yl)ethanamine was the similar to that of 2-(1-(6-(trifluoromethyl)pyridin-2-yl)-1H-indazol-6-yl)-6,7-dihydro-5H-cyclopenta[b]pyridin-7-amine. 97 mg, as a yellow solid, Y: 66%. ESI-MS (M+H)$^+$: 319.2. HPLC: 99.84%. $^1$H NMR (400 MHz, CD$_3$OD) δ: 8.76 (s, 1H), 8.09-8.07 (m, 1H), 7.83-7.81 (m, 1H), 7.73-7.65 (m, 3H), 7.53-7.51 (m, 1H), 7.20-7.18 (m, 1H), 6.45 (d, J=2.8 Hz, 1H), 4.03 (q, J=6.4 Hz, 1H), 2.85 (s, 3H), 1.36 (d, J=6.8 Hz, 3H).

Example 138. 1-(6-(1-(1-methyl-1H-imidazol-4-yl)-1H-indazol-6-yl)pyridin-2-yl)ethanamine Synthesis of 1-(6-(1-(1-methyl-1H-imidazol-4-yl)-1H-indazol-6-yl)pyridin-2-yl)ethanone

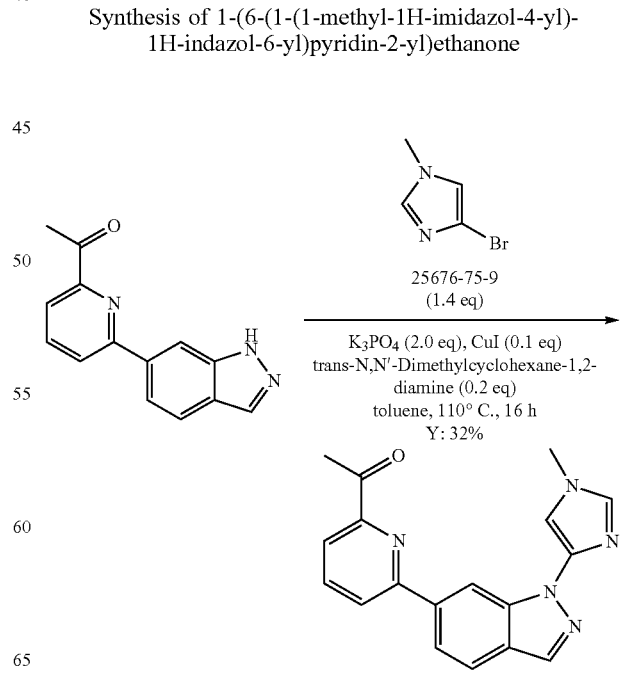

The preparation of 1-(6-(1-(1-methyl-1H-imidazol-4-yl)-1H-indazol-6-yl)pyridin-2-yl)ethanone was the similar to that of 1-(6-(1-(2-methylthiazol-4-yl)-1H-indazol-6-yl)pyridin-2-yl)ethanone. 200 mg, as a yellow solid, Y: 32%. ESI-MS (M+H)⁺: 318.1. ¹H NMR (400 MHz, CDCl₃) δ: 8.99 (s, 1H), 8.15 (d, J=0.8 Hz, 1H), 8.10 (dd, J=8.0, 1.2 Hz, 1H), 8.07 (dd, J=8.4, 1.6 Hz, 1H), 7.99 (dd, J=8.0, 1.2 Hz, 1H), 7.92 (t, J=7.6 Hz, 1H), 7.87 (dd, J=8.8, 0.8 Hz, 1H), 7.45 (d, J=1.2 Hz, 1H), 7.21 (d, J=2.0 Hz, 1H), 3.80 (s, 3H), 2.86 (s, 3H).

Synthesis of (Z)-1-(6-(1-(1-methyl-1H-imidazol-4-yl)-1H-indazol-6-yl)pyridin-2-yl)ethanone oxime

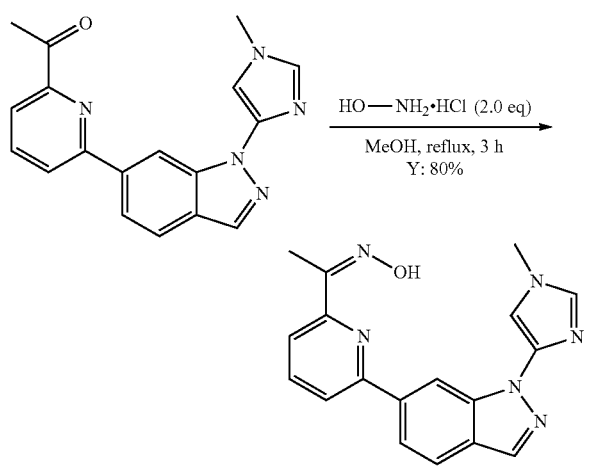

The preparation of (Z)-1-(6-(1-(1-methyl-1H-imidazol-4-yl)-1H-indazol-6-yl)pyridin-2-yl)ethanone oxime was the similar to that of 2-(1-(6-(trifluoromethyl)pyridin-2-yl)-1H-indazol-6-yl)-5H-cyclopenta[b]pyridin-7(6H)-one oxime. 167 mg, as a white solid, Y: 80%. ESI-MS (M+H)⁺: 333.1.

Synthesis of 1-(6-(1-(1-methyl-1H-imidazol-4-yl)-1H-indazol-6-yl)pyridin-2-yl)ethanamine

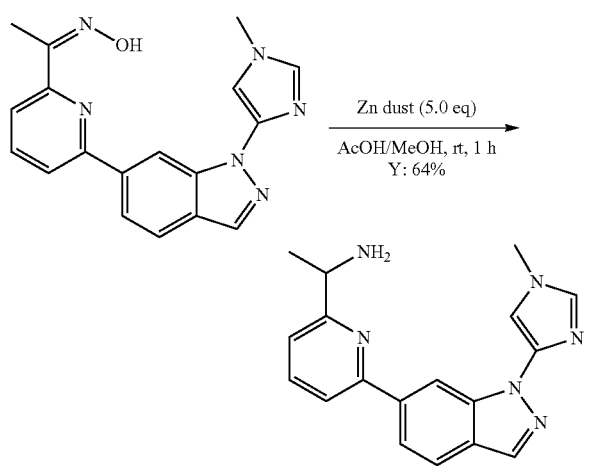

The preparation of 1-(6-(1-(1-methyl-1H-imidazol-4-yl)-1H-indazol-6-yl)pyridin-2-yl)ethanamine was the similar to that of 2-(1-(6-(trifluoromethyl)pyridin-2-yl)-1H-indazol-6-yl)-6,7-dihydro-5H-cyclopenta[b]pyridin-7-amine. 103 mg, as a yellow solid, Y: 64%. ESI-MS (M+H)⁺: 319.1. HPLC: 100.00%. ¹H NMR (400 MHz, CD₃OD) δ: 8.49 (s, 1H), 8.13-8.11 (m, 1H), 7.91-7.88 (m, 1H), 7.81-7.79 (m, 1H), 7.74-7.70 (m, 2H), 7.62-7.59 (m, 1H), 7.32-7.24 (m, 2H), 4.08 (q, J=6.8 Hz, 1H), 3.75 (s, 3H), 1.40 (d, J=6.8 Hz, 3H).

Example 139. (2-(1-(6-methylpyridin-2-yl)-1H-indazol-6-yl)thiazol-4-yl)methanamine Synthesis of 2-(1-(6-methylpyridin-2-yl)-1H-indazol-6-yl)thiazole-4-carbonitrile

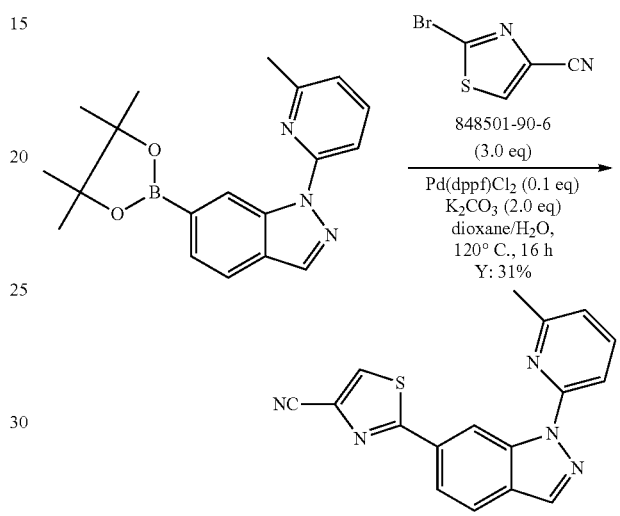

The preparation of 2-(1-(6-methylpyridin-2-yl)-1H-indazol-6-yl)thiazole-4-carbonitrile was the similar to that of tert-butyl (6-(6-acetylpyridin-2-yl)-1-(6-methylpyridin-2-yl)-1H-indazol-4-yl)carbamate. 60 mg, as a yellow solid, Y: 31%. ESI-MS (M+H)⁺: 317.1. ¹H NMR (400 MHz, CDCl₃) δ: 9.57 (s, 1H), 8.23 (d, J=0.7 Hz, 1H), 8.03 (s, 1H), 7.94 (dd, J=8.4, 1.5 Hz, 1H), 7.90-7.83 (m, 2H), 7.80-7.72 (m, 1H), 7.08 (d, J=7.4 Hz, 1H), 2.71 (s, 3H).

Synthesis of (2-(1-(6-methylpyridin-2-yl)-1H-indazol-6-yl)thiazol-4-yl)methanamine

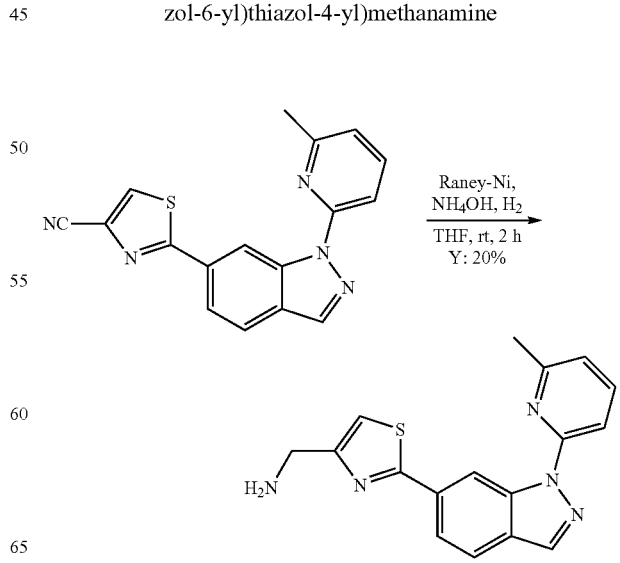

To a solution of 2-(1-(6-methylpyridin-2-yl)-1H-indazol-6-yl)thiazole-4-carbonitrile (59 mg, 0.19 mmol, 1.0 eq) in THF/NH₄OH (2 mL/0.5 mL) was added Raney-Ni (6 mg) at rt. The mixture was stirred at rt for 2 h under H₂. After filtration and concentration, the residue was purified by prep-HPLC (MeOH/H₂O with 0.05% NH₄OH as mobile phase from 5% to 95%) to afford (2-(1-(6-methylpyridin-2-yl)-1H-indazol-6-yl)thiazol-4-yl)methanamine as a pale yellow solid. 12 mg, Y: 20%. ESI-MS (M+H)⁺: 321.1. HPLC: 100.00%. ¹H NMR (400 MHz, CD₃OD) δ: 9.29 (s, 1H), 8.12 (s, 1H), 7.81-7.65 (m, 4H), 7.29 (s, 1H), 7.02-6.96 (m, 1H), 3.90 (s, 2H), 2.54 (s, 3H).

Example 140. (2-(1-(6-methylpyridin-2-yl)-1H-indazol-6-yl)thiazol-5-yl)methanamine Synthesis of 2-(1-(6-methylpyridin-2-yl)-1H-indazol-6-yl)thiazole-5-carbonitrile

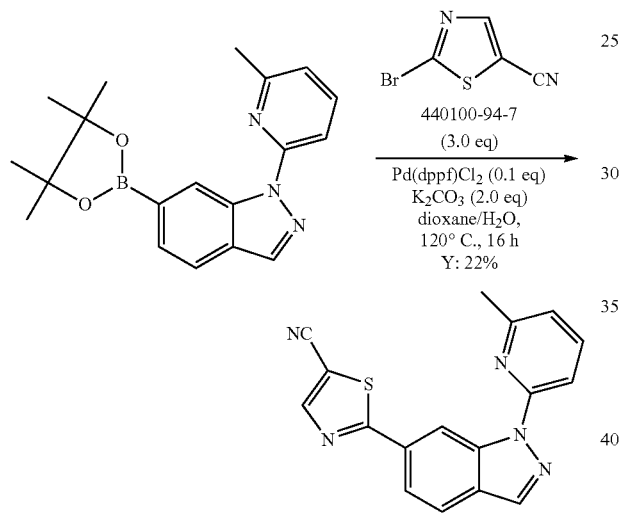

The preparation of 2-(1-(6-methylpyridin-2-yl)-1H-indazol-6-yl)thiazole-5-carbonitrile was the similar to that of tert-butyl (6-(6-acetylpyridin-2-yl)-1-(6-methylpyridin-2-yl)-1H-indazol-4-yl)carbamate. 87 mg, as a yellow solid, Y: 22%. ESI-MS (M+H)⁺: 317.1.

Synthesis of (2-(1-(6-methylpyridin-2-yl)-1H-indazol-6-yl)thiazol-5-yl)methanamine

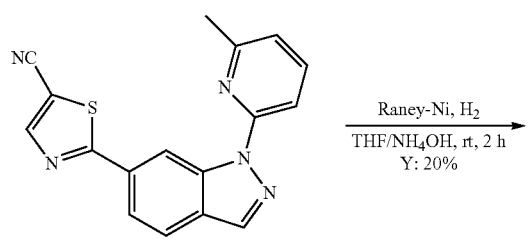

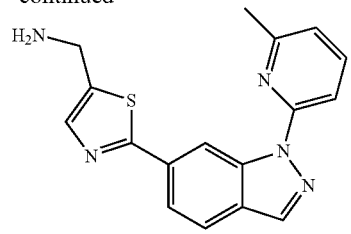

The preparation of (2-(1-(6-methylpyridin-2-yl)-1H-indazol-6-yl)thiazol-5-yl)methanamine was the similar to that of (2-(1-(6-methylpyridin-2-yl)-1H-indazol-6-yl)thiazol-4-yl)methanamine. 14 mg, as a pale green solid, Y: 20%. ESI-MS (M+H)⁺: 321.1. HPLC: 100.00%. ¹H NMR (400 MHz, CD₃OD) δ: 9.40 (s, 1H), 8.19 (s, 1H), 7.90-7.68 (m, 5H), 7.05 (d, J=5.8 Hz, 1H), 4.40 (s, 2H), 2.58 (s, 3H).

Example 141. (R)-1-(6-(1-(6-methylpyridin-2-yl)-1H-indazol-6-yl)pyridin-2-yl)ethanamine Synthesis of (R,E)-N-(1-(6-bromopyridin-2-yl)ethylidene)-2-methylpropane-2-sulfinamide

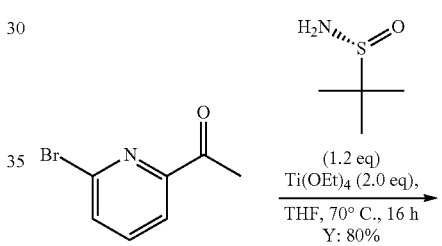

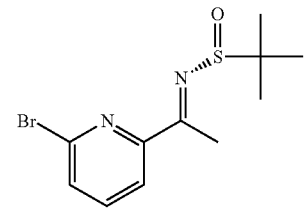

To a solution of 1-(6-bromopyridin-2-yl)ethanone (4.00 g, 20.0 mmol, 1.0 eq) and (R)-2-methylpropane-2-sulfinamide (2.42 g, 20.0 mmol, 1.0 eq) in THF (80 mL) was added Ti(OEt)₄ (9.12 g, 40.0 mmol, 2.0 eq) at room temperature. The mixture was stirred at 70° C. for 16 h. After cooling down to room temperature, the mixture was diluted with water (200 mL) and extracted with DCM (2×200 mL). The combined organic layers were dried over anhydrous Na₂SO₄. After concentration, the residue was purified by silica gel chromatography with PE/EA (10/1) as eluent to give (R,E)-N-(1-(6-bromopyridin-2-yl)ethylidene)-2-methylpropane-2-sulfinamide (4.83 g, yield: 80%) as a yellow solid. ESI-MS (M+H)⁺: 303.0. ¹H NMR (400 MHz, CDCl₃) δ: 8.06 (d, J=7.6 Hz, 1H), 7.63-7.54 (m, 2H), 2.81 (s, 3H), 1.30 (s, 9H).

277

Synthesis of (R)—N—((R)-1-(6-bromopyridin-2-yl)ethyl)-2-methylpropane-2-sulfinamide

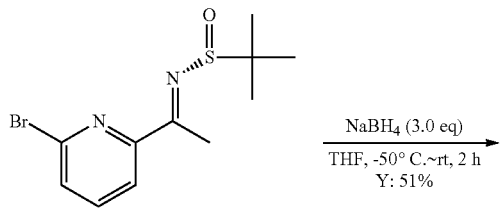

To a solution of (R,E)-N-(1-(6-bromopyridin-2-yl)ethylidene)-2-methylpropane-2-sulfinamide (4.40 g, 14.5 mmol, 1.0 eq) in THF (60 mL) was added NaBH$_4$ (1.65 g, 43.5 mmol, 3.0 eq) at −50° C. The mixture was warmed to room temperature over 3 h. The mixture was diluted with EA (200 mL) and washed with water (2×100 mL). The organics were dried (MgSO$_4$) and concentrated in vacuo. The residue was purified by silica gel chromatography with PE/EA (2/1) as eluent to give (R)—N—((R)-1-(6-bromopyridin-2-yl)ethyl)-2-methylpropane-2-sulfinamide (2.2 g, yield: 51%) as a white solid. ESI-MS (M+H)$^+$: 305.1, 307.1. $^1$H NMR (400 MHz, DMSO-d$_6$) δ: 7.76 (t, J=8.6 Hz, 1H), 7.59 (d, J=8.0 Hz, 1H), 7.52 (d, J=8.0 Hz, 1H), 5.84 (d, J=8.0 Hz, 1H), 4.41-4.37 (m, 1H), 1.41 (d, J=6.8 Hz, 3H), 1.13 (s, 9H).

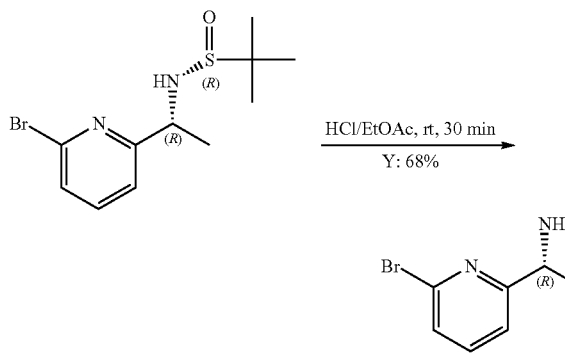

the R configuration was confirmed according to specific optical activity (Ref. Heterocycles 2000, 52, 719-732)

278

Synthesis of (R)-2-methyl-N—((R)-1-(6-(1-(6-methylpyridin-2-yl)-1H-indazol-6-yl)pyridin-2-yl)ethyl)propane-2-sulfinamide

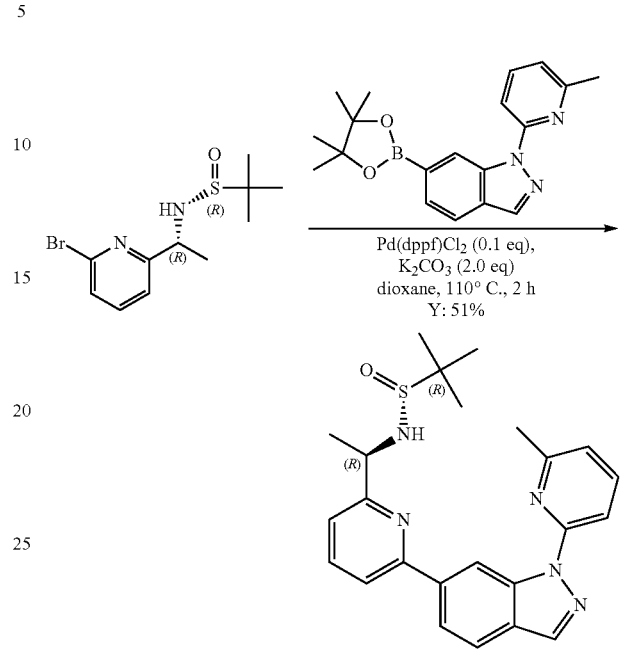

A mixture of (R)—N—((R)-1-(6-bromopyridin-2-yl)ethyl)-2-methylpropane-2-sulfinamide (185 mg, 0.6 mmol, 1.0 eq), 1-(6-methylpyridin-2-yl)-6-(4,4,5,5-tetramethyl-1,3,2-dioxaborolan-2-yl)-1H-indazole (201 mg, 0.6 mmol, 1.0 eq) and K$_2$CO$_3$ (167 mg, 1.2 mmol, 2.0 eq) in 1, 4-dioxane/H$_2$O (5 mL/0.5 mL) was stirred while purging N$_2$ at room temperature for 10 min. To this system was added Pd(dppf)Cl$_2$ (44 mg, 0.06 mmol, 0.1 eq) and heated to 110° C. for 2 h. The mixture was diluted with EA (50 mL), washed with water (50 mL) and brine (50 mL). The organics were dried (MgSO$_4$) and concentrated in vacuo. The residue was purified by silica gel chromatography with PE/EA (3/1) as eluent to give (R)-2-methyl-N—((R)-1-(6-(1-(6-methylpyridin-2-yl)-1H-indazol-6-yl)pyridin-2-yl)ethyl)propane-2-sulfinamide (132 mg, yield: 51%) as a white solid. ESI-MS (M+H)$^+$: 434.1.

Synthesis of (R)-1-(6-(1-(6-methylpyridin-2-yl)-1H-indazol-6-yl)pyridin-2-yl)ethanamine

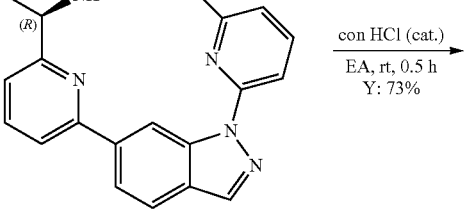

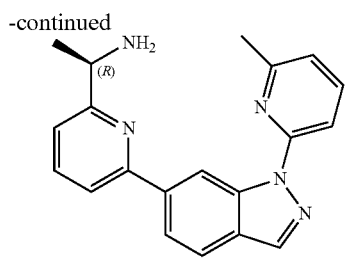

To a solution of (R)-2-methyl-N—((R)-1-(6-(1-(6-methylpyridin-2-yl)-1H-indazol-6-yl)pyridin-2-yl)ethyl)propane-2-sulfinamide (132 mg, 0.3 mmol, 1.0 eq) in EA (3 mL) was added. conc. HCl (cat.). The mixture was stirred for 0.5 h at room temperature. The resulting mixture was adjusted to pH=7-8 with sat NaHCO$_3$ and extracted with EA (2×50 mL). The combined organic layers were dried over anhydrous Na$_2$SO$_4$. After filtration and concentration, the residue was purified by pre-HPLC (MeCN/H$_2$O with 0.05% NH$_4$OH as mobile phase from 5% to 95%) to give (R)-1-(6-(1-(6-methylpyridin-2-yl)-1H-indazol-6-yl)pyridin-2-yl)ethanamine as a white solid (72 mg, yield: 73%). ESI-MS (M+H)$^+$: 330.0. HPLC: 94.94%. $^1$H NMR (400 MHz, CDCl$_3$) δ: 9.63 (s, 1H), 8.29 (s, 1H), 8.03 (d, J=8.4 Hz, 1H), 7.92-7.84 (m, 5H), 7.39 (d, J=6.4 Hz, 1H), 7.15 (d, J=6.4 Hz, 1H), 4.25-4.23 (m, 1H), 2.69 (s, 3H), 1.55 (d, J=6.4 Hz, 3H).

Example 142. (S)-1-(6-(1-(6-methylpyridin-2-yl)-1H-indazol-6-yl)pyridin-2-yl)ethanamine Synthesis of (R)—N—((S)-1-(6-bromopyridin-2-yl)ethyl)-2-methylpropane-2-sulfinamide

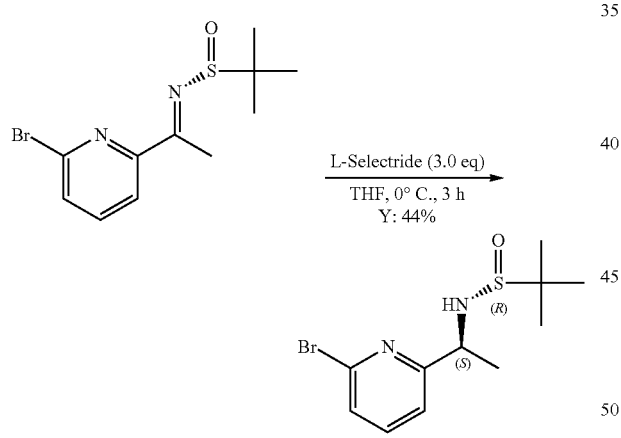

To a solution of (R,E)-N-(1-(6-bromopyridin-2-yl)ethylidene)-2-methylpropane-2-sulfinamide (3.4 g, 11.3 mmol, 1.0 eq) in THF (30 mL) was added L-selectride (34 mL, 34 mmol, 3.0 eq) at 0° C. The mixture was stirred at 0° C. for 3 h. The mixture was quenched with NH$_4$Cl (aq.) (5 mL) and extracted with EA (2×100 mL). The organics were dried (MgSO$_4$) and concentrated in vacuo. The residue was dissolved in DCM (5 mL) and a white solid was precipitated out while PE (100 mL) was added into the solution. After filtration, the white solid (R)—N—((S)-1-(6-bromopyridin-2-yl)ethyl)-2-methylpropane-2-sulfinamide was dried in vacuo. 1.5 g, yield: 44%. ESI-MS (M+H)$^+$: 305.1, 307.1. $^1$H NMR (400 MHz, CD$_3$OD) δ: 7.68 (t, J=8.0 Hz, 1H), 7.49-7.45 (m, 2H), 4.56 (q, J=6.8 Hz, 1H), 1.59 (d, J=6.8 Hz, 3H), 1.23 (s, 9H).

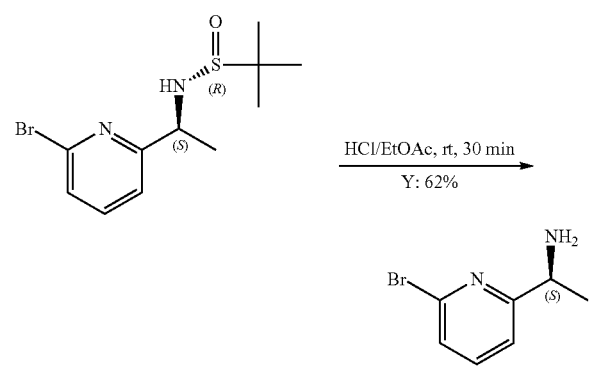

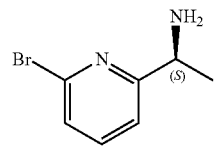

the s configuration was confirmed according to specific optical activity (Ref. Organometallics 2010, 29, 3563"C3570)

Synthesis of (R)-2-methyl-N—((S)-1-(6-(1-(6-methylpyridin-2-yl)-1H-indazol-6-yl)pyridin-2-yl)ethyl)propane-2-sulfinamide

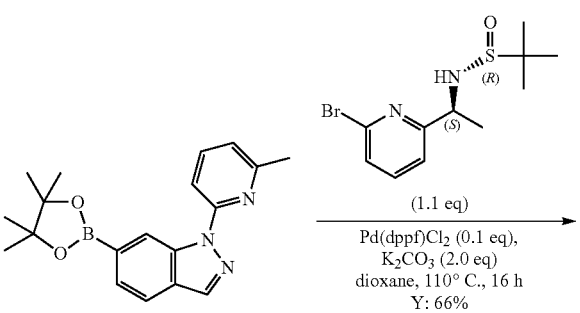

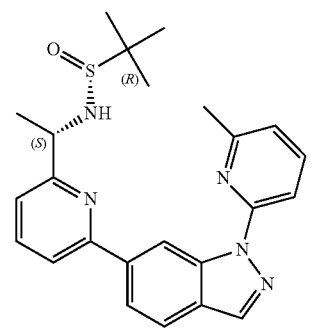

The preparation of (R)-2-methyl-N—((S)-1-(6-(1-(6-methylpyridin-2-yl)-1H-indazol-6-yl)pyridin-2-yl)ethyl)propane-2-sulfinamide was similar to that of (R)-2-methyl-N—((R)-1-(6-(1-(6-methylpyridin-2-yl)-1H-indazol-6-yl)pyridin-2-yl)ethyl)propane-2-sulfinamide to give 200 mg as a white solid, Y: 66%. ESI-MS (M+H)$^+$: 434.2. $^1$H NMR (400 MHz, CD$_3$OD) δ: 9.60 (s, 1H), 8.30 (s, 1H), 8.01 (dd, J=8.4, 1.2 Hz, 1H), 7.94-7.84 (m, 5H), 7.47 (dd, J=7.2, 1.2 Hz, 1H), 7.16 (dd, J=6.4, 1.6 Hz, 1H), 4.74 (q, J=6.8 Hz, 1H), 2.70 (s, 3H), 1.76 (d, J=7.2 Hz, 3H), 1.24 (s, 9H).

Synthesis of (S)-1-(6-(1-(6-methylpyridin-2-yl)-1H-indazol-6-yl)pyridin-2-yl)ethanamine

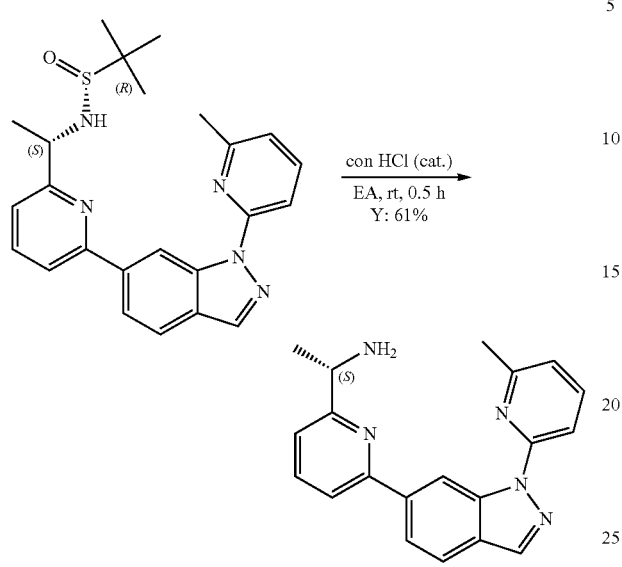

The preparation of (S)-1-(6-(1-(6-methylpyridin-2-yl)-1H-indazol-6-yl)pyridin-2-yl)ethanamine was similar to that of (R)-1-(6-(1-(6-methylpyridin-2-yl)-1H-indazol-6-yl)pyridin-2-yl)ethanamine to give 60 mg as a yellow solid, Y: 61%. ESI-MS (M+H)⁺: 330.1. HPLC: 94.21%. ¹H NMR (400 MHz, CD₃OD) δ: 9.38 (s, 1H), 8.05 (d, J=6.0 Hz, 1H), 7.79-7.77 (m, 1H), 7.69-7.57 (m, 5H), 7.19 (d, J=7.2 Hz, 1H), 6.91 (d, J=6.8 Hz, 1H), 4.04 (q, J=6.8 Hz, 1H), 2.46 (s, 3H), 1.39 (d, J=6.8 Hz, 3H).

Example 143. (S)-(6-(6-(6-(1-aminoethyl)pyridin-2-yl)-1H-indazol-1-yl)pyridin-2-yl)methanol Step 1. Synthesis of 2-bromo-6-(((tert-butyldimethylsilyl)oxy)methyl)pyridine

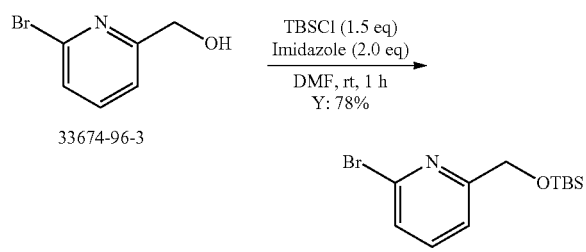

To a mixture of (6-bromopyridin-2-yl)methanol (CAS#33674-96-3) (1.87 g, 0.01 mol, 1.0 eq) and imidazole (1.36 g, 0.02 mmol, 2.0 eq) in DMF (10 mL) was added TBSCl (2.25 g, 0.015 mol, 1.5 eq) at rt. The mixture was stirred at room temperature for 1 h. The mixture was diluted with water (50 mL) and extracted with EA (3×20 mL). The combined organic phases were washed with brine (10 mL) and dried over Na₂SO₄. After filtration and concentration, the residue was purified by column chromatography (silica gel, PE/EA=50/1) to give 2-bromo-6-(((tert-butyldimethylsilyl)oxy)methyl)pyridine as yellow oil (2.35 g, Y: 78%). ESI-MS (M+H)⁺: 302.1.

Step 2. Synthesis of 6-bromo-1-(6-(((tert-butyldimethylsilyl)oxy)methyl)pyridin-2-yl)-1H-indazole

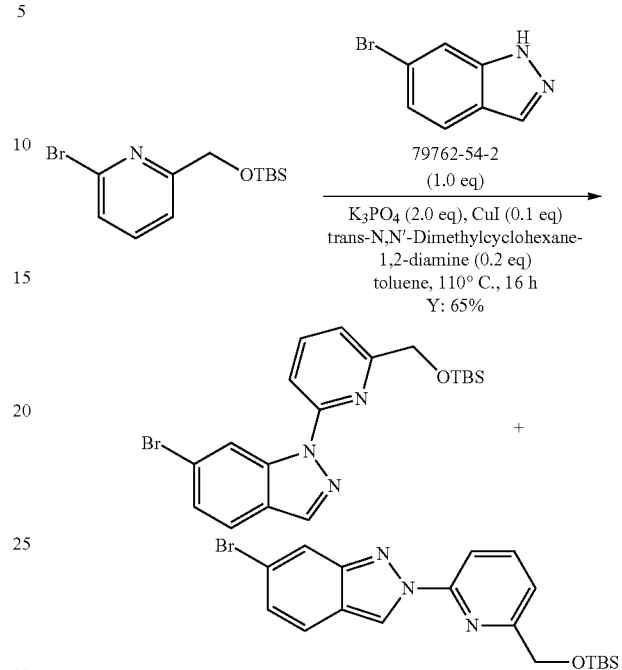

A mixture of 2-bromo-6-(((tert-butyldimethylsilyl)oxy)methyl)pyridine (1 g, 3.32 mmol), 6-bromo-1H-indazole (CAS#79762-54-2) (0.651 g, 3.32 mmol, 1.0 eq), K₃PO₄ (1.41 g, 6.64 mmol, 2.0 eq), CuI (63 mg, 0.33 mmol, 0.1 eq) and trans-N,N'-dimethylcyclohexane-1,2-diamine (93 mg, 0.66 mmol, 0.2 eq) in toluene (1 mL) was stirred at 110° C. for 16 h under N₂. After concentration, the residue was purified by column chromatography on silica gel (PE/EA=10/1) to give the mixture of 6-bromo-1-(6-(((tert-butyldimethylsilyl)oxy)methyl)pyridin-2-yl)-1H-indazole and 6-bromo-2-(6-(((tert-butyldimethylsilyl)oxy)methyl)pyridin-2-yl)-2H-indazole (the ratio 9/1) as a yellow solid. 0.91 g, Y: 65%. ESI-MS (M+H)⁺: 418.1. ¹H NMR (400 MHz, CDCl₃) δ: 9.03 (s, 1H), 8.15 (s, 1H), 7.87-7.84 (m, 2H), 7.62 (d, J=8.8 Hz, 1H), 7.40-7.37 (m, 2H), 4.93 (s, 2H), 1.00 (s, 9H), 0.20 (s, 6H).

Step 3. Synthesis of 1-(6-(((tert-butyldimethylsilyl)oxy)methyl)pyridin-2-yl)-6-(4,4,5,5-tetramethyl-1,3,2-dioxaborolan-2-yl)-1H-indazole

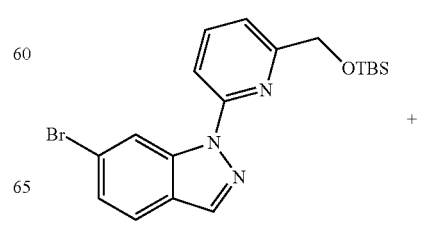

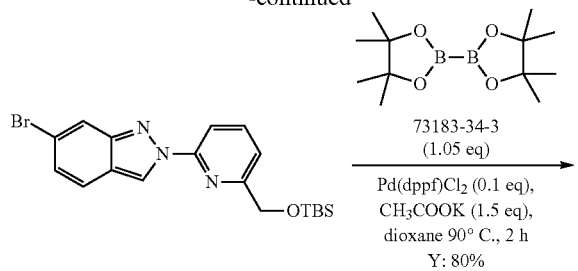
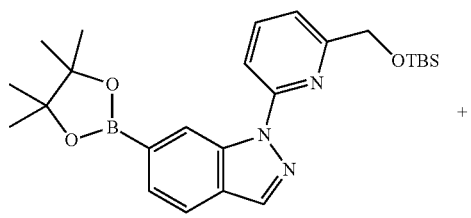
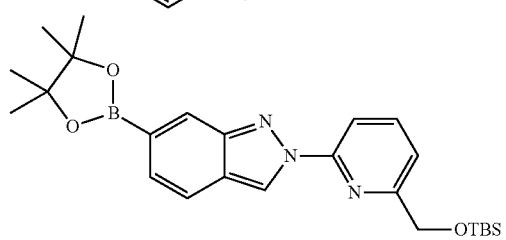

A mixture of 6-bromo-1-(6-(((tert-butyldimethylsilyl) oxy)methyl)pyridin-2-yl)-1H-indazole and 6-bromo-2-(6-(((tert-butyldimethylsilyl)oxy)methyl)pyridin-2-yl)-2H-indazole (0.83 g, 1.99 mmol), pinacol diborane (CAS#73183-34-3) (0.531 g, 2.09 mmol, 1.05 eq) and $CH_3COOK$ (0.39 g, 3.98 mmol, 2.0 eq) in 1, 4-dioxane (15 mL) was stirred while purging $N_2$ at room temperature for 10 min. To this system was added $Pd(dppf)Cl_2$ (0.326 g, 0.4 mmol, 0.1 eq) and heated to 90° C. for 2 h. The mixture was diluted with EA (50 mL) and washed with saturated aqueous $NaHCO_3$ solution (20 mL) and brine (20 mL). The organics were dried ($Na_2SO_4$) and concentrated in vacuo. The crude mixture was purified by silica gel chromatography with PE/EA (10/1) as eluent to give 1-(6-(((tert-butyldimethylsilyl)oxy)methyl) pyridin-2-yl)-6-(4,4,5,5-tetramethyl-1,3,2-dioxaborolan-2-yl)-1H-indazole and 2-(6-(((tert-butyldimethylsilyl)oxy) methyl)pyridin-2-yl)-6-(4,4,5,5-tetramethyl-1,3,2-dioxaborolan-2-yl)-2H-indazole (the ratio 9/1). 0.74 g, as a yellow solid, Y: 80%. ESI-MS $(M+H)^+$: 466.2.

Step 4. Synthesis of (R)—N—((S)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide

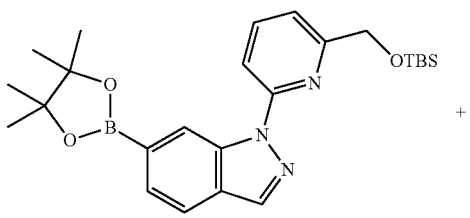
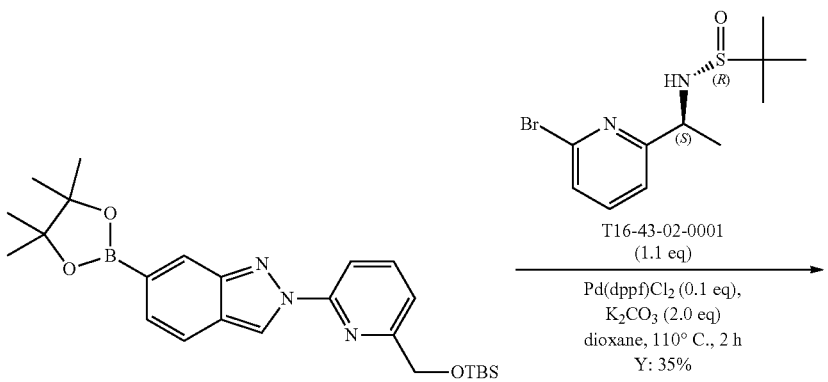

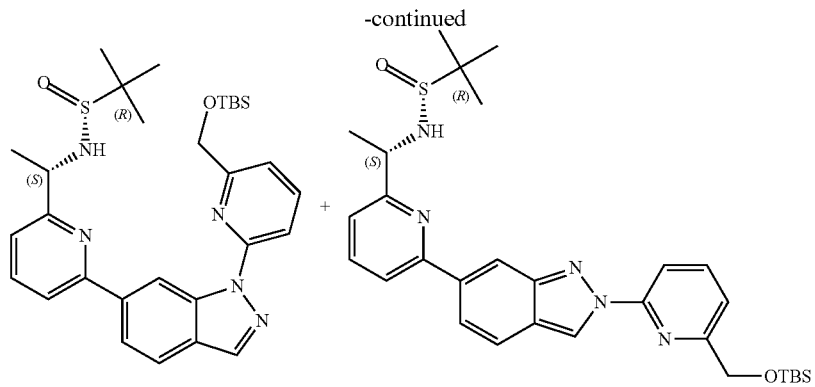

A mixture of 1-(6-(((tert-butyldimethylsilyl)oxy)methyl)pyridin-2-yl)-6-(4,4,5,5-tetramethyl-1,3,2-dioxaborolan-2-yl)-1H-indazole and 2-(6-(((tert-butyldimethylsilyl)oxy)methyl)pyridin-2-yl)-6-(4,4,5,5-tetramethyl-1,3,2-dioxaborolan-2-yl)-2H-indazole (0.74 g, 1.59 mmol), (R)—N—((S)-1-(6-bromopyridin-2-yl)ethyl)-2-methylpropane-2-sulfinamide (0.532 g, 1.75 mmol, 1.1 eq) and $K_2CO_3$ (0.439 g, 3.18 mmol, 2.0 eq) in 1,4-dioxane/$H_2O$ (10 mL/1 mL) was stirred while purging $N_2$ at room temperature for 10 min. To this system was added Pd(dppf)$Cl_2$ (0.131 g, 0.16 mmol, 0.1 eq) and heated to 110° C. for 2 h. The mixture was diluted with EA (50 mL) and washed with saturated aqueous $NaHCO_3$ solution (10 mL) and brine (10 mL). The organic phase was dried ($Na_2SO_4$) and concentrated in vacuo. The residue was purified by silica gel chromatography with PE/EA (3/1) as eluent to give (R)—N—((S)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide. 0.313 g, as a yellow solid, Y: 35%. ESI-MS (M+H)$^+$: 564.2. $^1$H NMR (400 MHz, CDCl3) δ: 9.43 (s, 1H), 8.22 (s, 1H), 8.00 (dd, J=8.4, 1.2 Hz, 1H), 7.93-7.84 (m, 3H), 7.79-7.75 (m, 2H), 7.40 (d, J=7.2 Hz, 1H), 7.29 (dd, J=6.8, 1.2 Hz, 1H), 5.30 (s, 2H), 4.98-4.95 (m, 1H), 4.05 (d, J=6.8 Hz, 1H), 1.76 (d, J=6.8 Hz, 3H), 1.22 (s, 9H), 0.99 (s, 9H), 0.17 (s, 6H).

Step 5. Synthesis of (S)-(6-(6-(6-(1-aminoethyl)pyridin-2-yl)-1H-indazol-1-yl)pyridin-2-yl)methanol

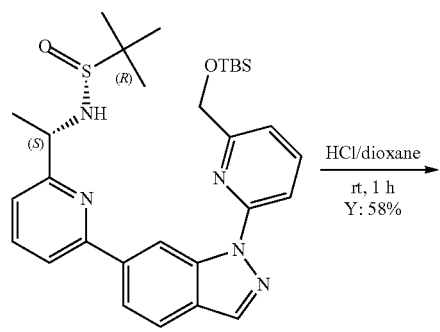

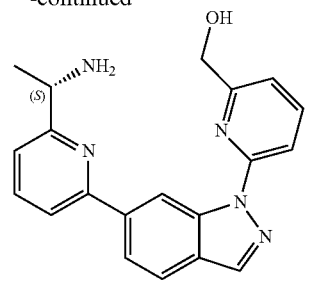

(S)-(6-(6-(6-(1-aminoethyl)pyridin-2-yl)-1H-indazol-1-yl)pyridin-2-yl)methanol

A solution of (R)—N—((S)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide (0.358 g, 0.636 mmol) in HCl/dioxane was stirred at room temperature for 1 h. After concentration, the residue was dissolved in THF (4 mL), adjusted pH=8 with 3 N NaOH and extracted with EA (10 mL). The organic phase was washed with water (4 mL), brine (4 mL) and dried over $Na_2SO_4$. After filtration and concentration, the residue was purified by prep-HPLC (MeOH/$H_2O$ with 0.05% $NH_4OH$ as mobile phase from 5% to 95%) to give (S)-(6-(6-(6-(1-aminoethyl)pyridin-2-yl)-1H-indazol-1-yl)pyridin-2-yl)methanol as a white solid. (0.127 g, Y: 58%). ESI-MS (M+H)$^+$: 346.1. HPLC: 100.00%. $^1$H NMR (400 MHz, $CD_3OD$) δ: 9.61 (s, 1H), 8.28 (s, 1H), 7.81 (dd, J=8.4, 0.8 Hz, 1H), 7.95-7.86 (m, 5H), 7.39-7.36 (m, 2H), 4.86 (s, 2H), 4.21 (q, J=6.4 Hz, 1H), 1.54 (d, J=6.8 Hz, 3H).

SFC (AD-H column, 4.6*250 mm 5 μm, MeOH with 0.1% DEA, $CO_2$ flow rate=1.95, Co-Solvent Flow Rate=1.05), $t_R$=2.88 min.

Example 144. (R)-(6-(6-(6-(1-aminoethyl)pyridin-2-yl)-1H-indazol-1-yl)pyridin-2-yl)methanol Synthesis of (R)—N—((R)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide

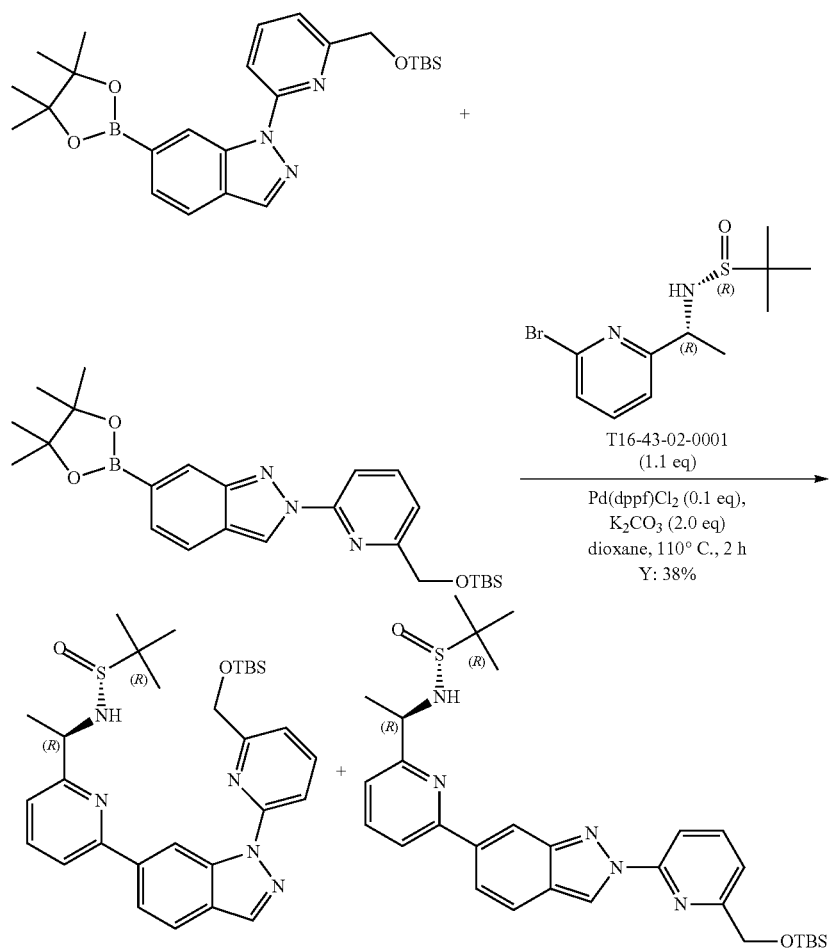

The preparation of (R)—N—((R)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide was similar to that of (R)—N—((S)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide to give 120 mg as a white solid, Y: 38%. ESI-MS (M+H)⁺: 564.2.

Synthesis of (R)-(6-(6-(6-(1-aminoethyl)pyridin-2-yl)-1H-indazol-1-yl)pyridin-2-yl)methanol

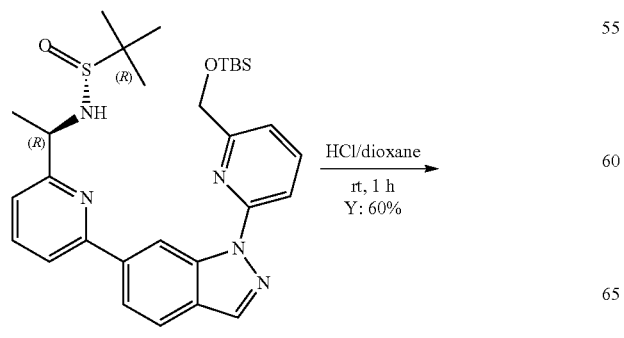

-continued

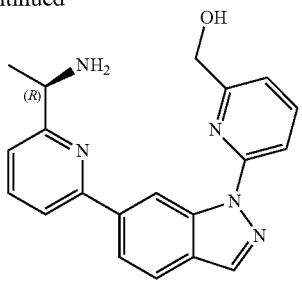

The preparation of (R)-(6-(6-(6-(1-aminoethyl)pyridin-2-yl)-1H-indazol-1-yl)pyridin-2-yl)methanol was similar to that of (S)-(6-(6-(6-(1-aminoethyl)pyridin-2-yl)-1H-indazol-1-yl)pyridin-2-yl)methanol to give 44 mg as a white solid, Y: 60%. ESI-MS (M+H)⁺: 346.1. HPLC: 100.00%. ¹H NMR (400 MHz, CD₃OD) δ: 9.66 (s, 1H), 8.31 (d, J=0.4 Hz, 1H), 8.05 (dd, J=8.4, 1.2 Hz, 1H), 7.98-7.88 (m, 5H), 7.42-7.38 (m, 2H), 4.87 (s, 2H), 4.29 (q, J=6.8 Hz, 1H), 1.57 (d, J=6.8 Hz, 3H).

SFC (AD-H column, 4.6*250 mm 5 μm, MeOH with 0.1% DEA, CO$_2$ flow rate=2.1, Co-Solvent Flow Rate=0.9), t$_R$=4.08 min.

Example 145. (S)-(6-(6-(6-(1-aminobutyl)pyridin-2-yl)-1H-indazol-1-yl)pyridin-2-yl)methanol Step 1. Synthesis of 6-bromo-N-methoxy-N-methylpicolinamide

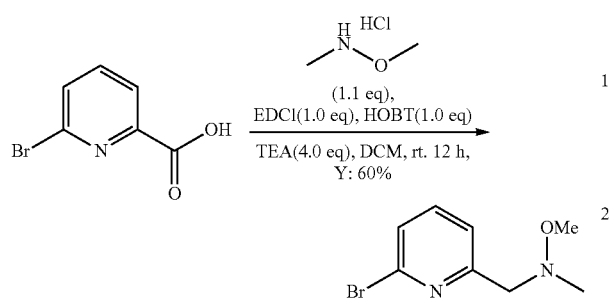

To a solution of 6-bromopicolinic acid (CAS#21190-87-4) (0.6 g, 2.98 mmol, 1.0 eq), N,O-dimethylhydroxylamine hydrochloride (CAS#6638-79-5) (0.319 g, 3.28 mmol, 1.1 eq) and TEA (1.2 g, 11.9 mmol, 4.0 eq) in DCM (30 mL) were added EDCI (0.57 g, 2.98 mmol, 1.0 eq) and HOBT (0.403 g, 2.98 mmol, 1.0 eq) in portions at 0° C. The reaction mixture was warmed up to room temperature and stirred for 12 h. The mixture was extracted with DCM (3×10 mL) and washed with brine. The combined organic phase was dried over Na$_2$SO$_4$ and concentrated in vacuo. The crude mixture was purified by silica gel chromatography with PE/EA (10/1) as eluent to give 6-bromo-N-methoxy-N-methylpicolinamide. 0.436 g, as colorless oil, Y: 60%. ESI-MS (M+H)$^+$: 245.0.

Step 2. Synthesis of 1-(6-bromopyridin-2-yl)butan-1-one

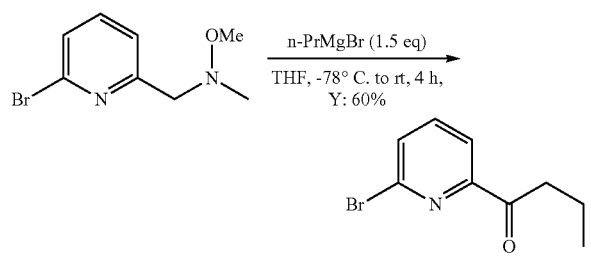

To a solution of 6-bromo-N-methoxy-N-methylpicolinamide (0.4 g, 1.63 mmol, 1.0 eq) in THF (5 mL) was slowly added n-PrMgBr (2.45 mL, 2.45 mmol, 1.5 eq, 1 M in THF) at −78° C. for 30 min. The mixture was warmed to room temperature and stirred at rt for 4 h. The mixture was quenched with NH$_4$Cl (aq.) (2 mL) and extracted with EA (2×10 mL). The combined organic phase was washed with brine and dried over Na$_2$SO$_4$. After filtration and concentration, the residue was purified by silica gel chromatography with PE/EA (10/1) as eluent to give 1-(6-bromopyridin-2-yl)butan-1-one. 0.22 g, as colorless oil, Y: 60%. ESI-MS (M+H)$^+$: 228.0.

Step 3. Synthesis of (R,E)-N-(1-(6-bromopyridin-2-yl)butylidene)-2-methylpropane-2-sulfinamide

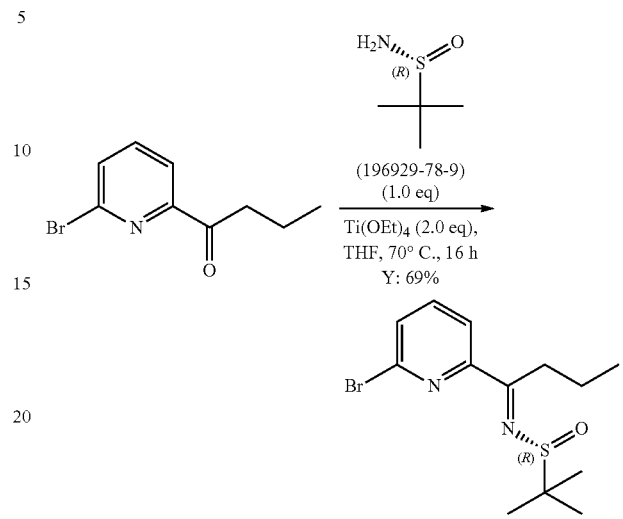

To a solution of 1-(6-bromopyridin-2-yl)butan-1-one (Example 145, Step 2, 0.2 g, 0.88 mmol, 1.0 eq) and (R)-2-methylpropane-2-sulfinamide (CAS#196929-78-9) (0.107 g, 0.88 mmol, 1.0 eq) in THF (2 mL) was added Ti(OEt)$_4$ (0.4 g, 1.76 mmol, 2.0 eq) at room temperature. The mixture was stirred at 70° C. for 16 h. After cooling down to rt, the mixture was diluted with water (10 mL) and extracted with DCM (2×10 mL). The combined organic layers were dried over anhydrous Na$_2$SO$_4$. After concentration, the residue was purified by silica gel chromatography with PE/EA (10/1) as eluent to give (R,E)-N-(1-(6-bromopyridin-2-yl)butylidene)-2-methylpropane-2-sulfinamide (0.183 g, Y: 69%) as a yellow solid. ESI-MS (M+H)$^+$: 331.0.

Step 4. Synthesis of (R)—N—((R)-1-(6-bromopyridin-2-yl)butyl)-2-methylpropane-2-sulfinamide

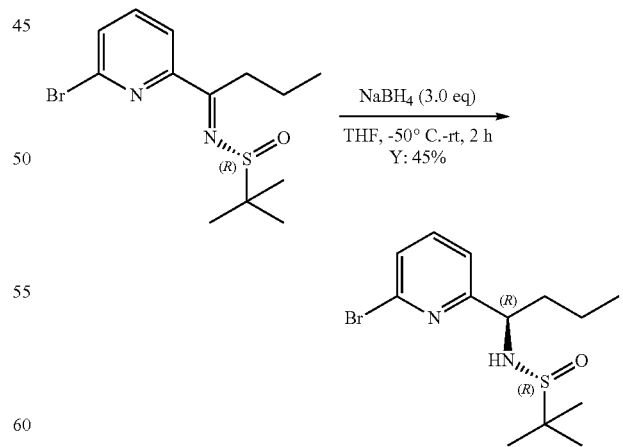

To a solution of (R,E)-N-(1-(6-bromopyridin-2-yl)butylidene)-2-methylpropane-2-sulfinamide (66 mg, 0.2 mmol, 1.0 eq) in THF (2 mL) was added NaBH$_4$ (22 mg, 0.6 mmol, 3.0 eq) at −50° C. The mixture was warmed to room temperature over 2 h. The mixture was diluted with EA (10 mL) and washed with water (2×5 mL). The organics were dried (MgSO$_4$) and concentrated in vacuo. The residue was purified by prep-HPLC (MeCN/H$_2$O with 0.05% NH$_4$OH as mobile phase from 5% to 95%) to give (R)—N—((R)-1-(6-bromopyridin-2-yl)butyl)-2-methylpropane-2-sulfinamide (30 mg, Y: 45%) as colorless oil. ESI-MS (M+H)$^+$: 333.1.

Step 5. Synthesis of (R)—N—((S)-1-(6-bromopyridin-2-yl)butyl)-2-methylpropane-2-sulfinamide

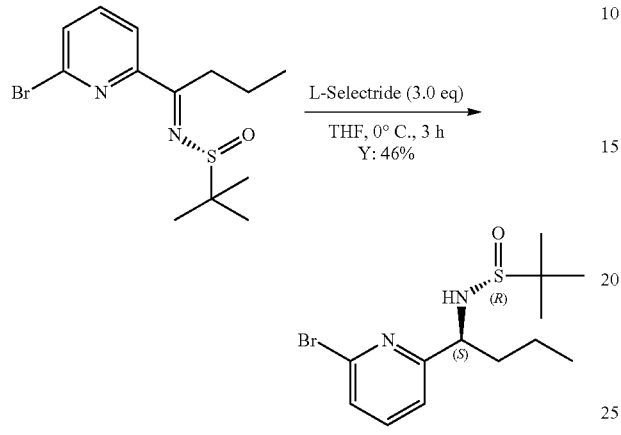

To a solution of (R)—N—((R)-1-(6-bromopyridin-2-yl)butyl)-2-methylpropane-2-sulfinamide (76 mg, 0.23 mmol, 1.0 eq) in THF (4 mL) was added L-Selectride (0.7 mL, 0.69 mmol, 3.0 eq) at 0° C. The mixture was stirred at 0° C. for 3 h. The reaction was quenched with NH$_4$Cl (aq) (2 mL) and extracted with EA (2×4 mL). The combined organic phase was washed with brine and dried over Na$_2$SO$_4$. After filtration and concentration, the residue was dissolved in DCM (0.5 mL) and a white solid was precipitated out while PE (10 mL) was added into the solution. After filtration, the white solid (R)—N—((S)-1-(6-bromopyridin-2-yl)butyl)-2-methylpropane-2-sulfinamide was dried in vacuo. 35 mg, Y: 46%. ESI-MS (M+H)$^+$: 333.1. $^1$H NMR (400 MHz, CDCl$_3$) δ: 7.51 (t, J=8.0 Hz, 1H), 7.38 (d, J=8.0 Hz, 1H), 7.22 (d, J=7.6 Hz, 1H), 4.46-4.41 (m, 1H), 1.92-1.85 (m, 2H), 1.38-1.24 (m, 2H), 1.18 (s, 9H), 0.92 (t, J=7.2 Hz, 3H).

Step 6. Synthesis of (R)—N—((S)-1-(6-(1-(6-(((tert-butyldimethylsilyl)oxy)methyl)pyridin-2-yl)-1H-indazol-6-yl)pyridin-2-yl)butyl)-2-methylpropane-2-sulfinamide

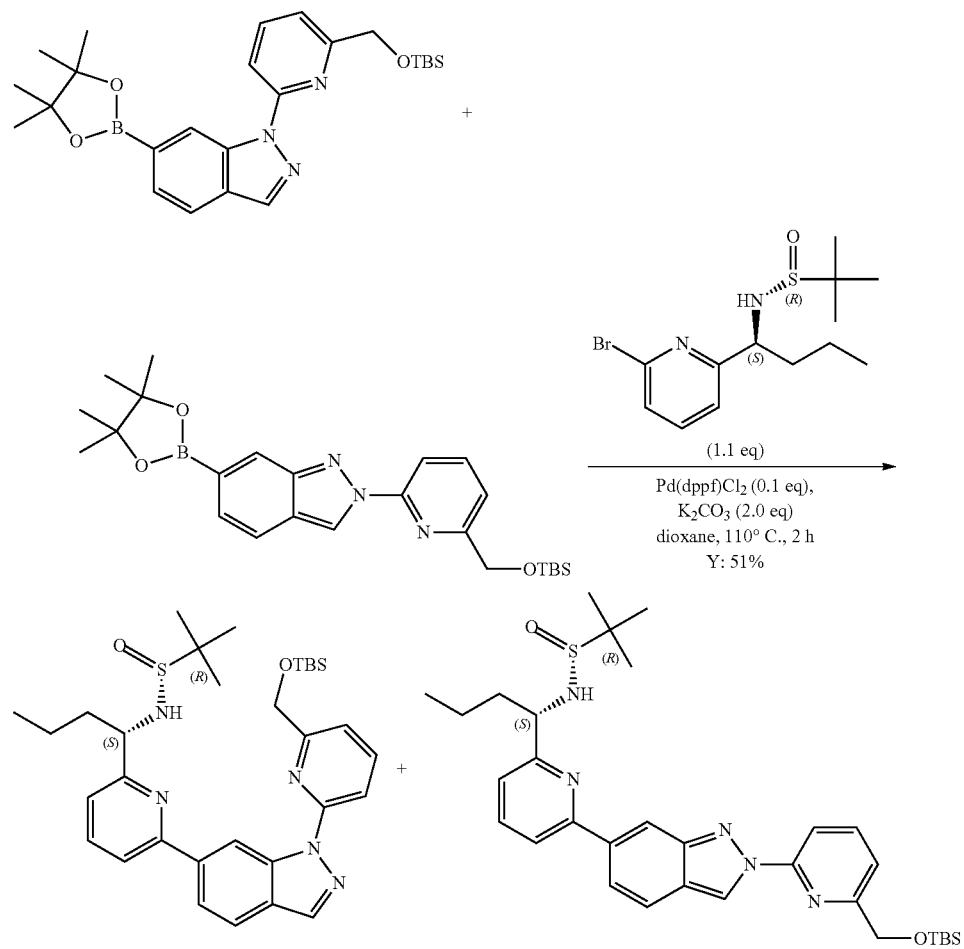

The preparation of (R)—N—((S)-1-(6-(1-(6-(((tert-butyldimethylsilyl)oxy)methyl)pyridin-2-yl)-1H-indazol-6-yl)pyridin-2-yl)butyl)-2-methylpropane-2-sulfinamide was similar to that of (R)—N—((S)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide to give 0.32 g as a white solid, Y: 51%. ESI-MS (M+H)$^+$: 592.2.

Step 7. Synthesis of (S)-(6-(6-(6-(1-aminobutyl)pyridin-2-yl)-1H-indazol-1-yl)pyridin-2-yl)methanol

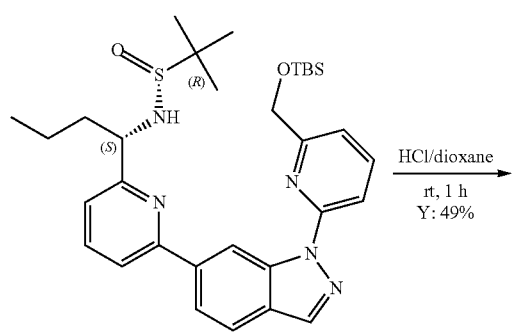

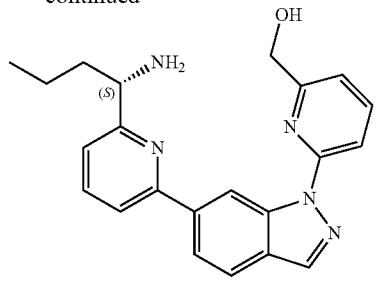

The preparation of (S)-(6-(6-(6-(1-aminobutyl)pyridin-2-yl)-1H-indazol-1-yl)pyridin-2-yl)methanol was similar to that of (S)-(6-(6-(6-(1-aminoethyl)pyridin-2-yl)-1H-indazol-1-yl)pyridin-2-yl)methanol to give 0.1 g as a white solid, Y: 49%. ESI-MS (M+H)$^+$: 374.1. HPLC: 100.00%. $^1$H NMR (400 MHz, CD$_3$OD) δ: 9.62 (s, 1H), 8.29 (s, 1H), 8.01 (d, J=8.8 Hz, 1H), 7.96-7.86 (m, 5H), 7.41-7.33 (m, 2H), 4.87 (s, 2H), 4.04 (t, J=6.8 Hz, 1H), 1.95-1.80 (m, 2H), 1.49-1.27 (m, 2H), 0.98 (t, J=6.8 Hz, 3H).

Example 146. (R)-(6-(6-(6-(1-aminobutyl)pyridin-2-yl)-1H-indazol-1-yl)pyridin-2-yl)methanol Synthesis of (R)—N—((R)-1-(6-(1-(6-(((tert-butyldimethylsilyl)oxy)methyl)pyridin-2-yl)-1H-indazol-6-yl)pyridin-2-yl)butyl)-2-methylpropane-2-sulfinamide

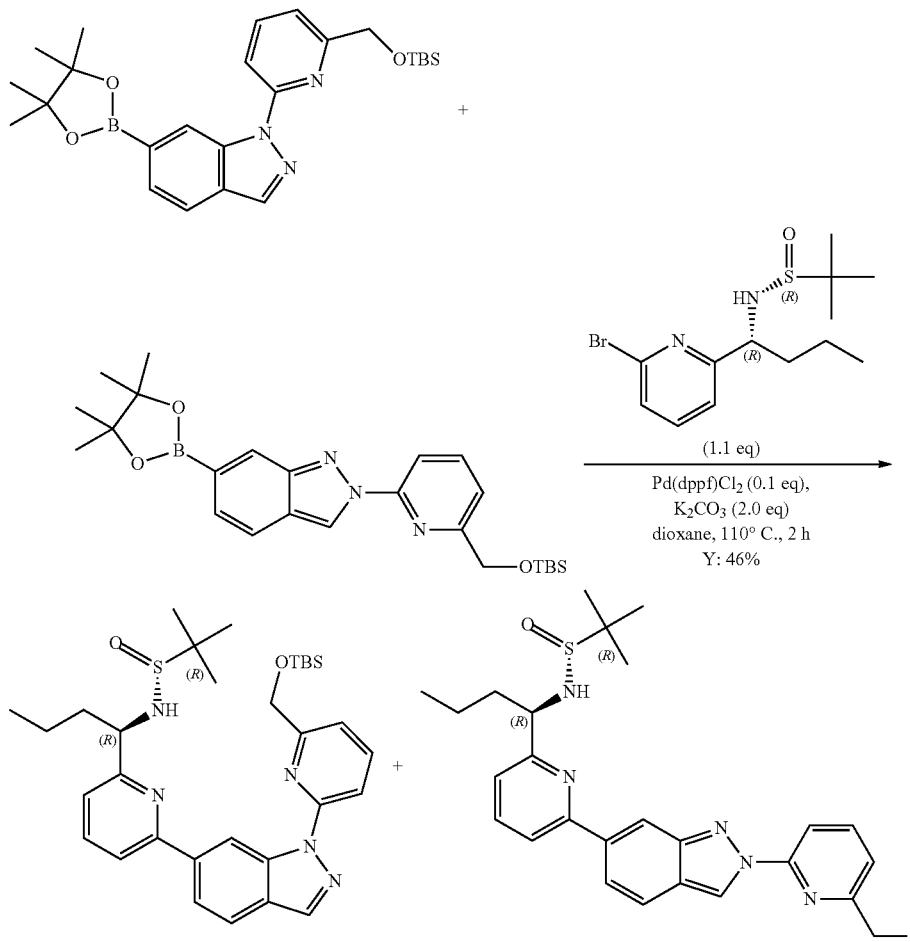

The preparation of (R)—N—((R)-1-(6-(1-(6-(((tert-butyldimethylsilyl)oxy)methyl)pyridin-2-yl)-1H-indazol-6-yl)pyridin-2-yl)butyl)-2-methylpropane-2-sulfinamide was similar to that of (R)—N—((S)-1-(6-(1-(6-(((tert-butyldimethylsilyl)oxy)methyl)pyridin-2-yl)-1H-indazol-6-yl)pyridin-2-yl)ethyl)-2-methylpropane-2-sulfinamide to give 210 mg as a white solid, Y: 46%. ESI-MS (M+H)+: 592.2.

Synthesis of (R)-(6-(6-(6-(1-aminobutyl)pyridin-2-yl)-1H-indazol-1-yl)pyridin-2-yl)methanol

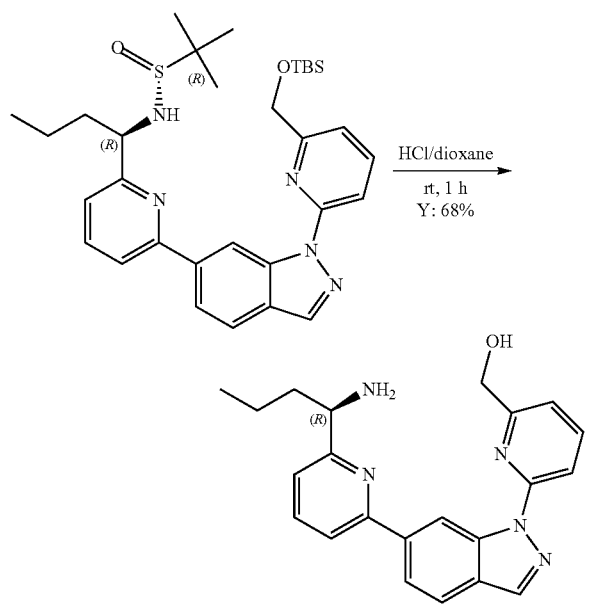

The preparation of (R)-(6-(6-(6-(1-aminobutyl)pyridin-2-yl)-1H-indazol-1-yl)pyridin-2-yl)methanol was similar to that of (S)-(6-(6-(6-(1-aminoethyl)pyridin-2-yl)-1H-indazol-1-yl)pyridin-2-yl)methanol to give 90 mg as a white solid, Y: 68%. ESI-MS (M+H)+: 374.1. HPLC: 100.00%. 1H NMR (400 MHz, CD3OD) δ: 9.61 (s, 1H), 8.29 (s, 1H), 8.01 (dd, J=8.8, 1.2 Hz, 1H), 7.95-7.86 (m, 5H), 7.40-7.32 (m, 2H), 4.86 (s, 2H), 4.04 (t, J=6.8 Hz, 1H), 1.95-1.80 (m, 2H), 1.49-1.27 (m, 2H), 0.97 (t, J=6.8 Hz, 3H).

Example 200. 1-(6-methylpyridin-2-yl)-1H-pyrazolo[4,3-c]pyridin-7-amine

Example 200 was synthesized according to the procedures described herein.
ESI-MS (M+H)+: 302.1.
1H NMR (400 MHz, CD3OD) δ: 9.06 (s, 1H), 8.26 (s, 1H), 8.13 (d, J=1.6 Hz, 1H), 7.98 (d, J=2.4 Hz, 1H), 7.89 (d, J=8.8 Hz, 1H), 7.83-7.77 (m, 2H), 7.51 (d, J=8.4 Hz, 1H), 7.41 (t, J=2.0 Hz, 1H), 7.11 (d, J=6.0 Hz, 1H), 2.63 (s, 3H).

Examples 201 to 323 can be synthesized according to the procedures described herein. In particular, Examples 201, 202, 203, 204, 205, 206, 209, 210, 211, 212, 213, 216, 220, 221, 228, 229, 230, 231, 232, 235, 236, 237, 239, 241, 242, 243, 244, 247, 248, 249, 252, 253, 254, 255, 256, 257, 258, 259, 260, 261, 262, 263, 264, 265, 266, 267, 268, 269, 270, 271, 272, 273, 274, 275, 279, 280, 281, 282, 283, 284, 285, 286, 287, 288, 289, 290, 291, 292, 294, 296, 297, 298, 299, 300, 301, 304, 305, 306, 308, 310, 312, 313, 314, 315, 318, 320, 322, 323 were synthesized similar to that of example 146. Examples 207, 240, and 321 were synthesized similar to that of example 106. Examples 208, 214, 215, and 217 were synthesized similar to that of example 105. Examples 218 and 219 were synthesized similar to that of example 106. Examples 222, 223, 224, 275, 276, 293, 302, 311, and 317 were synthesized similar to that of example 99. Examples 225, 226, 227, 233, 234 were synthesized similar to that of example 103. Examples 245, 246, 250, 251, and 307 were synthesized similar to that of example X (4-position ethoxy methoxy). Examples 295, 303, and 319 were synthesized similar to that of example X (4-position aryl). Example 309 was synthesized similar to that of example 114. Example 316 was synthesized similar to that of example 104.

| Example | Name | Structure |
| --- | --- | --- |
| 201 | 2-(1-(6-methylpyridin-2-yl)-1H-indazol-6-yl)isonicotinamide | 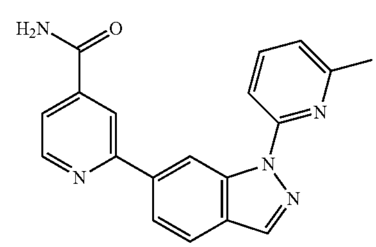 [SMILES: Cc1cccc(-n2ncc3ccc(-c4cc(C(N)=O)ccn4)cc32)n1] |
| 202 | N,N-dimethyl-5-(1-(6-methylpyridin-2-yl)-1H-indazol-6-yl)pyridin-3-amine | 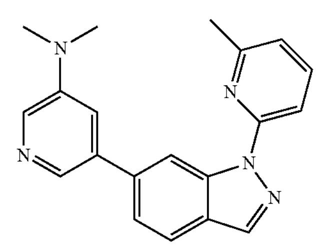 [SMILES: Cc1cccc(-n2ncc3ccc(-c4cncc(N(C)C)c4)cc32)n1] |

-continued

| Example | Name | Structure |
|---|---|---|
| 203 | 1-(6-methylpyridin-2-yl)-6-(5-(pyrrolidin-1-yl)pyridin-3-yl)-1H-indazole | 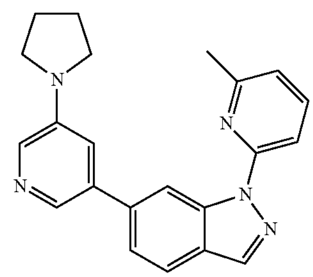 [SMILES: Cc1cccc(-n2ncc3ccc(-c4cncc(N5CCCC5)c4)cc32)n1] |
| 204 | 6-methyl-5-(1-(6-methylpyridin-2-yl)-1H-indazol-6-yl)pyridin-3-amine | 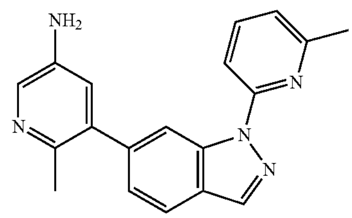 [SMILES: Cc1cccc(-n2ncc3ccc(-c4cc(N)cnc4C)cc32)n1] |
| 205 | 5-(1-(6-cyclopentylpyridin-2-yl)-1H-indazol-6-yl)pyridin-3-amine | 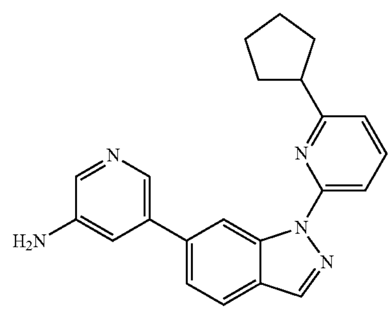 [SMILES: Nc1cncc(-c2ccc3cnn(-c4cccc(C5CCCC5)n4)c3c2)c1] |
| 206 | 5-(1-(6-methylpyridin-2-yl)-1H-indazol-6-yl)-3,4-dihydroisoquinolin-1(2H)-one | 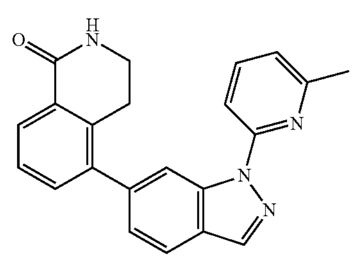 [SMILES: Cc1cccc(-n2ncc3ccc(-c4cccc5c4CCNC5=O)cc32)n1] |
| 207 | 1-(6-(4-fluoro-1-(6-(trifluoromethyl)pyridin-2-yl)-1H-indazol-6-yl)pyridin-2-yl)ethanone | 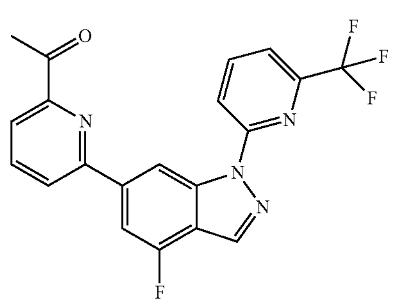 [SMILES: CC(=O)c1cccc(-c2cc(F)c3cnn(-c4cccc(C(F)(F)F)n4)c3c2)n1] |

| Example | Name | Structure |
|---|---|---|
| 208 | N-(5-(4-cyano-1-(6-(trifluoromethyl)pyridin-2-yl)-1H-indazol-6-yl)pyridin-3-yl)-2,2,2-trifluoroacetamide | 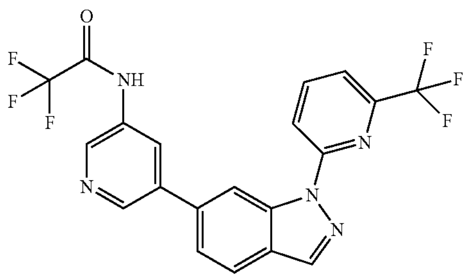 [SMILES: O=C(Nc1cncc(-c2ccc3cnn(-c4cccc(C(F)(F)F)n4)c3c2)c1)C(F)(F)F] |
| 209 | 1-(6-(1-(6-(trifluoromethyl)pyridin-2-yl)-1H-indazol-6-yl)pyridin-2-yl)ethanamine | 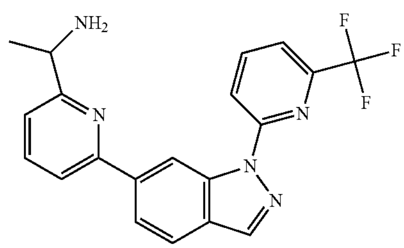 [SMILES: CC(N)c1cccc(-c2ccc3cnn(-c4cccc(C(F)(F)F)n4)c3c2)n1] |
| 210 | 2-(1-(6-(trifluoromethyl)pyridin-2-yl)-1H-indazol-6-yl)-5H-cyclopenta[b]pyridin-7(6H)-one | 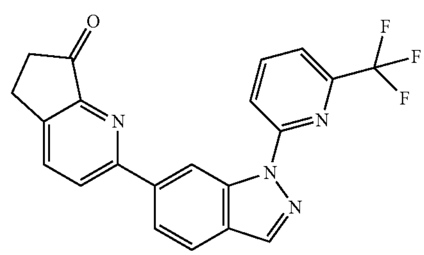 [SMILES: O=C1CCc2ccc(-c3ccc4cnn(-c5cccc(C(F)(F)F)n5)c4c3)nc21] |
| 211 | 6-(1-(6-(trifluoromethyl)pyridin-2-yl)-1H-indazol-6-yl)picolinonitrile | 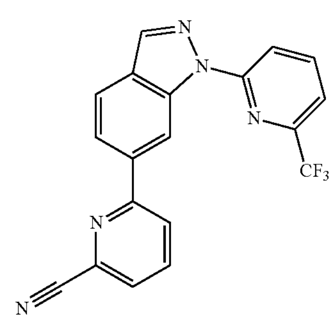 [SMILES: N#Cc1cccc(-c2ccc3cnn(-c4cccc(C(F)(F)F)n4)c3c2)n1] |
| 212 | 2-(1-(6-(trifluoromethyl)pyridin-2-yl)-1H-indazol-6-yl)-6,7-dihydroisoquinolin-8(5H)-one | 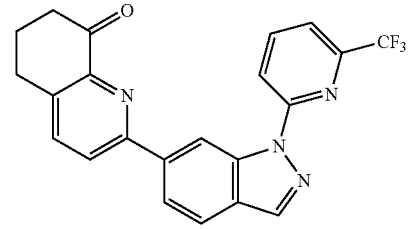 [SMILES: O=C1CCCc2ccc(-c3ccc4cnn(-c5cccc(C(F)(F)F)n5)c4c3)nc21] |

| Example | Name | Structure |
|---|---|---|
| 213 | 6-amino-4-(1-(6-(trifluoromethyl)pyridin-2-yl)-1H-indazol-6-yl)picolinic acid | 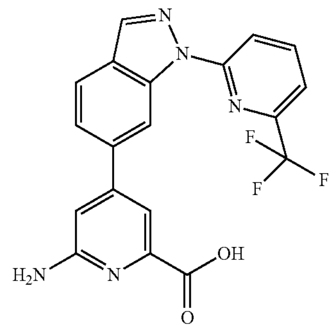 [SMILES: Nc1cc(-c2ccc3cnn(-c4cccc(C(F)(F)F)n4)c3c2)cc(C(=O)O)n1] |
| 214 | 6-(6-(1-aminoethyl)pyridin-2-yl)-1-(6-methylpyridin-2-yl)-1H-indazole-4-carbonitrile | 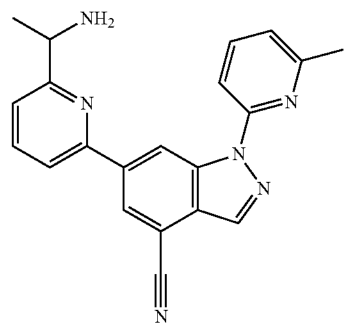 [SMILES: Cc1cccc(-n2ncc3c(C#N)cc(-c4cccc(C(C)N)n4)cc32)n1] |
| 215 | 1-(6-(4-(aminomethyl)-2-(6-methylpyridin-2-yl)-2H-indazol-6-yl)pyridin-2-yl)ethanamine | 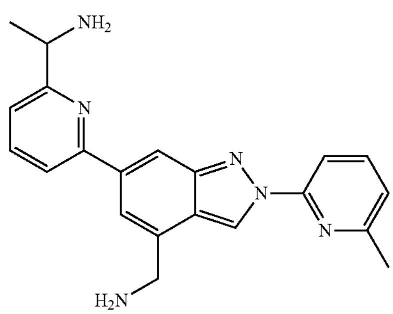 [SMILES: Cc1cccc(-n2cc3c(CN)cc(-c4cccc(C(C)N)n4)cc3n2)n1] |
| 216 | N,N-dimethyl-1-(6-(1-(6-(trifluoromethyl)pyridin-2-yl)-1H-indazol-6-yl)pyridin-2-yl)ethanamine | 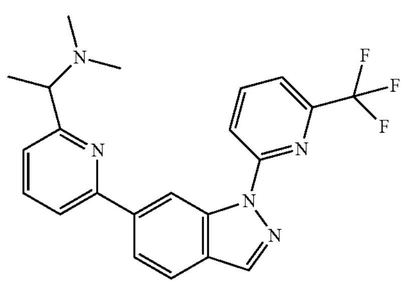 [SMILES: CC(c1cccc(-c2ccc3cnn(-c4cccc(C(F)(F)F)n4)c3c2)n1)N(C)C] |
| 217 | N-((6-(6-(1-aminoethyl)pyridin-2-yl)-2-(6-methylpyridin-2-yl)-2H-indazol-4-yl)methyl)acetamide | 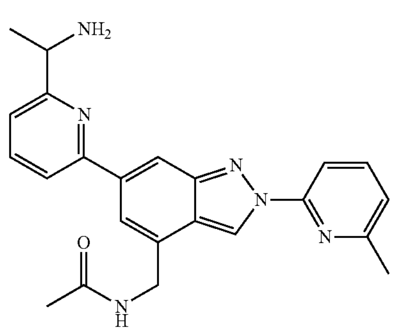 [SMILES: CC(=O)NCc1cc(-c2cccc(C(C)N)n2)cc2nn(-c3cccc(C)n3)cc12] |

-continued

| Example | Name |
|---|---|
| 218 | 1-(6-(4-chloro-1-(6-methylpyridin-2-yl)-1H-indazol-6-yl)pyridin-2-yl)ethanone |
| 219 | (Z)-1-(6-(4-chloro-1-(6-methylpyridin-2-yl)-1H-indazol-6-yl)pyridin-2-yl)ethanone oxime |
| 220 | N,N-dimethyl-1-(6-(1-(6-methylpyridin-2-yl)-1H-indazol-6-yl)pyridin-2-yl)ethanamine |
| 221 | N,N-dimethyl-1-(6-(1-(6-(trifluoromethyl)pyridin-2-yl)-1H-indazol-6-yl)pyridin-2-yl)ethanamine |
| 222 | 1-(6-(3-(6-(trifluoromethyl)pyridin-2-yl)imidazo[1,5-a]pyridin-6-yl)pyridin-2-yl)ethanamine |

| Example | Name | Structure |
|---|---|---|
| 223 | 1-(6-(3-(6-(trifluoromethyl)pyridin-2-yl)imidazo[1,5-a]pyridin-6-yl)pyridin-2-yl)ethanamine | 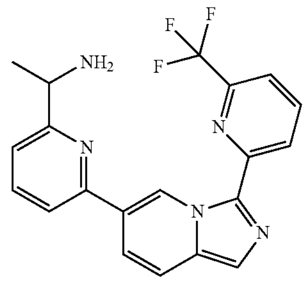 [SMILES: CC(N)c1cccc(-c2ccc3cnc(-c4cccc(C(F)(F)F)n4)n3c2)n1] |
| 224 | (Z)-1-(6-(3-(6-(trifluoromethyl)pyridin-2-yl)imidazo[1,5-a]pyridin-6-yl)pyridin-2-yl)ethanone oxime | 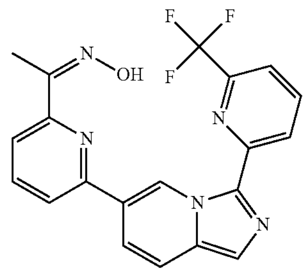 [SMILES: C/C(=N/O)c1cccc(-c2ccc3cnc(-c4cccc(C(F)(F)F)n4)n3c2)n1] |
| 225 | tert-butyl (6-(6-acetylpyridin-2-yl)-1-(6-methylpyridin-2-yl)-1H-indazol-4-yl)(methyl)carbamate | 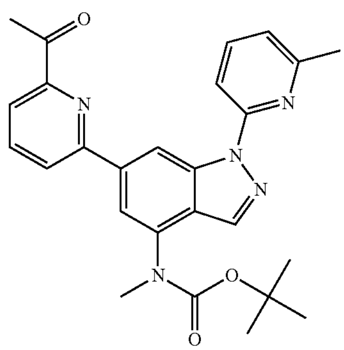 [SMILES: CC(=O)c1cccc(-c2cc(N(C)C(=O)OC(C)(C)C)c3cnn(-c4cccc(C)n4)c3c2)n1] |
| 226 | (Z)-tert-butyl (6-(6-(1-(hydroxyimino)ethyl)pyridin-2-yl)-1-(6-methylpyridin-2-yl)-1H-indazol-4-yl)(methyl)carbamate | 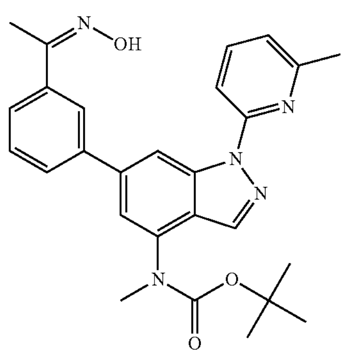 [SMILES: C/C(=N/O)c1cccc(-c2cc(N(C)C(=O)OC(C)(C)C)c3cnn(-c4cccc(C)n4)c3c2)c1] |
| 227 | (Z)-1-(6-(4-(methylamino)-1-(6-methylpyridin-2-yl)-1H-indazol-6-yl)pyridin-2-yl)ethanone oxime | 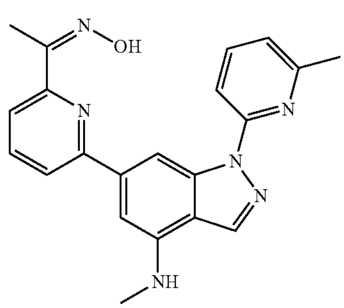 [SMILES: CNc1cc(-c2cccc(/C(C)=N\O)n2)cc2c1cnn2-c1cccc(C)n1] |

-continued

| Example | Name | Structure |
|---|---|---|
| 228 | 1-(6-(1-(6-ethylpyridin-2-yl)-1H-indazol-6-yl)pyridin-2-yl)ethanone | 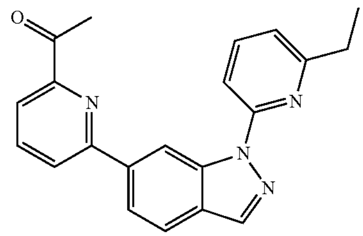 [SMILES: CCc1cccc(-n2ncc3ccc(-c4cccc(C(C)=O)n4)cc32)n1] |
| 229 | 1-(6-(1-(pyridin-2-yl)-1H-indazol-6-yl)pyridin-2-yl)ethanone | 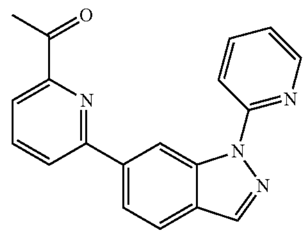 [SMILES: CC(=O)c1cccc(-c2ccc3cnn(-c4ccccn4)c3c2)n1] |
| 230 | (E)-1-(6-(1-(pyridin-2-yl)-1H-indazol-6-yl)pyridin-2-yl)ethanone oxime | 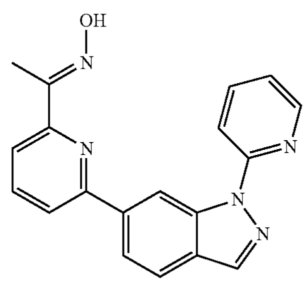 [SMILES: C/C(=N\O)c1cccc(-c2ccc3cnn(-c4ccccn4)c3c2)n1] |
| 231 | 2-(aminomethyl)-6-(1-(6-methylpyridin-2-yl)-1H-indazol-6-yl)pyridin-4-amine | 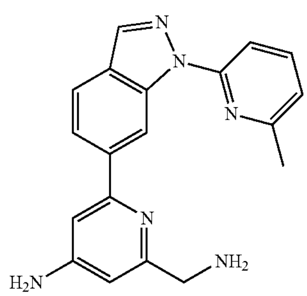 [SMILES: Cc1cccc(-n2ncc3ccc(-c4cc(N)cc(CN)n4)cc32)n1] |
| 232 | N,N-dimethyl-1-(6-(1-(6-methylpyridin-2-yl)-1H-indazol-6-yl)pyridin-2-yl)ethanamine | 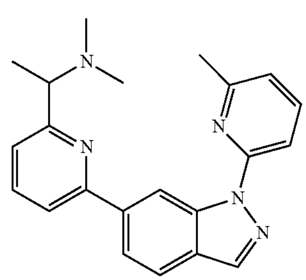 [SMILES: Cc1cccc(-n2ncc3ccc(-c4cccc(C(C)N(C)C)n4)cc32)n1] |

-continued

| Example | Name | Structure |
|---|---|---|
| 233 | 1-(6-(4-(dimethylamino)-1-(6-methylpyridin-2-yl)-1H-indazol-6-yl)pyridin-2-yl)ethanone | 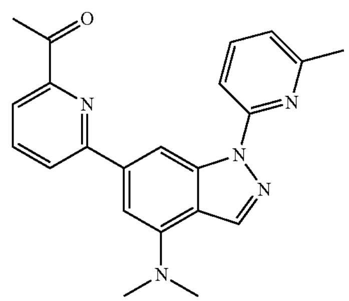 [SMILES: CC(=O)c1cccc(-c2cc(N(C)C)c3cnn(-c4cccc(C)n4)c3c2)n1] |
| 234 | (E)-1-(6-(4-(dimethylamino)-1-(6-methylpyridin-2-yl)-1H-indazol-6-yl)pyridin-2-yl)ethanone oxime | 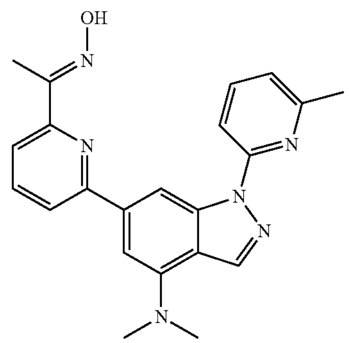 [SMILES: C/C(=N\O)c1cccc(-c2cc(N(C)C)c3cnn(-c4cccc(C)n4)c3c2)n1] |
| 235 | (E)-1-(6-(1-(6-ethylpyridin-2-yl)-1H-indazol-6-yl)pyridin-2-yl)ethanone oxime | 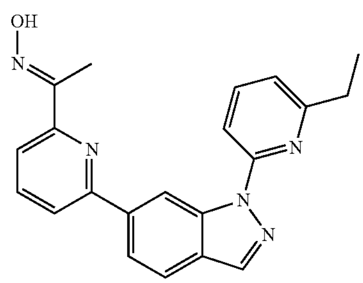 [SMILES: CCc1cccc(-n2ncc3ccc(-c4cccc(/C(C)=N/O)n4)cc32)n1] |
| 236 | 6-(6-(6-acet6ylpyridin-2-yl)-1H-indazol-1-yl)picolinonitrile | 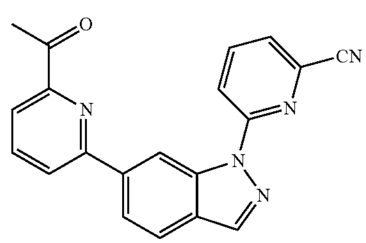 [SMILES: CC(=O)c1cccc(-c2ccc3cnn(-c4cccc(C#N)n4)c3c2)n1] |
| 237 | (E)-methyl 6-(6-(6-(1-(hydroxyimino)ethyl)pyridin-2-yl)-1H-indazol-1-yl)picolinate | 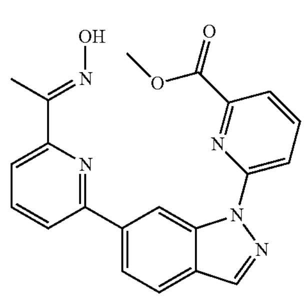 [SMILES: COC(=O)c1cccc(-n2ncc3ccc(-c4cccc(/C(C)=N/O)n4)cc32)n1] |

| Example | Name | Structure |
|---|---|---|
| 239 | 1-(6-(4-methylthiazol-2-yl)-1H-indazol-6-yl)pyridin-2-yl)ethanone | 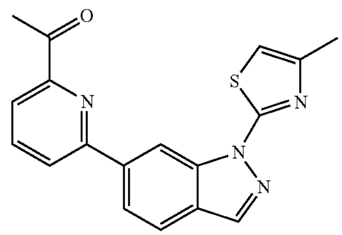 [SMILES: CC(=O)c1cccc(-c2ccc3cnn(-c4nc(C)cs4)c3c2)n1] |
| 240 | 1-(6-(4-fluoro-1-(6-(trifluoromethyl)pyridin-2-yl)-1H-indazol-6-yl)pyridin-2-yl)ethanamine | 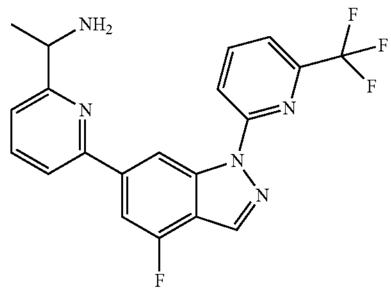 [SMILES: CC(N)c1cccc(-c2cc(F)c3cnn(-c4cccc(C(F)(F)F)n4)c3c2)n1] |
| 241 | (S)-1-(6-(1-(6-methylpyridin-2-yl)-1H-indazol-6-yl)pyridin-2-yl)ethanamine | 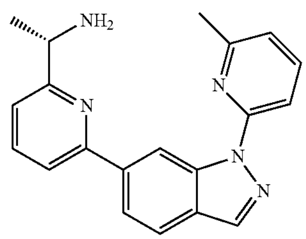 [SMILES: Cc1cccc(-n2ncc3ccc(-c4cccc([C@H](C)N)n4)cc32)n1] |
| 242 | 1-(3-fluoro-6-(1-(6-methylpyridin-2-yl)-1H-indazol-6-yl)pyridin-2-yl)ethanamine | 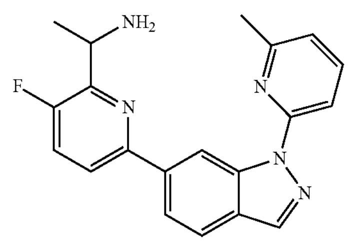 [SMILES: Cc1cccc(-n2ncc3ccc(-c4ccc(F)c(C(C)N)n4)cc32)n1] |
| 243 | methyl 3-amino-6-(1-(6-methylpyridin-2-yl)-1H-indazol-6-yl)picolinate | 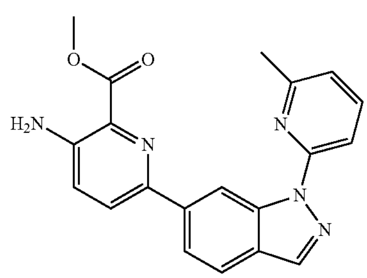 [SMILES: COC(=O)c1nc(-c2ccc3cnn(-c4cccc(C)n4)c3c2)ccc1N] |
| 244 | 2,2,2-trifluoro-1-(6-(1-(6-methylpyridin-2-yl)-1H-indazol-6-yl)pyridin-2-yl)ethanol | 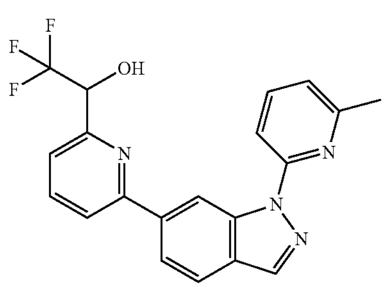 [SMILES: Cc1cccc(-n2ncc3ccc(-c4cccc(C(O)C(F)(F)F)n4)cc32)n1] |

| Example | Name | Structure |
|---|---|---|
| 245 | 1-(6-(4-ethoxy-1-(6-methylpyridin-2-yl)-1H-indazol-6-yl)pyridin-2-yl)ethanamine | 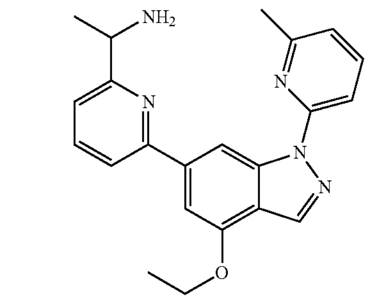 [SMILES: CCOc1cc(-c2cccc(C(C)N)n2)cc2c1cnn2-c1cccc(C)n1] |
| 246 | 1-(6-(4-methoxy-1-(6-methylpyridin-2-yl)-1H-indazol-6-yl)pyridin-2-yl)ethanamine | 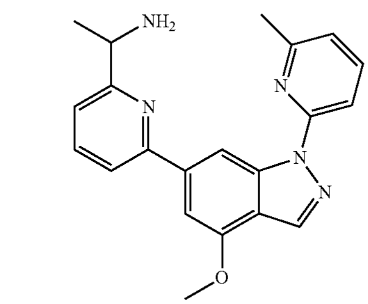 [SMILES: COc1cc(-c2cccc(C(C)N)n2)cc2c1cnn2-c1cccc(C)n1] |
| 247 | 3-amino-3-(6-(1-(6-methylpyridin-2-yl)-1H-indazol-6-yl)pyridin-2-yl)propan-1-ol | 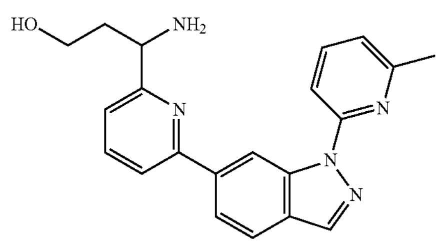 [SMILES: Cc1cccc(-n2ncc3ccc(-c4cccc(C(N)CCO)n4)cc32)n1] |
| 248 | 6-(1-(6-methylpyridin-2-yl)-1H-indazol-6-yl)picolinamide | 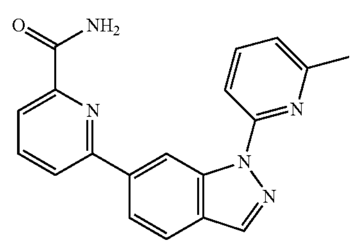 [SMILES: Cc1cccc(-n2ncc3ccc(-c4cccc(C(N)=O)n4)cc32)n1] |
| 249 | 2-(6-(1-(6-methylpyridin-2-yl)-1H-indazol-6-yl)pyridin-2-yl)acetonitrile | 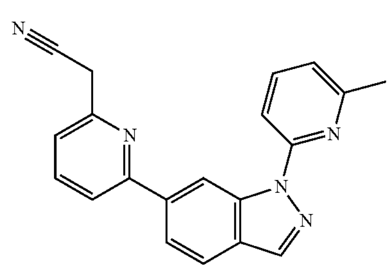 [SMILES: Cc1cccc(-n2ncc3ccc(-c4cccc(CC#N)n4)cc32)n1] |

| Example | Name | Structure |
|---|---|---|
| 250 | 6-(6-(1-aminoethyl)pyridin-2-yl)-1-(6-methylpyridin-2-yl)-1H-indazol-4-ol | 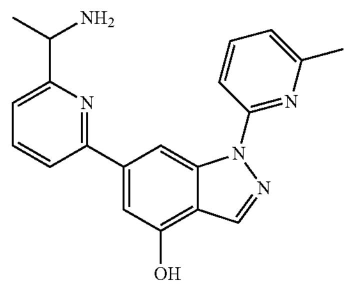 [SMILES: Cc1cccc(-n2ncc3c(O)cc(-c4cccc(C(C)N)n4)cc32)n1] |
| 251 | 1-(6-94-(cyclopropylmethoxy)-1-(6-methylpyridin-2-yl)-1H-indazol-6-yl)pyridin-2-yl)ethanamine | 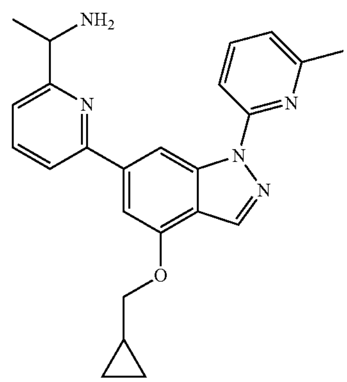 [SMILES: Cc1cccc(-n2ncc3c(OCC4CC4)cc(-c4cccc(C(C)N)n4)cc32)n1] |
| 252 | (4-(1-(6-methylpyridin-2-yl)-1H-indazol-6-yl)thiazol-2-yl)methanamine | 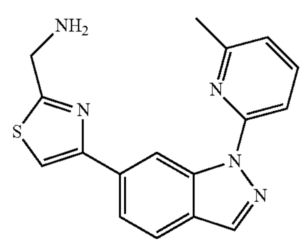 [SMILES: Cc1cccc(-n2ncc3ccc(-c4csc(CN)n4)cc32)n1] |
| 253 | N-((6-(1-(6-methylpyridin-2-yl)-1H-indazol-6-yl)pyridin-2-yl)methyl)acetamide | 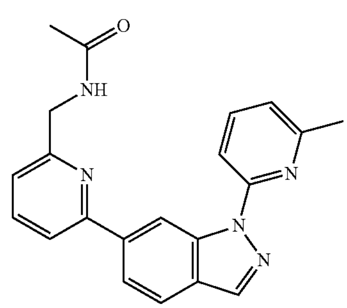 [SMILES: CC(=O)NCc1cccc(-c2ccc3cnn(-c4cccc(C)n4)c3c2)n1] |
| 254 | 2-(6-(1-(6-methylpyridin-2-yl)-1H-indazol-6-yl)pyridin-2-yl)ethanamine | 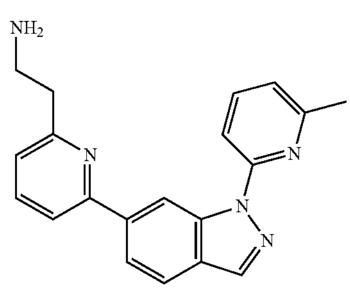 [SMILES: Cc1cccc(-n2ncc3ccc(-c4cccc(CCN)n4)cc32)n1] |

| Example | Name | Structure |
|---|---|---|
| 255 | 1-(6-(1-(6-methylpyridin-2-yl)-1H-indazol-6-yl)-3-(trifluoromethyl)pyridin-2-yl)ethanamine | 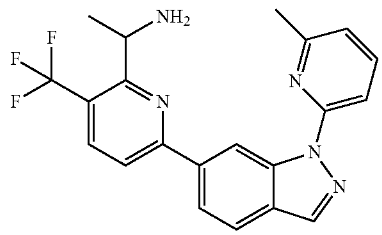 [SMILES: Cc1cccc(-n2ncc3ccc(-c4ccc(C(F)(F)F)c(C(C)N)n4)cc32)n1] |
| 256 | 2-(1-aminoethyl)-6-(1-(6-methylpyridin-2-yl)-1H-indazol-6-yl)pyridin-4-amine | 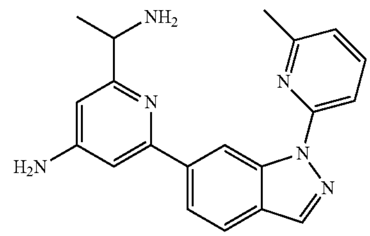 [SMILES: Cc1cccc(-n2ncc3ccc(-c4cc(N)cc(C(C)N)n4)cc32)n1] |
| 257 | (1-methyl-4-(1-(6-methylpyridin-2-yl)-1H-indazol-6-yl)-1H-imidazol-2-yl)methanol | 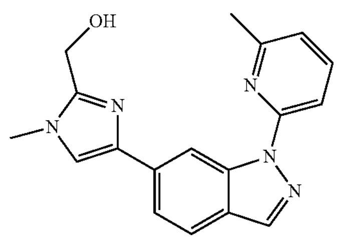 [SMILES: Cc1cccc(-n2ncc3ccc(-c4cn(C)c(CO)n4)cc32)n1] |
| 258 | 2-amino-2-(6-(1-(6-methylpyridin-2-yl)-1H-indazol-6-yl)pyridin-2-yl)acetonitrile | 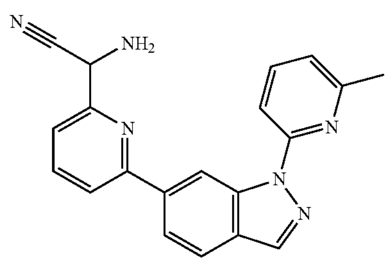 [SMILES: Cc1cccc(-n2ncc3ccc(-c4cccc(C(N)C#N)n4)cc32)n1] |
| 259 | 2,2,2-trifluoro-1-(6-(1-(6-methylpyridin-2-yl)-1H-indazol-6-yl)pyridin-2-yl)ethanamine | 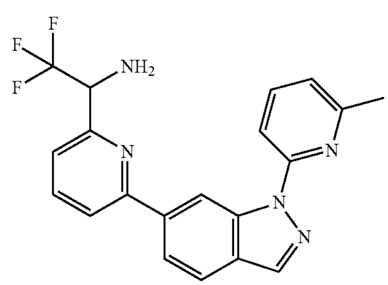 [SMILES: Cc1cccc(-n2ncc3ccc(-c4cccc(C(N)C(F)(F)F)n4)cc32)n1] |
| 260 | 3-amino-3-(6-(1-(6-methylpyridin-2-yl)-1H-indazol-6-yl)pyridin-2-yl)propanoic acid | 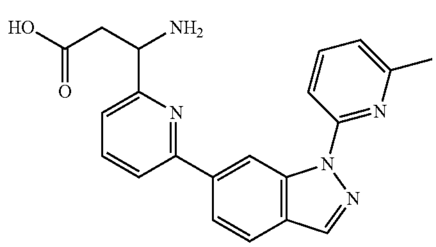 [SMILES: Cc1cccc(-n2ncc3ccc(-c4cccc(C(N)CC(=O)O)n4)cc32)n1] |

-continued

| Example | Name | Structure |
|---|---|---|
| 261 | methyl 3-amino-3-(6-(1-(6-methylpyridin-2-yl)-1H-indazol-6-yl)pyridin-2-yl)propanoate | 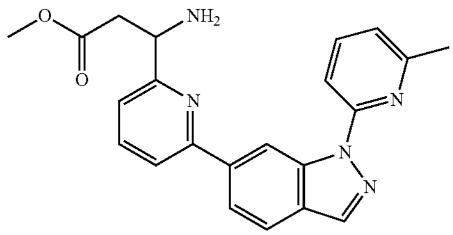 |
| 262 | 1-(6-(1-(6-methylpyridin-2-yl)-1H-indazol-6-yl)pyridin-2-yl)cyclopropanamine | 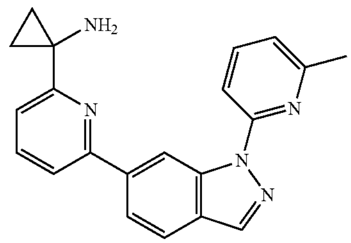 [SMILES: Cc1cccc(-n2ncc3ccc(-c4cccc(C5(N)CC5)n4)cc32)n1] |
| 263 | 1-(6-(1-(6-methylpyridin-2-yl)-1H-indazol-6-yl)pyridin-2-yl)propan-1-amine | 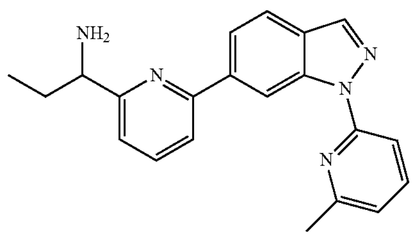 [SMILES: CCC(N)c1cccc(-c2ccc3cnn(-c4cccc(C)n4)c3c2)n1] |
| 264 | (R)-1-(6-(1-(6-methylpyridin-2-yl)-1H-indazol-6-yl)pyridin-2-yl)butan-1-amine | 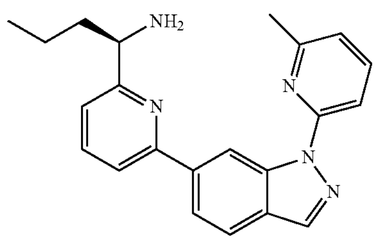 [SMILES: CCC[C@@H](N)c1cccc(-c2ccc3cnn(-c4cccc(C)n4)c3c2)n1] |
| 265 | (S)-1-(6-(1-(6-methylpyridin-2-yl)-1H-indazol-6-yl)pyridin-2-yl)butan-1-amine | 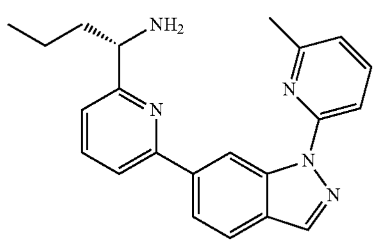 [SMILES: CCC[C@H](N)c1cccc(-c2ccc3cnn(-c4cccc(C)n4)c3c2)n1] |
| 266 | 1-(3-chloro-6-(1-(6-methylpyridin-2-yl)-1H-indazol-6-yl)pyridin-2-yl)ethanamine | 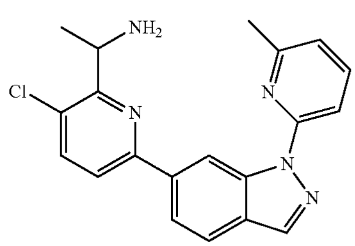 [SMILES: Cc1cccc(-n2ncc3ccc(-c4ccc(Cl)c(C(C)N)n4)cc32)n1] |

-continued

| Example | Name | Structure |
|---|---|---|
| 267 | 2-amino-2-(6-(1-(6-methylpyridin-2-yl)-1H-indazol-6-yl)pyridin-2-yl)acetamide | 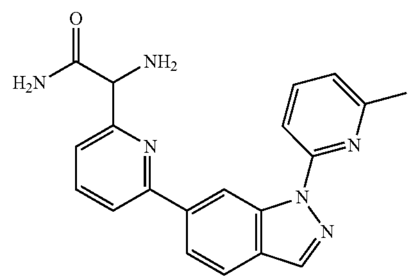 [SMILES: Cc1cccc(-n2ncc3ccc(-c4cccc(C(N)C(N)=O)n4)cc32)n1] |
| 268 | 1-(6-(1-(6-(trifluoromethyl)pyridin-2-yl)-1H-indazol-6-yl)pyridin-2-yl)butan-1-amine | 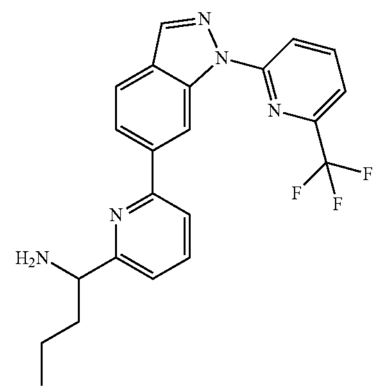 [SMILES: CCCC(N)c1cccc(-c2ccc3cnn(-c4cccc(C(F)(F)F)n4)c3c2)n1] |
| 269 | 6-(6-(6-(1-aminopropyl)pyridin-2-yl)-1H-indazol-1-yl)picolinamide | 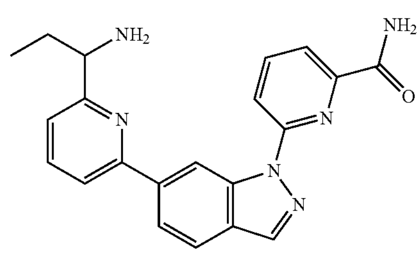 [SMILES: CCC(N)c1cccc(-c2ccc3cnn(-c4cccc(C(N)=O)n4)c3c2)n1] |
| 270 | 2-(1-aminoethyl)-6-(1-(6-(trifluoromethyl)pyridin-2-yl)-1H-indazol-6-yl)pyridin-4-amine | 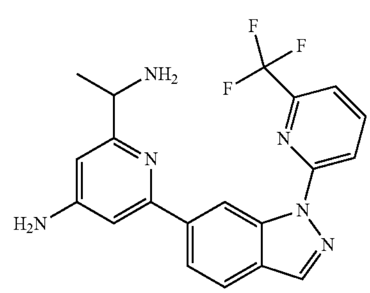 [SMILES: CC(N)c1cc(N)cc(-c2ccc3cnn(-c4cccc(C(F)(F)F)n4)c3c2)n1] |
| 271 | 2-amino-2-(6-(1-(6-methylpyridin-2-yl)-1H-indazol-6-yl)pyridin-2-yl)ethanol | 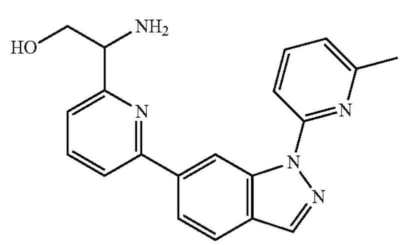 [SMILES: Cc1cccc(-n2ncc3ccc(-c4cccc(C(N)CO)n4)cc32)n1] |

| Example | Name | Structure |
|---|---|---|
| 272 | methyl 2-amino-2-(6-(1-(6-methylpyridin-2-yl)-1H-indazol-6-yl)pyridin-2-yl)acetate | 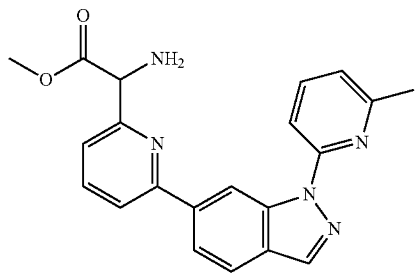 |
| 273 | 2-amino-2-(6-(1-(6-methylpyridin-2-yl)-1H-indazol-6-yl)pyridin-2-yl)acetic acid | 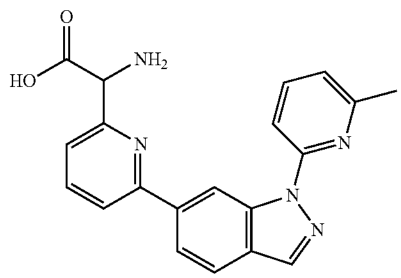 [SMILES: Cc1cccc(-n2ncc3ccc(-c4cccc(C(N)C(=O)O)n4)cc32)n1] |
| 274 | 6-(6-(6-(1-aminobutyl)pyridin-2-yl)-1H-indazol-1-yl)picolinamide | 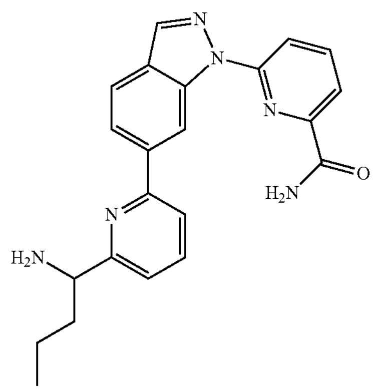 [SMILES: CCCC(N)c1cccc(-c2ccc3cnn(-c4cccc(C(N)=O)n4)c3c2)n1] |
| 275 | 1-(6-(3-(6-methylpyridin-2-yl)imidazo[1,5-a]pyridin-6-yl)pyridin-2-yl)propan-1-amine | 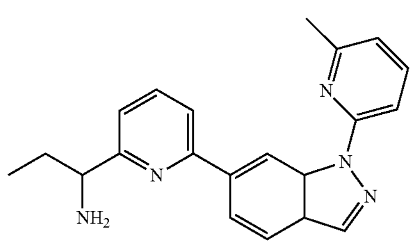 [SMILES: CCC(N)c1cccc(C2=CC3C(C=C2)C=NN3c2cccc(C)n2)n1] |
| 276 | 1-(6-(3-(6-methylpyridin-2-yl)imidazo[1,5-a]pyridin-6-yl)pyridin-2-yl)butan-1-amine | 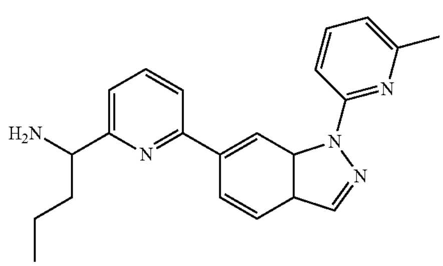 [SMILES: CCCC(N)c1cccc(C2=CC3C(C=C2)C=NN3c2cccc(C)n2)n1] |

| Example | Name | Structure |
|---|---|---|
| 278 | 2-(6-(6-(6-(1-aminoethyl)pyridin-2-yl)-1H-indazol-1-yl)pyridin-2-yl)propan-2-ol | 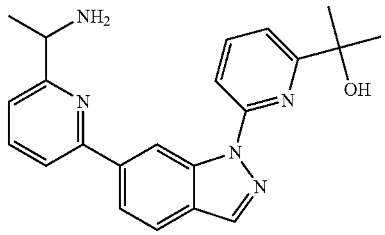 [SMILES: CC(N)c1cccc(-c2ccc3cnn(-c4cccc(C(C)(C)O)n4)c3c2)n1] |
| 279 | 1-(6-(1-(6-(methoxymethyl)pyridin-2-yl)-1H-indazol-6-yl)pyridin-2-yl)ethanamine | 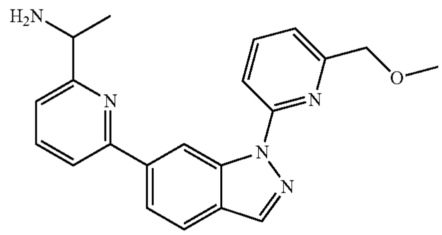 [SMILES: COCc1cccc(-n2ncc3ccc(-c4cccc(C(C)N)n4)cc32)n1] |
| 280 | (6-(6-(6-(1-aminobutyl)pyridin-2-yl)-1H-indazol-1-yl)pyridin-2-yl)methanol | 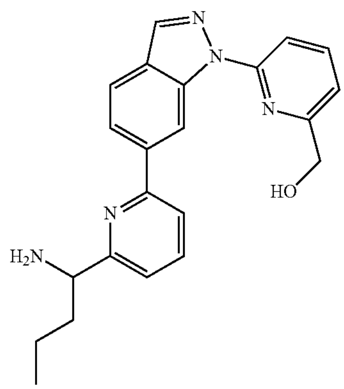 [SMILES: CCCC(N)c1cccc(-c2ccc3cnn(-c4cccc(CO)n4)c3c2)n1] |
| 281 | 1-(3-methyl-6-(1-(6-methylpyridin-2-yl)-1H-indazol-6-yl)pyridin-2-yl)ethanamine | 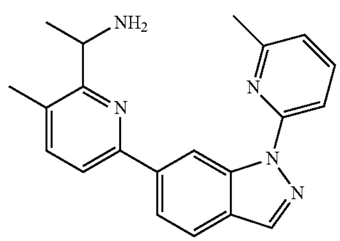 [SMILES: Cc1cccc(-n2ncc3ccc(-c4ccc(C)c(C(C)N)n4)cc32)n1] |
| 282 | 1-(6-(1-(4-methylthiophen-2-yl)-1H-indazol-6-yl)pyridin-2-yl)ethanamine | 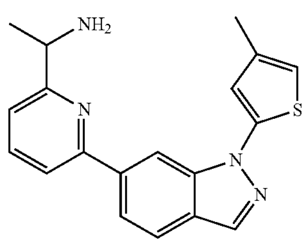 [SMILES: Cc1csc(-n2ncc3ccc(-c4cccc(C(C)N)n4)cc32)c1] |
| 283 | 1-(6-(1-(6-propylpyridin-2-yl)-1H-indazol-6-yl)pyridin-2-yl)ethanamine | 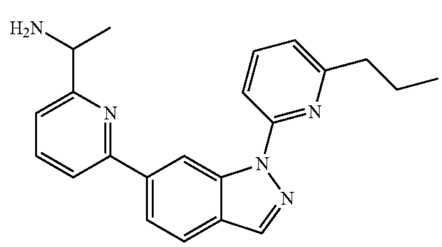 [SMILES: CCCc1cccc(-n2ncc3ccc(-c4cccc(C(C)N)n4)cc32)n1] |

| Example | Name | Structure |
|---|---|---|
| 284 | 1-(6-(6-(6-(1-aminoethyl)pyridin-2-yl)-1H-indazol-1-yl)pyridin-2-yl)ethanol | 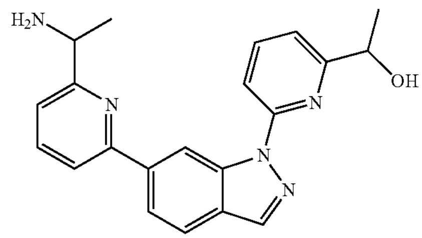 [SMILES: CC(N)c1cccc(-c2ccc3cnn(-c4cccc(C(C)O)n4)c3c2)n1] |
| 285 | (4-(1-(6-methylpyridin-2-yl)-1H-indazol-6-yl)oxazol-2-yl)methanamine | 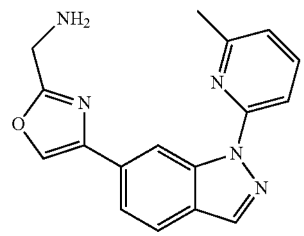 [SMILES: Cc1cccc(-n2ncc3ccc(-c4coc(CN)n4)cc32)n1] |
| 286 | 1-(6-(1-(6-(tert-butyl)pyridin-2-yl)-1H-indazol-6-yl)pyridin-2-yl)ethanamine | 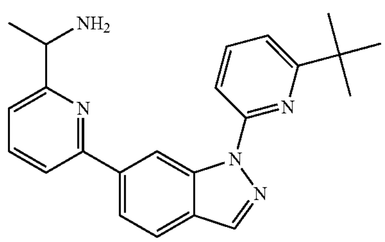 [SMILES: CC(N)c1cccc(-c2ccc3cnn(-c4cccc(C(C)(C)C)n4)c3c2)n1] |
| 287 | 1-(6-(1-(6-(aminomethyl)pyridin-2-yl)-1H-indazol-6-yl)pyridin-2-yl)ethanamine | 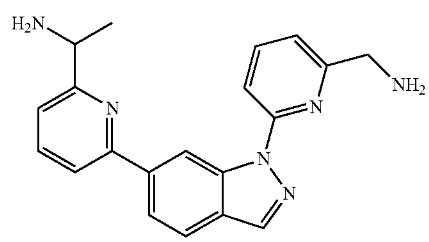 [SMILES: CC(N)c1cccc(-c2ccc3cnn(-c4cccc(CN)n4)c3c2)n1] |
| 288 | 2-(6-(6-(6-(1-aminoethyl)pyridin-2-yl)-1H-indazol-1-yl)pyridin-2-yl)-2-methylpropanenitrile | 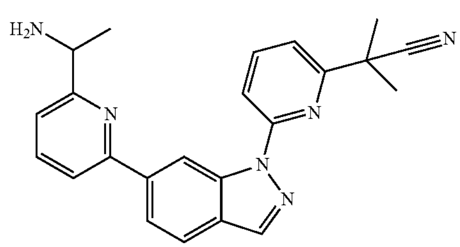 [SMILES: CC(N)c1cccc(-c2ccc3cnn(-c4cccc(C(C)(C)C#N)n4)c3c2)n1] |
| 289 | 1-(6-(1-(6-(2-(methylsulfonyl)propan-2-yl)pyridin-2-yl)-1H-indazol-6-yl)pyridin-2-yl)ethanamine | 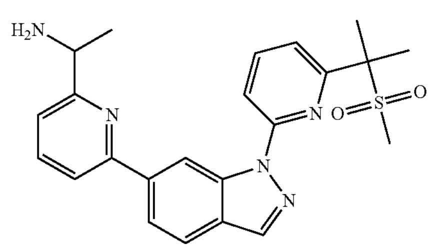 [SMILES: CC(N)c1cccc(-c2ccc3cnn(-c4cccc(C(C)(C)S(C)(=O)=O)n4)c3c2)n1] |

| Example | Name | Structure |
|---|---|---|
| 290 | 1-(6-(6-(6-(1-aminoethyl)pyridin-2-yl)-1H-indazole-1-yl)pyridin-2-yl)cyclopropanecarbonitrile | 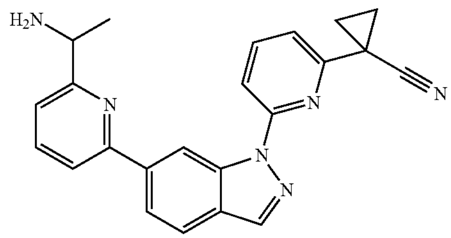 [SMILES: CC(N)c1cccc(-c2ccc3cnn(-c4cccc(C5(C#N)CC5)n4)c3c2)n1] |
| 291 | (6-(6-(6-(aminomethyl)pyridin-2-yl)-1H-indazol-1-yl)pyridin-2-yl)methanol | 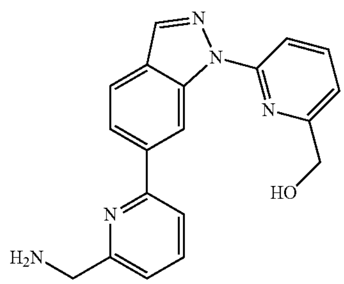 [SMILES: NCc1cccc(-c2ccc3cnn(-c4cccc(CO)n4)c3c2)n1] |
| 292 | 2-(6-(6-(6-(1-aminoethyl)pyridin-2-yl)-1H-indazol-1-yl)pyridin-2-yl)propan-2-amine | 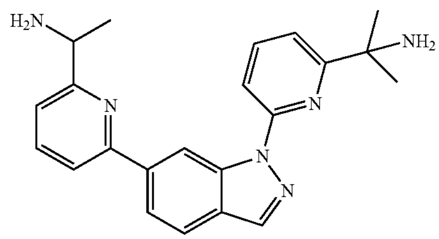 [SMILES: CC(N)c1cccc(-c2ccc3cnn(-c4cccc(C(C)(C)N)n4)c3c2)n1] |
| 293 | 1-(6-(3-(6-ethylpyridin-2-yl)imidazo[1,5-a]pyridin-6-yl)pyridin-2-yl)ethanamine | 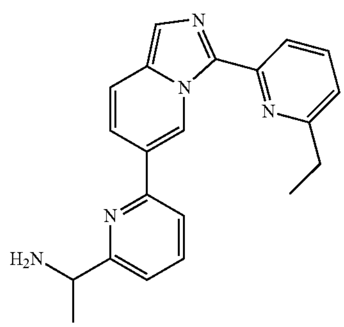 [SMILES: CCc1cccc(-c2ncc3ccc(-c4cccc(C(C)N)n4)cn23)n1] |
| 294 | (6-(6-(6-(1-aminopropyl)pyridin-2-yl)-1H-indazol-1-yl)pyridin-2-yl)methanol | 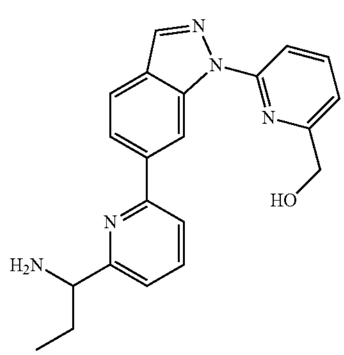 [SMILES: CCC(N)c1cccc(-c2ccc3cnn(-c4cccc(CO)n4)c3c2)n1] |

-continued

| Example | Name | Structure |
|---|---|---|
| 295 | 1-(6-(4-(1H-imidazol-2-yl)-1-(6-methylpyridin-2-yl)-1H-indazol-6-yl)pyridin-2-yl)ethanamine | 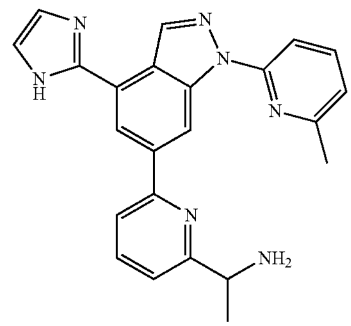 [SMILES: Cc1cccc(-n2ncc3c(-c4ncc[nH]4)cc(-c4cccc(C(C)N)n4)cc32)n1] |
| 296 | 1-(6-(1-(4-methylpyrimidin-2-yl)-1H-indazol-6-yl)pyridin-2-yl)ethanamine | 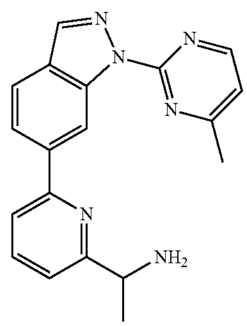 [SMILES: Cc1ccnc(-n2ncc3ccc(-c4cccc(C(C)N)n4)cc32)n1] |
| 297 | 1-(6-(1-(4-(trifluoromethyl)pyrimidin-2-yl)-1H-indazol-6-yl)pyridin-2-yl)ethanamine | 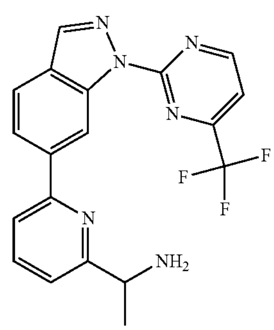 [SMILES: CC(N)c1cccc(-c2ccc3cnn(-c4nccc(C(F)(F)F)n4)c3c2)n1] |
| 298 | 2-(6-(1-(6-methylpyridin-2-yl)-1H-indazol-6-yl)pyridin-2-yl)propan-2-amine | 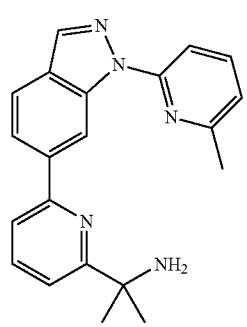 [SMILES: Cc1cccc(-n2ncc3ccc(-c4cccc(C(C)(C)N)n4)cc32)n1] |

-continued

| Example | Name |
|---|---|
| 299 | 1-(1-methyl-4-(1-(6-methylpyridin-2-yl)-1H-indazol-6-yl)-1H-imidazol-2-yl)ethanol |
| 300 | (1-methyl-4-(1-(6-methylpyridin-2-yl)-1H-indazol-6-yl)-1H-imidazol-2-yl)methanamine |
| 301 | 2-(6-(6-(6-(1-aminoethyl)pyridin-2-yl)-1H-indazol-1-yl)pyridin-2-yl)-2-methylpropanamide |
| 302 | (6-(6-(6-(1-aminoethyl)pyridin-2-yl)imidazo[1,5-a]pyridin-3-yl)pyridin-2-yl)methanol |
| 303 | 1-(6-(1-(6-methylpyridin-2-yl)-4-(thiazol-2-yl)-1H-indazol-6-yl)pyridin-2-yl)ethanamine |

-continued

| Example | Name | Structure |
|---|---|---|
| 304 | 1-(6-(1-(6-methylpyridin-2-yl)-1H-indazol-6-yl)pyridin-2-yl)cyclobutanecarbonitrile | 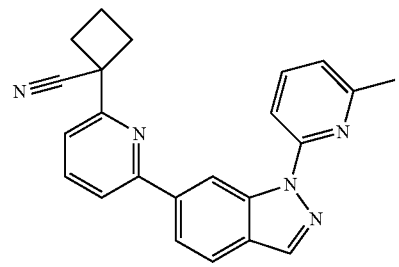 [SMILES: Cc1cccc(-n2ncc3ccc(-c4cccc(C5(C#N)CCC5)n4)cc32)n1] |
| 305 | 1-(1-methyl-4-(1-(6-methylpyridin-2-yl)-1H-indazol-6-yl)-1H-imidazol-2-yl)ethanamine | 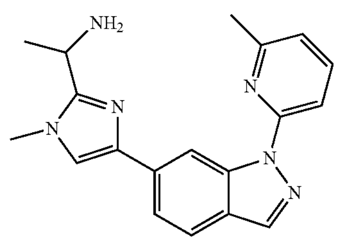 [SMILES: Cc1cccc(-n2ncc3ccc(-c4cn(C)c(C(C)N)n4)cc32)n1] |
| 306 | 1-(6-methylpyridin-2-yl)-6-(pyridin-2-yl)-1H-indazole | 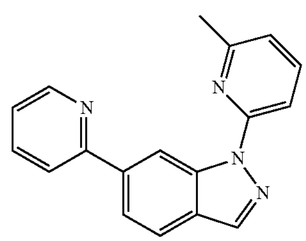 [SMILES: Cc1cccc(-n2ncc3ccc(-c4ccccn4)cc32)n1] |
| 307 | (6-(6-(6-(1-aminoethyl)pyridin-2-yl)-4-methoxy-1H-indazol-1-yl)pyridin-2-yl)methanol | 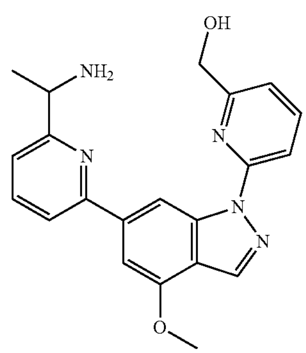 [SMILES: COc1cc(-c2cccc(C(C)N)n2)cc2c1cnn2-c1cccc(CO)n1] |
| 308 | 2-(1-(6-methylpyridin-2-yl)-1H-indazol-6-yl)-6,7,8,9-tetrahydro-5H-cyclohepta[b]pyridin-9-amine | 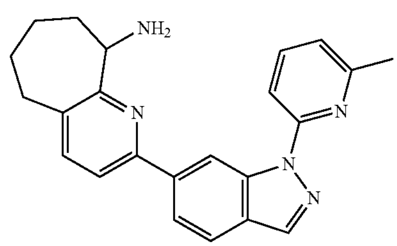 [SMILES: Cc1cccc(-n2ncc3ccc(-c4ccc5c(n4)C(N)CCCC5)cc32)n1] |

| Example | Name | Structure |
|---|---|---|
| 309 | (6-(6-(1-aminoethyl)pyridin-2-yl)-1-(6-(hydroxymethyl)pyridin-2-yl)-1H-indazol-4-yl)methanol | 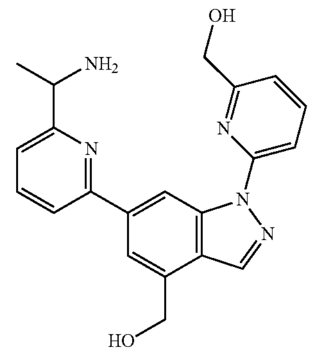 [SMILES: CC(N)c1cccc(-c2cc(CO)c3cnn(-c4cccc(CO)n4)c3c2)n1] |
| 310 | 1-(4-(1-(6-methylpyridin-2-yl)-1H-indazol-6-yl)thiazol-2-yl)ethanamine | 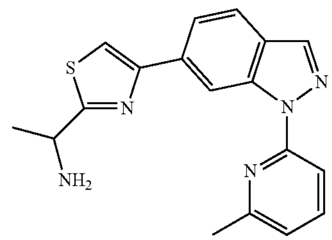 [SMILES: Cc1cccc(-n2ncc3ccc(-c4csc(C(C)N)n4)cc32)n1] |
| 311 | 1-(6-(8-chloro-3-(6-(trifluoromethyl)pyridin-2-yl)imidazo[1,5-a]pyridin-6-yl)pyridin-2-yl)ethanamine | 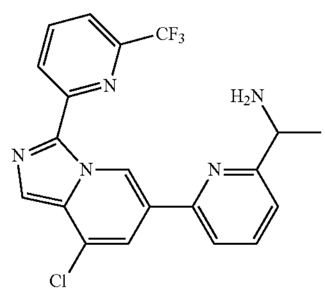 [SMILES: CC(N)c1cccc(-c2cc(Cl)c3cnc(-c4cccc(C(F)(F)F)n4)n3c2)n1] |
| 312 | 1-(6-(1-(6-methylpyridin-2-yl)-1H-indazol-6-yl)pyridin-2-yl)cyclobutanecarboxamide | 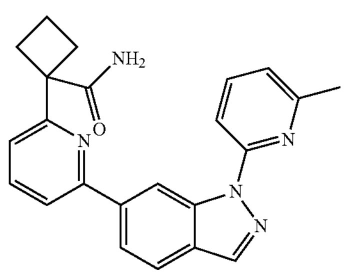 [SMILES: Cc1cccc(-n2ncc3ccc(-c4cccc(C5(C(N)=O)CCC5)n4)cc32)n1] |
| 313 | 1-(6-methylpyridin-2-yl)-6-(6-(3,3,3-trifluoropropyl)pyridin-2-yl)-1H-indazole | 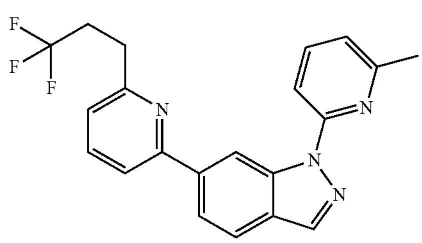 [SMILES: Cc1cccc(-n2ncc3ccc(-c4cccc(CCC(F)(F)F)n4)cc32)n1] |

| Example | Name | Structure |
|---|---|---|
| 314 | 2-(6-(6-(6-(1-aminoethyl)pyridin-2-yl)-1H-indazol-1-yl)pyridin-2-yl)ethanol | 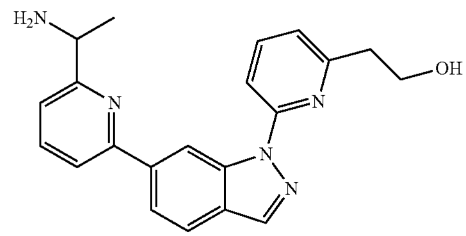 [SMILES: CC(N)c1cccc(-c2ccc3cnn(-c4cccc(CCO)n4)c3c2)n1] |
| 315 | 1-(6-(1-(4,6-dimethylpyridin-2-yl)-1H-indazol-6-yl)pyridin-2-yl)ethanamine | 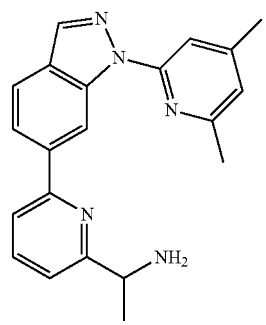 [SMILES: Cc1cc(C)nc(-n2ncc3ccc(-c4cccc(C(C)N)n4)cc32)c1] |
| 316 | 6-(6-(1-aminoethyl)pyridin-2-yl)-1-(6-(hydroxymethyl)pyridin-2-yl)-N-methyl-1H-indazole-4-carboxamide | 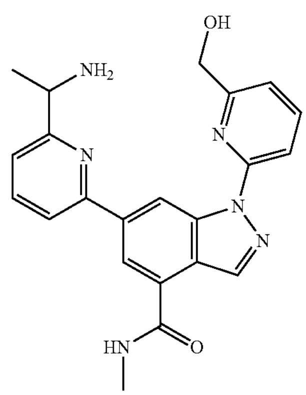 [SMILES: CNC(=O)c1cc(-c2cccc(C(C)N)n2)cc2c1cnn2-c1cccc(CO)n1] |
| 317 | 1-(6-(8-fluoro-3-(6-(trifluoromethyl)pyridin-2-yl)imidazo[1,5-a]pyridin-6-yl)pyridin-2-yl)ethanamine | 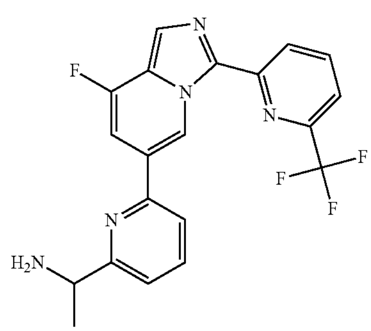 [SMILES: CC(N)c1cccc(-c2cc(F)c3cnc(-c4cccc(C(F)(F)F)n4)n3c2)n1] |
| 318 | (S)-(6-(6-(6-(1-aminopropyl)pyridin-2-yl)-1H-indazol-1-yl)pyridin-2-yl)methanol | 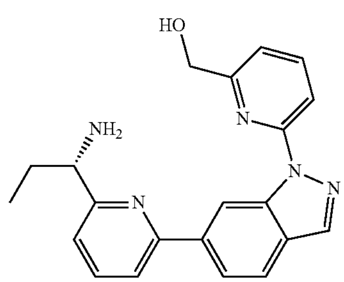 [SMILES: CC[C@H](N)c1cccc(-c2ccc3cnn(-c4cccc(CO)n4)c3c2)n1] |

| Example | Name | Structure |
|---|---|---|
| 319 | 1-(6-(1-(6-methylpyridin-2-yl)-4-(1H-pyrazol-3-yl)-1H-indazol-6-yl)pyridin-2-yl)ethanamine | 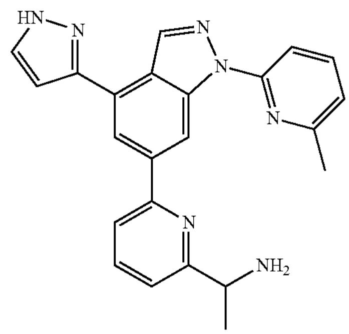 [SMILES: Cc1cccc(-n2ncc3c(-c4cc[nH]n4)cc(-c4cccc(C(C)N)n4)cc32)n1] |
| 320 | (4-(1-(6-methylpyridin-2-yl)-1H-indazol-6-yl)thiazol-2-yl)methanol | 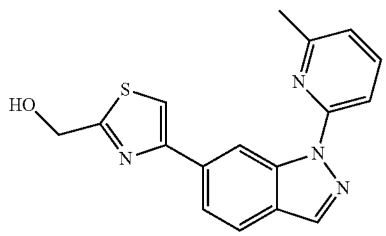 [SMILES: Cc1cccc(-n2ncc3ccc(-c4csc(CO)n4)cc32)n1] |
| 321 | (6-(6-(6-(1-aminoethyl)pyridin-2-yl)-4-fluoro-1H-indazol-1-yl)pyridin-2-yl)methanol | 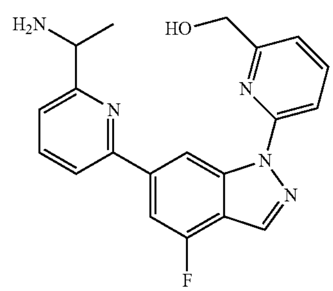 [SMILES: CC(N)c1cccc(-c2cc(F)c3cnn(-c4cccc(CO)n4)c3c2)n1] |
| 322 | (R)-(6-(6-(6-(1-aminopropyl)pyridin-2-yl)-1H-indazol-1-yl)pyridin-2-yl)methanol | 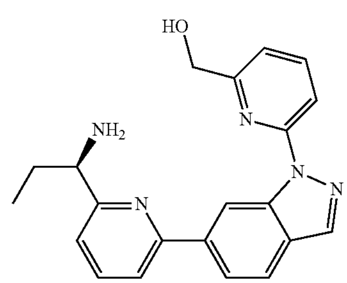 [SMILES: CC[C@@H](N)c1cccc(-c2ccc3cnn(-c4cccc(CO)n4)c3c2)n1] |
| 323 | 6-(1-methyl-1H-imidazol-4-yl)-1-(6-methylpyridin-2-yl)-1H-indazole | 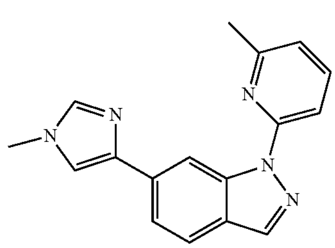 [SMILES: Cc1cccc(-n2ncc3ccc(-c4cn(C)cn4)cc32)n1] |

Example 324. (R)—N—((S)-1-(6-(1-(6-(((tert-butyldimethylsilyl)oxy)methyl)pyridin-2-yl)-4-(piperidin-1-yl)-1H-indazol-6-yl)pyridin-2-yl)butyl)-2-methylpropane-2-sulfinamide

Step 1 Synthesis of 4-bromo-2,6-difluorobenzaldehyde

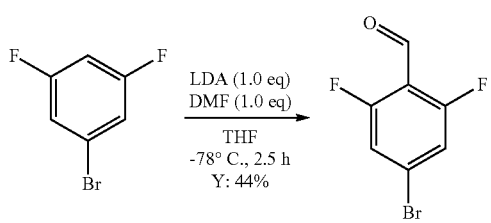 [SMILES: Fc1cc(F)cc(Br)c1 ; O=Cc1c(F)cc(Br)cc1F]

To a solution of 1-bromo-3,5-difluorobenzene (Cas No. 461-96-1, 210 g, 1.09 mol, 1.0 eq) in anhydrous THF (1000 mL), LDA/THF (545 mL, 1.09 mol, 1.0 eq, 2 M) was added slowly under nitrogen atmosphere at −78° C. The reaction solution was stirred for 2 h at −78° C., and then anhydrous DMF (79.6 g, 1.09 mol, 1.0 eq) was added dropwise. The reaction was stirred for 15 min at −78° C. and then a solution of AcOH in ethyl acetate (1/1, 300 mL) was added to adjusted pH=4-5 at −78° C. The reaction mixture was stirred at rt for 15 min, concentrated under reduced pressure, diluted with ethyl acetate (1000 mL) and washed with brine (600 mL×2). The organic layer was dried over anhydrous sodium sulfate, concentrated under reduced pressure and recrystallized from n-hexane to give the title compound (106 g, yield: 44%) as a light yellow solid. $^1$H NMR (400 MHz, CDCl$_3$) δ: 10.29 (s, 1H), 7.23 (s, 1H), 7.21 (s, 1H); ESI-MS (M+H)$^+$: 220.9, 222.9.

Step 2 Synthesis of 4-bromo-2-fluoro-6-methoxybenzaldehyde

To a solution of 4-bromo-2,6-difluorobenzaldehyde (106 g, 482 mmol, 1.0 eq) in methanol (150 mL), MeONa (26.0 g, 482 mmol, 1.0 eq) was added at rt. The reaction mixture was stirred for 2 h at 60° C. and concentrated under reduced pressure. The residue was purified by silica gel column (PE/EA=10/1) to give 4-bromo-2-fluoro-6-methoxybenzaldehyde (69 g, yield: 62%) as a light yellow solid. $^1$H NMR (400 MHz, CDCl$_3$) δ: 10.36 (s, 1H), 6.97-6.94 (m, 2H), 3.95 (s, 3H); ESI-MS (M+H)$^+$: 232.9, 234.9.

Step 3 Synthesis of 4-bromo-2-fluoro-6-hydroxybenzaldehyde

To a solution of 4-bromo-2-fluoro-6-methoxybenzaldehyde (69 g, 297 mmol, 1.0 eq) in DCM (800 mL) was added BBr$_3$ (223 g, 891 mmol, 3.0 eq) at −60° C. The reaction mixture was stirred at −60° C. for 3 h, quenched with water (300 mL) and extracted with DCM (2×300 mL). The combined organic phase was washed with brine and dried over Na$_2$SO$_4$. After filtration and concentration, the residue was directly used for next step without further purification. ESI-MS (M+H)$^+$: 218.9, 220.9.

Step 5 Synthesis of 4-bromo-2-fluoro-6-((4-methoxybenzyl)oxy)benzaldehyde

To a solution of 4-bromo-2-fluoro-6-hydroxybenzaldehyde (50 g, 229 mmol, 1.0 eq) and K$_2$CO$_3$ (63 g, 458 mmol, 2.0 eq) in DMF (100 mL) was added PMBCl (43 g, 275 mmol, 1.2 eq) at rt. The reaction mixture was stirred at rt for 16 h and diluted with water (600 mL). After filtration, the yellow solid was washed with water and dried in vacuo. 50 g, Y: 65%. ESI-MS (M+H)$^+$: 339.0, 341.0.

Step 6 Synthesis of 6-bromo-4-((4-methoxybenzyl)oxy)-1H-indazole

A mixture of 4-bromo-2-fluoro-6-((4-methoxybenzyl)oxy)benzaldehyde (50 g, 148 mmol, 1.0 eq) and NH$_2$NH$_2$.H$_2$O (22 g, 444 mmol, 3.0 eq) in DMSO (100 mL) was stirred at 135° C. for 2 h. The mixture was diluted with water (600 mL). After filtration, the yellow solid was purified by column chromatography (silica gel, PE/EA=4/1) to give 6-bromo-4-((4-methoxybenzyl)oxy)-1H-indazole as a yellow solid (34.4 g, Y: 70%). ESI-MS (M+H)$^+$: 333.1, 335.1.

Step 7 Synthesis of (6-(6-bromo-4-((4-methoxybenzyl)oxy)-1H-indazol-1-yl)pyridin-2-yl)methanol

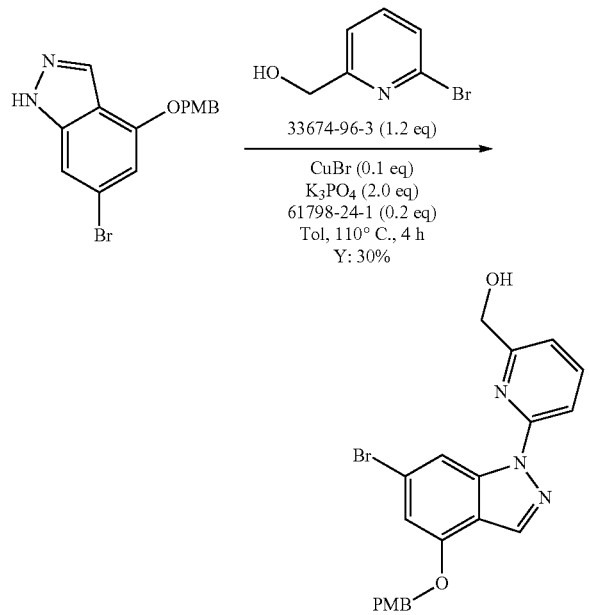

A mixture of 6-bromo-4-((4-methoxybenzyl)oxy)-1H-indazole (20 g, 60 mmol, 1.0 eq), (6-bromopyridin-2-yl)methanol Cas No. 33674-96-3 (13.5 g, 72 mmol, 1.2 eq), CuBr (858 mg, 6 mmol, 0.1 eq), K$_3$PO$_4$ (25.4 g, 120 mmol, 2.0 eq) and Cas. No. 61798-24-1 (1.7 g, 12 mmol, 0.2 eq) in toluene (200 mL) was stirred at 110° C. for 4 h under N$_2$. After concentration, the residue was purified by column chromatography (silica gel, PE/EA=2/1) to give (6-(6-bromo-4-((4-methoxybenzyl)oxy)-1H-indazol-1-yl)pyridin-2-yl)methanol as a yellow solid (7.9 g, Y: 30%). ESI-MS (M+H)$^+$: 440.1, 442.1.

Step 8 Synthesis of 6-bromo-1-(6-(((tert-butyldimethylsilyl)oxy)methyl)pyridin-2-yl)-4-((4-methoxybenzyl)oxy)-1H-indazole

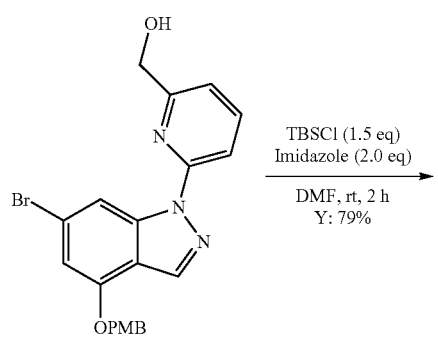

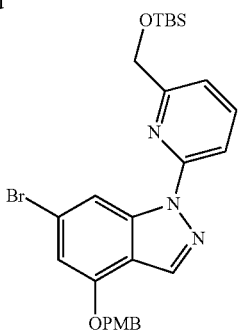

To a mixture of (6-(6-bromo-4-((4-methoxybenzyl)oxy)-1H-indazol-1-yl)pyridin-2-yl)methanol (2.35 g, 5.36 mmol, 1.0 eq) and imidazole (729 mg, 10.72 mmol, 2.0 eq) in DMF (30 mL) was added TBSCl (1.21 g, 8.04 mmol, 1.5 eq) at rt. The mixture was stirred at rt for 2 h. The mixture was diluted with water (300 mL) and extracted with EA (3×100 mL). The combined organic phases were washed with brine (100 mL) and dried over Na$_2$SO$_4$. After filtration and concentration, the residue was purified by column chromatography (silica gel, PE/EA=5/1) to give 6-bromo-1-(6-(((tert-butyldimethylsilyl)oxy)methyl)pyridin-2-yl)-4-((4-methoxybenzyl)oxy)-1H-indazole as a yellow solid (2.34 g, Y: 79%). ESI-MS (M+H)$^+$: 554.1.

Step 9 Synthesis of 1-(6-(((tert-butyldimethylsilyl)oxy)methyl)pyridin-2-yl)-4-((4-methoxybenzyl)oxy)-6-(4,4,5,5-tetramethyl-1,3,2-dioxaborolan-2-yl)-1H-indazole

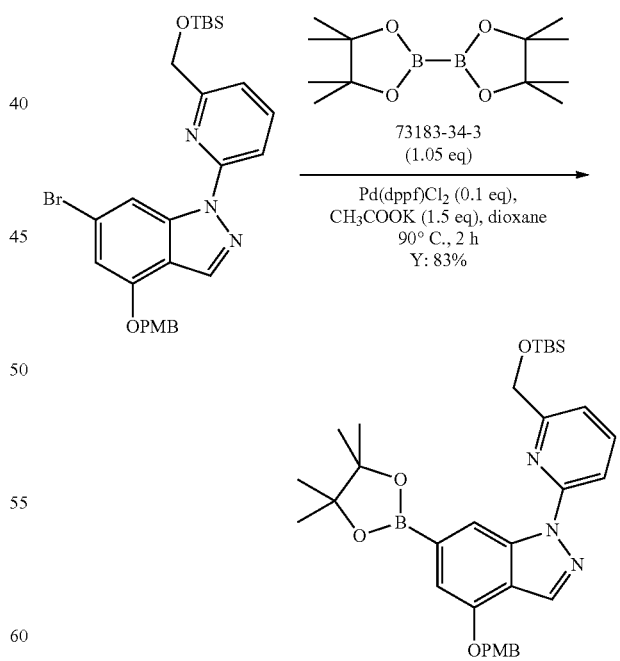

A mixture of 6-bromo-1-(6-(((tert-butyldimethylsilyl)oxy)methyl)pyridin-2-yl)-4-((4-methoxybenzyl)oxy)-1H-indazole (2.34 g, 4.23 mmol, 1.0 eq), Cas. No. 73183-34-3 (1.13 g, 4.44 mmol, 1.05 eq) and CH$_3$COOK (622 mg, 6.35 mmol, 1.5 eq) in 1, 4-dioxane (50 mL) was stirred while purging N₂ at rt for 10 min. To this system was added Pd(dppf)Cl₂ (343 mg, 0.42 mmol, 0.1 eq) and heated to 90° C. for 2 h. The mixture was diluted with EA (300 mL) and washed with saturated aqueous NaHCO₃ solution (100 mL) and brine (200 mL). The organics were dried (Na₂SO₄) and concentrated in vacuo. The residue was purified by silica gel chromatography with PE/EA (5/1) as eluent to give 1-(6-(((tert-butyldimethylsilyl)oxy)methyl)pyridin-2-yl)-4-((4-methoxybenzyl)oxy)-6-(4,4,5,5-tetramethyl-1,3,2-dioxaborolan-2-yl)-1H-indazole. 2.11 g, as a yellow solid, Y: 83%. ESI-MS (M+H)⁺: 602.3.

Step 10 Synthesis of (R)—N—((S)-1-(6-(1-(6-(((tert-butyldimethylsilyl)oxy)methyl)pyridin-2-yl)-4-((4-methoxybenzyl)oxy)-1H-indazol-6-yl)pyridin-2-yl)butyl)-2-methylpropane-2-sulfinamide

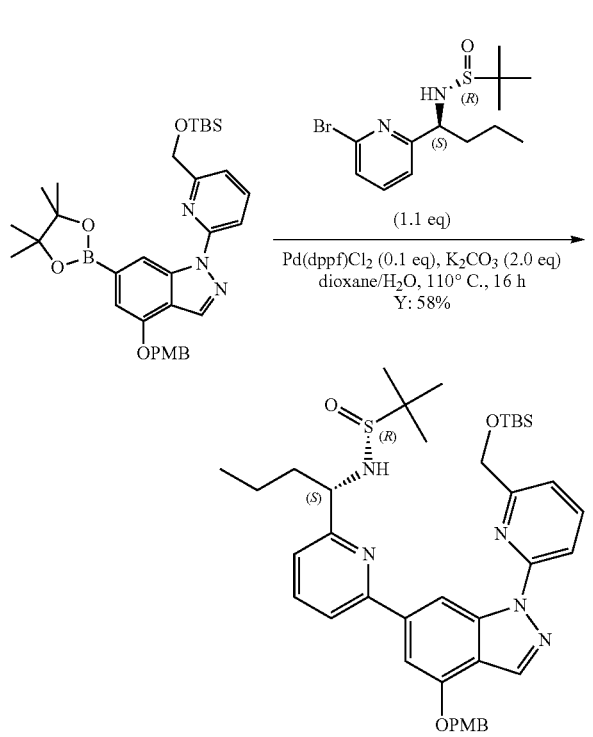

A mixture of 1-(6-(((tert-butyldimethylsilyl)oxy)methyl)pyridin-2-yl)-4-((4-methoxybenzyl)oxy)-6-(4,4,5,5-tetramethyl-1,3,2-dioxaborolan-2-yl)-1H-indazole (2.11 g, 3.51 mmol, 1.0 eq), (R)—N—((S)-1-(6-bromopyridin-2-yl)butyl)-2-methylpropane-2-sulfinamide (Example 145 step 5, 1.17 g, 3.51 mmol, 1.0 eq) and K₂CO₃ (969 mg, 7.02 mmol, 2.0 eq) in 1,4-dioxane/H₂O (30 mL/1.0 mL) was stirred while purging N₂ at rt for 10 min. To this system was added Pd(dppf)Cl₂ (286 mg, 0.35 mmol, 0.1 eq) and heated to 110° C. for 16 h. The mixture was diluted with EA (400 mL) and washed with saturated aqueous NaHCO₃ solution (100 mL) and brine (100 mL). The organics were dried (Na₂SO₄) and concentrated in vacuo. The crude mixture was purified by column chromatography (silica gel, PE/EA=2/1) to give (R)—N—((S)-1-(6-(1-(6-(((tert-butyldimethylsilyl)oxy)methyl)pyridin-2-yl)-4-((4-methoxybenzyl)oxy)-1H-indazol-6-yl)pyridin-2-yl)butyl)-2-methylpropane-2-sulfinamide as a yellow solid (1.48 g, Y: 58%). ESI-MS (M+H)⁺: 728.4.

Step 11 Synthesis of (R)—N—((S)-1-(6-(4-hydroxy-1-(6-(hydroxymethyl)pyridin-2-yl)-1H-indazol-6-yl)pyridin-2-yl)butyl)-2-methylpropane-2-sulfinamide

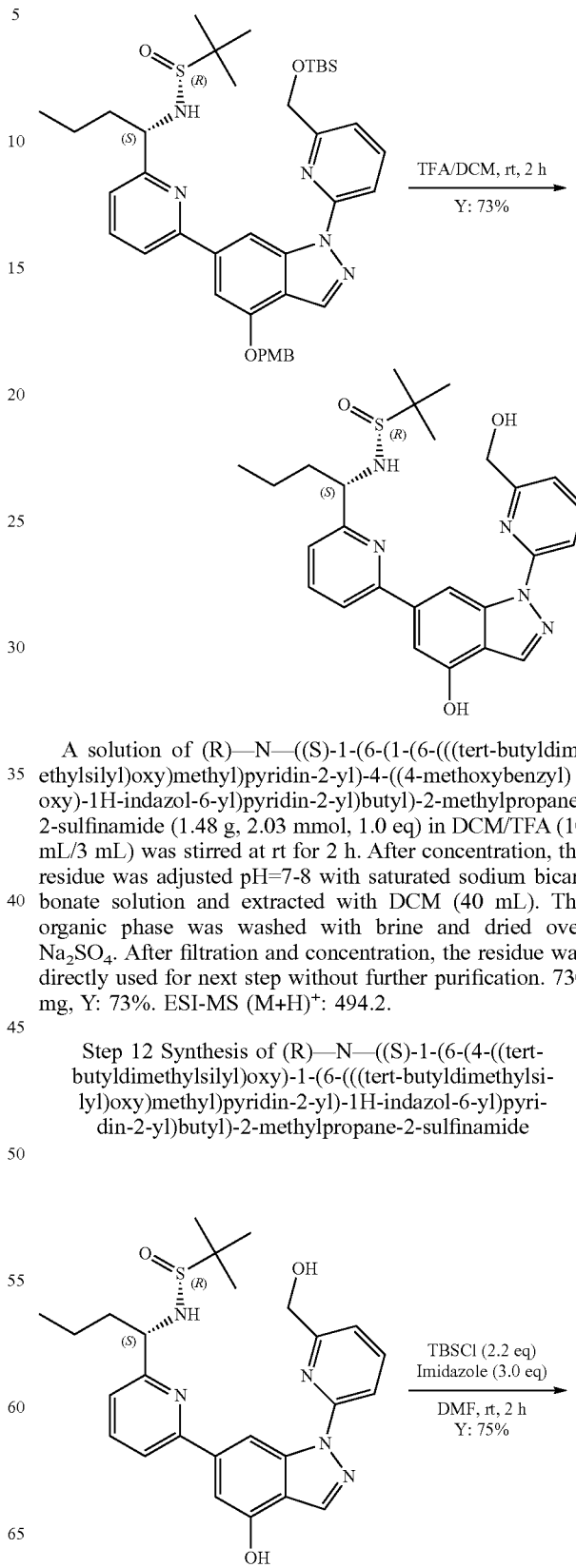

A solution of (R)—N—((S)-1-(6-(1-(6-(((tert-butyldimethylsilyl)oxy)methyl)pyridin-2-yl)-4-((4-methoxybenzyl)oxy)-1H-indazol-6-yl)pyridin-2-yl)butyl)-2-methylpropane-2-sulfinamide (1.48 g, 2.03 mmol, 1.0 eq) in DCM/TFA (10 mL/3 mL) was stirred at rt for 2 h. After concentration, the residue was adjusted pH=7-8 with saturated sodium bicarbonate solution and extracted with DCM (40 mL). The organic phase was washed with brine and dried over Na₂SO₄. After filtration and concentration, the residue was directly used for next step without further purification. 730 mg, Y: 73%. ESI-MS (M+H)⁺: 494.2.

Step 12 Synthesis of (R)—N—((S)-1-(6-(4-((tert-butyldimethylsilyl)oxy)-1-(6-(((tert-butyldimethylsilyl)oxy)methyl)pyridin-2-yl)-1H-indazol-6-yl)pyridin-2-yl)butyl)-2-methylpropane-2-sulfinamide 349
-continued

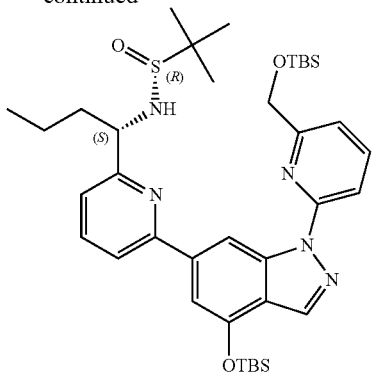

To a mixture of (R)—N—((S)-1-(6-(4-hydroxy-1-(6-(hydroxymethyl)pyridin-2-yl)-1H-indazol-6-yl)pyridin-2-yl)butyl)-2-methylpropane-2-sulfinamide (730 mg, 1.48 mmol, 1.0 eq) and imidazole (302 mg, 4.44 mmol, 3.0 eq) in DMF (10 mL) was added TBSCl (489 mg, 3.26 mmol, 2.2 eq) at rt. The mixture was stirred at rt for 2 h. The mixture was diluted with water (100 mL) and extracted with EA (3×50 mL). The combined organic phases were washed with brine (100 mL) and dried over Na₂SO₄. After filtration and concentration, the residue was purified by column chromatography (silica gel, PE/EA=2/1) to give (R)—N—((S)-1-(6-(4-((tert-butyldimethylsilyl)oxy)-1-(6-(((tert-butyldimethylsilyl)oxy)methyl)pyridin-2-yl)-1H-indazol-6-yl)pyridin-2-yl)butyl)-2-methylpropane-2-sulfinamide as a yellow solid (800 mg, Y: 75%). ESI-MS (M+H)⁺: 722.4.

Step 13 Synthesis of (R)—N—((S)-1-(6-(1-(6-(((tert-butyldimethylsilyl)oxy)methyl)pyridin-2-yl)-4-hydroxy-1H-indazol-6-yl)pyridin-2-yl)butyl)-2-methylpropane-2-sulfinamide

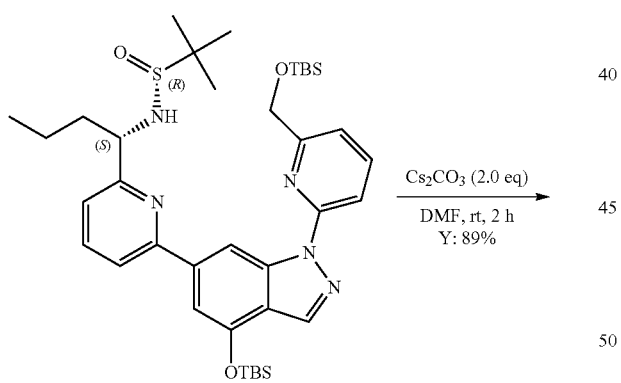

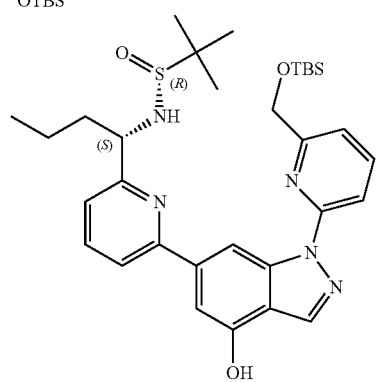

350

A mixture of (R)—N—((S)-1-(6-(4-((tert-butyldimethylsilyl)oxy)-1-(6-(((tert-butyldimethylsilyl)oxy)methyl)pyridin-2-yl)-1H-indazol-6-yl)pyridin-2-yl)butyl)-2-methylpropane-2-sulfinamide (800 mg, 1.11 mmol, 1.0 eq), Cs₂CO₃ (721 mg, 2.22 mmol, 2.0 eq) in DMF (10 mL) was stirred at rt for 2 h. The mixture was diluted with water (60 mL) and extracted with EA (90 mL). The organic phase was washed with brine and dried over Na₂SO₄. After filtration and concentration, the residue was purified by silica gel chromatography with PE/EA (1/2) as eluent to give (R)—N—((S)-1-(6-(1-(6-(((tert-butyldimethylsilyl)oxy)methyl)pyridin-2-yl)-4-hydroxy-1H-indazol-6-yl)pyridin-2-yl)butyl)-2-methylpropane-2-sulfinamide. 600 mg, as a yellow solid, Y: 89%. ESI-MS (M+H)⁺: 608.3.

Step 14 Synthesis of 1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl trifluoromethanesulfonate

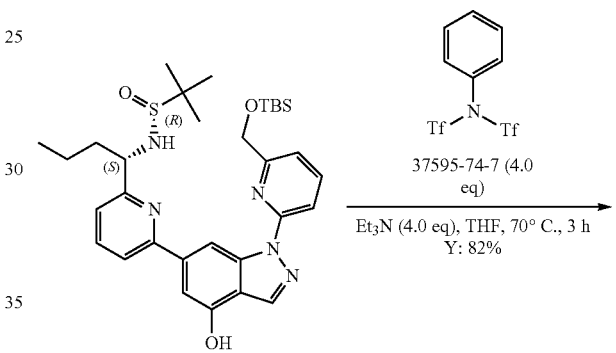

A mixture of (R)—N—((S)-1-(6-(1-(6-(((tert-butyldimethylsilyl)oxy)methyl)pyridin-2-yl)-4-hydroxy-1H-indazol-6-yl)pyridin-2-yl)butyl)-2-methylpropane-2-sulfinamide (607 mg, 1.0 mmol, 1.0 eq), Cas. No. 37595-74-7 (1.43 g, 4.0 mmol, 4.0 eq) and Et₃N (404 mg, 4.0 mmol, 4.0 eq) in THF (20 mL) was stirred at 70° C. for 3 h. After cooling down to rt, the mixture was poured into H₂O (50 mL) and extracted with DCM (50 mL×3). The combined organic fractions were dried, filtrated, concentrated and purified by silica gel chromatography with PE/EA (1/1) as eluent to give 1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl trifluoromethanesulfonate. 600 mg, as a yellow solid, Y: 82%. ESI-MS (M+H)⁺: 740.3.

Step 15. Synthesis of (R)—N—((S)-1-(6-(1-(6-(((tert-butyldimethylsilyl)oxy)methyl)pyridin-2-yl)-4-(piperidin-1-yl)-1H-indazol-6-yl)pyridin-2-yl)butyl)-2-methylpropane-2-sulfinamide

Step 16 Synthesis of (S)-(6-(6-(6-(1-aminobutyl)pyridin-2-yl)-4-(piperidin-1-yl)-1H-indazol-1-yl)pyridin-2-yl)methanol

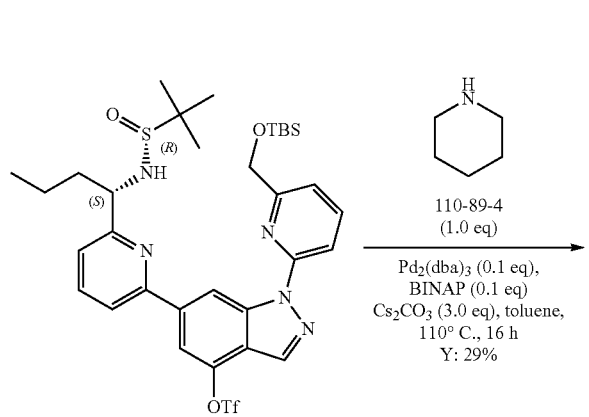

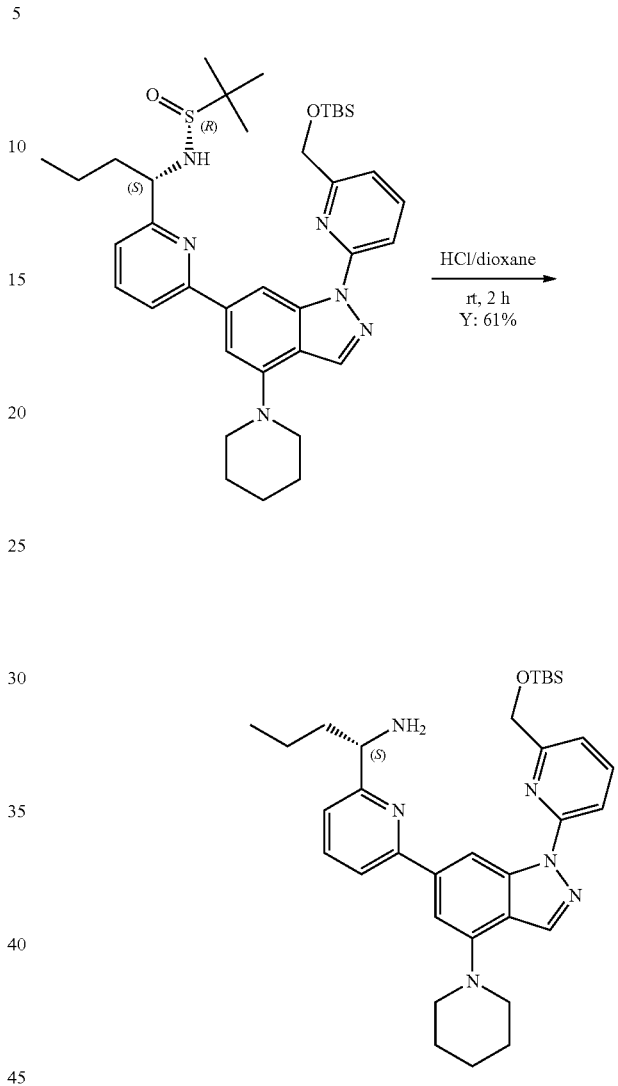

A mixture of 1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl trifluoromethanesulfonate (300 mg, 0.42 mmol, 1.0 eq), piperidine (CAS No. 110-89-4, 35 mg, 0.42 mmol, 1.0 eq), Pd$_2$(dba)$_3$ (38 mg, 0.042 mmol, 0.1 eq), BINAP (26 mg, 0.042 mmol, 0.1 eq) and Cs$_2$CO$_3$ (409 mg, 1.26 mmol, 3.0 eq) in toluene (10 mL) was stirred at 110° C. for 16 h. After concentration, the residue was purified by silica gel chromatography with PE/EA (1/1) as eluent to give (R)—N—((S)-1-(6-(1-(6-(((tert-butyldimethylsilyl)oxy)methyl)pyridin-2-yl)-4-(piperidin-1-yl)-1H-indazol-6-yl)pyridin-2-yl)butyl)-2-methylpropane-2-sulfinamide. 80 mg, as a yellow solid, Y: 29%. ESI-MS (M+H)$^+$: 675.4.

The preparation of (S)-(6-(6-(6-(1-aminobutyl)pyridin-2-yl)-4-(piperidin-1-yl)-1H-indazol-1-yl)pyridin-2-yl)methanol was similar to that of (S)-(6-(6-(6-(1-aminoethyl)pyridin-2-yl)-1H-indazol-1-yl)pyridin-2-yl)methanol (Example 143) to give 34 mg as a yellow solid, Y: 61%. ESI-MS (M+H)$^+$: 457.3. HPLC: 98%. $^1$H NMR (400 MHz, CD$_3$OD) δ: 9.32 (s, 1H), 8.33 (s, 1H), 8.04-7.95 (m, 4H), 7.52 (s, 1H), 7.42 (d, J=7.6 Hz, 1H), 7.36 (dd, J=6.4, 2.8 Hz, 1H), 4.86 (s, 2H), 4.53 (t, J=6.8 Hz, 1H), 3.44-3.42 (m, 4H), 2.08-1.97 (m, 2H), 1.94-1.89 (m, 4H), 1.77-1.73 (m, 2H), 1.48-1.38 (m, 2H), 1.01 (t, J=6.8 Hz, 3H).

The following examples were prepared as described in example 324 using the appropriate amine in place of piperidine (CAS No. 110-89-4)

| Example # | Structure | Name | LCMS (M+) | ¹H NMR |
|---|---|---|---|---|
| 325 | 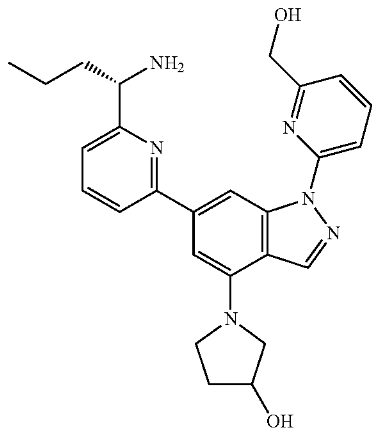 [SMILES: CCC[C@H](N)c1cccc(-c2cc(N3CCC(O)C3)c3cnn(-c4cccc(CO)n4)c3c2)n1] | 1-(6-(6-((S)-1-aminobutyl)pyridin-2-yl)-1-(6-(hydroxymethyl)pyridin-2-yl)-1H-indazol-4-yl)pyrrolidin-3-ol | 459.2 | ¹H NMR (400 MHz, DMSO-d₆) δ: 8.85 (s, 1H), 8.57 (s, 1H), 8.41-8.39 (m, 3H), 8.03-7.98 (m, 3H), 7.86 (d, J = 8.0 Hz, 1H), 7.51-7.46 (m, 1H), 7.38 (d, J = 7.2 Hz, 1H), 7.00 (s, 1H), 5.62-5.56 (m, 1H), 5.12-5.06 (m, 1H), 4.52-4.49 (m, 2H), 3.93-3.81 (m, 2H), 3.75-3.71 (m, 1H), 3.56-3.51 (m, 2H), 2.19-2.10 (m, 1H), 2.05-2.01 (m, 1H), 1.99-1.89 (m, 2H), 1.39-1.27 (m, 2H), 0.92 (t, J = 7.2 Hz, 3H). |
| 326 | 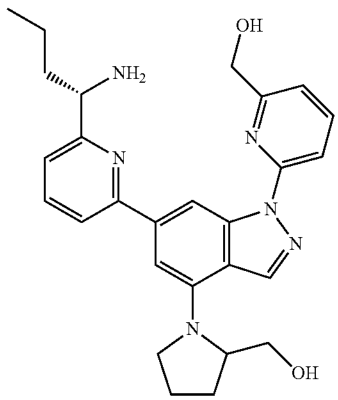 [SMILES: CCC[C@H](N)c1cccc(-c2cc(N3CCCC3CO)c3cnn(-c4cccc(CO)n4)c3c2)n1] | (1-(6-(6-((S)-1-aminobutyl)pyridin-2-yl)-1-(6-(hydroxymethyl)pyridin-2-yl)-1H-indazol-4-yl)pyrrolidin-2-yl)methanol | 473.2 | ¹H NMR (400 MHz, CD₃OD) δ: 9.00 (s, 1H), 8.49 (s, 1H), 8.03-7.92 (m, 4H), 7.42 (d, J = 6.8 Hz, 1H), 7.35 (d, J = 6.4 Hz, 1H), 7.14 (d, J = 3.2 Hz, 1H), 4.83 (s, 2H), 4.56-4.52 (m, 1H), 4.33-4.31 (m, 1H), 4.00-3.97 (m, 1H), 3.89-3.84 (m, 1H), 3.71-3.67 (m, 1H), 3.63-3.58 (m, 1H), 2.27-2.14 (m, 4H), 2.11-1.99 (m, 2H), 1.52-1.39 (m, 2H), 1.03 (t, J = 7.2 Hz, 3H). |
| 327 | 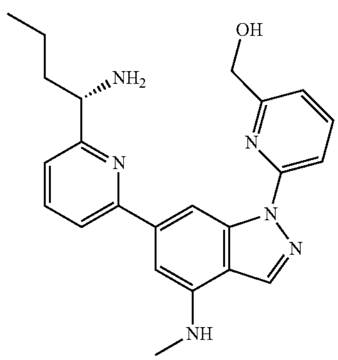 [SMILES: CCC[C@H](N)c1cccc(-c2cc(NC)c3cnn(-c4cccc(CO)n4)c3c2)n1] | (S)-(6-(6-(6-(1-aminobutyl)pyridin-2-yl)-4-(methylamino)-1H-indazol-1-yl)pyridin-2-yl)methanol | 403.1 | ¹H NMR (400 MHz, CD₃OD) δ: 8.90 (s, 1H), 8.34 (s, 1H), 8.02-7.90 (m, 4H), 7.40 (d, J = 7.2 Hz, 1H), 7.34 (d, J = 6.8 Hz, 1H), 7.04 (s, 1H), 4.85 (s, 2H), 4.53 (t, J = 6.8 Hz, 1H), 3.08 (s, 3H), 2.09-1.99 (m, 2H), 1.50-1.38 (m, 2H), 1.02 (t, J = 7.6 Hz, 3H). |
| 328 | 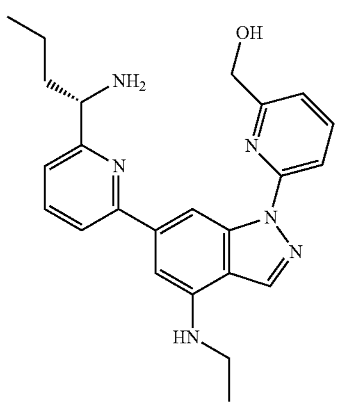 [SMILES: CCC[C@H](N)c1cccc(-c2cc(NCC)c3cnn(-c4cccc(CO)n4)c3c2)n1] | (S)-(6-(6-(6-(1-aminobutyl)pyridin-2-yl)-4-(ethylamino)-1H-indazol-1-yl)pyridin-2-yl)methanol | 417.1 | ¹H NMR (400 MHz, DMSO-d₆) δ: 8.74 (s, 1H), 8.59 (s, 1H), 8.39 (br, 2H), 8.02-7.96 (m, 3H), 7.84 (d, J = 2.8 Hz, 1H), 7.47 (dd, J = 5.2, 2.8 Hz, 1H), 7.37 (d, J = 7.6 Hz, 1H), 7.03 (s, 1H), 4.75 (s, 2H), 4.50-4.48 (m, 1H), 3.39 (q, J = 7.2 Hz, 2H), 1.96-1.91 (m, 2H), 1.37-1.23 (m, 5H), 0.92 (t, J = 7.2 Hz, 3H) |

| Example # | Structure | Name | LCMS (M+) | ¹H NMR |
|---|---|---|---|---|
| 329 | 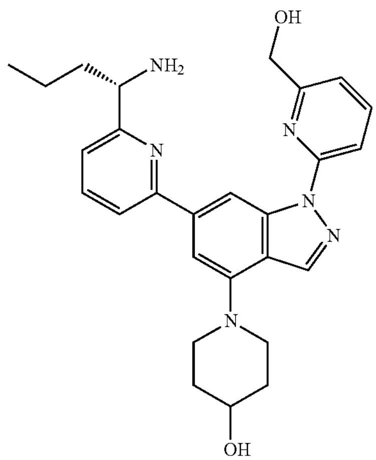 [SMILES: CCC[C@H](N)c1cccc(-c2cc(N3CCC(O)CC3)c3cnn(-c4cccc(CO)n4)c3c2)n1] | (S)-1-(6-(6-(1-aminobutyl)pyridin-2-yl)-1-(6-(hydroxymethyl)pyridin-2-yl)-1H-indazol-4-yl)piperidin-4-ol | 473.3 | ¹H NMR (400 MHz, CD₃OD) δ: 9.32 (s, 1H), 8.35 (s, 1H), 8.10-7.90 (m, 4H), 7.53 (d, J = 6.0 Hz, 1H), 7.44 (d, J = 7.2 Hz, 1H), 7.38 (dd, J = 5.6, 2.4 Hz, 1H), 4.88 (s, 2H), 4.55 (t, J = 6.8 Hz, 1H), 3.94-3.89 (m, 1H), 3.80-3.78 (m, 2H), 3.23-3.18 (m, 2H), 2.17-1.99 (m, 4H), 1.94-1.85 (m, 2H), 1.52-1.40 (m, 2H), 1.03 (t, J = 7.2 Hz, 3H). |
| 330 | 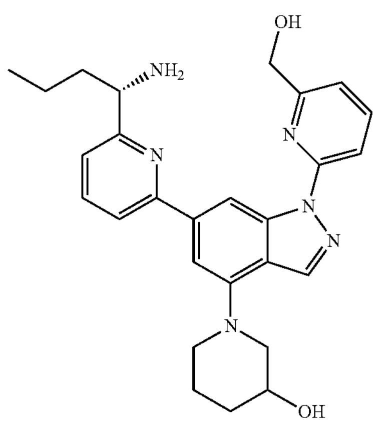 [SMILES: CCC[C@H](N)c1cccc(-c2cc(N3CCCC(O)C3)c3cnn(-c4cccc(CO)n4)c3c2)n1] | 1-(6-(6-((S)-1-aminobutyl)pyridin-2-yl)-1-(6-(hydroxymethyl)pyridin-2-yl)-1H-indazol-4-yl)piperidin-3-ol | 473.3 | ¹H NMR (400 MHz, CD₃OD) δ: 9.32 (s, 1H), 8.38 (s, 1H), 8.06-7.96 (m, 4H), 7.54 (s, 1H), 7.44 (d, J = 7.2 Hz, 1H), 7.37 (dd, J = 5.6, 2.0 Hz, 1H), 4.87 (s, 2H), 4.55 (t, J = 6.8 Hz, 1H), 4.07-4.03 (m, 1H), 3.79-3.76 (m, 1H), 3.66-3.62 (m, 1H), 3.18-3.14 (m, 2H), 2.12-2.02 (m, 4H), 1.92-1.89 (m, 1H), 1.64-1.59 (m, 1H), 1.50-1.40 (m, 2H), 1.03 (t, J = 7.2 Hz, 3H). |
| 331 | 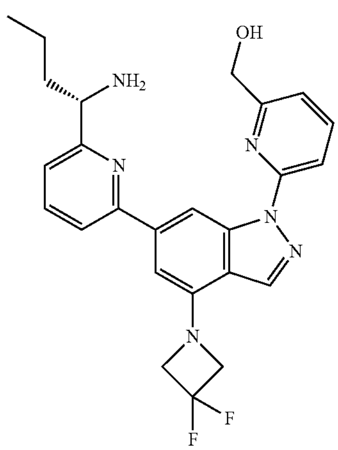 [SMILES: CCC[C@H](N)c1cccc(-c2cc(N3CC(F)(F)C3)c3cnn(-c4cccc(CO)n4)c3c2)n1] | (S)-(6-(6-(6-(1-aminobutyl)pyridin-2-yl)-4-(3,3-difluoroazetidin-1-yl)-1H-indazol-1-yl)pyridin-2-yl)methanol | 465.1 | ¹H NMR (400 MHz, CD₃OD) δ: 9.05 (s, 1H), 8.28 (s, 1H), 7.98-7.85 (m, 4H), 7.40 (d, J = 7.2 Hz, 1H), 7.35 (dd, J = 6.0, 1.6 Hz, 1H), 6.97 (s, 1H), 4.85 (s, 2H), 4.69-4.63 (m, 4H), 4.07 (t, J = 7.2 Hz, 1H), 1.93-1.83 (m, 2H), 1.46-1.31 (m, 2H), 0.99 (t, J = 7.6 Hz, 3H). |

-continued

| Example # | Structure | Name | LCMS (M+) | ¹H NMR |
|---|---|---|---|---|
| 332 | 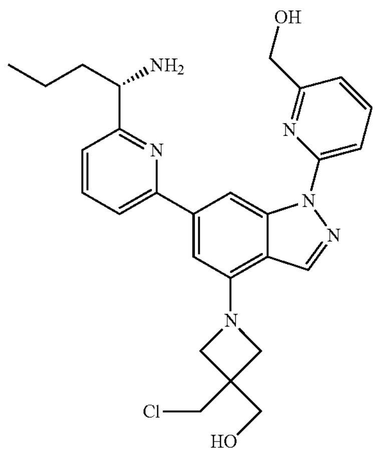 [SMILES: CCC[C@H](N)c1cccc(-c2cc(N3CC(CO)(CCl)C3)c3cnn(-c4cccc(CO)n4)c3c2)n1] | (S)-(1-(6-(6-(1-aminobutyl)pyridin-2-yl)-1-(6-(hydroxymethyl)pyridin-2-yl)-1H-indazol-4-yl)-3-(chloromethyl)azetidin-3-yl)methanol | 507.2 | ¹H NMR (400 MHz, CD₃OD) δ: 8.90 (s, 1H), 8.26 (s, 1H), 7.96-7.81 (m, 4H), 7.37 (d, J = 6.8 Hz, 1H), 7.33 (d, J = 7.2 Hz, 1H), 6.84 (s, 1H), 4.84 (s, 2H), 4.13-4.07 (m, 5H), 4.01 (s, 2H), 3.93 (s, 2H), 1.94-1.82 (m, 2H), 1.43-1.32 (m, 2H), 0.98 (t, J = 7.6 Hz, 3H). |
| 333 | 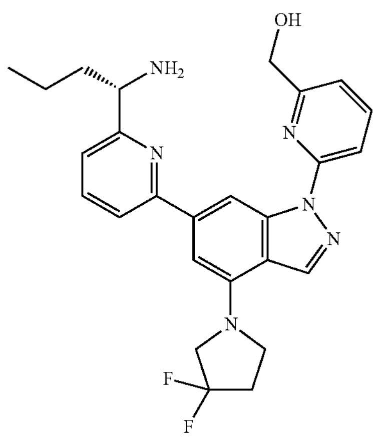 [SMILES: CCC[C@H](N)c1cccc(-c2cc(N3CCC(F)(F)C3)c3cnn(-c4cccc(CO)n4)c3c2)n1] | (S)-(6-(6-(6-(1-aminobutyl)pyridin-2-yl)-4-(3,3-difluoropyrrolidin-1-yl)-1H-indazol-1-yl)pyridin-2-yl)methanol | 479.2 | ¹H NMR (400 MHz, CD₃OD) δ: 9.08 (s, 1H), 8.45 (s, 1H), 8.01 (d, J = 7.2 Hz, 1H), 7.96-7.91 (m, 3H), 7.38 (d, J = 7.6 Hz, 1H), 7.32 (d, J = 10.0 Hz, 1H), 7.06 (s, 1H), 4.84 (s, 2H), 4.50 (t, J = 6.8 Hz, 1H), 4.15-4.09 (m, 2H), 3.99 (t, J = 6.8 Hz, 2H), 2.66-2.59 (m, 2H), 2.02-1.98 (m, 2H), 1.44-1.38 (m, 2H), 0.99 (t, J = 7.2 Hz, 3H). |
| 334 | 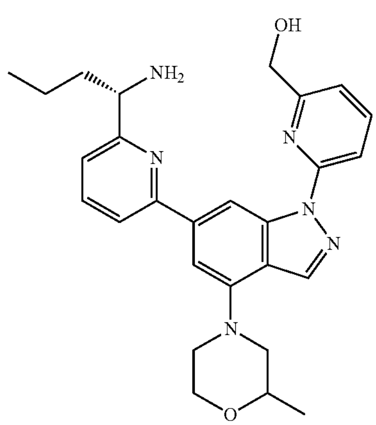 [SMILES: CCC[C@H](N)c1cccc(-c2cc(N3CCOC(C)C3)c3cnn(-c4cccc(CO)n4)c3c2)n1] | (6-(6-(6-((S)-1-aminobutyl)pyridin-2-yl)-4-(2-methylmorpholino)-1H-indazol-1-yl)pyridin-2-yl)methanol | 473.3 | ¹H NMR (400 MHz, CD₃OD) δ: 9.34 (s, 1H), 8.40 (s, 1H), 8.06 (d, J = 7.6 Hz, 1H), 8.01 (d, J = 7.6 Hz, 1H), 7.99-7.97 (m, 2H), 7.49 (s, 1H), 7.45 (d, J = 7.2 Hz, 1H), 7.39-7.37 (m, 1H), 4.87 (s, 2H), 4.56 (t, J = 7.2 Hz, 1H), 4.11-3.99 (m, 3H), 3.75-3.67 (m, 2H), 3.13-3.08 (m, 1H), 2.80-2.75 (m, 1H), 2.10-2.00 (m, 2H), 1.53-1.40 (m, 2H), 1.32 (d, J = 6.4 Hz, 3H), 1.04 (t, J = 7.2 Hz, 3H). |

| Example # | Structure | Name | LCMS (M+) | ¹H NMR |
|---|---|---|---|---|
| 335 | 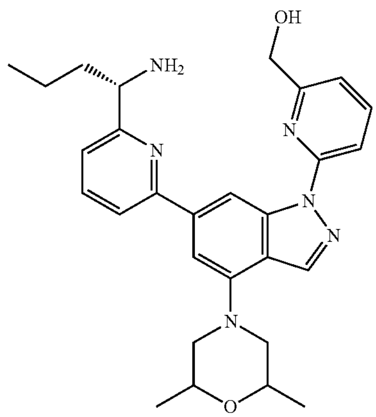 [SMILES: CCC[C@H](N)c1cccc(-c2cc(N3CC(C)OC(C)C3)c3cnn(-c4cccc(CO)n4)c3c2)n1] | (6-(6-(6-((S)-1-aminobutyl)pyridin-2-yl)-4-(2,6-dimethylmorpholino)-1H-indazol-1-yl)pyridin-2-yl)methanol | 487.2 | ¹H NMR (400 MHz, CD₃OD) δ: 9.33 (s, 1H), 8.39 (s, 1H), 8.07-7.97 (m, 4H), 7.46-7.43 (m, 2H), 7.39-7.37 (m, 1H), 4.87 (s, 2H), 4.56 (t, J = 6.8 Hz, 1H), 4.07-4.03 (m, 2H), 3.74-3.71 (m, 2H), 2.70 (t, J = 11.2 Hz, 2H), 2.11-2.02 (m, 2H), 1.51-1.42 (m, 3H), 1.32-1.31 (m, 5H), 1.04 (t, J = 7.2 Hz, 3H). |
| 336 | 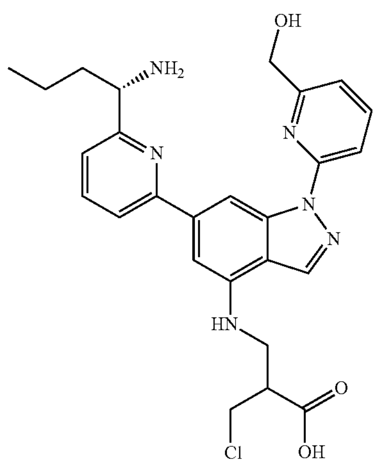 [SMILES: CCC[C@H](N)c1cccc(-c2cc(NCC(CCl)C(=O)O)c3cnn(-c4cccc(CO)n4)c3c2)n1] | 3-((6-(6-((S)-1-aminobutyl)pyridin-2-yl)-1-(6-(hydroxymethyl)pyridin-2-yl)-1H-indazol-4-yl)amino)-2-(chloromethyl)propanoic acid | 509.3 | ¹H NMR (400 MHz, CD₃OD) δ: 8.60 (d, J = 2.8 Hz, 1H), 8.20 (d, J = 3.2 Hz, 1H), 7.83-7.69 (m, 4H), 7.27-7.16 (m, 3H), 4.69 (s, 2H), 4.39-4.35 (m, 1H), 3.85-3.46 (m, 4H), 2.98-2.91 (m, 1H), 1.96-1.86 (m, 2H), 1.37-1.24 (m, 2H), 0.88 (t, J = 7.2 Hz, 3H). |
| 337 | 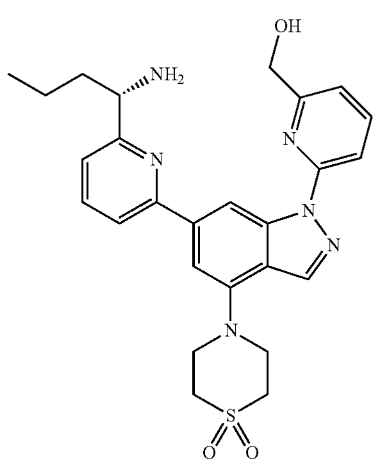 [SMILES: CCC[C@H](N)c1cccc(-c2cc(N3CCS(=O)(=O)CC3)c3cnn(-c4cccc(CO)n4)c3c2)n1] | (S)-4-(6-(6-(1-aminobutyl)pyridin-2-yl)-1-(6-(hydroxymethyl)pyridin-2-yl)-1H-indazol-4-yl)thiomorpholine 1,1-dioxide | 507.1 | ¹H NMR (400 MHz, CD₃OD) δ: 9.20 (s, 1H), 8.47 (s, 1H), 8.16-8.00 (m, 4H), 7.64 (s, 1H), 7.60-7.59 (m, 1H), 7.44 (d, J = 6.8 Hz, 1H), 4.89 (s, 2H), 4.71-4.68 (m, 1H), 3.97-3.96 (m, 4H), 3.44-3.43 (m, 4H), 2.13-2.07 (m, 2H), 1.56-1.39 (m, 2H), 1.04 (t, J = 7.2 Hz, 3H). |

| Example # | Structure | Name | LCMS (M+) | ¹H NMR |
|---|---|---|---|---|
| 338 | 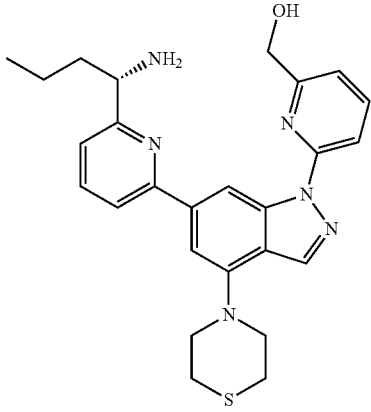 [SMILES: CCC[C@H](N)c1cccc(-c2cc(N3CCSCC3)c3cnn(-c4cccc(CO)n4)c3c2)n1] | (S)-(6-(6-(6-(1-aminobutyl)pyridin-2-yl)-4-thiomorpholino-1H-indazol-1-yl)pyridin-2-yl)methanol | 475.1 | ¹H NMR (400 MHz, CD$_3$OD) δ: 9.29 (s, 1H), 8.30 (s, 1H), 8.04-7.94 (m, 4H), 7.52 (s, 1H), 7.44 (d, J = 7.2 Hz, 1H), 7.36 (d, J = 6.0 Hz, 1H), 4.87 (s, 2H), 4.55 (t, J = 6.8 Hz, 1H), 3.71-3.68 (m, 4H), 2.97-2.95 (m, 4H), 2.08-2.02 (m, 2H), 1.49-1.43 (m, 2H), 1.03 (t, J = 7.2 Hz, 3H). |
| 339 | 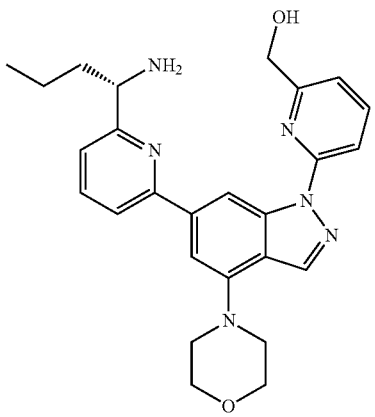 [SMILES: CCC[C@H](N)c1cccc(-c2cc(N3CCOCC3)c3cnn(-c4cccc(CO)n4)c3c2)n1] | (S)-(6-(6-(6-(1-aminobutyl)pyridin-2-yl)-4-morpholino-1H-indazol-1-yl)pyridin-2-yl)methanol | 457.3 | ¹H NMR (400 MHz, CD$_3$OD) δ: 9.32 (s, 1H), 8.37 (s, 1H), 8.04 (d, J = 7.6 Hz, 1H), 8.00-7.95 (m, 3H), 7.49 (s, 1H), 7.42 (d, J = 7.6 Hz, 1H), 7.37-7.35 (m, 1H), 4.86 (s, 2H), 4.54 (t, J = 7.2 Hz, 1H), 4.00-3.97 (m, 4H), 3.42-3.39 (m, 4H), 2.09-1.97 (m, 2H), 1.50-1.36 (m, 2H), 1.01 (t, J = 7.2 Hz, 3H). |
| 340 | 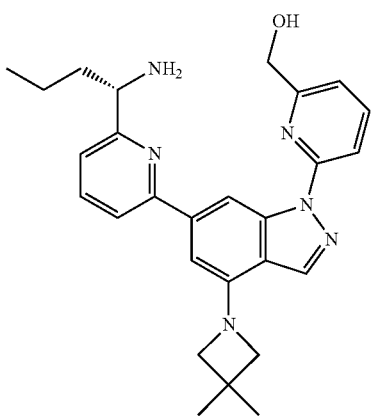 [SMILES: CCC[C@H](N)c1cccc(-c2cc(N3CC(C)(C)C3)c3cnn(-c4cccc(CO)n4)c3c2)n1] | (S)-(6-(6-(6-(1-aminobutyl)pyridin-2-yl)-4-(3,3-dimethylazetidin-1-yl)-1H-indazol-1-yl)pyridin-2-yl)methanol | 457.3 | ¹H NMR (400 MHz, CD$_3$OD) δ: 8.91 (s, 1H), 8.26 (s, 1H), 7.97-7.87 (m, 4H), 7.39-7.35 (m, 2H), 6.82 (s, 1H), 4.85 (s, 2H), 4.21-4.17 (m, 1H), 4.01 (s, 4H), 2.03-1.85 (m, 2H), 1.45 (s, 6H), 1.39-1.28 (m, 2H), 1.00 (t, J = 7.2 Hz, 3H). |

| Example # | Structure | Name | LCMS (M+) | ¹H NMR |
|---|---|---|---|---|
| 341 | 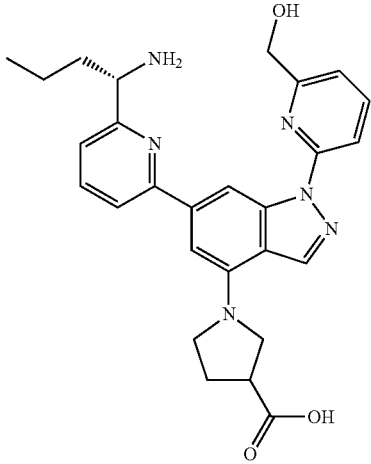 [SMILES: CCC[C@H](N)c1cccc(-c2cc(N3CCC(C(=O)O)C3)c3cnn(-c4cccc(CO)n4)c3c2)n1] | 1-(6-(6-((S)-1-aminobutyl)pyridin-2-yl)-1-(6-(hydroxymethyl)pyridin-2-yl)-1H-indazol-4-yl)pyrrolidine-3-carboxylic acid | 487.4 | ¹H NMR (400 MHz, CD₃OD) δ: 8.80 (s, 1H), 8.30 (s, 1H), 7.88-7.76 (m, 4H), 7.30-7.28 (m, 1H), 7.22 (d, J = 6.8 Hz, 1H), 6.87 (s, 1H), 4.74 (s, 2H), 4.42 (t, J = 7.2 Hz, 1H), 3.80 (d, J = 7.6 Hz, 2H), 3.75-3.60 (m, 2H), 3.14-3.09 (m, 1H), 2.27-2.22 (m, 2H), 1.98-1.90 (m, 2H), 1.39-1.28 (m, 2H), 0.91 (t, J = 7.2 Hz, 3H). |
| 342 | 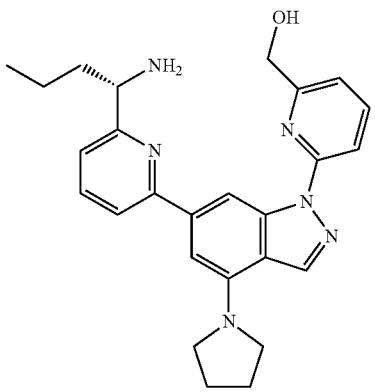 [SMILES: CCC[C@H](N)c1cccc(-c2cc(N3CCCC3)c3cnn(-c4cccc(CO)n4)c3c2)n1] | (S)-(6-(6-(6-(1-aminobutyl)pyridin-2-yl)-4-(pyrrolidin-1-yl)-1H-indazol-1-yl)pyridin-2-yl)methanol | 443.2 | ¹H NMR (400 MHz, CD₃OD) δ: 8.81 (s, 1H), 8.45 (s, 1H), 7.96-7.82 (m, 4H), 7.38-7.33 (m, 2H), 6.93 (s, 1H), 4.84 (s, 2H), 4.09 (t, J = 6.8 Hz, 1H), 3.76-3.73 (m, 4H), 2.17-2.14 (m, 4H), 1.93-1.84 (m, 2H), 1.46-1.31 (m, 2H), 0.98 (t, J = 7.6 Hz, 3H). |
| 343 | 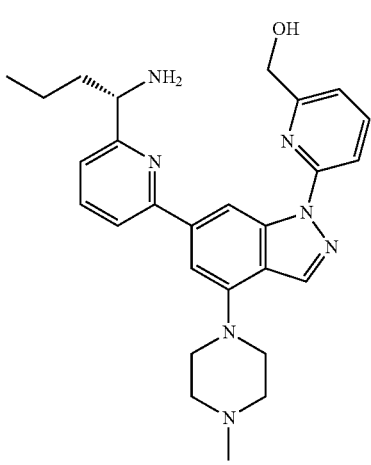 [SMILES: CCC[C@H](N)c1cccc(-c2cc(N3CCN(C)CC3)c3cnn(-c4cccc(CO)n4)c3c2)n1] | (S)-(6-(6-(6-(1-aminobutyl)pyridin-2-yl)-4-(4-methylpiperazin-1-yl)-1H-indazol-1-yl)pyridin-2-yl)methanol | 472.3 | ¹H NMR (400 MHz, CD₃OD) δ: 9.19 (s, 1H), 8.33 (s, 1H), 7.98-7.94 (m, 2H), 7.93-7.85 (m, 2H), 7.43 (s, 1H), 7.40 (d, J = 7.6 Hz, 1H), 7.35 (dd, J = 6.4, 2.0 Hz, 1H), 4.85 (s, 2H), 4.07 (t, J = 6.8 Hz, 1H), 3.46-3.44 (m, 4H), 2.80-2.78 (m, 4H), 2.44 (s, 3H), 1.95-1.81 (m, 2H), 1.47-1.29 (m, 2H), 0.98 (t, J = 7.6 Hz, 3H). |

| Example # | Structure | Name | LCMS (M+) | ¹H NMR |
|---|---|---|---|---|
| 344 | 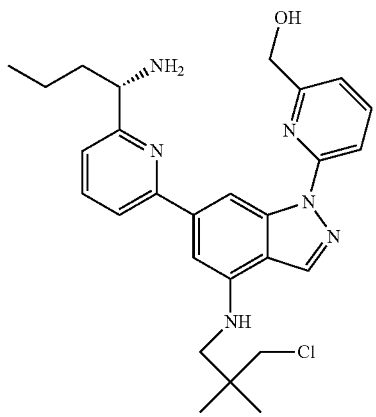 [SMILES: CCC[C@H](N)c1cccc(-c2cc(NCC(C)(C)CCl)c3cnn(-c4cccc(CO)n4)c3c2)n1] | (S)-(6-(6-(6-(1-aminobutyl)pyridin-2-yl)-4-((3-chloro-2,2-dimethylpropyl)amino)-1H-indazol-1-yl)pyridin-2-yl)methanol | 493.2 | ¹H NMR (400 MHz, CD$_3$OD) δ: 8.71 (s, 1H), 8.46 (s, 1H), 7.94-7.78 (m, 4H), 7.36 (d, J = 7.2 Hz, 1H), 7.29 (d, J = 7.2 Hz, 1H), 7.19 (s, 1H), 4.83 (s, 2H), 4.01 (t, J = 6.8 Hz, 1H), 3.62 (s, 2H), 3.40 (s, 2H), 1.92-1.80 (m, 2H), 1.43-1.31 (m, 2H), 1.16 (s, 6H), 0.97 (t, J = 7.6 Hz, 3H). |
| 345 | 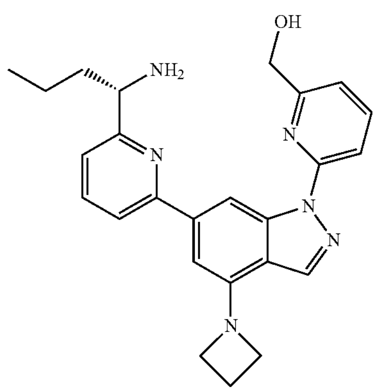 [SMILES: CCC[C@H](N)c1cccc(-c2cc(N3CCC3)c3cnn(-c4cccc(CO)n4)c3c2)n1] | (S)-(6-(6-(6-(1-aminobutyl)pyridin-2-yl)-4-(azetidin-1-yl)-1H-indazol-1-yl)pyridin-2-yl)methanol | 465.2 | ¹H NMR (400 MHz, CDCl$_3$) δ: 8.81-8.67 (m, 3H), 8.04 (s, 1H), 7.79-7.74 (m, 2H), 7.50 (d, J = 8.0 Hz, 1H), 7.42 (t, J = 8.0 Hz, 1H), 7.17 (d, J = 6.4 Hz, 1H), 6.71 (s, 1H), 6.64 (d, J = 7.2 Hz, 1H), 4.66-4.51 (m, 3H), 3.74 (t, J = 6.0 Hz, 2H), 3.50 (t, J = 6.8 Hz, 2H), 2.20 (t, J = 6.4 Hz, 2H), 2.06-1.94 (m, 2H), 1.32-1.25 (m, 2H), 0.88 (t, J = 7.2 Hz, 3H). |
| 346 | 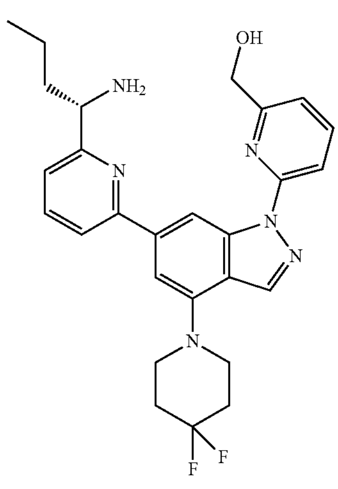 [SMILES: CCC[C@H](N)c1cccc(-c2cc(N3CCC(F)(F)CC3)c3cnn(-c4cccc(CO)n4)c3c2)n1] | (S)-(6-(6-(6-(1-aminobutyl)pyridin-2-yl)-4-(4,4-difluoropiperidin-1-yl)-1H-indazol-1-yl)pyridin-2-yl)methanol | 493.4 | ¹H NMR (400 MHz, CD$_3$OD) δ: 9.25 (s, 1H), 8.34 (s, 1H), 8.03-7.92 (m, 4H), 7.53 (s, 1H), 7.42 (d, J = 7.2 Hz, 1H), 7.34 (d, J = 4.0 Hz, 1H), 4.86 (s, 2H), 4.55 (t, J = 7.2 Hz, 1H), 3.53 (t, J = 5.2 Hz, 4H), 2.31-2.25 (m, 4H), 2.08-2.01 (m, 2H), 1.49-1.39 (m, 2H), 1.01 (t, J = 7.2 Hz, 3H). |

| Example # | Structure | Name | LCMS (M+) | ¹H NMR |
|---|---|---|---|---|
| 347 | 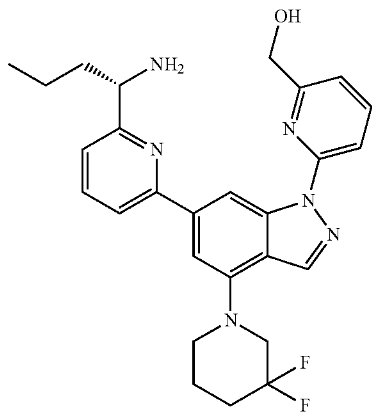 [SMILES: CCC[C@H](N)c1cccc(-c2cc(N3CCCC(F)(F)C3)c3cnn(-c4cccc(CO)n4)c3c2)n1] | (S)-(6-(6-(6-(1-aminobutyl)pyridin-2-yl)-4-(3,3-difluoropiperidin-1-yl)-1H-indazol-1-yl)pyridin-2-yl)methanol | 493.3 | ¹H NMR (400 MHz, CD$_3$OD) δ: 9.32 (s, 1H), 8.31 (s, 1H), 8.06-7.95 (m, 4H), 7.52 (s, 1H), 7.44 (d, J = 7.6 Hz, 1H), 7.37-7.36 (m, 1H), 4.88 (s, 2H), 4.56 (t, J = 6.8 Hz, 1H), 3.64 (t, J = 11.2 Hz, 2H), 3.49-3.46 (m, 2H), 2.20-2.02 (m, 6H), 1.51-1.42 (m, 2H), 1.03 (t, J = 7.6 Hz, 3H). |
| 348 | 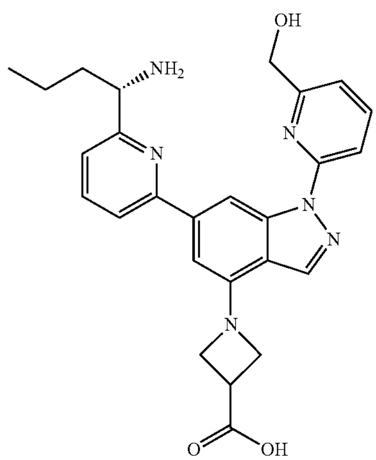 [SMILES: CCC[C@H](N)c1cccc(-c2cc(N3CC(C(=O)O)C3)c3cnn(-c4cccc(CO)n4)c3c2)n1] | (S)-1-(6-(6-(1-aminobutyl)pyridin-2-yl)-1-(6-(hydroxymethyl)pyridin-2-yl)-1H-indazol-4-yl)azetidine-3-carboxylic acid | 473.3 | ¹H NMR (400 MHz, CD$_3$OD) δ: 8.95 (s, 1H), 8.26 (s, 1H), 8.01-7.93 (m, 4H), 7.40 (d, J = 6.8 Hz, 1H), 7.35 (d, J = 6.0 Hz, 1H), 6.95 (s, 1H), 4.86 (s, 2H), 4.53 (t, J = 6.8 Hz, 1H), 4.45-4.43 (m, 2H), 4.36-4.34 (m, 2H), 3.61-3.53 (m, 1H), 2.06-2.02 (m, 2H), 1.46-1.44 (m, 2H), 1.03 (t, J = 7.6 Hz, 3H). |
| 349 | 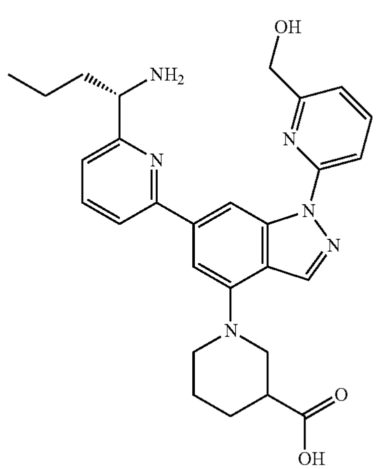 [SMILES: CCC[C@H](N)c1cccc(-c2cc(N3CCCC(C(=O)O)C3)c3cnn(-c4cccc(CO)n4)c3c2)n1] | 1-(6-(6-((S)-1-aminobutyl)pyridin-2-yl)-1-(6-(hydroxymethyl)pyridin-2-yl)-1H-indazol-4-yl)piperidine-3-carboxylic acid | 501.2 | ¹H NMR (400 MHz, CD$_3$OD) δ: 9.18 (s, 1H), 8.39 (s, 1H), 8.03 (dd, J = 8.0, 3.2 Hz, 1H), 7.98 (d, J = 7.6 Hz, 1H), 7.95-7.94 (m, 2H), 7.61-7.58 (m, 1H), 7.41 (d, J = 7.2 Hz, 1H), 7.37-7.35 (m, 1H), 4.87 (s, 2H), 4.52 (t, J = 6.8 Hz, 1H), 3.91-3.82 (m, 2H), 3.18-3.11 (m, 1H), 2.98-2.92 (m, 1H), 2.72-2.66 (m, 1H), 2.19-2.15 (m, 1H), 2.09-1.86 (m, 4H), 1.74-1.64 (m, 1H), 1.52-1.40 (m, 2H), 1.03 (t, J = 7.2 Hz, 3H). |

| Example # | Structure | Name | LCMS (M+) | ¹H NMR |
|---|---|---|---|---|
| 350 | 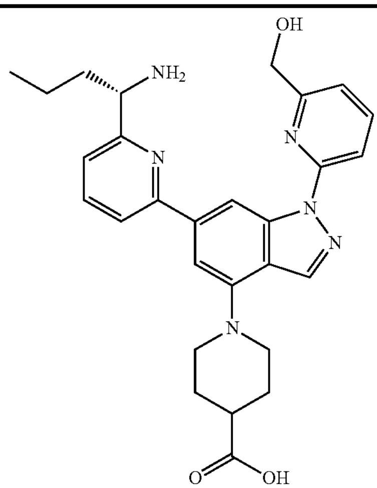 | (S)-1-(6-(6-(1-aminobutyl)pyridin-2-yl)-1-(6-(hydroxymethyl)pyridin-2-yl)-1H-indazol-4-yl)piperidine-4-carboxylic acid | 501.3 | ¹H NMR (400 MHz, CD₃OD) δ: 9.31 (s, 1H), 8.35 (s, 1H), 8.05-7.96 (m, 4H), 7.52 (s, 1H), 7.44 (d, J = 7.6 Hz, 1H), 7.38-7.36 (m, 1H), 4.87 (s, 2H), 4.55 (t, J = 6.8 Hz, 1H), 3.88-3.85 (m, 2H), 3.13-3.10 (m, 2H), 2.64-2.57 (m, 1H), 2.21-2.02 (m, 6H), 1.49-1.43 (m, 2H), 1.03 (t, J = 7.2 Hz, 3H). |
| 351 | 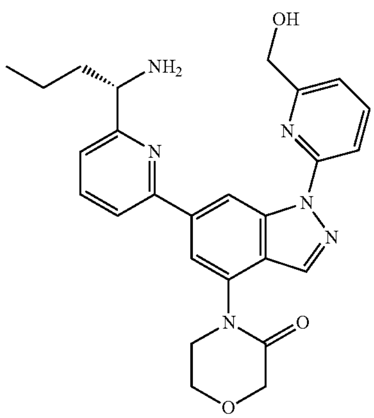 [SMILES: CCC[C@H](N)c1cccc(-c2cc(N3CCOCC3=O)c3cnn(-c4cccc(CO)n4)c3c2)n1] | (S)-4-(6-(6-(1-aminobutyl)pyridin-2-yl)-1-(6-(hydroxymethyl)pyridin-2-yl)-1H-indazol-4-yl)morpholin-3-one | 473.2 | ¹H NMR (400 MHz, CD₃OD) δ: 9.79 (s, 1H), 8.28 (s, 1H), 8.15 (s, 1H), 8.12-8.10 (m, 1H), 8.01-7.97 (m, 3H), 7.44 (d, J = 7.6 Hz, 1H), 7.37 (t, J = 4.0 Hz, 1H), 4.88 (s, 2H), 4.54 (t, J = 6.8 Hz, 1H), 4.45 (s, 2H), 4.21-4.18 (m, 2H), 4.03-4.00 (m, 2H), 2.06-1.98 (m, 2H), 1.48-1.38 (m, 2H), 1.00 (t, J = 7.6 Hz, 3H). |

Example 352

Step 1. Synthesis of 2-bromo-6-fluoro-4-hydroxybenzaldehyde

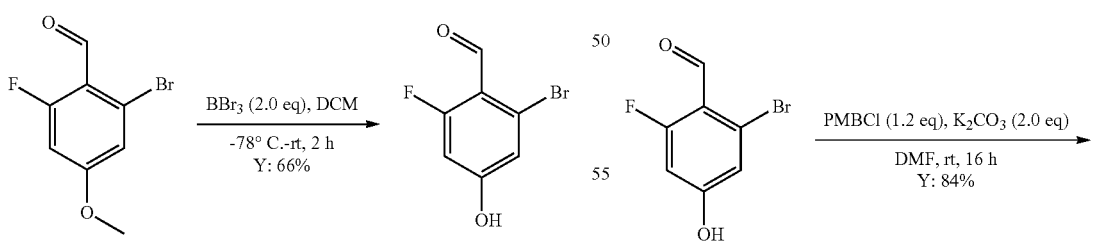

To a solution of 2-bromo-6-fluoro-4-methoxybenzaldehyde (21 g, 90 mmol, 1.0 eq) in DCM (100 mL) was added BBr₃ (46 g, 180 mmol, 2.0 eq) slowly at −78° C. The reaction mixture was stirred at rt for 2 h. The reaction was quenched with H₂O (50 mL). The mixture was filtrated and the precipitate was washed with DCM (200 mL×2). The filtrate was washed with H₂O (100 mL×2). The organic fraction was dried (Na₂SO₄), filtrated and concentrated to give 2-bromo-6-fluoro-4-hydroxybenzaldehyde (13.0 g, Y: 66%) as yellow oil. ESI-MS (M+H)⁺: 219.0.

Step 2. Synthesis of 2-bromo-6-fluoro-4-((4-methoxybenzyl)oxy)benzaldehyde

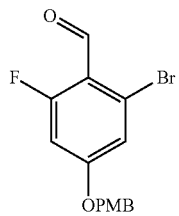

To a mixture of 2-bromo-6-fluoro-4-hydroxybenzaldehyde (13.0 g, 60 mmol, 1.0 eq) and K$_2$CO$_3$ (16.6 g, 120 mmol, 2.0 eq) in DMF (110 mL) was added p-Methoxybenzyl chloride (PMBCl, 11.2 g, 72 mmol, 1.2 eq) slowly at 0° C. The reaction mixture was stirred for 16 h at rt. Then H$_2$O (100 mL) was added to the mixture and stirred at rt for 30 min. The precipitate was collected by filtration and washed with H$_2$O (100 mL×2) and PE (100 mL×2) to give 2-bromo-6-fluoro-4-((4-methoxybenzyl)oxy)benzaldehyde (17 g, Y: 84%) as a yellow solid. ESI-MS (M+H)$^+$: 339.0.

Step 3. Synthesis of
4-bromo-6-((4-methoxybenzyl)oxy)-1H-indazole

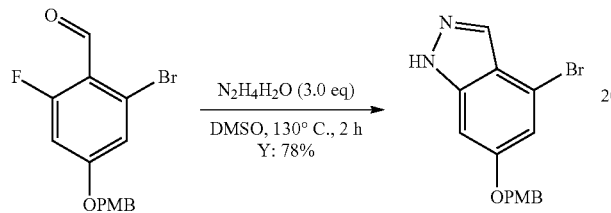

To a stirred solution of 2-bromo-6-fluoro-4-((4-methoxybenzyl)oxy)benzaldehyde (17 g, 50.3 mmol, 1.0 eq) in DMSO (100 mL) was added hydrazine monohydrate (7.5 g, 151 mmol, 3.0 eq). The reaction mixture was stirred at 130° C. for 2 h. After cooling down to rt, the reaction solution was diluted with water (500 mL) and stirred at rt for 30 min. The precipitate was collected by filtration and washed with water (50 mL×2) and PE (50 mL×2) to give 4-bromo-6-((4-methoxybenzyl)oxy)-1H-indazole (13 g, Y: 78%) as a light yellow solid. ESI-MS (M+H)$^+$: 333.0.

Step 4. Synthesis of (6-(4-bromo-6-((4-methoxybenzyl)oxy)-1H-indazol-1-yl)pyridin-2-yl)methanol

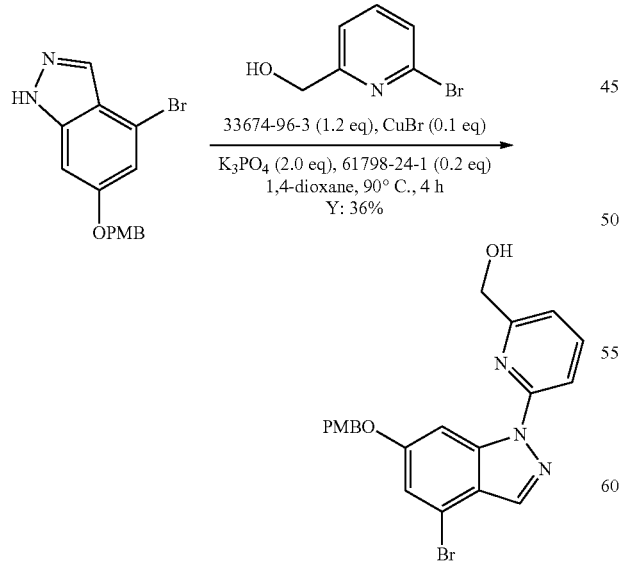

A mixture of 4-bromo-6-((4-methoxybenzyl)oxy)-1H-indazole (13 g, 39 mmol, 1.0 eq), (6-bromopyridin-2-yl)methanol (CAS No. 33674-96-3, 8.8 g, 47 mmol, 1.2 eq), CuBr (560 mg, 3.9 mmol, 0.1 eq), N,N'-Dimethyl-1,2-cyclohexanediamine (CAS No. 61798-24-1, 1.1 g, 7.8 mmol, 0.2 eq) and K$_3$PO$_4$ (16.6 g, 78 mmol, 2.0 eq) in 1,4-dioxane (120 mL) was stirred at 90° C. for 4 h under nitrogen atmosphere. After cooling down to rt, the mixture was filtrated and the filtrate was concentrated in vacuo. The residue was purified by silica gel column chromatography (PE/EA=4/1) to give (6-(4-bromo-6-((4-methoxybenzyl)oxy)-1H-indazol-1-yl)pyridin-2-yl)methanol (6 g, Y: 36%) as a light yellow solid. ESI-MS (M+H)$^+$: 440.1.

Step 5. Synthesis of 4-bromo-1-(6-(((tert-butyldimethylsilyl)oxy)methyl)pyridin-2-yl)-6-((4-methoxybenzyl)oxy)-1H-indazole

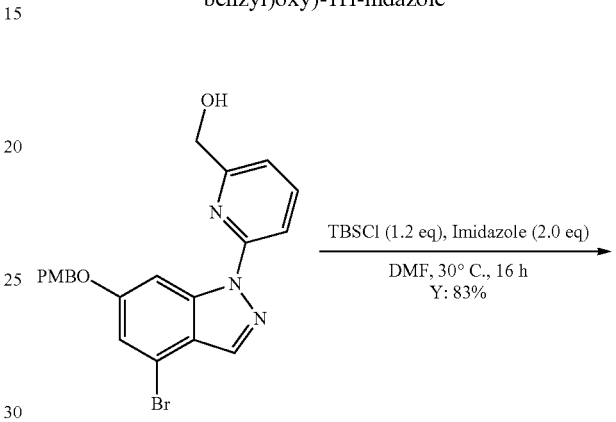

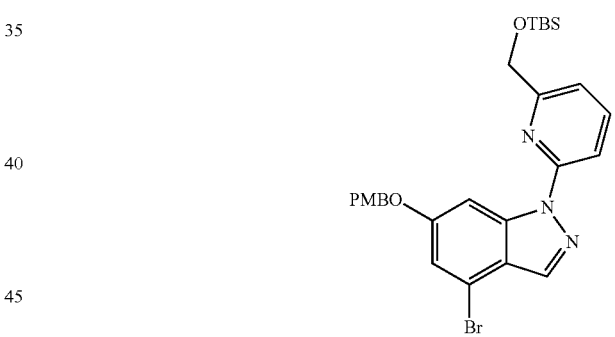

A mixture of (6-(4-bromo-6-((4-methoxybenzyl)oxy)-1H-indazol-1-yl)pyridin-2-yl)methanol (6 g, 13.6 mmol, 1.0 eq), tert-butyldimethylsilyl chloride (TBSCl, 2.5 g, 16.4 mmol, 1.2 eq) and imidazole (1.85 g, 27.2 mmol, 2.0 eq) in DMF (50 mL) was stirred at 30° C. for 16 h. The reaction solution was diluted with water (200 mL) and stirred at rt for 30 min. The precipitate was collected by filtration and washed with water (50 mL×2) and PE (50 mL×2) to give 4-bromo-1-(6-(((tert-butyldimethylsilyl)oxy)methyl)pyridin-2-yl)-6-((4-methoxybenzyl)oxy)-1H-indazole (6.3 g, Y: 83%) as a light yellow solid. ESI-MS (M+H)$^+$: 554.2. $^1$H NMR (400 MHz, CDCl$_3$) δ: 8.33 (s, 1H), 8.07 (s, 1H), 7.89-7.82 (m, 2H), 7.42-7.36 (m, 3H), 7.17 (d, J=2.0 Hz, 1H), 6.64 (d, J=8.4 Hz, 2H), 5.12 (s, 2H), 4.89 (s, 2H), 3.82 (s, 3H), 0.99 (s, 9H), 0.17 (s, 6H).

Step 6. Synthesis of 1-(6-(((tert-butyldimethylsilyl)oxy)methyl)pyridin-2-yl)-6-((4-methoxybenzyl)oxy)-4-(1H-pyrazol-1-yl)-1H-indazole

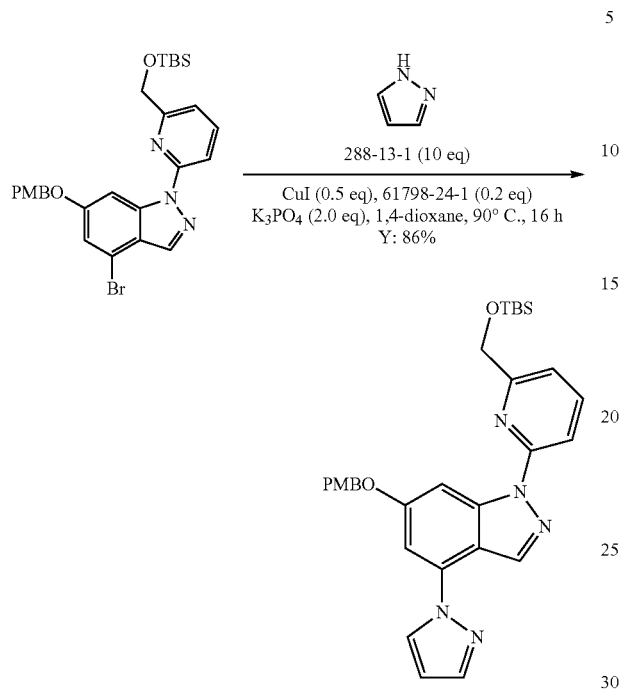

A mixture of 4-bromo-1-(6-(((tert-butyldimethylsilyl)oxy)methyl)pyridin-2-yl)-6-((4-methoxybenzyl)oxy)-1H-indazole (600 mg, 1.1 mmol, 1.0 eq), 288-13-1 (738 mg, 11 mmol, 10 eq), CuI (105 mg, 0.55 mmol, 0.5 eq), N,N'-Dimethyl-1,2-cyclohexanediamine (CAS No. 61798-24-1, 31 mg, 0.2 mmol, 0.2 eq) and K₃PO₄ (460 mg, 2.2 mmol, 2.0 eq) in 1,4-dioxane (5 mL) was stirred at 90° C. for 16 h under nitrogen atmosphere. After cooling down to rt, the mixture was filtered and the filtrate was concentrated in vacuo. The residue was purified by silica gel column chromatography (PE/EA=2/1) to give 1-(6-(((tert-butyldimethylsilyl)oxy)methyl)pyridin-2-yl)-6-((4-methoxybenzyl)oxy)-4-(1H-pyrazol-1-yl)-1H-indazole (520 mg, Y: 86%) as a light yellow solid. ESI-MS (M+H)⁺: 542.3.

Step 7. Synthesis of 1-(6-(((tert-butyldimethylsilyl)oxy)methyl)pyridin-2-yl)-4-(1H-pyrazol-1-yl)-1H-indazol-6-ol

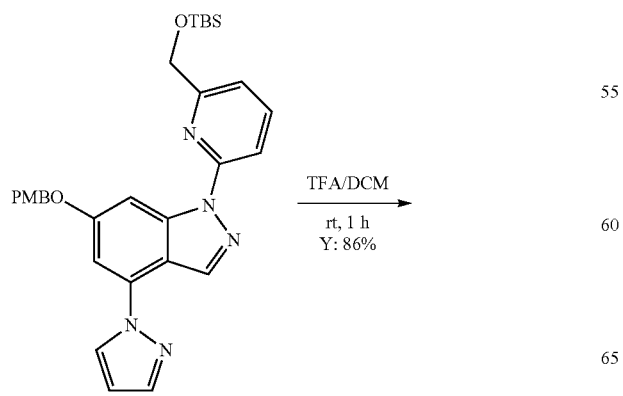

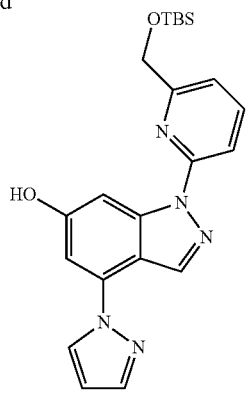

To a solution of 1-(6-(((tert-butyldimethylsilyl)oxy)methyl)pyridin-2-yl)-6-((4-methoxybenzyl)oxy)-4-(1H-pyrazol-1-yl)-1H-indazole (520 mg, 0.96 mmol, 1.0 eq) in DCM (3 mL) was added slowly TFA (3 mL). Then the mixture was stirred at rt for 1 h. The mixture was diluted with DCM (10 mL) and adjusted pH=7 with NaOH(aq). The mixture was extracted with DCM (30 mL×2). The combined organic fractions were washed with brine (50 mL×2), dried, filtrated and concentrated to give 1-(6-(((tert-butyldimethylsilyl)oxy)methyl)pyridin-2-yl)-4-(1H-pyrazol-1-yl)-1H-indazol-6-ol (350 mg, Y: 86%) as a light yellow solid. ESI-MS (M+H)⁺: 422.1.

Step 8. Synthesis of 1-(6-(((tert-butyldimethylsilyl)oxy)methyl)pyridin-2-yl)-4-(1H-pyrazol-1-yl)-1H-indazol-6-yl trifluoromethanesulfonate

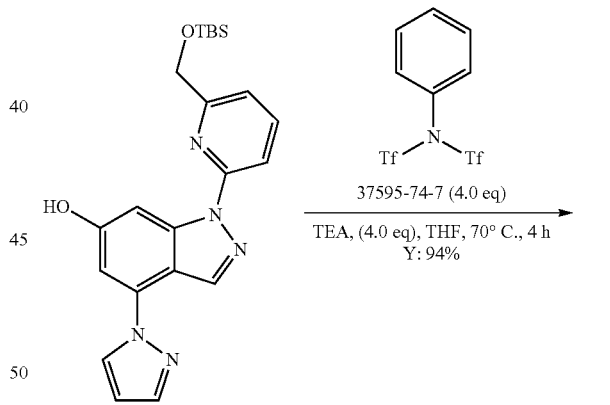

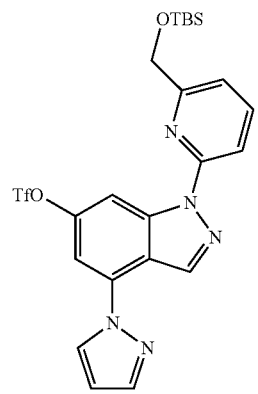

A mixture of 1-(6-(((tert-butyldimethylsilyl)oxy)methyl)pyridin-2-yl)-4-(1H-pyrazol-1-yl)-1H-indazol-6-ol (350 mg, 0.83 mmol, 1.0 eq), N-phenyl-bis(trifluoromethanesulfonimide) (CAS No. 37595-74-7, 1.2 g, 3.3 mmol, 4.0 eq) and TEA (340 mg, 3.3 mmol, 4.0 eq) in THF (50 mL) was stirred at 70° C. for 4 h. After cooling to rt, the reaction solution was concentrated in vacuo. The residue was purified by silica gel column chromatography (PE/EA=2/1) to give 1-(6-(((tert-butyldimethylsilyl)oxy)methyl)pyridin-2-yl)-4-(1H-pyrazol-1-yl)-1H-indazol-6-yl trifluoromethanesulfonate (430 mg, Y: 94%) as a light yellow solid. ESI-MS (M+H)⁺: 554.1.

Step 9. Synthesis of 1-(6-(((tert-butyldimethylsilyl)oxy)methyl)pyridin-2-yl)-4-(1H-pyrazol-1-yl)-6-(4,4,5,5-tetramethyl-1,3,2-dioxaborolan-2-yl)-1H-indazole

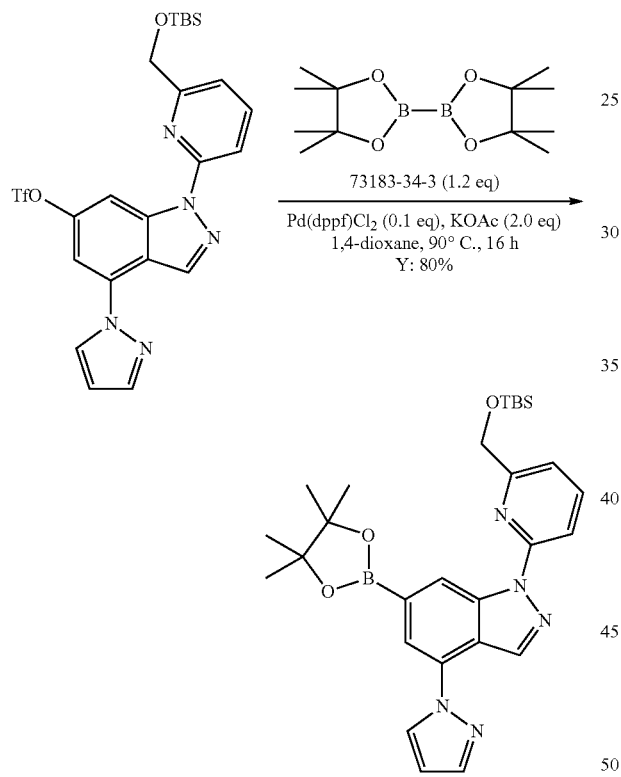

Step 10. Synthesis of (R)—N—((S)-1-(6-(1-(6-(((tert-butyldimethylsilyl)oxy)methyl)pyridin-2-yl)-4-(1H-pyrazol-1-yl)-1H-indazol-6-yl)pyridin-2-yl)ethyl)-2-methylpropane-2-sulfinamide

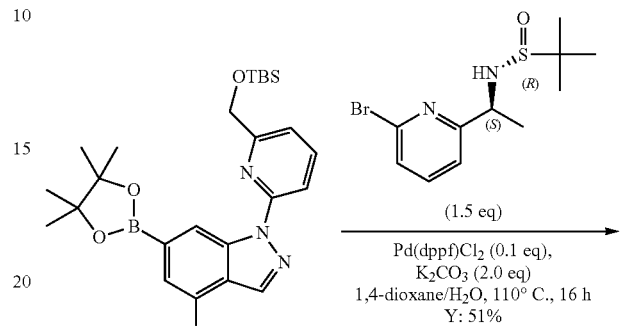

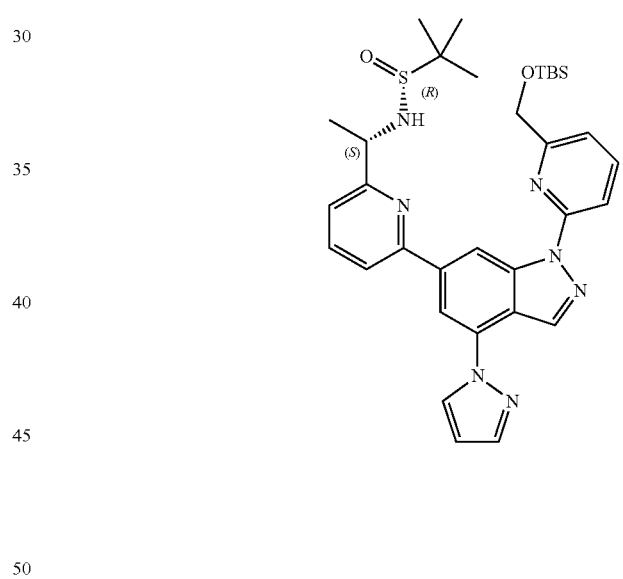

A mixture of 1-(6-(((tert-butyldimethylsilyl)oxy)methyl)pyridin-2-yl)-4-(1H-pyrazol-1-yl)-1H-indazol-6-yl trifluoromethanesulfonate (430 mg, 0.78 mmol, 1.0 eq), Bis(pinacolato)diboron (CAS No. 73183-34-3, 210 mg, 0.82 mmol, 1.05 eq) and CH₃COOK (160 mg, 1.6 mmol, 2.0 eq) in 1,4-dioxane (5 mL) was stirred while purging N₂ at rt for 10 min. To this system was added Pd(dppf)Cl₂ (70 mg, 0.08 mmol, 0.1 eq) and heated to 90° C. for 16 h. The mixture was diluted with EtOAc (50 mL) and washed with brine (50 mL×2). The organic was dried (Na₂SO₄) and concentrated to give 1-(6-(((tert-butyldimethylsilyl)oxy)methyl)pyridin-2-yl)-4-(1H-pyrazol-1-yl)-6-(4,4,5,5-tetramethyl-1,3,2-dioxaborolan-2-yl)-1H-indazole which was used for next step without further purification. 330 mg, as a brown solid, Y: 80%. ESI-MS (M+H)⁺: 532.3.

A mixture of 1-(6-(((tert-butyldimethylsilyl)oxy)methyl)pyridin-2-yl)-4-(1H-pyrazol-1-yl)-6-(4,4,5,5-tetramethyl-1,3,2-dioxaborolan-2-yl)-1H-indazole (330 mg, 0.62 mmol, 1.0 eq), (R)—N—((S)-1-(6-bromopyridin-2-yl)ethyl)-2-methylpropane-2-sulfinamide (Example 142, Step 1, 283 mg, 0.93 mmol, 1.5 eq) and K₂CO₃ (171 mg, 1.24 mmol, 2.0 eq) in 1,4-dioxane/H₂O (5 mL/0.5 mL) was stirred while purging N₂ at rt for 10 min. To this system was added Pd(dppf)Cl₂ (57 mg, 0.06 mmol, 0.1 eq) and heated to 110° C. for 16 h. After concentration, the residue was purified by silica gel column chromatography (PE/EA=2/1) to give (R)—N—((S)-1-(6-(1-(6-(((tert-butyldimethylsilyl)oxy)methyl)pyridin-2-yl)-4-(1H-pyrazol-1-yl)-1H-indazol-6-yl)pyridin-2-yl)ethyl)-2-methylpropane-2-sulfinamide (200 mg, Y: 51%) as a yellow solid. ESI-MS (M+H)⁺: 630.3.

377

Step 11. Synthesis of (S)-(6-(6-(6-(1-aminoethyl)pyridin-2-yl)-4-(1H-pyrazol-1-yl)-1H-indazol-1-yl)pyridin-2-yl)methanol

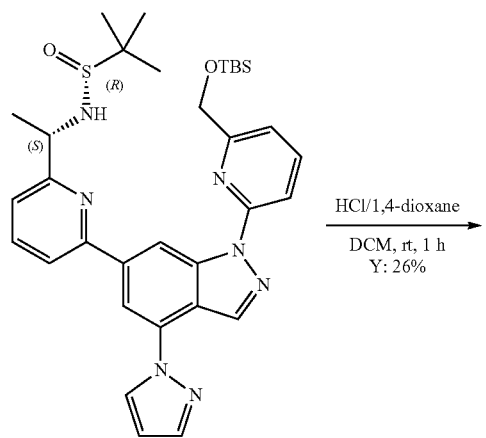

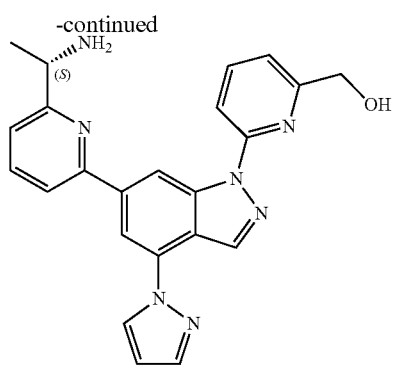

To a solution of —((S)-1-(6-(1-(6-(((tert-butyldimethylsilyl)oxy)methyl)pyridin-2-yl)-4-(1H-pyrazol-1-yl)-1H-indazol-6-yl)pyridin-2-yl)ethyl)-2-methylpropane-2-sulfinamide (200 mg, 0.32 mmol, 1.0 eq) in DCM (3 mL) was added slowly 4 M HCl in 1,4-dioxane (1 mL, excess). Then the mixture was stirred at rt for 1 h. After concentration, the residue was purified by prep-HPLC (CH$_3$CN/H$_2$O with 0.05% TFA as mobile phase from 5% to 95%) to give (S)-(6-(6-(6-(1-aminoethyl)pyridin-2-yl)-4-(1H-pyrazol-1-yl)-1H-indazol-1-yl)pyridin-2-yl)methanol. 34 mg, as a yellow solid, Y: 26%. ESI-MS (M+H)$^+$: 412.1. HPLC: 100%. $^1$H NMR (400 MHz, CD$_3$OD) δ: 9.73-9.70 (m, 1H), 8.73 (d, J=5.2 Hz, 1H), 8.54 (d, J=2.0 Hz, 1H), 8.41 (s, 1H), 8.14-7.89 (m, 5H), 7.47 (d, J=8.0 Hz, 1H), 7.37-7.33 (m, 1H), 6.65 (d, J=1.6 Hz, 1H), 4.86 (s, 2H), 4.72-4.67 (m, 1H), 1.69 (d, J=6.8 Hz, 3H).

The preparation of the following was similar to that of Example 352 using the appropriate heterocycle in place of pyrazole

| Example # | Structure | Name | LCMS (M+) | $^1$H NMR |
|---|---|---|---|---|
| 353 | 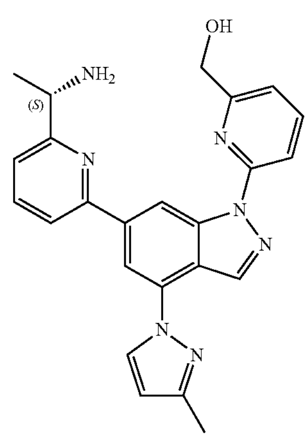 | (S)-(6-(6-(6-(1-aminoethyl)pyridin-2-yl)-4-(3-methyl-1H-pyrazol-1-yl)-1H-indazol-1-yl)pyridin-2-yl)methanol | 426.2 | $^1$H NMR (400 MHz, CD$_3$OD) δ: 9.63 (s, 1H), 8.69 (s, 1H), 8.39 (d, J = 2.0 Hz, 1H), 8.33 (s, 1H), 8.10 (d, J = 8.0 Hz, 1H), 8.01-7.92 (m, 3H), 7.47 (d, J = 7.6 Hz, 1H), 7.34 (t, J = 8.0 Hz, 1H), 6.44 (d, J = 2.4 Hz, 1H), 4.85 (s, 2H), 4.72-4.67 (m, 1H), 2.42 (s, 3H), 1.69 (d, J = 6.8 Hz, 3H). |

-continued

| Example # | Structure | Name | LCMS (M+) | ¹H NMR |
|---|---|---|---|---|
| 354 | 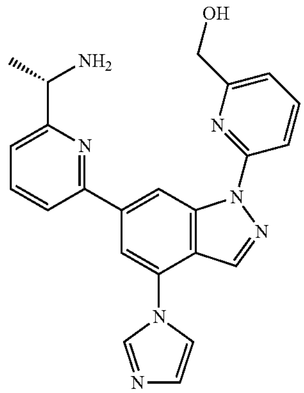 [SMILES: C[C@H](N)c1cccc(-c2cc(-n3ccnc3)c3cnn(-c4cccc(CO)n4)c3c2)n1] | (S)-(6-(6-(6-(1-aminoethyl)pyridin-2-yl)-4-(1H-imidazol-1-yl)-1H-indazol-1-yl)pyridin-2-yl)methanol | 412.2 | ¹H NMR (400 MHz, CD₃OD) δ: 9.73 (s, 1H), 8.36 (s, 1H), 8.32 (s, 1H), 8.18 (s, 1H), 7.99-7.88 (m, 4H), 7.79 (s, 1H), 7.41-7.38 (m, 2H), 7.27 (s, 1H), 4.85 (s, 2H), 4.34-4.29 (m, 1H), 1.54 (d, J = 6.4 Hz, 3H). |
| 355 | 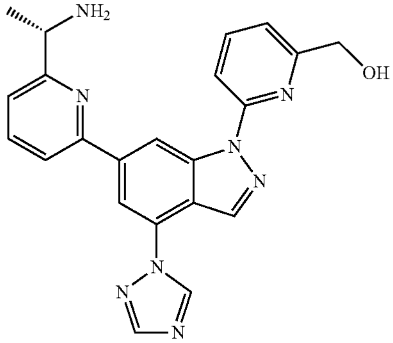 [SMILES: C[C@H](N)c1cccc(-c2cc(-n3cncn3)c3cnn(-c4cccc(CO)n4)c3c2)n1] | (S)-(6-(6-(6-(1-aminoethyl)pyridin-2-yl)-4-(1H-1,2,4-triazol-1-yl)-1H-indazol-1-yl)pyridin-2-yl)methanol | 413.2 | ¹H NMR (400 MHz, CD₃OD) δ: 9.89 (s, m1H), 9.42 (s, 1H), 8.78 (s, 1H), 8.62 (s, 1H), 8.40 (s, 1H), 8.21 (d, J = 6.8 Hz, 1H), 8.10-8.01′ (m, 3H), 7.55 (d, J = 7.6 Hz, 1H), 7.43-7.41 (m, 1H), 4.91 (s, 2H), 4.79-4.74 (m, 1H), 1.76 (d, J = 6.8 Hz, 3H). |
| 356 | 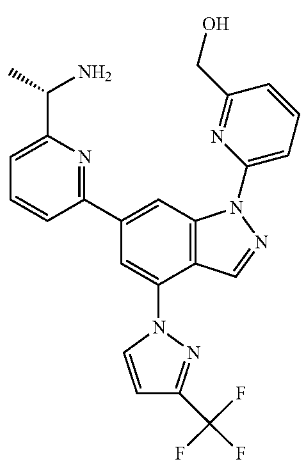 [SMILES: C[C@H](N)c1cccc(-c2cc(-n3ccc(C(F)(F)F)n3)c3cnn(-c4cccc(CO)n4)c3c2)n1] | (S)-(6-(6-(6-(1-aminoethyl)pyridin-2-yl)-4-(3-(trifluoromethyl)-1H-pyrazol-1-yl)-1H-indazol-1-yl)pyridin-2-yl)methanol | 480.1 | ¹H NMR (400 MHz, DMSO-d₆) δ: 9.72 (s, 1H), 9.14 (s, 1H), 8.80 (s, 1H), 8.63 (s, 1H), 8.54-8.52 (m, 2H), 8.26 (d, J = 8.0 Hz, 1H), 8.13-8.06 (m, 2H), 7.94 (d, J = 8.4 Hz, 1H), 7.61 (d, J = 8.0 Hz, 1H), 7.48 (d, J = 7.2 Hz, 1H), 7.27 (d, J = 2.4 Hz, 1H), 5.70 (br, 1H), 4.82 (d, J = 4.4 Hz, 2H), 4.70 (q, J = 6.8 Hz, 1H), 1.63 (d, J = 6.8 Hz, 3H). |

Example 357. (S)-(6-(6-(6-(1-aminoethyl)pyridin-2-yl)-4-(1-methyl-1H-pyrazol-3-yl)-1H-indazol-1-yl)pyridin-2-yl)methanol Step 1. Synthesis of 1-(6-(((tert-butyldimethylsilyl)oxy)methyl)pyridin-2-yl)-6-(6-((S)-1-((R)-1,1-dimethylethylsulfinamido)ethyl)pyridin-2-yl)-1H-indazol-4-yl trifluoromethanesulfonate

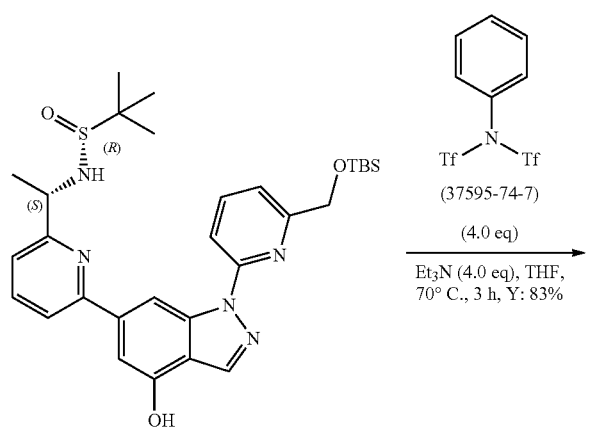

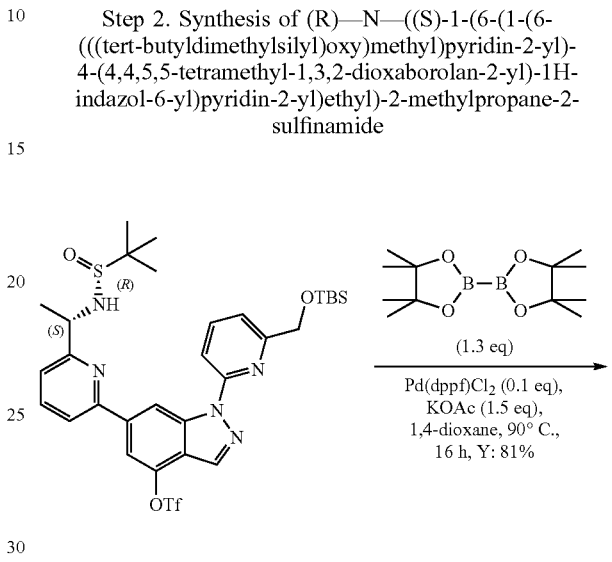

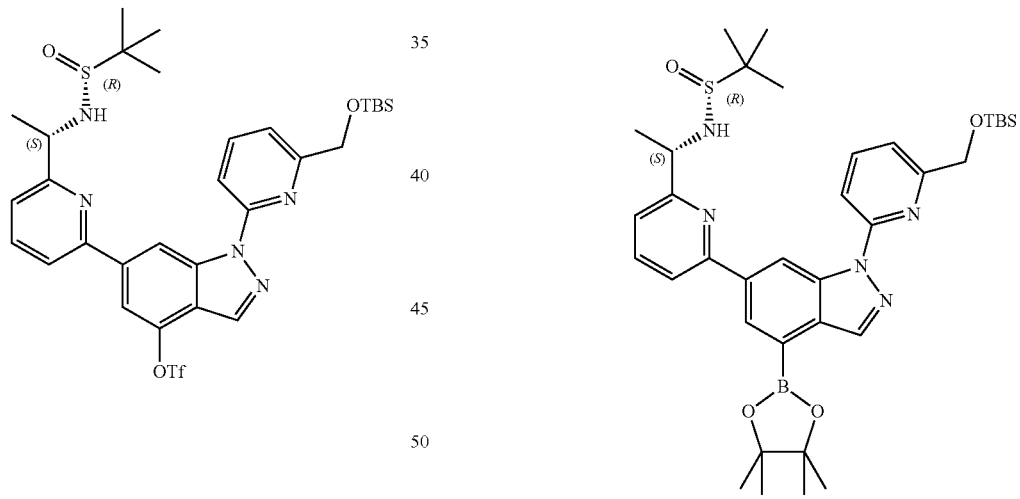

To a mixture of (S)-6-(6-(1-aminoethyl)pyridin-2-yl)-1-(6-(hydroxymethyl)pyridin-2-yl)-1H-indazol-4-ol (derived similar to that of Example 324 step 13 ((R)—N—((S)-1-(6-(1-(6-(((tert-butyldimethylsilyl)oxy)methyl)pyridin-2-yl)-4-hydroxy-1H-indazol-6-yl)pyridin-2-yl)butyl)-2-methylpropane-2-sulfinamide) utilizing (R)—N—((S)-1-(6-bromopyridin-2-yl)ethyl)-2-methylpropane-2-sulfinamide in step 10) (600 mg, 1.0 mmol, 1.0 eq) and Et$_3$N (419 mg, 4.0 mmol, 4.0 eq) in THF (30 mL) was added N-phenyl-bis(trifluoromethanesulfonimide) (CAS No. 37595-74-7, 1.5 g, 4.0 mmol, 4.0 eq) at rt. The mixture was stirred at 70° C. for 3 h. After concentration, the residue was purified by column chromatography (silica gel, PE/EA=3/1) to afford 1-(6-(((tert-butyldimethylsilyl)oxy)methyl)pyridin-2-yl)-6-(6-((S)-1-((R)-1,1-dimethylethylsulfinamido)ethyl)pyridin-2-yl)-1H-indazol-4-yl trifluoromethanesulfonate as brown oil (520 mg, Y: 83%). ESI-MS (M+H)$^+$: 712.2. $^1$H NMR (400 MHz, CDCl$_3$) δ: 9.47 (s, 1H), 8.28 (s, 1H), 8.01 (s, 1H), 7.96-7.89 (m, 2H), 7.82 (t, J=8.0 Hz, 1H), 7.75 (d, J=7.6 Hz, 1H), 7.46 (d, J=6.8 Hz, 1H), 7.34 (d, J=7.6 Hz, 1H), 4.96 (s, 2H), 4.77-4.73 (m, 1H), 4.07 (d, J=6.8 Hz, 1H), 1.73 (d, J=6.8 Hz, 3H), 1.20 (s, 9H), 0.99 (s, 9H), 0.17 (s, 6H).

Step 2. Synthesis of (R)—N—((S)-1-(6-(1-(6-(((tert-butyldimethylsilyl)oxy)methyl)pyridin-2-yl)-4-(4,4,5,5-tetramethyl-1,3,2-dioxaborolan-2-yl)-1H-indazol-6-yl)pyridin-2-yl)ethyl)-2-methylpropane-2-sulfinamide The preparation of (R)—N—((S)-1-(6-(1-(6-(((tert-butyldimethylsilyl)oxy)methyl)pyridin-2-yl)-4-(4,4,5,5-tetramethyl-1,3,2-dioxaborolan-2-yl)-1H-indazol-6-yl)pyridin-2-yl)ethyl)-2-methylpropane-2-sulfinamide was similar to that of 1-(6-(((tert-butyldimethylsilyl)oxy)methyl)pyridin-2-yl)-4-(1H-pyrazol-1-yl)-6-(4,4,5,5-tetramethyl-1,3,2-dioxaborolan-2-yl)-1H-indazole (Example 352, Step 9) to give 326 mg as a yellow solid, Y: 81%. ESI-MS (M+H)$^+$: 690.3

Step 3. Synthesis of (R)—N—((S)-1-(6-(1-(6-(((tert-butyldimethylsilyl)oxy)methyl)pyridin-2-yl)-4-(1-methyl-1H-pyrazol-3-yl)-1H-indazol-6-yl)pyridin-2-yl)ethyl)-2-methylpropane-2-sulfinamide

Step 4. Synthesis of (S)-(6-(6-(6-(1-aminoethyl)pyridin-2-yl)-4-(1-methyl-1H-pyrazol-3-yl)-1H-indazol-1-yl)pyridin-2-yl)methanol

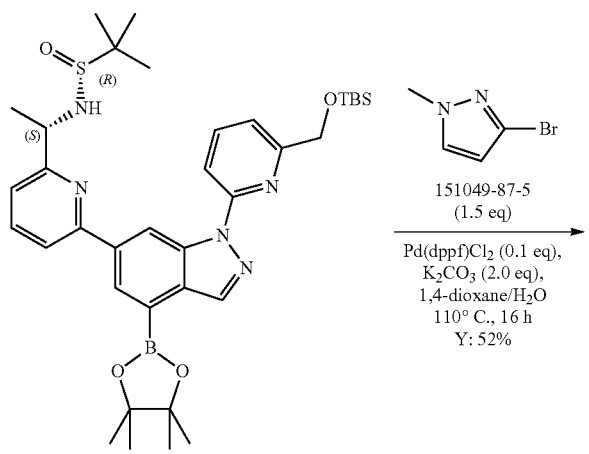

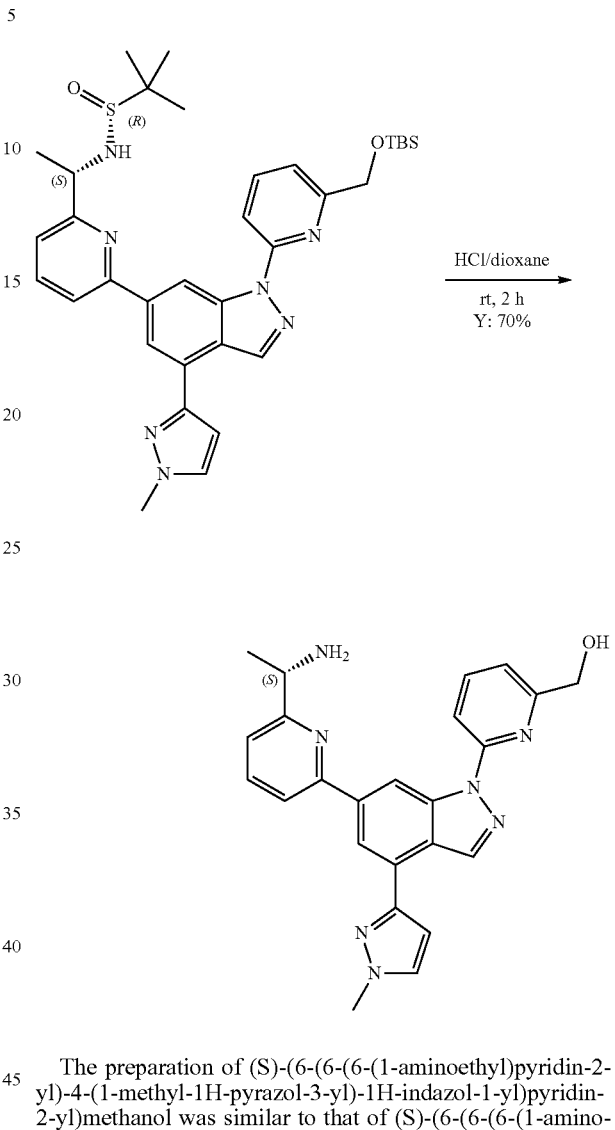

The preparation of (R)—N—((S)-1-(6-(1-(6-(((tert-butyldimethylsilyl)oxy)methyl)pyridin-2-yl)-4-(1-methyl-1H-pyrazol-3-yl)-1H-indazol-6-yl)pyridin-2-yl)ethyl)-2-methylpropane-2-sulfinamide was similar to that of (R)—N—((S)-1-(6-(1-(6-(((tert-butyldimethylsilyl)oxy)methyl)pyridin-2-yl)-4-(1H-pyrazol-1-yl)-1H-indazol-6-yl)pyridin-2-yl)ethyl)-2-methylpropane-2-sulfinamide (Example 352, Step 10) to give 150 mg as a yellow solid, Y: 52%. ESI-MS (M+H)⁺: 644.3. ¹H NMR (400 MHz, CDCl₃) δ: 9.21 (s, 1H), 8.71 (s, 1H), 8.13 (s, 1H), 7.79 (d, J=8.0 Hz, 1H), 7.72-7.60 (m, 3H), 7.33 (d, J=2.4 Hz, 1H), 7.23 (d, J=7.6 Hz, 1H), 7.12 (dd, J=7.2, 1.6 Hz, 1H), 6.64 (d, J=2.4 Hz, 1H), 4.80 (s, 2H), 4.59 (q, J=6.8 Hz, 1H), 3.89 (s, 3H), 1.60 (d, J=6.8 Hz, 3H), 1.06 (s, 9H), 0.82 (s, 9H), 0.00 (s, 6H).

The preparation of (S)-(6-(6-(6-(1-aminoethyl)pyridin-2-yl)-4-(1-methyl-1H-pyrazol-3-yl)-1H-indazol-1-yl)pyridin-2-yl)methanol was similar to that of (S)-(6-(6-(6-(1-aminoethyl)pyridin-2-yl)-4-(1H-pyrazol-1-yl)-1H-indazol-1-yl)pyridin-2-yl)methanol (Example 352, Step 11) to give 61 mg as a yellow solid, Y: 70%. ESI-MS (M+H)⁺: 426.0. HPLC: 100%. ¹H NMR (400 MHz, CD₃OD) δ: 9.70 (s, 1H), 8.82 (s, 1H), 8.48 (d, J=1.2 Hz, 1H), 8.13 (d, J=7.6 Hz, 1H), 8.03 (t, J=8.0 Hz, 1H), 7.98-7.95 (m, 2H), 7.76 (d, J=2.4 Hz, 1H), 7.49 (d, J=7.6 Hz, 1H), 7.40-7.32 (m, 1H), 6.99 (d, J=2.0 Hz, 1H), 4.89 (s, 2H), 4.73 (q, J=6.8 Hz, 1H), 4.07 (s, 3H), 1.75 (d, J=6.8 Hz, 3H).

The following examples were prepared similar to Example 357 by Suzuki coupling using the appropriate halogenated heterocycle in place of 3-Bromo-1-methyl-1H-pyrazole and/or (R)—N—((S)-1-(6-bromopyridin-2-yl)ethyl)-2-methylpropane-2-sulfinamide (Example 142, Step 1 and boranate in place of 1-(6-(((tert-butyldimethylsilyl)oxy)methyl)pyridin-2-yl)-4-methoxy-6-(4,4,5,5-tetramethyl-1,3,2-dioxaborolan-2-yl)-1H-indazole and/or (R)—N—((S)-1-(6-(1-(6-(((tert-butyldimethylsilyl)oxy)methyl)pyridin-2-yl)-4-(4,4,5,5-tetramethyl-1,3,2-dioxaborolan-2-yl)-1H-indazol-6-yl)pyridin-2-yl)ethyl)-2-methylpropane-2-sulfinamide

| Example # | Structure | Name | LCMS (M+) | ¹H NMR |
|---|---|---|---|---|
| 358 | 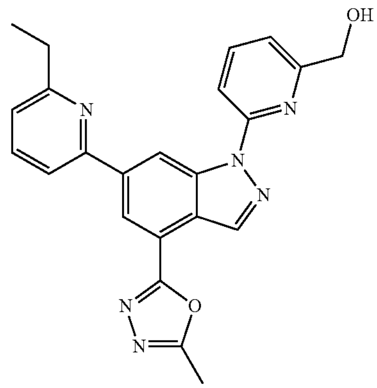 [SMILES: CCc1cccc(-c2cc(-c3nnc(C)o3)c3cnn(-c4cccc(CO)n4)c3c2)n1] | (6-(6-(6-ethylpyridin-2-yl)-4-(5-methyl-1,3,4-oxadiazol-2-yl)-1H-indazol-1-yl)pyridin-2-yl)methanol | 428.3 | ¹H NMR (400 MHz, CD₃OD) δ: 9.81 (s, 1H), 8.78 (s, 1H), 8.66 (s, 1H), 8.00-7.92 (m, 4H), 7.45-7.42 (m, 2H), 4.87 (s, 2H), 4.31 (q, J = 6.8 Hz, 1H), 2.74 (s, 3H), 1.59 (d, J = 6.8 Hz, 3H). |
| 359 | 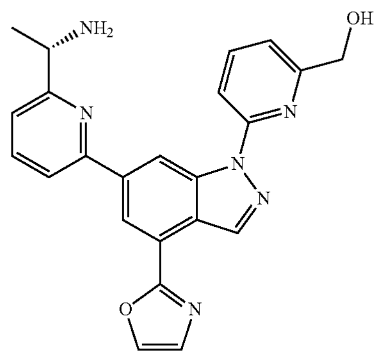 [SMILES: C[C@H](N)c1cccc(-c2cc(-c3ncco3)c3cnn(-c4cccc(CO)n4)c3c2)n1] | (S)-(6-(6-(6-(1-aminoethyl)pyridin-2-yl)-4-(oxazol-2-yl)-1H-indazol-1-yl)pyridin-2-yl)methanol | 413.3 | ¹H NMR (400 MHz, CD₃OD) δ: 9.82 (s, 1H), 8.73 (s, 1H), 8.55 (s, 1H), 8.47 (s, 1H), 8.15 (d, J = 8.0 Hz, 1H), 8.06-7.95 (m, 4H), 7.51 (d, J = 7.6 Hz, 1H), 7.39-7.37 (m, 1H), 4.89 (s, 2H), 4.72 (q, J = 6.8 Hz, 1H), 1.74 (d, J = 6.8 Hz, 3H). |
| 360 | 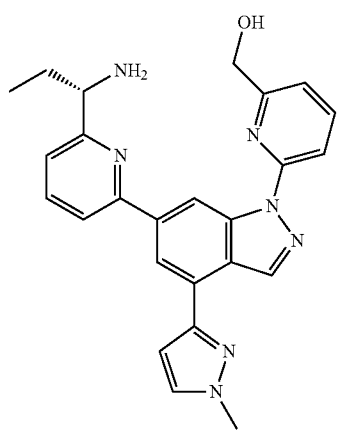 [SMILES: CC[C@H](N)c1cccc(-c2cc(-c3ccn(C)n3)c3cnn(-c4cccc(CO)n4)c3c2)n1] | (S)-(6-(6-(6-(1-aminopropyl)pyridin-2-yl)-4-(1-methyl-1H-pyrazol-3-yl)-1H-indazol-1-yl)pyridin-2-yl)methanol | 440.2 | ¹H NMR (400 MHz, CD₃OD) δ: 9.55 (s, 1H), 8.76 (s, 1H), 8.27 (s, 1H), 7.92-7.84 (m, 4H), 7.69 (d, J = 1.6 Hz, 1H), 7.36-7.31 (m, 2H), 7.88 (d, J = 2.0 Hz, 1H), 4.82 (s, 2H), 4.01-3.97 (m, 4H), 1.97-1.85 (m, 2H), 0.93 (t, J = 7.2 Hz, 3H). |
| 361 | 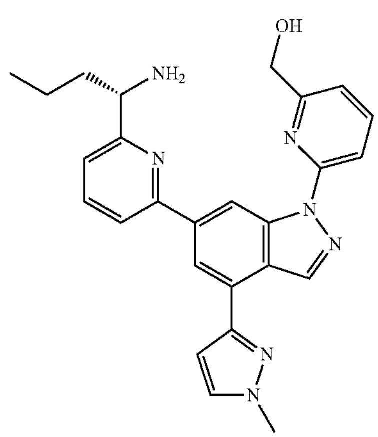 [SMILES: CCC[C@H](N)c1cccc(-c2cc(-c3ccn(C)n3)c3cnn(-c4cccc(CO)n4)c3c2)n1] | (S)-(6-(6-(6-(1-aminobutyl)pyridin-2-yl)-4-(1-methyl-1H-pyrazol-3-yl)-1H-indazol-1-yl)pyridin-2-yl)methanol | 454.2 | ¹H NMR (400 MHz, CD₃OD) δ: 9.71 (s, 1H), 8.81 (s, 1H), 8.44 (d, J = 1.2 Hz, 1H), 8.13 (d, J = 8.0 Hz, 1H), 8.02-7.96 (m, 3H), 7.74 (d, J = 2.0 Hz, 1H), 7.43 (d, J = 7.6 Hz, 1H), 7.37-7.35 (m, 1H), 6.97 (d, J = 2.4 Hz, 1H), 4.91 (s, 2H), 4.56-4.53 (m, 1H), 4.06 (s, 3H), 2.05-2.01 (m, 2H), 1.45-1.43 (m, 2H), 1.01 (t, J = 7.2 Hz, 3H). |

-continued

| Example # | Structure | Name | LCMS (M+) | ¹H NMR |
|---|---|---|---|---|
| 362 | 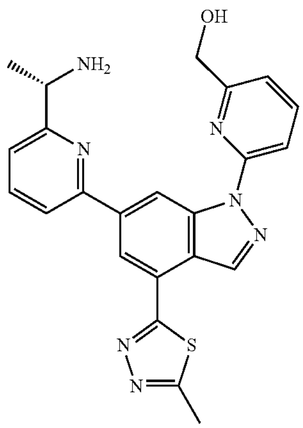 [SMILES: Cc1nnc(-c2cc(-c3cccc([C@H](C)N)n3)cc3c2cnn3-c2cccc(CO)n2)s1] | (S)-(6-(6-(6-(1-aminoethyl)pyridin-2-yl)-4-(5-methyl-1,3,4-thiadiazol-2-yl)-1H-indazol-1-yl)pyridin-2-yl)methanol | 444.1 | ¹H NMR (400 MHz, CD₃OD) δ: 9.83 (s, 1H), 8.78 (s, 1H), 8.54 (s, 1H), 8.09-8.02 (m, 2H), 7.99-7.85 (m, 2H), 7.53 (d, J = 7.2 Hz, 1H), 7.38 (d, J = 7.2 Hz, 1H), 4.89 (s, 2H), 4.77 (q, J = 6.8 Hz, 1H), 2.90 (s, 3H), 1.78 (d, J = 6.8 Hz, 3H). |
| 363 | 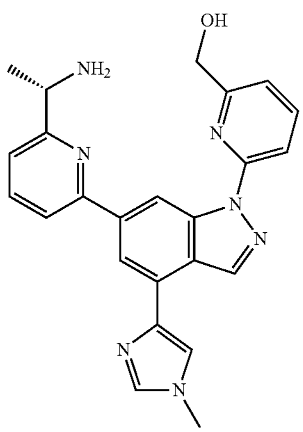 [SMILES: C[C@H](N)c1cccc(-c2cc(-c3cn(C)cn3)c3cnn(-c4cccc(CO)n4)c3c2)n1] | (S)-(6-(6-(6-(1-aminoethyl)pyridin-2-yl)-4-(1-methyl-1H-imidazol-4-yl)-1H-indazol-1-yl)pyridin-2-yl)methanol | 426.1 | ¹H NMR (400 MHz, CD₃OD) δ: 9.80 (s, 1H), 8.99 (xs, 1H), 8.56 (s, 1H), 8.50 (s, 1H), 8.19 (s, 1H), 8.13-7.84 (m, 4H), 7.51 (d, J = 7.2 Hz, 1H), 7.37 (d, J = 6.8 Hz, 1H), 4.89 (s, 2H), 4.75 (q, J = 6.8 Hz, 1H), 4.06 (s, 3H), 1.76 (d, J = 6.8 Hz, 3H). |
| 364 | 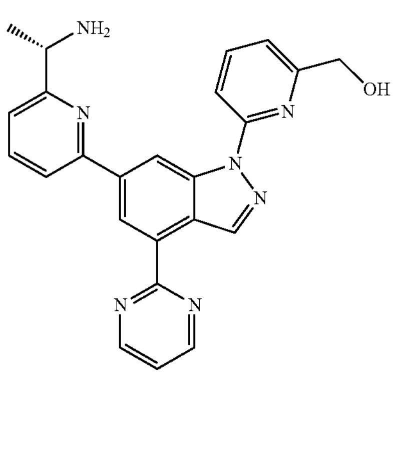 [SMILES: C[C@H](N)c1cccc(-c2cc(-c3ncccn3)c3cnn(-c4cccc(CO)n4)c3c2)n1] | (S)-(6-(6-(6-(1-aminoethyl)pyridin-2-yl)-4-(pyrimidin-2-yl)-1H-indazol-1-yl)pyridin-2-yl)methanol | 424.2 | ¹H NMR (400 MHz, CD₃OD) δ: 9.86 (s, 1H), 9.16-9.13 (m, 2H), 9.01 (d, J = 4.8 Hz, 2H), 8.05-7.95 (m, 4H), 7.48-7.39 (m, 3H), 4.89 (s, 2H), 4.49-4.48 (m, 1H), 1.67 (d, J = 6.8 Hz, 3H). |

-continued

| Example # | Structure | Name | LCMS (M+) | ¹H NMR |
|---|---|---|---|---|
| 365 | 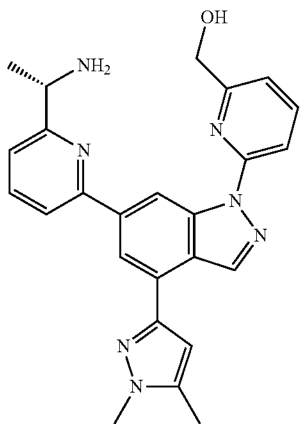 [SMILES: Cc1cc(-c2cc(-c3cccc([C@H](C)N)n3)cc3c2cnn3-c2cccc(CO)n2)nn1C] | (S)-(6-(6-(6-(1-aminoethyl)pyridin-2-yl)-4-(1,5-dimethyl-1H-pyrazol-3-yl)-1H-indazol-1-yl)pyridin-2-yl)methanol | 440.2 | ¹H NMR (400 MHz, CD₃OD) δ: 9.59 (s, 1H), 8.78 (s, 1H), 8.30 (s, 1H), 7.98-7.89 (m, 4H), 7.41 (d, J = 5.6 Hz, 2H), 6.72 (s, 1H), 4.88 (s, 2H), 4.28 (q, J = 6.8 Hz, 1H), 3.95 (s, 3H), 2.44 (s, 3H), 1.58 (d, J = 6.8 Hz, 3H). |
| 366 | 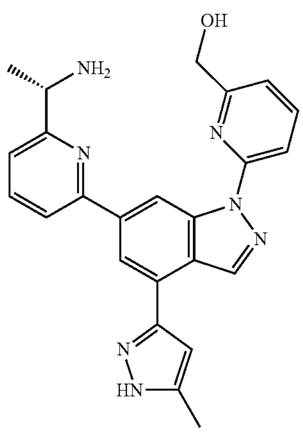 [SMILES: Cc1cc(-c2cc(-c3cccc([C@H](C)N)n3)cc3c2cnn3-c2cccc(CO)n2)n[nH]1] | (S)-(6-(6-(6-(1-aminoethyl)pyridin-2-yl)-4-(5-methyl-1H-pyrazol-3-yl)-1H-indazol-1-yl)pyridin-2-yl)methanol | 426.2 | ¹H NMR (400 MHz, CD₃OD) δ: 9.73 (s, 1H), 8.74 (s, 1H), 8.52 (s, 1H), 8.15 (d, J = 8.0 Hz, 1H), 8.11-7.87 (m, 3H), 7.50 (d, J = 7.6 Hz, 1H), 7.44-7.26 (m, 1H), 6.80 (s, 1H), 4.91 (s, 2H), 4.73 (q, J = 6.8 Hz, 1H), 2.47 (s, 3H), 1.75 (d, J = 6.8 Hz, 3H). |
| 367 | 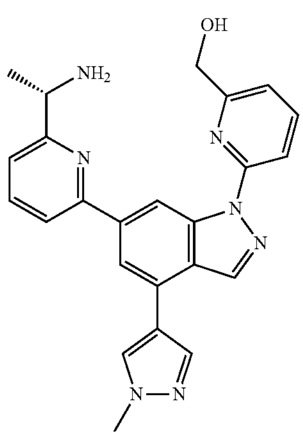 [SMILES: C[C@H](N)c1cccc(-c2cc(-c3cnn(C)c3)c3cnn(-c4cccc(CO)n4)c3c2)n1] | (S)-(6-(6-(6-(1-aminoethyl)pyridin-2-yl)-4-(1-methyl-1H-pyrazol-4-yl)-1H-indazol-1-yl)pyridin-2-yl)methanol | 426.2 | ¹H NMR (400 MHz, CD₃OD) δ: 9.56 (s, 1H), 8.56 (s, 1H), 8.31 (s, 1H), 8.16 (s, 1H), 8.12 (s, 1H), 8.05-7.86 (m, 4H), 7.44-7.41 (m, 2H), 4.89 (s, 2H), 4.34 (q, J = 6.8 Hz, 1H), 4.06 (s, 3H), 1.61 (d, J = 6.8 Hz, 3H). |

-continued

| Example # | Structure | Name | LCMS (M+) | ¹H NMR |
|---|---|---|---|---|
| 368 | 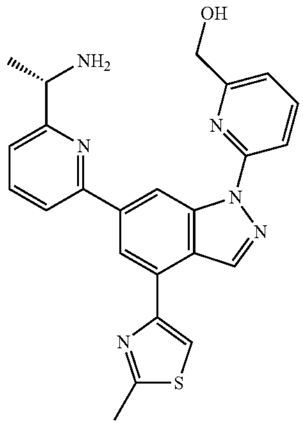 [SMILES: Cc1nc(-c2cc(-c3cccc([C@H](C)N)n3)cc3c2cnn3-c2cccc(CO)n2)cs1] | (S)-(6-(6-(6-(1-aminoethyl)pyridin-2-yl)-4-(2-methylthiazol-4-yl)-1H-indazol-1-yl)pyridin-2-yl)methanol | 443.2 | ¹H NMR (400 MHz, CD₃OD) δ: 9.70 (s, 1H), 8.82 (s, 1H), 8.51 (s, 1H), 8.03-7.93 (m, 5H), 7.45-7.41 (m, 2H), 4.90 (s, 2H), 4.34 (q, J = 6.8 Hz, 1H), 2.89 (s, 3H), 1.61 (d, J = 6.8 Hz, 3H). |
| 369 | 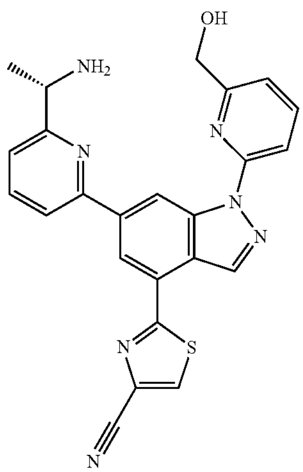 [SMILES: C[C@H](N)c1cccc(-c2cc(-c3nc(C#N)cs3)c3cnn(-c4cccc(CO)n4)c3c2)n1] | (S)-2-(6-(6-(1-aminoethyl)pyridin-2-yl)-1-(6-(hydroxymethyl)pyridin-2-yl)-1H-indazol-4-yl)thiazol-4-carbonitrile | 454.2 | ¹H NMR (400 MHz, CD₃OD) δ: 10.00 (s, 1H), 8.99 (s, 1H), 8.76 (s, 1H), 8.69 (s, 1H), 8.21 (d, J = 8.4 Hz, 1H), 8.11-8.02 (m, 3H), 7.56 (d, J = 8.0 Hz, 1H), 7.43 (d, J = 6.0 Hz, 1H), 4.93 (s, 2H), 4.77 (q, J = 6.8 Hz, 1H), 1.77 (d, J = 6.8 Hz, 3H). |
| 370 | 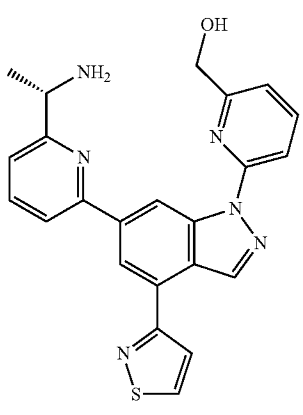 [SMILES: C[C@H](N)c1cccc(-c2cc(-c3ccsn3)c3cnn(-c4cccc(CO)n4)c3c2)n1] | (S)-(6-(6-(6-(1-aminoethyl)pyridi9n-2-yl)-4-(isothiazol-3-yl)-1H-indazol-1-yl)pyridin-2-yl)methanol | 429.1 | ¹H NMR (400 MHz, CD₃OD) δ: 9.82 (s, 1H), 9.08-9.07 (m, 1H), 8.98 (s, 1H), 8.65 (s, 1H), 8.16-8.14 (m, 2H), 8.03-7.93 (m, 3H), 7.47 (d, J = 7.6 Hz, 1H), 7.35 (d, J = 6.0 Hz, 1H), 4.80 (s, 2H), 4.75-4.67 (m, 1H), 1.71 (d, J = 6.8 Hz, 3H). |

-continued

| Example # | Structure | Name | LCMS (M+) | ¹H NMR |
|---|---|---|---|---|
| 371 | 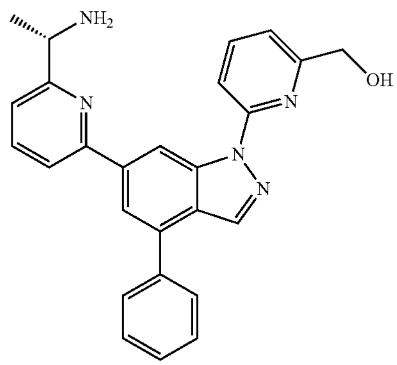 [SMILES: C[C@H](N)c1cccc(-c2cc(-c3ccccc3)c3cnn(-c4cccc(CO)n4)c3c2)n1] | (S)-(6-(6-(6-(1-aminoethyl)pyridin-2-yl)-4-phenyl-1H-indazol-1-yl)pyridin-2-yl)methanol | 422.1 | ¹H NMR (400 MHz, CD₃OD) δ: 9.78 (s, 1H), 8.39 (s, 1H), 8.24 (s, 1H), 8.15 (d, J = 8.0 Hz, 1H), 8.06-7.97 (m, 3H), 7.85 (s, 1H), 7.83 (s, 1H), 7.61 (t, J = 7.6 Hz, 2H), 7.51 (t, J = 8.0 Hz, 2H), 7.41-7.39 (m, 1H), 4.92 (s, 2H), 4.75-4.70 (m, 1H), 1.75 (d, J = 6.8 Hz, 3H). |
| 372 | 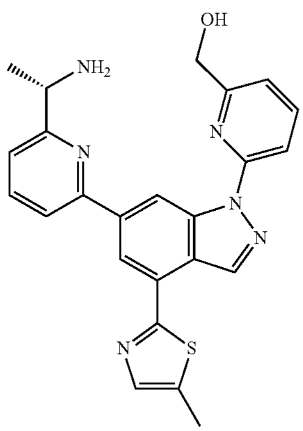 [SMILES: Cc1cnc(-c2cc(-c3cccc([C@H](C)N)n3)cc3c2cnn3-c2cccc(CO)n2)s1] | (S)-(6-(6-(6-(1-aminoethyl)pyridin-2-yl)-4-(5-methylthiazol-2-yl)-1H-indazol-1-yl)pyridin-2-yl)methanol | 443.2 | ¹H NMR (400 MHz, CD₃OD) δ: 9.83 (s, 1H), 8.89 (s, 1H), 8.65 (s, 1H), 8.13 (d, J = 8.0 Hz, 1H), 8.05 (t, J = 8.0 Hz, 1H), 7.99 (d, J = 8.4 Hz, 2H), 7.76 (s, 1H), 7.53 (d, J = 7.6 Hz, 1H), 7.40 (t, J = 4.0 Hz, 1H), 4.91 (s, 2H), 4.75 (q, J = 6.8 Hz, 1H), 2.65 (s, 3H), 1.76 (d, J = 6.8 Hz, 3H). |
| 373 | 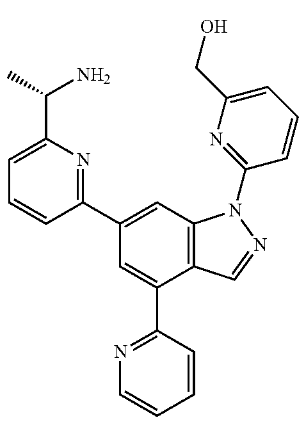 [SMILES: C[C@H](N)c1cccc(-c2cc(-c3ccccn3)c3cnn(-c4cccc(CO)n4)c3c2)n1] | (S)-(6-(6-(6-(1-aminoethyl)pyridin-2-yl)-4-(pyridin-2-yl)-1H-indazol-1-yl)pyridin-2-yl)methanol | 423.2 | ¹H NMR (400 MHz, CD₃OD) δ: 9.92 (s, 1H), 8.88 (d, J = 4.8 Hz, 1H), 8.71 (s, 1H), 8.62 (s, 1H), 8.27-8.17 (m, 3H), 8.05 (t, J = 8.0 Hz, 1H), 8.01-7.97 (m, 2H), 7.69-7.65 (m, 1H), 7.52 (d, J = 7.6 Hz, 1H), 7.41-7.39 (m, 1H), 4.92 (s, 2H), 4.75 (q, J = 6.8 Hz, 1H), 1.62 (d, J = 6.8 Hz, 3H). |

-continued

| Example # | Structure | Name | LCMS (M+) | ¹H NMR |
|---|---|---|---|---|
| 374 | 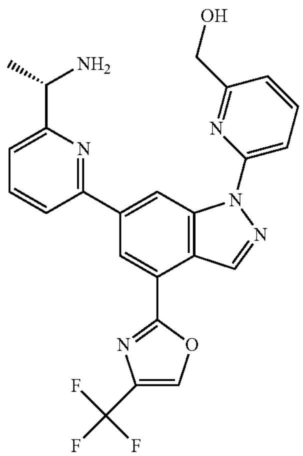 [SMILES: C[C@H](N)c1cccc(-c2cc(-c3nc(C(F)(F)F)co3)c3cnn(-c4cccc(CO)n4)c3c2)n1] | (S)-(6-(6-(6-(1-aminoethyl)pyridin-2-yl)-4-(4-(trifluoromethyl)oxazol-2-yl)-1H-indazol-1-yl)pyridin-2-yl)methanol | 481.1 | ¹H NMR (400 MHz, CD₃OD) δ: 9.92 (s, 1H), 8.87 (s, 1H), 8.83 (s, 1H), 8.72 (s, 1H), 8.10 (d, J = 8.0 Hz, 1H), 8.03 (t, J = 8.0 Hz, 1H), 7.96-7.95 (m, 2H), 7.51 (d, J = 7.6 Hz, 1H), 7.37 (t, J = 4.4 Hz, 1H), 4.87 (s, 2H), 4.74-4.72 (m, 1H), 1.74 (d, J = 6.8 Hz, 3H). |
| 375 | 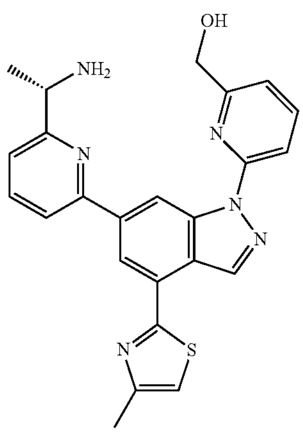 [SMILES: Cc1csc(-c2cc(-c3cccc([C@H](C)N)n3)cc3c2cnn3-c2cccc(CO)n2)n1] | (S)-(6-(6-(6-(1-aminoethyl)pyridin-2-yl)-4-(4-methylthiazol-2-yl)-1H-indazol-1-yl)pyridin-2-yl)methanol | 443.2 | ¹H NMR (400 MHz, DMSO-d₆) δ: 9.72 (s, 1H), 9.00 (s, 1H), 8.50 (s, 1H), 8.06-7.91 (m, 4H), 7.54-7.50 (m, 2H), 7.44 (d, J = 7.6 Hz, 1H), 5.66 (br, 1H), 4.76 (s, 2H), 4.13 (q, J = 6.8 Hz, 1H), 2.55 (s, 3H), 2.14 (br, 2H), 1.41 (d, J = 6.8 Hz, 3H). |
| 376 | 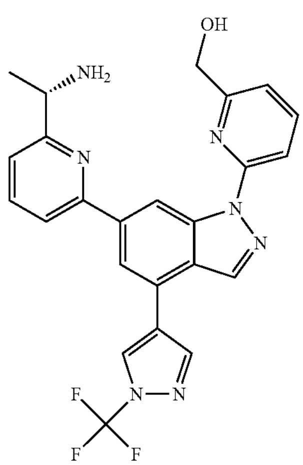 [SMILES: C[C@H](N)c1cccc(-c2cc(-c3cnn(C(F)(F)F)c3)c3cnn(-c4cccc(CO)n4)c3c2)n1] | (S)-(6-(6-(6-(1-aminoethyl)pyridin-2-yl)-4-(1-(trifluoromethyl)-1H-pyrazol-4-yl)-1H-indazol-1-yl)pyridin-2-yl)methanol | 480.2 | ¹H NMR (400 MHz, CD₃OD) δ: 9.80 (s, 1H), 8.92 (s, 1H), 8.64 (s, 1H), 8.56 (s, 1H), 8.42 (s, 1H), 8.19 (d, J = 7.6 Hz, 1H), 8.07-8.00 (m, 3H), 7.51 (d, J = 7.6 Hz, 1H), 7.42-7.40 (m, 1H), 4.91 (s, 2H), 4.77-4.72 (m, 1H), 1.75 (d, J = 7.2 Hz, 3H). |

| Example # | Structure | Name | LCMS (M+) | ¹H NMR |
|---|---|---|---|---|
| 377 | 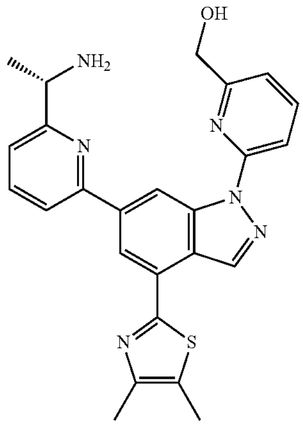 [SMILES: Cc1nc(-c2cc(-c3cccc([C@H](C)N)n3)cc3c2cnn3-c2cccc(CO)n2)sc1C] | (S)-(6-(6-(6-(1-aminoethyl)pyridin-2-yl)-4-(4,5-dimethylthiazol-2-yl)-1H-indazol-1-yl)pyridin-2-yl)methanol | 457.2 | ¹H NMR (400 MHz, CD₃OD) δ: 9.78 (s, 1H), 8.83 (s, 1H), 8.57 (s, 1H), 7.10-7.95 (m, 4H), 7.51 (d, J = 7.6 Hz, 1H), 7.39-7.37 (m, 1H), 4.10 (s, 2H), 4.75 (q, J = 6.8 Hz, 1H), 2.52 (s, 3H), 2.49 (s, 3H), 1.76 (d, J = 6.8 Hz, 3H). |
| 378 | 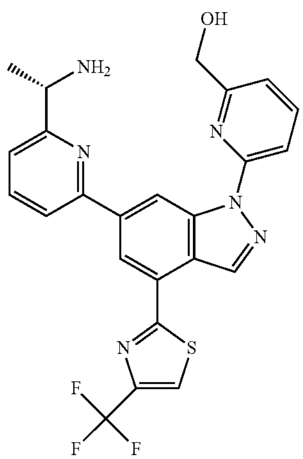 [SMILES: C[C@H](N)c1cccc(-c2cc(-c3nc(C(F)(F)F)cs3)c3cnn(-c4cccc(CO)n4)c3c2)n1] | (S)-(6-(6-(6-(1-aminoethyl)pyridin-2-yl)-4-(4-(trifluoromethyl)thiazol-2-yl)-1H-indazol-1-yl)pyridin-2-yl)methanol | 497.1 | ¹H NMR (400 MHz, DMSO-d₆) δ: 9.82 (s, 1H), 8.91 (s, 1H), 8.75 (s, 1H), 8.59 (s, 1H), 8.08-8.03 (m, 2H), 7.97-7.92 (m, 2H), 7.55 (d, J = 8.0 Hz, 1H), 7.47 (d, J = 7.2 Hz, 1H), 5.71 (br, 1H), 4.78 (s, 2H), 4.16 (q, J = 6.4 Hz, 1H), 2.20 (br, 2H), 1.44 (d, J = 6.4 Hz, 3H). |
| 379 | 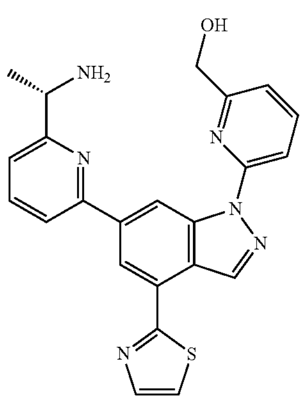 [SMILES: C[C@H](N)c1cccc(-c2cc(-c3nccs3)c3cnn(-c4cccc(CO)n4)c3c2)n1] | (S)-(6-(6-(6-(1-aminoethyl)pyridin-2-yl)-4-(thiazol-2-yl)-1H-indazol-1-yl)pyridin-2-yl)methanol | 428.9 | ¹H NMR (400 MHz, CD₃OD) δ: 9.87 (s, 1H), 8.94 (s, 1H), 8.73 (d, J = 1.2 Hz, 1H0, 8.15 (d, J = 7.6 Hz, 1H), 8.10 (d, J = 3.2 Hz, 1H), 8.06 (t, J = 7.2 Hz, 1H), 8.02-7.96 (m, 2H), 7.80 (d, J = 3.2 Hz, 1H), 7.52 (d, J = 7.6 Hz, 1H), 7.41-7.39 (m, 1H), 4.89 (s, 2H), 4.75 (q, J = 6.8 Hz, 1H), 1.76 (d, J = 6.8 Hz, 3H). |

| Example # | Structure | Name | LCMS (M+) | $^1$H NMR |
|---|---|---|---|---|
| 380 | 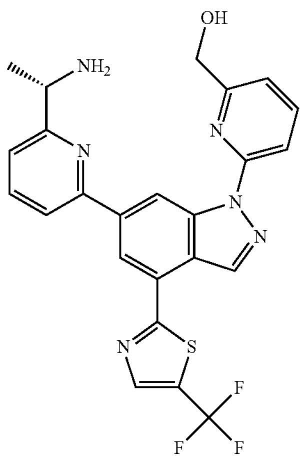 [SMILES: C[C@H](N)c1cccc(-c2cc(-c3ncc(C(F)(F)F)s3)c3cnn(-c4cccc(CO)n4)c3c2)n1] | (S)-(6-(6-(6-(1-aminoethyl)pyridin-2-yl)-4-(5-(trifluoromethyl)thiazol-2-yl)-1H-indazol-1-yl)pyridin-2-yl)methanol | 497.1 | $^1$H NMR (400 MHz, CD$_3$OD) δ: 9.92 (s, 1H), 8.95 (s, 1H), 8.72 (s, 1H), 8.44 (s, 1H), 8.13 (d, J = 8.0 Hz, 1H), 8.02 (t, J = 8.0 Hz, 1H), 7.97-7.94 (m, 2H), 7.48 (d, J = 7.6 Hz, 1H), 7.36 (d, J =6.0 Hz, 1H), 4.85 (s, 2H), 4.72-4.67 (m, 1H), 1.69 (d, J = 7.2 Hz, 3H). |
| 381 | 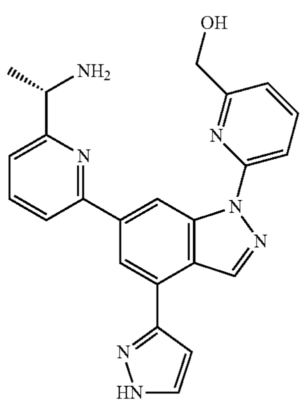 [SMILES: C[C@H](N)c1cccc(-c2cc(-c3cc[nH]n3)c3cnn(-c4cccc(CO)n4)c3c2)n1] | (S)-(6-(6-(6-(1-aminoethyl)pyridin-2-yl)-4-(1H-pyrazol-3-yl)-1H-indazol-1-yl)pyridin-2-yl)methanol | 412.0 | $^1$H NMR (400 MHz, CD$_3$OD) δ: 9.74 (s, 1H), 8.78 (s, 1H), 8.54 (d, J = 1.2 Hz, 1H), 8.15 (d, J = 8.0 Hz, 1H), 8.06-7.96 (m, 3H), 7.86 (d, J = 2.4 Hz, 1H), 7.49 (d, J = 7.6 Hz, 1H), 7.39-7.37 (m, 1H), 7.05 (d, J = 2.4 Hz, 1H), 4.90 (s, 2H), 4.73 (q, J = 6.8 Hz, 1H), 1.75 (d, J = 6.8 Hz, 3H). |
| 382 | 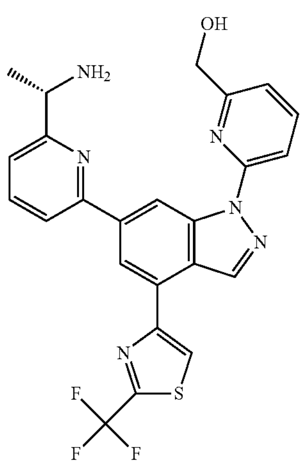 [SMILES: C[C@H](N)c1cccc(-c2cc(-c3csc(C(F)(F)F)n3)c3cnn(-c4cccc(CO)n4)c3c2)n1] | (S)-(6-(6-(6-(1-aminoethyl)pyridin-2-yl)-4-(2-(trifluoromethyl)thiazol-4-yl)-1H-indazol-1-yl)pyridin-2-yl)methanol | 497.1 | $^1$H NMR (400 MHz, CD$_3$OD) δ: 9.74-9.70 (m, 1H), 8.76-8.74 (m, 1H), 8.60-8.55 (m, 2H), 8.06-8.04 (m, 1H), 7.98-7.95 (m, 1H), 7.93-7.88 (m, 2H), 7.44 (d, J = 8.0 Hz, 1H), 7.30 (s, 1H), 4.83 (s, 2H), 4.68 (q, J = 6.8 Hz, 1H), 1.70 (d, J = 6.8 Hz, 3H). |

-continued

| Example # | Structure | Name | LCMS (M+) | ¹H NMR |
|---|---|---|---|---|
| 383 | 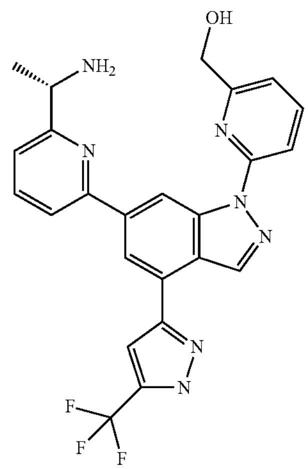 [SMILES: C[C@H](N)c1cccc(-c2cc(-c3cc(C(F)(F)F)[nH]n3)c3cnn(-c4cccc(CO)n4)c3c2)n1] | (S)-(6-(6-(6-(1-aminoethyl)pyridin-2-yl)-4-(5-(trifluoromethyl)-1H-pyrazol-3-yl)-1H-indazol-1-yl)pyridin-2-yl)methanol | 480.1 | ¹H NMR (400 MHz, CD₃OD) δ: 9.92 (s, 1H), 8.60 (s, 1H), 8.48 (s, 1H), 8.19 (d, J = 8.0 Hz, 1H), 8.13-7.92 (m, 3H), 7.53 (d, J = 7.2 Hz, 1H), 7.46-7.36 (m, 1H), 7.31 (s, 1H), 4.92 (s, 2H), 4.75 (q, J = 6.8 Hz, 1H), 1.76 (d, J = 6.8 Hz, 3H). |
| 384 | 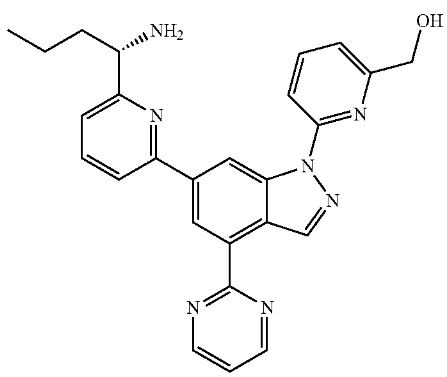 [SMILES: CCC[C@H](N)c1cccc(-c2cc(-c3ncccn3)c3cnn(-c4cccc(CO)n4)c3c2)n1] | (S)-(6-(6-(6-(1-aminobutyl)pyridin-2-yl)-4-(pyrimidin-2-yl)-1H-indazol-1-yl)pyridin-2-yl)methanol | 452.2 | ¹H NMR (400 MHz, CD₃OD) δ: 9.97-9.95 (m, 1H), 9.20-9.16 (m, 2H), 9.04-9.01 (m, 2H), 8.17-8.14 (m, 1H), 8.06-7.97 (m, 3H), 7.51-7.45 (m, 2H), 7.38-7.37 (m, 1H), 4.89 (s, 2H), 4.57 (t, J = 6.8 Hz, 1H), 2.10-2.02 (m, 2H), 1.52-1.39 (m, 2H), 1.02 (t, J = 7.2 Hz, 3H). |
| 385 | 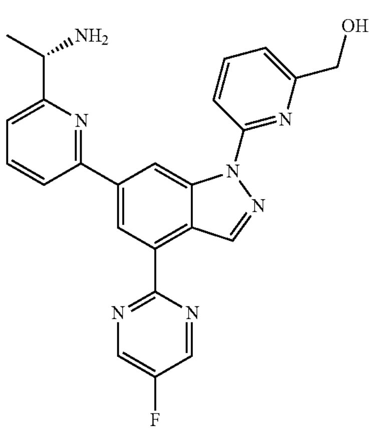 [SMILES: C[C@H](N)c1cccc(-c2cc(-c3ncc(F)cn3)c3cnn(-c4cccc(CO)n4)c3c2)n1] | (S)-(6-(6-(6-(1-aminoethyl)pyridin-2-yl)-4-(5-fluoropyrimidin-2-yl)-1H-indazol-1-yl)pyridin-2-yl)methanol | 442.1 | ¹H NMR (400 MHz, CD₃OD) δ: 9.75 (s, 1H), 9.05 (s, 1H), 9.02 (s, 1H), 8.87 (s, 2H), 8.05-7.91 (m, 4H), 7.48 (d, J = 7.6 Hz, 1H), 7.34 (d, J = 6.8 Hz, 1H), 4.84 (s, 2H), 4.73-4.68 (m, 1H), 1.71 (d, J = 7.2 Hz, 3H). |

-continued

| Example # | Structure | Name | LCMS (M+) | ¹H NMR |
|---|---|---|---|---|
| 386 | 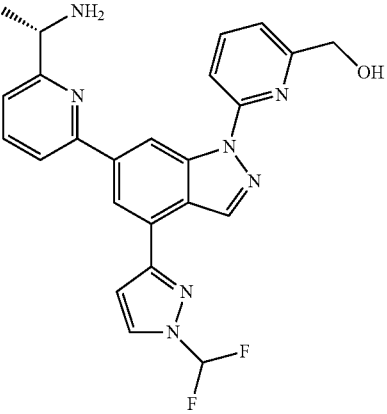 [SMILES: C[C@H](N)c1cccc(-c2cc(-c3ccn(C(F)F)n3)c3cnn(-c4cccc(CO)n4)c3c2)n1] | (S)-(6-(6-(6-(1-aminoethyl)pyridin-2-yl)-4-(1-(difluoromethyl)-1H-pyrazol-3-yl)-1H-indazol-1-yl)pyridin-2-yl)methanol | 462.1 | ¹H NMR (400 MHz, CD₃OD) δ: 9.80-9.76 (m, 1H), 8.92-8.90 (m, 1H), 8.54 (s, 1H), 8.21 (s, 1H), 8.16-7.96 (m, 4H), 7.68 (t, J = 6.0 Hz, 1H), 7.47 (d, J = 7.6 Hz, 1H), 7.35 (s, 1H), 7.28 (s, 1H), 4.87 (s, 2H), 4.73-4.68 (m, 1H), 1.72 (d, J = 6.8 Hz, 3H). |
| 387 | 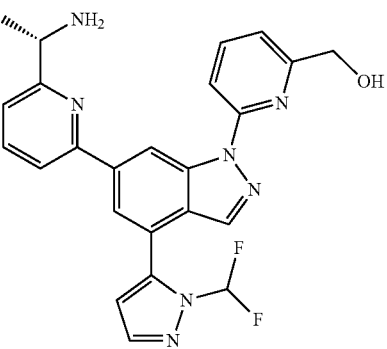 [SMILES: C[C@H](N)c1cccc(-c2cc(-c3ccnn3C(F)F)c3cnn(-c4cccc(CO)n4)c3c2)n1] | (S)-(6-(6-(6-(1-aminoethyl)pyridin-2-yl)-4-(1-(difluoromethyl)-1H-pyrazol-5-yl)-1H-indazol-1-yl)pyridin-2-yl)methanol | 462.1 | ¹H NMR (400 MHz, CD₃OD) δ: 9.90 (s, 1H), 8.28 (s, 1H), 8.20 (s, 1H), 8.11 (d, J = 8.0 Hz, 1H), 8.05-7.93 (m, 4H), 7.65-7.36 (m, 3H), 6.83 (d, J = 1.2 Hz, 1H), 4.89 (s, 2H), 4.72-4.67 (m, 1H), 1.70 (d, J = 6.8 Hz, 3H). |
| 388 | 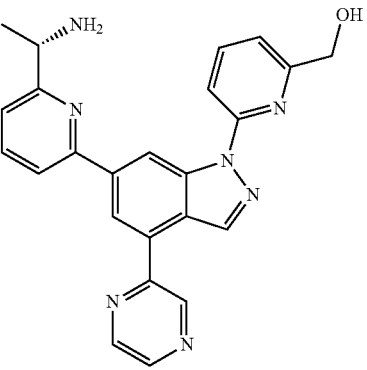 [SMILES: C[C@H](N)c1cccc(-c2cc(-c3cnccn3)c3cnn(-c4cccc(CO)n4)c3c2)n1] | (S)-(6-(6-(6-(1-aminoethyl)pyridin-2-yl)-4-(pyrazin-2-yl)-1H-indazol-1-yl)pyridin-2-yl)methanol | 424.1 | ¹H NMR (400 MHz, CD₃OD) δ: 9.79 (d, J = 5.2 Hz, 1H), 9.37 (s, 1H), 8.81-8.63 (m, 4H), 8.10-7.90 (m, 4H), 7.50 (d, J = 7.2 Hz, 1H), 7.35 (d, J = 5.6 Hz, 1H), 4.87 (s, 2H), 4.78-4.72 (m, 1H), 1.76 (d, J = 6.8 Hz, 3H). |
| 389 | 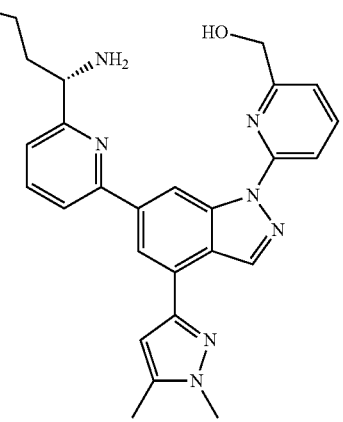 | (S)-(6-(6-(6-(1-aminobutyl)pyridin-2-yl)-4-(1,5-dimethyl-1H-pyrazol-3-yl)-1H-indazol-1-yl)pyridin-2-yl)methanol | 468.2 | ¹H NMR (400 MHz, DMSO-d₆) δ: 9.54 (s, 1H), 8.97 (s, 1H), 8.44 (s, 2H), 8.40 (s, 1H), 8.16 (d, J = 8.0 Hz, 1H), 8.08-8.02 (m, 2H), 7.91 (d, J = 8.0 Hz, 1H), 7.53 (d, J = 7.6 Hz, 1H), 7.43 (d, J = 7.2 Hz, 1H), 6.93 (s, 1H), 5.66 (br, 1H), 4.79 (s, 2H), 4.56-4.53 (m, 1H), 3.91 (s, 3H), 2.39 (s, 3H), 1.96-1.92 (m, 2H), 1.36-1.31 (m, 2H), 0.93 (t, J = 7.2 Hz, 3H). |

| Example # | Structure | Name | LCMS (M+) | ¹H NMR |
|---|---|---|---|---|
| 390 | 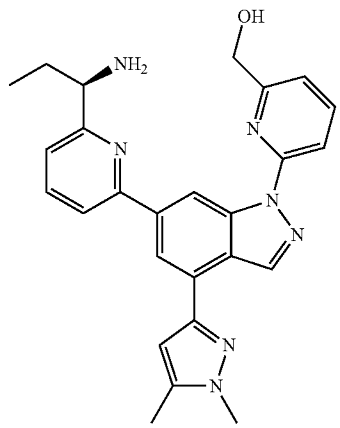 [SMILES: CC[C@@H](N)c1cccc(-c2cc(-c3cc(C)n(C)n3)c3cnn(-c4cccc(CO)n4)c3c2)n1] | (R)-(6-(6-(6-(1-aminopropyl)pyridin-2-yl)-4-(1,5-dimethyl-1H-pyrazol-3-yl)-1H-indazol-1-yl)pyridin-2-yl)methanol | 454.2 | ¹H NMR (400 MHz, CD₃OD) δ: 9.83 (s, 1H), 8.71 (s, 1H), 8.60 (s, 1H), 8.17 (d, J = 8.0 Hz, 1H), 8.07-7.99 (m, 3H), 7.51 (d, J = 7.6 Hz, 1H), 7.42 (dd, J = 5.6, 2.4 Hz, 1H), 7.10 (m, 1H), 4.91 (s, 2H), 4.55 (t, J = 6.4 Hz, 1H), 4.13 (s, 3H), 2.56 (s, 3H), 2.20-2.13 (m, 2H), 1.07 (t, J = 7.2 Hz, 3H). |
| 391 | 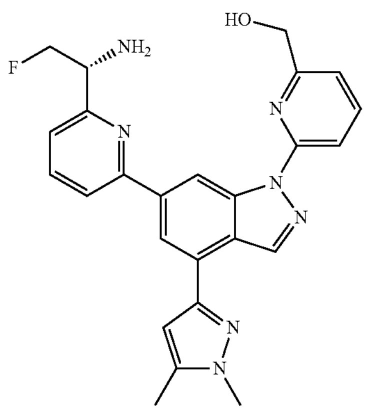 [SMILES: Cc1cc(-c2cc(-c3cccc([C@@H](N)CF)n3)cc3c2cnn3-c2cccc(CO)n2)nn1C] | (R)-(6-(6-(6-(1-amino-2-fluoroethyl)pyridin-2-yl)-4-(1,5-dimethyl-1H-pyrazol-3-yl)-1H-indazol-1-yl)pyridin-2-yl)methanol | 457.7 | ¹H NMR (400 MHz, CD₃OD) δ: 9.51 (s, 1H), 8.70 (s, 1H), 8.44 (s, 1H), 8.13-7.99 (m, 3H), 7.90 (d, J = 8.0 Hz, 1H), 7.63 (d, J = 7.2 Hz, 1H), 7.42 (d, J = 7.2 Hz, 1H), 6.77 (s, 1H), 5.16-4.94 (m, 3H), 4.92 (s, 2H), 3.98 (s, 3H), 2.47 (s, 3H). |
| 392 | 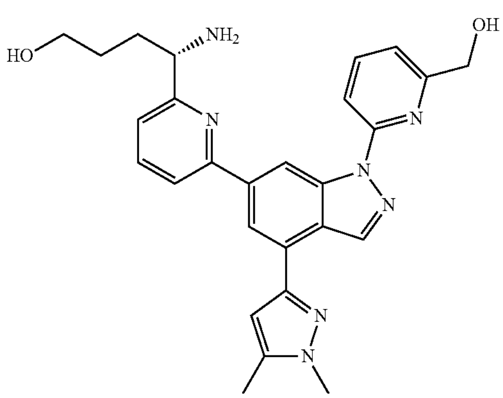 [SMILES: Cc1cc(-c2cc(-c3cccc([C@@H](N)CCCO)n3)cc3c2cnn3-c2cccc(CO)n2)nn1C] | (S)-4-amino-4-(6-(4-(1,5-dimethyl-1H-pyrazol-3-yl)-1-(6-(hydroxymethyl)pyridin-2-yl)-1H-indazol-6-yl)pyridin-2-yl)butan-1-ol | 484.2 | ¹H NMR (400 MHz, CD₃OD) δ: 9.71 (s, 1H), 8.80 (s, 1H), 8.44 (s, 1H), 8.15 (d, J = 8.0 Hz, 1H), 8.11-7.92 (m, 3H), 7.49 (d, J = 7.6 Hz, 1H), 7.43-7.32 (m, 1H), 6.79 (s, 1H), 4.91 (s, 2H), 4.63 (t, J = 6.8 Hz, 1H), 3.96 (s, 3H), 3.65 (t, J = 6.0 Hz, 2H), 2.45 (s, 3H), 2.21-2.16 (m, 2H), 1.71-1.62 (m, 2H). |

| Example # | Structure | Name | LCMS (M+) | $^1$H NMR |
|---|---|---|---|---|
| 393 | 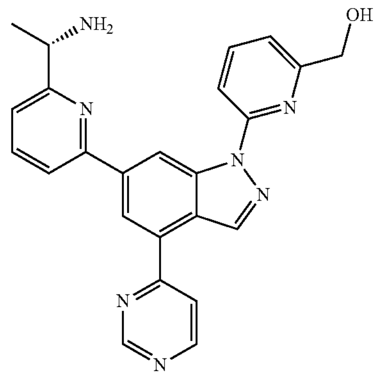 [SMILES: C[C@H](N)c1cccc(-c2cc(-c3ccncn3)c3cnn(-c4cccc(CO)n4)c3c2)n1] | (S)-(6-(6-(6-(1-aminoethyl)pyridin-2-yl)-4-(pyrimidin-4-yl)-1H-indazol-1-yl)pyridin-2-yl)methanol | 424.2 | $^1$H NMR (400 MHz, CD$_3$OD) δ: 10.12 (s, 1H), 9.55 (s, 1H), 9.12 (s, 1H), 9.08 (d, J = 4.8 Hz, 1H), 8.96 (s, 1H), 8.62 (d, J = 6.0 Hz, 1H), 8.26 (d, J = 7.6 Hz, 1H), 8.10 (t, J = 8.0 Hz, 1H), 8.06-8.00 (m, 2H), 7.56 (d, J = 8.0 Hz, 1H), 7.42 (dd, J = 1.6, 6.0 Hz, 1H), 4.93 (s, 2H), 4.80-4.75 (m, 1H), 1.78 (d, J = 6.8 Hz, 3H). |
| 394 | 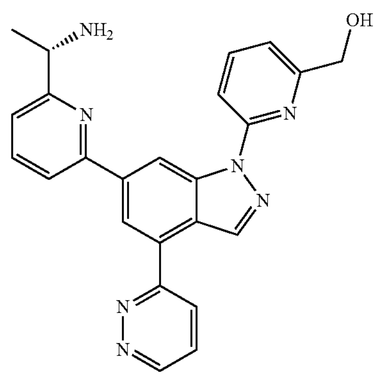 [SMILES: C[C@H](N)c1cccc(-c2cc(-c3cccnn3)c3cnn(-c4cccc(CO)n4)c3c2)n1] | (S)-(6-(6-(6-(1-aminoethyl)pyridin-2-yl)-4-(pyridazin-3-yl)-1H-indazol-1-yl)pyridin-2-yl)methanol | 424.1 | $^1$H NMR (400 MHz, CD$_3$OD) δ: 9.98 (s, 1H), 9.30 (dd, J = 5.2, 1.2 Hz, 1H), 8.86 (s, 1H), 8.72 (s, 1H), 8.52 (dd, J = 8.4, 1.6 Hz, 1H), 8.21 (d, J = 8.0 Hz, 1H), 8.08-7.94 (m, 4H), 7.52 (d, J = 7.6 Hz, 1H), 7.40 (dd, J = 6.0, 1.6 Hz, 1H), 4.91 (s, 2H), 4.75 (q, J = 6.8 Hz, 1H), 1.75 (d, J = 6.8 Hz, 3H). |

Example 395

Step 1. Synthesis of 1-(6-(((tert-butyldimethylsilyl)oxy)methyl)pyridin-2-yl)-6-((4-methoxybenzyl)oxy)-4-(4,4,5,5-tetramethyl-1,3,2-dioxaborolan-2-yl)-1H-indazole

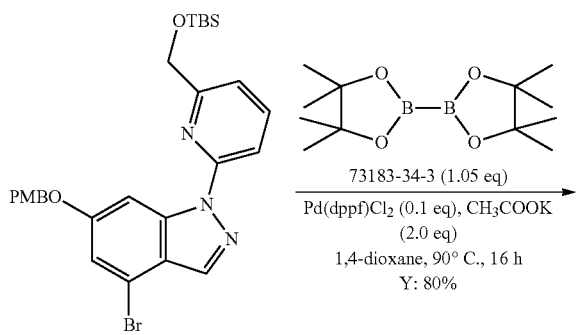

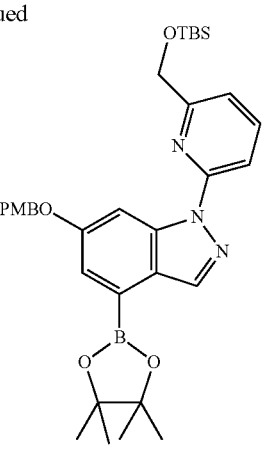

A mixture of 4-bromo-1-(6-(((tert-butyldimethylsilyl)oxy)methyl)pyridin-2-yl)-6-((4-methoxybenzyl)oxy)-1H-indazole (Example 352, step 5) (3.5 g, 6.3 mmol, 1.0 eq), 73183-34-3 (1.68 g, 6.6 mmol, 1.05 eq) and CH$_3$COOK (1.23 g, 12.6 mmol, 2.0 eq) in 1,4-dioxane (100 mL) was stirred while purging N$_2$ at rt for 10 min. To this system was added Pd(dppf)Cl$_2$ (576 mg, 0.63 mmol, 0.1 eq) and heated to 90° C. for 16 h. The mixture was diluted with EA (100 mL) and washed with saturated aqueous NaHCO₃ solution (100 mL) and brine (100 mL). The organic phase was dried (Na₂SO₄) and concentrated to give 1-(6-(((tert-butyldimethylsilyl)oxy)methyl)pyridin-2-yl)-6-((4-methoxybenzyl)oxy)-4-(4,4,5,5-tetramethyl-1,3,2-dioxaborolan-2-yl)-1H-indazole which was used for next step without further purification. 3.0 g, as a brown solid, Y: 80%. ESI-MS (M+H)⁺: 602.3.

Step 2. Synthesis of 1-(6-(((tert-butyldimethylsilyl)oxy)methyl)pyridin-2-yl)-6-((4-methoxybenzyl)oxy)-4-(1-methyl-1H-pyrazol-3-yl)-1H-indazole

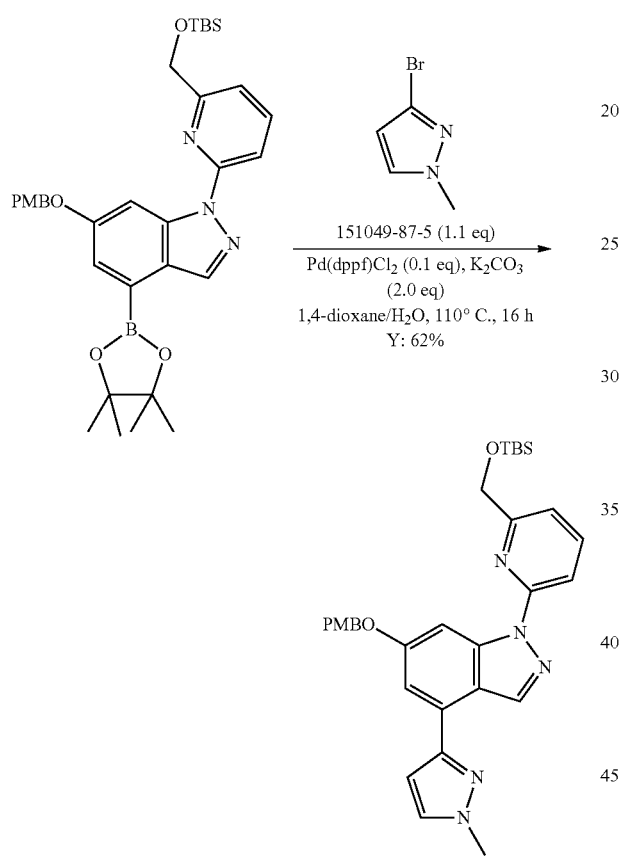

Step 3. Synthesis of 1-(6-(((tert-butyldimethylsilyl)oxy)methyl)pyridin-2-yl)-4-(1-methyl-1H-pyrazol-3-yl)-1H-indazol-6-ol

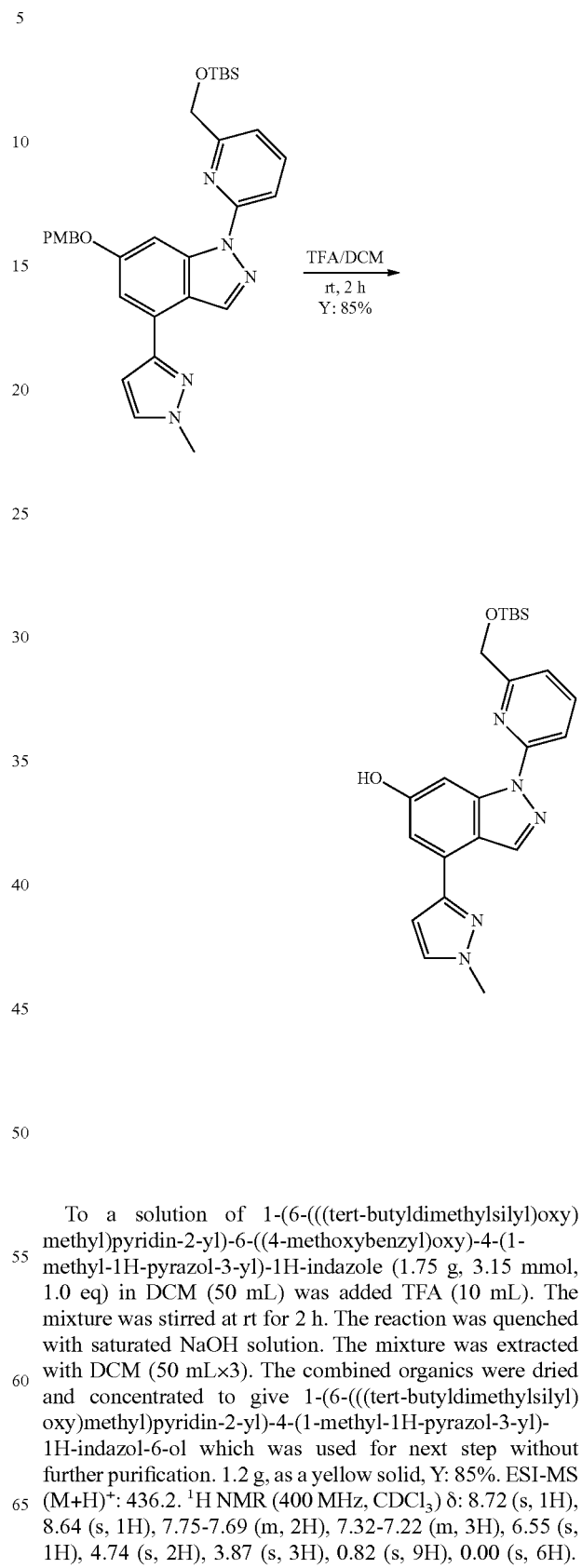

A mixture of 1-(6-(((tert-butyldimethylsilyl)oxy)methyl)pyridin-2-yl)-6-((4-methoxybenzyl)oxy)-4-(4,4,5,5-tetramethyl-1,3,2-dioxaborolan-2-yl)-1H-indazole (3.0 g, 5.0 mmol, 1.0 eq), 3-bromo-1-methyl-1H-pyrazole (151049-87-5) (880 mg, 5.5 mmol, 1.1 eq) and K₂CO₃ (1.38 g, 10.0 mmol, 2.0 eq) in 1,4-dioxane/H₂O (100 mL/5 mL) was stirred while purging N₂ at rt for 10 min. To this system was added Pd(dppf)Cl₂ (458 mg, 0.5 mmol, 0.1 eq) and heated to 110° C. for 16 h. The mixture was diluted with EA (100 mL) and washed with saturated aqueous NaHCO₃ solution (100 mL) and brine (100 mL). The organics were dried (Na₂SO₄) and concentrated in vacuo. The crude mixture was purified by silica gel chromatography using PE/EA (1/1) as eluent to give 1-(6-(((tert-butyldimethylsilyl)oxy)methyl)pyridin-2-yl)-6-((4-methoxybenzyl)oxy)-4-(1-methyl-H-pyrazol-3-yl)-1H-indazole. 1.75 g, as a yellow solid, Y: 62%. ESI-MS (M+H)⁺: 556.2.

To a solution of 1-(6-(((tert-butyldimethylsilyl)oxy)methyl)pyridin-2-yl)-6-((4-methoxybenzyl)oxy)-4-(1-methyl-1H-pyrazol-3-yl)-1H-indazole (1.75 g, 3.15 mmol, 1.0 eq) in DCM (50 mL) was added TFA (10 mL). The mixture was stirred at rt for 2 h. The reaction was quenched with saturated NaOH solution. The mixture was extracted with DCM (50 mL×3). The combined organics were dried and concentrated to give 1-(6-(((tert-butyldimethylsilyl)oxy)methyl)pyridin-2-yl)-4-(1-methyl-1H-pyrazol-3-yl)-1H-indazol-6-ol which was used for next step without further purification. 1.2 g, as a yellow solid, Y: 85%. ESI-MS (M+H)⁺: 436.2. ¹H NMR (400 MHz, CDCl₃) δ: 8.72 (s, 1H), 8.64 (s, 1H), 7.75-7.69 (m, 2H), 7.32-7.22 (m, 3H), 6.55 (s, 1H), 4.74 (s, 2H), 3.87 (s, 3H), 0.82 (s, 9H), 0.00 (s, 6H).

Step 4. Synthesis of 1-(6-(((tert-butyldimethylsilyl)oxy)methyl)pyridin-2-yl)-4-(1-methyl-1H-pyrazol-3-yl)-1H-indazol-6-yl trifluoromethanesulfonate

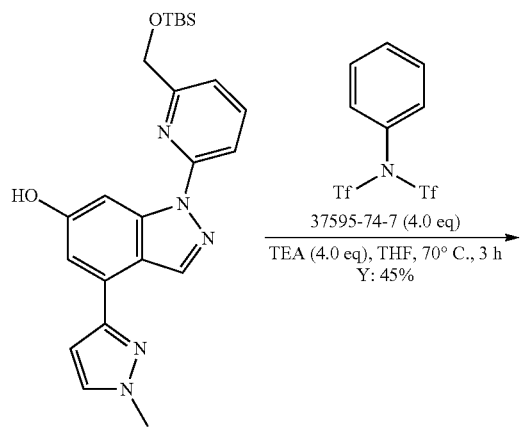

A mixture of 1-(6-(((tert-butyldimethylsilyl)oxy)methyl)pyridin-2-yl)-4-(1-methyl-1H-pyrazol-3-yl)-1H-indazol-6-ol (1.2 g, 2.76 mmol, 1.0 eq), Cas No 37595-74-7 (3.94 g, 11.04 mmol, 4.0 eq) and TEA (1.11 g, 11.04 mmol, 4.0 eq) in THF (50 mL) was stirred at 70° C. for 3 h. After concentration, the residue was purified by silica gel chromatography using PE/EA (5/1) as eluent give 1-(6-(((tert-butyldimethylsilyl)oxy)methyl)pyridin-2-yl)-4-(1-methyl-1H-pyrazol-3-yl)-1H-indazol-6-yl trifluoromethanesulfonate. 900 mg, as a yellow solid, Y: 45%. ESI-MS (M+H)+: 568.2. $^1$H NMR (400 MHz, CDCl$_3$) δ: 8.90 (s, 1H), 8.82 (s, 1H), 7.94 (d, J=7.6 Hz, 1H), 7.89-7.87 (m, 1H), 7.50-7.46 (m, 2H), 7.29-7.26 (m, 1H), 6.73 (d, J=2.0 Hz, 1H), 4.92 (s, 2H), 4.05 (s, 3H), 1.00 (s, 9H), 0.18 (s, 6H).

Step 5. Synthesis of 1-(6-(((tert-butyldimethylsilyl)oxy)methyl)pyridin-2-yl)-4-(1-methyl-1H-pyrazol-3-yl)-6-(4,4,5,5-tetramethyl-1,3,2-dioxaborolan-2-yl)-1H-indazole

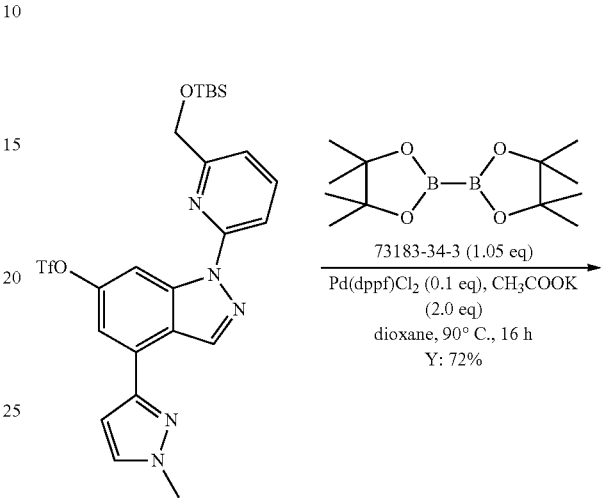

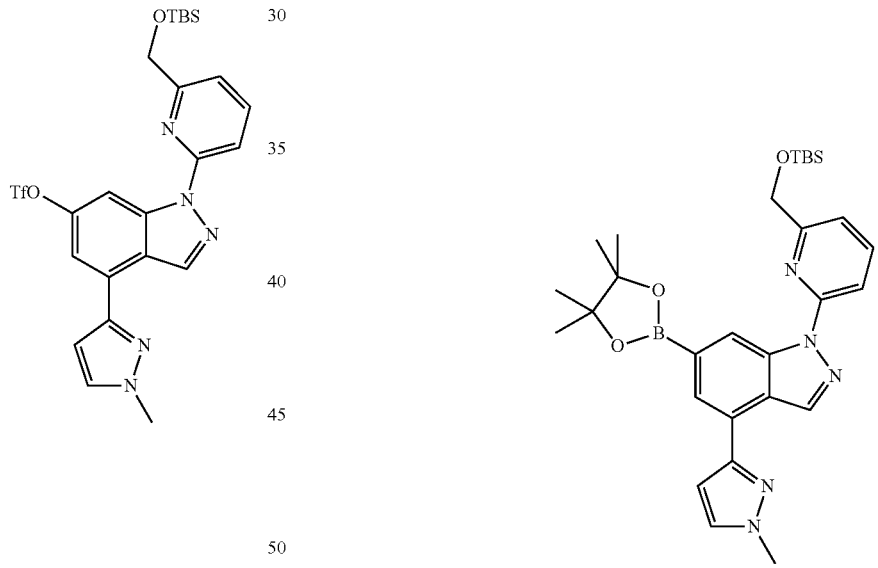

The preparation of 1-(6-(((tert-butyldimethylsilyl)oxy)methyl)pyridin-2-yl)-4-(1-methyl-1H-pyrazol-3-yl)-6-(4,4,5,5-tetramethyl-1,3,2-dioxaborolan-2-yl)-1H-indazole was similar to that of 1-(6-(((tert-butyldimethylsilyl)oxy)methyl)pyridin-2-yl)-6-((4-methoxybenzyl)oxy)-4-(4,4,5,5-tetramethyl-1,3,2-dioxaborolan-2-yl)-1H-indazole (Example 395, Step 1) to give 600 mg as a brown solid, Y: 72%. ESI-MS (M+H)+: 546.3.

Synthesis of (S)-tert-butyl (4-((tert-butyldimethylsilyl)oxy)-1-(6-(1-(6-(((tert-butyldimethylsilyl)oxy)methyl)pyridin-2-yl)-4-(1-methyl-1H-pyrazol-3-yl)-1H-indazol-6-yl)pyridin-2-yl)butyl)carbamate

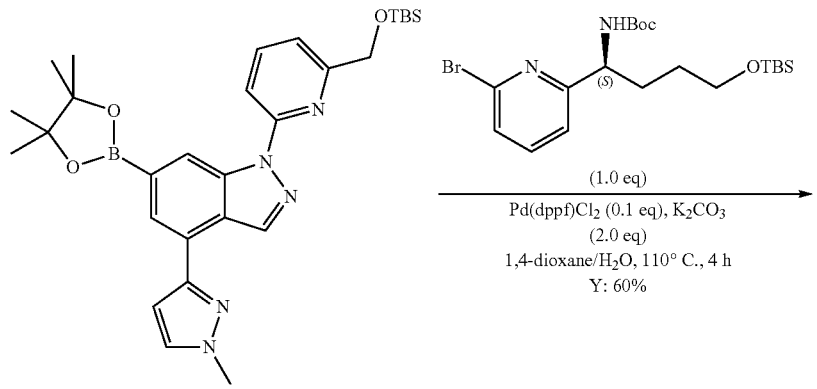

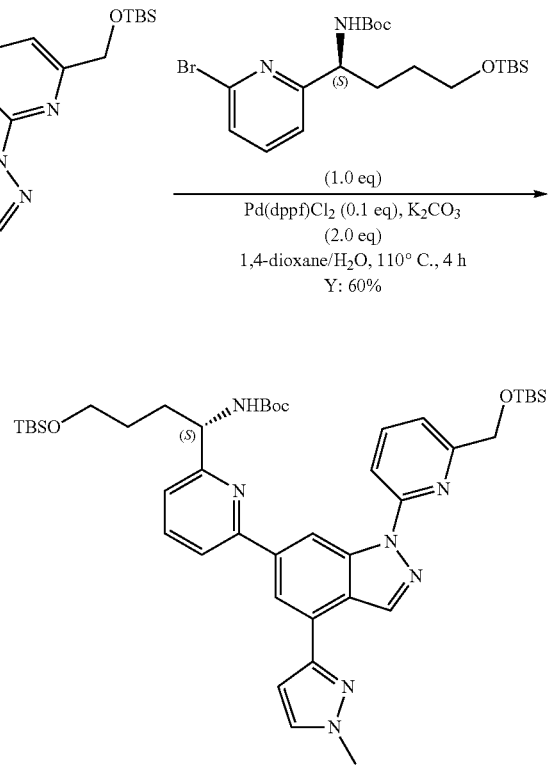

The preparation of (S)-tert-butyl (4-((tert-butyldimethylsilyl)oxy)-1-(6-(1-(6-(((tert-butyldimethylsilyl)oxy)methyl)pyridin-2-yl)-4-(1-methyl-1H-pyrazol-3-yl)-1H-indazol-6-yl)pyridin-2-yl)butyl)carbamate was similar to that of 1-(6-(((tert-butyldimethylsilyl)oxy)methyl)pyridin-2-yl)-6-((4-methoxybenzyl)oxy)-4-(1-methyl-1H-pyrazol-3-yl)-1H-indazole using (S)-tert-butyl (1-(6-bromopyridin-2-yl)-4-((tert-butyldimethylsilyl)oxy)butyl)carbamate from Example 396 to give 230 mg as a yellow solid, Y: 60%. ESI-MS (M+H)$^+$: 798.5.

Synthesis of (S)-4-amino-4-(6-(1-(6-(hydroxymethyl)pyridin-2-yl)-4-(1-methyl-1H-pyrazol-3-yl)-1H-indazol-6-yl)pyridin-2-yl)butan-1-ol

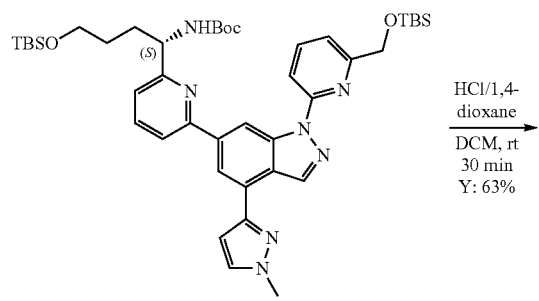

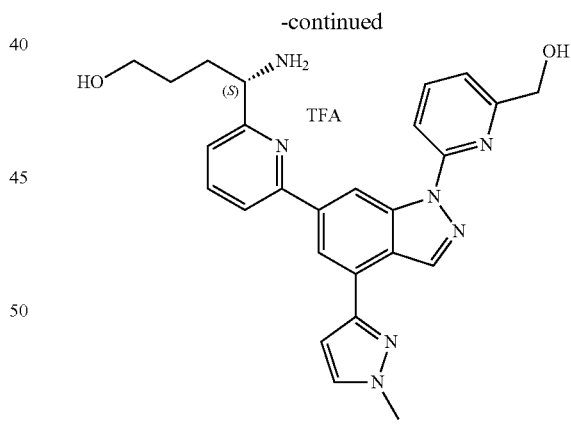

The preparation of (S)-4-amino-4-(6-(1-(6-(hydroxymethyl)pyridin-2-yl)-4-(1-methyl-1H-pyrazol-3-yl)-1H-indazol-6-yl)pyridin-2-yl)butan-1-ol was similar to that of (S)-4-amino-4-(6-(1-(6-(hydroxymethyl)pyridin-2-yl)-4-(2-methoxyethoxy)-1H-indazol-6-yl)pyridin-2-yl)butan-1-ol (Example 484, Step 2) to give 107 mg as a yellow solid, Y: 63%. ESI-MS (M+H)$^+$: 470.2. HPLC: 100%. $^1$H NMR (400 MHz, CD$_3$OD) δ: 9.70 (s, 1H), 8.82 (s, 1H), 8.47 (s, 1H), 8.14 (d, J=8.0 Hz, 1H), 8.09-7.89 (m, 3H), 7.77 (d, J=2.0 Hz, 1H), 7.49 (d, J=7.6 Hz, 1H), 7.44-7.27 (m, 1H), 7.00 (d, J=2.0 Hz, 1H), 4.90 (s, 2H), 4.63 (t, J=6.8 Hz, 1H), 4.08 (s, 3H), 3.66 (t, J=6.4 Hz, 2H), 2.23-2.16 (m, 2H), 1.87-1.47 (m, 2H).

Example 396

Synthesis of 1-(6-bromopyridin-2-yl)-4-methoxybutan-1-one

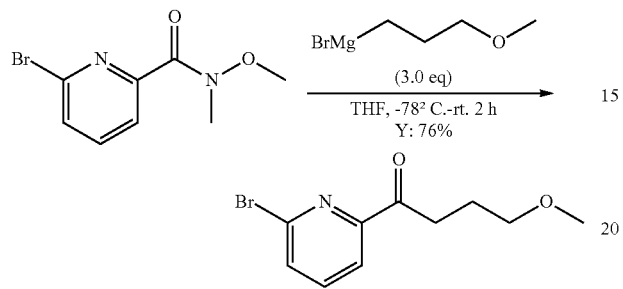

To a solution of 6-bromo-N-methoxy-N-methylpicolinamide (2.5 g, 10.2 mmol, 1.0 eq) in THF (20 mL) was added (3-methoxypropyl)magnesium bromide (15.3 mL (2M in THF), 30.6 mmol, 3.0 eq) at −78° C. The mixture was stirred at −78° C. for 2 h. Then saturated ammonium chloride aqueous solution (10 mL) was added to quench the reaction and the mixture was extracted with EA (3×50 mL). The organic phase was washed with brine and dried over Na$_2$SO$_4$. After filtration and concentration, the residue was purified by column chromatography (silica gel, PE/EA=6/1) to give 1-(6-bromopyridin-2-yl)-4-methoxybutan-1-one (2.0 g, yield: 76%) as light yellow oil. ESI-MS (M+H)$^+$: 258.1. $^1$H NMR (400 MHz, CDCl$_3$) δ: 7.98 (dd, J=7.2, 1.2 Hz, 1H), 7.76-7.55 (m, 2H), 3.48 (t, J=6.4 Hz, 2H), 3.32 (s, 3H), 3.27 (t, J=7.2 Hz, 2H), 2.09-1.90 (m, 2H).

Synthesis of (R,E)-N-(1-(6-bromopyridin-2-yl)-4-methoxybutylidene)-2-methylpropane-2-sulfinamide

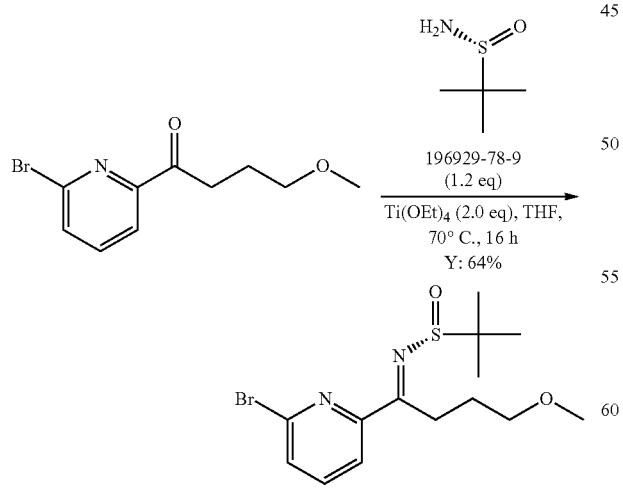

To a solution of 1-(6-bromopyridin-2-yl)-4-methoxybutan-1-one (2.0 g, 7.8 mmol, 1.0 eq) and (R)-(+)-2-Methyl-2-propanesulfinamide (CAS No. 196929-78-9, 1.1 g, 9.4 mmol, 1.2 eq) in THF (20 mL) was added Ti(OEt)$_4$ (3.6 g, 15.6 mmol, 2.0 eq) at rt. The mixture was stirred at 70° C. for 16 h. After cooling down to rt, the mixture was diluted with water (200 mL) and extracted with EA (50 mL×3). The combined organic layers were dried over anhydrous Na$_2$SO$_4$. After concentration, the residue was purified by silica gel chromatography with PE/EA (8/1) as eluent to give (R,E)-N-(1-(6-bromopyridin-2-yl)-4-methoxybutylidene)-2-methylpropane-2-sulfinamide (1.8 g, yield: 64%) as a yellow solid. ESI-MS (M+H)$^+$: 361.1.

Synthesis of (R)—N—((S)-1-(6-bromopyridin-2-yl)-4-methoxybutyl)-2-methylpropane-2-sulfinamide

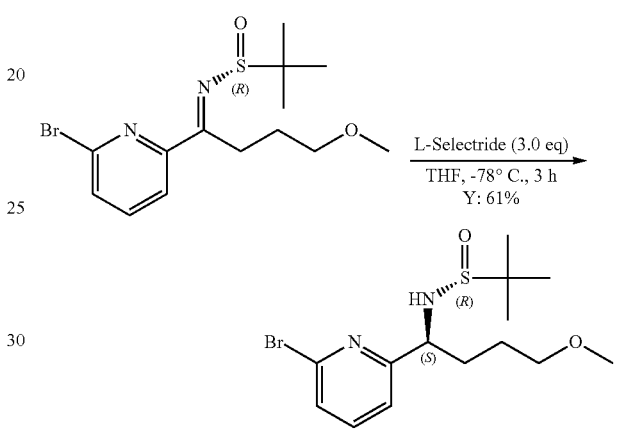

To a solution of (R,E)-N-(1-(6-bromopyridin-2-yl)-4-methoxybutylidene)-2-methylpropane-2-sulfinamide (1.8 g, 5.0 mmol, 1.0 eq) in THF (50 mL) was added L-selectride (15 mL, 15 mmol, 3.0 eq) at −78° C. The mixture was stirred at −78° C. for 3 h. The mixture was diluted with DCM (80 mL) and then Na$_2$SO$_4$.10H$_2$O was added to quench the reaction. After filtration and concentration, the residue was recrystallized by (DCM/PE=1/100) to give (R)—N—((S)-1-(6-bromopyridin-2-yl)-4-methoxybutyl)-2-methylpropane-2-sulfinamide (1.1 g, yield: 61%) as a white solid. ESI-MS (M+H)$^+$: 363.1. $^1$H NMR (400 MHz, CDCl$_3$) δ: 7.50 (t, J=8.0 Hz, 1H), 7.36 (d, J=8.0 Hz, 1H), 7.25 (d, J=7.2 Hz, 1H), 4.47 (q, J=6.4 Hz, 1H), 4.16 (d, J=6.0 Hz, 1H), 3.41-3.36 (m, 2H), 3.30 (s, 3H), 2.04-1.93 (m, 2H), 1.69-1.58 (m, 2H), 1.19 (s, 9H).

Synthesis of (S)-tert-butyl (1-(6-bromopyridin-2-yl)-4-hydroxybutyl)carbamate

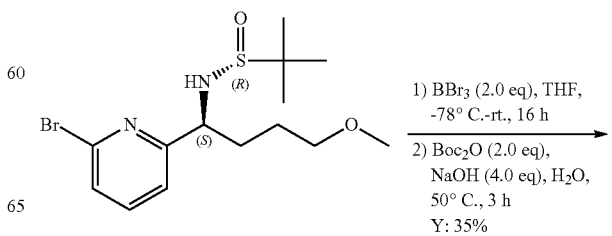

-continued

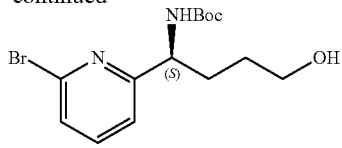

To a solution of (R)—N—((S)-1-(6-bromopyridin-2-yl)-4-methoxybutyl)-2-methylpropane-2-sulfinamide (1.1 g, 3.0 mmol, 1.0 eq) in THF (50 mL) was added BBr$_3$ (0.6 mL, 6.0 mmol, 2.0 eq) at −78° C. The mixture was stirred at −78° C. to rt for 16 h. Then Boc$_2$O (1.3 g, 6.0 mmol, 2.0 eq), NaOH (480 mg, 12.0 mmol, 4.0 eq) and H$_2$O (20 mL) was added to the mixture. The mixture was stirred at 50° C. for 3 h. After cooling down to rt, the mixture was extracted with EA (30 mL×3). The combined organic fractions were dried, filtered and concentrated. The residue was purified by silica gel chromatography (PE/EA=4/1) to give (S)-tert-butyl (1-(6-bromopyridin-2-yl)-4-hydroxybutyl)carbamate (370 mg, yield: 35%) as brown oil. ESI-MS (M+H)$^+$: 345.1.

Synthesis of (S)-tert-butyl (1-(6-bromopyridin-2-yl)-4-((tert-butyldimethylsilyl)oxy)butyl)carbamate

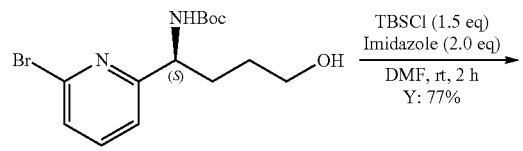

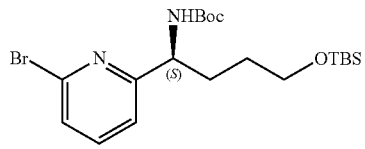

The preparation of (S)-tert-butyl (1-(6-bromopyridin-2-yl)-4-((tert-butyldimethylsilyl)oxy)butyl)carbamate was similar to that of 4-bromo-1-(6-(((tert-butyldimethylsilyl)oxy)methyl)pyridin-2-yl)-6-((4-methoxybenzyl)oxy)-1H-indazole (Example 352, Step 5) to give 380 mg, as a yellow solid, Y: 77%. ESI-MS (M+H)$^+$: 459.2.

Synthesis of (S)-tert-butyl (4-((tert-butyldimethylsilyl)oxy)-1-(6-(1-(6-(((tert-butyldimethylsilyl)oxy)methyl)pyridin-2-yl)-1H-indazol-6-yl)pyridin-2-yl)butyl)carbamate

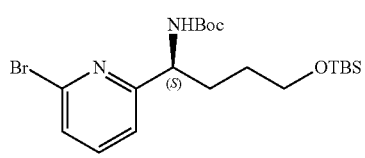

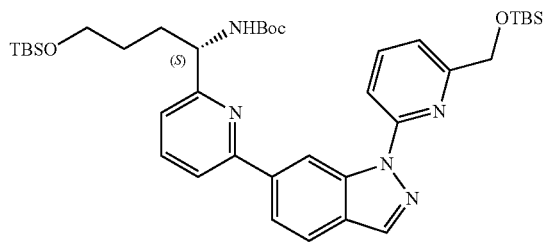

The preparation of (S)-tert-butyl (4-((tert-butyldimethylsilyl)oxy)-1-(6-(1-(6-(((tert-butyldimethylsilyl)oxy)methyl)pyridin-2-yl)-1H-indazol-6-yl)pyridin-2-yl)butyl)carbamate was similar to that of (R)—N—((S)-1-(6-(1-(6-(((tert-butyldimethylsilyl)oxy)methyl)pyridin-2-yl)-4-(1H-pyrazol-1-yl)-1H-indazol-6-yl)pyridin-2-yl)ethyl)-2-methylpropane-2-sulfinamide (Example 352, Step 10) using the borate from Example 145, Step 3 to give 270 mg, as a yellow solid, Y: 63%. ESI-MS (M+H)$^+$: 718.5. $^1$H NMR (400 MHz, CDCl$_3$) δ: 9.43 (s, 1H), 8.20 (s, 1H), 8.01 (d, J=8.4 Hz, 1H), 7.96-7.78 (m, 3H), 7.74 (d, J=4.0 Hz, 2H), 7.39 (d, J=7.2 Hz, 1H), 7.19 (t, J=4.0 Hz, 1H), 5.84 (d, J=8.4 Hz, 1H), 4.97 (s, 2H), 4.85-4.82 (m, 1H), 3.76-3.36 (m, 2H), 2.09-1.83 (m, 2H), 1.60-1.53 (m, 2H), 1.42 (s, 9H), 0.98 (s, 9H), 0.84 (s, 9H), 0.15 (s, 6H), 0.00 (s, 6H).

Synthesis of (S)-4-amino-4-(6-(1-(6-(hydroxymethyl)pyridin-2-yl)-1H-indazol-6-yl)pyridin-2-yl)butan-1-ol

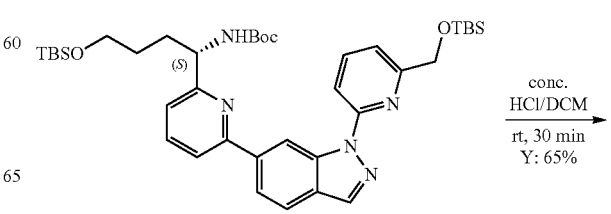

-continued

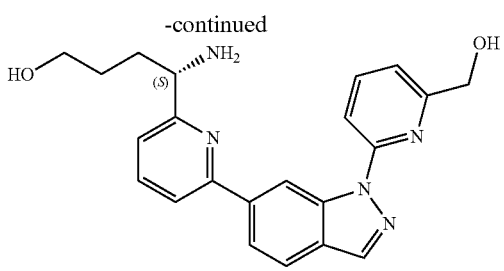

To a solution of (S)-tert-butyl (4-((tert-butyldimethylsilyl)oxy)-1-(6-(1-(6-(((tert-butyldimethylsilyl)oxy)methyl)pyridin-2-yl)-1H-indazol-6-yl)pyridin-2-yl)butyl)carbamate (270 mg, 0.38 mmol, 1.0 eq) in DCM (10 mL) was added conc. HCl (0.5 mL). The mixture was stirred at rt for 30 min. The solvent was removed in vacuo. The resulting mixture was diluted with DMF (3 mL) and adjusted to pH=7-8 with sodium hydroxide aqueous solution. The mixture was purified by prep-HPLC (MeOH/H$_2$O with 0.05% NH$_4$OH as mobile phase from 0% to 100%) to give (S)-4-amino-4-(6-(1-(6-(hydroxymethyl)pyridin-2-yl)-1H-indazol-6-yl)pyridin-2-yl)butan-1-ol (95 mg, yield: 65%) as a white solid. ESI-MS (M+H)$^+$: 390.3. HPLC: 96%. $^1$H NMR (400 MHz, CD$_3$OD) δ: 9.65 (s, 1H), 8.31 (s, 1H), 8.10-7.84 (m, 6H), 7.49-7.29 (m, 2H), 4.88 (s, 2H), 4.10 (t, J=6.8 Hz, 1H), 3.61 (t, J=6.8 Hz, 2H), 2.21-1.82 (m, 2H), 1.82-1.36 (m, 2H).

Example 397. (S)-(6-(6-(6-(1-aminoethyl)pyridin-2-yl)-1H-indazol-1-yl)pyrazin-2-yl)methanol Step 1. Synthesis of methyl 6-(6-bromo-1H-indazol-1-yl)pyrazine-2-carboxylate

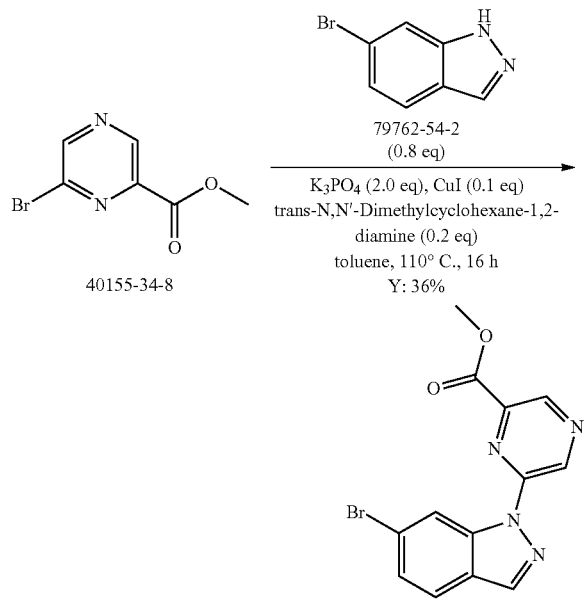

The preparation of methyl 6-(6-bromo-1H-indazol-1-yl)pyrazine-2-carboxylate was similar to that of (6-(4-bromo-6-((4-methoxybenzyl)oxy)-1H-indazol-1-yl)pyridin-2-yl)methanol (Example 352, Step 4) to give 1.1 g as a yellow solid, Y: 36%. ESI-MS (M+H)$^+$: 333.0. $^1$H NMR (400 MHz, CDCl$_3$) δ: 9.61 (s, 1H), 9.21 (s, 1H), 9.17 (s, 1H), 8.28 (s, 1H), 7.71 (d, J=8.4 Hz, 1H), 7.52 (dd, J=8.4, 1.2 Hz, 1H), 4.15 (s, 3H).

Step 2. Synthesis of (6-(6-bromo-1H-indazol-1-yl)pyrazin-2-yl)methanol

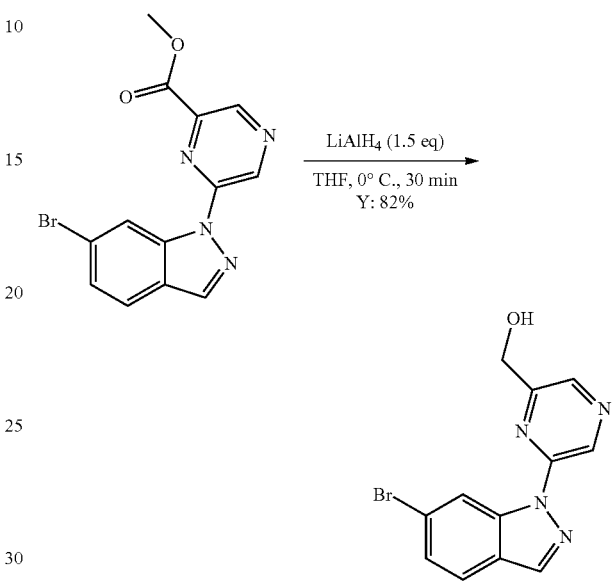

The preparation of (6-(6-bromo-1H-indazol-1-yl)pyrazin-2-yl)methanol was similar to that of (6-(6-(1-aminoethyl)pyridin-2-yl)-1-(6-(trifluoromethyl)pyridin-2-yl)-1H-indazol-4-yl)methanol (Example 57) to give 1.0 g as a yellow solid, Y: 82%. ESI-MS (M+H)$^+$: 305.0.

Step 3. Synthesis of 6-bromo-1-(6-(((tert-butyldimethylsilyl)oxy)methyl)pyrazin-2-yl)-1H-indazole

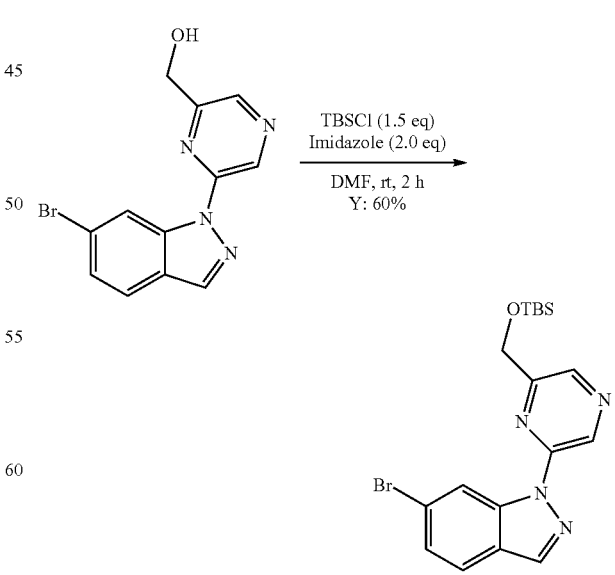

The preparation of 6-bromo-1-(6-(((tert-butyldimethylsilyl)oxy)methyl)pyrazin-2-yl)-1H-indazole was similar to that of 4-bromo-1-(6-(((tert-butyldimethylsilyl)oxy)methyl)pyridin-2-yl)-6-((4-methoxybenzyl)oxy)-1H-indazole (Example 352, Step 5) to give 830 mg as a yellow solid, Y: 60%. ESI-MS (M+H)⁺: 419.1. ¹H NMR (400 MHz, CDCl₃) δ: 9.29 (s, 1H), 8.93 (s, 1H), 8.63 (s, 1H), 8.21 (s, 1H), 7.66 (d, J=8.0 Hz, 1H), 7.44 (dd, J=8.8, 1.6 Hz, 1H), 4.98 (s, 2H), 1.01 (s, 9H), 0.19 (s, 6H).

Step 4. Synthesis of 1-(6-(((tert-butyldimethylsilyl)oxy)methyl)pyrazin-2-yl)-6-(4,4,5,5-tetramethyl-1,3,2-dioxaborolan-2-yl)-1H-indazole

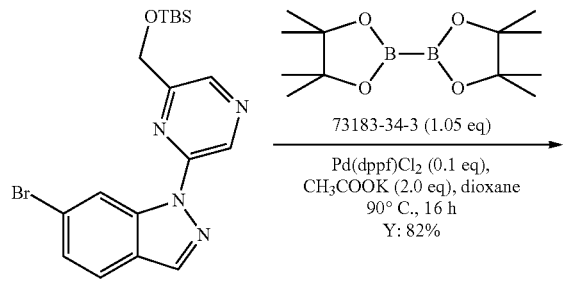

The preparation of 1-(6-(((tert-butyldimethylsilyl)oxy)methyl)pyrazin-2-yl)-6-(4,4,5,5-tetramethyl-1,3,2-dioxaborolan-2-yl)-1H-indazole was similar to that of 1-(6-(((tert-butyldimethylsilyl)oxy)methyl)pyridin-2-yl)-4-(1H-pyrazol-1-yl)-6-(4,4,5,5-tetramethyl-1,3,2-dioxaborolan-2-yl)-1H-indazole (Example 352, Step 9) to give 310 mg as a yellow solid, Y: 82%. ESI-MS (M+H)⁺: 467.3.

Step 5. Synthesis of (R)—N—((S)-1-(6-(1-(6-(((tert-butyldimethylsilyl)oxy)methyl)pyrazin-2-yl)-1H-indazol-6-yl)pyridin-2-yl)ethyl)-2-methylpropane-2-sulfinamide

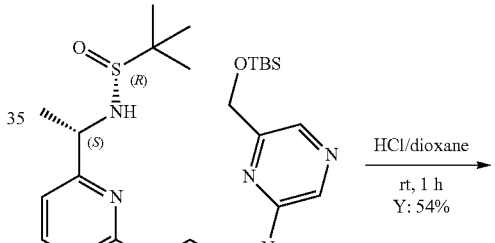

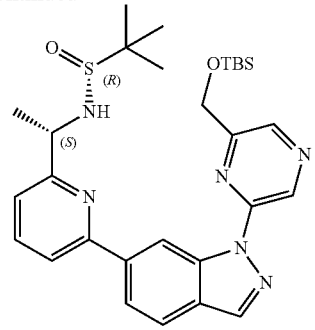

The preparation of (R)—N—((S)-1-(6-(1-(6-(((tert-butyldimethylsilyl)oxy)methyl)pyrazin-2-yl)-1H-indazol-6-yl)pyridin-2-yl)ethyl)-2-methylpropane-2-sulfinamide was similar to that of (R)—N—((S)-1-(6-(1-(6-(((tert-butyldimethylsilyl)oxy)methyl)pyridin-2-yl)-4-(1H-pyrazol-1-yl)-1H-indazol-6-yl)pyridin-2-yl)ethyl)-2-methylpropane-2-sulfinamide (Example 352, Step 10) to give 180 mg as a yellow solid, Y: 48%. ESI-MS (M+H)⁺: 565.3.

Step 6. Synthesis of (S)-(6-(6-(6-(1-aminoethyl)pyridin-2-yl)-1H-indazol-1-yl)pyrazin-2-yl)methanol

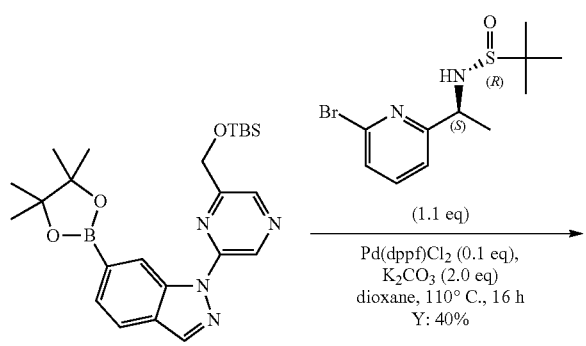

The preparation of (S)-(6-(6-(6-(1-aminoethyl)pyridin-2-yl)-1H-indazol-1-yl)pyrazin-2-yl)methanol was similar to that of (S)-(6-(6-(6-(1-aminoethyl)pyridin-2-yl)-4-(1H-pyrazol-1-yl)-1H-indazol-1-yl)pyridin-2-yl)methanol (Example 352, Step 11) to give 60 mg as a white solid, Y: 54%. ESI-MS (M+H)⁺: 347.2. HPLC: 100%. ¹H NMR (400 MHz, CD₃OD) δ: 9.57 (s, 1H), 9.25 (s, 1H), 8.56 (s, 1H), 8.39 (s, 1H), 8.08 (d, J=8.4 Hz, 1H), 7.95 (d, J=8.8 Hz, 1H), 7.89 (d, J=4.8 Hz, 2H), 7.39 (t, J=4.0 Hz, 1H), 4.92 (s, 2H), 4.25 (q, J=6.8 Hz, 1H), 1.55 (d, J=6.8 Hz, 3H).

The following were synthesized in a similar fashion to Example 397 using the appropriate pyridyl bromide.

| Example # | Structure | Name | LCMS (M+) | ¹H NMR |
|---|---|---|---|---|
| 398 | 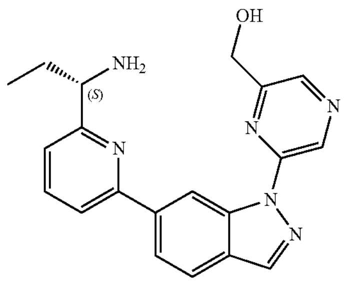 | (S)-(6-(6-(6-(1-aminopropyl)pyridin-2-yl)-1H-indazol-1-yl)pyrazin-2-yl)methanol | 361.2 | ¹H NMR (400 MHz, CD₃OD) δ: 9.55 (s, 1H), 9.25 (s, 1H), 8.56 (s, 1H), 8.38 (s, 1H), 8.07 (dd, J = 8.4, 1.2 Hz, 1H), 7.95 (d, J = 8.8 Hz, 1H), 7.89-7.88 (m, 2H), 7.35 (dd, J = 4.8, 3.6 Hz, 1H), 4.92 (s, 2H), 3.99 (t, J = 6.8 Hz, 1H), 2.03-1.87 (m, 2H), 0.95 (t, J = 7.2 Hz, 3H). |
| 399 | 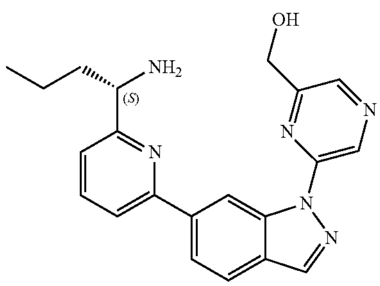 | (S)-(6-(6-(6-(1-aminobutyl)pyridin-2-yl)-1H-indazol-1-yl)pyrazin-2-yl)methanol | 375.2 | ¹H NMR (400 MHz, CD₃OD) δ: 9.51 (s, 1H), 9.22 (s, 1H), 8.54 (s, 1H), 8.36 (s, 1H), 8.04 (dd, J = 8.4, 1.6 Hz, 1H), 7.92 (d, J = 8.4 Hz, 1H), 7.87-7.86 (m, 2H), 7.34 (dd, J = 5.2, 3.6 Hz, 1H), 4.90 (s, 2H), 4.04 (t, J = 6.8 Hz, 1H), 1.92-1.80 (m, 2H), 1.44-1.27 (m, 2H), 0.96 (t, J = 7.6 Hz, 3H). |

Example 400 (S)-(4-(6-(6-(1-aminobutyl)pyridin-2-yl)-1H-indazol-1-yl)pyridin-2-yl)methanol Step 1. Synthesis of (4-(6-bromo-1H-indazol-1-yl)pyridin-2-yl)methanol A mixture of 6-Bromo-1H-indazole (CAS No. 79762-54-2, 1.5 g, 7.6 mmol, 1.0 eq), 4-Bromo-2-pyridinemethanol (CAS No. 131747-45-0, 1.85 g, 9.9 mmol, 1.3 eq), CuI (285 mg, 1.5 mmol, 0.2 eq), K₃PO₄ (3.2 g, 15.2 mmol, 2.0 eq) and 61798-24-1 (426 mg, 3.0 mmol, 0.4 eq) in 1,4-dioxane (15 mL) was stirred at 110° C. for 16 h. After concentration, the residue was purified by silica gel chromatography using PE/EA (3/1) as eluent to give (4-(6-bromo-1H-indazol-1-yl)pyridin-2-yl)methanol as a yellow solid. 750 mg, Y: 32%. ESI-MS (M+H)⁺: 304.1

Step 2. Synthesis of 6-bromo-1-(2-(((tert-butyldimethylsilyl)oxy)methyl)pyridin-4-yl)-1H-indazole

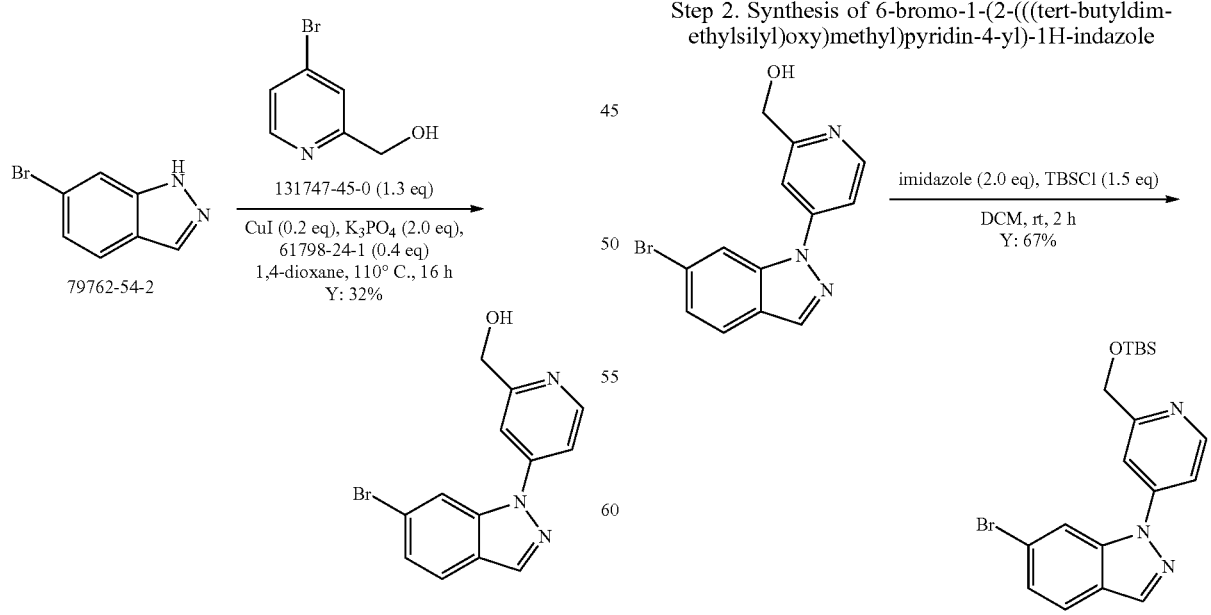

To a solution of (4-(6-bromo-1H-indazol-1-yl)pyridin-2-yl)methanol (750 mg, 2.5 mmol, 1.0 eq) in DCM (10 mL)

was added TBSCl (750 mg, 5.0 mmol, 2.0 eq) and imidazole (340 mg, 5.0 mmol, 2.0 eq). The mixture was stirred at rt for 2 h. After concentration, the residue was purified by silica gel chromatography using PE/EA (5/1) as eluent to give 6-bromo-1-(2-(((tert-butyldimethylsilyl)oxy)methyl)pyridin-4-yl)-1H-indazole. 750 mg, as a white solid, Y: 67%. ESI-MS (M+H)⁺: 418.1.

Step 3. Synthesis of 1-(2-(((tert-butyldimethylsilyl)oxy)methyl)pyridin-4-yl)-6-(4,4,5,5-tetramethyl-1,3,2-dioxaborolan-2-yl)-1H-indazole

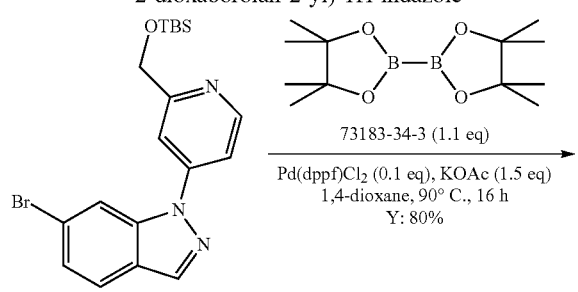

A mixture of 6-bromo-1-(2-(((tert-butyldimethylsilyl)oxy)methyl)pyridin-4-yl)-1H-indazole (700 mg, 1.7 mmol, 1.0 eq), Bis(pinacolato)diboron (CAS No. 73183-34-3, 475 mg, 1.9 mmol, 1.1 eq) and CH₃COOK (333 mg, 3.4 mmol, 2.0 eq) in 1,4-dioxane (10 mL) was stirred while purging N₂ at rt for 10 min. To this system was added Pd(dppf)Cl₂ (90 mg, 0.1 mmol, 0.1 eq) and heated to 90° C. for 16 h. The mixture was diluted with EtOAc (50 mL) and washed with and brine (50 mL×2). The organic phase was dried (Na₂SO₄) and concentrated to give 1-(2-(((tert-butyldimethylsilyl)oxy)methyl)pyridin-4-yl)-6-(4,4,5,5-tetramethyl-1,3,2-dioxaborolan-2-yl)-1H-indazole which was used for next step without further purification. 620 mg, as a brown solid, Y: 80%. ESI-MS (M+H)⁺: 466.3.

Step 4. Synthesis of (R)—N—((S)-1-(6-(1-(2-(((tert-butyldimethylsilyl)oxy)methyl)pyridin-4-yl)-1H-indazol-6-yl)pyridin-2-yl)butyl)-2-methylpropane-2-sulfinamide

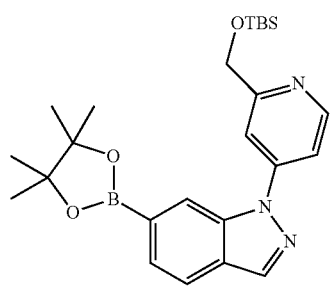

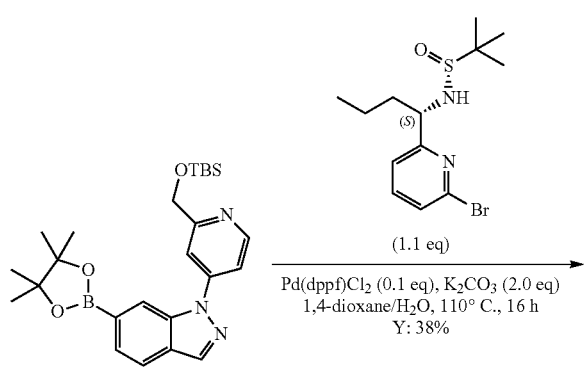

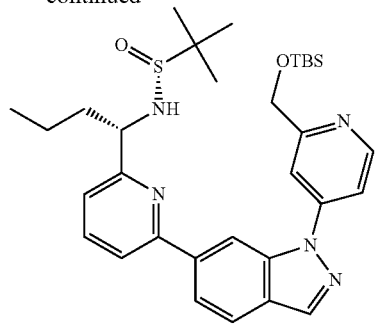

A mixture of 1-(2-(((tert-butyldimethylsilyl)oxy)methyl)pyridin-4-yl)-6-(4,4,5,5-tetramethyl-1,3,2-dioxaborolan-2-yl)-1H-indazole (520 mg, 1.1 mmol, 1.0 eq), (R)—N—((S)-1-(6-bromopyridin-2-yl)butyl)-2-methylpropane-2-sulfinamide (Example 145, Step 5, 402 mg, 1.2 mmol, 1.1 eq) and K₂CO₃ (304 mg, 2.2 mmol, 2.0 eq) in 1,4-dioxane/H₂O (10 mL/1 mL) was stirred while purging N₂ at rt for 10 min. To this system was added Pd(dppf)Cl₂ (92 mg, 0.1 mmol, 0.1 eq) and heated to 110° C. for 16 h. After concentration, the residue was purified by silica gel chromatography using PE/EA (1/1) as eluent to give (R)—N—((S)-1-(6-(1-(2-(((tert-butyldimethylsilyl)oxy)methyl)pyridin-4-yl)-1H-indazol-6-yl)pyridin-2-yl)butyl)-2-methylpropane-2-sulfinamide. 300 mg, as a brown solid, Y: 38%. ESI-MS (M+H)⁺: 592.3.

Step 5. Synthesis of (S)-(4-(6-(6-(1-aminobutyl)pyridin-2-yl)-1H-indazol-1-yl)pyridin-2-yl)methanol

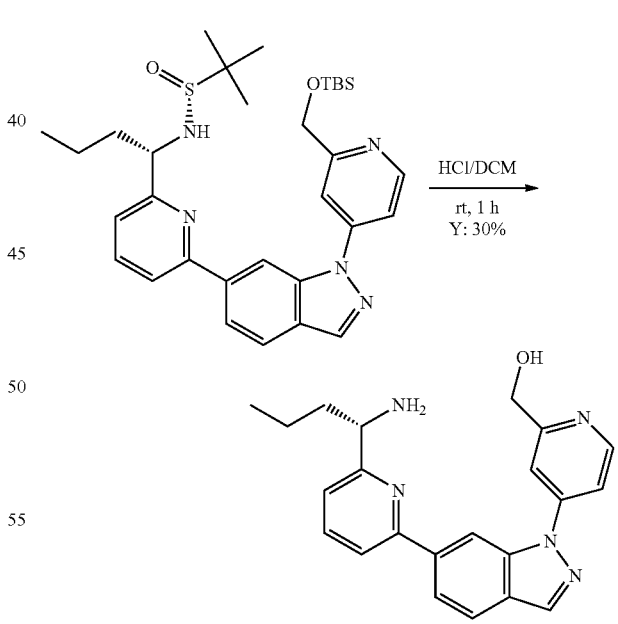

To a solution of (R)—N—((S)-1-(6-(1-(2-(((tert-butyldimethylsilyl)oxy)methyl)pyridin-4-yl)-1H-indazol-6-yl)pyridin-2-yl)butyl)-2-methylpropane-2-sulfinamide (200 mg, 0.34 mmol, 1.0 eq) in DCM (5 mL) was added conc. HCl (0.3 mL). Then the mixture was stirred at rt for 1 h. After concentration, the residue was purified by prep-HPLC (CH₃CN/H₂O with 0.05% NH₄HCO₃ as mobile phase from 5% to 95%) to afford the product (S)-(4-(6-(6-(1-aminobutyl)pyridin-2-yl)-1H-indazol-1-yl)pyridin-2-yl)methanol. 56 mg, as a white solid, Y: 30%. ESI-MS (M+H)+: 374.3. HPLC: 100%. ¹H NMR (400 MHz, CD₃OD) δ: 8.78 (s, 1H), 8.62 (s, 1H), 8.42-8.40 (m, 1H), 8.19 (s, 1H), 8.07-7.90 (m, 5H), 7.38 (d, J=7.6 Hz, 1H), 4.83 (s, 2H), 4.16 (t, J=6.8 Hz, 1H), 1.94-1.82 (m, 2H), 1.47-1.31 (m, 2H), 0.98 (t, J=7.2 Hz, 3H).

Example 401 (S)-(4-(6-(6-(1-aminobutyl)pyridin-2-yl)-1H-indazol-1-yl)pyrimidin-2-yl)methanol Synthesis of (R)-2-methyl-N-((1S)-1-(6-(1-(tetrahydro-2H-pyran-2-yl)-1H-indazol-6-yl)pyridin-2-yl)butyl)propane-2-sulfinamide

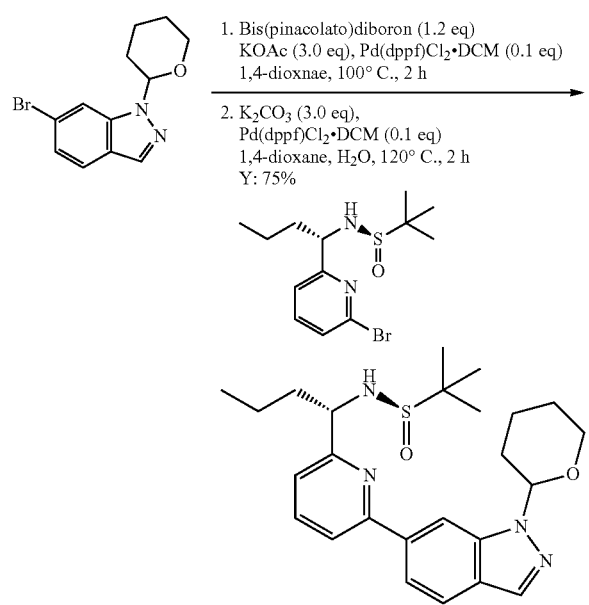

To a solution of 6-bromo-1-(tetrahydro-2H-pyran-2-yl)-1H-indazole (2.9 g, 10.36 mmol, 1.0 eq) in dry 1,4-dioxane (100 mL) were added bis(pinacolato)diboron (3.2 g, 12.43 mmol, 1.2 eq), KOAc (3.05 g, 31.07 mmol, 3.0 eq) and Pd(dppf)Cl₂.DCM (846 mg, 1.04 mmol, 0.1 eq). The mixture was stirred at 100° C. under N₂ for 2 h. After cooling down to rt, H₂O (10 mL), K₂CO₃ (4.3 g, 31.07 mmol, 3.0 eq), Pd(dppf)Cl₂.DCM (846 mg, 1.04 mmol, 0.1 eq) and (R)—N—((S)-1-(6-bromopyridin-2-yl)butyl)-2-methylpropane-2-sulfinamide (Example 145, Step 5, 3.44 g, 10.36 mmol, 1.0 eq) were added to the mixture. The mixture was stirred at 120° C. under N₂ for further 2 h. The mixture was diluted with water (200 mL) and extracted with EA (50 mL×3). The combined organic fractions were dried (Na₂SO₄), filtrated, concentrated and purified by silica gel chromatography (PE/EA=5/1) to give the title compound. 3.5 g, as a yellow solid, Y: 75%. ESI-MS (M+H)+: 455.2. ¹H NMR (400 MHz, CDCl₃) δ: 8.26 (d, J=13.2 Hz, 1H), 8.07 (s, 1H), 7.84-7.80 (m, 4H), 7.20 (d, J=6.4 Hz, 1H), 5.84 (dd, J=9.6, 2.4 Hz, 1H), 4.59-4.54 (m, 1H), 4.28-4.22 (m, 1H), 4.08-4.05 (m, 1H), 3.85-3.78 (m, 1H), 2.68-2.61 (m, 1H), 2.20-2.11 (m, 2H), 2.03-1.97 (m, 2H), 1.70-1.64 (m, 2H), 1.43-1.32 (m, 2H), 1.20 (s, 9H), 0.95 (t, J=7.2 Hz, 3H).

Synthesis of (R)—N—((S)-1-(6-(1H-indazol-6-yl)pyridin-2-yl)butyl)-2-methylpropane-2-sulfinamide

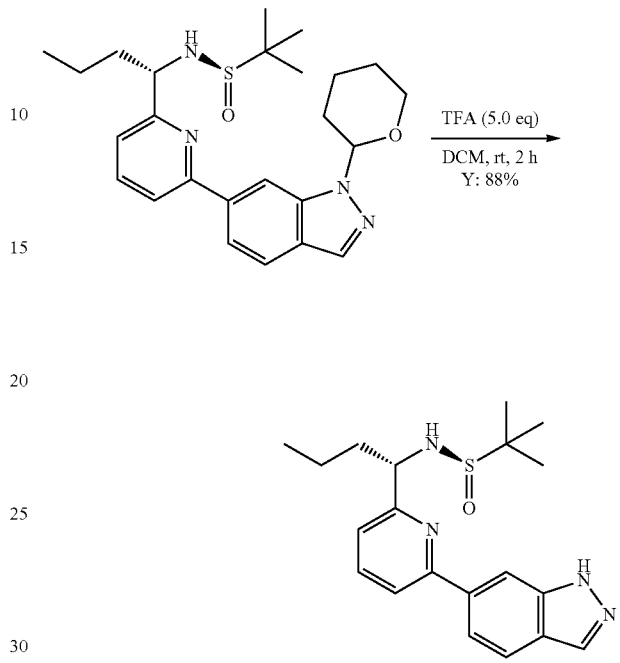

To a solution of (R)-2-methyl-N-((1S)-1-(6-(1-(tetrahydro-2H-pyran-2-yl)-1H-indazol-6-yl)pyridin-2-yl)butyl)propane-2-sulfinamide (3.5 g, 7.71 mmol, 1.0 eq) in DCM (100 mL) was added TFA (2.9 mL, 4.4 g, 38.55 mmol, 5.0 eq). The mixture was stirred at rt for 2 h and adjusted pH=7 with sat. NaHCO₃. The residue was extracted with EtOAc (50 mL×3). The combined organic fractions were dried (Na₂SO₄), filtrated and concentrated in vacuo to give (R)—N—((S)-1-(6-(1H-indazol-6-yl)pyridin-2-yl)butyl)-2-methylpropane-2-sulfinamide which was used for next step without further purification. 2.5 g, Y: 88%. ESI-MS (M+H)+: 371.2. ¹H NMR (400 MHz, CDCl₃) δ: 8.23 (s, 1H), 8.11 (s, 1H), 7.83-7.80 (m, 2H), 7.75-7.68 (m, 2H), 7.20 (d, J=7.2 Hz, 1H), 4.58-4.53 (m, 1H), 4.24-4.23 (m, 1H), 1.99-1.96 (m, 2H), 1.52-1.32 (m, 2H), 1.20 (s, 9H), 0.92 (t, J=7.2 Hz, 3H).

Synthesis of (R)—N—((S)-1-(6-(1-(2-chloropyrimidin-4-yl)-1H-indazol-6-yl)pyridin-2-yl)butyl)-2-methylpropane-2-sulfinamide

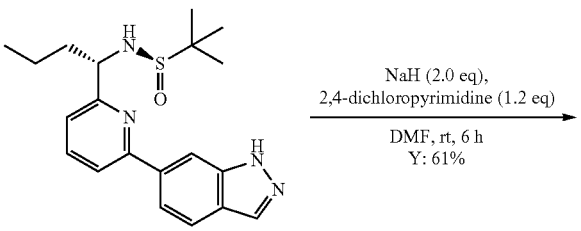

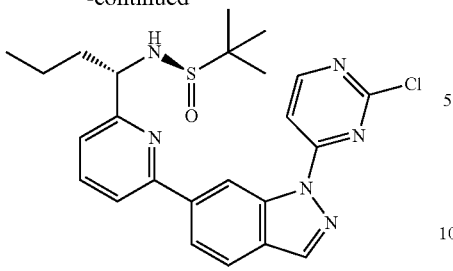

A solution of (R)—N—((S)-1-(6-(1H-indazol-6-yl)pyridin-2-yl)butyl)-2-methylpropane-2-sulfinamide (2.5 g, 6.76 mmol, 1.0 eq) in dry DMF (100 mL) cooled to 0° C. was treated with NaH (60%, 540 mg, 13.51 mmol, 2.0 eq) in portions. After stirring at rt for 2 h, 2,4-dichloropyrimidine (1.2 g, 8.11 mmol, 1.2 eq) was added and the mixture was stirred at rt for 4 h. The mixture was quenched with water and extracted with EA (50 mL×3). The combined organic layers were dried over $Na_2SO_4$ and evaporated. The residue was purified by column chromatography (PE/EA=3/1) to afford (R)—N—((S)-1-(6-(1-(2-chloropyrimidin-4-yl)-1H-indazol-6-yl)pyridin-2-yl)butyl)-2-methylpropane-2-sulfinamide. 2.0 g, as a white solid, Y: 61%. ESI-MS (M+H)$^+$: 483.2.

Synthesis of methyl 4-(6-(6-((S)-1-((R)-1,1-dimethylethylsulfinamido)butyl)pyridin-2-yl)-1H-indazol-1-yl)pyrimidine-2-carboxylate

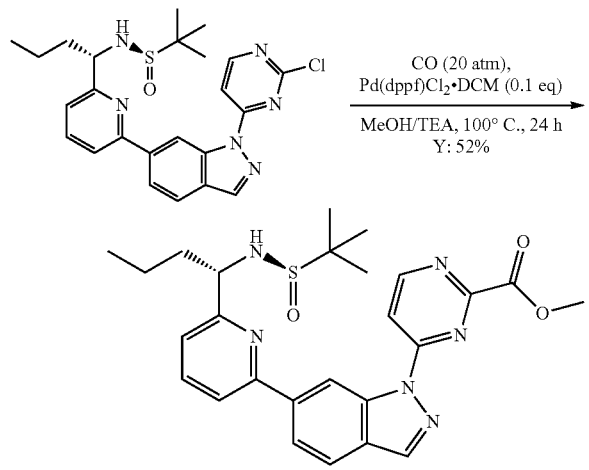

To a solution of (R)—N—((S)-1-(6-(1-(2-chloropyrimidin-4-yl)-1H-indazol-6-yl)pyridin-2-yl)butyl)-2-methylpropane-2-sulfinamide (2.0 g, 4.15 mmol, 1.0 eq) in MeOH (100 mL) were added Pd(dppf)Cl$_2$.DCM (380 mg, 0.42 mmol, 0.1 eq) and Et$_3$N (838 mg, 8.30 mmol, 2.0 eq). The mixture was stirred under an atmosphere of 20 atm CO at 100° C. for 24 h. After concentration, the residue was purified by chromatography (PE/EA=1/1) to give methyl 4-(6-(6-((S)-1-((R)-1,1-dimethylethylsulfinamido)butyl)pyridin-2-yl)-1H-indazol-1-yl)pyrimidine-2-carboxylate. 1.1 g, as a white solid, Y: 52%. ESI-MS (M+H)$^+$: 507.2. $^1$H NMR (400 MHz, CDCl$_3$) δ: 9.89 (s, 1H), 8.91 (d, J=6.0 Hz, 1H), 8.32 (s, 1H), 7.42 (dd, J=8.0, 1.2 Hz, 1H), 8.13 (d, J=5.6 Hz, 1H), 7.95-7.80 (m, 3H), 7.23 (d, J=7.2 Hz, 1H), 4.57-4.54 (m, 1H), 4.44-4.42 (m, 1H), 4.16 (s, 3H), 2.08-2.01 (m, 2H), 1.52-1.32 (m, 2H), 1.16 (s, 9H), 0.95 (t, J=7.2 Hz, 3H).

Synthesis of (R)—N—((S)-1-(6-(1-(2-(hydroxymethyl)pyrimidin-4-yl)-1H-indazol-6-yl)pyridin-2-yl)butyl)-2-methylpropane-2-sulfinamide

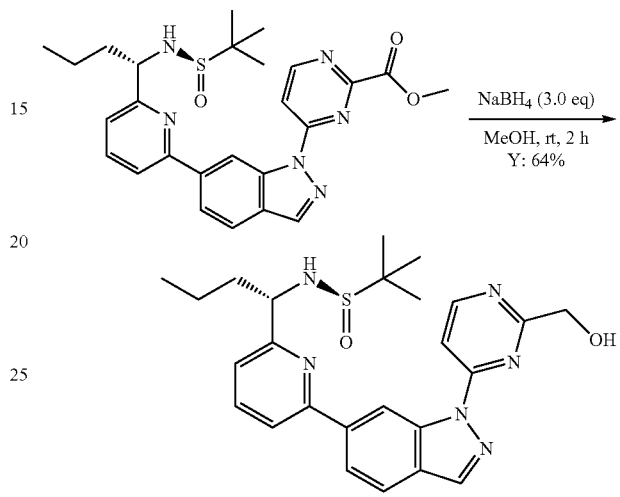

To a suspension of methyl 4-(6-(6-((S)-1-((R)-1,1-dimethylethylsulfinamido)butyl)pyridin-2-yl)-1H-indazol-1-yl)pyrimidine-2-carboxylate (500 mg, 0.99 mmol, 1.0 eq) in MeOH (50 mL) at 0° C. was added NaBH$_4$ (113 mg, 2.96 mmol, 3.0 eq). The reaction mixture was stirred at rt for 2 h. The solvent was removed by evaporation, and then the residue was diluted with water (100 mL) and extracted with EtOAc (30 mL×3). The combined organic layers were washed with brine (30 mL), dried (Na$_2$SO$_4$), concentrated and purified by prep-TLC (DCM/MeOH=20/1) to afford (R)—N—((S)-1-(6-(1-(2-(hydroxymethyl)pyrimidin-4-yl)-1H-indazol-6-yl)pyridin-2-yl)butyl)-2-methylpropane-2-sulfinamide. 300 mg, as a white solid, Y: 64%. ESI-MS (M+H)$^+$: 479.2. $^1$H NMR (400 MHz, CDCl$_3$) δ: 9.73 (s, 1H), 8.73 (d, J=5.6 Hz, 1H), 8.23 (s, 1H), 8.03-8.01 (m, 1H), 7.90-7.85 (m, 2H), 7.79-7.78 (m, 2H), 7.24-7.22 (m, 1H), 4.99 (d, J=4.4 Hz, 2H), 4.56-4.52 (m, 2H), 4.19-4.17 (m, 1H), 2.09-2.04 (m, 2H), 1.45-1.24 (m, 2H), 1.18 (s, 9H), 0.95 (t, J=7.2 Hz, 3H).

Synthesis of (S)-(4-(6-(6-(1-aminobutyl)pyridin-2-yl)-1H-indazol-1-yl)pyrimidin-2-yl)methanol

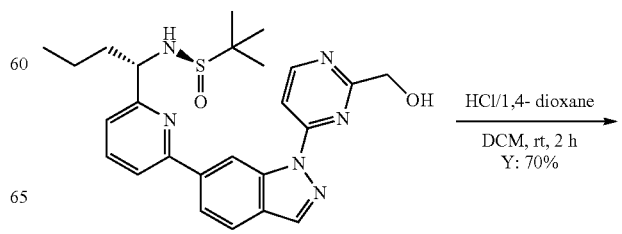

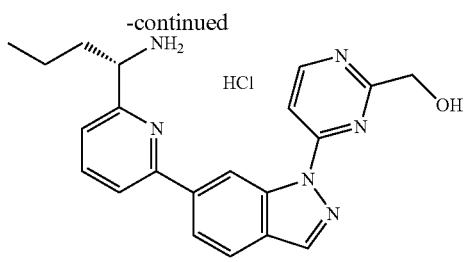

The preparation of (S)-(4-(6-(6-(1-aminobutyl)pyridin-2-yl)-1H-indazol-1-yl)pyrimidin-2-yl)methanol was similar to that of (S)-(4-(6-(6-(1-aminobutyl)pyridin-2-yl)-1H-indazol-1-yl)pyridin-2-yl)methanol (Example 400, Step 5) using 1,4-dioxane in place of DCM to give 220 mg as a yellow solid, Y: 70%. ESI-MS (M+H)⁺: 375.2. HPLC: 100%. ¹H NMR (400 MHz, CD₃OD) δ: 9.58 (s, 1H), 8.89 (d, J=7.2 Hz, 1H), 8.73 (s, 1H), 8.45-8.41 (m, 2H), 8.16-8.06 (m, 3H), 7.54 (d, J=7.2 Hz, 1H), 5.23 (s, 2H), 4.61 (t, J=6.8 Hz, 1H), 2.11-2.04 (m, 2H), 1.51-1.39 (m, 2H), 1.04 (t, J=7.2 Hz, 3H).

Example 402 (S)-(3-(6-(6-(1-aminobutyl)pyridin-2-yl)-1H-indazol-1-yl)phenyl)methanol Synthesis of (3-(6-bromo-1H-indazol-1-yl)phenyl)methanol

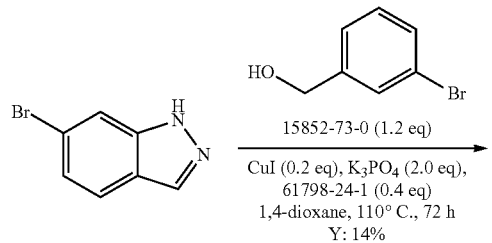

The preparation of (3-(6-bromo-1H-indazol-1-yl)phenyl)methanol was similar to that of (4-(6-bromo-1H-indazol-1-yl)pyridin-2-yl)methanol (Example 400, Step 1) to give 680 mg as a yellow solid, Y: 14%. ESI-MS (M+H)⁺: 303.1. ¹H NMR (400 MHz, CDCl₃) δ: 8.17 (s, 1H), 7.90 (s, 1H), 7.71-7.65 (m, 2H), 7.60 (d, J=8.0 Hz, 1H), 7.54 (d, J=8.0 Hz, 1H), 7.39 (d, J=7.6 Hz, 1H), 7.34 (dd, J=8.4, 1.2 Hz, 1H), 4.82 (d, J=4.4 Hz, 2H).

Synthesis of 6-bromo-1-(3-(((tert-butyldimethylsilyl)oxy)methyl)phenyl)-1H-indazole

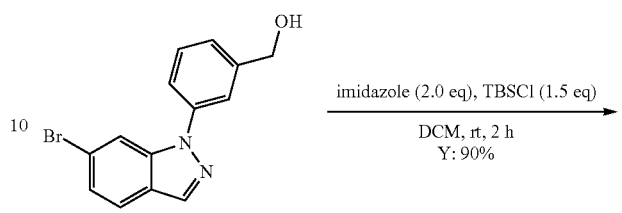

The preparation of 6-bromo-1-(3-(((tert-butyldimethylsilyl)oxy)methyl)phenyl)-1H-indazole was similar to that of 6-bromo-1-(2-(((tert-butyldimethylsilyl)oxy)methyl)pyridin-4-yl)-1H-indazole (Example 400, Step 2) to give 850 mg as a white solid, Y: 90%. ESI-MS (M+H)⁺: 417.1.

Synthesis of 1-(3-(((tert-butyldimethylsilyl)oxy)methyl)phenyl)-6-(4,4,5,5-tetramethyl-1,3,2-dioxaborolan-2-yl)-1H-indazole

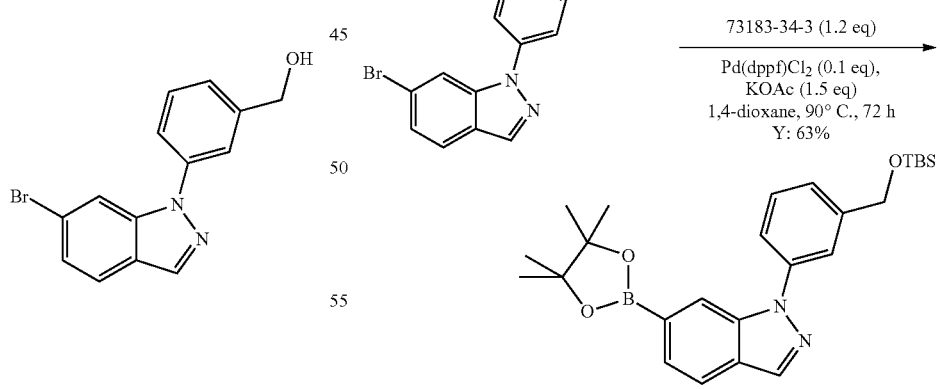

The preparation of 1-(3-(((tert-butyldimethylsilyl)oxy)methyl)phenyl)-6-(4,4,5,5-tetramethyl-1,3,2-dioxaborolan-2-yl)-1H-indazole was similar to that of 1-(2-(((tert-butyldimethylsilyl)oxy)methyl)pyridin-4-yl)-6-(4,4,5,5-tetramethyl-1,3,2-dioxaborolan-2-yl)-1H-indazole (Example 400, Step 3) to give 600 mg as a brown solid, Y: 63%. ESI-MS (M+H)⁺: 465.2.

433

Synthesis of (R)—N—((S)-1-(6-(1-(3-(((tert-butyldimethylsilyl)oxy)methyl)phenyl)-1H-indazol-6-yl)pyridin-2-yl)butyl)-2-methylpropane-2-sulfinamide

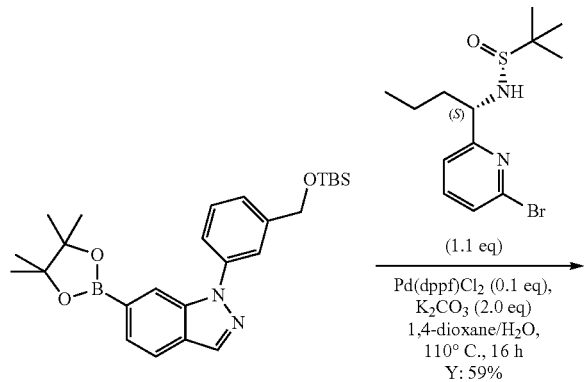

The preparation of (R)—N—((S)-1-(6-(1-(3-(((tert-butyldimethylsilyl)oxy)methyl)phenyl)-1H-indazol-6-yl)pyridin-2-yl)butyl)-2-methylpropane-2-sulfinamide was similar to that of (R)—N—((S)-1-(6-(1-(2-(((tert-butyldimethylsilyl)oxy)methyl)pyridin-4-yl)-1H-indazol-6-yl)pyridin-2-yl)butyl)-2-methylpropane-2-sulfinamide (Example 400, Step 4) to give 450 mg as a yellow solid, Y: 59%. ESI-MS (M+H)+: 591.3.

Synthesis of (S)-(3-(6-(6-(1-aminobutyl)pyridin-2-yl)-1H-indazol-1-yl)phenyl)methanol

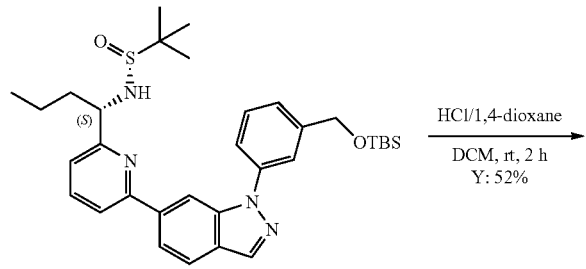

434

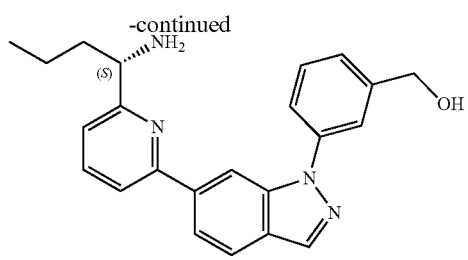

The preparation of (S)-(3-(6-(6-(1-aminobutyl)pyridin-2-yl)-1H-indazol-1-yl)phenyl)methanol was similar to that of (S)-(6-(6-(6-(1-aminoethyl)pyridin-2-yl)-1H-indazol-1-yl)pyrazin-2-yl)methanol (Example 397, Step 6) to give 150 mg as a white solid, Y: 52%. ESI-MS (M+H)+: 373.2. HPLC: 100%. 1H NMR (400 MHz, CD3OD) δ: 8.53 (s, 1H), 8.29 (s, 1H), 8.04 (dd, J=8.4, 1.2 Hz, 1H), 8.00 (d, J=8.0 Hz, 1H), 7.96-7.91 (m, 2H), 7.81 (s, 1H), 7.68 (d, J=8.0 Hz, 1H), 7.57 (t, J=8.0 Hz, 1H), 7.41-7.38 (m, 2H), 4.73 (s, 2H), 4.49 (t, J=6.8 Hz, 1H), 2.04-1.89 (m, 2H), 1.46-1.30 (m, 2H), 0.96 (t, J=7.6 Hz, 3H).

Example 403 (S)-(2-(6-(6-(1-aminobutyl)pyridin-2-yl)-1H-indazol-1-yl)pyrimidin-4-yl)methanol Synthesis of methyl 2-(6-bromo-1H-indazol-1-yl)pyrimidine-4-carboxylate

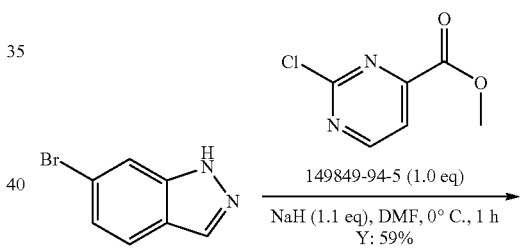

To a solution of 6-bromo-1H-indazole (Cas No. 79762-54-2, 400 mg, 2.04 mmol, 1.0 eq) in DMF (6 mL) was added NaH (90 mg, 2.24 mmol, 1.1 eq) at 0° C. After stirring at 0° C. for 15 min, Methyl 2-chloropyrimidine-4-carboxylate (CAS No. 149849-94-5, 352 mg, 2.04 mmol, 1.0 eq) dissolving in DMF (2 mL) was added and the reaction mixture was stirred at 0° C. for 1 h. The reaction mixture was poured into H2O (40 mL) and stirred at rt for 15 min. The precipitate was collected by filtration and dried to give methyl 2-(6-bromo-1H-indazol-1-yl)pyrimidine-4-carboxylate. 400 mg, as a yellow solid, Y: 59%. ESI-MS (M+H)+: 333.0.

435
Synthesis of (2-(6-bromo-1H-indazol-1-yl)pyrimidin-4-yl)methanol

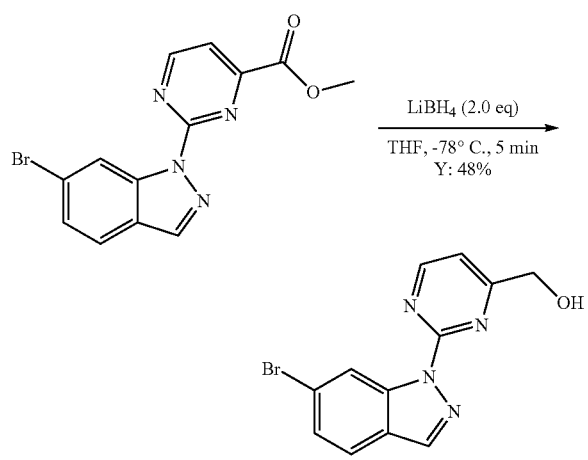

To a solution of methyl 2-(6-bromo-1H-indazol-1-yl)pyrimidine-4-carboxylate (300 mg, 0.9 mmol, 1.0 eq in THF (15 mL) was added LiBH₄ (1.8 mL, 1.8 mmol, 2.0 eq) dropwised at −78° C. After stirring at −78° C. for 5 min, the reaction was quenched with sat. NH₄Cl solution. The mixture was filtrated and the filtrate was extracted with EA (30 mL×3). The combined organic phases were dried and concentrated to give (2-(6-bromo-1H-indazol-1-yl)pyrimidin-4-yl)methanol. 110 mg, as a yellow solid, Y: 48%. ESI-MS (M+H)⁺: 305.0.

Synthesis of 6-bromo-1-(4-(((tert-butyldimethylsilyl)oxy)methyl)pyrimidin-2-yl)-1H-indazole

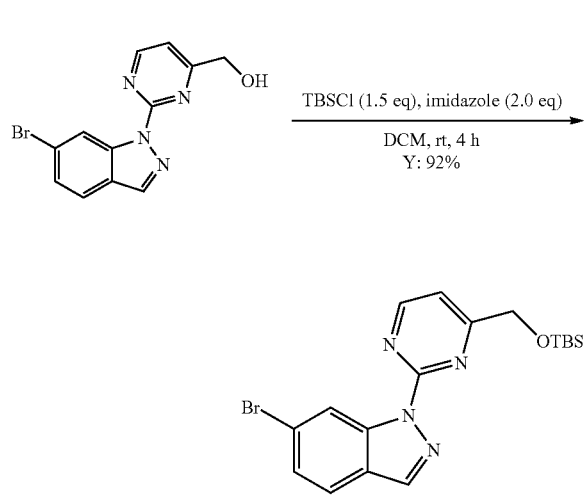

The preparation of 6-bromo-1-(4-(((tert-butyldimethylsilyl)oxy)methyl)pyrimidin-2-yl)-1H-indazole was similar to that of 6-bromo-1-(2-(((tert-butyldimethylsilyl)oxy)methyl)pyridin-4-yl)-1H-indazole (Example 400, Step 2) to give 140 mg as a white solid, Y: 92%. ESI-MS (M+H)⁺: 419.1. ¹H NMR (400 MHz, CDCl₃) δ: 9.02 (s, 1H), 8.83 (d, J=5.2 Hz, 1H), 8.27 (s, 1H), 7.65 (d, J=8.4 Hz, 1H), 7.47-7.44 (m, 2H), 4.95 (s, 2H), 0.92 (s, 9H), 0.08 (s, 6H).

436
Synthesis of 1-(4-(((tert-butyldimethylsilyl)oxy)methyl)pyrimidin-2-yl)-6-(4,4,5,5-tetramethyl-1,3,2-dioxaborolan-2-yl)-1H-indazole

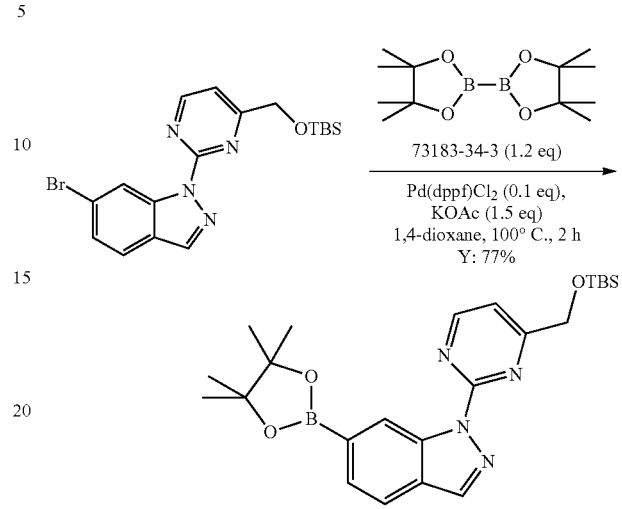

The preparation of 1-(4-(((tert-butyldimethylsilyl)oxy)methyl)pyrimidin-2-yl)-6-(4,4,5,5-tetramethyl-1,3,2-dioxaborolan-2-yl)-1H-indazole was similar to that of 1-(2-(((tert-butyldimethylsilyl)oxy)methyl)pyridin-4-yl)-6-(4,4,5,5-tetramethyl-1,3,2-dioxaborolan-2-yl)-1H-indazole (Example 400, Step 3) to give 120 mg as a brown solid, Y: 77%. ESI-MS (M+H)⁺: 467.2.

Synthesis of (R)—N—((S)-1-(6-(1-(4-(((tert-butyldimethylsilyl)oxy)methyl)pyrimidin-2-yl)-1H-indazol-6-yl)pyridin-2-yl)butyl)-2-methylpropane-2-sulfinamide The preparation of (R)—N—((S)-1-(6-(1-(4-(((tert-butyldimethylsilyl)oxy)methyl)pyrimidin-2-yl)-1H-indazol-6-yl)pyridin-2-yl)butyl)-2-methylpropane-2-sulfinamide was similar to that of (R)—N—((S)-1-(6-(1-(2-(((tert-butyldimethylsilyl)oxy)methyl)pyridin-4-yl)-1H-indazol-6-yl)pyridin-2-yl)butyl)-2-methylpropane-2-sulfinamide (Example 400, Step 4) to give 100 mg as yellow oil, Y: 66%. ESI-MS (M+H)⁺: 593.3.

Synthesis of (S)-(2-(6-(6-(1-aminobutyl)pyridin-2-yl)-1H-indazol-1-yl)pyrimidin-4-yl)methanol

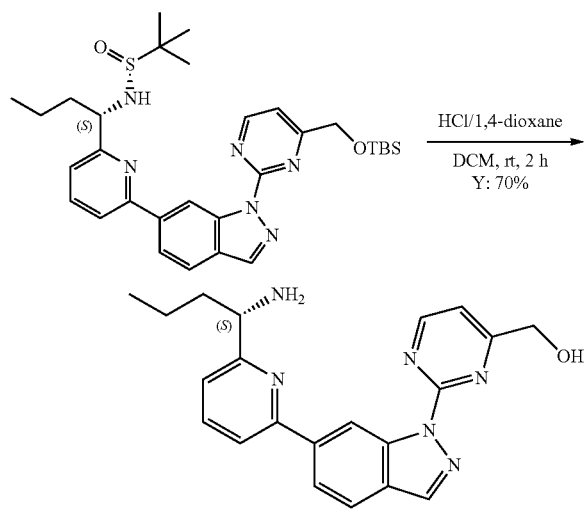

The preparation of (S)-(2-(6-(6-(1-aminobutyl)pyridin-2-yl)-1H-indazol-1-yl)pyrimidin-4-yl)methanol was similar to that of (S)-(6-(6-(6-(1-aminoethyl)pyridin-2-yl)-1H-indazol-1-yl)pyrazin-2-yl)methanol (Example 397, Step 6) to give 58 mg as a white solid, Y: 70%. ESI-MS (M+H)⁺: 375.2. HPLC: 100%. ¹H NMR (400 MHz, CD₃OD) δ: 9.57 (s, 1H), 8.86 (d, J=4.8 Hz, 1H), 8.44 (s, 1H), 8.22 (d, J=8.4 Hz, 1H), 8.09-7.98 (m, 3H), 7.48-7.46 (m, 2H), 4.87 (s, 2H), 4.58 (t, J=6.8 Hz, 1H), 2.11-2.03 (m, 2H), 1.51-1.41 (m, 2H), 1.04 (t, J=7.2 Hz, 3H).

Example 404. (S)-(6-(6-(4-(1-aminobutyl)pyridin-2-yl)-1H-indazol-1-yl)pyridin-2-yl)methanol Step 1. Synthesis of 2-bromo-N-methoxy-N-methylisonicotinamide

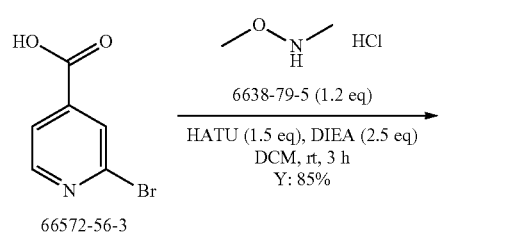

-continued

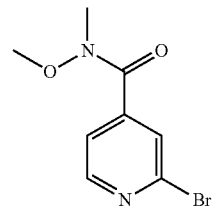

To a solution of 2-Bromopyridine-4-carboxylic acid (CAS no. 66572-56-3, 6.1 g, 30 mmol, 1.0 eq) in dichloromethane (100 mL) were added N,O-dimethylhydroxylamine hydrochloride (CAS No. 6638-79-5, 3.5 g, 36 mmol, 1.2 eq), HATU (17.0 g, 45 mmol, 1.5 eq) and DIEA (12.4 mL, 75 mmol, 2.5 eq). The mixture was stirred at room temperature for 16 h under N₂ atmosphere. The mixture was diluted with dichloromethane (200 mL) and washed with water (80 mL×3). The organic layer was dried over anhydrous sodium sulfate, filtrated and concentrated under reduced pressure. The residue was purified by silica gel column chromatography (PE/EA=2/1) to give 2-bromo-N-methoxy-N-methylisonicotinamide (6.3 g, Y: 85%) as colorless oil. ESI-MS (M+1)⁺: 247.0, 245.0.

Step 2. Synthesis of 1-(2-bromopyridin-4-yl)butan-1-one

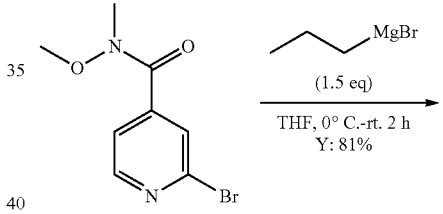

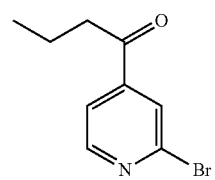

To a mixture of 2-bromo-N-methoxy-N-methylisonicotinamide (2.5 g, 10.2 mmol, 1.0 eq) in anhydrous THF (60 mL) was added propylmagnesium bromide (2.0 M in THF, 7.7 mL, 15.3 mmol, 1.5 eq) at 0° C. under N₂ atmosphere. The mixture was stirred at rt for 2 h. The reaction was quenched with saturated aqueous ammonium chloride (40 mL). The mixture was extracted with ethyl acetate (50 mL×2). The organic layers were dried over anhydrous sodium sulfate and concentrated under reduced pressure. The residue was purified by silica gel column chromatography (PE/EA=5/1) to give 1-(2-bromopyridin-4-yl)butan-1-one (1.9 g, Y: 81%) as colorless oil. ESI-MS (M+1)⁺: 228.0, 230.0. ¹H NMR (400 MHz, CDCl₃) δ: 8.55 (d, J=5.2 Hz, 1H), 7.91 (s, 1H), 7.69 (dd, J=5.2, 1.2 Hz, 1H), 2.94 (t, J=7.2 Hz, 2H), 1.82-1.72 (m, 2H), 1.03 (t, J=7.2 Hz, 3H).

Step 3. Synthesis of (R,E)-N-(1-(2-bromopyridin-4-yl)butylidene)-2-methylpropane-2-sulfinamide

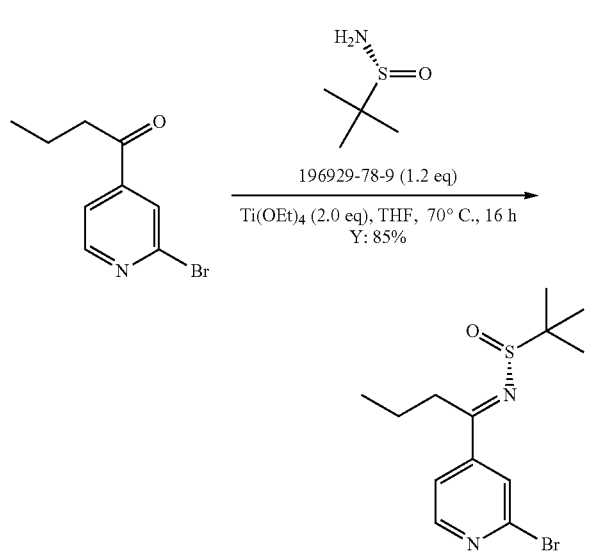

To a solution of 1-(2-bromopyridin-4-yl)butan-1-one (1.9 g, 8.4 mmol, 1.0 eq) in THF (60 mL) was added (R)-2-methylpropane-2-sulfinamide (CAS No. 196929-78-9, 1.2 g, 10.1 mmol, 1.2 eq) and titanium ethoxide (3.5 mL, 16.8 mmol, 2.0 eq). The mixture was stirred at 70° C. for 16 h under N₂ atmosphere. After cooling down to rt, the mixture was diluted with ethyl acetate (200 mL), and water (100 mL) was added. Then the mixture was filtered and washed with ethyl acetate (50 mL×3). The combined organic layers were dried over anhydrous sodium sulfate, filtrated and concentrated under reduced pressure. The residue was purified by silica gel column chromatography (PE/EA=2/1) to give (R,E)-N-(1-(2-bromopyridin-4-yl)butylidene)-2-methylpropane-2-sulfinamide (2.3 g, Y: 85%) as yellow oil. ESI-MS (M+1)⁺: 331.0, 333.0. ¹H NMR (400 MHz, CDCl₃) δ: 8.47 (d, J=5.2 Hz, 1H), 7.78 (s, 1H), 7.57 (dd, J=4.0 Hz, 1H), 3.27-3.07 (m, 2H), 1.71-1.59 (m, 2H), 1.33 (s, 9H), 1.05 (t, J=7.2 Hz, 3H).

Step 4. Synthesis of (R)—N—((S)-1-(2-bromopyridin-4-yl)butyl)-2-methylpropane-2-sulfinamide

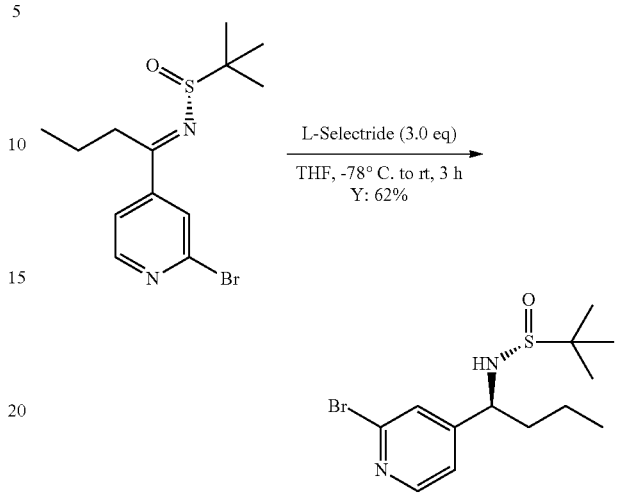

To a solution of (R,E)-N-(1-(2-bromopyridin-4-yl)butylidene)-2-methylpropane-2-sulfinamide (2.3 g, 7.0 mmol, 1.0 eq) in anhydrous THF (100 mL) was added L-selectride (1.0 M in THF, 21.0 mL, 21.0 mmol, 3.0 eq) at −78° C. under N₂ atmosphere. The mixture was stirred at rt for 3 h. The reaction was quenched with saturated aqueous ammonium chloride (60 mL). The mixture was extracted with ethyl acetate (50 mL×2). The combined organic layers were dried over anhydrous sodium sulfate, filtrated and concentrated under reduced pressure. The residue was purified by silica gel column chromatography (PE/EA=2/1) to give (R)—N—((S)-1-(2-bromopyridin-4-yl)butyl)-2-methylpropane-2-sulfinamide (1.4 g, Y: 62%) as colorless oil. ESI-MS (M+1)⁺: 333.0, 335.0. ¹H NMR (400 MHz, CDCl₃) δ: 8.33 (d, J=5.2 Hz, 1H), 7.43 (s, 1H), 7.19 (d, J=5.2 Hz, 1H), 4.38 (t, J=6.4 Hz, 1H), 3.39 (br, 1H), 1.81-1.69 (m, 2H), 1.37-1.21 (m, 2H), 1.21 (s, 9H), 0.95 (t, J=7.2 Hz, 3H).

Step 5. Synthesis of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide

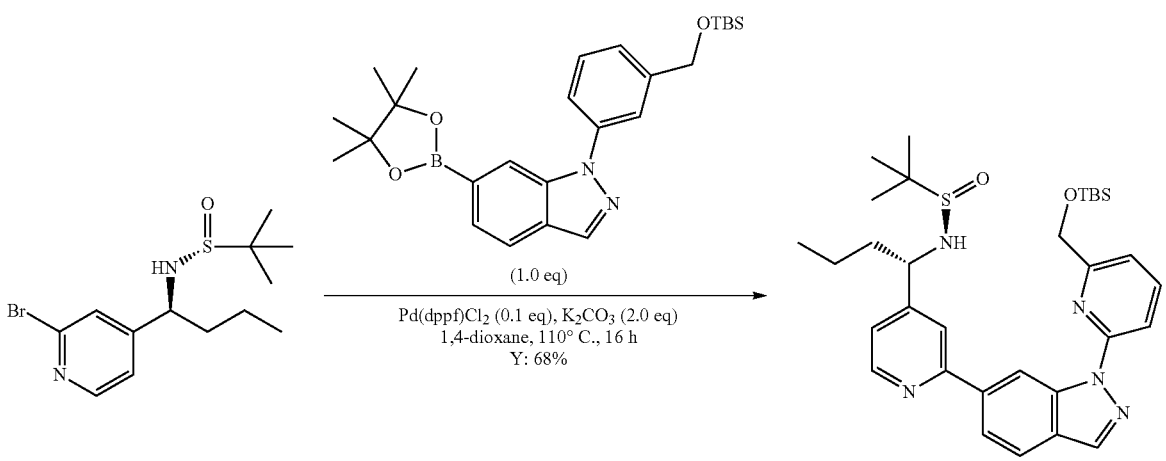

To a solution of (R)—N—((S)-1-(2-bromopyridin-4-yl)butyl)-2-methylpropane-2-sulfinamide (490 mg, 1.5 mmol, 1.0 eq) in 1,4-dioxane/H₂O (20 mL/1.0 mL) were added 1-(6-(((tert-butyldimethylsilyl)oxy)methyl)pyridin-2-yl)-6-(4,4,5,5-tetramethyl-1,3,2-dioxaborolan-2-yl)-1H-indazole, (Example 143, Step 3) 698 mg, 1.5 mmol, 1.0 eq), Pd(dppf)₂Cl₂ (122 mg, 0.15 mmol, 0.1 eq), K₂CO₃ (414 mg, 3.0 mmol, 2.0 eq). The mixture was stirred at 110° C. for 16 h under N₂ atmosphere. After concentration, the residue was purified by silica gel column chromatography (PE/EA=5/1) to give (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (595 mg, Y: 68%) as yellow oil. ESI-MS (M+1)⁺: 592.3. ¹H NMR (400 MHz, CDCl₃) δ: 9.38 (s, 1H), 8.72 (d, J=4.8 Hz, 1H), 8.22 (s, 1H), 7.94-7.85 (m, 4H), 7.78 (s, 1H), 7.42 (d, J=7.2 Hz, 1H), 7.24 (d, J=4.8 Hz, 1H), 4.98 (s, 2H), 4.52 (t, J=5.6 Hz, 1H), 3.45 (s, 1H), 1.90-1.83 (m, 2H), 1.42-1.25 (m, 2H), 1.22 (s, 9H), 1.00 (s, 9H), 0.99 (t, J=7.2 Hz, 3H), 0.17 (s, 6H).

Step 6. Synthesis of (S)-(6-(6-(4-(1-aminobutyl)pyridin-2-yl)-1H-indazol-1-yl)pyridin-2-yl)methanol

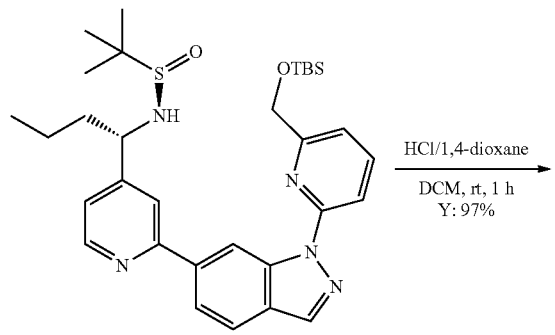

To a solution of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (590 mg, 1.0 mmol, 1.0 eq) in dichloromethane (30 mL) was added 4.0 M HCl in 1,4-dioxane (3 mL). The mixture was stirred at rt for 1 h. Then the solution was filtered and washed with dichloromethane to get (S)-(6-(6-(4-(1-aminobutyl)pyridin-2-yl)-1H-indazol-1-yl)pyridin-2-yl)methanol (400 mg, Y: 97%) as a yellow solid. ESI-MS (M+1)⁺: 374.2. HPLC: 95%. ¹H NMR (400 MHz, CD₃OD) δ: 9.64 (s, 1H), 9.03 (d, J=7.0 Hz, 1H), 8.59 (s, 1H), 8.49 (s, 1H), 8.21 (d, J=8.4 Hz, 1H), 8.13 (d, J=5.6 Hz, 1H), 8.07-8.01 (m, 2H), 7.92 (d, J=8.4 Hz, 1H), 7.44 (d, J=6.8 Hz, 1H), 4.91 (s, 2H), 4.81 (t, J=7.2 Hz, 1H), 2.17-2.09 (m, 2H), 1.55-1.40 (m, 2H), 1.07 (t, J=7.2 Hz, 3H).

Example 405 and 406 (S)-(6-(6-(2-(1-aminobutyl)pyrimidin-4-yl)-1H-indazol-1-yl)pyridin-2-yl)methanol and (R)-(6-(6-(2-(1-aminobutyl)pyrimidin-4-yl)-1H-indazol-1-yl)pyridin-2-yl)methanol Synthesis of 1-(6-(((tert-butyldimethylsilyl)oxy)methyl)pyridin-2-yl)-6-(2-chloropyrimidin-4-yl)-1H-indazole

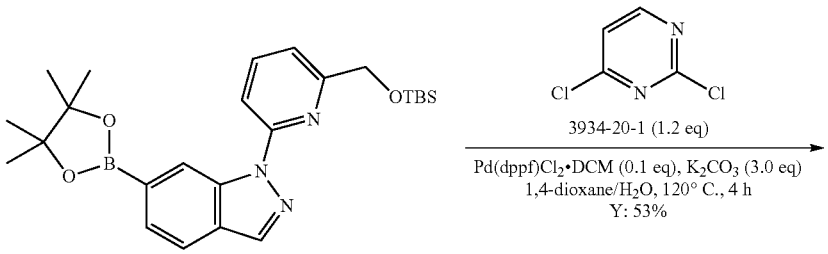

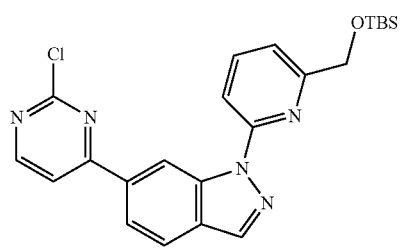

To a solution of 1-(6-(((tert-butyldimethylsilyl)oxy)methyl)pyridin-2-yl)-6-(4,4,5,5-tetramethyl-1,3,2-dioxaborolan-2-yl)-1H-indazole (Example 143, Step 3) (1.8 g, 3.87 mmol, 1.0 eq) in 1,4-dioxane/H$_2$O (40 mL/5 mL) were added 2,4-dichloropyrimidine (692 mg, 4.65 mmol, 1.2 eq), Pd(dppf)Cl$_2$DCM (316 mg, 0.387 mmol, 0.1 eq) and K$_2$CO$_3$ (1.6 g, 11.61 mmol, 3.0 eq). The mixture was stirred at 120° C. under N$_2$ for 4 h. After cooling down to rt, the mixture was diluted with water (100 mL) and extracted with EA (50 mL×3). The combined organic fractions were washed with brine, dried and evaporated. The residue was purified by chromatography (PE/EA=3/1) to give 1-(6-(((tert-butyldimethylsilyl)oxy)methyl)pyridin-2-yl)-6-(2-chloropyrimidin-4-yl)-1H-indazole (920 mg, Y: 53%) as a white solid. ESI-MS (M+H)$^+$: 452.2. $^1$H NMR (400 MHz, CDCl$_3$) δ: 9.66 (s, 1H), 8.70 (d, J=5.2 Hz, 1H), 8.25 (s, 1H), 8.01-7.99 (m, 1H), 7.93-7.87 (m, 3H), 7.78 (d, J=5.2 Hz, 1H), 7.44 (d, J=7.2 Hz, 1H), 5.01 (s, 2H), 1.01 (s, 9H), 0.19 (s, 6H).

Synthesis of 4-(1-(6-(((tert-butyldimethylsilyl)oxy)methyl)pyridin-2-yl)-1H-indazol-6-yl)pyrimidine-2-carbonitrile

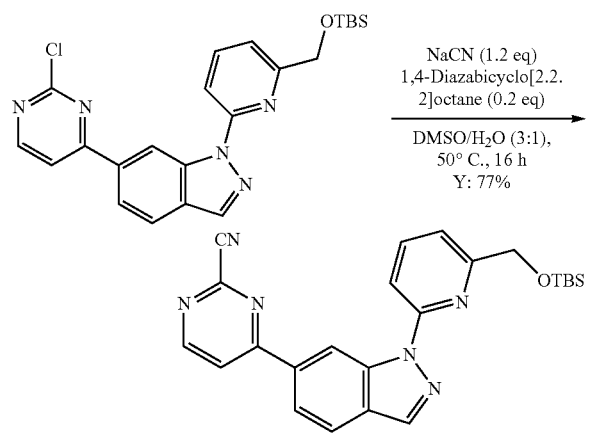

To a stirred solution of 1-(6-(((tert-butyldimethylsilyl)oxy)methyl)pyridin-2-yl)-6-(2-chloropyrimidin-4-yl)-1H-indazole (1.6 g, 3.55 mmol, 1.0 eq) in DMSO (30 mL) were added DABCO (80 mg, 0.71 mmol, 0.2 eq), NaCN (209 mg, 4.26 mmol, 1.2 eq) and drop-wise addition of H$_2$O (10 mL). The resulting solution was stirred at 50° C. for 16 h. After consumption of starting material by TLC, the reaction mixture was diluted with water (100 mL) and extracted with EA (50 mL×3). Combined organic layers were dried over Na$_2$SO$_4$, filtered, evaporated and purified by chromatography (PE/EA=2/1) to give 4-(1-(6-(((tert-butyldimethylsilyl)oxy)methyl)pyridin-2-yl)-1H-indazol-6-yl)pyrimidine-2-carbonitrile (1.2 g, Y: 77%) as a white solid. ESI-MS (M+H)$^+$: 443.2. $^1$H NMR (400 MHz, CDCl$_3$) δ: 9.70 (s, 1H), 8.90 (d, J=5.2 Hz, 1H), 8.26 (s, 1H), 8.04-8.01 (m, 2H), 7.94-7.90 (m, 3H), 7.45 (d, J=7.2 Hz, 1H), 5.01 (s, 2H), 1.01 (s, 9H), 0.19 (s, 6H).

Synthesis of 1-(4-(1-(6-(((tert-butyldimethylsilyl)oxy)methyl)pyridin-2-yl)-1H-indazol-6-yl)pyrimidin-2-yl)butan-1-one

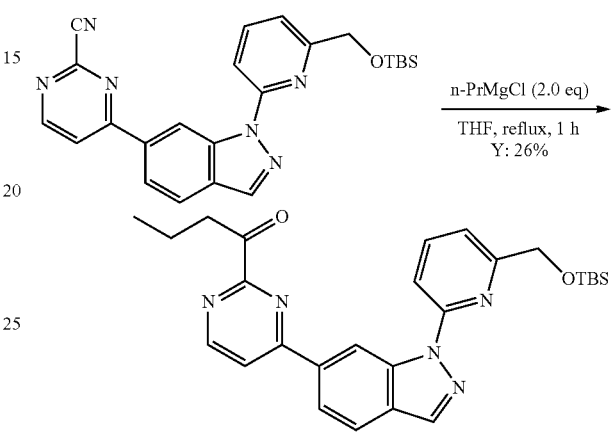

To a solution of 4-(1-(6-(((tert-butyldimethylsilyl)oxy)methyl)pyridin-2-yl)-1H-indazol-6-yl)pyrimidine-2-carbonitrile (900 mg, 2.04 mmol, 1.0 eq) in dry THF (50 mL) was added n-PrMgCl (1 M, 4.1 mL, 4.07 mmol, 2.0 eq). The mixture was refluxed under N$_2$ for 1 h. After cooling down to rt, the reaction was quenched with water (10 mL) and extracted with EA (30 mL×3). The combined organic fractions were washed with brine, dried, filtrated and evaporated. The residue was purified by chromatography (PE/EA=1/1) to give 1-(4-(1-(6-(((tert-butyldimethylsilyl)oxy)methyl)pyridin-2-yl)-1H-indazol-6-yl)pyrimidin-2-yl)butan-1-one (260 mg, Y: 26%) as colorless oil. ESI-MS (M+H)$^+$: 488.2. $^1$H NMR (400 MHz, CDCl$_3$) δ: 9.68 (s, 1H), 9.01 (d, J=5.2 Hz, 1H), 8.26 (s, 1H), 8.12-8.09 (m, 1H), 7.96-7.88 (m, 4H), 7.44 (d, J=7.2 Hz, 1H), 5.00 (s, 2H), 3.37 (t, J=7.2 Hz, 2H), 1.91-1.86 (m, 2H), 1.07 (t, J=7.2 Hz, 3H), 1.00 (s, 9H), 0.18 (s, 6H).

Synthesis of (R,E)-N-(1-(4-(1-(6-(((tert-butyldimethylsilyl)oxy)methyl)pyridin-2-yl)-1H-indazol-6-yl)pyrimidin-2-yl)butylidene)-2-methylpropane-2-sulfinamide

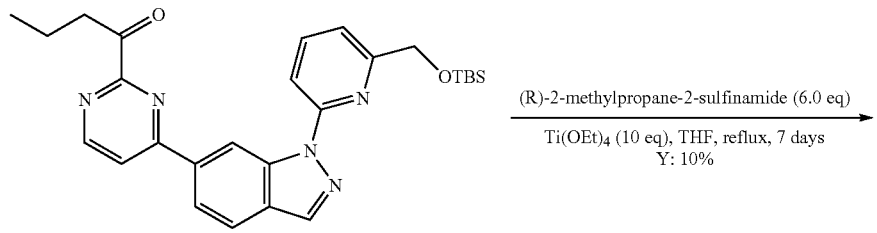

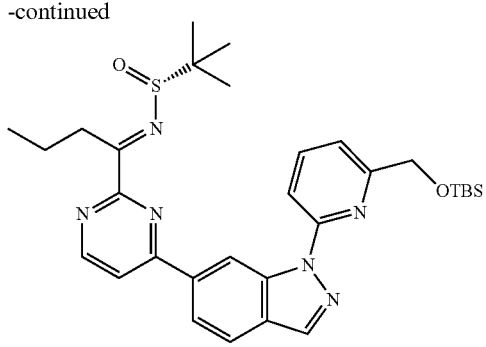

To a solution of 1-(4-(1-(6-(((tert-butyldimethylsilyl)oxy)methyl)pyridin-2-yl)-1H-indazol-6-yl)pyrimidin-2-yl)butan-1-one (260 mg, 0.53 mmol, 1.0 eq) in THF (50 mL) was added (R)-2-methylpropane-2-sulfinamide (388 mg, 3.20 mmol, 6.0 eq) and Ti(OEt)$_4$ (1.22 g, 5.34 mmol, 10.0 eq). The mixture was refluxed for 7 days. After cooling down to rt, the mixture was diluted with EA (20 mL) and washed with H$_2$O (20 mL×2) and brine. The organic was dried (Na$_2$SO$_4$) and concentrated in vacuo. The crude mixture was purified by silica gel chromatography (PE/EA=2/1) to give (R,E)-N-(1-(4-(1-(6-(((tert-butyldimethylsilyl)oxy)methyl)pyridin-2-yl)-1H-indazol-6-yl)pyrimidin-2-yl)butylidene)-2-methylpropane-2-sulfinamide (30 mg, Y: 10%) as a white solid. ESI-MS (M+H)$^+$: 591.3.

Synthesis of (R)—N—((S)-1-(4-(1-(6-(((tert-butyldimethylsilyl)oxy)methyl)pyridin-2-yl)-1H-indazol-6-yl)pyrimidin-2-yl)butyl)-2-methylpropane-2-sulfinamide and (R)—N—((R)-1-(4-(1-(6-(((tert-butyldimethylsilyl)oxy)methyl)pyridin-2-yl)-1H-indazol-6-yl)pyrimidin-2-yl)butyl)-2-methylpropane-2-sulfinamide

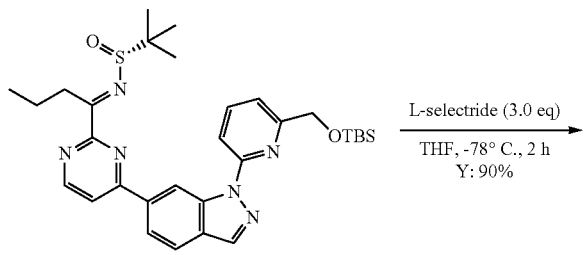

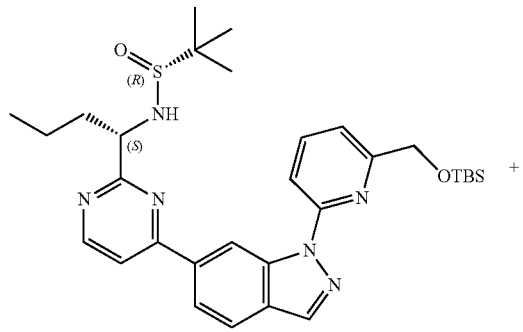

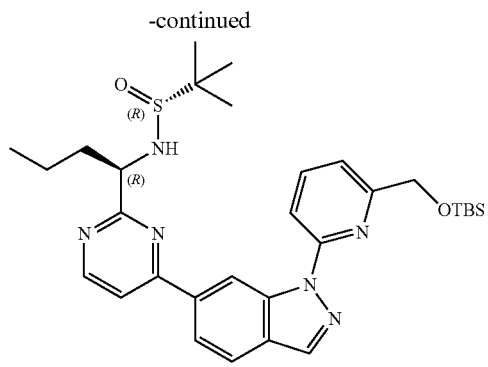

The preparation of (R)—N—((S)-1-(4-(1-(6-(((tert-butyldimethylsilyl)oxy)methyl)pyridin-2-yl)-1H-indazol-6-yl)pyrimidin-2-yl)butyl)-2-methylpropane-2-sulfinamide and (R)—N—((R)-1-(4-(1-(6-(((tert-butyldimethylsilyl)oxy)methyl)pyridin-2-yl)-1H-indazol-6-yl)pyrimidin-2-yl)butyl)-2-methylpropane-2-sulfinamide were similar to that of (R)—N—((S)-1-(2-bromopyridin-4-yl)butyl)-2-methylpropane-2-sulfinamide (Example 404, Step 4) to give (R)—N—((S)-1-(4-(1-(6-(((tert-butyldimethylsilyl)oxy)methyl)pyridin-2-yl)-1H-indazol-6-yl)pyrimidin-2-yl)butyl)-2-methylpropane-2-sulfinamide (16 mg, Y: 53%) and (R)—N—((R)-1-(4-(1-(6-(((tert-butyldimethylsilyl)oxy)methyl)pyridin-2-yl)-1H-indazol-6-yl)pyrimidin-2-yl)butyl)-2-methylpropane-2-sulfinamide (11 mg, Y: 37%) as separated by preparative TLC (PE/EA=1/1). ESI-MS (M+H)$^+$: 593.3.

Synthesis of (S)-(6-(6-(2-(1-aminobutyl)pyrimidin-4-yl)-1H-indazol-1-yl)pyridin-2-yl)methanol

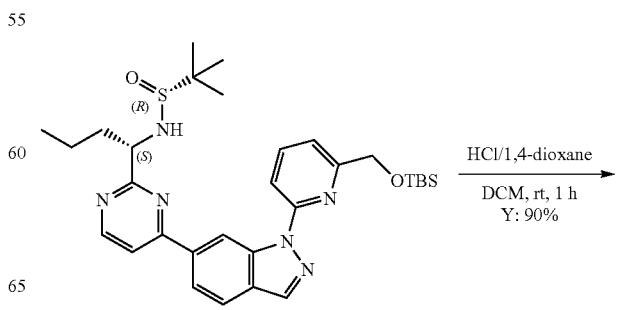

-continued

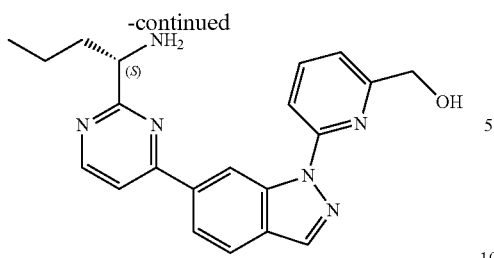

The preparation of (S)-(6-(6-(2-(1-aminobutyl)pyrimidin-4-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 7 mg as a yellow solid, Y: 90%. ESI-MS (M+H)⁺: 375.2. HPLC: 100%. ¹H NMR (400 MHz, CD₃OD) δ: 9.81 (s, 1H), 8.83 (d, J=5.6 Hz, 1H), 8.25 (s, 1H), 8.10-8.08 (m, 1H), 8.01 (d, J=5.6 Hz, 1H), 7.91-7.87 (m, 3H), 7.29-7.28 (m, 1H), 4.80 (s, 2H), 4.52 (t, J=6.8 Hz, 1H), 2.12-1.96 (m, 2H), 1.46-1.40 (m, 2H), 0.94 (t, J=7.2 Hz, 3H).

Synthesis of (R)-(6-(6-(2-(1-aminobutyl)pyrimidin-4-yl)-1H-indazol-1-yl)pyridin-2-yl)methanol

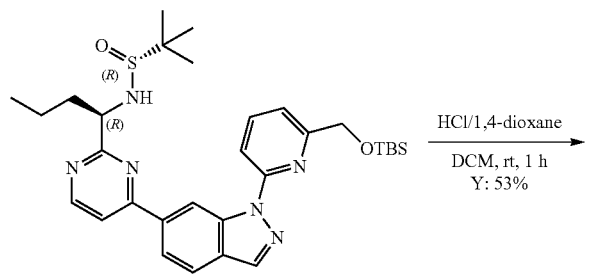

The preparation of (R)-(6-(6-(2-(1-aminobutyl)pyrimidin-4-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 4 mg as a yellow solid, Y: 53%. ESI-MS (M+H)⁺: 375.2. HPLC: 100%. ¹H NMR (400 MHz, CD₃OD) δ: 9.81 (s, 1H), 8.83 (d, J=5.6 Hz, 1H), 8.25 (s, 1H), 8.10-8.08 (m, 1H), 8.01 (d, J=5.6 Hz, 1H), 7.91-7.87 (m, 3H), 7.29-7.28 (m, 1H), 4.80 (s, 2H), 4.52 (t, J=6.8 Hz, 1H), 2.12-1.96 (m, 2H), 1.46-1.40 (m, 2H), 0.94 (t, J=7.2 Hz, 3H).

Example 407 and 408 (S)-(6-(6-(6-(1-aminobutyl)pyrazin-2-yl)-1H-indazol-1-yl)pyridin-2-yl)methanol and (R)-(6-(6-(6-(1-aminobutyl)pyrazin-2-yl)-1H-indazol-1-yl)pyridin-2-yl)methanol Synthesis of 1-(6-bromopyrazin-2-yl)butan-1-one

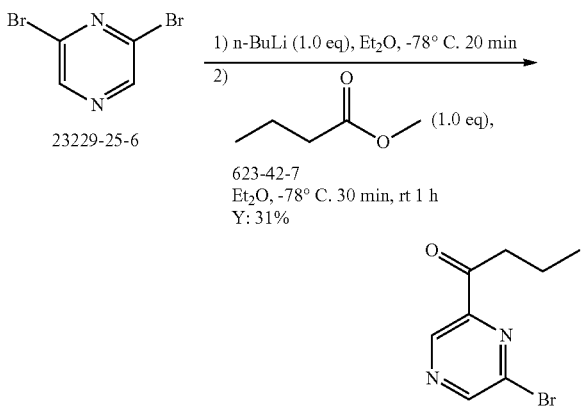

To a solution of 2,6-dibromopyrazine (CAS#23229-25-6, 1.5 g, 6.3 mmol, 1.0 eq) in anhydrous diethyl ether (30 mL) was added n-BuLi (2.4 M in THF, 2.6 mL, 6.3 mmol, 1.0 eq) at −78° C. under N₂ atmosphere. The mixture was stirred at −78° C. for 20 min. Then 623-42-7 (640 mg, 6.3 mmol, 1.0 eq) in anhydrous diethyl (5.0 mL) was added to the solution. After stirred at −78° C. for 30 min, the mixture was warmed to rt and stirred at rt for 1 h. Then the mixture was diluted with ethyl acetate (100 mL), and water (40 mL) was added. The aqueous layer was extracted with ethyl acetate (30 mL×2). The combined organic layers were dried over anhydrous sodium sulfate, filtrated and concentrated under reduced pressure. The residue was purified by silica gel column chromatography (PE/EA=5/1) to give 1-(6-bromopyrazin-2-yl)butan-1-one (450 mg, Y: 31%) as a yellow solid. ESI-MS (M+1)⁺: 229.0, 231.0.

¹H NMR (400 MHz, CDCl₃) δ: 9.13 (s, 1H), 8.86 (s, 1H), 3.16 (t, J=7.2 Hz, 2H), 1.81-1.72 (m, 2H), 1.04 (t, J=7.2 Hz, 3H).

Synthesis of (R,E)-N-(1-(6-bromopyrazin-2-yl)butylidene)propane-2-sulfinamide

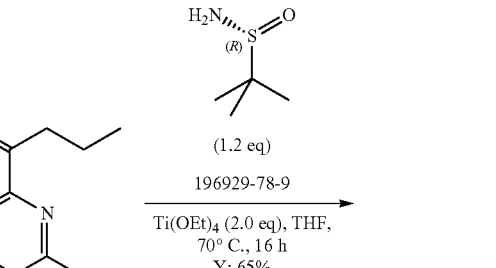

449
-continued

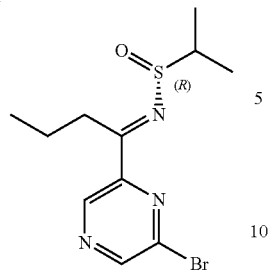

The preparation of (R,E)-N-(1-(6-bromopyrazin-2-yl)butylidene)propane-2-sulfinamide was similar to that of (R,E)-N-(1-(2-bromopyridin-4-yl)butylidene)-2-methylpropane-2-sulfinamide (Example 404, Step 3) to give 425 mg as a yellow solid, Y: 65%. ESI-MS (M+H)⁺: 332.0, 334.0. $^1$H NMR (400 MHz, CDCl$_3$) δ: 9.15 (s, 1H), 8.73 (s, 1H), 3.43-3.22 (m, 2H), 1.74-1.50 (m, 2H), 1.30 (s, 9H), 1.05 (t, J=7.2 Hz, 3H).

Synthesis of (R)—N—((R)-1-(6-bromopyrazin-2-yl)butyl)-2-methylpropane-2-sulfinamide and (R)—N—((S)-1-(6-bromopyrazin-2-yl)butyl)-2-methylpropane-2-sulfinamide

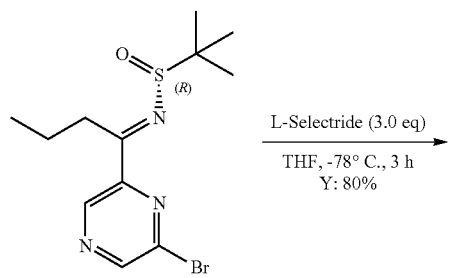

450
-continued

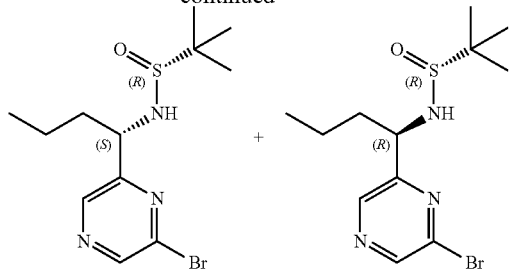

The preparation of the mixture of (R)—N—((R)-1-(6-bromopyrazin-2-yl)butyl)-2-methylpropane-2-sulfinamide and (R)—N—((S)-1-(6-bromopyrazin-2-yl)butyl)-2-methylpropane-2-sulfinamide was similar to that of (R)—N—((S)-1-(2-bromopyridin-4-yl)butyl)-2-methylpropane-2-sulfinamide (Example 404, Step 4) to give 340 mg as yellow oil, Y: 80%. ESI-MS (M+H)⁺: 334.0, 336.0.

Synthesis of (R)—N—((R)-1-(6-(1-(6-(((tert-butyldimethylsilyl)oxy)methyl)pyridin-2-yl)-1H-indazol-6-yl)pyrazin-2-yl)butyl)-2-methylpropane-2-sulfinamide and (R)—N—((S)-1-(6-(1-(6-(((tert-butyldimethylsilyl)oxy)methyl)pyridin-2-yl)-1H-indazol-6-yl)pyrazin-2-yl)butyl)-2-methylpropane-2-sulfinamide

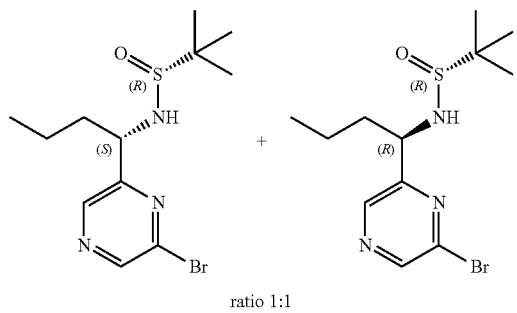

ratio 1:1

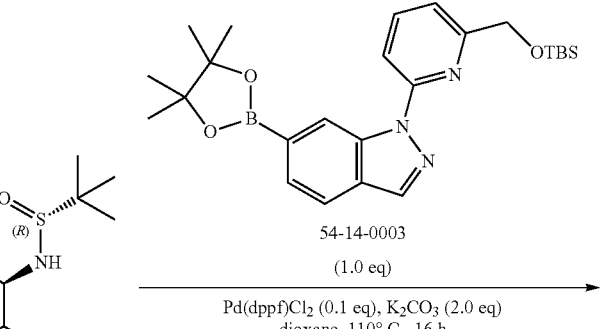

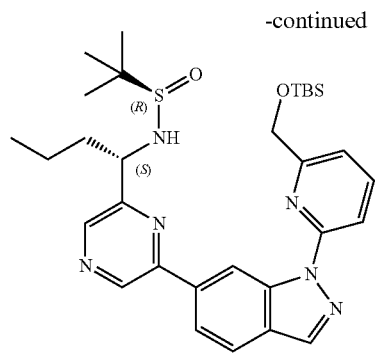
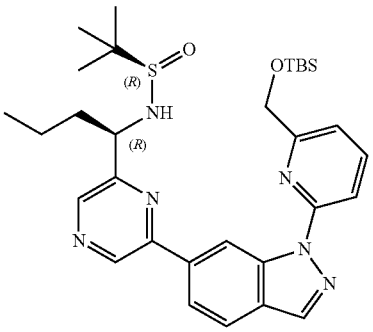

The preparation of the title compounds was similar to that of (S)—N—((S)-1-(2-(1-(6-(((tert-butyldimethylsilyl)oxy) methyl)pyridin-2-yl)-1H-indazol-6-yl)pyridin-4-yl)butyl)-2-methylpropane-2-sulfinamide (Example 404, Step 5) to give (R)—N—((S)-1-(6-(1-(6-(((tert-butyldimethylsilyl) oxy)methyl)pyridin-2-yl)-1H-indazol-6-yl)pyrazin-2-yl)butyl)-2-methylpropane-2-sulfinamide (300 mg, Y: 50%) and (R)—N—((R)-1-(6-(1-(6-(((tert-butyldimethylsilyl)oxy) methyl)pyridin-2-yl)-1H-indazol-6-yl)pyrazin-2-yl)butyl)-2-methylpropane-2-sulfinamide (260 mg, Y: 43%) as a yellow solid. ESI-MS (M+H)$^+$: 593.3. (R)—N—((S)-1-(6-(1-(6-(((tert-butyldimethylsilyl)oxy)methyl)pyridin-2-yl)-1H-indazol-6-yl)pyrazin-2-yl)butyl)-2-methylpropane-2-sulfinamide: $^1$H NMR (400 MHz, CDCl$_3$) δ: 9.46 (s, 1H), 9.08 (s, 1H), 8.55 (s, 1H), 8.25 (s, 1H), 8.04 (dd, J=8.4, 1.6 Hz, 1H), 7.96-7.87 (m, 3H), 7.44 (d, J=8.8 Hz, 1H), 4.97 (s, 2H), 4.70-4.65 (m, 1H), 4.13 (s, 1H), 2.10-2.03 (m, 2H), 1.46-1.25 (m, 2H), 1.21 (s, 9H), 1.00 (s, 9H), 0.99 (t, J=7.6 Hz, 3H), 0.18 (s, 6H). (R)—N—((R)-1-(6-(1-(6-(((tert-butyldimethylsilyl)oxy)methyl)pyridin-2-yl)-1H-indazol-6-yl) pyrazin-2-yl)butyl)-2-methylpropane-2-sulfinamide: $^1$H NMR (400 MHz, CDCl$_3$) δ: 9.41 (s, 1H), 9.05 (s, 1H), 8.55 (s, 1H), 8.24 (s, 1H), 7.99-7.86 (m, 4H), 7.44 (d, J=7.2 Hz, 1H), 4.96 (s, 2H), 4.76 (d, J=7.6 Hz, 1H), 4.60-4.54 (m, 1H), 2.04-1.88 (m, 2H), 1.50-1.39 (m, 2H), 1.21 (s, 9H), 0.99 (s, 9H), 0.97 (t, J=7.6 Hz, 3H), 0.17 (s, 6H).

Synthesis of (S)-(6-(6-(6-(1-aminobutyl)pyrazin-2-yl)-1H-indazol-1-yl)pyridin-2-yl)methanol (Example 407)

The preparation of (S)-(6-(6-(6-(1-aminobutyl)pyrazin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 190 mg as a yellow solid, Y: 91%. ESI-MS (M+H)$^+$: 375.2. HPLC: 100%. $^1$H NMR (400 MHz, CD$_3$OD) δ: 9.76 (s, 1H), 9.36 (s, 1H), 8.75 (s, 1H), 8.40 (s, 1H), 8.22 (d, J=8.4 Hz, 1H), 8.07-8.01 (m, 3H), 7.45 (d, J=6.0 Hz, 1H), 4.92 (s, 2H), 4.77 (t, J=7.2 Hz, 1H), 2.15-2.06 (m, 2H), 1.58-1.39 (m, 2H), 1.07 (t, J=7.2 Hz, 3H).

Synthesis of (R)-(6-(6-(6-(1-aminobutyl)pyrazin-2-yl)-1H-indazol-1-yl)pyridin-2-yl)methanol (Example 408)

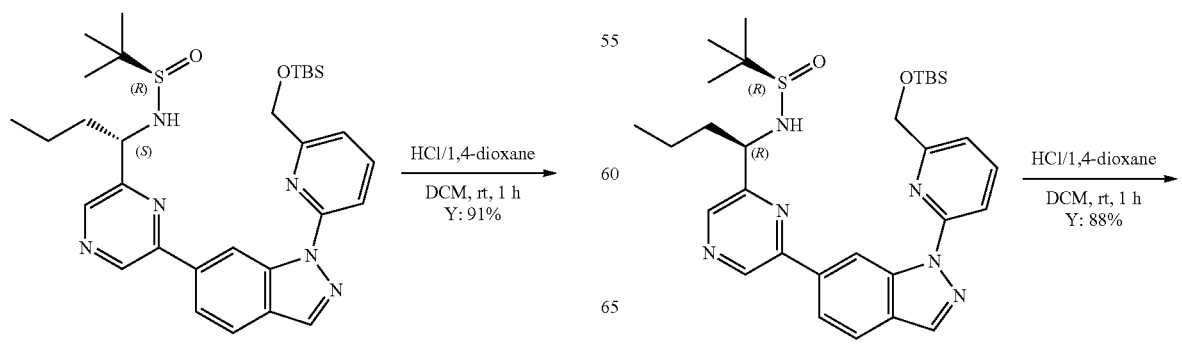

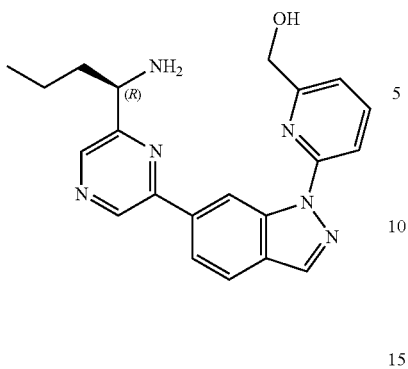

The preparation of (R)-(6-(6-(6-(1-aminobutyl)pyrazin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 160 mg as a yellow solid, Y: 88%. ESI-MS (M+H)⁺: 375.2. HPLC: 100%. $^1$H NMR (400 MHz, CD$_3$OD) δ: 9.76 (s, 1H), 9.36 (s, 1H), 8.75 (s, 1H), 8.41 (s, 1H), 8.22 (d, J=8.8 Hz, 1H), 8.09-8.03 (m, 3H), 7.45 (d, J=6.4 Hz, 1H), 4.92 (s, 2H), 4.77 (t, J=7.2 Hz, 1H), 2.15-2.09 (m, 2H), 1.58-1.41 (m, 2H), 1.07 (t, J=7.2 Hz, 3H).

Example 409 (S)-4-amino-4-(6-(1-(6-(hydroxymethyl)pyridin-2-yl)-4-methoxy-1H-indazol-6-yl)pyridin-2-yl)butan-1-ol Synthesis of (S)-tert-butyl (4-((tert-butyldimethylsilyl)oxy)-1-(6-(1-(6-(((tert-butyldimethylsilyl)oxy)methyl)pyridin-2-yl)-4-methoxy-1H-indazol-6-yl)pyridin-2-yl)butyl)carbamate

Step 1. Synthesis of 6-bromo-4-methoxy-1H-indazole

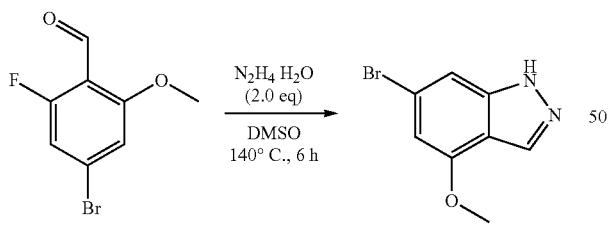

To a stirred solution of 4-bromo-2-fluoro-6-methoxybenzaldehyde (Example 324, Step 2; 16.5 g, 70.8 mmol) in DMSO (100 mL) was added hydrazine monohydrate (7.1 g, 141 mmol, 2.0 eq). The reaction mixture was stirred at 140° C. for 6 h. After cooled to rt, the reaction solution was diluted with water (100 mL). The precipitate was collected by filtration and washed with water (10 mL×2) to give 6-bromo-4-methoxy-1H-indazole (15.8 g, Y: 98%) as a light yellow solid. $^1$H NMR (400 MHz, CDCl$_3$) δ: 8.10 (s, 1H), 7.27 (s, 1H), 6.61 (d, J=1.2 Hz, 1H), 3.96 (s, 3H); ESI-MS (M+H)⁺: 229.0.

Step 4. Synthesis of (6-(6-bromo-4-methoxy-1H-indazol-1-yl)pyridin-2-yl)methanol

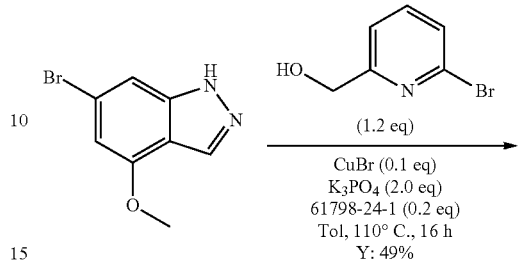

A mixture of 6-bromo-4-methoxy-1H-indazole (11.8 g, 52.0 mmol), (6-bromopyridin-2-yl)methanol (11.7 g, 62.4 mmol, 1.2 eq), CuBr (744 mg, 5.2 mmol, 0.1 eq), N,N'-Dimethyl-1,2-cyclohexanediamine (CAS No. 61798-24-1, 1.5 g, 10.4 mmol, 0.2 eq) and K$_3$PO$_4$ (22.0 g, 104.0 mmol, 2.0 eq) in toluene (300 mL) was stirred at 100° C. for 16 h under nitrogen atmosphere. After cooled to rt, the solution was filtered by Celite and the filtrate was concentrated in vacuo. The residue was purified by silica gel chromatography (PE/EA, 6:1) to give (6-(6-bromo-4-methoxy-1H-indazol-1-yl)pyridin-2-yl)methanol (8.5 g, Y: 49%) as a light yellow solid. ESI-MS (M+H)⁺: 336.1, 338.1.

Step 5. Synthesis of 6-bromo-1-(6-(((tert-butyldimethylsilyl)oxy)methyl)pyridin-2-yl)-4-methoxy-1H-indazole

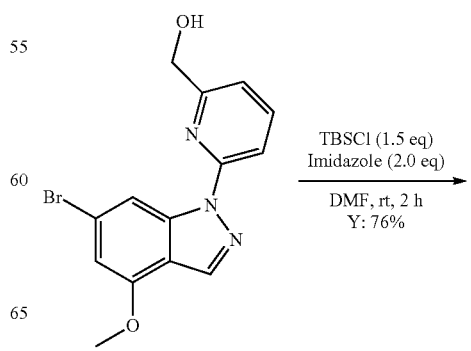

-continued

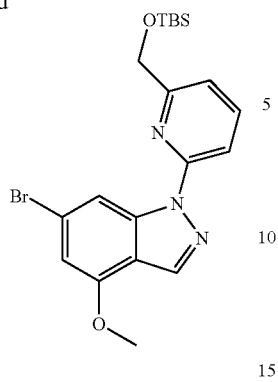

The preparation of 6-bromo-1-(6-(((tert-butyldimethylsilyl)oxy)methyl)pyridin-2-yl)-4-methoxy-1H-indazole was similar to that of 4-bromo-1-(6-(((tert-butyldimethylsilyl)oxy)methyl)pyridin-2-yl)-6-((4-methoxybenzyl)oxy)-1H-indazole (Example 352, Step 5) to give 677 mg as a white solid, Y: 76%. ESI-MS (M+H)$^+$: 448.1.

Step 6. Synthesis of 1-(6-(((tert-butyldimethylsilyl)oxy)methyl)pyridin-2-yl)-4-methoxy-6-(4,4,5,5-tetramethyl-1,3,2-dioxaborolan-2-yl)-1H-indazole

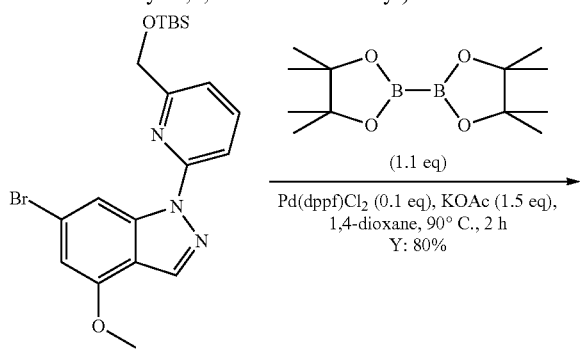

-continued

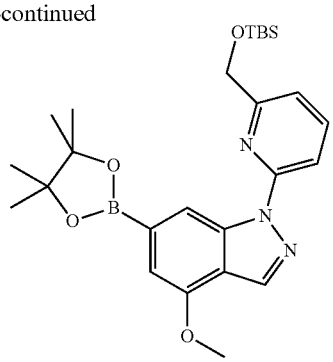

The preparation of 1-(6-(((tert-butyldimethylsilyl)oxy)methyl)pyridin-2-yl)-4-methoxy-6-(4,4,5,5-tetramethyl-1,3,2-dioxaborolan-2-yl)-1H-indazole was similar to that of 1-(6-(((tert-butyldimethylsilyl)oxy)methyl)pyridin-2-yl)-4-(1H-pyrazol-1-yl)-6-(4,4,5,5-tetramethyl-1,3,2-dioxaborolan-2-yl)-1H-indazole (Example 352, Step 9) to give 600 mg as a yellow solid, Y: 80%. ESI-MS (M+H)$^+$: 496.2.

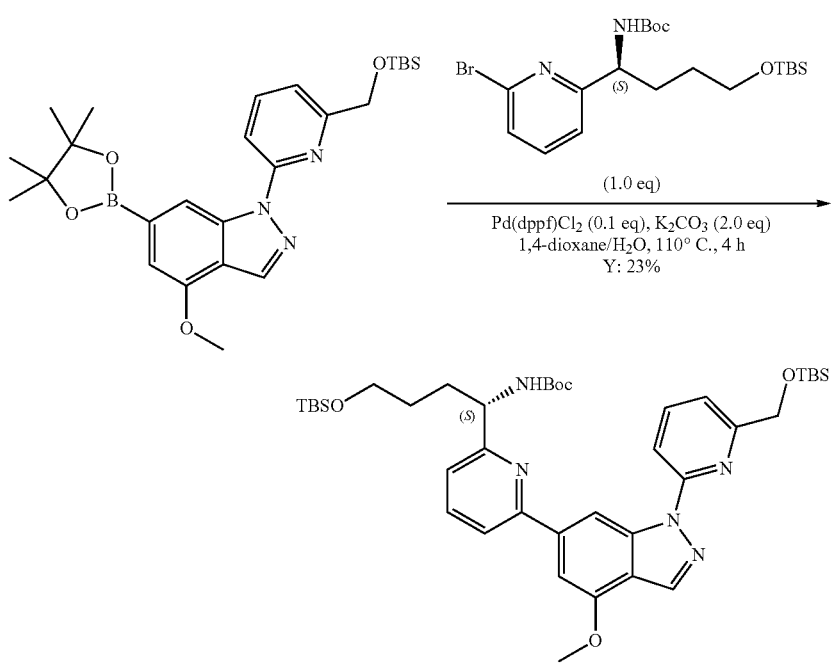

The preparation of (S)-tert-butyl (4-((tert-butyldimethylsilyl)oxy)-1-(6-(1-(6-(((tert-butyldimethylsilyl)oxy)methyl)pyridin-2-yl)-4-methoxy-1H-indazol-6-yl)pyridin-2-yl)butyl)carbamate was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 120 mg as a yellow solid, Y: 23%. ESI-MS (M+H)⁺: 748.5.

Synthesis of (S)-4-amino-4-(6-(1-(6-(hydroxymethyl)pyridin-2-yl)-4-methoxy-1H-indazol-6-yl)pyridin-2-yl)butan-1-ol

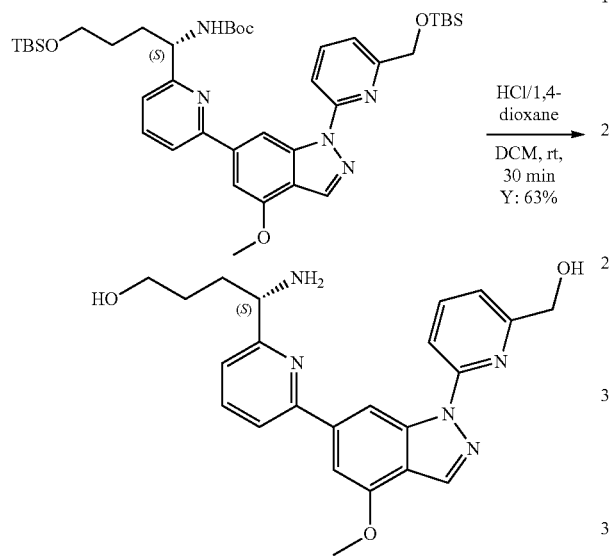

The preparation of (S)-4-amino-4-(6-(1-(6-(hydroxymethyl)pyridin-2-yl)-4-methoxy-1H-indazol-6-yl)pyridin-2-yl)butan-1-ol was similar to that of (S)-(6-(6-(4-(1-aminobutyl)pyridin-2-yl)-1H-indazol-1-yl)pyridin-2-yl)methanol (Example 404, Step 6) to give 53 mg as a yellow solid, Y: 63%. ESI-MS (M+H)⁺: 420.1. HPLC: 100%. ¹H NMR (400 MHz, CD₃OD) δ: 9.29 (s, 1H), 8.32 (s, 1H), 8.09 (d, J=7.2 Hz, 1H), 8.04-7.94 (m, 3H), 7.57 (s, 1H), 7.48 (d, J=7.2 Hz, 1H), 7.43-7.30 (m, 1H), 4.88 (s, 2H), 4.61 (t, J=6.8 Hz, 1H), 4.15 (s, 3H), 3.65 (t, J=6.4 Hz, 2H), 2.22-2.14 (m, 2H), 1.70-1.61 (m, 2H).

Example 410 (S)-4-amino-4-(6-(4-ethoxy-1-(6-(hydroxymethyl)pyridin-2-yl)-1H-indazol-6-yl)pyridin-2-yl)butan-1-ol Step 1. Synthesis of 4-bromo-2-ethoxy-6-fluorobenzaldehyde

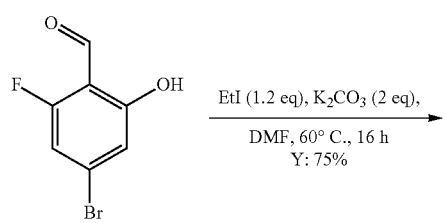

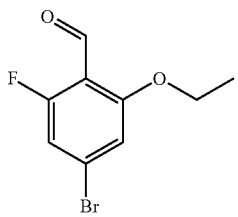

A mixture of 4-bromo-2-fluoro-6-hydroxybenzaldehyde (Cas No. 1427438-90-1, 50.0 g, 0.23 mmol, 1.0 eq), K2CO3 (63.5 g, 0.46 mmol, 2.0 eq) and EtI (43.0 g, 0.28 mmol, 1.2 eq) in DMF (80 mL) was stirred at 60° C. for 16 h. After cooling to rt, the mixture was poured into water (500 mL). After filtration, the yellow solid was directly used for next step without purification. (42.4 g, Y: 75%). ESI-MS (M+H)⁺: 246.9.

Step 2. Synthesis of 6-bromo-4-ethoxy-1H-indazole

The preparation of 6-bromo-4-ethoxy-1H-indazole was similar to that of 6-bromo-4-methoxy-1H-indazole (Example 409, Step 1) to give 28 g as a yellow solid, Y: 68%. ESI-MS (M+H)⁺: 240.9. ¹H NMR (400 MHz, CDCl₃) δ: 10.90 (br, 1H), 8.13 (s, 1H), 7.24 (s, 1H), 6.58 (s, 1H), 4.18 (q, J=6.8 Hz, 2H), 1.51 (t, J=6.8 Hz, 3H).

Step 3. Synthesis of (6-(6-bromo-4-ethoxy-1H-indazol-1-yl)pyridin-2-yl)methanol

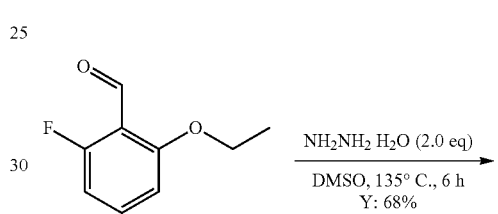

-continued

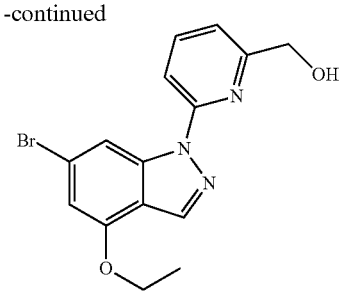

A mixture of 6-bromo-4-ethoxy-1H-indazole (7.0 g, 29 mmol, 1.0 eq), (6-bromopyridin-2-yl)methanol (CAS#33674-96-3, 7 g, 38 mmol, 1.3 eq), CuI (1.1 g, 5.8 mmol, 0.2 eq), $K_3PO_4$ (12 g, 58 mmol, 2.0 eq) and 61798-24-1 (1.7 g, 12 mmol, 0.4 eq) in 1,4-dioxane (60 mL) was stirred at 110° C. for 24 h. After concentration, the residue was purified by silica gel chromatography using PE/EA (4/1) as eluent to give (6-(6-bromo-4-ethoxy-1H-indazol-1-yl)pyridin-2-yl)methanol as a white solid. 1.5 g, Y: 13%. ESI-MS (M+H)$^+$: 348.1.

Step 4. Synthesis of 6-bromo-1-(6-(((tert-butyldimethylsilyl)oxy)methyl)pyridin-2-yl)-4-ethoxy-1H-indazole

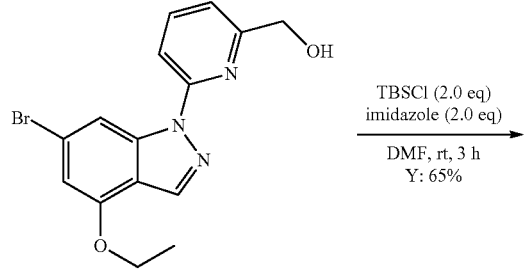

To a solution of (6-(6-bromo-4-ethoxy-1H-indazol-1-yl)pyridin-2-yl)methanol (1.5 g, 4.3 mmol, 1.0 eq) in DMF (8 mL) was added TBSCl (1.3 g, 8.6 mmol, 2.0 eq) and imidazole (585 mg, 8.6 mmol, 2.0 eq). The mixture was stirred at rt for 3 h. The mixture was poured into $H_2O$ (30 mL). The precipitate was collected by filtration and washed with water to give 6-bromo-1-(6-(((tert-butyldimethylsilyl)oxy)methyl)pyridin-2-yl)-4-ethoxy-1H-indazole as a yellow solid. 1.3 g, Y: 65%. ESI-MS (M+H)$^+$: 462.1.

Step 5. Synthesis of 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole

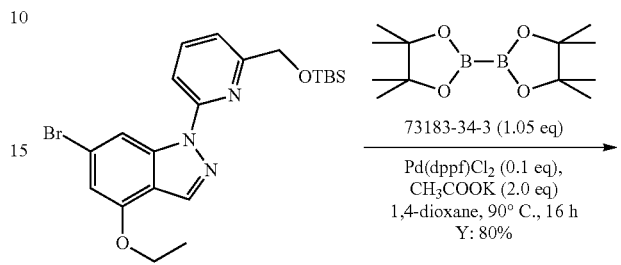

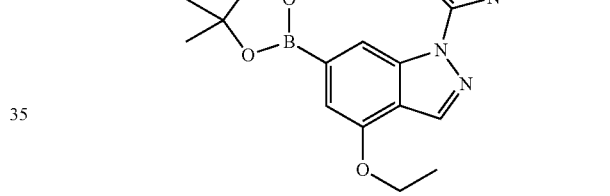

A mixture of 6-bromo-1-(6-(((tert-butyldimethylsilyl)oxy)methyl)pyridin-2-yl)-4-ethoxy-1H-indazole (500 mg, 1.09 mmol, 1.0 eq), Bis(pinacolato)diboron (CAS No. 73183-34-3, 289 mg, 1.14 mmol, 1.05 eq) and $CH_3COOK$ (214 mg, 2.18 mmol, 2.0 eq) in 1, 4-dioxane (10 mL) was stirred while purging $N_2$ at rt for 10 min. To this system was added Pd(dppf)Cl$_2$ (90 mg, 0.1 mmol, 0.1 eq) and heated to 90° C. for 16 h. The mixture was diluted with EtOAc (50 mL) and washed with saturated aqueous NaHCO$_3$ solution (50 mL) and brine (50 mL). The organics were dried (Na$_2$SO$_4$) and concentrated to give 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole which was used for next step without further purification. 400 mg, as a brown solid, Y: 80%. ESI-MS (M+H)$^+$: 510.2.

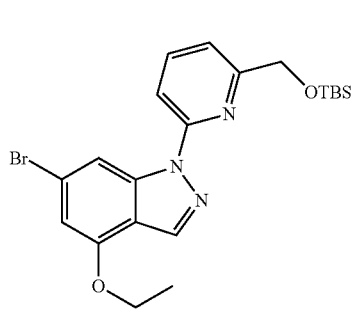

Step 6. Synthesis of (S)-tert-butyl (4-((tert-butyldimethylsilyl)oxy)-1-(6-(1-(6-(((tert-butyldimethylsilyl)oxy)methyl)pyridin-2-yl)-4-ethoxy-1H-indazol-6-yl)pyridin-2-yl)butyl)carbamate

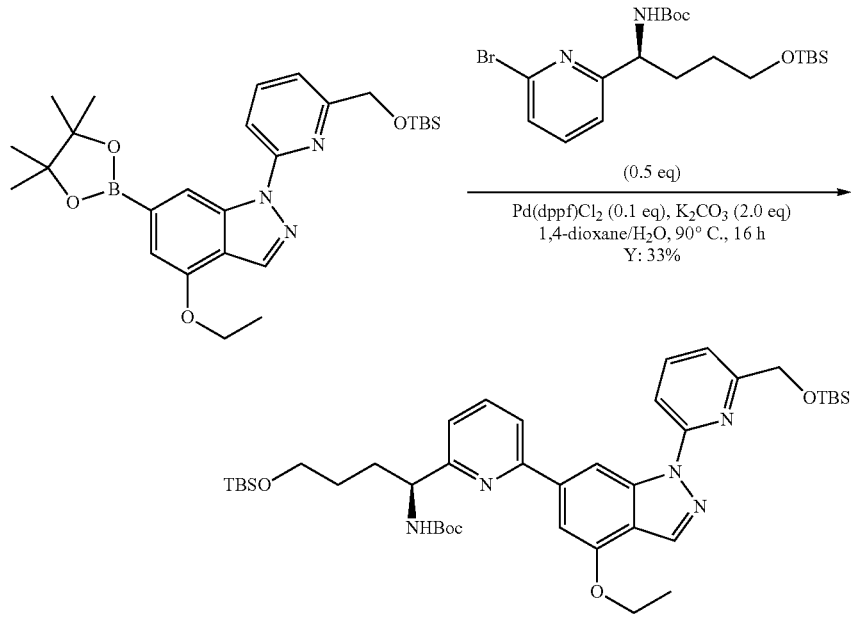

The preparation of (S)-tert-butyl (4-((tert-butyldimethylsilyl)oxy)-1-(6-(1-(6-(((tert-butyldimethylsilyl)oxy)methyl)pyridin-2-yl)-4-ethoxy-1H-indazol-6-yl)pyridin-2-yl)butyl)carbamate was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 130 mg as a yellow solid, Y: 33%. ESI-MS (M+H)$^+$: 762.3.

Step 7. Synthesis of (S)-4-amino-4-(6-(4-ethoxy-1-(6-(hydroxymethyl)pyridin-2-yl)-1H-indazol-6-yl)pyridin-2-yl)butan-1-ol

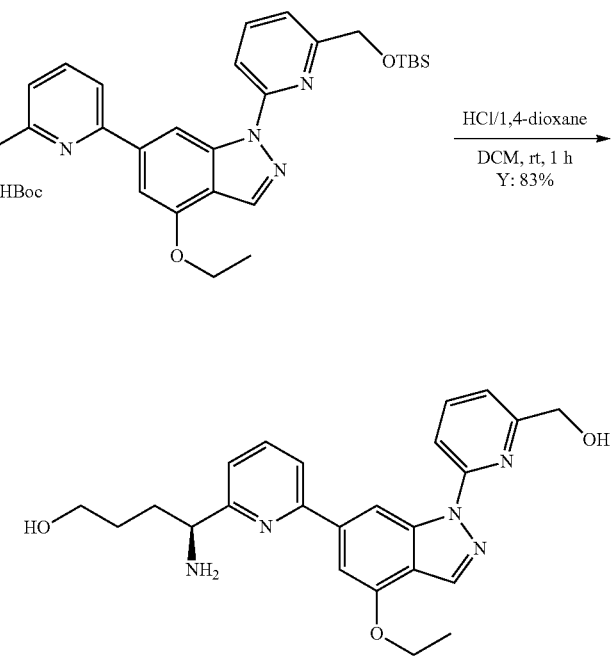

The preparation of (S)-4-amino-4-(6-(4-ethoxy-1-(6-(hydroxymethyl)pyridin-2-yl)-1H-indazol-6-yl)pyridin-2-yl)butan-1-ol was similar to that of (S)-(6-(6-(4-(1-aminobutyl)pyridin-2-yl)-1H-indazol-1-yl)pyridin-2-yl)methanol (Example 404, Step 6) to give 62 mg as a yellow solid, Y: 83%. ESI-MS (M+H)+: 434.2. HPLC: 100%. $^1$H NMR (400 MHz, CD$_3$OD) δ: 9.28 (s, 1H), 8.33 (s, 1H), 8.09-7.95 (m, 4H), 7.55 (s, 1H), 7.47 (d, J=7.6 Hz, 1H), 7.38 (d, J=7.6 Hz, 1H), 4.88 (s, 2H), 4.61 (t, J=7.2 Hz, 1H), 4.42 (q, J=6.8 Hz, 2H), 3.65 (t, J=6.0 Hz, 2H), 2.21-2.13 (m, 2H), 1.70-1.58 (m, 5H).

Example 411 and 412 (S)-(6-(6-(4-(1-aminoethyl)pyrimidin-2-yl)-1H-indazol-1-yl)pyridin-2-yl)methanol and (R)-(6-(6-(4-(1-aminoethyl)pyrimidin-2-yl)-1H-indazol-1-yl)pyridin-2-yl)methanol Synthesis of 1-(6-(((tert-butyldimethylsilyl)oxy)methyl)pyridin-2-yl)-6-(4-(1-ethoxyvinyl)pyrimidin-2-yl)-1H-indazole

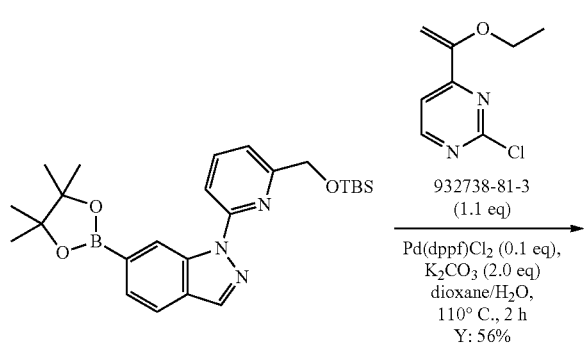

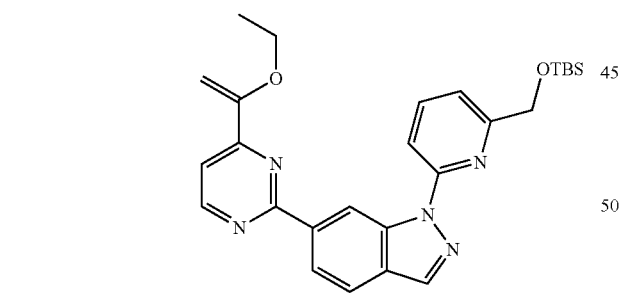

The preparation of 1-(6-(((tert-butyldimethylsilyl)oxy)methyl)pyridin-2-yl)-6-(4-(1-ethoxyvinyl)pyrimidin-2-yl)-1H-indazole was similar to that of (S)—N—((S)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide (Example 404, Step 5) to give 500 mg as a yellow solid, Y: 56%. ESI-MS (M+H)+: 488.1.

Synthesis of 1-(2-(1-(6-(hydroxymethyl)pyridin-2-yl)-1H-indazol-6-yl)pyrimidin-4-yl)ethanone

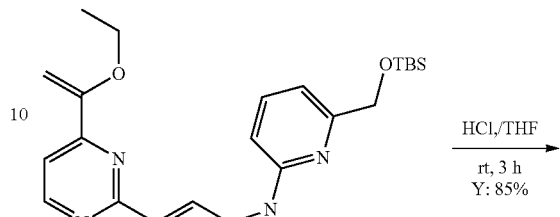

A solution of 1-(6-(((tert-butyldimethylsilyl)oxy)methyl)pyridin-2-yl)-6-(4-(1-ethoxyvinyl)pyrimidin-2-yl)-1H-indazole (500 mg, 1.03 mmol, 1.0 eq) in conc. HCl (1 mL)/THF (10 mL) was stirred at rt for 3 h. After concentration, the residue was directly used for next step without further purification. 300 mg, as a yellow solid, Y: 85%. ESI-MS (M+H)+: 346.1. $^1$H NMR (400 MHz, CDCl$_3$) δ: 9.93 (s, 1H), 9.08 (d, J=4.4 Hz, 1H), 8.49 (d, J=8.4 Hz, 1H), 8.27 (s, 1H), 7.99 (d, J=8.4 Hz, 1H), 7.92-7.86 (m, 2H), 7.80 (d, J=4.8 Hz, 1H), 7.20 (d, J=7.6 Hz, 1H), 4.94 (s, 2H), 2.92 (s, 3H).

Synthesis of (R,E)-N-(1-(2-(1-(6-(hydroxymethyl)pyridin-2-yl)-1H-indazol-6-yl)pyrimidin-4-yl)ethylidene)-2-methylpropane-2-sulfinamide

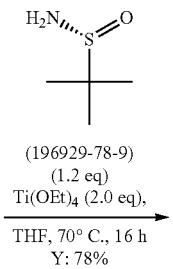

-continued

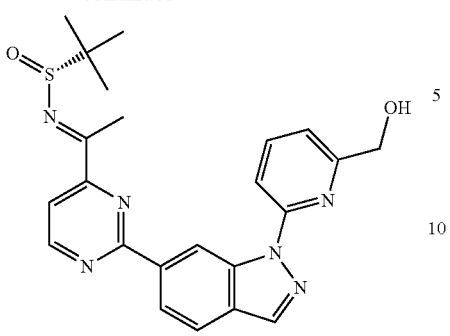

The preparation of (R,E)-N-(1-(2-(1-(6-(hydroxymethyl)pyridin-2-yl)-1H-indazol-6-yl)pyrimidin-4-yl)ethylidene)-2-methylpropane-2-sulfinamide was similar to that of (R,E)-N-(1-(2-bromopyridin-4-yl)butylidene)-2-methylpropane-2-sulfinamide (Example 404, Step 3) to give 305 mg as a yellow solid, Y: 78%. ESI-MS (M+H)$^+$: 449.1. $^1$H NMR (400 MHz, CDCl$_3$) δ: 9.92 (s, 1H), 8.96 (d, J=5.2 Hz, 1H), 8.47 (d, J=8.4 Hz, 1H), 8.26 (s, 1H), 7.98 (d, J=8.4 Hz, 1H), 7.90-7.86 (m, 3H), 7.21 (d, J=7.2 Hz, 1H), 4.93 (s, 2H), 3.05 (s, 3H), 1.38 (s, 9H).

Synthesis of (R)—N—((S)-1-(2-(1-(6-(hydroxymethyl)pyridin-2-yl)-1H-indazol-6-yl)pyrimidin-4-yl)ethyl)-2-methylpropane-2-sulfinamide and (R)—N—((R)-1-(2-(1-(6-(hydroxymethyl)pyridin-2-yl)-1H-indazol-6-yl)pyrimidin-4-yl)ethyl)-2-methylpropane-2-sulfinamide

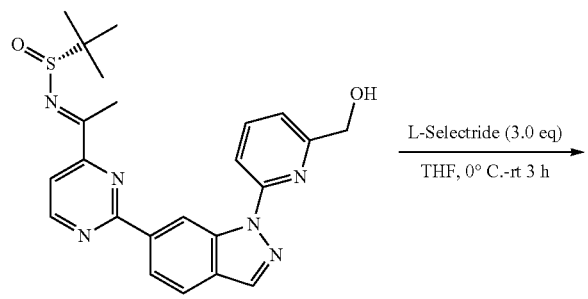

L-Selectride (3.0 eq)
THF, 0° C.-rt 3 h

-continued

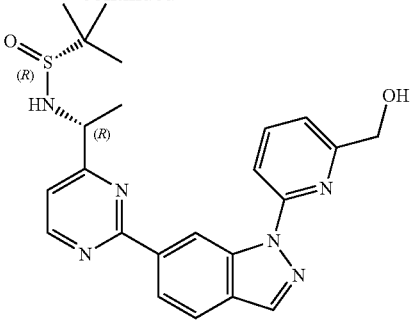

The preparation of (R)—N—((S)-1-(2-(1-(6-(hydroxymethyl)pyridin-2-yl)-1H-indazol-6-yl)pyrimidin-4-yl)ethyl)-2-methylpropane-2-sulfinamide and (R)—N—((R)-1-(2-(1-(6-(hydroxymethyl)pyridin-2-yl)-1H-indazol-6-yl)pyrimidin-4-yl)ethyl)-2-methylpropane-2-sulfinamide was similar to that of (R)—N—((S)-1-(2-bromopyridin-4-yl)butyl)-2-methylpropane-2-sulfinamide (Example 404, Step 4). (R)—N—((S)-1-(2-(1-(6-(hydroxymethyl)pyridin-2-yl)-1H-indazol-6-yl)pyrimidin-4-yl)ethyl)-2-methylpropane-2-sulfinamide (140 mg) and (R)—N—((R)-1-(2-(1-(6-(hydroxymethyl)pyridin-2-yl)-1H-indazol-6-yl)pyrimidin-4-yl)ethyl)-2-methylpropane-2-sulfinamide (40 mg) were separated by prep-TLC (PE/EA=1/1). ESI-MS (M+H)$^+$: 451.1.

(R)—N—((S)-1-(2-(1-(6-(hydroxymethyl)pyridin-2-yl)-1H-indazol-6-yl)pyrimidin-4-yl)ethyl)-2-methylpropane-2-sulfinamide (t$_R$: 6.31 min)

$^1$H NMR (400 MHz, CDCl$_3$) δ: 10.09 (s, 1H), 8.81 (d, J=4.8 Hz, 1H), 8.44-8.41 (m, 1H), 8.25 (d, J=0.8 Hz, 1H), 7.96 (d, J=8.0 Hz, 1H), 7.89-7.84 (m, 2H), 7.19-7.17 (m, 2H), 4.96 (s, 2H), 4.66-4.61 (m, 1H), 4.17-4.15 (m, 1H), 3.72-3.68 (m, 1H), 1.75 (d, J=6.4 Hz, 3H), 1.20 (s, 9H).

(R)—N—((R)-1-(2-(1-(6-(hydroxymethyl)pyridin-2-yl)-1H-indazol-6-yl)pyrimidin-4-yl)ethyl)-2-methylpropane-2-sulfinamide (t$_R$: 4.18 min)

$^1$H NMR (400 MHz, CDCl$_3$) δ: 9.96 (s, 1H), 8.83 (d, J=5.2 Hz, 1H), 8.38 (d, J=4.8 Hz, 1H), 8.25 (s, 1H), 7.95 (d, J=8.0 Hz, 1H), 7.88-7.85 (m, 2H), 7.25 (s, 1H), 7.18 (d, J=7.2 Hz, 1H), 4.94 (s, 2H), 4.66-4.60 (m, 1H), 4.13 (t, J=4.4 Hz, 1H), 3.75-3.72 (m, 1H), 1.64 (d, J=6.8 Hz, 3H), 1.25 (s, 9H).

Synthesis of (S)-(6-(6-(4-(1-aminoethyl)pyrimidin-2-yl)-1H-indazol-1-yl)pyridin-2-yl)methanol (Example 411)

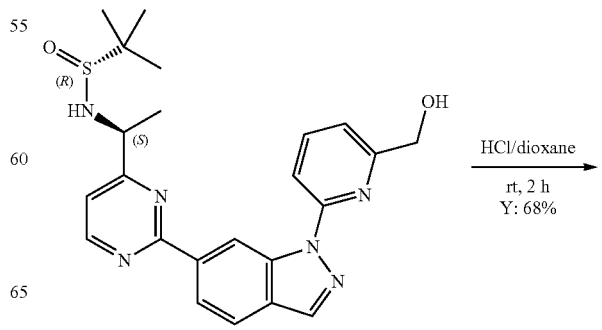

HCl/dioxane
rt, 2 h
Y: 68%

-continued

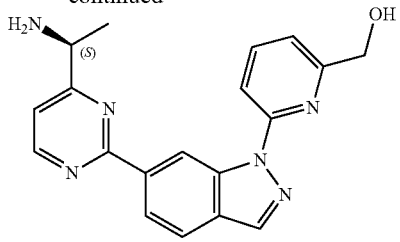

The preparation of (S)-(6-(6-(4-(1-aminoethyl)pyrimidin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 98 mg as a yellow solid, Y: 68%. ESI-MS (M+H)+: 347.1. HPLC: 99%. ¹H NMR (400 MHz, CD₃OD) δ: 10.07 (s, 1H), 8.91 (d, J=5.2 Hz, 1H), 8.45 (d, J=8.4 Hz, 1H), 8.27 (s, 1H), 7.91-7.87 (m, 3H), 7.46 (d, J=5.2 Hz, 1H), 7.33-7.31 (m, 1H), 4.86 (s, 2H), 4.70 (q, J=6.8 Hz, 1H), 1.69 (d, J=6.8 Hz, 3H).

Synthesis of (R)-(6-(6-(4-(1-aminoethyl)pyrimidin-2-yl)-1H-indazol-1-yl)pyridin-2-yl)methanol (Example 412)

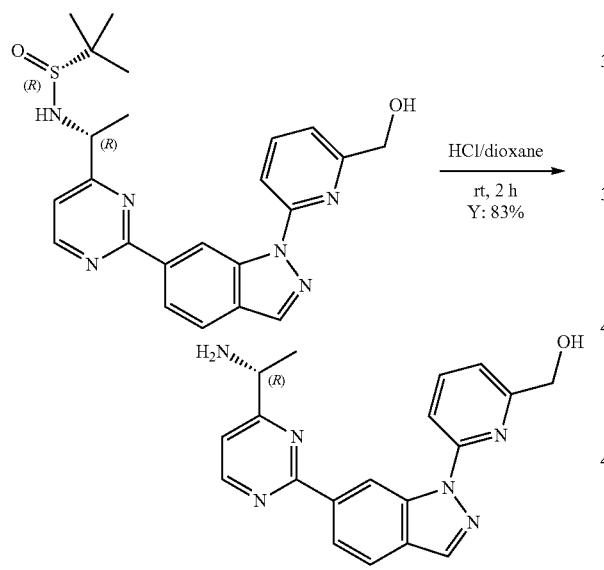

The preparation of (R)-(6-(6-(4-(1-aminoethyl)pyrimidin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 34 mg as a yellow solid, Y: 83%. ESI-MS (M+H)+: 347.1.HPLC: 97% ¹H NMR (400 MHz, CD₃OD) δ: 10.02 (s, 1H), 8.92 (d, J=7.6 Hz, 1H), 8.47 (t, J=1.2 Hz, 1H), 8.26 (s, 1H), 7.89-7.82 (m, 3H), 7.48 (d, J=7.2 Hz, 1H), 7.32 (d, J=7.2 Hz, 1H), 4.88 (s, 2H), 4.74 (q, J=6.8 Hz, 1H), 1.73 (d, J=6.8 Hz, 3H).

Example 413 and 414 (S)-(6-(6-(4-(1-aminobutyl)pyrimidin-2-yl)-1H-indazol-1-yl)pyridin-2-yl)methanol and (R)-(6-(6-(4-(1-aminobutyl)pyrimidin-2-yl)-1H-indazol-1-yl)pyridin-2-yl)methanol Synthesis of 2-chloro-N-methoxy-N-methylpyrimidine-4-carboxamide

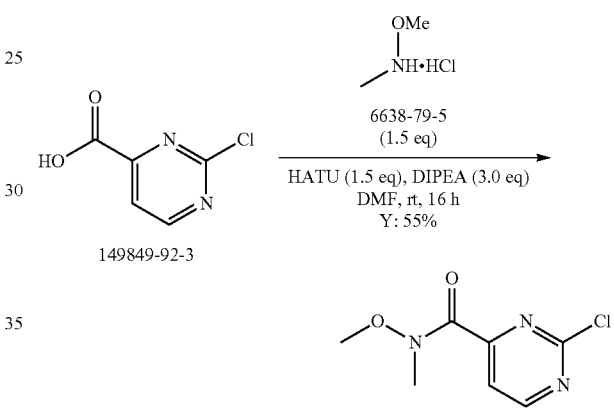

The preparation of 2-chloro-N-methoxy-N-methylpyrimidine-4-carboxamide was similar to that of 6-(6-(5-aminopyridin-3-yl)-1H-indazol-1-yl)-N-methylpicolinamide (Example 32) to give 400 mg as yellow oil, Y: 55%. ESI-MS (M+H)+: 202.1.

Synthesis of 2-(1-(6-(((tert-butyldimethylsilyl)oxy)methyl)pyridin-2-yl)-1H-indazol-6-yl)-N-methoxy-N-methylpyrimidine-4-carboxamide

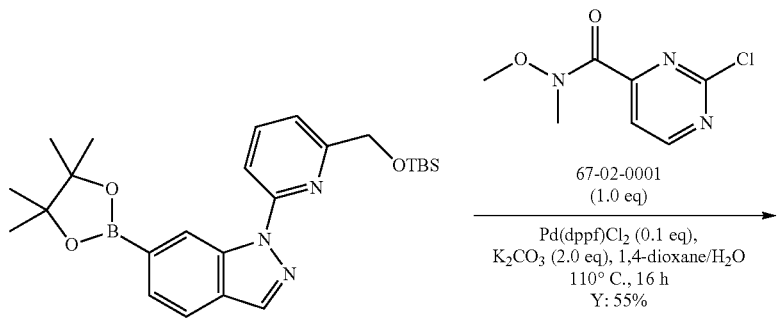

-continued

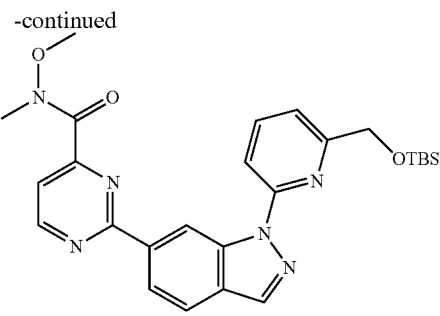

The preparation of 2-(1-(6-(((tert-butyldimethylsilyl)oxy)methyl)pyridin-2-yl)-1H-indazol-6-yl)-N-methoxy-N-methylpyrimidine-4-carboxamide was similar to that of (S)—N—((S)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide (Example 404, Step 5) to give 550 mg as a yellow solid, Y: 55%. ESI-MS (M+H)⁺: 505.2.

Synthesis of 1-(2-(1-(6-(((tert-butyldimethylsilyl)oxy)methyl)pyridin-2-yl)-1H-indazol-6-yl)pyrimidin-4-yl)butan-1-one

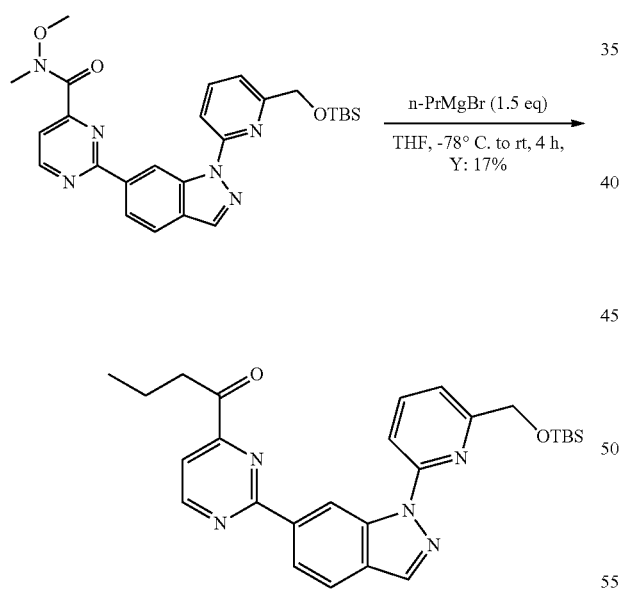

The preparation of 1-(2-(1-(6-(((tert-butyldimethylsilyl)oxy)methyl)pyridin-2-yl)-1H-indazol-6-yl)pyrimidin-4-yl)butan-1-one was similar to that of 1-(2-bromopyridin-4-yl)butan-1-one (Example 404, step 2) to give 90 mg as a white solid, Y: 17%. ESI-MS (M+H)⁺: 488.2. ¹H NMR (400 MHz, CDCl₃) δ: 9.75 (s, 1H), 8.91 (d, J=4.8 Hz, 1H), 8.29 (dd, J=8.4, 1.6 Hz, 1H), 8.08 (d, J=0.8 Hz, 1H), 7.78-7.70 (m, 3H), 7.63 (d, J=5.2 Hz, 1H), 7.27 (dd, J=7.2, 0.8 Hz, 1H), 4.85 (s, 2H), 3.22 (t, J=7.2 Hz, 2H), 1.73-1.67 (m, 2H), 0.91 (t, J=7.2 Hz, 3H), 0.83 (s, 9H), 0.00 (s, 6H).

Synthesis of (R,E)-N-(1-(2-(1-(6-(((tert-butyldimethylsilyl)oxy)methyl)pyridin-2-yl)-1H-indazol-6-yl)pyrimidin-4-yl)butylidene)-2-methylpropane-2-sulfinamide

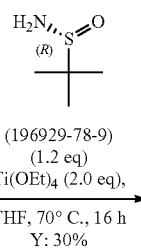

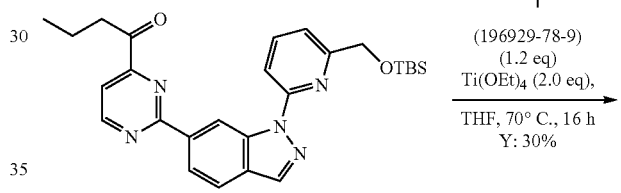

The preparation of (R,E)-N-(1-(2-(1-(6-(((tert-butyldimethylsilyl)oxy)methyl)pyridin-2-yl)-1H-indazol-6-yl)pyrimidin-4-yl)butylidene)-2-methylpropane-2-sulfinamide was similar to that of (R,E)-N-(1-(2-bromopyridin-4-yl)butylidene)-2-methylpropane-2-sulfinamide (Example 404, Step 3) to give 120 mg as a yellow solid, Y: 30%. ESI-MS (M+H)⁺: 591.3. ¹H NMR (400 MHz, CDCl₃) δ: 9.88 (s, 1H), 8.96 (d, J=5.2 Hz, 1H), 8.42 (dd, J=8.4, 1.2 Hz, 1H), 8.24 (s, 1H), 7.93-7.81 (m, 4H), 7.43 (d, J=6.8 Hz, 1H), 5.01 (s, 2H), 3.68-3.49 (m, 2H), 1.84-1.75 (m, 2H), 1.37 (s, 9H), 1.06 (t, J=7.2 Hz, 3H), 1.00 (s, 9H), 0.18 (s, 6H).

Synthesis of (R)—N—((S)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide and (R)—N—((R)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide

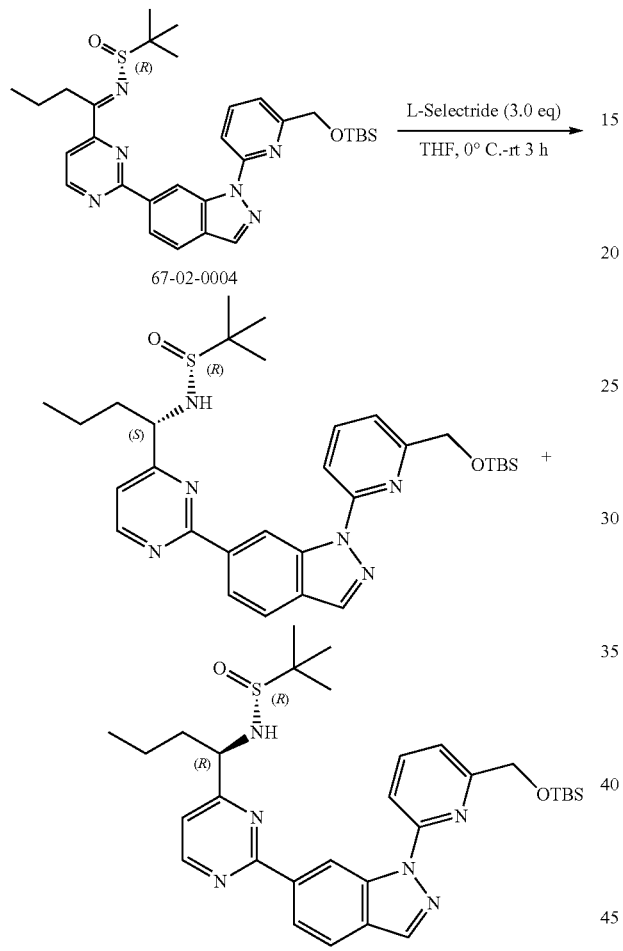

The preparation of (R)—N—((S)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide and (R)—N—((R)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide was similar to that of (R)—N—((S)-1-(2-bromopyridin-4-yl)butyl)-2-methylpropane-2-sulfinamide (Example 404, Step 4). (R)—N—((S)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide (40 mg) and (R)—N—((R)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide (30 mg) were separated by chiral resolution. ESI-MS (M+H)$^+$: 593.3.

(R)—N—((S)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide (t$_R$: 4.6 min)

$^1$H NMR (400 MHz, CD$_3$OD) δ: 9.67 (s, 1H), 8.67 (d, J=5.2 Hz, 1H), 8.22-8.19 (m, 1H), 8.10 (s, 1H), 7.78-7.70 (m, 3H), 7.25-7.22 (m, 2H), 4.81 (s, 2H), 4.34 (t, J=7.2 Hz, 1H), 1.88-1.79 (m, 2H), 1.39-1.17 (m, 2H), 1.01 (s, 9H), 0.83-0.79 (m, 12H), 0.00 (s, 6H).

(R)—N—((R)-1-(2-(1-(6-(((tert-butyldimethylsilyl)oxy)methyl)pyridin-2-yl)-1H-indazol-6-yl)pyrimidin-4-yl)butyl)-2-methylpropane-2-sulfinamide (t$_R$: 3.46 min)

$^1$H NMR (400 MHz, CD$_3$OD) δ: 9.63 (s, 1H), 8.64 (d, J=5.2 Hz, 1H), 8.18 (dd, J=8.4, 1.2 Hz, 1H), 8.05 (s, 1H), 7.78-7.59 (m, 3H), 7.30 (d, J=5.2 Hz, 1H), 7.20 (d, J=6.8 Hz, 1H), 6.74 (s, 1H), 4.79 (s, 2H), 4.30-4.26 (m, 1H), 1.81-1.73 (m, 2H), 1.38-1.25 (m, 2H), 1.22 (s, 9H), 0.81 (s, 12H), 0.00 (s, 6H).

Synthesis of (R)-(6-(6-(4-(1-aminobutyl)pyrimidin-2-yl)-1H-indazol-1-yl)pyridin-2-yl)methanol (Example 414)

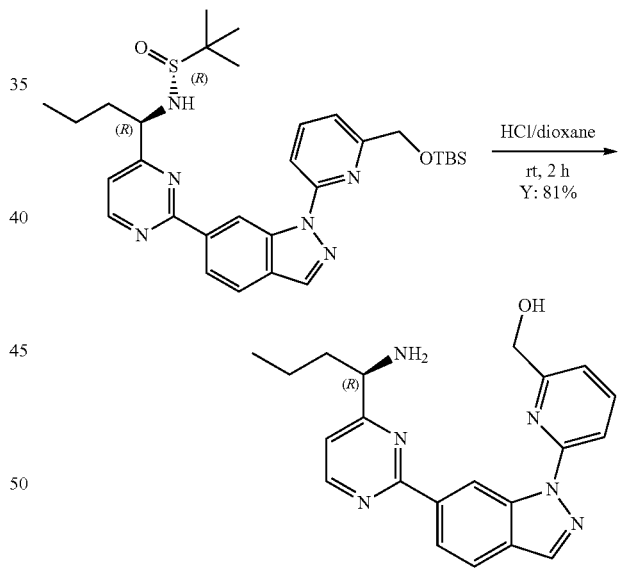

The preparation of (R)-(6-(6-(4-(1-aminobutyl)pyrimidin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to 20 mg as a yellow solid, Y: 81%. ESI-MS (M+H)$^+$: 375.2. HPLC: 100%. $^1$H NMR (400 MHz, CD$_3$OD) δ: 10.00 (s, 1H), 8.84 (d, J=4.8 Hz, 1H), 8.43 (dd, J=8.4, 1.6 Hz, 1H), 8.34 (s, 1H), 7.99-7.94 (m, 3H), 7.45-7.41 (m, 2H), 4.91 (s, 2H), 4.04 (t, J=6.8 Hz, 1H), 1.99-1.81 (m, 2H), 1.57-1.38 (m, 2H), 1.01 (t, J=7.2 Hz, 3H).

473

Synthesis of (S)-(6-(6-(4-(1-aminobutyl)pyrimidin-2-yl)-1H-indazol-1-yl)pyridin-2-yl)methanol (Example 413)

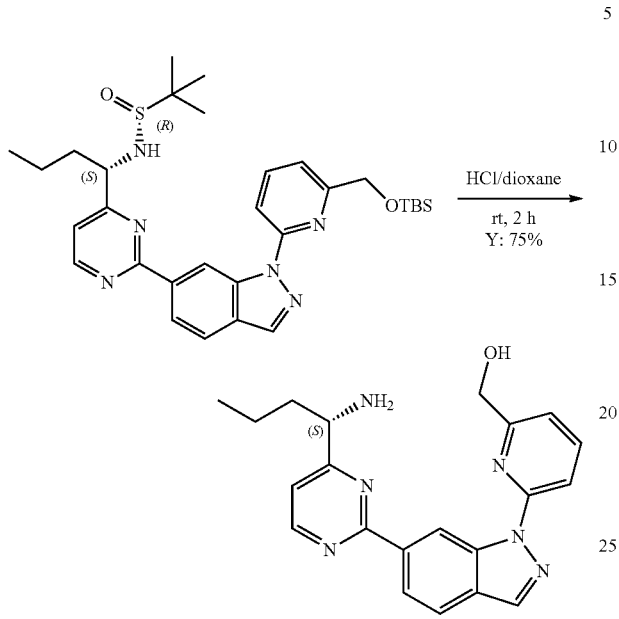

The preparation of (S)-(6-(6-(4-(1-aminobutyl)pyrimidin-2-yl)-1H-indazol-1-yl)pyridin-2-yl)methanol was similar to that of (S)-(6-(6-(4-(1-aminobutyl)pyrimidin-2-yl)-1H-indazol-1-yl)pyridin-2-yl)methanol (Example 404, Step 6) to give 25 mg as a yellow solid, Y: 75%. ESI-MS (M+H)$^+$: 375.2. HPLC: 100%. $^1$H NMR (400 MHz, CD$_3$OD) δ: 9.83 (s, 1H), 8.74 (d, J=5.2 Hz, 1H), 8.30 (dd, J=8.4, 1.2 Hz, 1H), 8.20 (s, 1H), 7.90-7.79 (m, 3H), 7.34 (d, J=6.8 Hz, 1H), 7.30 (d, J=5.2 Hz, 1H), 4.83 (s, 2H), 3.95 (t, J=6.8 Hz, 1H), 1.91-1.72 (m, 2H), 1.48-1.28 (m, 2H), 0.96 (t, J=7.2 Hz, 3H).

Example 415 and 416 1-(6-(6-(6-((S)-1-aminoethyl)pyridin-2-yl)-1H-indazol-1-yl)pyridin-2-yl)ethanol—Peak 1 and 1-(6-(6-(6-((S)-1-aminoethyl)pyridin-2-yl)-1H-indazol-1-yl)pyridin-2-yl)ethanol—Peak 2

Step 1. Synthesis of 1-(6-(6-bromo-1H-indazol-1-yl)pyridin-2-yl)ethanone

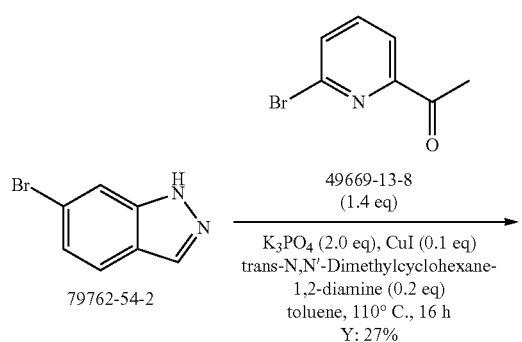

474

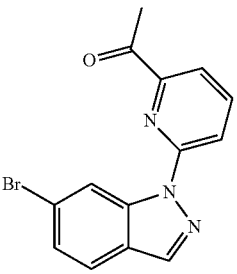

The preparation of 1-(6-(6-bromo-1H-indazol-1-yl)pyridin-2-yl)ethanone was similar to that of (4-(6-bromo-1H-indazol-1-yl)pyridin-2-yl)methanol (Example 400, Step 1) to give 1.65 g as a yellow solid, Y: 27%. ESI-MS (M+H)$^+$: 316.0.

Step 2. Synthesis of 1-(6-(6-(4,4,5,5-tetramethyl-1,3,2-dioxaborolan-2-yl)-1H-indazol-1-yl)pyridin-2-yl)ethanone

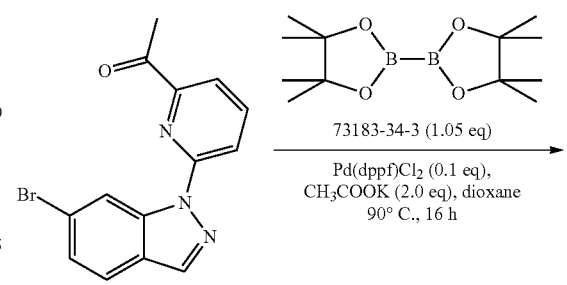

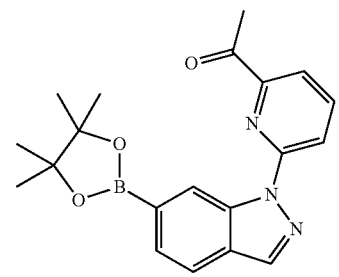

The preparation of 1-(6-(6-(4,4,5,5-tetramethyl-1,3,2-dioxaborolan-2-yl)-1H-indazol-1-yl)pyridin-2-yl)ethanone was similar to that of 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) to give 1.73 g (crude) as a yellow solid. ESI-MS (M+H)$^+$: 364.2.

Step 3. Synthesis of (R)—N—((S)-1-(6-(1-(6-acetylpyridin-2-yl)-1H-indazol-6-yl)pyridin-2-yl)ethyl)-2-methylpropane-2-sulfinamide

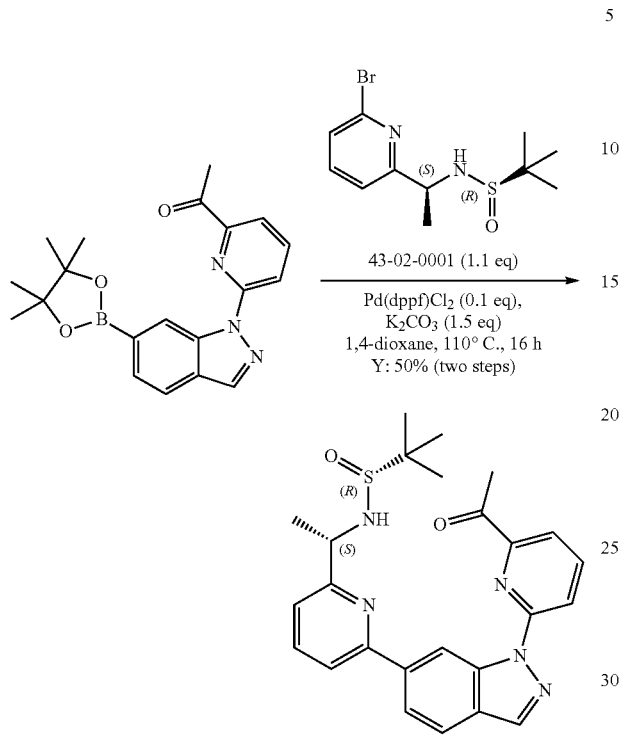

The preparation of (R)—N—((S)-1-(6-(1-(6-acetylpyridin-2-yl)-1H-indazol-6-yl)pyridin-2-yl)ethyl)-2-methylpropane-2-sulfinamide was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 2.0 g as a yellow solid, Y: 50% (two steps). ESI-MS (M+H)+: 462.2. $^1$H NMR (400 MHz, CDCl$_3$) δ: 9.57 (s, 1H), 8.33 (d, J=8.4 Hz, 1H), 8.27 (s, 1H), 8.05-7.99 (m, 2H), 7.95-7.89 (m, 2H), 7.81-7.79 (m, 2H), 7.34-7.29 (m, 1H), 5.31-5.29 (m, 1H), 2.99 (s, 3H), 1.69 (d, J=6.4 Hz, 3H), 1.23 (s, 9H).

Step 4. Synthesis of (R)—N—((1S)-1-(6-(1-(6-(1-hydroxyethyl)pyridin-2-yl)-1H-indazol-6-yl)pyridin-2-yl)ethyl)-2-methylpropane-2-sulfinamide

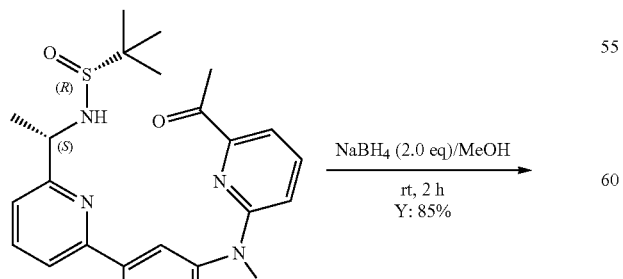

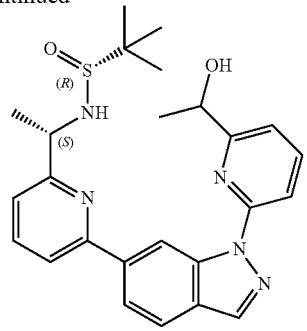

To a solution of (R)—N—((S)-1-(6-(1-(6-acetylpyridin-2-yl)-1H-indazol-6-yl)pyridin-2-yl)ethyl)-2-methylpropane-2-sulfinamide (2.0 g, 4.33 mmol, 1.0 eq) in MeOH (30 mL) was added NaBH$_4$ (320 mg, 8.66 mmol, 2.0 eq) at rt. The mixture was stirred at rt for 2 h. After concentration, the residue was dissolved in DCM (50 mL) and washed with water (15 mL). The organic phase washed with brine and dried over Na$_2$SO$_4$. After filtration and concentration, the residue was directly used for next step without further purification. 1.23 g, as a yellow solid, Y: 85%. ESI-MS (M+H)+: 464.2.

Step 5. Synthesis of 1-(6-(6-(6-((S)-1-aminoethyl)pyridin-2-yl)-1H-indazol-1-yl)pyridin-2-yl)ethanol

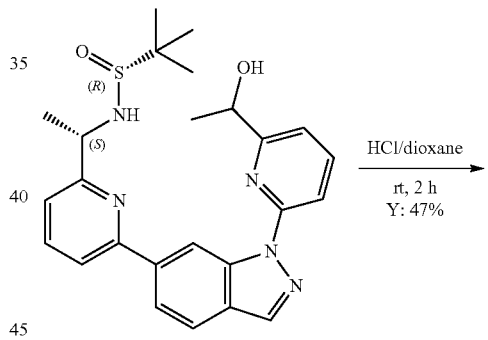

The preparation of 1-(6-(6-(6-((S)-1-aminoethyl)pyridin-2-yl)-1H-indazol-1-yl)pyridin-2-yl)ethanol was similar to that of (S)-(6-(6-(4-(1-aminobutyl)pyridin-2-yl)-1H-indazol-1-yl)pyridin-2-yl)methanol (Example 404, Step 6) to give 450 mg as a yellow solid, Y: 47%. ESI-MS (M+H)+: 360.2.

Step 6. Chiral Resolution of 1-(6-(6-(6-((S)-1-aminoethyl)pyridin-2-yl)-1H-indazol-1-yl)pyridin-2-yl)ethanol

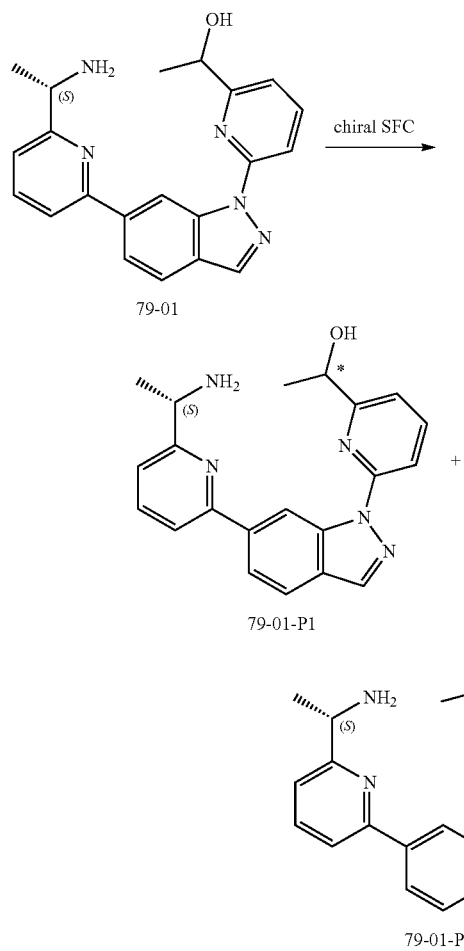

SFC (Chiralpak IC column, 4.6*250 mm 5 m, MeOH with 0.1% NH₄OH, CO₂ flow rate=1.65, Co-Solvent Flow Rate=1.35). $t_R$=3.66 min, 4.86 min.

1-(6-(6-(6-((S)-1-aminoethyl)pyridin-2-yl)-1H-indazol-1-yl)pyridin-2-yl)ethanol—Peak 1 (104 mg) and 1-(6-(6-(6-((S)-1-aminoethyl)pyridin-2-yl)-1H-indazol-1-yl)pyridin-2-yl)ethanol—Peak 2 (138 mg) were separated by chiral resolution from 1-(6-(6-(6-((S)-1-aminoethyl)pyridin-2-yl)-1H-indazol-1-yl)pyridin-2-yl)ethanol (450 mg).

1-(6-(6-(6-((S)-1-aminoethyl)pyridin-2-yl)-1H-indazol-1-yl)pyridin-2-yl)ethanol—Peak 1

¹H NMR (400 MHz, CD₃OD) δ: 9.64 (s, 1H), 8.28 (s, 1H), 8.03 (dd, J=8.4, 2.8 Hz, 1H), 7.97-7.87 (m, 5H), 7.44-7.39 (m, 2H), 5.05 (q, J=6.4 Hz, 1H), 4.26 (q, J=6.8 Hz, 1H), 1.68 (d, J=6.4 Hz, 3H), 1.54 (d, J=6.8 Hz, 3H). ESI-MS (M+H)⁺: 360.2. HPLC: 100%.

1-(6-(6-(6-((S)-1-aminoethyl)pyridin-2-yl)-1H-indazol-1-yl)pyridin-2-yl)ethanol—Peak 2

¹H NMR (400 MHz, CD₃OD) δ: 9.63 (s, 1H), 8.30 (s, 1H), 8.01 (dd, J=8.4, 1.6 Hz, 1H), 7.95-7.84 (m, 5H), 7.42-7.37 (m, 2H), 5.02 (q, J=6.8 Hz, 1H), 4.21 (q, J=6.8 Hz, 1H), 1.69 (d, J=6.8 Hz, 3H), 1.53 (d, J=6.8 Hz, 3H). ESI-MS (M+H)⁺: 360.2. HPLC: 100%.

Example 417 and 418 1-(6-(6-(6-((S)-1-aminobutyl)pyridin-2-yl)-1H-indazol-1-yl)pyridin-2-yl)ethanol-Peak 1 1-(6-(6-(6-((S)-1-aminobutyl)pyridin-2-yl)-1H-indazol-1-yl)pyridin-2-yl)ethanol-Peak 2

Synthesis of (R)—N—((S)-1-(6-(1-(6-acetylpyridin-2-yl)-1H-indazol-6-yl)pyridin-2-yl)butyl)-2-methylpropane-2-sulfinamide

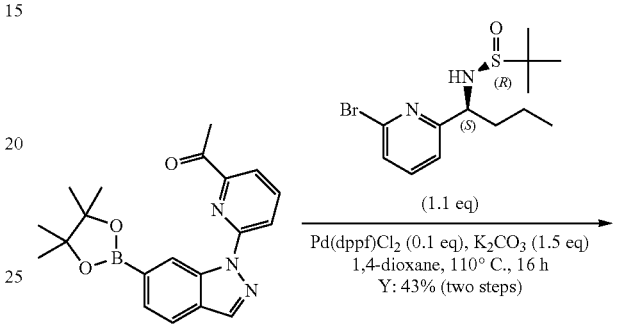

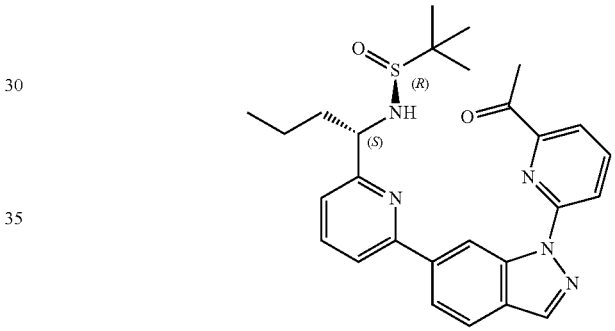

The preparation of (R)—N—((S)-1-(6-(1-(6-acetylpyridin-2-yl)-1H-indazol-6-yl)pyridin-2-yl)butyl)-2-methylpropane-2-sulfinamide was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 415, Step 2) to give 600 mg as a yellow solid, Y: 43% (two steps). ESI-MS (M+H)⁺: 490.2.

Synthesis of (R)—N—((1S)-1-(6-(1-(6-(1-hydroxyethyl)pyridin-2-yl)-1H-indazol-6-yl)pyridin-2-yl)butyl)-2-methylpropane-2-sulfinamide

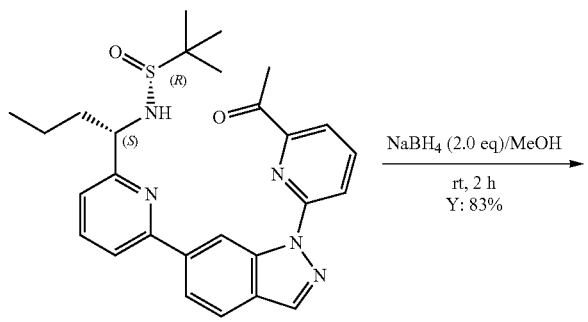

-continued

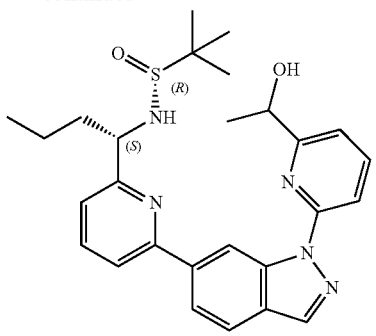

The preparation of (R)—N—((1S)-1-(6-(1-(6-(1-hydroxyethyl)pyridin-2-yl)-1H-indazol-6-yl)pyridin-2-yl)butyl)-2-methylpropane-2-sulfinamide was similar to that of (R)—N—((1S)-1-(6-(1-(6-(1-hydroxyethyl)pyridin-2-yl)-1H-indazol-6-yl)pyridin-2-yl)ethyl)-2-methylpropane-2-sulfinamide (Example 415/416, Step 4) to give 500 mg as a yellow solid, Y: 83%. ESI-MS (M+H)+: 492.2.

Synthesis of 1-(6-(6-(6-((S)-1-aminobutyl)pyridin-2-yl)-1H-indazol-1-yl)pyridin-2-yl)ethanol

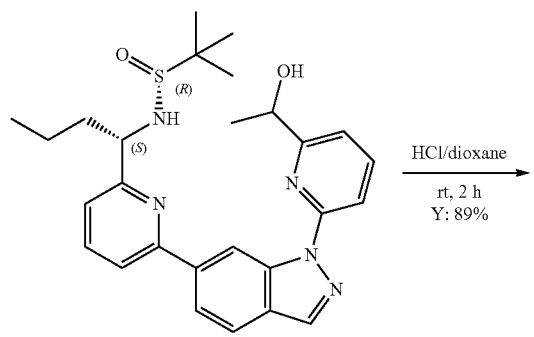

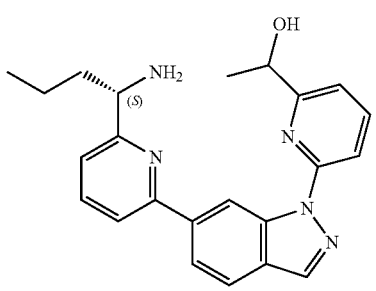

The preparation of 1-(6-(6-(6-((S)-1-aminobutyl)pyridin-2-yl)-1H-indazol-1-yl)pyridin-2-yl)ethanol was similar to that of (S)-(6-(6-(4-(1-aminobutyl)pyridin-2-yl)-1H-indazol-1-yl)pyridin-2-yl)methanol (Example 404, Step 6) to give 350 mg as a yellow solid, Y: 89%. ESI-MS (M+H)+: 388.2.

Chiral Resolution of 1-(6-(6-(6-((S)-1-aminobutyl)pyridin-2-yl)-1H-indazol-1-yl)pyridin-2-yl)ethanol

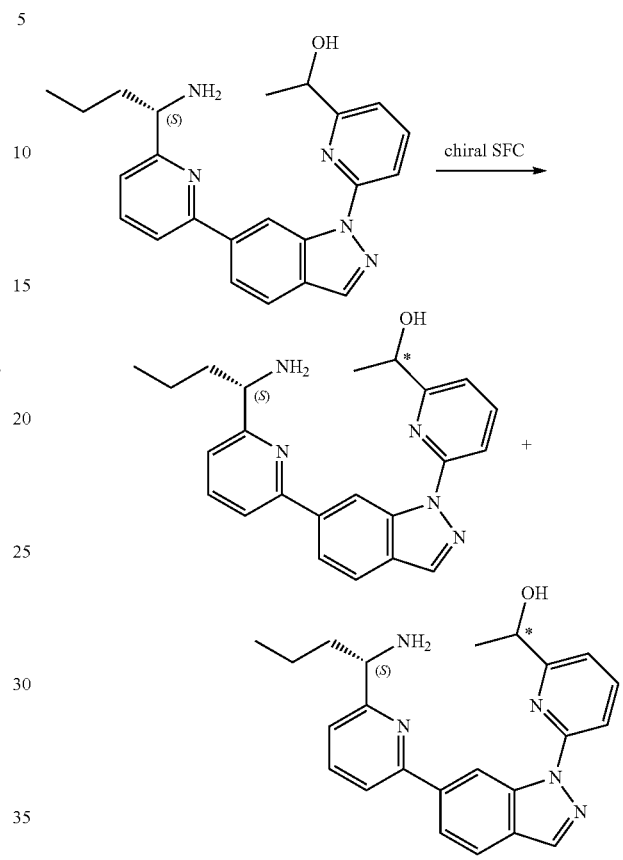

SFC (Chiralpak IC column, 4.6*250 mm 5 μm, MeOH with 0.1% NH$_4$OH, CO$_2$ flow rate=2.25, Co-Solvent Flow Rate=0.75). t$_R$=5.26 min, 6.11 min.

1-(6-(6-(6-((S)-1-aminobutyl)pyridin-2-yl)-1H-indazol-1-yl)pyridin-2-yl)ethanol—Peak 1 (149 mg) and 1-(6-(6-(6-((S)-1-aminobutyl)pyridin-2-yl)-1H-indazol-1-yl)pyridin-2-yl)ethanol—Peak 2 (61 mg) were separated by chiral resolution from 1-(6-(6-(6-((S)-1-aminobutyl)pyridin-2-yl)-1H-indazol-1-yl)pyridin-2-yl)ethanol (350 mg).

1-(6-(6-(6-((S)-1-aminobutyl)pyridin-2-yl)-1H-indazol-1-yl)pyridin-2-yl)ethanol—Peak 1

$^1$H NMR (400 MHz, CD$_3$OD) δ: 9.57 (s, 1H), 8.24 (s, 1H), 7.94-7.80 (m, 6H), 7.40-7.38 (m, 1H), 7.31-7.28 (m, 1H), 5.01 (q, J=6.4 Hz, 1H), 3.99 (t, J=6.8 Hz, 1H), 1.88-1.78 (m, 2H), 1.66 (d, J=6.4 Hz, 3H), 1.43-1.27 (m, 2H), 0.95 (t, J=7.2 Hz, 3H). ESI-MS (M+H)+: 388.2. HPLC: 98.34%.

1-(6-(6-(6-((S)-1-aminobutyl)pyridin-2-yl)-1H-indazol-1-yl)pyridin-2-yl)ethanol—Peak 2

$^1$H NMR (400 MHz, CD$_3$OD) δ: 9.62 (s, 1H), 8.29 (s, 1H), 8.00-7.68 (m, 6H), 7.43-7.40 (m, 1H), 7.35-7.32 (m, 1H), 5.03 (q, J=6.4 Hz, 1H), 4.02 (t, J=6.8 Hz, 1H), 1.91-1.80 (m, 2H), 1.68 (d, J=6.8 Hz, 3H), 1.44-1.30 (m, 2H), 0.94 (t, J=7.2 Hz, 3H). ESI-MS (M+H)+: 388.2. HPLC: 100%.

Example 419

Synthesis of Deutero (R)—N—((S)-1-(6-bromopyridin-2-yl)butyl)-2-methylpropane-2-sulfinamide

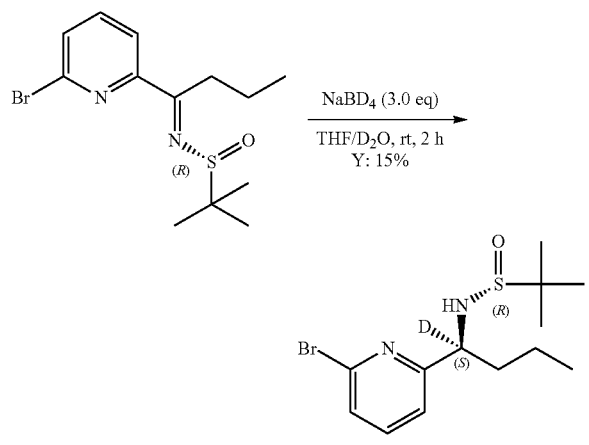

To a solution of (R,E)-N-(1-(6-bromopyridin-2-yl)butylidene)-2-methylpropane-2-sulfinamide (2.3 g, 7.0 mmol, 1.0 eq) and D₂O (1.5 g, excess) in THF (10 mL) was added NaBD₄ (882 mg, 21.0 mmol, 3.0 eq) at rt. The mixture was stirred at rt for 2 h. The reaction was quenched with NH₄Cl (aq.) and extracted with DCM (20 mL×3). The combined organic fractions were dried and concentrated. The residue was recrystallized from PE/DCM (10/1) to give the title compound. 350 mg, as a white solid, Y: 15%. ESI-MS (M+H)⁺: 333.9. ¹H NMR (400 MHz, CDCl₃) δ: 7.50 (t, J=7.6 Hz, 1H), 7.36 (d, J=8.0 Hz, 1H), 7.21 (d, J=7.2 Hz, 1H), 3.84 (br, 1H), 1.90-1.85 (m, 2H), 1.37-1.22 (m, 2H), 1.18 (s, 9H), 0.91 (t, J=7.2 Hz, 3H).

Synthesis of Deutero (R)—N—((S)-1-(6-(1-(6-(((tert-butyldimethylsilyl)oxy)methyl)pyridin-2-yl)-1H-indazol-6-yl)pyridin-2-yl)butyl)-2-methylpropane-2-sulfinamide

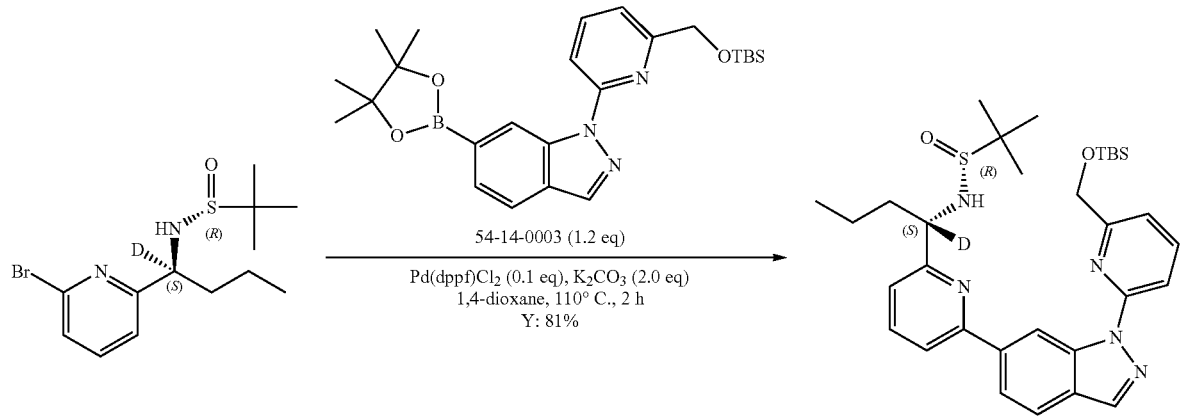

A mixture of Deutero (R)—N—((S)-1-(6-bromopyridin-2-yl)butyl)-2-methylpropane-2-sulfinamide (200 mg, 0.6 mmol, 1.0 eq), 1-(6-(((tert-butyldimethylsilyl)oxy)methyl) pyridin-2-yl)-6-(4,4,5,5-tetramethyl-1,3,2-dioxaborolan-2-yl)-1H-indazole (CAS No. 54-14-0003, (Example 143, Step 3) 335 mg, 0.72 mmol, 1.2 eq) and K₂CO₃ (170 mg, 1.2 mmol, 2.0 eq) in 1,4-dioxane/H₂O (10 mL/1 mL) was stirred while purging N₂ at rt for 10 min. To this system was added Pd(dppf)Cl₂ (50 mg, 0.06 mmol, 0.1 eq) and heated to 110° C. for 2 h. After concentration, the residue was purified by silica gel chromatography using PE/EA (1/1) as eluent to give the title compound. 290 mg, as a yellow solid, Y: 81%. ESI-MS (M+H)⁺: 593.3.

Synthesis of deutero (S)-(6-(6-(6-(1-aminobutyl)pyridin-2-yl)-1H-indazol-1-yl)pyridin-2-yl)methanol

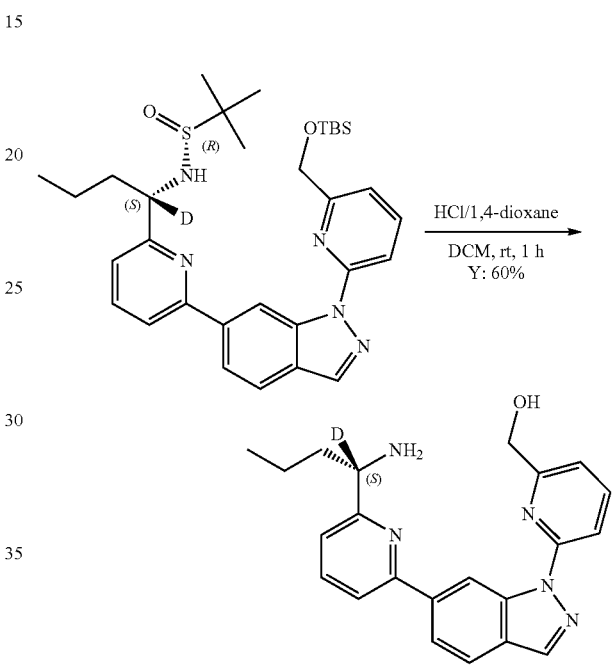

To a solution of the starting material (290 mg, 0.49 mmol, 1.0 eq) in DCM (3 mL) was added slowly 4 M HCl in 1,4-dioxane (1.0 mL, excess). Then the mixture was stirred at rt for 1 h. After concentration, the residue was dissolved in THF, adjusted pH=7-8 and extracted with EA (2×50 mL). The combined organic phase was washed with brine and dried over Na₂SO₄. After filtration and concentration, the residue was purified by prep-HPLC (CH$_3$CN/H$_2$O with 0.05% TFA as mobile phase from 5% to 95%) to give the title compound. 110 mg, as a yellow solid, Y: 60%. ESI-MS (M+H)$^+$: 375.0. HPLC: 100%. $^1$H NMR (400 MHz, CD$_3$OD) δ: 9.74 (s, 1H), 8.29 (s, 1H), 8.10 (dd, J=8.4, 0.8 Hz, 1H), 8.05-7.91 (m, 5H), 7.41 (d, J=7.6 Hz, 1H), 7.33 (t, J=8.0 Hz, 1H), 4.85 (s, 2H), 2.07-1.97 (m, 2H), 1.48-1.35 (m, 2H), 0.99 (t, J=7.2 Hz, 3H).

Example 420 (6-(6-(8-amino-8-methyl-5,6,7,8-tetra-hydroquinolin-2-yl)-1H-indazol-1-yl)pyridin-2-yl) methanol Step 1. Synthesis of 2-chloro-8-methyl-5,6,7,8-tetrahydroquinolin-8-ol

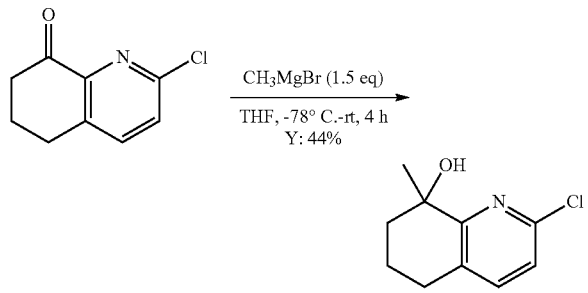

To a solution of 2-chloro-6,7-dihydroquinolin-8(5H)-one (Example 63, Step 4, 630 mg, 3.5 mmol, 1.0 eq) in THF (10 mL) was slowly added CH$_3$MgBr (2 M in hexane, 2.6 mL, 5.3 mmol, 1.5 eq) at −78° C. After stirring at rt for 4 h, the reaction was quenched with NH$_4$Cl (aq.). The mixture was extracted with EA (20 mL×3). The combined organic phases were dried, filtrated and concentrated. The residue was purified by column chromatography on silica gel (PE/EA=10/1) to give 2-chloro-8-methyl-5,6,7,8-tetrahydroquinolin-8-ol as colorless oil. 300 mg, Y: 44%. ESI-MS (M+H)$^+$: 198.1.

Step 2. Synthesis of 8-azido-2-chloro-8-methyl-5,6,7,8-tetrahydroquinoline

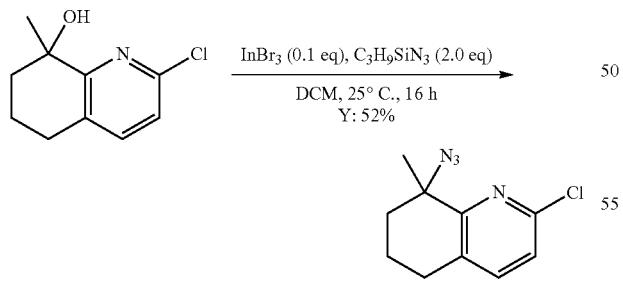

To a round bottom flask equipped was added InBr$_3$ (54 mg, 0.15 mmol, 0.1 eq) in DCM (10 mL) was added C$_3$H$_9$SiN$_3$ (350 mg, 3.0 mmol, 2.0 eq) under N$_2$. 2-chloro-8-methyl-5,6,7,8-tetrahydroquinolin-8-ol (300 mg, 1.5 mmol, 1.0 eq) in DCM (10 mL) was added to this mixture dropwise. The mixture was stirred at 25° C. for 16 h and concentrated. The residue was purified by column chromatography on silica gel (PE/EA=50/1) to give 8-azido-2-chloro-8-methyl-5,6,7,8-tetrahydroquinoline as yellow oil. 200 mg, Y: 52%. ESI-MS (M+H)$^+$: 223.1. $^1$H NMR (400 MHz, CDCl$_3$) δ: 7.31 (d, J=8.0 Hz, 1H), 7.08 (d, J=8.0 Hz, 1H), 2.75-2.61 (m, 2H), 2.00-1.71 (m, 4H), 1.66 (s, 3H).

Step 3. Synthesis of 2-chloro-8-methyl-5,6,7,8-tetrahydroquinolin-8-amine

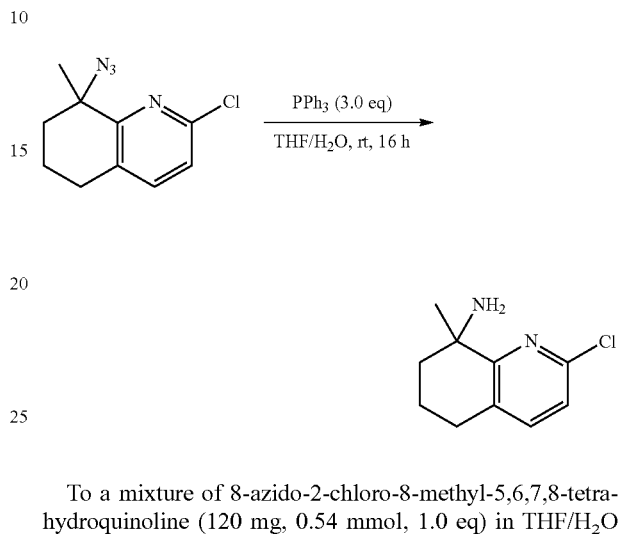

To a mixture of 8-azido-2-chloro-8-methyl-5,6,7,8-tetrahydroquinoline (120 mg, 0.54 mmol, 1.0 eq) in THF/H$_2$O (10 mL/0.5 mL) was added PPh$_3$ (425 mg, 1.6 mmol, 3.0 eq). The mixture was stirred at rt for 16 h. Then it was used directly in the next step without further purification. ESI-MS (M+H)$^+$: 197.1.

Step 4. Synthesis of tert-butyl (2-chloro-8-methyl-5,6,7,8-tetrahydroquinolin-8-yl)carbamate

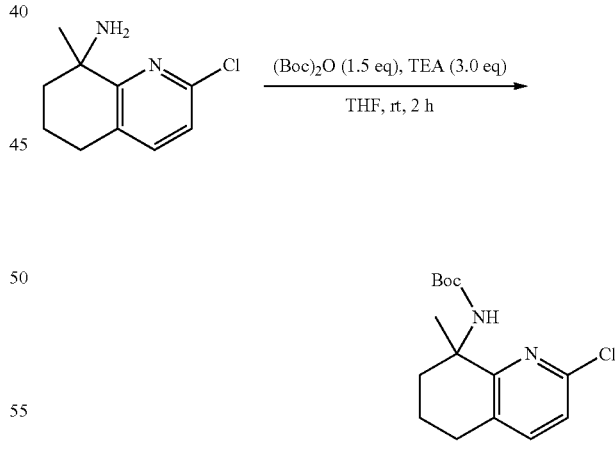

To a mixture of 2-chloro-8-methyl-5,6,7,8-tetrahydroquinolin-8-amine (0.54 mmol, 1.0 eq) in THF (5 mL) was added (Boc)$_2$O (177 mg, 0.81 mmol, 1.5 eq) and TEA (164 mg, 1.62 mmol, 3.0 eq). The mixture was stirred at rt for 2 h. After concentration, the residue was purified by column chromatography on silica gel (PE/EA=10/1) to give tert-butyl (2-chloro-8-methyl-5,6,7,8-tetrahydroquinolin-8-yl) carbamate as colorless oil. 300 mg (crude), ESI-MS (M+H)$^+$: 297.1.

Step 5. Synthesis of tert-butyl (2-(1-(6-(((tert-butyldimethylsilyl)oxy)methyl)pyridin-2-yl)-1H-indazol-6-yl)-8-methyl-5,6,7,8-tetrahydroquinolin-8-yl)carbamate

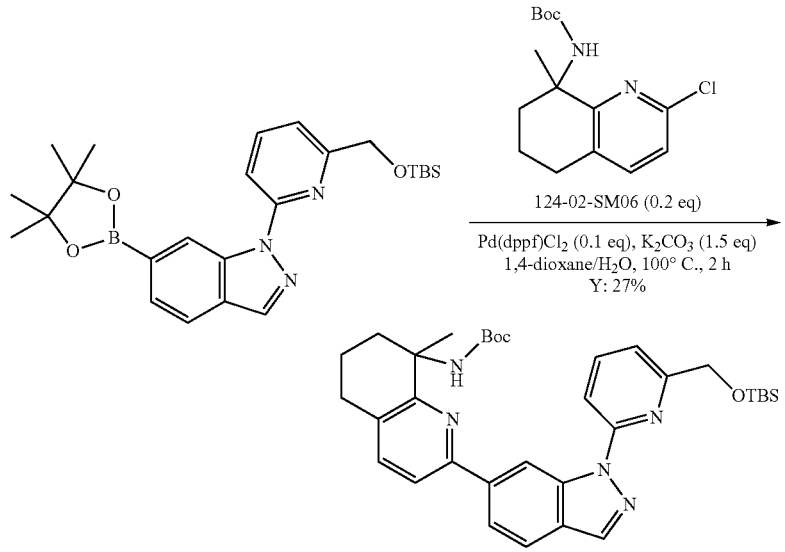

The preparation of tert-butyl (2-(1-(6-(((tert-butyldimethylsilyl)oxy)methyl)pyridin-2-yl)-1H-indazol-6-yl)-8-methyl-5,6,7,8-tetrahydroquinolin-8-yl)carbamate was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 100 mg as a yellow solid, Y: 27%. ESI-MS (M+H)+: 600.3.

Step 6. Synthesis of (6-(6-(8-amino-8-methyl-5,6,7,8-tetrahydroquinolin-2-yl)-1H-indazol-1-yl)pyridin-2-yl)methanol

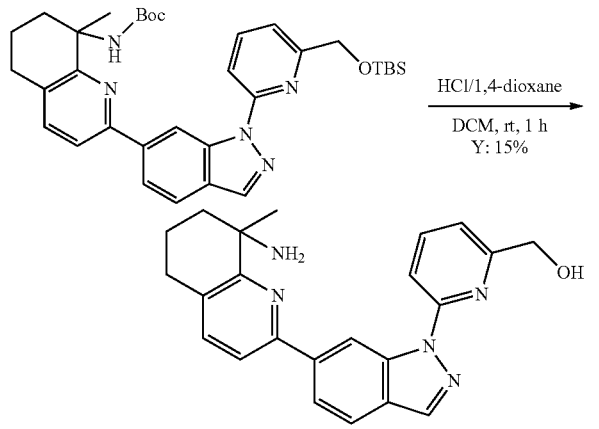

The preparation of (6-(6-(8-amino-8-methyl-5,6,7,8-tetrahydroquinolin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 5 mg as a yellow solid, Y: 15%. ESI-MS (M+H)+: 386.1. HPLC: 97%. 1H NMR (400 MHz, CD3OD) δ: 9.54 (s, 1H), 8.18 (s, 1H), 7.94-7.91 (m, 1H), 7.86-7.85 (m, 2H), 7.81-7.79 (m, 1H), 7.70-7.68 (m, 1H), 7.52-7.50 (m, 1H), 7.30-7.28 (m, 1H), 4.86 (s, 2H), 2.80 (t, J=5.6 Hz, 2H), 2.02-1.85 (m, 4H), 1.52 (s, 3H).

Example 421 (6-(6-(8-amino-8-propyl-5,6,7,8-tetrahydroquinolin-2-yl)-1H-indazol-1-yl)pyridin-2-yl)methanol Synthesis of 2-chloro-8-propyl-5,6,7,8-tetrahydroquinolin-8-ol

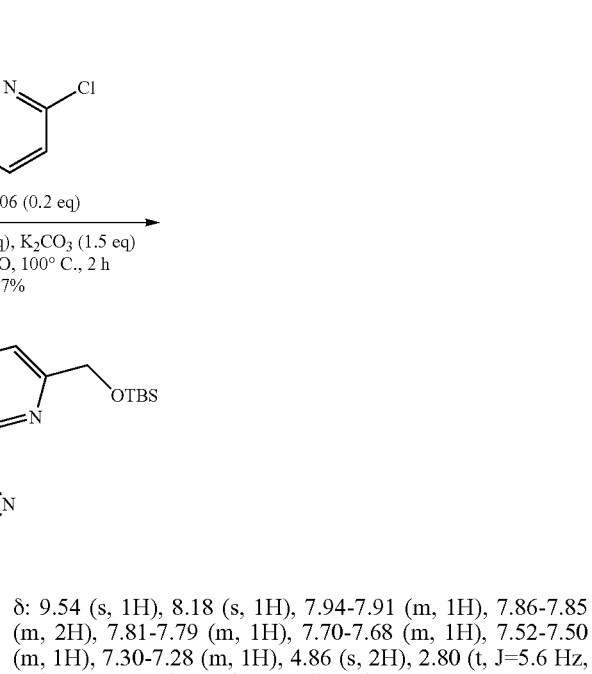

The preparation of 2-chloro-8-propyl-5,6,7,8-tetrahydroquinolin-8-ol was similar to that 2-chloro-8-methyl-5,6,7,8-tetrahydroquinolin-8-ol (Example 420, Step 1) to give 880 mg as colorless oil, Y: 42%. ESI-MS (M+H)+: 226.1.

Synthesis of 8-azido-2-chloro-8-propyl-5,6,7,8-tetrahydroquinoline

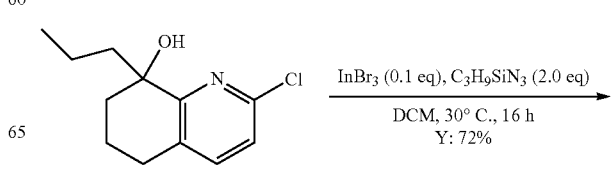

-continued

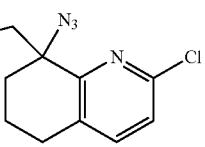

The preparation of 8-azido-2-chloro-8-propyl-5,6,7,8-tetrahydroquinoline was similar to that of 8-azido-2-chloro-8-methyl-5,6,7,8-tetrahydroquinoline (Example 420, Step 2) to give 880 mg as yellow oil, Y: 72%. ESI-MS (M+H)+: 251.1. $^1$H NMR (400 MHz, CDCl$_3$) δ: 7.38 (d, J=8.0 Hz, 1H), 7.15 (d, J=8.0 Hz, 1H), 2.80-2.62 (m, 2H), 2.25-2.17 (m, 1H), 2.06-1.77 (m, 5H), 1.48-1.36 (m, 1H), 1.28-1.16 (m, 1H), 0.97 (t, J=7.2 Hz, 3H).

Synthesis of 2-chloro-8-propyl-5,6,7,8-tetrahydroquinolin-8-amine

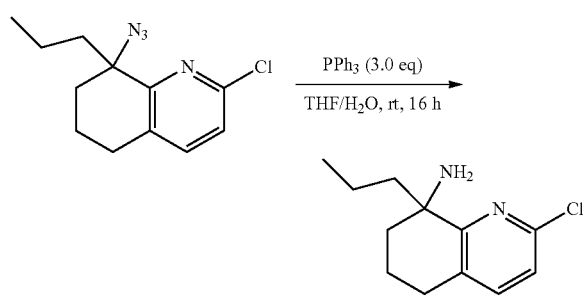

The preparation of 2-chloro-8-propyl-5,6,7,8-tetrahydroquinolin-8-amine was similar to that of 2-chloro-8-methyl-5,6,7,8-tetrahydroquinolin-8-amine (Example 420, Step 3). ESI-MS (M+H)+: 225.1.

Synthesis of tert-butyl (2-chloro-8-propyl-5,6,7,8-tetrahydroquinolin-8-yl)carbamate

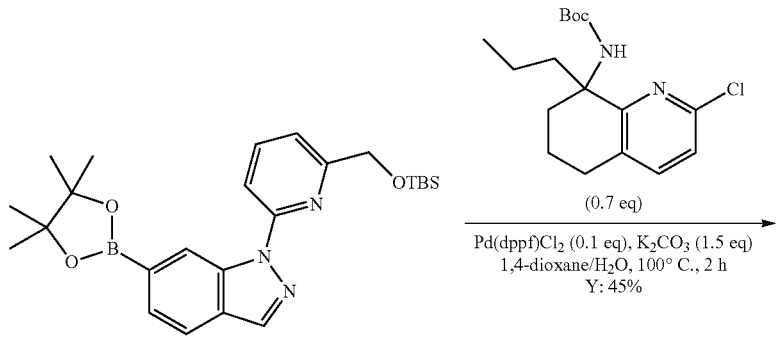

The preparation of tert-butyl (2-chloro-8-propyl-5,6,7,8-tetrahydroquinolin-8-yl)carbamate was similar to that of tert-butyl (2-chloro-8-methyl-5,6,7,8-tetrahydroquinolin-8-yl)carbamate (Example 404, Step 4) to give 200 mg as colorless oil, Y: 22% for two steps. ESI-MS (M+H)+: 325.1.

Synthesis of tert-butyl (2-(1-(6-(((tert-butyldimethylsilyl)oxy)methyl)pyridin-2-yl)-1H-indazol-6-yl)-8-propyl-5,6,7,8-tetrahydroquinolin-8-yl)carbamate

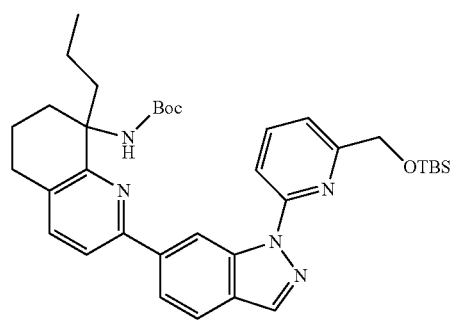

The preparation of tert-butyl (2-(1-(6-(((tert-butyldimethylsilyl)oxy)methyl)pyridin-2-yl)-1H-indazol-6-yl)-8-propyl-5,6,7,8-tetrahydroquinolin-8-yl)carbamate was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 230 mg as a yellow solid, Y: 45%. ESI-MS (M+H)⁺: 628.2.

Synthesis of (6-(6-(8-amino-8-propyl-5,6,7,8-tetrahydroquinolin-2-yl)-1H-indazol-1-yl)pyridin-2-yl)methanol

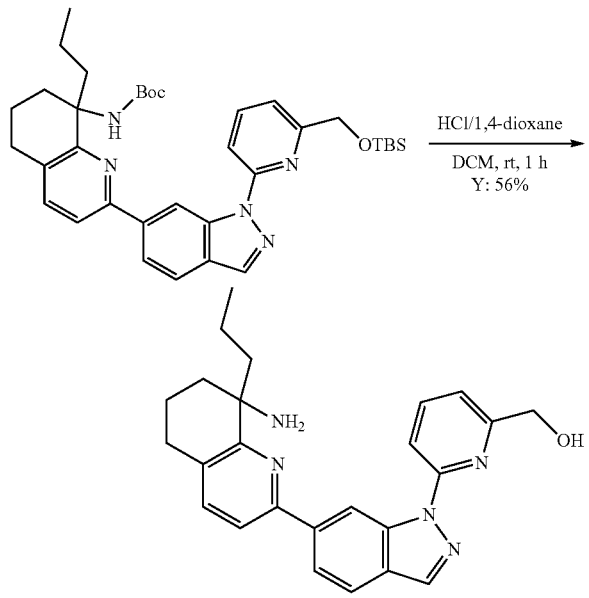

The preparation of (6-(6-(8-amino-8-propyl-5,6,7,8-tetrahydroquinolin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 73 mg as a white solid, Y: 56%. ESI-MS (M+H)⁺: 414.2. HPLC: 100%. ¹H NMR (400 MHz, CD₃OD) δ: 9.60 (s, 1H), 8.27 (s, 1H), 8.03-7.87 (m, 4H), 7.76 (d, J=8.4 Hz, 1H), 7.57 (d, J=8.4 Hz, 1H), 7.41-7.39 (m, 1H), 4.88 (s, 2H), 2.89-2.85 (m, 2H), 2.17-2.12 (m, 1H), 2.05-1.82 (m, 5H), 1.54-1.45 (m, 1H), 1.31-1.23 (m, 1H), 0.93 (t, J=7.2 Hz, 3H).

Example 422 (S)-(6-(6-(6-(amino(cyclobutyl)methyl)pyridin-2-yl)-1H-indazol-1-yl)pyridin-2-yl)methanol Synthesis of (6-bromopyridin-2-yl)(cyclobutyl)methanone

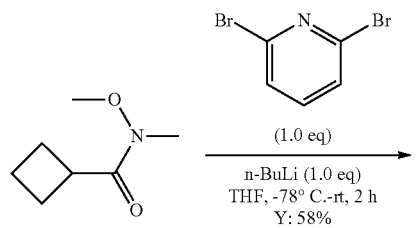

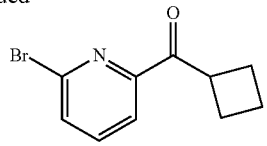

To a solution of 2,6-Dibromopyridine (CAS No. 626-05-1) (6.0 g, 25.3 mmol, 1.0 eq) in dry THF (30 mL) at −78° C. was added n-BuLi (1 M in THF, 25.3 mL, 25.3 mmol, 1.0 eq) dropwise. After stirring at −78° C. for 10 min, N-methoxy-N-methylcyclobutanecarboxamide (CAS No. 640768-72-5, 3.62 g, 25.3 mmol, 1.0 eq) in THF (10 mL) was added and the reaction mixture was stirred at −78° C. for 2 h. The reaction mixture was quenched with saturated aqueous NH₄Cl (10 mL) and extracted with EtOAc (30 mL×3). The combined organic layers were dried over anhydrous Na₂SO₄ and filtered. The filtrate was concentrated in vacuo and purified by silica gel column chromatography (PE/EA=5/1) to obtain (6-bromopyridin-2-yl)(cyclobutyl)methanone (3.5 g, Y: 58%) as colorless oil. ESI-MS (M+1): 240.1.

Synthesis of (R,E)-N-((6-bromopyridin-2-yl)(cyclobutyl)methylene)-2-methylpropane-2-sulfinamide

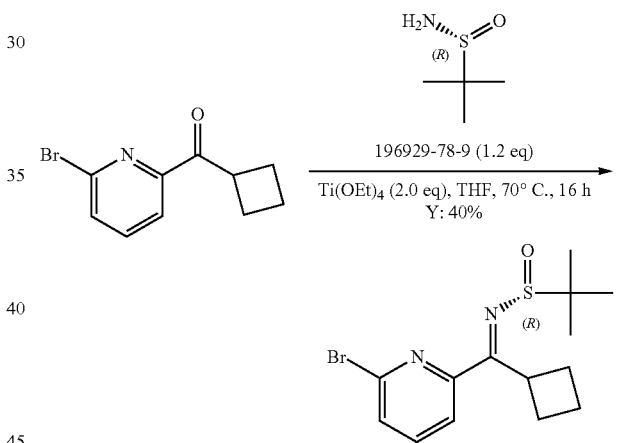

The preparation of (R,E)-N-((6-bromopyridin-2-yl)(cyclobutyl)methylene)-2-methylpropane-2-sulfinamide was similar to that of (R,E)-N-(1-(2-bromopyridin-4-yl)butylidene)-2-methylpropane-2-sulfinamide (Example 404, Step 3) to give 2.0 g as a yellow solid, Y: 40%. ESI-MS (M+1): 343.1.

Synthesis of (R)—N—((S)-(6-bromopyridin-2-yl)(cyclobutyl)methyl)-2-methylpropane-2-sulfinamide

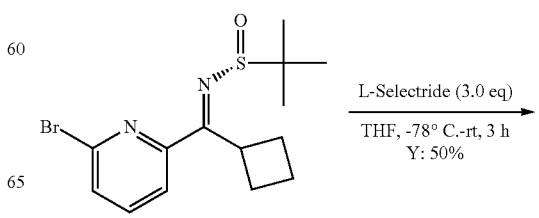

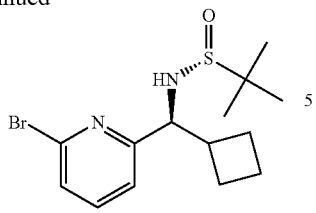

The preparation of (R)—N—((S)-(6-bromopyridin-2-yl)(cyclobutyl)methyl)-2-methylpropane-2-sulfinamide was similar to that of (R)—N—((S)-1-(2-bromopyridin-4-yl)butyl)-2-methylpropane-2-sulfinamide (Example 404, Step 4) to give 1.0 g as a white solid, Y: 50%. ESI-MS (M+1): 345.1. $^1$H NMR (400 MHz, CDCl$_3$) δ: 7.50 (t, J=7.6 Hz, 1H), 7.36 (d, J=8.0 Hz, 1H), 7.19 (d, J=7.2 Hz, 1H), 3.76-3.74 (m, 1H), 2.80-2.78 (m, 1H), 1.83-1.80 (m, 1H), 1.77-1.74 (m, 6H), 1.17 (s, 9H).

Synthesis of (R)—N—((S)-(6-(1-(6-(((tert-butyldimethylsilyl)oxy)methyl)pyridin-2-yl)-1H-indazol-6-yl)pyridin-2-yl)(cyclobutyl)methyl)-2-methylpropane-2-sulfinamide

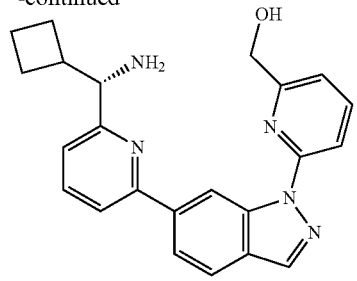

The preparation of (S)-(6-(6-(6-(amino(cyclobutyl)methyl)pyridin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 200 mg as a white solid, Y: 75%. ESI-MS (M+H)$^+$: 386.1. HPLC: 100%. $^1$H NMR (400 MHz, DMSO-d$_6$) δ: 9.60 (s, 1H), 8.51 (s, 1H), 8.39 (s, 2H), 8.23-8.20 (m, 1H), 8.09-8.01 (m, 4H), 7.89 (d, J=8.4 Hz, 1H), 7.49 (d, J=7.2 Hz, 1H), 7.42 (d, J=7.6 Hz, 1H), 5.65 (br, 1H), 4.80 (s, 2H), 4.51-4.47 (m, 1H), 2.82 (d, J=8.4 Hz, 1H), 2.11-1.75 (m, 6H).

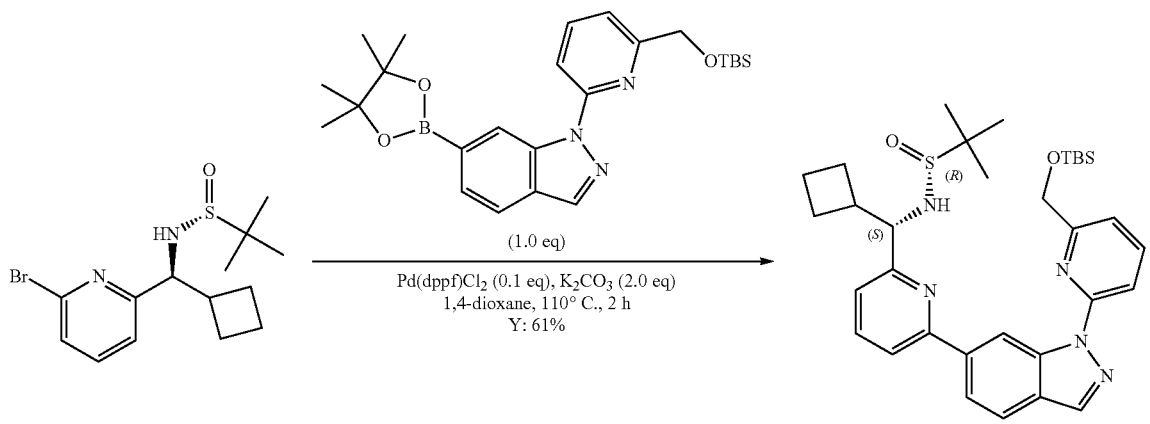

The preparation of (R)—N—((S)-(6-(1-(6-(((tert-butyldimethylsilyl)oxy)methyl)pyridin-2-yl)-1H-indazol-6-yl)pyridin-2-yl)(cyclobutyl)methyl)-2-methylpropane-2-sulfinamide was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 320 mg as light yellow oil, Y: 61%. ESI-MS (M+1): 604.2.

Synthesis of (S)-(6-(6-(6-(amino(cyclobutyl)methyl)pyridin-2-yl)-1H-indazol-1-yl)pyridin-2-yl)methanol

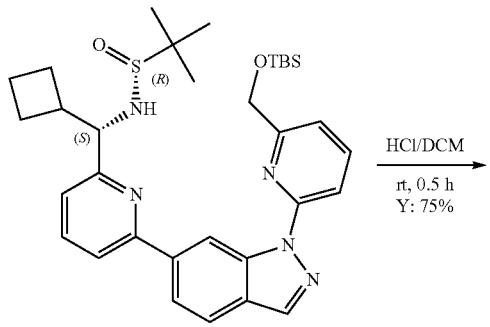

Example 423 (S)-(6-(6-(6-(1-aminobutyl)pyridin-2-yl)-4-(1-methyl-1,2,3,6-tetrahydropyridin-4-yl)-1H-indazol-1-yl)pyridin-2-yl)methanol Step 1. Synthesis of tert-butyl 4-(1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl)-5,6-dihydropyridine-1(2H)-carboxylate

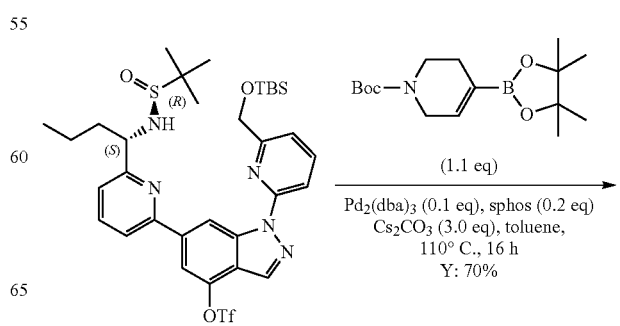

493

-continued

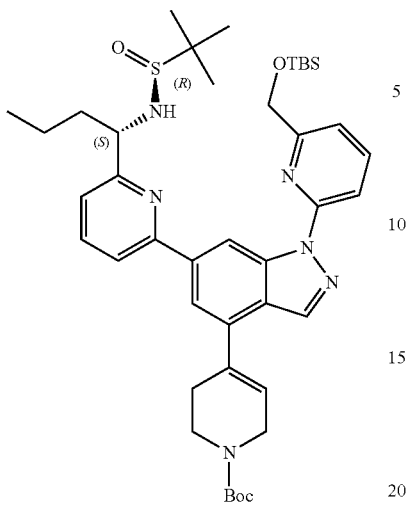

494

-continued

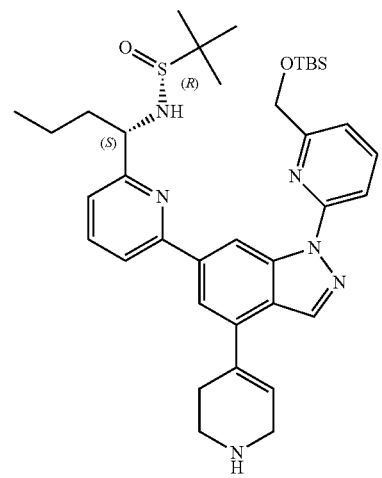

The preparation of tert-butyl 4-(1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl)-5,6-dihydropyridine-1(2H)-carboxylate was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) using 1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl trifluoromethanesulfonate (Example 324, Step 14) to give 1.1 g as a yellow solid, Y: 70%. ESI-MS (M+H)⁺: 773.4.

Step 2. Synthesis of (R)—N—((S)-1-(6-(1-(6-(((tert-butyldimethylsilyl)oxy)methyl)pyridin-2-yl)-4-(1,2,3,6-tetrahydropyridin-4-yl)-1H-indazol-6-yl)pyridin-2-yl)butyl)-2-methylpropane-2-sulfinamide A mixture of tert-butyl 4-(1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl)-5,6-dihydropyridine-1(2H)-carboxylate (1.1 g, 1.4 mmol, 1.0 eq) in DCM/TFA (30 mL/5 mL) was stirred at rt for 2 h. The reaction was quenched with saturated NaHCO₃ solution and extracted with DCM (50 mL×3). The combined organic layers were dried and concentrated to afford (R)—N—((S)-1-(6-(1-(6-(((tert-butyldimethylsilyl)oxy)methyl)pyridin-2-yl)-4-(1,2,3,6-tetrahydropyridin-4-yl)-1H-indazol-6-yl)pyridin-2-yl)butyl)-2-methylpropane-2-sulfinamide. 800 mg, as a yellow solid, Y: 83%. ESI-MS (M+H)⁺: 673.4.

Step 3. Synthesis of (R)—N—((S)-1-(6-(1-(6-(((tert-butyldimethylsilyl)oxy)methyl)pyridin-2-yl)-4-(1-methyl-1,2,3,6-tetrahydropyridin-4-yl)-1H-indazol-6-yl)pyridin-2-yl)butyl)-2-methylpropane-2-sulfinamide

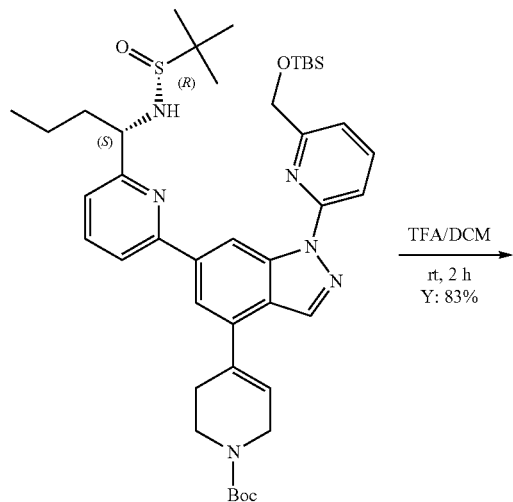

TFA/DCM
rt, 2 h
Y: 83%

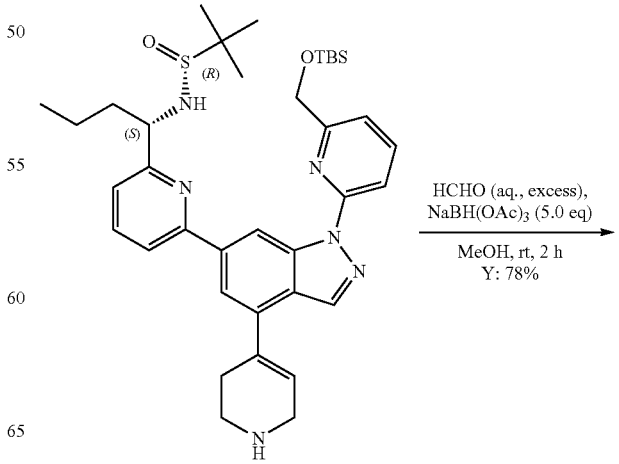

HCHO (aq., excess),
NaBH(OAc)₃ (5.0 eq)
MeOH, rt, 2 h
Y: 78%

495

-continued

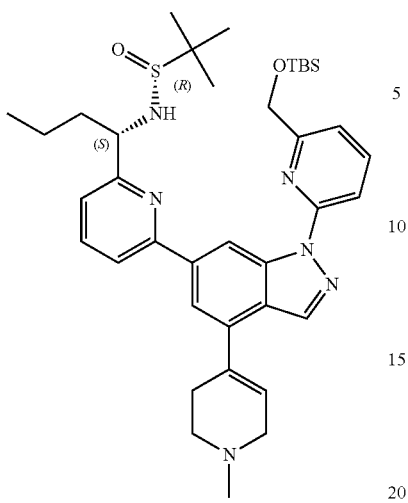

To a mixture of (R)—N—((S)-1-(6-(1-(6-(((tert-butyldimethylsilyl)oxy)methyl)pyridin-2-yl)-4-(1,2,3,6-tetrahydropyridin-4-yl)-1H-indazol-6-yl)pyridin-2-yl)butyl)-2-methylpropane-2-sulfinamide (150 mg, 0.22 mmol, 1.0 eq) and HCHO (aq., excess) in MeOH (10 mL) was added NaBH(OAc)$_3$ (233 mg, 1.10 mmol, 5.0 eq) at rt. The mixture was stirred at rt for 2 h. After concentration, the residue was purified by silica gel chromatography with PE/EA (1/1) as eluent to give (R)—N—((S)-1-(6-(1-(6-(((tert-butyldimethylsilyl)oxy)methyl)pyridin-2-yl)-4-(1-methyl-1,2,3,6-tetrahydropyridin-4-yl)-1H-indazol-6-yl)pyridin-2-yl)butyl)-2-methylpropane-2-sulfinamide 120 mg as a yellow solid, Y: 78%. ESI-MS (M+H)$^+$: 687.4.

Step 4. Synthesis of (S)-(6-(6-(6-(1-aminobutyl)pyridin-2-yl)-4-(1-methyl-1,2,3,6-tetrahydropyridin-4-yl)-1H-indazol-1-yl)pyridin-2-yl)methanol

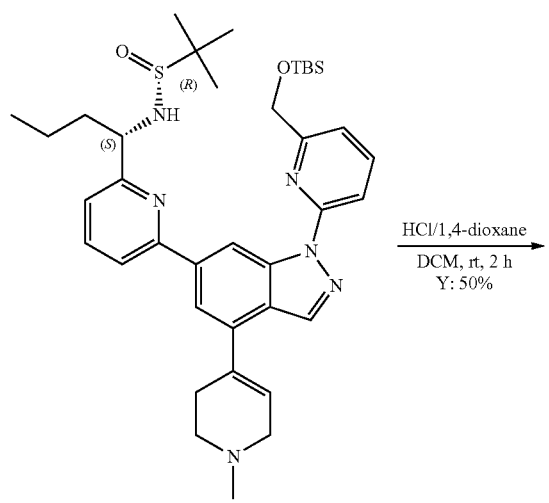

496

-continued

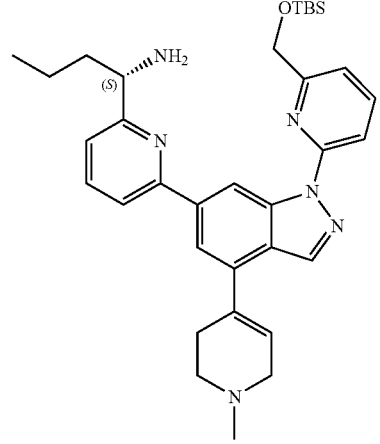

The preparation of (S)-(6-(6-(6-(1-aminobutyl)pyridin-2-yl)-4-(1-methyl-1,2,3,6-tetrahydropyridin-4-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 42 mg as a yellow solid, Y: 50%. ESI-MS (M+H)$^+$: 469.3. HPLC: 94%. $^1$H NMR (400 MHz, CD$_3$OD) δ: 9.59 (s, 1H), 8.44 (s, 1H), 7.98-7.90 (m, 5H), 7.42-7.37 (m, 2H), 6.29 (s, 1H), 4.85 (s, 2H), 4.19 (t, J=6.8 Hz, 1H), 3.33-3.30 (m, 2H), 2.87-2.86 (m, 4H), 2.50 (s, 3H), 1.96-1.88 (m, 2H), 1.48-1.37 (m, 2H), 1.00 (t, J=7.2 Hz, 3H).

Example 424 (S)-(6-(6-(6-(1-aminobutyl)pyridin-2-yl)-4-(1-methylpiperidin-4-yl)-1H-indazol-1-yl)pyridin-2-yl)methanol Step 1. Synthesis of (R)—N—((S)-1-(6-(1-(6-(((tert-butyldimethylsilyl)oxy)methyl)pyridin-2-yl)-4-(piperidin-4-yl)-1H-indazol-6-yl)pyridin-2-yl)butyl)-2-methylpropane-2-sulfinamide

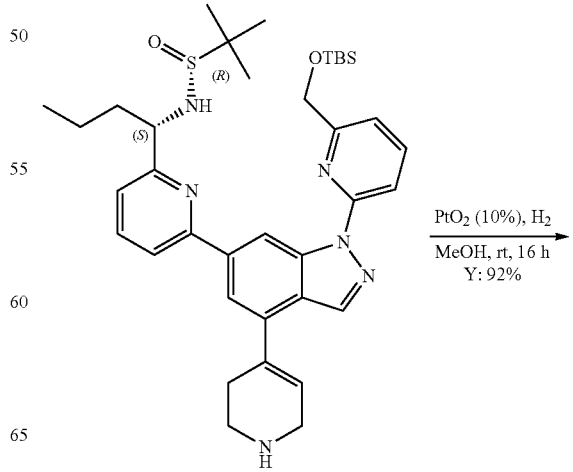

497

-continued

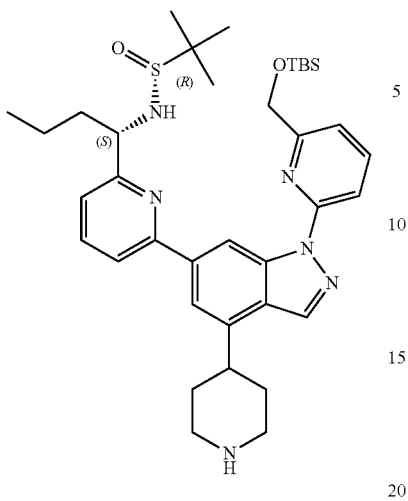

498

-continued

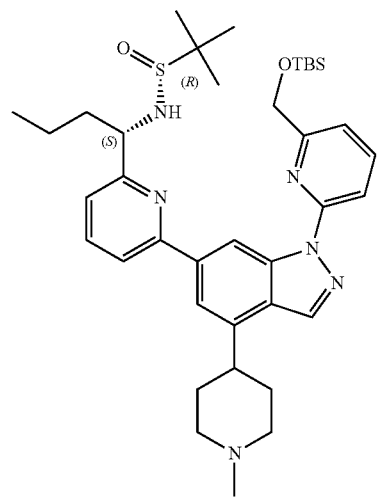

A mixture of (R)—N—((S)-1-(6-(1-(6-(((tert-butyldimethylsilyl)oxy)methyl)pyridin-2-yl)-4-(1,2,3,6-tetrahydropyridin-4-yl)-1H-indazol-6-yl)pyridin-2-yl)butyl)-2-methylpropane-2-sulfinamide (Example 423, Step 2, 500 mg, 0.74 mmol, 1.0 eq) and PtO$_2$ (50 mg, 10% w/w) in MeOH (20 mL) was stirred at rt for 16 h under H$_2$ atmosphere. The mixture was filtrated and concentrated to give (R)—N—((S)-1-(6-(1-(6-(((tert-butyldimethylsilyl)oxy)methyl)pyridin-2-yl)-4-(piperidin-4-yl)-1H-indazol-6-yl)pyridin-2-yl)butyl)-2-methylpropane-2-sulfinamide as a yellow solid which was used for next step without further purification. 460 mg, Y: 92%. ESI-MS (M+H)$^+$: 675.4.

Step 2. Synthesis of (R)—N—((S)-1-(6-(1-(6-(((tert-butyldimethylsilyl)oxy)methyl)pyridin-2-yl)-4-(1-methylpiperidin-4-yl)-1H-indazol-6-yl)pyridin-2-yl)butyl)-2-methylpropane-2-sulfinamide The preparation of (R)—N—((S)-1-(6-(1-(6-(((tert-butyldimethylsilyl)oxy)methyl)pyridin-2-yl)-4-(1-methylpiperidin-4-yl)-1H-indazol-6-yl)pyridin-2-yl)butyl)-2-methylpropane-2-sulfinamide was similar to that of (R)—N—((S)-1-(6-(1-(6-(((tert-butyldimethylsilyl)oxy)methyl)pyridin-2-yl)-4-(1-methyl-1,2,3,6-tetrahydropyridin-4-yl)-1H-indazol-6-yl)pyridin-2-yl)butyl)-2-methylpropane-2-sulfinamide (Example 423, Step 3) to give 110 mg as a yellow solid, Y: 47%. ESI-MS (M+H)$^+$: 689.4.

Step 3. Synthesis of (S)-(6-(6-(6-(1-aminobutyl)pyridin-2-yl)-4-(1-methylpiperidin-4-yl)-1H-indazol-1-yl)pyridin-2-yl)methanol

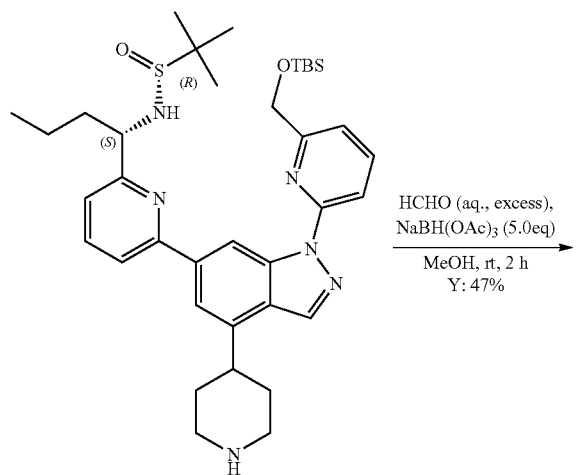

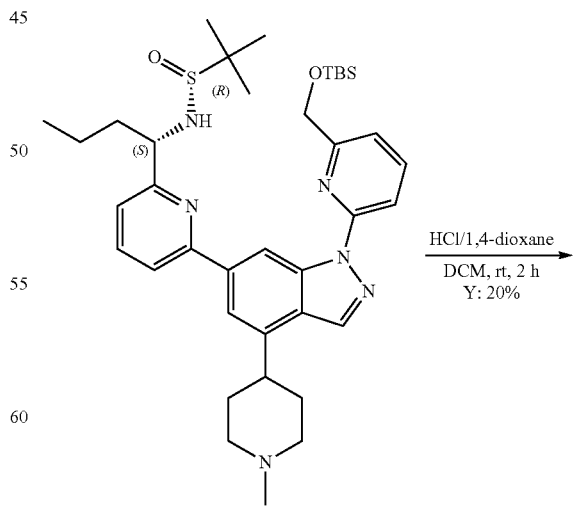

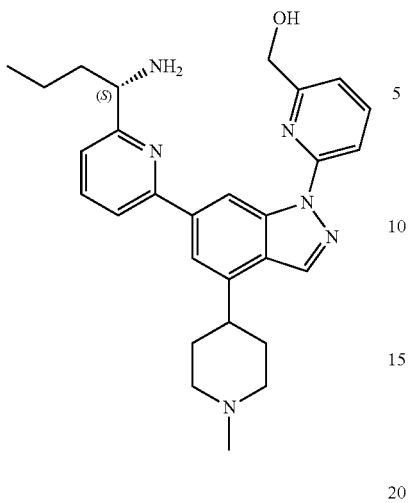

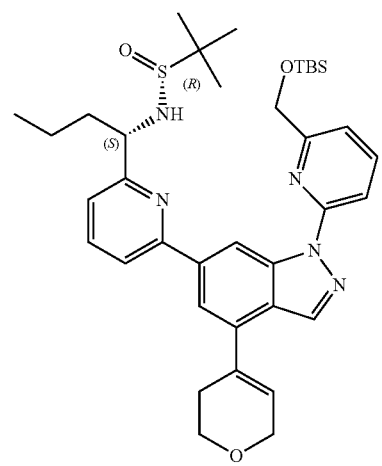

The preparation of (S)-(6-(6-(6-(1-aminobutyl)pyridin-2-yl)-4-(1-methylpiperidin-4-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 15 mg as a white solid, Y: 20%. ESI-MS (M+H)$^+$: 471.3. HPLC: 93%. $^1$H NMR (400 MHz, CD$_3$OD) δ: 9.46 (s, 1H), 8.47 (s, 1H), 7.94-7.87 (m, 5H), 7.38-7.36 (m, 1H), 7.32 (t, J=4.0 Hz, 1H), 4.83 (s, 2H), 4.07-4.03 (m, 1H), 3.18-3.04 (m, 3H), 2.38 (s, 3H), 2.31-2.29 (m, 2H), 2.15-2.01 (m, 4H), 1.91-1.80 (m, 2H), 1.44-1.26 (m, 2H), 0.95 (t, J=7.2 Hz, 3H).

Example 425 (S)-(6-(6-(6-(1-aminobutyl)pyridin-2-yl)-4-(tetrahydro-2H-pyran-4-yl)-1H-indazol-1-yl)pyridin-2-yl)methanol Synthesis of (R)—N—((S)-1-(6-(1-(6-(((tert-butyldimethylsilyl)oxy)methyl)pyridin-2-yl)-4-(3,6-dihydro-2H-pyran-4-yl)-1H-indazol-6-yl)pyridin-2-yl)butyl)-2-methylpropane-2-sulfinamide

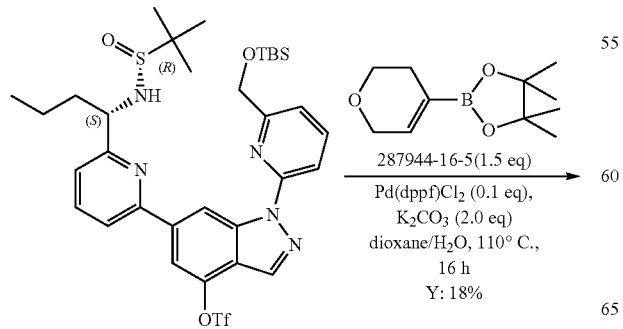

The preparation of (R)—N—((S)-1-(6-(1-(6-(((tert-butyldimethylsilyl)oxy)methyl)pyridin-2-yl)-4-(3,6-dihydro-2H-pyran-4-yl)-1H-indazol-6-yl)pyridin-2-yl)butyl)-2-methylpropane-2-sulfinamide was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) using 1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl trifluoromethanesulfonate (Example 324, Step 14) to give 100 mg as a yellow solid, Y: 18%. ESI-MS (M+H)$^+$: 674.3.

Synthesis of (R)—N—((S)-1-(6-(1-(6-(((tert-butyldimethylsilyl)oxy)methyl)pyridin-2-yl)-4-(tetrahydro-2H-pyran-4-yl)-1H-indazol-6-yl)pyridin-2-yl)butyl)-2-methylpropane-2-sulfinamide

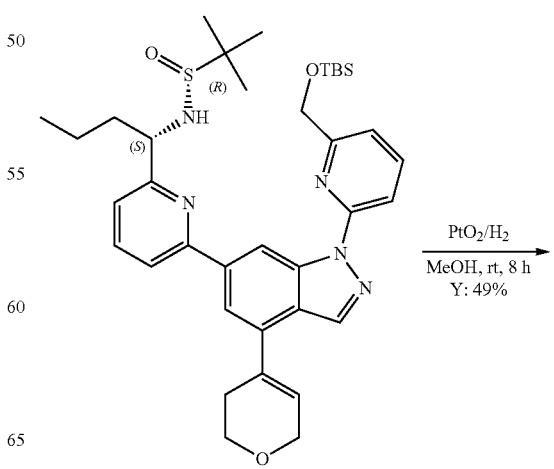

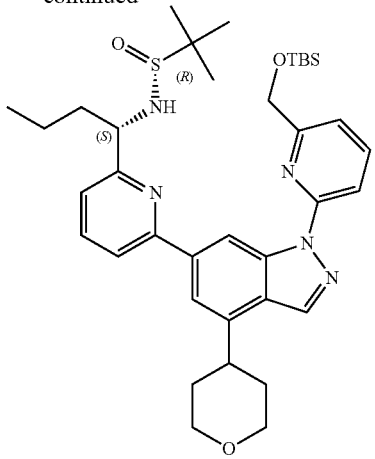

The preparation of (R)—N—((S)-1-(6-(1-(6-(((tert-butyldimethylsilyl)oxy)methyl)pyridin-2-yl)-4-(tetrahydro-2H-pyran-4-yl)-1H-indazol-6-yl)pyridin-2-yl)butyl)-2-methylpropane-2-sulfinamide was similar to that of (R)—N—((S)-1-(6-(1-(6-(((tert-butyldimethylsilyl)oxy)methyl)pyridin-2-yl)-4-(piperidin-4-yl)-1H-indazol-6-yl)pyridin-2-yl)butyl)-2-methylpropane-2-sulfinamide (Example 424, Step 1) to give 50 mg as a yellow solid, Y: 49%. ESI-MS (M+H)⁺: 676.4.

Synthesis of (S)-(6-(6-(6-(1-aminobutyl)pyridin-2-yl)-4-(tetrahydro-2H-pyran-4-yl)-1H-indazol-1-yl)pyridin-2-yl)methanol

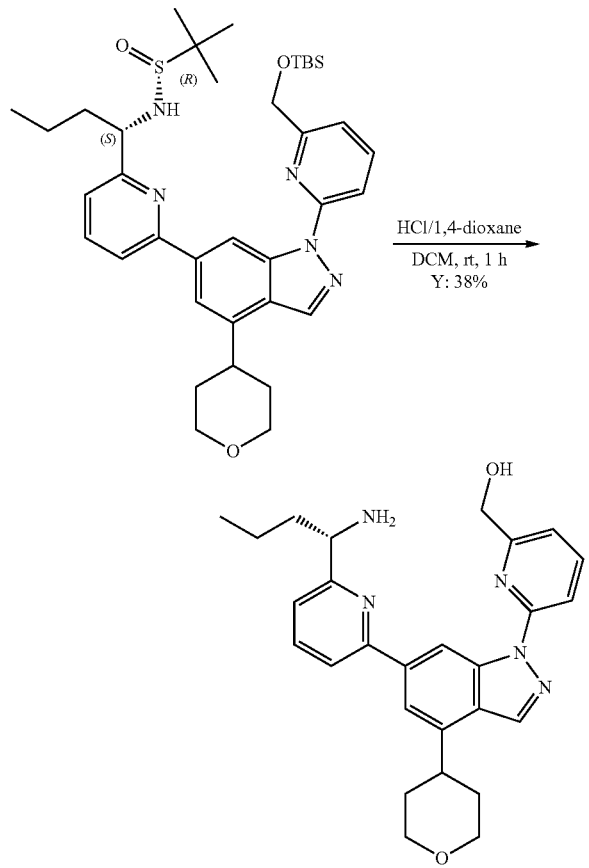

The preparation of (S)-(6-(6-(6-(1-aminobutyl)pyridin-2-yl)-4-(tetrahydro-2H-pyran-4-yl)-1H-indazol-1-yl)pyridin-2-yl)methanol was similar to that of (S)-(6-(6-(4-(1-aminobutyl)pyridin-2-yl)-1H-indazol-6-yl)pyridin-2-yl)methanol (Example 404, Step 6) to give 16 mg as a yellow solid, Y: 38%. ESI-MS (M+H)⁺: 458.2. HPLC: 100%. ¹H NMR (400 MHz, CD₃OD) δ: 9.59 (s, 1H), 8.49 (s, 1H), 8.06-7.94 (m, 5H), 7.41 (d, J=7.6 Hz, 1H), 7.34 (t, J=4.0 Hz, 1H), 4.85 (s, 2H), 4.53 (t, J=6.8 Hz, 1H), 4.15-4.11 (m, 2H), 3.74-3.72 (m, 2H), 3.49-3.43 (m, 1H), 2.15-1.93 (m, 6H), 1.49-1.36 (m, 2H), 1.00 (t, J=7.6 Hz, 3H).

Example 426 (S)-2-((6-(6-(1-aminobutyl)pyridin-2-yl)-1-(6-(hydroxymethyl)pyridin-2-yl)-1H-indazol-4-yl)oxy)ethanol Step 1 Synthesis of (6-(6-bromo-4-methoxy-1H-indazol-1-yl)pyridin-2-yl)methanol

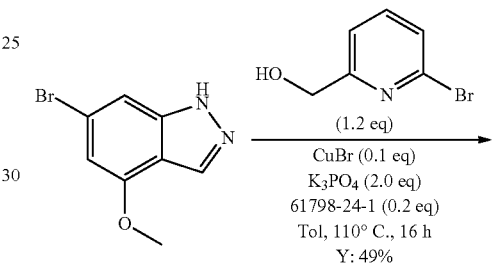

A mixture of 6-bromo-4-methoxy-1H-indazole (Cas No. 885519-21-1, 11.8 g, 52.0 mmol), (6-bromopyridin-2-yl)methanol (11.7 g, 62.4 mmol, 1.2 eq), CuBr (744 mg, 5.2 mmol), N,N'-Dimethyl-1,2-cyclohexanediamine (CAS No. 61798-24-1, 1.5 g, 10.4 mmol) and K₃PO₄ (22.0 g, 104.0 mmol) in toluene (300 mL) was stirred at 100° C. for 16 h under nitrogen atmosphere. After cooling to rt, the solution was filtered through Celite and the filtrate was concentrated in vacuo. The residue was purified by silica gel chromatography (PE/EtOAc, 6:1) to give the product as a light yellow solid (8.5 g, 49%).

ES (+) MS m/e=336/338 (M+1)

Step 2 Synthesis of 6-bromo-1-(6-(hydroxymethyl)pyridin-2-yl)-1H-indazol-4-ol

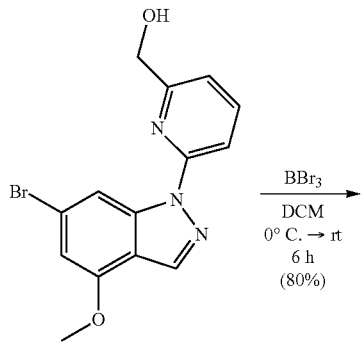

To a suspension of (6-(6-bromo-4-methoxy-1H-indazol-1-yl)pyridin-2-yl)methanol (8.0 g, 24.0 mmol) in DCM (100 mL) was added 3 M BBr₃ in DCM (24 mL, 72.0 mmol) slowly at 0° C. The reaction mixture was stirred for 6 h at rt. The reaction was quenched with MeOH (50 mL) and the product was collected by filtration and washed with MeOH (5 mL×2) to give the title compound (6.2 g, 80%) as a yellow solid. ES (+) MS m/e=321/323 (M+1)

Step 3 Synthesis of 6-bromo-4-((tert-butyldimethylsilyl)oxy)-1-(6-(((tert-butyldimethylsilyl)oxy)methyl)pyridin-2-yl)-1H-indazole

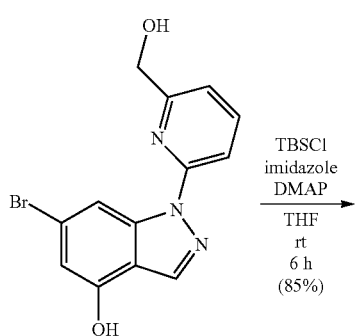

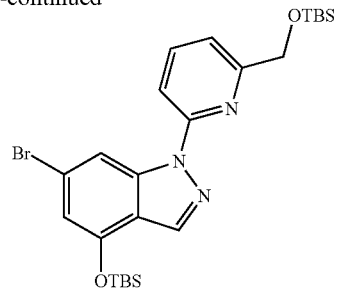

To a solution of 6-bromo-1-(6-(hydroxymethyl)pyridin-2-yl)-1H-indazol-4-ol (6.0 g, 18.75 mmol) in THF (150 mL) were added TBSCl (14.1 g, 93.75 mmol), 1H-imidazole (6.4 g, 93.75 mmol) and DMAP (230 mg, 1.88 mmol). The mixture was stirred at rt for 6 h, diluted with H₂O (200 mL) and extracted with EtOAc (100 mL×3). The combined organic layers were washed with brine (200 mL×2), dried over anhydrous Na₂SO₄, concentrated under reduced pressure to give the product (8.7 g, 85%) as a yellow solid.

ES (+) MS m/e=548/550 (M+1)

Step 4 Synthesis of 6-bromo-1-(6-(((tert-butyldimethylsilyl)oxy)methyl)pyridin-2-yl)-1H-indazol-4-ol

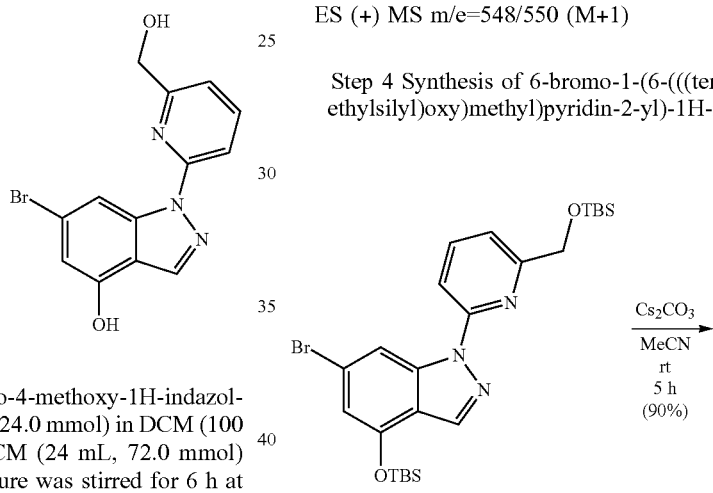

To a solution of 6-bromo-4-((tert-butyldimethylsilyl)oxy)-1-(6-(((tert-butyldimethylsilyl)oxy)methyl)pyridin-2-yl)-1H-indazole (8.0 g, 14.6 mmol) in MeCN (200 mL) were added Cs₂CO₃ (4.8 g, 14.6 mmol). The mixture was stirred at rt for 5 h, filtered through Celite before concentrating the filtrate in vacuo. The residue was purified by flash chromatography (silica gel, PE/EtOAc, 4:1) to give 6-bromo-1-(6-(((tert-butyldimethylsilyl)oxy)methyl)pyridin-2-yl)-1H-indazol-4-ol (5.7 g, 90%) as a light yellow solid. ¹H NMR (400 MHz, d₆-DMSO) δ 8.48 (s, 1H), 8.21 (s, 1H), 7.84-7.82 (m, 2H), 7.39-7.36 (m, 1H), 6.70 (d, J=1.2 Hz, 1H), 4.92 (s, 2H), 1.00 (s, 9H), 0.08 (s, 6H).

ES (+) MS m/e=434/436 (M+1)

Step 5. Synthesis of 6-bromo-4-(2-((tert-butyldimethylsilyl)oxy)ethoxy)-1-(6-(((tert-butyldimethylsilyl)oxy)methyl)pyridin-2-yl)-1H-indazole

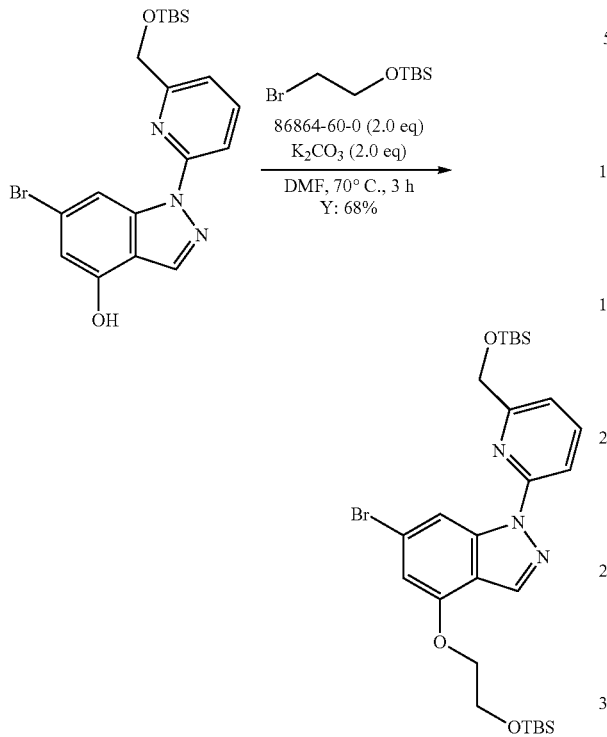

To a mixture of 6-bromo-1-(6-(((tert-butyldimethylsilyl)oxy)methyl)pyridin-2-yl)-1H-indazol-4-ol (600 mg, 1.4 mmol, 1.0 eq) and K₂CO₃ (382 mg, 2.8 mmol, 2.0 eq) in DMF (5 mL) was added (2-Bromoethoxy)-tert-butyldimethylsilane (CAS No. 86864-60-0, 660 mg, 2.8 mmol, 2.0 eq). The resulting mixture was stirred at 70° C. for 3 h. The mixture was diluted with water (50 mL) and extracted with EA (50 mL×3). The combined organic phase was washed with brine and dried over Na₂SO₄. After filtration and concentration, the residue was purified by silica gel column chromatography (PE/EA=10/1) to give 6-bromo-4-(2-((tert-butyldimethylsilyl)oxy)ethoxy)-1-(6-(((tert-butyldimethylsilyl)oxy)methyl)pyridin-2-yl)-1H-indazole. 560 mg, as colorless oil, Y: 68%. ESI-MS (M+H)⁺: 592.2.

Step 6. Synthesis of 4-(2-((tert-butyldimethylsilyl)oxy)ethoxy)-1-(6-(((tert-butyldimethylsilyl)oxy)methyl)pyridin-2-yl)-6-(4,4,5,5-tetramethyl-1,3,2-dioxaborolan-2-yl)-1H-indazole

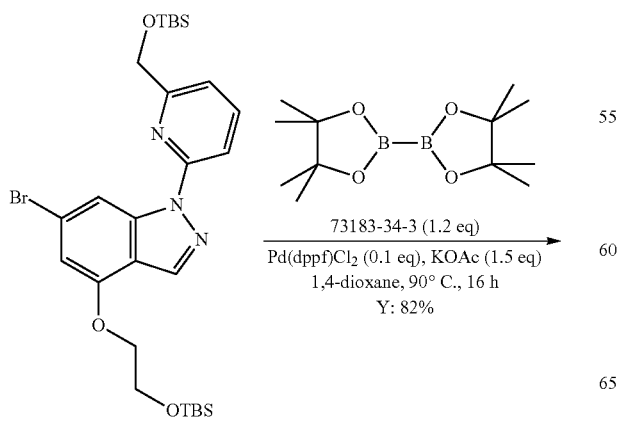

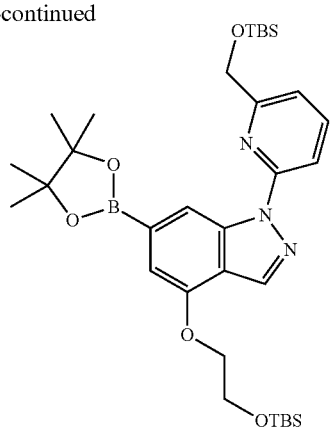

The preparation of 4-(2-((tert-butyldimethylsilyl)oxy)ethoxy)-1-(6-(((tert-butyldimethylsilyl)oxy)methyl)pyridin-2-yl)-6-(4,4,5,5-tetramethyl-1,3,2-dioxaborolan-2-yl)-1H-indazole was similar to that of 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) to give 500 mg as a white solid, Y: 82%. ESI-MS (M+H)⁺: 640.3.

Step 7. Synthesis of N—((S)-1-(6-(4-(2-((tert-butyldimethylsilyl)oxy)ethoxy)-1-(6-(((tert-butyldimethylsilyl)oxy)methyl)pyridin-2-yl)-1H-indazol-6-yl)pyridin-2-yl)butyl)-2-methylpropane-2-sulfinamide

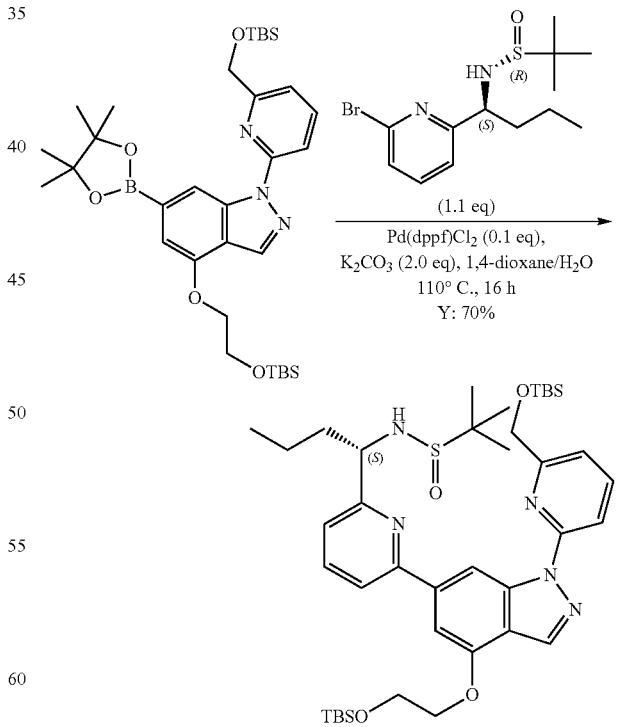

The preparation of N—((S)-1-(6-(4-(2-((tert-butyldimethylsilyl)oxy)ethoxy)-1-(6-(((tert-butyldimethylsilyl)oxy)methyl)pyridin-2-yl)-1H-indazol-6-yl)pyridin-2-yl)butyl)-2-methylpropane-2-sulfinamide was similar to that of (S)—

N—((S)-1-(2-(1-(6-((((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 420 mg as a yellow solid, Y: 70%. ESI-MS (M+H)⁺: 766.3.

Step 8. Synthesis of (S)-2-((6-(6-(1-aminobutyl)pyridin-2-yl)-1-(6-(hydroxymethyl)pyridin-2-yl)-1H-indazol-4-yl)oxy)ethanol

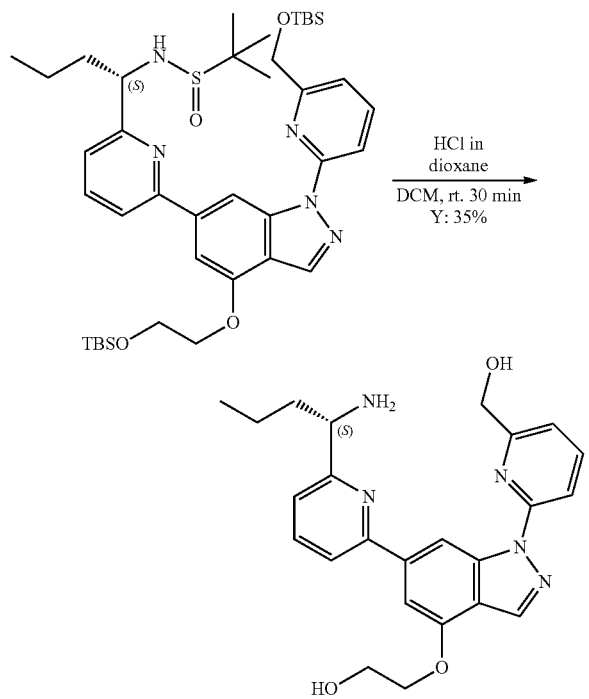

The preparation of (S)-2-((6-(6-(1-aminobutyl)pyridin-2-yl)-1-(6-(hydroxymethyl)pyridin-2-yl)-1H-indazol-4-yl)oxy)ethanol was similar to that of (S)-(6-(6-(4-(1-aminobutyl)pyridin-2-yl)-1H-indazol-1-yl)pyridin-2-yl)methanol (Example 404, Step 6) to give 82 mg as a yellow solid, Y: 35%. ESI-MS (M+H)⁺: 434.2. HPLC: 100% ¹H NMR (400 MHz, CD₃OD) δ: 9.18 (s, 1H), 8.29 (s, 1H), 7.97 (d, J=8.0 Hz, 1H), 7.91-7.85 (m, 3H), 7.46 (s, 1H), 7.33 (d, J=7.2 Hz, 1H), 7.26 (d, J=6.0 Hz, 1H), 4.78 (s, 2H), 4.45 (t, J=6.4 Hz, 1H), 4.32 (t, J=4.4 Hz, 2H), 3.96 (t, J=4.4 Hz, 2H), 1.96-1.90 (m, 2H), 1.37-1.30 (m, 2H), 0.92 (t, J=7.2 Hz, 3H).

Example 427 (S)-(6-(6-(6-(1-amino-4,4,4-trifluorobutyl)pyridin-2-yl)-1H-indazol-1-yl)pyridin-2-yl)methanol Synthesis of 1-(6-bromopyridin-2-yl)-4,4,4-trifluorobutan-1-one

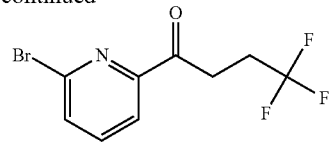

The preparation of 1-(6-bromopyridin-2-yl)-4,4,4-trifluorobutan-1-one was similar to that of 1-(2-bromopyridin-4-yl)butan-1-one (Example 404, Step 2) using 6-bromo-N-methoxy-N-methylpicolinamide (Example 145, Step 1) as the starting material to give 900 mg as colorless oil, Y: 78%. ESI-MS (M+H)⁺: 282.0. ¹H NMR (400 MHz, CDCl₃) δ: 8.02-8.00 (m, 1H), 7.75-7.68 (m, 2H), 3.49 (t, J=7.6 Hz, 2H), 2.61-2.53 (m, 2H).

Synthesis of (R,E)-N-(1-(6-bromopyridin-2-yl)-4,4,4-trifluorobutylidene)-2-methylpropane-2-sulfinamide

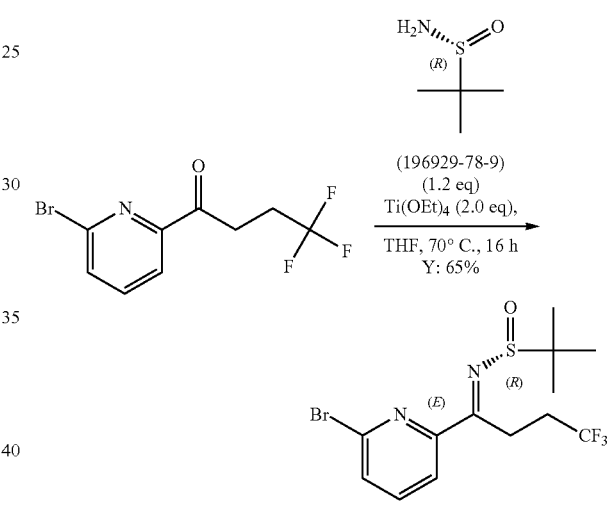

The preparation of (R,E)-N-(1-(6-bromopyridin-2-yl)-4,4,4-trifluorobutylidene)-2-methylpropane-2-sulfinamide was similar to that of (R,E)-N-(1-(2-bromopyridin-4-yl)butylidene)-2-methylpropane-2-sulfinamide (Example 404, Step 3) to give 800 mg as a white solid, Y: 65%. ESI-MS (M+H)⁺: 385.1. ¹H NMR (400 MHz, CDCl₃) δ: 7.98-7.97 (m, 1H), 7.66-7.58 (m, 2H), 3.79-3.75 (m, 1H), 3.53-3.49 (m, 1H), 2.62-2.50 (m, 2H), 1.34 (s, 9H).

Synthesis of (R)—N—((S)-1-(6-bromopyridin-2-yl)-4,4,4-trifluorobutyl)-2-methylpropane-2-sulfinamide

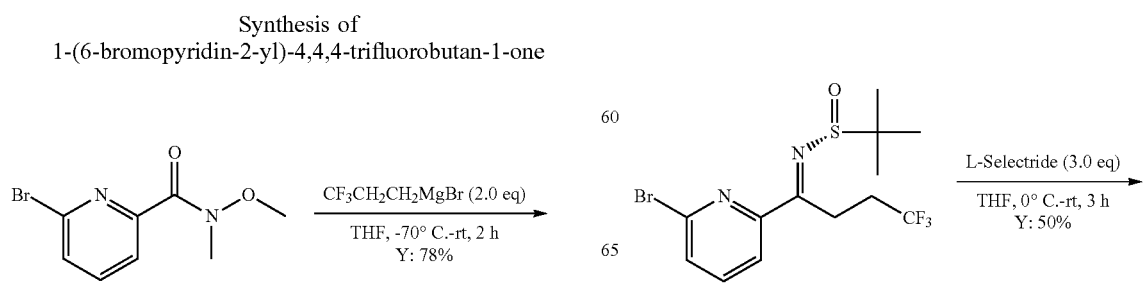

509

-continued

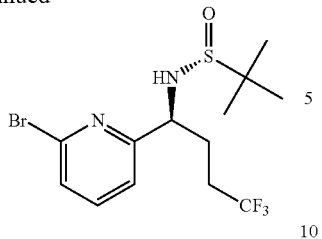

The preparation of (R)—N—((S)-1-(6-bromopyridin-2-yl)-4,4,4-trifluorobutyl)-2-methylpropane-2-sulfinamide was similar to that of (R)—N—((S)-1-(2-bromopyridin-4-yl)butyl)-2-methylpropane-2-sulfinamide (Example 404, Step 4) to give 900 mg as a white solid, Y: 50%. ESI-MS (M+H)+: 387.1. ¹H NMR (400 MHz, CDCl₃) δ: 7.57-7.53 (m, 1H), 7.43-7.41 (m, 1H), 7.26-7.22 (m, 1H), 4.47-4.44 (m, 1H), 4.08-4.06 (m, 1H), 2.25-2.13 (m, 4H), 1.19 (s, 9H).

Synthesis of (R)—N—((S)-1-(6-(1-(6-(((tert-butyldimethylsilyl)oxy)methyl)pyridin-2-yl)-1H-indazol-6-yl)pyridin-2-yl)-4-(4-trifluorobutyl)-2-methylpropane-2-sulfinamide

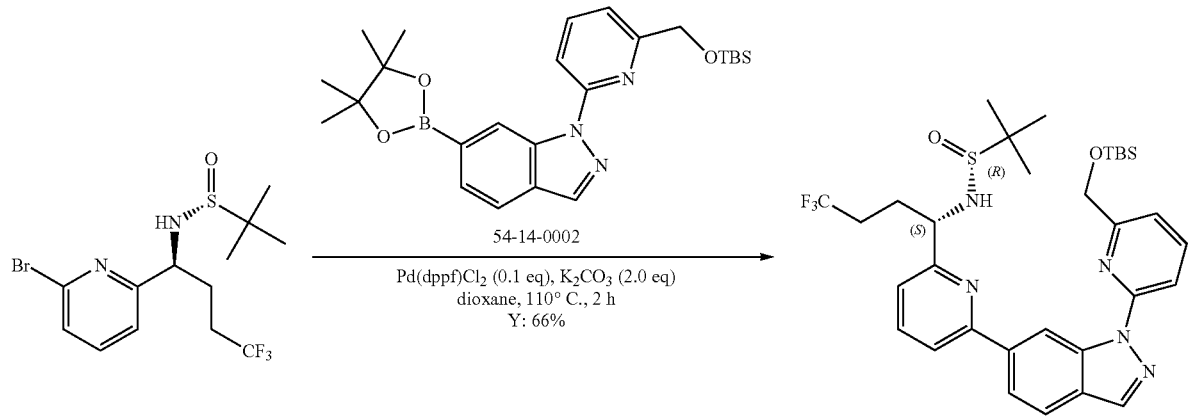

The preparation of (R)—N—((S)-1-(6-(1-(6-(((tert-butyldimethylsilyl)oxy)methyl)pyridin-2-yl)-1H-indazol-6-yl)pyridin-2-yl)-4,4,4-trifluorobutyl)-2-methylpropane-2-sulfinamide was similar to that of (S)—N—((S)-1-(2-(1-(6-(((tert-butyldimethylsilyl)oxy)methyl)pyridin-2-yl)-1H-indazol-6-yl)pyridin-4-yl)butyl)-2-methylpropane-2-sulfinamide (Example 404, Step 5) to give 300 mg as a brown solid, Y: 66%. ESI-MS (M+H)+: 646.3.

Synthesis of (S)-(6-(6-(6-(1-amino-4,4,4-trifluorobutyl)pyridin-2-yl)-1H-indazol-1-yl)pyridin-2-yl)methanol

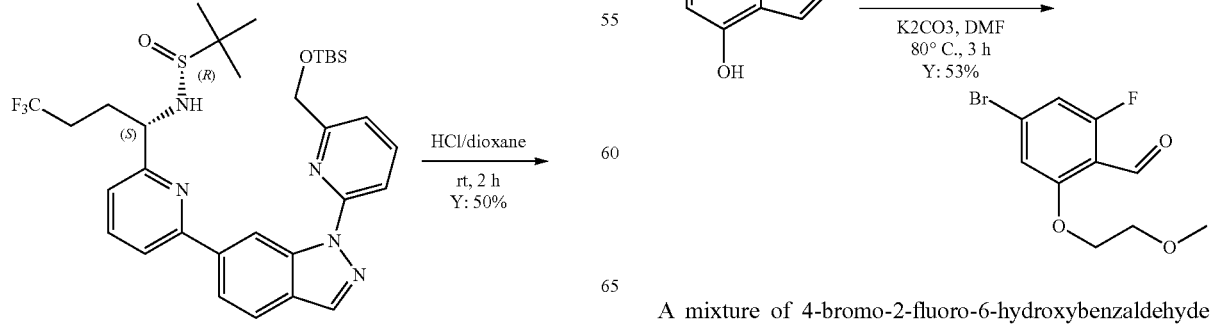

510

-continued

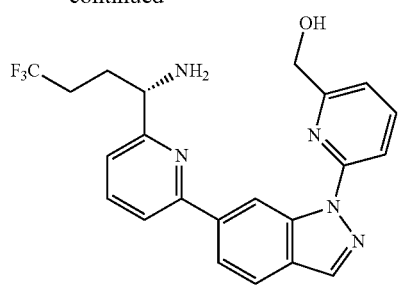

The preparation of (S)-(6-(6-(6-(1-amino-4,4,4-trifluorobutyl)pyridin-2-yl)-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 100 mg as a yellow solid, Y: 50%. ESI-MS (M+H)+: 428.2. HPLC: 100%. ¹H NMR (400 MHz, CD₃OD) δ: 9.63 (s, 1H), 8.29 (s, 1H), 8.14-7.91 (m, 6H), 7.53 (d, J=5.2 Hz, 1H), 7.35 (d, J=5.6 Hz, 1H), 4.87 (s, 2H), 4.74-4.72 (m, 1H), 2.41-2.22 (m, 4H).

Example 428 (S)-4-amino-4-(6-(1-(6-(hydroxymethyl)pyrazin-2-yl)-4-(2-methoxyethoxy)-1H-indazol-6-yl)pyridin-2-yl)butan-1-ol Step 1. Synthesis of 4-bromo-2-fluoro-6-(2-methoxyethoxy)benzaldehyde

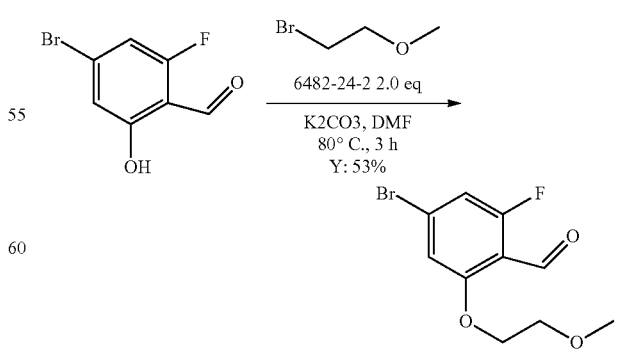

A mixture of 4-bromo-2-fluoro-6-hydroxybenzaldehyde (CAS No. 1427438-90-1; 12.0 g, 55.3 mmol, 1.0 eq), 2-Bromoethyl methyl ether (CAS No. 6482-24-2, 15.2 g, 110.6 mmol, 2.0 eq), K₂CO₃ (15.3 g, 110.6 mmol, 2.0 eq) in DMF (60 mL) was stirred at 80° C. for 3 h. The mixture was quenched with water (300 mL) and extracted with DCM (3×100 mL). After concentration, the residue was purified by column chromatography on silica gel (PE/EA=5/1) to give 4-bromo-2-fluoro-6-(2-methoxyethoxy)benzaldehydeas a yellow solid. 8.1 g, Y: 53%. ESI-MS (M+H)⁺: 277.0.

Step 2. Synthesis of 6-bromo-4-(2-methoxyethoxy)-1H-indazole

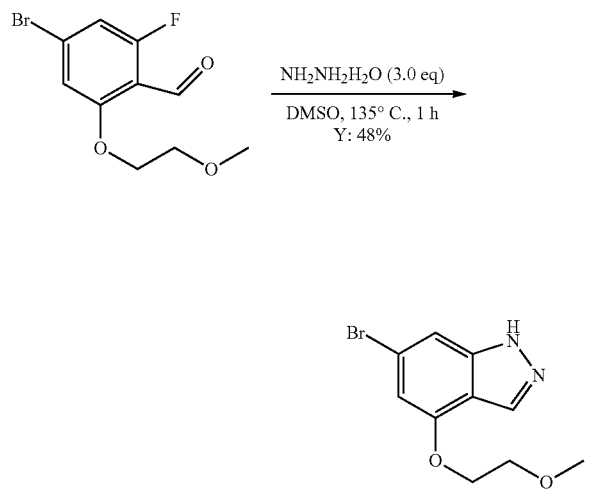

A mixture of 4-bromo-2-fluoro-6-(2-methoxyethoxy)benzaldehyde (8.1 g, 29.1 mmol, 1.0 eq), NH₂NH₂H₂O (4.37 g, 87.3 mmol, 3.0 eq) in DMSO (80 mL) was stirred at 135° C. for 1 h. The mixture was quenched with water (400 mL) and extracted with DCM (3×100 mL). The organic phase was washed with brine and dried over Na₂SO₄. After filtration and concentration, the residue was purified by column chromatography on silica gel (PE/EA=5/1) to give 6-bromo-4-(2-methoxyethoxy)-1H-indazole as a white solid. 3.8 g, Y: 48%. ESI-MS (M+H)⁺: 271.0.

Step 3. Synthesis of methyl 6-(6-bromo-4-(2-methoxyethoxy)-1H-indazol-1-yl)pyrazine-2-carboxylate

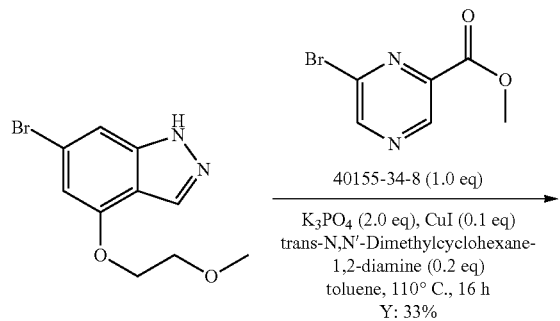

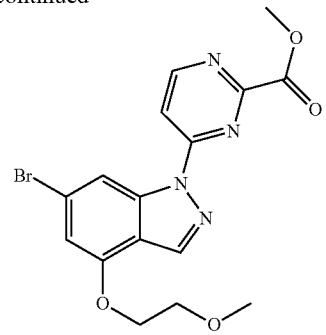

A mixture of 6-bromo-4-(2-methoxyethoxy)-1H-indazole (4.0 g, 14.8 mmol, 1.0 eq), methyl 6-bromopyrazine-2-carboxylate (CAS No. 40155-34-8, 3.19 g, 14.8 mmol, 1.0 eq), K₃PO₄ (6.28 g, 29.6 mmol, 2.0 eq), CuI (284 mg, 1.48 mmol, 0.1 eq) and trans-N,N'-Dimethylcyclohexane-1,2-diamine (420 mg, 2.96 mmol, 0.2 eq) in toluene (30 mL) was stirred at 110° C. for 16 h under N₂. After concentration, the residue was purified by column chromatography on silica gel (PE/EA=3/1) to give methyl 6-(6-bromo-4-(2-methoxyethoxy)-1H-indazol-1-yl)pyrazine-2-carboxylate as a white solid. 2.0 g, Y: 33%. ESI-MS (M+H)⁺: 407.0. ¹H NMR (400 MHz, CDCl₃) δ: 9.55 (s, 1H), 9.12 (s, 1H), 8.73 (s, 1H), 8.32 (d, J=4.8 Hz, 1H), 6.85 (s, 1H), 4.32-4.30 (m, 2H), 4.11 (s, 3H), 3.88-3.86 (m, 2H), 3.50 (s, 3H).

Step 4. Synthesis of (6-(6-bromo-4-(2-methoxyethoxy)-1H-indazol-1-yl)pyrazin-2-yl)methanol

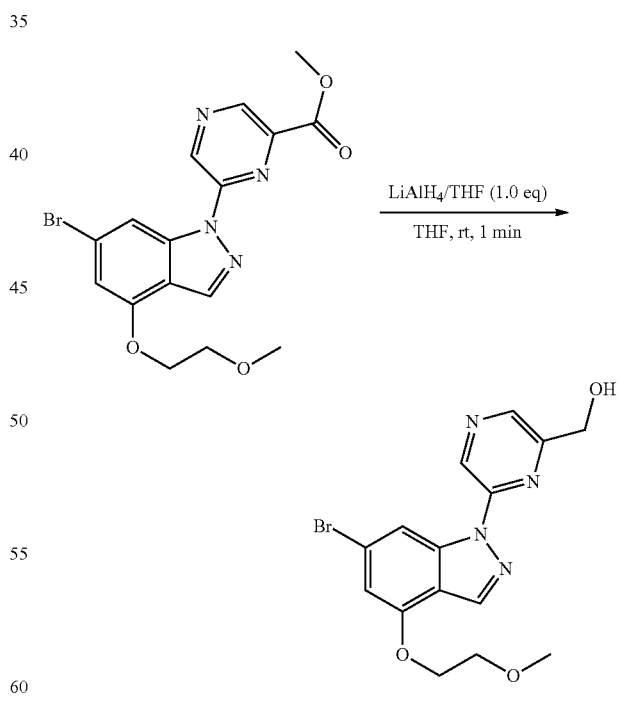

To a solution of methyl 6-(6-bromo-4-(2-methoxyethoxy)-1H-indazol-1-yl)pyrazine-2-carboxylate (400 mg, 1.0 mmol, 1.0 eq) in THF (10 mL) was added LiAlH₄ (1.0 mL, 1.0 mmol, 1.0 eq, 1 M in THF) at rt. The mixture was stirred at rt for 1 min. The reaction was quenched with Na₂SO₄·10H₂O. After filtration and concentrated to (6-(6- bromo-4-(2-methoxyethoxy)-1H-indazol-1-yl)pyrazin-2-yl)methanol, which was directly used for next step without further purification. ESI-MS (M+H)+: 379.0

Step 5. Synthesis of 6-bromo-1-(6-(((tert-butyldimethylsilyl)oxy)methyl)pyrazin-2-yl)-4-(2-methoxyethoxy)-1H-indazole

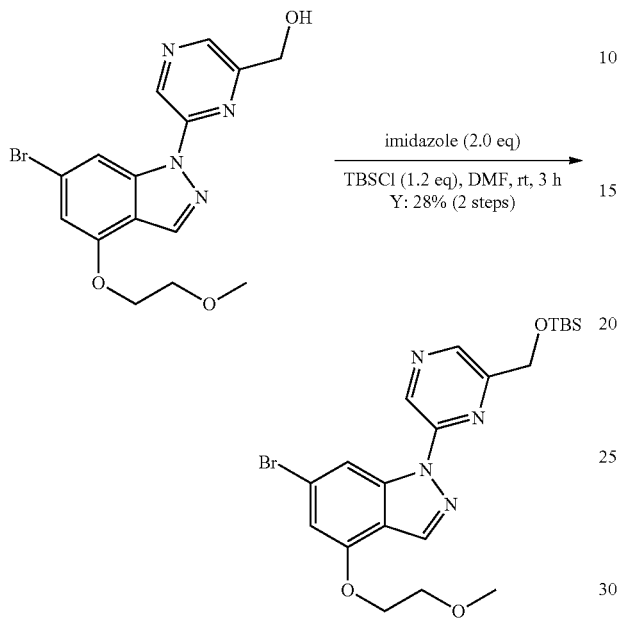

To a mixture of (6-(6-bromo-4-(2-methoxyethoxy)-1H-indazol-1-yl)pyrazin-2-yl)methanol and imidazole (432 mg, 6.36 mmol, 2.0 eq) in DMF (25 mL) was added TBSCl (572 mg, 3.82 mol, 1.2 eq) at rt. The mixture was stirred at rt for 3 h. The mixture was diluted with water (300 mL) and extracted with DCM (3×90 mL). The combined organic phases were washed with brine and dried over Na$_2$SO$_4$. After filtration and concentration, the residue was purified by column chromatography on silica gel (PE/EA=10/1) to give 6-bromo-1-(6-(((tert-butyldimethylsilyl)oxy)methyl)pyrazin-2-yl)-4-(2-methoxyethoxy)-1H-indazole as a yellow solid. 700 mg, Y: 28% (2 steps). ESI-MS (M+H)+: 493.1. $^1$H NMR (400 MHz, CDCl$_3$) δ: 9.27 (s, 1H), 8.61 (s, 1H), 8.48 (s, 1H), 8.29 (s, 1H), 6.80 (s, 1H), 4.96 (s, 2H), 4.31-4.29 (m, 2H), 3.87-3.85 (m, 2H), 3.50 (s, 3H), 1.00 (s, 9H), 0.21 (s, 6H).

Step 6. Synthesis of 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole

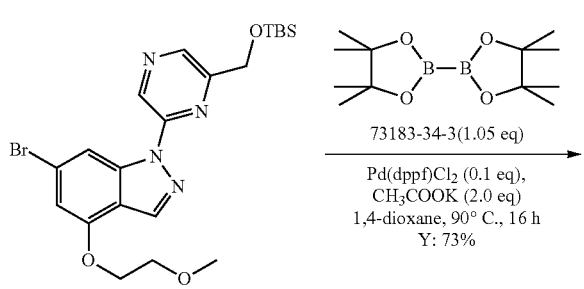

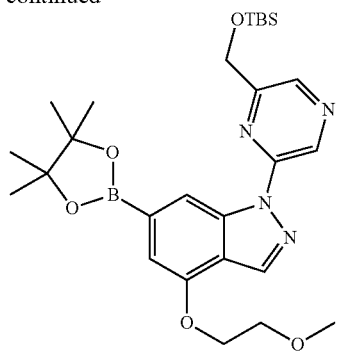

A mixture of 6-bromo-1-(6-(((tert-butyldimethylsilyl)oxy)methyl)pyrazin-2-yl)-4-(2-methoxyethoxy)-1H-indazole (350 mg, 0.71 mmol, 1.0 eq), Bis(pinacolato)diboron (CAS No. 73183-34-3, 190 mg, 0.75 mmol, 1.05 eq), Pd(dppf)Cl$_2$ (58 mg, 0.071 mmol, 0.1 eq) and CH$_3$COOK (139 mg, 1.42 mmol, 2.0 eq) in 1,4-dioxane (10 mL) stirred at 90° C. for 16 h under N$_2$. After concentration, the residue was purified by column chromatography on silica gel (PE/EA=5/1) to give 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole as a yellow solid. 280 mg, Y: 73%. ESI-MS (M+H)+: 541.3.

Step 7A. Synthesis of 1-(6-bromopyridin-2-yl)-4-hydroxybutan-1-one

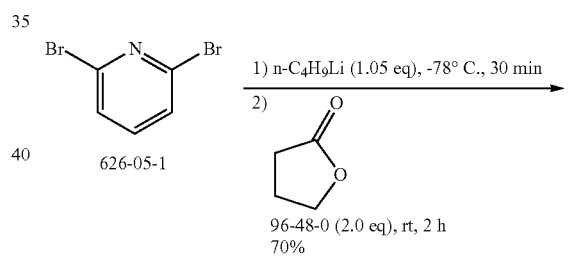

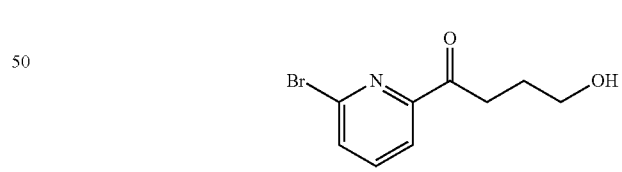

To a solution of Cas No. 626-05-1 (80 g, 340 mmol, 1.0 eq) in dry Et$_2$O (600 mL) was slowly added n-BuLi (2.4 M in hexane, 149 mL, 357 mmol, 1.05 eq) at −78° C. After stirring at −78° C. for 30 min, Cas No 96-48-0 (58.5 g, 680 mmol, 2.0 eq) was added to the mixture. Then the mixture was stirred at −78° C. for 2 h. The reaction was quenched with saturated NH$_4$Cl solution and extracted with EtOAc (500 mL×3). The combined organics were dried (Na$_2$SO$_4$) and concentrated in vacuo. The residue was used for next step without further purification. 58 g, as yellow oil, Y: 70%. ESI-MS (M+H)+: 244.1.

Step 7B. Synthesis of 1-(6-bromopyridin-2-yl)-4-((tert-butyldimethylsilyl)oxy)butan-1-one

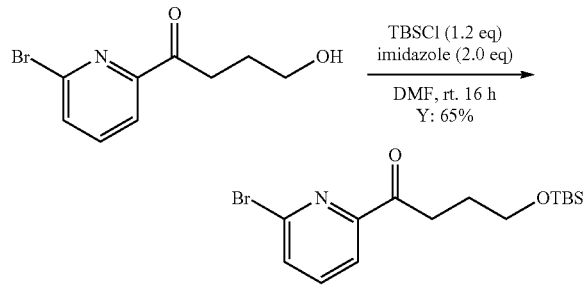

To a solution of 1-(6-bromopyridin-2-yl)-4-hydroxybutan-1-one (58 g, 237 mmol, 1.0 eq) in DMF (200 mL) was added TBSCl (43 g, 286 mmol, 1.2 eq) and imidazole (32 g, 477 mmol, 2.0 eq). The resulting mixture was stirred at rt for 16 h. The mixture was diluted with water (1000 mL) and extracted with EA (300 mL×3). The organic phase was washed with brine and dried over $Na_2SO_4$. After filtration and concentration, the residue was purified by silica gel chromatography using PE/EtOAc (50/1) as eluent to give the title compound (56 g, Y: 65%) as yellow solid; ESI-MS (M+1): 358.0.

Step 7C. Synthesis of (R,E)-N-(1-(6-bromopyridin-2-yl)-4-((tert-butyldimethylsilyl)oxy)butylidene)-2-methylpropane-2-sulfinamide

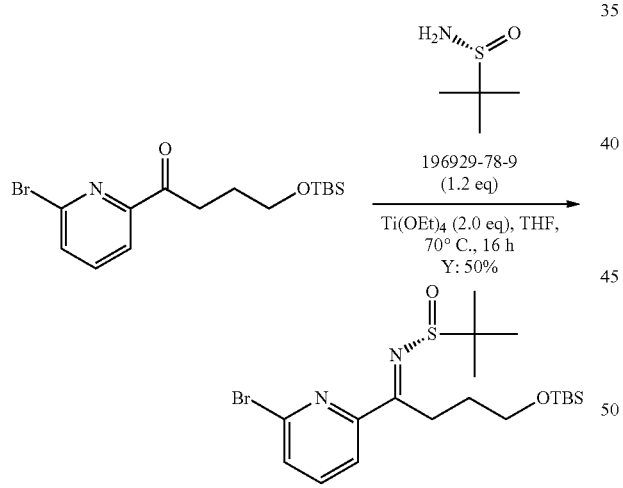

A mixture of 1-(6-bromopyridin-2-yl)-4-((tert-butyldimethylsilyl)oxy)butan-1-one (56 g, 157 mmol, 1.0 eq), Cas No. 196929-78-9 (23 g, 188 mmol, 1.2 eq) and Ti(OEt)$_4$ (72 g, 314 mmol, 2.0 eq) in THF (500 mL) was stirred while purging $N_2$ at 70° C. for 16 h. The mixture was diluted with H$_2$O (1000 mL) and extracted with EA (500 mL×3). The organic phase was washed with brine (200 mL) and dried over $Na_2SO_4$. After filtration and concentration, the residue was purified by silica gel chromatography using PE/EA (10/1) as eluent to give (R,E)-N-(1-(6-bromopyridin-2-yl)-4-((tert-butyldimethylsilyl)oxy)butylidene)-2-methylpropane-2-sulfinamide (36 g, Y: 50%) as a yellow oil, Y: 50%. ESI-MS (M+H)$^+$: 461.1.

Step 7D. Synthesis of (R)—N—((S)-1-(6-bromopyridin-2-yl)-4-((tert-butyldimethylsilyl)oxy)butyl)-2-methylpropane-2-sulfinamide

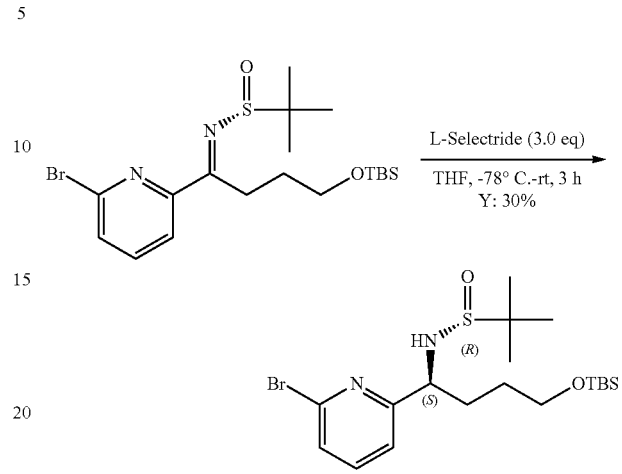

To a mixture of (R,E)-N-(1-(6-bromopyridin-2-yl)-4-((tert-butyldimethylsilyl)oxy)butylidene)-2-methylpropane-2-sulfinamide (36 g, 78 mmol, 1.0 eq) in THF (300 mL) was stirred while purging $N_2$ at −78° C. for 10 min. To this system was added L-Selectride (234 mL, 1 M, 234 mmol, 3.0 eq) dropwise at −78° C. for 3 h. The mixture was diluted with aqueous NH$_4$Cl solution (100 mL) dropwise and extracted with EA (300 mL×3). The organic phase was washed with brine (200 mL) and dried over $Na_2SO_4$. After filtration and concentration, the residue was purified by silica gel chromatography with PE/EA (10/1) as eluent to give (R)—N—((S)-1-(6-bromopyridin-2-yl)-4-((tert-butyldimethylsilyl)oxy)butyl)-2-methylpropane-2-sulfinamide (11 g, Y: 30%) as a white solid, ESI-MS (M+H)$^+$: 463.1. HPLC: 100%. $^1$H NMR (400 MHz, CD$_3$OD) δ: 7.69 (t, J=7.6 Hz, 1H), 7.51-7.49 (m, 1H), 7.43 (d, J=8.0 Hz, 1H), 4.43 (t, J=7.2 Hz, 1H), 3.69-3.66 (m, 2H), 2.04-1.98 (m, 2H), 1.49-1.47 (m, 2H), 1.20 (s, 9H), 0.92 (s, 9H), 0.07 (s, 6H)

Step 7. Synthesis of (R)—N—((S)-4-((tert-butyldimethylsilyl)oxy)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide

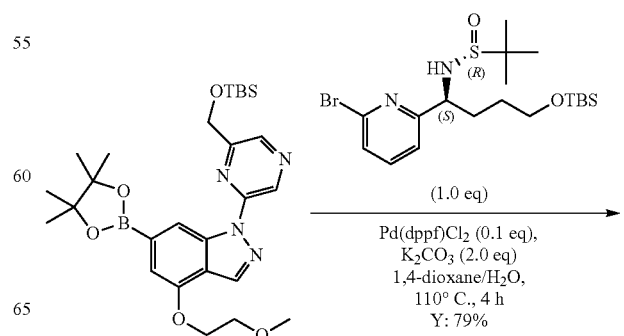

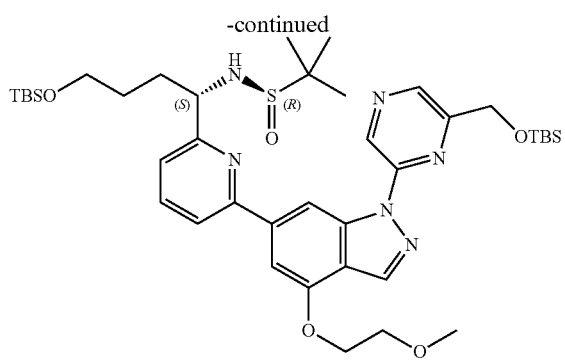

A mixture of 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole (360 mg, 0.67 mmol, 1.0 eq), (R)—N—((S)-1-(6-bromopyridin-2-yl)-4-((tert-butyldimethylsilyl)oxy)butyl)-2-methylpropane-2-sulfinamide (310 mg, 0.67 mmol, 1.0 eq) and K$_2$CO$_3$ (190 mg, 1.4 mmol, 2.0 eq) in 1, 4-dioxane/H$_2$O (4 mL/1 mL) was stirred while purging N$_2$ at rt for 10 min. To this system was added Pd(dppf)Cl$_2$ (50 mg, 0.06 mmol, 0.1 eq) and heated to 110° C. for 4 h. After concentration, the residue was purified by silica gel chromatography using PE/EA (1/1) as eluent to give (R)—N—((S)-4-((tert-butyldimethylsilyl)oxy)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide as a yellow solid. 420 mg, Y: 79%, ESI-MS (M+H)$^+$: 797.4.

Step 8. Synthesis of (S)-4-amino-4-(6-(1-(6-(hydroxymethyl)pyrazin-2-yl)-4-(2-methoxyethoxy)-1H-indazol-6-yl)pyridin-2-yl)butan-1-ol

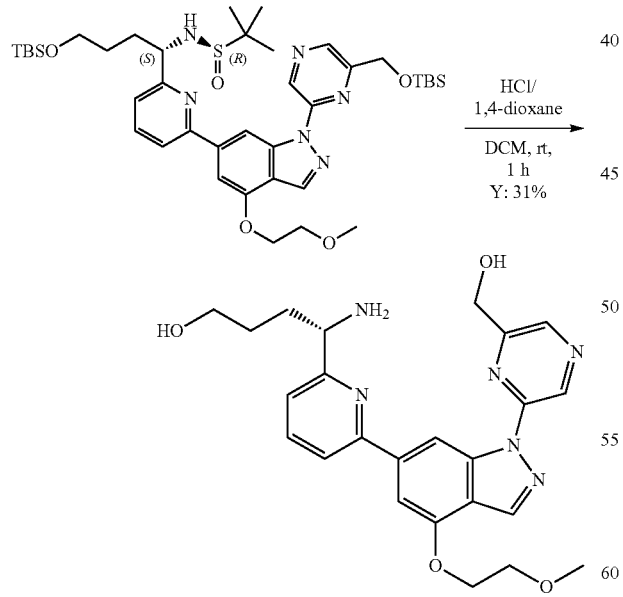

To a solution of (R)—N—((S)-4-((tert-butyldimethylsilyl)oxy)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide (420 mg, 0.53 mmol, 1.0 eq) in DCM (3 mL) was added 4 M HCl in 1,4-dioxane (1.0 mL). Then the mixture was stirred at rt for 1 h. After concentration, the residue was dissolved in THF (10 mL) and adjusted pH=7 with NaOH (aq.). The mixture was extracted with DCM (10 mL×3). The combined organic layers were dried, filtrated, concentrated and purified by prep-HPLC (CH$_3$CN/H$_2$O with 0.05% NH$_3$.H$_2$O as mobile phase from 5% to 95%) to give (S)-4-amino-4-(6-(1-(6-(hydroxymethyl)pyrazin-2-yl)-4-(2-methoxyethoxy)-1H-indazol-6-yl)pyridin-2-yl)butan-1-ol as a yellow solid. 75 mg, Y: 31%. ESI-MS (M+H)$^+$: 465.2. HPLC: 98%. $^1$H NMR (400 MHz, CD$_3$OD) δ: 9.08-9.06 (m, 1H), 8.90-8.87 (m, 1H), 8.47 (d, J=4.4 Hz, 1H), 8.28 (d, J=8.0 Hz, 1H), 7.92-7.82 (m, 2H), 7.46-7.39 (m, 2H), 4.84 (s, 2H), 4.41 (t, J=3.6 Hz, 2H), 4.26-4.23 (m, 1H), 3.91 (t, J=4.0 Hz, 2H), 3.63 (t, J=6.0 Hz, 2H), 3.53 (s, 3H), 2.10-1.95 (m, 2H), 1.72-1.55 (m, 2H).

Example 429, 430, 431, and 432

Step 1. Synthesis of 3-fluorodihydrofuran-2(3H)-one

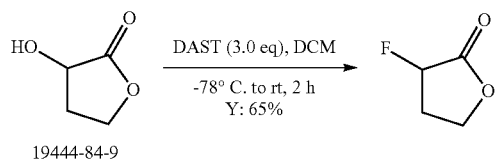 [SMILES: O=C1OCCC1O ; O=C1OCCC1F]

To a solution of α-Hydroxy-γ-butyrolactone (CAS No. 19444-84-9, 3.3 g, 32.3 mmol, 1.0 eq) in DCM (100 mL) was added DAST (13.0 mL, 96.9 mmol, 3.0 eq) at −78° C. under N$_2$ atmosphere. The mixture was stirred at −78° C. for 1 h and stirred at rt for 1 h. The mixture was then slowly poured into saturated aqueous NaHCO$_3$ solution (200 mL) at 0° C., and extracted with DCM (60 mL×2). The organic layers were dried over anhydrous Na$_2$SO$_4$ and concentrated under reduced pressure. The residue was purified by silica gel column chromatography (PE/EA=10/1) to give 3-fluorodihydrofuran-2(3H)-one (2.2 g, Y: 65%) as colorless oil. $^1$H NMR (400 MHz, CDCl$_3$) δ: 5.29-5.12 (m, 1H), 4.53-4.78 (m, 1H), 4.35-4.29 (m, 1H), 2.75-2.64 (m, 1H), 2.59-2.44 (m, 1H).

Step 2. Synthesis of 1-(6-bromopyridin-2-yl)-2-fluoro-4-hydroxybutan-1-one

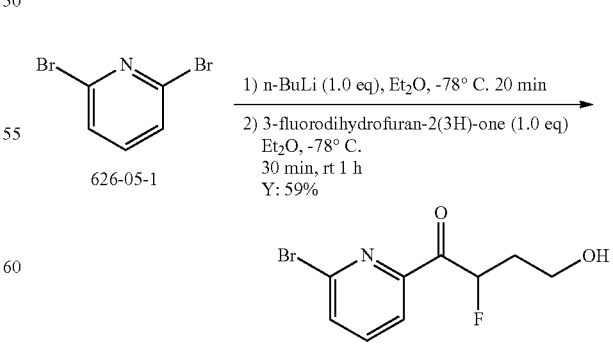

To a mixture of 2,6-Dibromopyridine (CAS No. 626-05-1, 5.6 g, 23.6 mmol, 1.1 eq) in anhydrous diethyl ether (60 mL) was added 2.4 M n-BuLi THF solution (10.0 mL, 23.6 mmol, 1.1 eq) at −78° C. under N₂ atmosphere. The mixture was stirred at −78° C. for 20 min. Then 3-fluorodihydrofuran-2(3H)-one (2.2 g, 21.1 mmol, 1.0 eq) in anhydrous diethyl ether (10.0 mL) was added to the solution. After stirred at −78° C. for 20 min, the mixture was stirred at rt for 1 h. Then the mixture was diluted with ethyl acetate (100 mL), and water (40 mL) was added. The aqueous layer was extracted with ethyl acetate (60 mL×2). The combined organic layers were dried over anhydrous Na₂SO₄ and concentrated under reduced pressure. The residue was purified by silica gel column chromatography (PE/EA=2/1) to give 1-(6-bromopyridin-2-yl)-2-fluoro-4-hydroxybutan-1-one (3.3 g, Y: 59%) as a yellow solid. ESI-MS (M+H)⁺: 264.0, 262.0. ¹H NMR (400 MHz, CDCl₃) δ: 7.66-7.60 (m, 2H), 7.54-7.46 (m, 1H), 4.91-4.88 (m, 1H), 4.45-4.30 (m, 2H), 2.71-2.53 (m, 1H), 2.38-2.05 (m, 1H).

Step 3. Synthesis of 1-(6-bromopyridin-2-yl)-4-((tert-butyldimethylsilyl)oxy)-2-fluorobutan-1-one

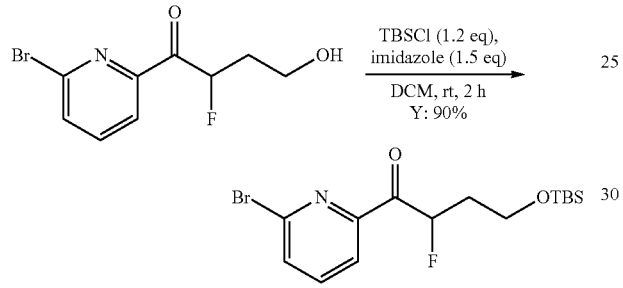

To a solution of 1-(6-bromopyridin-2-yl)-2-fluoro-4-hydroxybutan-1-one (2.6 g, 10 mmol, 1.0 eq) in DCM (60 mL) was added TBSCl (1.8 g, 12 mmol, 1.2 eq) and imidazole (1.0 g, 15 mmol, 1.5 eq). The mixture was stirred at rt for 2 h. The solution was then diluted with DCM (100 mL), and washed with water (80 mL). The organic layer was dried over anhydrous Na₂SO₄ and concentrated under reduced pressure. The residue was purified by silica gel column chromatography (PE/EA=10/1) to give 1-(6-bromopyridin-2-yl)-4-((tert-butyldimethylsilyl)oxy)-2-fluorobutan-1-one (3.9 g, Y: 90%) as yellow oil. ESI-MS (M+1)⁺: 378.1, 376.1. ¹H NMR (400 MHz, CDCl₃) δ: 8.04-8.02 (m, 1H), 7.74-7.67 (m, 2H), 6.32-6.17 (m, 1H), 3.88-3.83 (m, 2H), 2.37-2.20 (m, 2H), 0.84 (s, 9H), 0.10 (s, 6H).

Step 4. Synthesis of (R,E)-N-(1-(6-bromopyridin-2-yl)-4-((tert-butyldimethylsilyl)oxy)-2-fluorobutylidene)-2-methylpropane-2-sulfinamide

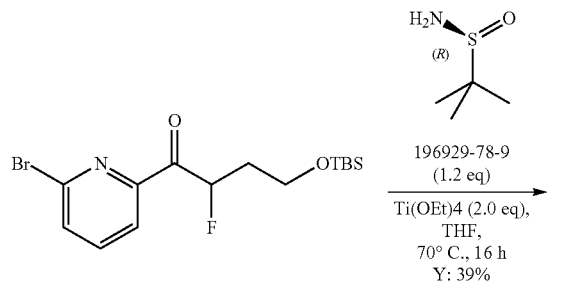

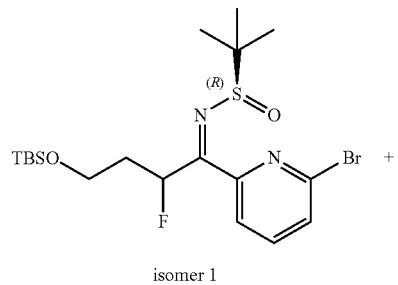

isomer 1

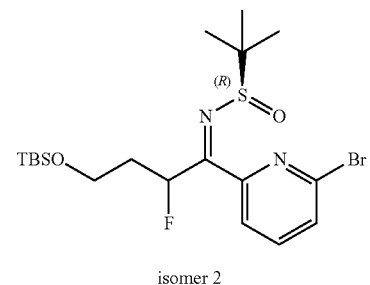

isomer 2

To a solution of give 1-(6-bromopyridin-2-yl)-4-((tert-butyldimethylsilyl)oxy)-2-fluorobutan-1-one (3.9 g, 9.6 mmol, 1.0 eq) in anhydrous THF (100 mL) was added (R)-(+)-2-Methyl-2-propanesulfinamide (CAS no. 196929-78-9 (1.4 g, 11.5 mmol, 1.2 eq) and titanium ethoxide (4.0 mL, 19.2 mmol, 2.0 eq). The mixture was stirred at 70° C. for 16 h under N₂ atmosphere. The solution was then cooled to rt and diluted with ethyl acetate (200 mL), and water (100 mL) was added. Then the mixture was filtered and washed with ethyl acetate. The organic layer was dried over anhydrous sodium sulfate and concentrated under reduced pressure. The residue was purified by silica gel column chromatography (PE/EA=2/1) to give (R,E)-N-(1-(6-bromopyridin-2-yl)-4-((tert-butyldimethylsilyl)oxy)-2-fluorobutylidene)-2-methylpropane-2-sulfinamide-1 (905 mg, Y: 18%) and (R,E)-N-(1-(6-bromopyridin-2-yl)-4-((tert-butyldimethylsilyl)oxy)-2-fluorobutylidene)-2-methylpropane-2-sulfinamide-2 (1.1 g, Y: 21%) as yellow oil. ESI-MS (M+1)⁺: 481.1, 479.1.

(R,E)-N-(1-(6-bromopyridin-2-yl)-4-((tert-butyldimethylsilyl)oxy)-2-fluorobutylidene)-2-methylpropane-2-sulfinamide-1

8.04-8.02 (m, 1H), 7.72-7.67 (m, 1H), 7.54 (d, J=8.8 Hz, 1H), 3.85-3.83 (m, 3H), 2.30-2.14 (m, 2H), 1.30 (s, 9H), 0.90 (s, 9H), 0.07 (s, 6H).

(R,E)-N-(1-(6-bromopyridin-2-yl)-4-((tert-butyldimethylsilyl)oxy)-2-fluorobutylidene)-2-methylpropane-2-sulfinamide-2

8.02-7.52 (m, 3H), 3.94-3.79 (m, 3H), 2.39-2.08 (m, 2H), 1.31 (s, 9H), 0.91 (s, 9H), 0.08 (s, 6H).

521

Step 5. Synthesis of (R)—N—((1S)-1-(6-bromopyridin-2-yl)-4-((tert-butyldimethylsilyl)oxy)-2-fluorobutyl)-2-methylpropane-2-sulfinamide and (R)—N—((1R)-1-(6-bromopyridin-2-yl)-4-((tert-butyldimethylsilyl)oxy)-2-fluorobutyl)-2-methylpropane-2-sulfinamide

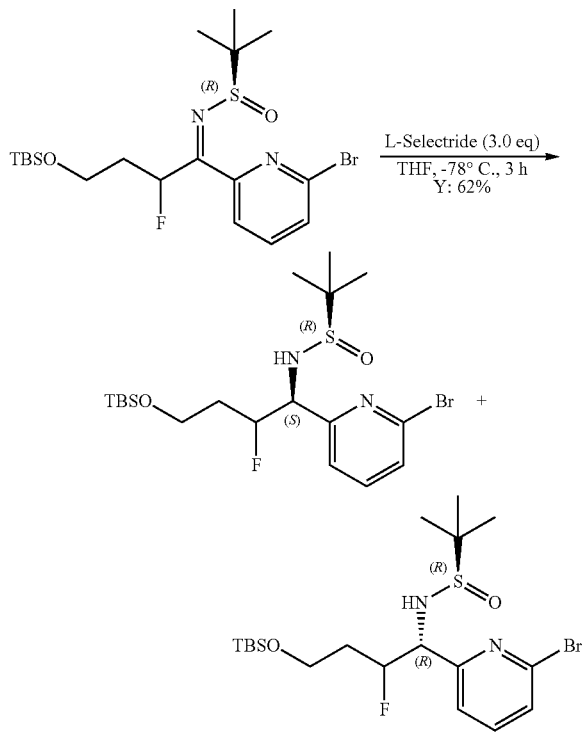

To a solution of (R,E)-N-(1-(6-bromopyridin-2-yl)-4-((tert-butyldimethylsilyl)oxy)-2-fluorobutylidene)-2-methylpropane-2-sulfinamide-1 (905 mg, 1.9 mmol, 1.0 eq) in anhydrous THF (30 mL) was added 1.0 M L-selectride THF solution (5.7 mL, 5.7 mmol, 3.0 eq) at −78° C. under N₂ atmosphere. The mixture was stirred at −78° C. for 2 h. The solution was then diluted with ethyl acetate (100 mL), and saturated aqueous ammonium chloride (30 mL) was added. The aqueous layer was extracted with ethyl acetate (50 mL×2). The organic layer was dried over anhydrous sodium sulfate and concentrated under reduced pressure. The residue was purified by prep-TLC (silica gel, PE/EA=2/1) to give (R)—N—((1S)-1-(6-bromopyridin-2-yl)-4-((tert-butyldimethylsilyl)oxy)-2-fluorobutyl)-2-methylpropane-2-sulfinamide (220 mg, Y: 27%) and (R)—N—((1R)-1-(6-bromopyridin-2-yl)-4-((tert-butyldimethylsilyl)oxy)-2-fluorobutyl)-2-methylpropane-2-sulfinamide (280 mg, Y: 35%) as yellow oil. ESI-MS (M+H)⁺: 483.1, 481.1.

(R)—N—((1S)-1-(6-bromopyridin-2-yl)-4-((tert-butyldimethylsilyl)oxy)-2-fluorobutyl)-2-methylpropane-2-sulfinamide $^1$H NMR (400 MHz, CDCl₃) δ: 7.53 (t, J=8.0 Hz, 1H), 7.39 (d, J=8.0 Hz, 1H), 7.30 (d, J=8.0 Hz, 1H), 5.15-4.99 (m, 1H), 4.63-4.55 (m, 1H), 4.27 (d, J=5.6 Hz, 1H), 3.72-3.68 (m, 2H), 1.92-1.71 (m, 2H), 1.21 (s, 9H), 0.86 (s, 9H), 0.03 (s, 6H).

522

(R)—N—((1R)-1-(6-bromopyridin-2-yl)-4-((tert-butyldimethylsilyl)oxy)-2-fluorobutyl)-2-methylpropane-2-sulfinamide $^1$H NMR (400 MHz, CDCl₃) δ: 7.55 (t, J=8.0 Hz, 1H), 7.42 (d, J=8.0 Hz, 1H), 7.31 (d, J=8.0 Hz, 1H), 4.93-4.75 (m, 1H), 4.59-4.52 (m, 1H), 3.76-3.72 (m, 2H), 1.89-1.79 (m, 2H), 1.28 (s, 9H), 0.87 (s, 9H), 0.04 (s, 6H).

Step 6. Synthesis of R)—N—((1S)-1-(6-bromopyridin-2-yl)-4-((tert-butyldimethylsilyl)oxy)-2-fluorobutyl)-2-methylpropane-2-sulfinamide and (R)—N—((1R)-1-(6-bromopyridin-2-yl)-4-((tert-butyldimethylsilyl)oxy)-2-fluorobutyl)-2-methylpropane-2-sulfinamide

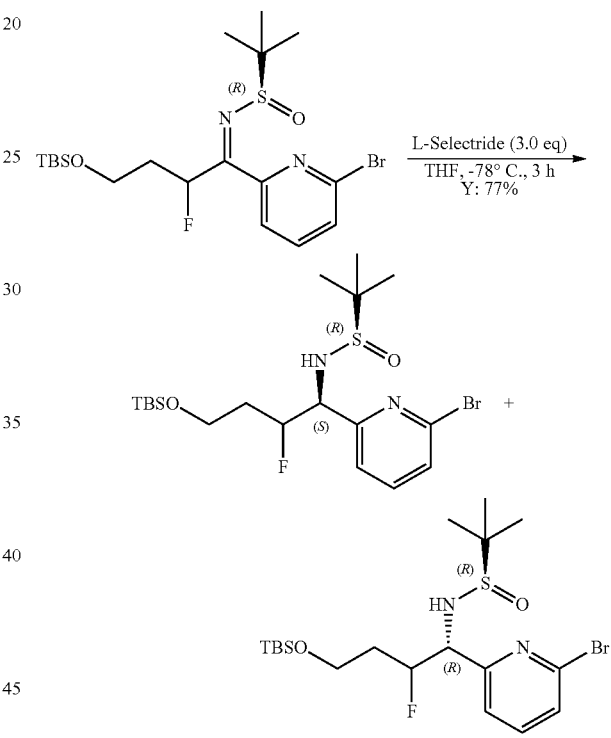

The preparation of the title compounds was similar to that of (R)—N—((S)-1-(2-bromopyridin-4-yl)butyl)-2-methylpropane-2-sulfinamide (Example 404, Step 4) to give 180 mg of (R)—N—((1S)-1-(6-bromopyridin-2-yl)-4-((tert-butyldimethylsilyl)oxy)-2-fluorobutyl)-2-methylpropane-2-sulfinamide (Y: 20%) and 510 mg of (R)—N—((1R)-1-(6-bromopyridin-2-yl)-4-((tert-butyldimethylsilyl)oxy)-2-fluorobutyl)-2-methylpropane-2-sulfinamide (Y: 57%) as yellow oil. ESI-MS (M+H)⁺: 483.1, 481.1.

(R)—N—((1S)-1-(6-bromopyridin-2-yl)-4-((tert-butyldimethylsilyl)oxy)-2-fluorobutyl)-2-methylpropane-2-sulfinamide $^1$H NMR (400 MHz, CDCl₃) δ: 7.57 (t, J=8.0 Hz, 1H), 7.42-7.31 (m, 2H), 5.08-4.92 (m, 1H), 4.66-4.58 (m, 1H), 3.76-3.70 (m, 2H), 1.87-1.67 (m, 2H), 1.29 (s, 9H), 0.89 (s, 9H), 0.04 (s, 6H).

(R)—N—((1R)-1-(6-bromopyridin-2-yl)-4-((tert-butyldimethylsilyl)oxy)-2-fluorobutyl)-2-methylpropane-2-sulfinamide $^1$H NMR (400 MHz, CDCl$_3$) δ: 7.56 (t, J=7.6 Hz, 1H), 7.43 (d, J=8.0 Hz, 1H), 7.29 (d, J=7.6 Hz, 1H), 5.10-0.94 (m, 1H), 4.73-0.65 (m, 1H), 4.44 (d, J=7.2 Hz, 1H), 3.75-0.72 (m, 2H), 1.97-0.70 (m, 2H), 1.21 (s, 9H), 0.86 (s, 9H), 0.04 (s, 6H).

Step 7. Synthesis of (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide

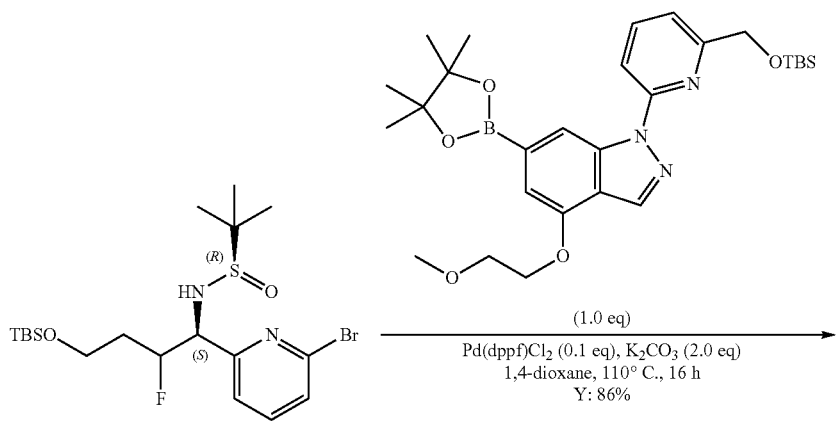

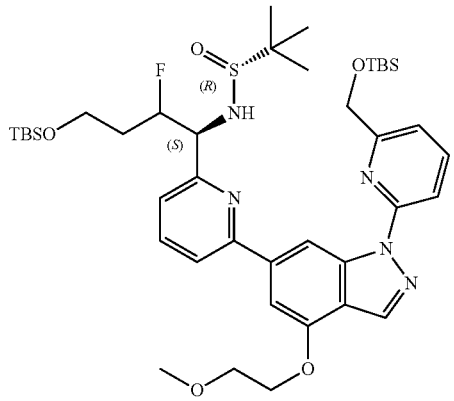

To a solution of (R)—N—((1S)-1-(6-bromopyridin-2-yl)-4-((tert-butyldimethylsilyl)oxy)-2-fluorobutyl)-2-methylpropane-2-sulfinamide from Step 5 (120 mg, 0.25 mmol, 1.0 eq) in 1,4-dioxane (10 mL) were added 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2, 135 mg, 0.25 mmol, 1.0 eq), Pd(dppf)Cl$_2$ (25 mg, 0.03 mmol, 0.1 eq), K$_2$CO$_3$ (69 mg, 0.5 mmol, 2.0 eq) and water (0.5 mL). The mixture was stirred at 110° C. for 4 h under N$_2$ atmosphere. The solution was then cooled to rt and diluted with ethyl acetate (100 mL), and washed with water (20 mL). The organic layer was dried over anhydrous sodium sulfate and concentrated under reduced pressure. The residue was purified by silica gel column chromatography (PE/EA=2/1) to give (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (175 mg, Y: 86%) as yellow oil. ESI-MS (M+H)$^+$: 814.4.

Step 8. Synthesis of (R)—N—((1R)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide

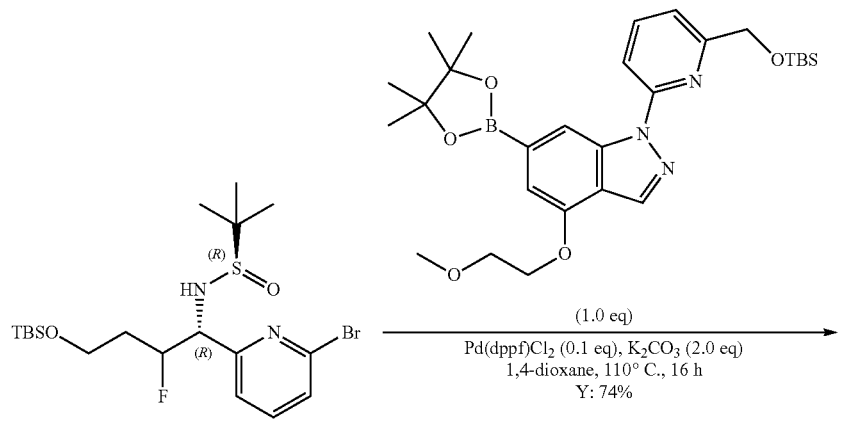

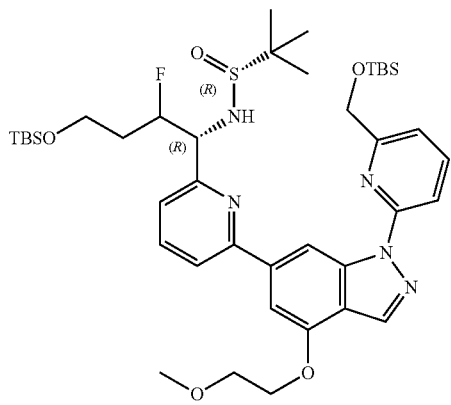

The preparation of (R)—N—((1R)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide was similar to that of (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (Step 7) except that (R)—N—((1R)-1-(6-bromopyridin-2-yl)-4-((tert-butyldimethylsilyl)oxy)-2-fluorobutyl)-2-methylpropane-2-sulfinamide from Step 5 was used to give 150 mg as yellow oil, Y: 74%. ESI-MS (M+H)$^+$: 814.4.

Step 9. Synthesis of (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide

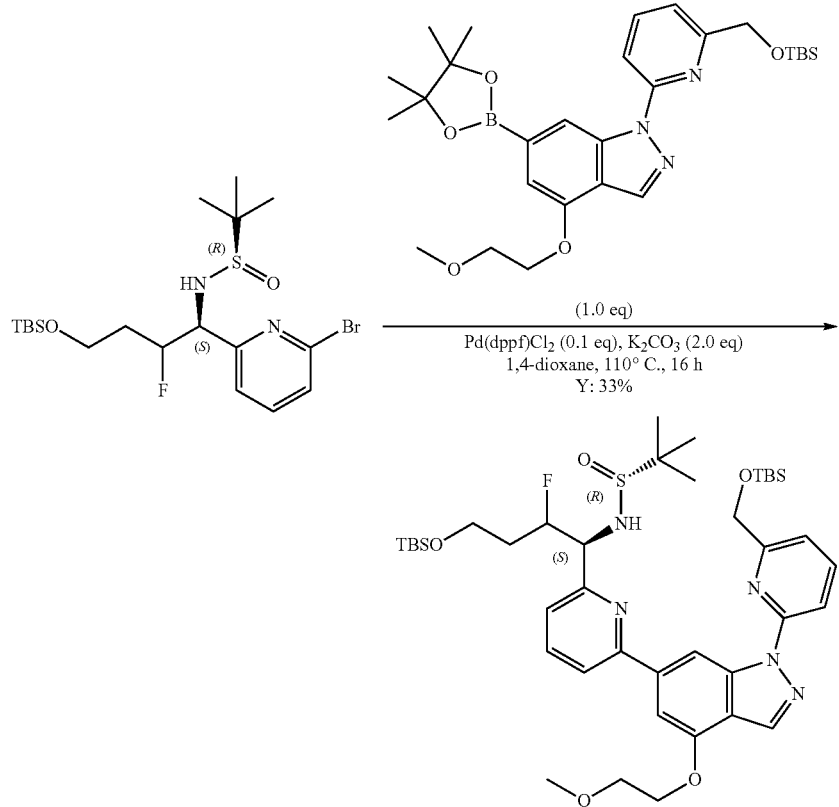

The preparation of (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide was similar to that of (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (Step 7) except that (R)—N—((1S)-1-(6-bromopyridin-2-yl)-4-((tert-butyldimethylsilyl)oxy)-2-fluorobutyl)-2-methylpropane-2-sulfinamide from Step 6 was used to give 160 mg as yellow oil, Y: 33%. ESI-MS (M+H)+: 814.4.

Step 10. Synthesis of (R)—N—((1R)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide

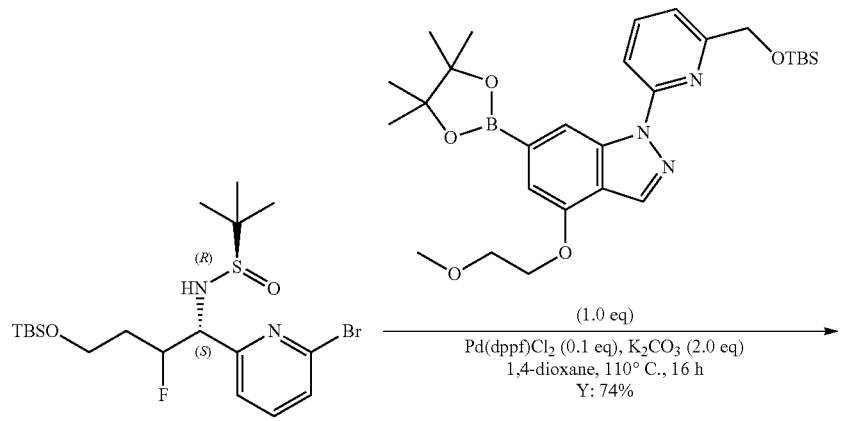

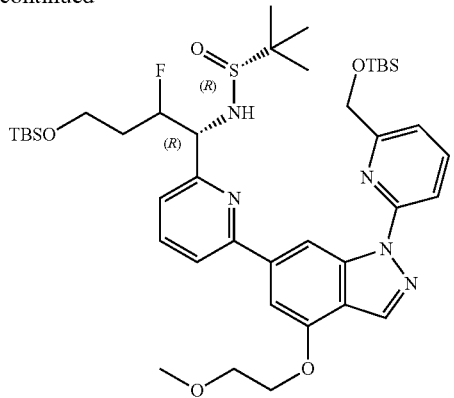

The preparation of (R)—N—((1R)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide was similar to that of (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (Step 7) except that (R)—N—((1R)-1-(6-bromopyridin-2-yl)-4-((tert-butyldimethylsilyl)oxy)-2-fluorobutyl)-2-methylpropane-2-sulfinamide from Step 6 was used to give 450 mg as yellow oil, Y: 52%. ESI-MS (M+H)⁺: 814.4.

Example 429 (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol To a solution of (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (Step 7, 175 mg, 0.21 mmol, 1.0 eq) in dichloromethane (20 mL) was added 4.0 M HCl dioxane solution (5.0 mL). The mixture was stirred at rt for 1 h. The solution was then filtered and washed with DCM to get (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol (69 mg, Y: 97%) as a yellow solid. ESI-MS (M+1)⁺: 482.2. HPLC: 100%. ¹H NMR (400 MHz, CD₃OD) δ: 9.26 (s, 1H), 8.36 (s, 1H), 8.16 (d, J=8.0 Hz, 1H), 8.08 (t, J=7.6 Hz, 1H), 8.01-7.95 (m, 2H), 7.59-7.57 (m, 2H), 7.40 (d, J=6.4 Hz, 1H), 5.39-5.23 (m, 1H), 4.85 (s, 2H), 4.85-4.82 (m, 1H), 4.52 (t, J=4.8 Hz, 2H), 3.96 (t, J=4.8 Hz, 2H), 3.76-3.61 (m, 2H), 3.54 (s, 3H), 2.02-1.73 (m, 2H).

Example 430 (4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol

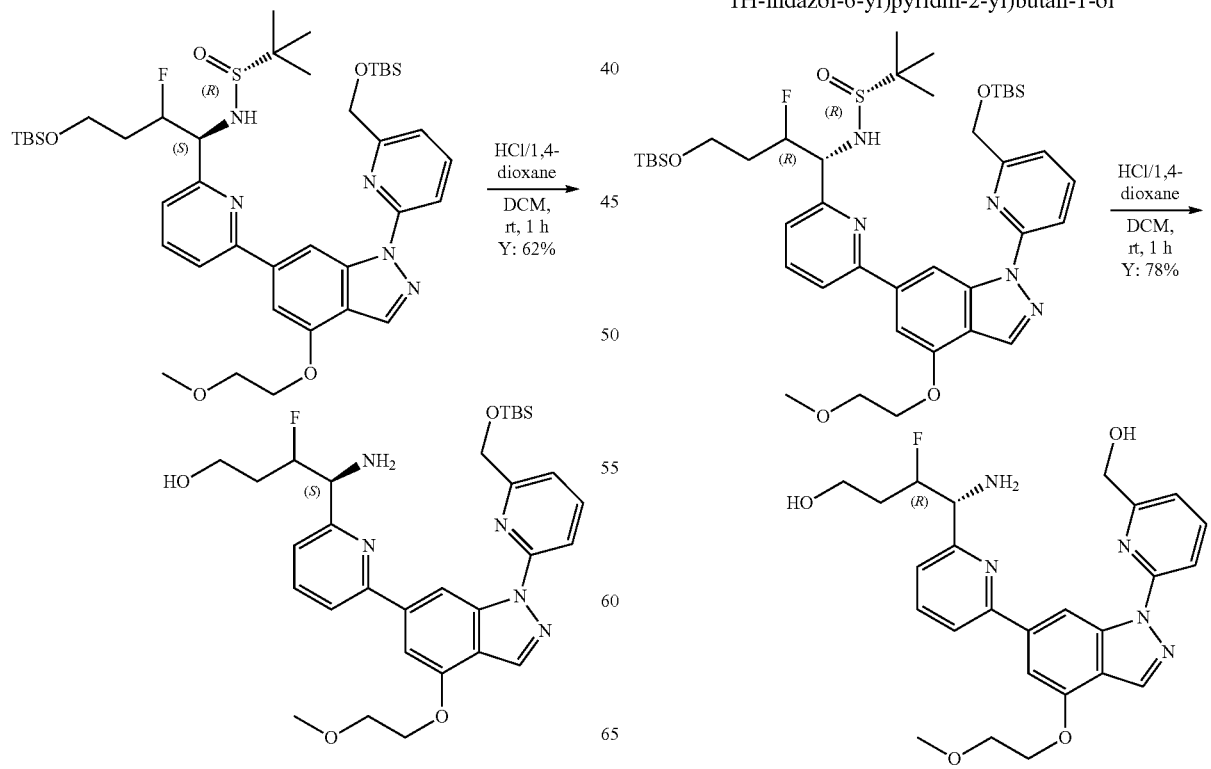

The preparation of (4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol was similar to that of (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol (Example 429), but (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (Step 8), to give 75 mg as a yellow solid, Y: 78%. ESI-MS (M+H)+: 482.2. HPLC: 100%. ¹H NMR (400 MHz, CD₃OD) δ: 9.26 (s, 1H), 8.36 (s, 1H), 8.14 (d, J=8.0 Hz, 1H), 8.08-7.95 (m, 3H), 7.59-7.56 (m, 2H), 7.40 (d, J=6.4 Hz, 1H), 5.41-5.25 (m, 1H), 5.05-4.93 (m, 1H), 4.89 (s, 2H), 4.51 (t, J=4.4 Hz, 2H), 3.96 (t, J=4.4 Hz, 2H), 3.80-3.62 (m, 2H), 3.53 (s, 3H), 1.99-1.60 (m, 2H).

Example 431 Synthesis of (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol

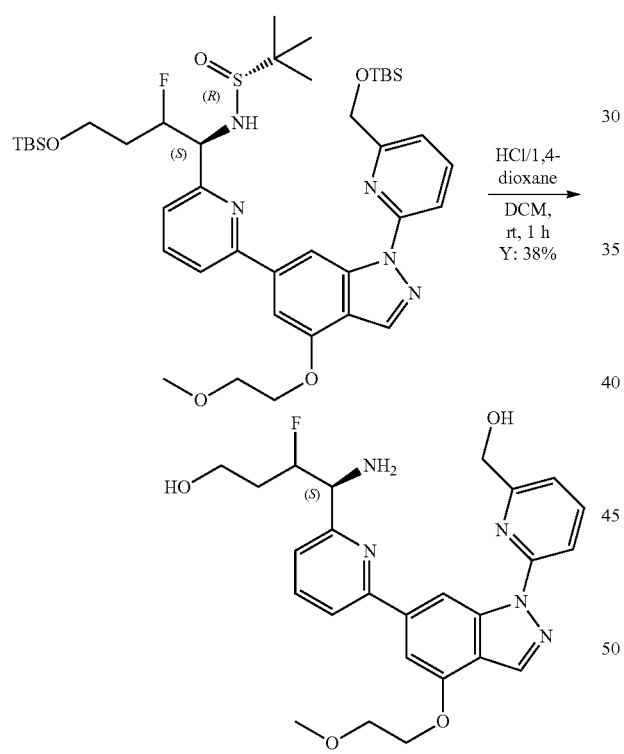

The preparation of (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol was similar to that of (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol (Example 429), but (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (Step 9), to give 39 mg as a yellow solid, Y: 38%. ESI-MS (M+H)+: 482.2. HPLC: 100%. ¹H NMR (400 MHz, CD₃OD) δ: 9.26 (s, 1H), 8.50 (s, 1H), 8.36 (s, 1H), 8.12 (d, J=8.0 Hz, 1H), 8.05 (t, J=7.6 Hz, 1H), 8.00-7.92 (m, 2H), 7.57-7.55 (m, 1H), 7.39 (d, J=6.4 Hz, 1H), 5.39-5.18 (m, 1H), 4.88 (s, 2H), 4.76-4.70 (m, 1H), 4.51 (t, J=4.4 Hz, 2H), 3.96 (t, J=4.4 Hz, 2H), 3.75-3.72 (m, 2H), 3.54 (s, 3H), 2.00-1.74 (m, 2H).

Example 432 (4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol

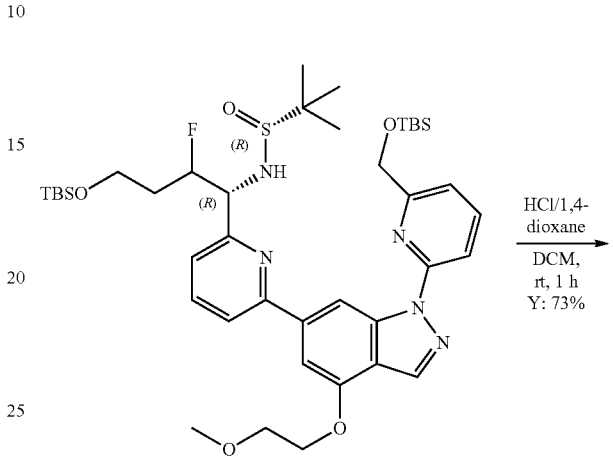

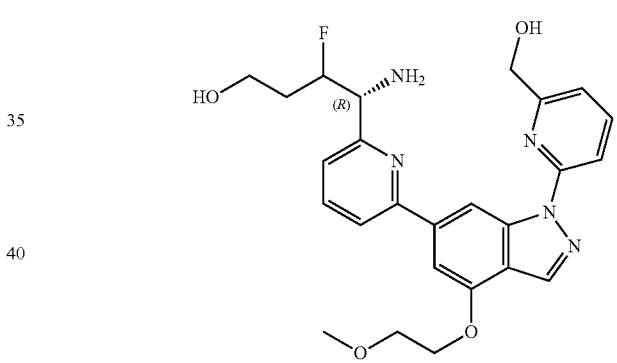

The preparation of (4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol was similar to that of (4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol (Example 429), but (R)—N—((1S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide (Step 10), to give 210 mg as a yellow solid, Y: 73%. ESI-MS (M+H)+: 482.2. HPLC: 100%. ¹H NMR (400 MHz, CD₃OD) δ: 9.18 (s, 1H), 8.38 (s, 1H), 8.15 (d, J=8.0 Hz, 1H), 8.08-7.98 (m, 3H), 7.59-7.57 (m, 2H), 7.43 (d, J=7.2 Hz, 1H), 5.41-5.26 (m, 1H), 5.06-5.01 (m, 1H), 4.89 (s, 2H), 4.52 (t, J=4.4 Hz, 2H), 3.95 (t, J=4.4 Hz, 2H), 3.78-3.69 (m, 2H), 3.53 (s, 3H), 1.98-1.87 (m, 2H).

Example 433 and 434

Step 1. Synthesis of 1-(6-bromopyridin-2-yl)-2-fluoropropan-1-one

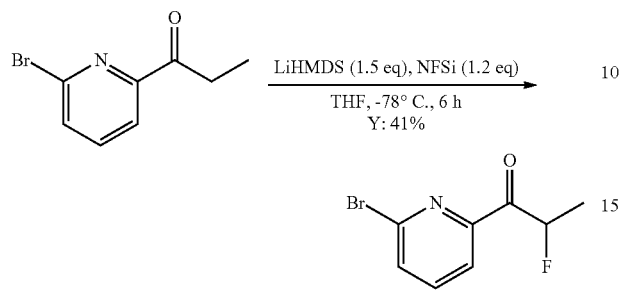

To a solution of 1-(6-bromopyridin-2-yl)propan-1-one (prepared similarly to Example 145 Steps 1 and 2, 11.2 g, 52.6 mmol, 1.0 eq) in anhydrous THF (40 mL) was added LiHMDS (78.9 mL, 78.9 mmol, 1.5 eq) dropwise at −78° C. under nitrogen atmosphere. After stirring 30 min, NFSi (19.9 g, 63.1 mmol, 1.2 eq) in anhydrous THF (10 mL) was added dropwise under nitrogen atmosphere. The reaction mixture was stirred at −78° C. to rt for 5 h under nitrogen atmosphere. The reaction mixture was quenched with saturated aqueous NH$_4$Cl (8 mL) and extracted with EtOAc (50 mL×3). The organic layer thus obtained was dried over anhydrous Na$_2$SO$_4$ and filtered. The filtrate was concentrated in vacuo and purified by silica gel column chromatography (PE/EA=9/1) to obtain 1-(6-bromopyridin-2-yl)-2-fluoropropan-1-one (4.8 g, Y: 41%) as colorless oil. ESI-MS (M+H)$^+$: 231.9. $^1$H NMR (400 MHz, CD$_3$OD) δ: 7.94 (d, J=8.0 Hz, 1H), 7.79-7.75 (m, 2H), 6.11-6.09 (m, 1H), 1.55 (d, J=6.8 Hz, 3H).

Step 2. Synthesis of (R,E)-N-(1-(6-bromopyridin-2-yl)-2-fluoropropylidene)-2-methylpropane-2-sulfinamide

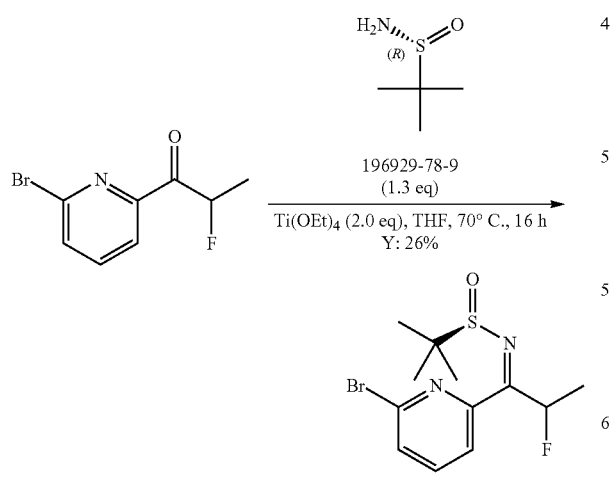

To a solution of 1-(6-bromopyridin-2-yl)-2-fluoropropan-1-one (4.8 g, 20.8 mmol, 1.0 eq) in anhydrous THF (40 mL) were added (R)-(+)-2-Methyl-2-propanesulfinamide (CAS No. 196929-78-9 (3.3 g, 27.0 mmol, 1.3 eq) and Ti(OEt)$_4$ (9.5 g, 41.6 mmol, 2.0 eq) under nitrogen atmosphere. The resulting mixture was stirred at 70° C. for 16 h. The reaction mixture was quenched with saturated aqueous NH$_4$Cl (5 mL) and dried over anhydrous Na$_2$SO$_4$. After filtration, the filtrate was concentrated in vacuo and purified by silica gel column chromatography (PE/EA=6/1) to obtain (R,E)-N-(1-(6-bromopyridin-2-yl)-2-fluoropropylidene)-2-methylpropane-2-sulfinamide (1.8 g, Y: 26%) as yellow oil. ESI-MS (M+H)$^+$: 335.1.

Step 3. Synthesis of (R)—N—((1R)-1-(6-bromopyridin-2-yl)-2-fluoropropyl)-2-methylpropane-2-sulfinamide and (R)—N—((1S)-1-(6-bromopyridin-2-yl)-2-fluoropropyl)-2-methylpropane-2-sulfinamide

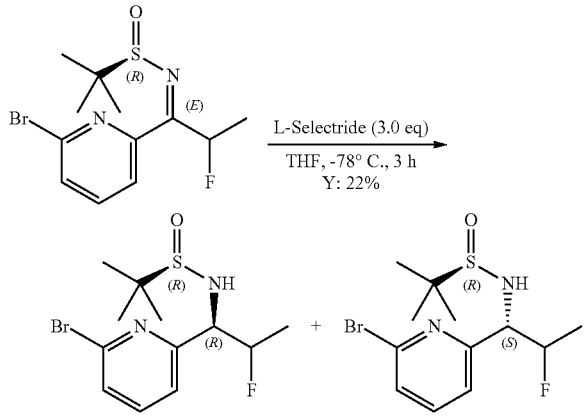

To a stirred solution of (R,E)-N-(1-(6-bromopyridin-2-yl)-2-fluoropropylidene)-2-methylpropane-2-sulfinamide (1.8 g, 5.4 mmol, 1.0 eq) in anhydrous THF (60 mL) at −78° C. was added L-Selectride (1.0 M in THF, 16.2 mL, 16.2 mmol, 3.0 eq) dropwise. The resulting mixture was stirred at −78° C. for 3 h. Then the reaction mixture was quenched with saturated aqueous NH$_4$Cl (6 mL) and dried over anhydrous Na$_2$SO$_4$. After filtration, the filtrate was concentrated in vacuo. Then the residue was purified by prep-HPLC (CH$_3$CN/H$_2$O with 0.05% TFA as mobile phase from 5% to 95%) to obtain (R)—N—((1R)-1-(6-bromopyridin-2-yl)-2-fluoropropyl)-2-methylpropane-2-sulfinamide (400 mg, as a white solid, Y: 22%) and (R)—N—((1S)-1-(6-bromopyridin-2-yl)-2-fluoropropyl)-2-methylpropane-2-sulfinamide (200 mg, as a colorless oil, Y: 11%). ESI-MS (M+H)$^+$: 336.1.

Step 4. Synthesis of (R)—N—((1R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide

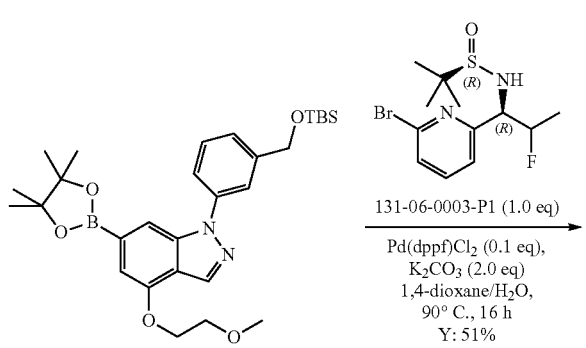

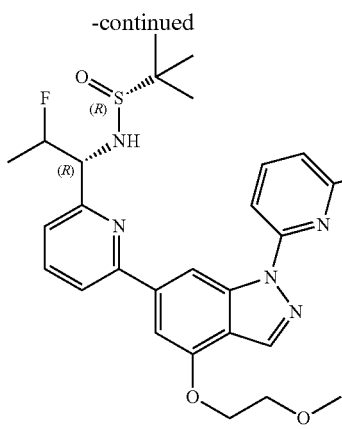

To a mixture of (R)—N—((1R)-1-(6-bromopyridin-2-yl)-2-fluoropropyl)-2-methylpropane-2-sulfinamide (400 mg, 1.19 mmol, 1.0 eq), 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2, 640 mg, 1.19 mmol, 1.0 eq) and K₂CO₃ (329 mg, 2.38 mmol, 2.0 eq) in 1,4-dioxane/H₂O (5 mL/0.3 mL) was added Pd(dppf)Cl₂ (98 mg, 0.12 mmol, 0.1 eq) under nitrogen atmosphere. The mixture was stirred at 90° C. for 16 h under nitrogen atmosphere. The mixture was concentrated in vacuo and purified by silica gel column chromatography (PE/EA=1/1) to obtain (R)—N—((1R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide (400 mg, Y: 51%) as colorless oil. ESI-MS (M+H)⁺: 670.1.

Step 5. Synthesis of (R)—N—((1S)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide

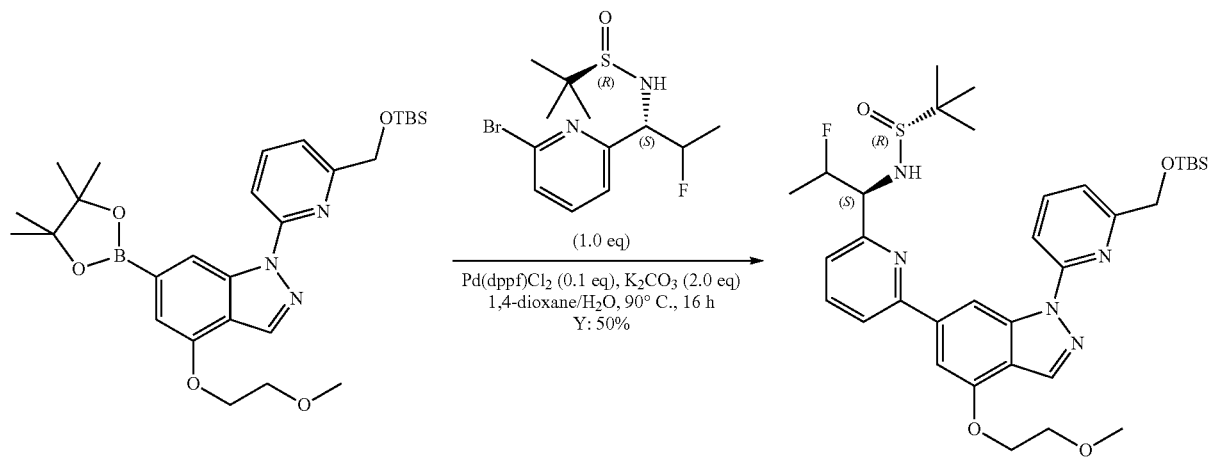

The preparation of (R)—N—((1S)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide was similar to that of (R)—N—((1R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide to give 200 mg as colorless oil, Y: 50%. ESI-MS (M+H)⁺: 670.1.

Step 5. Synthesis of (6-(6-(6-((1R)-1-amino-2-fluoropropyl)pyridin-2-yl)-4-(2-methoxyethoxy)-1H-indazol-1-yl)pyridin-2-yl)methanol (Example 433)

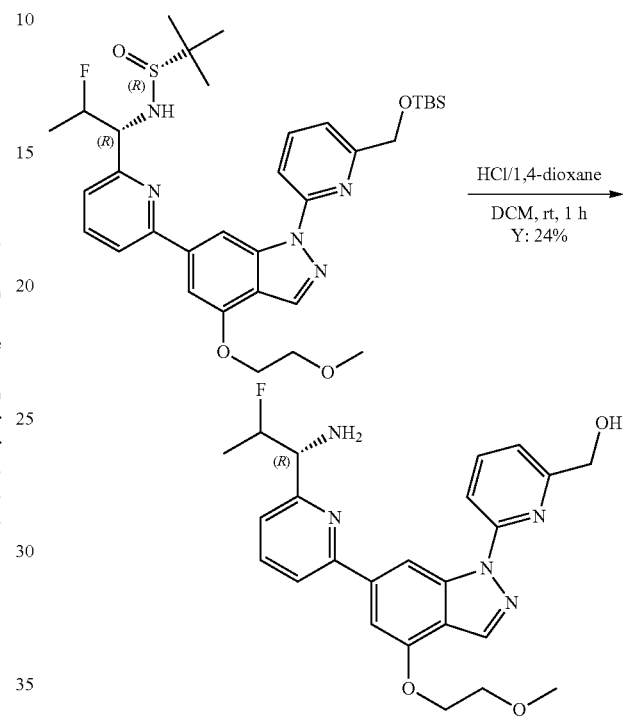

To a stirred solution of (R)—N—((1R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide (400 mg, 0.60 mmol, 1.0 eq) in DCM (5 mL) was added HCl (4 M in 1,4-dioxane, 2 mL). The resulting mixture was stirred at rt for 1 h. The reaction mixture was concentrated in vacuo and the residue was dissolved in H₂O (20 mL). The mixture was adjusted pH=7 with saturated NaHCO₃ solution. The precipitate was collected by filtration and purified by prep-HPLC (H₃CN/H₂O with 0.05% TFA as mobile phase from 5% to 95%) to give (6-(6-(6-((1R)-1-amino-2-fluoropropyl)pyridin-2-yl)-4-(2-methoxyethoxy)-1H-indazol-1-yl)pyridin-2-yl)methanol (66 mg, Y: 24%) as a yellow solid. ESI-MS (M+H)⁺: 452.2. HPLC: 98%. ¹H NMR (400 MHz, CD₃OD) δ: 9.28 (s, 1H), 8.37 (s, 1H), 8.13 (d, J=8.0 Hz, 1H), 8.05 (t, J=7.6 Hz, 1H), 7.98-7.95 (m, 2H), 7.56-7.52 (m, 2H), 7.37 (d, J=6.0 Hz, 1H), 5.36-5.23 (m, 1H), 4.96-4.92 (m, 1H), 4.87 (s, 2H), 4.50 (t, J=4.4 Hz, 2H), 3.94 (t, J=4.4 Hz, 2H), 3.53 (s, 3H), 1.47-1.39 (m, 3H).

Step 6. Synthesis of (6-(6-(6-((1S)-1-amino-2-fluoropropyl)pyridin-2-yl)-4-(2-methoxyethoxy)-1H-indazol-1-yl)pyridin-2-yl)methanol (Example 434)

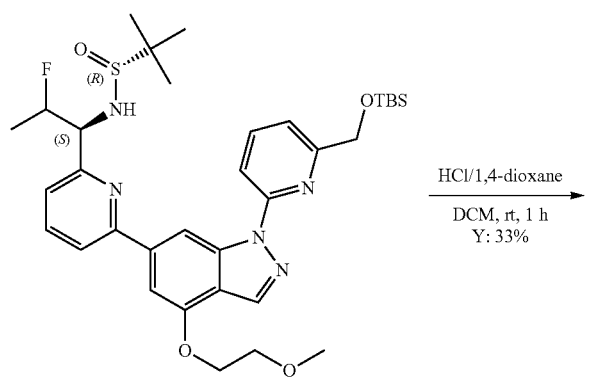

The preparation of (6-(6-(6-((1S)-1-amino-2-fluoropropyl)pyridin-2-yl)-4-(2-methoxyethoxy)-1H-indazol-1-yl)pyridin-2-yl)methanol was similar to that of (6-(6-(6-((1R)-1-amino-2-fluoropropyl)pyridin-2-yl)-4-(2-methoxyethoxy)-1H-indazol-1-yl)pyridin-2-yl)methanol to give 45 mg as a yellow solid, Y: 33%. ESI-MS (M+H)⁺: 452.2. HPLC: 92%. ¹H NMR (400 MHz, CD₃OD) δ: 9.28 (s, 1H), 8.36 (s, 1H), 8.14 (t, J=7.2 Hz, 1H), 8.07-8.03 (m, 1H), 8.00-7.94 (m, 2H), 7.57-7.52 (m, 2H), 7.39-7.37 (m, 1H), 5.37-5.16 (m, 1H), 4.96-4.88 (m, 1H), 4.87 (s, 2H), 4.50 (t, J=4.4 Hz, 2H), 3.94 (t, J=4.4 Hz, 2H), 3.53 (s, 3H), 1.48-1.39 (m, 3H).

Example 435 (S)-(6-(6-(6-(1-aminobut-3-en-1-yl)pyridin-2-yl)-1H-indazol-1-yl)pyridin-2-yl)methanol Step 1. Synthesis of (S,Z)—N-((6-bromopyridin-2-yl)methylene)-2-methylpropane-2-sulfinamide

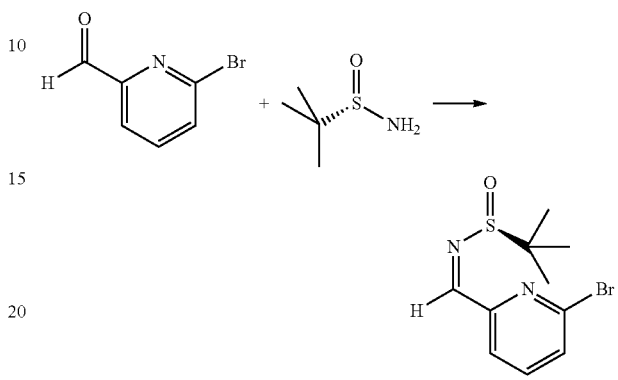

6-Bromo-pyridine-2-carbaldehyde (CAS NO. 34160-40-2; 2.5 g, 13 mmol) and (S)-(−)-2-Methyl-2-propanesulfinamide (CAS NO. 343338-28-3; 1.8 g, 15 mmol) and Copper (II) sulfate (4.3 g, 27 mmol) were combined in 100 mL of anhydrous dichloromethane. The mixture was stirred at RT under an atmosphere of Nitrogen overnight. The reaction was filtered and the filter cake was rinsed with dichloromethane. The filtrate was concentrated and purified using 10% ethyl acetate in heptane on 40 g 30 uM silica column to afford 3.9 g of a yellow oil which solidified upon standing. ¹H NMR (400 MHz, DMSO-d₆) δ ppm 8.35-8.46 (m, 1H) 8.11 (dd, J=7.5, 0.8 Hz, 1H) 7.95 (dd, J=7.8, 0.5 Hz, 1H) 7.87 (dd, J=8.0, 1.0 Hz, 1H) 1.21 (s, 9H).

Step 2. Synthesis of (S)—N—((S)-1-(6-bromopyridin-2-yl)but-3-en-1-yl)-2-methylpropane-2-sulfinamide

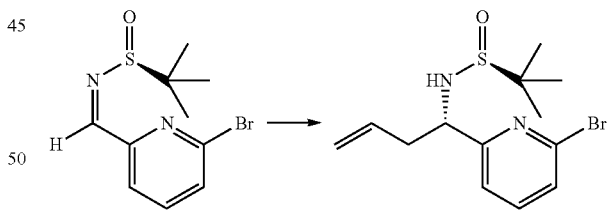

To a solution of (S,Z)—N-((6-bromopyridin-2-yl)methylene)-2-methylpropane-2-sulfinamide (1.10 g, 3.80 mmol) in 15 mL anhydrous THF at −78° C. was added allylmagnesium bromide (0.872 g, 6.00 mmol) as a 1M solution in THF (6.0 mL) using a syringe pump over 30 minutes. The reaction was allowed to stir at −78° C. for 1.5 h. The reaction was quenched by addition of sat. NH₄Cl and ethyl ether. The layers were separated and the organic phase was washed with brine, dried over MgSO₄, filtered, and concentrated. Purification by column chromatography using 5-25% acetone in heptane on a 40 g 30 μM silica gel column afforded (S)—N—((S)-1-(6-bromopyridin-2-yl)but-3-en-1-yl)-2-methylpropane-2-sulfinamide (0.58 g; Yield=46%). ¹H NMR (400 MHz, CHLOROFORM-d) δ ppm 7.47-7.56 (m,

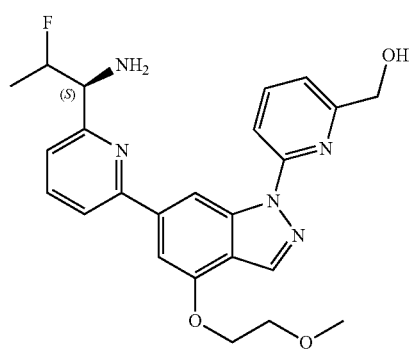

1H) 7.47-7.56 (m, 1H) 7.37 (dd, J=7.8, 0.8 Hz, 1H) 7.27-7.31 (m, 1H) 5.58-5.82 (m, 1H) 5.03-5.11 (m, 2H) 4.38-4.54 (m, 2H) 2.54-2.68 (m, 2H) 1.26 (s, 9H).

Step 3. Synthesis of 1-(6-(((tert-butyldimethylsilyl)oxy)methyl)pyridin-2-yl)-6-(4,4,5,5-tetramethyl-1,3,2-dioxaborolan-2-yl)-1H-indazole

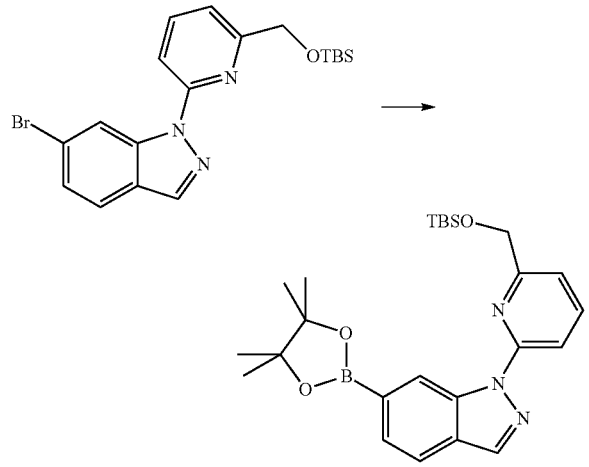

A reaction vessel containing 6-Bromo-1-[6-(tert-butyl-dimethyl-silanyloxymethyl)-pyridin-2-yl]-1H-indazole (Example 432, step 2, 2.5 g, 6.0 mmol), Potassium acetate (1.76 g, 17.9 mmol), bis(pinacolato)diboron (1.67 g, 6.57 mmol) and 1,1'-bis(diphenylphosphino)ferrocene-palladium(II)dichloride dichloromethane complex (0.244 g, 0.299 mmol) and a stir bar was fitted with a reflux condenser and rubber septum and purged with a stream of nitrogen for 1 h. 1,4-Dioxane (3.0E1 mL, 380 mmol) was added and the reaction was heated to 90° C. After 24 h, an additional charge of 0.5 eq bis(pinacolato)diboron was added and the bath temperature was raised to 100° C. After an addition 6 h at temperature, the reaction was cooled to RT and diluted with ethyl acetate and brine. The layers were separated and the organic phase was dried over MgSO₄, filtered, and concentrated. Purification by column chromatography (5% ethyl acetate in heptane) afforded 1-(6-(((tert-butyldimethylsilyl)oxy)methyl)pyridin-2-yl)-6-(4,4,5,5-tetramethyl-1,3,2-dioxaborolan-2-yl)-1H-indazole (2.5 g; Yield=90%). ¹H NMR (400 MHz, CHLOROFORM-d) δ ppm 9.21 (s, 1H) 8.19 (s, 1H) 7.81-7.97 (m, 2H) 7.59-7.80 (m, 2H) 7.35-7.46 (m, 1H) 4.99 (s, 2H) 1.40 (s, 12H) 1.01 (s, 9H) 0.19 (s, 6H).

Step 4. Synthesis of (S)—N—((S)-1-(6-(1-(6-(((tert-butyldimethylsilyl)oxy)methyl)pyridin-2-yl)-1H-indazol-6-yl)pyridin-2-yl)but-3-en-1-yl)-2-methylpropane-2-sulfinamide

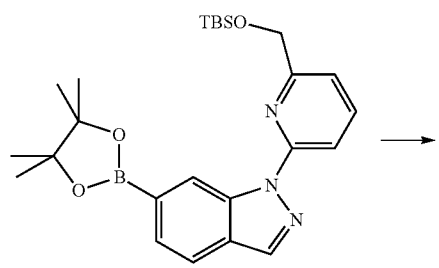

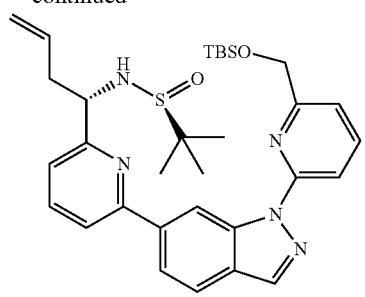

1-(6-(((tert-butyldimethylsilyl)oxy)methyl)pyridin-2-yl)-6-(4,4,5,5-tetramethyl-1,3,2-dioxaborolan-2-yl)-1H-indazole (252.9 mg, 0.5434 mmol), (S)—N—((S)-1-(6-bromopyridin-2-yl)but-3-en-1-yl)-2-methylpropane-2-sulfinamide (216.0 mg, 0.6520 mmol), Potassium carbonate (0.15 g, 1.1 mmol), and 1,1'-bis(diphenylphosphino)ferrocene-palladium(II)dichloride dichloromethane complex (0.023 g, 0.028 mmol) were combined in a 40 mL reaction vial, sealed, evacuated, and backfilled with N₂ two times. 2.0 mL of water and 8.0 mL of 1,4 dioxane were added. The reaction was heated to 90° C. for 2 h. The reaction was deemed complete by LC/MS. The reaction was cooled to RT and diluted with ethyl acetate. The organic phase was washed with brine twice. The organic phase was dried over MgSO₄, filtered, and concentrated. Purification using 10-50% ethyl acetate in heptanes on 12 g 30 M silica gel column afforded (S)—N—((S)-1-(6-(1-(6-(((tert-butyldimethylsilyl)oxy)methyl)pyridin-2-yl)-1H-indazol-6-yl)pyridin-2-yl)but-3-en-1-yl)-2-methylpropane-2-sulfinamide (290 mg; Yield=90%). ¹H NMR (400 MHz, CHLOROFORM-d) δ ppm 9.35-9.40 (m, 1H) 8.22 (d, J=0.8 Hz, 1H) 8.00 (dd, J=8.5, 1.5 Hz, 1H) 7.91-7.95 (m, 1H) 7.89 (d, J=7.5 Hz, 1H) 7.82-7.86 (m, 1H) 7.77-7.82 (m, 1H) 7.73-7.77 (m, 1H) 7.41 (dd, J=7.3, 1.0 Hz, 1H) 7.31 (dd, J=7.3, 1.0 Hz, 1H) 5.80 (ddt, J=17.1, 10.1, 7.0, 7.0 Hz, 1H) 5.01-5.15 (m, 3H) 4.62 (q, J=6.7 Hz, 1H) 2.72-2.86 (m, 2H) 1.25 (s, 9H) 1.00 (s, 9H) 0.17 (s, 6H).

Step 5. Synthesis of (S)-(6-(6-(6-(1-aminobut-3-en-1-yl)pyridin-2-yl)-1H-indazol-1-yl)pyridin-2-yl)methanol

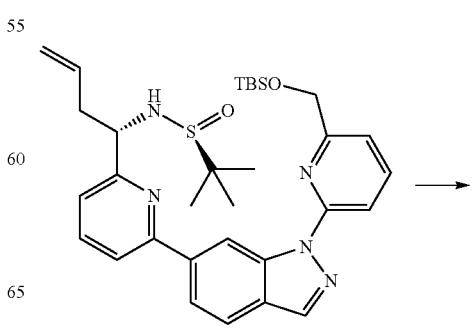

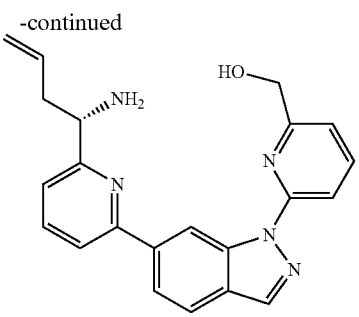

To a reaction vessel containing (S)—N—((S)-1-(6-(1-(6-(((tert-butyldimethylsilyl)oxy)methyl)pyridin-2-yl)-1H-indazol-6-yl)pyridin-2-yl)but-3-en-1-yl)-2-methylpropane-2-sulfinamide (125 mg, 0.212 mmol) in 4 mL of anhydrous DCM was added 4 M of Hydrogen Chloride in 1,4-Dioxane (1.06 mL, 4.24 mmol). After 1 h, the reaction was diluted with 10 mL of diethyl ether and filtered. The solid was washed with 10 mL of diethyl ether and dried under vacuum to afford (S)-(6-(6-(6-(1-aminobut-3-en-1-yl)pyridin-2-yl)-1H-indazol-1-yl)pyridin-2-yl)methanol as a hydrochloride salt (67 mg; Yield=71%). $^1$H NMR (400 MHz, DMSO-$d_6$) δ ppm 9.49-9.71 (m, 1H) 8.62 (br s, 3H) 8.50 (d, J=0.8 Hz, 1H) 8.24 (dd, J=8.4, 1.6 Hz, 1H) 7.99-8.10 (m, 4H) 7.86-7.91 (m, 1H) 7.52 (dd, J=7.3, 1.0 Hz, 1H) 7.42 (dd, J=7.5, 0.8 Hz, 1H) 5.69-5.84 (m, 1H) 5.05-5.16 (m, 2H) 4.72-4.86 (m, 2H) 4.53-4.68 (m, 1H) 2.73-2.89 (m, 2H). LC/MS (M+H)=372.

Example 436. (S)-(6-(6-(6-(1-amino-3-methylbut-3-en-1-yl)pyridin-2-yl)-1H-indazol-1-yl)pyridin-2-yl)methanol Step 1. Synthesis of (S)—N—((S)-1-(6-bromopyridin-2-yl)-3-methylbut-3-en-1-yl)-2-methylpropane-2-sulfinamide

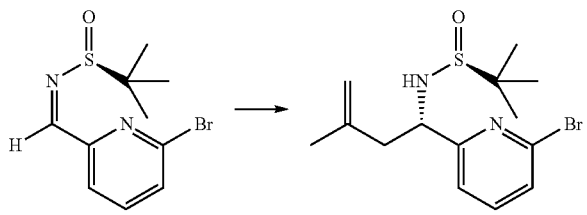 [SMILES: CC(C)(C)[S@](=O)/N=C\c1cccc(Br)n1 ; C=C(C)C[C@H](N[S@@](=O)C(C)(C)C)c1cccc(Br)n1]

To a solution of (S,Z)—N-((6-bromopyridin-2-yl)methylene)-2-methylpropane-2-sulfinamide (Example, 435, Step 1, 0.440 g, 1.52 mmol) in 5 mL anhydrous THF at −78° C. was added 2-methallylmagnesium bromide (0.303 g, 1.90 mmol) as a 0.5 solution in THF (3.8 mL). The reaction was allowed to stir at −78° C. for 30 minutes. The reaction was quenched by addition of sat. NH$_4$Cl solution. The mixture was warmed to RT and diluted with ethyl ether and brine. The layers were separated. The organic phase was washed with brine, dried over MgSO$_4$, filtered and concentrated. Column chromatographic purification using 15% acetone in heptane on 40 g silica gel column (30 μM silica) afforded (S)—N—((S)-1-(6-bromopyridin-2-yl)-3-methylbut-3-en-1-yl)-2-methylpropane-2-sulfinamide (0.182 g; Yield=34.6%). $^1$H NMR (400 MHz, CHLOROFORM-d) δ ppm 7.51 (t, J=7.8 Hz, 1H) 7.36 (dd, J=7.8, 0.8 Hz, 1H) 7.30 (d, J=7.5 Hz, 1H) 4.76-4.90 (m, 1H) 4.65-4.76 (m, 1H) 4.51 (q, J=7.5 Hz, 1H) 4.41 (d, J=8.0 Hz, 1H) 2.53 (d, J=7.0 Hz, 2H) 1.73 (s, 3H) 1.24 (s, 9H).

Step 2. Synthesis of (S)-(6-(6-(6-(1-amino-3-methylbut-3-en-1-yl)pyridin-2-yl)-1H-indazol-1-yl)pyridin-2-yl)methanol

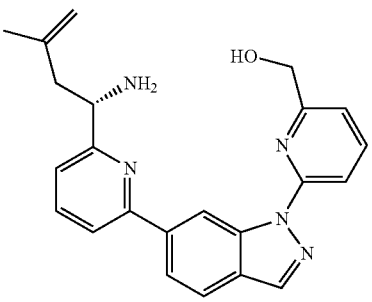 [SMILES: C=C(C)C[C@H](N)c1cccc(-c2ccc3cnn(-c4cccc(CO)n4)c3c2)n1]

(S)-(6-(6-(6-(1-amino-3-methylbut-3-en-1-yl)pyridin-2-yl)-1H-indazol-1-yl)pyridin-2-yl)methanol was made as the hydrochloride salt from (S)—N—((S)-1-(6-bromopyridin-2-yl)-3-methylbut-3-en-1-yl)-2-methylpropane-2-sulfinamide and 1-(6-(((tert-butyldimethylsilyl)oxy)methyl)pyridin-2-yl)-6-(4,4,5,5-tetramethyl-1,3,2-dioxaborolan-2-yl)-1H-indazole (Example 143, Step 3) in a manner analogous to that used to prepare (S)-(6-(6-(6-(1-aminobut-3-en-1-yl)pyridin-2-yl)-1H-indazol-1-yl)pyridin-2-yl)methanol (Example 435) described above. $^1$H NMR (400 MHz, DMSO-$d_6$) δ ppm 9.49-9.68 (m, 1H) 8.45-8.57 (m, 4H) 8.22 (dd, J=8.3, 1.5 Hz, 1H) 8.08 (dd, J=7.8, 1.0 Hz, 1H) 7.99-8.05 (m, 3H) 7.89 (dd, J=8.3, 0.8 Hz, 1H) 7.51-7.54 (m, 1H) 7.38-7.45 (m, 1H) 4.59-4.92 (m, 5H) 2.74 (d, J=7.5 Hz, 2H) 1.75 (s, 3H). LC/MS (M+H)=386.0.

Example 437 (S)-(6-(6-(6-(1-amino-3,3-difluorobutyl)pyridin-2-yl)-1H-indazol-1-yl)pyridin-2-yl)methanol Step 1. Synthesis of 4-(6-bromopyridin-2-yl)-4-hydroxybutan-2-one

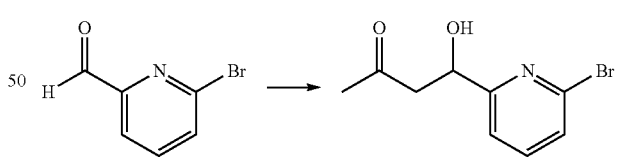

6-Bromo-pyridine-2-carbaldehyde (CAS NO. 34160-40-2, 1.86 g, 10.0 mmol) was dissolved in acetone (60.66 mL) and water (120 g). To this solution was added zinc(proline)$_2$ complex (0.294 g, 1.00 mmol) and the reaction was allowed to stir for 72 h. The reaction was concentrated to remove acetone and the resultant mixture was extracted with ethyl acetate three times. The organic phase was washed with brine, dried over MgSO$_4$, filtered, and concentrated. Purification by column chromatography eluted with 20% ethyl acetate in heptane afforded 4-(6-bromopyridin-2-yl)-4-hydroxybutan-2-one (2.1 g; Yield=86%). $^1$H NMR (400 MHz, CHLOROFORM-d) δ ppm 7.59 (t, J=7.5 Hz, 1H) 7.53 (dt, J=7.8, 0.8 Hz, 1H) 7.40 (s, 1H) 5.17 (ddd, J=8.5, 5.2, 3.4 Hz, 1H) 3.85 (d, J=5.3 Hz, 1H) 3.17 (dd, J=17.8, 3.3 Hz, 1H) 2.92 (dd, J=17.7, 8.4 Hz, 1H) 2.25 (s, 3H).

Step 2. Synthesis of 1-(6-bromopyridin-2-yl)-3-oxobutyl acetate

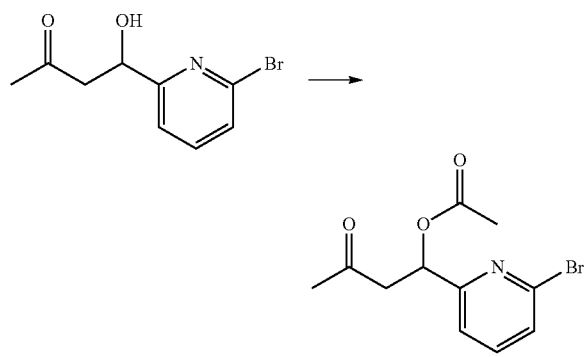

4-(6-bromopyridin-2-yl)-4-hydroxybutan-2-one (1.00 g, 4.10 mmol) in 10 mL ethyl ether was treated with acetic anhydride (0.502 g, 4.92 mmol) and a catalytic amount of DMAP. The reaction was stirred at RT overnight. A white solid precipitated. The reaction was diluted with sat. NaHCO$_3$ solution and ethyl acetate. The layers were separated and the organic phase was washed with brine, dried over MgSO$_4$, filtered, and concentrated to afford a white solid, 1-(6-bromopyridin-2-yl)-3-oxobutyl acetate (1.1 g; Yield=94%). $^1$H NMR (400 MHz, CHLOROFORM-d) δ ppm 7.40-7.52 (m, 1H) 7.33 (d, J=8.0 Hz, 1H) 7.26 (d, J=7.5 Hz, 1H) 6.12 (dd, J=7.5, 5.5 Hz, 1H) 3.14 (dd, J=16.8, 5.5 Hz, 1H) 3.06 (dd, J=17.3, 7.3 Hz, 1H) 2.13 (s, 3H) 1.96-2.05 (s, 3H).

Step 3. Synthesis of 1-(6-bromopyridin-2-yl)-3,3-difluorobutyl acetate

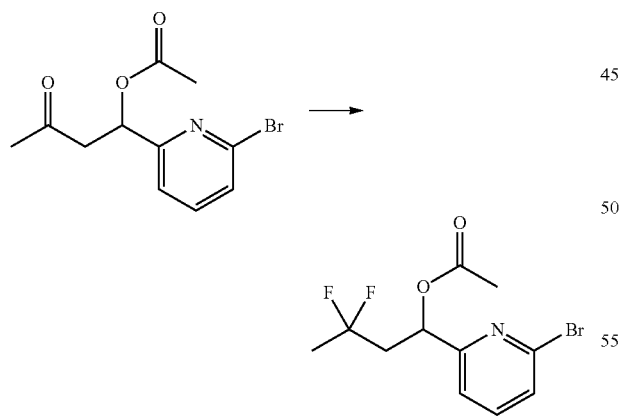

In a plastic reaction vessel, 1-(6-bromopyridin-2-yl)-3-oxobutyl acetate (0.57 g, 2.0 mmol) was dissolved in 1 mL of CH$_2$Cl$_2$. To this solution was added Deoxofluor™ (0.75 g, 3.4 mmol) followed by ethanol (0.018 g, 0.40 mmol). The reaction was allowed to stir at RT for 48 h. The reaction was quenched by careful addition of sat NaHCO$_3$ at RT. Purification by column chromatography on 40 g silica gel column using 10-20% ethyl acetate in heptane afforded 1-(6-bromopyridin-2-yl)-3,3-difluorobutyl acetate (212 mg; Yield=34). $^1$H NMR (400 MHz, CHLOROFORM-d) δ ppm 7.47 (t, J=7.8 Hz, 1H) 7.35 (dd, J=8.0, 0.8 Hz, 1H) 7.25 (d, J=7.5 Hz, 1H) 6.02 (dd, J=8.0, 4.5 Hz, 1H) 2.40-2.65 (m, 2H) 2.06 (s, 3H) 1.59 (t, J=18.7 Hz, 3H).

Step 4. Synthesis of 1-(6-bromopyridin-2-yl)-3,3-difluorobutan-1-ol

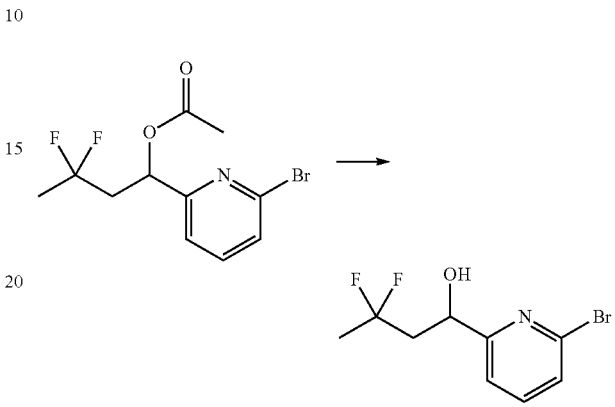

A solution of 1-(6-bromopyridin-2-yl)-3,3-difluorobutyl acetate (375 mg, 1.22 mmol) in 12 mL of anhydrous methanol was treated with solid Potassium carbonate (0.185 g, 1.34 mmol). After 15 minutes, the reaction was concentrated in vacuo and the resultant mixture was partioned between ethyl ether and brine. The pH of the aqueous phase was adjusted to neutral using 1N HCL. The layers were separated and the aqueous layer was extracted with ethyl ether. The combined organic phases were dried over MgSO$_4$, filtered, and concentrated to afford 1-(6-bromopyridin-2-yl)-3,3-difluorobutan-1-ol (330 mg; Yield=100%) as a pale yellow liquid. $^1$H NMR (400 MHz, CHLOROFORM-d) δ ppm 7.58 (t, J=7.8 Hz, 1H) 7.42 (d, J=8.0 Hz, 1H) 7.38 (d, J=7.5 Hz, 1H) 5.05 (ddd, J=9.1, 5.7, 3.0 Hz, 1H) 3.36 (dt, J=5.3, 1.0 Hz, 1H) 2.36-2.59 (m, 1H) 2.26 (qd, J=15.6, 9.3 Hz, 1H) 1.76 (t, J=19.1 Hz, 3H).

Step 5. Synthesis of 1-(6-bromopyridin-2-yl)-3,3-difluorobutan-1-one

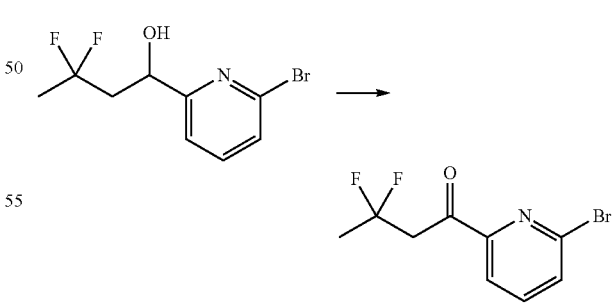

To a solution of 1-(6-bromopyridin-2-yl)-3,3-difluorobutan-1-ol (330 mg, 1.2 mmol) in 12 mL anhydrous CH$_2$Cl$_2$ was added Dess-Martin periodinane (0.63 g, 1.5 mmol). The reaction was stirred at RT for 1 h. To the solution was added 20 mL of 1:1 10% sodium thiosulfate solution/sat. sodium bicarbonate solution. The biphasic mixture was stirred vigorously for 1.5 h. To this mixture was added 100 mL of ethyl ether and the layers were separated. The organic phase was washed with 20 mL of the sodium thiosulfate/sodium bicarbonate solution used above, followed by sat. NaHCO₃ solution, and then brine. The organic phase was dried over MgSO₄, filtered and concentrated to afford 1-(6-bromopyridin-2-yl)-3,3-difluorobutan-1-one (0.33 g; Yield=100%). $^1$H NMR (400 MHz, CHLOROFORM-d) δ ppm 8.03 (dd, J=7.0, 1.8 Hz, 1H) 7.72-7.76 (m, 1H) 7.68-7.72 (m, 1H) 3.86 (t, J=14.1 Hz, 2H) 1.83 (t, J=18.9 Hz, 3H).

Step 6. Synthesis of N-(1-(6-bromopyridin-2-yl)-3,3-difluorobutylidene)-2-methylpropane-2-sulfinamide

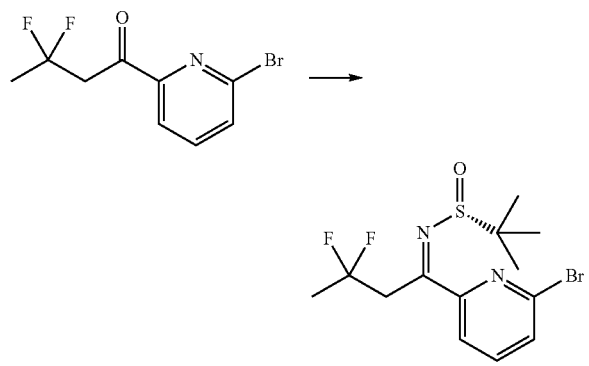

In a round-bottomed flask, 1-(6-bromopyridin-2-yl)-3,3-difluorobutan-1-one (330 mg, 1.2 mmol) in 10 mL anhydrous THF was treated with (R)-(+)-2-Methyl-2-propanesulfinamide ((CAS No. 196929-78-9, 0.198 g, 1.62 mmol) and Titanium tetraisopropoxide (0.71 g, 2.5 mmol). The reaction was heated to 70 C for 14 h. The reaction was cooled to room temperature and quenched with 3 mL of water and 6 mL of ethyl acetate. The mixture was filtered through Celite™ and the filter cake was rinsed with ethyl acetate. The filtrate was concentrated and purified by column chromatography using 10% ethyl acetate in heltane to afford (R,Z)—N-(1-(6-bromopyridin-2-yl)-3,3-difluorobutylidene)-2-methylpropane-2-sulfinamide (226 mg; Yield=49%) as an orange oil. $^1$H NMR (400 MHz, CHLOROFORM-d) δ ppm 7.94 (br d, J=7.8 Hz, 1H) 7.64 (t, J=7.8 Hz, 1H) 7.57 (dd, J=8.0, 1.0 Hz, 1H) 3.96-4.62 (m, 2H) 1.72 (t, J=18.4 Hz, 3H) 1.35 (s, 9H).

Step 7. Synthesis of (R)—N—((S)-1-(6-bromopyridin-2-yl)-3,3-difluorobutyl)-2-methylpropane-2-sulfinamide

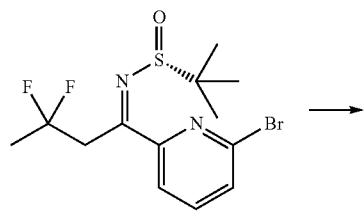

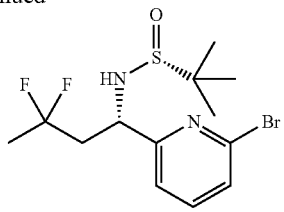

To a solution of (R,Z)—N-(1-(6-bromopyridin-2-yl)-3,3-difluorobutylidene)-2-methylpropane-2-sulfinamide (220 mg, 0.60 mmol) in 5 mL anhydrous THF at −78° C. was added [B] 1 M of L-Selectride® in tetrahydrofuran (1.2 mL, 1.2 mmol) dropwise. The reaction was stirred for 20 minutes at −78° C. The reaction was allowed to warm to −15° C. and stir for 15 min. The reaction was quenched by addition of sat. NH₄Cl solution and the aqueous phase was extracted with ethyl acetate. The combined organic phases were washed with brine, sat NaHCO₃, and brine. The organic phase was dried over MgSO₄, filtered, and concentrated to afford a yellow solid. Column chromatographic purification using 20% acetone in heptane afforded a white solid, (R)—N—((S)-1-(6-bromopyridin-2-yl)-3,3-difluorobutyl)-2-methylpropane-2-sulfinamide (0.18 g; Yield=81%). $^1$H NMR (400 MHz, CHLOROFORM-d) δ ppm 7.53 (t, J=7.5 Hz, 1H) 7.40 (dd, J=8.0, 0.8 Hz, 1H) 7.31 (d, J=7.5 Hz, 1H) 4.79 (q, J=6.3 Hz, 1H) 4.17 (br s, 1H) 2.44-2.73 (m, 2H) 1.65 (t, J=18.8 Hz, 3H) 1.21 (s, 9H).

Step 8. Synthesis of (S)-(6-(6-(6-(1-amino-3,3-difluorobutyl)pyridin-2-yl)-1H-indazol-1-yl)pyridin-2-yl)methanol

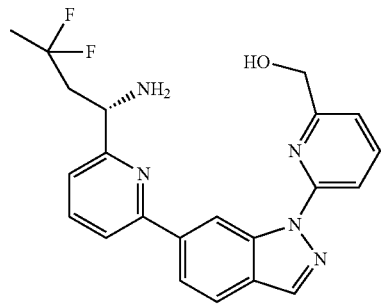 [SMILES: CC(F)(F)C[C@H](N)c1cccc(-c2ccc3cnn(-c4cccc(CO)n4)c3c2)n1]

(S)-(6-(6-(6-(1-amino-3,3-difluorobutyl)pyridin-2-yl)-1H-indazol-1-yl)pyridin-2-yl)methanol was made as a hydrochloride salt from (R)—N—((S)-1-(6-bromopyridin-2-yl)-3,3-difluorobutyl)-2-methylpropane-2-sulfinamide (Example 437, Step 7) and 1-(6-(((tert-butyldimethylsilyl)oxy)methyl)pyridin-2-yl)-6-(4,4,5,5-tetramethyl-1,3,2-dioxaborolan-2-yl)-1H-indazole (Example 143, Step 3) in a manner analogous to that described for (S)-(6-(6-(6-(1-aminobut-3-en-1-yl)pyridin-2-yl)-1H-indazol-1-yl)pyridin-2-yl)methanol (Example 435). $^1$H NMR (400 MHz, DMSO-d₆) δ ppm 9.61 (s, 1H) 8.70 (br s, 3H) 8.51 (d, J=1.0 Hz, 1H) 8.23 (dd, J=8.5, 1.5 Hz, 1H) 7.99-8.14 (m, 4H) 7.89 (d, J=8.3 Hz, 1H) 7.63 (d, J=7.5 Hz, 1H) 7.42 (d, J=7.5 Hz, 1H) 4.64-4.89 (m, 3H) 2.82-3.02 (m, 1H) 2.61-2.81 (m, 1H) 1.66 (t, J=19.2 Hz, 3H). LC/MS (M+H)=410.0

Example 438. (S)-(6-(6-(6-(1-amino-3,3-difluorobutyl)pyridin-2-yl)-4-ethoxy-1H-indazol-1-yl)pyridin-2-yl)methanol

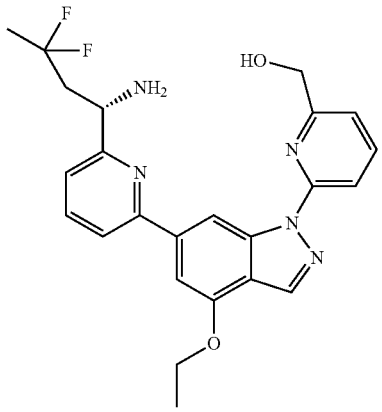 [SMILES: CCOc1cc(-c2cccc([C@@H](N)CC(C)(F)F)n2)cc2c1cnn2-c1cccc(CO)n1]

(S)-(6-(6-(6-(1-amino-3,3-difluorobutyl)pyridin-2-yl)-4-ethoxy-1H-indazol-1-yl)pyridin-2-yl)methanol was made as a hydrochloride salt from (R)—N—((S)-1-(6-bromopyridin-2-yl)-3,3-difluorobutyl)-2-methylpropane-2-sulfinamide (Example 437, Step 7) and 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) in similar manner to procedure described for (S)-(6-(6-(6-(1-aminobut-3-en-1-yl)pyridin-2-yl)-1H-indazol-1-yl)pyridin-2-yl)methanol (Example 435). $^1$H NMR (400 MHz, DMSO-d$_6$) δ ppm 9.16 (s, 1H) 8.75 (br s, 3H) 8.43 (s, 1H) 8.08-8.15 (m, 1H) 7.97-8.07 (m, 2H) 7.87 (d, J=8.3 Hz, 1H) 7.63 (t, J=3.8 Hz, 2H) 7.42 (d, J=7.5 Hz, 1H) 4.68-4.85 (m, 3H) 4.43 (q, J=7.1 Hz, 2H) 2.64-2.99 (m, 2H) 1.67 (t, J=19.3 Hz, 3H) 1.51 (t, J=6.9 Hz, 3H). LC/MS (M+H)=454.2.

Example 439 and 440 (R)-(6-(6-(6-(amino(phenyl)methyl)pyridin-2-yl)-4-ethoxy-1H-indazol-1-yl)pyridin-2-yl)methanol and (S)-(6-(6-(6-(amino(phenyl)methyl)pyridin-2-yl)-4-ethoxy-1H-indazol-1-yl)pyridin-2-yl)methanol Synthesis of (S)—N-((6-bromopyridin-2-yl)(phenyl)methyl)-2-methylpropane-2-sulfinamide

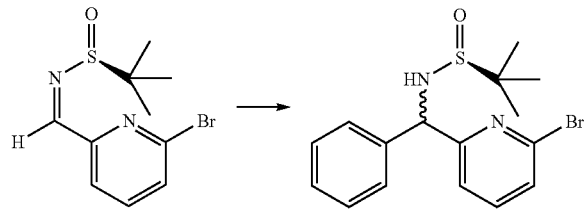 [SMILES: CC(C)(C)[S@](=O)/N=C\c1cccc(Br)n1 ; CC(C)(C)[S@](=O)NC(c1ccccc1)c1cccc(Br)n1]

(S,Z)—N-((6-bromopyridin-2-yl)methylene)-2-methylpropane-2-sulfinamide (Example 435, Step 1, 400.0 mg, 1.383 mmol) in 6.5 mL THF at −78 C was treated with 3 M of Phenylmagnesium bromide in Ether (0.6155 mL, 1.846 mmol) at −78° C. The reaction was allowed to stir for 1 h. The reaction was warmed to 0° C. and stirred for 15 min. The reaction was quenched by addition of sat. NH$_4$Cl solution. Purification by column chromatography (using acetone in heptane) afforded a 3:1 mixture of diastereomers. LC/MS=367.1.

Synthesis of (R)-(6-(6-(6-(amino(phenyl)methyl)pyridin-2-yl)-4-ethoxy-1H-indazol-1-yl)pyridin-2-yl)methanol and (S)-(6-(6-(6-(amino(phenyl)methyl)pyridin-2-yl)-4-ethoxy-1H-indazol-1-yl)pyridin-2-yl)methanol

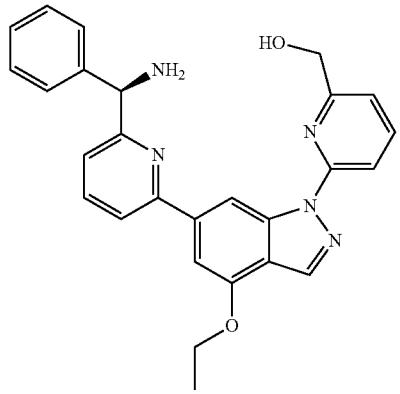

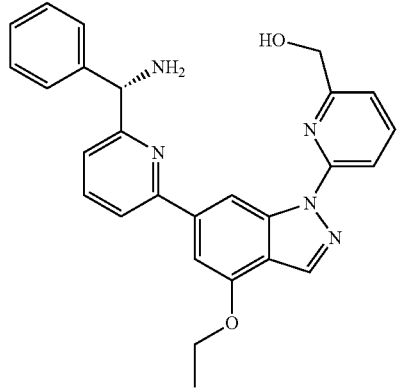

(R)-(6-(6-(6-(amino(phenyl)methyl)pyridin-2-yl)-4-ethoxy-1H-indazol-1-yl)pyridin-2-yl)methanol and (S)-(6-(6-(6-(amino(phenyl)methyl)pyridin-2-yl)-4-ethoxy-1H-indazol-1-yl)pyridin-2-yl)methanol were made as a hydrochloride salt in a manner analogous to that described for (S)-(6-(6-(6-(1-aminobut-3-en-1-yl)pyridin-2-yl)-1H-indazol-1-yl)pyridin-2-yl)methanol (Example 435) starting from (S,Z)—N-((6-bromopyridin-2-yl)methylene)-2-methylpropane-2-sulfinamide (Example 435, Step 1) and 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5). A major and minor isomer were obtained. Data for major isomer: $^1$H NMR (400 MHz, DMSO-d$_6$) δ ppm 9.15 (s, 1H) 9.07 (br s, 3H) 8.44 (d, J=1.0 Hz, 1H) 8.07 (d, J=7.8 Hz, 1H) 7.97-8.05 (m, 2H) 7.88 (d, J=7.8 Hz, 1H) 7.71 (d, J=1.0 Hz, 1H) 7.57-7.66 (m, 2H) 7.44-7.50 (m, 2H) 7.37-7.43 (m, 3H) 5.86 (br d, J=4.8 Hz, 1H) 4.78 (s, 2H) 4.35-4.57 (m, 2H) 1.52 (t, J=6.9 Hz, 3H). LC/MS (M+H)=452.2. Data for minor isomer: $^1$H NMR (400 MHz, DMSO-d$_6$) δ ppm 9.15 (s, 1H) 9.03 (br s, 3H) 8.44 (d, J=0.8 Hz, 1H) 8.08 (d, J=7.0 Hz, 1H) 7.95-8.05 (m, 2H) 7.88 (d, J=8.0 Hz, 1H) 7.70 (d, J=1.0 Hz, 1H) 7.58-7.64

(m, 2H) 7.44-7.52 (m, 2H) 7.37-7.44 (m, 3H) 5.80-5.91 (m, 1H) 4.78 (s, 2H) 4.42-4.50 (m, 2H) 1.53 (t, J=7.0 Hz, 3H). LC/MS (M+H)=452.2.

Example 441 (S)-(6-(6-(6-(1-aminopent-3-yn-1-yl)pyridin-2-yl)-4-ethoxy-1H-indazol-1-yl)pyridin-2-yl)methanol Synthesis of (S)—N—((S)-1-(6-bromopyridin-2-yl)-4-(trimethylsilyl)but-3-yn-1-yl)-2-methylpropane-2-sulfinamide

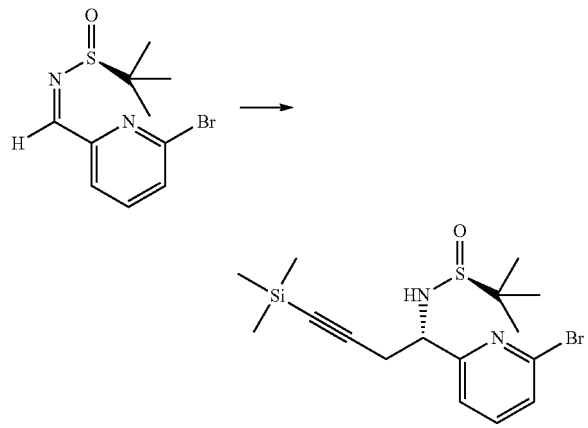

(S,Z)—N-((6-bromopyridin-2-yl)methylene)-2-methylpropane-2-sulfinamide (Example 435, Step 1, 445 mg, 1.54 mmol) 3-Bromo-1-(trimethylsilyl)-1-propyne (CAS No. 38002-45-8; 0.9265 g, 4.847 mmol) and Indium (0.5565 g, 4.847 mmol) were sonicated in 5 mL of anhydrous THF for 5 hours. The reaction was allowed to stir for three days at ambient temperature. The reaction was diluted with 5 mL water and extracted with 3×20 mL EtOAc. The combined organic phase was washed twice with brine, dried over MgSO₄, filtered, and concentrated. Purification using 2-5% isopropanol in heptane afforded (S)—N—((S)-1-(6-bromopyridin-2-yl)-4-(trimethylsilyl)but-3-yn-1-yl)-2-methylpropane-2-sulfinamide (0.500 g; Yield=80.9%). ¹H NMR (400 MHz, CHLOROFORM-d) δ ppm 7.48-7.58 (m, 1H) 7.34-7.43 (m, 2H) 4.61-4.70 (m, 1H) 4.49-4.60 (m, 1H) 2.63-2.87 (m, 2H) 1.29 (s, 9H), 0.11 (s, 9H).

Synthesis of (S)—N—((S)-1-(6-bromopyridin-2-yl)but-3-yn-1-yl)-2-methylpropane-2-sulfinamide

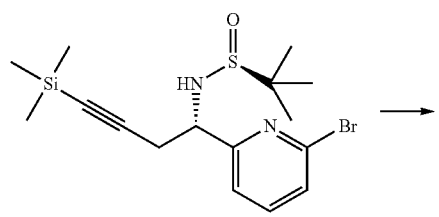

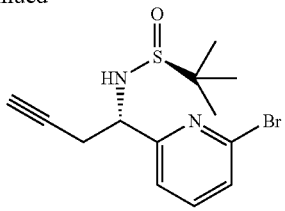

(S)—N—((S)-1-(6-bromopyridin-2-yl)-4-(trimethylsilyl)but-3-yn-1-yl)-2-methylpropane-2-sulfinamide (0.500 g, 1.24 mmol) in 5 mL methanol was treated with Potassium carbonate (0.189 g, 1.37 mmol). The reaction was allowed to stir for 1 h. The solvent was removed in vacuo. The reaction was partitioned between ethyl acetate and water and the pH was adjusted to 9 using 1N HCl. The organic phase was washed with brine twice, dried over MgSO₄, filtered, and concentrated. Column chromatographic purification using heptane/ethyl acetate plug (4 g silica gel) afforded (S)—N—((S)-1-(6-bromopyridin-2-yl)but-3-yn-1-yl)-2-methylpropane-2-sulfinamide (360 mg; Yield=88%; Supplier=BIOGEN) as a red oil. ¹H NMR (400 MHz, CHLOROFORM-d) δ ppm 7.51-7.58 (m, 1H) 7.41 (dd, J=7.7, 4.9 Hz, 2H) 4.51-4.63 (m, 2H) 2.61-2.92 (m, 2H) 1.94-2.01 (m, 1H) 1.28 (s, 9H).

Synthesis of (S)—N—((S)-1-(6-bromopyridin-2-yl)pent-3-yn-1-yl)-2-methylpropane-2-sulfinamide

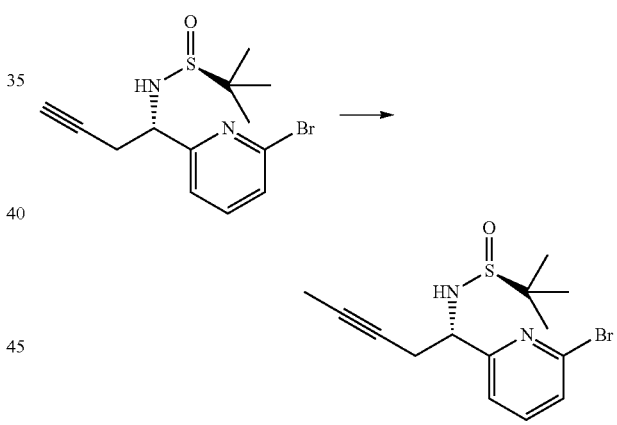

To a solution of (S)—N—((S)-1-(6-bromopyridin-2-yl)but-3-yn-1-yl)-2-methylpropane-2-sulfinamide (350 mg, 1.1 mmol) in 5 mL of THF at −78° C. was added freshly prepared 1M Lithium Diisopropylamide in THF/Hexane (2.15 mL, 2.23 mmol). The reaction was stirred for 1 h. Methyl iodide (0.166 g, 1.17 mmol) (density=2.28 g/mL) (73 uL) was added and the reaction was stirred for 1 h then allowed to warm to RT and stir for 3 h. The reaction was quenched with sat. NH₄Cl and extracted with EtOAc. The organic phase was washed with brine and concentrated. Purification using 15% acetone in heptane on a 2×25 g (stacked) 30 uM Interchim™ silica gel cartridge setup afforded (S)—N—((S)-1-(6-bromopyridin-2-yl)pent-3-yn-1-yl)-2-methylpropane-2-sulfinamide (0.125 g; Yield=34%). ¹H NMR (400 MHz, CHLOROFORM-d) δ ppm 7.43-7.49 (m, 1H) 7.27-7.36 (m, 2H) 4.48-4.54 (m, 1H) 4.39-4.47 (m, 1H) 2.47-2.73 (m, 2H) 1.65 (t, J=2.5 Hz, 3H) 1.20 (s, 9H).

Synthesis of (S)-(6-(6-(6-(1-aminopent-3-yn-1-yl)pyridin-2-yl)-4-ethoxy-1H-indazol-1-yl)pyridin-2-yl)methanol

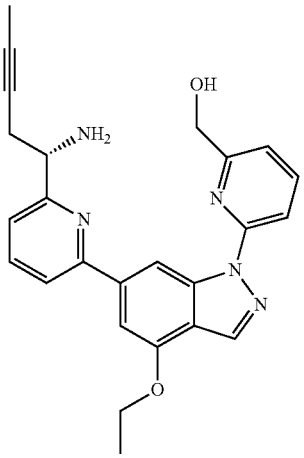 [SMILES: CC#CC[C@H](N)c1cccc(-c2cc(OCC)c3cnn(-c4cccc(CO)n4)c3c2)n1]

(S)-(6-(6-(6-(1-aminopent-3-yn-1-yl)pyridin-2-yl)-4-ethoxy-1H-indazol-1-yl)pyridin-2-yl)methanol was made as a hydrochloride salt starting from (S)—N—((S)-1-(6-bromopyridin-2-yl)pent-3-yn-1-yl)-2-methylpropane-2-sulfinamide and 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) in similar manner to procedure described for (S)-(6-(6-(6-(1-aminobut-3-en-1-yl)pyridin-2-yl)-1H-indazol-1-yl)pyridin-2-yl)methanol (Example 435). $^1$H NMR (400 MHz, DMSO-d$_6$) δ ppm 9.14 (s, 1H) 8.71 (br s, 3H) 8.43 (d, J=1.0 Hz, 1H) 8.08-8.13 (m, 1H) 7.98-8.07 (m, 2H) 7.87 (d, J=8.3 Hz, 1H) 7.67 (d, J=1.0 Hz, 1H) 7.58 (d, J=7.5 Hz, 1H) 7.41 (dd, J=7.5, 0.8 Hz, 1H) 4.78 (s, 2H) 4.54-4.70 (m, 1H) 4.43 (q, J=7.0 Hz, 2H) 2.83-3.03 (m, 2H) 1.71 (t, J=2.5 Hz, 3H) 1.51 (t, J=6.9 Hz, 3H). LC/MS (M+H)=428.2.

Examples 442 and 443 (6-(6-(6-((1R,2S)-1-amino-2-fluorobutyl)pyridin-2-yl)-4-ethoxy-1H-indazol-1-yl)pyridin-2-yl)methanol and (6-(6-(6-((1R,2R)-1-amino-2-fluorobutyl)pyridin-2-yl)-4-ethoxy-1H-indazol-1-yl)pyridin-2-yl)methanol Step 1. Synthesis of 1-(6-bromopyridin-2-yl)-2-fluorobutan-1-one

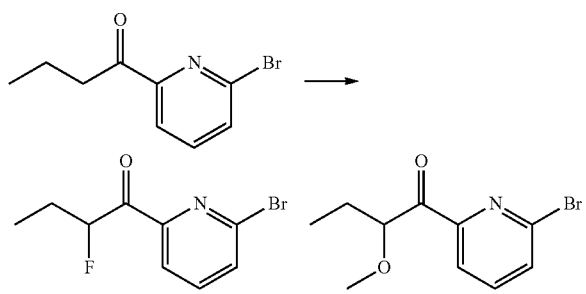

1-(6-bromopyridin-2-yl)butan-1-one (Example 145, Step 2, 1200 mg, 5.3 mmol) in 3 mL of methanol was treated with Selectfluor™ (2.24 g, 6.31 mmol) and Sulfuric acid (0.0516 g, 0.526 mmol). The vial was heated to 50° C. overnight. The reaction was cooled to RT and filtered through Celite®. The solid was rinsed with dichlormethane and the combined organic washes were concentrated. Purification on 40 g 30 M silica gel column using 0-5% ethyl acetate in heptane to afford three main components, recovered 1-(6-bromopyridin-2-yl)butan-1-one (400 mg; Yield=33%) as the first eluting product, 1-(6-bromopyridin-2-yl)-2-fluorobutan-1-one (520 mg; Yield=40%) as the second eluting compound and 1-(6-bromopyridin-2-yl)-2-methoxybutan-1-one (280 mg, 21%) as the third eluting product. Data for 1-(6-bromopyridin-2-yl)-2-fluorobutan-1-one: $^1$H NMR (400 MHz, CHLOROFORM-d) δ ppm 8.05 (dd, J=7.3, 1.3 Hz, 1H) 7.67-7.83 (m, 2H) 6.12 (ddd, J=50.2, 7.3, 4.0 Hz, 1H) 2.09-2.28 (m, 1H) 1.88-2.08 (m, 1H) 1.08 (t, J=7.4 Hz, 3H). Data for and 1-(6-bromopyridin-2-yl)-2-methoxybutan-1-one: $^1$H NMR (400 MHz, CHLOROFORM-d) δ ppm 8.03 (dd, J=7.2, 1.4 Hz, 1H) 7.66-7.76 (m, 2H) 5.12 (dd, J=6.8, 4.3 Hz, 1H) 3.44 (s, 3H) 1.99 (dqd, J=14.5, 7.4, 7.4, 7.4, 4.3 Hz, 1H) 1.77 (dquin, J=14.3, 7.2, 7.2, 7.2, 7.2 Hz, 1H) 0.99 (t, J=7.4 Hz, 3H).

Step 2. Synthesis of (R,E)-N—((S)-1-(6-bromopyridin-2-yl)-2-fluorobutylidene)-2-methylpropane-2-sulfinamide and (R,E)-N—((R)-1-(6-bromopyridin-2-yl)-2-fluorobutylidene)-2-methylpropane-2-sulfinamide

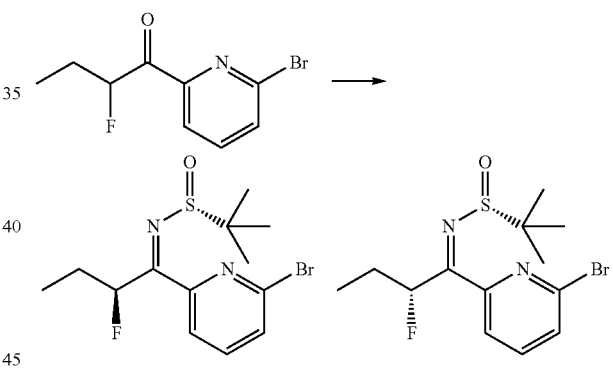

1-(6-bromopyridin-2-yl)-2-fluorobutan-1-one (520 mg, 2.1 mmol) in 10 mL anhydrous THF was treated with (R)-(+)-2-Methyl-2-propanesulfinamide ((CAS No. 196929-78-9, 0.336 g, 2.75 mmol) and Titanium tetraisopropoxide (1.20 g, 4.23 mmol). The reaction was heated to 70° C. overnight. The reaction was cooled to RT and quenched by addition of 4 mL water and 8 mL EtOAc. The mixture was filtered through Celite® and rinsed with EtOAc. The reaction was concentrated and deposited on 4 g silica gel and purified on a 40 g silica gel column eluted with 20% ethyl acetate in heptane to afford two diastereomers: (R,E)-N—((S)-1-(6-bromopyridin-2-yl)-2-fluorobutylidene)-2-methylpropane-2-sulfinamide and (R,E)-N—((R)-1-(6-bromopyridin-2-yl)-2-fluorobutylidene)-2-methylpropane-2-sulfinamide. 190 mg of the first eluting diastereomer was obtained (Yield=26%). 180 mg of the second eluting diastereomer was obtained (Yield=24%). Data for 1$^{st}$ eluting diastereomer: $^1$H NMR (400 MHz, CHLOROFORM-d) δ ppm 7.49-7.71 (m, 3H) 5.87 (br s, 1H) 2.31 (br s, 1H) 1.88-2.17 (m, 1H) 1.30 (s, 9H) 1.13 (t, J=7.4 Hz, 3H). Data for 2nd eluting diastereomer: $^1$H NMR (400 MHz, CHLO- ROFORM-d) δ ppm 7.71-8.08 (m, 1H) 7.50-7.68 (m, 2H) 5.82-6.47 (m, 1H) 1.91-2.31 (m, 2H) 1.26-1.37 (m, 9H) 1.13 (t, J=7.4 Hz, 3H).

Step 3. Synthesis of (R)—N—((1R,2S)-1-(6-bromopyridin-2-yl)-2-fluorobutyl)-2-methylpropane-2-sulfinamide

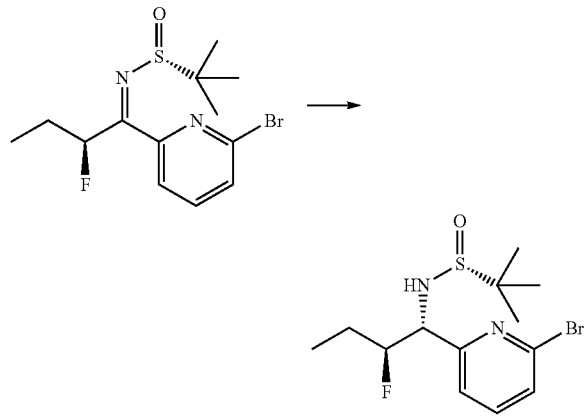

To a solution of (R,E)-N—((S)-1-(6-bromopyridin-2-yl)-2-fluorobutylidene)-2-methylpropane-2-sulfinamide (85 mg, 0.24 mmol) in 2 mL anhydrous THF at −78° C. was added 1 M L-Selectride (R) in Tetrahydrofuran (0.49 mL, 0.49 mmol) dropwise. The reaction was stirred for 20 minutes at −78° C. and allowed warm to −15° C. and stir for 15 min. The reaction was quenched by addition of sat NH₄Cl and extracted with ethyl acetate. The organic phase was washed with brine, sat NahCO₃, and brine. The organic phase was then dried over MgSO₄, filtered, and concentrated to afford a yellow oil. Purification by silica gel column chromatography using 10-15% acetone in heptane afforded a white solid, (R)—N—((1R,2S)-1-(6-bromopyridin-2-yl)-2-fluorobutyl)-2-methylpropane-2-sulfinamide (0.065 g; Yield=76%). ¹H NMR (400 MHz, CHLOROFORM-d) δ ppm 7.52-7.60 (m, 1H) 7.43 (d, J=7.8 Hz, 1H) 7.35 (d, J=7.5 Hz, 1H) 4.84 (ddt, J=47.2, 8.8, 4.0, 4.0 Hz, 1H) 4.56-4.68 (m, 1H) 4.25 (br d, J=6.3 Hz, 1H) 1.59-1.80 (m, 2H) 1.25 (s, 9H) 1.03 (t, J=7.5 Hz, 3H).

Synthesis of (6-(6-(6-((1R,2S)-1-amino-2-fluorobutyl)pyridin-2-yl)-4-ethoxy-1H-indazol-1-yl)pyridin-2-yl)methanol (Example 442)

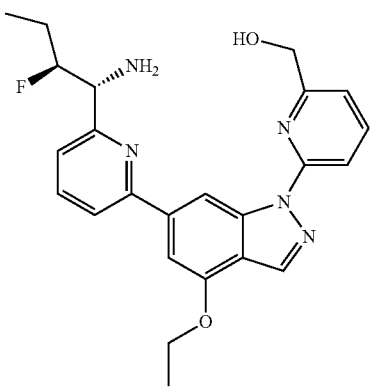 [SMILES: CCOc1cc(-c2cccc([C@@H](N)[C@@H](F)CC)n2)cc2c1cnn2-c1cccc(CO)n1]

(6-(6-(6-((1R,2S)-1-amino-2-fluorobutyl)pyridin-2-yl)-4-ethoxy-1H-indazol-1-yl)pyridin-2-yl)methanol was made as a hydrochloride salt starting from (R)—N—((1R,2S)-1-(6-bromopyridin-2-yl)-2-fluorobutyl)-2-methylpropane-2-sulfinamide and 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) in similar manner to procedure described for (S)-(6-(6-(6-(1-aminobut-3-en-1-yl)pyridin-2-yl)-1H-indazol-1-yl)pyridin-2-yl)methanol (Example 435) ¹H NMR (400 MHz, DMSO-d₆) δ ppm 9.08-9.16 (m, 1H) 8.88 (br s, 3H) 8.43 (d, J=0.8 Hz, 1H) 8.12-8.17 (m, 1H) 8.05-8.11 (m, 1H) 7.99-8.05 (m, 1H) 7.87 (d, J=8.0 Hz, 1H) 7.62-7.69 (m, 2H) 7.41 (dd, J=7.5, 0.8 Hz, 1H) 4.92-5.14 (m, 1H) 4.77 (s, 3H) 4.35-4.52 (m, 2H) 1.53-1.75 (m, 2H) 1.51 (t, J=6.9 Hz, 3H) 0.96 (t, J=7.4 Hz, 3H). LC/MS (M+H)=436.2.

Synthesis of (R)—N—((1R,2S)-1-(6-bromopyridin-2-yl)-2-fluorobutyl)-2-methylpropane-2-sulfinamide

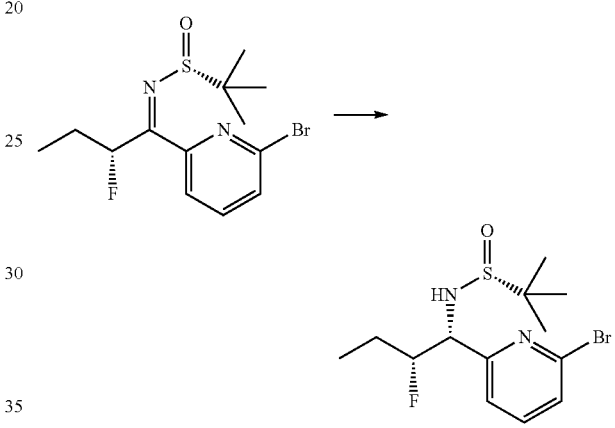

(R)—N—((1R,2R)-1-(6-bromopyridin-2-yl)-2-fluorobutyl)-2-methylpropane-2-sulfinamide was made in a manner similar to that described for (R)—N—((1R,2S)-1-(6-bromopyridin-2-yl)-2-fluorobutyl)-2-methylpropane-2-sulfinamide. ¹H NMR (300 MHz, CHLOROFORM-d) δ ppm 7.50-7.60 (m, 1H) 7.43 (dd, J=7.9, 0.8 Hz, 1H) 7.25-7.30 (m, 1H) 4.52-4.85 (m, 2H) 4.38 (br d, J=7.9 Hz, 1H) 1.54-1.97 (m, 2H) 1.20 (s, 9H) 1.03 (t, J=7.4 Hz, 3H).

Synthesis of (6-(6-(6-((1R,2R)-1-amino-2-fluorobutyl)pyridin-2-yl)-4-ethoxy-1H-indazol-1-yl)pyridin-2-yl)methanol (Example 443)

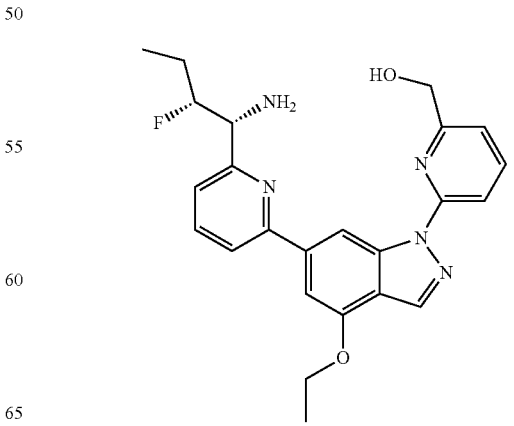

(6-(6-(6-((1R,2R)-1-amino-2-fluorobutyl)pyridin-2-yl)-4-ethoxy-1H-indazol-1-yl)pyridin-2-yl)methanol was made as a hydrochloride salt starting from (R)—N—((1R,2R)-1-(6-bromopyridin-2-yl)-2-fluorobutyl)-2-methylpropane-2-sulfinamide and 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) in similar manner to procedure described for (S)-(6-(6-(6-(1-aminobut-3-en-1-yl)pyridin-2-yl)-1H-indazol-1-yl)pyridin-2-yl)methanol (Example 435). $^1$H NMR (400 MHz, DMSO-d$_6$) δ ppm 9.11 (s, 1H) 8.90 (br d, J=3.8 Hz, 3H) 8.43 (d, J=1.0 Hz, 1H) 8.10-8.15 (m, 1H) 8.04-8.09 (m, 1H) 7.99-8.04 (m, 1H) 7.87 (d, J=8.0 Hz, 1H) 7.55-7.60 (m, 2H) 7.42 (d, J=7.5 Hz, 1H) 4.93-5.14 (m, 1H) 4.80-4.91 (m, 1H) 4.76 (s, 2H) 4.34-4.49 (m, 2H) 1.55-1.85 (m, 2H) 1.50 (t, J=7.0 Hz, 3H) 0.99 (t, J=7.3 Hz, 3H). LC/MS (M+H)=436.2.

Example 444 and 445. (6-(6-(6-((1R,2S)-1-amino-2-methoxybutyl)pyridin-2-yl)-4-ethoxy-1H-indazol-1-yl)pyridin-2-yl)methanol and (6-(6-(6-((1R,2R)-1-amino-2-methoxybutyl)pyridin-2-yl)-4-ethoxy-1H-indazol-1-yl)pyridin-2-yl)methanol

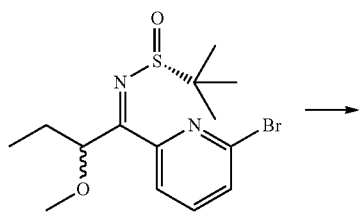

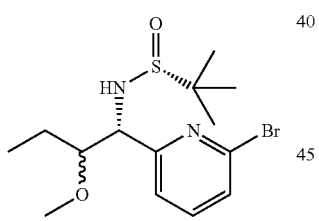

(R)—N—((1R)-1-(6-bromopyridin-2-yl)-2-methoxybutyl)-2-methylpropane-2-sulfinamide was made in a manner similar to that described for (R)—N—((1R,2S)-1-(6-bromopyridin-2-yl)-2-fluorobutyl)-2-methylpropane-2-sulfinamide (Example 442/443, Step 3) and was obtained as −6:4 mixture of diastereomers. $^1$H NMR (400 MHz, CHLOROFORM-d) δ ppm 7.48-7.57 (m, 1H) 7.31-7.42 (m, 2H) 4.79 (t, J=4.4 Hz, 0.4H) 4.52 (t, J=4.9 Hz, 0.6H) 4.37 (br d, J=5.0 Hz, 0.6H) 4.14 (d, J=3.8 Hz, 0.4H) 3.79-3.80 (m, 1H) 3.53-3.68 (m, 1H) 3.44 (s, 1.2H) 3.26 (s, 1.8H) 1.41-1.69 (m, 2H) 1.25 (s, 4H) 1.24 (s, 5H) 0.96 (t, J=7.5 Hz, 1.8H) 0.91 (t, J=7.4 Hz, 1.2H).

Synthesis of (6-(6-(6-((1R,2S)-1-amino-2-methoxybutyl)pyridin-2-yl)-4-ethoxy-1H-indazol-1-yl)pyridin-2-yl)methanol (Example 444)

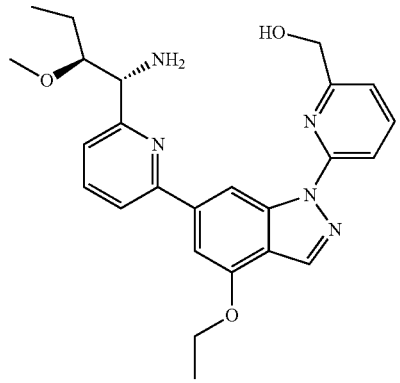 [SMILES: CCOc1cc(-c2cccc([C@@H](N)[C@H](CC)OC)n2)cc2c1cnn2-c1cccc(CO)n1]

(6-(6-(6-((1R,2S)-1-amino-2-methoxybutyl)pyridin-2-yl)-4-ethoxy-1H-indazol-1-yl)pyridin-2-yl)methanol was made as a hydrochloride salt starting from (R)—N—((1R)-1-(6-bromopyridin-2-yl)-2-methoxybutyl)-2-methylpropane-2-sulfinamide and 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) in similar manner to procedure described for (S)-(6-(6-(6-(1-aminobut-3-en-1-yl)pyridin-2-yl)-1H-indazol-1-yl)pyridin-2-yl)methanol (Example 435). $^1$H NMR (400 MHz, DMSO-d$_6$) δ ppm 9.00-9.20 (m, 1H) 8.57 (br s, 3H) 8.43 (d, J=1.0 Hz, 1H) 7.98-8.12 (m, 3H) 7.87 (d, J=7.5 Hz, 1H) 7.59 (d, J=1.0 Hz, 1H) 7.55 (d, J=6.5 Hz, 1H) 7.41 (dd, J=7.5, 0.8 Hz, 1H) 4.77 (s, 3H) 4.33-4.52 (m, 2H) 3.61-3.77 (m, 1H) 3.38 (s, 3H) 1.57 (dt, J=14.9, 7.5 Hz, 1H) 1.50 (t, J=6.9 Hz, 3H) 1.34 (ddd, J=14.1, 7.5, 4.8 Hz, 1H) 0.92 (t, J=7.4 Hz, 3H). LC/MS=448.2.

Synthesis of (6-(6-(6-((1R,2R)-1-amino-2-methoxybutyl)pyridin-2-yl)-4-ethoxy-1H-indazol-1-yl)pyridin-2-yl)methanol (Example 445)

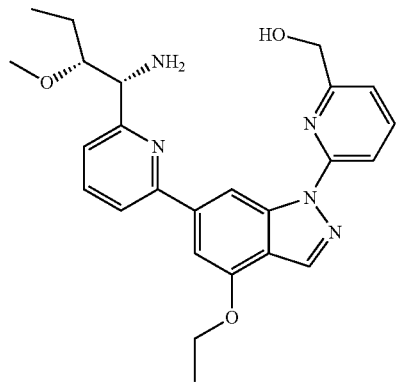 [SMILES: CCOc1cc(-c2cccc([C@@H](N)[C@@H](CC)OC)n2)cc2c1cnn2-c1cccc(CO)n1]

(6-(6-(6-((1R,2R)-1-amino-2-methoxybutyl)pyridin-2-yl)-4-ethoxy-1H-indazol-1-yl)pyridin-2-yl)methanol was made as a hydrochloride salt starting from (R)—N—((1R)-1-(6-bromopyridin-2-yl)-2-methoxybutyl)-2-methylpropane-2-sulfinamide and 1-(6-(((tert-butyldimethylsilyl)oxy)

methyl)pyridin-2-yl)-4-ethoxy-6-(4,4,5,5-tetramethyl-1,3,2-dioxaborolan-2-yl)-1H-indazole (Example 410, Step 5) in similar manner to procedure described for (S)-(6-(6-(6-(1-aminobut-3-en-1-yl)pyridin-2-yl)-1H-indazol-1-yl)pyridin-2-yl)methanol (Example 435)$^1$H NMR (400 MHz, DMSO-d$_6$) δ ppm 9.10-9.16 (m, 1H) 8.55 (br s, 3H) 8.43 (d, J=0.8 Hz, 1H) 8.08-8.15 (m, 1H) 7.99-8.08 (m, 2H) 7.87 (d, J=8.0 Hz, 1H) 7.62 (d, J=6.8 Hz, 1H) 7.59 (d, J=1.0 Hz, 1H) 7.42 (d, J=7.5 Hz, 1H) 4.72-4.83 (m, 2H) 4.47-4.58 (m, 1H) 4.36-4.47 (m, 2H) 3.73-3.85 (m, 1H) 3.39 (s, 3H) 1.64 (ddd, J=14.7, 7.5, 4.6 Hz, 1H) 1.50 (t, J=6.9 Hz, 3H) 1.15-1.34 (m, 1H) 0.87 (t, J=7.4 Hz, 3H). LC/MS=448.2.

Example 446 Synthesis of (6-(6-(6-(amino(oxetan-3-yl)methyl)pyridin-2-yl)-1H-indazol-1-yl)pyridin-2-yl)methanol Synthesis of (6-bromopyridin-2-yl)(oxetan-3-yl)methanol Step 1

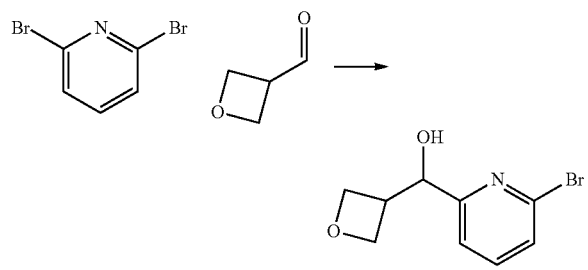

To a slurry of 2,6-Dibromopyridine ((CAS No. 626-05-1, 0.82 g, 3.5 mmol) in 35 mL of anhydrous ethyl ether at −78° C. was added 2.5 M of n-Butyllithium in hexanes (1.28 mL, 3.19 mmol). The reaction turned yellowish-orange in color. After 30 min, oxetane-3-carbaldehyde (CAS No. 1305207-52-6, 250 mg, 2.9 mmol) was added dropwise. The reaction was allowed to stir at −78° C. for 30 min then warmed to −20° C. and then quenched with sat. NH$_4$Cl solution. The layers were separated and the aqueous phase was extracted with diethyl ether. The combined organics were washed with brine, dried over MgSO$_4$, filtered, and concentrated. Column chromatographic purification using 40-80% ethyl acetate in heptane afforded (6-bromopyridin-2-yl)(oxetan-3-yl)methanol (0.45 g; Yield=63%). $^1$H NMR (400 MHz, CHLOROFORM-d) δ ppm 7.56 (t, J=7.5 Hz, 1H) 7.39-7.45 (m, 1H) 7.20-7.25 (m, 1H) 4.96 (t, J=6.7 Hz, 1H) 4.62-4.80 (m, 4H) 3.48 (d, J=6.3 Hz, 1H) 3.31-3.42 (m, 1H).

Step 2. Synthesis of 2-(azido(oxetan-3-yl)methyl)-6-bromopyridine

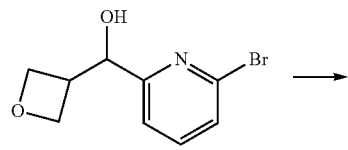

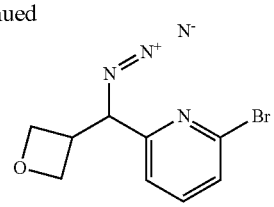

To a solution of Triphenylphosphine (0.317 g, 1.21 mmol) in 5 mL of anhydrous THF at 0° C. was added diisopropyl azodicarboxylate (0.224 g, 1.11 mmol) followed by (6-bromopyridin-2-yl)(oxetan-3-yl)methanol (260 mg, 1.1 mmol) in 2.6 mL of anhydrous THF, followed by diphenylphosphonic azide (0.554 g, 2.01 mmol). The reaction was allowed to warm to RT and stir for 2 h. The reaction was diluted with ethyl ether and washed with sat. NaHCO$_3$ and brine. The organic phase was dried over MgSO$_4$, filtered, and concentrated. Purification using 15-25% acetone in heptane on a 12 g silica gel cartridge afforded 2-(azido(oxetan-3-yl)methyl)-6-bromopyridine (0.24 g; Yield=84%). $^1$H NMR (400 MHz, CHLOROFORM-d) δ ppm 7.60 (t, J=7.8 Hz, 1H) 7.47 (dd, J=8.0, 0.8 Hz, 1H) 7.31 (dt, J=7.5, 0.5 Hz, 1H) 4.79-4.89 (m, 2H) 4.67-4.75 (m, 2H) 4.54 (t, J=6.4 Hz, 1H) 3.59 (s, 1H) 3.51-3.63 (m, 1H).

Step 3. Synthesis of 6-(6-(azido(oxetan-3-yl)methyl)pyridin-2-yl)-1-(6-(((tert-butyldimethylsilyl)oxy)methyl)pyridin-2-yl)-1H-indazole

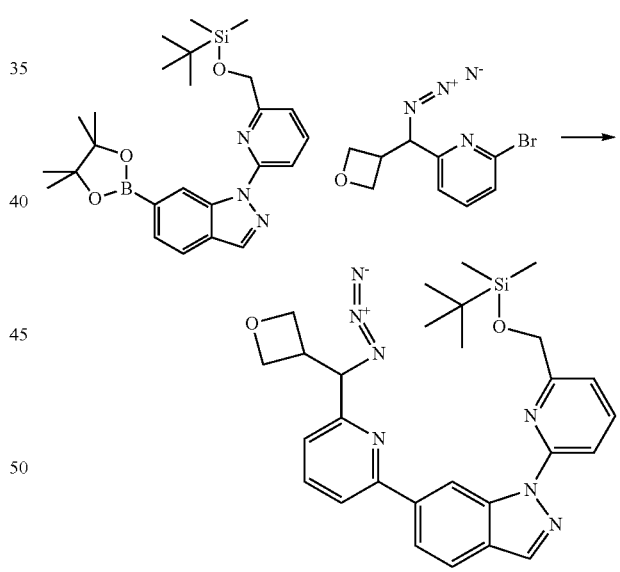

To a 40 mL reaction vial was added 1-(6-(((tert-butyldimethylsilyl)oxy)methyl)pyridin-2-yl)-6-(4,4,5,5-tetramethyl-1,3,2-dioxaborolan-2-yl)-1H-indazole (Example 143, Step 3, 345.9 mg, 0.7432 mmol), 2-(azido(oxetan-3-yl)methyl)-6-bromopyridine (240 mg, 0.89 mmol), Potassium carbonate (0.21 g, 1.5 mmol), and 1,1'-bis(diphenylphosphino)ferrocene-palladium(II)dichloride dichloromethane complex (0.031 g, 0.038 mmol) The vial was sealed, evacuated, and backfilled with N$_2$ two times. Water (2.0 mL) and 1,4 dioxane (8.0 mL) were added. The reaction was heated to 90° C. for 1 h. The reaction was cooled to RT and diluted with 150 mL of ethyl acetate. The reaction mixture was poured into a separatory funnel and washed twice with 15 mL of brine. The organic phase was dried over MgSO₄, filtered, and concentrated. Purification by column chromatography using 5-25% ethyl acetate in heptane afforded 6-(6-(azido(oxetan-3-yl)methyl)pyridin-2-yl)-1-(6-(((tert-butyldimethylsilyl)oxy)methyl)pyridin-2-yl)-1H-indazole (360 mg; Yield=92%). ¹H NMR (400 MHz, CHLOROFORM-d) δ ppm 9.44 (dt, J=1.6, 0.8 Hz, 1H) 8.23 (d, J=0.8 Hz, 1H) 7.84-7.99 (m, 6H) 7.40-7.44 (m, 1H) 7.28-7.34 (m, 1H) 5.00 (s, 2H) 4.89-4.98 (m, 2H) 4.73-4.87 (m, 2H) 4.63 (t, J=6.4 Hz, 1H) 3.74 (dtt, J=9.2, 7.8, 7.8, 6.2, 6.2 Hz, 1H) 0.97-1.05 (m, 9H) 0.19 (s, 6H).

Step 4. Synthesis of (6-(6-(6-(azido(oxetan-3-yl)methyl)pyridin-2-yl)-1H-indazol-1-yl)pyridin-2-yl)methanol

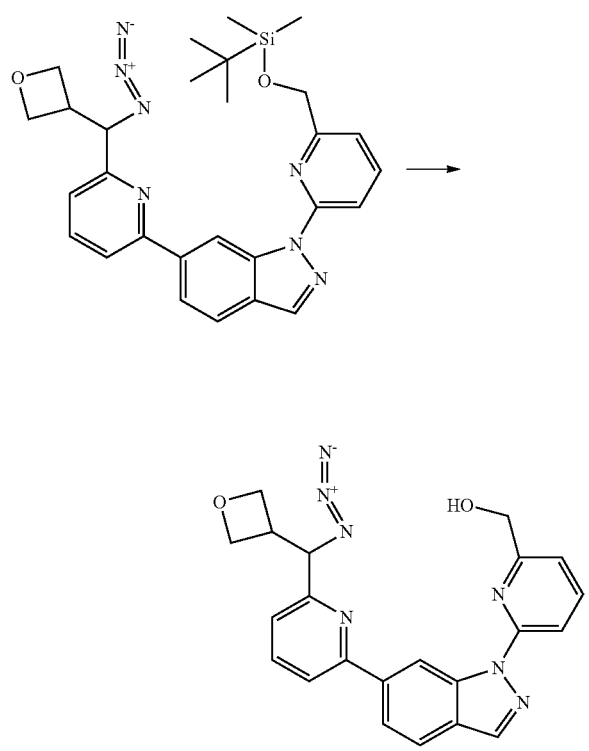 [SMILES: CC(C)(C)[Si](C)(C)OCc1cccc(-n2ncc3ccc(-c4cccc(C(N=[N+]=[N-])C5COC5)n4)cc32)n1 ; [N-]=[N+]=NC(c1cccc(-c2ccc3cnn(-c4cccc(CO)n4)c3c2)n1)C1COC1]

A solution of 6-(6-(azido(oxetan-3-yl)methyl)pyridin-2-yl)-1-(6-(((tert-butyldimethylsilyl)oxy)methyl)pyridin-2-yl)-1H-indazole (0.324 g, 0.614 mmol) in 6 mL of anhydrous THF at 0° C. was treated dropwise with 1 M of Tetra-n-butylammonium fluoride in Tetrahydrofuran (0.675 mL, 0.675 mmol). After 1 h, the reaction was diluted with ethyl ether and washed with water, sat. NaHCO₃, and brine. The organic phase was dried over MgSO₄, filtered, and concentrated. Purification on a 4 g 30 μM silica gel cartridge eluted with 50-100% ethyl acetate in heptane afforded (6-(6-(6-(azido(oxetan-3-yl)methyl)pyridin-2-yl)-1H-indazol-1-yl)pyridin-2-yl)methanol (245 mg; Yield=96.5%) as a yellow oil. ¹H NMR (400 MHz, CHLOROFORM-d) δ ppm 9.47 (dt, J=1.5, 0.8 Hz, 1H) 8.25 (d, J=1.0 Hz, 1H) 7.94-8.00 (m, 2H) 7.83-7.91 (m, 4H) 7.29-7.35 (m, 1H) 7.23 (dd, J=7.3, 0.8 Hz, 1H) 4.90-5.02 (m, 4H) 4.83-4.88 (m, 1H) 4.81 (dd, J=8.2, 6.4 Hz, 1H) 4.67-4.73 (m, 1H) 3.66-3.86 (m, 1H) 3.33 (t, J=5.4 Hz, 1H).

Step 5. Synthesis of (6-(6-(6-(amino(oxetan-3-yl)methyl)pyridin-2-yl)-1H-indazol-1-yl)pyridin-2-yl)methanol

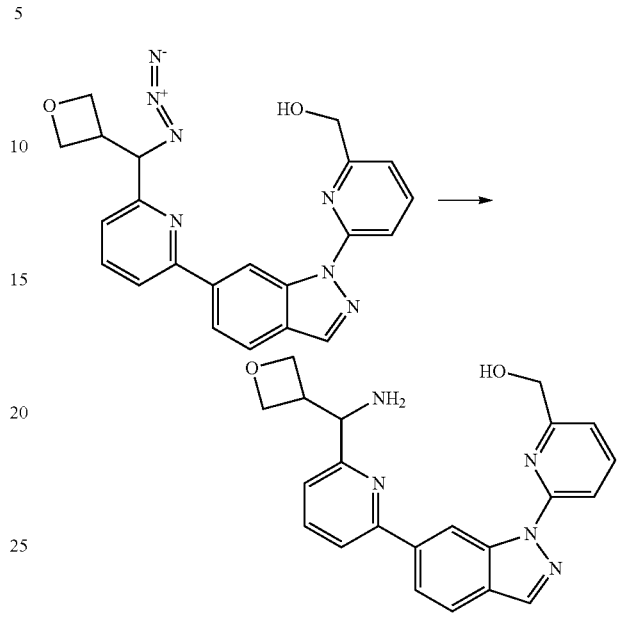

To a 100 mL round-bottomed flask containing (6-(6-(6-(azido(oxetan-3-yl)methyl)pyridin-2-yl)-1H-indazol-1-yl)pyridin-2-yl)methanol (34 mg, 0.082 mmol) and Sodium Bicarbonate (0.041 g, 0.49 mmol) in 1 mL ethanol was added Palladium (0.0088 g, 0.0082 mmol) (10% on carbon, Degussa type). The vessel was purged with nitrogen then the atmosphere was replaced with hydrogen. After 3 h, the reaction appears to have progressed completely. The reaction was purged with nitrogen, diluted with 25 mL of ethyl acetate, filtered through Celite™ and concentrated to afford (6-(6-(6-(amino(oxetan-3-yl)methyl)pyridin-2-yl)-1H-indazol-1-yl)pyridin-2-yl)methanol. LC/MS (M+H)=388.1. ¹H NMR (400 MHz, DMSO-d₆) δ ppm 9.57 (d, J=0.8 Hz, 1H) 8.48 (d, J=1.0 Hz, 1H) 8.00-8.06 (m, 2H) 7.95-7.99 (m, 1H) 7.86-7.94 (m, 3H) 7.48 (dd, J=6.4, 2.1 Hz, 1H) 7.42 (dd, J=7.4, 0.9 Hz, 1H) 4.79 (s, 2H) 4.62-4.72 (m, 2H) 4.51-4.59 (m, 2H) 4.21 (d, J=8.8 Hz, 1H) 3.35-3.42 (m, 1H).

Example 447 (6-(6-(6-(amino(oxetan-3-yl)methyl)pyridin-2-yl)-4-ethoxy-1H-indazol-1-yl)pyridin-2-yl)methanol

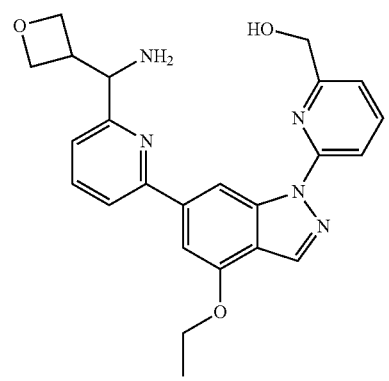 [SMILES: CCOc1cc(-c2cccc(C(N)C3COC3)n2)cc2c1cnn2-c1cccc(CO)n1]

(6-(6-(6-(amino(oxetan-3-yl)methyl)pyridin-2-yl)-4-ethoxy-1H-indazol-1-yl)pyridin-2-yl)methanol was made from 2-(azido(oxetan-3-yl)methyl)-6-bromopyridine (Example 446, Step 2) and 1-(6-(((tert-butyldimethylsilyl)oxy)methyl)pyridin-2-yl)-4-ethoxy-6-(4,4,5,5-tetramethyl-1,3,2-dioxaborolan-2-yl)-1H-indazole (Example 410, Step 5) in similar manner to procedure described for (6-(6-(6-(amino(oxetan-3-yl)methyl)pyridin-2-yl)-1H-indazol-1-yl)pyridin-2-yl)methanol (Example 446). ¹H NMR (400 MHz, CHLOROFORM-d) δ ppm 9.02 (s, 1H) 8.32 (d, J=0.8 Hz, 1H) 7.97 (d, J=8.0 Hz, 1H) 7.82-7.90 (m, 1H) 7.68-7.80 (m, 2H) 7.31 (d, J=1.0 Hz, 1H) 7.22 (dd, J=6.8, 1.8 Hz, 1H) 7.18 (d, J=7.5 Hz, 1H) 4.89-4.97 (m, 3H) 4.81-4.88 (m, 1H) 4.72 (dd, J=8.0, 6.3 Hz, 1H) 4.59-4.66 (m, 1H) 4.35 (q, J=6.9 Hz, 3H) 3.39-3.61 (m, 2H) 1.84-1.86 (m, 1H) 1.82-1.97 (m, 1H) 1.52-1.67 (m, 3H).

Example 448 (6-(6-(6-(1-amino-2-(3-methyloxetan-3-yl)ethyl)pyridin-2-yl)-1H-indazol-1-yl)pyridin-2-yl)methanol Synthesis of 2-(1-azido-2-(3-methyloxetan-3-yl)ethyl)-6-bromopyridine

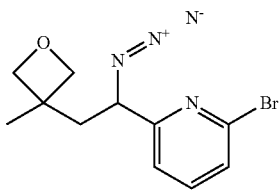

2-(1-azido-2-(3-methyloxetan-3-yl)ethyl)-6-bromopyridine was made in a manner analogous to 2-(azido(oxetan-3-yl)methyl)-6-bromopyridine (Example 446, Step 2) starting from 2,6-Dibromopyridine and 2-(3-methyloxetan-3-yl)acetaldehyde. ¹H NMR (400 MHz, CHLOROFORM-d) δ ppm 7.56-7.69 (m, 1H) 7.46 (d, J=8.0 Hz, 1H) 7.37 (d, J=7.5 Hz, 1H) 4.66 (d, J=6.0 Hz, 1H) 4.59 (dd, J=9.7, 5.1 Hz, 1H) 4.38 (d, J=6.0 Hz, 1H) 4.32 (d, J=5.8 Hz, 1H) 4.24 (d, J=5.8 Hz, 1H) 2.26 (dd, J=14.3, 9.8 Hz, 1H) 2.09 (dd, J=14.2, 5.1 Hz, 1H) 1.50 (s, 3H).

Synthesis of (6-(6-(6-(1-amino-2-(3-methyloxetan-3-yl)ethyl)pyridin-2-yl)-1H-indazol-1-yl)pyridin-2-yl)methanol

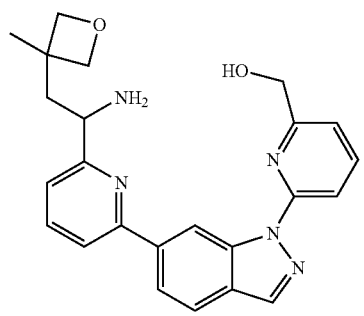 [SMILES: CC1(CC(N)c2cccc(-c3ccc4cnn(-c5cccc(CO)n5)c4c3)n2)COC1]

(6-(6-(6-(1-amino-2-(3-methyloxetan-3-yl)ethyl)pyridin-2-yl)-1H-indazol-1-yl)pyridin-2-yl)methanol was obtained from 1-(6-(((tert-butyldimethylsilyl)oxy)methyl)pyridin-2-yl)-6-(4,4,5,5-tetramethyl-1,3,2-dioxaborolan-2-yl)-1H-indazole (Example 143, Step 3) and 2-(1-azido-2-(3-methyloxetan-3-yl)ethyl)-6-bromopyridine in an analogous manner to that described for the synthesis of (6-(6-(6-(amino(oxetan-3-yl)methyl)pyridin-2-yl)-1H-indazol-1-yl)pyridin-2-yl)methanol (Example 446). ¹H NMR (400 MHz, CHLOROFORM-d) δ ppm 9.63 (s, 1H) 8.22 (s, 1H) 7.87-7.98 (m, 2H) 7.79-7.87 (m, 2H) 7.65-7.77 (m, 2H) 7.19 (d, J=7.5 Hz, 1H) 7.13 (br d, J=7.3 Hz, 1H) 4.89-5.02 (m, 2H) 4.75 (d, J=5.8 Hz, 1H) 4.42 (d, J=5.8 Hz, 1H) 4.02-4.27 (m, 3H) 2.86 (br s, 4H) 2.30 (dd, J=13.6, 8.3 Hz, 1H) 2.03-2.21 (m, 1H) 1.52 (s, 3H). LC/MS (M+H)=416.2.

Example 449 (S)-4-amino-4-(6-(1-(6-(hydroxymethyl)pyridin-2-yl)-1H-indazol-6-yl)pyridin-2-yl)butan-2-one Synthesis of (S)-1-(6-bromopyridin-2-yl)-3-methylbut-3-en-1-amine

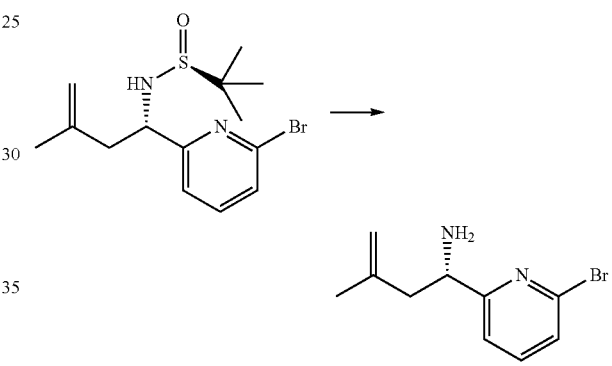

To a solution of (S)—N—((S)-1-(6-bromopyridin-2-yl)-3-methylbut-3-en-1-yl)-2-methylpropane-2-sulfinamide (Example 436, Step 1, 1.00 g, 2.90 mmol) in 15 mL anhydrous DCM was added 4 M of Hydrogen chloride in 1,4-Dioxane (3.62 mL, 14.5 mmol). A white solid precipitated. After 1 h, the reaction was diluted with 20 mL of ethyl ether and the mixture was filtered. The solid product was washed with 20 mL of ethyl ether to afford 930 mg (S)-1-(6-bromopyridin-2-yl)-3-methylbut-3-en-1-amine as a hydrogen chloride salt. Yield=100%. ¹H NMR (400 MHz, DMSO-d₆) δ ppm 8.59 (br s, 3H) 7.82 (t, J=8.0 Hz, 1H) 7.67 (dd, J=8.0, 0.8 Hz, 1H) 7.60 (dd, J=7.8, 0.8 Hz, 1H) 4.76 (t, J=1.6 Hz, 1H) 4.61 (d, J=1.0 Hz, 1H) 4.54 (dt, J=8.6, 5.9 Hz, 1H) 2.52-2.70 (m, 2H) 1.68 (s, 3H).

Synthesis of (S)-tert-butyl (1-(6-bromopyridin-2-yl)-3-methylbut-3-en-1-yl)carbamate

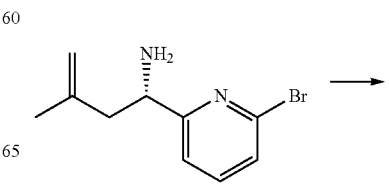

-continued

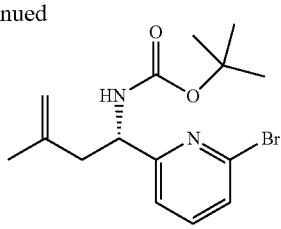

To (S)-1-(6-bromopyridin-2-yl)-3-methylbut-3-en-1-amine hydrogen chloride salt (930 mg, 3.0 mmol) in THF (10 ml) was added triethylamine (0.90 g, 8.9 mmol) followed by di-tert-Butyldicarbonate (0.97 g, 4.4 mmol) and 4-Dimethylaminopyridine (0.0072 g, 0.059 mmol). The reaction was heated to 40° C. After 1 h, the reaction was quenched with sat NaHCO$_3$. The reaction was diluted with ethyl ether and washed with brine. The organic phase was dried over MgSO$_4$, filtered, and concentrated to afford 1.3 g crude material Purification on 25 g silica cartridge using 0-20% ethyl acetate in heptane afforded (S)-tert-butyl (1-(6-bromopyridin-2-yl)-3-methylbut-3-en-1-yl)carbamate (0.787 g; Yield=78%) as a crystalline white solid. $^1$H NMR (400 MHz, CHLOROFORM-d) δ ppm 7.49 (t, J=8.0 Hz, 1H) 7.36 (d, J=7.5 Hz, 1H) 7.19 (d, J=7.5 Hz, 1H) 5.31 (br s, 1H) 4.74-4.99 (m, 2H) 4.68 (br s, 1H) 2.36-2.63 (m, 2H) 1.74 (s, 3H) 1.43 (br s, 9H).

Synthesis of (S)-tert-butyl (1-(6-bromopyridin-2-yl)-3-oxobutyl)carbamate

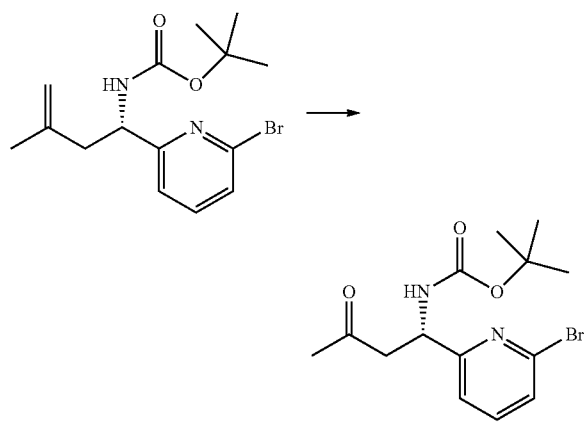

To a reaction vessel containing (S)-tert-butyl (1-(6-bromopyridin-2-yl)-3-methylbut-3-en-1-yl)carbamate (750 mg, 2.2 mmol) and sodium periodate (1.88 g, 8.79 mmol) in 15 mL 1,4 dioxane and 3 mL water was added 2,6-Lutidine (0.471 g, 4.40 mmol), Osmium tetroxide, 2.5 wt. % solution in 2-methyl-2-propanol (0.577 g, 0.0440 mmol), and Sodium periodate. After 3 h, water was added (10 mL) and the aqueous phase was extracted three times with dichloromethane. The combined dichloromethane extracts were washed with brine, dried over MgSO$_4$, filtered, and concentrated. Purification by column chromatography using 10-40% ethyl acetate in heptane afforded (S)-tert-butyl (1-(6-bromopyridin-2-yl)-3-oxobutyl)carbamate (0.72 g; Yield=95%) as a thick clear oil. $^1$H NMR (400 MHz, CHLOROFORM-d) δ ppm 7.51 (t, J=7.8 Hz, 1H) 7.39 (d, J=7.5 Hz, 1H) 7.34 (d, J=7.8 Hz, 1H) 5.73 (br d, J=7.8 Hz, 1H) 5.14 (br s, 1H) 3.32 (br dd, J=17.2, 3.9 Hz, 1H) 2.99 (br dd, J=17.3, 6.5 Hz, 1H) 2.16 (s, 3H) 1.46 (s, 9H).

Synthesis of (S)-4-amino-4-(6-(1-(6-(hydroxymethyl)pyridin-2-yl)-1H-indazol-6-yl)pyridin-2-yl)butan-2-one

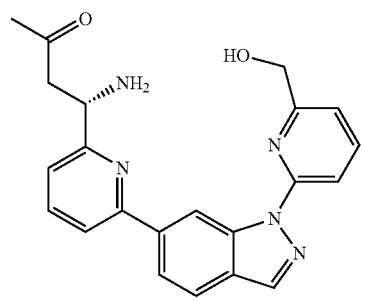 [SMILES: CC(=O)C[C@H](N)c1cccc(-c2ccc3cnn(-c4cccc(CO)n4)c3c2)n1]

(S)-4-amino-4-(6-(1-(6-(hydroxymethyl)pyridin-2-yl)-1H-indazol-6-yl)pyridin-2-yl)butan-2-one was made as a hydrochloride salt starting from (S)-tert-butyl (1-(6-bromopyridin-2-yl)-3-oxobutyl)carbamate and 1-(6-(((tert-butyldimethylsilyl)oxy)methyl)pyridin-2-yl)-6-(4,4,5,5-tetramethyl-1,3,2-dioxaborolan-2-yl)-1H-indazole (Example 143, Step 3) in a manner analogous to that described for the synthesis of (6-(6-(6-(amino(oxetan-3-yl)methyl)pyridin-2-yl)-1H-indazol-1-yl)pyridin-2-yl)methanol (Example 446). $^1$H NMR (400 MHz, DMSO-d$_6$) δ ppm 9.45-9.67 (m, 1H) 8.56 (m, J=4.3 Hz, 3H) 8.50 (d, J=0.8 Hz, 1H) 8.20 (dd, J=8.5, 1.5 Hz, 1H) 8.00-8.11 (m, 4H) 7.86-7.91 (m, 1H) 7.57 (dd, J=7.3, 1.0 Hz, 1H) 7.42 (dd, J=7.5, 0.8 Hz, 1H) 4.86 (q, J=5.8 Hz, 1H) 4.81 (s, 2H) 3.41 (dd, J=18.1, 6.5 Hz, 1H) 3.30 (dd, J=17.8, 6.3 Hz, 1H). LC/MS (M+H) 388.1.

Example 450 (S)-6-(6-(6-(1-aminobutyl)pyridin-2-yl)-1H-indazol-1-yl)picolinaldehyde Step 1. Synthesis of (R)—N—((S)-1-(6-(1-(6-(hydroxymethyl)pyridin-2-yl)-1H-indazol-6-yl)pyridin-2-yl)butyl)-2-methylpropane-2-sulfinamide

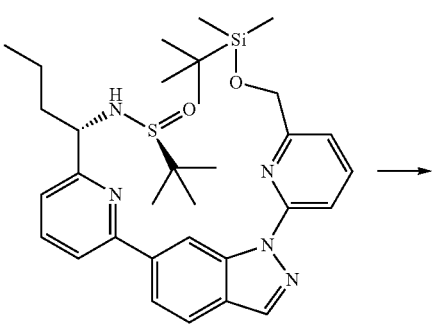

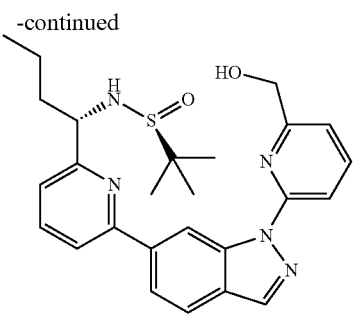

To a solution of (R)—N—((S)-1-(6-(1-(6-(((tert-butyldimethylsilyl)oxy)methyl)pyridin-2-yl)-1H-indazol-6-yl)pyridin-2-yl)butyl)-2-methylpropane-2-sulfinamide (Example 145, Step 6, 2.16 g, 3.65 mmol) in 20 mL THF was added 1 M of Tetra-n-butylammonium fluoride in Tetrahydrofuran (4.38 mL, 4.38 mmol). After 15 minutes, the reaction was diluted with ether and washed with water, sat NaHCO$_3$, brine. The reaction flask and aqueous layers were reextracted with ethyl acetate to afford additional crude material. Purification using 70% ethyl acetate in heptane afforded (R)—N—((S)-1-(6-(1-(6-(hydroxymethyl)pyridin-2-yl)-1H-indazol-6-yl)pyridin-2-yl)butyl)-2-methylpropane-2-sulfinamide (1.3 g; Yield=74%). $^1$H NMR (400 MHz, CHLOROFORM-d) δ ppm 9.84 (s, 1H) 8.25 (d, J=0.8 Hz, 1H) 7.92-8.02 (m, 2H) 7.88 (t, J=8.0 Hz, 2H) 7.81-7.85 (m, 1H) 7.74-7.81 (m, 1H) 7.22-7.27 (m, 1H) 7.15-7.21 (m, 1H) 4.90-5.04 (m, 2H) 4.86 (d, J=7.3 Hz, 1H) 4.20 (t, J=4.9 Hz, 1H) 2.07-2.17 (m, 3H) 1.31-1.51 (m, 2H) 1.16 (s, 9H) 0.96 (t, J=7.4 Hz, 3H).

Step 2. Synthesis of (R)—N—((S)-1-(6-(1-(6-formylpyridin-2-yl)-1H-indazol-6-yl)pyridin-2-yl)butyl)-2-methylpropane-2-sulfinamide

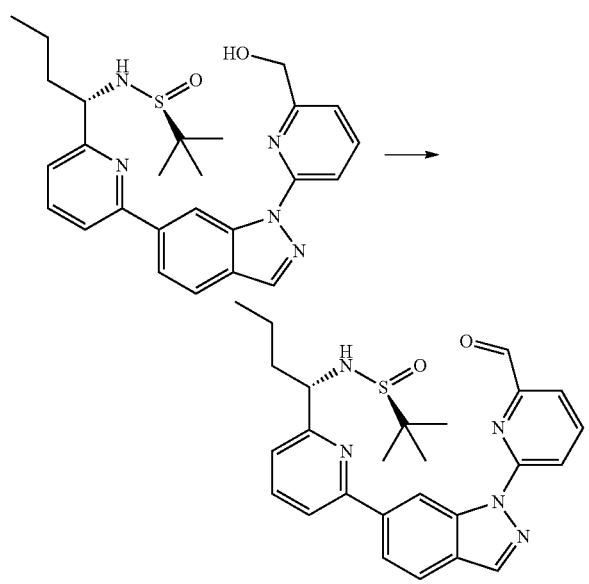

To a reaction flask containing (R)—N—((S)-1-(6-(1-(6-(hydroxymethyl)pyridin-2-yl)-1H-indazol-6-yl)pyridin-2-yl)butyl)-2-methylpropane-2-sulfinamide (1.0 g, 2.1 mmol) in 20 mL of anhydrous dichloromethane was added Dess-Martin periodinane (1.1 g, 2.5 mmol). After 1 h, Water (0.045 g, 2.5 mmol) was added dropwise. After 30 min, Sat. NaHCO$_3$/10% sodium thiosulfate solution was added and the reaction was stirred vigorously for 1 h. The reaction was diluted with ethyl acetate and washed with Sat. NaHCO$_3$/10% sodium thiosulfate solution, then sat. NaHCO$_3$ solution, then brine. The organic phase was dried over MgSO$_4$, filtered and concentrated to afford (R)—N—((S)-1-(6-(1-(6-formylpyridin-2-yl)-1H-indazol-6-yl)pyridin-2-yl)butyl)-2-methylpropane-2-sulfinamide (1.0 g; Yield=100%) The sample was further purified by column chromatography using 30-60% ethyl acetate in heptane. $^1$H NMR (400 MHz, CHLOROFORM-d) δ ppm 10.26 (d, J=0.8 Hz, 1H) 9.49-9.77 (m, 1H) 8.37 (dd, J=8.3, 1.0 Hz, 1H) 8.28 (d, J=0.8 Hz, 1H) 8.10 (dd, J=8.5, 1.5 Hz, 1H) 8.05 (ddd, J=8.3, 7.5, 0.8 Hz, 1H) 7.90 (dd, J=8.5, 0.8 Hz, 1H) 7.86 (dd, J=7.4, 0.9 Hz, 1H) 7.78-7.84 (m, 2H) 4.60 (q, J=6.7 Hz, 1H) 4.18 (d, J=6.3 Hz, 1H) 1.95-2.14 (m, 2H) 1.30-1.51 (m, 2H) 1.20 (s, 8H) 0.92-1.00 (m, 3H).

Step 3. Synthesis of (S)-6-(6-(6-(1-aminobutyl)pyridin-2-yl)-1H-indazol-1-yl)picolinaldehyde

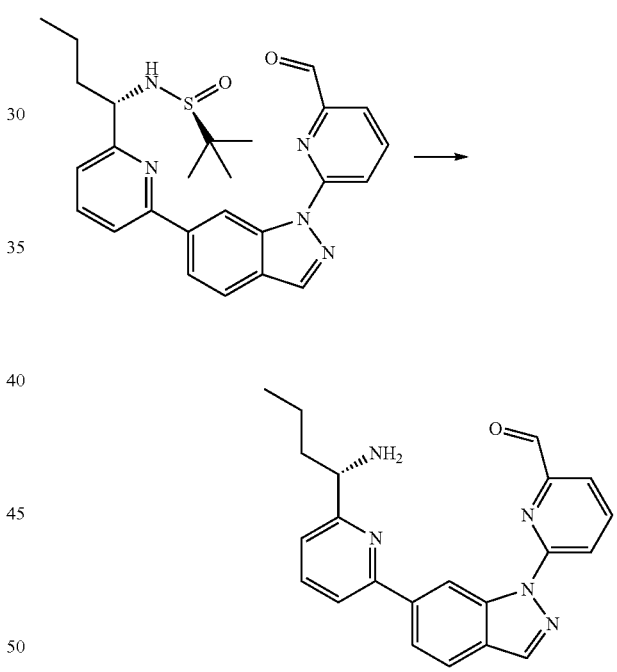

To a solution of (R)—N—((S)-1-(6-(1-(6-formylpyridin-2-yl)-1H-indazol-6-yl)pyridin-2-yl)butyl)-2-methylpropane-2-sulfinamide (90 mg, 0.2 mmol) in 4 mL of anhydrous dichloromethane was added 4 M of Hydrogen Chloride in 1,4-Dioxane (0.9 mL, 4 mmol). After 30 minutes, the reaction was diluted with diethyl ether, filtered, and rinsed with diethyl ether. The solid was dried in vacuo to afford a yellow hydrochloride salt of (S)-6-(6-(6-(1-aminobutyl)pyridin-2-yl)-1H-indazol-1-yl)picolinaldehyde. $^1$H NMR (400 MHz, DMSO-d$_6$) δ ppm 10.21 (s, 1H) 9.63-9.88 (m, 1H) 8.63 (br s, 3H) 8.59 (d, J=1.0 Hz, 1H) 8.23-8.37 (m, 3H) 8.16 (dd, J=8.0, 0.8 Hz, 1H) 7.99-8.09 (m, 2H) 7.91 (dd, J=7.2, 1.1 Hz, 1H) 7.52-7.62 (m, 1H) 6.15 (br d, J=12.0 Hz, 3H) 4.44-4.57 (m, 1H) 1.85-2.05 (m, 2H) 1.20-1.43 (m, 2H) 0.86-0.94 (m, 3H). LC/MS(M+H)=372.2.

Example 451 and 452 (R)-1-(6-(6-(6-((S)-1-aminobutyl)pyridin-2-yl)-1H-indazol-1-yl)pyridin-2-yl)-2,2,2-trifluoroethanol and (S)-1-(6-(6-(6-((S)-1-aminobutyl)pyridin-2-yl)-1H-indazol-1-yl)pyridin-2-yl)-2,2,2-trifluoroethanol Step 1. Synthesis of (R)-2-methyl-N—((S)-1-(6-(1-(6-((R)-2,2,2-trifluoro-1-hydroxyethyl)pyridin-2-yl)-1H-indazol-6-yl)pyridin-2-yl)butyl)propane-2-sulfinamide and (R)-2-methyl-N—((S)-1-(6-(1-(6-((S)-2,2,2-trifluoro-1-hydroxyethyl)pyridin-2-yl)-1H-indazol-6-yl)pyridin-2-yl)butyl)propane-2-sulfinamide

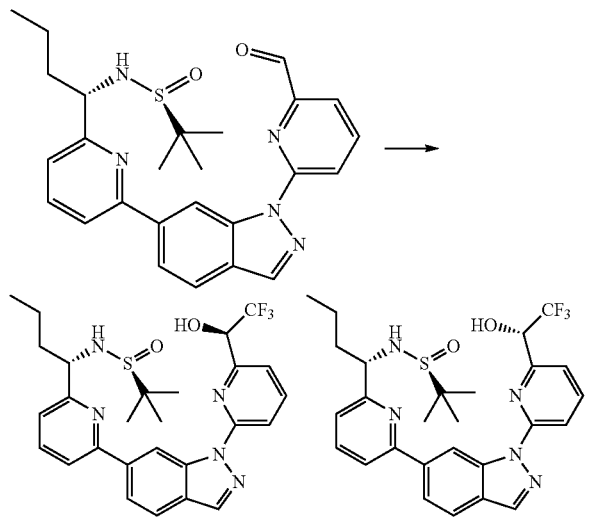

To a solution of (R)—N—((S)-1-(6-(1-(6-formylpyridin-2-yl)-1H-indazol-6-yl)pyridin-2-yl)butyl)-2-methylpropane-2-sulfinamide (Example 450, Step 2, 240 mg, 0.50 mmol) in 2 mL of anhydrous DMF at RT was added (Trifluoromethyl)trimethylsilane (0.100 g, 0.706 mmol) followed by Potassium carbonate (0.0139 g, 0.101 mmol). The reaction was allowed to stir at RT. After 3 h, the reaction was quenched by addition of 3 mL of water. The reaction was diluted with ethyl acetate and washed with sat. NaHCO$_3$ and brine. The reaction was dried over MgSO$_4$, filtered, and concentrated to afford a crude material that was purified using 30-50% ethyl acetate in heptane on a 25 g 30 μM silica gel column to yield (R)-2-methyl-N—((S)-1-(6-(1-(6-((R)-2,2,2-trifluoro-1-hydroxyethyl)pyridin-2-yl)-1H-indazol-6-yl)pyridin-2-yl)butyl)propane-2-sulfinamide and (R)-2-methyl-N—((S)-1-(6-(1-(6-((S)-2,2,2-trifluoro-1-hydroxyethyl)pyridin-2-yl)-1H-indazol-6-yl)pyridin-2-yl)butyl)propane-2-sulfinamide. 75 mg of the first eluting material was obtained (Yield=27%). 55 mg of the second eluting material was obtained (Yield=21%). Data for 1$^{st}$ eluting isomer: $^1$H NMR (400 MHz, CHLOROFORM-d) δ ppm 10.03 (s, 1H) 8.25 (d, J=0.8 Hz, 1H) 8.10 (d, J=8.3 Hz, 1H) 7.93-8.00 (m, 1H) 7.83-7.92 (m, 3H) 7.75-7.82 (m, 1H) 7.48-7.57 (m, 1H) 7.17 (d, J=7.5 Hz, 1H) 6.44 (d, J=7.3 Hz, 1H) 5.21-5.50 (m, 2H) 4.44-4.68 (m, 1H) 4.05-4.06 (m, 1H) 1.97-2.22 (m, 2H) 1.35-1.45 (m, 2H) 1.11 (s, 9H) 0.95 (t, J=7.4 Hz, 3H). Data for 2nd eluting isomer: $^1$H NMR (400 MHz, CHLOROFORM-d) δ ppm 9.66 (s, 1H) 8.26 (d, J=0.8 Hz, 1H) 8.13 (d, J=8.0 Hz, 1H) 7.91-8.00 (m, 2H) 7.87 (d, J=8.5 Hz, 1H) 7.72-7.83 (m, 2H) 7.32 (d, J=7.5 Hz, 1H) 7.19 (dd, J=7.0, 1.5 Hz, 1H) 5.51 (d, J=7.0 Hz, 1H) 5.19-5.31 (m, 1H) 4.47-4.62 (m, 2H) 2.06 (q, J=7.3 Hz, 2H) 1.38-1.49 (m, 1H) 1.29-1.37 (m, 2H) 1.15 (s, 9H) 0.94 (t, J=7.4 Hz, 3H).

Step 2. Synthesis of (R)-1-(6-(6-(6-((S)-1-aminobutyl)pyridin-2-yl)-1H-indazol-1-yl)pyridin-2-yl)-2,2,2-trifluoroethanol (Example 451)

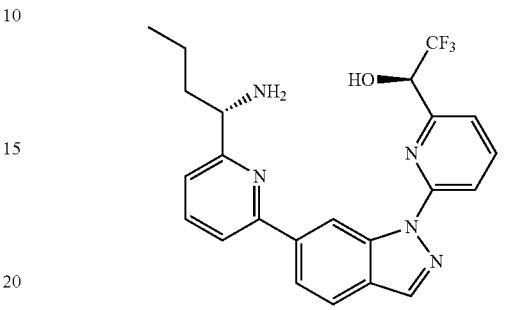

(R)-1-(6-(6-(6-((S)-1-aminobutyl)pyridin-2-yl)-1H-indazol-1-yl)pyridin-2-yl)-2,2,2-trifluoroethanol was obtained as a hydrochloride salt starting from (R)-2-methyl-N—((S)-1-(6-(1-(6-((R)-2,2,2-trifluoro-1-hydroxyethyl)pyridin-2-yl)-1H-indazol-6-yl)pyridin-2-yl)butyl)propane-2-sulfinamide in a similar manner to that described for the synthesis of (S)-6-(6-(6-(1-aminobutyl)pyridin-2-yl)-1H-indazol-1-yl)picolinaldehyde (Example 450). $^1$H NMR (400 MHz, DMSO-d$_6$) δ ppm 9.35-9.63 (m, 1H) 8.55 (d, J=0.8 Hz, 1H) 8.48 (br s, 3H) 8.32 (dd, J=8.3, 1.5 Hz, 1H) 8.10-8.22 (m, 1H) 8.03-8.09 (m, 4H) 7.60 (d, J=7.0 Hz, 1H) 7.51-7.58 (m, 1H) 5.45 (q, J=7.5 Hz, 1H) 4.67 (br s, 4H) 4.40-4.53 (m, 1H) 1.84-1.98 (m, 2H) 1.21-1.44 (m, 2H) 0.86-0.95 (m, 3H). LC/MS (M+H)=442.2.

Step 2. Synthesis of (S)-1-(6-(6-(6-((S)-1-aminobutyl)pyridin-2-yl)-1H-indazol-1-yl)pyridin-2-yl)-2,2,2-trifluoroethanol (Example 452)

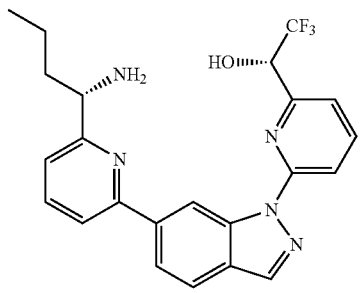 [SMILES: CCC[C@H](N)c1cccc(-c2ccc3cnn(-c4cccc([C@H](O)C(F)(F)F)n4)c3c2)n1]

(S)-1-(6-(6-(6-((S)-1-aminobutyl)pyridin-2-yl)-1H-indazol-1-yl)pyridin-2-yl)-2,2,2-trifluoroethanol was obtained as a hydrochloride salt starting from (R)-2-methyl-N—((S)-1-(6-(1-(6-((S)-2,2,2-trifluoro-1-hydroxyethyl)pyridin-2-yl)-1H-indazol-6-yl)pyridin-2-yl)butyl)propane-2-sulfinamide in a similar manner to that described for the synthesis of (S)-6-(6-(6-(1-aminobutyl)pyridin-2-yl)-1H-indazol-1-yl)picolinaldehyde (Example 450). $^1$H NMR (400 MHz, DMSO-d$_6$) δ ppm 9.16-9.76 (m, 1H) 8.54 (d, J=0.8 Hz, 1H) 8.46 (br s, 3H) 8.29 (dd, J=8.3, 1.5 Hz, 1H) 8.10-8.17 (m, 1H) 8.00-8.09 (m, 4H) 7.60 (d, J=7.3 Hz, 1H) 7.47-7.57 (m, 1H) 5.47 (q, J=7.8 Hz, 1H) 4.58-4.89 (m, 4H) 4.48 (br d, J=6.8 Hz, 1H) 1.87-1.98 (m, 2H) 1.21-1.44 (m, 2H) 0.86-0.94 (m, 3H). LC/MS (M+H)=442.2.

Example 453 (6-(6-(6-(((1R,2R)-1-amino-2-fluorobutyl)pyridin-2-yl)-4-(2-methoxyethoxy)-1H-indazol-1-yl)pyridin-2-yl)methanol Step 1. Synthesis of 6-bromo-1-(6-(((tert-butyldimethylsilyl)oxy)methyl)pyridin-2-yl)-4-(2-methoxyethoxy)-1H-indazole

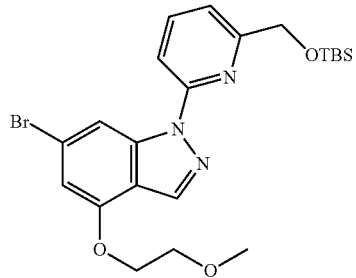 [SMILES: COCCOc1cc(Br)cc2c1cnn2-c1cccc(CO[Si](C)(C)C(C)(C)C)n1]

Triphenylphosphine (4.2 g, 16 mmol) was added to a solution of 6-bromo-1-[6-(tert-butyl-dimethyl-silanyloxymethyl)-pyridin-2-yl]-1H-indazol-4-ol (Example 426, Step 4, 5.0 g, 12 mmol) and 2-methoxyethanol (1.3 mL, 16 mol) in dry tetrahydrofuran (100 mL). The mixture was cooled in an ice/water bath and diisopropyl azodicarboxylate (3.2 mL, 16 mol) was slowly added. The reaction was then stirred at rt for 1 h. The mixture was diluted with EtOAc, washed with brine. The organic phase was separated, dried over MgSO₄, and concentrated. The crude was purified by ISCO (0-20%, ethyl acetate in heptane gradient) to give the title compound as a white solid (4.8 g). LCMS: RT 2.67 min; MH+ 491.9 & 493.9; ¹H NMR (400 MHz, CHLOROFORM-d) δ 8.59 (s, 1H), 8.24 (s, 1H), 7.87 (s, 2H), 7.34-7.43 (m, 1H), 6.75 (d, J=0.75 Hz, 1H), 4.93 (s, 2H), 4.29 (d, J=4.77 Hz, 2H), 3.82-3.92 (m, 2H), 3.51 (s, 3H), 1.01 (s, 9H), 0.20 (s, 6H).

Step 2. Synthesis of 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole

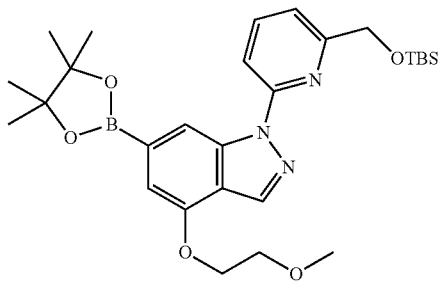 [SMILES: COCCOc1cc(B2OC(C)(C)C(C)(C)O2)cc2c1cnn2-c1cccc(CO[Si](C)(C)C(C)(C)C)n1]

To a mixture of 6-bromo-1-[6-(tert-butyl-dimethyl-silanyloxymethyl)-pyridin-2-yl]-4-(2-methoxy-ethoxy)-1H-indazole (5.0 g, 10 mmol), potassium acetate (3.0 g, 30 mmol) in 1,4-dioxane (60 mL) under nitrogen was added [1,1'-bis(diphenylphosphino)ferrocene]dichloropalladium(II), complex with dichloromethane (1:1) (0.41 g, 0.5 mmol) and bis(pinacolato)diboron (3.9 g, 15 mmol). The reaction was heated at 90° C. for 6 hours. The reaction was cooled to room temperature and diluted with ethyl acetate, and then filtered through celite. The filtrate was concentrated, and purified by ISCO (0% to 50% EtOAc/heptane gradient) to give the title compound as a white solid (5.1 g). LCMS: RT 2.71 min.; MH+ 540.1; ¹H NMR (400 MHz, CHLOROFORM-d) δ 8.76 (s, 1H), 8.31 (s, 1H), 7.79-7.89 (m, 2H), 7.39 (dd, J=3.14, 5.40 Hz, 1H), 6.99 (s, 1H), 4.98 (s, 2H), 4.34-4.44 (m, 2H), 3.83-3.93 (m, 2H), 3.51 (s, 3H), 1.39 (s, 12H), 1.01 (s, 9H), 0.19 (s, 6H).

Step 3. Synthesis of (R)—N—((1R,2R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide

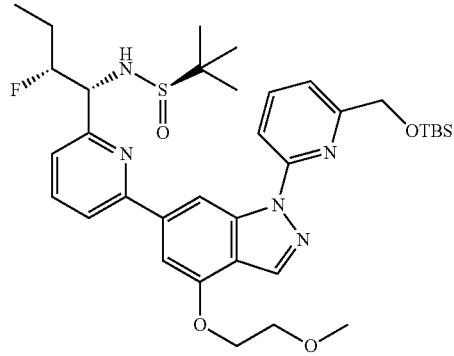 [SMILES: CC[C@@H](F)[C@H](N[S@](=O)C(C)(C)C)c1cccc(-c2cc(OCCOC)c3cnn(-c4cccc(CO[Si](C)(C)C(C)(C)C)n4)c3c2)n1]

To a mixture of 1-[6-(tert-butyl-dimethyl-silanyloxymethyl)-pyridin-2-yl]-4-(3-methoxy-propoxy)-6-(4,4,5,5-tetramethyl-1,3,2-dioxaborolan-2-yl)-1H-indazole (100 mg, 0.18 mmol) and 2-Methyl-propane-2-sulfinic acid [(S)-1-(6-bromo-pyridin-2-yl)-butyl]-amide (prepared similar to (R)—N—((1R,2S)-1-(6-bromopyridin-2-yl)-2-fluorobutyl)-2-methylpropane-2-sulfinamide (Example 442, step 3), 90 mg, 0.27 mmol) in 1,4-dioxane (2.0 mL) under nitrogen was added 1,1'-bis(diphenylphosphino)ferrocene-palladium(ii) dichloride dichloromethane complex (15 mg, 0.018 mmol) and a solution of potassium carbonate (50 mg, 0.36 mmol) in water (0.5 mL). The reaction was heated at 90° C. for 2 hours. Cooled to room temperature and diluted with ethyl acetate and washed with brine. The organic layer was separated, dried over MgSO₄, filtered, and concentrated. The crude was purified using ISCO (0% to 30% ethyl acetate in heptane gradient) to give the title compound as an oil: LCMS: RT 2.48 min; MH+ 680.1. The compound was used in the next step without further purifications.

Step 4. Synthesis of (6-(6-(6-(((1R,2R)-1-amino-2-fluorobutyl)pyridin-2-yl)-4-(2-methoxyethoxy)-1H-indazol-1-yl)pyridin-2-yl)methanol (Example 453)

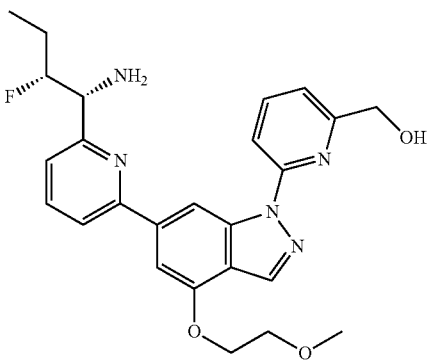 [SMILES: CC[C@@H](F)[C@H](N)c1cccc(-c2cc(OCCOC)c3cnn(-c4cccc(CO)n4)c3c2)n1]

(R)—N-((1R,2R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluorobutyl)-2-methylpropane-2-sulfinamide was then dissolved in methylene chloride (2.0 mL). 4 M of hydrogen chloride in 1,4-dioxane (0.9 mL, 3.6 mmol) was then added. The reaction stirred at rt for 1 h. Remove the solvent, the residue was purified by HPLC to give the title compound as a TFA salt (42 mg). LCMS: RT 1.22 min.; MH+ 462.0; $^1$H NMR (400 MHz, METHANOL-d4) d 9.27 (s, 1H), 8.32 (s, 1H), 8.03-8.10 (m, 1H), 7.90-8.02 (m, 3H), 7.54 (s, 1H), 7.43 (d, J=7.53 Hz, 1H), 7.36 (dd, J=2.13, 6.15 Hz, 1H), 4.86 (br. s., 2H), 4.54 (t, J=7.03 Hz, 1H), 4.43 (t, J=6.15 Hz, 2H), 3.70 (t, J=6.15 Hz, 2H), 3.40 (s, 3H), 2.21 (quin, J=6.21 Hz, 2H), 1.90-2.14 (m, 2H), 1.32-1.56 (m, 2H), 1.02 (t, J=7.40 Hz, 3H).

Example 454 Synthesis of (6-(6-(6-((1R,2S)-1-amino-2-fluorobutyl)pyridin-2-yl)-4-(2-methoxyethoxy)-1H-indazol-1-yl)pyridin-2-yl)methanol

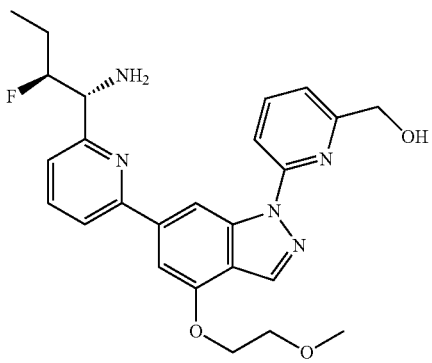 [SMILES: CC[C@H](F)[C@H](N)c1cccc(-c2cc(OCCOC)c3cnn(-c4cccc(CO)n4)c3c2)n1]

The same procedure described in (6-(6-(6-((1R,2R)-1-amino-2-fluorobutyl)pyridin-2-yl)-4-(2-methoxyethoxy)-1H-indazol-1-yl)pyridin-2-yl)methanol (Example 453) was used in synthesizing the title compound from 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2) and (R)—N—((1R,2S)-1-(6-bromopyridin-2-yl)-2-fluorobutyl)-2-methylpropane-2-sulfinamide (Example 442/443, Step 3) gave (6-(6-(6-((1R,2S)-1-amino-2-fluorobutyl)pyridin-2-yl)-4-(2-methoxyethoxy)-1H-indazol-1-yl)pyridin-2-yl)methanol as a TFA salt (68 mg, 78%). LCMS: RT 1.12 min.; MH+ 466.1; 1H NMR (400 MHz, METHANOL-d4) d 9.27 (s, 1H), 8.35 (s, 1H), 8.11 (d, J=7.78 Hz, 1H), 7.99-8.06 (m, 1H), 7.90-7.99 (m, 2H), 7.45-7.59 (m, 2H), 7.36 (dd, J=2.13, 6.15 Hz, 1H), 4.88-5.08 (m, 2H), 4.86-4.88 (m, 2H), 4.41-4.56 (m, 2H), 3.93 (dd, J=3.76, 5.27 Hz, 2H), 3.49-3.56 (m, 3H), 1.53-1.81 (m, 2H), 1.07 (t, J=7.40 Hz, 3H).

Example 455 (S)-(6-(6-(6-(1-amino-3,3-difluorobutyl)pyridin-2-yl)-4-(2-methoxyethoxy)-1H-indazol-1-yl)pyridin-2-yl)methanol

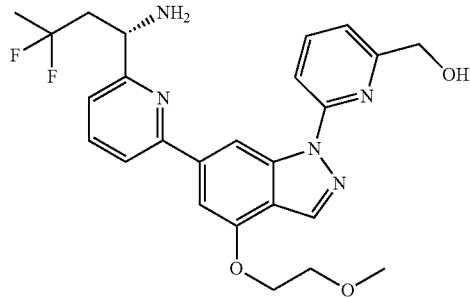 [SMILES: COCCOc1cc(-c2cccc([C@@H](N)CC(C)(F)F)n2)cc2c1cnn2-c1cccc(CO)n1]

The same procedure described in (6-(6-(6-((1R,2R)-1-amino-2-fluorobutyl)pyridin-2-yl)-4-(2-methoxyethoxy)-1H-indazol-1-yl)pyridin-2-yl)methanol (Example 453) was used in synthesizing the title compound from 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2) and (R)—N—((S)-1-(6-bromopyridin-2-yl)-3,3-difluorobutyl)-2-methylpropane-2-sulfinamide (Example 437, Step 7) gave (S)-(6-(6-(6-(1-amino-3,3-difluorobutyl)pyridin-2-yl)-4-(2-methoxyethoxy)-1H-indazol-1-yl)pyridin-2-yl)methanol as a TFA salt (73 mg, 69%). LCMS: RT 1.11 min.; MH+ 484.0; $^1$H NMR (400 MHz, METHANOL-d4) δ 9.28 (s, 1H), 8.34 (s, 1H), 8.05-8.13 (m, 1H), 7.89-8.05 (m, 3H), 7.57 (s, 1H), 7.50 (d, J=7.53 Hz, 1H), 7.36 (dd, J=1.76, 6.27 Hz, 1H), 4.92 (dd, J=5.52, 7.78 Hz, 1H), 4.86 (br. s., 2H), 4.40-4.55 (m, 2H), 3.93 (dd, J=3.76, 5.27 Hz, 2H), 3.52 (s, 3H), 2.58-2.94 (m, 2H), 1.74 (t, J=18.95 Hz, 3H).

Example 456 (S)-(6-(6-(6-(1-aminobutyl)pyridin-2-yl)-4-(3-methoxypropoxy)-1H-indazol-1-yl)pyridin-2-yl)methanol Step 1. Synthesis of 6-bromo-1-(6-(((tert-butyldimethylsilyl)oxy)methyl)pyridin-2-yl)-4-(3-methoxypropoxy)-1H-indazole

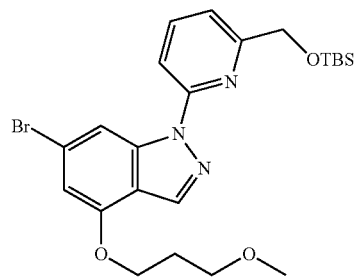 [SMILES: COCCCOc1cc(Br)cc2c1cnn2-c1cccc(CO[Si](C)(C)C(C)(C)C)n1]

The same procedure described in 6-bromo-1-(6-(((tert-butyldimethylsilyl)oxy)methyl)pyridin-2-yl)-4-(2-methoxyethoxy)-1H-indazole (Example 453) was used in synthesizing the title compound from 6-bromo-1-(6-(((tert-butyldimethylsilyl)oxy)methyl)pyridin-2-yl)-1H-indazol-4-ol (Example 426, Step 4) and 3-methoxy-propan-1-ol (CAS No. 1589-49-7) gave 6-bromo-1-(6-((((tert-butyldimethylsilyl)oxy)methyl)pyridin-2-yl)-4-(3-methoxy-propoxy)-1H-indazole as a white solid (1.4 g, 92%). LCMS: RT 2.88 min; MH+ 505.9 & 507.9; ¹H NMR (400 MHz, CHLOROFORM-d) δ 8.57 (s, 1H), 8.20 (s, 1H), 7.78-7.94 (m, 2H), 7.38 (d, J=6.78 Hz, 1H), 6.77 (d, J=1.00 Hz, 1H), 4.93 (s, 2H), 4.24 (t, J=6.27 Hz, 2H), 3.62 (t, J=6.02 Hz, 2H), 3.39 (s, 3H), 2.17 (quin, J=6.21 Hz, 2H), 1.01 (s, 9H), 0.20 (s, 6H).

Step 2. Synthesis of 1-(6-(((tert-butyldimethylsilyl)oxy)methyl)pyridin-2-yl)-4-(3-methoxypropoxy)-6-(4,4,5,5-tetramethyl-1,3,2-dioxaborolan-2-yl)-1H-indazole

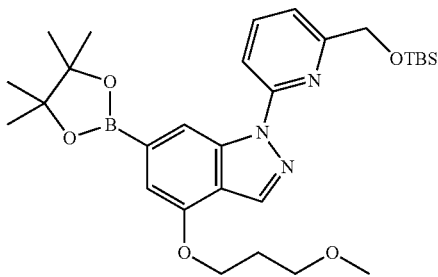 [SMILES: COCCCOc1cc(B2OC(C)(C)C(C)(C)O2)cc2c1cnn2-c1cccc(CO[Si](C)(C)C(C)(C)C)n1]

The same procedure described in 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2) was used in synthesizing the title compound from 6-bromo-1-(6-(((tert-butyldimethylsilyl)oxy)methyl)pyridin-2-yl)-4-(3-methoxy-propoxy)-1H-indazole (see Example 456, step 1) gave 1-(6-(((tert-butyldimethylsilyl)oxy)methyl)pyridin-2-yl)-4-(3-methoxypropoxy)-6-(4,4,5,5-tetramethyl-1,3,2-dioxaborolan-2-yl)-1H-indazole as a white solid (0.51 g, 52%). LCMS: RT 2.77 min.; MH+ 554.4; ¹H NMR (400 MHz, CHLOROFORM-d) δ 8.73 (s, 1H), 8.27 (s, 1H), 7.78-7.91 (m, 2H), 7.35-7.45 (m, 1H), 7.01 (s, 1H), 4.99 (s, 2H), 4.31 (t, J=6.15 Hz, 2H), 3.64 (t, J=6.15 Hz, 2H), 3.39 (s, 3H), 2.18 (quin, J=6.21 Hz, 2H), 1.39 (s, 12H), 1.01 (s, 9H), 0.19 (s, 6H).

Synthesis of Step 3 (S)-(6-(6-(6-(1-aminobutyl)pyridin-2-yl)-4-(3-methoxypropoxy)-1H-indazol-1-yl)pyridin-2-yl)methanol (Example 456)

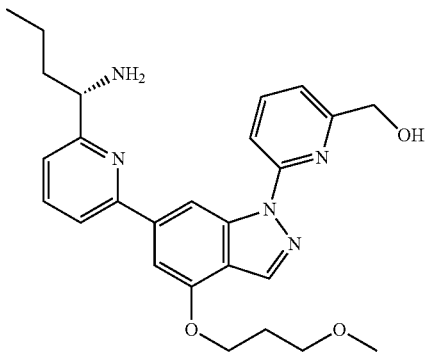 [SMILES: CCC[C@H](N)c1cccc(-c2cc(OCCCOC)c3cnn(-c4cccc(CO)n4)c3c2)n1]

To a mixture of 1-[6-(tert-Butyl-dimethyl-silanyloxymethyl)-pyridin-2-yl]-4-(3-methoxy-propoxy)-6-(4,4,5,5-tetramethyl-1,3,2-dioxaborolan-2-yl)-1H-indazole (100 mg, 0.18 mmol) and 2-methyl-propane-2-sulfinic acid [(S)-1-(6-bromo-pyridin-2-yl)-butyl]-amide (See Example 145, 90 mg, 0.27 mmol) in 1,4-dioxane (2.0 mL) under nitrogen was added 1,1'-bis(diphenylphosphino)ferrocene-palladium(ii) dichloride dichloromethane complex (15 mg, 0.018 mmol) and a solution of potassium carbonate (50 mg, 0.3613 mmol) in water (0.5 mL). The reaction was heated at 90° C. for 2 h. The reaction mixture was cooled to room temperature, and diluted with ethyl acetate, washed with brine. The organic layer was separated, dried over MgSO₄, filtered, and concentrated. The crude was purified using ISCO (0% to 30% ethyl acetate in heptane gradient) to give (R)—N—((S)-1-(6-(1-(6-(((tert-butyldimethylsilyl)oxy)methyl)pyridin-2-yl)-4-(3-methoxypropoxy)-1H-indazol-6-yl)pyridin-2-yl)butyl)-2-methylpropane-2-sulfinamide as an oil (LCMS: RT 2.48 min; MH+ 680.1) which was then dissolved in methylene chloride (2.0 mL, 31 mmol). 4 M of hydrogen chloride in 1,4-dioxane (0.9 mL, 3.6 mmol) was then added. The reaction stirred at RT for 1 h. Remove the solvent, the crude was purified by HPLC to give compound (S)-(6-(6-(6-(1-aminobutyl)pyridin-2-yl)-4-(3-methoxypropoxy)-1H-indazol-1-yl)pyridin-2-yl)methanol as a TFA salt (42 mg). LCMS: RT 1.22 min.; MH+ 462.0; ¹H NMR (400 MHz, METHANOL-d4) δ 9.27 (s, 1H), 8.32 (s, 1H), 8.03-8.10 (m, 1H), 7.90-8.02 (m, 3H), 7.54 (s, 1H), 7.43 (d, J=7.53 Hz, 1H), 7.36 (dd, J=2.13, 6.15 Hz, 1H), 4.86 (br. s., 2H), 4.54 (t, J=7.03 Hz, 1H), 4.43 (t, J=6.15 Hz, 2H), 3.70 (t, J=6.15 Hz, 2H), 3.40 (s, 3H), 2.21 (quin, J=6.21 Hz, 2H), 1.90-2.14 (m, 2H), 1.32-1.56 (m, 2H), 1.02 (t, J=7.40 Hz, 3H).

Example 457 (S)-(6-(6-(6-(1-aminopropyl)pyridin-2-yl)-4-(3-methoxypropoxy)-1H-indazol-1-yl)pyridin-2-yl)methanol

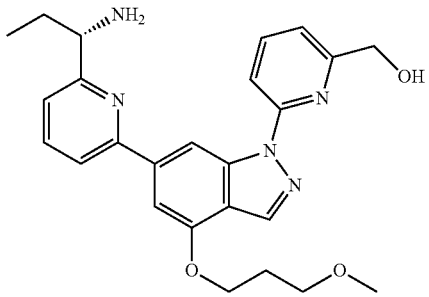 [SMILES: CC[C@H](N)c1cccc(-c2cc(OCCCOC)c3cnn(-c4cccc(CO)n4)c3c2)n1]

The same procedure described in (S)-(6-(6-(6-(1-aminobutyl)pyridin-2-yl)-4-(3-methoxypropoxy)-1H-indazol-1-yl)pyridin-2-yl)methanol (Example 456) was used in synthesizing the title compound from 1-(6-(((tert-butyldimethylsilyl)oxy)methyl)pyridin-2-yl)-4-(3-methoxypropoxy)-6-(4,4,5,5-tetra-methyl-1,3,2-dioxaborolan-2-yl)-1H-indazole (Example 456, step 2) and (R)—N—((S)-1-(6-bromopyridin-2-yl)propyl)-2-methylpropane-2-sulfinamide (similar to Example 145, steps 1-5) gave (S)-(6-(6-(6-(1-aminopropyl)pyridin-2-yl)-4-(3-methoxy-propoxy)-1H-indazol-1-yl)pyridin-2-yl)methanol as TFA salt (48 mg, 59%). LCMS: RT 1.15 min.; MH+ 448.0; ¹H NMR (400 MHz, METHANOL-d4) 9.27 (s, 1H), 8.32 (s, 1H), 8.03-8.10 (m, 1H), 7.90-8.03 (m, 3H), 7.54 (s, 1H), 7.43 (d, J=7.53 Hz, 1H), 7.36 (dd, J=2.13, 6.15 Hz, 1H), 4.86-4.88 (m, 2H), 4.34-4.55 (m, 3H), 3.70 (t, J=6.15 Hz, 2H), 3.40 (s, 3H), 1.99-2.32 (m, 4H), 1.04 (t, J=7.53 Hz, 3H)

Example 458 (S)-(6-(6-(6-(1-aminoethyl)pyridin-2-yl)-4-(3-methoxypropoxy)-1H-indazol-1-yl)pyridin-2-yl)methanol

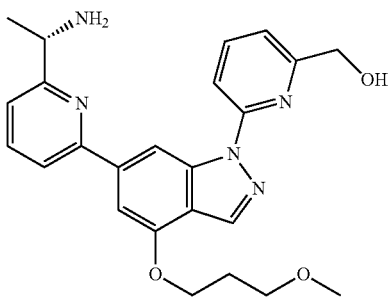 [SMILES: COCCCOc1cc(-c2cccc([C@H](C)N)n2)cc2c1cnn2-c1cccc(CO)n1]

The same procedure described in (S)-(6-(6-(6-(1-aminobutyl)pyridin-2-yl)-4-(3-methoxypropoxy)-1H-indazol-1-yl)pyridin-2-yl)methanol (Example 456) was used in synthesizing the title compound from 1-(6-(((tert-butyldimethylsilyl)oxy)methyl)pyridin-2-yl)-4-(3-methoxypropoxy)-6-(4,4,5,5-tetra-methyl-1,3,2-dioxaborolan-2-yl)-1H-indazole (See Example 456, Step 2) and (R)—N—((S)-1-(6-bromopyridin-2-yl)ethyl)-2-methylpropane-2-sulfinamide (Example 142) gave (S)-(6-(6-(6-(1-aminoethyl)pyridin-2-yl)-4-(3-methoxypropoxy)-1H-indazol-1-yl)pyridin-2-yl)methanol as TFA salt (52 mg, 66%). LCMS: RT 1.09 min.; MH+ 434.0; $^1$H NMR (400 MHz, METHANOL-d4) δ 9.27 (s, 1H), 8.31 (s, 1H), 7.88-8.10 (m, 4H), 7.58 (s, 1H), 7.46 (d, J=7.28 Hz, 1H), 7.36 (dd, J=1.88, 6.15 Hz, 1H), 4.86 (br. s., 2H), 4.70 (q, J=6.78 Hz, 1H), 4.43 (t, J=6.27 Hz, 2H), 3.70 (t, J=6.15 Hz, 2H), 3.40 (s, 3H), 2.21 (quin, J=6.21 Hz, 2H), 1.73 (d, J=6.78 Hz, 3H).

Example 459 (S)-3-((6-(6-(1-aminoethyl)pyridin-2-yl)-1-(6-(hydroxymethyl)pyridin-2-yl)-1H-indazol-4-yl)oxy)propan-1-ol Synthesis of 3-((6-bromo-1-(6-(((tert-butyldimethylsilyl)oxy)methyl)pyridin-2-yl)-1H-indazol-4-yl)oxy)propan-1-ol

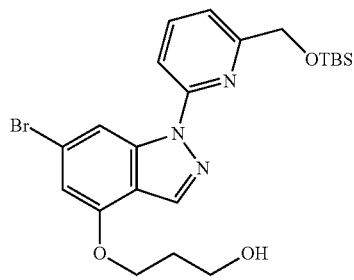 [SMILES: CC(C)(C)[Si](C)(C)OCc1cccc(-n2ncc3c(OCCCO)cc(Br)cc32)n1]

Triphenylphosphine (0.90 g, 3.4 mmol) was added to a solution of 6-bromo-1-[6-(tert-butyl-dimethyl-silanyloxymethyl)-pyridin-2-yl]-1H-indazol-4-ol (Example 426, Step 4, 1.0 g, 2.3 mol) and 1,3-propanediol (0.25 mL, 3.4 mmol) in dry tetrahydrofuran (25 mL). The mixture was cooled in an ice/water bath and diisopropyl azodicarboxylate (0.7 mL, 3.4 mmol) was slowly added. The reaction was then stirred at RT for 1 h. The mixture was diluted with EtOAc, washed with brine. The organic phase was dried over MgSO$_4$, filtered, concentrated. The crude was purified by ISCO (5-100% ethyl acetate in heptane gradient) to give the title compound as a white solid (0.79 g). LCMS: RT 2.45 min; MH+ 491.9; 493.9; $^1$H NMR (400 MHz, DMSO-d6) δ 8.56 (s, 1H), 8.40 (s, 1H), 7.96-8.11 (m, 1H), 7.87 (d, J=8.03 Hz, 1H), 7.37 (d, J=7.28 Hz, 1H), 6.97 (d, J=1.00 Hz, 1H), 4.87 (s, 2H), 4.60 (t, J=5.27 Hz, 1H), 4.28 (t, J=6.27 Hz, 2H), 3.63 (q, J=6.02 Hz, 2H), 1.96 (quin, J=6.21 Hz, 2H), 0.95 (s, 9H), 0.16 (s, 6H).

Synthesis of 3-((1-(6-(((tert-butyldimethylsilyl)oxy)methyl)pyridin-2-yl)-6-(4,4,5,5-tetramethyl-1,3,2-dioxaborolan-2-1)-1H-indazol-4-yl)oxy)propan-1-ol

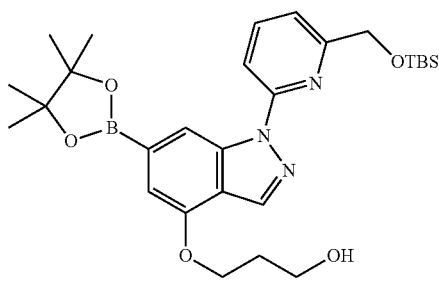 [SMILES: CC1(C)OB(c2cc(OCCCO)c3cnn(-c4cccc(CO[Si](C)(C)C(C)(C)C)n4)c3c2)OC1(C)C]

To a mixture of 3-{6-bromo-1-[6-(tert-butyl-dimethyl-silanyloxymethyl)-pyridin-2-yl]-1H-indazol-4-yloxy}-propan-1-ol (690 mg, 1.4 mmol), potassium acetate (413 mg, 4.2 mmol) in 1,4-dioxane (12 mL) under nitrogen was added [1,1'-bis(diphenylphosphino)ferrocene]dichloro-palladium (II), complex with dichloromethane (1:1) (115 mg, 0.14 mmol), followed by bis(pinacolato)diboron (534 mg, 2.1 mmol). The reaction was heated at 100° C. for 30 min. Cooled down. The reaction was diluted with EtOAc, washed with brine, dried over magnesium sulfate, filtered and concentrated. The crude was purified by ISCO (0-60% EtOAc/heptane gradient) to give the title compound as a white solid (0.68 g). LCMS: RT 2.43 min.; MH+ 540.3; $^1$H NMR (400 MHz, DMSO-d6) 8.74 (s, 1H), 8.40 (s, 1H), 7.96-8.08 (m, 1H), 7.87 (d, J=8.03 Hz, 1H), 7.37 (d, J=7.28 Hz, 1H), 6.93 (s, 1H), 4.86 (s, 2H), 4.60 (t, J=5.15 Hz, 1H), 4.26 (t, J=6.40 Hz, 2H), 3.64 (q, J=6.02 Hz, 2H), 1.99 (quin, J=6.27 Hz, 2H), 1.34 (s, 12H), 0.94 (s, 9H), 0.16 (s, 6H).

Synthesis of (R)—N—((S)-1-(6-(1-(6-(((tert-butyldimethylsilyl)oxy)methyl)pyridin-2-yl)-4-(3-hydroxypropoxy)-1H-indazol-6-yl)pyridin-2-yl)ethyl)-2-methylpropane-2-sulfinamide and (S)-3-((6-(6-(1-aminoethyl)pyridin-2-yl)-1-(6-(hydroxymethyl)pyridin-2-yl)-1H-indazol-4-yl)oxy)propan-1-ol (Example 459)

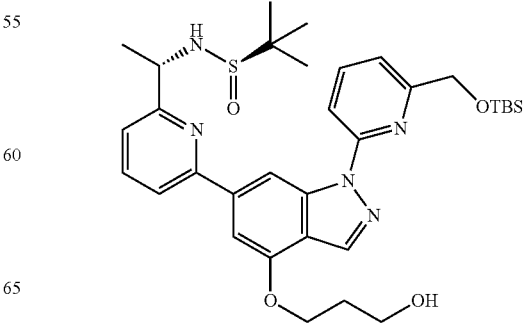

-continued

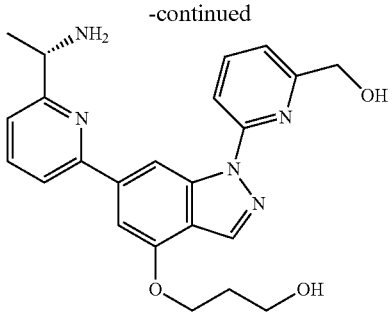

To a mixture of 3-[1-[6-(tert-butyl-dimethyl-silanyloxymethyl)-pyridin-2-yl]-6-(4,4,5,5-tetramethyl-1,3,2-dioxaborolan-2-yl)-1H-indazol-4-yloxy]-propan-1-ol (120.0 mg, 0.20 mmol) and (R)—N—((S)-1-(6-bromopyridin-2-yl)ethyl)-2-methylpropane-2-sulfinamide (Example 142, 91 mg, 0.30 mmol) in 1,4-dioxane (2.0 mL) under nitrogen was added 1,1'-bis(diphenylphosphino)ferrocene-palladium(ii) dichloride dichloromethane complex (16 mg, 0.02 mmol), followed by a solution of potassium carbonate (55 mg, 0.40 mmol) in water (0.5 mL). The reaction was heated at 90° C. for 2 h. Cooled to room temperature. The reaction was diluted with ethyl acetate, and washed with brine. The organic layer was separated, dried over MgSO$_4$, filtered, and concentrated. The crude was purified by HPLC to give (R)—N—((S)-1-(6-(1-(6-(((tert-butyldimethylsilyl)oxy)methyl)pyridin-2-yl)-4-(3-hydroxypropoxy)-1H-indazol-6-yl)pyridin-2-yl)ethyl)-2-methylpropane-2-sulfinamide (7.3) as an oil (LCMS: RT 2.08 min; MH+ 638.3) which was then dissolved in methylene chloride (2.0 mL). 4 M of hydrogen chloride in 1,4-dioxane (1.0 mL, 4.0 mmol) was then added. The reaction stirred at RT for 1 h. Remove the solvent, the crude was purified by HPLC to give the title compound as a TFA salt (42 mg). LCMS: RT 0.95 min.; MH+ 420.0; $^1$H NMR (400 MHz, DMSO-d6) δ 9.15-9.25 (m, 1H), 8.44 (s, 4H), 7.96-8.17 (m, 3H), 7.88 (d, J=8.03 Hz, 1H), 7.64 (s, 1H), 7.54 (d, J=7.53 Hz, 1H), 7.42 (d, J=7.53 Hz, 1H), 4.78 (s, 2H), 4.69 (td, J=6.21, 8.91 Hz, 1H), 4.35-4.52 (m, 2H), 3.70 (t, J=6.15 Hz, 2H), 2.04 (quin, J=6.15 Hz, 2H), 1.62 (d, J=6.78 Hz, 3H).

Example 460 (S)-3-((6-(6-(1-aminobutyl)pyridin-2-yl)-1-(6-(hydroxymethyl)pyridin-2-yl)-1H-indazol-4-yl)oxy)propan-1-ol

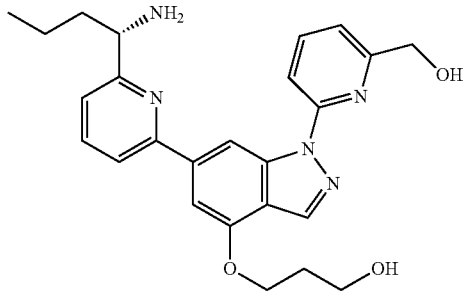 [SMILES: CCC[C@H](N)c1cccc(-c2cc(OCCCO)c3cnn(-c4cccc(CO)n4)c3c2)n1]

The same procedure described in (S)-3-((6-(6-(1-aminoethyl)pyridin-2-yl)-1-(6-(hydroxymethyl)pyridin-2-yl)-1H-indazol-4-yl)oxy)propan-1-ol (Example 459) was used in synthesizing the title compound from 3-((1-(6-(((tert-butyldimethylsilyl)oxy)methyl)pyridin-2-yl)-6-(4,4,5,5-tetramethyl-1,3,2-dioxaboro-lan-2-yl)-1H-indazol-4-yl)oxy)propan-1-ol (See Example 459, step 2) and (R)—N—((S)-1-(6-bromopyridin-2-yl)butyl)-2-methyl-propane-2-sulfinamide (see Example 145, step 5) gave (S)-3-((6-(6-(1-aminobutyl)pyridin-2-yl)-1-(6-(hydroxymethyl)pyridin-2-yl)-1H-indazol-4-yl)oxy)propan-1-ol as TFA salt (32 mg, 36%). LCMS: RT 1.07 min.; MH+ 448.0; $^1$H NMR (400 MHz, DMSO-d6) δ 9.12-9.21 (m, 1H), 8.28-8.54 (m, 4H), 7.97-8.14 (m, 3H), 7.88 (d, J=8.03 Hz, 1H), 7.60 (s, 1H), 7.51 (d, J=7.28 Hz, 1H), 7.42 (d, J=7.53 Hz, 1H), 4.77 (s, 2H), 4.34-4.61 (m, 3H), 3.45-3.76 (m, 3H), 1.83-2.12 (m, 4H), 1.19-1.45 (m, 2H), 0.92 (t, J=7.28 Hz, 3H).

Example 461 (S)-3-((6-(6-(1-aminopropyl)pyridin-2-yl)-1-(6-(hydroxymethyl)pyridin-2-yl)-1H-indazol-4-yl)oxy)propan-1-ol

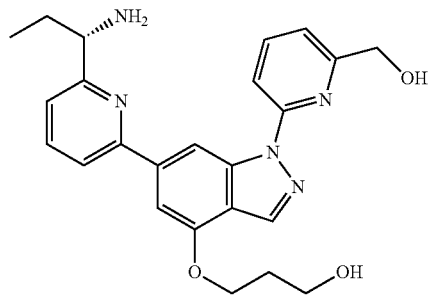 [SMILES: CC[C@H](N)c1cccc(-c2cc(OCCCO)c3cnn(-c4cccc(CO)n4)c3c2)n1]

The same procedure described in (S)-3-((6-(6-(1-aminoethyl)pyridin-2-yl)-1-(6-(hydroxymethyl)pyridin-2-yl)-1H-indazol-4-yl)oxy)propan-1-ol (Example 459) was used in synthesizing the title compound from 3-((1-(6-(((tert-butyldimethylsilyl)oxy)methyl)pyridin-2-yl)-6-(4,4,5,5-tetramethyl-1,3,2-dioxaboro-lan-2-yl)-1H-indazol-4-yl)oxy)propan-1-ol (See Example 459, step 2) and (R)—N—((S)-1-(6-bromopyridin-2-yl)propyl)-2-methylpropane-2-sulfinamide (see Example 145, steps 1-5) gave (S)-3-((6-(6-(1-aminopropyl)pyridin-2-yl)-1-(6-(hydroxymethyl)-pyridin-2-yl)-1H-indazol-4-yl)oxy)propan-1-ol as TFA salt (36 mg, 41%). LCMS: RT 1.00 min.; MH+ 434.0; $^1$H NMR (400 MHz, DMSO-d6) δ 9.16 (s, 1H), 8.32-8.52 (m, 4H), 7.95-8.15 (m, 3H), 7.88 (d, J=8.03 Hz, 1H), 7.60 (s, 1H), 7.51 (d, J=7.28 Hz, 1H), 7.42 (d, J=7.53 Hz, 1H), 4.64-4.86 (m, 2H), 4.34-4.57 (m, 3H), 3.70 (t, J=6.15 Hz, 3H), 1.90-2.15 (m, 4H), 0.92 (t, J=7.40 Hz, 3H).

Example 462. (S)-4-(6-(6-(1-aminobutyl)pyridin-2-yl)-1-(6-(hydroxymethyl)pyridin-2-yl)-1H-indazol-4-yl)-2-methylbut-3-yn-2-ol Synthesis of (R)—N—((S)-1-(6-(1-(6-(((tert-butyldimethylsilyl)oxy)methyl)pyridin-2-yl)-4-(3-hydroxy-3-methylbut-1-yn-1-yl)-1H-indazol-6-yl)pyridin-2-yl)butyl)-2-methylpropane-2-sulfinamide

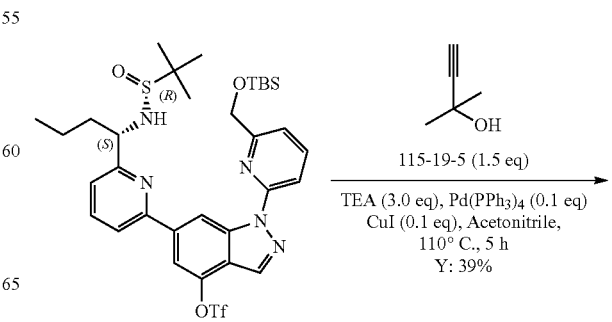

115-19-5 (1.5 eq)

TEA (3.0 eq), Pd(PPh$_3$)$_4$ (0.1 eq)
CuI (0.1 eq), Acetonitrile,
110° C., 5 h
Y: 39%

579

-continued

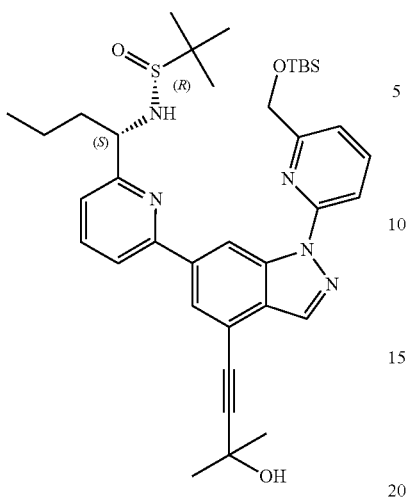

A mixture of 1-(6-(((tert-butyldimethylsilyl)oxy)methyl)pyridin-2-yl)-6-(6-((S)-1-((R)-1,1-dimethylethylsulfinamido)butyl)pyridin-2-yl)-1H-indazol-4-yl trifluoromethanesulfonate (Example 324, Step 14, 1.0 g, 1.35 mmol, 1.0 eq), 2-Methyl-3-butyn-2-ol (CAS No. 115-19-5, 170 mg, 2.03 mmol, 1.5 eq), TEA (412 mg, 4.05 mmol, 3.0 eq), CuI (26 mg, 0.136 mmol, 0.1 eq) and Pd(PPh$_3$)$_4$(156 mg, 0.136 mmol, 0.1 eq) in CH$_3$CN (20 mL) was stirred at 110° C. for 5 h under N$_2$. After concentration, the residue was purified by column (PE/EA=3/1) to give (R)—N—((S)-1-(6-(1-(6-(((tert-butyldimethylsilyl)oxy)methyl)pyridin-2-yl)-4-(3-hydroxy-3-methylbut-1-yn-1-yl)-1H-indazol-6-yl)pyridin-2-yl)butyl)-2-methylpropane-2-sulfinamide as a yellow solid (350 mg, Y: 39%). ESI-MS (M+H)$^+$: 674.3.

Synthesis of (S)-4-(6-(6-(1-aminobutyl)pyridin-2-yl)-1-(6-(hydroxymethyl)pyridin-2-yl)-1H-indazol-4-yl)-2-methylbut-3-yn-2-ol

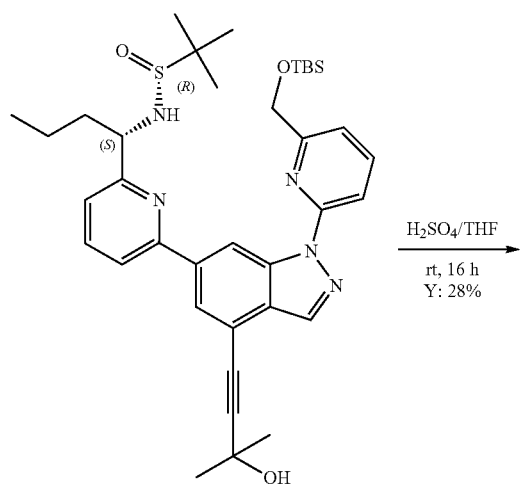

H$_2$SO$_4$/THF rt, 16 h
Y: 28%

580

-continued

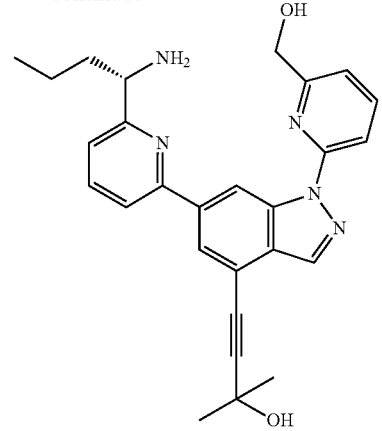

A mixture of (R)—N—((S)-1-(6-(1-(6-(((tert-butyldimethylsilyl)oxy)methyl)pyridin-2-yl)-4-(3-hydroxy-3-methylbut-1-yn-1-yl)-1H-indazol-6-yl)pyridin-2-yl)butyl)-2-methylpropane-2-sulfinamide (350 mg, 0.52 mmol, 1.0 eq) in H$_2$SO$_4$/THF (0.5 mL/10 mL) was stirred at rt for 16 h. The mixture was diluted with water (30 mL), adjusted to pH=7 with saturated NaHCO$_3$ solution and extracted with DCM (10 mL×3). The combined organic layers were concentrated and purified by pre-HPLC (0.05% TFA in H$_2$O/ACN from 5%-95%) to afford (S)-4-(6-(6-(1-aminobutyl)pyridin-2-yl)-1-dimet(6-(hydroxymethyl)pyridin-2-yl)-H-indazol-4-yl)-2-methylbut-3-yn-2-ol)-H-ind. 67 mg, as a brown solid, Y: 28-yl)butyl. ES-MS (M+H)ylpro: 456.2. HPLC: 100%. $^1$H NMR (400 MHz, CD$_3$OD) δ: 9.24 (s, 1H), 8.43 (s, 1H), 8.12-8.07 (m, 2H), 8.03-1.98 (m, 2H), 7.92 (t, J=7.6 Hz, 1H), 7.53 (d, J=7.2 Hz, H), 7.37 (d, J=7.6 Hz, H), 4.77 (s, 2H), 4.48 (t, J=7.2 Hz, H), 1.99-1.92 (m, 2H), 1.63 (s, 6H), 1.41-1.32 (m, 2H), 0.95 (t, J=7.2 Hz, 3H).

Example 463

Synthesis of (R)—N—((S)-1-(6-(1-(6-(((tert-butyldimethylsilyl)oxy)methyl)pyridin-2-yl)-4-methoxy-1H-indazol-6-yl)pyridin-2-yl)butyl)-2-methylpropane-2-sulfinamide

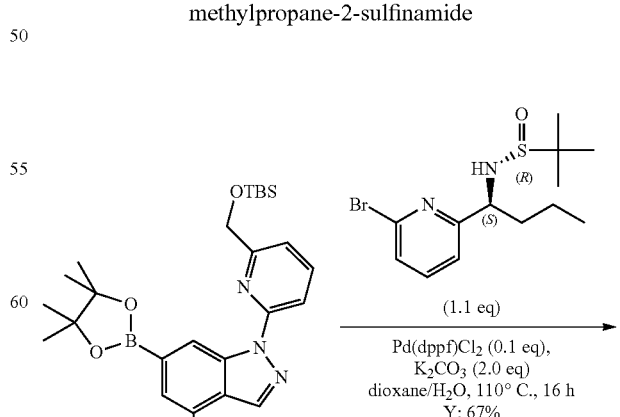

(1.1 eq)

Pd(dppf)Cl$_2$ (0.1 eq),
K$_2$CO$_3$ (2.0 eq)
dioxane/H$_2$O, 110° C., 16 h
Y: 67%

581
-continued

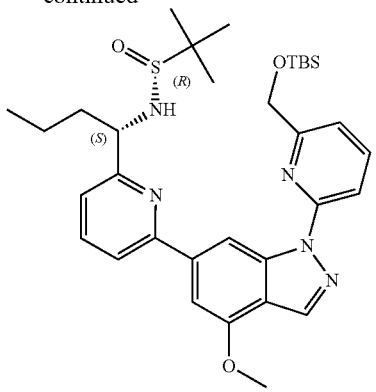

The preparation of (R)—N—((S)-1-(6-(1-(6-(((tert-butyldimethylsilyl)oxy)methyl)pyridin-2-yl)-4-methoxy-1H-indazol-6-yl)pyridin-2-yl)butyl)-2-methylpropane-2-sulfinamide was similar to that of (R)—N—((1R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide (Example 433/434, Step 4) to give 240 mg as a yellow solid, Y: 67%, ESI-MS (M+H)⁺: 622.1. ¹H NMR (400 MHz, CDCl₃) δ: 8.84 (s, 1H), 8.22 (s, 1H), 7.83-7.79 (m, 2H), 7.71-7.69 (m, 2H), 7.40 (s, 1H), 7.33 (d, J=7.2 Hz, 1H), 7.17-7.15 (m, 1H), 4.95 (s, 2H), 4.52-4.51 (m, 1H), 4.15 (d, J=6.4 Hz, 1H), 4.01 (s, 3H), 3.44-3.40 (m, 2H), 1.97-1.93 (m, 2H), 1.13 (s, 9H), 0.92 (s, 9H), 0.87 (d, J=6.8 Hz, 3H), 0.10 (s, 6H).

Synthesis of (S)-(6-(6-(6-(1-aminobutyl)pyridin-2-yl)-4-methoxy-1H-indazol-1-yl)pyridin-2-yl)methanol

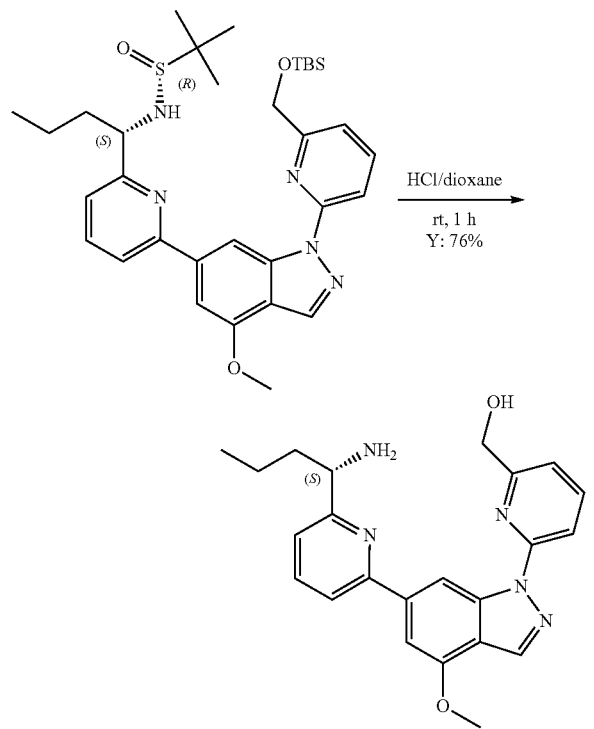

The preparation of (S)-(6-(6-(6-(1-aminobutyl)pyridin-2-yl)-4-methoxy-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 89 mg as a white solid, Y: 76%. ESI-MS (M+H)⁺: 404.2. HPLC: 98%. ¹H NMR (400 MHz, CD₃OD) δ: 9.15 (s, 1H), 8.29 (s, 1H), 7.99-7.87 (m, 4H), 7.46 (s, 1H), 7.41-7.34 (m, 2H), 4.86 (s, 2H), 4.12 (s, 3H), 4.04 (t, J=6.8 Hz, 1H), 1.92-1.81 (m, 2H), 1.46-1.30 (m, 2H), 0.97 (t, J=6.8 Hz, 3H).

Example 464. (S)-(6-(6-(6-(1-aminobutyl)pyridin-2-yl)-4-ethoxy-1H-indazol-1-yl)pyridin-2-yl)methanol Synthesis of (R)—N—((S)-1-(6-(1-(6-(((tert-butyldimethylsilyl)oxy)methyl)pyridin-2-yl)-4-ethoxy-1H-indazol-6-yl)pyridin-2-yl)butyl)-2-methylpropane-2-sulfinamide

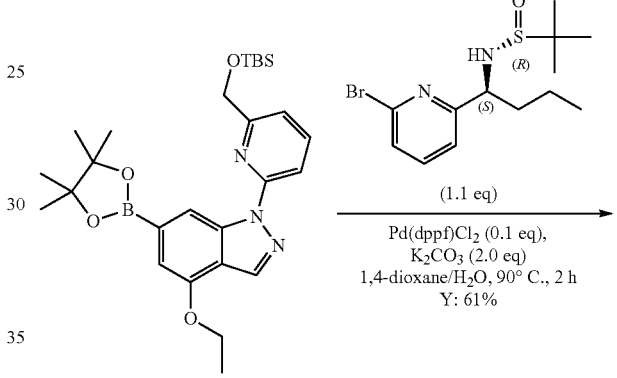

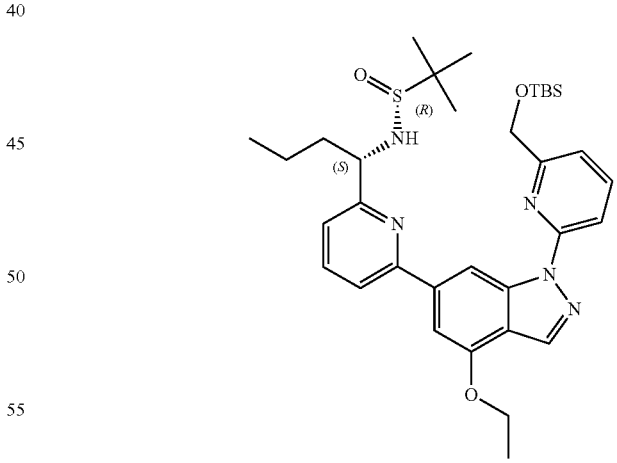

The preparation of (R)—N—((S)-1-(6-(1-(6-(((tert-butyldimethylsilyl)oxy)methyl)pyridin-2-yl)-4-ethoxy-1H-indazol-6-yl)pyridin-2-yl)butyl)-2-methylpropane-2-sulfinamide was similar to that of (R)—N—((1R)-1-(6-(1-(6-(((tert-butyldimethylsilyl)oxy)methyl)pyridin-2-yl)-4-(2-methoxyethoxy)-1H-indazol-6-yl)pyridin-2-yl)-2-fluoropropyl)-2-methylpropane-2-sulfinamide (Example 433/434, Step 4) to give 230 mg as a white solid, Y: 61%. ESI-MS (M+H)⁺: 636.3.

Synthesis of (S)-(6-(6-(6-(1-aminobutyl)pyridin-2-yl)-4-ethoxy-1H-indazol-1-yl)pyridin-2-yl)methanol

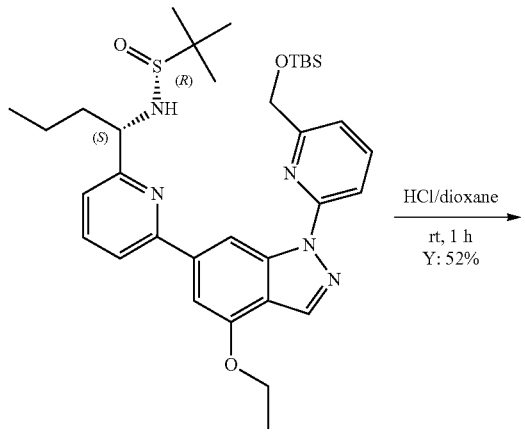

The preparation of (S)-(6-(6-(6-(1-aminobutyl)pyridin-2-yl)-4-ethoxy-1H-indazol-1-yl)pyridin-2-yl)methanol was similar to that of (S)-(6-(6-(4-(1-aminobutyl)pyridin-2-yl)-1H-indazol-1-yl)pyridin-2-yl)methanol (Example 404, Step 6) to give 79 mg as a white solid, Y: 52%. ESI-MS (M+H)⁺: 418.2. HPLC: 100%. ¹H NMR (400 MHz, CD₃OD) δ: 9.11 (s, 1H), 8.28 (s, 1H), 7.97-7.91 (m, 2H), 7.89-7.84 (m, 2H), 7.42 (s, 1H), 7.40 (d, J=6.8 Hz, 1H), 7.35 (dd, J=6.8, 1.6 Hz, 1H), 4.85 (s, 2H), 4.37 (q, J=6.8 Hz, 2H), 4.04 (t, J=6.8 Hz, 1H), 1.92-1.79 (m, 2H), 1.58 (t, J=6.8 Hz, 3H), 1.45-1.29 (m, 2H), 0.99 (t, J=7.2 Hz, 3H).

Example 465 (6-(6-(6-(3-aminooxetan-3-yl)pyridin-2-yl)-4-(2-methoxyethoxy)-1H-indazol-1-yl)pyridin-2-yl)methanol Step 1. Synthesis of (R)-2-methyl-N-(oxetan-3-ylidene)propane-2-sulfinamide

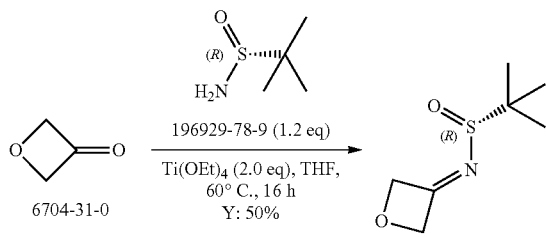

To a solution of 3-Oxetanone (CAS No. 6704-31-0, 1.6 g, 22.2 mmol, 1.0 eq) in THF (40 mL) was added (R)-(+)-2-Methyl-2-propanesulfinamide (CAS No. 196929-78-9 (3.2 g, 26.6 mmol, 1.2 eq) and titanium ethoxide (9.3 mL, 44.4 mmol, 2.0 eq). The mixture was stirred at 60° C. for 16 h under N₂ atmosphere. After cooling down to rt, the mixture was diluted with ethyl acetate (200 mL), and water (100 mL) was added. Then the mixture was filtered and washed with ethyl acetate. The filtrate was extracted with ethyl acetate (100 mL×2). The combined organic layers were dried over anhydrous sodium sulfate, filtrated and concentrated under reduced pressure. The residue was purified by silica gel column chromatography (PE/EA=2/1) to give (R)-2-methyl-N-(oxetan-3-ylidene)propane-2-sulfinamide (2.0 g, Y: 50%) as colorless oil. ESI-MS (M+H)⁺: 176.1. ¹H NMR (400 MHz, CDCl₃) δ: 5.82-5.77 (m, 1H), 5.68-5.63 (m, 1H), 5.51-5.30 (m, 2H), 1.27 (s, 9H).

Step 2. Synthesis of (R)—N-(3-(6-bromopyridin-2-yl)oxetan-3-yl)-2-methylpropane-2-sulfinamide

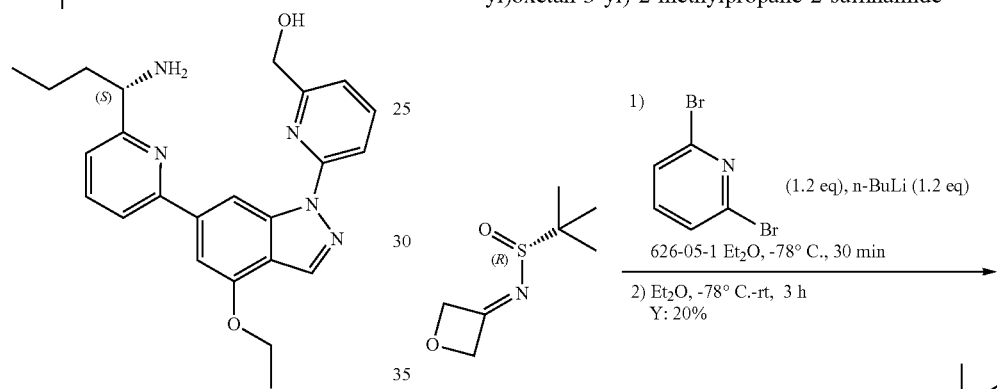

To a mixture of 2,6-Dibromopyridine (CAS No. 626-05-1, 3.1 g, 13.2 mmol, 1.2 eq) in anhydrous diethyl ether (40 mL) was added n-BuLi (2.4 M in THF, 5.5 mL, 13.2 mmol, 1.2 eq) at −78° C. under N₂ atmosphere. The mixture was stirred at −78° C. for 30 min. Then (R)-2-methyl-N-(oxetan-3-ylidene)propane-2-sulfinamide (1.9 g, 11.0 mmol, 1.0 eq) in anhydrous diethyl ether (20 mL) was added to the solution. After stirring at −78° C. for 30 min, the mixture was stirred at rt for 1.5 h. The reaction was quenched with saturated NH₄Cl solution. The mixture was extracted with ethyl acetate (30 mL×2). The combined organic layers were dried over anhydrous sodium sulfate, filtrated and concentrated under reduced pressure. The residue was purified by silica gel column chromatography (PE/EA=1/1) to give (R)—N-(3-(6-bromopyridin-2-yl)oxetan-3-yl)-2-methylpropane-2-sulfinamide (750 mg, Y: 20%) as yellow oil. ESI-MS (M+H)⁺: 333.0. ¹H NMR (400 MHz, CDCl₃) δ: 7.79 (dd, J=7.6, 0.8 Hz, 1H), 7.70 (t, J=8.0 Hz, 1H), 7.49 (dd, J=7.6, 0.8 Hz, 1H), 5.36-5.33 (m, 2H), 5.08 (d, J=6.8 Hz, 1H), 4.95 (d, J=6.8 Hz, 1H), 4.88 (d, J=6.8 Hz, 1H), 1.30 (s, 9H).

Step 3. Synthesis of (R)—N-(3-(6-(1-(6-(((tert-butyldimethylsilyl)oxy)methyl)pyridin-2-yl)-4-(2-methoxyethoxy)-1H-indazol-6-yl)pyridin-2-yl)oxetan-3-yl)-2-methylpropane-2-sulfinamide Step 4. Synthesis of 2-amino-3-chloro-2-(6-(1-(6-(hydroxymethyl)pyridin-2-yl)-4-(2-methoxyethoxy)-1H-indazol-6-yl)pyridin-2-yl)propan-1-ol

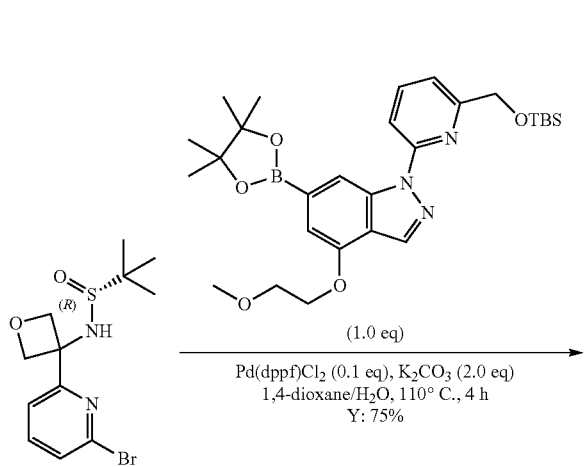

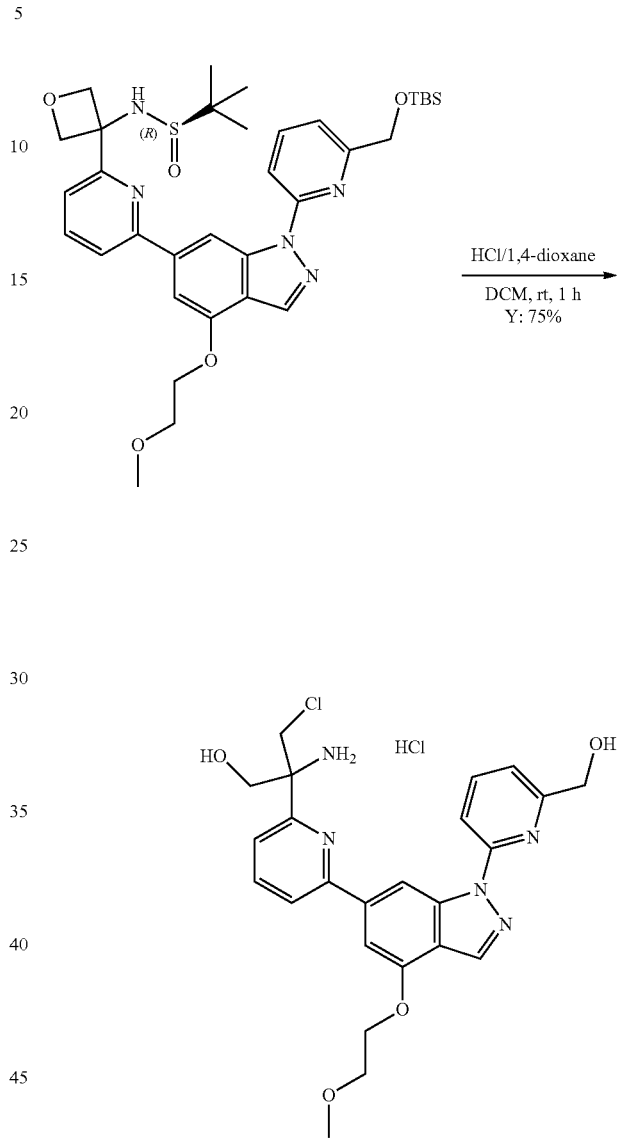

A mixture of (R)—N-(3-(6-bromopyridin-2-yl)oxetan-3-yl)-2-methylpropane-2-sulfinamide (240 mg, 0.72 mmol, 1.0 eq), 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2, 388 mg, 0.72 mmol, 1.0 eq), Pd(dppf)$_2$Cl$_2$ (57 mg, 0.07 mmol, 0.1 eq), K$_2$CO$_3$ (199 mg, 1.44 mmol, 2.0 eq) in 1,4-dioxane/H$_2$O (10 mL/0.5 mL) was stirred at 110° C. for 4 h under N$_2$ atmosphere. After concentration, the residue was purified by silica gel column chromatography (PE/EA=1/1) to give (R)—N-(3-(6-(1-(6-(((tert-butyldimethylsilyl)oxy)methyl)pyridin-2-yl)-4-(2-methoxyethoxy)-1H-indazol-6-yl)pyridin-2-yl)oxetan-3-yl)-2-methylpropane-2-sulfinamide (360 mg, Y: 75%) as yellow oil. ESI-MS (M+1)$^+$: 666.3. $^1$H NMR (400 MHz, CDCl$_3$) δ: 8.92 (s, 1H), 8.33 (s, 1H), 7.99-7.85 (m, 5H), 7.42-7.38 (m, 2H), 5.97 (s, 1H), 5.53 (d, J=6.8 Hz, 1H), 5.18 (d, J=6.4 Hz, 1H), 5.08 (d, J=6.4 Hz, 1H), 4.98-4.94 (m, 3H), 4.41 (dd, J=7.6, 4.4 Hz, 2H), 3.91 (dd, J=5.2, 4.0 Hz, 2H), 3.52 (s, 3H), 1.33 (s, 9H), 1.00 (s, 9H), 0.17 (s, 6H).

To a mixture of (R)—N-(3-(6-(1-(6-(((tert-butyldimethylsilyl)oxy)methyl)pyridin-2-yl)-4-(2-methoxyethoxy)-1H-indazol-6-yl)pyridin-2-yl)oxetan-3-yl)-2-methylpropane-2-sulfinamide (360 mg, 0.54 mmol, 1.0 eq) in dichloromethane (10 mL) was added 4 M HCl in 1,4-dioxane (5 mL). The mixture was stirred at rt for 1 h. The solution was then filtered and washed with dichloromethane to get 2-amino-3-chloro-2-(6-(1-(6-(hydroxymethyl)pyridin-2-yl)-4-(2-methoxyethoxy)-1H-indazol-6-yl)pyridin-2-yl)propan-1-ol (210 mg, Y: 75%) as a yellow solid. ESI-MS (M+1)$^+$: 484.2.

Step 5. Synthesis of (6-(6-(6-(3-aminooxetan-3-yl)pyridin-2-yl)-4-(2-methoxyethoxy)-1H-indazol-1-yl)pyridin-2-yl)methanol

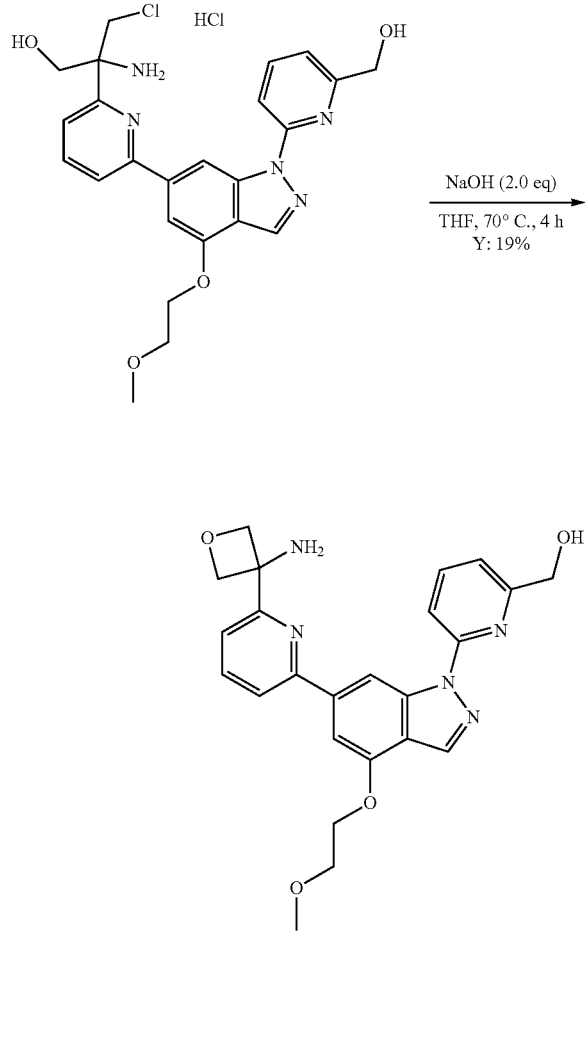

To a mixture of 2-amino-3-chloro-2-(6-(1-(6-(hydroxymethyl)pyridin-2-yl)-4-(2-methoxyethoxy)-1H-indazol-6-yl)pyridin-2-yl)propan-1-ol (150 mg, 0.29 mmol, 1.0 eq) in THF (10 mL) was added NaOH (23 mg, 0.58 mmol, 2.0 eq). The mixture was stirred at 70° C. for 4 h under N₂ atmosphere. After cooling down to rt, the mixture was diluted with ethyl acetate (80 mL) and washed with water (30 mL). The combined organic layers were dried over anhydrous sodium sulfate, filtrated and concentrated under reduced pressure. The residue was purified by prep-TLC (silica gel, EA) to give (6-(6-(6-(3-aminooxetan-3-yl)pyridin-2-yl)-4-(2-methoxyethoxy)-1H-indazol-1-yl)pyridin-2-yl)methanol (25 mg, Y: 19%) as a yellow solid. ESI-MS (M+1)$^+$: 448.2. HPLC: 100%. $^1$H NMR (400 MHz, CDCl$_3$) δ: 8.97 (s, 1H), 8.28 (s, 1H), 7.95 (d, J=8.4 Hz, 1H), 7.86 (t, J=7.6 Hz, 1H), 7.76 (t, J=8.0 Hz, 1H), 7.65 (d, J=7.6 Hz, 1H), 7.42 (d, J=7.6 Hz, 1H), 7.20 (d, J=7.2 Hz, 1H), 7.13 (s, 1H), 4.86 (s, 2H), 4.39-4.37 (m, 2H), 4.37-4.24 (m, 2H), 4.07-4.03 (m, 2H), 3.92-3.89 (m, 2H), 3.53 (s, 3H), 2.15 (br, 2H).

Example 466. (6-(6-(6-(3-aminotetrahydrofuran-3-yl)pyridin-2-yl)-4-(2-methoxyethoxy)-1H-indazol-1-yl)pyridin-2-yl)methanol Synthesis of (R,Z)—N-(dihydrofuran-3(2H)-ylidene)-2-methylpropane-2-sulfinamide

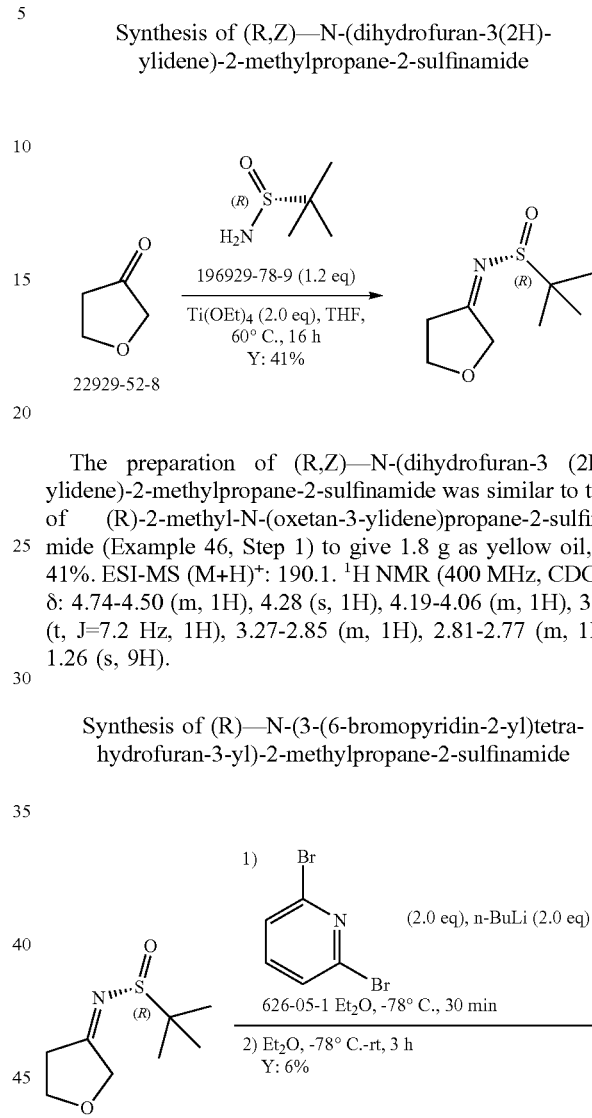

The preparation of (R,Z)—N-(dihydrofuran-3(2H)-ylidene)-2-methylpropane-2-sulfinamide was similar to that of (R)-2-methyl-N-(oxetan-3-ylidene)propane-2-sulfinamide (Example 46, Step 1) to give 1.8 g as yellow oil, Y: 41%. ESI-MS (M+H)$^+$: 190.1. $^1$H NMR (400 MHz, CDCl$_3$) δ: 4.74-4.50 (m, 1H), 4.28 (s, 1H), 4.19-4.06 (m, 1H), 3.96 (t, J=7.2 Hz, 1H), 3.27-2.85 (m, 1H), 2.81-2.77 (m, 1H), 1.26 (s, 9H).

Synthesis of (R)—N-(3-(6-bromopyridin-2-yl)tetrahydrofuran-3-yl)-2-methylpropane-2-sulfinamide The preparation of (R)—N-(3-(6-bromopyridin-2-yl)tetrahydrofuran-3-yl)-2-methylpropane-2-sulfinamide was similar to that of (R)—N-(3-(6-bromopyridin-2-yl)oxetan-3-yl)-2-methylpropane-2-sulfinamide (Example 465, Step 2) to give 90 mg as colorless oil, Y: 6%. ESI-MS (M+H)$^+$: 347.0, 348.0. $^1$H NMR (400 MHz, CDCl$_3$) δ: 7.57-7.53 (m, 1H), 7.48-7.47 (m, 1H), 7.41-7.39 (m, 1H), 4.24-4.16 (m, 3H), 4.12-4.07 (m, 1H), 4.03-4.01 (m, 1H), 2.78-2.71 (m, 1H), 2.59-2.55 (m, 1H), 1.22 (s, 9H).

Synthesis of (R)—N-(3-(6-(1-(6-(((tert-butyldimethylsilyl)oxy)methyl)pyridin-2-yl)-4-(2-methoxyethoxy)-1H-indazol-6-yl)pyridin-2-yl)tetrahydrofuran-3-yl)-2-methylpropane-2-sulfinamide

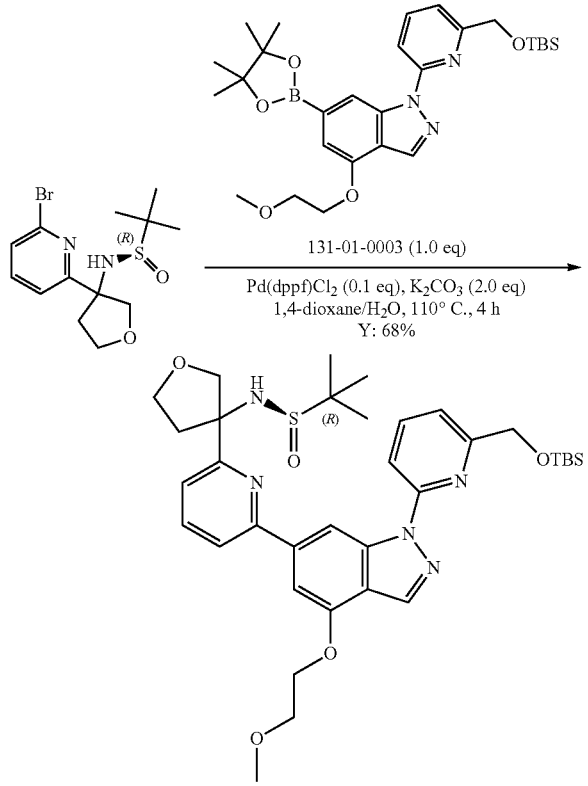

The preparation of (R)—N-(3-(6-(1-(6-(((tert-butyldimethylsilyl)oxy)methyl)pyridin-2-yl)-4-(2-methoxyethoxy)-1H-indazol-6-yl)pyridin-2-yl)tetrahydrofuran-3-yl)-2-methylpropane-2-sulfinamide was similar to that of (R)—N-(3-(6-(1-(6-(((tert-butyldimethylsilyl)oxy)methyl)pyridin-2-yl)-4-(2-methoxyethoxy)-1H-indazol-6-yl)pyridin-2-yl)oxetan-3-yl)-2-methylpropane-2-sulfinamide (Example 465, Step 3) to give 120 mg as a white solid, Y: 68%. ESI-MS (M+H)$^+$: 680.3. $^1$H NMR (400 MHz, CDCl3) δ: 8.93 (s, 1H), 8.33 (s, 1H), 7.93-7.77 (m, 4H), 7.52-7.39 (m, 3H), 5.06 (s, 1H), 4.95 (s, 2H), 4.44-4.41 (m, 2H), 4.29-4.12 (m, 4H), 3.92-3.90 (m, 2H), 3.53 (s, 3H), 2.74-2.67 (m, 1H), 2.54-2.46 (m, 1H), 1.10 (s, 9H), 0.83 (s, 9H), 0.17 (s, 6H).

Synthesis of (6-(6-(6-(3-aminotetrahydrofuran-3-yl)pyridin-2-yl)-4-(2-methoxyethoxy)-1H-indazol-1-yl)pyridin-2-yl)methanol

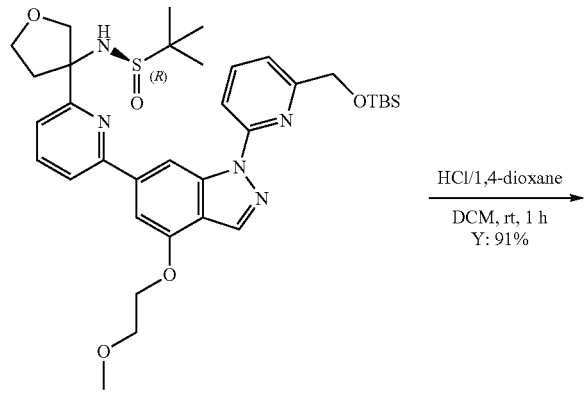

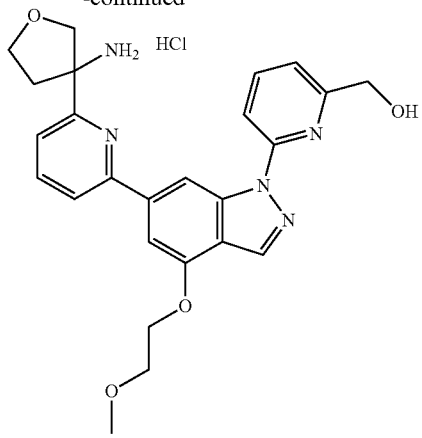

The preparation of (6-(6-(6-(3-aminotetrahydrofuran-3-yl)pyridin-2-yl)-4-(2-methoxyethoxy)-1H-indazol-1-yl)pyridin-2-yl)methanol was similar to that of 2-amino-3-chloro-2-(6-(1-(6-(hydroxymethyl)pyridin-2-yl)-4-(2-methoxyethoxy)-1H-indazol-6-yl)pyridin-2-yl)propan-1-ol (Example 465, Step 4) to give 80 mg as a yellow solid, Y: 91%. ESI-MS (M+H)$^+$: 462.2. HPLC: 100%. $^1$H NMR (400 MHz, CD$_3$OD) δ: 9.29 (s, 1H), 8.37 (s, 1H), 8.14-8.06 (m, 2H), 8.01-7.95 (m, 2H), 7.67-7.64 (m, 2H), 7.41-7.39 (m, 1H), 4.89 (s, 2H), 4.52-4.50 (m, 2H), 4.37-4.24 (m, 3H), 4.16-4.13 (m, 1H), 3.96-3.94 (m, 2H), 3.54 (s, 3H), 2.83-2.75 (m, 1H), 2.62-2.57 (m, 1H).

Example 467 (6-(6-(6-(1-aminocyclobutyl)pyridin-2-yl)-4-(2-methoxyethoxy)-1H-indazol-1-yl)pyridin-2-yl)methanol

Step 1. Synthesis of (R)—N-cyclobutylidene-2-methylpropane-2-sulfinamide

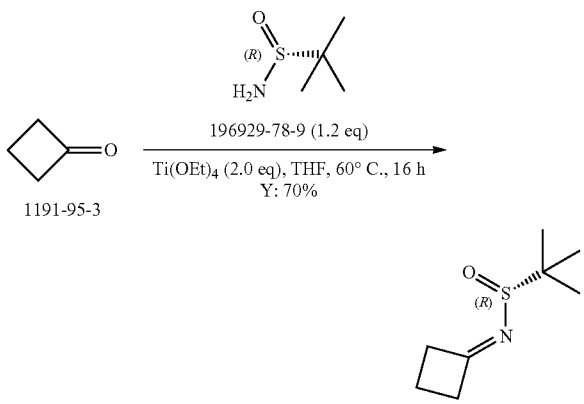

To a solution of Cyclobutanone (CAS No. 1191-95-3, 10.0 g, 143 mmol, 1.0 eq) in THF (100 mL) were added (R)-(+)-2-Methyl-2-propanesulfinamide (CAS No. 196929-78-9, 20.7 g, 171 mmol, 1.2 eq) and titanium ethoxide (60.0 mL, 286 mmol, 2.0 eq). The mixture was stirred at 60° C. for 16 h under N$_2$ atmosphere. After cooling down to rt, the mixture was diluted with EA (400 mL) and water (200 mL) was added. Then the mixture was filtered and washed with EA. The organic layer was dried over anhydrous sodium sulfate and concentrated under reduced pressure. The residue was purified by silica gel column chromatography (PE/EA=2/1) to give (R)—N-cyclobutylidene-2-methylpropane-2-sulfinamide (17.2 g, Y: 70%) as colorless oil. ESI-MS (M+1)⁺: 174.1. ¹H NMR (400 MHz, CDCl₃) δ: 3.55-3.46 (m, 1H), 3.32-3.23 (m, 1H), 3.15-3.09 (m, 2H), 2.16-2.05 (m, 2H), 1.26 (s, 9H).

Step 2. Synthesis of (R)—N-(1-(6-bromopyridin-2-yl)cyclobutyl)-2-methylpropane-2-sulfinamide

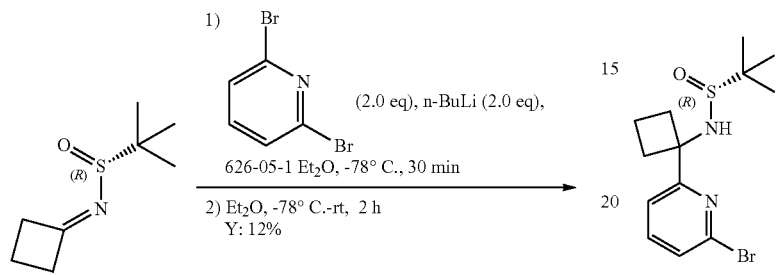

To a solution of 2,6-Dibromopyridine (CAS No. 626-05-1, 14.2 g, 60 mmol, 2.0 eq) in anhydrous diethyl ether (120 mL) was added n-BuLi (2.4 M in THF, 25.0 mL, 60 mmol, 2.0 eq) at −78° C. under N₂ atmosphere. After stirring at −78° C. for 30 min (R)—N-cyclobutylidene-2-methylpropane-2-sulfinamide (5.2 g, 30 mmol, 1.0 eq) in anhydrous diethyl ether (20 mL) was added to the mixture. After stirring at −78° C. for 30 min, the mixture was stirred at rt for 1.5 h. The reaction was quenched with saturated NH₄Cl solution. The mixture was extracted with EA (50 mL×2). The organic layers were dried over anhydrous sodium sulfate and concentrated under reduced pressure. The residue was purified by silica gel column chromatography (PE/EA=1/1) to give (R)—N-(1-(6-bromopyridin-2-yl)cyclobutyl)-2-methylpropane-2-sulfinamide (1.2 g, Y: 12%) as yellow oil. ESI-MS (M+1)⁺: 331.0. ¹H NMR (400 MHz, CDCl₃) δ: 7.57 (t, J=7.6 Hz, 1H), 7.48 (dd, J=7.6, 0.8 Hz, 1H), 7.37 (dd, J=7.6, 0.8 Hz, 1H), 4.32 (br, 1H), 2.69-2.61 (m, 3H), 2.55-2.41 (m, 1H), 2.11-2.04 (m, 1H), 1.91-1.81 (m, 1H), 1.22 (s, 9H).

Step 3. Synthesis of (R)—N-(1-(6-(1-(6-(((tert-butyldimethylsilyl)oxy)methyl)pyridin-2-yl)-4-(2-methoxyethoxy)-1H-indazol-6-yl)pyridin-2-yl)cyclobutyl)-2-methylpropane-2-sulfinamide

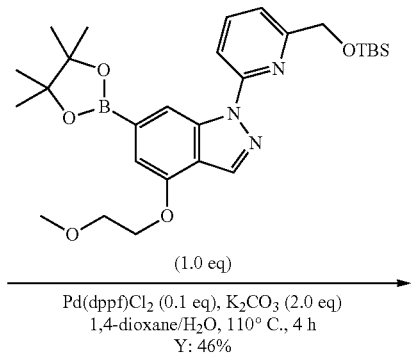

A mixture of (R)—N-(1-(6-bromopyridin-2-yl)cyclobutyl)-2-methylpropane-2-sulfinamide (260 mg, 0.8 mmol, 1.0 eq), 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2, 431 mg, 0.8 mmol, 1.0 eq), Pd(dppf)Cl₂ (65 mg, 0.08 mmol, 0.1 eq) and K₂CO₃ (220 mg, 1.6 mmol, 2.0 eq) in 1,4-dioxane/H₂O (10 mL/0.5 mL) was stirred at 110° C. for 4 h under N₂ atmosphere. After concentration, the residue was purified by silica gel column chromatography (PE/EA=1/1) to give (R)—N-(1-(6-(1-(6-(((tert-butyldimethylsilyl)oxy)methyl)pyridin-2-yl)-4-(2-methoxyethoxy)-1H-indazol-6-yl)pyridin-2-yl)cyclobutyl)-2-methylpropane-2-sulfinamide (240 mg, Y: 46%) as yellow oil. ESI-MS (M+1)⁺: 664.3.

593

Step 4. Synthesis of (6-(6-(6-(1-aminocyclobutyl)pyridin-2-yl)-4-(2-methoxyethoxy)-1H-indazol-1-yl)pyridin-2-yl)methanol

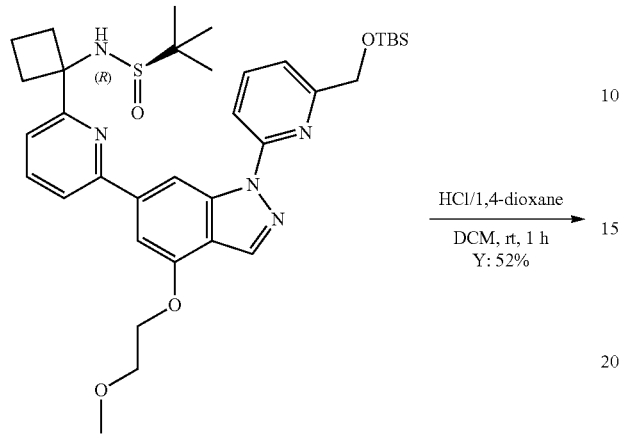

To a solution of (R)—N-(1-(6-(1-(6-(((tert-butyldimethylsilyl)oxy)methyl)pyridin-2-yl)-4-(2-methoxyethoxy)-1H-indazol-6-yl)pyridin-2-yl)cyclobutyl)-2-methylpropane-2-sulfinamide (240 mg, 0.36 mmol, 1.0 eq) in DCM (10 mL) was added 4.0 M HCl (2 mL) in 1,4-dioxane. The mixture was stirred at rt for 1 h. The solution was filtered and washed with DCM to get (6-(6-(6-(1-aminocyclobutyl)pyridin-2-yl)-4-(2-methoxyethoxy)-1H-indazol-1-yl)pyridin-2-yl)methanol (90 mg, Y: 52%) as a yellow solid. ESI-MS (M+1)+: 446.2. HPLC: 100%. ¹H NMR (400 MHz, CD₃OD) δ: 9.29 (s, 1H), 8.36 (s, 1H), 8.12-8.09 (m, 2H), 8.01-7.95 (m, 2H), 7.86 (dd, J=5.6, 3.2 Hz, 1H), 7.61 (s, 1H), 7.40 (d, J=6.8 Hz, 1H), 4.88 (s, 2H), 4.51-4.49 (m, 2H), 3.96-3.93 (m, 2H), 3.62 (s, 3H), 2.88-2.71 (m, 4H), 2.40-2.30 (m, 2H).

594

Example 468. (6-(6-(6-(1-aminocyclobutyl)pyridin-2-yl)-4-(2-methoxyethoxy)-1H-indazol-1-yl)pyrazin-2-yl)methanol Synthesis of (R)—N-(1-(6-(1-(6-(((tert-butyldimethylsilyl)oxy)methyl)pyrazin-2-yl)-4-(2-methoxyethoxy)-1H-indazol-6-yl)pyridin-2-yl)cyclobutyl)-2-methylpropane-2-sulfinamide

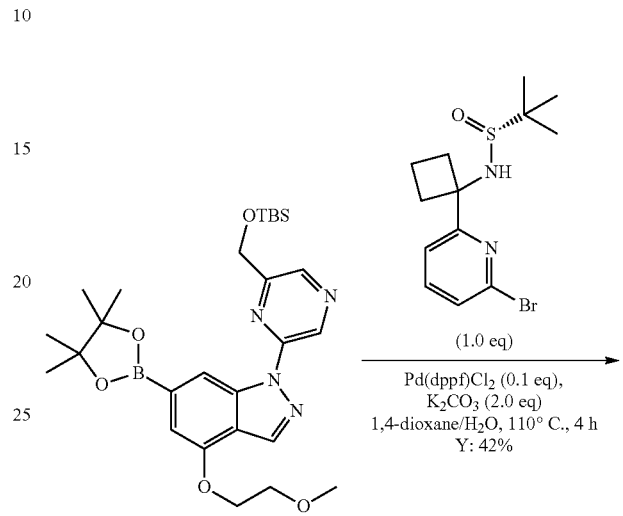

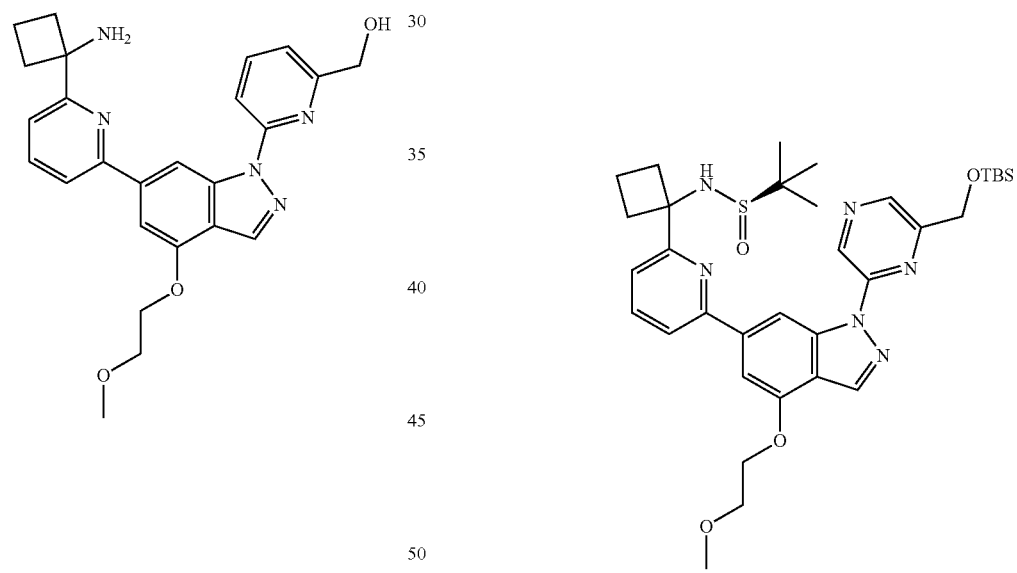

The preparation of (R)—N-(1-(6-(1-(6-(((tert-butyldimethylsilyl)oxy)methyl)pyrazin-2-yl)-4-(2-methoxyethoxy)-1H-indazol-6-yl)pyridin-2-yl)cyclobutyl)-2-methylpropane-2-sulfinamide was similar to that of (R)—N-(1-(6-(1-(6-(((tert-butyldimethylsilyl)oxy)methyl)pyridin-2-yl)-4-(2-methoxyethoxy)-1H-indazol-6-yl)pyridin-2-yl)cyclobutyl)-2-methylpropane-2-sulfinamide (Example 467, Step 3) to give 230 mg as a yellow solid, Y: 42%. ESI-MS (M+H)+: 665.3.

Synthesis of (6-(6-(6-(1-aminocyclobutyl)pyridin-2-yl)-4-(2-methoxyethoxy)-1H-indazol-1-yl)pyrazin-2-yl)methanol

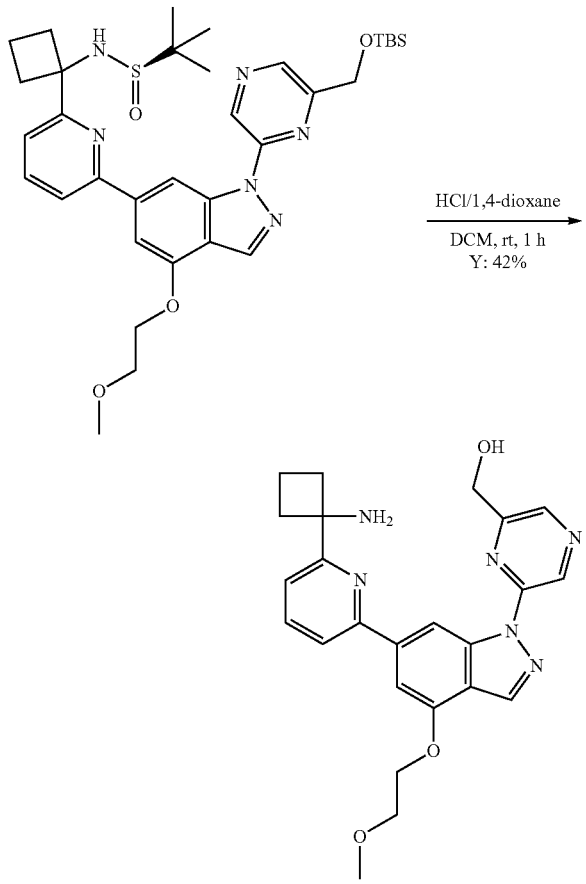

The preparation of (6-(6-(6-(1-aminocyclobutyl)pyridin-2-yl)-4-(2-methoxyethoxy)-1H-indazol-1-yl)pyrazin-2-yl)methanol was similar to that of (6-(6-(6-(1-aminocyclobutyl)pyridin-2-yl)-4-(2-methoxyethoxy)-1H-indazol-1-yl)pyridin-2-yl)methanol (Example 467, Step 4) to give 70 mg as a yellow solid, Y: 42%. ESI-MS (M+H)$^+$: 447.2. HPLC: 98%. $^1$H NMR (400 MHz, CD$_3$OD) δ: 9.22 (s, 1H), 9.15 (s, 1H), 8.55 (s, 1H), 8.42 (s, 1H), 8.14-8.08 (m, 2H), 7.87-7.84 (m, 1H), 7.65 (s, 1H), 4.93 (s, 2H), 4.50-4.48 (m, 2H), 3.95-3.92 (m, 2H), 3.52 (s, 3H), 32.85-2.71 (m, 4H), 2.39-2.31 (m, 2H).

Example 469. (6-(6-(6-(1-aminocyclopentyl)pyridin-2-yl)-4-(2-methoxyethoxy)-1H-indazol-1-yl)pyridin-2-yl)methanol Synthesis of (R)—N-cyclopentylidene-2-methylpropane-2-sulfinamide

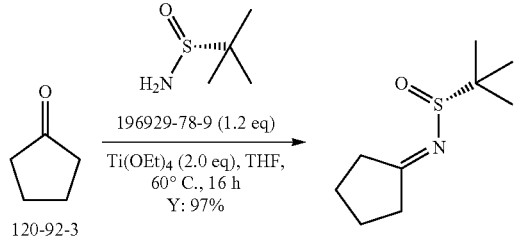

The preparation of (R)—N-cyclopentylidene-2-methylpropane-2-sulfinamide was similar to that of (R)—N-cyclobutylidene-2-methylpropane-2-sulfinamide (Example 467, Step 1) to give 4.3 g as yellow oil, Y: 97%. ESI-MS (M+H)$^+$: 188.1. $^1$H NMR (400 MHz, CDCl$_3$) δ: 2.93-2.57 (m, 2H), 2.51-2.47 (m, 2H), 1.94-1.73 (m, 4H), 1.22 (s, 9H).

Synthesis of (R)—N-(1-(6-bromopyridin-2-yl)cyclopentyl)-2-methylpropane-2-sulfinamide

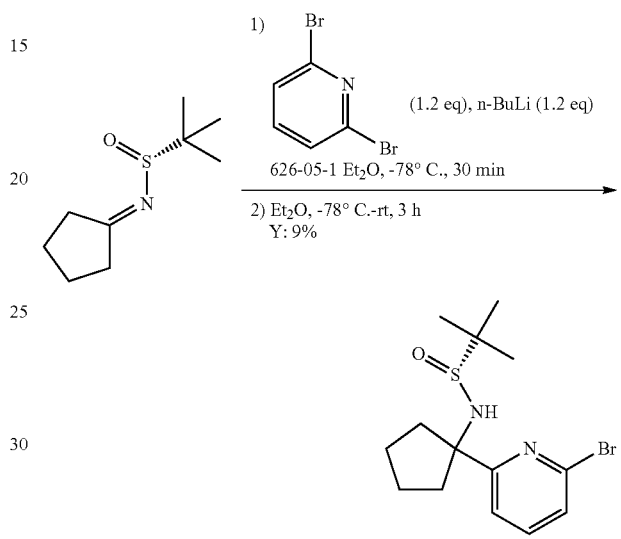

The preparation of (R)—N-(1-(6-bromopyridin-2-yl)cyclopentyl)-2-methylpropane-2-sulfinamide was similar to that of (R)—N-(1-(6-bromopyridin-2-yl)cyclobutyl)-2-methylpropane-2-sulfinamide (Example 467, Step 2) to give 400 mg as yellow oil, Y: 9%. ESI-MS (M+H)$^+$: 345.0, 347.0. $^1$H NMR (400 MHz, CDCl$_3$) δ: 7.51-7.45 (m, 2H), 7.31 (dd, J=6.8, 1.6 Hz, 1H), 4.09 (s, 1H), 2.36-2.12 (m, 4H), 1.90-1.76 (m, 4H), 1.20 (s, 9H).

Synthesis of N-(1-(6-(1-(6-(((tert-butyldimethylsilyl)oxy)methyl)pyridin-2-yl)-4-(2-methoxyethoxy)-1H-indazol-6-yl)pyridin-2-yl)cyclopentyl)-2-methylpropane-2-sulfinamide

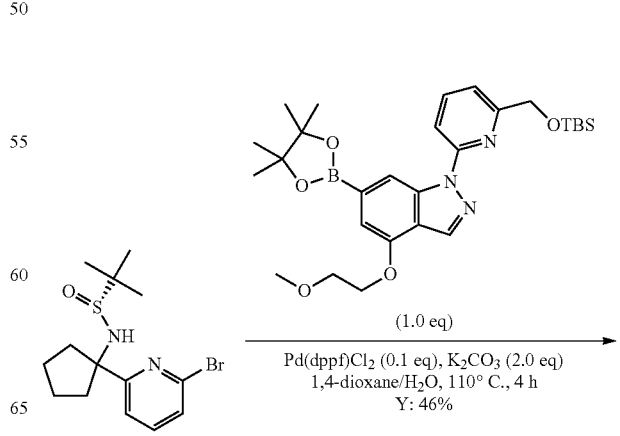

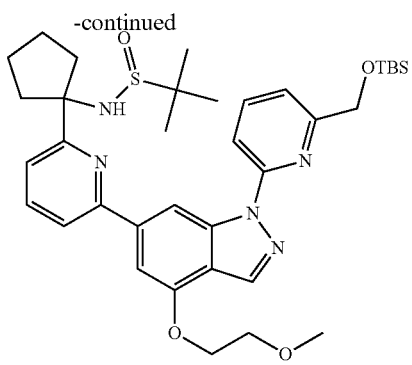

The preparation of N-(1-(6-(1-(6-(((tert-butyldimethylsilyl)oxy)methyl)pyridin-2-yl)-4-(2-methoxyethoxy)-1H-indazol-6-yl)pyridin-2-yl)cyclopentyl)-2-methylpropane-2-sulfinamide was similar to that of (R)—N-(1-(6-(1-(6-(((tert-butyldimethylsilyl)oxy)methyl)pyridin-2-yl)-4-(2-methoxyethoxy)-1H-indazol-6-yl)pyridin-2-yl)cyclobutyl)-2-methylpropane-2-sulfinamide (Example 467, Step 3) to give 360 mg as a yellow solid, Y: 46%. ESI-MS (M+H)$^+$: 678.3.

Synthesis of (6-(6-(6-(1-aminocyclopentyl)pyridin-2-yl)-4-(2-methoxyethoxy)-1H-indazol-1-yl)pyridin-2-yl)methanol

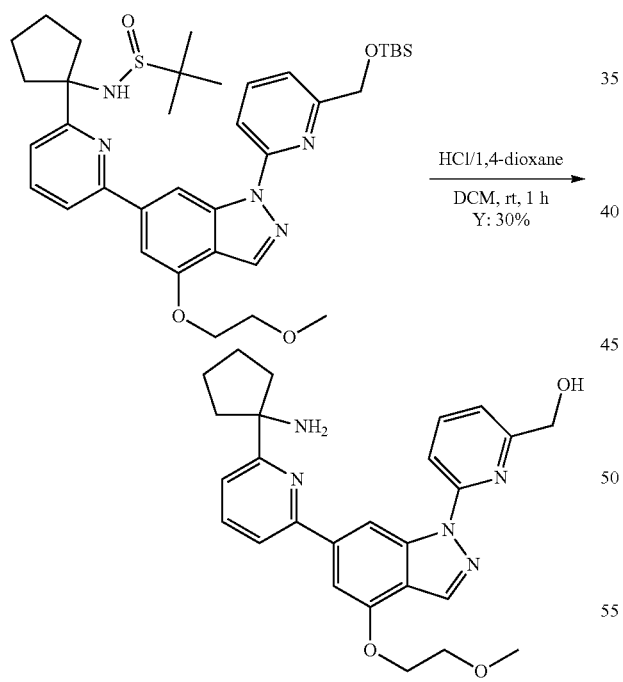

The preparation of (6-(6-(6-(1-aminocyclopentyl)pyridin-2-yl)-4-(2-methoxyethoxy)-1H-indazol-1-yl)pyridin-2-yl)methanol was similar to that of (6-(6-(6-(1-aminocyclobutyl)pyridin-2-yl)-4-(2-methoxyethoxy)-1H-indazol-1-yl)pyridin-2-yl)methanol (Example 467, Step 4) to give 80 mg as a yellow solid, Y: 30%. ESI-MS (M+H)$^+$: 460.2. HPLC: 100%. $^1$H NMR (400 MHz, CD$_3$OD) δ: 9.23 (s, 1H), 8.33 (s, 1H), 8.05-7.92 (m, 4H), 7.60 (s, 1H), 7.55 (dd, J=7.2, 1.2 Hz, 1H), 7.36 (d, J=6.4 Hz, 1H), 4.85 (s, 2H), 4.47 (t, J=4.8 Hz, 2H), 3.92 (t, J=4.8 Hz, 2H), 3.50 (s, 3H), 2.43-2.21 (m, 4H), 2.10-2.07 (m, 4H).

Example 470. (S)-(6-(6-(6-(1-aminobutyl)pyridin-2-yl)-4-(2-(methylsulfonyl)ethoxy)-1H-indazol-1-yl)pyridin-2-yl)methanol Synthesis of (6-(6-bromo-4-(2-(methylsulfonyl)ethoxy)-1H-indazol-1-yl)pyridin-2-yl)methanol

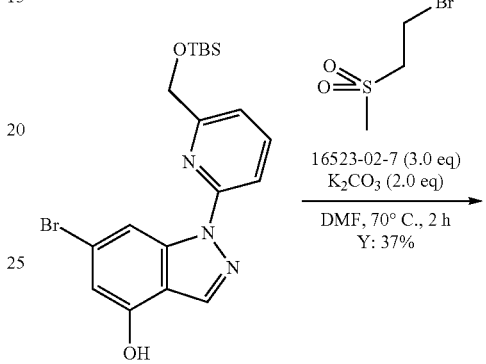

To a mixture of 6-bromo-1-(6-(((tert-butyldimethylsilyl)oxy)methyl)pyridin-2-yl)-1H-indazol-4-ol (Example 426, Step 4, 00 mg, 1.2 mmol, 1.0 eq) and K$_2$CO$_3$ (318 mg, 2.4 mmol, 2.0 eq) in DMF (100 mL) was added 16523-02-7 (644 mg, 3.4 mmol, 3.0 eq). The resulting mixture was stirred at 70° C. for 2 h. The mixture was diluted with water (500 mL), extracted with EA (300 mL×3) and concentrated in vacuo. The residue was purified by silica gel chromatography using PE/EA (5/1) as eluent to give (6-(6-bromo-4-(2-(methylsulfonyl)ethoxy)-1H-indazol-1-yl)pyridin-2-yl)methanol (180 mg, Y: 37%) as a yellow solid. ESI-MS (M+H)$^+$: 426.0.

599

Synthesis of (6-(4-(2-(methylsulfonyl)ethoxy)-6-(4,4,5,5-tetramethyl-1,3,2-dioxaborolan-2-yl)-1H-indazol-1-yl)pyridin-2-yl)methanol

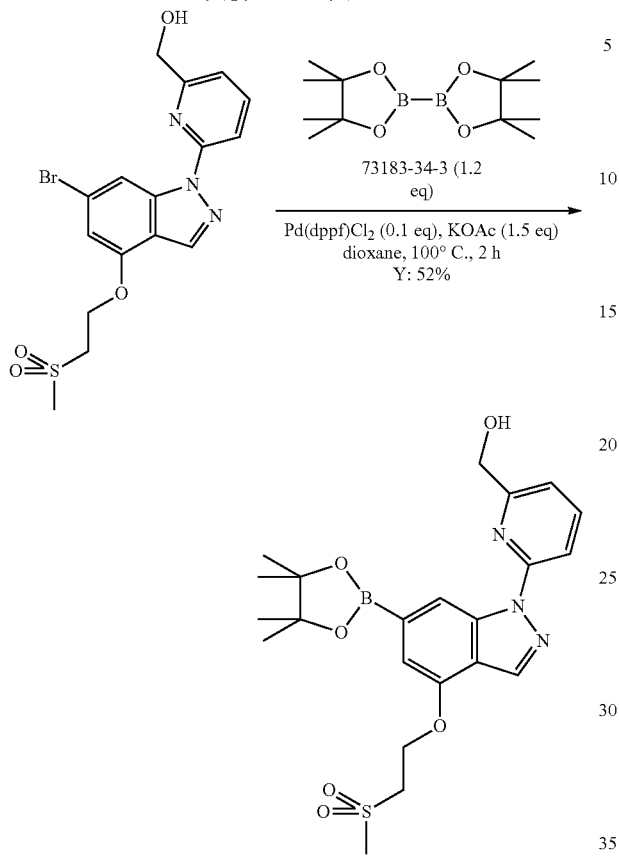

The preparation of (6-(4-(2-(methylsulfonyl)ethoxy)-6-(4,4,5,5-tetramethyl-1,3,2-dioxaborolan-2-yl)-1H-indazol-1-yl)pyridin-2-yl)methanol was similar to that of 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole (Example 428, Step 6) to give 104 mg as a white solid, Y: 52%. ESI-MS (M+H)⁺: 474.2.

Synthesis of (R)—N—((S)-1-(6-(1-(6-(hydroxymethyl)pyridin-2-yl)-4-(2-(methylsulfonyl)ethoxy)-1H-indazol-6-yl)pyridin-2-yl)butyl)-2-methylpropane-2-sulfinamide

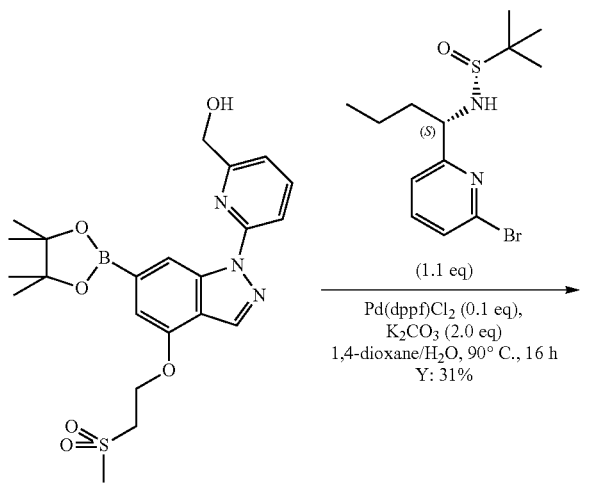

600

-continued

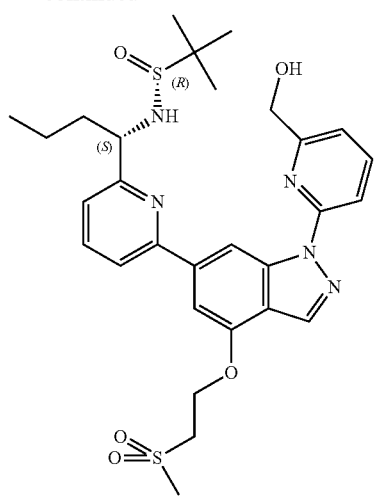

The preparation of (R)—N—((S)-1-(6-(1-(6-(hydroxymethyl)pyridin-2-yl)-4-(2-(methylsulfonyl)ethoxy)-1H-indazol-6-yl)pyridin-2-yl)butyl)-2-methylpropane-2-sulfinamide was similar to that of (R)—N-(1-(6-(1-(6-(((tert-butyldimethylsilyl)oxy)methyl)pyridin-2-yl)-4-(2-methoxyethoxy)-1H-indazol-6-yl)pyridin-2-yl)cyclobutyl)-2-methylpropane-2-sulfinamide (Example 467, Step 3) to give 40 mg as a yellow solid, Y: 31%. ESI-MS (M+H)⁺: 600.0.

Synthesis of (S)-(6-(6-(6-(1-aminobutyl)pyridin-2-yl)-4-(2-(methylsulfonyl)ethoxy)-1H-indazol-1-yl)pyridin-2-yl)methanol

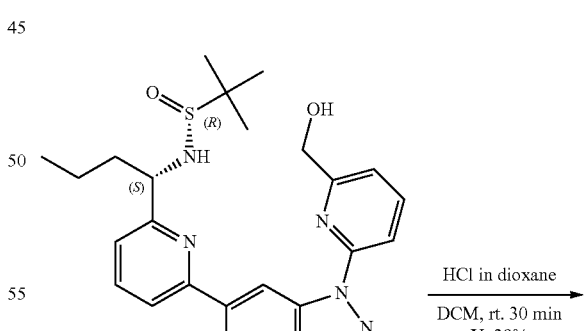

-continued

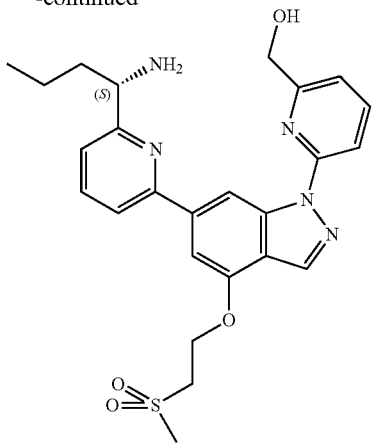

The preparation of (S)-(6-(6-(6-(1-aminobutyl)pyridin-2-yl)-4-(2-(methylsulfonyl)ethoxy)-1H-indazol-1-yl)pyridin-2-yl)methanol was similar to that of (6-(6-(6-(1-aminocyclobutyl)pyridin-2-yl)-4-(2-methoxyethoxy)-1H-indazol-1-yl)pyridin-2-yl)methanol (Example 467, Step 4) to give 13 mg as a yellow solid, Y: 39%. ESI-MS (M+H)+: 491.1. HPLC: 100%. 1H NMR (400 MHz, CD3OD) δ: 9.02 (s, 1H), 8.35 (s, 1H), 8.02-7.97 (m, 4H), 7.46-7.40 (m, 3H), 4.88 (s, 2H), 4.55 (t, J=7.2 Hz, 1H), 4.10 (t, J=5.2 Hz, 2H), 3.45 (t, J=5.2 Hz, 2H), 3.01 (s, 3H), 2.06-2.04 (m, 2H), 1.34-1.29 (m, 2H), 1.03 (t, J=7.2 Hz, 3H).

Example 471. (S)-1-((6-(6-(1-aminobutyl)pyridin-2-yl)-1-(6-(hydroxymethyl)pyridin-2-yl)-1H-indazol-4-yl)oxy)-2-methylpropan-2-ol Synthesis of 1-((6-bromo-1-(6-(((tert-butyldimethylsilyl)oxy)methyl)pyridin-2-yl)-1H-indazol-4-yl)oxy)propan-2-one

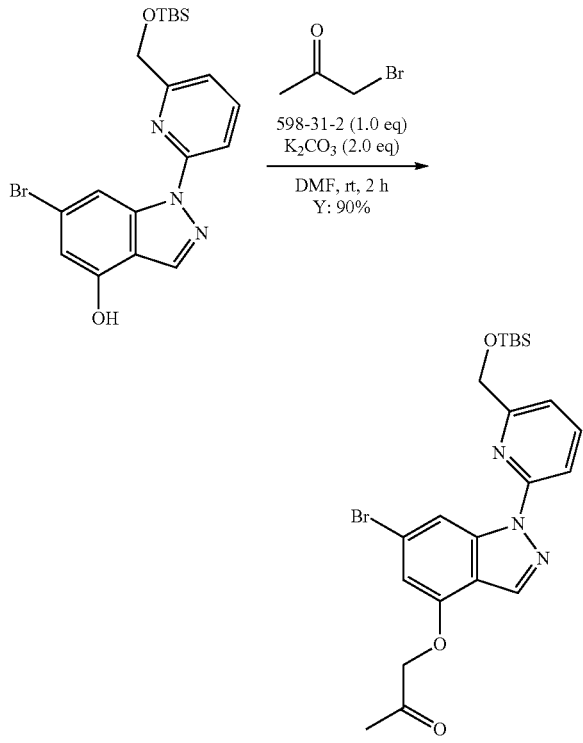

To a mixture of 6-bromo-1-(6-(((tert-butyldimethylsilyl)oxy)methyl)pyridin-2-yl)-1H-indazol-4-ol (Example 426, Step 4, 500 mg, 1.2 mmol, 1.0 eq) and K2CO3 (318 mg, 2.4 mmol, 2.0 eq) in DMF (100 mL) was added 598-31-2 (156 mg, 1.2 mmol, 1.0 eq). The resulting mixture was stirred at rt for 2 h. The mixture was diluted with water (500 mL), extracted with EA (300 mL×3) and concentrated in vacuo. The residue was purified by silica gel chromatography using PE/EA (5/1) as eluent to give 1-((6-bromo-1-(6-(((tert-butyldimethylsilyl)oxy)methyl)pyridin-2-yl)-1H-indazol-4-yl)oxy)propan-2-one (510 mg, Y: 90%) as a yellow solid. ESI-MS (M+H)+: 490.1.

Synthesis of 1-((6-bromo-1-(6-(((tert-butyldimethylsilyl)oxy)methyl)pyridin-2-yl)-1H-indazol-4-yl)oxy)-2-methylpropan-2-ol

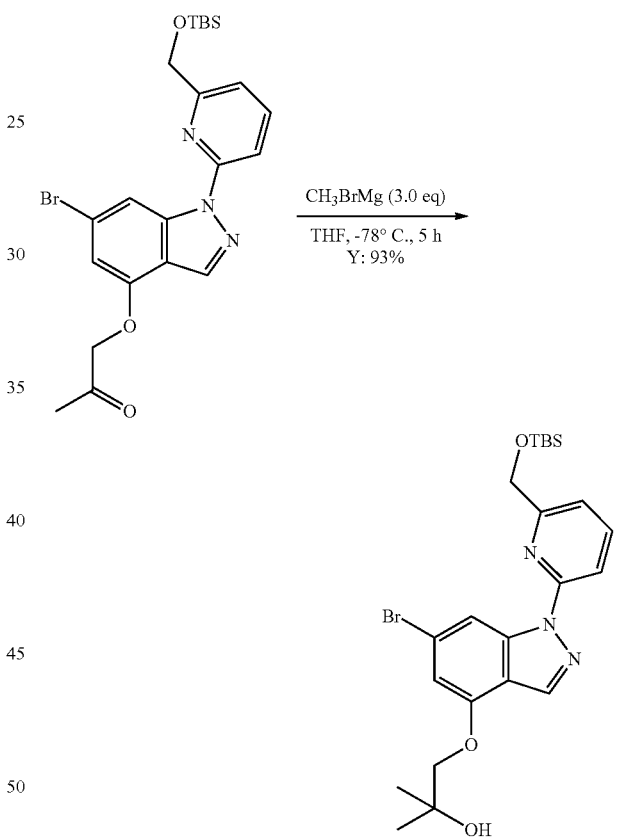

To a solution of 1-((6-bromo-1-(6-(((tert-butyldimethylsilyl)oxy)methyl)pyridin-2-yl)-1H-indazol-4-yl)oxy)propan-2-one (510 mg, 1.0 mmol, 1.0 eq) in THF (100 mL) was added CH3MgBr (1.5 mL, 3 mmol, 3.0 eq, 2 M in THF) at −78° C. The mixture was stirred at −78° C. for 5 h. The mixture was quenched with NH4Cl (aq.) and extracted with EA (100 mL×3). The combined organic phase was washed with brine and dried over Na2SO4. After filtration and concentration, the residue was purified by silica gel chromatography using PE/EA (8/1) as eluent to give 1-((6-bromo-1-(6-(((tert-butyldimethylsilyl)oxy)methyl)pyridin-2-yl)-1H-indazol-4-yl)oxy)-2-methylpropan-2-ol (400 mg, Y: 93%) as a yellow solid. ESI-MS (M+H)+: 506.1.

Synthesis of 1-((1-(6-(((tert-butyldimethylsilyl)oxy)methyl)pyridin-2-yl)-6-(4,4,5,5-tetramethyl-1,3,2-dioxaborolan-2-yl)-1H-indazol-4-yl)oxy)-2-methylpropan-2-ol

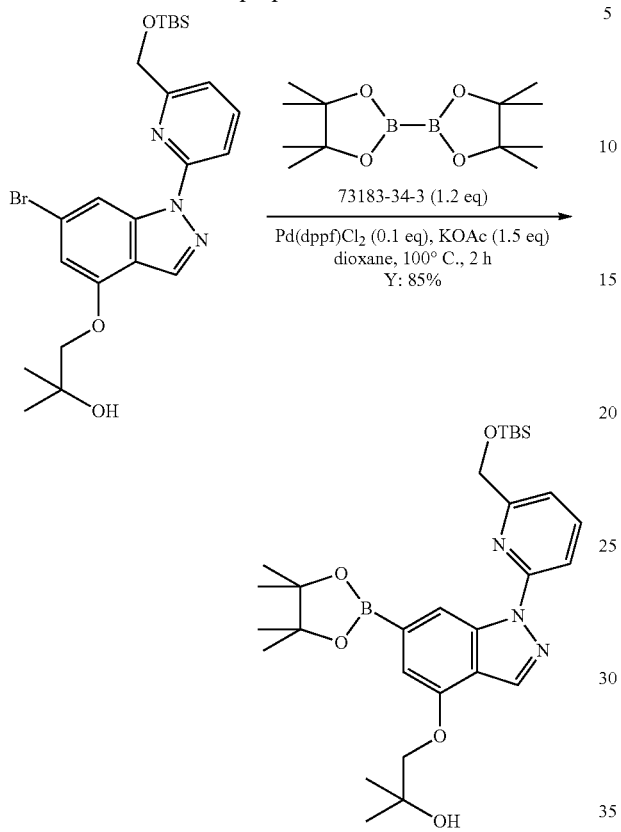

The preparation of 1-((1-(6-(((tert-butyldimethylsilyl)oxy)methyl)pyridin-2-yl)-6-(4,4,5,5-tetramethyl-1,3,2-dioxaborolan-2-yl)-1H-indazol-4-yl)oxy)-2-methylpropan-2-ol was similar to that of 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole (Example 428, Step 6) to give 370 mg as a yellow solid, Y: 85%. ESI-MS (M+H)⁺: 554.3.

Synthesis of (R)—N—((S)-1-(6-(1-(6-(((tert-butyldimethylsilyl)oxy)methyl)pyridin-2-yl)-4-(2-hydroxy-2-methylpropoxy)-1H-indazol-6-yl)pyridin-2-yl)butyl)-2-methylpropane-2-sulfinamide

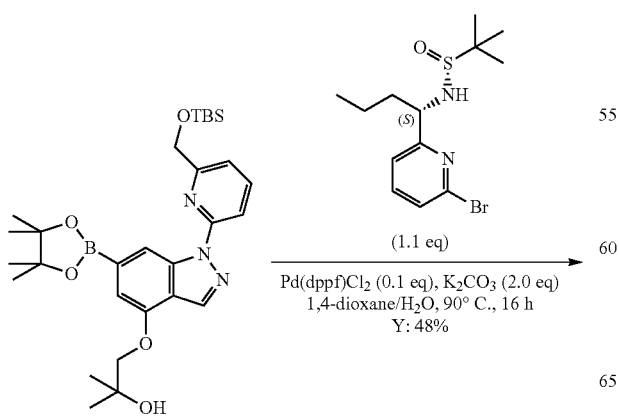

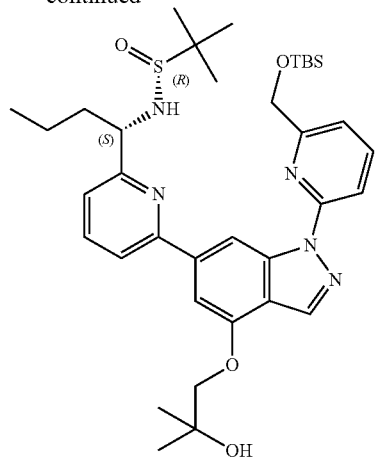

The preparation of (R)—N—((S)-1-(6-(1-(6-(((tert-butyldimethylsilyl)oxy)methyl)pyridin-2-yl)-4-(2-hydroxy-2-methylpropoxy)-1H-indazol-6-yl)pyridin-2-yl)butyl)-2-methylpropane-2-sulfinamide was similar to that of (R)—N-(1-(6-(1-(6-(((tert-butyldimethylsilyl)oxy)methyl)pyridin-2-yl)-4-(2-methoxyethoxy)-1H-indazol-6-yl)pyridin-2-yl)cyclobutyl)-2-methylpropane-2-sulfinamide (Example 467, Step 3) to give 218 mg as a yellow solid, Y: 48%. ESI-MS (M+H)⁺: 680.4.

Synthesis of (S)-1-((6-(6-(1-aminobutyl)pyridin-2-yl)-1-(6-(hydroxymethyl)pyridin-2-yl)-1H-indazol-4-yl)oxy)-2-methylpropan-2-ol

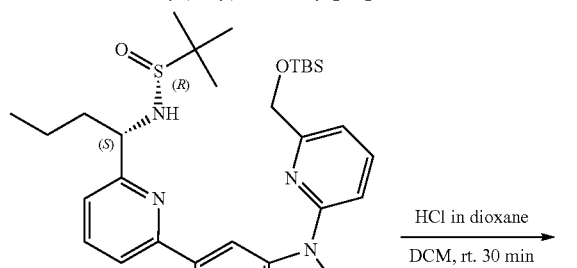

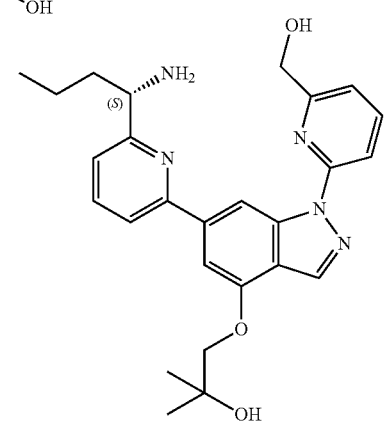

The preparation of (S)-1-((6-(6-(1-aminobutyl)pyridin-2-yl)-1-(6-(hydroxymethyl)pyridin-2-yl)-1H-indazol-4-yl)oxy)-2-methylpropan-2-ol was similar to that of (6-(6-(6-(1-aminocyclobutyl)pyridin-2-yl)-4-(2-methoxyethoxy)-1H-indazol-1-yl)pyridin-2-yl)methanol (Example 467, Step 4) to give 89 mg as a yellow solid, Y: 56%. ESI-MS (M+H)⁺: 462.2. HPLC: 96%. ¹H NMR (400 MHz, CD₃OD) δ: 9.14 (s, 1H), 8.45 (s, 1H), 8.08-8.01 (m, 4H), 7.53 (s, 1H), 7.49 (d, J=7.2 Hz, 1H), 7.41 (d, J=7.2 Hz, 1H), 4.87 (s, 2H), 4.58 (t, J=7.2 Hz, 1H), 4.15 (s, 2H), 2.01-1.97 (m, 2H), 1.46-1.43 (m, 8H), 1.01 (t, J=7.2 Hz, 3H).

Example 472 6-{6-[6-((S)-1-Amino-ethyl)-pyridin-2-yl]-indazol-1-yl}-pyridine-2-carboxylic

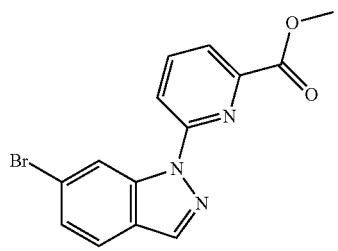 [SMILES: COC(=O)c1cccc(-n2ncc3ccc(Br)cc32)n1]

Synthesis of 6-(6-Bromo-indazol-1-yl)-pyridine-2-carboxylic acid methyl ester

6-Bromo-1H-indazole (CAS No. 79762-54-2 0.501 g, 2.54 mmol) and 6-fluoro-pyridine-2-carboxylic acid methyl ester (CAS No. 455-71-0; 0.510 g, 3.29 mmol) were dissolved in DMF (10 mL) before 60% sodium hydride dispersion in mineral oil (0.149 g, 3.72 mmol) was added portionwise. The reaction was then stirred at rt for 2 h, before heating at 40° C. for 2 h. The reaction was quenched with 1 mL MeOH, followed by an excess of a 5% Citric acid aqueous solution. The mixture was extracted with 100 mL EtOAc and the organic phase was washed with water, aqueous NaHCO₃, and brine. The organic phase was dried over anhydrous MgSO₄, evaporated, and purified by flash chromatography (0-100% DCM:heptane). Collected 0.216 g of a white powder (26%).

ES (+) MS m/e=332 (M+1). ¹H NMR (400 MHz, CDCl₃) δ 9.37 (s, 1H), 8.23 (dd, J=3.01, 6.27 Hz, 1H), 8.18 (s, 1H), 7.97-8.03 (m, 2H), 7.65 (d, J=8.53 Hz, 1H), 7.44 (dd, J=1.51, 8.53 Hz, 1H), 4.11 (s, 3H).

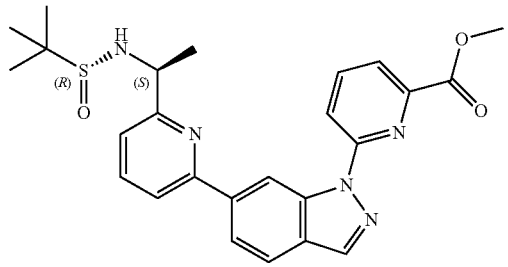

Synthesis of 6-(6-{6-[(S)-1-((R)-2-Methyl-propane-2-sulfinylamino)-ethyl]-pyridin-2-yl}-indazol-1-yl)-pyridine-2-carboxylic acid methyl ester 6-(6-Bromo-indazol-1-yl)-pyridine-2-carboxylic acid methyl ester (0.216 g, 0.650 mmol), bis(pinacolato)diboron (188 mg, 0.740 mmol), KOAc (193 mg, 1.97 mmol) and [1,1'-bis(diphenylphosphino)ferrocene]dichloropalladium (II), complex with dichloromethane (1:1) (37 mg, 0.045 mmol) were charged to a vial, evacuated, and flushed with nitrogen gas. 1,4-Dioxane (3.00 mL, 38.4 mmol) was added and the vial was then heated at 90° C. for 3 h. The reaction was cooled before adding (R)—N—((S)-1-(6-bromopyridin-2-yl)ethyl)-2-methylpropane-2-sulfinamide (Example 142, 218 mg, 0.715 mmol), 1.88 M of aqueous Na₂CO₃ (0.692 mL, 1.30 mmol) and [1,1'-bis(diphenylphosphino)ferrocene]dichloropalladium(II), complex with dichloromethane (1:1) (36 mg, 0.044 mmol) and then heating at 90° C. for 6 h. The reaction was cooled to room temperature, and treated with ethyl acetate (10 mL) and water (10 mL) before filtering through Celite. To the filtrate was added aqueous NaHCO₃ (50 mL) and extracted with 75 mL ethyl acetate. The organic phase was then washed with water, followed by brine, before drying over anhydrous MgSO₄, evaporating, and purifying by flash chromatography. Collected 170 mg of an off-white solid.

ES (+) MS m/e=478 (M+1). ¹H NMR (400 MHz, CDCl₃) δ 9.78 (s, 1H), 8.12-8.22 (m, 3H), 7.86-7.95 (m, 3H), 7.80 (d, J=8.28 Hz, 1H), 7.76 (t, J=7.65 Hz, 1H), 7.25 (d, J=7.53 Hz, 1H), 4.72 (quin, J=6.80 Hz, 1H), 4.34 (d, J=6.78 Hz, 1H), 4.04 (s, 3H), 1.73 (d, J=6.78 Hz, 3H), 1.21 (s, 9H).

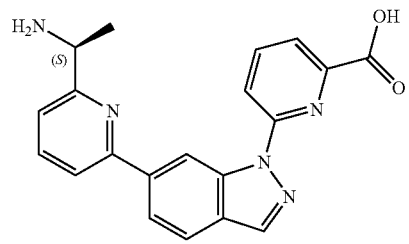

Synthesis of 6-{6-[6-((S)-1-Amino-ethyl)-pyridin-2-yl]-indazol-1-yl}-pyridine-2-carboxylic acid (Example 472)

6-(6-{6-[(S)-1-((R)-2-methyl-propane-2-sulfinylamino)-ethyl]-pyridin-2-yl}-indazol-1-yl)-pyridine-2-carboxylic acid methyl ester (170 mg, 0.356 mmol), 1.0 M of aqueous NaOH (0.392 mL, 0.392 mmol) and MeOH (1.0 mL, 25 mmol) were stirred at 40° C. for 1 h. Added 1.0 M of aqueous HCl (1.0 mL, 1.0 mmol) and continued to heat at 60° C. for 3 h. Concentrated and purified by reverse-phase flash chromatography (C18 silica, 0-50% MeCN:H₂O w/0.1% TFA). The product was collected after lyophilization. Collected product as a TFA salt (27.8 mg, 22%).

ES (+) MS m/e=360 (M+1). ¹H NMR (400 MHz, d₄-MeOH) δ 9.96 (s, 1H), 8.25 (s, 1H), 8.20 (d, J=8.03 Hz, 1H), 8.11 (d, J=7.53 Hz, 1H), 7.97-8.06 (m, 2H), 7.87-7.97 (m, 2H), 7.85 (d, J=8.28 Hz, 1H), 7.37 (d, J=7.53 Hz, 1H), 4.61 (q, J=6.78 Hz, 1H), 1.64 (d, J=6.78 Hz, 3H).

Example 473. (6-{6-[6-((S)-1-Amino-butyl)-pyridin-2-yl]-4-fluoro-indazol-1-yl}-pyridin-2-yl)-methanol

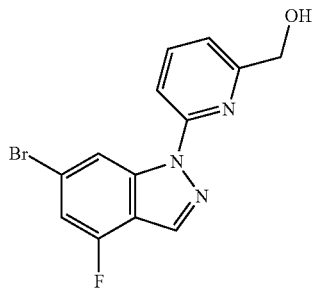 [SMILES: OCc1cccc(-n2ncc3c(F)cc(Br)cc32)n1]

Step 1. Synthesis of [6-(6-Bromo-4-fluoro-indazol-1-yl)-pyridin-2-yl]-methanol

6-Bromo-4-fluoro-1H-indazole (CAS No. 885520-23-0; 2.00 g, 9.30 mmol), 2-bromo-6-(hydroxylmethyl)pyridine (CAS No. 33674-96-3; 2.01 g, 10.7 mmol), $K_3PO_4$ (3.95 g, 18.6 mmol) and copper(I) iodide (214 mg, 1.12 mmol) were charged to a flask and dried under vacuum for 10 minutes before flushing with nitrogen. Added toluene (38 mL) and trans-N,N'-dimethyl-cyclohexyl-1,2-diamine (350 uL, 2.2 mmol) before heating at 110° C. for 1 h. Filtered through Celite and washed with ethyl acetate. Concentrated and purified by flash chromatography (0-30% EtOAc:heptane). Collected 1.32 g of an off-white powder (44%). $^1$H NMR (400 MHz, CDCL$_3$) δ 8.72 (s, 1H), 8.23 (s, 1H), 7.79-7.97 (m, 2H), 7.29 (s, 1H), 7.10 (d, J=8.28 Hz, 1H), 4.91 (s, 2H).

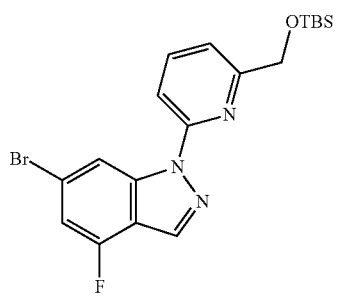 [SMILES: CC(C)(C)[Si](C)(C)OCc1cccc(-n2ncc3c(F)cc(Br)cc32)n1]

Step 2. Synthesis of 6-Bromo-1-[6-(tert-butyl-dimethyl-silanyloxymethyl)-pyridin-2-yl]-4-fluoro-1H-indazole

[6-(6-Bromo-4-fluoro-indazol-1-yl)-pyridin-2-yl]-methanol (1.38 g, 4.28 mmol), tert-butyldimethylsilyl chloride (814 mg, 5.40 mmol), and 1H-imidazole (577 mg, 8.48 mmol) were dissolved in DMF (14 mL, 180 mmol) and stirred at rt overnight. Added EtOAc (75 mL) and washed with aqueous sodium bicarbonate (50 mL), water (50 mL), and then brine (50 mL). The organic phase was dried over anhydrous $MgSO_4$, filtered, evaporated and purified by flash chromatography (silica gel, 0-10% EtOAc:heptane). Collected 1.76 g of a white powder (94%). $^1$H NMR (400 MHz, CDCl$_3$) δ 8.82 (s, 1H), 8.21 (s, 1H), 7.78-7.96 (m, 2H), 7.41 (d, J=6.27 Hz, 1H), 7.10 (d, J=9.04 Hz, 1H), 4.93 (s, 2H), 1.01 (s, 9H), 0.20 (s, 6H).

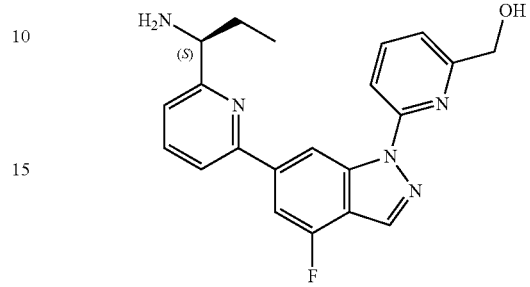

Step 3. Synthesis of (S)-(6-(6-(6-(1-aminopropyl)pyridin-2-yl)-4-fluoro-1H-indazol-1-yl)pyridin-2-yl)methanol 6-Bromo-1-[6-(tert-butyl-dimethyl-silanyloxymethyl)-pyridin-2-yl]-4-fluoro-1H-indazole (100 mg, 0.229 mmol), bis(pinacolato)diboron (79.0 mg, 0.311 mmol), KOAc (67.5 mg, 0.687 mmol), [1,1'-bis(diphenylphosphino)ferrocene]dichloropalladium(II), complex with DCM (1:1) (9.36 mg, 0.0114 mmol) and 1,4-dioxane (1.00 mL, 12.8 mmol) were charged to a vial and heated at 90° C. for 5 hours.

Added (R)—N—((S)-1-(6-bromopyridin-2-yl)propyl)-2-methylpropane-2-sulfinamide (prepared as in Example 145, Steps 1-5, 72.3 mg, 0.226 mmol), [1,1'-bis(diphenylphosphino)ferrocene]dichloropalladium(II), complex with DCM (1:1) (10.9 mg, 0.0133 mmol), and 1.88 M of aqueous $Na_2CO_3$ (0.244 mL, 0.458 mmol) before heating at 110° C. for 3 hours. Cooled to rt. Added EtOAc and water before filtering through Celite. The organic phase was washed with aqueous $NaHCO_3$, and brine before drying over anhydrous $MgSO_4$, filtering and evaporating. The crude product was purified by flash chromatography (silica gel, 0-100% EtOAc:heptane). Concentrated to an oil.

ES (+) MS m/e=596 (M+1).

The oil was dissolved in MeOH (1.0 mL) and treated with 1.0 M of aqueous HCl (1.0 mL, 1.0 mmol) before heating at 65° C. for 2 hours. Added 20 mL EtOAc, and extracted twice with dilute aqueous HCl. The aqueous extracts were neutralized with saturated $Na_2CO_3$ before extracting with 3×20 mL EtOAc. The organic phase was dried over anhydrous $MgSO_4$, filtered, and evaporated. Collected 32.5 mg of an off-white powder (38% over 3 steps).

ES (+) MS m/e=378 (M+1). $^1$H NMR (400 MHz, CDCl$_3$) δ 9.43 (s, 1H), 8.25 (s, 1H), 7.82 (d, J=8.28 Hz, 1H), 7.78 (t, J=7.78 Hz, 1H), 7.71 (t, J=7.03 Hz, 2H), 7.51 (d, J=11.04 Hz, 1H), 7.21 (d, J=7.53 Hz, 1H), 6.98 (d, J=7.53 Hz, 1H), 4.80 (d, J=6.53 Hz, 2H), 4.18 (t, J=6.65 Hz, 1H), 2.74 (br. s., 2H), 1.86-2.07 (m, 2H), 1.22-1.29 (m, 1H), 0.94 (t, J=7.40 Hz, 3H).

Example 474. (6-{6-[6-((S)-1-Amino-butyl)-pyridin-2-yl]-4-fluoro-indazol-1-yl}-pyridin-2-yl)-methanol

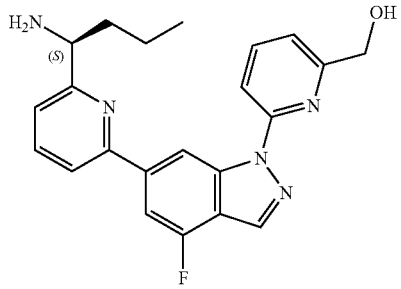

The synthesis of the title compound was conducted using the procedure for (S)-(6-(6-(6-(1-aminopropyl)pyridin-2-yl)-4-fluoro-1H-indazol-1-yl)pyridin-2-yl)methanol (Example 473) using (R)—N—((S)-1-(6-bromopyridin-2-yl)butyl)-2-methylpropane-2-sulfinamide instead of (R)—N—((S)-1-(6-bromopyridin-2-yl)propyl)-2-methylpropane-2-sulfinamide (preparied similarly to Example 145, Step 5, and purifying the final compound by flash chromatography (C18 silica, 10-50% MeCN:H$_2$O w/0.1% TFA). The TFA salt was collected as a yellow powder (48.3 mg, 28% over 3 steps).

ES (+) MS m/e=392.1 (M+1).

$^1$H NMR (400 MHz, CDCl3) δ 9.50 (s, 1H), 8.18 (s, 1H), 7.85 (t, J=7.65 Hz, 1H), 7.79 (d, J=7.78 Hz, 1H), 7.66 (d, J=8.28 Hz, 1H), 7.56 (t, J=7.78 Hz, 1H), 7.39 (d, J=10.79 Hz, 1H), 7.25 (s, 1H), 6.71 (d, J=7.28 Hz, 1H), 4.68 (d, J=14.06 Hz, 1H), 4.56 (d, J=13.80 Hz, 2H), 3.03 (br. s., 3H), 2.00-2.16 (m, 1H), 1.96 (br. s., 1H), 1.30 (dd, J=7.15, 15.44 Hz, 2H), 0.90 (t, J=7.15 Hz, 3H).

Example 475. (6-{6-[6-((S)-1-Amino-ethyl)-pyridin-2-yl]-4-fluoro-indazol-1-yl}-pyridin-2-yl)-methanol

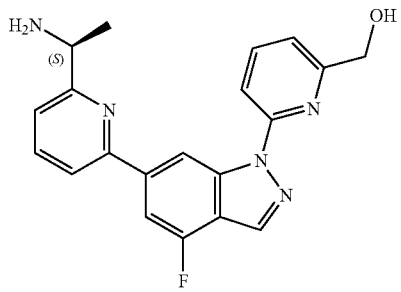

The synthesis of (6-{6-[6-((S)-1-Amino-ethyl)-pyridin-2-yl]-4-fluoro-indazol-1-yl}-pyridin-2-yl)-methanol was conducted using the procedure for (S)-(6-(6-(6-(1-aminopropyl)pyridin-2-yl)-4-fluoro-1H-indazol-1-yl)pyridin-2-yl)methanol (Example 473) using (R)—N—((S)-1-(6-bromopyridin-2-yl)ethyl)-2-methylpropane-2-sulfinamide (Example 142) instead of (R)—N—((S)-1-(6-bromopyridin-2-yl)propyl)-2-methylpropane-2-sulfinamide, and purifying the final compound by flash chromatography (silica gel, 0-100% EtOAc:heptane). Collected 161 mg of an oil (82%).

ES (+) MS m/e=582 (M+1).

$^1$H NMR (400 MHz, CDCl$_3$) δ 9.23 (s, 1H), 8.30 (s, 1H), 7.87-7.99 (m, 2H), 7.84 (t, J=7.78 Hz, 1H), 7.76 (d, J=7.78 Hz, 1H), 7.72 (d, J=11.04 Hz, 1H), 7.44 (d, J=7.03 Hz, 1H), 7.36 (d, J=7.53 Hz, 1H), 5.31 (s, 1H), 4.97 (s, 2H), 4.80 (q, J=6.19 Hz, 1H), 1.76 (d, J=6.78 Hz, 3H), 1.25 (s, 9H), 1.00 (s, 9H), 0.18 (s, 6H).

Example 476. (S)-(6-(6-(6-(1-aminobutyl)pyridin-2-yl)-4-(2-methoxyethoxy)-1H-indazol-1-yl)pyridin-2-yl)methanol

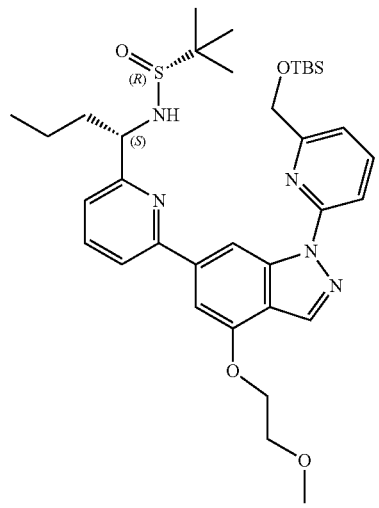

Synthesis of 2-Methyl-propane-2-sulfinic acid ((S)-1-{6-[1-[6-(tert-butyl-dimethyl-silanyloxymethyl)-pyridin-2-yl]-4-(2-methoxy-ethoxy)-1H-indazol-6-yl]-pyridin-2-yl}-butyl)-amide 1-[6-(tert-Butyl-dimethyl-silanyloxymethyl)-pyridin-2-yl]-4-(2-methoxy-ethoxy)-6-(4,4,5,5-tetramethyl-1,3,2-dioxaborolan-2-yl)-1H-indazole ((Example 453, step 2, 210.1 mg, 0.3894 mmol), 2-methyl-propane-2-sulfinic acid [(S)-1-(6-bromo-pyridin-2-yl)-butyl]-amide (Example 145, Step 5, 136.7 mg, 0.4102 mmol), [1,1'-bis(diphenylphosphino)ferrocene]dichloropalladium(II), complex with DCM (14.9 mg, 0.0182 mmol), 1,4-dioxane (2.6 mL), saturated aqueous Na$_2$CO$_3$ (0.415 mL, 0.780 mmol) and H$_2$O (0.415 mL) were charged to a vial and heated at 110° C. for 2 hours. The reaction was extracted with 2×3 mL DCM, concentrated and purified by flash chromatography (0-100% EtOAc:heptane). Collected 192.7 mg of a yellow film (78%). ES (+) MS m/e=666 (M+1) $^1$H NMR (400 MHz, CDCl$_3$) δ 8.92 (s, 1H), 8.34 (s, 1H), 7.75-7.97 (m, 4H), 7.52 (s, 1H), 7.40 (d, J=7.28 Hz, 1H), 7.34 (br. s., 1H), 4.95 (s, 2H), 4.58-4.88 (m, 1H), 4.38-4.57 (m, 2H), 3.92 (t, J=4.52 Hz, 2H), 3.53 (s, 3H), 1.97-2.15 (m, 2H), 1.26-1.29 (m, 2H), 1.23 (s, 9H), 1.00 (s, 9H), 0.98 (t, J=7.30 Hz, 3H), 0.17 (s, 6H)

Synthesis of (S)-(6-(6-(6-(1-aminobutyl)pyridin-2-yl)-4-(2-methoxyethoxy)-1H-indazol-1-yl)pyridin-2-yl)methanol

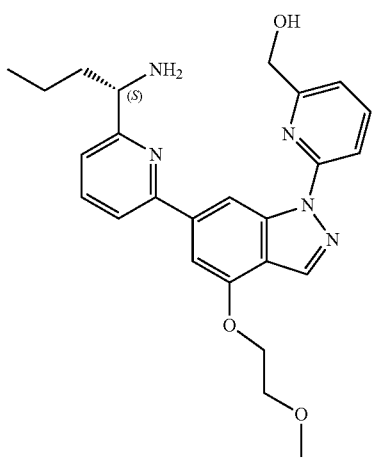

2-Methyl-propane-2-sulfinic acid ((S)-1-{6-[1-[6-(tert-butyl-dimethyl-silanyloxymethyl)-pyridin-2-yl]-4-(2-methoxy-ethoxy)-1H-indazol-6-yl]-pyridin-2-yl}-butyl)-amide (192.7 mg, 0.2894 mmol) was dissolved in DCM (3.0 mL) before treatment with 4.0 M of HCl in 1,4-dioxane (0.75 mL) for 1 h. The reaction was concentrated, and the crude material was stirred with 10 mL of DCM, before heating at 65° C. for 5 minutes. The material was chilled in an ice bath and filtered. The solid was washed with 10 mL of DCM and vacuum dried over the weekend. Collected 122.2 mg of a bright yellow powder (87%).

ES (+) MS m/e=448 (M+1)

$^1$H NMR (400 MHz, CD$_3$OD) δ 9.22 (s, 1H), 8.38 (s, 1H), 8.07-8.15 (m, 1H), 7.95-8.07 (m, 3H), 7.59 (s, 1H), 7.49 (d, J=7.28 Hz, 1H), 7.41 (d, J=7.03 Hz, 1H), 4.89 (br. s., 2H), 4.59 (t, J=7.03 Hz, 1H), 4.51 (dd, J=3.39, 5.40 Hz, 2H), 3.95 (dd, J=3.64, 5.15 Hz, 2H), 3.54 (s, 3H), 1.97-2.18 (m, 2H), 1.36-1.59 (m, 2H), 1.04 (t, J=7.40 Hz, 3H)

Example 477. (6-(6-(6-((S)-1-aminobutyl)pyridin-2-yl)-4-(tetrahydrofuran-2-yl)-1H-indazol-1-yl)pyridin-2-yl)methanol Step 1. Synthesis of (6-(6-bromo-4-chloro-1H-indazol-1-yl)pyridin-2-yl)methanol

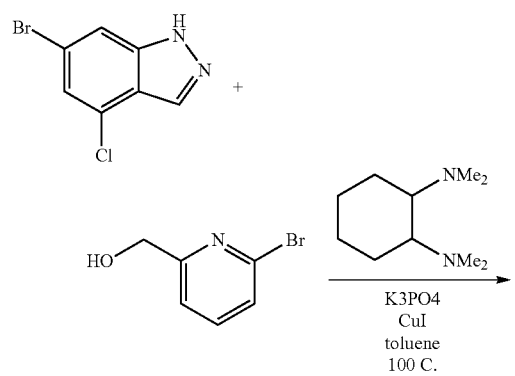

A mixture of 6-bromo-4-chloro-1H-indazole Cas. No. 885518-99-0 (2.415 g, 10.43 mmol), 2-Bromo-6-(hydroxylmethyl)pyridine (2.16 g, 11.5 mmol), Potassium phosphate (4.43 g, 20.9 mmol), Trans N,N'-dimethyl-cyclohexyl-1,2-diamine (164 uL, 1.04 mmol), and Copper(I) iodide (99.3 mg, 0.522 mmol) in Toluene (30 mL) was sparged with N2. The reaction was heated at 110 C for 3 h. The reaction was filtered through celite, evaporated, and purified (SiO2 DCM→EtOAc) to afford 750 mg of the product. MS m/z 337 (M+1); 1H NMR (400 MHz, DMSO-d6) δ ppm 8.96 (s, 9H), 8.52 (s, 9H), 8.03 (t, J=7.9 Hz, 11H), 7.85 (d, J=8.0 Hz, 10H), 7.64 (d, J=1.5 Hz, 8H), 7.44 (d, J=7.5 Hz, 11H), 5.61 (t, J=5.9 Hz, 1H), 4.70 (d, J=5.8 Hz, 2H)

Step 2 Synthesis of 6-bromo-1-(6-(((tert-butyldimethylsilyl)oxy)methyl)pyridin-2-yl)-4-chloro-1H-indazole

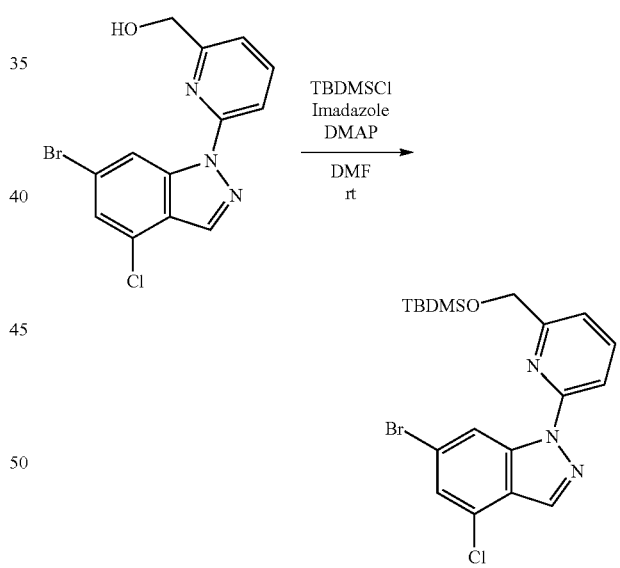

A mixture of [6-(6-Bromo-4-chloro-indazol-1-yl)-pyridin-2-yl]-methanol (0.750 g, 2.22 mmol), 1H-Imidazole (0.302 g, 4.43 mmol), tert-Butyldimethylsilyl chloride (0.401 g, 2.66 mmol) and 4-Dimethylaminopyridine (0.01 g, 0.08 mmol) in N,N-Dimethylformamide (6.86 mL, 88.6 mmol) was stirred for 48 h at rt. The reaction was diluted (DCM), washed (NaHCO3), and evaporated. The residue was purified (SiO2 40 g heptane→EtOAc) to afford 600 mg of clear solid. MS m/z 452 (M+1); 1H NMR (400 MHz, CHLOROFORM-d) ä ppm 8.81 (br s, 1H), 8.08 (br s, 1H), 7.66-7.83 (m, 2H), 7.27 (br s, 1H), 7.12 (s, 1H), 4.79 (s, 2H), 0.77 (s, 9H), 0.12 (s, 6H)

Step 3 Synthesis of 1-(6-(((tert-butyldimethylsilyl)oxy)methyl)pyridin-2-yl)-4-chloro-6-(4,4,5,5-tetramethyl-1,3,2-dioxaborolan-2-yl)-1H-indazole

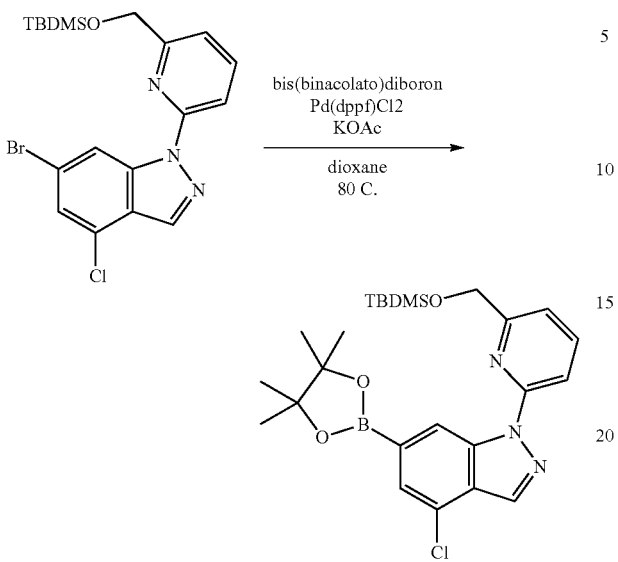

A mixture of 6-Bromo-1-[6-(tert-butyl-dimethyl-silanyloxymethyl)-pyridin-2-yl]-4-chloro-1H-indazole (0.600 g, 1.32 mmol), bis(pinacolato)diboron (0.505 g, 1.99 mmol), Potassium acetate (0.390 g, 3.97 mmol), and [1,1'-Bis(diphenylphosphino)ferrocene]dichloropalladium(II), complex with dichloromethane (1:1) (0.108 g, 0.132 mmol) in 1,4-Dioxane (4 mL, 50 mmol) was degassed under N2. The reaction was heated at 80 C for 4 h. The reaction was then filtered, evaporated and purified (SiO2 heptane→40% EtOAc) to afford 230 mg of clear solid. MS m/z 500 (M+1); 1H NMR (400 MHz, CHLOROFORM-d)™ ppm 9.10 (s, 1H), 8.27 (d, J=0.8 Hz, 1H), 7.85-7.88 (m, 2H), 7.65 (s, 1H), 7.42 (dd, J=5.8, 2.8 Hz, 1H), 4.98 (s, 2H), 1.39 (s, 12H), 1.01 (s, 9H), 0.19 (s, 6H)

Step 4 Synthesis of N—((S)-1-(6-(1-(6-(((tert-butyldimethylsilyl)oxy)methyl)pyridin-2-yl)-4-chloro-1H-indazol-6-yl)pyridin-2-yl)butyl)-2-methylpropane-2-sulfinamide

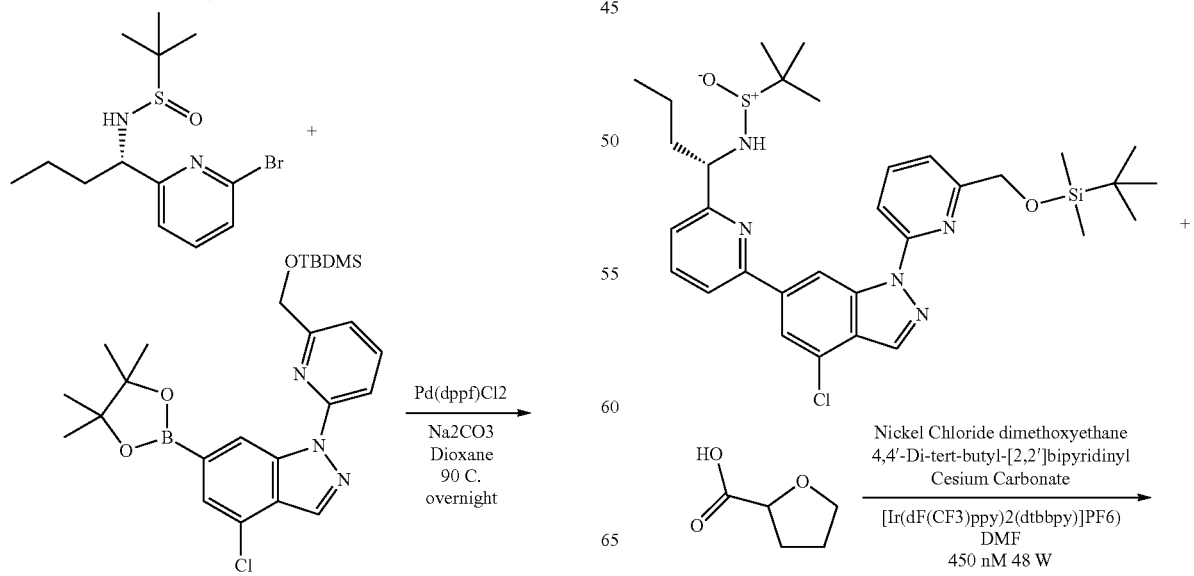

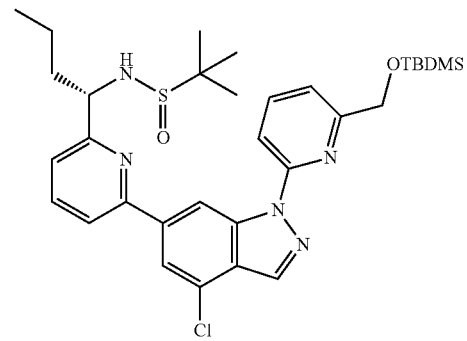

A mixture of 2-Methyl-propane-2-sulfinic acid [(S)-1-(6-bromo-pyridin-2-yl)-butyl]-amide (0.230 g, 0.690 mmol), 1-[6-(tert-Butyl-dimethyl-silanyloxymethyl)-pyridin-2-yl]-4-chloro-6-(4,4,5,5-tetramethyl-1,3,2-dioxaborolan-2-yl)-1H-indazole (0.230 g, 0.460 mmol), [1,1'-Bis(diphenylphosphino)ferrocene]dichloropalladium(II), complex with dichloromethane (1:1) (0.0376 g, 0.0460 mmol), 2 M of Sodium carbonate in Water (0.920 mL, 1.84 mmol) in 1,4-Dioxane (4 mL, 50 mmol) was degassed under N2. The reaction was heated at 90 C overnight. The reaction was filtered through celite, layers where separated, and evaporated. The residue was purified (SiO2 12 g heptane→EtOAc) to afford 150 mg of clear solid. MS m/z 626 (M+1); 1H NMR (400 MHz, CHLOROFORM-d) ppm 9.29 (t, J=0.9 Hz, 1H), 8.27 (d, J=0.8 Hz, 1H), 8.04 (d, J=1.3 Hz, 1H), 7.90-7.94 (m, 1H), 7.85-7.90 (m, 1H), 7.76-7.81 (m, 1H), 7.72-7.75 (m, 1H), 7.42 (dd, J=7.3, 1.0 Hz, 1H), 7.25 (d, J=1.0 Hz, 1H), 4.96 (s, 2H), 4.59 (q, J=6.7 Hz, 1H), 4.06-4.20 (m, 2H), 1.96-2.10 (m, 4H), 1.29-1.51 (m, 2H), 1.20 (s, 10H), 1.00 (s, 9H), 0.92-0.98 (m, 4H), 0.17 (s, 6H)

Step 5 Synthesis of N-((1S)-1-(6-(1-(6-(((tert-butyldimethylsilyl)oxy)methyl)pyridin-2-yl)-4-(tetrahydrofuran-2-yl)-1H-indazol-6-yl)pyridin-2-yl)butyl)-2-methylpropane-2-sulfinamide

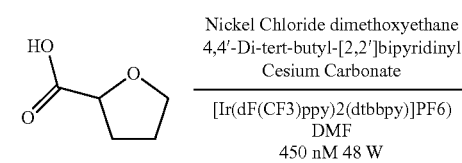

Nickel Chloride dimethoxyethane
4,4'-Di-tert-butyl-[2,2']bipyridinyl
Cesium Carbonate

[Ir(dF(CF3)ppy)2(dtbbpy)]PF6]
DMF
450 nM 48 W

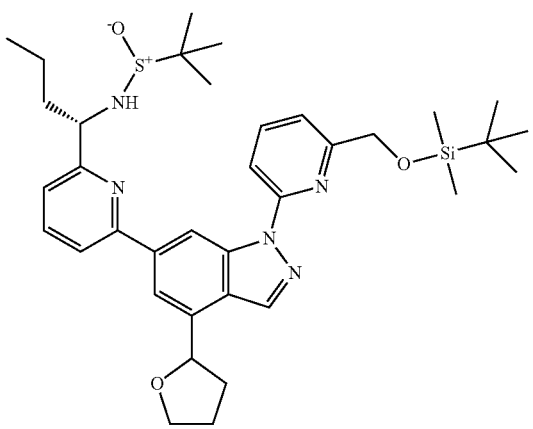

A mixture of N—((S)-1-(6-(1-(6-(((tert-butyldimethylsilyl)oxy)methyl)pyridin-2-yl)-4-chloro-1H-indazol-6-yl)pyridin-2-yl)butyl)-2-methylpropane-2-sulfinamide (126 mg, 0.201 mmol), 2-Furancarboxylic acid, tetrahydro-(88 mg, 0.76 mmol), 4,4'-Di-tert-butyl-[2,2']bipyridinyl (10.80 mg, 0.04023 mmol), Cesium Carbonate (249.1 mg, 0.7644 mmol), Nickel Chloride dimethoxyethane (8.840 mg, 0.04023 mmol), and [Ir(dF(CF3)ppy)2(dtbbpy)](PF6) (4.514 mg, 0.004023 mmol) in (new bottle, oxygen free) N,N-Dimethylformamide (20 mL, 200 mmol) was degassed under high vacuum. The reaction was cooled to maintain 30 C. The reaction was irradiated with a 48 W 450 nm lamp for 4 h. The reaction was filtered and evaporated. The residue was purified (SiO2, Heptane to EtOAc) to afford 80 mg of clear solid. MS 622 (M+1). 1H NMR (400 MHz, CHLOROFORM-d) δ ppm 9.29 (s, 1H), 8.33 (s, 1H), 7.99 (s, 1H), 7.91-7.95 (m, 1H), 7.84-7.90 (m, 1H), 7.79 (br. s., 2H), 7.41 (d, J=7.3 Hz, 1H), 7.25 (br. s., 1H), 5.37 (td, J=7.0, 4.0 Hz, 1H), 4.97 (s, 2H), 4.62 (br. s., 1H), 4.26 (q, J=7.1 Hz, 1H), 4.10-4.16 (m, 1H), 4.04-4.09 (m, 1H), 2.48-2.59 (m, 1H), 2.10-2.20 (m, 2H), 2.01-2.09 (m, 4H), 1.34-1.52 (m, 2H), 1.20 (d, J=1.0 Hz, 9H), 1.00 (s, 10H), 0.92-0.98 (m, 3H), 0.17 (s, 10H)

Synthesis of (6-(6-(6-((S)-1-aminobutyl)pyridin-2-yl)-4-(tetrahydrofuran-2-yl)-1H-indazol-1-yl)pyridin-2-yl)methanol

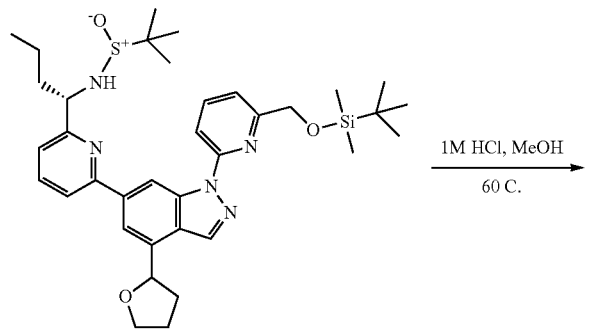

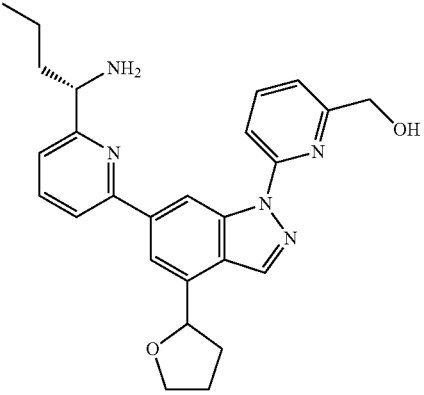

A solution of N-((1S)-1-(6-(1-(6-(((tert-butyldimethylsilyl)oxy)methyl)pyridin-2-yl)-4-(tetrahydrofuran-2-yl)-1H-indazol-6-yl)pyridin-2-yl)butyl)-2-methylpropane-2-sulfinamide (0.08 g, 0.1 mmol) and 1 M of Hydrogen chloride in water (2 mL, 2 mmol) in Methanol (2 mL, 60 mmol) was heated at 60 C for 2 h. The solvent was removed invacuo. The residue was purified by HPLC to afford 28 mg of the product. MS mz 444 (M+1) 1H NMR (400 MHz, METHANOL-d4) δ ppm 9.67 (s, 1H), 8.43 (s, 1H), 8.06 (d, J=3.8 Hz, 2H), 7.98-8.03 (m, 1H), 7.96 (d, J=4.0 Hz, 2H), 7.45 (d, J=7.5 Hz, 1H), 7.37 (t, J=4.0 Hz, 1H), 5.39 (t, J=7.4 Hz, 1H), 4.56 (t, J=7.0 Hz, 1H), 4.24-4.37 (m, 1H), 4.09 (q, J=7.3 Hz, 1H), 3.37 (s, 2H), 2.61 (dq, J=12.3, 6.3 Hz, 1H), 2.20 (quin, J=7.0 Hz, 2H), 1.97-2.13 (m, 3H), 1.36-1.58 (m, 2H), 1.03 (t, J=7.3 Hz, 3H).

Example 478. (6-(6-(6-((S)-1-aminobutyl)pyridin-2-yl)-4-((2R,5R)-5-methyltetrahydrofuran-2-yl)-1H-indazol-1-yl)pyridin-2-yl)methanol

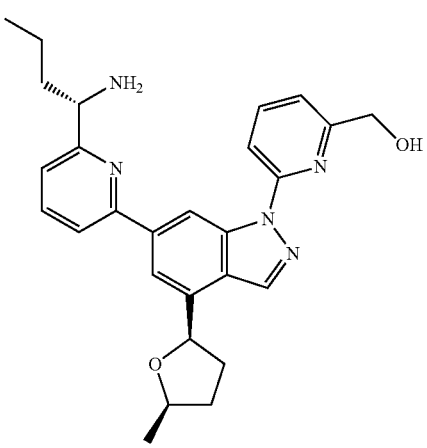 [SMILES: CCC[C@H](N)c1cccc(-c2cc([C@H]3CC[C@@H](C)O3)c3cnn(-c4cccc(CO)n4)c3c2)n1]

The title compound was synthesized in a similar fashion to that of (6-(6-(6-((S)-1-aminobutyl)pyridin-2-yl)-4-(tetrahydrofuran-2-yl)-1H-indazol-1-yl)pyridin-2-yl)methanol (Example 477) utilizing a two step procedure and the appropriate acid. MS m/z 458 (M+1) 1H NMR (400 MHz, METHANOL-d4) δ ppm 9.55 (d, J=1.0 Hz, 1H), 8.54 (s, 1H), 8.02-8.14 (m, 6H), 7.50-7.56 (m, 1H), 7.41-7.48 (m, 1H), 5.41 (td, J=7.4, 2.3 Hz, 1H), 4.62 (t, J=6.9 Hz, 1H), 4.34 (sxt, J=6.2 Hz, 1H), 2.54-2.68 (m, 1H), 2.25-2.36 (m, 1H), 2.00-2.16 (m, 3H), 1.71-1.85 (m, 1H), 1.52 (d, J=6.0 Hz, 4H), 1.04 (t, J=7.4 Hz, 4H)

Example 479. (6-(6-(6-((S)-1-aminobutyl)pyridin-2-yl)-4-((2S,5R)-5-methyltetrahydrofuran-2-yl)-1H-indazol-1-yl)pyridin-2-yl)methanol

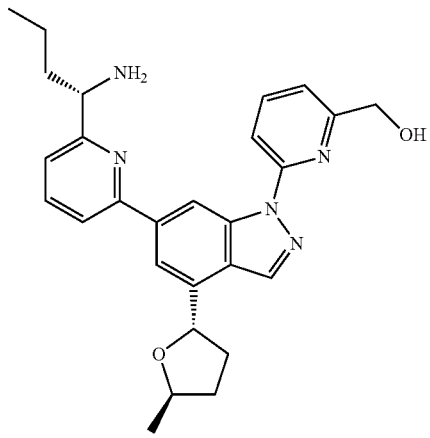 [SMILES: CCC[C@H](N)c1cccc(-c2cc([C@@H]3CC[C@@H](C)O3)c3cnn(-c4cccc(CO)n4)c3c2)n1]

The title compound was synthesized in a similar fashion to that of (6-(6-(6-((S)-1-aminobutyl)pyridin-2-yl)-4-(tetrahydrofuran-2-yl)-1H-indazol-1-yl)pyridin-2-yl)methanol (Example 477) utilizing a two step procedure and the appropriate acid. MS m/z 458 (M+1) 1H NMR (400 MHz, METHANOL-d4) δ ppm 9.59 (s, 1H), 8.49 (s, 1H), 8.01-8.14 (m, 12H), 7.51 (d, J=7.3 Hz, 1H), 7.43 (dd, J=6.1, 2.1 Hz, 1H), 5.58 (dd, J=8.3, 6.8 Hz, 1H), 4.60 (t, J=6.5 Hz, 2H), 2.62-2.76 (m, 1H), 2.29-2.41 (m, 1H), 2.00-2.18 (m, 4H), 1.78-1.91 (m, 1H), 1.44 (d, J=6.0 Hz, 4H), 1.04 (t, J=7.3 Hz, 4H)

Example 480 (S)-(6-(6-(6-(1-aminobutyl)pyridin-2-yl)-4-(2-methoxyethoxy)-1H-indazol-1-yl)pyrazin-2-yl)methanol Step 1. Synthesis of 4-bromo-2-fluoro-6-(2-methoxyethoxy)benzaldehyde

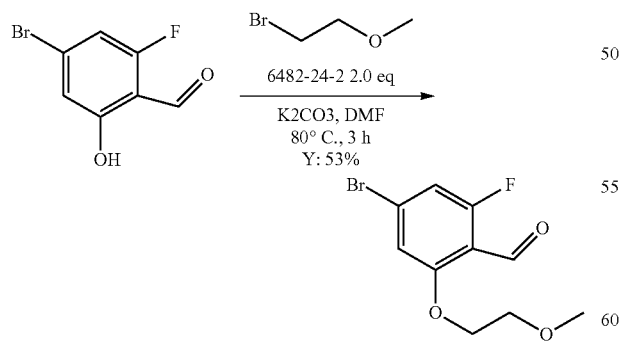

A mixture of 4-bromo-2-fluoro-6-hydroxybenzaldehyde (12.0 g, 55.3 mmol, 1.0 eq), 6482-24-2 (15.2 g, 110.6 mmol, 2.0 eq), K$_2$CO$_3$ (15.3 g, 110.6 mmol, 2.0 eq) in DMF (60 mL) was stirred at 80° C. for 3 h. The mixture was quenched with water (300 mL) and extracted with DCM (3×100 mL). After concentration, the residue was purified by column chromatography on silica gel (PE/EA=5/1) to give 4-bromo-2-fluoro-6-(2-methoxyethoxy)benzaldehydeas a yellow solid. 8.1 g, Y: 53%. ESI-MS (M+H)$^+$: 277.0.

Step 2. Synthesis of 6-bromo-4-(2-methoxyethoxy)-1H-indazole

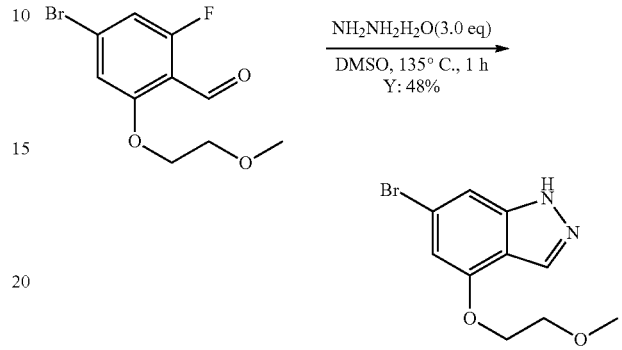

A mixture of 4-bromo-2-fluoro-6-(2-methoxyethoxy)benzaldehyde (8.1 g, 29.1 mmol, 1.0 eq), NH$_2$NH$_2$H$_2$O (4.37 g, 87.3 mmol, 3.0 eq) in DMSO (80 mL) was stirred at 135° C. for 1 h. The mixture was quenched with water (400 mL) and extracted with DCM (3×100 mL). The organic phase was washed with brine and dried over Na$_2$SO$_4$. After filtration and concentration, the residue was purified by column chromatography on silica gel (PE/EA=5/1) to give 6-bromo-4-(2-methoxyethoxy)-1H-indazole as a white solid. 3.8 g, Y: 48%. ESI-MS (M+H)$^+$: 271.0.

Step 3. Synthesis of methyl 6-(6-bromo-4-(2-methoxyethoxy)-1H-indazol-1-yl)pyrazine-2-carboxylate

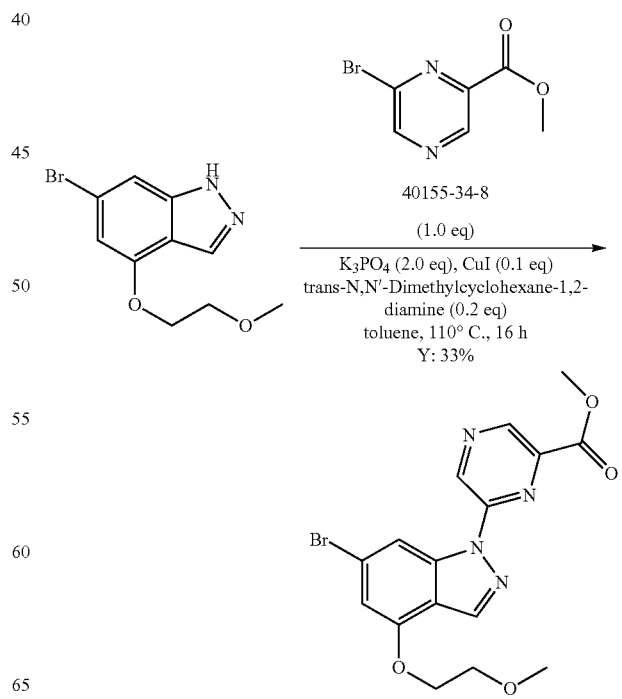

A mixture of 6-bromo-4-(2-methoxyethoxy)-1H-indazole (4.0 g, 14.8 mmol, 1.0 eq), 40155-34-8 (3.19 g, 14.8 mmol, 1.0 eq), K$_3$PO$_4$ (6.28 g, 29.6 mmol, 2.0 eq), CuI (284 mg, 1.48 mmol, 0.1 eq) and trans-N,N'-Dimethylcyclohexane-1,2-diamine (420 mg, 2.96 mmol, 0.2 eq) in toluene (30 mL) was stirred at 110° C. for 16 h under N$_2$. After concentration, the residue was purified by column chromatography on silica gel (PE/EA=3/1) to give methyl 6-(6-bromo-4-(2-methoxyethoxy)-1H-indazol-1-yl)pyrazine-2-carboxylate as a white solid. 2.0 g, Y: 33%. ESI-MS (M+H)$^+$: 407.0. $^1$H NMR (400 MHz, CDCl$_3$) δ: 9.55 (s, 1H), 9.12 (s, 1H), 8.73 (s, 1H), 8.32 (d, J=4.8 Hz, 1H), 6.85 (s, 1H), 4.32-4.30 (m, 2H), 4.11 (s, 3H), 3.88-3.86 (m, 2H), 3.50 (s, 3H).

Step 4. Synthesis of (6-(6-bromo-4-(2-methoxyethoxy)-1H-indazol-1-yl)pyrazin-2-yl)methanol

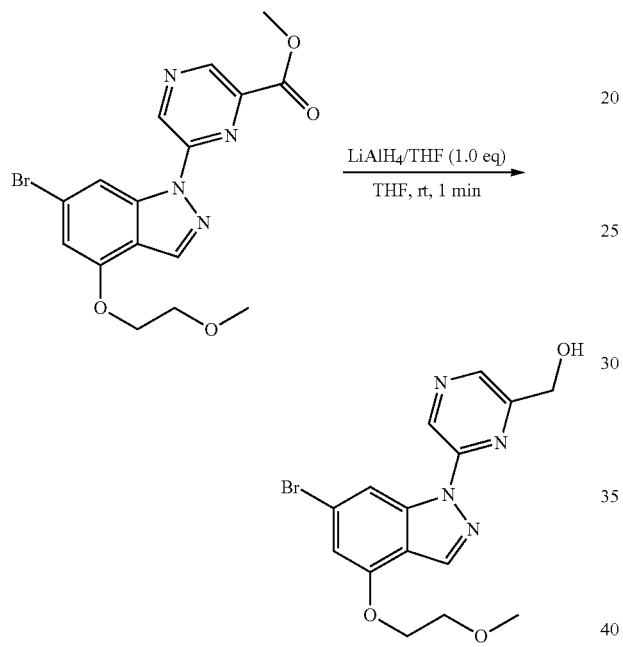

To a solution of methyl 6-(6-bromo-4-(2-methoxyethoxy)-1H-indazol-1-yl)pyrazine-2-carboxylate (400 mg, 1.0 mmol, 1.0 eq) in THF (10 mL) was added LiAlH$_4$ (1.0 mL, 1.0 mmol, 1.0 eq, 1 M in THF) at rt. The mixture was stirred at rt for 1 min. The reaction was quenched with Na$_2$SO$_4$ 10H$_2$O. After filtration and concentrated to give (6-(6-bromo-4-(2-methoxyethoxy)-1H-indazol-1-yl)pyrazin-2-yl)methanol, which was directly used for next step without further purification. ESI-MS (M+H)$^+$: 379.0

Step 5. Synthesis of 6-bromo-1-(6-(((tert-butyldimethylsilyl)oxy)methyl)pyrazin-2-yl)-4-(2-methoxyethoxy)-1H-indazole

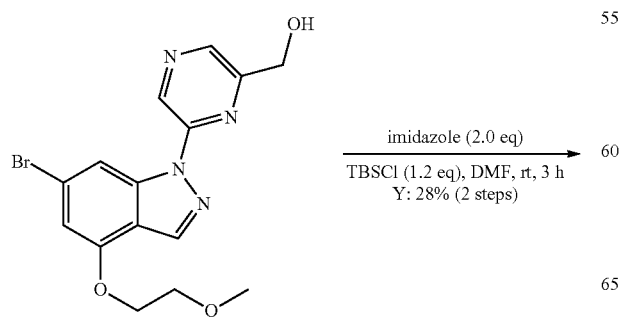

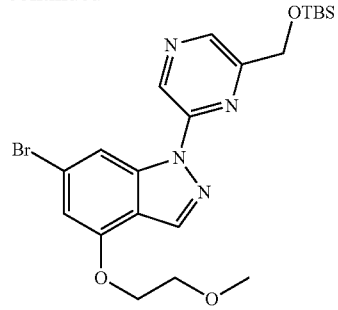

To a mixture of give (6-(6-bromo-4-(2-methoxyethoxy)-1H-indazol-1-yl)pyrazin-2-yl)methanol, and imidazole (432 mg, 6.36 mmol, 2.0 eq) in DMF (25 mL) was added TBSCl (572 mg, 3.82 mol, 1.2 eq) at rt. The mixture was stirred at rt for 3 h. The mixture was diluted with water (300 mL) and extracted with DCM (3×90 mL). The combined organic phases were washed with brine and dried over Na$_2$SO$_4$. After filtration and concentration, the residue was purified by column chromatography on silica gel (PE/EA=10/1) to give 6-bromo-1-(6-(((tert-butyldimethylsilyl)oxy)methyl)pyrazin-2-yl)-4-(2-methoxyethoxy)-1H-indazole as a yellow solid. 700 mg, Y: 28% (2 steps). ESI-MS (M+H)$^+$: 493.1. $^1$H NMR (400 MHz, CDCl$_3$) δ: 9.27 (s, 1H), 8.61 (s, 1H), 8.48 (s, 1H), 8.29 (s, 1H), 6.80 (s, 1H), 4.96 (s, 2H), 4.31-4.29 (m, 2H), 3.87-3.85 (m, 2H), 3.50 (s, 3H), 1.00 (s, 9H), 0.21 (s, 6H).

Step 6. Synthesis of 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole

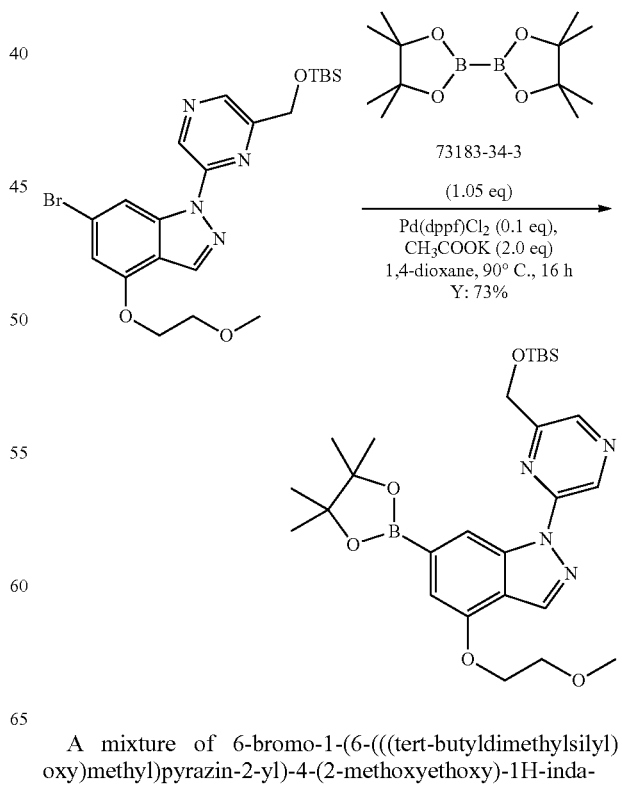

A mixture of 6-bromo-1-(6-(((tert-butyldimethylsilyl)oxy)methyl)pyrazin-2-yl)-4-(2-methoxyethoxy)-1H-indazole (350 mg, 0.71 mmol, 1.0 eq), 73183-34-3 (190 mg, 0.75 mmol, 1.05 eq), Pd(dppf)Cl$_2$ (58 mg, 0.071 mmol, 0.1 eq) and CH$_3$COOK (139 mg, 1.42 mmol, 2.0 eq) in 1,4-dioxane (10 mL) stirred at 90° C. for 16 h under N$_2$. After concentration, the residue was purified by column chromatography on silica gel (PE/EA=5/1) to give 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole as a yellow solid. 280 mg, Y: 73%. ESI-MS (M+H)$^+$: 541.3.

Step 7. Synthesis of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide

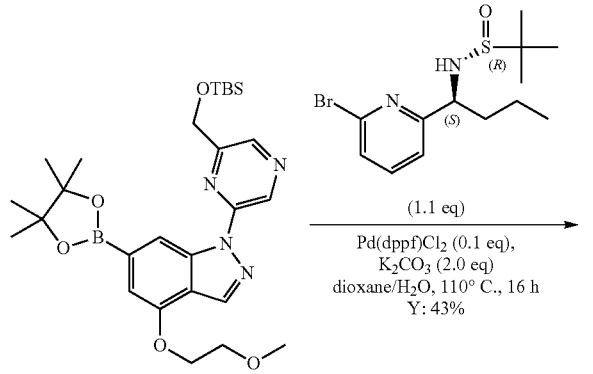

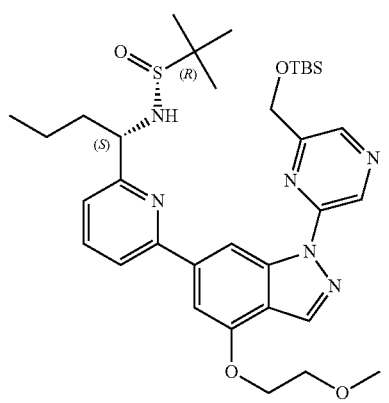

A mixture of 1-(6-(((tert-butyldimethylsilyl)oxy)methyl)pyrazin-2-yl)-4-(2-methoxyethoxy)-6-(4,4,5,5-tetramethyl-1,3,2-dioxaborolan-2-yl)-1H-indazole (280 mg, 0.52 mmol, 1.0 eq), (R)—N—((S)-1-(6-bromopyridin-2-yl)butyl)-2-methylpropane-2-sulfinamide (189 mg, 0.57 mmol, 1.1 eq), Pd(dppf)Cl$_2$ (42 mg, 0.052 mmol, 0.1 eq) and K$_2$CO$_3$ (143 mg, 1.04 mmol, 2.0 eq) in dioxane/H$_2$O (15 mL/2 mL) was stirred at 110° C. for 16 h under N$_2$. After concentration, the residue was purified by column chromatography on silica gel (PE/EA=1/1) to give (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide as a yellow solid. 150 mg, Y: 43%. ESI-MS (M+H)$^+$: 667.3.

Step 8. Synthesis of (S)-(6-(6-(6-(1-aminobutyl)pyridin-2-yl)-4-(2-methoxyethoxy)-1H-indazol-1-yl)pyrazin-2-yl)methanol

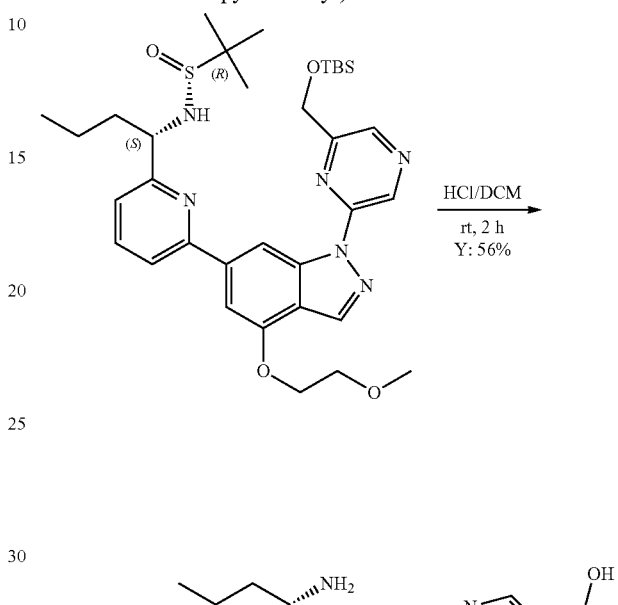

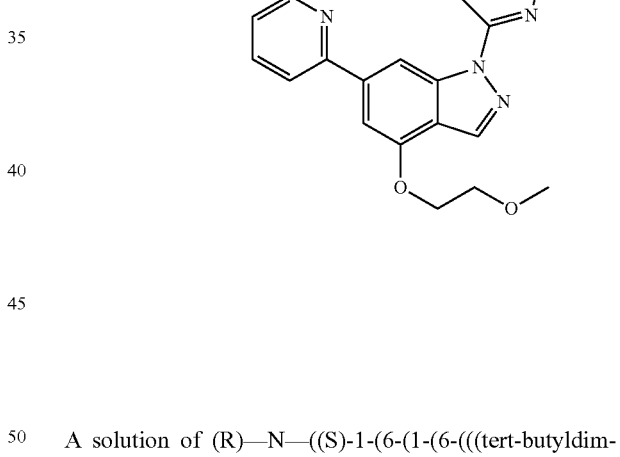

A solution of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide (150 mg, 0.23 mmol, 1.0 eq) in DCM (8 mL) was added conc. HCl (0.8 mL). The mixture was stirred at rt for 2 h. After concentration, the residue was recrystallized from DCM (20 mL) to give (S)-(6-(6-(6-(1-aminobutyl)pyridin-2-yl)-4-(2-methoxyethoxy)-1H-indazol-1-yl)pyrazin-2-yl)methanol. 61 mg, as a yellow solid, Y: 56%. ESI-MS (M+H)$^+$: 449.2. HPLC: 96%. $^1$H NMR (400 MHz, CD$_3$OD) δ: 9.17 (s, 1H), 9.07 (s, 1H), 8.50 (s, 1H), 8.38 (s, 1H), 8.02 (d, J=7.6 Hz, 1H), 7.97 (t, J=7.2 Hz, 1H), 7.58 (s, 1H), 7.42 (d, J=7.2 Hz, 1H), 4.88 (s, 2H), 4.53 (t, J=6.8 Hz, 1H), 4.46-4.44 (m, 2H), 3.90-3.88 (m, 2H), 3.47 (s, 3H), 2.02-1.98 (m, 2H), 1.42-1.39 (m, 2H), 0.98 (t, J=7.2 Hz, 3H).

623

Example 481 (S)-(6-(6-(6-(1-aminoethyl)pyridin-2-yl)-4-(2-methoxyethoxy)-1H-indazol-1-yl)pyrazin-2-yl)methanol Synthesis of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)ethyl)-2-methylpropane-2-sulfinamide

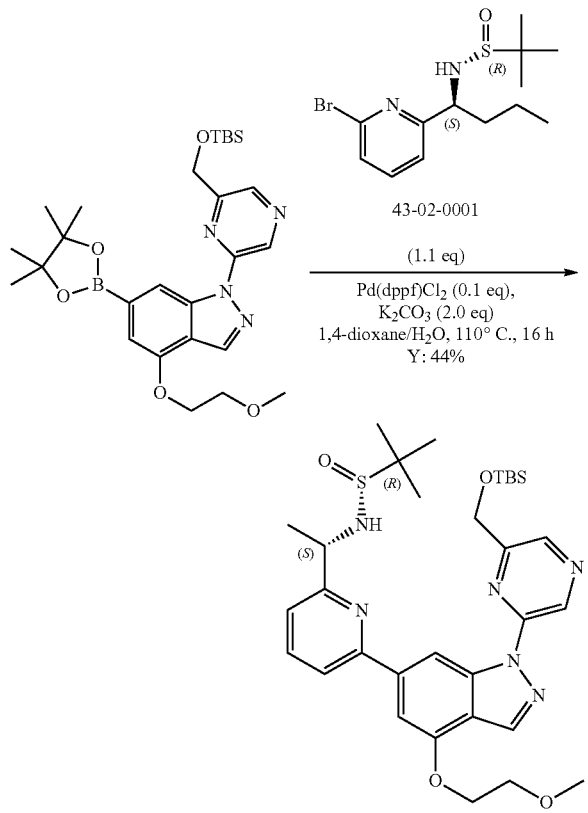

The preparation of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)ethyl)-2-methylpropane-2-sulfinamide was similar to that of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide (Example 480, Step 7) to give 140 mg as a yellow solid, Y: 44%. ESI-MS (M+H)$^+$: 639.3.

Synthesis of (S)-(6-(6-(6-(1-aminoethyl)pyridin-2-yl)-4-(2-methoxyethoxy)-1H-indazol-1-yl)pyrazin-2-yl)methanol

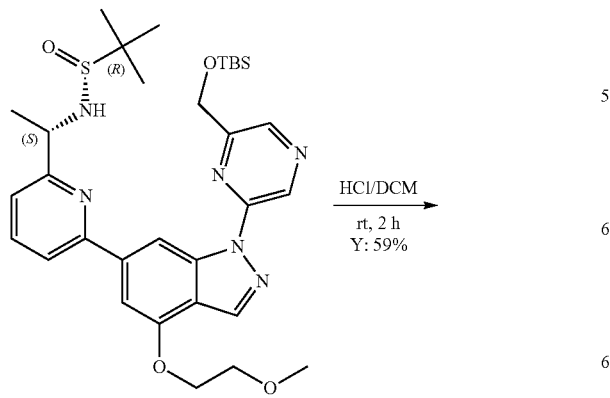

624

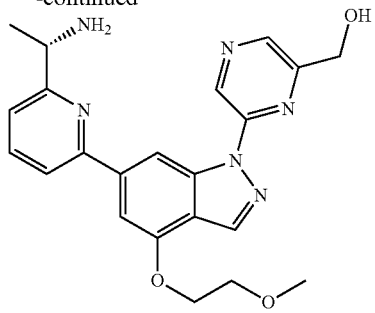

The preparation of (S)-(6-(6-(6-(1-aminoethyl)pyridin-2-yl)-4-(2-methoxyethoxy)-1H-indazol-1-yl)pyrazin-2-yl)methanol was similar to that of (S)-(6-(6-(6-(1-aminobutyl)pyridin-2-yl)-4-(2-methoxyethoxy)-1H-indazol-1-yl)pyrazin-2-yl)methanol (Example 480, Step 8) to give 59 mg as a yellow solid, Y: 59%. ESI-MS (M+H)$^+$: 421.2. HPLC: 97%. $^1$H NMR (400 MHz, CD$_3$OD) δ: 9.20 (s, 1H), 9.11 (s, 1H), 8.51 (s, 1H), 8.39 (s, 1H), 8.04 (d, J=7.6 Hz, 1H), 7.98 (t, J=7.6 Hz, 1H), 7.63 (s, 1H), 7.45 (d, J=7.6 Hz, 1H), 4.89 (s, 2H), 4.68 (q, J=7.2 Hz, 1H), 4.47-4.44 (m, 2H), 3.90-3.88 (m, 2H), 3.47 (s, 3H), 1.69 (d, J=7.2 Hz, 3H).

Example 482 (S)-(6-(6-(6-(1-aminopropyl)pyridin-2-yl)-4-(2-methoxyethoxy)-1H-indazol-1-yl)pyrazin-2-yl)methanol Synthesis of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)propyl)-2-methylpropane-2-sulfinamide

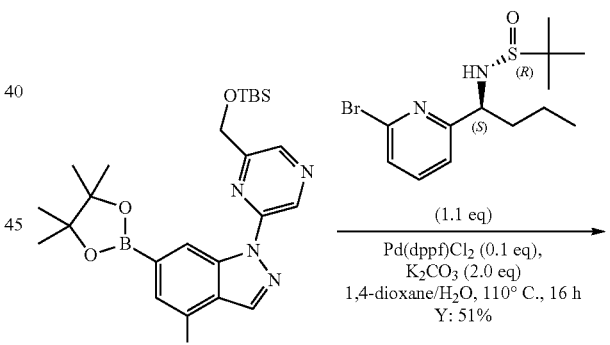

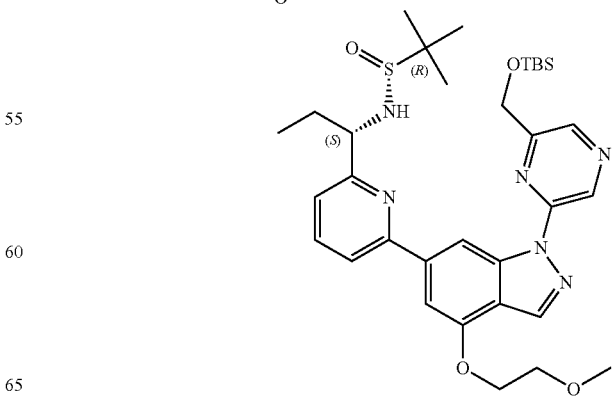

The preparation of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)propyl)-2-methylpropane-2-sulfinamide was similar to that of (R)—N—((S)-1-(6-(1-(6-(((tert-butyldimethylsilyl)oxy)methyl)pyrazin-2-yl)-4-(2-methoxyethoxy)-1H-indazol-6-yl)pyridin-2-yl)butyl)-2-methylpropane-2-sulfinamide (Example 480, Step 7) to give 160 mg as a yellow solid, Y: 51%. ESI-MS (M+H)+: 653.3.

Synthesis of (S)-(6-(6-(6-(1-aminopropyl)pyridin-2-yl)-4-(2-methoxyethoxy)-1H-indazol-1-yl)pyrazin-2-yl)methanol

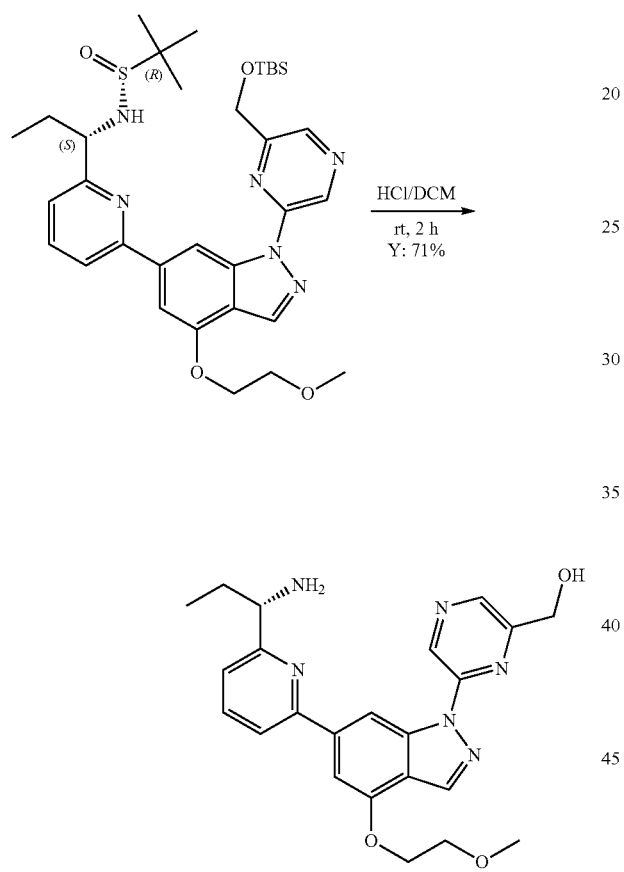

The preparation of (S)-(6-(6-(6-(1-aminopropyl)pyridin-2-yl)-4-(2-methoxyethoxy)-1H-indazol-1-yl)pyrazin-2-yl)methanol was similar to that of (S)-(6-(6-(6-(1-aminobutyl)pyridin-2-yl)-4-(2-methoxyethoxy)-1H-indazol-1-yl)pyrazin-2-yl)methanol to give 82 mg as a yellow solid, Y: 71%. ESI-MS (M+H)+: 435.2. HPLC: 98%. 1H NMR (400 MHz, CD3OD) δ: 9.22 (s, 1H), 9.13 (s, 1H), 8.53 (s, 1H), 8.41 (s, 1H), 8.06 (d, J=8.0 Hz, 1H), 8.01-7.98 (m, 1H), 7.61 (s, 1H), 7.44 (d, J=7.6 Hz, 1H), 4.91 (s, 2H), 4.48-4.47 (m, 3H), 3.92-3.90 (m, 2H), 3.49 (s, 3H), 2.10-2.07 (m, 2H), 1.02 (t, J=7.2 Hz, 3H).

Example 483 (6-{6-[6-((S)-1-Amino-butyl)-pyridin-2-yl]-4-isopropoxy-indazol-1-yl}-pyridin-2-yl)-methanol Synthesis of 6-Bromo-1-[6-(tert-butyl-dimethyl-silanyloxymethyl)-pyridin-2-yl]-4-isopropoxy-1H-indazole

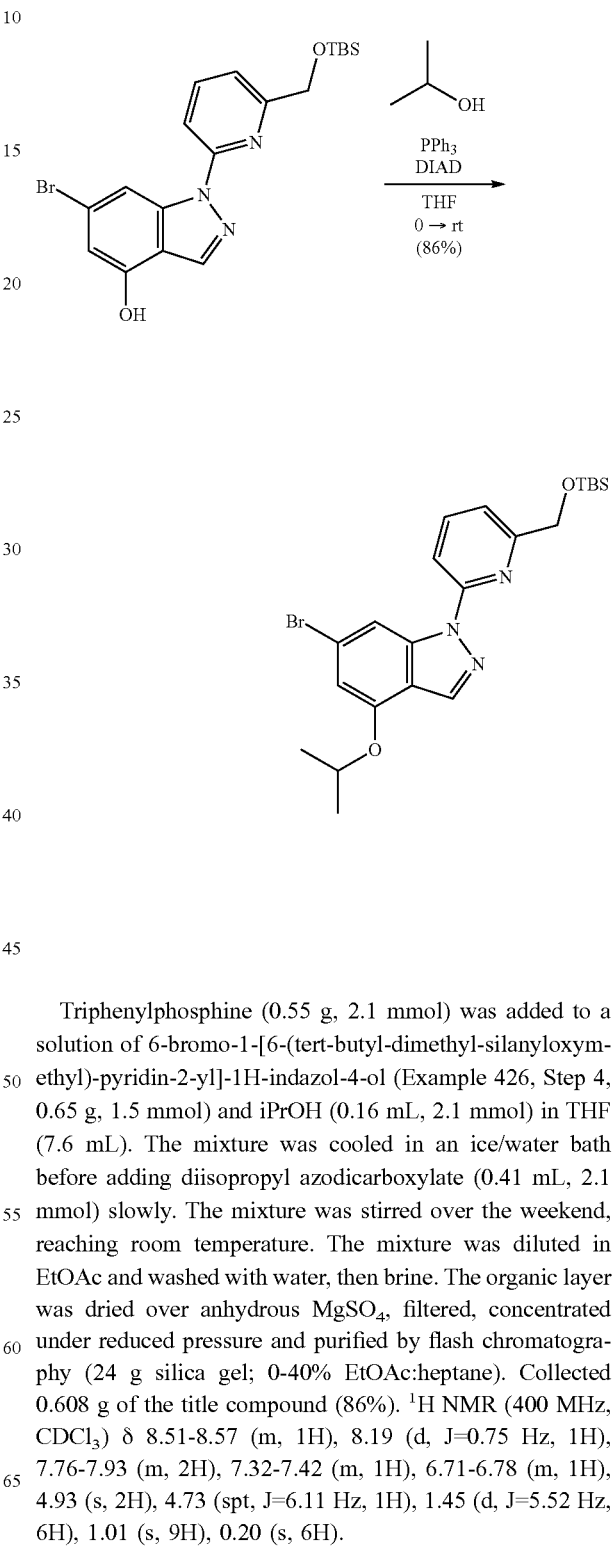

Triphenylphosphine (0.55 g, 2.1 mmol) was added to a solution of 6-bromo-1-[6-(tert-butyl-dimethyl-silanyloxymethyl)-pyridin-2-yl]-1H-indazol-4-ol (Example 426, Step 4, 0.65 g, 1.5 mmol) and iPrOH (0.16 mL, 2.1 mmol) in THF (7.6 mL). The mixture was cooled in an ice/water bath before adding diisopropyl azodicarboxylate (0.41 mL, 2.1 mmol) slowly. The mixture was stirred over the weekend, reaching room temperature. The mixture was diluted in EtOAc and washed with water, then brine. The organic layer was dried over anhydrous MgSO4, filtered, concentrated under reduced pressure and purified by flash chromatography (24 g silica gel; 0-40% EtOAc:heptane). Collected 0.608 g of the title compound (86%). 1H NMR (400 MHz, CDCl3) δ 8.51-8.57 (m, 1H), 8.19 (d, J=0.75 Hz, 1H), 7.76-7.93 (m, 2H), 7.32-7.42 (m, 1H), 6.71-6.78 (m, 1H), 4.93 (s, 2H), 4.73 (spt, J=6.11 Hz, 1H), 1.45 (d, J=5.52 Hz, 6H), 1.01 (s, 9H), 0.20 (s, 6H).

Synthesis of 2-Methyl-propane-2-sulfinic acid [(S)-1-(6-{1-[6-(tert-butyl-dimethyl-silanyloxymethyl)-pyridin-2-yl]-4-isopropoxy-1H-indazol-6-yl}-pyridin-2-yl)-butyl]-amide

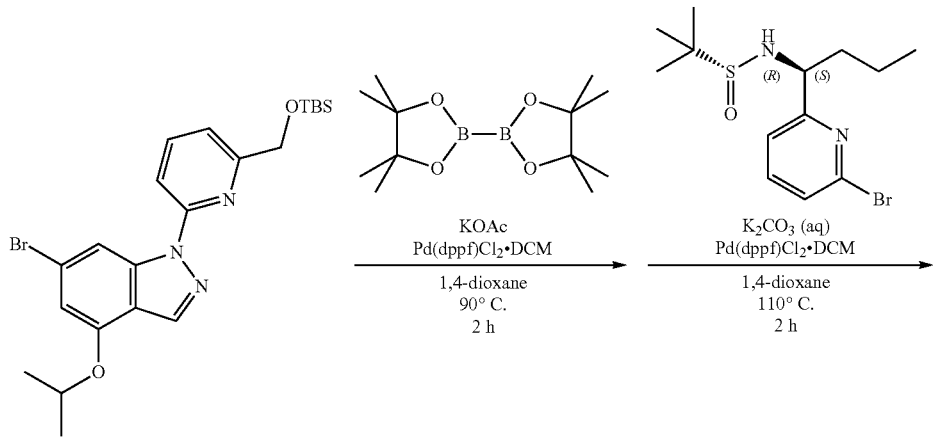

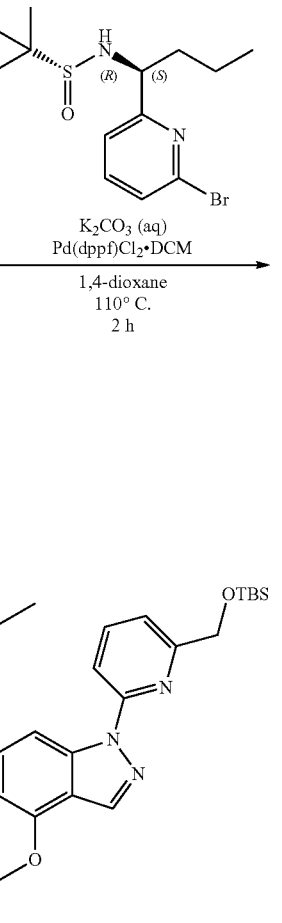

6-Bromo-1-[6-(tert-butyl-dimethyl-silanyloxymethyl)-pyridin-2-yl]-4-isopropoxy-1H-indazole (0.239 g, 0.501 mmol), bis(pinacolato)diboron (0.140 g, 0.551 mmol), KOAc (0.148 g, 1.51 mmol), [1,1'-bis(diphenylphosphino)ferrocene]dichloropalladium(II), complex with DCM (40.9 mg, 0.0501 mmol), and 1,4-dioxane (3 mL) were charged to a vial and heated at 90° C. for 2 hours. Cooled reaction to room temperature and added 2-methyl-propane-2-sulfinic acid [(S)-1-(6-bromo-pyridin-2-yl)-butyl]-amide (Example 145, Step 5. 0.200 g, 0.601 mmol), [1,1'-bis(diphenylphosphino)ferrocene]dichloropalladium(II), complex with DCM (40.9 mg, 0.0501 mmol) $K_2CO_3$ (0.138 g, 1.00 mmol), and $H_2O$ (2 mL). The mixture was then heated at 110° C. for 2 h. Cooled to rt. Added EtOAc and $H_2O$ before filtering through Celite. The organic phase was washed with brine, dried over $MgSO_4$, filtered and evaporated to dryness under reduced pressure. The crude product was purified by flash chromatography (silica gel, 0-10% MeOH:DCM) to give the title compound (0.38 g, 95%).

ES (+) MS m/e=651 (M+1).

Synthesis of (6-{6-[6-((S)-1-Amino-butyl)-pyridin-2-yl]-4-isopropoxy-indazol-1-yl}-pyridin-2-yl)-methanol)

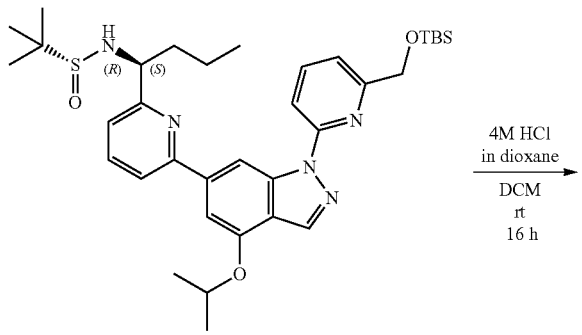

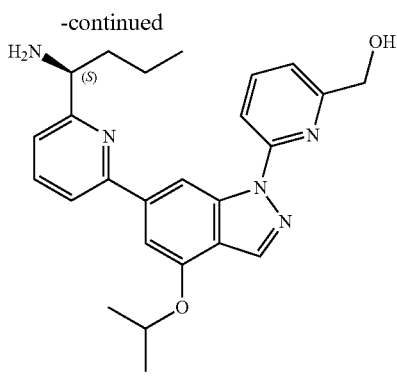

A solution of 2-methyl-propane-2-sulfinic acid [(S)-1-(6-{1-[6-(tert-butyl-dimethyl-silanyloxymethyl)-pyridin-2-yl]-4-isopropoxy-1H-indazol-6-yl}-pyridin-2-yl)-butyl]-amide (0.368 g, 0.567 mmol) in DCM (5 mL) was treated with 4 M of HCl in 1,4-dioxane (1 mL). The reaction mixture was allowed to stir overnight at rt. The reaction was then concentrated to dryness under reduced pressure. The resulting residue was dissolved in MeCN (2 mL), H₂O (0.5 mL) with a few drops of TFA prior to purification by prep HPLC. Collected the title compound as a TFA salt (65 mg). ES (+) MS m/e=432 (M+1) ¹H NMR (400 MHz, CDCl₃) δ 9.25 (s, 1H), 8.21 (d, J=0.63 Hz, 1H), 7.79-7.89 (m, 2H), 7.61-7.66 (m, 1H), 7.42-7.50 (m, 1H), 7.22-7.27 (m, 1H), 7.06-7.11 (m, 1H), 6.57-6.63 (m, 1H), 4.86-4.96 (m, 1H), 4.55-4.74 (m, 2H), 1.93-2.17 (m, 2H), 1.57 (d, J=6.02 Hz, 3H), 1.53 (d, J=6.02 Hz, 3H), 1.26-1.44 (m, 2H), 0.88-0.95 (m, 3H)

Example 484 (S)-4-amino-4-(6-(1-(6-(hydroxymethyl)pyridin-2-yl)-4-(2-methoxyethoxy)-1H-indazol-6-yl)pyridin-2-yl)butan-1-ol Step 1. Synthesis of (R)—N—((S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)butyl)-2-methylpropane-2-sulfinamide A mixture of 1-(6-(((tert-butyldimethylsilyl)oxy)methyl)pyridin-2-yl)-4-(2-methoxyethoxy)-6-(4,4,5,5-tetramethyl-1,3,2-dioxaborolan-2-yl)-1H-indazole (Example 453, Step 2, 260 mg, 0.48 mmol, 1.0 eq), (R)—N—((S)-1-(6-bromopyridin-2-yl)-4-((tert-butyldimethylsilyl)oxy)butyl)-2-methylpropane-2-sulfinamide (Example 428, Step 7D, 222 mg, 0.48 mmol, 1.0 eq) and K₂CO₃ (132 mg, 0.96 mmol, 2.0 eq) in 1,4-dioxane/H₂O (20 mL/0.5 mL) was stirred while purging N₂ at rt for 10 min. To this system was added Pd(dppf)Cl₂ (39 mg, 0.048 mmol, 0.1 eq) and heated to 110° C. for 4 h. After concentration, the residue was purified by silica gel chromatography using PE/EA (2/1) as eluent to give (R)—N—((S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)butyl)-2-methylpropane-2-sulfinamide. 160 mg, as a yellow solid, Y: 42%. ESI-MS (M+H)⁺: 796.5.

Step 2. Synthesis of (S)-4-amino-4-(6-(1-(6-(hydroxymethyl)pyridin-2-yl)-4-(2-methoxyethoxy)-1H-indazol-6-yl)pyridin-2-yl)butan-1-ol

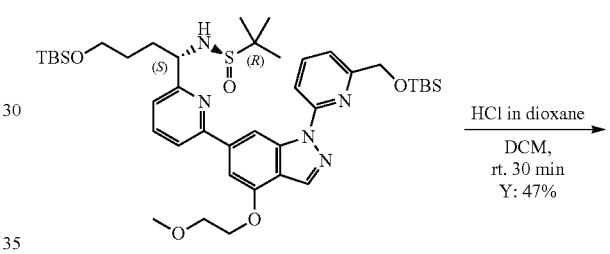

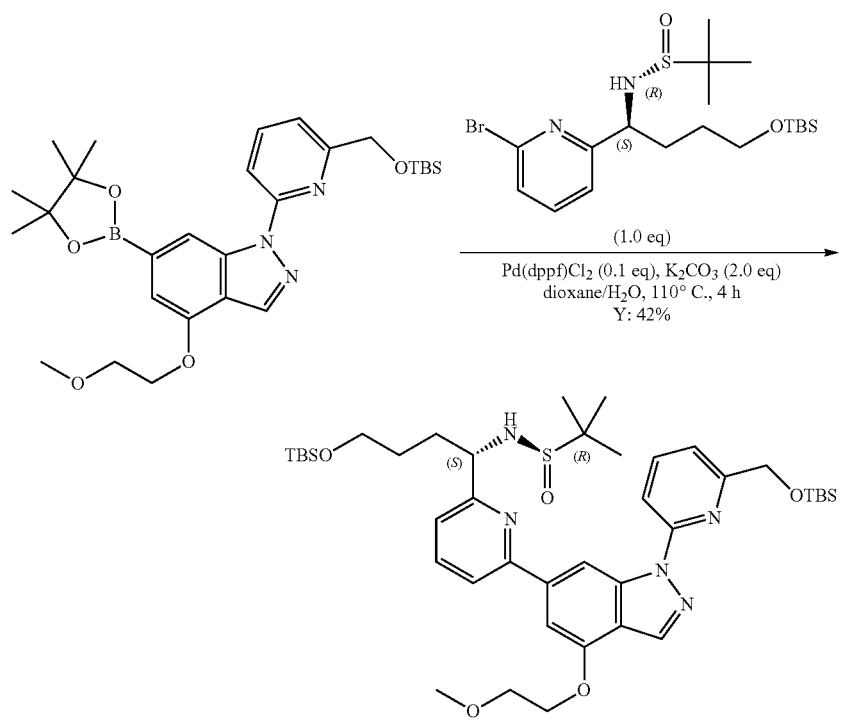

-continued

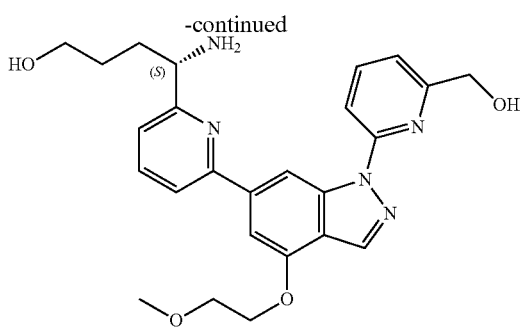

To a solution of (R)—N—((S)-4-((tert-butyldimethylsilyl)oxy)-1-(6-(1-(6-(((tert-butyldimethylsilyl)oxy)methyl)pyridin-2-yl)-4-(2-methoxyethoxy)-1H-indazol-6-yl)pyridin-2-yl)butyl)-2-methylpropane-2-sulfinamide (160 mg, 0.2 mmol, 1.0 eq) in DCM (10 mL) was added HCl in dioxane (0.5 mL). The mixture was stirred at rt for 0.5 h. After concentration, the residue dissolved in THF, adjusted pH=7-8 with NaOH solution and extracted with EA (2×50 mL). The combined organic phase was washed with brine and dried over $Na_2SO_4$. After filtration and concentration, the residue was purified by prep-HPLC (MeCN/$H_2O$ with 0.05% TFA as mobile phase from 5% to 95%) to give (S)-4-amino-4-(6-(1-(6-(hydroxymethyl)pyridin-2-yl)-4-(2-methoxyethoxy)-1H-indazol-6-yl)pyridin-2-yl)butan-1-ol. 55 mg (TFA salt), as a yellow solid, Y: 47%. ESI-MS (M+H)$^+$: 464.2. $^1$H NMR (400 MHz, $CD_3OD$) δ: 9.29 (s, 1H), 8.36 (s, 1H), 8.09-7.94 (m, 4H), 7.59 (s, 1H), 7.47 (d, J=7.6 Hz, 1H), 7.37 (d, J=6.4 Hz, 1H), 4.88 (s, 2H), 4.61 (t, J=6.8 Hz, 1H), 4.55-4.38 (m, 2H), 4.03-3.86 (m, 2H), 3.65 (t, J=6.0 Hz, 2H), 3.54 (s, 3H), 2.22-2.14 (m, 2H), 1.70-1.61 (m, 2H).

The following compounds were also synthesized using a synthesis as indicated in the table below.

| Example # | Structure | Compound name | similar to synthesis |
|---|---|---|---|
| 485 | 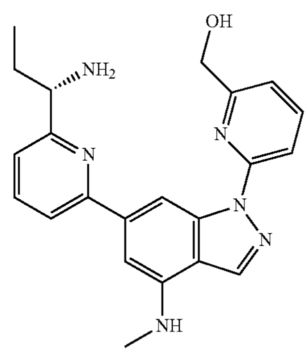 [SMILES: CC[C@H](N)c1cccc(-c2cc(NC)c3cnn(-c4cccc(CO)n4)c3c2)n1] | (S)-(6-(6-(6-(1-aminopropyl)pyridin-2-yl)-4-(methylamino)-1H-indazol-1-yl)pyridin-2-yl)methanol | example 101 |
| 486 | 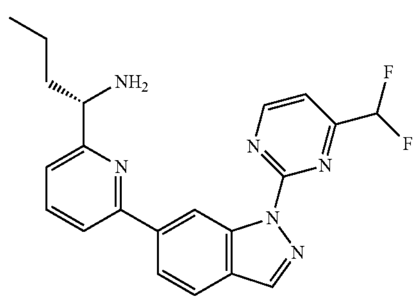 [SMILES: CCC[C@H](N)c1cccc(-c2ccc3cnn(-c4nccc(C(F)F)n4)c3c2)n1] | (S)-1-(6-(1-(4-(difluoromethyl)pyrimidin-2-yl)-1H-indazol-6-yl)pyridin-2-yl)butan-1-amine | example 145 |
| 487 | 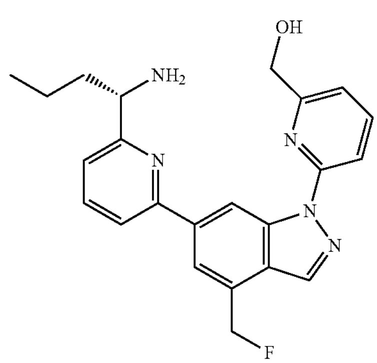 [SMILES: CCC[C@H](N)c1cccc(-c2cc(CF)c3cnn(-c4cccc(CO)n4)c3c2)n1] | (S)-(6-(6-(6-(1-aminobutyl)pyridin-2-yl)-4-(fluoromethyl)-1H-indazol-1-yl)pyridin-2-yl)methanol | example 114 |

-continued

| Example # | Structure | Compound name | similar to synthesis |
|---|---|---|---|
| 488 | 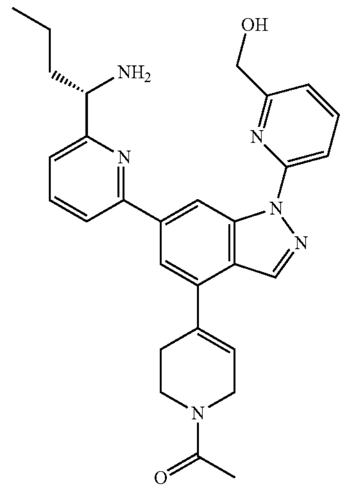 [SMILES: CCC[C@H](N)c1cccc(-c2cc(C3=CCN(C(C)=O)CC3)c3cnn(-c4cccc(CO)n4)c3c2)n1] | (S)-1-(4-(6-(6-(1-aminobutyl)pyridin-2-yl)-1-(6-(hydroxymethyl)pyridin-2-yl)-1H-indazol-4-yl)-5,6-dihydropyridin-1(2H)-yl)ethanone | example 424 |
| 489 | 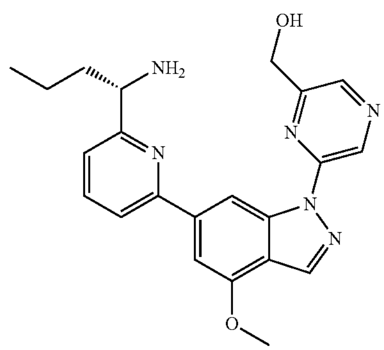 [SMILES: CCC[C@H](N)c1cccc(-c2cc(OC)c3cnn(-c4cncc(CO)n4)c3c2)n1] | (S)-(6-(6-(6-(1-aminobutyl)pyridin-2-yl)-4-methoxy-1H-indazol-1-yl)pyrazin-2-yl)methanol | example 410 |
| 490 | 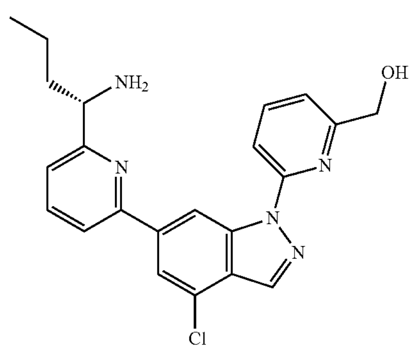 [SMILES: CCC[C@H](N)c1cccc(-c2cc(Cl)c3cnn(-c4cccc(CO)n4)c3c2)n1] | (S)-(6-(6-(6-(1-aminobutyl)pyridin-2-yl)-4-chloro-1H-indazol-1-yl)pyridin-2-yl)methanol | example 473 |
| 491 | 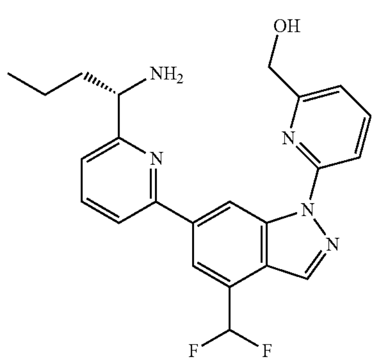 [SMILES: CCC[C@H](N)c1cccc(-c2cc(C(F)F)c3cnn(-c4cccc(CO)n4)c3c2)n1] | (S)-(6-(6-(6-(1-aminobutyl)pyridin-2-yl)-4-(difluoromethyl)-1H-indazol-1-yl)pyridin-2-yl)methanol | example 114 |

-continued

| Example # | Structure | Compound name | similar to synthesis |
|---|---|---|---|
| 492 | 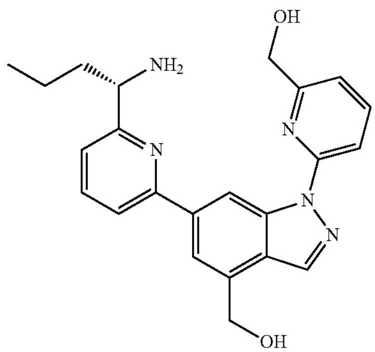 [SMILES: CCC[C@H](N)c1cccc(-c2cc(CO)c3cnn(-c4cccc(CO)n4)c3c2)n1] | (S)-(6-(6-(1-aminobutyl)pyridin-2-yl)-1-(6-(hydroxymethyl)pyridin-2-yl)-1H-indazol-4-yl)methanol | example 114 |
| 493 | 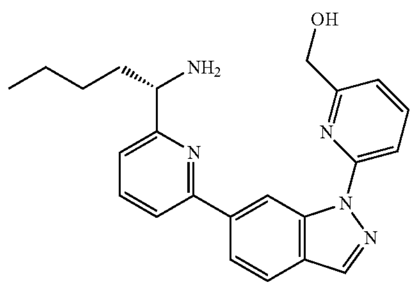 [SMILES: CCCC[C@H](N)c1cccc(-c2ccc3cnn(-c4cccc(CO)n4)c3c2)n1] | (S)-(6-(6-(6-(1-aminopentyl)pyridin-2-yl)-1H-indazol-1-yl)pyridin-2-yl)methanol | example 404 |
| 494 | 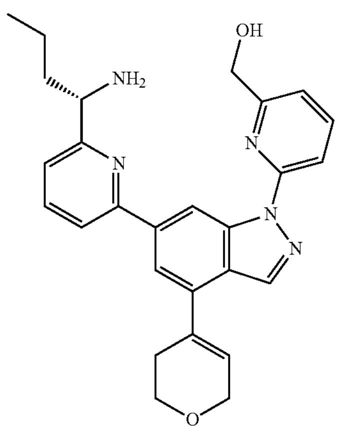 [SMILES: CCC[C@H](N)c1cccc(-c2cc(C3=CCOCC3)c3cnn(-c4cccc(CO)n4)c3c2)n1] | (S)-(6-(6-(6-(1-aminobutyl)pyridin-2-yl)-4-(3,6-dihydro-2H-pyran-4-yl)-1H-indazol-1-yl)pyridin-2-yl)methanol | example 424 |
| 495 | 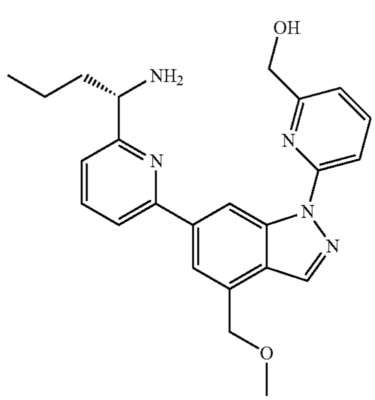 [SMILES: CCC[C@H](N)c1cccc(-c2cc(COC)c3cnn(-c4cccc(CO)n4)c3c2)n1] | (S)-(6-(6-(6-(1-aminobutyl)pyridin-2-yl)-4-(methoxymethyl)-1H-indazol-1-yl)pyridin-2-yl)methanol | example 114 |

-continued

| Example # | Structure | Compound name | similar to synthesis |
|---|---|---|---|
| 496 | 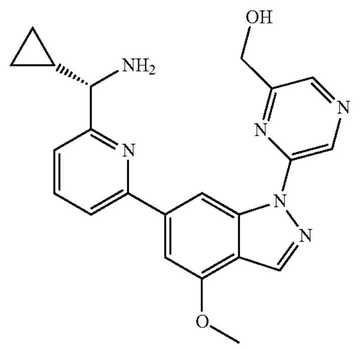 [SMILES: COc1cc(-c2cccc([C@@H](N)C3CC3)n2)cc2c1cnn2-c1cncc(CO)n1] | (S)-(6-(6-(6-(amino(cyclopropyl)methyl)pyridin-2-yl)-4-methoxy-1H-indazol-1-yl)pyrazin-2-yl)methanol | example 410 |
| 497 | 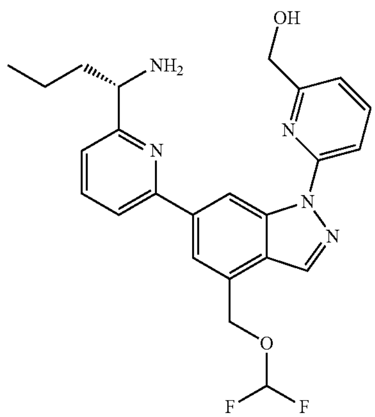 [SMILES: CCC[C@H](N)c1cccc(-c2cc(COC(F)F)c3cnn(-c4cccc(CO)n4)c3c2)n1] | (S)-(6-(6-(6-(1-aminobutyl)pyridin-2-yl)-4-((difluoromethoxy)methyl)-1H-indazol-1-yl)pyridin-2-yl)methanol | example 114 |
| 498 | 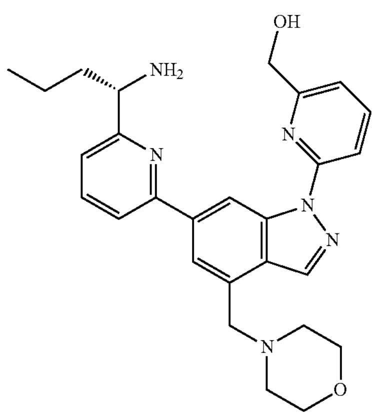 [SMILES: CCC[C@H](N)c1cccc(-c2cc(CN3CCOCC3)c3cnn(-c4cccc(CO)n4)c3c2)n1] | (S)-(6-(6-(6-(1-aminobutyl)pyridin-2-yl)-4-(morpholinomethyl)-1H-indazol-1-yl)pyridin-2-yl)methanol | example 104 |
| 499 | 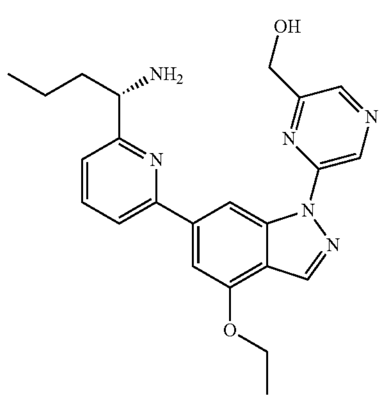 [SMILES: CCC[C@H](N)c1cccc(-c2cc(OCC)c3cnn(-c4cncc(CO)n4)c3c2)n1] | (S)-(6-(6-(6-(1-aminobutyl)pyridin-2-yl)-4-ethoxy-1H-indazol-1-yl)pyrazin-2-yl)methanol | example 410 |

-continued

| Example # | Structure | Compound name | similar to synthesis |
|---|---|---|---|
| 500 | 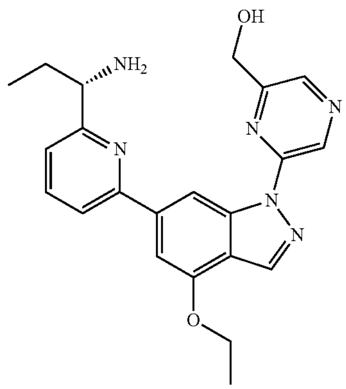 [SMILES: CCOc1cc(-c2cccc([C@@H](N)CC)n2)cc2c1cnn2-c1cncc(CO)n1] | (S)-(6-(6-(6-(1-aminopropyl)pyridin-2-yl)-4-ethoxy-1H-indazol-1-yl)pyrazin-2-yl)methanol | example 410 |
| 501 | 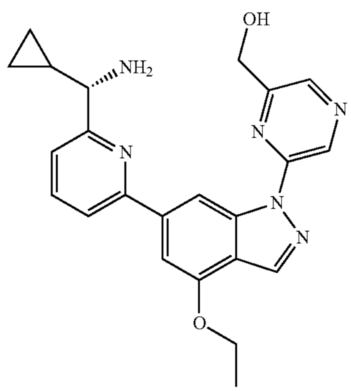 [SMILES: CCOc1cc(-c2cccc([C@@H](N)C3CC3)n2)cc2c1cnn2-c1cncc(CO)n1] | (S)-(6-(6-(6-(amino(cyclopropyl)methyl)pyridin-2-yl)-4-ethoxy-1H-indazol-1-yl)pyrazin-2-yl)methanol | example 410 |
| 502 | 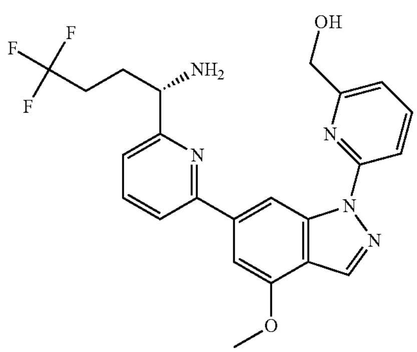 [SMILES: COc1cc(-c2cccc([C@@H](N)CCC(F)(F)F)n2)cc2c1cnn2-c1cccc(CO)n1] | (S)-(6-(6-(6-(1-amino-4,4,4-trifluorobutyl)pyridin-2-yl)-4-methoxy-1H-indazol-1-yl)pyridin-2-yl)methanol | example 410 |
| 503 | 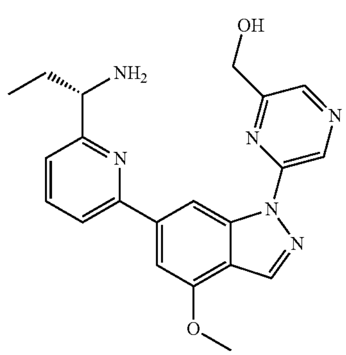 [SMILES: CC[C@H](N)c1cccc(-c2cc(OC)c3cnn(-c4cncc(CO)n4)c3c2)n1] | (S)-(6-(6-(6-(1-aminopropyl)pyridin-2-yl)-4-methoxy-1H-indazol-1-yl)pyrazin-2-yl)methanol | example 410 |

-continued

| Example # | Structure | Compound name | similar to synthesis |
|---|---|---|---|
| 504 | 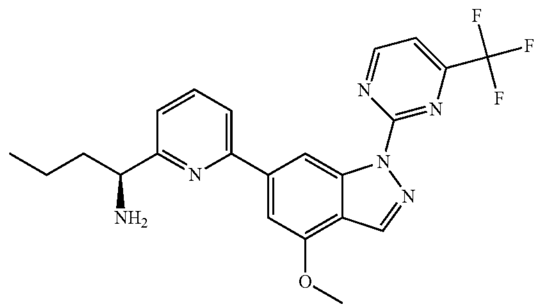 [SMILES: CCC[C@H](N)c1cccc(-c2cc(OC)c3cnn(-c4nccc(C(F)(F)F)n4)c3c2)n1] | (S)-1-(6-(4-methoxy-1-(4-(trifluoromethyl)pyrimidin-2-yl)-1H-indazol-6-yl)pyridin-2-yl)butan-1-amine | example 410 |
| 505 | 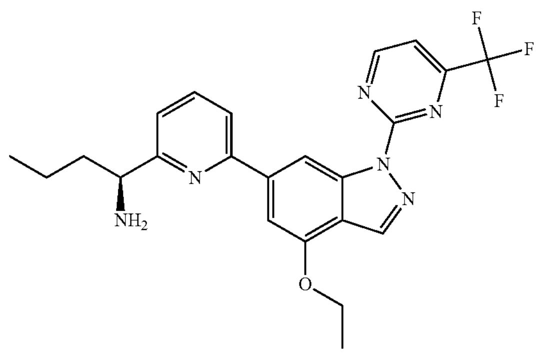 [SMILES: CCC[C@H](N)c1cccc(-c2cc(OCC)c3cnn(-c4nccc(C(F)(F)F)n4)c3c2)n1] | (S)-1-(6-(4-ethoxy-1-(4-(trifluoromethyl)pyrimidin-2-yl)-1H-indazol-6-yl)pyridin-2-yl)butan-1-amine | example 410 |
| 506 | 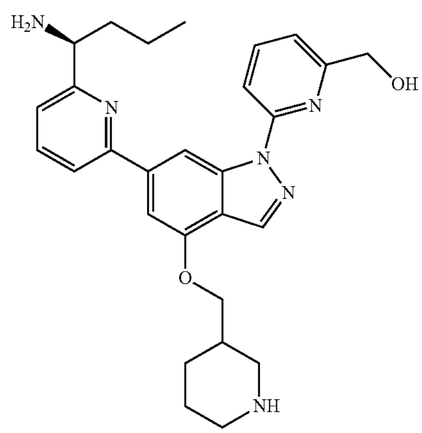 [SMILES: CCC[C@H](N)c1cccc(-c2cc(OCC3CCCNC3)c3cnn(-c4cccc(CO)n4)c3c2)n1] | (6-(6-(6-((S)-1-aminobutyl)pyridin-2-yl)-4-(piperidin-3-ylmethoxy)-1H-indazol-1-yl)pyridin-2-yl)methanol | example 476 |
| 507 | 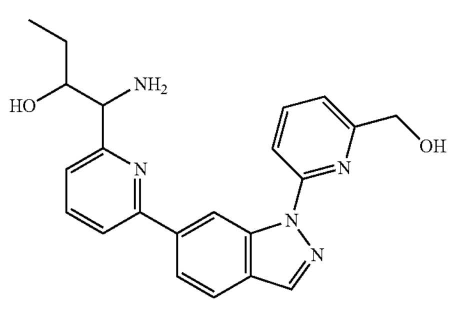 [SMILES: CCC(O)C(N)c1cccc(-c2ccc3cnn(-c4cccc(CO)n4)c3c2)n1] | 1-amino-1-(6-(1-(6-(hydroxymethyl)pyridin-2-yl)-1H-indazol-6-yl)pyridin-2-yl)butan-2-ol | example 145 |

-continued

| Example # | Structure | Compound name | similar to synthesis |
|---|---|---|---|
| 508 | 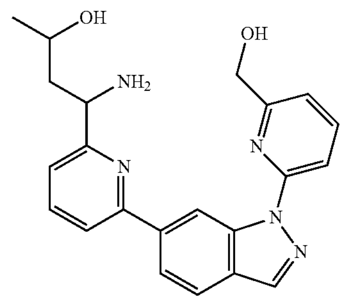 [SMILES: CC(O)CC(N)c1cccc(-c2ccc3cnn(-c4cccc(CO)n4)c3c2)n1] | 4-amino-4-(6-(1-(6-(hydroxymethyl)pyridin-2-yl)-1H-indazol-6-yl)pyridin-2-yl)butan-2-ol | example 145 |
| 509 | 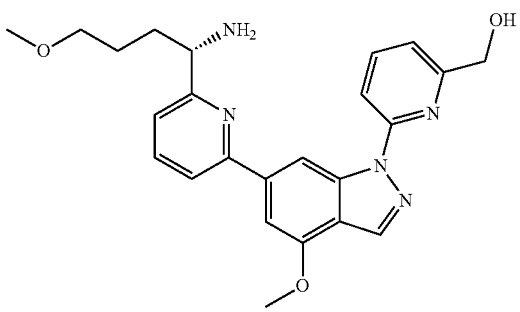 [SMILES: COCCC[C@H](N)c1cccc(-c2cc(OC)c3cnn(-c4cccc(CO)n4)c3c2)n1] | (S)-(6-(6-(6-(1-amino-4-methoxybutyl)pyridin-2-yl)-4-methoxy-1H-indazol-1-yl)pyridin-2-yl)methanol | example 410 |
| 510 | 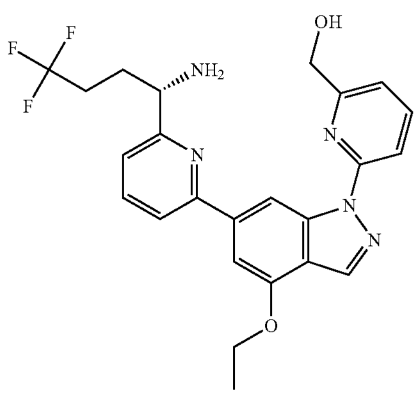 [SMILES: CCOc1cc(-c2cccc([C@@H](N)CCC(F)(F)F)n2)cc2c1cnn2-c1cccc(CO)n1] | (S)-(6-(6-(6-(1-amino-4,4,4-trifluorobutyl)pyridin-2-yl)-4-ethoxy-1H-indazol-1-yl)pyridin-2-yl)methanol | example 410 |
| 511 | 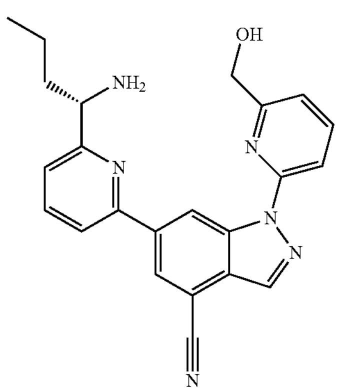 [SMILES: CCC[C@H](N)c1cccc(-c2cc(C#N)c3cnn(-c4cccc(CO)n4)c3c2)n1] | (S)-6-(6-(1-aminobutyl)pyridin-2-yl)-1-(6-(hydroxymethyl)pyridin-2-yl)-1H-indazole-4-carbonitrile | example 105 |

-continued

| Example # | Structure | Compound name | similar to synthesis |
|---|---|---|---|
| 512 | 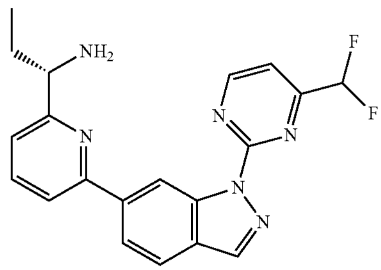 [SMILES: CC[C@H](N)c1cccc(-c2ccc3cnn(-c4nccc(C(F)F)n4)c3c2)n1] | (S)-1-(6-(1-(4-(difluoromethyl)pyrimidin-2-yl)-1H-indazol-6-yl)pyridin-2-yl)propan-1-amine | example 145 |
| 513 | 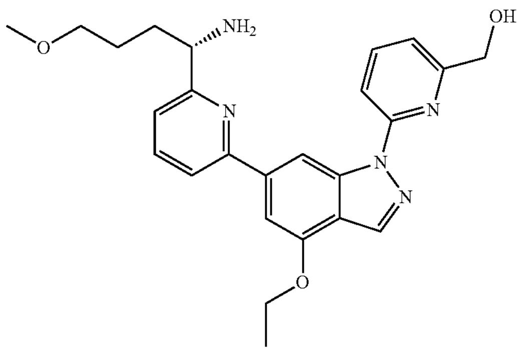 [SMILES: CCOc1cc(-c2cccc([C@@H](N)CCCOC)n2)cc2c1cnn2-c1cccc(CO)n1] | (S)-(6-(6-(6-(1-amino-4-methoxybutyl)pyridin-2-yl)-4-ethoxy-1H-indazol-1-yl)pyridin-2-yl)methanol | example 410 |
| 514 | 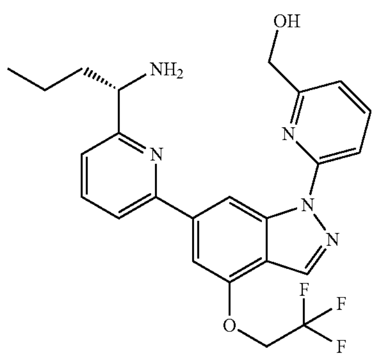 [SMILES: CCC[C@H](N)c1cccc(-c2cc(OCC(F)(F)F)c3cnn(-c4cccc(CO)n4)c3c2)n1] | (S)-(6-(6-(6-(1-aminobutyl)pyridin-2-yl)-4-(2,2,2-trifluoroethoxy)-1H-indazol-1-yl)pyridin-2-yl)methanol | example 476 |
| 515 | 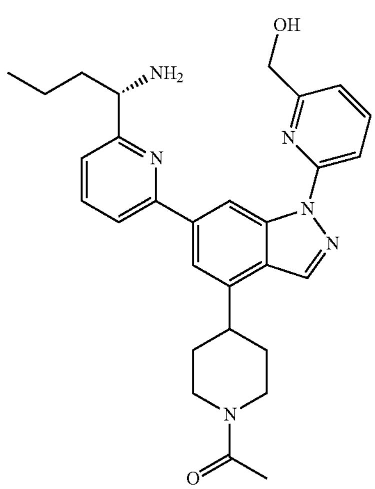 [SMILES: CCC[C@H](N)c1cccc(-c2cc(C3CCN(C(C)=O)CC3)c3cnn(-c4cccc(CO)n4)c3c2)n1] | (S)-1-(4-(6-(6-(1-aminobutyl)pyridin-2-yl)-1-(6-(hydroxymethyl)pyridin-2-yl)-1H-indazol-4-yl)piperidin-1-yl)ethanone | example 424 |

-continued

| Example # | Structure | Compound name | similar to synthesis |
|---|---|---|---|
| 516 | 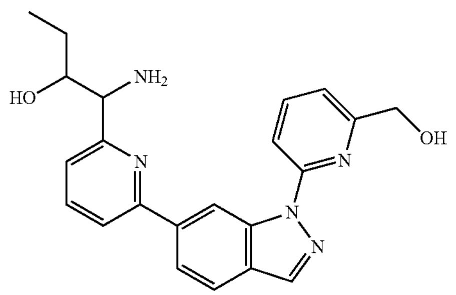 [SMILES: CCC(O)C(N)c1cccc(-c2ccc3cnn(-c4cccc(CO)n4)c3c2)n1] | 1-amino-1-(6-(1-(6-(hydroxymethyl)pyridin-2-yl)-1H-indazol-6-yl)pyridin-2-yl)butan-2-ol | example 145 |
| 517 | 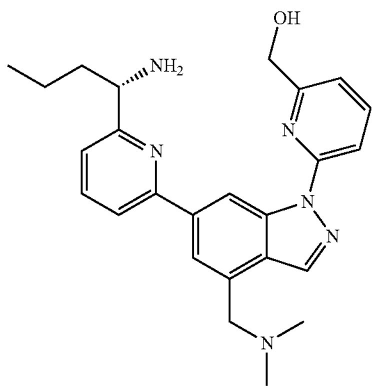 [SMILES: CCC[C@H](N)c1cccc(-c2cc(CN(C)C)c3cnn(-c4cccc(CO)n4)c3c2)n1] | (S)-(6-(6-(6-(1-aminobutyl)pyridin-2-yl)-4-((dimethylamino)methyl)-1H-indazol-1-yl)pyridin-2-yl)methanol | example 104 |
| 518 | 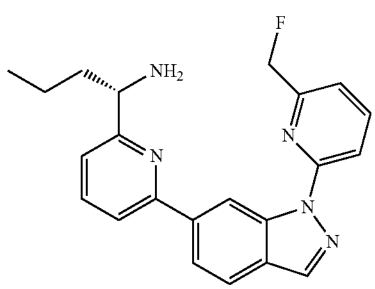 [SMILES: CCC[C@H](N)c1cccc(-c2ccc3cnn(-c4cccc(CF)n4)c3c2)n1] | (S)-1-(6-(1-(6-(fluoromethyl)pyridin-2-yl)-1H-indazol-6-yl)pyridin-2-yl)butan-1-amine | example 145 |
| 519 | 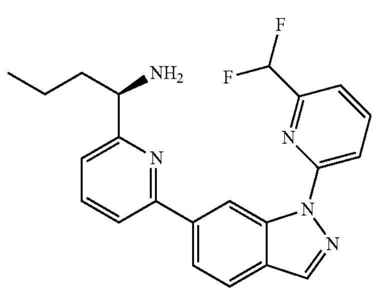 [SMILES: CCC[C@@H](N)c1cccc(-c2ccc3cnn(-c4cccc(C(F)F)n4)c3c2)n1] | (S)-1-(6-(1-(6-(difluoromethyl)pyridin-2-yl)-1H-indazol-6-yl)pyridin-2-yl)butan-1-amine | example 145 |
| 520 | 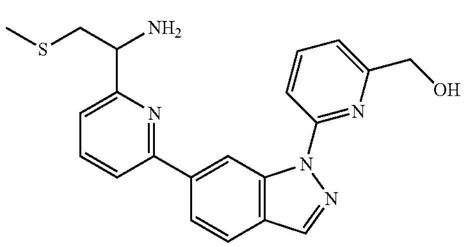 [SMILES: CSCC(N)c1cccc(-c2ccc3cnn(-c4cccc(CO)n4)c3c2)n1] | (6-(6-(6-(1-amino-2-(methylthio)ethyl)pyridin-2-yl)-1H-indazol-1-yl)pyridin-2-yl)methanol | example 145 |

-continued

| Example # | Structure | Compound name | similar to synthesis |
|---|---|---|---|
| 521 | 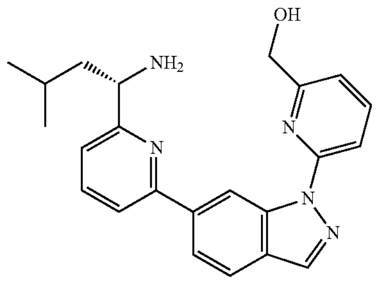 [SMILES: CC(C)C[C@H](N)c1cccc(-c2ccc3cnn(-c4cccc(CO)n4)c3c2)n1] | (S)-(6-(6-(6-(1-amino-3-methylbutyl)pyridin-2-yl)-1H-indazol-1-yl)pyridin-2-yl)methanol | example 145 |
| 522 | 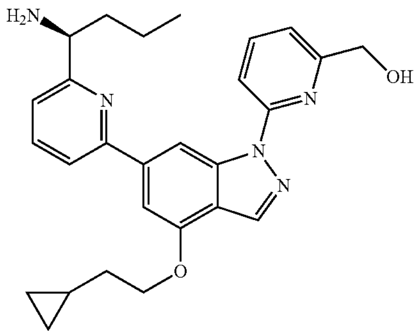 [SMILES: CCC[C@H](N)c1cccc(-c2cc(OCCC3CC3)c3cnn(-c4cccc(CO)n4)c3c2)n1] | (S)-(6-(6-(6-(1-aminobutyl)pyridin-2-yl)-4-(2-cyclopropylethoxy)-1H-indazol-1-yl)pyridin-2-yl)methanol | example 476 |
| 523 | 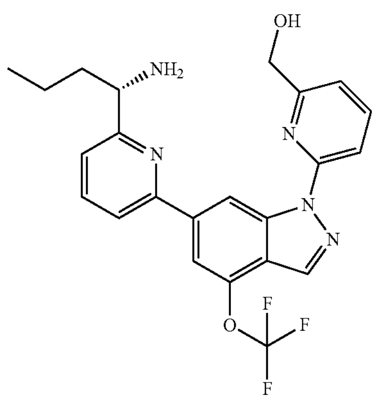 [SMILES: CCC[C@H](N)c1cccc(-c2cc(OC(F)(F)F)c3cnn(-c4cccc(CO)n4)c3c2)n1] | (S)-(6-(6-(6-(1-aminobutyl)pyridin-2-yl)-4-(trifluoromethoxy)-1H-indazol-1-yl)pyridin-2-yl)methanol | example 476 |
| 524 | 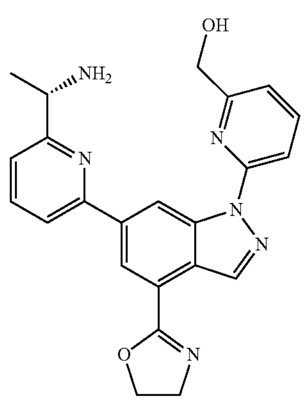 [SMILES: C[C@H](N)c1cccc(-c2cc(C3=NCCO3)c3cnn(-c4cccc(CO)n4)c3c2)n1] | (S)-(6-(6-(6-(1-aminoethyl)pyridin-2-yl)-4-(4,5-dihydrooxazol-2-yl)-1H-indazol-1-yl)pyridin-2-yl)methanol | example 357 |

-continued

| Example # | Structure | Compound name | similar to synthesis |
|---|---|---|---|
| 525 | 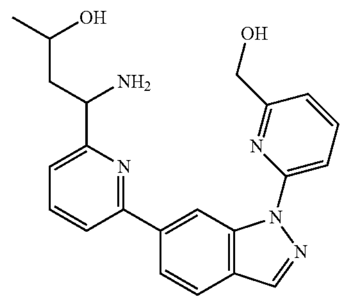 [SMILES: CC(O)CC(N)c1cccc(-c2ccc3cnn(-c4cccc(CO)n4)c3c2)n1] | 4-amino-4-(6-(1-(6-(hydroxymethyl)pyridin-2-yl)-1H-indazol-6-yl)pyridin-2-yl)butan-2-ol | example 145 |
| 526 | 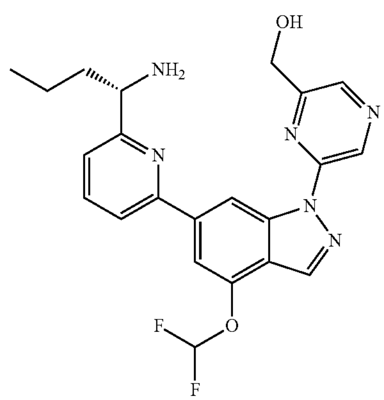 [SMILES: CCC[C@H](N)c1cccc(-c2cc(OC(F)F)c3cnn(-c4cncc(CO)n4)c3c2)n1] | (S)-(6-(6-(6-(1-aminobutyl)pyridin-2-yl)-4-(difluoromethoxy)-1H-indazol-1-yl)pyrazin-2-yl)methanol | example 476 |
| 527 | 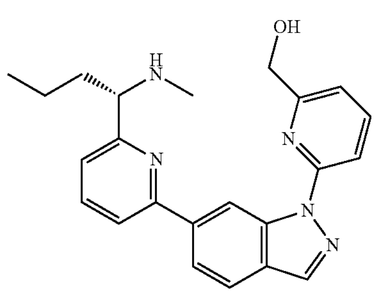 [SMILES: CCC[C@H](NC)c1cccc(-c2ccc3cnn(-c4cccc(CO)n4)c3c2)n1] | (S)-(6-(6-(6-(1-(methylamino)butyl)pyridin-2-yl)-1H-indazol-1-yl)pyridin-2-yl)methanol | example 145 |
| 528 | 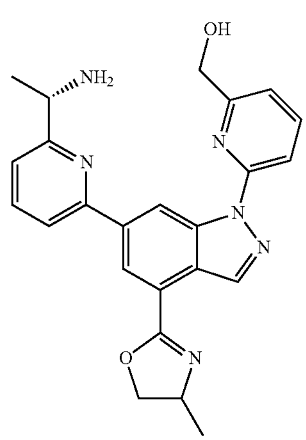 [SMILES: CC1COC(c2cc(-c3cccc([C@H](C)N)n3)cc3c2cnn3-c2cccc(CO)n2)=N1] | (6-(6-(6-((S)-1-aminoethyl)pyridin-2-yl)-4-(4-methyl-4,5-dihydrooxazol-2-yl)-1H-indazol-1-yl)pyridin-2-yl)methanol | example 357 |

-continued

| Example # | Structure | Compound name | similar to synthesis |
|---|---|---|---|
| 529 | 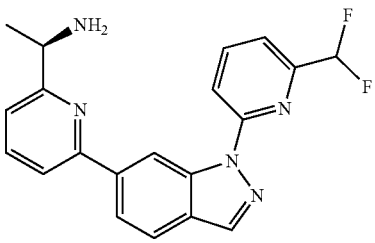 [SMILES: C[C@@H](N)c1cccc(-c2ccc3cnn(-c4cccc(C(F)F)n4)c3c2)n1] | (S)-1-(6-(1-(6-(difluoromethyl)pyridin-2-yl)-1H-indazol-6-yl)pyridin-2-yl)ethanamine | example 145 |
| 530 | 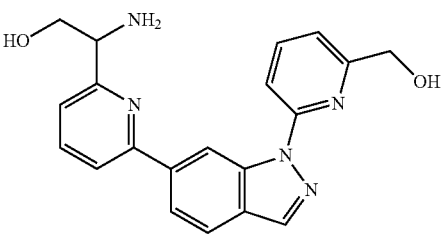 [SMILES: NC(CO)c1cccc(-c2ccc3cnn(-c4cccc(CO)n4)c3c2)n1] | 2-amino-2-(6-(1-(6-(hydroxymethyl)pyridin-2-yl)-1H-indazol-6-yl)pyridin-2-yl)ethanol | example 145 |
| 531 | 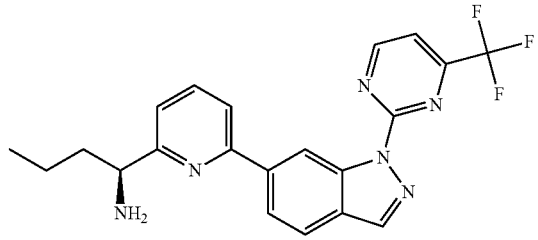 [SMILES: CCC[C@H](N)c1cccc(-c2ccc3cnn(-c4nccc(C(F)(F)F)n4)c3c2)n1] | (S)-1-(6-(1-(4-(trifluoromethyl)pyrimidin-2-yl)-1H-indazol-6-yl)pyridin-2-yl)butan-1-amine | example 145 |
| 532 | 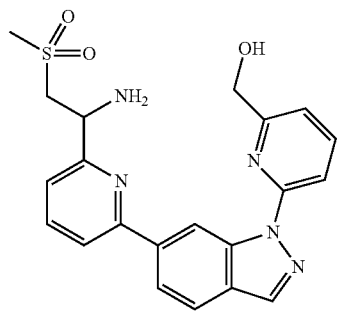 [SMILES: CS(=O)(=O)CC(N)c1cccc(-c2ccc3cnn(-c4cccc(CO)n4)c3c2)n1] | (6-(6-(6-(1-amino-2-(methylsulfonyl)ethyl)pyridin-2-yl)-1H-indazol-1-yl)pyridin-2-yl)methanol | example 145 |
| 533 | 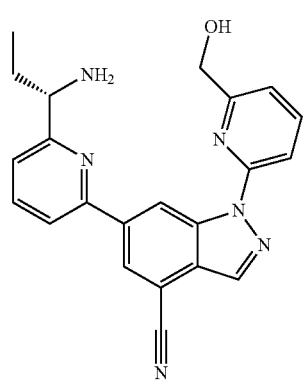 [SMILES: CC[C@H](N)c1cccc(-c2cc(C#N)c3cnn(-c4cccc(CO)n4)c3c2)n1] | (S)-6-(6-(1-aminopropyl)pyridin-2-yl)-1-(6-(hydroxymethyl)pyridin-2-yl)-1H-indazole-4-carbonitrile | example 105 |

-continued

| Example # | Structure | Compound name | similar to synthesis |
|---|---|---|---|
| 535 | 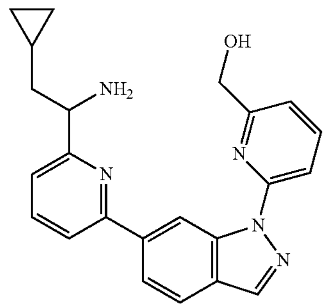 [SMILES: NC(CC1CC1)c1cccc(-c2ccc3cnn(-c4cccc(CO)n4)c3c2)n1] | (6-(6-(6-(1-amino-2-cyclopropylethyl)pyridin-2-yl)-1H-indazol-1-yl)pyridin-2-yl)methanol | example 145 |
| 536 | 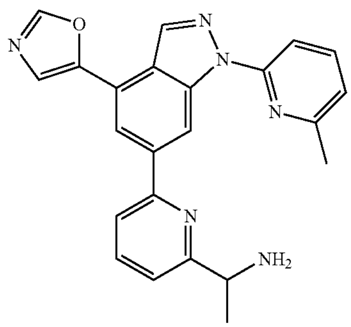 [SMILES: Cc1cccc(-n2ncc3c(-c4cnco4)cc(-c4cccc(C(C)N)n4)cc32)n1] | 1-(6-(1-(6-methylpyridin-2-yl)-4-(oxazol-5-yl)-1H-indazol-6-yl)pyridin-2-yl)ethanamine | example 357 |
| 537 | 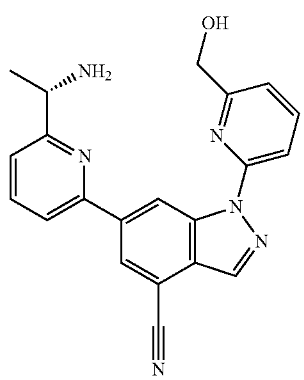 [SMILES: C[C@H](N)c1cccc(-c2cc(C#N)c3cnn(-c4cccc(CO)n4)c3c2)n1] | (S)-6-(6-(1-aminoethyl)pyridin-2-yl)-1-(6-(hydroxymethyl)pyridin-2-yl)-1H-indazole-4-carbonitrile | example 105 |
| 538 | 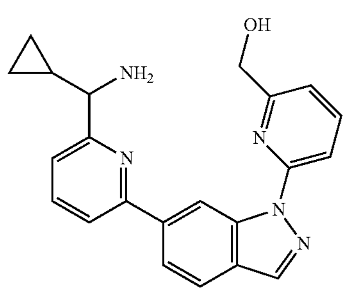 [SMILES: NC(c1cccc(-c2ccc3cnn(-c4cccc(CO)n4)c3c2)n1)C1CC1] | (6-(6-(6-(amino(cyclopropyl)methyl)pyridin-2-yl)-1H-indazol-1-yl)pyridin-2-yl)methanol | example 145 |
| 539 | 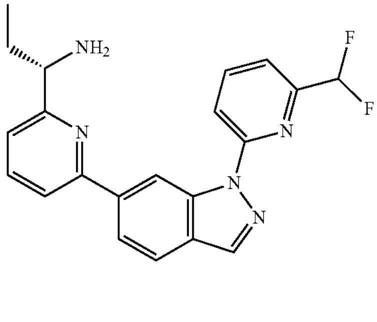 [SMILES: CC[C@H](N)c1cccc(-c2ccc3cnn(-c4cccc(C(F)F)n4)c3c2)n1] | (S)-1-(6-(1-(6-(difluoromethyl)pyridin-2-yl)-1H-indazol-6-yl)pyridin-2-yl)propan-1-amine | example 145 |

-continued

| Example # | Structure | Compound name | similar to synthesis |
|---|---|---|---|
| 540 | 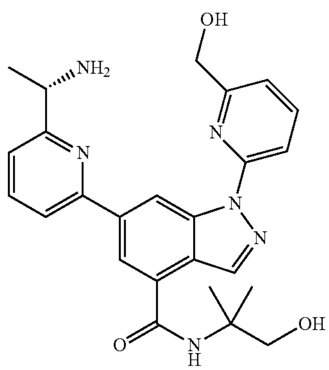 [SMILES: C[C@H](N)c1cccc(-c2cc(C(=O)NC(C)(C)CO)c3cnn(-c4cccc(CO)n4)c3c2)n1] | (S)-6-(6-(1-aminoethyl)pyridin-2-yl)-N-(1-hydroxy-2-methylpropan-2-yl)-1-(6-(hydroxymethyl)pyridin-2-yl)-1H-indazole-4-carboxamide | example 104 |
| 541 | 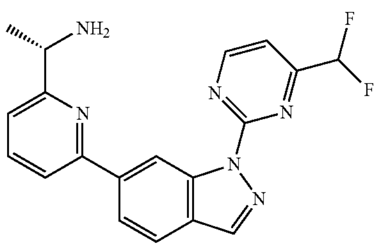 [SMILES: C[C@H](N)c1cccc(-c2ccc3cnn(-c4nccc(C(F)F)n4)c3c2)n1] | (S)-1-(6-(1-(4-(difluoromethyl)pyrimidin-2-yl)-1H-indazol-6-yl)pyridin-2-yl)ethanamine | example 145 |
| 542 | 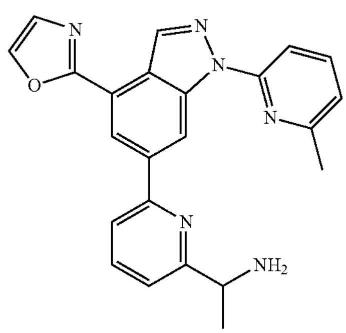 [SMILES: Cc1cccc(-n2ncc3c(-c4ncco4)cc(-c4cccc(C(C)N)n4)cc32)n1] | 1-(6-(1-(6-methylpyridin-2-yl)-4-(oxazol-2-yl)-1H-indazol-6-yl)pyridin-2-yl)ethanamine | example 357 |
| 543 | 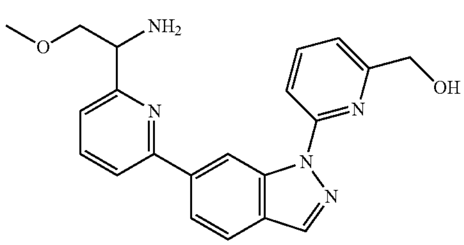 [SMILES: COCC(N)c1cccc(-c2ccc3cnn(-c4cccc(CO)n4)c3c2)n1] | (6-(6-(6-(1-amino-2-methoxyethyl)pyridin-2-yl)-1H-indazol-1-yl)pyridin-2-yl)methanol | example 145 |
| 544 | 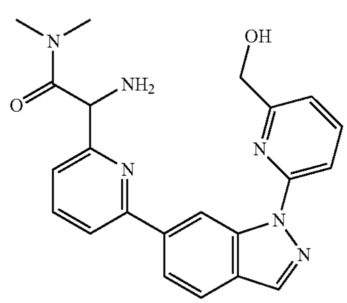 [SMILES: CN(C)C(=O)C(N)c1cccc(-c2ccc3cnn(-c4cccc(CO)n4)c3c2)n1] | 2-amino-2-(6-(1-(6-(hydroxymethyl)pyridin-2-yl)-1H-indazol-6-yl)pyridin-2-yl)-N,N-dimethylacetamide | example 145 |

-continued

| Example # | Structure | Compound name | similar to synthesis |
|---|---|---|---|
| 545 | 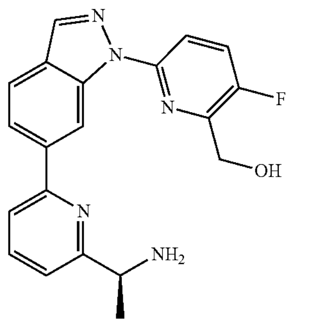 [SMILES: C[C@H](N)c1cccc(-c2ccc3cnn(-c4ccc(F)c(CO)n4)c3c2)n1] | (S)-(6-(6-(6-(1-aminoethyl)pyridin-2-yl)-1H-indazol-1-yl)-3-fluoropyridin-2-yl)methanol | example 145 |
| 546 | 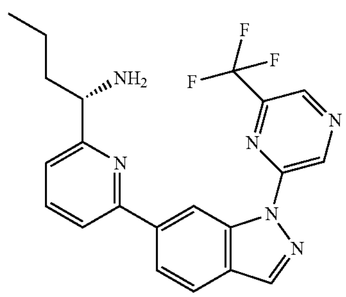 [SMILES: CCC[C@H](N)c1cccc(-c2ccc3cnn(-c4cncc(C(F)(F)F)n4)c3c2)n1] | (S)-1-(6-(1-(6-(trifluoromethyl)pyrazin-2-yl)-1H-indazol-6-yl)pyridin-2-yl)butan-1-amine | example 145 |
| 548 | 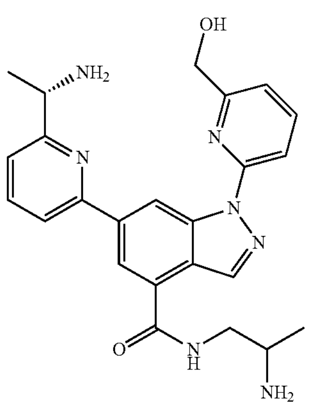 [SMILES: CC(N)CNC(=O)c1cc(-c2cccc([C@H](C)N)n2)cc2c1cnn2-c1cccc(CO)n1] | 6-(6-((S)-1-aminoethyl)pyridin-2-yl)-N-(2-aminopropyl)-1-(6-(hydroxymethyl)pyridin-2-yl)-1H-indazole-4-carboxamide | example 104 |
| 549 | 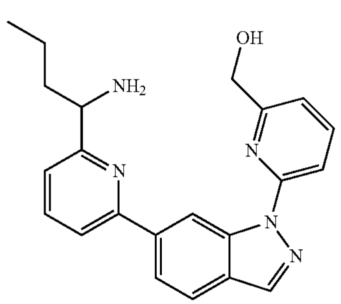 [SMILES: CCCC(N)c1cccc(-c2ccc3cnn(-c4cccc(CO)n4)c3c2)n1] | 1-(6-(1-(6-(hydroxymethyl)pyridin-2-yl)-1H-indazol-6-yl)pyridin-2-yl)butan-1-ol | example 145 |

-continued

| Example # | Structure | Compound name | similar to synthesis |
|---|---|---|---|
| 550 | 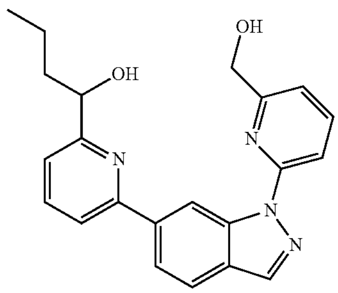 [SMILES: CCCC(O)c1cccc(-c2ccc3cnn(-c4cccc(CO)n4)c3c2)n1] | 1-(6-(1-(6-(hydroxymethyl)pyridin-2-yl)-1H-indazol-6-yl)pyridin-2-yl)butan-1-ol | example 145 |
| 551 | 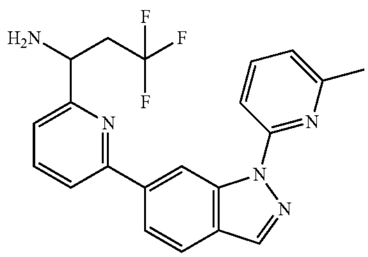 [SMILES: Cc1cccc(-n2ncc3ccc(-c4cccc(C(N)CC(F)(F)F)n4)cc32)n1] | 3,3,3-trifluoro-1-(6-(1-(6-methylpyridin-2-yl)-1H-indazol-6-yl)pyridin-2-yl)propan-1-amine | example 145 |
| 557 | 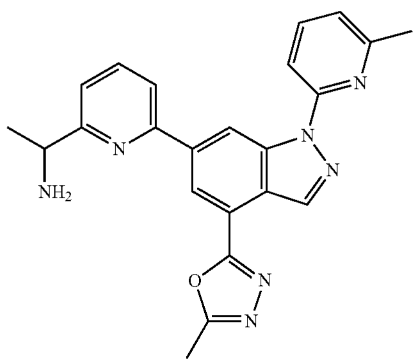 [SMILES: Cc1cccc(-n2ncc3c(-c4nnc(C)o4)cc(-c4cccc(C(C)N)n4)cc32)n1] | 1-(6-(4-(5-methyl-1,3,4-oxadiazol-2-yl)-1-(6-methylpyridin-2-yl)-1H-indazol-6-yl)pyridin-2-yl)ethanamine | example 357 |
| 559 | 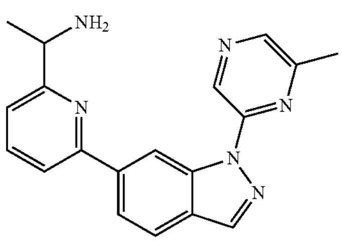 [SMILES: Cc1cncc(-n2ncc3ccc(-c4cccc(C(C)N)n4)cc32)n1] | 1-(6-(1-(6-methylpyrazin-2-yl)-1H-indazol-6-yl)pyridin-2-yl)ethanamine | example 145 |
| 560 | 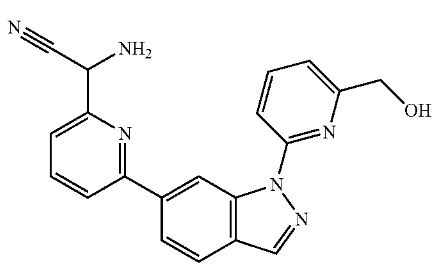 [SMILES: N#CC(N)c1cccc(-c2ccc3cnn(-c4cccc(CO)n4)c3c2)n1] | 2-amino-2-(6-(1-(6-(hydroxymethyl)pyridin-2-yl)-1H-indazol-6-yl)pyridin-2-yl)acetonitrile | example 145 |

-continued

| Example # | Structure | Compound name | similar to synthesis |
|---|---|---|---|
| 561 | 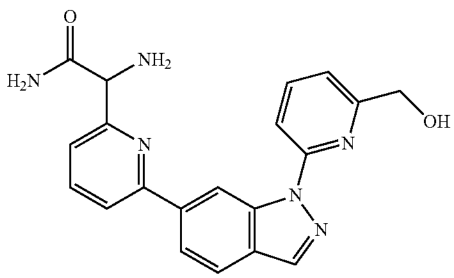 [SMILES: NC(=O)C(N)c1cccc(-c2ccc3cnn(-c4cccc(CO)n4)c3c2)n1] | 2-amino-2-(6-(1-(6-(hydroxymethyl)pyridin-2-yl)-1H-indazol-6-yl)pyridin-2-yl)acetamide | example 145 |
| 562 | 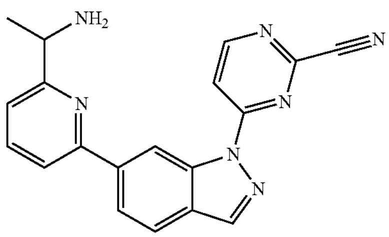 [SMILES: CC(N)c1cccc(-c2ccc3cnn(-c4ccnc(C#N)n4)c3c2)n1] | 4-(6-(6-(1-aminoethyl)pyridin-2-yl)-1H-indazol-1-yl)pyrimidine-2-carbonitrile | example 145 |
| 563 | 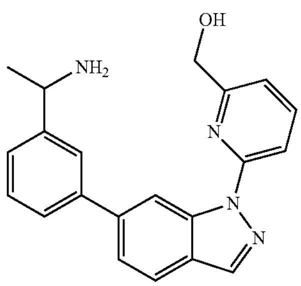 [SMILES: CC(N)c1cccc(-c2ccc3cnn(-c4cccc(CO)n4)c3c2)c1] | (6-(6-(3-(1-aminoethyl)phenyl)-1H-indazol-1-yl)pyridin-2-yl)methanol | example 145 |
| 564 | 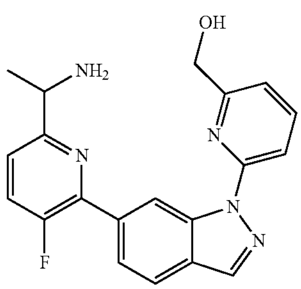 [SMILES: CC(N)c1ccc(F)c(-c2ccc3cnn(-c4cccc(CO)n4)c3c2)n1] | (6-(6-(6-(1-aminoethyl)-3-fluoropyridin-2-yl)-1H-indazol-1-yl)pyridin-2-yl)methanol | example 145 |
| 565 | 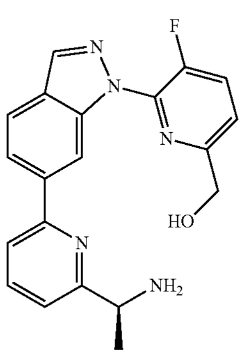 [SMILES: C[C@H](N)c1cccc(-c2ccc3cnn(-c4nc(CO)ccc4F)c3c2)n1] | (S)-(6-(6-(6-(1-aminoethyl)pyridin-2-yl)-1H-indazol-1-yl)-5-fluoropyridin-2-yl)methanol | example 145 |

-continued

| Example # | Structure | Compound name | similar to synthesis |
|---|---|---|---|
| 566 | 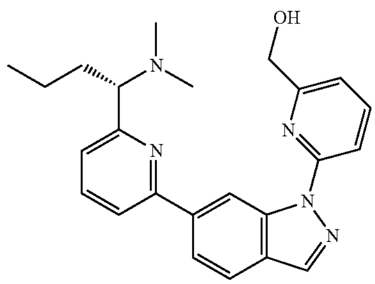 [SMILES: CCC[C@@H](c1cccc(-c2ccc3cnn(-c4cccc(CO)n4)c3c2)n1)N(C)C] | (S)-(6-(6-(6-(1-(dimethylamino)butyl)pyridin-2-yl)-1H-indazol-1-yl)pyridin-2-yl)methanol | example 145 |
| 567 | 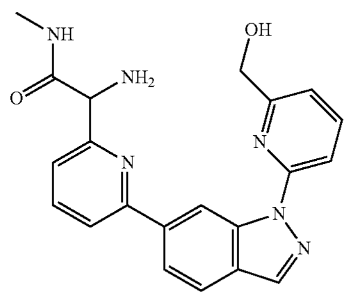 [SMILES: CNC(=O)C(N)c1cccc(-c2ccc3cnn(-c4cccc(CO)n4)c3c2)n1] | 2-amino-2-(6-(1-(6-(hydroxymethyl)pyridin-2-yl)-1H-indazol-6-yl)pyridin-2-yl)-N-methylacetamide | example 145 |
| 568 | 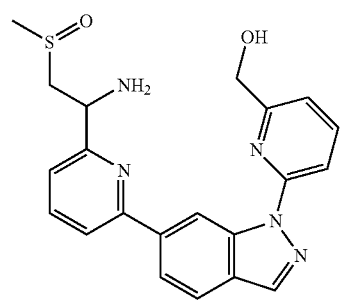 [SMILES: CS(=O)CC(N)c1cccc(-c2ccc3cnn(-c4cccc(CO)n4)c3c2)n1] | (6-(6-(6-(1-amino-2-(methylsulfinyl)ethyl)pyridin-2-yl)-1H-indazol-1-yl)pyridin-2-yl)methanol | example 145 |
| 569 | 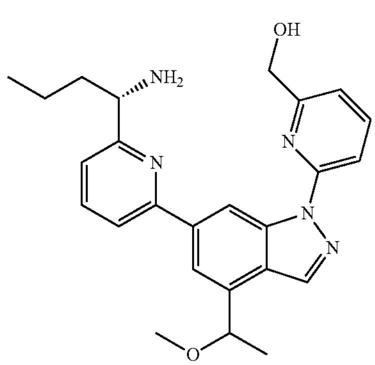 [SMILES: CCC[C@H](N)c1cccc(-c2cc(C(C)OC)c3cnn(-c4cccc(CO)n4)c3c2)n1] | (6-(6-(6-((S)-1-aminobutyl)pyridin-2-yl)-4-(1-methoxyethyl)-1H-indazol-1-yl)pyridin-2-yl)methanol | example 114 |

-continued

| Example # | Structure | Compound name | similar to synthesis |
|---|---|---|---|
| 570 | 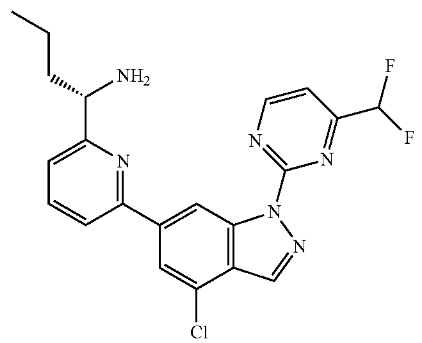 [SMILES: CCC[C@H](N)c1cccc(-c2cc(Cl)c3cnn(-c4nccc(C(F)F)n4)c3c2)n1] | (S)-1-(6-(4-chloro-1-(4-(difluoromethyl)pyrimidin-2-yl)-1H-indazol-6-yl)pyridin-2-yl)butan-1-amine | example 473 |
| 571 | 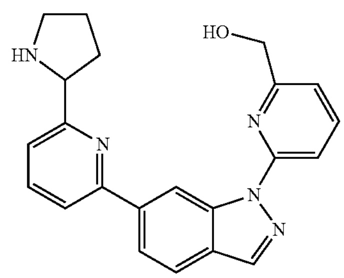 [SMILES: OCc1cccc(-n2ncc3ccc(-c4cccc(C5CCCN5)n4)cc32)n1] | (6-(6-(6-(pyrrolidin-2-yl)pyridin-2-yl)-1H-indazol-1-yl)pyridin-2-yl)methanol | example 145 |
| 572 | 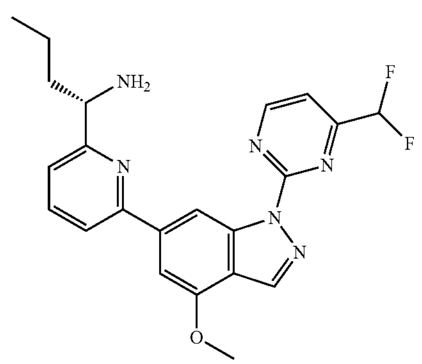 [SMILES: CCC[C@H](N)c1cccc(-c2cc(OC)c3cnn(-c4nccc(C(F)F)n4)c3c2)n1] | (S)-1-(6-(1-(4-(difluoromethyl)pyrimidin-2-yl)-4-methoxy-1H-indazol-6-yl)pyridin-2-yl)butan-1-amine | example 410 |
| 573 | 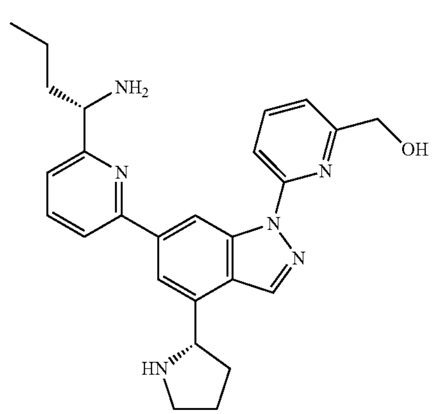 [SMILES: CCC[C@H](N)c1cccc(-c2cc([C@@H]3CCCN3)c3cnn(-c4cccc(CO)n4)c3c2)n1] | (6-(6-(6-((S)-1-aminobutyl)pyridin-2-yl)-4-((S)-pyrrolidin-2-yl)-1H-indazol-1-yl)pyridin-2-yl)methanol | example 477 |

| Example # | Structure | Compound name | similar to synthesis |
|---|---|---|---|
| 574 | 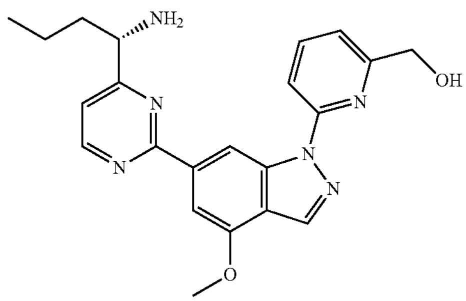 [SMILES: CCC[C@H](N)c1ccnc(-c2cc(OC)c3cnn(-c4cccc(CO)n4)c3c2)n1] | (S)-(6-(6-(4-(1-aminobutyl)pyrimidin-2-yl)-4-methoxy-1H-indazol-1-yl)pyridin-2-yl)methanol | example 413 |
| 575 | 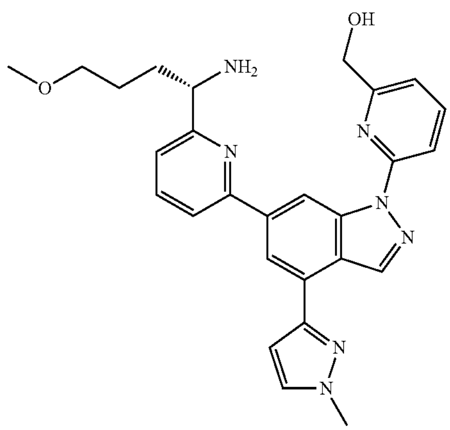 [SMILES: COCCC[C@H](N)c1cccc(-c2cc(-c3ccn(C)n3)c3cnn(-c4cccc(CO)n4)c3c2)n1] | (S)-(6-(6-(6-(1-amino-4-methoxybutyl)pyridin-2-yl)-4-(1-methyl-1H-pyrazol-3-yl)-1H-indazol-1-yl)pyridin-2-yl)methanol | example 357 |
| 576 | 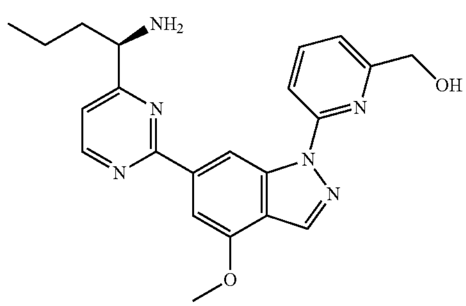 [SMILES: CCC[C@@H](N)c1ccnc(-c2cc(OC)c3cnn(-c4cccc(CO)n4)c3c2)n1] | (R)-(6-(6-(4-(1-aminobutyl)pyrimidin-2-yl)-4-methoxy-1H-indazol-1-yl)pyridin-2-yl)methanol | example 413 |
| 577 | 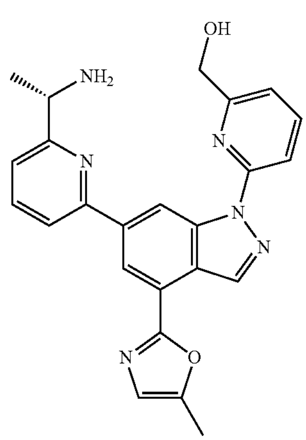 [SMILES: Cc1cnc(-c2cc(-c3cccc([C@H](C)N)n3)cc3c2cnn3-c2cccc(CO)n2)o1] | (S)-(6-(6-(6-(1-aminoethyl)pyridin-2-yl)-4-(5-methyloxazol-2-yl)-1H-indazol-1-yl)pyridin-2-yl)methanol | example 357 |

| Example # | Structure | Compound name | similar to synthesis |
|---|---|---|---|
| 578 | 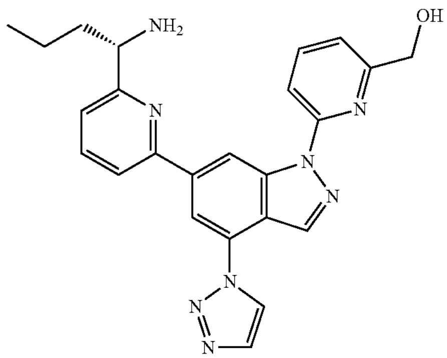 [SMILES: CCC[C@H](N)c1cccc(-c2cc(-n3ccnn3)c3cnn(-c4cccc(CO)n4)c3c2)n1] | (S)-(6-(6-(6-(1-aminobutyl)pyridin-2-yl)-4-(1H-1,2,3-triazol-1-yl)-1H-indazol-1-yl)pyridin-2-yl)methanol | example 352 |
| 579 | 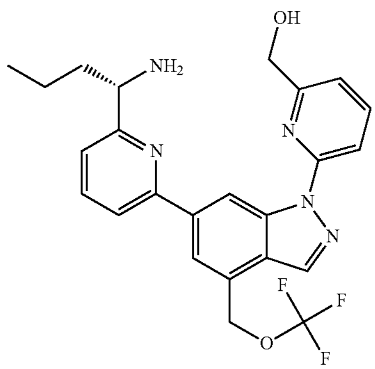 [SMILES: CCC[C@H](N)c1cccc(-c2cc(COC(F)(F)F)c3cnn(-c4cccc(CO)n4)c3c2)n1] | (S)-(6-(6-(6-(1-aminobutyl)pyridin-2-yl)-4-((trifluoromethoxy)methyl)-1H-indazol-1-yl)pyridin-2-yl)methanol | example 114 |
| 580 | 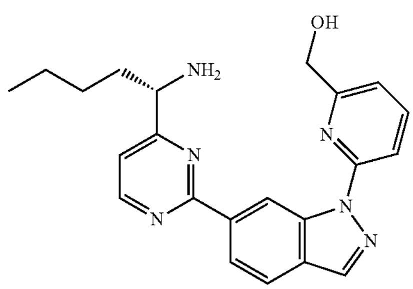 [SMILES: CCCC[C@H](N)c1ccnc(-c2ccc3cnn(-c4cccc(CO)n4)c3c2)n1] | (S)-(6-(6-(4-(1-aminopentyl)pyrimidin-2-yl)-1H-indazol-1-yl)pyridin-2-yl)methanol | example 413 |
| 581 | 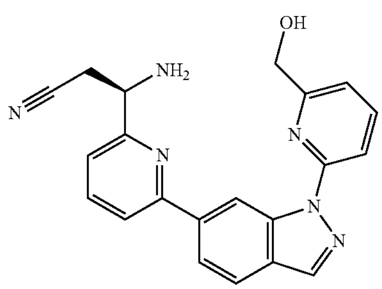 [SMILES: N#CC[C@@H](N)c1cccc(-c2ccc3cnn(-c4cccc(CO)n4)c3c2)n1] | (R)-3-amino-3-(6-(1-(6-(hydroxymethyl)pyridin-2-yl)-1H-indazol-6-yl)pyridin-2-yl)propanenitrile | example 146 |

-continued

| Example # | Structure | Compound name | similar to synthesis |
|---|---|---|---|
| 582 | 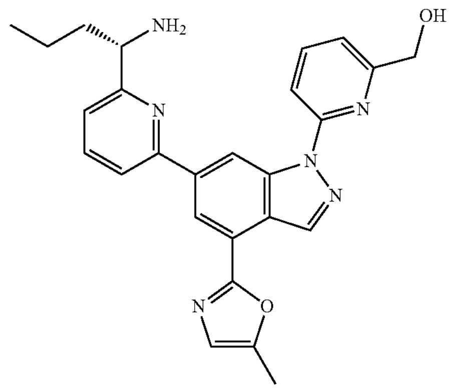 [SMILES: CCC[C@H](N)c1cccc(-c2cc(-c3ncc(C)o3)c3cnn(-c4cccc(CO)n4)c3c2)n1] | (S)-(6-(6-(6-(1-aminobutyl)pyridin-2-yl)-4-(5-methyloxazol-2-yl)-1H-indazol-1-yl)pyridin-2-yl)methanol | example 357 |
| 583 | 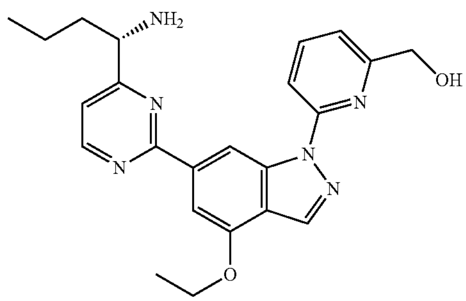 [SMILES: CCC[C@H](N)c1ccnc(-c2cc(OCC)c3cnn(-c4cccc(CO)n4)c3c2)n1] | (S)-(6-(6-(4-(1-aminobutyl)pyrimidin-2-yl)-4-ethoxy-1H-indazol-1-yl)pyridin-2-yl)methanol | example 413 |
| 584 | 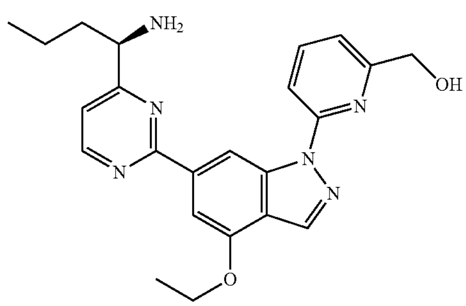 [SMILES: CCC[C@@H](N)c1ccnc(-c2cc(OCC)c3cnn(-c4cccc(CO)n4)c3c2)n1] | (R)-(6-(6-(4-(1-aminobutyl)pyrimidin-2-yl)-4-ethoxy-1H-indazol-1-yl)pyridin-2-yl)methanol | example 413 |
| 585 | 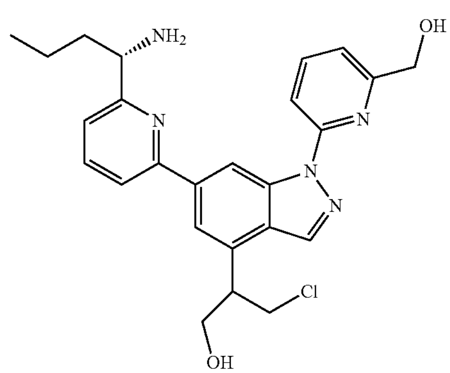 [SMILES: CCC[C@H](N)c1cccc(-c2cc(C(CO)CCl)c3cnn(-c4cccc(CO)n4)c3c2)n1] | 2-(6-(6-((S)-1-aminobutyl)pyridin-2-yl)-1-(6-(hydroxymethyl)pyridin-2-yl)-1H-indazol-4-yl)-3-chloropropan-1-ol | example 114 |

-continued

| Example # | Structure | Compound name | similar to synthesis |
|---|---|---|---|
| 586 | 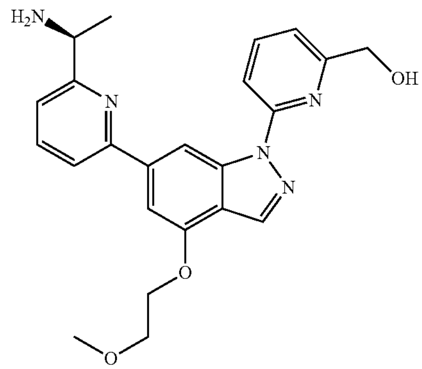 [SMILES: COCCOc1cc(-c2cccc([C@H](C)N)n2)cc2c1cnn2-c1cccc(CO)n1] | (S)-(6-(6-(6-(1-aminoethyl)pyridin-2-yl)-4-(2-methoxyethoxy)-1H-indazol-1-yl)pyridin-2-yl)methanol | example 456 |
| 587 | 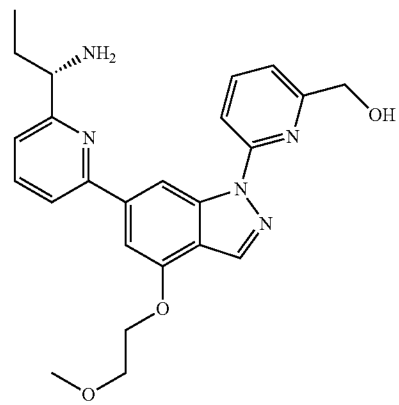 [SMILES: CC[C@H](N)c1cccc(-c2cc(OCCOC)c3cnn(-c4cccc(CO)n4)c3c2)n1] | (S)-(6-(6-(6-(1-aminopropyl)pyridin-2-yl)-4-(2-methoxyethoxy)-1H-indazol-1-yl)pyridin-2-yl)methanol | example 456 |
| 588 | 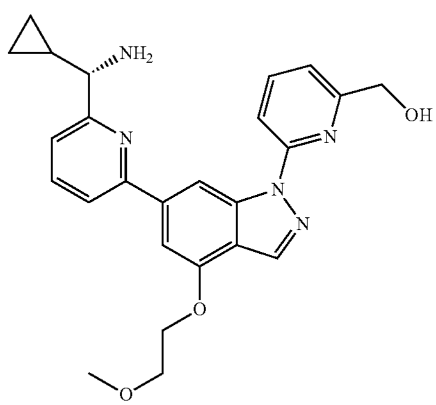 [SMILES: COCCOc1cc(-c2cccc([C@@H](N)C3CC3)n2)cc2c1cnn2-c1cccc(CO)n1] | (S)-(6-(6-(6-(amino(cyclopropyl)methyl)pyridin-2-yl)-4-(2-methoxyethoxy)-1H-indazol-1-yl)pyridin-2-yl)methanol | example 456 |
| 589 | 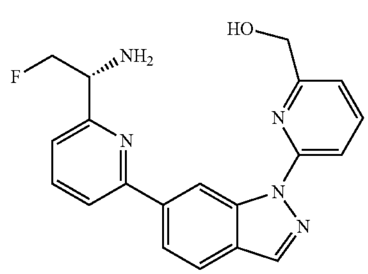 [SMILES: N[C@@H](CF)c1cccc(-c2ccc3cnn(-c4cccc(CO)n4)c3c2)n1] | (R)-(6-(6-(6-(1-amino-2-fluoroethyl)pyridin-2-yl)-1H-indazol-1-yl)pyridin-2-yl)methanol | example 145 |

-continued

| Example # | Structure | Compound name | similar to synthesis |
|---|---|---|---|
| 590 | 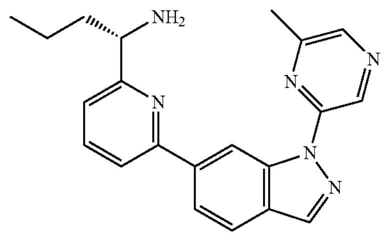 [SMILES: CCC[C@H](N)c1cccc(-c2ccc3cnn(-c4cncc(C)n4)c3c2)n1] | (S)-1-(6-(1-(6-methylpyrazin-2-yl)-1H-indazol-6-yl)pyridin-2-yl)butan-1-amine | example 145 |
| 591 | 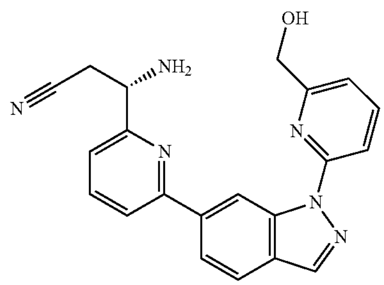 [SMILES: N#CC[C@H](N)c1cccc(-c2ccc3cnn(-c4cccc(CO)n4)c3c2)n1] | (S)-3-amino-3-(6-(1-(6-(hydroxymethyl)pyridin-2-yl)-1H-indazol-6-yl)pyridin-2-yl)propanenitrile | example 145 |
| 592 | 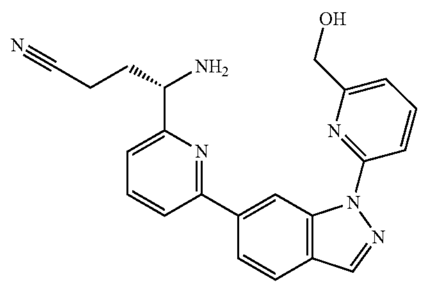 [SMILES: N#CCC[C@H](N)c1cccc(-c2ccc3cnn(-c4cccc(CO)n4)c3c2)n1] | (S)-4-amino-4-(6-(1-(6-(hydroxymethyl)pyridin-2-yl)-1H-indazol-6-yl)pyridin-2-yl)butanenitrile | example 145 |
| 593 | 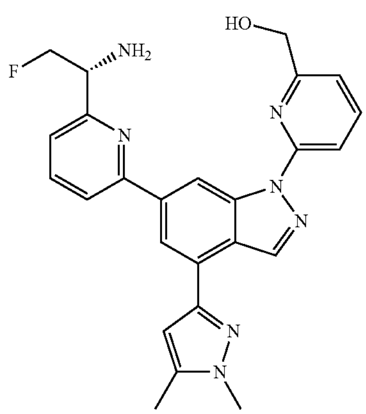 [SMILES: Cc1cc(-c2cc(-c3cccc([C@@H](N)CF)n3)cc3c2cnn3-c2cccc(CO)n2)nn1C] | (R)-(6-(6-(6-(1-amino-2-fluoroethyl)pyridin-2-yl)-4-(1,5-dimethyl-1H-pyrazol-3-yl)-1H-indazol-1-yl)pyridin-2-yl)methanol | example 357 |
| 594 | 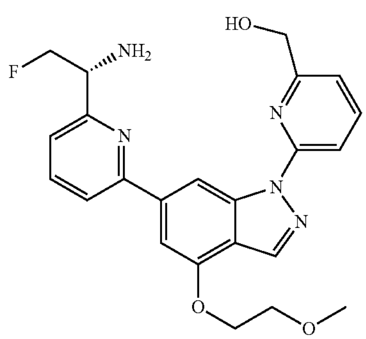 [SMILES: COCCOc1cc(-c2cccc([C@@H](N)CF)n2)cc2c1cnn2-c1cccc(CO)n1] | (R)-(6-(6-(6-(1-amino-2-fluoroethyl)pyridin-2-yl)-4-(2-methoxyethoxy)-1H-indazol-1-yl)pyridin-2-yl)methanol | example 476 |

| Example # | Structure | Compound name | similar to synthesis |
|---|---|---|---|
| 595 | 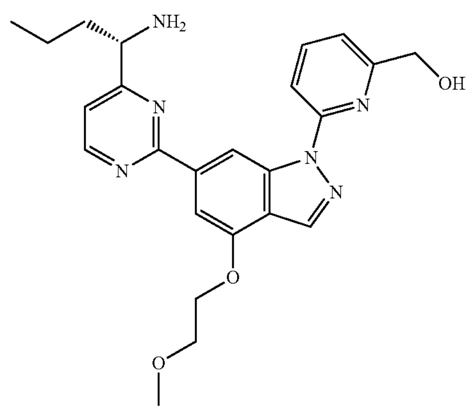 [SMILES: CCC[C@H](N)c1ccnc(-c2cc(OCCOC)c3cnn(-c4cccc(CO)n4)c3c2)n1] | (S)-(6-(6-(4-(1-aminobutyl)pyrimidin-2-yl)-4-(2-methoxyethoxy)-1H-indazol-1-yl)pyridin-2-yl)methanol | example 413 |
| 596 | 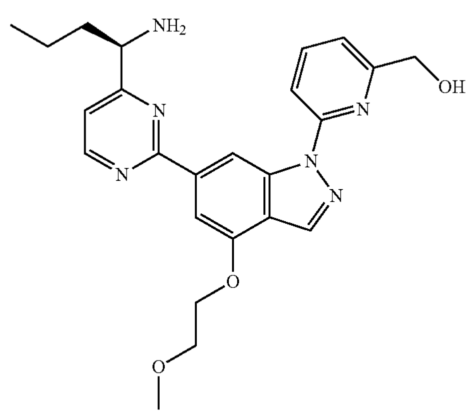 [SMILES: CCC[C@@H](N)c1ccnc(-c2cc(OCCOC)c3cnn(-c4cccc(CO)n4)c3c2)n1] | (R)-(6-(6-(4-(1-aminobutyl)pyrimidin-2-yl)-4-(2-methoxyethoxy)-1H-indazol-1-yl)pyridin-2-yl)methanol | example 413 |
| 597 | 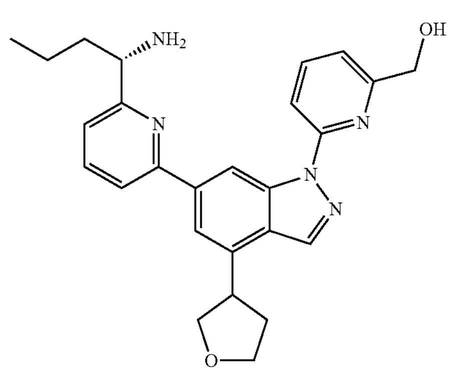 [SMILES: CCC[C@H](N)c1cccc(-c2cc(C3CCOC3)c3cnn(-c4cccc(CO)n4)c3c2)n1] | (6-(6-(6-((S)-1-aminobutyl)pyridin-2-yl)-4-(tetrahydrofuran-3-yl)-1H-indazol-1-yl)pyridin-2-yl)methanol | example 424 |

| Example # | Structure | Compound name | similar to synthesis |
|---|---|---|---|
| 598 | 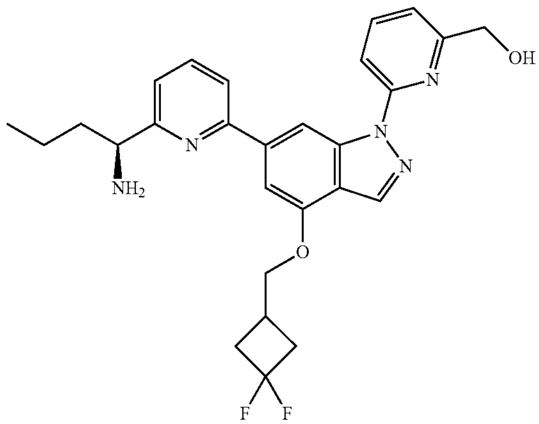 [SMILES: CCC[C@H](N)c1cccc(-c2cc(OCC3CC(F)(F)C3)c3cnn(-c4cccc(CO)n4)c3c2)n1] | (S)-(6-(6-(6-(1-aminobutyl)pyridin-2-yl)-4-((3,3-difluorocyclobutyl)methoxy)-1H-indazol-1-yl)pyridin-2-yl)methanol | example 476 |

Example 599

Biochemical Assay:

The biochemical assay is in a AlphaScreen format. The kinase reaction is based on the IRAK-4 phosphorylation of a biotin labeled peptide. The phosphopeptide is incubated with anti-phosphothreonine antibody as well as streptavidin- and protein A-coated beads. Binding of the protein-A coated beads to the antibody and the streptavidin beads to the peptide, leads to an energy transfer from one bead to the other, ultimately producing a luminescent/fluorescent signal.

Generally, the kinase reaction is carried out at 1 nM IRAK4, 1.6 µM peptide, 1 mM ATP in reaction buffer 50 mM Hepes, 60 mM NaCl, 5 mM MgCl2, 0.25 mM MnCl2, 2 mM DTT, 0.01% BSA, 0.01% Tween-20) for 3.5 h at RT.

The compounds described herein were tested for in the above biochemical assay. The results are provided below, wherein the compound number corresponds to the numbers set forth in the examples above, "+" represents an IC50 of less than 10 uM, but greater than 1 uM, "++" represents an IC50 of less than or equal to 1 uM but greater than 0.1 uM, and a "+++" represents an IC50 of less than or equal to 0.1 uM.

| IC50 | Compounds |
|---|---|
| +++ | 18, 22, 25, 27, 29, 31, 36, 37, 40, 41, 42, 47, 48, 49, 50, 51, 52, 54, 55, 56, 57, 59, 61, 63, 72, 76, 78, 79, 80, 83, 84, 85, 86, 88, 89, 90, 99, 100, 101, 102, 106, 108, 112, 114, 115, 117, 118, 119, 120, 121, 123, 124, 126, 127, 128, 129, 131, 132, 141, 142, 143, 144, 145, 146, 200, 209, 214, 216, 221, 222, 223, 231, 240, 241, 242, 245, 246, 247, 250, 256, 257, 261, 263, 264, 265, 268, 269, 270, 271, 273, 274, 275, 276, 278, 279, 280, 281, 283, 284, 286, 290, 291, 293, 294, 295, 297, 302, 303, 304, 307, 309, 310, 311, 312, 314, 316, 317, 318, 319, 321, 322, 324, 325, 326, 327, 328, 329, 330, 331, 332, 333, 334, 335, 336, 337, 338, 339, 340, 341, 342, 343, 344, 345, 346, 347, 348, 349, 350, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 398, 399, 401, 402, 403, 405, 406, 407, 408, 409, 410, 411, 413, 414, 416, 417, 418, 419, 420, 421, 422, 423, 424, 425, 426, 427, 428, 429, 430, 432, 433, 435, 436, 437, 438, 439, 440, 441, 442, 443, 444, 445, 446, 447, 448, 449, 450, 451, 452, 453, 454, 455, 456, 457, 458, 459, 460, 461, 463, 464, 466, 467, 468, 469, 471, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502 503, 504, 505, 506, 507, 508, 509, 510, 511, 512, 513, 514, 515, 516, 517, 518, 519, 520, 521, 522, 523, 524, 525, 526, 527, 528, 529, 531, 532, 533, 535, 536, 537, 538, 539, 542, 543, 544, 545, 546, 569, 570, 572, 573, 574, 575, 576, 577, 578, 579, 580, 582, 583, 584, 586, 587, 588, 589, 590, 591, 592, 594, 595, 596, 597, and 598. |
| ++ | 1, 4, 6, 8, 9, 13, 14, 20, 21, 30, 32, 33, 34, 35, 39, 43, 46, 53, 58, 64, 65, 66, 68, 71, 77, 81, 87, 91, 96, 97, 103, 105, 107, 109, 110, 111, 113, 116, 122, 125, 130, 134, 135, 136, 137, 138, 139, 140, 202, 204, 220, 228, 232, 234, 244, 248, 249, 251, 252, 254, 255, 258, 259, 260, 262, 266, 267, 272, 287, 288, 298, 301, 305, 306, 308, 320, 323, 351, 397, 400, 404, 415, 431, 465, 470, 530, 540, 541, 548, 551, 557, 559, 561, 563, 564, 565, 566, 567, 571, 581, and 585. |
| + | 2, 3, 5, 10, 11, 12, 15, 16, 17, 23, 24, 26, 28, 38, 44, 60, 62, 67, 69, 70, 73, 74, 75, 82, 92, 93, 94, 95, 98, 104, 138, 203, 207, 211, 213, 215, 217, 218, 219, 225, 227, 229, 233, 235, 243, 253, 282, 285, 289, 292, 296, 299, 300, 313, 315, 412, 462, 472, 549, 550, 560, 562, and 568. |
| greater than 10 µM | 201, 205, 206, 208, 210, 212, 224, 226, 230, 236, 237, and 239 |

Cell-Based Assay:

The cell-based assays is based on IL-6 ELISA quantification. Briefly, A549 cells are cultured in DMEM with 10% FBS medium. When cells reach 80% confluence they are trypsin treated and seeded 180 ul/well in 96-well plate at 2.5×10^4 cells/well. Then, 20 ul of compound serial dilutions (starting at 10 uM, 10 points) are added to the cell plate; incubate for 30 min at 37 C and stimulated with 2 ng/ml human IL-1beta 37 C, 5% $CO_2$ overnight. The next day 100 ul of cell supernatant per well are analyzed on a Human IL-6 Quantikine ELISA kit from R&D Systems.

The compounds described herein were tested for in the above biochemical and cell-based assays. The results are provided below, wherein the compound number corresponds to the numbers set forth in the examples above, "†" represents an EC50 of greater than 10 uM, "††" represents an EC50 of equal to or less than 10 uM but greater than 1 uM, and "†††" represents an EC50 of equal to or less than 1 uM.

| EC50 | Compounds |
|---|---|
| ††† | 324, 325, 326, 327, 328, 329, 330, 331, 332, 333, 334, 335, 336, 337, 338, 339, 340, 341, 342, 343, 344, 345, 346, 347, 348, 349, 354, 355, 357, 358, 359, 360, 361, 362, 363, 364, 365, 366, 367, 368, 369, 370, 371, 372, 373, 374, 375, 376, 377, 397, 398, 399, 411, 413, 414, 415, 416, 418, 422, 423, 425, 427, 436, 437, 438, 439, 442, 443, 445, 446, 447, 451, 453, 454, 456, 457, 458, 463, 464, 473, 474, 475, 476, 483, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 535, 536, 537, and 538. |
| †† | 350, 356, 378, 379, 380, 381, 444, 448, 450, 452, 539, 540, 541, 542, 543, 544, 545, 546, 548, 549, and 550. |
| † | |

Example 600—IRAK4 Inhibits Injury Responses in Human and Mouse Fibroblasts

Primary mouse kidney fibroblasts were treated for 24 hours with 10 ng/ml recombinant IL-1β (FIG. 1 (a)) or 100 ng/ml ultrapure LPS (FIG. 1 (b)). Inflammatory responses were measured by detection of secreted IL-6 in supernatants using ELISA. Both IL-1β induced Interleukin-1 Receptor responses and LPS-induced Toll-like Receptor responses are mediated by MyD88 and they showed significantly decreased activation in the presence of one of the exemplified compounds ("IRAK4 inhibitor") in the dose-dependent manner (FIGS. 1 (a) and (b)).

Primary human kidney fibroblasts were stimulated with a variety of treatments that model injury in vitro: kidney Danger Associated Molecular Patters, or DAMPs, 10 ng/ml TGFβ or 10 μg/ml histones. Inflammatory responses measured by expression of Il6 and Ccl2 using qPCR as well fibroblast activation as indicated by TGFβ-induced Acta2 expression measured by qPCR or histone-induced migration (scratch wound assays, See Methods as described below) were reduced in the presence one of the exemplified compounds ("IRAK4 inhibitor"). These data presented in the table below demonstrate that the IRAK4 inhibitor is able to efficiently inhibit injury responses (e.g., Il6 expression, Ccl2 expression, Acta2 expression, and migration) in human fibroblasts.

| Measurement | Assay | Description | No Compound | IRAK4 inhibitor 100 nM | IRAK4 inhibitor 1000 nM |
|---|---|---|---|---|---|
| Il6 expression (qPCR) | Fibroblasts stimulated with diseased kidney DAMPs | Inflammatory response | 100% | 64.30% | 52.46% |
| Ccl2 expression (qPCR) | Fibroblasts stimulated with diseased kidney DAMPs | Inflammatory response | 100% | 46.87% | 35.78% |
| Acta2 expression (qPCR) | Fibroblasts stimulated with diseased kidney TGFβs | Fibroblast activation | 100% | 96% | 80.69% |
| Migration | Scratch Wound Assay in fibroblasts activated with histones | Fibroblast activation | 100% | 46.78% | 19.61% |

Example 601—Inhibition of IRAK4 Reduces Inflammation, Tubular Damage and Extracellular Matrix Deposition in Mouse Models of Ischemic Kidney Injury (IRI)

Figure 2:
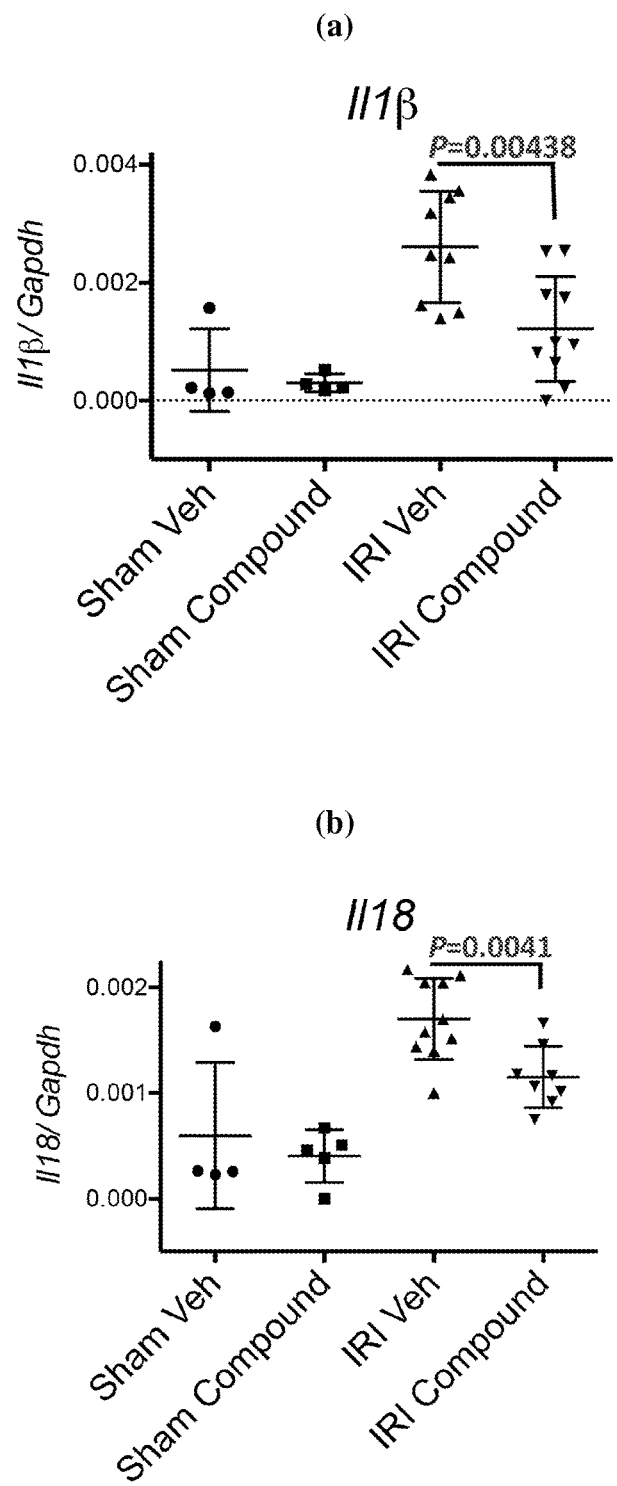
FIG. 2 is a graph showing that inhibition of IRAK4 reduces inflammation (a) and (b), tubular damage (c), and extracellular matrix deposition (d) in mouse models of ischemic kidney injury.
Figure 2:
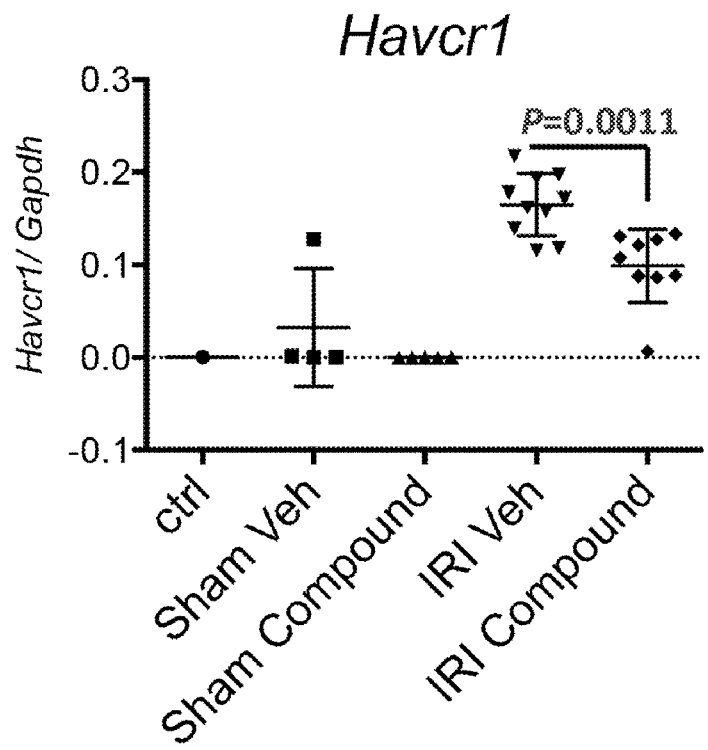
Figure 2:
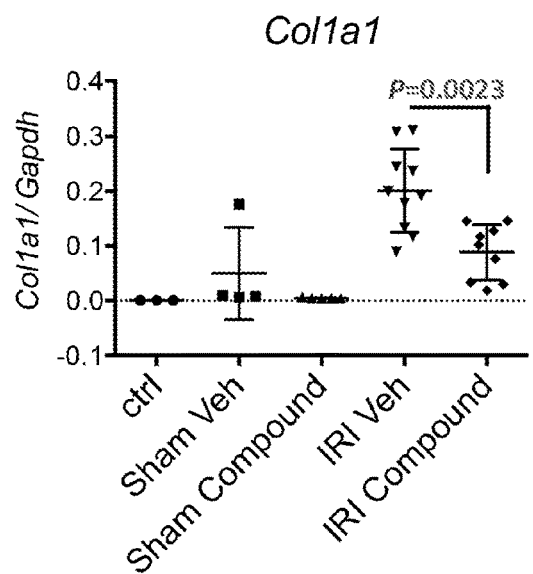

To evaluate the effect of IRAK4 inhibitor on fibrotic kidney disease mice, were subjected to ischemic kidney injury (IRI) and a subgroup was treated with one of the exemplified compounds ("IRAK4 inhibitor"). On Day 7 of the study mice were sacrificed and their kidneys were collected. Kidney RNA was isolated and used to quantify the expression of fibrotic disease and inflammation markers by qPCR. Mice that received a treatment showed significant protection from disease as indicated by reduced expression pro-inflammatory cytokines Il1β (FIG. 2 (a)) and Il18 (FIG. 2 (b)), kidney tubular damage marker Havcr1 (FIG. 2 (c)) and extracellular matrix Collagen1 (Col1a1)(FIG. 2 (d)).

Study Design:

| Day | −1 | 0 | 1 | 2 | 3 | 4 | 5 | 6 | 7 |
|---|---|---|---|---|---|---|---|---|---|
| Bi-daily dosing with an IRAK4 inhibitor or vehicle | X | IRI | X | | | X | | X | Endpoint |

Mice Groups:

| Group | Number of Mice | Procedure | Compound | Dose | Route |
|---|---|---|---|---|---|
| 1 | 10 | IRI | Vehicle | N/A | PO |
| 2 | 10 | IRI | IRAK4 inhibitor | 75 mg/kg | PO |
| 3 | 10 | IRI | IRAK4 inhibitor | 15 mg/kg | PO |
| 4 | 5 | Sham | Vehicle | N/A | PO |
| 5 | 5 | Sham | IRAK4 inhibitor | 75 mg/kg | PO |

Methods for Examples 600 and 601

Pericyte Purification and Culture.

Mouse pericytes were purified from normal kidneys of wild-type C57BL/6 by magnetic affinity cell sorting system (Miltenyi Biotech) as described previously.[1] Human pericytes were purified from fetal human kidneys obtained following voluntary pregnancy interruptions (d110 to d130 of gestation) performed at the University of Washington Medical Center, (IRB447773EA University of Washington) or from Novogenix, Los Angeles, Calif. as described.[2] Informed consents for the use of fetal tissues were obtained from all patients. The single cell preparation was depleted of epithelial cells by passing through an anti-CD326 magnetic bead Column (Miltenyi Biotech). Pericytes were further sorted as PDGFRP (300 μg/ml, Biolegend, Cat. No. 323608) and NG2 (R&D, Cat. No. FAB2585F) positive populations. Pericytes were cultured in pericyte medium as described[1] on 0.2% gelatin-coated plates. Purity of pericyte cultures was confirmed by FACS to represent >90% PDGFRβ+populations free of CD45+, CD326+ or CD31+ cells. All pericytes were studied at low passages (below passage 5).

Cell Culture Assays

Pericytes (P3-P5) were cultured in 6-well gelatin-coated plates at a density of $4*10^5$ cells/mL for 24 h in pericyte medium. Cells were then washed five times with PBS and cultured overnight in serum-free pericyte medium followed by the following treatments:

ultrapure LPS (100 ng/mL) from Invivogen, IL-13 (10 ng/mL) from Peprotech, histones (10 μg/ml) or 10-20% kidney DAMPs.

Migration was evaluated in a wound healing scratch assay in 96-well plates using IncuCyte from Essen BioScience.

Quantification of Secreted Proteins

Secreted proteins were collected in cell culture supernatants as described.[3] Secreted IL-6 was measured by ELISA (R&D systems).

DAMPs Preparation

IRI and healthy kidney DAMPs were collected 24 hours post-surgery under sterile conditions using methods as described.[3] Histones (Worthington Biochemical) were used at a final concentration of 10 μg/ml.

Animals and Animal Studies

Foxd1$^{+/Cre}$; Myd88$^{fl/fl}$ mice on the C57BL6 genetic background were generated by crossing female Foxd1$^{1+/Cre}$; Myd88$^{+/flox}$ mice with male Myd88$^{flox/flox}$ mice. Myd88$^{flox/flox}$ mice were obtained from Jackson Labs (CBy.1129P2(B6)-Myd88tm1Defr/J). Foxd1$^{+/Cre}$ were generated as described.[4] Experimental mice were identified by PCR to identify the floxed allele and the Cre insertion at the Foxd1 locus using primers as described.[5] Kidney ischemia reperfusion injury (IRI) studies were performed as described.[6] Mice were euthanized at either 24 hours or 5 days post-surgery. All studies were performed under protocols approved by Institutional Animal Care and Use Committees at the University of Washington, Center for Infectious Disease Research, or Biogen.

Quantitative RT-PCR

Total RNA was extracted using RNeasy Plus Mini Kit (Qiagen). Purity was determined by the A260 to A280 ratio. cDNA was synthesized using oligo(dT) and random primers (iScript Reverse Transcription Supermix, BioRad). Quantitative PCR was performed using QuantStudio™ 7 Flex Real-Time PCR System (Life Technologies), TaqMan® Gene Expression Assays using manufacturer's instructions (Life Technologies). The specific Taqman probe sets used in Q-PCR are listed below (Life Technologies). All values were normalized to Gapdh.

| Gene   | Vendor           | Format                          | Assay ID      |
|--------|------------------|---------------------------------|---------------|
| Col1a1 | Life Technologies | TaqMan ® Gene Expression Assays | Mm00801666_g1 |
| Il1b   | Life Technologies | TaqMan ® Gene Expression Assays | Mm00434228_m1 |
| Il18   | Life Technologies | TaqMan ® Gene Expression Assays | Mm00434225_m1 |
| Hacvr1 | Life Technologies | TaqMan ® Gene Expression Assays | Mm00506686_m1 |
| Gapdh  | Life Technologies | TaqMan ® Gene Expression Assays | Mm99999915_g1 |

Statistical Analysis

Data are presented as the means±s.e.m. Statistically significant differences between groups were determined by Student's t test, One-Way ANOVA, or Two-Way ANOVA with Bonferroni correction for multiple comparisons with a 95% confidence interval

REFERENCES

1. Lin, S. L., Kisseleva, T., Brenner, D. A. & Duffield, J. S. Pericytes and perivascular fibroblasts are the primary source of collagen-producing cells in obstructive fibrosis of the kidney. *The American journal of pathology* 173, 1617-1627 (2008).
2. Gomez, I. G., et al. Anti-microRNA-21 oligonucleotides prevent Alport nephropathy progression by stimulating metabolic pathways. *The Journal of clinical investigation* 125, 141-156 (2015).
3. Campanholle, G., et al. TLR-2/TLR-4 TREM-1 signaling pathway is dispensablein inflammatory myeloid cells during sterile kidney injury. *PloS one* 8, e68640 (2013).
4. Humphreys, B. D., et al. Fate tracing reveals the pericyte and not epithelial origin of myofibroblasts in kidney fibrosis. *The American journal of pathology* 176, 85-97 (2010).
5. Nakagawa, N., et al. Dicer1 activity in the stromal compartment regulates nephron differentiation and vascular patterning during mammalian kidneyorganogenesis. *Kidney international* 87, 1125-1140 (2015).
6. Duffield, J. S., et al. Restoration of tubular epithelial cells during repair of the postischemic kidney occurs independently of bone marrow-derived stem cells. *The Journal of clinical investigation* 115, 1743-1755 (2005).

What is claimed is:

1. A compound selected from:
   6-(1-(6-methylpyridin-2-yl)-1H-indazol-6-yl)pyridine-2-amine;
   2-(1-(6-methylpyridin-2-yl)-1H-indazol-6-yl)pyrimidin-4-amine;
   2-(1-(6-methylpyridin-2-yl)-1H-indazol-6-yl)pyridin-4-amine;
   (6-(1-(6-methylpyridin-2-yl)-1H-indazol-6-yl)pyridin-2-yl)methanamine;
   (2-(1-(6-methylpyridin-2-yl)-1H-indazol-6-yl)pyridin-4-yl)methanamine;
   4-(1-(6-methylpyridin-2-yl)-1H-indazol-6-yl)pyridin-2-amine;
   5-(1-(6-methylpyridin-2-yl)-1H-indazol-6-yl)pyridin-3-amine;
   (2-(1-(6-methylpyridin-2-yl)-1H-indazol-6-yl)pyrimidin-4-yl)methanamine;
   4-methyl-5-(1-(6-methylpyridin-2-yl)-1H-indazol-6-yl)pyridin-3-amine;
   3-(1-(6-methylpyridin-2-yl)-1H-indazol-6-yl)-5-nitropyridin-2-ol;
   3-amino-5-(1-(6-methylpyridin-2-yl)-1H-indazol-6-yl)pyridin-4-ol;
   N-methyl-5-(1-(6-methylpyridin-2-yl)-1H-indazol-6-yl)pyridin-3-amine;

N,N-dimethyl-1-(6-(1-(6-methylpyridin-2-yl)-1H-indazol-6-yl)pyridin-2-yl)methanamine;
N-methyl-1-(3-(1-(6-methylpyridin-2-yl)-1H-indazol-6-yl)phenyl)methanamine;
6-(6-(5-aminopyridin-3-yl)-1H-indazol-1-yl)picolinonitrile;
6-(6-(5-aminopyridin-3-yl)-1H-indazol-1-yl)picolinic acid;
6-(6-(5-aminopyridin-3-yl)-1H-indazol-1-yl)picolinamide;
6-(6-(5-aminopyridin-3-yl)-1H-indazol-1-yl)-N-methylpicolinamide;
2-(6-(5-aminopyridin-3-yl)-1H-indazol-1-yl)pyrimidine-4-carbonitrile;
5-(1-(3-chloro-6-methylpyridin-2-yl)-1H-indazol-6-yl)pyridin-3-amine;
5-(1-(4-methylpyridin-2-yl)-1H-indazol-6-yl)pyridin-3-amine;
5-(1-(6-(trifluoromethyl)pyridin-2-yl)-1H-indazol-6-yl)pyridin-3-amine;
5-(5-fluoro-1-(6-methylpyridin-2-yl)-1H-indazol-6-yl)pyridin-3-amine;
5-(5-methyl-1-(6-methylpyridin-2-yl)-1H-indazol-6-yl)pyridin-3-amine;
6-(6-(6-(aminomethyl)pyridin-2-yl)-1H-indazol-1-yl)picolinonitrile;
6-(6-(6-(aminomethyl)pyridin-2-yl)-1H-indazol-1-yl)picolinamide;
(6-(1-(6-(trifluoromethyl)pyridin-2-yl)-1H-indazol-6-yl)pyridin-2-yl)methanamine;
methyl 6-(5-aminopyridin-3-yl)-1-(6-cyanopyridin-2-yl)-1H-indazole-4-carboxylate;
methyl 6-(5-aminopyridin-3-yl)-1-(6-(trifluoromethyl)pyridin-2-yl)-1H-indazole-4-carboxylate;
6-(5-aminopyridin-3-yl)-1-(6-(trifluoromethyl)pyridin-2-yl)-1H-indazole-4-carboxylic acid;
6-(5-aminopyridin-3-yl)-1-(6-(trifluoromethyl)pyridin-2-yl)-1H-indazole-4-carboxamide;
5-(4-(aminomethyl)-1-(6-(trifluoromethyl)pyridin-2-yl)-1H-indazol-6-yl)pyridin-3-amine;
(6-(5-aminopyridin-3-yl)-1-(6-(trifluoromethyl)pyridin-2-yl)-1H-indazol-4-yl)methanol;
1-(6-(1-(6-methylpyridin-2-yl)-1H-indazol-6-yl)pyridin-2-yl)ethanamine;
methyl 6-(6-(1-aminoethyl)pyridin-2-yl)-1-(6-(trifluoromethyl)pyridin-2-yl)-1H-indazole-4-carboxylate;
(6-(6-(1-aminoethyl)pyridin-2-yl)-1-(6-(trifluoromethyl)pyridin-2-yl)-1H-indazol-4-yl)methanol;
6-(6-(1-aminoethyl)pyridin-2-yl)-N,N-dimethyl-1-(6-(trifluoromethyl)pyridin-2-yl)-1H-indazole-4-carboxamide;
6-(6-(1-aminoethyl)pyridin-2-yl)-N-methyl-1-(6-(trifluoromethyl)pyridin-2-yl)-1H-indazole-4-carboxamide;
6-(5-aminopyridin-3-yl)-N,N-dimethyl-1-(6-(trifluoromethyl)pyridin-2-yl)-1H-indazole-4-carboxamide;
6-(5-aminopyridin-3-yl)-N-methyl-1-(6-(trifluoromethyl)pyridin-2-yl)-1H-indazole-4-carboxamide;
2-(1-(6-(trifluoromethyl)pyridin-2-yl)-1H-indazol-6-yl)-6,7-dihydro-5H-cyclopenta[b]pyridin-7-amine;
2-(1-(6-(trifluoromethyl)pyridin-2-yl)-1H-indazol-6-yl)-5,6,7,8-tetrahydroquinolin-8-amine;
6-(6-(5-aminopyridin-3-yl)-1H-indazol-1-yl)-N,N-dimethylpicolinamide;
6-(6-(5-aminopyridin-3-yl)-1H-indazol-1-yl)-N-(2-hydroxyethyl)picolinamide;
6-(6-(5-aminopyridin-3-yl)-1H-indazol-1-yl)-N-(3-hydroxypropyl)picolinamide;
6-(6-(5-aminopyridin-3-yl)-1H-indazol-1-yl)-N-(2-hydroxypropyl)picolinamide;
(6-(6-(5-aminopyridin-3-yl)-1H-indazol-1-yl)pyridin-2-yl)(3-hydroxyazetidin-1-yl)methanone;
6-(6-(5-aminopyridin-3-yl)-1H-indazol-1-yl)-N-(2-(dimethylamino)ethyl)picolinamide;
6-(6-(5-aminopyridin-3-yl)-1H-indazol-1-yl)-N-(2-cyanoethyl)picolinamide;
N-(2-aminoethyl)-6-(6-(5-aminopyridin-3-yl)-1H-indazol-1-yl)picolinamide;
6-(6-(5-aminopyridin-3-yl)-1H-indazol-1-yl)-N-(cyanomethyl)picolinamide;
6-(6-(5-aminopyridin-3-yl)-1H-indazol-1-yl)-N-(2-(methylsulfonyl)ethyl)picolinamide;
2-(aminomethyl)-6-(1-(6-(trifluoromethyl)pyridin-2-yl)-1H-indazol-6-yl)pyridin-4-amine;
2-(6-(6-(5-aminopyridin-3-yl)-1H-indazol-1-yl)pyridin-2-yl)acetonitrile;
2-(6-(6-(5-aminopyridin-3-yl)-1H-indazol-1-yl)pyridin-2-yl)acetic acid;
1-(6-(1-(6-(trifluoromethyl)pyridin-2-yl)-1H-indazol-6-yl)pyridin-2-yl)ethanamine;
6-amino-N-(cyanomethyl)-4-(1-(6-(trifluoromethyl)pyridin-2-yl)-1H-indazol-6-yl)picolinamide;
1-(5-(1-(6-(trifluoromethyl)pyridin-2-yl)-1H-indazol-6-yl)pyridin-3-yl)ethanamine;
1-(4-(1-(6-(trifluoromethyl)pyridin-2-yl)-1H-indazol-6-yl)pyridin-2-yl)ethanamine;
6-(1-(6-(trifluoromethyl)pyridin-2-yl)-1H-indazol-6-yl)pyrazine-2-carbonitrile;
(6-(1-(6-(trifluoromethyl)pyridin-2-yl)-1H-indazol-6-yl)pyrazin-2-yl)methanamine;
4-(1-(6-(trifluoromethyl)pyridin-2-yl)-1H-indazol-6-yl)pyrimidine-2-carbonitrile;
(4-(1-(6-(trifluoromethyl)pyridin-2-yl)-1H-indazol-6-yl)pyrimidin-2-yl)methanamine;
6-(1-(6-(trifluoromethyl)pyridin-2-yl)-1H-indazol-6-yl)pyrazin-2-amine;
6-(6-(pyrrolidin-2-yl)pyridin-2-yl)-1-(6-(trifluoromethyl)pyridin-2-yl)-1H-indazole;
6-(6-(1-methylpyrrolidin-2-yl)pyridin-2-yl)-1-(6-(trifluoromethyl)pyridin-2-yl)-1H-indazole;
6-(6-(1-aminoethyl)pyridin-2-yl)-1-(6-methylpyridin-2-yl)-1H-indazol-4-amine;
6-(6-(1-aminoethyl)pyridin-2-yl)-N-methyl-1-(6-methylpyridin-2-yl)-1H-indazol-4-amine;
6-(6-(1-aminoethyl)pyridin-2-yl)-N,N-dimethyl-1-(6-methylpyridin-2-yl)-1H-indazol-4-amine;
N-(6-(6-(1-aminoethyl)pyridin-2-yl)-1-(6-methylpyridin-2-yl)-1H-indazol-4-yl)acetamide;
1-(6-(4-(aminomethyl)-1-(6-methylpyridin-2-yl)-1H-indazol-6-yl)pyridin-2-yl)ethanamine;
N-((6-(6-(1-aminoethyl)pyridin-2-yl)-1-(6-methylpyridin-2-yl)-1H-indazol-4-yl)methyl)acetamide;
1-(6-(4-chloro-1-(6-methylpyridin-2-yl)-1H-indazol-6-yl)pyridin-2-yl)ethanamine;
1-(6-(4-cyclopropyl-1-(6-methylpyridin-2-yl)-1H-indazol-6-yl)pyridin-2-yl)ethanamine;
1-(6-(1-(6-methylpyridin-2-yl)-4-(prop-1-en-2-yl)-1H-indazol-6-yl)pyridin-2-yl)ethanamine;
1-(6-(4-ethyl-1-(6-methylpyridin-2-yl)-1H-indazol-6-yl)pyridin-2-yl)ethanamine;
1-(6-(4-isopropyl-1-(6-methylpyridin-2-yl)-1H-indazol-6-yl)pyridin-2-yl)ethanamine;
1-(6-(1-(6-methylpyridin-2-yl)-4-(trifluoromethyl)-1H-indazol-6-yl)pyridin-2-yl)ethanamine;

methyl 6-(6-(1-aminoethyl)pyridin-2-yl)-1-(6-methylpyridin-2-yl)-1H-indazole-4-carboxylate;
6-(6-(1-aminoethyl)pyridin-2-yl)-1-(6-methylpyridin-2-yl)-1H-indazole-4-carboxylic acid;
6-(6-(1-aminoethyl)pyridin-2-yl)-1-(6-methylpyridin-2-yl)-1H-indazol-4-yl)methanol;
6-(6-(1-aminoethyl)pyridin-2-yl)-N-methyl-1-(6-methylpyridin-2-yl)-1H-indazole-4-carboxamide;
N-methyl-1-(6-(1-(6-methylpyridin-2-yl)-1H-indazol-6-yl)pyridin-2-yl)ethanamine;
N-methyl-1-(6-(1-(6-(trifluoromethyl)pyridin-2-yl)-1H-indazol-6-yl)pyridin-2-yl)ethanamine;
N-methyl-1-(6-(1-(6-(trifluoromethyl)pyridin-2-yl)-1H-indazol-6-yl)pyridin-2-yl)ethanamine;
1-(6-(1-(6-cyclopropylpyridin-2-yl)-1H-indazol-6-yl)pyridin-2-yl)ethanamine;
1-(6-(1-(6-ethylpyridin-2-yl)-1H-indazol-6-yl)pyridin-2-yl)ethanamine;
1-(6-(1-(6-isopropylpyridin-2-yl)-1H-indazol-6-yl)pyridin-2-yl)ethanamine;
1-(6-(1-(pyridin-2-yl)-1H-indazol-6-yl)pyridin-2-yl)ethanamine;
(6-(6-(6-(1-aminoethyl)pyridin-2-yl)-1H-indazol-1-yl)pyridin-2-yl)methanol;
1-(4-methyl-6-(1-(6-methylpyridin-2-yl)-1H-indazol-6-yl)pyridin-2-yl)ethanamine;
1-(6-(1-(6-methylpyridin-2-yl)-1H-indazol-6-yl)-4-(trifluoromethyl)pyridin-2-yl)ethanamine;
6-(6-(6-(1-aminoethyl)pyridin-2-yl)-1H-indazol-1-yl)picolinamide;
1-(6-(1-(6-(trifluoromethyl)pyridin-2-yl)-1H-indazol-6-yl)pyridin-2-yl)propan-1-amine;
cyclopropyl(6-(1-(6-(trifluoromethyl)pyridin-2-yl)-1H-indazol-6-yl)pyridin-2-yl)methanamine;
2-(6-(1-(6-(trifluoromethyl)pyridin-2-yl)-1H-indazol-6-yl)pyridin-2-yl)propan-2-amine;
1-(6-(1-(6-methylpyridin-2-yl)-1H-indazol-6-yl)pyridin-2-yl)ethanol;
cyclopropyl(6-(1-(6-methylpyridin-2-yl)-1H-indazol-6-yl)pyridin-2-yl)methanamine;
1-(6-(1-(6-methylpyridin-2-yl)-1H-indazol-6-yl)pyridin-2-yl)butan-1-amine;
1-(6-(1-(4-methylthiazol-2-yl)-1H-indazol-6-yl)pyridin-2-yl)ethanamine;
1-(6-(1-(5-methylthiazol-2-yl)-1H-indazol-6-yl)pyridin-2-yl)ethanamine;
1-(6-(1-(2-methylthiazol-4-yl)-1H-indazol-6-yl)pyridin-2-yl)ethanamine;
1-(6-(1-(1-methyl-1H-pyrazol-3-yl)-1H-indazol-6-yl)pyridin-2-yl)ethanamine;
1-(6-(1-(1-methyl-1H-imidazol-4-yl)-1H-indazol-6-yl)pyridin-2-yl)ethanamine;
(2-(1-(6-methylpyridin-2-yl)-1H-indazol-6-yl)thiazol-4-yl)methanamine;
(2-(1-(6-methylpyridin-2-yl)-1H-indazol-6-yl)thiazol-5-yl)methanamine;
(2-(1-(6-methylpyridin-2-yl)-1H-indazol-6-yl)thiazol-5-yl)methanamine;
(S)-1-(6-(1-(6-methylpyridin-2-yl)-1H-indazol-6-yl)pyridin-2-yl)ethanamine;
(S)-(6-(6-(6-(1-aminoethyl)pyridin-2-yl)-1H-indazol-1-yl)pyridin-2-yl)methanol;
(R)-(6-(6-(6-(1-aminoethyl)pyridin-2-yl)-1H-indazol-1-yl)pyridin-2-yl)methanol;
(S)-(6-(6-(6-(1-aminobutyl)pyridin-2-yl)-1H-indazol-1-yl)pyridin-2-yl)methanol;
(R)-(6-(6-(6-(1-aminobutyl)pyridin-2-yl)-1H-indazol-1-yl)pyridin-2-yl)methanol;
2-(1-(6-methylpyridin-2-yl)-1H-indazol-6-yl)isonicotinamide;
N,N-dimethyl-5-(1-(6-methylpyridin-2-yl)-1H-indazol-6-yl)pyridin-3-amine;
1-(6-methylpyridin-2-yl)-6-(5-(pyrrolidin-1-yl)pyridin-3-yl)-1H-indazole;
6-methyl-5-(1-(6-methylpyridin-2-yl)-1H-indazol-6-yl)pyridin-3-amine;
5-(1-(6-cyclopentylpyridin-2-yl)-1H-indazol-6-yl)pyridin-3-amine;
1-(6-(4-fluoro-1-(6-(trifluoromethyl)pyridin-2-yl)-1H-indazol-6-yl)pyridin-2-yl)ethanone;
N-(5-(4-cyano-1-(6-(trifluoromethyl)pyridin-2-yl)-1H-indazol-6-yl)pyridin-3-yl)-2,2,2-trifluoroacetamide;
1-(6-(1-(6-(trifluoromethyl)pyridin-2-yl)-1H-indazol-6-yl)pyridin-2-yl)ethanamine;
2-(1-(6-(trifluoromethyl)pyridin-2-yl)-1H-indazol-6-yl)-5H-cyclopenta[b]pyridin-7(6H)-one;
6-(1-(6-(trifluoromethyl)pyridin-2-yl)-1H-indazol-6-yl)picolinonitrile;
2-(1-(6-(trifluoromethyl)pyridin-2-yl)-1H-indazol-6-yl)-6,7-dihydroquinolin-8(5H)-one;
6-amino-4-(1-(6-(trifluoromethyl)pyridin-2-yl)-1H-indazol-6-yl)picolinic acid;
6-(6-(1-aminoethyl)pyridin-2-yl)-1-(6-methylpyridin-2-yl)-1H-indazole-4-carbonitrile;
1-(6-(4-(aminomethyl)-2-(6-methylpyridin-2-yl)-2H-indazol-6-yl)pyridin-2-yl)ethanamine;
N,N-dimethyl-1-(6-(1-(6-(trifluoromethyl)pyridin-2-yl)-1H-indazol-6-yl)pyridin-2-yl)ethanamine;
1-(6-(4-chloro-1-(6-methylpyridin-2-yl)-1H-indazol-6-yl)pyridin-2-yl)ethanone;
(Z)-1-(6-(4-chloro-1-(6-methylpyridin-2-yl)-1H-indazol-6-yl)pyridin-2-yl)ethanone oxime;
N,N-dimethyl-1-(6-(1-(6-methylpyridin-2-yl)-1H-indazol-6-yl)pyridin-2-yl)ethanamine;
N,N-dimethyl-1-(6-(1-(6-(trifluoromethyl)pyridin-2-yl)-1H-indazol-6-yl)pyridin-2-yl)ethanamine;
tert-butyl (6-(6-acetylpyridin-2-yl)-1-(6-methylpyridin-2-yl)-1H-indazol-4-yl)(methyl)carbamate;
(Z)-tert-butyl (6-(6-(1-(hydroxyimino)ethyl)pyridin-2-yl)-1-(6-methylpyridin-2-yl)-1H-indazol-4-yl)(methyl)carbamate;
(Z)-1-(6-(4-(methylamino)-1-(6-methylpyridin-2-yl)-1H-indazol-6-yl)pyridin-2-yl)ethanone oxime;
1-(6-(1-(6-ethylpyridin-2-yl)-1H-indazol-6-yl)pyridin-2-yl)ethanone;
1-(6-(1-(pyridin-2-yl)-1H-indazol-6-yl)pyridin-2-yl)ethanone;
(E)-1-(6-(1-(pyridin-2-yl)-1H-indazol-6-yl)pyridin-2-yl)ethanone oxime;
2-(aminomethyl)-6-(1-(6-methylpyridin-2-yl)-1H-indazol-6-yl)pyridin-4-amine;
N,N-dimethyl-1-(6-(1-(6-methylpyridin-2-yl)-1H-indazol-6-yl)pyridin-2-yl)ethanamine;
1-(6-(4-(dimethylamino)-1-(6-methylpyridin-2-yl)-1H-indazol-6-yl)pyridin-2-yl)ethanone;
(E)-1-(6-(4-(dimethylamino)-1-(6-methylpyridin-2-yl)-1H-indazol-6-yl)pyridin-2-yl)ethanone oxime;
(E)-1-(6-(4-(dimethylamino)-1-(6-methylpyridin-2-yl)-1H-indazol-6-yl)pyridin-2-yl)ethanone oxime;
6-(6-acetylpyridin-2-yl)-1H-indazol-1-yl)picolinonitrile;
(E)-methyl 6-(6-(6-(1-(hydroxyimino)ethyl)pyridin-2-yl)-1H-indazol-1-yl)picolinate;

1-(6-(1-(4-methylthiazol-2-yl)-1H-indazol-6-yl)pyridin-2-yl)ethanone;
1-(6-(4-fluoro-1-(6-(trifluoromethyl)pyridin-2-yl)-1H-indazol-6-yl)pyridin-2-yl)ethanamine;
(S)-1-(6-(1-(6-methylpyridin-2-yl)-1H-indazol-6-yl)pyridin-2-yl)ethanamine;
1-(3-fluoro-6-(1-(6-methylpyridin-2-yl)-1H-indazol-6-yl)pyridin-2-yl)ethanamine;
methyl 3-amino-6-(1-(6-methylpyridin-2-yl)-1H-indazol-6-yl)picolinate;
2,2,2-trifluoro-1-(6-(1-(6-methylpyridin-2-yl)-1H-indazol-6-yl)pyridin-2-yl)ethanol;
1-(6-(4-ethoxy-1-(6-methylpyridin-2-yl)-1H-indazol-6-yl)pyridin-2-yl)ethanamine;
1-(6-(4-methoxy-1-(6-methylpyridin-2-yl)-1H-indazol-6-yl)pyridin-2-yl)ethanamine;
3-amino-3-(6-(1-(6-methylpyridin-2-yl)-1H-indazol-6-yl)pyridin-2-yl)propan-1-ol;
6-(1-(6-methylpyridin-2-yl)-1H-indazol-6-yl)picolinamide;
2-(6-(1-(6-methylpyridin-2-yl)-1H-indazol-6-yl)pyridin-2-yl)acetonitrile;
6-(6-(1-aminoethyl)pyridin-2-yl)-1-(6-methylpyridin-2-yl)-1H-indazol-4-ol;
1-(6-(4-(cyclopropylmethoxy)-1-(6-methylpyridin-2-yl)-1H-indazol-6-yl)pyridin-2-yl)ethanamine;
(4-(1-(6-methylpyridin-2-yl)-1H-indazol-6-yl)thiazol-2-yl)methanamine;
N-((6-(1-(6-methylpyridin-2-yl)-1H-indazol-6-yl)pyridin-2-yl)methyl)acetamide;
2-(6-(1-(6-methylpyridin-2-yl)-1H-indazol-6-yl)pyridin-2-yl)ethanamine;
1-(6-(1-(6-methylpyridin-2-yl)-1H-indazol-6-yl)-3-(trifluoromethyl)pyridin-2-yl)ethanamine;
2-(1-aminoethyl)-6-(1-(6-methylpyridin-2-yl)-1H-indazol-6-yl)pyridin-4-amine;
(1-methyl-4-(1-(6-methylpyridin-2-yl)-1H-indazol-6-yl)-1H-imidazol-2-yl)methanol;
2-amino-2-(6-(1-(6-methylpyridin-2-yl)-1H-indazol-6-yl)pyridin-2-yl)acetonitrile;
2,2,2-trifluoro-1-(6-(1-(6-methylpyridin-2-yl)-1H-indazol-6-yl)pyridin-2-yl)ethanamine;
3-amino-3-(6-(1-(6-methylpyridin-2-yl)-1H-indazol-6-yl)pyridin-2-yl)propanoic acid;
methyl 3-amino-3-(6-(1-(6-methylpyridin-2-yl)-1H-indazol-6-yl)pyridin-2-yl)propanoate;
1-(6-(1-(6-methylpyridin-2-yl)-1H-indazol-6-yl)pyridin-2-yl)cyclopropanamine;
1-(6-(1-(6-methylpyridin-2-yl)-1H-indazol-6-yl)pyridin-2-yl)propan-1-amine;
(R)-1-(6-(1-(6-methylpyridin-2-yl)-1H-indazol-6-yl)pyridin-2-yl)butan-1-amine;
(S)-1-(6-(1-(6-methylpyridin-2-yl)-1H-indazol-6-yl)pyridin-2-yl)butan-1-amine;
1-(3-chloro-6-(1-(6-methylpyridin-2-yl)-1H-indazol-6-yl)pyridin-2-yl)ethanamine;
2-amino-2-(6-(1-(6-methylpyridin-2-yl)-1H-indazol-6-yl)pyridin-2-yl)acetamide;
1-(6-(1-(6-(trifluoromethyl)pyridin-2-yl)-1H-indazol-6-yl)pyridin-2-yl)butan-1-amine;
6-(6-(6-(1-aminopropyl)pyridin-2-yl)-1H-indazol-1-yl)picolinamide;
2-(1-aminoethyl)-6-(1-(6-(trifluoromethyl)pyridin-2-yl)-1H-indazol-6-yl)pyridin-4-amine;
2-amino-2-(6-(1-(6-methylpyridin-2-yl)-1H-indazol-6-yl)pyridin-2-yl)ethanol;
methyl 2-amino-2-(6-(1-(6-methylpyridin-2-yl)-1H-indazol-6-yl)pyridin-2-yl)acetate;
2-amino-2-(6-(1-(6-methylpyridin-2-yl)-1H-indazol-6-yl)pyridin-2-yl)acetic acid;
6-(6-(1-aminobutyl)pyridin-2-yl)-1H-indazol-1-yl)picolinamide;
2-(6-(6-(1-aminoethyl)pyridin-2-yl)-1H-indazol-1-yl)pyridin-2-yl)propan-2-ol;
1-(6-(1-(6-(methoxymethyl)pyridin-2-yl)-1H-indazol-6-yl)pyridin-2-yl)ethanamine;
(6-(6-(6-(1-aminobutyl)pyridin-2-yl)-1H-indazol-1-yl)pyridin-2-yl)methanol;
1-(3-methyl-6-(1-(6-methylpyridin-2-yl)-1H-indazol-6-yl)pyridin-2-yl)ethanamine;
1-(6-(1-(4-methylthiophen-2-yl)-1H-indazol-6-yl)pyridin-2-yl)ethanamine;
1-(6-(1-(6-propylpyridin-2-yl)-1H-indazol-6-yl)pyridin-2-yl)ethanamine;
1-(6-(6-(6-(1-aminoethyl)pyridin-2-yl)-1H-indazol-1-yl)pyridin-2-yl)ethanol;
(4-(1-(6-methylpyridin-2-yl)-1H-indazol-6-yl)oxazol-2-yl)methanamine;
1-(6-(1-(6-(tert-butyl)pyridin-2-yl)-1H-indazol-6-yl)pyridin-2-yl)ethanamine;
1-(6-(1-(6-(aminomethyl)pyridin-2-yl)-1H-indazol-6-yl)pyridin-2-yl)ethanamine;
2-(6-(6-(6-(1-aminoethyl)pyridin-2-yl)-1H-indazol-1-yl)pyridin-2-yl)-2-methylpropanenitrile;
1-(6-(1-(6-(2-(methylsulfonyl)propan-2-yl)pyridin-2-yl)-1H-indazol-6-yl)pyridin-2-yl)ethanamine;
1-(6-(6-(6-(1-aminoethyl)pyridin-2-yl)-1H-indazol-1-yl)pyridin-2-yl)cyclopropanecarbonitrile;
(6-(6-(6-(aminomethyl)pyridin-2-yl)-1H-indazol-1-yl)pyridin-2-yl)methanol;
2-(6-(6-(6-(1-aminoethyl)pyridin-2-yl)-1H-indazol-1-yl)pyridin-2-yl)propan-2-amine;
(6-(6-(6-(1-aminopropyl)pyridin-2-yl)-1H-indazol-1-yl)pyridin-2-yl)methanol;
1-(6-(4-(1H-imidazol-2-yl)-1-(6-methylpyridin-2-yl)-1H-indazol-6-yl)pyridin-2-yl)ethanamine;
1-(6-(1-(4-methylpyrimidin-2-yl)-1H-indazol-6-yl)pyridin-2-yl)ethanamine;
1-(6-(1-(4-(trifluoromethyl)pyrimidin-2-yl)-1H-indazol-6-yl)pyridin-2-yl)ethanamine;
2-(6-(1-(6-methylpyridin-2-yl)-1H-indazol-6-yl)pyridin-2-yl)propan-2-amine;
1-(1-methyl-4-(1-(6-methylpyridin-2-yl)-1H-indazol-6-yl)-1H-imidazol-2-yl)ethanol;
(1-methyl-4-(1-(6-methylpyridin-2-yl)-1H-indazol-6-yl)-1H-imidazol-2-yl)methanamine;
2-(6-(6-(6-(1-aminoethyl)pyridin-2-yl)-1H-indazol-1-yl)pyridin-2-yl)-2-methylpropanamide;
1-(6-(1-(6-methylpyridin-2-yl)-4-(thiazol-2-yl)-1H-indazol-6-yl)pyridin-2-yl)ethanamine;
1-(6-(1-(6-methylpyridin-2-yl)-1H-indazol-6-yl)pyridin-2-yl)cyclobutanecarbonitrile;
1-(1-methyl-4-(1-(6-methylpyridin-2-yl)-1H-indazol-6-yl)-1H-imidazol-2-yl)ethanamine;
1-(6-methylpyridin-2-yl)-6-(pyridin-2-yl)-1H-indazole;
(6-(6-(1-aminoethyl)pyridin-2-yl)-4-methoxy-1H-indazol-1-yl)pyridin-2-yl)methanol;
2-(1-(6-methylpyridin-2-yl)-1H-indazol-6-yl)-6,7,8,9-tetrahydro-5H-cyclohepta[b]pyridin-9-amine;
(6-(6-(1-aminoethyl)pyridin-2-yl)-1-(6-(hydroxymethyl)pyridin-2-yl)-1H-indazol-4-yl)methanol;
1-(4-(1-(6-methylpyridin-2-yl)-1H-indazol-6-yl)thiazol-2-yl)ethanamine;

1-(6-(1-(6-methylpyridin-2-yl)-1H-indazol-6-yl)pyridin-2-yl)cyclobutanecarboxamide;

1-(6-methylpyridin-2-yl)-6-(6-(3,3,3-trifluoropropyl)pyridin-2-yl)-1H-indazole;

2-(6-(6-(6-(1-aminoethyl)pyridin-2-yl)-1H-indazol-1-yl)pyridin-2-yl)ethanol;

1-(6-(1-(4,6-dimethylpyridin-2-yl)-1H-indazol-6-yl)pyridin-2-yl)ethanamine;

6-(6-(1-aminoethyl)pyridin-2-yl)-1-(6-(hydroxymethyl)pyridin-2-yl)-N-methyl-1H-indazole-4-carboxamide;

(S)-(6-(6-(6-(1-aminopropyl)pyridin-2-yl)-1H-indazol-1-yl)pyridin-2-yl)methanol;

1-(6-(1-(6-methylpyridin-2-yl)-4-(1H-pyrazol-3-yl)-1H-indazol-6-yl)pyridin-2-yl)ethanamine;

(4-(1-(6-methylpyridin-2-yl)-1H-indazol-6-yl)thiazol-2-yl)methanol;

(6-(6-(6-(1-aminoethyl)pyridin-2-yl)-4-fluoro-1H-indazol-1-yl)pyridin-2-yl)methanol;

(R)-(6-(6-(6-(1-aminopropyl)pyridin-2-yl)-1H-indazol-1-yl)pyridin-2-yl)methanol;

6-(1-methyl-1H-imidazol-4-yl)-1-(6-methylpyridin-2-yl)-1H-indazole;

(S)-(6-(6-(6-(1-aminobutyl)pyridin-2-yl)-4-(piperidin-1-yl)-1H-indazol-1-yl)pyridin-2-yl)methanol;

1-(6-(6-((S)-1-aminobutyl)pyridin-2-yl)-1-(6-(hydroxymethyl)pyridin-2-yl)-1H-indazol-4-yl)pyrrolidin-3-ol;

(1-(6-(6-((S)-1-aminobutyl)pyridin-2-yl)-1-(6-(hydroxymethyl)pyridin-2-yl)-1H-indazol-4-yl)pyrrolidin-2-yl)methanol;

(S)-(6-(6-(6-(1-aminobutyl)pyridin-2-yl)-4-(methylamino)-1H-indazol-1-yl)pyridin-2-yl)methanol;

(S)-(6-(6-(6-(1-aminobutyl)pyridin-2-yl)-4-(ethylamino)-1H-indazol-1-yl)pyridin-2-yl)methanol;

(S)-1-(6-(6-(1-aminobutyl)pyridin-2-yl)-1-(6-(hydroxymethyl)pyridin-2-yl)-1H-indazol-4-yl)piperidin-4-ol;

1-(6-(6-((S)-1-aminobutyl)pyridin-2-yl)-1-(6-(hydroxymethyl)pyridin-2-yl)-1H-indazol-4-yl)piperidin-3-ol;

(S)-(6-(6-(6-(1-aminobutyl)pyridin-2-yl)-4-(3,3-difluoroazetidin-1-yl)-1H-indazol-1-yl)pyridin-2-yl)methanol;

(S)-(1-(6-(6-(1-aminobutyl)pyridin-2-yl)-1-(6-(hydroxymethyl)pyridin-2-yl)-1H-indazol-4-yl)-3-(chloromethyl)azetidin-3-yl)methanol;

(S)-(6-(6-(6-(1-aminobutyl)pyridin-2-yl)-4-(3,3-difluoropyrrolidin-1-yl)-1H-indazol-1-yl)pyridin-2-yl)methanol;

(6-(6-(6-((S)-1-aminobutyl)pyridin-2-yl)-4-(2-methylmorpholino)-1H-indazol-1-yl)pyridin-2-yl)methanol;

(6-(6-(6-((S)-1-aminobutyl)pyridin-2-yl)-4-(2,6-dimethylmorpholino)-1H-indazol-1-yl)pyridin-2-yl)methanol;

3-((6-(6-((S)-1-aminobutyl)pyridin-2-yl)-1-(6-(hydroxymethyl)pyridin-2-yl)-1H-indazol-4-yl)amino)-2-(chloromethyl)propanoic acid;

(S)-4-(6-(6-(1-aminobutyl)pyridin-2-yl)-1-(6-(hydroxymethyl)pyridin-2-yl)-1H-indazol-4-yl)thiomorpholine 1,1-dioxide;

(S)-(6-(6-(6-(1-aminobutyl)pyridin-2-yl)-4-thiomorpholino-1H-indazol-1-yl)pyridin-2-yl)methanol;

(S)-(6-(6-(6-(1-aminobutyl)pyridin-2-yl)-4-morpholino-1H-indazol-1-yl)pyridin-2-yl)methanol;

(S)-(6-(6-(6-(1-aminobutyl)pyridin-2-yl)-4-(3,3-dimethylazetidin-1-yl)-1H-indazol-1-yl)pyridin-2-yl)methanol;

1-(6-(6-((S)-1-aminobutyl)pyridin-2-yl)-1-(6-(hydroxymethyl)pyridin-2-yl)-1H-indazol-4-yl)pyrrolidine-3-carboxylic acid;

(S)-(6-(6-(6-(1-aminobutyl)pyridin-2-yl)-4-(pyrrolidin-1-yl)-1H-indazol-1-yl)pyridin-2-yl)methanol;

(S)-(6-(6-(6-(1-aminobutyl)pyridin-2-yl)-4-(4-methylpiperazin-1-yl)-1H-indazol-1-yl)pyridin-2-yl)methanol;

(S)-(6-(6-(6-(1-aminobutyl)pyridin-2-yl)-4-((3-chloro-2,2-dimethylpropyl)amino)-1H-indazol-1-yl)pyridin-2-yl)methanol;

(S)-(6-(6-(6-(1-aminobutyl)pyridin-2-yl)-4-(azetidin-1-yl)-1H-indazol-1-yl)pyridin-2-yl)methanol;

(S)-(6-(6-(6-(1-aminobutyl)pyridin-2-yl)-4-(4,4-difluoropiperidin-1-yl)-1H-indazol-1-yl)pyridin-2-yl)methanol;

(S)-(6-(6-(6-(1-aminobutyl)pyridin-2-yl)-4-(3,3-difluoropiperidin-1-yl)-1H-indazol-1-yl)pyridin-2-yl)methanol;

(S)-1-(6-(6-(1-aminobutyl)pyridin-2-yl)-1-(6-(hydroxymethyl)pyridin-2-yl)-1H-indazol-4-yl)azetidine-3-carboxylic acid;

1-(6-(6-((S)-1-aminobutyl)pyridin-2-yl)-1-(6-(hydroxymethyl)pyridin-2-yl)-1H-indazol-4-yl)piperidine-3-carboxylic acid;

(S)-1-(6-(6-(1-aminobutyl)pyridin-2-yl)-1-(6-(hydroxymethyl)pyridin-2-yl)-1H-indazol-4-yl)piperidine-4-carboxylic acid;

(S)-4-(6-(6-(1-aminobutyl)pyridin-2-yl)-1-(6-(hydroxymethyl)pyridin-2-yl)-1H-indazol-4-yl)morpholin-3-one;

(S)-(6-(6-(6-(1-aminoethyl)pyridin-2-yl)-4-(1H-pyrazol-1-yl)-1H-indazol-1-yl)pyridin-2-yl)methanol;

(S)-(6-(6-(6-(1-aminoethyl)pyridin-2-yl)-4-(3-methyl-1H-pyrazol-1-yl)-1H-indazol-1-yl)pyridin-2-yl)methanol;

(S)-(6-(6-(6-(1-aminoethyl)pyridin-2-yl)-4-(1H-imidazol-1-yl)-1H-indazol-1-yl)pyridin-2-yl)methanol;

(S)-(6-(6-(6-(1-aminoethyl)pyridin-2-yl)-4-(1H-1,2,4-triazol-1-yl)-1H-indazol-1-yl)pyridin-2-yl)methanol;

(S)-(6-(6-(6-(1-aminoethyl)pyridin-2-yl)-4-(3-(trifluoromethyl)-1H-pyrazol-1-yl)-1H-indazol-1-yl)pyridin-2-yl)methanol;

(S)-(6-(6-(6-(1-aminoethyl)pyridin-2-yl)-4-(1-methyl-1H-pyrazol-3-yl)-1H-indazol-1-yl)pyridin-2-yl)methanol;

(6-(6-(6-ethylpyridin-2-yl)-4-(5-methyl-1,3,4-oxadiazol-2-yl)-1H-indazol-1-yl)pyridin-2-yl)methanol;

(S)-(6-(6-(6-(1-aminoethyl)pyridin-2-yl)-4-(oxazol-2-yl)-1H-indazol-1-yl)pyridin-2-yl)methanol;

(S)-(6-(6-(6-(1-aminopropyl)pyridin-2-yl)-4-(1-methyl-1H-pyrazol-3-yl)-1H-indazol-1-yl)pyridin-2-yl)methanol;

(S)-(6-(6-(6-(1-aminobutyl)pyridin-2-yl)-4-(1-methyl-1H-pyrazol-3-yl)-1H-indazol-1-yl)pyridin-2-yl)methanol;

(S)-(6-(6-(6-(1-aminoethyl)pyridin-2-yl)-4-(5-methyl-1,3,4-thiadiazol-2-yl)-1H-indazol-1-yl)pyridin-2-yl)methanol;

(S)-(6-(6-(6-(1-aminoethyl)pyridin-2-yl)-4-(1-methyl-1H-imidazol-4-yl)-1H-indazol-1-yl)pyridin-2-yl)methanol;

(S)-(6-(6-(6-(1-aminoethyl)pyridin-2-yl)-4-(pyrimidin-2-yl)-1H-indazol-1-yl)pyridin-2-yl)methanol;

(S)-(6-(6-(6-(1-aminoethyl)pyridin-2-yl)-4-(1,5-dimethyl-1H-pyrazol-3-yl)-1H-indazol-1-yl)pyridin-2-yl)methanol;

(S)-(6-(6-(6-(1-aminoethyl)pyridin-2-yl)-4-(5-methyl-1H-pyrazol-3-yl)-1H-indazol-1-yl)pyridin-2-yl)methanol;

(S)-(6-(6-(6-(1-aminoethyl)pyridin-2-yl)-4-(1-methyl-1H-pyrazol-4-yl)-1H-indazol-1-yl)pyridin-2-yl)methanol;

(S)-(6-(6-(6-(1-aminoethyl)pyridin-2-yl)-4-(2-methylthiazol-4-yl)-1H-indazol-1-yl)pyridin-2-yl)methanol;

(S)-2-(6-(6-(1-aminoethyl)pyridin-2-yl)-1-(6-(hydroxymethyl)pyridin-2-yl)-1H-indazol-4-yl)thiazole-4-carbonitrile;

(S)-(6-(6-(6-(1-aminoethyl)pyridin-2-yl)-4-(isothiazol-3-yl)-1H-indazol-1-yl)pyridin-2-yl)methanol;

(S)-(6-(6-(6-(1-aminoethyl)pyridin-2-yl)-4-phenyl-1H-indazol-1-yl)pyridin-2-yl)methanol;

(S)-(6-(6-(6-(1-aminoethyl)pyridin-2-yl)-4-(5-methylthiazol-2-yl)-1H-indazol-1-yl)pyridin-2-yl)methanol;

(S)-(6-(6-(6-(1-aminoethyl)pyridin-2-yl)-4-(pyridin-2-yl)-1H-indazol-1-yl)pyridin-2-yl)methanol;

(S)-(6-(6-(6-(1-aminoethyl)pyridin-2-yl)-4-(4-(trifluoromethyl)oxazol-2-yl)-1H-indazol-1-yl)pyridin-2-yl)methanol;

(S)-(6-(6-(6-(1-aminoethyl)pyridin-2-yl)-4-(4-methylthiazol-2-yl)-1H-indazol-1-yl)pyridin-2-yl)methanol;

(S)-(6-(6-(6-(1-aminoethyl)pyridin-2-yl)-4-(1-(trifluoromethyl)-1H-pyrazol-4-yl)-1H-indazol-1-yl)pyridin-2-yl)methanol;

(S)-(6-(6-(6-(1-aminoethyl)pyridin-2-yl)-4-(4,5-dimethylthiazol-2-yl)-1H-indazol-1-yl)pyridin-2-yl)methanol;

(S)-(6-(6-(6-(1-aminoethyl)pyridin-2-yl)-4-(4-(trifluoromethyl)thiazol-2-yl)-1H-indazol-1-yl)pyridin-2-yl)methanol;

(S)-(6-(6-(6-(1-aminoethyl)pyridin-2-yl)-4-(thiazol-2-yl)-1H-indazol-1-yl)pyridin-2-yl)methanol;

(S)-(6-(6-(6-(1-aminoethyl)pyridin-2-yl)-4-(5-(trifluoromethyl)thiazol-2-yl)-1H-indazol-1-yl)pyridin-2-yl)methanol;

(S)-(6-(6-(6-(1-aminoethyl)pyridin-2-yl)-4-(1H-pyrazol-3-yl)-1H-indazol-1-yl)pyridin-2-yl)methanol;

(S)-(6-(6-(6-(1-aminoethyl)pyridin-2-yl)-4-(2-(trifluoromethyl)thiazol-4-yl)-1H-indazol-1-yl)pyridin-2-yl)methanol;

(S)-(6-(6-(6-(1-aminoethyl)pyridin-2-yl)-4-(5-(trifluoromethyl)-1H-pyrazol-3-yl)-1H-indazol-1-yl)pyridin-2-yl)methanol;

(S)-(6-(6-(6-(1-aminobutyl)pyridin-2-yl)-4-(pyrimidin-2-yl)-1H-indazol-1-yl)pyridin-2-yl)methanol;

(S)-(6-(6-(6-(1-aminoethyl)pyridin-2-yl)-4-(5-fluoropyrimidin-2-yl)-1H-indazol-1-yl)pyridin-2-yl)methanol;

(S)-(6-(6-(6-(1-aminoethyl)pyridin-2-yl)-4-(1-(difluoromethyl)-1H-pyrazol-3-yl)-1H-indazol-1-yl)pyridin-2-yl)methanol;

(S)-(6-(6-(6-(1-aminoethyl)pyridin-2-yl)-4-(1-(difluoromethyl)-1H-pyrazol-5-yl)-1H-indazol-1-yl)pyridin-2-yl)methanol;

(S)-(6-(6-(6-(1-aminoethyl)pyridin-2-yl)-4-(pyrazin-2-yl)-1H-indazol-1-yl)pyridin-2-yl)methanol;

(S)-(6-(6-(6-(1-aminobutyl)pyridin-2-yl)-4-(1,5-dimethyl-1H-pyrazol-3-yl)-1H-indazol-1-yl)pyridin-2-yl)methanol;

(R)-(6-(6-(6-(1-aminopropyl)pyridin-2-yl)-4-(1,5-dimethyl-1H-pyrazol-3-yl)-1H-indazol-1-yl)pyridin-2-yl)methanol;

(R)-(6-(6-(6-(1-amino-2-fluoroethyl)pyridin-2-yl)-4-(1,5-dimethyl-1H-pyrazol-3-yl)-1H-indazol-1-yl)pyridin-2-yl)methanol;

(R)-(6-(6-(6-(1-amino-2-fluoroethyl)pyridin-2-yl)-4-(1,5-dimethyl-1H-pyrazol-3-yl)-1H-indazol-1-yl)pyridin-2-yl)methanol;

(S)-4-amino-4-(6-(4-(1,5-dimethyl-1H-pyrazol-3-yl)-1-(6-(hydroxymethyl)pyridin-2-yl)-1H-indazol-6-yl)pyridin-2-yl)butan-1-ol;

(S)-(6-(6-(6-(1-aminoethyl)pyridin-2-yl)-4-(pyrimidin-4-yl)-1H-indazol-1-yl)pyridin-2-yl)methanol;

(S)-(6-(6-(6-(1-aminoethyl)pyridin-2-yl)-4-(pyridazin-3-yl)-1H-indazol-1-yl)pyridin-2-yl)methanol;

(S)-4-amino-4-(6-(1-(6-(hydroxymethyl)pyridin-2-yl)-4-(1-methyl-1H-pyrazol-3-yl)-1H-indazol-6-yl)pyridin-2-yl)butan-1-ol;

(S)-4-amino-4-(6-(1-(6-(hydroxymethyl)pyridin-2-yl)-1H-indazol-6-yl)pyridin-2-yl)butan-1-ol;

(S)-(6-(6-(6-(1-aminoethyl)pyridin-2-yl)-1H-indazol-1-yl)pyrazin-2-yl)methanol;

(S)-(6-(6-(6-(1-aminopropyl)pyridin-2-yl)-1H-indazol-1-yl)pyrazin-2-yl)methanol;

(S)-(6-(6-(6-(1-aminobutyl)pyridin-2-yl)-1H-indazol-1-yl)pyrazin-2-yl)methanol;

(S)-(4-(6-(6-(1-aminobutyl)pyridin-2-yl)-1H-indazol-1-yl)pyridin-2-yl)methanol;

(S)-(4-(6-(6-(1-aminobutyl)pyridin-2-yl)-1H-indazol-1-yl)pyrimidin-2-yl)methanol;

(S)-(3-(6-(6-(1-aminobutyl)pyridin-2-yl)-1H-indazol-1-yl)phenyl)methanol;

(S)-(2-(6-(6-(1-aminobutyl)pyridin-2-yl)-1H-indazol-1-yl)pyrimidin-4-yl)methanol;

(S)-(6-(6-(4-(1-aminobutyl)pyridin-2-yl)-1H-indazol-1-yl)pyridin-2-yl)methanol;

(S)-(6-(6-(2-(1-aminobutyl)pyrimidin-4-yl)-1H-indazol-1-yl)pyridin-2-yl)methanol;

(R)-(6-(6-(2-(1-aminobutyl)pyrimidin-4-yl)-1H-indazol-1-yl)pyridin-2-yl)methanol;

(S)-(6-(6-(6-(1-aminobutyl)pyrazin-2-yl)-1H-indazol-1-yl)pyridin-2-yl)methanol;

(R)-(6-(6-(6-(1-aminobutyl)pyrazin-2-yl)-1H-indazol-1-yl)pyridin-2-yl)methanol;

(S)-4-amino-4-(6-(1-(6-(hydroxymethyl)pyridin-2-yl)-4-methoxy-1H-indazol-6-yl)pyridin-2-yl)butan-1-ol;

(S)-(6-(6-(4-(1-aminoethyl)pyrimidin-2-yl)-1H-indazol-1-yl)pyridin-2-yl)methanol;

(R)-(6-(6-(4-(1-aminoethyl)pyrimidin-2-yl)-1H-indazol-1-yl)pyridin-2-yl)methanol;

(S)-(6-(6-(4-(1-aminobutyl)pyrimidin-2-yl)-1H-indazol-1-yl)pyridin-2-yl)methanol;

(R)-(6-(6-(4-(1-aminobutyl)pyrimidin-2-yl)-1H-indazol-1-yl)pyridin-2-yl)methanol;

1-(6-(6-(6-((S)-1-aminoethyl)pyridin-2-yl)-1H-indazol-1-yl)pyridin-2-yl)ethanol;

1-(6-(6-(6-((S)-1-aminobutyl)pyridin-2-yl)-1H-indazol-1-yl)pyridin-2-yl)ethanol;

deutero (S)-(6-(6-(6-(1-aminobutyl)pyridin-2-yl)-1H-indazol-1-yl)pyridin-2-yl)methanol;

(6-(6-(8-amino-8-methyl-5,6,7,8-tetrahydroquinolin-2-yl)-1H-indazol-1-yl)pyridin-2-yl)methanol;

(6-(6-(8-amino-8-propyl-5,6,7,8-tetrahydroquinolin-2-yl)-1H-indazol-1-yl)pyridin-2-yl)methanol;

(S)-(6-(6-(6-(amino(cyclobutyl)methyl)pyridin-2-yl)-1H-indazol-1-yl)pyridin-2-yl)methanol;

(S)-(6-(6-(6-(1-aminobutyl)pyridin-2-yl)-4-(1-methyl-1,2,3,6-tetrahydropyridin-4-yl)-1H-indazol-1-yl)pyridin-2-yl)methanol;

(S)-(6-(6-(6-(1-aminobutyl)pyridin-2-yl)-4-(1-methylpiperidin-4-yl)-1H-indazol-1-yl)pyridin-2-yl)methanol;

(S)-(6-(6-(6-(1-aminobutyl)pyridin-2-yl)-4-(tetrahydro-2H-pyran-4-yl)-1H-indazol-1-yl)pyridin-2-yl)methanol;

(S)-2-((6-(6-(1-aminobutyl)pyridin-2-yl)-1-(6-(hydroxymethyl)pyridin-2-yl)-1H-indazol-4-yl)oxy)ethanol;

(S)-(6-(6-(6-(1-amino-4,4,4-trifluorobutyl)pyridin-2-yl)-1H-indazol-1-yl)pyridin-2-yl)methanol;

(S)-4-amino-4-(6-(1-(6-(hydroxymethyl)pyrazin-2-yl)-4-(2-methoxyethoxy)-1H-indazol-6-yl)pyridin-2-yl)butan-1-ol;

(4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;

(4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;

(4S)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;

(4R)-4-amino-3-fluoro-4-(6-(1-(6-(hydroxymethyl)pyridin-2-yl)-4-(2-methoxyethoxy)-1H-indazol-6-yl)pyridin-2-yl)butan-1-ol;

(6-(6-(6-((1R)-1-amino-2-fluoropropyl)pyridin-2-yl)-4-(2-methoxyethoxy)-1H-indazol-1-yl)pyridin-2-yl)methanol;

(6-(6-(6-((1S)-1-amino-2-fluoropropyl)pyridin-2-yl)-4-(2-methoxyethoxy)-1H-indazol-1-yl)pyridin-2-yl)methanol;

(S)-(6-(6-(6-(1-aminobut-3-en-1-yl)pyridin-2-yl)-1H-indazol-1-yl)pyridin-2-yl)methanol;

(S)-(6-(6-(6-(1-amino-3-methylbut-3-en-1-yl)pyridin-2-yl)-1H-indazol-1-yl)pyridin-2-yl)methanol;

(S)-(6-(6-(6-(1-amino-3,3-difluorobutyl)pyridin-2-yl)-1H-indazol-1-yl)pyridin-2-yl)methanol;

(S)-(6-(6-(6-(1-amino-3,3-difluorobutyl)pyridin-2-yl)-4-ethoxy-1H-indazol-1-yl)pyridin-2-yl)methanol;

(R)-(6-(6-(6-(amino(phenyl)methyl)pyridin-2-yl)-4-ethoxy-1H-indazol-1-yl)pyridin-2-yl)methanol;

(S)-(6-(6-(6-(amino(phenyl)methyl)pyridin-2-yl)-4-ethoxy-1H-indazol-1-yl)pyridin-2-yl)methanol;

(S)-(6-(6-(6-(1-aminopent-3-yn-1-yl)pyridin-2-yl)-4-ethoxy-1H-indazol-1-yl)pyridin-2-yl)methanol;

(6-(6-(6-((1R,2S)-1-amino-2-fluorobutyl)pyridin-2-yl)-4-ethoxy-1H-indazol-1-yl)pyridin-2-yl)methanol;

(6-(6-(6-((1R,2R)-1-amino-2-fluorobutyl)pyridin-2-yl)-4-ethoxy-1H-indazol-1-yl)pyridin-2-yl)methanol;

(6-(6-(6-(amino(oxetan-3-yl)methyl)pyridin-2-yl)-1H-indazol-1-yl)pyridin-2-yl)methanol;

(6-(6-(6-(amino(oxetan-3-yl)methyl)pyridin-2-yl)-4-ethoxy-1H-indazol-1-yl)pyridin-2-yl)methanol;

(6-(6-(6-(1-amino-2-(3-methyloxetan-3-yl)ethyl)pyridin-2-yl)-1H-indazol-1-yl)pyridin-2-yl)methanol;

(S)-4-amino-4-(6-(1-(6-(hydroxymethyl)pyridin-2-yl)-1H-indazol-6-yl)pyridin-2-yl)butan-2-one;

(S)-6-(6-(6-(1-aminobutyl)pyridin-2-yl)-1H-indazol-1-yl)picolinaldehyde;

(R)-1-(6-(6-(6-((S)-1-aminobutyl)pyridin-2-yl)-1H-indazol-1-yl)pyridin-2-yl)-2,2,2-trifluoroethanol;

(S)-1-(6-(6-(6-((S)-1-aminobutyl)pyridin-2-yl)-1H-indazol-1-yl)pyridin-2-yl)-2,2,2-trifluoroethanol;

(6-(6-(6-((1R,2S)-1-amino-2-fluorobutyl)pyridin-2-yl)-4-(2-methoxyethoxy)-1H-indazol-1-yl)pyridin-2-yl)methanol;

(6-(6-(6-((1R,2S)-1-amino-2-fluorobutyl)pyridin-2-yl)-4-(2-methoxyethoxy)-1H-indazol-1-yl)pyridin-2-yl)methanol;

(S)-(6-(6-(6-(1-amino-3,3-difluorobutyl)pyridin-2-yl)-4-(2-methoxyethoxy)-1H-indazol-1-yl)pyridin-2-yl)methanol;

(S)-(6-(6-(6-(1-aminobutyl)pyridin-2-yl)-4-(3-methoxypropoxy)-1H-indazol-1-yl)pyridin-2-yl)methanol;

(S)-(6-(6-(6-(1-aminopropyl)pyridin-2-yl)-4-(3-methoxypropoxy)-1H-indazol-1-yl)pyridin-2-yl)methanol;

(S)-(6-(6-(6-(1-aminoethyl)pyridin-2-yl)-4-(3-methoxypropoxy)-1H-indazol-1-yl)pyridin-2-yl)methanol;

(S)-3-((6-(6-(1-aminoethyl)pyridin-2-yl)-1-(6-(hydroxymethyl)pyridin-2-yl)-1H-indazol-4-yl)oxy)propan-1-ol;

(S)-3-((6-(6-(1-aminobutyl)pyridin-2-yl)-1-(6-(hydroxymethyl)pyridin-2-yl)-1H-indazol-4-yl)oxy)propan-1-ol;

(S)-3-((6-(6-(1-aminopropyl)pyridin-2-yl)-1-(6-(hydroxymethyl)pyridin-2-yl)-1H-indazol-4-yl)oxy)propan-1-ol;

(S)-4-(6-(6-(1-aminobutyl)pyridin-2-yl)-1-(6-(hydroxymethyl)pyridin-2-yl)-1H-indazol-4-yl)-2-methylbut-3-yn-2-ol;

(S)-(6-(6-(6-(1-aminobutyl)pyridin-2-yl)-4-methoxy-1H-indazol-1-yl)pyridin-2-yl)methanol;

(S)-(6-(6-(6-(1-aminobutyl)pyridin-2-yl)-4-ethoxy-1H-indazol-1-yl)pyridin-2-yl)methanol;

(6-(6-(6-(3-aminooxetan-3-yl)pyridin-2-yl)-4-(2-methoxyethoxy)-1H-indazol-1-yl)pyridin-2-yl)methanol;

(6-(6-(6-(3-aminotetrahydrofuran-3-yl)pyridin-2-yl)-4-(2-methoxyethoxy)-1H-indazol-1-yl)pyridin-2-yl)methanol;

(6-(6-(6-(1-aminocyclobutyl)pyridin-2-yl)-4-(2-methoxyethoxy)-1H-indazol-1-yl)pyridin-2-yl)methanol;

(6-(6-(6-(1-aminocyclobutyl)pyridin-2-yl)-4-(2-methoxyethoxy)-1H-indazol-1-yl)pyrazin-2-yl)methanol;

(6-(6-(6-(1-aminocyclopentyl)pyridin-2-yl)-4-(2-methoxyethoxy)-1H-indazol-1-yl)pyridin-2-yl)methanol;

(S)-(6-(6-(6-(1-aminobutyl)pyridin-2-yl)-4-(2-(methylsulfonyl)ethoxy)-1H-indazol-1-yl)pyridin-2-yl)methanol;

(S)-1-((6-(6-(1-aminobutyl)pyridin-2-yl)-1-(6-(hydroxymethyl)pyridin-2-yl)-1H-indazol-4-yl)oxy)-2-methylpropan-2-ol;

6-{6-[6-((S)-1-Amino-ethyl)-pyridin-2-yl]-indazol-1-yl}-pyridine-2-carboxylic;

(6-{6-[6-((S)-1-Amino-butyl)-pyridin-2-yl]-4-fluoro-indazol-1-yl}-pyridin-2-yl)-methanol;

(6-{6-[6-((S)-1-Amino-butyl)-pyridin-2-yl]-4-fluoro-indazol-1-yl}-pyridin-2-yl)-methanol;

(6-{6-[6-((S)-1-Amino-ethyl)-pyridin-2-yl]-4-fluoro-indazol-1-yl}-pyridin-2-yl)-methanol;

(S)-(6-(6-(6-(1-aminobutyl)pyridin-2-yl)-4-(2-methoxyethoxy)-1H-indazol-1-yl)pyridin-2-yl)methanol;

(6-(6-(6-((S)-1-aminobutyl)pyridin-2-yl)-4-(tetrahydrofuran-2-yl)-1H-indazol-1-yl)pyridin-2-yl)methanol;

(6-(6-(6-((S)-1-aminobutyl)pyridin-2-yl)-4-((2R,5R)-5-methyltetrahydrofuran-2-yl)-1H-indazol-1-yl)pyridin-2-yl)methanol;

(6-(6-(6-((S)-1-aminobutyl)pyridin-2-yl)-4-((2S,5R)-5-methyltetrahydrofuran-2-yl)-1H-indazol-1-yl)pyridin-2-yl)methanol;

(S)-(6-(6-(6-(1-aminobutyl)pyridin-2-yl)-4-(2-methoxyethoxy)-1H-indazol-1-yl)pyrazin-2-yl)methanol;

(S)-(6-(6-(6-(1-aminoethyl)pyridin-2-yl)-4-(2-methoxyethoxy)-1H-indazol-1-yl)pyrazin-2-yl)methanol;
(S)-(6-(6-(6-(1-aminopropyl)pyridin-2-yl)-4-(2-methoxyethoxy)-1H-indazol-1-yl)pyrazin-2-yl)methanol;
(6-{6-[6-((S)-1-Amino-butyl)-pyridin-2-yl]-4-isopropoxy-indazol-1-yl}-pyridin-2-yl)-methanol;
(S)-4-amino-4-(6-(1-(6-(hydroxymethyl)pyridin-2-yl)-4-(2-methoxyethoxy)-1H-indazol-6-yl)pyridin-2-yl)butan-1-ol;
(S)-(6-(6-(6-(1-aminopropyl)pyridin-2-yl)-4-(methylamino)-1H-indazol-1-yl)pyridin-2-yl)methanol;
(S)-1-(6-(1-(4-(difluoromethyl)pyrimidin-2-yl)-1H-indazol-6-yl)pyridin-2-yl)butan-1-amine;
(S)-(6-(6-(6-(1-aminobutyl)pyridin-2-yl)-4-(fluoromethyl)-1H-indazol-1-yl)pyridin-2-yl)methanol;
(S)-1-(4-(6-(6-(1-aminobutyl)pyridin-2-yl)-1-(6-(hydroxymethyl)pyridin-2-yl)-1H-indazol-4-yl)-5,6-dihydropyridin-1(2H)-yl)ethanone;
(S)-(6-(6-(6-(1-aminobutyl)pyridin-2-yl)-4-methoxy-1H-indazol-1-yl)pyrazin-2-yl)methanol;
(S)-(6-(6-(6-(1-aminobutyl)pyridin-2-yl)-4-chloro-1H-indazol-1-yl)pyridin-2-yl)methanol;
(S)-(6-(6-(6-(1-aminobutyl)pyridin-2-yl)-4-(difluoromethyl)-1H-indazol-1-yl)pyridin-2-yl)methanol;
(S)-(6-(6-(1-aminobutyl)pyridin-2-yl)-1-(6-(hydroxymethyl)pyridin-2-yl)-1H-indazol-4-yl)methanol;
(S)-(6-(6-(6-(1-aminopentyl)pyridin-2-yl)-1H-indazol-1-yl)pyridin-2-yl)methanol;
(S)-(6-(6-(6-(1-aminobutyl)pyridin-2-yl)-4-(3,6-dihydro-2H-pyran-4-yl)-1H-indazol-1-yl)pyridin-2-yl)methanol;
(S)-(6-(6-(6-(1-aminobutyl)pyridin-2-yl)-4-(methoxymethyl)-1H-indazol-1-yl)pyridin-2-yl)methanol;
(S)-(6-(6-(6-(amino(cyclopropyl)methyl)pyridin-2-yl)-4-methoxy-1H-indazol-1-yl)pyrazin-2-yl)methanol;
(S)-(6-(6-(6-(1-aminobutyl)pyridin-2-yl)-4-((difluoromethoxy)methyl)-1H-indazol-1-yl)pyridin-2-yl)methanol;
(S)-(6-(6-(6-(1-aminobutyl)pyridin-2-yl)-4-(morpholinomethyl)-1H-indazol-1-yl)pyridin-2-yl)methanol;
(S)-(6-(6-(6-(1-aminobutyl)pyridin-2-yl)-4-ethoxy-1H-indazol-1-yl)pyrazin-2-yl)methanol;
(S)-(6-(6-(6-(1-aminopropyl)pyridin-2-yl)-4-ethoxy-1H-indazol-1-yl)pyrazin-2-yl)methanol;
(S)-(6-(6-(6-(amino(cyclopropyl)methyl)pyridin-2-yl)-4-ethoxy-1H-indazol-1-yl)pyrazin-2-yl)methanol;
(S)-(6-(6-(6-(1-amino-4,4,4-trifluorobutyl)pyridin-2-yl)-4-methoxy-1H-indazol-1-yl)pyridin-2-yl)methanol;
(S)-(6-(6-(6-(1-aminopropyl)pyridin-2-yl)-4-methoxy-1H-indazol-1-yl)pyrazin-2-yl)methanol;
(S)-1-(6-(4-methoxy-1-(4-(trifluoromethyl)pyrimidin-2-yl)-1H-indazol-6-yl)pyridin-2-yl)butan-1-amine;
(S)-1-(6-(4-ethoxy-1-(4-(trifluoromethyl)pyrimidin-2-yl)-1H-indazol-6-yl)pyridin-2-yl)butan-1-amine;
(6-(6-(6-((S)-1-aminobutyl)pyridin-2-yl)-4-(piperidin-3-ylmethoxy)-1H-indazol-1-yl)pyridin-2-yl)methanol;
1-amino-1-(6-(1-(6-(hydroxymethyl)pyridin-2-yl)-1H-indazol-6-yl)pyridin-2-yl)butan-2-ol;
4-amino-4-(6-(1-(6-(hydroxymethyl)pyridin-2-yl)-1H-indazol-6-yl)pyridin-2-yl)butan-2-ol;
(S)-(6-(6-(6-(1-amino-4-methoxybutyl)pyridin-2-yl)-4-methoxy-1H-indazol-1-yl)pyridin-2-yl)methanol;
(S)-(6-(6-(6-(1-amino-4,4,4-trifluorobutyl)pyridin-2-yl)-4-ethoxy-1H-indazol-1-yl)pyridin-2-yl)methanol;
(S)-6-(6-(1-aminobutyl)pyridin-2-yl)-1-(6-(hydroxymethyl)pyridin-2-yl)-1H-indazole-4-carbonitrile;
(S)-1-(6-(1-(4-(difluoromethyl)pyrimidin-2-yl)-1H-indazol-6-yl)pyridin-2-yl)propan-1-amine;
(S)-(6-(6-(6-(1-amino-4-methoxybutyl)pyridin-2-yl)-4-ethoxy-1H-indazol-1-yl)pyridin-2-yl)methanol;
(S)-(6-(6-(6-(1-aminobutyl)pyridin-2-yl)-4-(2,2,2-trifluoroethoxy)-1H-indazol-1-yl)pyridin-2-yl)methanol;
(S)-1-(4-(6-(6-(1-aminobutyl)pyridin-2-yl)-1-(6-(hydroxymethyl)pyridin-2-yl)-1H-indazol-4-yl)piperidin-1-yl)ethanone;
1-amino-1-(6-(1-(6-(hydroxymethyl)pyridin-2-yl)-1H-indazol-6-yl)pyridin-2-yl)butan-2-ol;
(S)-(6-(6-(6-(1-aminobutyl)pyridin-2-yl)-4-((dimethylamino)methyl)-1H-indazol-1-yl)pyridin-2-yl)methanol;
(S)-1-(6-(1-(6-(fluoromethyl)pyridin-2-yl)-1H-indazol-6-yl)pyridin-2-yl)butan-1-amine;
(S)-1-(6-(1-(6-(difluoromethyl)pyridin-2-yl)-1H-indazol-6-yl)pyridin-2-yl)butan-1-amine;
(6-(6-(6-(1-amino-2-(methylthio)ethyl)pyridin-2-yl)-1H-indazol-1-yl)pyridin-2-yl)methanol;
(S)-(6-(6-(6-(1-amino-3-methylbutyl)pyridin-2-yl)-1H-indazol-1-yl)pyridin-2-yl)methanol;
(S)-(6-(6-(6-(1-aminobutyl)pyridin-2-yl)-4-(2-cyclopropylethoxy)-1H-indazol-1-yl)pyridin-2-yl)methanol;
(S)-(6-(6-(6-(1-aminobutyl)pyridin-2-yl)-4-(trifluoromethoxy)-1H-indazol-1-yl)pyridin-2-yl)methanol;
(S)-(6-(6-(6-(1-aminoethyl)pyridin-2-yl)-4-(4,5-dihydrooxazol-2-yl)-1H-indazol-1-yl)pyridin-2-yl)methanol;
4-amino-4-(6-(1-(6-(hydroxymethyl)pyridin-2-yl)-1H-indazol-6-yl)pyridin-2-yl)butan-2-ol;
(S)-(6-(6-(6-(1-aminobutyl)pyridin-2-yl)-4-(difluoromethoxy)-1H-indazol-1-yl)pyrazin-2-yl)methanol;
(S)-(6-(6-(6-(1-(methylamino)butyl)pyridin-2-yl)-1H-indazol-1-yl)pyridin-2-yl)methanol;
(6-(6-(6-((S)-1-aminoethyl)pyridin-2-yl)-4-(4-methyl-4,5-dihydrooxazol-2-yl)-1H-indazol-1-yl)pyridin-2-yl)methanol;
(S)-1-(6-(1-(6-(difluoromethyl)pyridin-2-yl)-1H-indazol-6-yl)pyridin-2-yl)ethanamine;
2-amino-2-(6-(1-(6-(hydroxymethyl)pyridin-2-yl)-1H-indazol-6-yl)pyridin-2-yl)ethanol;
(S)-1-(6-(1-(4-(trifluoromethyl)pyrimidin-2-yl)-1H-indazol-6-yl)pyridin-2-yl)butan-1-amine;
(6-(6-(6-(1-amino-2-(methylsulfonyl)ethyl)pyridin-2-yl)-1H-indazol-1-yl)pyridin-2-yl)methanol;
(S)-6-(6-(1-aminopropyl)pyridin-2-yl)-1-(6-(hydroxymethyl)pyridin-2-yl)-1H-indazole-4-carbonitrile;
(6-(6-(6-(1-amino-2-cyclopropylethyl)pyridin-2-yl)-1H-indazol-1-yl)pyridin-2-yl)methanol;
1-(6-(1-(6-methylpyridin-2-yl)-4-(oxazol-5-yl)-1H-indazol-6-yl)pyridin-2-yl)ethanamine;
(S)-6-(6-(1-aminoethyl)pyridin-2-yl)-1-(6-(hydroxymethyl)pyridin-2-yl)-1H-indazole-4-carbonitrile;
(6-(6-(6-(amino(cyclopropyl)methyl)pyridin-2-yl)-1H-indazol-1-yl)pyridin-2-yl)methanol;
(S)-1-(6-(1-(6-(difluoromethyl)pyridin-2-yl)-1H-indazol-6-yl)pyridin-2-yl)propan-1-amine;
(S)-6-(6-(1-aminoethyl)pyridin-2-yl)-N-(1-hydroxy-2-methylpropan-2-yl)-1-(6-(hydroxymethyl)pyridin-2-yl)-1H-indazole-4-carboxamide;
(S)-1-(6-(1-(4-(difluoromethyl)pyrimidin-2-yl)-1H-indazol-6-yl)pyridin-2-yl)ethanamine;
1-(6-(1-(6-methylpyridin-2-yl)-4-(oxazol-2-yl)-1H-indazol-6-yl)pyridin-2-yl)ethanamine;
(6-(6-(6-(1-amino-2-methoxyethyl)pyridin-2-yl)-1H-indazol-1-yl)pyridin-2-yl)methanol;

2-amino-2-(6-(1-(6-(hydroxymethyl)pyridin-2-yl)-1H-indazol-6-yl)pyridin-2-yl)-N,N-dimethylacetamide;
(S)-(6-(6-(6-(1-aminoethyl)pyridin-2-yl)-1H-indazol-1-yl)-3-fluoropyridin-2-yl)methanol;
(S)-1-(6-(1-(6-(trifluoromethyl)pyrazin-2-yl)-1H-indazol-6-yl)pyridin-2-yl)butan-1-amine;
6-(6-((S)-1-aminoethyl)pyridin-2-yl)-N-(2-aminopropyl)-1-(6-(hydroxymethyl)pyridin-2-yl)-1H-indazole-4-carboxamide;
1-(6-(1-(6-(hydroxymethyl)pyridin-2-yl)-1H-indazol-6-yl)pyridin-2-yl)butan-1-ol;
1-(6-(1-(6-(hydroxymethyl)pyridin-2-yl)-1H-indazol-6-yl)pyridin-2-yl)butan-1-ol;
3,3,3-trifluoro-1-(6-(1-(6-methylpyridin-2-yl)-1H-indazol-6-yl)pyridin-2-yl)propan-1-amine;
1-(6-(4-(5-methyl-1,3,4-oxadiazol-2-yl)-1-(6-methylpyridin-2-yl)-1H-indazol-6-yl)pyridin-2-yl)ethanamine;
1-(6-(1-(6-methylpyrazin-2-yl)-1H-indazol-6-yl)pyridin-2-yl)ethanamine;
2-amino-2-(6-(1-(6-(hydroxymethyl)pyridin-2-yl)-1H-indazol-6-yl)pyridin-2-yl)acetonitrile;
2-amino-2-(6-(1-(6-(hydroxymethyl)pyridin-2-yl)-1H-indazol-6-yl)pyridin-2-yl)acetamide;
4-(6-(6-(1-aminoethyl)pyridin-2-yl)-1H-indazol-1-yl)pyrimidine-2-carbonitrile;
(6-(6-(3-(1-aminoethyl)phenyl)-1H-indazol-1-yl)pyridin-2-yl)methanol;
(6-(6-(6-(1-aminoethyl)-3-fluoropyridin-2-yl)-1H-indazol-1-yl)pyridin-2-yl)methanol;
(S)-(6-(6-(6-(1-aminoethyl)pyridin-2-yl)-1H-indazol-1-yl)-5-fluoropyridin-2-yl)methanol;
(S)-(6-(6-(6-(1-(dimethylamino)butyl)pyridin-2-yl)-1H-indazol-1-yl)pyridin-2-yl)methanol;
2-amino-2-(6-(1-(6-(hydroxymethyl)pyridin-2-yl)-1H-indazol-6-yl)pyridin-2-yl)-N-methylacetamide;
(6-(6-(6-(1-amino-2-(methylsulfinyl)ethyl)pyridin-2-yl)-1H-indazol-1-yl)pyridin-2-yl)methanol;
(6-(6-(6-((S)-1-aminobutyl)pyridin-2-yl)-4-(1-methoxyethyl)-1H-indazol-1-yl)pyridin-2-yl)methanol;
(S)-1-(6-(4-chloro-1-(4-(difluoromethyl)pyrimidin-2-yl)-1H-indazol-6-yl)pyridin-2-yl)butan-1-amine;
(6-(6-(6-(pyrrolidin-2-yl)pyridin-2-yl)-1H-indazol-1-yl)pyridin-2-yl)methanol;
(S)-1-(6-(1-(4-(difluoromethyl)pyrimidin-2-yl)-4-methoxy-1H-indazol-6-yl)pyridin-2-yl)butan-1-amine;
(6-(6-(6-((S)-1-aminobutyl)pyridin-2-yl)-4-((S)-pyrrolidin-2-yl)-1H-indazol-1-yl)pyridin-2-yl)methanol;
(S)-(6-(6-(4-(1-aminobutyl)pyrimidin-2-yl)-4-methoxy-1H-indazol-1-yl)pyridin-2-yl)methanol;
(S)-(6-(6-(6-(1-amino-4-methoxybutyl)pyridin-2-yl)-4-(1-methyl-1H-pyrazol-3-yl)-1H-indazol-1-yl)pyridin-2-yl)methanol;
(R)-(6-(6-(4-(1-aminobutyl)pyrimidin-2-yl)-4-methoxy-1H-indazol-1-yl)pyridin-2-yl)methanol;
(S)-(6-(6-(6-(1-aminoethyl)pyridin-2-yl)-4-(5-methyloxazol-2-yl)-1H-indazol-1-yl)pyridin-2-yl)methanol;
(S)-(6-(6-(6-(1-aminobutyl)pyridin-2-yl)-4-(1H-1,2,3-triazol-1-yl)-1H-indazol-1-yl)pyridin-2-yl)methanol;
(S)-(6-(6-(6-(1-aminobutyl)pyridin-2-yl)-4-((trifluoromethoxy)methyl)-1H-indazol-1-yl)pyridin-2-yl)methanol;
(S)-(6-(6-(4-(1-aminopentyl)pyrimidin-2-yl)-1H-indazol-1-yl)pyridin-2-yl)methanol;
(R)-3-amino-3-(6-(1-(6-(hydroxymethyl)pyridin-2-yl)-1H-indazol-6-yl)pyridin-2-yl)propanenitrile;
(S)-(6-(6-(6-(1-aminobutyl)pyridin-2-yl)-4-(5-methyloxazol-2-yl)-1H-indazol-1-yl)pyridin-2-yl)methanol;
(S)-(6-(6-(4-(1-aminobutyl)pyrimidin-2-yl)-4-ethoxy-1H-indazol-1-yl)pyridin-2-yl)methanol;
(R)-(6-(6-(4-(1-aminobutyl)pyrimidin-2-yl)-4-ethoxy-1H-indazol-1-yl)pyridin-2-yl)methanol;
2-(6-(6-((S)-1-aminobutyl)pyridin-2-yl)-1-(6-(hydroxymethyl)pyridin-2-yl)-1H-indazol-4-yl)-3-chloropropan-1-ol;
(S)-(6-(6-(6-(1-aminoethyl)pyridin-2-yl)-4-(2-methoxyethoxy)-1H-indazol-1-yl)pyridin-2-yl)methanol;
(S)-(6-(6-(6-(1-aminopropyl)pyridin-2-yl)-4-(2-methoxyethoxy)-1H-indazol-1-yl)pyridin-2-yl)methanol;
(S)-(6-(6-(6-(amino(cyclopropyl)methyl)pyridin-2-yl)-4-(2-methoxyethoxy)-1H-indazol-1-yl)pyridin-2-yl)methanol;
(R)-(6-(6-(6-(1-amino-2-fluoroethyl)pyridin-2-yl)-1H-indazol-1-yl)pyridin-2-yl)methanol;
(S)-1-(6-(1-(6-methylpyrazin-2-yl)-1H-indazol-6-yl)pyridin-2-yl)butan-1-amine;
(S)-3-amino-3-(6-(1-(6-(hydroxymethyl)pyridin-2-yl)-1H-indazol-6-yl)pyridin-2-yl)propanenitrile;
(S)-4-amino-4-(6-(1-(6-(hydroxymethyl)pyridin-2-yl)-1H-indazol-6-yl)pyridin-2-yl)butanenitrile;
(R)-(6-(6-(6-(1-amino-2-fluoroethyl)pyridin-2-yl)-4-(1,5-dimethyl-1H-pyrazol-3-yl)-1H-indazol-1-yl)pyridin-2-yl)methanol;
(R)-(6-(6-(6-(1-amino-2-fluoroethyl)pyridin-2-yl)-4-(2-methoxyethoxy)-1H-indazol-1-yl)pyridin-2-yl)methanol;
(S)-(6-(6-(4-(1-aminobutyl)pyrimidin-2-yl)-4-(2-methoxyethoxy)-1H-indazol-1-yl)pyridin-2-yl)methanol;
(R)-(6-(6-(4-(1-aminobutyl)pyrimidin-2-yl)-4-(2-methoxyethoxy)-1H-indazol-1-yl)pyridin-2-yl)methanol;
(6-(6-(6-((S)-1-aminobutyl)pyridin-2-yl)-4-(tetrahydrofuran-3-yl)-1H-indazol-1-yl)pyridin-2-yl)methanol; and
(S)-(6-(6-(6-(1-aminobutyl)pyridin-2-yl)-4-((3,3-difluorocyclobutyl)methoxy)-1H-indazol-1-yl)pyridin-2-yl)methanol;
or a pharmaceutically acceptable salt thereof.

2. A pharmaceutical composition comprising at least one compound of claim 1, or a pharmaceutically acceptable salt thereof, and at least one pharmaceutically acceptable excipient.

3. A method for treating rheumatoid arthritis or ischemic kidney injury in a subject, comprising administering to the patient a therapeutically effective amount of a compound of claim 1, or a pharmaceutically acceptable salt thereof, thereby treating rheumatoid arthritis or ischemic kidney injury.

4. The method of claim 3, wherein the method is for treating rheumatoid arthritis.

* * * * *